US009181307B2

(12) United States Patent
Cusack et al.

(10) Patent No.: US 9,181,307 B2
(45) Date of Patent: Nov. 10, 2015

(54) INFLUENZA A 2009 PANDEMIC H1N1 POLYPEPTIDE FRAGMENTS COMPRISING ENDONUCLEASE ACTIVITY AND THEIR USE

(75) Inventors: Stephen Cusack, Seyssinet-Pariset (FR); Eva Kowalinski, Hirschberg (DE); Chloe Zubieta, Le Fontanil-Cornillon (FR)

(73) Assignee: European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 13/635,064

(22) PCT Filed: Mar. 15, 2011

(86) PCT No.: PCT/EP2011/001274

§ 371 (c)(1), (2), (4) Date: Sep. 14, 2012

(87) PCT Pub. No.: WO2011/113579

PCT Pub. Date: Sep. 22, 2011

(65) Prior Publication Data

US 2013/0023565 A1 Jan. 24, 2013

Related U.S. Application Data

(60) Provisional application No. 61/340,335, filed on Mar. 16, 2010.

(51) Int. Cl.

*C12N 9/22* (2006.01)
*C07K 14/005* (2006.01)

(Continued)

(52) U.S. Cl.

CPC ............... *C07K 14/005* (2013.01); *A61K 31/33* (2013.01); *A61K 38/00* (2013.01); *C07K 2299/00* (2013.01); *C12N 9/22* (2013.01); *C12N 2760/16122* (2013.01)

(58) Field of Classification Search

None

See application file for complete search history.

(56) References Cited

U.S. PATENT DOCUMENTS

2005/0143402 A1 * 6/2005 Cheetham et al. ....... 514/266.21

OTHER PUBLICATIONS

Wiencek, J. M. Ann. Rev. Biomed. Eng. 1999, 1, 505-534.*

(Continued)

*Primary Examiner* — Nashaat Nashed

(74) *Attorney, Agent, or Firm* — Faegre Baker Daniels LLP

(57) ABSTRACT

The present invention relates to polypeptide fragments comprising an amino-terminal fragment of the PA subunit of a viral RNA-dependent RNA polymerase possessing endonuclease activity, wherein said PA subunit is from Influenza A 2009 pandemic H1N1 virus or is a variant thereof. This invention also relates to (i) crystals of the polypeptide fragments which are suitable for structure determination of said polypeptide fragments using X-ray crystallography and (ii) computational methods using the structural coordinates of said polypeptide to screen for and design compounds that modulate, preferably inhibit the endonucleolytically active site within the polypeptide fragment. In addition, this invention relates to methods identifying compounds that bind to the PA polypeptide fragments possessing endonuclease activity and preferably inhibit said endonucleolytic activity, preferably in a high throughput setting. This invention also relates to compounds which are able to modulate, preferably to inhibit, the endonuclease activity of the PA subunit polypeptide fragment or variant thereof of the present invention and pharmaceutical compositions comprising said compounds for the treatment of disease conditions caused by viral infections with viruses of the Orthomyxoviridae family, Bunyaviridae family and/or Arenviridae family, preferably caused by viral infections with Influenza A 2009 pandemic H1N1 virus. Preferably, said compounds are identifiable by the methods disclosed herein or said pharmaceutical compositions are producible by the methods disclosed herein.

14 Claims, 209 Drawing Sheets

H1N1 PA structure (Chain A) native

(51) Int. Cl.
*A61K 31/33* (2006.01)
*A61K 38/00* (2006.01)

(56) References Cited

OTHER PUBLICATIONS

Gerloff et al., Sep. 1, 2009; "SubName: Full-Polymerase acidic protein; flags: Fragment:"; XP002637949, retrieved from EBI accession No. UNIPROT: C6HOY9; database accession No. C6HOY9; compound.
Eshaghi et al., Oct. 13, 2009; "Subname: Full+Polymerase PA; Flags: Fragment;", XP002637950, retrieved from EBI accession No. UNIPROT: C8CTT5; Database accession No. C8CTT5; compound.
Garten, Rebecca J. et al; "Antigenic and Genetic Characterics of Swine-Origin 2009 A(H1N1) Influenza Viruses Circulating in Humans:, Science (Washington, D.C.), vol. 325, No. 5937, Jul. 2009, pp. 197-201, XP002637951, ISSN: 0036-8075, the whole document & Garten et al.:" Supporting online Material for Antigenic and Genetic Characterics of the Early Isolates of Swine-Origin 2009 A(H1N1) Influenza Viruses Circulating in Humans.
Kuzuhara et al.: "Green tea catechins inhibit the endonuclease activity of influenza A virus RNA polymerse", PLOS Currents; Oct. 13, 2009, XP002637952, retrieved from the Internet: URL:http://www.ncbi.nlm.nih.gov/pmc/articles/PMC2762814, retrieved on May 19, 2011], the whole document.
Hayden Frederick: "Developing New Antiviral Agents for Influenza Treatment: What Does the Future Hold?", Clinical Infectious Diseases, The University of Chicago Press, Chicago, IL, US, vol. 48, No. Suppl. 1, Jan. 1, 2009, pp. S3-S13, XP002604650, ISSN: 1058-4838, DOI: DOI:10, 1086/591851, the whole document.
Sleeman Katrina et al.: "In Vitro Antiviral Activity of Favipiravir (T-705) against Drug-Resistance Influenza and 2009 A (H1N1) Viruses", Antimicrobial Agents and Chemotherapy, vol. 54, No. 6, Jun. 2010, pp. 2517-2524, XP002637953, the whole document.
Zhao Cong et al.: "Nucleoside Monophosphate Complex Structures of the Endonuclease Domain from the Influenza Virus Polymerase PA Subunit Reveal the Substrate Binding Site inside the Catalytic Center", Journal of Virology, vol. 83, No. 18, Sep. 2009, pp. 9024-9030, XP002675566, the whole documents.
Alexandre Dias et al: "The cap-snatching endonuclease of influenza virus polymerase resides in the PA subunit", Nature, vol. 458, No. 7240, Feb. 4, 2009, pp. 914-918, XP55022148, ISSN: 0028-0836, DOI: 10.1038/nature07745, the whole document.
Nistal-Villan Estanislao et al: "New prospects for the rational design of antivirals", Nature Medicine Nov. 2009 LNKD-PBUMED: 19893557, vol. 15, No. 11, Nov. 2009, pp. 1253-1254, XP002675567, ISSN: 1546-170X, the whole document.
Hastings J C et al: Anti-influenza virus activities of 4-Substituted 2,4-dioxobutanoic acid inhibitors:, Antimicrobial Agents and Chemotherapy, vol. 40, No. 5, 1996, pp. 1304-1307, XP002675568, ISSN: 055-4804, the whole document.
Dias A. et al., The Cap-Snatching Endonuclease of Influenza Virus Polymerase Resides in the PA Subunit, Nature Letters, Apr. 16, 2009, vol. 458, pp. 914-918.
Dubois R. M. et al., Structural and Biochemical Basis for Development of Influenza Virus Inhibitors Targeting the PA Endonuclease, PLOS Pathogens, Aug. 2012, vol. 8, No. 8, pp. 1-13.

* cited by examiner

FIG. 1-1

Figure 1: Native H1N1 polypeptide fragment (Chain A)

```
HEADER    ----                                     XX-XXX-XX   xxxx
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.10
REMARK   3   RESOLUTION RANGE LOW  (ANGSTROMS) :  20.00
REMARK   3   DATA CUTOFF            (SIGMA(F)) : NONE
REMARK   3   COMPLETENESS FOR RANGE        (%) :  98.97
REMARK   3   NUMBER OF REFLECTIONS             :   63279
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.22341
REMARK   3   R VALUE            (WORKING SET) :  0.22159
REMARK   3   FREE R VALUE                     :  0.26801
REMARK   3   FREE R VALUE TEST SET SIZE   (%) :  4.0
REMARK   3   FREE R VALUE TEST SET COUNT      :  2639
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    2.100
REMARK   3   BIN RESOLUTION RANGE LOW            :    2.154
REMARK   3   REFLECTION IN BIN     (WORKING SET) :     4547
REMARK   3   BIN COMPLETENESS (WORKING+TEST) (%) :    97.48
REMARK   3   BIN R VALUE           (WORKING SET) :    0.248
REMARK   3   BIN FREE R VALUE SET COUNT          :      204
REMARK   3   BIN FREE R VALUE                    :    0.291
REMARK   3
REMARK   3  NUMBER OF NON-HYDROGEN ATOMS USED IN REFINEMENT.
REMARK   3   ALL ATOMS                :     6568
REMARK   3
REMARK   3  B VALUES.
REMARK   3   FROM WILSON PLOT           (A**2) : NULL
REMARK   3   MEAN B VALUE      (OVERALL, A**2) :  33.980
REMARK   3   OVERALL ANISOTROPIC B VALUE.
REMARK   3    B11 (A**2) :     0.00
REMARK   3    B22 (A**2) :     0.04
REMARK   3    B33 (A**2) :    -0.04
REMARK   3    B12 (A**2) :     0.00
REMARK   3    B13 (A**2) :    -0.02
REMARK   3    B23 (A**2) :     0.00
REMARK   3
REMARK   3  ESTIMATED OVERALL COORDINATE ERROR.
REMARK   3   ESU BASED ON R VALUE                            (A):   0.199
REMARK   3   ESU BASED ON FREE R VALUE                       (A):   0.184
REMARK   3   ESU BASED ON MAXIMUM LIKELIHOOD                 (A):   0.131
REMARK   3   ESU FOR B VALUES BASED ON MAXIMUM LIKELIHOOD (A**2):   4.762
REMARK   3
REMARK   3 CORRELATION COEFFICIENTS.
REMARK   3   CORRELATION COEFFICIENT FO-FC      :   0.928
REMARK   3   CORRELATION COEFFICIENT FO-FC FREE :   0.893
REMARK   3
```

FIG. 1-2

```
REMARK   3  RMS DEVIATIONS FROM IDEAL VALUES        COUNT    RMS    WEIGHT
REMARK   3   BOND LENGTHS REFINED ATOMS        (A):  6502 ; 0.026 ; 0.022
REMARK   3   BOND ANGLES REFINED ATOMS   (DEGREES):  8730 ; 2.114 ; 1.941
REMARK   3   TORSION ANGLES, PERIOD 1    (DEGREES):   758 ; 7.213 ; 5.000
REMARK   3   TORSION ANGLES, PERIOD 2    (DEGREES):   346 ;35.310 ;23.526
REMARK   3   TORSION ANGLES, PERIOD 3    (DEGREES):  1222 ;19.330 ;15.000
REMARK   3   TORSION ANGLES, PERIOD 4    (DEGREES):    56 ;20.187 ;15.000
REMARK   3   CHIRAL-CENTER RESTRAINTS       (A**3):   938 ; 0.155 ; 0.200
REMARK   3   GENERAL PLANES REFINED ATOMS      (A):  4900 ; 0.012 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):  3820 ; 1.364 ; 1.500
REMARK   3   MAIN-CHAIN ANGLE REFINED ATOMS (A**2):  6192 ; 2.379 ; 2.000
REMARK   3   SIDE-CHAIN BOND REFINED ATOMS  (A**2):  2682 ; 3.867 ; 3.000
REMARK   3   SIDE-CHAIN ANGLE REFINED ATOMS (A**2):  2538 ; 5.937 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  U VALUES      : REFINED INDIVIDUALLY
REMARK   3
LINKR            GLU A  64                     ASN A  69                gap
LINKR            GLU C  64                     ASN C  69                gap
LINKR            ILE C 138                     ASN C 142                gap
LINKR            GLU B  64                     ASN B  69                gap
LINKR            GLU D  64                     ASN D  69                gap
LINKR            ILE D 138                     ASN D 142                gap
CRYST1  263.630   66.240   66.320  90.00  95.98  90.00 C 1 2 1
SCALE1      0.003793  0.000000  0.000397        0.00000
SCALE2      0.000000  0.015097  0.000000        0.00000
SCALE3      0.000000  0.000000  0.015161        0.00000
ATOM      1  N   GLY A  -2     106.920  36.113 -16.120  1.00 42.11           N
ATOM      2  CA  GLY A  -2     107.197  36.607 -14.722  1.00 42.42           C
ATOM      3  C   GLY A  -2     106.306  37.763 -14.247  1.00 42.64           C
ATOM      4  O   GLY A  -2     106.398  38.220 -13.071  1.00 42.95           O
ATOM      5  N   MET A  -1     105.422  38.235 -15.136  1.00 42.19           N
ATOM      6  CA  MET A  -1     104.454  39.289 -14.808  1.00 41.62           C
ATOM      7  CB  MET A  -1     103.457  39.402 -15.946  1.00 42.52           C
ATOM      8  CG  MET A  -1     102.421  40.555 -15.917  1.00 47.58           C
ATOM      9  SD  MET A  -1     100.922  40.056 -16.866  1.00 59.76           S
ATOM     10  CE  MET A  -1      99.977  39.071 -15.666  1.00 58.22           C
ATOM     11  C   MET A  -1     103.711  38.952 -13.499  1.00 40.62           C
ATOM     12  O   MET A  -1     103.430  39.841 -12.678  1.00 38.80           O
ATOM     13  N   ALA A   0     103.391  37.665 -13.306  1.00 38.62           N
ATOM     14  CA  ALA A   0     102.561  37.313 -12.164  1.00 37.98           C
ATOM     15  CB  ALA A   0     102.144  35.841 -12.242  1.00 38.44           C
ATOM     16  C   ALA A   0     103.311  37.598 -10.850  1.00 35.87           C
```

FIG. 1-3

| | | | | | | | | | | | |
|---|---|---|---|---|---|---|---|---|---|---|---|
| ATOM | 17 | O | ALA | A | 0 | 102.751 | 38.144 | -9.897 | 1.00 | 34.89 | O |
| ATOM | 18 | N | MET | A | 1 | 104.590 | 37.247 | -10.790 | 1.00 | 33.89 | N |
| ATOM | 19 | CA | MET | A | 1 | 105.271 | 37.492 | -9.543 | 1.00 | 33.49 | C |
| ATOM | 20 | CB | MET | A | 1 | 106.518 | 36.611 | -9.384 | 1.00 | 34.19 | C |
| ATOM | 21 | CG | MET | A | 1 | 107.436 | 37.038 | -8.233 | 1.00 | 33.79 | C |
| ATOM | 22 | SD | MET | A | 1 | 106.782 | 36.651 | -6.599 | 1.00 | 37.21 | S |
| ATOM | 23 | CE | MET | A | 1 | 107.366 | 34.945 | -6.546 | 1.00 | 34.04 | C |
| ATOM | 24 | C | MET | A | 1 | 105.561 | 38.983 | -9.344 | 1.00 | 32.13 | C |
| ATOM | 25 | O | MET | A | 1 | 105.475 | 39.490 | -8.218 | 1.00 | 30.65 | O |
| ATOM | 26 | N | GLU | A | 2 | 105.805 | 39.692 | -10.432 | 1.00 | 32.04 | N |
| ATOM | 27 | CA | GLU | A | 2 | 106.093 | 41.143 | -10.347 | 1.00 | 33.26 | C |
| ATOM | 28 | CB | GLU | A | 2 | 106.453 | 41.711 | -11.741 | 1.00 | 34.23 | C |
| ATOM | 29 | CG | GLU | A | 2 | 106.964 | 43.179 | -11.676 | 1.00 | 37.06 | C |
| ATOM | 30 | CD | GLU | A | 2 | 106.799 | 44.010 | -13.027 | 1.00 | 43.24 | C |
| ATOM | 31 | OE1 | GLU | A | 2 | 106.583 | 43.427 | -14.154 | 1.00 | 36.15 | O |
| ATOM | 32 | OE2 | GLU | A | 2 | 106.889 | 45.274 | -12.911 | 1.00 | 44.58 | O |
| ATOM | 33 | C | GLU | A | 2 | 104.889 | 41.897 | -9.827 | 1.00 | 33.56 | C |
| ATOM | 34 | O | GLU | A | 2 | 105.031 | 42.794 | -9.016 | 1.00 | 34.09 | O |
| ATOM | 35 | N | ASP | A | 3 | 103.706 | 41.593 | -10.377 | 1.00 | 33.72 | N |
| ATOM | 36 | CA | ASP | A | 3 | 102.423 | 42.039 | -9.798 | 1.00 | 34.07 | C |
| ATOM | 37 | CB | ASP | A | 3 | 101.300 | 41.380 | -10.599 | 1.00 | 36.24 | C |
| ATOM | 38 | CG | ASP | A | 3 | 101.268 | 41.859 | -12.022 | 1.00 | 39.95 | C |
| ATOM | 39 | OD1 | ASP | A | 3 | 102.165 | 42.658 | -12.371 | 1.00 | 46.54 | O |
| ATOM | 40 | OD2 | ASP | A | 3 | 100.368 | 41.438 | -12.778 | 1.00 | 46.06 | O |
| ATOM | 41 | C | ASP | A | 3 | 102.185 | 41.651 | -8.323 | 1.00 | 32.78 | C |
| ATOM | 42 | O | ASP | A | 3 | 101.657 | 42.422 | -7.544 | 1.00 | 31.80 | O |
| ATOM | 43 | N | PHE | A | 4 | 102.489 | 40.415 | -7.950 | 1.00 | 31.44 | N |
| ATOM | 44 | CA | PHE | A | 4 | 102.310 | 40.074 | -6.547 | 1.00 | 30.67 | C |
| ATOM | 45 | CB | PHE | A | 4 | 102.654 | 38.598 | -6.293 | 1.00 | 30.24 | C |
| ATOM | 46 | CG | PHE | A | 4 | 102.680 | 38.280 | -4.850 | 1.00 | 29.43 | C |
| ATOM | 47 | CD1 | PHE | A | 4 | 101.477 | 38.056 | -4.165 | 1.00 | 30.86 | C |
| ATOM | 48 | CE1 | PHE | A | 4 | 101.487 | 37.848 | -2.742 | 1.00 | 30.63 | C |
| ATOM | 49 | CZ | PHE | A | 4 | 102.726 | 37.837 | -2.039 | 1.00 | 29.79 | C |
| ATOM | 50 | CE2 | PHE | A | 4 | 103.933 | 38.077 | -2.737 | 1.00 | 30.85 | C |
| ATOM | 51 | CD2 | PHE | A | 4 | 103.872 | 38.292 | -4.150 | 1.00 | 26.32 | C |
| ATOM | 52 | C | PHE | A | 4 | 103.170 | 40.984 | -5.646 | 1.00 | 29.79 | C |
| ATOM | 53 | O | PHE | A | 4 | 102.736 | 41.450 | -4.558 | 1.00 | 30.94 | O |
| ATOM | 54 | N | VAL | A | 5 | 104.420 | 41.216 | -6.064 | 1.00 | 30.48 | N |
| ATOM | 55 | CA | VAL | A | 5 | 105.391 | 41.980 | -5.260 | 1.00 | 29.36 | C |
| ATOM | 56 | CB | VAL | A | 5 | 106.750 | 41.975 | -5.963 | 1.00 | 29.08 | C |
| ATOM | 57 | CG1 | VAL | A | 5 | 107.689 | 42.974 | -5.341 | 1.00 | 30.12 | C |
| ATOM | 58 | CG2 | VAL | A | 5 | 107.379 | 40.663 | -5.854 | 1.00 | 28.29 | C |
| ATOM | 59 | C | VAL | A | 5 | 104.893 | 43.391 | -5.079 | 1.00 | 30.37 | C |
| ATOM | 60 | O | VAL | A | 5 | 104.839 | 43.988 | -3.974 | 1.00 | 29.91 | O |
| ATOM | 61 | N | ARG | A | 6 | 104.447 | 43.938 | -6.185 | 1.00 | 31.19 | N |
| ATOM | 62 | CA | ARG | A | 6 | 103.939 | 45.319 | -6.118 | 1.00 | 33.22 | C |
| ATOM | 63 | CB | ARG | A | 6 | 103.770 | 45.939 | -7.538 | 1.00 | 32.70 | C |
| ATOM | 64 | CG | ARG | A | 6 | 105.082 | 46.029 | -8.302 | 1.00 | 32.45 | C |
| ATOM | 65 | CD | ARG | A | 6 | 104.899 | 46.627 | -9.647 | 1.00 | 35.90 | C |
| ATOM | 66 | NE | ARG | A | 6 | 106.156 | 46.609 | -10.372 | 1.00 | 38.38 | N |
| ATOM | 67 | CZ | ARG | A | 6 | 107.124 | 47.499 | -10.167 | 1.00 | 39.22 | C |
| ATOM | 68 | NH1 | ARG | A | 6 | 106.951 | 48.504 | -9.313 | 1.00 | 38.07 | N |
| ATOM | 69 | NH2 | ARG | A | 6 | 108.242 | 47.408 | -10.846 | 1.00 | 39.11 | N |
| ATOM | 70 | C | ARG | A | 6 | 102.703 | 45.545 | -5.228 | 1.00 | 32.81 | C |
| ATOM | 71 | O | ARG | A | 6 | 102.496 | 46.644 | -4.772 | 1.00 | 33.19 | O |
| ATOM | 72 | N | GLN | A | 7 | 101.881 | 44.519 | -4.973 | 1.00 | 33.24 | N |
| ATOM | 73 | CA | GLN | A | 7 | 100.780 | 44.711 | -4.058 | 1.00 | 32.91 | C |
| ATOM | 74 | CB | GLN | A | 7 | 99.476 | 44.128 | -4.612 | 1.00 | 33.20 | C |
| ATOM | 75 | CG | GLN | A | 7 | 99.463 | 42.611 | -4.729 | 1.00 | 37.26 | C |
| ATOM | 76 | CD | GLN | A | 7 | 98.171 | 42.066 | -5.417 | 1.00 | 48.45 | C |
| ATOM | 77 | OE1 | GLN | A | 7 | 97.277 | 42.847 | -5.795 | 1.00 | 50.00 | O |
| ATOM | 78 | NE2 | GLN | A | 7 | 98.102 | 40.727 | -5.626 | 1.00 | 48.29 | N |
| ATOM | 79 | C | GLN | A | 7 | 101.079 | 44.182 | -2.654 | 1.00 | 33.62 | C |

FIG. 1-4

| | | | | | | | | | | | |
|---|---|---|---|---|---|---|---|---|---|---|---|
| ATOM | 80 | O | GLN | A | 7 | 100.299 | 44.397 | -1.770 | 1.00 | 32.93 | O |
| ATOM | 81 | N | CYS | A | 8 | 102.177 | 43.440 | -2.474 | 1.00 | 33.35 | N |
| ATOM | 82 | CA | CYS | A | 8 | 102.481 | 42.866 | -1.192 | 1.00 | 33.91 | C |
| ATOM | 83 | CB | CYS | A | 8 | 103.316 | 41.566 | -1.329 | 1.00 | 32.63 | C |
| ATOM | 84 | SG | CYS | A | 8 | 103.610 | 40.718 | 0.309 | 1.00 | 39.98 | S |
| ATOM | 85 | C | CYS | A | 8 | 103.208 | 43.872 | -0.253 | 1.00 | 33.14 | C |
| ATOM | 86 | O | CYS | A | 8 | 102.930 | 43.932 | 0.938 | 1.00 | 33.37 | O |
| ATOM | 87 | N | PHE | A | 9 | 104.104 | 44.667 | -0.814 | 1.00 | 31.55 | N |
| ATOM | 88 | CA | PHE | A | 9 | 105.010 | 45.524 | -0.030 | 1.00 | 30.40 | C |
| ATOM | 89 | CB | PHE | A | 9 | 106.448 | 45.248 | -0.499 | 1.00 | 27.69 | C |
| ATOM | 90 | CG | PHE | A | 9 | 106.903 | 43.833 | -0.211 | 1.00 | 25.63 | C |
| ATOM | 91 | CD1 | PHE | A | 9 | 107.353 | 43.466 | 1.062 | 1.00 | 26.07 | C |
| ATOM | 92 | CE1 | PHE | A | 9 | 107.793 | 42.130 | 1.319 | 1.00 | 27.24 | C |
| ATOM | 93 | CZ | PHE | A | 9 | 107.717 | 41.166 | 0.272 | 1.00 | 23.99 | C |
| ATOM | 94 | CE2 | PHE | A | 9 | 107.294 | 41.550 | -0.973 | 1.00 | 23.73 | C |
| ATOM | 95 | CD2 | PHE | A | 9 | 106.831 | 42.891 | -1.179 | 1.00 | 21.08 | C |
| ATOM | 96 | C | PHE | A | 9 | 104.685 | 47.015 | -0.164 | 1.00 | 29.41 | C |
| ATOM | 97 | O | PHE | A | 9 | 104.147 | 47.376 | -1.159 | 1.00 | 30.84 | O |
| ATOM | 98 | N | ASN | A | 10 | 105.003 | 47.836 | 0.845 | 1.00 | 31.48 | N |
| ATOM | 99 | CA | ASN | A | 10 | 104.954 | 49.343 | 0.796 | 1.00 | 32.81 | C |
| ATOM | 100 | CB | ASN | A | 10 | 106.003 | 49.954 | 1.744 | 1.00 | 33.17 | C |
| ATOM | 101 | CG | ASN | A | 10 | 105.617 | 49.821 | 3.046 | 1.00 | 37.36 | C |
| ATOM | 102 | OD1 | ASN | A | 10 | 104.483 | 49.355 | 3.258 | 1.00 | 47.16 | O |
| ATOM | 103 | ND2 | ASN | A | 10 | 106.489 | 50.111 | 3.990 | 1.00 | 40.42 | N |
| ATOM | 104 | C | ASN | A | 10 | 105.505 | 49.853 | -0.488 | 1.00 | 31.88 | C |
| ATOM | 105 | O | ASN | A | 10 | 106.470 | 49.265 | -0.938 | 1.00 | 32.03 | O |
| ATOM | 106 | N | PRO | A | 11 | 105.010 | 51.024 | -0.977 | 1.00 | 31.02 | N |
| ATOM | 107 | CA | PRO | A | 11 | 105.727 | 51.649 | -2.085 | 1.00 | 29.85 | C |
| ATOM | 108 | CB | PRO | A | 11 | 104.879 | 52.908 | -2.416 | 1.00 | 29.84 | C |
| ATOM | 109 | CG | PRO | A | 11 | 103.380 | 52.433 | -2.010 | 1.00 | 32.11 | C |
| ATOM | 110 | CD | PRO | A | 11 | 103.694 | 51.680 | -0.689 | 1.00 | 32.04 | C |
| ATOM | 111 | C | PRO | A | 11 | 107.203 | 52.062 | -1.713 | 1.00 | 28.66 | C |
| ATOM | 112 | O | PRO | A | 11 | 107.988 | 52.180 | -2.609 | 1.00 | 27.80 | O |
| ATOM | 113 | N | MET | A | 12 | 107.494 | 52.332 | -0.437 | 1.00 | 25.87 | N |
| ATOM | 114 | CA | MET | A | 12 | 108.820 | 52.670 | 0.038 | 1.00 | 28.94 | C |
| ATOM | 115 | CB | MET | A | 12 | 108.774 | 53.099 | 1.545 | 1.00 | 30.09 | C |
| ATOM | 116 | CG | MET | A | 12 | 110.174 | 53.272 | 2.135 | 1.00 | 37.54 | C |
| ATOM | 117 | SD | MET | A | 12 | 110.304 | 53.494 | 3.953 | 1.00 | 56.33 | S |
| ATOM | 118 | CE | MET | A | 12 | 109.646 | 51.934 | 4.573 | 1.00 | 50.08 | C |
| ATOM | 119 | C | MET | A | 12 | 109.771 | 51.479 | -0.139 | 1.00 | 26.98 | C |
| ATOM | 120 | O | MET | A | 12 | 110.867 | 51.607 | -0.653 | 1.00 | 25.63 | O |
| ATOM | 121 | N | ILE | A | 13 | 109.308 | 50.300 | 0.239 | 1.00 | 26.06 | N |
| ATOM | 122 | CA | ILE | A | 13 | 110.072 | 49.065 | 0.002 | 1.00 | 25.53 | C |
| ATOM | 123 | CB | ILE | A | 13 | 109.369 | 47.853 | 0.646 | 1.00 | 26.04 | C |
| ATOM | 124 | CG1 | ILE | A | 13 | 109.158 | 48.098 | 2.166 | 1.00 | 27.13 | C |
| ATOM | 125 | CD1 | ILE | A | 13 | 110.363 | 48.591 | 2.856 | 1.00 | 31.35 | C |
| ATOM | 126 | CG2 | ILE | A | 13 | 110.138 | 46.504 | 0.450 | 1.00 | 23.46 | C |
| ATOM | 127 | C | ILE | A | 13 | 110.272 | 48.842 | -1.508 | 1.00 | 25.48 | C |
| ATOM | 128 | O | ILE | A | 13 | 111.392 | 48.579 | -1.975 | 1.00 | 24.10 | O |
| ATOM | 129 | N | VAL | A | 14 | 109.210 | 48.994 | -2.276 | 1.00 | 25.92 | N |
| ATOM | 130 | CA | VAL | A | 14 | 109.285 | 48.591 | -3.719 | 1.00 | 25.96 | C |
| ATOM | 131 | CB | VAL | A | 14 | 107.930 | 48.586 | -4.414 | 1.00 | 25.30 | C |
| ATOM | 132 | CG1 | VAL | A | 14 | 108.071 | 48.477 | -5.978 | 1.00 | 26.39 | C |
| ATOM | 133 | CG2 | VAL | A | 14 | 106.973 | 47.441 | -3.805 | 1.00 | 27.53 | C |
| ATOM | 134 | C | VAL | A | 14 | 110.296 | 49.496 | -4.433 | 1.00 | 25.98 | C |
| ATOM | 135 | O | VAL | A | 14 | 111.114 | 49.020 | -5.291 | 1.00 | 23.87 | O |
| ATOM | 136 | N | GLU | A | 15 | 110.274 | 50.764 | -4.043 | 1.00 | 25.35 | N |
| ATOM | 137 | CA | GLU | A | 15 | 111.147 | 51.772 | -4.683 | 1.00 | 27.71 | C |
| ATOM | 138 | CB | GLU | A | 15 | 110.803 | 53.205 | -4.179 | 1.00 | 27.39 | C |
| ATOM | 139 | CG | GLU | A | 15 | 111.648 | 54.380 | -4.744 | 1.00 | 33.50 | C |
| ATOM | 140 | CD | GLU | A | 15 | 110.861 | 55.741 | -4.786 | 1.00 | 39.08 | C |
| ATOM | 141 | OE1 | GLU | A | 15 | 110.621 | 56.357 | -3.718 | 1.00 | 37.10 | O |
| ATOM | 142 | OE2 | GLU | A | 15 | 110.448 | 56.155 | -5.906 | 1.00 | 44.04 | O |

FIG. 1-5

| | | | | | | | | | | | |
|---|---|---|---|---|---|---|---|---|---|---|---|
| ATOM | 143 | C | GLU | A | 15 | 112.612 | 51.454 | -4.349 | 1.00 | 27.40 | C |
| ATOM | 144 | O | GLU | A | 15 | 113.381 | 51.391 | -5.271 | 1.00 | 29.50 | O |
| ATOM | 145 | N | LEU | A | 16 | 112.953 | 51.231 | -3.059 | 1.00 | 26.00 | N |
| ATOM | 146 | CA | LEU | A | 16 | 114.324 | 50.797 | -2.607 | 1.00 | 25.66 | C |
| ATOM | 147 | CB | LEU | A | 16 | 114.463 | 50.615 | -1.022 | 1.00 | 24.84 | C |
| ATOM | 148 | CG | LEU | A | 16 | 114.470 | 51.912 | -0.120 | 1.00 | 28.10 | C |
| ATOM | 149 | CD1 | LEU | A | 16 | 114.169 | 51.812 | 1.363 | 1.00 | 24.50 | C |
| ATOM | 150 | CD2 | LEU | A | 16 | 115.819 | 52.795 | -0.228 | 1.00 | 27.58 | C |
| ATOM | 151 | C | LEU | A | 16 | 114.825 | 49.601 | -3.355 | 1.00 | 25.50 | C |
| ATOM | 152 | O | LEU | A | 16 | 115.972 | 49.577 | -3.769 | 1.00 | 25.71 | O |
| ATOM | 153 | N | ALA | A | 17 | 113.952 | 48.600 | -3.540 | 1.00 | 23.82 | N |
| ATOM | 154 | CA | ALA | A | 17 | 114.260 | 47.399 | -4.263 | 1.00 | 23.96 | C |
| ATOM | 155 | CB | ALA | A | 17 | 113.053 | 46.340 | -4.077 | 1.00 | 23.48 | C |
| ATOM | 156 | C | ALA | A | 17 | 114.552 | 47.651 | -5.768 | 1.00 | 23.90 | C |
| ATOM | 157 | O | ALA | A | 17 | 115.585 | 47.145 | -6.326 | 1.00 | 22.52 | O |
| ATOM | 158 | N | GLU | A | 18 | 113.709 | 48.454 | -6.433 | 1.00 | 23.41 | N |
| ATOM | 159 | CA | GLU | A | 18 | 113.972 | 48.771 | -7.837 | 1.00 | 25.58 | C |
| ATOM | 160 | CB | GLU | A | 18 | 112.837 | 49.559 | -8.481 | 1.00 | 27.82 | C |
| ATOM | 161 | CG | GLU | A | 18 | 111.423 | 48.914 | -8.429 | 1.00 | 29.86 | C |
| ATOM | 162 | CD | GLU | A | 18 | 110.354 | 49.936 | -8.798 | 1.00 | 35.01 | C |
| ATOM | 163 | OE1 | GLU | A | 18 | 110.439 | 51.101 | -8.318 | 1.00 | 42.13 | O |
| ATOM | 164 | OE2 | GLU | A | 18 | 109.441 | 49.604 | -9.572 | 1.00 | 37.55 | O |
| ATOM | 165 | C | GLU | A | 18 | 115.299 | 49.595 | -7.982 | 1.00 | 26.84 | C |
| ATOM | 166 | O | GLU | A | 18 | 116.003 | 49.428 | -8.947 | 1.00 | 27.35 | O |
| ATOM | 167 | N | LYS | A | 19 | 115.580 | 50.489 | -7.035 | 1.00 | 27.67 | N |
| ATOM | 168 | CA | LYS | A | 19 | 116.789 | 51.304 | -7.104 | 1.00 | 30.64 | C |
| ATOM | 169 | CB | LYS | A | 19 | 116.835 | 52.322 | -5.956 | 1.00 | 29.91 | C |
| ATOM | 170 | CG | LYS | A | 19 | 115.802 | 53.446 | -6.099 | 1.00 | 36.63 | C |
| ATOM | 171 | CD | LYS | A | 19 | 115.807 | 54.399 | -4.881 | 1.00 | 36.59 | C |
| ATOM | 172 | CE | LYS | A | 19 | 115.309 | 55.763 | -5.323 | 1.00 | 42.22 | C |
| ATOM | 173 | NZ | LYS | A | 19 | 115.724 | 56.847 | -4.358 | 1.00 | 43.08 | N |
| ATOM | 174 | C | LYS | A | 19 | 117.988 | 50.373 | -6.987 | 1.00 | 29.27 | C |
| ATOM | 175 | O | LYS | A | 19 | 118.927 | 50.487 | -7.800 | 1.00 | 29.84 | O |
| ATOM | 176 | N | ALA | A | 20 | 117.913 | 49.420 | -6.044 | 1.00 | 28.62 | N |
| ATOM | 177 | CA | ALA | A | 20 | 119.038 | 48.541 | -5.829 | 1.00 | 29.09 | C |
| ATOM | 178 | CB | ALA | A | 20 | 118.866 | 47.679 | -4.563 | 1.00 | 28.93 | C |
| ATOM | 179 | C | ALA | A | 20 | 119.296 | 47.714 | -7.075 | 1.00 | 29.58 | C |
| ATOM | 180 | O | ALA | A | 20 | 120.446 | 47.526 | -7.525 | 1.00 | 28.61 | O |
| ATOM | 181 | N | MET | A | 21 | 118.227 | 47.198 | -7.633 | 1.00 | 30.20 | N |
| ATOM | 182 | CA | MET | A | 21 | 118.381 | 46.327 | -8.765 | 1.00 | 31.07 | C |
| ATOM | 183 | CB | MET | A | 21 | 117.115 | 45.554 | -9.068 | 1.00 | 29.96 | C |
| ATOM | 184 | CG | MET | A | 21 | 116.890 | 44.360 | -8.192 | 1.00 | 28.70 | C |
| ATOM | 185 | SD | MET | A | 21 | 115.271 | 43.605 | -8.539 | 1.00 | 30.60 | S |
| ATOM | 186 | CE | MET | A | 21 | 115.692 | 42.772 | -10.043 | 1.00 | 32.06 | C |
| ATOM | 187 | C | MET | A | 21 | 118.829 | 47.125 | -10.007 | 1.00 | 32.07 | C |
| ATOM | 188 | O | MET | A | 21 | 119.651 | 46.628 | -10.738 | 1.00 | 32.00 | O |
| ATOM | 189 | N | LYS | A | 22 | 118.302 | 48.331 | -10.227 | 1.00 | 32.88 | N |
| ATOM | 190 | CA | LYS | A | 22 | 118.768 | 49.175 | -11.353 | 1.00 | 34.41 | C |
| ATOM | 191 | CB | LYS | A | 22 | 118.000 | 50.488 | -11.432 | 1.00 | 33.51 | C |
| ATOM | 192 | CG | LYS | A | 22 | 118.217 | 51.117 | -12.801 | 1.00 | 40.97 | C |
| ATOM | 193 | CD | LYS | A | 22 | 117.597 | 52.548 | -12.899 | 1.00 | 47.64 | C |
| ATOM | 194 | CE | LYS | A | 22 | 118.111 | 53.312 | -14.126 | 1.00 | 48.65 | C |
| ATOM | 195 | NZ | LYS | A | 22 | 117.521 | 54.691 | -14.031 | 1.00 | 51.01 | N |
| ATOM | 196 | C | LYS | A | 22 | 120.280 | 49.525 | -11.283 | 1.00 | 33.38 | C |
| ATOM | 197 | O | LYS | A | 22 | 121.009 | 49.461 | -12.294 | 1.00 | 33.44 | O |
| ATOM | 198 | N | GLU | A | 23 | 120.718 | 49.860 | -10.082 | 1.00 | 33.00 | N |
| ATOM | 199 | CA | GLU | A | 23 | 122.076 | 50.205 | -9.764 | 1.00 | 33.25 | C |
| ATOM | 200 | CB | GLU | A | 23 | 122.188 | 50.431 | -8.248 | 1.00 | 33.36 | C |
| ATOM | 201 | CG | GLU | A | 23 | 123.655 | 50.643 | -7.695 | 1.00 | 39.45 | C |
| ATOM | 202 | CD | GLU | A | 23 | 124.099 | 52.084 | -7.546 | 1.00 | 42.41 | C |
| ATOM | 203 | OE1 | GLU | A | 23 | 123.884 | 52.865 | -8.486 | 1.00 | 47.54 | O |
| ATOM | 204 | OE2 | GLU | A | 23 | 124.663 | 52.456 | -6.467 | 1.00 | 45.45 | O |
| ATOM | 205 | C | GLU | A | 23 | 123.119 | 49.160 | -10.244 | 1.00 | 32.51 | C |

FIG. 1-6

| | | | | | | | | | | | |
|---|---|---|---|---|---|---|---|---|---|---|---|
| ATOM | 206 | O | GLU | A | 23 | 124.209 | 49.559 | -10.663 | 1.00 | 33.04 | O |
| ATOM | 207 | N | TYR | A | 24 | 122.798 | 47.854 | -10.190 | 1.00 | 31.10 | N |
| ATOM | 208 | CA | TYR | A | 24 | 123.737 | 46.822 | -10.622 | 1.00 | 30.25 | C |
| ATOM | 209 | CB | TYR | A | 24 | 124.091 | 45.813 | -9.509 | 1.00 | 29.88 | C |
| ATOM | 210 | CG | TYR | A | 24 | 124.517 | 46.501 | -8.232 | 1.00 | 30.66 | C |
| ATOM | 211 | CD1 | TYR | A | 24 | 125.845 | 47.015 | -8.087 | 1.00 | 28.09 | C |
| ATOM | 212 | CE1 | TYR | A | 24 | 126.245 | 47.603 | -6.969 | 1.00 | 28.22 | C |
| ATOM | 213 | CZ | TYR | A | 24 | 125.308 | 47.835 | -5.957 | 1.00 | 34.66 | C |
| ATOM | 214 | OH | TYR | A | 24 | 125.704 | 48.479 | -4.834 | 1.00 | 34.37 | O |
| ATOM | 215 | CE2 | TYR | A | 24 | 123.989 | 47.384 | -6.070 | 1.00 | 31.70 | C |
| ATOM | 216 | CD2 | TYR | A | 24 | 123.617 | 46.730 | -7.235 | 1.00 | 29.48 | C |
| ATOM | 217 | C | TYR | A | 24 | 123.221 | 46.146 | -11.871 | 1.00 | 31.20 | C |
| ATOM | 218 | O | TYR | A | 24 | 123.556 | 45.006 | -12.127 | 1.00 | 30.08 | O |
| ATOM | 219 | N | GLY | A | 25 | 122.392 | 46.858 | -12.632 | 1.00 | 31.07 | N |
| ATOM | 220 | CA | GLY | A | 25 | 121.974 | 46.381 | -13.945 | 1.00 | 34.02 | C |
| ATOM | 221 | C | GLY | A | 25 | 120.985 | 45.184 | -13.877 | 1.00 | 34.74 | C |
| ATOM | 222 | O | GLY | A | 25 | 120.931 | 44.376 | -14.757 | 1.00 | 35.69 | O |
| ATOM | 223 | N | GLU | A | 26 | 120.251 | 45.020 | -12.800 | 1.00 | 34.56 | N |
| ATOM | 224 | CA | GLU | A | 26 | 119.269 | 43.951 | -12.808 | 1.00 | 35.34 | C |
| ATOM | 225 | CB | GLU | A | 26 | 119.283 | 43.228 | -11.465 | 1.00 | 33.83 | C |
| ATOM | 226 | CG | GLU | A | 26 | 120.503 | 42.336 | -11.172 | 1.00 | 32.93 | C |
| ATOM | 227 | CD | GLU | A | 26 | 120.790 | 42.208 | -9.664 | 1.00 | 33.15 | C |
| ATOM | 228 | OE1 | GLU | A | 26 | 120.240 | 43.008 | -8.868 | 1.00 | 35.33 | O |
| ATOM | 229 | OE2 | GLU | A | 26 | 121.564 | 41.330 | -9.234 | 1.00 | 37.78 | O |
| ATOM | 230 | C | GLU | A | 26 | 117.884 | 44.567 | -13.123 | 1.00 | 36.09 | C |
| ATOM | 231 | O | GLU | A | 26 | 117.529 | 45.645 | -12.584 | 1.00 | 36.21 | O |
| ATOM | 232 | N | ASP | A | 27 | 117.067 | 43.894 | -13.939 | 1.00 | 35.84 | N |
| ATOM | 233 | CA | ASP | A | 27 | 115.737 | 44.450 | -14.258 | 1.00 | 36.21 | C |
| ATOM | 234 | CB | ASP | A | 27 | 115.489 | 44.325 | -15.767 | 1.00 | 36.31 | C |
| ATOM | 235 | CG | ASP | A | 27 | 114.170 | 44.955 | -16.193 | 1.00 | 39.03 | C |
| ATOM | 236 | OD1 | ASP | A | 27 | 113.361 | 45.405 | -15.312 | 1.00 | 43.45 | O |
| ATOM | 237 | OD2 | ASP | A | 27 | 113.942 | 44.994 | -17.416 | 1.00 | 37.86 | O |
| ATOM | 238 | C | ASP | A | 27 | 114.571 | 43.748 | -13.484 | 1.00 | 36.73 | C |
| ATOM | 239 | O | ASP | A | 27 | 114.350 | 42.541 | -13.682 | 1.00 | 34.87 | O |
| ATOM | 240 | N | PRO | A | 28 | 113.814 | 44.494 | -12.625 | 1.00 | 36.93 | N |
| ATOM | 241 | CA | PRO | A | 28 | 112.786 | 43.801 | -11.812 | 1.00 | 37.09 | C |
| ATOM | 242 | CB | PRO | A | 28 | 112.158 | 44.951 | -11.003 | 1.00 | 36.98 | C |
| ATOM | 243 | CG | PRO | A | 28 | 113.296 | 45.905 | -10.848 | 1.00 | 38.10 | C |
| ATOM | 244 | CD | PRO | A | 28 | 113.970 | 45.897 | -12.196 | 1.00 | 36.43 | C |
| ATOM | 245 | C | PRO | A | 28 | 111.710 | 43.016 | -12.617 | 1.00 | 37.10 | C |
| ATOM | 246 | O | PRO | A | 28 | 111.159 | 42.070 | -12.091 | 1.00 | 37.74 | O |
| ATOM | 247 | N | LYS | A | 29 | 111.459 | 43.375 | -13.882 | 1.00 | 37.20 | N |
| ATOM | 248 | CA | LYS | A | 29 | 110.421 | 42.731 | -14.707 | 1.00 | 37.12 | C |
| ATOM | 249 | CB | LYS | A | 29 | 110.063 | 43.605 | -15.891 | 1.00 | 37.66 | C |
| ATOM | 250 | CG | LYS | A | 29 | 109.449 | 44.938 | -15.509 | 1.00 | 38.59 | C |
| ATOM | 251 | CD | LYS | A | 29 | 109.174 | 45.767 | -16.782 | 1.00 | 43.47 | C |
| ATOM | 252 | CE | LYS | A | 29 | 108.421 | 47.016 | -16.418 | 1.00 | 41.22 | C |
| ATOM | 253 | NZ | LYS | A | 29 | 108.888 | 47.398 | -15.082 | 1.00 | 43.48 | N |
| ATOM | 254 | C | LYS | A | 29 | 110.909 | 41.363 | -15.153 | 1.00 | 36.54 | C |
| ATOM | 255 | O | LYS | A | 29 | 110.125 | 40.456 | -15.431 | 1.00 | 35.83 | O |
| ATOM | 256 | N | ILE | A | 30 | 112.225 | 41.197 | -15.146 | 1.00 | 35.98 | N |
| ATOM | 257 | CA | ILE | A | 30 | 112.794 | 39.948 | -15.564 | 1.00 | 36.07 | C |
| ATOM | 258 | CB | ILE | A | 30 | 113.893 | 40.186 | -16.641 | 1.00 | 37.76 | C |
| ATOM | 259 | CG1 | ILE | A | 30 | 113.335 | 41.004 | -17.846 | 1.00 | 37.27 | C |
| ATOM | 260 | CD1 | ILE | A | 30 | 114.434 | 41.663 | -18.646 | 1.00 | 38.51 | C |
| ATOM | 261 | CG2 | ILE | A | 30 | 114.643 | 38.790 | -17.038 | 1.00 | 37.36 | C |
| ATOM | 262 | C | ILE | A | 30 | 113.258 | 39.054 | -14.380 | 1.00 | 35.15 | C |
| ATOM | 263 | O | ILE | A | 30 | 112.998 | 37.819 | -14.335 | 1.00 | 34.62 | O |
| ATOM | 264 | N | GLU | A | 31 | 113.966 | 39.627 | -13.428 | 1.00 | 32.56 | N |
| ATOM | 265 | CA | GLU | A | 31 | 114.387 | 38.810 | -12.285 | 1.00 | 31.04 | C |
| ATOM | 266 | CB | GLU | A | 31 | 115.813 | 39.228 | -11.847 | 1.00 | 31.30 | C |
| ATOM | 267 | CG | GLU | A | 31 | 116.857 | 38.566 | -12.666 | 1.00 | 33.30 | C |
| ATOM | 268 | CD | GLU | A | 31 | 118.271 | 39.046 | -12.332 | 1.00 | 34.64 | C |

FIG. 1-7

| | | | | | | | | | | | |
|---|---|---|---|---|---|---|---|---|---|---|---|
| ATOM | 269 | OE1 | GLU | A | 31 | 118.964 | 38.310 | -11.587 | 1.00 | 38.54 | O |
| ATOM | 270 | OE2 | GLU | A | 31 | 118.688 | 40.120 | -12.828 | 1.00 | 38.37 | O |
| ATOM | 271 | C | GLU | A | 31 | 113.349 | 38.971 | -11.201 | 1.00 | 29.15 | C |
| ATOM | 272 | O | GLU | A | 31 | 113.592 | 39.601 | -10.208 | 1.00 | 29.02 | O |
| ATOM | 273 | N | THR | A | 32 | 112.159 | 38.405 | -11.408 | 1.00 | 28.35 | N |
| ATOM | 274 | CA | THR | A | 32 | 111.080 | 38.662 | -10.529 | 1.00 | 25.14 | C |
| ATOM | 275 | CB | THR | A | 32 | 109.691 | 38.308 | -11.199 | 1.00 | 26.11 | C |
| ATOM | 276 | OG1 | THR | A | 32 | 109.722 | 36.935 | -11.584 | 1.00 | 23.73 | O |
| ATOM | 277 | CG2 | THR | A | 32 | 109.484 | 39.127 | -12.468 | 1.00 | 26.65 | C |
| ATOM | 278 | C | THR | A | 32 | 111.241 | 37.956 | -9.206 | 1.00 | 24.47 | C |
| ATOM | 279 | O | THR | A | 32 | 110.782 | 38.481 | -8.214 | 1.00 | 22.40 | O |
| ATOM | 280 | N | ASN | A | 33 | 111.914 | 36.783 | -9.146 | 1.00 | 25.61 | N |
| ATOM | 281 | CA | ASN | A | 33 | 112.121 | 36.141 | -7.851 | 1.00 | 25.65 | C |
| ATOM | 282 | CB | ASN | A | 33 | 112.519 | 34.640 | -7.967 | 1.00 | 27.21 | C |
| ATOM | 283 | CG | ASN | A | 33 | 111.359 | 33.816 | -8.499 | 1.00 | 28.50 | C |
| ATOM | 284 | OD1 | ASN | A | 33 | 111.547 | 33.021 | -9.402 | 1.00 | 36.25 | O |
| ATOM | 285 | ND2 | ASN | A | 33 | 110.153 | 34.146 | -8.082 | 1.00 | 22.48 | N |
| ATOM | 286 | C | ASN | A | 33 | 113.141 | 36.898 | -6.983 | 1.00 | 24.71 | C |
| ATOM | 287 | O | ASN | A | 33 | 112.991 | 37.015 | -5.750 | 1.00 | 23.62 | O |
| ATOM | 288 | N | LYS | A | 34 | 114.163 | 37.395 | -7.653 | 1.00 | 24.60 | N |
| ATOM | 289 | CA | LYS | A | 34 | 115.119 | 38.352 | -7.043 | 1.00 | 25.52 | C |
| ATOM | 290 | CB | LYS | A | 34 | 116.271 | 38.653 | -8.013 | 1.00 | 25.03 | C |
| ATOM | 291 | CG | LYS | A | 34 | 117.398 | 39.618 | -7.386 | 1.00 | 31.00 | C |
| ATOM | 292 | CD | LYS | A | 34 | 118.579 | 39.745 | -8.336 | 1.00 | 37.80 | C |
| ATOM | 293 | CE | LYS | A | 34 | 119.522 | 38.493 | -8.233 | 1.00 | 38.22 | C |
| ATOM | 294 | NZ | LYS | A | 34 | 120.773 | 38.795 | -9.012 | 1.00 | 39.96 | N |
| ATOM | 295 | C | LYS | A | 34 | 114.430 | 39.650 | -6.544 | 1.00 | 24.86 | C |
| ATOM | 296 | O | LYS | A | 34 | 114.581 | 40.044 | -5.351 | 1.00 | 25.65 | O |
| ATOM | 297 | N | PHE | A | 35 | 113.654 | 40.297 | -7.417 | 1.00 | 24.43 | N |
| ATOM | 298 | CA | PHE | A | 35 | 112.809 | 41.415 | -6.937 | 1.00 | 24.24 | C |
| ATOM | 299 | CB | PHE | A | 35 | 111.793 | 41.709 | -8.025 | 1.00 | 25.49 | C |
| ATOM | 300 | CG | PHE | A | 35 | 111.020 | 42.979 | -7.844 | 1.00 | 27.31 | C |
| ATOM | 301 | CD1 | PHE | A | 35 | 111.564 | 44.076 | -7.167 | 1.00 | 23.80 | C |
| ATOM | 302 | CE1 | PHE | A | 35 | 110.818 | 45.286 | -7.086 | 1.00 | 28.99 | C |
| ATOM | 303 | CZ | PHE | A | 35 | 109.554 | 45.385 | -7.706 | 1.00 | 24.27 | C |
| ATOM | 304 | CE2 | PHE | A | 35 | 109.038 | 44.301 | -8.395 | 1.00 | 26.04 | C |
| ATOM | 305 | CD2 | PHE | A | 35 | 109.749 | 43.104 | -8.447 | 1.00 | 26.96 | C |
| ATOM | 306 | C | PHE | A | 35 | 112.117 | 41.127 | -5.567 | 1.00 | 23.64 | C |
| ATOM | 307 | O | PHE | A | 35 | 112.262 | 41.855 | -4.606 | 1.00 | 20.80 | O |
| ATOM | 308 | N | ALA | A | 36 | 111.394 | 40.012 | -5.464 | 1.00 | 25.29 | N |
| ATOM | 309 | CA | ALA | A | 36 | 110.791 | 39.587 | -4.203 | 1.00 | 23.01 | C |
| ATOM | 310 | CB | ALA | A | 36 | 109.813 | 38.378 | -4.474 | 1.00 | 23.96 | C |
| ATOM | 311 | C | ALA | A | 36 | 111.694 | 39.296 | -3.030 | 1.00 | 22.15 | C |
| ATOM | 312 | O | ALA | A | 36 | 111.330 | 39.570 | -1.885 | 1.00 | 21.47 | O |
| ATOM | 313 | N | ALA | A | 37 | 112.884 | 38.739 | -3.270 | 1.00 | 22.04 | N |
| ATOM | 314 | CA | ALA | A | 37 | 113.718 | 38.343 | -2.202 | 1.00 | 19.77 | C |
| ATOM | 315 | CB | ALA | A | 37 | 114.948 | 37.380 | -2.703 | 1.00 | 19.56 | C |
| ATOM | 316 | C | ALA | A | 37 | 114.287 | 39.694 | -1.688 | 1.00 | 21.30 | C |
| ATOM | 317 | O | ALA | A | 37 | 114.417 | 39.867 | -0.467 | 1.00 | 20.64 | O |
| ATOM | 318 | N | ILE | A | 38 | 114.531 | 40.644 | -2.583 | 1.00 | 20.77 | N |
| ATOM | 319 | CA | ILE | A | 38 | 115.086 | 42.013 | -2.119 | 1.00 | 21.63 | C |
| ATOM | 320 | CB | ILE | A | 38 | 115.527 | 42.981 | -3.290 | 1.00 | 22.23 | C |
| ATOM | 321 | CG1 | ILE | A | 38 | 116.592 | 42.401 | -4.242 | 1.00 | 26.72 | C |
| ATOM | 322 | CD1 | ILE | A | 38 | 117.648 | 41.799 | -3.507 | 1.00 | 29.37 | C |
| ATOM | 323 | CG2 | ILE | A | 38 | 116.050 | 44.370 | -2.694 | 1.00 | 18.26 | C |
| ATOM | 324 | C | ILE | A | 38 | 114.066 | 42.755 | -1.191 | 1.00 | 21.39 | C |
| ATOM | 325 | O | ILE | A | 38 | 114.369 | 43.176 | -0.038 | 1.00 | 21.05 | O |
| ATOM | 326 | N | CYS | A | 39 | 112.804 | 42.802 | -1.656 | 1.00 | 23.05 | N |
| ATOM | 327 | CA | CYS | A | 39 | 111.754 | 43.498 | -0.877 | 1.00 | 23.02 | C |
| ATOM | 328 | CB | CYS | A | 39 | 110.359 | 43.473 | -1.615 | 1.00 | 21.00 | C |
| ATOM | 329 | SG | CYS | A | 39 | 110.343 | 44.408 | -3.128 | 1.00 | 27.59 | S |
| ATOM | 330 | C | CYS | A | 39 | 111.592 | 42.888 | 0.464 | 1.00 | 22.06 | C |
| ATOM | 331 | O | CYS | A | 39 | 111.417 | 43.620 | 1.437 | 1.00 | 20.89 | O |

FIG. 1-8

| | | | | | | | | | | | |
|---|---|---|---|---|---|---|---|---|---|---|---|
| ATOM | 332 | N | THR | A | 40 | 111.577 | 41.546 | 0.512 | 1.00 | 22.10 | N |
| ATOM | 333 | CA | THR | A | 40 | 111.449 | 40.812 | 1.751 | 1.00 | 21.04 | C |
| ATOM | 334 | CB | THR | A | 40 | 111.403 | 39.228 | 1.509 | 1.00 | 23.25 | C |
| ATOM | 335 | OG1 | THR | A | 40 | 110.391 | 38.893 | 0.580 | 1.00 | 21.80 | O |
| ATOM | 336 | CG2 | THR | A | 40 | 110.932 | 38.491 | 2.814 | 1.00 | 22.85 | C |
| ATOM | 337 | C | THR | A | 40 | 112.565 | 41.111 | 2.745 | 1.00 | 21.93 | C |
| ATOM | 338 | O | THR | A | 40 | 112.354 | 41.300 | 3.949 | 1.00 | 21.15 | O |
| ATOM | 339 | N | HIS | A | 41 | 113.798 | 41.021 | 2.247 | 1.00 | 21.54 | N |
| ATOM | 340 | CA | HIS | A | 41 | 114.916 | 41.325 | 3.035 | 1.00 | 21.49 | C |
| ATOM | 341 | CB | HIS | A | 41 | 116.177 | 41.157 | 2.212 | 1.00 | 22.12 | C |
| ATOM | 342 | CG | HIS | A | 41 | 117.403 | 41.340 | 3.023 | 1.00 | 26.08 | C |
| ATOM | 343 | ND1 | HIS | A | 41 | 118.143 | 42.501 | 2.989 | 1.00 | 25.08 | N |
| ATOM | 344 | CE1 | HIS | A | 41 | 119.173 | 42.389 | 3.804 | 1.00 | 19.14 | C |
| ATOM | 345 | NE2 | HIS | A | 41 | 119.130 | 41.191 | 4.359 | 1.00 | 28.46 | N |
| ATOM | 346 | CD2 | HIS | A | 41 | 118.049 | 40.501 | 3.866 | 1.00 | 26.32 | C |
| ATOM | 347 | C | HIS | A | 41 | 114.820 | 42.781 | 3.560 | 1.00 | 19.08 | C |
| ATOM | 348 | O | HIS | A | 41 | 114.944 | 43.029 | 4.764 | 1.00 | 14.92 | O |
| ATOM | 349 | N | LEU | A | 42 | 114.527 | 43.705 | 2.637 | 1.00 | 20.28 | N |
| ATOM | 350 | CA | LEU | A | 42 | 114.220 | 45.068 | 3.084 | 1.00 | 20.07 | C |
| ATOM | 351 | CB | LEU | A | 42 | 113.991 | 46.070 | 1.930 | 1.00 | 20.76 | C |
| ATOM | 352 | CG | LEU | A | 42 | 115.136 | 46.439 | 0.970 | 1.00 | 22.35 | C |
| ATOM | 353 | CD1 | LEU | A | 42 | 114.681 | 46.964 | -0.436 | 1.00 | 20.75 | C |
| ATOM | 354 | CD2 | LEU | A | 42 | 116.058 | 47.459 | 1.643 | 1.00 | 27.69 | C |
| ATOM | 355 | C | LEU | A | 42 | 113.148 | 45.111 | 4.139 | 1.00 | 19.88 | C |
| ATOM | 356 | O | LEU | A | 42 | 113.377 | 45.702 | 5.223 | 1.00 | 17.77 | O |
| ATOM | 357 | N | GLU | A | 43 | 111.997 | 44.439 | 3.908 | 1.00 | 21.82 | N |
| ATOM | 358 | CA | GLU | A | 43 | 110.892 | 44.570 | 4.900 | 1.00 | 20.65 | C |
| ATOM | 359 | CB | GLU | A | 43 | 109.515 | 43.943 | 4.470 | 1.00 | 22.30 | C |
| ATOM | 360 | CG | GLU | A | 43 | 108.430 | 45.007 | 4.881 | 1.00 | 25.46 | C |
| ATOM | 361 | CD | GLU | A | 43 | 107.038 | 44.589 | 4.789 | 1.00 | 37.53 | C |
| ATOM | 362 | OE1 | GLU | A | 43 | 106.699 | 43.527 | 5.324 | 1.00 | 41.59 | O |
| ATOM | 363 | OE2 | GLU | A | 43 | 106.226 | 45.379 | 4.206 | 1.00 | 48.75 | O |
| ATOM | 364 | C | GLU | A | 43 | 111.317 | 44.055 | 6.219 | 1.00 | 20.03 | C |
| ATOM | 365 | O | GLU | A | 43 | 111.061 | 44.669 | 7.268 | 1.00 | 22.15 | O |
| ATOM | 366 | N | VAL | A | 44 | 112.035 | 42.931 | 6.233 | 1.00 | 19.16 | N |
| ATOM | 367 | CA | VAL | A | 44 | 112.503 | 42.424 | 7.522 | 1.00 | 18.30 | C |
| ATOM | 368 | CB | VAL | A | 44 | 113.201 | 41.005 | 7.320 | 1.00 | 19.74 | C |
| ATOM | 369 | CG1 | VAL | A | 44 | 113.865 | 40.613 | 8.652 | 1.00 | 20.11 | C |
| ATOM | 370 | CG2 | VAL | A | 44 | 112.076 | 39.996 | 6.816 | 1.00 | 21.24 | C |
| ATOM | 371 | C | VAL | A | 44 | 113.420 | 43.346 | 8.326 | 1.00 | 19.87 | C |
| ATOM | 372 | O | VAL | A | 44 | 113.315 | 43.462 | 9.570 | 1.00 | 19.37 | O |
| ATOM | 373 | N | CYS | A | 45 | 114.348 | 43.995 | 7.624 | 1.00 | 20.59 | N |
| ATOM | 374 | CA | CYS | A | 45 | 115.312 | 44.966 | 8.259 | 1.00 | 22.34 | C |
| ATOM | 375 | CB | CYS | A | 45 | 116.368 | 45.493 | 7.237 | 1.00 | 21.83 | C |
| ATOM | 376 | SG | CYS | A | 45 | 117.587 | 44.252 | 6.771 | 1.00 | 26.82 | S |
| ATOM | 377 | C | CYS | A | 45 | 114.582 | 46.155 | 8.912 | 1.00 | 21.91 | C |
| ATOM | 378 | O | CYS | A | 45 | 114.729 | 46.408 | 10.111 | 1.00 | 22.11 | O |
| ATOM | 379 | N | PHE | A | 46 | 113.714 | 46.794 | 8.155 | 1.00 | 22.73 | N |
| ATOM | 380 | CA | PHE | A | 46 | 112.823 | 47.796 | 8.764 | 1.00 | 24.28 | C |
| ATOM | 381 | CB | PHE | A | 46 | 111.922 | 48.394 | 7.735 | 1.00 | 24.77 | C |
| ATOM | 382 | CG | PHE | A | 46 | 112.628 | 49.239 | 6.744 | 1.00 | 29.86 | C |
| ATOM | 383 | CD1 | PHE | A | 46 | 113.030 | 50.553 | 7.089 | 1.00 | 36.82 | C |
| ATOM | 384 | CE1 | PHE | A | 46 | 113.665 | 51.350 | 6.139 | 1.00 | 35.81 | C |
| ATOM | 385 | CZ | PHE | A | 46 | 113.882 | 50.840 | 4.858 | 1.00 | 38.37 | C |
| ATOM | 386 | CE2 | PHE | A | 46 | 113.469 | 49.607 | 4.518 | 1.00 | 36.57 | C |
| ATOM | 387 | CD2 | PHE | A | 46 | 112.820 | 48.803 | 5.465 | 1.00 | 31.36 | C |
| ATOM | 388 | C | PHE | A | 46 | 111.983 | 47.338 | 9.940 | 1.00 | 23.58 | C |
| ATOM | 389 | O | PHE | A | 46 | 111.850 | 48.077 | 10.902 | 1.00 | 24.26 | O |
| ATOM | 390 | N | MET | A | 47 | 111.348 | 46.156 | 9.874 | 1.00 | 23.87 | N |
| ATOM | 391 | CA | MET | A | 47 | 110.578 | 45.664 | 11.039 | 1.00 | 23.27 | C |
| ATOM | 392 | CB | MET | A | 47 | 109.832 | 44.332 | 10.639 | 1.00 | 24.23 | C |
| ATOM | 393 | CG | MET | A | 47 | 108.665 | 44.510 | 9.651 | 1.00 | 23.95 | C |
| ATOM | 394 | SD | MET | A | 47 | 107.762 | 42.932 | 9.293 | 1.00 | 32.59 | S |

FIG. 1-9

| | | | | | | | | | | | |
|---|---|---|---|---|---|---|---|---|---|---|---|
| ATOM | 395 | CE | MET | A | 47 | 106.999 | 42.762 | 10.891 | 1.00 | 24.89 | C |
| ATOM | 396 | C | MET | A | 47 | 111.372 | 45.397 | 12.307 | 1.00 | 23.14 | C |
| ATOM | 397 | O | MET | A | 47 | 110.901 | 45.537 | 13.467 | 1.00 | 21.96 | O |
| ATOM | 398 | N | TYR | A | 48 | 112.606 | 44.958 | 12.091 | 1.00 | 22.19 | N |
| ATOM | 399 | CA | TYR | A | 48 | 113.462 | 44.585 | 13.136 | 1.00 | 21.11 | C |
| ATOM | 400 | CB | TYR | A | 48 | 114.754 | 44.010 | 12.506 | 1.00 | 19.64 | C |
| ATOM | 401 | CG | TYR | A | 48 | 115.615 | 43.198 | 13.444 | 1.00 | 19.63 | C |
| ATOM | 402 | CD1 | TYR | A | 48 | 115.667 | 41.797 | 13.347 | 1.00 | 23.15 | C |
| ATOM | 403 | CE1 | TYR | A | 48 | 116.517 | 41.048 | 14.189 | 1.00 | 20.73 | C |
| ATOM | 404 | CZ | TYR | A | 48 | 117.274 | 41.635 | 15.172 | 1.00 | 23.31 | C |
| ATOM | 405 | OH | TYR | A | 48 | 118.038 | 40.821 | 16.043 | 1.00 | 21.51 | O |
| ATOM | 406 | CE2 | TYR | A | 48 | 117.231 | 43.047 | 15.333 | 1.00 | 20.56 | C |
| ATOM | 407 | CD2 | TYR | A | 48 | 116.385 | 43.803 | 14.470 | 1.00 | 23.79 | C |
| ATOM | 408 | C | TYR | A | 48 | 113.713 | 45.865 | 13.963 | 1.00 | 23.18 | C |
| ATOM | 409 | O | TYR | A | 48 | 113.791 | 45.866 | 15.205 | 1.00 | 20.86 | O |
| ATOM | 410 | N | SER | A | 49 | 113.743 | 46.972 | 13.247 | 1.00 | 25.22 | N |
| ATOM | 411 | CA | SER | A | 49 | 114.167 | 48.218 | 13.852 | 1.00 | 28.76 | C |
| ATOM | 412 | CB | SER | A | 49 | 114.856 | 49.040 | 12.790 | 1.00 | 28.94 | C |
| ATOM | 413 | OG | SER | A | 49 | 113.912 | 49.388 | 11.783 | 1.00 | 32.93 | O |
| ATOM | 414 | C | SER | A | 49 | 112.932 | 48.981 | 14.418 | 1.00 | 30.63 | C |
| ATOM | 415 | O | SER | A | 49 | 113.077 | 49.678 | 15.395 | 1.00 | 29.11 | O |
| ATOM | 416 | N | ASP | A | 50 | 111.739 | 48.749 | 13.839 | 1.00 | 31.70 | N |
| ATOM | 417 | CA | ASP | A | 50 | 110.465 | 49.377 | 14.301 | 1.00 | 33.27 | C |
| ATOM | 418 | CB | ASP | A | 50 | 109.215 | 48.604 | 13.749 | 1.00 | 33.14 | C |
| ATOM | 419 | CG | ASP | A | 50 | 108.724 | 49.144 | 12.449 | 1.00 | 36.94 | C |
| ATOM | 420 | OD1 | ASP | A | 50 | 109.142 | 50.281 | 12.102 | 1.00 | 42.74 | O |
| ATOM | 421 | OD2 | ASP | A | 50 | 107.939 | 48.427 | 11.747 | 1.00 | 37.80 | O |
| ATOM | 422 | C | ASP | A | 50 | 110.310 | 49.429 | 15.819 | 1.00 | 32.77 | C |
| ATOM | 423 | O | ASP | A | 50 | 110.406 | 48.411 | 16.493 | 1.00 | 33.85 | O |
| ATOM | 424 | N | PHE | A | 51 | 110.074 | 50.610 | 16.369 | 1.00 | 32.76 | N |
| ATOM | 425 | CA | PHE | A | 51 | 109.477 | 50.740 | 17.743 | 1.00 | 31.19 | C |
| ATOM | 426 | CB | PHE | A | 51 | 108.442 | 49.613 | 18.063 | 1.00 | 32.43 | C |
| ATOM | 427 | CG | PHE | A | 51 | 107.329 | 49.501 | 17.083 | 1.00 | 33.43 | C |
| ATOM | 428 | CD1 | PHE | A | 51 | 106.787 | 50.656 | 16.473 | 1.00 | 38.68 | C |
| ATOM | 429 | CE1 | PHE | A | 51 | 105.755 | 50.565 | 15.527 | 1.00 | 39.63 | C |
| ATOM | 430 | CZ | PHE | A | 51 | 105.235 | 49.277 | 15.189 | 1.00 | 40.25 | C |
| ATOM | 431 | CE2 | PHE | A | 51 | 105.777 | 48.108 | 15.807 | 1.00 | 41.18 | C |
| ATOM | 432 | CD2 | PHE | A | 51 | 106.831 | 48.242 | 16.736 | 1.00 | 38.51 | C |
| ATOM | 433 | C | PHE | A | 51 | 110.494 | 50.683 | 18.813 | 1.00 | 29.39 | C |
| ATOM | 434 | O | PHE | A | 51 | 110.116 | 50.767 | 19.986 | 1.00 | 28.70 | O |
| ATOM | 435 | N | HIS | A | 52 | 111.768 | 50.444 | 18.458 | 1.00 | 28.72 | N |
| ATOM | 436 | CA | HIS | A | 52 | 112.796 | 50.265 | 19.472 | 1.00 | 27.24 | C |
| ATOM | 437 | CB | HIS | A | 52 | 113.687 | 49.063 | 19.164 | 1.00 | 27.74 | C |
| ATOM | 438 | CG | HIS | A | 52 | 112.950 | 47.754 | 19.087 | 1.00 | 29.30 | C |
| ATOM | 439 | ND1 | HIS | A | 52 | 112.717 | 46.977 | 20.198 | 1.00 | 29.47 | N |
| ATOM | 440 | CE1 | HIS | A | 52 | 112.012 | 45.913 | 19.844 | 1.00 | 33.01 | C |
| ATOM | 441 | NE2 | HIS | A | 52 | 111.839 | 45.940 | 18.528 | 1.00 | 33.69 | N |
| ATOM | 442 | CD2 | HIS | A | 52 | 112.405 | 47.092 | 18.032 | 1.00 | 28.21 | C |
| ATOM | 443 | C | HIS | A | 52 | 113.665 | 51.545 | 19.614 | 1.00 | 28.97 | C |
| ATOM | 444 | O | HIS | A | 52 | 114.308 | 52.025 | 18.646 | 1.00 | 25.35 | O |
| ATOM | 445 | N | PHE | A | 53 | 113.718 | 52.019 | 20.842 | 1.00 | 30.92 | N |
| ATOM | 446 | CA | PHE | A | 53 | 114.325 | 53.320 | 21.167 | 1.00 | 34.45 | C |
| ATOM | 447 | CB | PHE | A | 53 | 113.222 | 54.406 | 21.335 | 1.00 | 34.83 | C |
| ATOM | 448 | CG | PHE | A | 53 | 112.563 | 54.748 | 20.068 | 1.00 | 35.99 | C |
| ATOM | 449 | CD1 | PHE | A | 53 | 113.166 | 55.609 | 19.183 | 1.00 | 40.04 | C |
| ATOM | 450 | CE1 | PHE | A | 53 | 112.583 | 55.880 | 17.958 | 1.00 | 40.10 | C |
| ATOM | 451 | CZ | PHE | A | 53 | 111.395 | 55.278 | 17.608 | 1.00 | 40.74 | C |
| ATOM | 452 | CE2 | PHE | A | 53 | 110.781 | 54.386 | 18.481 | 1.00 | 39.70 | C |
| ATOM | 453 | CD2 | PHE | A | 53 | 111.375 | 54.112 | 19.698 | 1.00 | 42.11 | C |
| ATOM | 454 | C | PHE | A | 53 | 115.141 | 53.254 | 22.408 | 1.00 | 35.34 | C |
| ATOM | 455 | O | PHE | A | 53 | 114.946 | 52.398 | 23.229 | 1.00 | 37.62 | O |
| ATOM | 456 | N | ILE | A | 54 | 116.126 | 54.137 | 22.520 | 1.00 | 39.00 | N |
| ATOM | 457 | CA | ILE | A | 54 | 116.812 | 54.358 | 23.775 | 1.00 | 40.31 | C |

FIG. 1-10

| | | | | | | | | | | | |
|---|---|---|---|---|---|---|---|---|---|---|---|
| ATOM | 458 | CB | ILE | A | 54 | 118.338 | 54.234 | 23.570 | 1.00 | 42.04 | C |
| ATOM | 459 | CG1 | ILE | A | 54 | 118.734 | 52.738 | 23.535 | 1.00 | 40.76 | C |
| ATOM | 460 | CD1 | ILE | A | 54 | 119.572 | 52.504 | 22.328 | 1.00 | 39.39 | C |
| ATOM | 461 | CG2 | ILE | A | 54 | 119.145 | 55.027 | 24.592 | 1.00 | 36.99 | C |
| ATOM | 462 | C | ILE | A | 54 | 116.403 | 55.764 | 24.163 | 1.00 | 42.94 | C |
| ATOM | 463 | O | ILE | A | 54 | 116.412 | 56.662 | 23.336 | 1.00 | 42.66 | O |
| ATOM | 464 | N | ASP | A | 55 | 116.017 | 55.963 | 25.410 | 1.00 | 45.93 | N |
| ATOM | 465 | CA | ASP | A | 55 | 115.441 | 57.267 | 25.756 | 1.00 | 49.47 | C |
| ATOM | 466 | CB | ASP | A | 55 | 114.317 | 57.120 | 26.780 | 1.00 | 50.32 | C |
| ATOM | 467 | CG | ASP | A | 55 | 114.802 | 56.476 | 28.097 | 1.00 | 51.50 | C |
| ATOM | 468 | OD1 | ASP | A | 55 | 114.018 | 55.762 | 28.748 | 1.00 | 52.94 | O |
| ATOM | 469 | OD2 | ASP | A | 55 | 115.973 | 56.681 | 28.482 | 1.00 | 53.29 | O |
| ATOM | 470 | C | ASP | A | 55 | 116.505 | 58.213 | 26.277 | 1.00 | 51.12 | C |
| ATOM | 471 | O | ASP | A | 55 | 117.702 | 58.051 | 25.994 | 1.00 | 51.23 | O |
| ATOM | 472 | N | GLU | A | 56 | 116.047 | 59.174 | 27.071 | 1.00 | 53.58 | N |
| ATOM | 473 | CA | GLU | A | 56 | 116.852 | 60.286 | 27.601 | 1.00 | 55.53 | C |
| ATOM | 474 | CB | GLU | A | 56 | 115.889 | 61.333 | 28.161 | 1.00 | 56.20 | C |
| ATOM | 475 | CG | GLU | A | 56 | 114.414 | 60.990 | 27.806 | 1.00 | 57.21 | C |
| ATOM | 476 | CD | GLU | A | 56 | 113.486 | 61.253 | 28.921 | 1.00 | 59.52 | C |
| ATOM | 477 | OE1 | GLU | A | 56 | 112.285 | 61.089 | 28.689 | 1.00 | 61.14 | O |
| ATOM | 478 | OE2 | GLU | A | 56 | 113.938 | 61.631 | 30.033 | 1.00 | 63.69 | O |
| ATOM | 479 | C | GLU | A | 56 | 117.785 | 59.810 | 28.713 | 1.00 | 56.99 | C |
| ATOM | 480 | O | GLU | A | 56 | 118.983 | 60.144 | 28.750 | 1.00 | 58.03 | O |
| ATOM | 481 | N | ARG | A | 57 | 117.226 | 59.025 | 29.615 | 1.00 | 58.21 | N |
| ATOM | 482 | CA | ARG | A | 57 | 117.955 | 58.472 | 30.722 | 1.00 | 59.56 | C |
| ATOM | 483 | CB | ARG | A | 57 | 116.976 | 58.077 | 31.858 | 1.00 | 59.94 | C |
| ATOM | 484 | CG | ARG | A | 57 | 115.743 | 59.025 | 32.020 | 1.00 | 63.90 | C |
| ATOM | 485 | CD | ARG | A | 57 | 115.248 | 59.206 | 33.478 | 1.00 | 68.93 | C |
| ATOM | 486 | NE | ARG | A | 57 | 116.099 | 60.116 | 34.274 | 1.00 | 72.68 | N |
| ATOM | 487 | CZ | ARG | A | 57 | 116.324 | 60.006 | 35.596 | 1.00 | 74.39 | C |
| ATOM | 488 | NH1 | ARG | A | 57 | 115.758 | 59.027 | 36.307 | 1.00 | 74.29 | N |
| ATOM | 489 | NH2 | ARG | A | 57 | 117.119 | 60.878 | 36.224 | 1.00 | 73.92 | N |
| ATOM | 490 | C | ARG | A | 57 | 118.808 | 57.287 | 30.215 | 1.00 | 59.66 | C |
| ATOM | 491 | O | ARG | A | 57 | 119.564 | 56.694 | 30.983 | 1.00 | 59.63 | O |
| ATOM | 492 | N | GLY | A | 58 | 118.660 | 56.937 | 28.929 | 1.00 | 59.68 | N |
| ATOM | 493 | CA | GLY | A | 58 | 119.575 | 56.030 | 28.225 | 1.00 | 59.05 | C |
| ATOM | 494 | C | GLY | A | 58 | 119.293 | 54.534 | 28.200 | 1.00 | 59.03 | C |
| ATOM | 495 | O | GLY | A | 58 | 120.222 | 53.716 | 27.981 | 1.00 | 58.74 | O |
| ATOM | 496 | N | GLU | A | 59 | 118.037 | 54.152 | 28.416 | 1.00 | 58.42 | N |
| ATOM | 497 | CA | GLU | A | 59 | 117.682 | 52.717 | 28.360 | 1.00 | 58.36 | C |
| ATOM | 498 | CB | GLU | A | 59 | 117.211 | 52.146 | 29.716 | 1.00 | 58.91 | C |
| ATOM | 499 | CG | GLU | A | 59 | 116.727 | 53.161 | 30.735 | 1.00 | 60.56 | C |
| ATOM | 500 | CD | GLU | A | 59 | 117.838 | 54.105 | 31.246 | 1.00 | 62.98 | C |
| ATOM | 501 | OE1 | GLU | A | 59 | 117.462 | 55.219 | 31.670 | 1.00 | 62.31 | O |
| ATOM | 502 | OE2 | GLU | A | 59 | 119.064 | 53.757 | 31.222 | 1.00 | 62.07 | O |
| ATOM | 503 | C | GLU | A | 59 | 116.715 | 52.380 | 27.230 | 1.00 | 57.44 | C |
| ATOM | 504 | O | GLU | A | 59 | 115.942 | 53.243 | 26.786 | 1.00 | 56.78 | O |
| ATOM | 505 | N | SER | A | 60 | 116.776 | 51.127 | 26.773 | 1.00 | 56.20 | N |
| ATOM | 506 | CA | SER | A | 60 | 115.984 | 50.691 | 25.616 | 1.00 | 56.01 | C |
| ATOM | 507 | CB | SER | A | 60 | 116.631 | 49.510 | 24.903 | 1.00 | 55.49 | C |
| ATOM | 508 | OG | SER | A | 60 | 116.990 | 48.533 | 25.856 | 1.00 | 56.45 | O |
| ATOM | 509 | C | SER | A | 60 | 114.578 | 50.335 | 26.005 | 1.00 | 55.06 | C |
| ATOM | 510 | O | SER | A | 60 | 114.366 | 49.481 | 26.850 | 1.00 | 54.75 | O |
| ATOM | 511 | N | ILE | A | 61 | 113.632 | 51.000 | 25.351 | 1.00 | 55.19 | N |
| ATOM | 512 | CA | ILE | A | 61 | 112.190 | 50.864 | 25.610 | 1.00 | 54.35 | C |
| ATOM | 513 | CB | ILE | A | 61 | 111.631 | 52.139 | 26.278 | 1.00 | 54.74 | C |
| ATOM | 514 | CG1 | ILE | A | 61 | 111.996 | 53.371 | 25.450 | 1.00 | 55.79 | C |
| ATOM | 515 | CD1 | ILE | A | 61 | 111.169 | 54.621 | 25.788 | 1.00 | 58.32 | C |
| ATOM | 516 | CG2 | ILE | A | 61 | 112.126 | 52.282 | 27.748 | 1.00 | 55.82 | C |
| ATOM | 517 | C | ILE | A | 61 | 111.436 | 50.639 | 24.292 | 1.00 | 53.30 | C |
| ATOM | 518 | O | ILE | A | 61 | 111.963 | 50.958 | 23.211 | 1.00 | 51.29 | O |
| ATOM | 519 | N | ILE | A | 62 | 110.203 | 50.123 | 24.398 | 1.00 | 52.71 | N |
| ATOM | 520 | CA | ILE | A | 62 | 109.306 | 49.964 | 23.248 | 1.00 | 52.41 | C |

FIG. 1-11

| | | | | | | | | | | | |
|---|---|---|---|---|---|---|---|---|---|---|---|
| ATOM | 521 | CB | ILE | A | 62 | 108.640 | 48.535 | 23.194 | 1.00 | 52.13 | C |
| ATOM | 522 | CG1 | ILE | A | 62 | 109.725 | 47.431 | 23.123 | 1.00 | 52.63 | C |
| ATOM | 523 | CD1 | ILE | A | 62 | 109.325 | 46.065 | 23.710 | 1.00 | 47.97 | C |
| ATOM | 524 | CG2 | ILE | A | 62 | 107.749 | 48.398 | 21.973 | 1.00 | 51.39 | C |
| ATOM | 525 | C | ILE | A | 62 | 108.287 | 51.122 | 23.174 | 1.00 | 52.81 | C |
| ATOM | 526 | O | ILE | A | 62 | 107.639 | 51.442 | 24.160 | 1.00 | 52.03 | O |
| ATOM | 527 | N | VAL | A | 63 | 108.208 | 51.760 | 22.008 | 1.00 | 53.12 | N |
| ATOM | 528 | CA | VAL | A | 63 | 107.306 | 52.875 | 21.725 | 1.00 | 54.51 | C |
| ATOM | 529 | CB | VAL | A | 63 | 108.119 | 54.201 | 21.551 | 1.00 | 54.25 | C |
| ATOM | 530 | CG1 | VAL | A | 63 | 107.251 | 55.318 | 20.983 | 1.00 | 55.15 | C |
| ATOM | 531 | CG2 | VAL | A | 63 | 108.783 | 54.618 | 22.834 | 1.00 | 52.54 | C |
| ATOM | 532 | C | VAL | A | 63 | 106.592 | 52.591 | 20.400 | 1.00 | 55.49 | C |
| ATOM | 533 | O | VAL | A | 63 | 107.255 | 52.429 | 19.414 | 1.00 | 55.99 | O |
| ATOM | 534 | N | GLU | A | 64 | 105.262 | 52.597 | 20.353 | 1.00 | 57.01 | N |
| ATOM | 535 | CA | GLU | A | 64 | 104.527 | 52.232 | 19.134 | 1.00 | 58.58 | C |
| ATOM | 536 | CB | GLU | A | 64 | 103.499 | 51.142 | 19.456 | 1.00 | 59.63 | C |
| ATOM | 537 | CG | GLU | A | 64 | 104.074 | 50.011 | 20.315 | 1.00 | 62.16 | C |
| ATOM | 538 | CD | GLU | A | 64 | 103.900 | 48.633 | 19.697 | 1.00 | 65.82 | C |
| ATOM | 539 | OE1 | GLU | A | 64 | 102.788 | 48.326 | 19.205 | 1.00 | 66.64 | O |
| ATOM | 540 | OE2 | GLU | A | 64 | 104.888 | 47.848 | 19.727 | 1.00 | 68.44 | O |
| ATOM | 541 | C | GLU | A | 64 | 103.847 | 53.350 | 18.334 | 1.00 | 58.80 | C |
| ATOM | 542 | O | GLU | A | 64 | 103.720 | 54.477 | 18.787 | 1.00 | 58.79 | O |
| ATOM | 543 | N | ASN | A | 69 | 108.491 | 60.891 | 20.150 | 1.00 | 47.33 | N |
| ATOM | 544 | CA | ASN | A | 69 | 108.881 | 61.505 | 21.428 | 1.00 | 49.37 | C |
| ATOM | 545 | CB | ASN | A | 69 | 108.591 | 60.477 | 22.512 | 1.00 | 49.40 | C |
| ATOM | 546 | CG | ASN | A | 69 | 109.061 | 60.887 | 23.884 | 1.00 | 52.60 | C |
| ATOM | 547 | OD1 | ASN | A | 69 | 109.932 | 61.749 | 24.046 | 1.00 | 54.70 | O |
| ATOM | 548 | ND2 | ASN | A | 69 | 108.517 | 60.206 | 24.901 | 1.00 | 54.58 | N |
| ATOM | 549 | C | ASN | A | 69 | 110.358 | 62.047 | 21.403 | 1.00 | 49.37 | C |
| ATOM | 550 | O | ASN | A | 69 | 111.311 | 61.289 | 21.601 | 1.00 | 50.10 | O |
| ATOM | 551 | N | ALA | A | 70 | 110.527 | 63.352 | 21.135 | 1.00 | 49.25 | N |
| ATOM | 552 | CA | ALA | A | 70 | 111.761 | 63.913 | 20.517 | 1.00 | 47.76 | C |
| ATOM | 553 | CB | ALA | A | 70 | 111.534 | 65.425 | 20.191 | 1.00 | 48.77 | C |
| ATOM | 554 | C | ALA | A | 70 | 113.182 | 63.655 | 21.163 | 1.00 | 47.17 | C |
| ATOM | 555 | O | ALA | A | 70 | 114.244 | 63.836 | 20.515 | 1.00 | 46.79 | O |
| ATOM | 556 | N | LEU | A | 71 | 113.226 | 63.215 | 22.420 | 1.00 | 45.43 | N |
| ATOM | 557 | CA | LEU | A | 71 | 114.508 | 62.950 | 23.061 | 1.00 | 44.08 | C |
| ATOM | 558 | CB | LEU | A | 71 | 114.449 | 63.312 | 24.533 | 1.00 | 43.97 | C |
| ATOM | 559 | CG | LEU | A | 71 | 114.368 | 64.799 | 24.880 | 1.00 | 42.01 | C |
| ATOM | 560 | CD1 | LEU | A | 71 | 114.114 | 64.902 | 26.375 | 1.00 | 38.92 | C |
| ATOM | 561 | CD2 | LEU | A | 71 | 115.669 | 65.502 | 24.496 | 1.00 | 38.65 | C |
| ATOM | 562 | C | LEU | A | 71 | 115.005 | 61.520 | 22.932 | 1.00 | 44.74 | C |
| ATOM | 563 | O | LEU | A | 71 | 116.169 | 61.231 | 23.154 | 1.00 | 44.38 | O |
| ATOM | 564 | N | LEU | A | 72 | 114.135 | 60.595 | 22.587 | 1.00 | 45.46 | N |
| ATOM | 565 | CA | LEU | A | 72 | 114.654 | 59.244 | 22.453 | 1.00 | 46.52 | C |
| ATOM | 566 | CB | LEU | A | 72 | 113.571 | 58.194 | 22.706 | 1.00 | 47.21 | C |
| ATOM | 567 | CG | LEU | A | 72 | 112.105 | 58.530 | 22.676 | 1.00 | 49.53 | C |
| ATOM | 568 | CD1 | LEU | A | 72 | 111.594 | 58.547 | 21.240 | 1.00 | 49.94 | C |
| ATOM | 569 | CD2 | LEU | A | 72 | 111.461 | 57.436 | 23.473 | 1.00 | 53.22 | C |
| ATOM | 570 | C | LEU | A | 72 | 115.385 | 59.064 | 21.113 | 1.00 | 45.34 | C |
| ATOM | 571 | O | LEU | A | 72 | 115.002 | 59.701 | 20.102 | 1.00 | 45.79 | O |
| ATOM | 572 | N | LYS | A | 73 | 116.449 | 58.242 | 21.160 | 1.00 | 43.11 | N |
| ATOM | 573 | CA | LYS | A | 73 | 117.261 | 57.828 | 19.997 | 1.00 | 42.14 | C |
| ATOM | 574 | CB | LYS | A | 73 | 118.730 | 57.715 | 20.418 | 1.00 | 42.49 | C |
| ATOM | 575 | CG | LYS | A | 73 | 119.729 | 57.159 | 19.308 | 1.00 | 45.81 | C |
| ATOM | 576 | CD | LYS | A | 73 | 121.142 | 56.826 | 19.913 | 1.00 | 48.57 | C |
| ATOM | 577 | CE | LYS | A | 73 | 122.229 | 56.680 | 18.853 | 1.00 | 50.87 | C |
| ATOM | 578 | NZ | LYS | A | 73 | 122.068 | 57.614 | 17.676 | 1.00 | 52.28 | N |
| ATOM | 579 | C | LYS | A | 73 | 116.832 | 56.429 | 19.509 | 1.00 | 39.34 | C |
| ATOM | 580 | O | LYS | A | 73 | 116.624 | 55.549 | 20.340 | 1.00 | 37.81 | O |
| ATOM | 581 | N | HIS | A | 74 | 116.725 | 56.284 | 18.185 | 1.00 | 36.23 | N |
| ATOM | 582 | CA | HIS | A | 74 | 116.502 | 55.024 | 17.496 | 1.00 | 35.73 | C |
| ATOM | 583 | CB | HIS | A | 74 | 116.736 | 55.212 | 15.975 | 1.00 | 36.37 | C |

FIG. 1-12

| | | | | | | | | | | | |
|---|---|---|---|---|---|---|---|---|---|---|---|
| ATOM | 584 | CG | HIS | A | 74 | 115.507 | 55.632 | 15.206 | 1.00 | 40.54 | C |
| ATOM | 585 | ND1 | HIS | A | 74 | 114.560 | 54.727 | 14.750 | 1.00 | 41.72 | N |
| ATOM | 586 | CE1 | HIS | A | 74 | 113.624 | 55.374 | 14.072 | 1.00 | 43.42 | C |
| ATOM | 587 | NE2 | HIS | A | 74 | 113.941 | 56.663 | 14.051 | 1.00 | 42.94 | N |
| ATOM | 588 | CD2 | HIS | A | 74 | 115.101 | 56.854 | 14.768 | 1.00 | 37.66 | C |
| ATOM | 589 | C | HIS | A | 74 | 117.493 | 53.972 | 18.008 | 1.00 | 32.26 | C |
| ATOM | 590 | O | HIS | A | 74 | 118.724 | 54.233 | 18.054 | 1.00 | 31.60 | O |
| ATOM | 591 | N | ARG | A | 75 | 116.995 | 52.810 | 18.408 | 1.00 | 29.08 | N |
| ATOM | 592 | CA | ARG | A | 75 | 117.904 | 51.718 | 18.901 | 1.00 | 27.67 | C |
| ATOM | 593 | CB | ARG | A | 75 | 117.146 | 50.597 | 19.648 | 1.00 | 28.19 | C |
| ATOM | 594 | CG | ARG | A | 75 | 118.139 | 49.532 | 20.388 | 1.00 | 27.31 | C |
| ATOM | 595 | CD | ARG | A | 75 | 117.422 | 48.267 | 20.769 | 1.00 | 31.20 | C |
| ATOM | 596 | NE | ARG | A | 75 | 118.389 | 47.181 | 21.055 | 1.00 | 31.60 | N |
| ATOM | 597 | CZ | ARG | A | 75 | 118.065 | 46.050 | 21.678 | 1.00 | 32.06 | C |
| ATOM | 598 | NH1 | ARG | A | 75 | 116.800 | 45.873 | 22.074 | 1.00 | 30.78 | N |
| ATOM | 599 | NH2 | ARG | A | 75 | 118.991 | 45.101 | 21.920 | 1.00 | 33.97 | N |
| ATOM | 600 | C | ARG | A | 75 | 118.873 | 51.139 | 17.802 | 1.00 | 26.98 | C |
| ATOM | 601 | O | ARG | A | 75 | 120.051 | 50.868 | 18.087 | 1.00 | 28.42 | O |
| ATOM | 602 | N | PHE | A | 76 | 118.391 | 51.028 | 16.573 | 1.00 | 26.49 | N |
| ATOM | 603 | CA | PHE | A | 76 | 119.110 | 50.428 | 15.442 | 1.00 | 26.90 | C |
| ATOM | 604 | CB | PHE | A | 76 | 118.263 | 49.299 | 14.823 | 1.00 | 26.78 | C |
| ATOM | 605 | CG | PHE | A | 76 | 117.963 | 48.158 | 15.786 | 1.00 | 27.51 | C |
| ATOM | 606 | CD1 | PHE | A | 76 | 118.977 | 47.227 | 16.147 | 1.00 | 27.11 | C |
| ATOM | 607 | CE1 | PHE | A | 76 | 118.710 | 46.166 | 17.101 | 1.00 | 20.93 | C |
| ATOM | 608 | CZ | PHE | A | 76 | 117.443 | 46.075 | 17.647 | 1.00 | 21.48 | C |
| ATOM | 609 | CE2 | PHE | A | 76 | 116.419 | 47.006 | 17.277 | 1.00 | 23.38 | C |
| ATOM | 610 | CD2 | PHE | A | 76 | 116.679 | 48.017 | 16.371 | 1.00 | 26.20 | C |
| ATOM | 611 | C | PHE | A | 76 | 119.438 | 51.511 | 14.394 | 1.00 | 27.87 | C |
| ATOM | 612 | O | PHE | A | 76 | 118.580 | 52.340 | 14.081 | 1.00 | 28.54 | O |
| ATOM | 613 | N | GLU | A | 77 | 120.673 | 51.562 | 13.909 | 1.00 | 25.24 | N |
| ATOM | 614 | CA | GLU | A | 77 | 120.965 | 52.250 | 12.656 | 1.00 | 26.74 | C |
| ATOM | 615 | CB | GLU | A | 77 | 122.473 | 52.499 | 12.640 | 1.00 | 26.83 | C |
| ATOM | 616 | CG | GLU | A | 77 | 123.077 | 53.793 | 12.198 | 1.00 | 32.19 | C |
| ATOM | 617 | CD | GLU | A | 77 | 122.239 | 55.065 | 12.460 | 1.00 | 30.31 | C |
| ATOM | 618 | OE1 | GLU | A | 77 | 121.468 | 55.454 | 11.582 | 1.00 | 35.51 | O |
| ATOM | 619 | OE2 | GLU | A | 77 | 122.386 | 55.638 | 13.515 | 1.00 | 32.50 | O |
| ATOM | 620 | C | GLU | A | 77 | 120.659 | 51.218 | 11.560 | 1.00 | 25.79 | C |
| ATOM | 621 | O | GLU | A | 77 | 121.008 | 50.031 | 11.734 | 1.00 | 24.39 | O |
| ATOM | 622 | N | ILE | A | 78 | 120.125 | 51.657 | 10.419 | 1.00 | 24.55 | N |
| ATOM | 623 | CA | ILE | A | 78 | 119.883 | 50.760 | 9.347 | 1.00 | 25.64 | C |
| ATOM | 624 | CB | ILE | A | 78 | 118.448 | 50.859 | 8.776 | 1.00 | 25.37 | C |
| ATOM | 625 | CG1 | ILE | A | 78 | 117.389 | 50.439 | 9.853 | 1.00 | 30.17 | C |
| ATOM | 626 | CD1 | ILE | A | 78 | 116.483 | 51.585 | 10.530 | 1.00 | 34.64 | C |
| ATOM | 627 | CG2 | ILE | A | 78 | 118.333 | 49.789 | 7.709 | 1.00 | 27.85 | C |
| ATOM | 628 | C | ILE | A | 78 | 120.886 | 51.000 | 8.209 | 1.00 | 26.64 | C |
| ATOM | 629 | O | ILE | A | 78 | 121.053 | 52.149 | 7.781 | 1.00 | 26.38 | O |
| ATOM | 630 | N | ILE | A | 79 | 121.516 | 49.922 | 7.699 | 1.00 | 23.83 | N |
| ATOM | 631 | CA | ILE | A | 79 | 122.585 | 50.100 | 6.764 | 1.00 | 22.98 | C |
| ATOM | 632 | CB | ILE | A | 79 | 123.951 | 49.382 | 7.310 | 1.00 | 23.51 | C |
| ATOM | 633 | CG1 | ILE | A | 79 | 124.300 | 49.862 | 8.720 | 1.00 | 22.81 | C |
| ATOM | 634 | CD1 | ILE | A | 79 | 125.273 | 48.966 | 9.523 | 1.00 | 26.88 | C |
| ATOM | 635 | CG2 | ILE | A | 79 | 125.077 | 49.497 | 6.306 | 1.00 | 20.50 | C |
| ATOM | 636 | C | ILE | A | 79 | 122.134 | 49.641 | 5.382 | 1.00 | 23.00 | C |
| ATOM | 637 | O | ILE | A | 79 | 122.437 | 50.247 | 4.395 | 1.00 | 21.80 | O |
| ATOM | 638 | N | GLU | A | 80 | 121.459 | 48.508 | 5.329 | 1.00 | 23.94 | N |
| ATOM | 639 | CA | GLU | A | 80 | 120.755 | 48.052 | 4.174 | 1.00 | 25.99 | C |
| ATOM | 640 | CB | GLU | A | 80 | 119.922 | 46.837 | 4.593 | 1.00 | 26.50 | C |
| ATOM | 641 | CG | GLU | A | 80 | 119.194 | 46.095 | 3.498 | 1.00 | 30.22 | C |
| ATOM | 642 | CD | GLU | A | 80 | 120.088 | 45.520 | 2.424 | 1.00 | 36.91 | C |
| ATOM | 643 | OE1 | GLU | A | 80 | 121.264 | 45.170 | 2.689 | 1.00 | 42.16 | O |
| ATOM | 644 | OE2 | GLU | A | 80 | 119.593 | 45.383 | 1.292 | 1.00 | 42.25 | O |
| ATOM | 645 | C | GLU | A | 80 | 119.812 | 49.178 | 3.708 | 1.00 | 26.68 | C |
| ATOM | 646 | O | GLU | A | 80 | 119.318 | 49.987 | 4.538 | 1.00 | 26.87 | O |

FIG. 1-13

| | | | | | | | | | | | |
|---|---|---|---|---|---|---|---|---|---|---|---|
| ATOM | 647 | N | GLY | A | 81 | 119.597 | 49.256 | 2.409 | 1.00 | 25.00 | N |
| ATOM | 648 | CA | GLY | A | 81 | 118.737 | 50.303 | 1.848 | 1.00 | 25.66 | C |
| ATOM | 649 | C | GLY | A | 81 | 119.566 | 51.452 | 1.296 | 1.00 | 27.49 | C |
| ATOM | 650 | O | GLY | A | 81 | 119.066 | 52.211 | 0.524 | 1.00 | 28.91 | O |
| ATOM | 651 | N | ARG | A | 82 | 120.832 | 51.578 | 1.679 | 1.00 | 25.71 | N |
| ATOM | 652 | CA | ARG | A | 82 | 121.684 | 52.695 | 1.153 | 1.00 | 27.02 | C |
| ATOM | 653 | CB | ARG | A | 82 | 122.514 | 53.299 | 2.254 | 1.00 | 22.81 | C |
| ATOM | 654 | CG | ARG | A | 82 | 121.735 | 53.488 | 3.594 | 1.00 | 25.76 | C |
| ATOM | 655 | CD | ARG | A | 82 | 122.605 | 54.074 | 4.702 | 1.00 | 22.32 | C |
| ATOM | 656 | NE | ARG | A | 82 | 121.858 | 54.133 | 5.980 | 1.00 | 29.84 | N |
| ATOM | 657 | CZ | ARG | A | 82 | 121.140 | 55.205 | 6.347 | 1.00 | 32.60 | C |
| ATOM | 658 | NH1 | ARG | A | 82 | 121.107 | 56.262 | 5.544 | 1.00 | 28.57 | N |
| ATOM | 659 | NH2 | ARG | A | 82 | 120.443 | 55.215 | 7.487 | 1.00 | 31.43 | N |
| ATOM | 660 | C | ARG | A | 82 | 122.618 | 52.221 | 0.049 | 1.00 | 28.24 | C |
| ATOM | 661 | O | ARG | A | 82 | 122.981 | 51.039 | -0.045 | 1.00 | 26.51 | O |
| ATOM | 662 | N | ASP | A | 83 | 123.044 | 53.156 | -0.769 | 1.00 | 29.07 | N |
| ATOM | 663 | CA | ASP | A | 83 | 123.972 | 52.797 | -1.821 | 1.00 | 29.79 | C |
| ATOM | 664 | CB | ASP | A | 83 | 123.922 | 53.845 | -2.938 | 1.00 | 29.55 | C |
| ATOM | 665 | CG | ASP | A | 83 | 124.780 | 55.113 | -2.614 | 1.00 | 36.23 | C |
| ATOM | 666 | OD1 | ASP | A | 83 | 125.172 | 55.334 | -1.455 | 1.00 | 43.86 | O |
| ATOM | 667 | OD2 | ASP | A | 83 | 125.064 | 55.914 | -3.547 | 1.00 | 43.76 | O |
| ATOM | 668 | C | ASP | A | 83 | 125.365 | 52.596 | -1.157 | 1.00 | 27.22 | C |
| ATOM | 669 | O | ASP | A | 83 | 125.540 | 52.902 | 0.023 | 1.00 | 25.99 | O |
| ATOM | 670 | N | ARG | A | 84 | 126.342 | 52.064 | -1.890 | 1.00 | 24.65 | N |
| ATOM | 671 | CA | ARG | A | 84 | 127.605 | 51.719 | -1.219 | 1.00 | 24.50 | C |
| ATOM | 672 | CB | ARG | A | 84 | 128.518 | 50.936 | -2.190 | 1.00 | 23.17 | C |
| ATOM | 673 | CG | ARG | A | 84 | 127.913 | 49.574 | -2.510 | 1.00 | 27.83 | C |
| ATOM | 674 | CD | ARG | A | 84 | 128.382 | 48.423 | -1.562 | 1.00 | 30.58 | C |
| ATOM | 675 | NE | ARG | A | 84 | 128.176 | 47.187 | -2.298 | 1.00 | 33.27 | N |
| ATOM | 676 | CZ | ARG | A | 84 | 126.990 | 46.558 | -2.387 | 1.00 | 38.36 | C |
| ATOM | 677 | NH1 | ARG | A | 84 | 125.928 | 47.080 | -1.785 | 1.00 | 37.14 | N |
| ATOM | 678 | NH2 | ARG | A | 84 | 126.826 | 45.443 | -3.131 | 1.00 | 37.61 | N |
| ATOM | 679 | C | ARG | A | 84 | 128.344 | 52.887 | -0.497 | 1.00 | 23.58 | C |
| ATOM | 680 | O | ARG | A | 84 | 128.793 | 52.747 | 0.634 | 1.00 | 22.35 | O |
| ATOM | 681 | N | ILE | A | 85 | 128.393 | 54.067 | -1.117 | 1.00 | 25.70 | N |
| ATOM | 682 | CA | ILE | A | 85 | 129.092 | 55.228 | -0.509 | 1.00 | 24.40 | C |
| ATOM | 683 | CB | ILE | A | 85 | 129.068 | 56.423 | -1.444 | 1.00 | 26.28 | C |
| ATOM | 684 | CG1 | ILE | A | 85 | 129.783 | 56.105 | -2.761 | 1.00 | 29.93 | C |
| ATOM | 685 | CD1 | ILE | A | 85 | 131.106 | 55.591 | -2.555 | 1.00 | 34.08 | C |
| ATOM | 686 | CG2 | ILE | A | 85 | 129.755 | 57.666 | -0.783 | 1.00 | 27.71 | C |
| ATOM | 687 | C | ILE | A | 85 | 128.439 | 55.558 | 0.809 | 1.00 | 24.36 | C |
| ATOM | 688 | O | ILE | A | 85 | 129.097 | 55.567 | 1.824 | 1.00 | 24.48 | O |
| ATOM | 689 | N | MET | A | 86 | 127.095 | 55.709 | 0.842 | 1.00 | 25.64 | N |
| ATOM | 690 | CA | MET | A | 86 | 126.443 | 56.186 | 2.028 | 1.00 | 24.45 | C |
| ATOM | 691 | CB | MET | A | 86 | 124.953 | 56.436 | 1.752 | 1.00 | 25.98 | C |
| ATOM | 692 | CG | MET | A | 86 | 124.689 | 57.628 | 0.955 | 1.00 | 32.14 | C |
| ATOM | 693 | SD | MET | A | 86 | 125.740 | 59.004 | 1.491 | 1.00 | 44.80 | S |
| ATOM | 694 | CE | MET | A | 86 | 126.135 | 59.636 | -0.158 | 1.00 | 38.55 | C |
| ATOM | 695 | C | MET | A | 86 | 126.494 | 55.177 | 3.117 | 1.00 | 23.73 | C |
| ATOM | 696 | O | MET | A | 86 | 126.565 | 55.531 | 4.305 | 1.00 | 23.45 | O |
| ATOM | 697 | N | ALA | A | 87 | 126.314 | 53.902 | 2.754 | 1.00 | 23.19 | N |
| ATOM | 698 | CA | ALA | A | 87 | 126.461 | 52.825 | 3.766 | 1.00 | 22.63 | C |
| ATOM | 699 | CB | ALA | A | 87 | 126.153 | 51.381 | 3.070 | 1.00 | 19.72 | C |
| ATOM | 700 | C | ALA | A | 87 | 127.746 | 52.775 | 4.552 | 1.00 | 19.18 | C |
| ATOM | 701 | O | ALA | A | 87 | 127.800 | 52.676 | 5.791 | 1.00 | 20.92 | O |
| ATOM | 702 | N | TRP | A | 88 | 128.831 | 52.786 | 3.828 | 1.00 | 22.50 | N |
| ATOM | 703 | CA | TRP | A | 88 | 130.159 | 52.751 | 4.434 | 1.00 | 20.36 | C |
| ATOM | 704 | CB | TRP | A | 88 | 131.225 | 52.618 | 3.346 | 1.00 | 20.71 | C |
| ATOM | 705 | CG | TRP | A | 88 | 131.428 | 51.252 | 2.946 | 1.00 | 23.65 | C |
| ATOM | 706 | CD1 | TRP | A | 88 | 131.074 | 50.665 | 1.793 | 1.00 | 23.39 | C |
| ATOM | 707 | NE1 | TRP | A | 88 | 131.408 | 49.330 | 1.845 | 1.00 | 24.15 | N |
| ATOM | 708 | CE2 | TRP | A | 88 | 131.949 | 49.051 | 3.075 | 1.00 | 20.66 | C |
| ATOM | 709 | CD2 | TRP | A | 88 | 131.937 | 50.224 | 3.805 | 1.00 | 22.48 | C |

FIG. 1-14

| | | | | | | | | | | | |
|---|---|---|---|---|---|---|---|---|---|---|---|
| ATOM | 710 | CE3 | TRP | A | 88 | 132.494 | 50.242 | 5.105 | 1.00 | 24.89 | C |
| ATOM | 711 | CZ3 | TRP | A | 88 | 132.986 | 49.032 | 5.640 | 1.00 | 28.04 | C |
| ATOM | 712 | CH2 | TRP | A | 88 | 132.913 | 47.838 | 4.886 | 1.00 | 24.59 | C |
| ATOM | 713 | CZ2 | TRP | A | 88 | 132.421 | 47.823 | 3.601 | 1.00 | 23.83 | C |
| ATOM | 714 | C | TRP | A | 88 | 130.333 | 54.119 | 5.133 | 1.00 | 21.55 | C |
| ATOM | 715 | O | TRP | A | 88 | 131.074 | 54.202 | 6.097 | 1.00 | 21.31 | O |
| ATOM | 716 | N | THR | A | 89 | 129.641 | 55.157 | 4.669 | 1.00 | 22.55 | N |
| ATOM | 717 | CA | THR | A | 89 | 129.718 | 56.470 | 5.431 | 1.00 | 23.74 | C |
| ATOM | 718 | CB | THR | A | 89 | 129.028 | 57.623 | 4.642 | 1.00 | 23.90 | C |
| ATOM | 719 | OG1 | THR | A | 89 | 129.757 | 57.813 | 3.440 | 1.00 | 26.28 | O |
| ATOM | 720 | CG2 | THR | A | 89 | 129.005 | 58.954 | 5.435 | 1.00 | 27.11 | C |
| ATOM | 721 | C | THR | A | 89 | 129.071 | 56.316 | 6.765 | 1.00 | 21.64 | C |
| ATOM | 722 | O | THR | A | 89 | 129.604 | 56.792 | 7.778 | 1.00 | 24.13 | O |
| ATOM | 723 | N | VAL | A | 90 | 127.938 | 55.606 | 6.802 | 1.00 | 20.19 | N |
| ATOM | 724 | CA | VAL | A | 90 | 127.269 | 55.366 | 8.099 | 1.00 | 21.17 | C |
| ATOM | 725 | CB | VAL | A | 90 | 125.840 | 54.848 | 7.772 | 1.00 | 21.45 | C |
| ATOM | 726 | CG1 | VAL | A | 90 | 125.136 | 54.314 | 8.980 | 1.00 | 23.14 | C |
| ATOM | 727 | CG2 | VAL | A | 90 | 125.006 | 56.025 | 7.161 | 1.00 | 25.54 | C |
| ATOM | 728 | C | VAL | A | 90 | 128.118 | 54.410 | 8.956 | 1.00 | 20.25 | C |
| ATOM | 729 | O | VAL | A | 90 | 128.440 | 54.638 | 10.117 | 1.00 | 22.52 | O |
| ATOM | 730 | N | VAL | A | 91 | 128.523 | 53.290 | 8.384 | 1.00 | 20.69 | N |
| ATOM | 731 | CA | VAL | A | 91 | 129.428 | 52.423 | 9.157 | 1.00 | 21.28 | C |
| ATOM | 732 | CB | VAL | A | 91 | 129.899 | 51.253 | 8.315 | 1.00 | 18.74 | C |
| ATOM | 733 | CG1 | VAL | A | 91 | 131.108 | 50.627 | 9.004 | 1.00 | 21.12 | C |
| ATOM | 734 | CG2 | VAL | A | 91 | 128.642 | 50.226 | 8.134 | 1.00 | 18.85 | C |
| ATOM | 735 | C | VAL | A | 91 | 130.663 | 53.199 | 9.694 | 1.00 | 22.68 | C |
| ATOM | 736 | O | VAL | A | 91 | 131.080 | 52.976 | 10.816 | 1.00 | 23.09 | O |
| ATOM | 737 | N | ASN | A | 92 | 131.267 | 54.060 | 8.895 | 1.00 | 24.25 | N |
| ATOM | 738 | CA | ASN | A | 92 | 132.554 | 54.763 | 9.373 | 1.00 | 26.98 | C |
| ATOM | 739 | CB | ASN | A | 92 | 133.244 | 55.584 | 8.261 | 1.00 | 26.36 | C |
| ATOM | 740 | CG | ASN | A | 92 | 133.911 | 54.759 | 7.173 | 1.00 | 32.55 | C |
| ATOM | 741 | OD1 | ASN | A | 92 | 134.164 | 53.518 | 7.296 | 1.00 | 40.81 | O |
| ATOM | 742 | ND2 | ASN | A | 92 | 134.184 | 55.436 | 6.044 | 1.00 | 33.67 | N |
| ATOM | 743 | C | ASN | A | 92 | 132.182 | 55.736 | 10.512 | 1.00 | 27.38 | C |
| ATOM | 744 | O | ASN | A | 92 | 132.840 | 55.867 | 11.497 | 1.00 | 28.44 | O |
| ATOM | 745 | N | SER | A | 93 | 131.056 | 56.388 | 10.382 | 1.00 | 28.83 | N |
| ATOM | 746 | CA | SER | A | 93 | 130.588 | 57.280 | 11.476 | 1.00 | 29.39 | C |
| ATOM | 747 | CB | SER | A | 93 | 129.422 | 58.157 | 10.960 | 1.00 | 29.20 | C |
| ATOM | 748 | OG | SER | A | 93 | 128.668 | 58.681 | 12.031 | 1.00 | 36.15 | O |
| ATOM | 749 | C | SER | A | 93 | 130.223 | 56.530 | 12.703 | 1.00 | 27.81 | C |
| ATOM | 750 | O | SER | A | 93 | 130.458 | 56.998 | 13.829 | 1.00 | 27.63 | O |
| ATOM | 751 | N | ILE | A | 94 | 129.682 | 55.314 | 12.531 | 1.00 | 27.52 | N |
| ATOM | 752 | CA | ILE | A | 94 | 129.370 | 54.491 | 13.683 | 1.00 | 24.71 | C |
| ATOM | 753 | CB | ILE | A | 94 | 128.529 | 53.258 | 13.280 | 1.00 | 26.27 | C |
| ATOM | 754 | CG1 | ILE | A | 94 | 127.159 | 53.670 | 12.712 | 1.00 | 24.93 | C |
| ATOM | 755 | CD1 | ILE | A | 94 | 126.349 | 52.474 | 12.155 | 1.00 | 23.61 | C |
| ATOM | 756 | CG2 | ILE | A | 94 | 128.351 | 52.417 | 14.523 | 1.00 | 24.62 | C |
| ATOM | 757 | C | ILE | A | 94 | 130.622 | 53.978 | 14.398 | 1.00 | 25.53 | C |
| ATOM | 758 | O | ILE | A | 94 | 130.719 | 53.958 | 15.632 | 1.00 | 25.48 | O |
| ATOM | 759 | N | CYS | A | 95 | 131.591 | 53.501 | 13.653 | 1.00 | 24.91 | N |
| ATOM | 760 | CA | CYS | A | 95 | 132.861 | 53.178 | 14.281 | 1.00 | 28.68 | C |
| ATOM | 761 | CB | CYS | A | 95 | 133.812 | 52.447 | 13.302 | 1.00 | 27.47 | C |
| ATOM | 762 | SG | CYS | A | 95 | 132.943 | 50.957 | 12.676 | 1.00 | 33.60 | S |
| ATOM | 763 | C | CYS | A | 95 | 133.542 | 54.397 | 15.039 | 1.00 | 30.70 | C |
| ATOM | 764 | O | CYS | A | 95 | 134.003 | 54.243 | 16.159 | 1.00 | 32.47 | O |
| ATOM | 765 | N | ASN | A | 96 | 133.455 | 55.606 | 14.517 | 1.00 | 31.17 | N |
| ATOM | 766 | CA | ASN | A | 96 | 133.886 | 56.772 | 15.342 | 1.00 | 34.29 | C |
| ATOM | 767 | CB | ASN | A | 96 | 133.859 | 58.056 | 14.510 | 1.00 | 34.06 | C |
| ATOM | 768 | CG | ASN | A | 96 | 134.879 | 58.038 | 13.453 | 1.00 | 37.04 | C |
| ATOM | 769 | OD1 | ASN | A | 96 | 135.975 | 57.501 | 13.686 | 1.00 | 45.12 | O |
| ATOM | 770 | ND2 | ASN | A | 96 | 134.545 | 58.544 | 12.256 | 1.00 | 37.27 | N |
| ATOM | 771 | C | ASN | A | 96 | 133.119 | 57.009 | 16.625 | 1.00 | 34.55 | C |
| ATOM | 772 | O | ASN | A | 96 | 133.709 | 57.374 | 17.648 | 1.00 | 37.18 | O |

FIG. 1-15

| | | | | | | | | | | | |
|---|---|---|---|---|---|---|---|---|---|---|---|
| ATOM | 773 | N | THR | A | 97 | 131.801 | 56.806 | 16.590 | 1.00 | 34.97 | N |
| ATOM | 774 | CA | THR | A | 97 | 130.957 | 57.079 | 17.746 | 1.00 | 33.78 | C |
| ATOM | 775 | CB | THR | A | 97 | 129.505 | 56.848 | 17.350 | 1.00 | 34.91 | C |
| ATOM | 776 | OG1 | THR | A | 97 | 129.269 | 57.549 | 16.135 | 1.00 | 38.47 | O |
| ATOM | 777 | CG2 | THR | A | 97 | 128.484 | 57.284 | 18.448 | 1.00 | 30.89 | C |
| ATOM | 778 | C | THR | A | 97 | 131.237 | 56.141 | 18.888 | 1.00 | 34.63 | C |
| ATOM | 779 | O | THR | A | 97 | 131.252 | 56.583 | 20.069 | 1.00 | 35.31 | O |
| ATOM | 780 | N | THR | A | 98 | 131.383 | 54.845 | 18.578 | 1.00 | 32.27 | N |
| ATOM | 781 | CA | THR | A | 98 | 131.299 | 53.823 | 19.602 | 1.00 | 32.11 | C |
| ATOM | 782 | CB | THR | A | 98 | 130.294 | 52.634 | 19.277 | 1.00 | 34.31 | C |
| ATOM | 783 | OG1 | THR | A | 98 | 130.817 | 51.901 | 18.172 | 1.00 | 29.27 | O |
| ATOM | 784 | CG2 | THR | A | 98 | 128.798 | 53.106 | 18.997 | 1.00 | 32.15 | C |
| ATOM | 785 | C | THR | A | 98 | 132.658 | 53.191 | 19.764 | 1.00 | 30.79 | C |
| ATOM | 786 | O | THR | A | 98 | 132.964 | 52.655 | 20.828 | 1.00 | 29.82 | O |
| ATOM | 787 | N | GLY | A | 99 | 133.451 | 53.245 | 18.722 | 1.00 | 30.71 | N |
| ATOM | 788 | CA | GLY | A | 99 | 134.799 | 52.674 | 18.770 | 1.00 | 33.01 | C |
| ATOM | 789 | C | GLY | A | 99 | 134.797 | 51.167 | 18.530 | 1.00 | 33.78 | C |
| ATOM | 790 | O | GLY | A | 99 | 135.782 | 50.441 | 18.851 | 1.00 | 35.21 | O |
| ATOM | 791 | N | VAL | A | 100 | 133.676 | 50.700 | 17.984 | 1.00 | 32.38 | N |
| ATOM | 792 | CA | VAL | A | 100 | 133.510 | 49.319 | 17.605 | 1.00 | 31.73 | C |
| ATOM | 793 | CB | VAL | A | 100 | 132.022 | 49.029 | 17.297 | 1.00 | 30.21 | C |
| ATOM | 794 | CG1 | VAL | A | 100 | 131.627 | 49.696 | 15.965 | 1.00 | 29.23 | C |
| ATOM | 795 | CG2 | VAL | A | 100 | 131.741 | 47.503 | 17.320 | 1.00 | 33.80 | C |
| ATOM | 796 | C | VAL | A | 100 | 134.357 | 49.027 | 16.375 | 1.00 | 29.68 | C |
| ATOM | 797 | O | VAL | A | 100 | 134.462 | 49.843 | 15.509 | 1.00 | 27.97 | O |
| ATOM | 798 | N | GLU | A | 101 | 134.979 | 47.847 | 16.348 | 1.00 | 30.40 | N |
| ATOM | 799 | CA | GLU | A | 101 | 135.787 | 47.408 | 15.230 | 1.00 | 29.78 | C |
| ATOM | 800 | CB | GLU | A | 101 | 136.290 | 45.985 | 15.510 | 1.00 | 30.19 | C |
| ATOM | 801 | CG | GLU | A | 101 | 137.453 | 45.557 | 14.676 | 1.00 | 35.18 | C |
| ATOM | 802 | CD | GLU | A | 101 | 138.065 | 44.217 | 15.194 | 1.00 | 41.01 | C |
| ATOM | 803 | OE1 | GLU | A | 101 | 137.468 | 43.156 | 14.899 | 1.00 | 34.44 | O |
| ATOM | 804 | OE2 | GLU | A | 101 | 139.115 | 44.265 | 15.898 | 1.00 | 43.44 | O |
| ATOM | 805 | C | GLU | A | 101 | 134.980 | 47.455 | 13.928 | 1.00 | 28.95 | C |
| ATOM | 806 | O | GLU | A | 101 | 133.789 | 47.037 | 13.866 | 1.00 | 27.32 | O |
| ATOM | 807 | N | LYS | A | 102 | 135.599 | 48.025 | 12.910 | 1.00 | 26.95 | N |
| ATOM | 808 | CA | LYS | A | 102 | 134.976 | 48.090 | 11.614 | 1.00 | 26.95 | C |
| ATOM | 809 | CB | LYS | A | 102 | 135.659 | 49.128 | 10.752 | 1.00 | 27.08 | C |
| ATOM | 810 | CG | LYS | A | 102 | 134.920 | 49.455 | 9.444 | 1.00 | 31.11 | C |
| ATOM | 811 | CD | LYS | A | 102 | 135.721 | 50.466 | 8.606 | 1.00 | 37.88 | C |
| ATOM | 812 | CE | LYS | A | 102 | 136.068 | 51.667 | 9.490 | 1.00 | 39.44 | C |
| ATOM | 813 | NZ | LYS | A | 102 | 136.109 | 52.904 | 8.671 | 1.00 | 42.90 | N |
| ATOM | 814 | C | LYS | A | 102 | 134.956 | 46.701 | 10.898 | 1.00 | 26.48 | C |
| ATOM | 815 | O | LYS | A | 102 | 135.966 | 46.025 | 10.814 | 1.00 | 24.28 | O |
| ATOM | 816 | N | PRO | A | 103 | 133.785 | 46.282 | 10.424 | 1.00 | 26.52 | N |
| ATOM | 817 | CA | PRO | A | 103 | 133.661 | 44.977 | 9.755 | 1.00 | 26.25 | C |
| ATOM | 818 | CB | PRO | A | 103 | 132.158 | 44.681 | 9.835 | 1.00 | 26.53 | C |
| ATOM | 819 | CG | PRO | A | 103 | 131.493 | 46.120 | 9.778 | 1.00 | 26.84 | C |
| ATOM | 820 | CD | PRO | A | 103 | 132.546 | 47.089 | 10.386 | 1.00 | 25.64 | C |
| ATOM | 821 | C | PRO | A | 103 | 134.096 | 45.225 | 8.301 | 1.00 | 27.05 | C |
| ATOM | 822 | O | PRO | A | 103 | 134.032 | 46.371 | 7.832 | 1.00 | 26.40 | O |
| ATOM | 823 | N | LYS | A | 104 | 134.549 | 44.169 | 7.636 | 1.00 | 26.71 | N |
| ATOM | 824 | CA | LYS | A | 104 | 135.044 | 44.181 | 6.243 | 1.00 | 29.35 | C |
| ATOM | 825 | CB | LYS | A | 104 | 136.008 | 42.980 | 6.066 | 1.00 | 28.99 | C |
| ATOM | 826 | CG | LYS | A | 104 | 137.325 | 43.212 | 6.750 | 1.00 | 29.89 | C |
| ATOM | 827 | CD | LYS | A | 104 | 138.216 | 41.953 | 6.664 | 1.00 | 34.14 | C |
| ATOM | 828 | CE | LYS | A | 104 | 139.444 | 42.210 | 7.460 | 1.00 | 33.97 | C |
| ATOM | 829 | NZ | LYS | A | 104 | 140.592 | 41.452 | 6.906 | 1.00 | 38.04 | N |
| ATOM | 830 | C | LYS | A | 104 | 134.007 | 44.126 | 5.126 | 1.00 | 28.96 | C |
| ATOM | 831 | O | LYS | A | 104 | 134.283 | 44.443 | 3.946 | 1.00 | 29.54 | O |
| ATOM | 832 | N | PHE | A | 105 | 132.812 | 43.720 | 5.479 | 1.00 | 29.04 | N |
| ATOM | 833 | CA | PHE | A | 105 | 131.708 | 43.743 | 4.520 | 1.00 | 30.31 | C |
| ATOM | 834 | CB | PHE | A | 105 | 131.232 | 42.302 | 4.442 | 1.00 | 31.46 | C |
| ATOM | 835 | CG | PHE | A | 105 | 130.672 | 41.867 | 5.705 | 1.00 | 36.41 | C |

FIG. 1-16

| | | | | | | | | | | | |
|---|---|---|---|---|---|---|---|---|---|---|---|
| ATOM | 836 | CD1 | PHE | A | 105 | 129.290 | 41.812 | 5.879 | 1.00 | 45.29 | C |
| ATOM | 837 | CE1 | PHE | A | 105 | 128.735 | 41.454 | 7.116 | 1.00 | 44.10 | C |
| ATOM | 838 | CZ | PHE | A | 105 | 129.571 | 41.201 | 8.191 | 1.00 | 44.12 | C |
| ATOM | 839 | CE2 | PHE | A | 105 | 130.936 | 41.266 | 8.054 | 1.00 | 41.63 | C |
| ATOM | 840 | CD2 | PHE | A | 105 | 131.505 | 41.619 | 6.801 | 1.00 | 42.87 | C |
| ATOM | 841 | C | PHE | A | 105 | 130.586 | 44.579 | 5.147 | 1.00 | 27.91 | C |
| ATOM | 842 | O | PHE | A | 105 | 130.584 | 44.743 | 6.344 | 1.00 | 28.94 | O |
| ATOM | 843 | N | LEU | A | 106 | 129.619 | 45.052 | 4.377 | 1.00 | 26.08 | N |
| ATOM | 844 | CA | LEU | A | 106 | 128.495 | 45.800 | 4.948 | 1.00 | 25.85 | C |
| ATOM | 845 | CB | LEU | A | 106 | 127.801 | 46.539 | 3.813 | 1.00 | 25.11 | C |
| ATOM | 846 | CG | LEU | A | 106 | 128.658 | 47.729 | 3.333 | 1.00 | 28.47 | C |
| ATOM | 847 | CD1 | LEU | A | 106 | 128.032 | 48.268 | 2.020 | 1.00 | 25.00 | C |
| ATOM | 848 | CD2 | LEU | A | 106 | 128.789 | 48.852 | 4.393 | 1.00 | 26.80 | C |
| ATOM | 849 | C | LEU | A | 106 | 127.459 | 44.873 | 5.625 | 1.00 | 23.67 | C |
| ATOM | 850 | O | LEU | A | 106 | 126.841 | 44.064 | 4.979 | 1.00 | 22.75 | O |
| ATOM | 851 | N | PRO | A | 107 | 127.239 | 45.006 | 6.911 | 1.00 | 21.65 | N |
| ATOM | 852 | CA | PRO | A | 107 | 126.107 | 44.250 | 7.445 | 1.00 | 21.50 | C |
| ATOM | 853 | CB | PRO | A | 107 | 126.495 | 44.050 | 8.916 | 1.00 | 21.01 | C |
| ATOM | 854 | CG | PRO | A | 107 | 127.423 | 45.181 | 9.206 | 1.00 | 25.92 | C |
| ATOM | 855 | CD | PRO | A | 107 | 127.928 | 45.804 | 7.929 | 1.00 | 23.21 | C |
| ATOM | 856 | C | PRO | A | 107 | 124.772 | 45.074 | 7.337 | 1.00 | 20.47 | C |
| ATOM | 857 | O | PRO | A | 107 | 124.819 | 46.181 | 6.787 | 1.00 | 21.40 | O |
| ATOM | 858 | N | ASP | A | 108 | 123.683 | 44.651 | 7.994 | 1.00 | 18.13 | N |
| ATOM | 859 | CA | ASP | A | 108 | 122.347 | 45.269 | 7.759 | 1.00 | 19.87 | C |
| ATOM | 860 | CB | ASP | A | 108 | 121.259 | 44.137 | 7.728 | 1.00 | 18.23 | C |
| ATOM | 861 | CG | ASP | A | 108 | 121.537 | 43.177 | 6.613 | 1.00 | 19.12 | C |
| ATOM | 862 | OD1 | ASP | A | 108 | 121.573 | 43.526 | 5.408 | 1.00 | 22.66 | O |
| ATOM | 863 | OD2 | ASP | A | 108 | 121.803 | 42.066 | 6.937 | 1.00 | 27.04 | O |
| ATOM | 864 | C | ASP | A | 108 | 121.958 | 46.266 | 8.763 | 1.00 | 18.51 | C |
| ATOM | 865 | O | ASP | A | 108 | 121.254 | 47.171 | 8.421 | 1.00 | 24.12 | O |
| ATOM | 866 | N | LEU | A | 109 | 122.239 | 45.992 | 10.017 | 1.00 | 20.09 | N |
| ATOM | 867 | CA | LEU | A | 109 | 121.941 | 46.871 | 11.117 | 1.00 | 20.75 | C |
| ATOM | 868 | CB | LEU | A | 109 | 120.740 | 46.364 | 11.965 | 1.00 | 22.01 | C |
| ATOM | 869 | CG | LEU | A | 109 | 119.437 | 46.024 | 11.201 | 1.00 | 23.61 | C |
| ATOM | 870 | CD1 | LEU | A | 109 | 118.556 | 44.988 | 11.897 | 1.00 | 25.56 | C |
| ATOM | 871 | CD2 | LEU | A | 109 | 118.659 | 47.297 | 10.951 | 1.00 | 21.63 | C |
| ATOM | 872 | C | LEU | A | 109 | 123.145 | 47.077 | 12.052 | 1.00 | 21.13 | C |
| ATOM | 873 | O | LEU | A | 109 | 124.139 | 46.248 | 12.116 | 1.00 | 19.84 | O |
| ATOM | 874 | N | TYR | A | 110 | 123.026 | 48.139 | 12.862 | 1.00 | 18.38 | N |
| ATOM | 875 | CA | TYR | A | 110 | 123.835 | 48.314 | 14.042 | 1.00 | 18.86 | C |
| ATOM | 876 | CB | TYR | A | 110 | 124.738 | 49.545 | 13.875 | 1.00 | 19.35 | C |
| ATOM | 877 | CG | TYR | A | 110 | 125.608 | 49.673 | 15.059 | 1.00 | 20.54 | C |
| ATOM | 878 | CD1 | TYR | A | 110 | 126.630 | 48.755 | 15.253 | 1.00 | 21.69 | C |
| ATOM | 879 | CE1 | TYR | A | 110 | 127.368 | 48.772 | 16.386 | 1.00 | 20.34 | C |
| ATOM | 880 | CZ | TYR | A | 110 | 127.138 | 49.755 | 17.370 | 1.00 | 27.19 | C |
| ATOM | 881 | OH | TYR | A | 110 | 127.959 | 49.778 | 18.497 | 1.00 | 27.25 | O |
| ATOM | 882 | CE2 | TYR | A | 110 | 126.072 | 50.662 | 17.228 | 1.00 | 22.47 | C |
| ATOM | 883 | CD2 | TYR | A | 110 | 125.331 | 50.614 | 16.071 | 1.00 | 25.73 | C |
| ATOM | 884 | C | TYR | A | 110 | 122.965 | 48.494 | 15.278 | 1.00 | 20.38 | C |
| ATOM | 885 | O | TYR | A | 110 | 121.993 | 49.249 | 15.278 | 1.00 | 20.57 | O |
| ATOM | 886 | N | ASP | A | 111 | 123.326 | 47.857 | 16.358 | 1.00 | 20.65 | N |
| ATOM | 887 | CA | ASP | A | 111 | 122.465 | 47.877 | 17.553 | 1.00 | 24.59 | C |
| ATOM | 888 | CB | ASP | A | 111 | 122.243 | 46.427 | 18.028 | 1.00 | 23.42 | C |
| ATOM | 889 | CG | ASP | A | 111 | 121.488 | 46.310 | 19.310 | 1.00 | 23.58 | C |
| ATOM | 890 | OD1 | ASP | A | 111 | 121.168 | 47.299 | 19.907 | 1.00 | 21.89 | O |
| ATOM | 891 | OD2 | ASP | A | 111 | 121.136 | 45.158 | 19.712 | 1.00 | 27.24 | O |
| ATOM | 892 | C | ASP | A | 111 | 123.179 | 48.671 | 18.613 | 1.00 | 24.74 | C |
| ATOM | 893 | O | ASP | A | 111 | 124.200 | 48.229 | 19.054 | 1.00 | 25.21 | O |
| ATOM | 894 | N | TYR | A | 112 | 122.633 | 49.832 | 19.006 | 1.00 | 26.40 | N |
| ATOM | 895 | CA | TYR | A | 112 | 123.326 | 50.766 | 19.956 | 1.00 | 26.77 | C |
| ATOM | 896 | CB | TYR | A | 112 | 122.802 | 52.196 | 19.880 | 1.00 | 26.44 | C |
| ATOM | 897 | CG | TYR | A | 112 | 123.312 | 52.933 | 18.711 | 1.00 | 27.42 | C |
| ATOM | 898 | CD1 | TYR | A | 112 | 122.503 | 53.117 | 17.629 | 1.00 | 30.73 | C |

FIG. 1-17

| | | | | | | | | | | | |
|---|---|---|---|---|---|---|---|---|---|---|---|
| ATOM | 899 | CE1 | TYR | A | 112 | 122.937 | 53.801 | 16.512 | 1.00 | 34.75 | C |
| ATOM | 900 | CZ | TYR | A | 112 | 124.251 | 54.322 | 16.463 | 1.00 | 29.86 | C |
| ATOM | 901 | OH | TYR | A | 112 | 124.579 | 54.954 | 15.262 | 1.00 | 29.23 | O |
| ATOM | 902 | CE2 | TYR | A | 112 | 125.107 | 54.156 | 17.518 | 1.00 | 27.39 | C |
| ATOM | 903 | CD2 | TYR | A | 112 | 124.638 | 53.490 | 18.682 | 1.00 | 31.22 | C |
| ATOM | 904 | C | TYR | A | 112 | 123.159 | 50.289 | 21.370 | 1.00 | 27.89 | C |
| ATOM | 905 | O | TYR | A | 112 | 123.926 | 50.687 | 22.261 | 1.00 | 27.99 | O |
| ATOM | 906 | N | LYS | A | 113 | 122.240 | 49.359 | 21.605 | 1.00 | 29.22 | N |
| ATOM | 907 | CA | LYS | A | 113 | 122.257 | 48.819 | 22.955 | 1.00 | 30.96 | C |
| ATOM | 908 | CB | LYS | A | 113 | 120.919 | 48.223 | 23.365 | 1.00 | 32.31 | C |
| ATOM | 909 | CG | LYS | A | 113 | 120.822 | 47.797 | 24.848 | 1.00 | 34.11 | C |
| ATOM | 910 | CD | LYS | A | 113 | 119.778 | 46.717 | 24.972 | 1.00 | 42.13 | C |
| ATOM | 911 | CE | LYS | A | 113 | 119.274 | 46.559 | 26.400 | 1.00 | 44.42 | C |
| ATOM | 912 | NZ | LYS | A | 113 | 118.071 | 45.698 | 26.322 | 1.00 | 49.89 | N |
| ATOM | 913 | C | LYS | A | 113 | 123.360 | 47.770 | 23.156 | 1.00 | 32.96 | C |
| ATOM | 914 | O | LYS | A | 113 | 124.047 | 47.810 | 24.178 | 1.00 | 33.42 | O |
| ATOM | 915 | N | GLU | A | 114 | 123.467 | 46.766 | 22.276 | 1.00 | 32.57 | N |
| ATOM | 916 | CA | GLU | A | 114 | 124.380 | 45.593 | 22.565 | 1.00 | 32.04 | C |
| ATOM | 917 | CB | GLU | A | 114 | 123.857 | 44.308 | 21.919 | 1.00 | 31.51 | C |
| ATOM | 918 | CG | GLU | A | 114 | 122.469 | 43.836 | 22.471 | 1.00 | 31.86 | C |
| ATOM | 919 | CD | GLU | A | 114 | 122.625 | 43.183 | 23.815 | 1.00 | 37.94 | C |
| ATOM | 920 | OE1 | GLU | A | 114 | 123.781 | 42.998 | 24.277 | 1.00 | 39.64 | O |
| ATOM | 921 | OE2 | GLU | A | 114 | 121.613 | 42.818 | 24.429 | 1.00 | 43.07 | O |
| ATOM | 922 | C | GLU | A | 114 | 125.756 | 45.954 | 22.026 | 1.00 | 32.14 | C |
| ATOM | 923 | O | GLU | A | 114 | 126.747 | 45.271 | 22.266 | 1.00 | 32.02 | O |
| ATOM | 924 | N | ASN | A | 115 | 125.775 | 47.077 | 21.311 | 1.00 | 31.99 | N |
| ATOM | 925 | CA | ASN | A | 115 | 126.875 | 47.553 | 20.497 | 1.00 | 31.56 | C |
| ATOM | 926 | CB | ASN | A | 115 | 127.980 | 48.185 | 21.360 | 1.00 | 31.25 | C |
| ATOM | 927 | CG | ASN | A | 115 | 127.597 | 49.552 | 21.871 | 1.00 | 34.17 | C |
| ATOM | 928 | OD1 | ASN | A | 115 | 127.374 | 49.713 | 23.065 | 1.00 | 37.89 | O |
| ATOM | 929 | ND2 | ASN | A | 115 | 127.557 | 50.553 | 20.990 | 1.00 | 32.94 | N |
| ATOM | 930 | C | ASN | A | 115 | 127.467 | 46.562 | 19.507 | 1.00 | 29.75 | C |
| ATOM | 931 | O | ASN | A | 115 | 128.653 | 46.329 | 19.520 | 1.00 | 29.27 | O |
| ATOM | 932 | N | ARG | A | 116 | 126.652 | 45.951 | 18.676 | 1.00 | 28.67 | N |
| ATOM | 933 | CA | ARG | A | 116 | 127.218 | 45.144 | 17.602 | 1.00 | 25.74 | C |
| ATOM | 934 | CB | ARG | A | 116 | 127.204 | 43.671 | 18.025 | 1.00 | 27.34 | C |
| ATOM | 935 | CG | ARG | A | 116 | 125.776 | 43.205 | 18.372 | 1.00 | 28.20 | C |
| ATOM | 936 | CD | ARG | A | 116 | 125.710 | 42.102 | 19.438 | 1.00 | 25.80 | C |
| ATOM | 937 | NE | ARG | A | 116 | 124.300 | 41.665 | 19.571 | 1.00 | 25.41 | N |
| ATOM | 938 | CZ | ARG | A | 116 | 123.820 | 40.823 | 20.499 | 1.00 | 26.84 | C |
| ATOM | 939 | NH1 | ARG | A | 116 | 124.610 | 40.265 | 21.384 | 1.00 | 27.39 | N |
| ATOM | 940 | NH2 | ARG | A | 116 | 122.533 | 40.505 | 20.531 | 1.00 | 28.58 | N |
| ATOM | 941 | C | ARG | A | 116 | 126.453 | 45.415 | 16.312 | 1.00 | 24.65 | C |
| ATOM | 942 | O | ARG | A | 116 | 125.378 | 45.966 | 16.325 | 1.00 | 22.53 | O |
| ATOM | 943 | N | PHE | A | 117 | 127.092 | 45.123 | 15.189 | 1.00 | 22.12 | N |
| ATOM | 944 | CA | PHE | A | 117 | 126.475 | 45.053 | 13.958 | 1.00 | 22.26 | C |
| ATOM | 945 | CB | PHE | A | 117 | 127.492 | 45.108 | 12.829 | 1.00 | 21.72 | C |
| ATOM | 946 | CG | PHE | A | 117 | 128.183 | 46.450 | 12.698 | 1.00 | 22.55 | C |
| ATOM | 947 | CD1 | PHE | A | 117 | 127.539 | 47.474 | 12.101 | 1.00 | 19.09 | C |
| ATOM | 948 | CE1 | PHE | A | 117 | 128.182 | 48.769 | 11.990 | 1.00 | 27.35 | C |
| ATOM | 949 | CZ | PHE | A | 117 | 129.423 | 49.008 | 12.467 | 1.00 | 22.15 | C |
| ATOM | 950 | CE2 | PHE | A | 117 | 130.137 | 47.972 | 13.055 | 1.00 | 21.26 | C |
| ATOM | 951 | CD2 | PHE | A | 117 | 129.485 | 46.651 | 13.152 | 1.00 | 19.95 | C |
| ATOM | 952 | C | PHE | A | 117 | 125.675 | 43.719 | 13.875 | 1.00 | 22.96 | C |
| ATOM | 953 | O | PHE | A | 117 | 125.989 | 42.731 | 14.541 | 1.00 | 25.10 | O |
| ATOM | 954 | N | ILE | A | 118 | 124.686 | 43.712 | 13.003 | 1.00 | 24.15 | N |
| ATOM | 955 | CA | ILE | A | 118 | 123.789 | 42.546 | 12.755 | 1.00 | 21.86 | C |
| ATOM | 956 | CB | ILE | A | 118 | 122.370 | 42.822 | 13.179 | 1.00 | 22.55 | C |
| ATOM | 957 | CG1 | ILE | A | 118 | 122.365 | 43.631 | 14.455 | 1.00 | 26.73 | C |
| ATOM | 958 | CD1 | ILE | A | 118 | 121.691 | 43.061 | 15.549 | 1.00 | 35.89 | C |
| ATOM | 959 | CG2 | ILE | A | 118 | 121.456 | 41.470 | 13.204 | 1.00 | 19.31 | C |
| ATOM | 960 | C | ILE | A | 118 | 123.741 | 42.310 | 11.267 | 1.00 | 20.89 | C |
| ATOM | 961 | O | ILE | A | 118 | 123.533 | 43.232 | 10.474 | 1.00 | 17.21 | O |

FIG. 1-18

| | | | | | | | | | | | |
|---|---|---|---|---|---|---|---|---|---|---|---|
| ATOM | 962 | N | GLU | A | 119 | 123.915 | 41.039 | 10.902 | 1.00 | 20.10 | N |
| ATOM | 963 | CA | GLU | A | 119 | 123.743 | 40.632 | 9.559 | 1.00 | 20.80 | C |
| ATOM | 964 | CB | GLU | A | 119 | 124.965 | 39.722 | 9.159 | 1.00 | 21.09 | C |
| ATOM | 965 | CG | GLU | A | 119 | 124.703 | 38.961 | 7.898 | 1.00 | 26.34 | C |
| ATOM | 966 | CD | GLU | A | 119 | 124.413 | 39.937 | 6.720 | 1.00 | 29.79 | C |
| ATOM | 967 | OE1 | GLU | A | 119 | 125.044 | 41.001 | 6.633 | 1.00 | 35.89 | O |
| ATOM | 968 | OE2 | GLU | A | 119 | 123.570 | 39.648 | 5.878 | 1.00 | 30.35 | O |
| ATOM | 969 | C | GLU | A | 119 | 122.435 | 39.871 | 9.626 | 1.00 | 21.24 | C |
| ATOM | 970 | O | GLU | A | 119 | 122.242 | 38.967 | 10.425 | 1.00 | 18.50 | O |
| ATOM | 971 | N | ILE | A | 120 | 121.492 | 40.283 | 8.801 | 1.00 | 23.72 | N |
| ATOM | 972 | CA | ILE | A | 120 | 120.180 | 39.652 | 8.763 | 1.00 | 23.23 | C |
| ATOM | 973 | CB | ILE | A | 120 | 119.058 | 40.710 | 8.511 | 1.00 | 23.83 | C |
| ATOM | 974 | CG1 | ILE | A | 120 | 118.935 | 41.682 | 9.709 | 1.00 | 23.83 | C |
| ATOM | 975 | CD1 | ILE | A | 120 | 118.508 | 40.916 | 10.991 | 1.00 | 22.81 | C |
| ATOM | 976 | CG2 | ILE | A | 120 | 117.745 | 39.983 | 8.239 | 1.00 | 20.21 | C |
| ATOM | 977 | C | ILE | A | 120 | 120.097 | 38.700 | 7.609 | 1.00 | 23.86 | C |
| ATOM | 978 | O | ILE | A | 120 | 120.582 | 38.993 | 6.526 | 1.00 | 22.92 | O |
| ATOM | 979 | N | GLY | A | 121 | 119.426 | 37.560 | 7.803 | 1.00 | 25.01 | N |
| ATOM | 980 | CA | GLY | A | 121 | 119.232 | 36.658 | 6.659 | 1.00 | 24.61 | C |
| ATOM | 981 | C | GLY | A | 121 | 117.769 | 36.223 | 6.636 | 1.00 | 23.18 | C |
| ATOM | 982 | O | GLY | A | 121 | 117.158 | 36.076 | 7.665 | 1.00 | 22.81 | O |
| ATOM | 983 | N | VAL | A | 122 | 117.223 | 36.109 | 5.445 | 1.00 | 24.10 | N |
| ATOM | 984 | CA | VAL | A | 122 | 115.869 | 35.612 | 5.177 | 1.00 | 23.11 | C |
| ATOM | 985 | CB | VAL | A | 122 | 114.904 | 36.735 | 4.643 | 1.00 | 22.67 | C |
| ATOM | 986 | CG1 | VAL | A | 122 | 113.495 | 36.113 | 4.539 | 1.00 | 22.36 | C |
| ATOM | 987 | CG2 | VAL | A | 122 | 114.848 | 37.914 | 5.619 | 1.00 | 19.79 | C |
| ATOM | 988 | C | VAL | A | 122 | 115.975 | 34.511 | 4.140 | 1.00 | 23.74 | C |
| ATOM | 989 | O | VAL | A | 122 | 116.410 | 34.746 | 3.015 | 1.00 | 24.81 | O |
| ATOM | 990 | N | THR | A | 123 | 115.576 | 33.293 | 4.514 | 1.00 | 24.85 | N |
| ATOM | 991 | CA | THR | A | 123 | 115.754 | 32.159 | 3.617 | 1.00 | 24.26 | C |
| ATOM | 992 | CB | THR | A | 123 | 116.843 | 31.104 | 4.163 | 1.00 | 25.22 | C |
| ATOM | 993 | OG1 | THR | A | 123 | 116.857 | 29.972 | 3.288 | 1.00 | 27.18 | O |
| ATOM | 994 | CG2 | THR | A | 123 | 116.491 | 30.621 | 5.538 | 1.00 | 23.74 | C |
| ATOM | 995 | C | THR | A | 123 | 114.448 | 31.426 | 3.377 | 1.00 | 23.31 | C |
| ATOM | 996 | O | THR | A | 123 | 113.616 | 31.321 | 4.267 | 1.00 | 21.78 | O |
| ATOM | 997 | N | ARG | A | 124 | 114.303 | 30.903 | 2.163 | 1.00 | 25.09 | N |
| ATOM | 998 | CA | ARG | A | 124 | 113.220 | 29.963 | 1.794 | 1.00 | 27.08 | C |
| ATOM | 999 | CB | ARG | A | 124 | 112.892 | 30.113 | 0.287 | 1.00 | 25.27 | C |
| ATOM | 1000 | CG | ARG | A | 124 | 112.201 | 31.455 | -0.079 | 1.00 | 28.12 | C |
| ATOM | 1001 | CD | ARG | A | 124 | 113.240 | 32.483 | -0.446 | 1.00 | 25.39 | C |
| ATOM | 1002 | NE | ARG | A | 124 | 113.468 | 32.338 | -1.876 | 1.00 | 29.12 | N |
| ATOM | 1003 | CZ | ARG | A | 124 | 114.397 | 32.959 | -2.571 | 1.00 | 31.04 | C |
| ATOM | 1004 | NH1 | ARG | A | 124 | 115.255 | 33.762 | -1.985 | 1.00 | 32.81 | N |
| ATOM | 1005 | NH2 | ARG | A | 124 | 114.455 | 32.774 | -3.864 | 1.00 | 29.63 | N |
| ATOM | 1006 | C | ARG | A | 124 | 113.643 | 28.482 | 2.045 | 1.00 | 29.45 | C |
| ATOM | 1007 | O | ARG | A | 124 | 112.879 | 27.552 | 1.718 | 1.00 | 30.42 | O |
| ATOM | 1008 | N | ARG | A | 125 | 114.888 | 28.255 | 2.451 | 1.00 | 30.37 | N |
| ATOM | 1009 | CA | ARG | A | 125 | 115.335 | 26.867 | 2.766 | 1.00 | 33.50 | C |
| ATOM | 1010 | CB | ARG | A | 125 | 116.751 | 26.608 | 2.296 | 1.00 | 33.86 | C |
| ATOM | 1011 | CG | ARG | A | 125 | 117.004 | 26.792 | 0.812 | 1.00 | 38.17 | C |
| ATOM | 1012 | CD | ARG | A | 125 | 118.397 | 27.434 | 0.639 | 1.00 | 38.05 | C |
| ATOM | 1013 | NE | ARG | A | 125 | 119.447 | 26.467 | 1.022 | 1.00 | 43.50 | N |
| ATOM | 1014 | CZ | ARG | A | 125 | 120.717 | 26.763 | 1.272 | 1.00 | 44.97 | C |
| ATOM | 1015 | NH1 | ARG | A | 125 | 121.145 | 28.022 | 1.221 | 1.00 | 45.26 | N |
| ATOM | 1016 | NH2 | ARG | A | 125 | 121.564 | 25.796 | 1.614 | 1.00 | 47.76 | N |
| ATOM | 1017 | C | ARG | A | 125 | 115.280 | 26.654 | 4.273 | 1.00 | 32.67 | C |
| ATOM | 1018 | O | ARG | A | 125 | 114.366 | 27.065 | 4.950 | 1.00 | 36.32 | O |
| ATOM | 1019 | N | GLU | A | 126 | 116.260 | 26.030 | 4.840 | 1.00 | 33.04 | N |
| ATOM | 1020 | CA | GLU | A | 126 | 116.131 | 25.695 | 6.247 | 1.00 | 31.85 | C |
| ATOM | 1021 | CB | GLU | A | 126 | 116.552 | 24.241 | 6.397 | 1.00 | 33.19 | C |
| ATOM | 1022 | CG | GLU | A | 126 | 116.246 | 23.646 | 7.743 | 1.00 | 36.91 | C |
| ATOM | 1023 | CD | GLU | A | 126 | 117.399 | 23.846 | 8.698 | 1.00 | 42.26 | C |
| ATOM | 1024 | OE1 | GLU | A | 126 | 117.112 | 24.348 | 9.850 | 1.00 | 42.79 | O |

FIG. 1-19

| | | | | | | | | | | | |
|---|---|---|---|---|---|---|---|---|---|---|---|
| ATOM | 1025 | OE2 | GLU | A | 126 | 118.570 | 23.493 | 8.309 | 1.00 | 37.69 | O |
| ATOM | 1026 | C | GLU | A | 126 | 116.982 | 26.678 | 7.037 | 1.00 | 30.31 | C |
| ATOM | 1027 | O | GLU | A | 126 | 118.039 | 27.091 | 6.585 | 1.00 | 30.05 | O |
| ATOM | 1028 | N | VAL | A | 127 | 116.535 | 27.044 | 8.221 | 1.00 | 29.36 | N |
| ATOM | 1029 | CA | VAL | A | 127 | 117.161 | 28.084 | 8.983 | 1.00 | 29.64 | C |
| ATOM | 1030 | CB | VAL | A | 127 | 116.200 | 28.526 | 10.146 | 1.00 | 31.07 | C |
| ATOM | 1031 | CG1 | VAL | A | 127 | 116.721 | 28.187 | 11.511 | 1.00 | 30.66 | C |
| ATOM | 1032 | CG2 | VAL | A | 127 | 115.922 | 29.997 | 10.064 | 1.00 | 31.21 | C |
| ATOM | 1033 | C | VAL | A | 127 | 118.629 | 27.726 | 9.380 | 1.00 | 29.43 | C |
| ATOM | 1034 | O | VAL | A | 127 | 119.588 | 28.550 | 9.175 | 1.00 | 27.52 | O |
| ATOM | 1035 | N | HIS | A | 128 | 118.820 | 26.487 | 9.881 | 1.00 | 27.13 | N |
| ATOM | 1036 | CA | HIS | A | 128 | 120.123 | 26.064 | 10.345 | 1.00 | 28.16 | C |
| ATOM | 1037 | CB | HIS | A | 128 | 120.010 | 24.701 | 11.160 | 1.00 | 28.60 | C |
| ATOM | 1038 | CG | HIS | A | 128 | 121.196 | 24.418 | 12.014 | 1.00 | 29.94 | C |
| ATOM | 1039 | ND1 | HIS | A | 128 | 121.352 | 23.250 | 12.720 | 1.00 | 29.01 | N |
| ATOM | 1040 | CE1 | HIS | A | 128 | 122.490 | 23.294 | 13.383 | 1.00 | 30.53 | C |
| ATOM | 1041 | NE2 | HIS | A | 128 | 123.126 | 24.397 | 13.048 | 1.00 | 30.25 | N |
| ATOM | 1042 | CD2 | HIS | A | 128 | 122.351 | 25.109 | 12.178 | 1.00 | 32.97 | C |
| ATOM | 1043 | C | HIS | A | 128 | 121.228 | 26.123 | 9.271 | 1.00 | 27.06 | C |
| ATOM | 1044 | O | HIS | A | 128 | 122.275 | 26.768 | 9.459 | 1.00 | 27.42 | O |
| ATOM | 1045 | N | ILE | A | 129 | 120.983 | 25.497 | 8.144 | 1.00 | 27.67 | N |
| ATOM | 1046 | CA | ILE | A | 129 | 121.965 | 25.389 | 7.084 | 1.00 | 29.76 | C |
| ATOM | 1047 | CB | ILE | A | 129 | 121.637 | 24.267 | 6.007 | 1.00 | 32.02 | C |
| ATOM | 1048 | CG1 | ILE | A | 129 | 122.898 | 23.958 | 5.225 | 1.00 | 31.34 | C |
| ATOM | 1049 | CD1 | ILE | A | 129 | 122.711 | 22.950 | 4.122 | 1.00 | 43.21 | C |
| ATOM | 1050 | CG2 | ILE | A | 129 | 120.493 | 24.647 | 5.091 | 1.00 | 32.48 | C |
| ATOM | 1051 | C | ILE | A | 129 | 122.298 | 26.739 | 6.458 | 1.00 | 28.92 | C |
| ATOM | 1052 | O | ILE | A | 129 | 123.477 | 27.029 | 6.174 | 1.00 | 26.57 | O |
| ATOM | 1053 | N | TYR | A | 130 | 121.289 | 27.595 | 6.383 | 1.00 | 26.94 | N |
| ATOM | 1054 | CA | TYR | A | 130 | 121.513 | 28.921 | 5.944 | 1.00 | 27.00 | C |
| ATOM | 1055 | CB | TYR | A | 130 | 120.146 | 29.665 | 5.719 | 1.00 | 25.76 | C |
| ATOM | 1056 | CG | TYR | A | 130 | 120.335 | 30.993 | 5.027 | 1.00 | 28.67 | C |
| ATOM | 1057 | CD1 | TYR | A | 130 | 120.631 | 31.052 | 3.684 | 1.00 | 29.98 | C |
| ATOM | 1058 | CE1 | TYR | A | 130 | 120.841 | 32.281 | 3.053 | 1.00 | 35.41 | C |
| ATOM | 1059 | CZ | TYR | A | 130 | 120.726 | 33.473 | 3.752 | 1.00 | 28.23 | C |
| ATOM | 1060 | OH | TYR | A | 130 | 120.908 | 34.640 | 3.064 | 1.00 | 34.08 | O |
| ATOM | 1061 | CE2 | TYR | A | 130 | 120.464 | 33.445 | 5.095 | 1.00 | 29.64 | C |
| ATOM | 1062 | CD2 | TYR | A | 130 | 120.256 | 32.197 | 5.729 | 1.00 | 29.56 | C |
| ATOM | 1063 | C | TYR | A | 130 | 122.417 | 29.647 | 6.924 | 1.00 | 25.09 | C |
| ATOM | 1064 | O | TYR | A | 130 | 123.366 | 30.256 | 6.504 | 1.00 | 25.63 | O |
| ATOM | 1065 | N | TYR | A | 131 | 122.148 | 29.514 | 8.217 | 1.00 | 23.85 | N |
| ATOM | 1066 | CA | TYR | A | 131 | 122.915 | 30.114 | 9.217 | 1.00 | 23.89 | C |
| ATOM | 1067 | CB | TYR | A | 131 | 122.348 | 29.743 | 10.620 | 1.00 | 24.32 | C |
| ATOM | 1068 | CG | TYR | A | 131 | 123.233 | 30.277 | 11.701 | 1.00 | 27.01 | C |
| ATOM | 1069 | CD1 | TYR | A | 131 | 123.019 | 31.548 | 12.222 | 1.00 | 30.13 | C |
| ATOM | 1070 | CE1 | TYR | A | 131 | 123.857 | 32.084 | 13.168 | 1.00 | 30.19 | C |
| ATOM | 1071 | CZ | TYR | A | 131 | 124.958 | 31.387 | 13.583 | 1.00 | 37.38 | C |
| ATOM | 1072 | OH | TYR | A | 131 | 125.783 | 31.979 | 14.511 | 1.00 | 42.12 | O |
| ATOM | 1073 | CE2 | TYR | A | 131 | 125.244 | 30.121 | 13.066 | 1.00 | 36.83 | C |
| ATOM | 1074 | CD2 | TYR | A | 131 | 124.360 | 29.559 | 12.141 | 1.00 | 34.49 | C |
| ATOM | 1075 | C | TYR | A | 131 | 124.433 | 29.754 | 9.052 | 1.00 | 26.44 | C |
| ATOM | 1076 | O | TYR | A | 131 | 125.349 | 30.661 | 9.187 | 1.00 | 24.68 | O |
| ATOM | 1077 | N | LEU | A | 132 | 124.689 | 28.462 | 8.769 | 1.00 | 25.67 | N |
| ATOM | 1078 | CA | LEU | A | 132 | 126.054 | 27.902 | 8.775 | 1.00 | 27.57 | C |
| ATOM | 1079 | CB | LEU | A | 132 | 126.081 | 26.337 | 8.684 | 1.00 | 26.28 | C |
| ATOM | 1080 | CG | LEU | A | 132 | 125.458 | 25.542 | 9.824 | 1.00 | 23.94 | C |
| ATOM | 1081 | CD1 | LEU | A | 132 | 125.611 | 23.951 | 9.620 | 1.00 | 26.89 | C |
| ATOM | 1082 | CD2 | LEU | A | 132 | 126.083 | 25.979 | 11.185 | 1.00 | 23.18 | C |
| ATOM | 1083 | C | LEU | A | 132 | 126.737 | 28.483 | 7.586 | 1.00 | 28.21 | C |
| ATOM | 1084 | O | LEU | A | 132 | 127.853 | 29.013 | 7.725 | 1.00 | 28.68 | O |
| ATOM | 1085 | N | GLU | A | 133 | 126.040 | 28.488 | 6.450 | 1.00 | 29.62 | N |
| ATOM | 1086 | CA | GLU | A | 133 | 126.633 | 29.063 | 5.258 | 1.00 | 32.24 | C |
| ATOM | 1087 | CB | GLU | A | 133 | 125.763 | 28.842 | 4.087 | 1.00 | 31.82 | C |

FIG. 1-20

| | | | | | | | | | | | |
|---|---|---|---|---|---|---|---|---|---|---|---|
| ATOM | 1088 | CG | GLU | A | 133 | 125.769 | 27.365 | 3.691 | 1.00 | 37.61 | C |
| ATOM | 1089 | CD | GLU | A | 133 | 124.755 | 27.093 | 2.605 | 1.00 | 43.83 | C |
| ATOM | 1090 | OE1 | GLU | A | 133 | 124.067 | 28.032 | 2.161 | 1.00 | 48.18 | O |
| ATOM | 1091 | OE2 | GLU | A | 133 | 124.630 | 25.929 | 2.186 | 1.00 | 51.10 | O |
| ATOM | 1092 | C | GLU | A | 133 | 126.946 | 30.562 | 5.418 | 1.00 | 33.05 | C |
| ATOM | 1093 | O | GLU | A | 133 | 127.993 | 31.019 | 4.947 | 1.00 | 32.39 | O |
| ATOM | 1094 | N | LYS | A | 134 | 126.101 | 31.295 | 6.162 | 1.00 | 34.52 | N |
| ATOM | 1095 | CA | LYS | A | 134 | 126.379 | 32.722 | 6.436 | 1.00 | 36.37 | C |
| ATOM | 1096 | CB | LYS | A | 134 | 125.146 | 33.484 | 6.952 | 1.00 | 35.60 | C |
| ATOM | 1097 | CG | LYS | A | 134 | 124.347 | 34.204 | 5.875 | 1.00 | 40.77 | C |
| ATOM | 1098 | CD | LYS | A | 134 | 124.789 | 35.662 | 5.801 | 1.00 | 43.36 | C |
| ATOM | 1099 | CE | LYS | A | 134 | 123.626 | 36.588 | 5.423 | 1.00 | 42.20 | C |
| ATOM | 1100 | NZ | LYS | A | 134 | 123.671 | 37.059 | 3.981 | 1.00 | 36.67 | N |
| ATOM | 1101 | C | LYS | A | 134 | 127.544 | 32.916 | 7.384 | 1.00 | 36.06 | C |
| ATOM | 1102 | O | LYS | A | 134 | 128.350 | 33.835 | 7.170 | 1.00 | 36.67 | O |
| ATOM | 1103 | N | ALA | A | 135 | 127.605 | 32.108 | 8.444 | 1.00 | 37.11 | N |
| ATOM | 1104 | CA | ALA | A | 135 | 128.692 | 32.198 | 9.444 | 1.00 | 38.75 | C |
| ATOM | 1105 | CB | ALA | A | 135 | 128.355 | 31.440 | 10.690 | 1.00 | 37.18 | C |
| ATOM | 1106 | C | ALA | A | 135 | 130.071 | 31.789 | 8.888 | 1.00 | 40.80 | C |
| ATOM | 1107 | O | ALA | A | 135 | 131.118 | 32.394 | 9.238 | 1.00 | 40.99 | O |
| ATOM | 1108 | N | ASN | A | 136 | 130.082 | 30.792 | 8.015 | 1.00 | 41.49 | N |
| ATOM | 1109 | CA | ASN | A | 136 | 131.282 | 30.511 | 7.203 | 1.00 | 44.23 | C |
| ATOM | 1110 | CB | ASN | A | 136 | 130.978 | 29.413 | 6.190 | 1.00 | 43.80 | C |
| ATOM | 1111 | CG | ASN | A | 136 | 132.208 | 28.676 | 5.747 | 1.00 | 45.24 | C |
| ATOM | 1112 | OD1 | ASN | A | 136 | 132.593 | 28.745 | 4.586 | 1.00 | 50.31 | O |
| ATOM | 1113 | ND2 | ASN | A | 136 | 132.836 | 27.969 | 6.661 | 1.00 | 45.35 | N |
| ATOM | 1114 | C | ASN | A | 136 | 131.772 | 31.732 | 6.423 | 1.00 | 45.73 | C |
| ATOM | 1115 | O | ASN | A | 136 | 132.936 | 32.097 | 6.496 | 1.00 | 46.33 | O |
| ATOM | 1116 | N | LYS | A | 137 | 130.851 | 32.360 | 5.692 | 1.00 | 47.91 | N |
| ATOM | 1117 | CA | LYS | A | 137 | 131.163 | 33.359 | 4.682 | 1.00 | 50.18 | C |
| ATOM | 1118 | CB | LYS | A | 137 | 129.972 | 33.541 | 3.743 | 1.00 | 50.21 | C |
| ATOM | 1119 | CG | LYS | A | 137 | 130.224 | 34.510 | 2.650 | 1.00 | 52.51 | C |
| ATOM | 1120 | CD | LYS | A | 137 | 128.981 | 35.312 | 2.356 | 1.00 | 56.82 | C |
| ATOM | 1121 | CE | LYS | A | 137 | 129.306 | 36.494 | 1.421 | 1.00 | 57.58 | C |
| ATOM | 1122 | NZ | LYS | A | 137 | 128.066 | 37.179 | 0.927 | 1.00 | 58.58 | N |
| ATOM | 1123 | C | LYS | A | 137 | 131.576 | 34.685 | 5.309 | 1.00 | 51.35 | C |
| ATOM | 1124 | O | LYS | A | 137 | 132.452 | 35.375 | 4.790 | 1.00 | 50.74 | O |
| ATOM | 1125 | N | ILE | A | 138 | 130.943 | 35.037 | 6.427 | 1.00 | 53.13 | N |
| ATOM | 1126 | CA | ILE | A | 138 | 131.298 | 36.251 | 7.154 | 1.00 | 54.46 | C |
| ATOM | 1127 | CB | ILE | A | 138 | 130.359 | 36.547 | 8.370 | 1.00 | 53.81 | C |
| ATOM | 1128 | CG1 | ILE | A | 138 | 129.005 | 37.052 | 7.925 | 1.00 | 52.73 | C |
| ATOM | 1129 | CD1 | ILE | A | 138 | 128.232 | 37.686 | 9.077 | 1.00 | 50.31 | C |
| ATOM | 1130 | CG2 | ILE | A | 138 | 130.945 | 37.615 | 9.255 | 1.00 | 55.84 | C |
| ATOM | 1131 | C | ILE | A | 138 | 132.680 | 35.968 | 7.664 | 1.00 | 55.71 | C |
| ATOM | 1132 | O | ILE | A | 138 | 133.659 | 36.551 | 7.163 | 1.00 | 56.60 | O |
| ATOM | 1133 | N | LYS | A | 139 | 132.748 | 35.063 | 8.646 | 1.00 | 56.77 | N |
| ATOM | 1134 | CA | LYS | A | 139 | 133.969 | 34.720 | 9.358 | 1.00 | 57.96 | C |
| ATOM | 1135 | CB | LYS | A | 139 | 135.003 | 34.034 | 8.452 | 1.00 | 58.98 | C |
| ATOM | 1136 | CG | LYS | A | 139 | 135.190 | 32.534 | 8.752 | 1.00 | 59.51 | C |
| ATOM | 1137 | CD | LYS | A | 139 | 136.671 | 32.152 | 8.904 | 1.00 | 59.96 | C |
| ATOM | 1138 | CE | LYS | A | 139 | 136.873 | 30.618 | 8.745 | 1.00 | 59.03 | C |
| ATOM | 1139 | NZ | LYS | A | 139 | 138.018 | 30.068 | 9.494 | 1.00 | 58.17 | N |
| ATOM | 1140 | C | LYS | A | 139 | 134.590 | 35.885 | 10.132 | 1.00 | 58.82 | C |
| ATOM | 1141 | O | LYS | A | 139 | 135.804 | 35.895 | 10.379 | 1.00 | 58.81 | O |
| ATOM | 1142 | N | SER | A | 140 | 133.747 | 36.858 | 10.516 | 1.00 | 58.84 | N |
| ATOM | 1143 | CA | SER | A | 140 | 134.048 | 37.754 | 11.654 | 1.00 | 58.34 | C |
| ATOM | 1144 | CB | SER | A | 140 | 134.033 | 39.253 | 11.295 | 1.00 | 58.21 | C |
| ATOM | 1145 | OG | SER | A | 140 | 133.098 | 39.582 | 10.279 | 1.00 | 57.99 | O |
| ATOM | 1146 | C | SER | A | 140 | 133.161 | 37.454 | 12.878 | 1.00 | 57.93 | C |
| ATOM | 1147 | O | SER | A | 140 | 131.926 | 37.491 | 12.797 | 1.00 | 58.35 | O |
| ATOM | 1148 | N | GLU | A | 141 | 133.820 | 37.121 | 13.991 | 1.00 | 57.36 | N |
| ATOM | 1149 | CA | GLU | A | 141 | 133.186 | 36.838 | 15.301 | 1.00 | 56.53 | C |
| ATOM | 1150 | CB | GLU | A | 141 | 134.214 | 36.164 | 16.278 | 1.00 | 56.69 | C |

FIG. 1-21

| | | | | | | | | | | | |
|---|---|---|---|---|---|---|---|---|---|---|---|
| ATOM | 1151 | CG | GLU | A | 141 | 133.666 | 35.616 | 17.664 | 1.00 | 57.49 | C |
| ATOM | 1152 | CD | GLU | A | 141 | 133.195 | 34.108 | 17.687 | 1.00 | 57.93 | C |
| ATOM | 1153 | OE1 | GLU | A | 141 | 132.589 | 33.608 | 16.703 | 1.00 | 56.39 | O |
| ATOM | 1154 | OE2 | GLU | A | 141 | 133.406 | 33.435 | 18.732 | 1.00 | 56.13 | O |
| ATOM | 1155 | C | GLU | A | 141 | 132.594 | 38.166 | 15.846 | 1.00 | 55.02 | C |
| ATOM | 1156 | O | GLU | A | 141 | 131.938 | 38.210 | 16.907 | 1.00 | 55.80 | O |
| ATOM | 1157 | N | ASN | A | 142 | 132.823 | 39.234 | 15.089 | 1.00 | 51.90 | N |
| ATOM | 1158 | CA | ASN | A | 142 | 132.262 | 40.534 | 15.388 | 1.00 | 50.18 | C |
| ATOM | 1159 | CB | ASN | A | 142 | 132.830 | 41.557 | 14.397 | 1.00 | 51.86 | C |
| ATOM | 1160 | CG | ASN | A | 142 | 134.368 | 41.496 | 14.299 | 1.00 | 58.45 | C |
| ATOM | 1161 | OD1 | ASN | A | 142 | 135.054 | 41.091 | 15.263 | 1.00 | 64.09 | O |
| ATOM | 1162 | ND2 | ASN | A | 142 | 134.916 | 41.892 | 13.133 | 1.00 | 62.16 | N |
| ATOM | 1163 | C | ASN | A | 142 | 130.746 | 40.552 | 15.262 | 1.00 | 45.54 | C |
| ATOM | 1164 | O | ASN | A | 142 | 130.008 | 40.846 | 16.204 | 1.00 | 44.71 | O |
| ATOM | 1165 | N | THR | A | 143 | 130.333 | 40.242 | 14.057 | 1.00 | 40.26 | N |
| ATOM | 1166 | CA | THR | A | 143 | 129.026 | 40.551 | 13.569 | 1.00 | 37.76 | C |
| ATOM | 1167 | CB | THR | A | 143 | 129.107 | 40.626 | 12.037 | 1.00 | 37.80 | C |
| ATOM | 1168 | OG1 | THR | A | 143 | 130.010 | 41.669 | 11.695 | 1.00 | 41.40 | O |
| ATOM | 1169 | CG2 | THR | A | 143 | 127.772 | 40.969 | 11.397 | 1.00 | 38.66 | C |
| ATOM | 1170 | C | THR | A | 143 | 128.064 | 39.445 | 13.980 | 1.00 | 34.31 | C |
| ATOM | 1171 | O | THR | A | 143 | 128.274 | 38.308 | 13.565 | 1.00 | 31.88 | O |
| ATOM | 1172 | N | HIS | A | 144 | 127.001 | 39.808 | 14.725 | 1.00 | 31.19 | N |
| ATOM | 1173 | CA | HIS | A | 144 | 125.919 | 38.897 | 15.139 | 1.00 | 28.43 | C |
| ATOM | 1174 | CB | HIS | A | 144 | 125.062 | 39.636 | 16.150 | 1.00 | 29.67 | C |
| ATOM | 1175 | CG | HIS | A | 144 | 124.470 | 38.772 | 17.203 | 1.00 | 27.10 | C |
| ATOM | 1176 | ND1 | HIS | A | 144 | 125.215 | 38.173 | 18.194 | 1.00 | 27.40 | N |
| ATOM | 1177 | CE1 | HIS | A | 144 | 124.434 | 37.442 | 18.957 | 1.00 | 25.64 | C |
| ATOM | 1178 | NE2 | HIS | A | 144 | 123.203 | 37.552 | 18.497 | 1.00 | 29.95 | N |
| ATOM | 1179 | CD2 | HIS | A | 144 | 123.192 | 38.433 | 17.442 | 1.00 | 28.08 | C |
| ATOM | 1180 | C | HIS | A | 144 | 125.077 | 38.498 | 13.918 | 1.00 | 27.35 | C |
| ATOM | 1181 | O | HIS | A | 144 | 124.945 | 39.259 | 12.970 | 1.00 | 26.80 | O |
| ATOM | 1182 | N | ILE | A | 145 | 124.501 | 37.298 | 13.903 | 1.00 | 26.07 | N |
| ATOM | 1183 | CA | ILE | A | 145 | 123.781 | 36.900 | 12.707 | 1.00 | 24.79 | C |
| ATOM | 1184 | CB | ILE | A | 145 | 124.475 | 35.688 | 11.994 | 1.00 | 25.87 | C |
| ATOM | 1185 | CG1 | ILE | A | 145 | 125.841 | 36.096 | 11.450 | 1.00 | 24.90 | C |
| ATOM | 1186 | CD1 | ILE | A | 145 | 126.765 | 34.892 | 11.080 | 1.00 | 27.25 | C |
| ATOM | 1187 | CG2 | ILE | A | 145 | 123.588 | 35.132 | 10.892 | 1.00 | 22.14 | C |
| ATOM | 1188 | C | ILE | A | 145 | 122.389 | 36.514 | 13.162 | 1.00 | 22.86 | C |
| ATOM | 1189 | O | ILE | A | 145 | 122.240 | 35.954 | 14.192 | 1.00 | 20.58 | O |
| ATOM | 1190 | N | HIS | A | 146 | 121.371 | 36.947 | 12.453 | 1.00 | 22.20 | N |
| ATOM | 1191 | CA | HIS | A | 146 | 120.014 | 36.580 | 12.820 | 1.00 | 22.79 | C |
| ATOM | 1192 | CB | HIS | A | 146 | 119.324 | 37.715 | 13.590 | 1.00 | 22.24 | C |
| ATOM | 1193 | CG | HIS | A | 146 | 118.098 | 37.311 | 14.323 | 1.00 | 20.41 | C |
| ATOM | 1194 | ND1 | HIS | A | 146 | 117.700 | 37.911 | 15.504 | 1.00 | 21.91 | N |
| ATOM | 1195 | CE1 | HIS | A | 146 | 116.567 | 37.362 | 15.908 | 1.00 | 18.49 | C |
| ATOM | 1196 | NE2 | HIS | A | 146 | 116.244 | 36.403 | 15.054 | 1.00 | 21.16 | N |
| ATOM | 1197 | CD2 | HIS | A | 146 | 117.152 | 36.383 | 14.028 | 1.00 | 19.39 | C |
| ATOM | 1198 | C | HIS | A | 146 | 119.288 | 36.240 | 11.555 | 1.00 | 22.31 | C |
| ATOM | 1199 | O | HIS | A | 146 | 119.186 | 37.079 | 10.613 | 1.00 | 20.78 | O |
| ATOM | 1200 | N | ILE | A | 147 | 118.811 | 34.998 | 11.522 | 1.00 | 22.70 | N |
| ATOM | 1201 | CA | ILE | A | 147 | 118.213 | 34.362 | 10.313 | 1.00 | 21.45 | C |
| ATOM | 1202 | CB | ILE | A | 147 | 118.817 | 33.003 | 9.982 | 1.00 | 22.08 | C |
| ATOM | 1203 | CG1 | ILE | A | 147 | 120.356 | 33.072 | 9.878 | 1.00 | 25.84 | C |
| ATOM | 1204 | CD1 | ILE | A | 147 | 120.868 | 34.126 | 8.883 | 1.00 | 22.00 | C |
| ATOM | 1205 | CG2 | ILE | A | 147 | 118.274 | 32.466 | 8.631 | 1.00 | 22.00 | C |
| ATOM | 1206 | C | ILE | A | 147 | 116.739 | 34.130 | 10.508 | 1.00 | 21.15 | C |
| ATOM | 1207 | O | ILE | A | 147 | 116.317 | 33.706 | 11.542 | 1.00 | 21.00 | O |
| ATOM | 1208 | N | PHE | A | 148 | 115.925 | 34.446 | 9.510 | 1.00 | 20.82 | N |
| ATOM | 1209 | CA | PHE | A | 148 | 114.485 | 34.142 | 9.641 | 1.00 | 20.72 | C |
| ATOM | 1210 | CB | PHE | A | 148 | 113.612 | 35.452 | 9.555 | 1.00 | 19.83 | C |
| ATOM | 1211 | CG | PHE | A | 148 | 113.771 | 36.320 | 10.733 | 1.00 | 21.73 | C |
| ATOM | 1212 | CD1 | PHE | A | 148 | 113.122 | 36.025 | 11.903 | 1.00 | 20.89 | C |
| ATOM | 1213 | CE1 | PHE | A | 148 | 113.223 | 36.844 | 13.044 | 1.00 | 23.63 | C |

FIG. 1-22

| | | | | | | | | | | | |
|---|---|---|---|---|---|---|---|---|---|---|---|
| ATOM | 1214 | CZ | PHE | A | 148 | 114.105 | 37.934 | 13.023 | 1.00 | 22.51 | C |
| ATOM | 1215 | CE2 | PHE | A | 148 | 114.818 | 38.209 | 11.823 | 1.00 | 18.18 | C |
| ATOM | 1216 | CD2 | PHE | A | 148 | 114.629 | 37.415 | 10.688 | 1.00 | 20.44 | C |
| ATOM | 1217 | C | PHE | A | 148 | 114.085 | 33.290 | 8.533 | 1.00 | 20.52 | C |
| ATOM | 1218 | O | PHE | A | 148 | 114.632 | 33.433 | 7.470 | 1.00 | 21.54 | O |
| ATOM | 1219 | N | SER | A | 149 | 113.049 | 32.454 | 8.725 | 1.00 | 24.56 | N |
| ATOM | 1220 | CA | SER | A | 149 | 112.560 | 31.700 | 7.605 | 1.00 | 26.69 | C |
| ATOM | 1221 | CB | SER | A | 149 | 112.827 | 30.194 | 7.820 | 1.00 | 24.67 | C |
| ATOM | 1222 | OG | SER | A | 149 | 111.719 | 29.628 | 8.427 | 1.00 | 27.98 | O |
| ATOM | 1223 | C | SER | A | 149 | 111.052 | 32.032 | 7.379 | 1.00 | 27.64 | C |
| ATOM | 1224 | O | SER | A | 149 | 110.435 | 32.628 | 8.256 | 1.00 | 29.66 | O |
| ATOM | 1225 | N | PHE | A | 150 | 110.502 | 31.661 | 6.224 | 1.00 | 29.30 | N |
| ATOM | 1226 | CA | PHE | A | 150 | 109.056 | 31.796 | 5.863 | 1.00 | 31.71 | C |
| ATOM | 1227 | CB | PHE | A | 150 | 108.920 | 31.651 | 4.336 | 1.00 | 32.58 | C |
| ATOM | 1228 | CG | PHE | A | 150 | 109.451 | 32.832 | 3.576 | 1.00 | 29.17 | C |
| ATOM | 1229 | CD1 | PHE | A | 150 | 108.601 | 33.893 | 3.258 | 1.00 | 21.99 | C |
| ATOM | 1230 | CE1 | PHE | A | 150 | 109.069 | 34.990 | 2.562 | 1.00 | 26.89 | C |
| ATOM | 1231 | CZ | PHE | A | 150 | 110.440 | 35.024 | 2.191 | 1.00 | 23.00 | C |
| ATOM | 1232 | CE2 | PHE | A | 150 | 111.250 | 33.977 | 2.462 | 1.00 | 24.93 | C |
| ATOM | 1233 | CD2 | PHE | A | 150 | 110.761 | 32.865 | 3.158 | 1.00 | 28.36 | C |
| ATOM | 1234 | C | PHE | A | 150 | 108.102 | 30.774 | 6.487 | 1.00 | 33.92 | C |
| ATOM | 1235 | O | PHE | A | 150 | 106.884 | 30.819 | 6.299 | 1.00 | 33.98 | O |
| ATOM | 1236 | N | THR | A | 151 | 108.669 | 29.835 | 7.222 | 1.00 | 35.95 | N |
| ATOM | 1237 | CA | THR | A | 151 | 107.916 | 28.803 | 7.911 | 1.00 | 36.83 | C |
| ATOM | 1238 | CB | THR | A | 151 | 108.551 | 27.462 | 7.578 | 1.00 | 37.62 | C |
| ATOM | 1239 | OG1 | THR | A | 151 | 108.019 | 26.533 | 8.506 | 1.00 | 45.95 | O |
| ATOM | 1240 | CG2 | THR | A | 151 | 110.062 | 27.511 | 7.753 | 1.00 | 35.76 | C |
| ATOM | 1241 | C | THR | A | 151 | 107.844 | 29.067 | 9.444 | 1.00 | 36.33 | C |
| ATOM | 1242 | O | THR | A | 151 | 107.544 | 28.184 | 10.264 | 1.00 | 35.35 | O |
| ATOM | 1243 | N | GLY | A | 152 | 108.168 | 30.304 | 9.834 | 1.00 | 36.00 | N |
| ATOM | 1244 | CA | GLY | A | 152 | 108.131 | 30.669 | 11.247 | 1.00 | 33.94 | C |
| ATOM | 1245 | C | GLY | A | 152 | 109.344 | 30.408 | 12.101 | 1.00 | 32.46 | C |
| ATOM | 1246 | O | GLY | A | 152 | 109.262 | 30.382 | 13.352 | 1.00 | 32.26 | O |
| ATOM | 1247 | N | GLU | A | 153 | 110.489 | 30.183 | 11.487 | 1.00 | 30.42 | N |
| ATOM | 1248 | CA | GLU | A | 153 | 111.610 | 29.822 | 12.359 | 1.00 | 30.30 | C |
| ATOM | 1249 | CB | GLU | A | 153 | 112.237 | 28.530 | 11.878 | 1.00 | 30.48 | C |
| ATOM | 1250 | CG | GLU | A | 153 | 111.125 | 27.502 | 11.689 | 1.00 | 38.02 | C |
| ATOM | 1251 | CD | GLU | A | 153 | 111.659 | 26.100 | 11.590 | 1.00 | 44.11 | C |
| ATOM | 1252 | OE1 | GLU | A | 153 | 112.880 | 25.930 | 11.336 | 1.00 | 48.04 | O |
| ATOM | 1253 | OE2 | GLU | A | 153 | 110.849 | 25.166 | 11.813 | 1.00 | 51.52 | O |
| ATOM | 1254 | C | GLU | A | 153 | 112.638 | 30.916 | 12.344 | 1.00 | 27.40 | C |
| ATOM | 1255 | O | GLU | A | 153 | 112.682 | 31.707 | 11.385 | 1.00 | 25.25 | O |
| ATOM | 1256 | N | GLU | A | 154 | 113.482 | 30.926 | 13.384 | 1.00 | 27.06 | N |
| ATOM | 1257 | CA | GLU | A | 154 | 114.687 | 31.835 | 13.399 | 1.00 | 26.77 | C |
| ATOM | 1258 | CB | GLU | A | 154 | 114.439 | 33.092 | 14.206 | 1.00 | 25.11 | C |
| ATOM | 1259 | CG | GLU | A | 154 | 113.856 | 32.751 | 15.637 | 1.00 | 27.82 | C |
| ATOM | 1260 | CD | GLU | A | 154 | 113.414 | 33.966 | 16.435 | 1.00 | 32.69 | C |
| ATOM | 1261 | OE1 | GLU | A | 154 | 113.886 | 35.109 | 16.175 | 1.00 | 33.69 | O |
| ATOM | 1262 | OE2 | GLU | A | 154 | 112.630 | 33.784 | 17.372 | 1.00 | 36.65 | O |
| ATOM | 1263 | C | GLU | A | 154 | 115.871 | 31.096 | 13.981 | 1.00 | 25.56 | C |
| ATOM | 1264 | O | GLU | A | 154 | 115.698 | 30.175 | 14.779 | 1.00 | 24.36 | O |
| ATOM | 1265 | N | MET | A | 155 | 117.073 | 31.517 | 13.591 | 1.00 | 23.57 | N |
| ATOM | 1266 | CA | MET | A | 155 | 118.275 | 31.107 | 14.316 | 1.00 | 23.80 | C |
| ATOM | 1267 | CB | MET | A | 155 | 119.017 | 30.054 | 13.568 | 1.00 | 21.29 | C |
| ATOM | 1268 | CG | MET | A | 155 | 120.178 | 29.493 | 14.390 | 1.00 | 29.12 | C |
| ATOM | 1269 | SD | MET | A | 155 | 120.809 | 27.962 | 13.614 | 1.00 | 35.15 | S |
| ATOM | 1270 | CE | MET | A | 155 | 119.387 | 26.985 | 14.088 | 1.00 | 36.95 | C |
| ATOM | 1271 | C | MET | A | 155 | 119.240 | 32.283 | 14.463 | 1.00 | 23.67 | C |
| ATOM | 1272 | O | MET | A | 155 | 119.507 | 32.977 | 13.466 | 1.00 | 22.85 | O |
| ATOM | 1273 | N | ALA | A | 156 | 119.788 | 32.461 | 15.651 | 1.00 | 21.76 | N |
| ATOM | 1274 | CA | ALA | A | 156 | 120.684 | 33.626 | 15.895 | 1.00 | 25.54 | C |
| ATOM | 1275 | CB | ALA | A | 156 | 119.924 | 34.733 | 16.666 | 1.00 | 24.12 | C |
| ATOM | 1276 | C | ALA | A | 156 | 121.901 | 33.240 | 16.657 | 1.00 | 25.34 | C |

FIG. 1-23

| | | | | | | | | | | | |
|---|---|---|---|---|---|---|---|---|---|---|---|
| ATOM | 1277 | O | ALA | A | 156 | 121.836 | 32.399 | 17.563 | 1.00 | 28.10 | O |
| ATOM | 1278 | N | THR | A | 157 | 123.010 | 33.882 | 16.335 | 1.00 | 26.62 | N |
| ATOM | 1279 | CA | THR | A | 157 | 124.237 | 33.748 | 17.093 | 1.00 | 25.56 | C |
| ATOM | 1280 | CB | THR | A | 157 | 125.146 | 34.995 | 16.863 | 1.00 | 26.58 | C |
| ATOM | 1281 | OG1 | THR | A | 157 | 125.352 | 35.125 | 15.482 | 1.00 | 23.30 | O |
| ATOM | 1282 | CG2 | THR | A | 157 | 126.478 | 34.814 | 17.590 | 1.00 | 25.53 | C |
| ATOM | 1283 | C | THR | A | 157 | 124.091 | 33.556 | 18.581 | 1.00 | 27.17 | C |
| ATOM | 1284 | O | THR | A | 157 | 123.459 | 34.338 | 19.285 | 1.00 | 26.05 | O |
| ATOM | 1285 | N | LYS | A | 158 | 124.743 | 32.500 | 19.068 | 1.00 | 29.56 | N |
| ATOM | 1286 | CA | LYS | A | 158 | 124.823 | 32.154 | 20.498 | 1.00 | 30.33 | C |
| ATOM | 1287 | CB | LYS | A | 158 | 125.674 | 33.157 | 21.305 | 1.00 | 30.65 | C |
| ATOM | 1288 | CG | LYS | A | 158 | 127.097 | 33.113 | 21.036 | 1.00 | 35.27 | C |
| ATOM | 1289 | CD | LYS | A | 158 | 127.744 | 32.251 | 22.154 | 1.00 | 44.59 | C |
| ATOM | 1290 | CE | LYS | A | 158 | 129.262 | 32.191 | 22.003 | 1.00 | 45.76 | C |
| ATOM | 1291 | NZ | LYS | A | 158 | 129.668 | 31.511 | 20.776 | 1.00 | 49.48 | N |
| ATOM | 1292 | C | LYS | A | 158 | 123.497 | 32.018 | 21.144 | 1.00 | 30.12 | C |
| ATOM | 1293 | O | LYS | A | 158 | 123.440 | 32.030 | 22.369 | 1.00 | 30.20 | O |
| ATOM | 1294 | N | ALA | A | 159 | 122.461 | 31.768 | 20.339 | 1.00 | 30.87 | N |
| ATOM | 1295 | CA | ALA | A | 159 | 121.068 | 31.752 | 20.835 | 1.00 | 31.80 | C |
| ATOM | 1296 | CB | ALA | A | 159 | 120.807 | 30.529 | 21.784 | 1.00 | 30.34 | C |
| ATOM | 1297 | C | ALA | A | 159 | 120.681 | 33.100 | 21.526 | 1.00 | 30.61 | C |
| ATOM | 1298 | O | ALA | A | 159 | 119.897 | 33.152 | 22.461 | 1.00 | 31.33 | O |
| ATOM | 1299 | N | ASP | A | 160 | 121.237 | 34.191 | 21.050 | 1.00 | 31.03 | N |
| ATOM | 1300 | CA | ASP | A | 160 | 120.860 | 35.488 | 21.584 | 1.00 | 28.96 | C |
| ATOM | 1301 | CB | ASP | A | 160 | 122.167 | 36.184 | 22.013 | 1.00 | 30.00 | C |
| ATOM | 1302 | CG | ASP | A | 160 | 121.986 | 37.598 | 22.394 | 1.00 | 30.68 | C |
| ATOM | 1303 | OD1 | ASP | A | 160 | 120.823 | 38.120 | 22.280 | 1.00 | 34.16 | O |
| ATOM | 1304 | OD2 | ASP | A | 160 | 123.012 | 38.196 | 22.784 | 1.00 | 29.55 | O |
| ATOM | 1305 | C | ASP | A | 160 | 120.009 | 36.152 | 20.461 | 1.00 | 28.49 | C |
| ATOM | 1306 | O | ASP | A | 160 | 120.462 | 36.486 | 19.347 | 1.00 | 29.35 | O |
| ATOM | 1307 | N | TYR | A | 161 | 118.725 | 36.218 | 20.757 | 1.00 | 29.18 | N |
| ATOM | 1308 | CA | TYR | A | 161 | 117.719 | 36.613 | 19.837 | 1.00 | 28.85 | C |
| ATOM | 1309 | CB | TYR | A | 161 | 116.422 | 35.696 | 19.949 | 1.00 | 29.41 | C |
| ATOM | 1310 | CG | TYR | A | 161 | 116.766 | 34.353 | 19.404 | 1.00 | 30.32 | C |
| ATOM | 1311 | CD1 | TYR | A | 161 | 116.680 | 34.086 | 18.045 | 1.00 | 32.04 | C |
| ATOM | 1312 | CE1 | TYR | A | 161 | 117.078 | 32.826 | 17.505 | 1.00 | 33.00 | C |
| ATOM | 1313 | CZ | TYR | A | 161 | 117.657 | 31.836 | 18.367 | 1.00 | 37.47 | C |
| ATOM | 1314 | OH | TYR | A | 161 | 118.174 | 30.617 | 17.871 | 1.00 | 35.26 | O |
| ATOM | 1315 | CE2 | TYR | A | 161 | 117.781 | 32.115 | 19.726 | 1.00 | 37.19 | C |
| ATOM | 1316 | CD2 | TYR | A | 161 | 117.354 | 33.369 | 20.239 | 1.00 | 35.58 | C |
| ATOM | 1317 | C | TYR | A | 161 | 117.517 | 38.162 | 19.756 | 1.00 | 28.13 | C |
| ATOM | 1318 | O | TYR | A | 161 | 116.714 | 38.643 | 18.946 | 1.00 | 27.44 | O |
| ATOM | 1319 | N | THR | A | 162 | 118.291 | 38.914 | 20.561 | 1.00 | 27.88 | N |
| ATOM | 1320 | CA | THR | A | 162 | 118.344 | 40.387 | 20.519 | 1.00 | 27.05 | C |
| ATOM | 1321 | CB | THR | A | 162 | 118.830 | 40.940 | 19.129 | 1.00 | 25.80 | C |
| ATOM | 1322 | OG1 | THR | A | 162 | 120.196 | 40.513 | 18.949 | 1.00 | 26.05 | O |
| ATOM | 1323 | CG2 | THR | A | 162 | 118.809 | 42.529 | 19.044 | 1.00 | 22.66 | C |
| ATOM | 1324 | C | THR | A | 162 | 117.031 | 40.999 | 20.943 | 1.00 | 28.86 | C |
| ATOM | 1325 | O | THR | A | 162 | 117.013 | 41.670 | 21.937 | 1.00 | 29.35 | O |
| ATOM | 1326 | N | LEU | A | 163 | 115.939 | 40.702 | 20.221 | 1.00 | 29.90 | N |
| ATOM | 1327 | CA | LEU | A | 163 | 114.665 | 41.426 | 20.384 | 1.00 | 30.80 | C |
| ATOM | 1328 | CB | LEU | A | 163 | 113.992 | 41.496 | 19.049 | 1.00 | 29.73 | C |
| ATOM | 1329 | CG | LEU | A | 163 | 114.635 | 42.351 | 17.947 | 1.00 | 29.60 | C |
| ATOM | 1330 | CD1 | LEU | A | 163 | 113.788 | 42.182 | 16.648 | 1.00 | 24.71 | C |
| ATOM | 1331 | CD2 | LEU | A | 163 | 114.736 | 43.834 | 18.370 | 1.00 | 24.30 | C |
| ATOM | 1332 | C | LEU | A | 163 | 113.745 | 40.735 | 21.355 | 1.00 | 32.39 | C |
| ATOM | 1333 | O | LEU | A | 163 | 114.014 | 39.588 | 21.701 | 1.00 | 33.64 | O |
| ATOM | 1334 | N | ASP | A | 164 | 112.655 | 41.372 | 21.789 | 1.00 | 33.97 | N |
| ATOM | 1335 | CA | ASP | A | 164 | 111.723 | 40.634 | 22.689 | 1.00 | 35.55 | C |
| ATOM | 1336 | CB | ASP | A | 164 | 110.623 | 41.549 | 23.225 | 1.00 | 37.24 | C |
| ATOM | 1337 | CG | ASP | A | 164 | 110.066 | 42.424 | 22.132 | 1.00 | 37.16 | C |
| ATOM | 1338 | OD1 | ASP | A | 164 | 110.872 | 43.169 | 21.565 | 1.00 | 35.69 | O |
| ATOM | 1339 | OD2 | ASP | A | 164 | 108.862 | 42.341 | 21.811 | 1.00 | 42.57 | O |

FIG. 1-24

| | | | | | | | | | | | |
|---|---|---|---|---|---|---|---|---|---|---|---|
| ATOM | 1340 | C | ASP | A | 164 | 111.057 | 39.628 | 21.797 | 1.00 | 35.46 | C |
| ATOM | 1341 | O | ASP | A | 164 | 111.129 | 39.739 | 20.550 | 1.00 | 33.31 | O |
| ATOM | 1342 | N | GLU | A | 165 | 110.353 | 38.685 | 22.412 | 1.00 | 35.82 | N |
| ATOM | 1343 | CA | GLU | A | 165 | 109.581 | 37.697 | 21.661 | 1.00 | 36.75 | C |
| ATOM | 1344 | CB | GLU | A | 165 | 108.911 | 36.782 | 22.671 | 1.00 | 38.41 | C |
| ATOM | 1345 | CG | GLU | A | 165 | 109.814 | 35.841 | 23.310 | 1.00 | 45.07 | C |
| ATOM | 1346 | CD | GLU | A | 165 | 109.125 | 34.490 | 23.450 | 1.00 | 52.54 | C |
| ATOM | 1347 | OE1 | GLU | A | 165 | 109.135 | 33.762 | 22.414 | 1.00 | 49.98 | O |
| ATOM | 1348 | OE2 | GLU | A | 165 | 108.578 | 34.195 | 24.565 | 1.00 | 48.11 | O |
| ATOM | 1349 | C | GLU | A | 165 | 108.455 | 38.274 | 20.768 | 1.00 | 36.08 | C |
| ATOM | 1350 | O | GLU | A | 165 | 108.118 | 37.715 | 19.701 | 1.00 | 35.12 | O |
| ATOM | 1351 | N | GLU | A | 166 | 107.838 | 39.360 | 21.228 | 1.00 | 35.44 | N |
| ATOM | 1352 | CA | GLU | A | 166 | 106.673 | 39.888 | 20.535 | 1.00 | 35.56 | C |
| ATOM | 1353 | CB | GLU | A | 166 | 105.890 | 40.878 | 21.461 | 1.00 | 37.07 | C |
| ATOM | 1354 | CG | GLU | A | 166 | 104.381 | 40.608 | 21.543 | 1.00 | 40.70 | C |
| ATOM | 1355 | CD | GLU | A | 166 | 103.566 | 41.902 | 21.668 | 1.00 | 50.09 | C |
| ATOM | 1356 | OE1 | GLU | A | 166 | 102.959 | 42.361 | 20.658 | 1.00 | 53.45 | O |
| ATOM | 1357 | OE2 | GLU | A | 166 | 103.543 | 42.482 | 22.782 | 1.00 | 53.92 | O |
| ATOM | 1358 | C | GLU | A | 166 | 107.097 | 40.512 | 19.186 | 1.00 | 33.77 | C |
| ATOM | 1359 | O | GLU | A | 166 | 106.529 | 40.193 | 18.146 | 1.00 | 33.36 | O |
| ATOM | 1360 | N | SER | A | 167 | 108.124 | 41.380 | 19.194 | 1.00 | 32.33 | N |
| ATOM | 1361 | CA | SER | A | 167 | 108.760 | 41.843 | 17.954 | 1.00 | 29.96 | C |
| ATOM | 1362 | CB | SER | A | 167 | 109.984 | 42.656 | 18.349 | 1.00 | 30.89 | C |
| ATOM | 1363 | OG | SER | A | 167 | 109.643 | 43.712 | 19.240 | 1.00 | 29.23 | O |
| ATOM | 1364 | C | SER | A | 167 | 109.198 | 40.756 | 16.927 | 1.00 | 27.93 | C |
| ATOM | 1365 | O | SER | A | 167 | 108.985 | 40.860 | 15.781 | 1.00 | 29.09 | O |
| ATOM | 1366 | N | ARG | A | 168 | 109.866 | 39.728 | 17.374 | 1.00 | 28.03 | N |
| ATOM | 1367 | CA | ARG | A | 168 | 110.277 | 38.638 | 16.572 | 1.00 | 26.71 | C |
| ATOM | 1368 | CB | ARG | A | 168 | 111.057 | 37.736 | 17.489 | 1.00 | 27.66 | C |
| ATOM | 1369 | CG | ARG | A | 168 | 112.520 | 38.077 | 17.586 | 1.00 | 30.76 | C |
| ATOM | 1370 | CD | ARG | A | 168 | 113.230 | 36.889 | 18.088 | 1.00 | 31.97 | C |
| ATOM | 1371 | NE | ARG | A | 168 | 113.062 | 36.916 | 19.479 | 1.00 | 35.28 | N |
| ATOM | 1372 | CZ | ARG | A | 168 | 113.127 | 35.894 | 20.326 | 1.00 | 37.96 | C |
| ATOM | 1373 | NH1 | ARG | A | 168 | 113.318 | 34.662 | 19.930 | 1.00 | 36.85 | N |
| ATOM | 1374 | NH2 | ARG | A | 168 | 112.992 | 36.172 | 21.626 | 1.00 | 34.61 | N |
| ATOM | 1375 | C | ARG | A | 168 | 109.086 | 37.833 | 16.017 | 1.00 | 25.51 | C |
| ATOM | 1376 | O | ARG | A | 168 | 109.130 | 37.375 | 14.851 | 1.00 | 23.96 | O |
| ATOM | 1377 | N | ALA | A | 169 | 108.046 | 37.640 | 16.847 | 1.00 | 25.04 | N |
| ATOM | 1378 | CA | ALA | A | 169 | 106.794 | 36.943 | 16.382 | 1.00 | 26.61 | C |
| ATOM | 1379 | CB | ALA | A | 169 | 105.772 | 36.680 | 17.583 | 1.00 | 26.61 | C |
| ATOM | 1380 | C | ALA | A | 169 | 106.136 | 37.715 | 15.276 | 1.00 | 27.19 | C |
| ATOM | 1381 | O | ALA | A | 169 | 105.585 | 37.110 | 14.369 | 1.00 | 28.22 | O |
| ATOM | 1382 | N | ARG | A | 170 | 106.184 | 39.066 | 15.345 | 1.00 | 26.67 | N |
| ATOM | 1383 | CA | ARG | A | 170 | 105.587 | 39.967 | 14.346 | 1.00 | 26.51 | C |
| ATOM | 1384 | CB | ARG | A | 170 | 105.845 | 41.413 | 14.818 | 1.00 | 27.54 | C |
| ATOM | 1385 | CG | ARG | A | 170 | 104.818 | 42.492 | 14.422 | 1.00 | 31.56 | C |
| ATOM | 1386 | CD | ARG | A | 170 | 105.348 | 43.878 | 14.934 | 1.00 | 37.15 | C |
| ATOM | 1387 | NE | ARG | A | 170 | 105.402 | 44.889 | 13.855 | 1.00 | 45.81 | N |
| ATOM | 1388 | CZ | ARG | A | 170 | 106.505 | 45.478 | 13.347 | 1.00 | 48.22 | C |
| ATOM | 1389 | NH1 | ARG | A | 170 | 107.711 | 45.195 | 13.818 | 1.00 | 43.46 | N |
| ATOM | 1390 | NH2 | ARG | A | 170 | 106.386 | 46.405 | 12.366 | 1.00 | 48.54 | N |
| ATOM | 1391 | C | ARG | A | 170 | 106.295 | 39.794 | 12.979 | 1.00 | 25.43 | C |
| ATOM | 1392 | O | ARG | A | 170 | 105.658 | 39.670 | 11.938 | 1.00 | 26.10 | O |
| ATOM | 1393 | N | ILE | A | 171 | 107.628 | 39.687 | 13.008 | 1.00 | 22.73 | N |
| ATOM | 1394 | CA | ILE | A | 171 | 108.357 | 39.356 | 11.786 | 1.00 | 22.29 | C |
| ATOM | 1395 | CB | ILE | A | 171 | 109.877 | 39.514 | 11.963 | 1.00 | 20.69 | C |
| ATOM | 1396 | CG1 | ILE | A | 171 | 110.223 | 40.994 | 12.215 | 1.00 | 20.55 | C |
| ATOM | 1397 | CD1 | ILE | A | 171 | 111.587 | 41.116 | 12.878 | 1.00 | 24.73 | C |
| ATOM | 1398 | CG2 | ILE | A | 171 | 110.649 | 39.013 | 10.625 | 1.00 | 17.15 | C |
| ATOM | 1399 | C | ILE | A | 171 | 108.092 | 37.925 | 11.224 | 1.00 | 24.02 | C |
| ATOM | 1400 | O | ILE | A | 171 | 107.930 | 37.775 | 10.032 | 1.00 | 22.47 | O |
| ATOM | 1401 | N | LYS | A | 172 | 108.210 | 36.894 | 12.073 | 1.00 | 26.04 | N |
| ATOM | 1402 | CA | LYS | A | 172 | 107.944 | 35.495 | 11.671 | 1.00 | 27.04 | C |

FIG. 1-25

| | | | | | | | | | | | |
|---|---|---|---|---|---|---|---|---|---|---|---|
| ATOM | 1403 | CB | LYS | A | 172 | 108.159 | 34.558 | 12.842 | 1.00 | 26.24 | C |
| ATOM | 1404 | CG | LYS | A | 172 | 109.602 | 34.325 | 13.140 | 1.00 | 30.50 | C |
| ATOM | 1405 | CD | LYS | A | 172 | 109.812 | 33.378 | 14.336 | 1.00 | 34.18 | C |
| ATOM | 1406 | CE | LYS | A | 172 | 109.383 | 33.989 | 15.642 | 1.00 | 34.48 | C |
| ATOM | 1407 | NZ | LYS | A | 172 | 110.181 | 33.278 | 16.690 | 1.00 | 34.27 | N |
| ATOM | 1408 | C | LYS | A | 172 | 106.510 | 35.365 | 11.131 | 1.00 | 27.01 | C |
| ATOM | 1409 | O | LYS | A | 172 | 106.262 | 34.685 | 10.141 | 1.00 | 28.03 | O |
| ATOM | 1410 | N | THR | A | 173 | 105.565 | 36.060 | 11.743 | 1.00 | 29.93 | N |
| ATOM | 1411 | CA | THR | A | 173 | 104.151 | 36.102 | 11.217 | 1.00 | 30.29 | C |
| ATOM | 1412 | CB | THR | A | 173 | 103.260 | 36.717 | 12.246 | 1.00 | 31.89 | C |
| ATOM | 1413 | OG1 | THR | A | 173 | 103.316 | 35.832 | 13.368 | 1.00 | 33.85 | O |
| ATOM | 1414 | CG2 | THR | A | 173 | 101.752 | 36.862 | 11.757 | 1.00 | 31.43 | C |
| ATOM | 1415 | C | THR | A | 173 | 104.004 | 36.764 | 9.840 | 1.00 | 30.75 | C |
| ATOM | 1416 | O | THR | A | 173 | 103.257 | 36.293 | 8.986 | 1.00 | 30.39 | O |
| ATOM | 1417 | N | ARG | A | 174 | 104.784 | 37.817 | 9.583 | 1.00 | 30.40 | N |
| ATOM | 1418 | CA | ARG | A | 174 | 104.700 | 38.466 | 8.324 | 1.00 | 28.17 | C |
| ATOM | 1419 | CB | ARG | A | 174 | 105.447 | 39.811 | 8.340 | 1.00 | 29.56 | C |
| ATOM | 1420 | CG | ARG | A | 174 | 105.689 | 40.402 | 6.958 | 1.00 | 30.31 | C |
| ATOM | 1421 | CD | ARG | A | 174 | 104.403 | 41.001 | 6.402 | 1.00 | 37.43 | C |
| ATOM | 1422 | NE | ARG | A | 174 | 104.725 | 41.826 | 5.245 | 1.00 | 35.70 | N |
| ATOM | 1423 | CZ | ARG | A | 174 | 103.943 | 42.058 | 4.186 | 1.00 | 41.01 | C |
| ATOM | 1424 | NH1 | ARG | A | 174 | 102.730 | 41.533 | 4.072 | 1.00 | 40.42 | N |
| ATOM | 1425 | NH2 | ARG | A | 174 | 104.392 | 42.854 | 3.219 | 1.00 | 39.63 | N |
| ATOM | 1426 | C | ARG | A | 174 | 105.223 | 37.586 | 7.221 | 1.00 | 26.53 | C |
| ATOM | 1427 | O | ARG | A | 174 | 104.617 | 37.512 | 6.216 | 1.00 | 25.92 | O |
| ATOM | 1428 | N | LEU | A | 175 | 106.377 | 36.942 | 7.408 | 1.00 | 26.25 | N |
| ATOM | 1429 | CA | LEU | A | 175 | 106.986 | 36.062 | 6.409 | 1.00 | 24.97 | C |
| ATOM | 1430 | CB | LEU | A | 175 | 108.353 | 35.565 | 6.936 | 1.00 | 23.61 | C |
| ATOM | 1431 | CG | LEU | A | 175 | 109.369 | 36.726 | 7.147 | 1.00 | 24.02 | C |
| ATOM | 1432 | CD1 | LEU | A | 175 | 110.717 | 36.198 | 7.619 | 1.00 | 21.67 | C |
| ATOM | 1433 | CD2 | LEU | A | 175 | 109.528 | 37.491 | 5.821 | 1.00 | 16.97 | C |
| ATOM | 1434 | C | LEU | A | 175 | 106.039 | 34.849 | 6.077 | 1.00 | 25.23 | C |
| ATOM | 1435 | O | LEU | A | 175 | 105.838 | 34.478 | 4.885 | 1.00 | 22.05 | O |
| ATOM | 1436 | N | PHE | A | 176 | 105.467 | 34.329 | 7.125 | 1.00 | 25.41 | N |
| ATOM | 1437 | CA | PHE | A | 176 | 104.505 | 33.154 | 7.078 | 1.00 | 28.69 | C |
| ATOM | 1438 | CB | PHE | A | 176 | 104.077 | 32.744 | 8.510 | 1.00 | 28.11 | C |
| ATOM | 1439 | CG | PHE | A | 176 | 103.256 | 31.438 | 8.550 | 1.00 | 32.78 | C |
| ATOM | 1440 | CD1 | PHE | A | 176 | 103.901 | 30.210 | 8.560 | 1.00 | 34.00 | C |
| ATOM | 1441 | CE1 | PHE | A | 176 | 103.144 | 28.991 | 8.607 | 1.00 | 38.40 | C |
| ATOM | 1442 | CZ | PHE | A | 176 | 101.757 | 29.043 | 8.620 | 1.00 | 35.28 | C |
| ATOM | 1443 | CE2 | PHE | A | 176 | 101.095 | 30.272 | 8.627 | 1.00 | 36.37 | C |
| ATOM | 1444 | CD2 | PHE | A | 176 | 101.857 | 31.471 | 8.598 | 1.00 | 31.25 | C |
| ATOM | 1445 | C | PHE | A | 176 | 103.309 | 33.559 | 6.232 | 1.00 | 27.87 | C |
| ATOM | 1446 | O | PHE | A | 176 | 102.995 | 32.929 | 5.255 | 1.00 | 29.43 | O |
| ATOM | 1447 | N | THR | A | 177 | 102.720 | 34.703 | 6.523 | 1.00 | 30.69 | N |
| ATOM | 1448 | CA | THR | A | 177 | 101.618 | 35.269 | 5.710 | 1.00 | 30.39 | C |
| ATOM | 1449 | CB | THR | A | 177 | 101.209 | 36.530 | 6.331 | 1.00 | 31.43 | C |
| ATOM | 1450 | OG1 | THR | A | 177 | 101.167 | 36.272 | 7.727 | 1.00 | 38.77 | O |
| ATOM | 1451 | CG2 | THR | A | 177 | 99.780 | 37.023 | 5.913 | 1.00 | 31.72 | C |
| ATOM | 1452 | C | THR | A | 177 | 102.021 | 35.506 | 4.257 | 1.00 | 30.26 | C |
| ATOM | 1453 | O | THR | A | 177 | 101.218 | 35.221 | 3.347 | 1.00 | 31.11 | O |
| ATOM | 1454 | N | ILE | A | 178 | 103.254 | 35.951 | 3.992 | 1.00 | 27.30 | N |
| ATOM | 1455 | CA | ILE | A | 178 | 103.698 | 36.128 | 2.561 | 1.00 | 25.45 | C |
| ATOM | 1456 | CB | ILE | A | 178 | 105.101 | 36.843 | 2.401 | 1.00 | 23.58 | C |
| ATOM | 1457 | CG1 | ILE | A | 178 | 105.036 | 38.269 | 2.985 | 1.00 | 25.77 | C |
| ATOM | 1458 | CD1 | ILE | A | 178 | 106.506 | 38.868 | 3.316 | 1.00 | 23.14 | C |
| ATOM | 1459 | CG2 | ILE | A | 178 | 105.652 | 36.759 | 0.910 | 1.00 | 19.72 | C |
| ATOM | 1460 | C | ILE | A | 178 | 103.831 | 34.824 | 1.794 | 1.00 | 26.04 | C |
| ATOM | 1461 | O | ILE | A | 178 | 103.546 | 34.773 | 0.598 | 1.00 | 26.19 | O |
| ATOM | 1462 | N | ARG | A | 179 | 104.374 | 33.800 | 2.436 | 1.00 | 25.98 | N |
| ATOM | 1463 | CA | ARG | A | 179 | 104.498 | 32.508 | 1.824 | 1.00 | 27.03 | C |
| ATOM | 1464 | CB | ARG | A | 179 | 105.217 | 31.554 | 2.765 | 1.00 | 26.80 | C |
| ATOM | 1465 | CG | ARG | A | 179 | 105.288 | 30.121 | 2.260 | 1.00 | 27.93 | C |

FIG. 1-26

| | | | | | | | | | | | |
|---|---|---|---|---|---|---|---|---|---|---|---|
| ATOM | 1466 | CD | ARG | A | 179 | 105.910 | 29.169 | 3.249 | 1.00 | 32.90 | C |
| ATOM | 1467 | NE | ARG | A | 179 | 105.117 | 29.142 | 4.463 | 1.00 | 44.55 | N |
| ATOM | 1468 | CZ | ARG | A | 179 | 104.068 | 28.335 | 4.659 | 1.00 | 45.92 | C |
| ATOM | 1469 | NH1 | ARG | A | 179 | 103.690 | 27.477 | 3.711 | 1.00 | 43.01 | N |
| ATOM | 1470 | NH2 | ARG | A | 179 | 103.392 | 28.411 | 5.794 | 1.00 | 44.90 | N |
| ATOM | 1471 | C | ARG | A | 179 | 103.091 | 31.921 | 1.556 | 1.00 | 29.37 | C |
| ATOM | 1472 | O | ARG | A | 179 | 102.828 | 31.432 | 0.429 | 1.00 | 28.76 | O |
| ATOM | 1473 | N | GLN | A | 180 | 102.213 | 31.937 | 2.576 | 1.00 | 29.72 | N |
| ATOM | 1474 | CA | GLN | A | 180 | 100.786 | 31.496 | 2.340 | 1.00 | 33.09 | C |
| ATOM | 1475 | CB | GLN | A | 180 | 99.884 | 31.807 | 3.496 | 1.00 | 31.60 | C |
| ATOM | 1476 | CG | GLN | A | 180 | 99.988 | 30.864 | 4.596 | 1.00 | 38.26 | C |
| ATOM | 1477 | CD | GLN | A | 180 | 99.076 | 31.268 | 5.703 | 1.00 | 44.59 | C |
| ATOM | 1478 | OE1 | GLN | A | 180 | 99.076 | 32.430 | 6.120 | 1.00 | 45.64 | O |
| ATOM | 1479 | NE2 | GLN | A | 180 | 98.244 | 30.333 | 6.164 | 1.00 | 45.94 | N |
| ATOM | 1480 | C | GLN | A | 180 | 100.189 | 32.226 | 1.136 | 1.00 | 33.43 | C |
| ATOM | 1481 | O | GLN | A | 180 | 99.525 | 31.619 | 0.324 | 1.00 | 35.33 | O |
| ATOM | 1482 | N | GLU | A | 181 | 100.398 | 33.542 | 1.038 | 1.00 | 33.86 | N |
| ATOM | 1483 | CA | GLU | A | 181 | 99.844 | 34.326 | -0.061 | 1.00 | 32.37 | C |
| ATOM | 1484 | CB | GLU | A | 181 | 100.030 | 35.836 | 0.174 | 1.00 | 34.20 | C |
| ATOM | 1485 | CG | GLU | A | 181 | 99.071 | 36.445 | 1.211 | 1.00 | 39.61 | C |
| ATOM | 1486 | CD | GLU | A | 181 | 97.556 | 36.514 | 0.781 | 1.00 | 47.38 | C |
| ATOM | 1487 | OE1 | GLU | A | 181 | 97.189 | 36.466 | -0.439 | 1.00 | 49.01 | O |
| ATOM | 1488 | OE2 | GLU | A | 181 | 96.703 | 36.659 | 1.706 | 1.00 | 52.25 | O |
| ATOM | 1489 | C | GLU | A | 181 | 100.425 | 33.870 | -1.386 | 1.00 | 31.75 | C |
| ATOM | 1490 | O | GLU | A | 181 | 99.660 | 33.574 | -2.336 | 1.00 | 30.87 | O |
| ATOM | 1491 | N | MET | A | 182 | 101.754 | 33.723 | -1.448 | 1.00 | 29.72 | N |
| ATOM | 1492 | CA | MET | A | 182 | 102.383 | 33.124 | -2.637 | 1.00 | 28.02 | C |
| ATOM | 1493 | CB | MET | A | 182 | 103.892 | 32.991 | -2.427 | 1.00 | 27.79 | C |
| ATOM | 1494 | CG | MET | A | 182 | 104.633 | 34.344 | -2.260 | 1.00 | 29.70 | C |
| ATOM | 1495 | SD | MET | A | 182 | 106.417 | 34.208 | -2.460 | 1.00 | 29.37 | S |
| ATOM | 1496 | CE | MET | A | 182 | 106.663 | 33.894 | -4.197 | 1.00 | 36.51 | C |
| ATOM | 1497 | C | MET | A | 182 | 101.819 | 31.722 | -2.981 | 1.00 | 26.97 | C |
| ATOM | 1498 | O | MET | A | 182 | 101.676 | 31.353 | -4.157 | 1.00 | 24.81 | O |
| ATOM | 1499 | N | ALA | A | 183 | 101.626 | 30.914 | -1.967 | 1.00 | 26.40 | N |
| ATOM | 1500 | CA | ALA | A | 183 | 101.298 | 29.487 | -2.171 | 1.00 | 28.90 | C |
| ATOM | 1501 | CB | ALA | A | 183 | 101.454 | 28.606 | -0.815 | 1.00 | 27.54 | C |
| ATOM | 1502 | C | ALA | A | 183 | 99.868 | 29.428 | -2.749 | 1.00 | 30.70 | C |
| ATOM | 1503 | O | ALA | A | 183 | 99.632 | 28.742 | -3.748 | 1.00 | 33.28 | O |
| ATOM | 1504 | N | SER | A | 184 | 98.967 | 30.212 | -2.178 | 1.00 | 31.25 | N |
| ATOM | 1505 | CA | SER | A | 184 | 97.610 | 30.432 | -2.739 | 1.00 | 31.98 | C |
| ATOM | 1506 | CB | SER | A | 184 | 96.876 | 31.462 | -1.907 | 1.00 | 31.89 | C |
| ATOM | 1507 | OG | SER | A | 184 | 96.797 | 30.826 | -0.617 | 1.00 | 35.96 | O |
| ATOM | 1508 | C | SER | A | 184 | 97.563 | 30.745 | -4.221 | 1.00 | 31.47 | C |
| ATOM | 1509 | O | SER | A | 184 | 96.784 | 30.128 | -4.988 | 1.00 | 29.22 | O |
| ATOM | 1510 | N | ARG | A | 185 | 98.491 | 31.588 | -4.658 | 1.00 | 31.19 | N |
| ATOM | 1511 | CA | ARG | A | 185 | 98.608 | 31.897 | -6.085 | 1.00 | 31.27 | C |
| ATOM | 1512 | CB | ARG | A | 185 | 99.111 | 33.334 | -6.291 | 1.00 | 32.55 | C |
| ATOM | 1513 | CG | ARG | A | 185 | 98.169 | 34.391 | -5.760 | 1.00 | 29.13 | C |
| ATOM | 1514 | CD | ARG | A | 185 | 98.996 | 35.668 | -5.456 | 1.00 | 27.62 | C |
| ATOM | 1515 | NE | ARG | A | 185 | 98.198 | 36.845 | -5.103 | 1.00 | 24.61 | N |
| ATOM | 1516 | CZ | ARG | A | 185 | 97.702 | 37.075 | -3.886 | 1.00 | 29.07 | C |
| ATOM | 1517 | NH1 | ARG | A | 185 | 97.901 | 36.222 | -2.922 | 1.00 | 24.68 | N |
| ATOM | 1518 | NH2 | ARG | A | 185 | 97.002 | 38.179 | -3.619 | 1.00 | 32.34 | N |
| ATOM | 1519 | C | ARG | A | 185 | 99.554 | 30.935 | -6.764 | 1.00 | 31.46 | C |
| ATOM | 1520 | O | ARG | A | 185 | 99.934 | 31.156 | -7.904 | 1.00 | 33.55 | O |
| ATOM | 1521 | N | SER | A | 186 | 99.936 | 29.850 | -6.100 | 1.00 | 31.68 | N |
| ATOM | 1522 | CA | SER | A | 186 | 100.956 | 28.920 | -6.680 | 1.00 | 32.13 | C |
| ATOM | 1523 | CB | SER | A | 186 | 100.287 | 27.806 | -7.480 | 1.00 | 32.50 | C |
| ATOM | 1524 | OG | SER | A | 186 | 100.162 | 28.137 | -8.820 | 1.00 | 38.14 | O |
| ATOM | 1525 | C | SER | A | 186 | 102.269 | 29.583 | -7.301 | 1.00 | 32.44 | C |
| ATOM | 1526 | O | SER | A | 186 | 102.794 | 29.286 | -8.441 | 1.00 | 30.76 | O |
| ATOM | 1527 | N | LEU | A | 187 | 102.813 | 30.479 | -6.485 | 1.00 | 31.52 | N |
| ATOM | 1528 | CA | LEU | A | 187 | 103.988 | 31.198 | -6.814 | 1.00 | 32.49 | C |

FIG. 1-27

| | | | | | | | | | | | |
|---|---|---|---|---|---|---|---|---|---|---|---|
| ATOM | 1529 | CB | LEU | A | 187 | 103.760 | 32.704 | -6.634 | 1.00 | 31.67 | C |
| ATOM | 1530 | CG | LEU | A | 187 | 102.934 | 33.440 | -7.724 | 1.00 | 34.94 | C |
| ATOM | 1531 | CD1 | LEU | A | 187 | 102.652 | 34.952 | -7.322 | 1.00 | 34.90 | C |
| ATOM | 1532 | CD2 | LEU | A | 187 | 103.593 | 33.337 | -9.078 | 1.00 | 34.12 | C |
| ATOM | 1533 | C | LEU | A | 187 | 105.110 | 30.753 | -5.930 | 1.00 | 32.67 | C |
| ATOM | 1534 | O | LEU | A | 187 | 106.272 | 31.115 | -6.181 | 1.00 | 32.59 | O |
| ATOM | 1535 | N | TRP | A | 188 | 104.770 | 29.948 | -4.926 | 1.00 | 31.57 | N |
| ATOM | 1536 | CA | TRP | A | 188 | 105.672 | 29.686 | -3.860 | 1.00 | 33.33 | C |
| ATOM | 1537 | CB | TRP | A | 188 | 104.935 | 29.227 | -2.575 | 1.00 | 32.39 | C |
| ATOM | 1538 | CG | TRP | A | 188 | 105.893 | 28.718 | -1.582 | 1.00 | 33.07 | C |
| ATOM | 1539 | CD1 | TRP | A | 188 | 106.086 | 27.410 | -1.226 | 1.00 | 35.84 | C |
| ATOM | 1540 | NE1 | TRP | A | 188 | 107.081 | 27.299 | -0.286 | 1.00 | 31.40 | N |
| ATOM | 1541 | CE2 | TRP | A | 188 | 107.583 | 28.545 | -0.011 | 1.00 | 32.33 | C |
| ATOM | 1542 | CD2 | TRP | A | 188 | 106.849 | 29.482 | -0.820 | 1.00 | 32.66 | C |
| ATOM | 1543 | CE3 | TRP | A | 188 | 107.160 | 30.862 | -0.725 | 1.00 | 30.49 | C |
| ATOM | 1544 | CZ3 | TRP | A | 188 | 108.189 | 31.262 | 0.175 | 1.00 | 23.09 | C |
| ATOM | 1545 | CH2 | TRP | A | 188 | 108.904 | 30.308 | 0.949 | 1.00 | 28.37 | C |
| ATOM | 1546 | CZ2 | TRP | A | 188 | 108.601 | 28.941 | 0.886 | 1.00 | 26.38 | C |
| ATOM | 1547 | C | TRP | A | 188 | 106.777 | 28.710 | -4.257 | 1.00 | 33.89 | C |
| ATOM | 1548 | O | TRP | A | 188 | 107.960 | 28.953 | -4.003 | 1.00 | 33.34 | O |
| ATOM | 1549 | N | ASP | A | 189 | 106.398 | 27.610 | -4.889 | 1.00 | 34.35 | N |
| ATOM | 1550 | CA | ASP | A | 189 | 107.384 | 26.648 | -5.317 | 1.00 | 34.70 | C |
| ATOM | 1551 | CB | ASP | A | 189 | 106.643 | 25.448 | -5.915 | 1.00 | 36.28 | C |
| ATOM | 1552 | CG | ASP | A | 189 | 107.547 | 24.255 | -6.183 | 1.00 | 43.70 | C |
| ATOM | 1553 | OD1 | ASP | A | 189 | 108.521 | 23.999 | -5.400 | 1.00 | 48.58 | O |
| ATOM | 1554 | OD2 | ASP | A | 189 | 107.273 | 23.560 | -7.213 | 1.00 | 51.52 | O |
| ATOM | 1555 | C | ASP | A | 189 | 108.442 | 27.253 | -6.285 | 1.00 | 35.16 | C |
| ATOM | 1556 | O | ASP | A | 189 | 109.611 | 26.867 | -6.264 | 1.00 | 35.34 | O |
| ATOM | 1557 | N | SER | A | 190 | 108.043 | 28.161 | -7.168 | 1.00 | 34.10 | N |
| ATOM | 1558 | CA | SER | A | 190 | 109.005 | 28.833 | -8.018 | 1.00 | 34.32 | C |
| ATOM | 1559 | CB | SER | A | 190 | 108.278 | 29.654 | -9.058 | 1.00 | 33.89 | C |
| ATOM | 1560 | OG | SER | A | 190 | 109.280 | 30.065 | -9.990 | 1.00 | 41.67 | O |
| ATOM | 1561 | C | SER | A | 190 | 109.971 | 29.771 | -7.237 | 1.00 | 33.71 | C |
| ATOM | 1562 | O | SER | A | 190 | 111.170 | 29.851 | -7.500 | 1.00 | 33.55 | O |
| ATOM | 1563 | N | PHE | A | 191 | 109.429 | 30.490 | -6.278 | 1.00 | 33.61 | N |
| ATOM | 1564 | CA | PHE | A | 191 | 110.246 | 31.346 | -5.409 | 1.00 | 33.24 | C |
| ATOM | 1565 | CB | PHE | A | 191 | 109.323 | 32.260 | -4.637 | 1.00 | 30.51 | C |
| ATOM | 1566 | CG | PHE | A | 191 | 110.012 | 33.216 | -3.692 | 1.00 | 24.21 | C |
| ATOM | 1567 | CD1 | PHE | A | 191 | 110.874 | 34.201 | -4.165 | 1.00 | 27.54 | C |
| ATOM | 1568 | CE1 | PHE | A | 191 | 111.429 | 35.157 | -3.278 | 1.00 | 26.58 | C |
| ATOM | 1569 | CZ | PHE | A | 191 | 111.150 | 35.091 | -1.901 | 1.00 | 22.84 | C |
| ATOM | 1570 | CE2 | PHE | A | 191 | 110.268 | 34.130 | -1.439 | 1.00 | 27.35 | C |
| ATOM | 1571 | CD2 | PHE | A | 191 | 109.722 | 33.185 | -2.360 | 1.00 | 21.84 | C |
| ATOM | 1572 | C | PHE | A | 191 | 111.122 | 30.528 | -4.454 | 1.00 | 34.72 | C |
| ATOM | 1573 | O | PHE | A | 191 | 112.264 | 30.884 | -4.212 | 1.00 | 34.69 | O |
| ATOM | 1574 | N | ARG | A | 192 | 110.581 | 29.462 | -3.862 | 1.00 | 37.55 | N |
| ATOM | 1575 | CA | ARG | A | 192 | 111.446 | 28.585 | -3.085 | 1.00 | 39.47 | C |
| ATOM | 1576 | CB | ARG | A | 192 | 110.653 | 27.506 | -2.313 | 1.00 | 40.04 | C |
| ATOM | 1577 | CG | ARG | A | 192 | 111.539 | 26.596 | -1.374 | 1.00 | 43.76 | C |
| ATOM | 1578 | CD | ARG | A | 192 | 110.760 | 25.562 | -0.517 | 1.00 | 44.57 | C |
| ATOM | 1579 | NE | ARG | A | 192 | 109.696 | 24.935 | -1.286 | 1.00 | 51.11 | N |
| ATOM | 1580 | CZ | ARG | A | 192 | 109.851 | 24.024 | -2.255 | 1.00 | 52.22 | C |
| ATOM | 1581 | NH1 | ARG | A | 192 | 111.055 | 23.557 | -2.583 | 1.00 | 53.29 | N |
| ATOM | 1582 | NH2 | ARG | A | 192 | 108.777 | 23.579 | -2.897 | 1.00 | 52.31 | N |
| ATOM | 1583 | C | ARG | A | 192 | 112.573 | 28.025 | -3.965 | 1.00 | 40.71 | C |
| ATOM | 1584 | O | ARG | A | 192 | 113.765 | 28.151 | -3.596 | 1.00 | 41.21 | O |
| ATOM | 1585 | N | GLN | A | 193 | 112.244 | 27.501 | -5.151 | 1.00 | 41.42 | N |
| ATOM | 1586 | CA | GLN | A | 193 | 113.278 | 26.837 | -5.989 | 1.00 | 41.77 | C |
| ATOM | 1587 | CB | GLN | A | 193 | 112.681 | 26.081 | -7.152 | 1.00 | 41.08 | C |
| ATOM | 1588 | CG | GLN | A | 193 | 111.610 | 25.146 | -6.682 | 1.00 | 46.62 | C |
| ATOM | 1589 | CD | GLN | A | 193 | 112.115 | 23.826 | -6.160 | 1.00 | 52.45 | C |
| ATOM | 1590 | OE1 | GLN | A | 193 | 113.110 | 23.758 | -5.408 | 1.00 | 55.27 | O |
| ATOM | 1591 | NE2 | GLN | A | 193 | 111.411 | 22.745 | -6.537 | 1.00 | 53.32 | N |

FIG. 1-28

| | | | | | | | | | | | | |
|---|---|---|---|---|---|---|---|---|---|---|---|---|
| ATOM | 1592 | C | GLN | A | 193 | 114.399 | 27.698 | -6.519 | 1.00 | 41.51 | | C |
| ATOM | 1593 | O | GLN | A | 193 | 115.491 | 27.185 | -6.745 | 1.00 | 40.65 | | O |
| ATOM | 1594 | N | SER | A | 194 | 114.130 | 28.981 | -6.739 | 1.00 | 41.28 | | N |
| ATOM | 1595 | CA | SER | A | 194 | 115.136 | 29.862 | -7.274 | 1.00 | 42.17 | | C |
| ATOM | 1596 | CB | SER | A | 194 | 114.482 | 31.132 | -7.846 | 1.00 | 42.35 | | C |
| ATOM | 1597 | OG | SER | A | 194 | 113.938 | 31.877 | -6.778 | 1.00 | 42.42 | | O |
| ATOM | 1598 | C | SER | A | 194 | 116.207 | 30.223 | -6.202 | 1.00 | 42.12 | | C |
| ATOM | 1599 | O | SER | A | 194 | 117.230 | 30.768 | -6.528 | 1.00 | 41.95 | | O |
| ATOM | 1600 | N | GLU | A | 195 | 115.983 | 29.933 | -4.926 | 1.00 | 43.28 | | N |
| ATOM | 1601 | CA | GLU | A | 195 | 117.016 | 30.275 | -3.927 | 1.00 | 44.25 | | C |
| ATOM | 1602 | CB | GLU | A | 195 | 116.525 | 30.078 | -2.478 | 1.00 | 43.64 | | C |
| ATOM | 1603 | CG | GLU | A | 195 | 117.634 | 30.320 | -1.461 | 1.00 | 44.63 | | C |
| ATOM | 1604 | CD | GLU | A | 195 | 117.166 | 30.739 | -0.095 | 1.00 | 44.42 | | C |
| ATOM | 1605 | OE1 | GLU | A | 195 | 117.981 | 30.661 | 0.829 | 1.00 | 41.25 | | O |
| ATOM | 1606 | OE2 | GLU | A | 195 | 116.000 | 31.174 | 0.068 | 1.00 | 46.92 | | O |
| ATOM | 1607 | C | GLU | A | 195 | 118.368 | 29.554 | -4.156 | 1.00 | 44.00 | | C |
| ATOM | 1608 | O | GLU | A | 195 | 118.374 | 28.347 | -4.469 | 1.00 | 45.08 | | O |
| ATOM | 1609 | MN | MN | A | 901 | 121.549 | 40.494 | 5.133 | 1.00 | 44.36 | | MN |
| ATOM | 1610 | MG | MG | A | 902 | 122.916 | 43.816 | 3.714 | 1.00 | 40.56 | | MG |
| ATOM | 6389 | OH2 | WAT | A | 901 | 122.045 | 42.811 | 18.783 | 1.00 | 26.44 | A | O |
| ATOM | 6392 | OH2 | WAT | A | 902 | 119.887 | 38.331 | 17.323 | 1.00 | 26.18 | A | O |
| ATOM | 6394 | OH2 | WAT | A | 903 | 110.707 | 45.442 | 15.972 | 1.00 | 27.34 | A | O |
| ATOM | 6395 | OH2 | WAT | A | 904 | 123.764 | 46.193 | 3.887 | 1.00 | 25.43 | A | O |
| ATOM | 6396 | OH2 | WAT | A | 904 | 118.775 | 46.035 | -1.122 | 1.00 | 33.31 | A | O |
| ATOM | 6397 | OH2 | WAT | A | 905 | 118.343 | 33.451 | 0.684 | 1.00 | 39.92 | A | O |
| ATOM | 6399 | OH2 | WAT | A | 906 | 127.719 | 38.320 | 18.733 | 1.00 | 33.07 | A | O |
| ATOM | 6400 | OH2 | WAT | A | 907 | 101.260 | 28.674 | 4.136 | 1.00 | 44.78 | A | O |
| ATOM | 6402 | OH2 | WAT | A | 908 | 108.131 | 51.963 | -7.683 | 1.00 | 40.55 | A | O |
| ATOM | 6403 | OH2 | WAT | A | 909 | 120.504 | 30.149 | 0.243 | 1.00 | 35.40 | A | O |
| ATOM | 6404 | OH2 | WAT | A | 910 | 119.491 | 54.349 | 10.527 | 1.00 | 25.13 | A | O |
| ATOM | 6405 | OH2 | WAT | A | 911 | 112.965 | 34.751 | 24.069 | 1.00 | 47.07 | A | O |
| ATOM | 6406 | OH2 | WAT | A | 912 | 120.559 | 43.926 | -6.265 | 1.00 | 43.93 | A | O |
| ATOM | 6407 | OH2 | WAT | A | 913 | 126.036 | 24.176 | 3.064 | 1.00 | 49.41 | A | O |
| ATOM | 6408 | OH2 | WAT | A | 914 | 117.926 | 41.407 | -15.080 | 1.00 | 48.12 | A | O |
| ATOM | 6409 | OH2 | WAT | A | 915 | 125.405 | 36.981 | 22.518 | 1.00 | 43.66 | A | O |
| ATOM | 6410 | OH2 | WAT | A | 916 | 124.778 | 42.688 | 4.758 | 1.00 | 29.14 | A | O |
| ATOM | 6411 | OH2 | WAT | A | 917 | 104.308 | 44.947 | -12.185 | 1.00 | 56.88 | A | O |
| ATOM | 6412 | OH2 | WAT | A | 918 | 107.575 | 32.972 | -8.947 | 1.00 | 64.71 | A | O |
| ATOM | 6413 | OH2 | WAT | A | 919 | 119.018 | 43.026 | 23.298 | 1.00 | 44.05 | A | O |
| ATOM | 6415 | OH2 | WAT | A | 920 | 125.055 | 50.783 | 24.110 | 1.00 | 45.48 | A | O |

END

FIG. 2-1

Figure 2: H1N1 polypeptide fragment (Chain A) with bound EMBL-R05-3

```
HEADER    ----                                 XX-XXX-9-   xxxx
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.50
REMARK   3   RESOLUTION RANGE LOW  (ANGSTROMS) :  89.10
REMARK   3   DATA CUTOFF            (SIGMA(F)) : NONE
REMARK   3   COMPLETENESS FOR RANGE        (%) :  99.04
REMARK   3   NUMBER OF REFLECTIONS             :   28997
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.20822
REMARK   3   R VALUE            (WORKING SET) :  0.20459
REMARK   3   FREE R VALUE                     :  0.27625
REMARK   3   FREE R VALUE TEST SET SIZE   (%) :  5.1
REMARK   3   FREE R VALUE TEST SET COUNT      :  1545
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    2.502
REMARK   3   BIN RESOLUTION RANGE LOW            :    2.567
REMARK   3   REFLECTION IN BIN     (WORKING SET) :     1968
REMARK   3   BIN COMPLETENESS (WORKING+TEST) (%) :    93.65
REMARK   3   BIN R VALUE           (WORKING SET) :    0.268
REMARK   3   BIN FREE R VALUE SET COUNT          :      113
REMARK   3   BIN FREE R VALUE                    :    0.378
REMARK   3
REMARK   3  NUMBER OF NON-HYDROGEN ATOMS USED IN REFINEMENT.
REMARK   3   ALL ATOMS                :     6523
REMARK   3
REMARK   3  B VALUES.
REMARK   3   FROM WILSON PLOT           (A**2) : NULL
REMARK   3   MEAN B VALUE      (OVERALL, A**2) :  29.083
REMARK   3   OVERALL ANISOTROPIC B VALUE.
REMARK   3    B11 (A**2) :     0.24
REMARK   3    B22 (A**2) :    -0.24
REMARK   3    B33 (A**2) :     0.00
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.783
REMARK   3   ESU BASED ON FREE R VALUE                       (A):   0.335
REMARK   3   ESU BASED ON MAXIMUM LIKELIHOOD                 (A):   0.240
REMARK   3   ESU FOR B VALUES BASED ON MAXIMUM LIKELIHOOD (A**2):  23.556
REMARK   3
REMARK   3 CORRELATION COEFFICIENTS.
REMARK   3   CORRELATION COEFFICIENT FO-FC      :   0.937
REMARK   3   CORRELATION COEFFICIENT FO-FC FREE :   0.891
REMARK   3
```

FIG. 2-2

```
REMARK   3  RMS DEVIATIONS FROM IDEAL VALUES        COUNT    RMS    WEIGHT
REMARK   3   BOND LENGTHS REFINED ATOMS        (A):  6520 ; 0.016 ; 0.022
REMARK   3   BOND LENGTHS OTHERS               (A):  4574 ; 0.001 ; 0.020
REMARK   3   BOND ANGLES REFINED ATOMS   (DEGREES):  8769 ; 1.513 ; 1.974
REMARK   3   BOND ANGLES OTHERS          (DEGREES): 11027 ; 0.893 ; 3.000
REMARK   3   TORSION ANGLES, PERIOD 1    (DEGREES):   741 ; 6.052 ; 5.000
REMARK   3   TORSION ANGLES, PERIOD 2    (DEGREES):   332 ;35.152 ;23.373
REMARK   3   TORSION ANGLES, PERIOD 3    (DEGREES):  1193 ;19.051 ;15.000
REMARK   3   TORSION ANGLES, PERIOD 4    (DEGREES):    55 ;19.093 ;15.000
REMARK   3   CHIRAL-CENTER RESTRAINTS       (A**3):   920 ; 0.086 ; 0.200
REMARK   3   GENERAL PLANES REFINED ATOMS      (A):  7058 ; 0.006 ; 0.020
REMARK   3   GENERAL PLANES OTHERS             (A):  1441 ; 0.001 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):  3740 ; 0.632 ; 1.500
REMARK   3   MAIN-CHAIN BOND OTHER ATOMS    (A**2):  1503 ; 0.123 ; 1.500
REMARK   3   MAIN-CHAIN ANGLE REFINED ATOMS (A**2):  6055 ; 1.173 ; 2.000
REMARK   3   SIDE-CHAIN BOND REFINED ATOMS  (A**2):  2780 ; 1.839 ; 3.000
REMARK   3   SIDE-CHAIN ANGLE REFINED ATOMS (A**2):  2714 ; 2.962 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  :    4
REMARK   3   ATOM RECORD CONTAINS SUM OF TLS AND RESIDUAL B FACTORS
REMARK   3
REMARK   3   TLS GROUP :     1
REMARK   3    NUMBER OF COMPONENTS GROUP :    4
REMARK   3    COMPONENTS        C SSSEQI   TO  C SSSEQI
REMARK   3    RESIDUE RANGE :   A    -2        A   194
REMARK   3    RESIDUE RANGE :   A   901        A   902
REMARK   3    RESIDUE RANGE :   A   401        A   404
REMARK   3    RESIDUE RANGE :   A   801        A   801
REMARK   3    ORIGIN FOR THE GROUP (A): -18.7820 -18.3467  15.6409
REMARK   3    T TENSOR
REMARK   3      T11:   0.0626 T22:   0.0601
REMARK   3      T33:   0.0370 T12:   0.0477
REMARK   3      T13:   0.0061 T23:  -0.0096
REMARK   3    L TENSOR
REMARK   3      L11:   3.8491 L22:   3.1615
REMARK   3      L33:   2.2199 L12:   0.4794
REMARK   3      L13:   0.2562 L23:  -0.2521
REMARK   3    S TENSOR
REMARK   3      S11:   0.0271 S12:  -0.0426 S13:   0.3012
REMARK   3      S21:   0.1037 S22:   0.0068 S23:   0.2311
REMARK   3      S31:  -0.2046 S32:   0.0173 S33:  -0.0339
REMARK   3
REMARK   3   TLS GROUP :     2
REMARK   3    NUMBER OF COMPONENTS GROUP :    4
REMARK   3    COMPONENTS        C SSSEQI   TO  C SSSEQI
REMARK   3    RESIDUE RANGE :   B    -2        B   193
REMARK   3    RESIDUE RANGE :   B   901        B   902
REMARK   3    RESIDUE RANGE :   B   401        B   404
REMARK   3    RESIDUE RANGE :   B   801        B   801
REMARK   3    ORIGIN FOR THE GROUP (A):  -9.5592 -43.9684  15.4406
REMARK   3    T TENSOR
REMARK   3      T11:   0.0655 T22:   0.0616
REMARK   3      T33:   0.0284 T12:   0.0424
```

FIG. 2-3

```
REMARK   3      T13:  -0.0096 T23:   0.0116
REMARK   3    L TENSOR
REMARK   3      L11:   3.5209 L22:   2.7524
REMARK   3      L33:   2.1675 L12:   0.0213
REMARK   3      L13:  -0.8001 L23:   0.2855
REMARK   3    S TENSOR
REMARK   3      S11:   0.0173 S12:  -0.0992 S13:  -0.2131
REMARK   3      S21:   0.1239 S22:  -0.0222 S23:  -0.2049
REMARK   3      S31:   0.2223 S32:  -0.0015 S33:   0.0049
REMARK   3
REMARK   3   TLS GROUP :     3
REMARK   3    NUMBER OF COMPONENTS GROUP :    4
REMARK   3    COMPONENTS          C SSSEQI   TO  C SSSEQI
REMARK   3    RESIDUE RANGE :   C     0        C   195
REMARK   3    RESIDUE RANGE :   C   901        C   902
REMARK   3    RESIDUE RANGE :   C   401        C   403
REMARK   3    RESIDUE RANGE :   C   801        C   801
REMARK   3    ORIGIN FOR THE GROUP (A):  -4.3952 -15.1378  52.3445
REMARK   3    T TENSOR
REMARK   3      T11:   0.0906 T22:   0.0725
REMARK   3      T33:   0.0515 T12:  -0.0225
REMARK   3      T13:  -0.0351 T23:  -0.0026
REMARK   3    L TENSOR
REMARK   3      L11:   3.4910 L22:   2.7740
REMARK   3      L33:   2.4480 L12:   1.0609
REMARK   3      L13:  -0.2109 L23:  -1.3961
REMARK   3    S TENSOR
REMARK   3      S11:  -0.0152 S12:   0.1383 S13:  -0.1047
REMARK   3      S21:  -0.2065 S22:  -0.0565 S23:  -0.0793
REMARK   3      S31:   0.1206 S32:   0.1449 S33:   0.0717
REMARK   3
REMARK   3   TLS GROUP :     4
REMARK   3    NUMBER OF COMPONENTS GROUP :    4
REMARK   3    COMPONENTS          C SSSEQI   TO  C SSSEQI
REMARK   3    RESIDUE RANGE :   D     0        D   195
REMARK   3    RESIDUE RANGE :   D   901        D   902
REMARK   3    RESIDUE RANGE :   D   401        D   403
REMARK   3    RESIDUE RANGE :   D   801        D   801
REMARK   3    ORIGIN FOR THE GROUP (A): -21.2945 -45.7592  51.4140
REMARK   3    T TENSOR
REMARK   3      T11:   0.1308 T22:   0.1190
REMARK   3      T33:   0.0216 T12:  -0.0416
REMARK   3      T13:  -0.0097 T23:   0.0186
REMARK   3    L TENSOR
REMARK   3      L11:   3.6692 L22:   2.1484
REMARK   3      L33:   2.5225 L12:  -0.2058
REMARK   3      L13:  -0.3579 L23:   1.1039
REMARK   3    S TENSOR
REMARK   3      S11:   0.0541 S12:   0.3685 S13:  -0.0165
REMARK   3      S21:  -0.1313 S22:  -0.0722 S23:   0.0569
REMARK   3      S31:   0.0558 S32:  -0.2205 S33:   0.0181
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : WITH TLS ADDED
```

FIG. 2-4

```
REMARK    3
LINKR          GLU A  64                            LEU A  71                 gap
LINKR          LYS A 137                            LYS A 142                 gap
LINKR          GLU B  64                            LEU B  71                 gap
LINKR          PHE D  51                            LEU D  72                 gap
CRYST1    54.570  122.540  129.780  90.00  90.00  90.00 P 21 21 21
SCALE1      0.018325  0.000000  0.000000        0.00000
SCALE2      0.000000  0.008161  0.000000        0.00000
SCALE3      0.000000  0.000000  0.007705        0.00000
ATOM      1  N   GLY A  -2      -38.519 -32.846  21.771  1.00 50.75      A    N
ATOM      2  CA  GLY A  -2      -37.114 -32.422  21.506  1.00 47.67      A    C
ATOM      3  C   GLY A  -2      -36.272 -33.439  20.743  1.00 46.67      A    C
ATOM      4  O   GLY A  -2      -35.234 -33.069  20.155  1.00 45.44      A    O
ATOM      5  N   MET A  -1      -36.681 -34.712  20.738  1.00 47.85      A    N
ATOM      6  CA  MET A  -1      -35.956 -35.754  19.979  1.00 46.83      A    C
ATOM      7  CB  MET A  -1      -36.686 -37.113  20.044  1.00 49.48      A    C
ATOM      8  C   MET A  -1      -35.726 -35.349  18.511  1.00 44.43      A    C
ATOM      9  O   MET A  -1      -34.666 -35.599  17.955  1.00 43.39      A    O
ATOM     10  N   ALA A   0      -36.720 -34.719  17.900  1.00 44.28      A    N
ATOM     11  CA  ALA A   0      -36.655 -34.339  16.497  1.00 42.51      A    C
ATOM     12  CB  ALA A   0      -37.986 -33.694  16.075  1.00 43.78      A    C
ATOM     13  C   ALA A   0      -35.474 -33.389  16.265  1.00 39.35      A    C
ATOM     14  O   ALA A   0      -34.733 -33.539  15.297  1.00 38.08      A    O
ATOM     15  N   MET A   1      -35.292 -32.433  17.169  1.00 38.01      A    N
ATOM     16  CA  MET A   1      -34.191 -31.470  17.075  1.00 35.93      A    C
ATOM     17  CB  MET A   1      -34.381 -30.323  18.074  1.00 35.54      A    C
ATOM     18  CG  MET A   1      -33.244 -29.325  18.087  1.00 34.33      A    C
ATOM     19  SD  MET A   1      -33.022 -28.423  16.534  1.00 33.65      A    S
ATOM     20  CE  MET A   1      -33.808 -26.859  16.941  1.00 31.82      A    C
ATOM     21  C   MET A   1      -32.846 -32.119  17.336  1.00 34.49      A    C
ATOM     22  O   MET A   1      -31.846 -31.792  16.687  1.00 32.19      A    O
ATOM     23  N   GLU A   2      -32.812 -33.015  18.317  1.00 35.64      A    N
ATOM     24  CA  GLU A   2      -31.568 -33.679  18.636  1.00 34.77      A    C
ATOM     25  CB  GLU A   2      -31.717 -34.578  19.855  1.00 36.86      A    C
ATOM     26  CG  GLU A   2      -30.425 -34.762  20.606  1.00 37.45      A    C
ATOM     27  CD  GLU A   2      -30.412 -36.006  21.476  1.00 43.71      A    C
ATOM     28  OE1 GLU A   2      -31.509 -36.429  21.931  1.00 47.97      A    O
ATOM     29  OE2 GLU A   2      -29.299 -36.551  21.719  1.00 43.85      A    O
ATOM     30  C   GLU A   2      -31.147 -34.488  17.419  1.00 34.14      A    C
ATOM     31  O   GLU A   2      -29.985 -34.482  17.006  1.00 32.33      A    O
ATOM     32  N   ASP A   3      -32.100 -35.177  16.818  1.00 34.95      A    N
ATOM     33  CA  ASP A   3      -31.771 -35.929  15.636  1.00 34.86      A    C
ATOM     34  CB  ASP A   3      -32.951 -36.772  15.208  1.00 38.04      A    C
ATOM     35  CG  ASP A   3      -33.054 -38.043  16.010  1.00 42.67      A    C
ATOM     36  OD1 ASP A   3      -33.714 -38.974  15.522  1.00 48.58      A    O
ATOM     37  OD2 ASP A   3      -32.445 -38.125  17.107  1.00 45.54      A    O
ATOM     38  C   ASP A   3      -31.316 -34.990  14.532  1.00 31.91      A    C
ATOM     39  O   ASP A   3      -30.341 -35.265  13.839  1.00 30.97      A    O
ATOM     40  N   PHE A   4      -32.002 -33.866  14.402  1.00 29.93      A    N
ATOM     41  CA  PHE A   4      -31.671 -32.913  13.370  1.00 27.51      A    C
ATOM     42  CB  PHE A   4      -32.603 -31.719  13.404  1.00 26.94      A    C
ATOM     43  CG  PHE A   4      -32.205 -30.665  12.461  1.00 25.87      A    C
ATOM     44  CD1 PHE A   4      -32.405 -30.843  11.101  1.00 27.98      A    C
ATOM     45  CE1 PHE A   4      -31.974 -29.878  10.188  1.00 29.31      A    C
ATOM     46  CZ  PHE A   4      -31.333 -28.704  10.653  1.00 26.48      A    C
ATOM     47  CE2 PHE A   4      -31.116 -28.546  11.995  1.00 24.77      A    C
ATOM     48  CD2 PHE A   4      -31.549 -29.527  12.901  1.00 24.87      A    C
ATOM     49  C   PHE A   4      -30.251 -32.415  13.524  1.00 24.87      A    C
ATOM     50  O   PHE A   4      -29.479 -32.359  12.569  1.00 24.18      A    O
ATOM     51  N   VAL A   5      -29.915 -32.020  14.731  1.00 23.79      A    N
ATOM     52  CA  VAL A   5      -28.585 -31.554  14.998  1.00 21.57      A    C
ATOM     53  CB  VAL A   5      -28.420 -31.160  16.467  1.00 21.39      A    C
ATOM     54  CG1 VAL A   5      -26.932 -31.024  16.833  1.00 20.32      A    C
```

FIG. 2-5

| | | | | | | | | | | | | |
|---|---|---|---|---|---|---|---|---|---|---|---|---|
| ATOM | 55 | CG2 | VAL | A | 5 | -29.181 | -29.876 | 16.730 | 1.00 | 17.95 | A | C |
| ATOM | 56 | C | VAL | A | 5 | -27.576 | -32.599 | 14.597 | 1.00 | 21.42 | A | C |
| ATOM | 57 | O | VAL | A | 5 | -26.613 | -32.293 | 13.908 | 1.00 | 20.79 | A | O |
| ATOM | 58 | N | ARG | A | 6 | -27.802 | -33.839 | 14.981 | 1.00 | 23.52 | A | N |
| ATOM | 59 | CA | ARG | A | 6 | -26.811 | -34.885 | 14.715 | 1.00 | 24.60 | A | C |
| ATOM | 60 | CB | ARG | A | 6 | -27.158 | -36.180 | 15.456 | 1.00 | 26.20 | A | C |
| ATOM | 61 | CG | ARG | A | 6 | -26.996 | -35.977 | 16.943 | 1.00 | 26.38 | A | C |
| ATOM | 62 | CD | ARG | A | 6 | -27.362 | -37.122 | 17.837 | 1.00 | 30.58 | A | C |
| ATOM | 63 | NE | ARG | A | 6 | -27.377 | -36.649 | 19.238 | 1.00 | 33.78 | A | N |
| ATOM | 64 | CZ | ARG | A | 6 | -26.311 | -36.377 | 20.015 | 1.00 | 33.11 | A | C |
| ATOM | 65 | NH1 | ARG | A | 6 | -25.067 | -36.568 | 19.606 | 1.00 | 31.54 | A | N |
| ATOM | 66 | NH2 | ARG | A | 6 | -26.501 | -35.918 | 21.251 | 1.00 | 34.64 | A | N |
| ATOM | 67 | C | ARG | A | 6 | -26.637 | -35.086 | 13.226 | 1.00 | 25.83 | A | C |
| ATOM | 68 | O | ARG | A | 6 | -25.550 | -35.332 | 12.782 | 1.00 | 26.84 | A | O |
| ATOM | 69 | N | GLN | A | 7 | -27.688 | -34.913 | 12.440 | 1.00 | 27.44 | A | N |
| ATOM | 70 | CA | GLN | A | 7 | -27.585 | -35.097 | 11.014 | 1.00 | 28.35 | A | C |
| ATOM | 71 | CB | GLN | A | 7 | -28.937 | -35.504 | 10.426 | 1.00 | 30.34 | A | C |
| ATOM | 72 | CG | GLN | A | 7 | -29.292 | -36.929 | 10.705 | 1.00 | 33.32 | A | C |
| ATOM | 73 | CD | GLN | A | 7 | -30.564 | -37.407 | 10.001 | 1.00 | 36.08 | A | C |
| ATOM | 74 | OE1 | GLN | A | 7 | -31.086 | -36.771 | 9.079 | 1.00 | 33.80 | A | O |
| ATOM | 75 | NE2 | GLN | A | 7 | -31.054 | -38.562 | 10.441 | 1.00 | 38.66 | A | N |
| ATOM | 76 | C | GLN | A | 7 | -27.085 | -33.861 | 10.297 | 1.00 | 27.47 | A | C |
| ATOM | 77 | O | GLN | A | 7 | -26.649 | -33.939 | 9.153 | 1.00 | 29.12 | A | O |
| ATOM | 78 | N | CYS | A | 8 | -27.169 | -32.707 | 10.931 | 1.00 | 25.80 | A | N |
| ATOM | 79 | CA | CYS | A | 8 | -26.876 | -31.460 | 10.242 | 1.00 | 24.20 | A | C |
| ATOM | 80 | CB | CYS | A | 8 | -27.829 | -30.402 | 10.771 | 1.00 | 24.13 | A | C |
| ATOM | 81 | SG | CYS | A | 8 | -27.679 | -28.858 | 10.002 | 1.00 | 25.78 | A | S |
| ATOM | 82 | C | CYS | A | 8 | -25.417 | -30.998 | 10.402 | 1.00 | 21.96 | A | C |
| ATOM | 83 | O | CYS | A | 8 | -24.829 | -30.431 | 9.482 | 1.00 | 20.81 | A | O |
| ATOM | 84 | N | PHE | A | 9 | -24.837 | -31.210 | 11.576 | 1.00 | 20.93 | A | N |
| ATOM | 85 | CA | PHE | A | 9 | -23.491 | -30.717 | 11.835 | 1.00 | 19.41 | A | C |
| ATOM | 86 | CB | PHE | A | 9 | -23.416 | -29.960 | 13.156 | 1.00 | 18.35 | A | C |
| ATOM | 87 | CG | PHE | A | 9 | -24.257 | -28.764 | 13.175 | 1.00 | 17.85 | A | C |
| ATOM | 88 | CD1 | PHE | A | 9 | -23.801 | -27.582 | 12.635 | 1.00 | 18.20 | A | C |
| ATOM | 89 | CE1 | PHE | A | 9 | -24.604 | -26.492 | 12.606 | 1.00 | 17.55 | A | C |
| ATOM | 90 | CZ | PHE | A | 9 | -25.904 | -26.553 | 13.103 | 1.00 | 15.93 | A | C |
| ATOM | 91 | CE2 | PHE | A | 9 | -26.372 | -27.703 | 13.609 | 1.00 | 16.98 | A | C |
| ATOM | 92 | CD2 | PHE | A | 9 | -25.555 | -28.820 | 13.641 | 1.00 | 19.53 | A | C |
| ATOM | 93 | C | PHE | A | 9 | -22.526 | -31.860 | 11.827 | 1.00 | 20.11 | A | C |
| ATOM | 94 | O | PHE | A | 9 | -22.891 | -32.984 | 12.129 | 1.00 | 22.44 | A | O |
| ATOM | 95 | N | ASN | A | 10 | -21.297 | -31.556 | 11.425 | 1.00 | 19.59 | A | N |
| ATOM | 96 | CA | ASN | A | 10 | -20.165 | -32.464 | 11.531 | 1.00 | 19.31 | A | C |
| ATOM | 97 | CB | ASN | A | 10 | -18.866 | -31.678 | 11.312 | 1.00 | 18.53 | A | C |
| ATOM | 98 | CG | ASN | A | 10 | -17.725 | -32.563 | 11.032 | 1.00 | 20.99 | A | C |
| ATOM | 99 | OD1 | ASN | A | 10 | -17.170 | -33.208 | 11.931 | 1.00 | 25.13 | A | O |
| ATOM | 100 | ND2 | ASN | A | 10 | -17.353 | -32.633 | 9.776 | 1.00 | 22.16 | A | N |
| ATOM | 101 | C | ASN | A | 10 | -20.111 | -33.072 | 12.918 | 1.00 | 17.98 | A | C |
| ATOM | 102 | O | ASN | A | 10 | -20.383 | -32.396 | 13.895 | 1.00 | 16.58 | A | O |
| ATOM | 103 | N | PRO | A | 11 | -19.758 | -34.337 | 13.005 | 1.00 | 18.37 | A | N |
| ATOM | 104 | CA | PRO | A | 11 | -19.655 | -34.938 | 14.315 | 1.00 | 19.57 | A | C |
| ATOM | 105 | CB | PRO | A | 11 | -19.239 | -36.371 | 14.006 | 1.00 | 20.39 | A | C |
| ATOM | 106 | CG | PRO | A | 11 | -19.666 | -36.594 | 12.648 | 1.00 | 20.94 | A | C |
| ATOM | 107 | CD | PRO | A | 11 | -19.656 | -35.334 | 11.929 | 1.00 | 19.75 | A | C |
| ATOM | 108 | C | PRO | A | 11 | -18.625 | -34.259 | 15.224 | 1.00 | 19.98 | A | C |
| ATOM | 109 | O | PRO | A | 11 | -18.788 | -34.265 | 16.440 | 1.00 | 19.39 | A | O |
| ATOM | 110 | N | MET | A | 12 | -17.592 | -33.656 | 14.626 | 1.00 | 20.46 | A | N |
| ATOM | 111 | CA | MET | A | 12 | -16.610 | -32.943 | 15.400 | 1.00 | 20.47 | A | C |
| ATOM | 112 | CB | MET | A | 12 | -15.419 | -32.504 | 14.542 | 1.00 | 20.73 | A | C |
| ATOM | 113 | CG | MET | A | 12 | -14.529 | -33.634 | 14.064 | 1.00 | 24.64 | A | C |
| ATOM | 114 | SD | MET | A | 12 | -13.560 | -33.183 | 12.568 | 1.00 | 32.34 | A | S |
| ATOM | 115 | CE | MET | A | 12 | -12.195 | -32.490 | 13.401 | 1.00 | 30.42 | A | C |
| ATOM | 116 | C | MET | A | 12 | -17.276 | -31.757 | 16.087 | 1.00 | 18.94 | A | C |
| ATOM | 117 | O | MET | A | 12 | -17.098 | -31.579 | 17.289 | 1.00 | 19.31 | A | O |

FIG. 2-6

| | | | | | | | | | | | | |
|---|---|---|---|---|---|---|---|---|---|---|---|---|
| ATOM | 118 | N | ILE | A | 13 | -18.059 | -30.970 | 15.346 | 1.00 | 17.39 | A | N |
| ATOM | 119 | CA | ILE | A | 13 | -18.776 | -29.809 | 15.909 | 1.00 | 15.91 | A | C |
| ATOM | 120 | CB | ILE | A | 13 | -19.720 | -29.184 | 14.906 | 1.00 | 16.36 | A | C |
| ATOM | 121 | CG1 | ILE | A | 13 | -18.967 | -28.565 | 13.733 | 1.00 | 16.97 | A | C |
| ATOM | 122 | CD1 | ILE | A | 13 | -17.918 | -27.616 | 14.160 | 1.00 | 19.34 | A | C |
| ATOM | 123 | CG2 | ILE | A | 13 | -20.622 | -28.130 | 15.569 | 1.00 | 14.69 | A | C |
| ATOM | 124 | C | ILE | A | 13 | -19.675 | -30.251 | 17.064 | 1.00 | 16.26 | A | C |
| ATOM | 125 | O | ILE | A | 13 | -19.704 | -29.615 | 18.131 | 1.00 | 15.30 | A | O |
| ATOM | 126 | N | VAL | A | 14 | -20.368 | -31.360 | 16.834 | 1.00 | 16.18 | A | N |
| ATOM | 127 | CA | VAL | A | 14 | -21.317 | -31.891 | 17.777 | 1.00 | 17.15 | A | C |
| ATOM | 128 | CB | VAL | A | 14 | -22.166 | -32.995 | 17.123 | 1.00 | 18.61 | A | C |
| ATOM | 129 | CG1 | VAL | A | 14 | -23.052 | -33.625 | 18.133 | 1.00 | 20.90 | A | C |
| ATOM | 130 | CG2 | VAL | A | 14 | -23.022 | -32.419 | 15.921 | 1.00 | 17.70 | A | C |
| ATOM | 131 | C | VAL | A | 14 | -20.612 | -32.385 | 19.039 | 1.00 | 18.00 | A | C |
| ATOM | 132 | O | VAL | A | 14 | -21.056 | -32.099 | 20.145 | 1.00 | 18.86 | A | O |
| ATOM | 133 | N | GLU | A | 15 | -19.501 | -33.105 | 18.899 | 1.00 | 18.33 | A | N |
| ATOM | 134 | CA | GLU | A | 15 | -18.707 | -33.444 | 20.067 | 1.00 | 18.94 | A | C |
| ATOM | 135 | CB | GLU | A | 15 | -17.487 | -34.258 | 19.697 | 1.00 | 19.34 | A | C |
| ATOM | 136 | CG | GLU | A | 15 | -17.805 | -35.639 | 19.181 | 1.00 | 22.29 | A | C |
| ATOM | 137 | CD | GLU | A | 15 | -16.685 | -36.607 | 19.410 | 1.00 | 23.71 | A | C |
| ATOM | 138 | OE1 | GLU | A | 15 | -15.565 | -36.170 | 19.714 | 1.00 | 27.78 | A | O |
| ATOM | 139 | OE2 | GLU | A | 15 | -16.922 | -37.813 | 19.333 | 1.00 | 27.67 | A | O |
| ATOM | 140 | C | GLU | A | 15 | -18.272 | -32.198 | 20.886 | 1.00 | 18.08 | A | C |
| ATOM | 141 | O | GLU | A | 15 | -18.275 | -32.237 | 22.124 | 1.00 | 18.57 | A | O |
| ATOM | 142 | N | LEU | A | 16 | -17.898 | -31.114 | 20.211 | 1.00 | 17.01 | A | N |
| ATOM | 143 | CA | LEU | A | 16 | -17.514 | -29.878 | 20.928 | 1.00 | 16.98 | A | C |
| ATOM | 144 | CB | LEU | A | 16 | -16.799 | -28.848 | 20.041 | 1.00 | 15.14 | A | C |
| ATOM | 145 | CG | LEU | A | 16 | -15.438 | -29.310 | 19.469 | 1.00 | 16.38 | A | C |
| ATOM | 146 | CD1 | LEU | A | 16 | -15.069 | -28.378 | 18.317 | 1.00 | 13.21 | A | C |
| ATOM | 147 | CD2 | LEU | A | 16 | -14.281 | -29.384 | 20.520 | 1.00 | 14.19 | A | C |
| ATOM | 148 | C | LEU | A | 16 | -18.713 | -29.249 | 21.589 | 1.00 | 16.38 | A | C |
| ATOM | 149 | O | LEU | A | 16 | -18.609 | -28.816 | 22.706 | 1.00 | 18.12 | A | O |
| ATOM | 150 | N | ALA | A | 17 | -19.859 | -29.246 | 20.923 | 1.00 | 15.62 | A | N |
| ATOM | 151 | CA | ALA | A | 17 | -21.048 | -28.606 | 21.489 | 1.00 | 15.78 | A | C |
| ATOM | 152 | CB | ALA | A | 17 | -22.204 | -28.590 | 20.509 | 1.00 | 14.60 | A | C |
| ATOM | 153 | C | ALA | A | 17 | -21.452 | -29.312 | 22.780 | 1.00 | 17.05 | A | C |
| ATOM | 154 | O | ALA | A | 17 | -21.773 | -28.662 | 23.741 | 1.00 | 17.12 | A | O |
| ATOM | 155 | N | GLU | A | 18 | -21.403 | -30.642 | 22.776 | 1.00 | 17.83 | A | N |
| ATOM | 156 | CA | GLU | A | 18 | -21.733 | -31.453 | 23.930 | 1.00 | 19.84 | A | C |
| ATOM | 157 | CB | GLU | A | 18 | -21.597 | -32.942 | 23.584 | 1.00 | 21.03 | A | C |
| ATOM | 158 | CG | GLU | A | 18 | -22.694 | -33.505 | 22.703 | 1.00 | 21.16 | A | C |
| ATOM | 159 | CD | GLU | A | 18 | -22.538 | -34.988 | 22.429 | 1.00 | 22.58 | A | C |
| ATOM | 160 | OE1 | GLU | A | 18 | -21.430 | -35.493 | 22.704 | 1.00 | 22.98 | A | O |
| ATOM | 161 | OE2 | GLU | A | 18 | -23.504 | -35.639 | 21.927 | 1.00 | 23.47 | A | O |
| ATOM | 162 | C | GLU | A | 18 | -20.858 | -31.138 | 25.150 | 1.00 | 20.89 | A | C |
| ATOM | 163 | O | GLU | A | 18 | -21.352 | -31.123 | 26.296 | 1.00 | 21.49 | A | O |
| ATOM | 164 | N | LYS | A | 19 | -19.568 | -30.897 | 24.915 | 1.00 | 20.66 | A | N |
| ATOM | 165 | CA | LYS | A | 19 | -18.627 | -30.577 | 26.037 | 1.00 | 21.79 | A | C |
| ATOM | 166 | CB | LYS | A | 19 | -17.169 | -30.693 | 25.605 | 1.00 | 20.61 | A | C |
| ATOM | 167 | CG | LYS | A | 19 | -16.773 | -32.098 | 25.329 | 1.00 | 21.87 | A | C |
| ATOM | 168 | CD | LYS | A | 19 | -15.479 | -32.193 | 24.532 | 1.00 | 21.08 | A | C |
| ATOM | 169 | CE | LYS | A | 19 | -15.017 | -33.678 | 24.362 | 1.00 | 23.20 | A | C |
| ATOM | 170 | NZ | LYS | A | 19 | -14.869 | -34.470 | 25.633 | 1.00 | 22.35 | A | N |
| ATOM | 171 | C | LYS | A | 19 | -18.893 | -29.162 | 26.519 | 1.00 | 21.37 | A | C |
| ATOM | 172 | O | LYS | A | 19 | -18.859 | -28.877 | 27.739 | 1.00 | 23.73 | A | O |
| ATOM | 173 | N | ALA | A | 20 | -19.193 | -28.307 | 25.555 | 1.00 | 18.73 | A | N |
| ATOM | 174 | CA | ALA | A | 20 | -19.483 | -26.929 | 25.837 | 1.00 | 19.32 | A | C |
| ATOM | 175 | CB | ALA | A | 20 | -19.753 | -26.157 | 24.557 | 1.00 | 16.73 | A | C |
| ATOM | 176 | C | ALA | A | 20 | -20.672 | -26.878 | 26.769 | 1.00 | 20.89 | A | C |
| ATOM | 177 | O | ALA | A | 20 | -20.591 | -26.270 | 27.823 | 1.00 | 23.74 | A | O |
| ATOM | 178 | N | MET | A | 21 | -21.739 | -27.574 | 26.426 | 1.00 | 20.70 | A | N |
| ATOM | 179 | CA | MET | A | 21 | -22.901 | -27.563 | 27.251 | 1.00 | 22.97 | A | C |
| ATOM | 180 | CB | MET | A | 21 | -24.045 | -28.281 | 26.556 | 1.00 | 23.11 | A | C |

FIG. 2-7

| | | | | | | | | | | | | |
|---|---|---|---|---|---|---|---|---|---|---|---|---|
| ATOM | 181 | CG | MET | A | 21 | -24.530 | -27.534 | 25.314 | 1.00 | 23.06 | A | C |
| ATOM | 182 | SD | MET | A | 21 | -26.174 | -28.016 | 24.724 | 1.00 | 26.35 | A | S |
| ATOM | 183 | CE | MET | A | 21 | -27.199 | -27.416 | 26.072 | 1.00 | 25.56 | A | C |
| ATOM | 184 | C | MET | A | 21 | -22.639 | -28.118 | 28.648 | 1.00 | 25.25 | A | C |
| ATOM | 185 | O | MET | A | 21 | -23.143 | -27.574 | 29.638 | 1.00 | 26.92 | A | O |
| ATOM | 186 | N | LYS | A | 22 | -21.829 | -29.165 | 28.730 | 1.00 | 26.13 | A | N |
| ATOM | 187 | CA | LYS | A | 22 | -21.489 | -29.773 | 30.020 | 1.00 | 29.17 | A | C |
| ATOM | 188 | CB | LYS | A | 22 | -20.665 | -31.035 | 29.833 | 1.00 | 29.20 | A | C |
| ATOM | 189 | CG | LYS | A | 22 | -20.517 | -31.813 | 31.101 | 1.00 | 33.11 | A | C |
| ATOM | 190 | CD | LYS | A | 22 | -19.465 | -32.898 | 30.998 | 1.00 | 36.31 | A | C |
| ATOM | 191 | CE | LYS | A | 22 | -19.953 | -34.225 | 31.598 | 1.00 | 40.17 | A | C |
| ATOM | 192 | NZ | LYS | A | 22 | -18.954 | -35.315 | 31.374 | 1.00 | 42.12 | A | N |
| ATOM | 193 | C | LYS | A | 22 | -20.763 | -28.783 | 30.952 | 1.00 | 30.09 | A | C |
| ATOM | 194 | O | LYS | A | 22 | -21.119 | -28.665 | 32.135 | 1.00 | 31.19 | A | O |
| ATOM | 195 | N | GLU | A | 23 | -19.802 | -28.060 | 30.376 | 1.00 | 28.37 | A | N |
| ATOM | 196 | CA | GLU | A | 23 | -19.168 | -26.908 | 31.013 | 1.00 | 29.67 | A | C |
| ATOM | 197 | CB | GLU | A | 23 | -18.219 | -26.222 | 30.021 | 1.00 | 27.78 | A | C |
| ATOM | 198 | CG | GLU | A | 23 | -17.129 | -25.370 | 30.606 | 1.00 | 28.78 | A | C |
| ATOM | 199 | CD | GLU | A | 23 | -16.143 | -24.850 | 29.545 | 1.00 | 28.63 | A | C |
| ATOM | 200 | OE1 | GLU | A | 23 | -16.335 | -25.079 | 28.335 | 1.00 | 29.68 | A | O |
| ATOM | 201 | OE2 | GLU | A | 23 | -15.164 | -24.176 | 29.913 | 1.00 | 31.53 | A | O |
| ATOM | 202 | C | GLU | A | 23 | -20.241 | -25.922 | 31.488 | 1.00 | 31.64 | A | C |
| ATOM | 203 | O | GLU | A | 23 | -20.312 | -25.584 | 32.697 | 1.00 | 33.74 | A | O |
| ATOM | 204 | N | TYR | A | 24 | -21.131 | -25.515 | 30.575 | 1.00 | 30.64 | A | N |
| ATOM | 205 | CA | TYR | A | 24 | -22.137 | -24.519 | 30.947 | 1.00 | 32.37 | A | C |
| ATOM | 206 | CB | TYR | A | 24 | -22.914 | -23.970 | 29.754 | 1.00 | 31.23 | A | C |
| ATOM | 207 | CG | TYR | A | 24 | -22.085 | -23.591 | 28.586 | 1.00 | 28.21 | A | C |
| ATOM | 208 | CD1 | TYR | A | 24 | -22.619 | -23.581 | 27.330 | 1.00 | 26.36 | A | C |
| ATOM | 209 | CE1 | TYR | A | 24 | -21.845 | -23.230 | 26.230 | 1.00 | 27.39 | A | C |
| ATOM | 210 | CZ | TYR | A | 24 | -20.518 | -22.910 | 26.417 | 1.00 | 27.75 | A | C |
| ATOM | 211 | OH | TYR | A | 24 | -19.693 | -22.577 | 25.369 | 1.00 | 24.23 | A | O |
| ATOM | 212 | CE2 | TYR | A | 24 | -19.981 | -22.934 | 27.672 | 1.00 | 28.48 | A | C |
| ATOM | 213 | CD2 | TYR | A | 24 | -20.760 | -23.265 | 28.742 | 1.00 | 29.94 | A | C |
| ATOM | 214 | C | TYR | A | 24 | -23.148 | -25.039 | 31.950 | 1.00 | 35.13 | A | C |
| ATOM | 215 | O | TYR | A | 24 | -23.948 | -24.251 | 32.413 | 1.00 | 36.84 | A | O |
| ATOM | 216 | N | GLY | A | 25 | -23.104 | -26.338 | 32.278 | 1.00 | 36.28 | A | N |
| ATOM | 217 | CA | GLY | A | 25 | -24.021 | -26.966 | 33.237 | 1.00 | 38.88 | A | C |
| ATOM | 218 | C | GLY | A | 25 | -25.284 | -27.483 | 32.568 | 1.00 | 38.95 | A | C |
| ATOM | 219 | O | GLY | A | 25 | -26.202 | -27.884 | 33.219 | 1.00 | 40.13 | A | O |
| ATOM | 220 | N | GLU | A | 26 | -25.307 | -27.494 | 31.244 | 1.00 | 37.74 | A | N |
| ATOM | 221 | CA | GLU | A | 26 | -26.493 | -27.858 | 30.501 | 1.00 | 38.12 | A | C |
| ATOM | 222 | CB | GLU | A | 26 | -26.690 | -26.821 | 29.421 | 1.00 | 36.54 | A | C |
| ATOM | 223 | CG | GLU | A | 26 | -27.092 | -25.451 | 30.032 | 1.00 | 39.91 | A | C |
| ATOM | 224 | CD | GLU | A | 26 | -26.490 | -24.262 | 29.316 | 1.00 | 39.81 | A | C |
| ATOM | 225 | OE1 | GLU | A | 26 | -25.942 | -24.435 | 28.211 | 1.00 | 42.01 | A | O |
| ATOM | 226 | OE2 | GLU | A | 26 | -26.558 | -23.144 | 29.859 | 1.00 | 41.95 | A | O |
| ATOM | 227 | C | GLU | A | 26 | -26.427 | -29.266 | 29.914 | 1.00 | 37.96 | A | C |
| ATOM | 228 | O | GLU | A | 26 | -25.342 | -29.809 | 29.727 | 1.00 | 37.23 | A | O |
| ATOM | 229 | N | ASP | A | 27 | -27.606 | -29.849 | 29.667 | 1.00 | 39.12 | A | N |
| ATOM | 230 | CA | ASP | A | 27 | -27.764 | -31.177 | 29.082 | 1.00 | 39.25 | A | C |
| ATOM | 231 | CB | ASP | A | 27 | -28.707 | -32.025 | 29.928 | 1.00 | 42.22 | A | C |
| ATOM | 232 | CG | ASP | A | 27 | -28.894 | -33.440 | 29.376 | 1.00 | 44.32 | A | C |
| ATOM | 233 | OD1 | ASP | A | 27 | -28.229 | -33.814 | 28.376 | 1.00 | 44.76 | A | O |
| ATOM | 234 | OD2 | ASP | A | 27 | -29.714 | -34.196 | 29.947 | 1.00 | 47.21 | A | O |
| ATOM | 235 | C | ASP | A | 27 | -28.343 | -31.030 | 27.681 | 1.00 | 37.87 | A | C |
| ATOM | 236 | O | ASP | A | 27 | -29.436 | -30.489 | 27.520 | 1.00 | 38.80 | A | O |
| ATOM | 237 | N | PRO | A | 28 | -27.615 | -31.499 | 26.654 | 1.00 | 36.28 | A | N |
| ATOM | 238 | CA | PRO | A | 28 | -28.056 | -31.269 | 25.280 | 1.00 | 35.00 | A | C |
| ATOM | 239 | CB | PRO | A | 28 | -26.913 | -31.846 | 24.438 | 1.00 | 33.33 | A | C |
| ATOM | 240 | CG | PRO | A | 28 | -26.148 | -32.681 | 25.355 | 1.00 | 34.90 | A | C |
| ATOM | 241 | CD | PRO | A | 28 | -26.269 | -32.079 | 26.693 | 1.00 | 35.29 | A | C |
| ATOM | 242 | C | PRO | A | 28 | -29.369 | -31.931 | 24.904 | 1.00 | 36.56 | A | C |
| ATOM | 243 | O | PRO | A | 28 | -30.044 | -31.465 | 23.979 | 1.00 | 35.66 | A | O |

FIG. 2-8

| | | | | | | | | | | | | |
|---|---|---|---|---|---|---|---|---|---|---|---|---|
| ATOM | 244 | N | LYS | A | 29 | -29.713 | -33.017 | 25.594 | 1.00 | 38.93 | A | N |
| ATOM | 245 | CA | LYS | A | 29 | -30.986 | -33.706 | 25.356 | 1.00 | 41.06 | A | C |
| ATOM | 246 | CB | LYS | A | 29 | -30.915 | -35.149 | 25.867 | 1.00 | 43.29 | A | C |
| ATOM | 247 | CG | LYS | A | 29 | -30.426 | -36.155 | 24.825 | 1.00 | 44.43 | A | C |
| ATOM | 248 | CD | LYS | A | 29 | -30.115 | -37.532 | 25.440 | 1.00 | 50.57 | A | C |
| ATOM | 249 | CE | LYS | A | 29 | -30.527 | -38.696 | 24.510 | 1.00 | 53.55 | A | C |
| ATOM | 250 | NZ | LYS | A | 29 | -29.737 | -38.688 | 23.223 | 1.00 | 52.09 | A | N |
| ATOM | 251 | C | LYS | A | 29 | -32.161 | -32.960 | 25.989 | 1.00 | 42.43 | A | C |
| ATOM | 252 | O | LYS | A | 29 | -33.291 | -33.106 | 25.551 | 1.00 | 43.23 | A | O |
| ATOM | 253 | N | ILE | A | 30 | -31.887 | -32.178 | 27.030 | 1.00 | 43.17 | A | N |
| ATOM | 254 | CA | ILE | A | 30 | -32.903 | -31.342 | 27.663 | 1.00 | 45.15 | A | C |
| ATOM | 255 | CB | ILE | A | 30 | -32.619 | -31.102 | 29.193 | 1.00 | 47.04 | A | C |
| ATOM | 256 | CG1 | ILE | A | 30 | -32.764 | -32.417 | 29.971 | 1.00 | 49.74 | A | C |
| ATOM | 257 | CD1 | ILE | A | 30 | -32.450 | -32.330 | 31.480 | 1.00 | 51.74 | A | C |
| ATOM | 258 | CG2 | ILE | A | 30 | -33.596 | -30.095 | 29.790 | 1.00 | 48.66 | A | C |
| ATOM | 259 | C | ILE | A | 30 | -32.980 | -30.027 | 26.885 | 1.00 | 43.30 | A | C |
| ATOM | 260 | O | ILE | A | 30 | -34.012 | -29.715 | 26.307 | 1.00 | 42.91 | A | O |
| ATOM | 261 | N | GLU | A | 31 | -31.865 | -29.293 | 26.823 | 1.00 | 41.69 | A | N |
| ATOM | 262 | CA | GLU | A | 31 | -31.827 | -27.955 | 26.167 | 1.00 | 39.92 | A | C |
| ATOM | 263 | CB | GLU | A | 31 | -30.974 | -26.960 | 26.983 | 1.00 | 39.98 | A | C |
| ATOM | 264 | CG | GLU | A | 31 | -31.647 | -26.570 | 28.318 | 1.00 | 44.32 | A | C |
| ATOM | 265 | CD | GLU | A | 31 | -31.051 | -25.334 | 28.993 | 1.00 | 47.24 | A | C |
| ATOM | 266 | OE1 | GLU | A | 31 | -31.081 | -24.241 | 28.380 | 1.00 | 48.73 | A | O |
| ATOM | 267 | OE2 | GLU | A | 31 | -30.601 | -25.446 | 30.163 | 1.00 | 49.73 | A | O |
| ATOM | 268 | C | GLU | A | 31 | -31.419 | -28.051 | 24.693 | 1.00 | 36.66 | A | C |
| ATOM | 269 | O | GLU | A | 31 | -30.393 | -27.509 | 24.240 | 1.00 | 34.58 | A | O |
| ATOM | 270 | N | THR | A | 32 | -32.268 | -28.748 | 23.947 | 1.00 | 36.29 | A | N |
| ATOM | 271 | CA | THR | A | 32 | -32.001 | -29.045 | 22.555 | 1.00 | 34.03 | A | C |
| ATOM | 272 | CB | THR | A | 32 | -33.077 | -29.979 | 21.957 | 1.00 | 35.51 | A | C |
| ATOM | 273 | OG1 | THR | A | 32 | -34.351 | -29.327 | 21.960 | 1.00 | 38.58 | A | O |
| ATOM | 274 | CG2 | THR | A | 32 | -33.179 | -31.259 | 22.746 | 1.00 | 36.42 | A | C |
| ATOM | 275 | C | THR | A | 32 | -31.864 | -27.790 | 21.697 | 1.00 | 31.73 | A | C |
| ATOM | 276 | O | THR | A | 32 | -31.005 | -27.753 | 20.813 | 1.00 | 30.28 | A | O |
| ATOM | 277 | N | ASN | A | 33 | -32.667 | -26.755 | 21.954 | 1.00 | 31.40 | A | N |
| ATOM | 278 | CA | ASN | A | 33 | -32.523 | -25.511 | 21.179 | 1.00 | 29.99 | A | C |
| ATOM | 279 | CB | ASN | A | 33 | -33.665 | -24.495 | 21.407 | 1.00 | 31.18 | A | C |
| ATOM | 280 | CG | ASN | A | 33 | -34.978 | -24.895 | 20.728 | 1.00 | 33.33 | A | C |
| ATOM | 281 | OD1 | ASN | A | 33 | -36.075 | -24.692 | 21.273 | 1.00 | 38.17 | A | O |
| ATOM | 282 | ND2 | ASN | A | 33 | -34.878 | -25.464 | 19.548 | 1.00 | 34.83 | A | N |
| ATOM | 283 | C | ASN | A | 33 | -31.173 | -24.825 | 21.406 | 1.00 | 28.09 | A | C |
| ATOM | 284 | O | ASN | A | 33 | -30.518 | -24.410 | 20.464 | 1.00 | 26.28 | A | O |
| ATOM | 285 | N | LYS | A | 34 | -30.766 | -24.683 | 22.652 | 1.00 | 28.62 | A | N |
| ATOM | 286 | CA | LYS | A | 34 | -29.479 | -24.117 | 22.917 | 1.00 | 28.25 | A | C |
| ATOM | 287 | CB | LYS | A | 34 | -29.251 | -23.923 | 24.416 | 1.00 | 30.26 | A | C |
| ATOM | 288 | CG | LYS | A | 34 | -27.921 | -23.202 | 24.718 | 1.00 | 31.82 | A | C |
| ATOM | 289 | CD | LYS | A | 34 | -27.857 | -22.715 | 26.179 | 1.00 | 36.92 | A | C |
| ATOM | 290 | CE | LYS | A | 34 | -26.500 | -22.043 | 26.503 | 1.00 | 37.85 | A | C |
| ATOM | 291 | NZ | LYS | A | 34 | -26.418 | -21.555 | 27.963 | 1.00 | 39.77 | A | N |
| ATOM | 292 | C | LYS | A | 34 | -28.386 | -24.993 | 22.313 | 1.00 | 26.26 | A | C |
| ATOM | 293 | O | LYS | A | 34 | -27.344 | -24.489 | 21.962 | 1.00 | 25.42 | A | O |
| ATOM | 294 | N | PHE | A | 35 | -28.625 | -26.303 | 22.226 | 1.00 | 26.66 | A | N |
| ATOM | 295 | CA | PHE | A | 35 | -27.695 | -27.259 | 21.570 | 1.00 | 25.28 | A | C |
| ATOM | 296 | CB | PHE | A | 35 | -28.263 | -28.688 | 21.714 | 1.00 | 26.97 | A | C |
| ATOM | 297 | CG | PHE | A | 35 | -27.340 | -29.815 | 21.283 | 1.00 | 26.72 | A | C |
| ATOM | 298 | CD1 | PHE | A | 35 | -25.971 | -29.792 | 21.536 | 1.00 | 28.20 | A | C |
| ATOM | 299 | CE1 | PHE | A | 35 | -25.145 | -30.864 | 21.151 | 1.00 | 26.51 | A | C |
| ATOM | 300 | CZ | PHE | A | 35 | -25.696 | -31.956 | 20.545 | 1.00 | 28.02 | A | C |
| ATOM | 301 | CE2 | PHE | A | 35 | -27.089 | -31.996 | 20.296 | 1.00 | 27.80 | A | C |
| ATOM | 302 | CD2 | PHE | A | 35 | -27.882 | -30.953 | 20.689 | 1.00 | 27.70 | A | C |
| ATOM | 303 | C | PHE | A | 35 | -27.484 | -26.888 | 20.106 | 1.00 | 23.16 | A | C |
| ATOM | 304 | O | PHE | A | 35 | -26.327 | -26.742 | 19.678 | 1.00 | 21.73 | A | O |
| ATOM | 305 | N | ALA | A | 36 | -28.584 | -26.693 | 19.365 | 1.00 | 22.28 | A | N |
| ATOM | 306 | CA | ALA | A | 36 | -28.507 | -26.232 | 17.959 | 1.00 | 21.27 | A | C |

FIG. 2-9

| | | | | | | | | | | | | |
|---|---|---|---|---|---|---|---|---|---|---|---|---|
| ATOM | 307 | CB | ALA | A | 36 | -29.875 | -26.152 | 17.307 | 1.00 | 21.28 | A | C |
| ATOM | 308 | C | ALA | A | 36 | -27.784 | -24.891 | 17.805 | 1.00 | 20.58 | A | C |
| ATOM | 309 | O | ALA | A | 36 | -26.921 | -24.739 | 16.907 | 1.00 | 19.84 | A | O |
| ATOM | 310 | N | ALA | A | 37 | -28.121 | -23.929 | 18.662 | 1.00 | 20.84 | A | N |
| ATOM | 311 | CA | ALA | A | 37 | -27.501 | -22.604 | 18.566 | 1.00 | 20.81 | A | C |
| ATOM | 312 | CB | ALA | A | 37 | -28.131 | -21.587 | 19.582 | 1.00 | 20.93 | A | C |
| ATOM | 313 | C | ALA | A | 37 | -25.998 | -22.715 | 18.814 | 1.00 | 19.61 | A | C |
| ATOM | 314 | O | ALA | A | 37 | -25.194 | -22.007 | 18.204 | 1.00 | 19.55 | A | O |
| ATOM | 315 | N | ILE | A | 38 | -25.623 | -23.573 | 19.743 | 1.00 | 19.45 | A | N |
| ATOM | 316 | CA | ILE | A | 38 | -24.243 | -23.656 | 20.083 | 1.00 | 19.17 | A | C |
| ATOM | 317 | CB | ILE | A | 38 | -24.019 | -24.341 | 21.439 | 1.00 | 20.89 | A | C |
| ATOM | 318 | CG1 | ILE | A | 38 | -24.493 | -23.419 | 22.551 | 1.00 | 21.15 | A | C |
| ATOM | 319 | CD1 | ILE | A | 38 | -24.610 | -24.148 | 23.852 | 1.00 | 24.96 | A | C |
| ATOM | 320 | CG2 | ILE | A | 38 | -22.500 | -24.733 | 21.641 | 1.00 | 18.93 | A | C |
| ATOM | 321 | C | ILE | A | 38 | -23.488 | -24.341 | 18.960 | 1.00 | 17.60 | A | C |
| ATOM | 322 | O | ILE | A | 38 | -22.420 | -23.884 | 18.630 | 1.00 | 17.30 | A | O |
| ATOM | 323 | N | CYS | A | 39 | -24.028 | -25.414 | 18.373 | 1.00 | 17.62 | A | N |
| ATOM | 324 | CA | CYS | A | 39 | -23.441 | -25.979 | 17.137 | 1.00 | 16.85 | A | C |
| ATOM | 325 | CB | CYS | A | 39 | -24.222 | -27.186 | 16.634 | 1.00 | 18.19 | A | C |
| ATOM | 326 | SG | CYS | A | 39 | -24.155 | -28.635 | 17.642 | 1.00 | 15.81 | A | S |
| ATOM | 327 | C | CYS | A | 39 | -23.377 | -24.965 | 15.982 | 1.00 | 16.18 | A | C |
| ATOM | 328 | O | CYS | A | 39 | -22.406 | -24.910 | 15.261 | 1.00 | 16.46 | A | O |
| ATOM | 329 | N | THR | A | 40 | -24.384 | -24.137 | 15.825 | 1.00 | 16.58 | A | N |
| ATOM | 330 | CA | THR | A | 40 | -24.388 | -23.191 | 14.721 | 1.00 | 16.57 | A | C |
| ATOM | 331 | CB | THR | A | 40 | -25.731 | -22.469 | 14.608 | 1.00 | 17.81 | A | C |
| ATOM | 332 | OG1 | THR | A | 40 | -26.813 | -23.438 | 14.570 | 1.00 | 17.65 | A | O |
| ATOM | 333 | CG2 | THR | A | 40 | -25.734 | -21.609 | 13.345 | 1.00 | 17.88 | A | C |
| ATOM | 334 | C | THR | A | 40 | -23.269 | -22.186 | 14.865 | 1.00 | 16.76 | A | C |
| ATOM | 335 | O | THR | A | 40 | -22.500 | -21.963 | 13.946 | 1.00 | 18.19 | A | O |
| ATOM | 336 | N | HIS | A | 41 | -23.156 | -21.591 | 16.039 | 1.00 | 17.23 | A | N |
| ATOM | 337 | CA | HIS | A | 41 | -22.100 | -20.648 | 16.340 | 1.00 | 16.15 | A | C |
| ATOM | 338 | CB | HIS | A | 41 | -22.220 | -20.238 | 17.784 | 1.00 | 16.60 | A | C |
| ATOM | 339 | CG | HIS | A | 41 | -21.284 | -19.148 | 18.190 | 1.00 | 15.39 | A | C |
| ATOM | 340 | ND1 | HIS | A | 41 | -20.070 | -19.397 | 18.797 | 1.00 | 12.33 | A | N |
| ATOM | 341 | CE1 | HIS | A | 41 | -19.486 | -18.246 | 19.071 | 1.00 | 14.61 | A | C |
| ATOM | 342 | NE2 | HIS | A | 41 | -20.268 | -17.264 | 18.666 | 1.00 | 14.41 | A | N |
| ATOM | 343 | CD2 | HIS | A | 41 | -21.403 | -17.803 | 18.114 | 1.00 | 14.71 | A | C |
| ATOM | 344 | C | HIS | A | 41 | -20.726 | -21.233 | 16.102 | 1.00 | 16.02 | A | C |
| ATOM | 345 | O | HIS | A | 41 | -19.892 | -20.616 | 15.438 | 1.00 | 16.87 | A | O |
| ATOM | 346 | N | LEU | A | 42 | -20.475 | -22.422 | 16.625 | 1.00 | 16.35 | A | N |
| ATOM | 347 | CA | LEU | A | 42 | -19.175 | -23.073 | 16.432 | 1.00 | 15.82 | A | C |
| ATOM | 348 | CB | LEU | A | 42 | -19.107 | -24.409 | 17.136 | 1.00 | 16.48 | A | C |
| ATOM | 349 | CG | LEU | A | 42 | -18.593 | -24.388 | 18.590 | 1.00 | 18.28 | A | C |
| ATOM | 350 | CD1 | LEU | A | 42 | -19.483 | -25.258 | 19.436 | 1.00 | 20.28 | A | C |
| ATOM | 351 | CD2 | LEU | A | 42 | -17.168 | -24.838 | 18.695 | 1.00 | 13.65 | A | C |
| ATOM | 352 | C | LEU | A | 42 | -18.942 | -23.273 | 14.959 | 1.00 | 15.64 | A | C |
| ATOM | 353 | O | LEU | A | 42 | -17.877 | -22.885 | 14.470 | 1.00 | 16.50 | A | O |
| ATOM | 354 | N | GLU | A | 43 | -19.936 | -23.776 | 14.211 | 1.00 | 15.26 | A | N |
| ATOM | 355 | CA | GLU | A | 43 | -19.687 | -23.932 | 12.796 | 1.00 | 16.02 | A | C |
| ATOM | 356 | CB | GLU | A | 43 | -20.840 | -24.582 | 12.009 | 1.00 | 18.04 | A | C |
| ATOM | 357 | CG | GLU | A | 43 | -20.263 | -25.433 | 10.859 | 1.00 | 20.41 | A | C |
| ATOM | 358 | CD | GLU | A | 43 | -21.292 | -26.232 | 10.118 | 1.00 | 26.88 | A | C |
| ATOM | 359 | OE1 | GLU | A | 43 | -22.217 | -25.602 | 9.579 | 1.00 | 26.20 | A | O |
| ATOM | 360 | OE2 | GLU | A | 43 | -21.148 | -27.495 | 10.049 | 1.00 | 33.05 | A | O |
| ATOM | 361 | C | GLU | A | 43 | -19.272 | -22.616 | 12.131 | 1.00 | 15.14 | A | C |
| ATOM | 362 | O | GLU | A | 43 | -18.337 | -22.594 | 11.351 | 1.00 | 14.71 | A | O |
| ATOM | 363 | N | VAL | A | 44 | -19.940 | -21.521 | 12.470 | 1.00 | 14.64 | A | N |
| ATOM | 364 | CA | VAL | A | 44 | -19.607 | -20.259 | 11.868 | 1.00 | 14.99 | A | C |
| ATOM | 365 | CB | VAL | A | 44 | -20.672 | -19.222 | 12.222 | 1.00 | 16.08 | A | C |
| ATOM | 366 | CG1 | VAL | A | 44 | -20.278 | -17.844 | 11.727 | 1.00 | 15.24 | A | C |
| ATOM | 367 | CG2 | VAL | A | 44 | -22.015 | -19.641 | 11.610 | 1.00 | 16.62 | A | C |
| ATOM | 368 | C | VAL | A | 44 | -18.174 | -19.808 | 12.219 | 1.00 | 15.20 | A | C |
| ATOM | 369 | O | VAL | A | 44 | -17.426 | -19.405 | 11.340 | 1.00 | 15.01 | A | O |

FIG. 2-10

| | | | | | | | | | | | | |
|---|---|---|---|---|---|---|---|---|---|---|---|---|
| ATOM | 370 | N | CYS | A | 45 | -17.787 | -19.943 | 13.492 | 1.00 | 15.02 | A | N |
| ATOM | 371 | CA | CYS | A | 45 | -16.418 | -19.703 | 13.917 | 1.00 | 15.09 | A | C |
| ATOM | 372 | CB | CYS | A | 45 | -16.237 | -20.043 | 15.393 | 1.00 | 15.14 | A | C |
| ATOM | 373 | SG | CYS | A | 45 | -17.126 | -18.860 | 16.494 | 1.00 | 17.74 | A | S |
| ATOM | 374 | C | CYS | A | 45 | -15.405 | -20.476 | 13.081 | 1.00 | 15.35 | A | C |
| ATOM | 375 | O | CYS | A | 45 | -14.442 | -19.893 | 12.640 | 1.00 | 14.54 | A | O |
| ATOM | 376 | N | PHE | A | 46 | -15.616 | -21.780 | 12.877 | 1.00 | 16.14 | A | N |
| ATOM | 377 | CA | PHE | A | 46 | -14.668 | -22.606 | 12.105 | 1.00 | 16.71 | A | C |
| ATOM | 378 | CB | PHE | A | 46 | -14.859 | -24.095 | 12.351 | 1.00 | 16.76 | A | C |
| ATOM | 379 | CG | PHE | A | 46 | -14.377 | -24.544 | 13.710 | 1.00 | 18.56 | A | C |
| ATOM | 380 | CD1 | PHE | A | 46 | -13.031 | -24.565 | 14.013 | 1.00 | 16.99 | A | C |
| ATOM | 381 | CE1 | PHE | A | 46 | -12.581 | -24.945 | 15.277 | 1.00 | 18.86 | A | C |
| ATOM | 382 | CZ | PHE | A | 46 | -13.459 | -25.320 | 16.246 | 1.00 | 18.27 | A | C |
| ATOM | 383 | CE2 | PHE | A | 46 | -14.819 | -25.313 | 15.967 | 1.00 | 21.68 | A | C |
| ATOM | 384 | CD2 | PHE | A | 46 | -15.279 | -24.934 | 14.699 | 1.00 | 20.78 | A | C |
| ATOM | 385 | C | PHE | A | 46 | -14.764 | -22.334 | 10.620 | 1.00 | 17.91 | A | C |
| ATOM | 386 | O | PHE | A | 46 | -13.767 | -22.384 | 9.909 | 1.00 | 18.58 | A | O |
| ATOM | 387 | N | MET | A | 47 | -15.958 | -22.029 | 10.132 | 1.00 | 18.70 | A | N |
| ATOM | 388 | CA | MET | A | 47 | -16.070 | -21.621 | 8.740 | 1.00 | 19.52 | A | C |
| ATOM | 389 | CB | MET | A | 47 | -17.515 | -21.445 | 8.333 | 1.00 | 19.81 | A | C |
| ATOM | 390 | CG | MET | A | 47 | -18.260 | -22.739 | 8.144 | 1.00 | 20.59 | A | C |
| ATOM | 391 | SD | MET | A | 47 | -19.892 | -22.374 | 7.501 | 1.00 | 21.22 | A | S |
| ATOM | 392 | CE | MET | A | 47 | -19.486 | -22.150 | 5.806 | 1.00 | 22.09 | A | C |
| ATOM | 393 | C | MET | A | 47 | -15.321 | -20.325 | 8.506 | 1.00 | 19.33 | A | C |
| ATOM | 394 | O | MET | A | 47 | -14.673 | -20.161 | 7.502 | 1.00 | 20.61 | A | O |
| ATOM | 395 | N | TYR | A | 48 | -15.412 | -19.408 | 9.445 | 1.00 | 19.41 | A | N |
| ATOM | 396 | CA | TYR | A | 48 | -14.788 | -18.082 | 9.295 | 1.00 | 20.50 | A | C |
| ATOM | 397 | CB | TYR | A | 48 | -15.066 | -17.243 | 10.560 | 1.00 | 19.66 | A | C |
| ATOM | 398 | CG | TYR | A | 48 | -14.976 | -15.735 | 10.449 | 1.00 | 19.41 | A | C |
| ATOM | 399 | CD1 | TYR | A | 48 | -16.121 | -14.956 | 10.339 | 1.00 | 18.97 | A | C |
| ATOM | 400 | CE1 | TYR | A | 48 | -16.057 | -13.595 | 10.270 | 1.00 | 18.30 | A | C |
| ATOM | 401 | CZ | TYR | A | 48 | -14.851 | -12.956 | 10.353 | 1.00 | 18.88 | A | C |
| ATOM | 402 | OH | TYR | A | 48 | -14.814 | -11.588 | 10.293 | 1.00 | 19.64 | A | O |
| ATOM | 403 | CE2 | TYR | A | 48 | -13.696 | -13.678 | 10.485 | 1.00 | 20.51 | A | C |
| ATOM | 404 | CD2 | TYR | A | 48 | -13.764 | -15.075 | 10.553 | 1.00 | 21.06 | A | C |
| ATOM | 405 | C | TYR | A | 48 | -13.268 | -18.297 | 9.048 | 1.00 | 21.22 | A | C |
| ATOM | 406 | O | TYR | A | 48 | -12.646 | -17.587 | 8.249 | 1.00 | 21.95 | A | O |
| ATOM | 407 | N | SER | A | 49 | -12.715 | -19.323 | 9.700 | 1.00 | 20.73 | A | N |
| ATOM | 408 | CA | SER | A | 49 | -11.292 | -19.622 | 9.643 | 1.00 | 21.92 | A | C |
| ATOM | 409 | CB | SER | A | 49 | -10.869 | -20.369 | 10.904 | 1.00 | 21.47 | A | C |
| ATOM | 410 | OG | SER | A | 49 | -9.881 | -21.354 | 10.617 | 1.00 | 24.24 | A | O |
| ATOM | 411 | C | SER | A | 49 | -10.851 | -20.398 | 8.404 | 1.00 | 22.71 | A | C |
| ATOM | 412 | O | SER | A | 49 | -9.750 | -20.200 | 7.938 | 1.00 | 23.74 | A | O |
| ATOM | 413 | N | ASP | A | 50 | -11.697 | -21.284 | 7.891 | 1.00 | 23.37 | A | N |
| ATOM | 414 | CA | ASP | A | 50 | -11.408 | -22.051 | 6.690 | 1.00 | 25.48 | A | C |
| ATOM | 415 | CB | ASP | A | 50 | -12.703 | -22.647 | 6.137 | 1.00 | 26.38 | A | C |
| ATOM | 416 | CG | ASP | A | 50 | -13.187 | -23.856 | 6.916 | 1.00 | 26.94 | A | C |
| ATOM | 417 | OD1 | ASP | A | 50 | -12.375 | -24.528 | 7.527 | 1.00 | 27.01 | A | O |
| ATOM | 418 | OD2 | ASP | A | 50 | -14.401 | -24.151 | 6.884 | 1.00 | 32.80 | A | O |
| ATOM | 419 | C | ASP | A | 50 | -10.777 | -21.232 | 5.556 | 1.00 | 27.02 | A | C |
| ATOM | 420 | O | ASP | A | 50 | -11.207 | -20.127 | 5.236 | 1.00 | 27.66 | A | O |
| ATOM | 421 | N | PHE | A | 51 | -9.762 | -21.795 | 4.928 | 1.00 | 28.32 | A | N |
| ATOM | 422 | CA | PHE | A | 51 | -9.218 | -21.253 | 3.680 | 1.00 | 30.00 | A | C |
| ATOM | 423 | CB | PHE | A | 51 | -10.300 | -20.841 | 2.666 | 1.00 | 30.77 | A | C |
| ATOM | 424 | CG | PHE | A | 51 | -11.406 | -21.809 | 2.519 | 1.00 | 31.84 | A | C |
| ATOM | 425 | CD1 | PHE | A | 51 | -11.146 | -23.165 | 2.385 | 1.00 | 35.15 | A | C |
| ATOM | 426 | CE1 | PHE | A | 51 | -12.193 | -24.068 | 2.237 | 1.00 | 35.39 | A | C |
| ATOM | 427 | CZ | PHE | A | 51 | -13.507 | -23.603 | 2.208 | 1.00 | 34.54 | A | C |
| ATOM | 428 | CE2 | PHE | A | 51 | -13.766 | -22.247 | 2.328 | 1.00 | 32.66 | A | C |
| ATOM | 429 | CD2 | PHE | A | 51 | -12.723 | -21.364 | 2.486 | 1.00 | 32.53 | A | C |
| ATOM | 430 | C | PHE | A | 51 | -8.333 | -20.059 | 3.851 | 1.00 | 29.55 | A | C |
| ATOM | 431 | O | PHE | A | 51 | -7.718 | -19.646 | 2.868 | 1.00 | 31.06 | A | O |
| ATOM | 432 | N | HIS | A | 52 | -8.270 | -19.511 | 5.063 | 1.00 | 27.47 | A | N |

FIG. 2-11

| | | | | | | | | | | | | |
|---|---|---|---|---|---|---|---|---|---|---|---|---|
| ATOM | 433 | CA | HIS | A | 52 | -7.437 | -18.330 | 5.348 | 1.00 | 27.94 | A | C |
| ATOM | 434 | CB | HIS | A | 52 | -8.221 | -17.342 | 6.196 | 1.00 | 26.83 | A | C |
| ATOM | 435 | CG | HIS | A | 52 | -9.395 | -16.764 | 5.476 | 1.00 | 28.10 | A | C |
| ATOM | 436 | ND1 | HIS | A | 52 | -9.269 | -15.736 | 4.564 | 1.00 | 30.46 | A | N |
| ATOM | 437 | CE1 | HIS | A | 52 | -10.456 | -15.446 | 4.067 | 1.00 | 30.64 | A | C |
| ATOM | 438 | NE2 | HIS | A | 52 | -11.344 | -16.264 | 4.609 | 1.00 | 29.75 | A | N |
| ATOM | 439 | CD2 | HIS | A | 52 | -10.704 | -17.111 | 5.478 | 1.00 | 27.35 | A | C |
| ATOM | 440 | C | HIS | A | 52 | -6.104 | -18.662 | 6.022 | 1.00 | 27.57 | A | C |
| ATOM | 441 | O | HIS | A | 52 | -6.058 | -19.355 | 7.020 | 1.00 | 26.50 | A | O |
| ATOM | 442 | N | PHE | A | 53 | -5.007 | -18.188 | 5.445 | 1.00 | 28.94 | A | N |
| ATOM | 443 | CA | PHE | A | 53 | -3.668 | -18.522 | 5.950 | 1.00 | 28.70 | A | C |
| ATOM | 444 | CB | PHE | A | 53 | -3.054 | -19.634 | 5.084 | 1.00 | 30.26 | A | C |
| ATOM | 445 | CG | PHE | A | 53 | -3.883 | -20.872 | 5.043 | 1.00 | 27.97 | A | C |
| ATOM | 446 | CD1 | PHE | A | 53 | -3.801 | -21.797 | 6.065 | 1.00 | 26.02 | A | C |
| ATOM | 447 | CE1 | PHE | A | 53 | -4.595 | -22.938 | 6.040 | 1.00 | 27.12 | A | C |
| ATOM | 448 | CZ | PHE | A | 53 | -5.502 | -23.147 | 4.976 | 1.00 | 27.38 | A | C |
| ATOM | 449 | CE2 | PHE | A | 53 | -5.603 | -22.220 | 3.978 | 1.00 | 26.47 | A | C |
| ATOM | 450 | CD2 | PHE | A | 53 | -4.796 | -21.080 | 4.012 | 1.00 | 28.15 | A | C |
| ATOM | 451 | C | PHE | A | 53 | -2.755 | -17.319 | 5.991 | 1.00 | 29.18 | A | C |
| ATOM | 452 | O | PHE | A | 53 | -3.152 | -16.225 | 5.633 | 1.00 | 28.10 | A | O |
| ATOM | 453 | N | ILE | A | 54 | -1.540 | -17.540 | 6.474 | 1.00 | 30.67 | A | N |
| ATOM | 454 | CA | ILE | A | 54 | -0.461 | -16.534 | 6.439 | 1.00 | 33.09 | A | C |
| ATOM | 455 | CB | ILE | A | 54 | -0.171 | -16.011 | 7.871 | 1.00 | 32.95 | A | C |
| ATOM | 456 | CG1 | ILE | A | 54 | -1.306 | -15.081 | 8.306 | 1.00 | 32.29 | A | C |
| ATOM | 457 | CD1 | ILE | A | 54 | -1.222 | -14.731 | 9.768 | 1.00 | 33.16 | A | C |
| ATOM | 458 | CG2 | ILE | A | 54 | 1.171 | -15.266 | 7.959 | 1.00 | 34.00 | A | C |
| ATOM | 459 | C | ILE | A | 54 | 0.781 | -17.171 | 5.828 | 1.00 | 35.14 | A | C |
| ATOM | 460 | O | ILE | A | 54 | 1.062 | -18.342 | 6.078 | 1.00 | 34.60 | A | O |
| ATOM | 461 | N | ASP | A | 55 | 1.509 | -16.409 | 5.018 | 1.00 | 38.12 | A | N |
| ATOM | 462 | CA | ASP | A | 55 | 2.678 | -16.934 | 4.304 | 1.00 | 40.92 | A | C |
| ATOM | 463 | CB | ASP | A | 55 | 2.691 | -16.424 | 2.857 | 1.00 | 42.73 | A | C |
| ATOM | 464 | CG | ASP | A | 55 | 3.250 | -15.033 | 2.723 | 1.00 | 44.02 | A | C |
| ATOM | 465 | OD1 | ASP | A | 55 | 3.704 | -14.675 | 1.612 | 1.00 | 45.40 | A | O |
| ATOM | 466 | OD2 | ASP | A | 55 | 3.246 | -14.302 | 3.725 | 1.00 | 43.03 | A | O |
| ATOM | 467 | C | ASP | A | 55 | 3.943 | -16.580 | 5.094 | 1.00 | 43.06 | A | C |
| ATOM | 468 | O | ASP | A | 55 | 3.813 | -16.109 | 6.219 | 1.00 | 41.80 | A | O |
| ATOM | 469 | N | GLU | A | 56 | 5.138 | -16.801 | 4.538 | 1.00 | 46.51 | A | N |
| ATOM | 470 | CA | GLU | A | 56 | 6.377 | -16.603 | 5.303 | 1.00 | 49.50 | A | C |
| ATOM | 471 | CB | GLU | A | 56 | 7.627 | -17.215 | 4.620 | 1.00 | 53.21 | A | C |
| ATOM | 472 | CG | GLU | A | 56 | 7.558 | -18.663 | 4.150 | 1.00 | 54.84 | A | C |
| ATOM | 473 | CD | GLU | A | 56 | 7.256 | -19.677 | 5.256 | 1.00 | 56.52 | A | C |
| ATOM | 474 | OE1 | GLU | A | 56 | 6.878 | -19.298 | 6.393 | 1.00 | 56.80 | A | O |
| ATOM | 475 | OE2 | GLU | A | 56 | 7.376 | -20.889 | 4.971 | 1.00 | 59.29 | A | O |
| ATOM | 476 | C | GLU | A | 56 | 6.732 | -15.157 | 5.629 | 1.00 | 51.05 | A | C |
| ATOM | 477 | O | GLU | A | 56 | 7.622 | -14.945 | 6.451 | 1.00 | 52.87 | A | O |
| ATOM | 478 | N | ARG | A | 57 | 6.115 | -14.171 | 4.976 | 1.00 | 51.60 | A | N |
| ATOM | 479 | CA | ARG | A | 57 | 6.412 | -12.744 | 5.257 | 1.00 | 52.92 | A | C |
| ATOM | 480 | CB | ARG | A | 57 | 6.699 | -11.942 | 3.961 | 1.00 | 55.63 | A | C |
| ATOM | 481 | CG | ARG | A | 57 | 8.197 | -11.818 | 3.571 | 1.00 | 60.48 | A | C |
| ATOM | 482 | CD | ARG | A | 57 | 8.607 | -10.393 | 3.084 | 1.00 | 63.64 | A | C |
| ATOM | 483 | NE | ARG | A | 57 | 10.012 | -10.323 | 2.632 | 1.00 | 68.09 | A | N |
| ATOM | 484 | CZ | ARG | A | 57 | 10.738 | -9.198 | 2.526 | 1.00 | 72.13 | A | C |
| ATOM | 485 | NH1 | ARG | A | 57 | 10.205 | -8.021 | 2.853 | 1.00 | 72.40 | A | N |
| ATOM | 486 | NH2 | ARG | A | 57 | 12.011 | -9.233 | 2.095 | 1.00 | 74.08 | A | N |
| ATOM | 487 | C | ARG | A | 57 | 5.298 | -12.055 | 6.052 | 1.00 | 50.34 | A | C |
| ATOM | 488 | O | ARG | A | 57 | 5.345 | -10.841 | 6.256 | 1.00 | 52.01 | A | O |
| ATOM | 489 | N | GLY | A | 58 | 4.301 | -12.811 | 6.496 | 1.00 | 46.96 | A | N |
| ATOM | 490 | CA | GLY | A | 58 | 3.133 | -12.227 | 7.169 | 1.00 | 44.46 | A | C |
| ATOM | 491 | C | GLY | A | 58 | 1.970 | -11.773 | 6.285 | 1.00 | 43.35 | A | C |
| ATOM | 492 | O | GLY | A | 58 | 0.990 | -11.190 | 6.778 | 1.00 | 41.65 | A | O |
| ATOM | 493 | N | GLU | A | 59 | 2.051 | -12.058 | 4.989 | 1.00 | 43.75 | A | N |
| ATOM | 494 | CA | GLU | A | 59 | 0.999 | -11.670 | 4.052 | 1.00 | 43.17 | A | C |
| ATOM | 495 | CB | GLU | A | 59 | 1.551 | -11.641 | 2.604 | 1.00 | 46.48 | A | C |

FIG. 2-12

| | | | | | | | | | | | | |
|---|---|---|---|---|---|---|---|---|---|---|---|---|
| ATOM | 496 | CG | GLU | A | 59 | 2.920 | -10.834 | 2.475 | 1.00 | 51.44 | A | C |
| ATOM | 497 | CD | GLU | A | 59 | 3.599 | -10.849 | 1.058 | 1.00 | 57.39 | A | C |
| ATOM | 498 | OE1 | GLU | A | 59 | 4.797 | -11.237 | 0.973 | 1.00 | 60.23 | A | O |
| ATOM | 499 | OE2 | GLU | A | 59 | 2.962 | -10.439 | 0.048 | 1.00 | 58.61 | A | O |
| ATOM | 500 | C | GLU | A | 59 | -0.177 | -12.635 | 4.223 | 1.00 | 39.22 | A | C |
| ATOM | 501 | O | GLU | A | 59 | 0.008 | -13.845 | 4.367 | 1.00 | 37.74 | A | O |
| ATOM | 502 | N | SER | A | 60 | -1.389 | -12.098 | 4.273 | 1.00 | 37.25 | A | N |
| ATOM | 503 | CA | SER | A | 60 | -2.576 | -12.951 | 4.386 | 1.00 | 34.87 | A | C |
| ATOM | 504 | CB | SER | A | 60 | -3.782 | -12.167 | 4.899 | 1.00 | 33.32 | A | C |
| ATOM | 505 | OG | SER | A | 60 | -4.110 | -11.118 | 3.999 | 1.00 | 36.85 | A | O |
| ATOM | 506 | C | SER | A | 60 | -2.858 | -13.579 | 3.026 | 1.00 | 35.08 | A | C |
| ATOM | 507 | O | SER | A | 60 | -2.465 | -13.038 | 1.996 | 1.00 | 37.89 | A | O |
| ATOM | 508 | N | ILE | A | 61 | -3.507 | -14.729 | 3.023 | 1.00 | 33.23 | A | N |
| ATOM | 509 | CA | ILE | A | 61 | -3.706 | -15.477 | 1.805 | 1.00 | 34.51 | A | C |
| ATOM | 510 | CB | ILE | A | 61 | -2.431 | -16.291 | 1.448 | 1.00 | 36.25 | A | C |
| ATOM | 511 | CG1 | ILE | A | 61 | -2.151 | -17.423 | 2.422 | 1.00 | 34.55 | A | C |
| ATOM | 512 | CD1 | ILE | A | 61 | -0.658 | -17.912 | 2.382 | 1.00 | 34.18 | A | C |
| ATOM | 513 | CG2 | ILE | A | 61 | -1.208 | -15.397 | 1.466 | 1.00 | 39.05 | A | C |
| ATOM | 514 | C | ILE | A | 61 | -4.945 | -16.371 | 1.847 | 1.00 | 33.17 | A | C |
| ATOM | 515 | O | ILE | A | 61 | -5.222 | -17.023 | 2.846 | 1.00 | 30.98 | A | O |
| ATOM | 516 | N | ILE | A | 62 | -5.677 | -16.400 | 0.737 | 1.00 | 35.18 | A | N |
| ATOM | 517 | CA | ILE | A | 62 | -6.905 | -17.171 | 0.617 | 1.00 | 34.43 | A | C |
| ATOM | 518 | CB | ILE | A | 62 | -8.055 | -16.309 | 0.032 | 1.00 | 35.05 | A | C |
| ATOM | 519 | CG1 | ILE | A | 62 | -8.295 | -15.087 | 0.940 | 1.00 | 34.22 | A | C |
| ATOM | 520 | CD1 | ILE | A | 62 | -9.396 | -14.138 | 0.465 | 1.00 | 34.75 | A | C |
| ATOM | 521 | CG2 | ILE | A | 62 | -9.336 | -17.160 | -0.173 | 1.00 | 30.76 | A | C |
| ATOM | 522 | C | ILE | A | 62 | -6.646 | -18.353 | -0.293 | 1.00 | 37.27 | A | C |
| ATOM | 523 | O | ILE | A | 62 | -6.224 | -18.164 | -1.429 | 1.00 | 37.86 | A | O |
| ATOM | 524 | N | VAL | A | 63 | -6.936 | -19.562 | 0.221 | 1.00 | 38.57 | A | N |
| ATOM | 525 | CA | VAL | A | 63 | -6.563 | -20.838 | -0.426 | 1.00 | 41.42 | A | C |
| ATOM | 526 | CB | VAL | A | 63 | -5.277 | -21.378 | 0.201 | 1.00 | 41.01 | A | C |
| ATOM | 527 | CG1 | VAL | A | 63 | -4.850 | -22.657 | -0.492 | 1.00 | 43.16 | A | C |
| ATOM | 528 | CG2 | VAL | A | 63 | -4.173 | -20.337 | 0.137 | 1.00 | 42.58 | A | C |
| ATOM | 529 | C | VAL | A | 63 | -7.619 | -21.947 | -0.270 | 1.00 | 42.62 | A | C |
| ATOM | 530 | O | VAL | A | 63 | -7.934 | -22.335 | 0.869 | 1.00 | 40.60 | A | O |
| ATOM | 531 | N | GLU | A | 64 | -8.126 | -22.494 | -1.393 | 1.00 | 46.80 | A | N |
| ATOM | 532 | CA | GLU | A | 64 | -9.155 | -23.586 | -1.356 | 1.00 | 47.65 | A | C |
| ATOM | 533 | CB | GLU | A | 64 | -9.568 | -24.028 | -2.768 | 1.00 | 50.96 | A | C |
| ATOM | 534 | CG | GLU | A | 64 | -10.681 | -23.204 | -3.401 | 1.00 | 54.65 | A | C |
| ATOM | 535 | CD | GLU | A | 64 | -11.841 | -22.925 | -2.443 | 1.00 | 56.63 | A | C |
| ATOM | 536 | OE1 | GLU | A | 64 | -12.296 | -23.875 | -1.733 | 1.00 | 58.48 | A | O |
| ATOM | 537 | OE2 | GLU | A | 64 | -12.277 | -21.744 | -2.396 | 1.00 | 56.99 | A | O |
| ATOM | 538 | C | GLU | A | 64 | -8.729 | -24.829 | -0.565 | 1.00 | 47.56 | A | C |
| ATOM | 539 | O | GLU | A | 64 | -8.195 | -25.801 | -1.128 | 1.00 | 50.63 | A | O |
| ATOM | 540 | N | LEU | A | 71 | 0.780 | -27.601 | 4.107 | 1.00 | 40.62 | A | N |
| ATOM | 541 | CA | LEU | A | 71 | 0.706 | -27.176 | 5.491 | 1.00 | 38.62 | A | C |
| ATOM | 542 | CB | LEU | A | 71 | 1.727 | -27.947 | 6.335 | 1.00 | 40.34 | A | C |
| ATOM | 543 | CG | LEU | A | 71 | 1.696 | -29.475 | 6.258 | 1.00 | 41.81 | A | C |
| ATOM | 544 | CD1 | LEU | A | 71 | 2.947 | -30.014 | 6.868 | 1.00 | 44.76 | A | C |
| ATOM | 545 | CD2 | LEU | A | 71 | 0.486 | -30.066 | 6.934 | 1.00 | 38.80 | A | C |
| ATOM | 546 | C | LEU | A | 71 | 1.037 | -25.700 | 5.576 | 1.00 | 37.67 | A | C |
| ATOM | 547 | O | LEU | A | 71 | 2.038 | -25.272 | 5.015 | 1.00 | 39.52 | A | O |
| ATOM | 548 | N | LEU | A | 72 | 0.218 | -24.939 | 6.303 | 1.00 | 34.72 | A | N |
| ATOM | 549 | CA | LEU | A | 72 | 0.293 | -23.478 | 6.293 | 1.00 | 34.00 | A | C |
| ATOM | 550 | CB | LEU | A | 72 | -0.677 | -22.963 | 5.250 | 1.00 | 33.74 | A | C |
| ATOM | 551 | CG | LEU | A | 72 | -0.154 | -23.121 | 3.834 | 1.00 | 36.99 | A | C |
| ATOM | 552 | CD1 | LEU | A | 72 | -1.230 | -22.825 | 2.806 | 1.00 | 37.53 | A | C |
| ATOM | 553 | CD2 | LEU | A | 72 | 1.057 | -22.236 | 3.666 | 1.00 | 39.80 | A | C |
| ATOM | 554 | C | LEU | A | 72 | -0.075 | -22.869 | 7.618 | 1.00 | 31.35 | A | C |
| ATOM | 555 | O | LEU | A | 72 | -0.939 | -23.406 | 8.274 | 1.00 | 30.25 | A | O |
| ATOM | 556 | N | LYS | A | 73 | 0.537 | -21.744 | 8.018 | 1.00 | 31.38 | A | N |
| ATOM | 557 | CA | LYS | A | 73 | 0.094 | -21.078 | 9.284 | 1.00 | 29.65 | A | C |
| ATOM | 558 | CB | LYS | A | 73 | 0.986 | -19.934 | 9.753 | 1.00 | 30.49 | A | C |

FIG. 2-13

| | | | | | | | | | | | | |
|---|---|---|---|---|---|---|---|---|---|---|---|---|
| ATOM | 559 | CG | LYS | A | 73 | 2.505 | -20.207 | 9.780 | 1.00 | 36.77 | A | C |
| ATOM | 560 | CD | LYS | A | 73 | 3.335 | -18.896 | 9.514 | 1.00 | 40.46 | A | C |
| ATOM | 561 | CE | LYS | A | 73 | 4.764 | -19.184 | 9.082 | 1.00 | 45.72 | A | C |
| ATOM | 562 | NZ | LYS | A | 73 | 5.681 | -17.976 | 9.164 | 1.00 | 48.12 | A | N |
| ATOM | 563 | C | LYS | A | 73 | -1.326 | -20.529 | 9.101 | 1.00 | 26.75 | A | C |
| ATOM | 564 | O | LYS | A | 73 | -1.584 | -19.752 | 8.168 | 1.00 | 26.71 | A | O |
| ATOM | 565 | N | HIS | A | 74 | -2.227 | -20.952 | 9.984 | 1.00 | 24.13 | A | N |
| ATOM | 566 | CA | HIS | A | 74 | -3.587 | -20.426 | 10.037 | 1.00 | 22.22 | A | C |
| ATOM | 567 | CB | HIS | A | 74 | -4.400 | -21.157 | 11.104 | 1.00 | 20.82 | A | C |
| ATOM | 568 | CG | HIS | A | 74 | -4.543 | -22.609 | 10.823 | 1.00 | 20.84 | A | C |
| ATOM | 569 | ND1 | HIS | A | 74 | -5.595 | -23.114 | 10.104 | 1.00 | 22.21 | A | N |
| ATOM | 570 | CE1 | HIS | A | 74 | -5.427 | -24.414 | 9.934 | 1.00 | 23.54 | A | C |
| ATOM | 571 | NE2 | HIS | A | 74 | -4.292 | -24.764 | 10.508 | 1.00 | 25.28 | A | N |
| ATOM | 572 | CD2 | HIS | A | 74 | -3.714 | -23.649 | 11.061 | 1.00 | 24.28 | A | C |
| ATOM | 573 | C | HIS | A | 74 | -3.581 | -18.936 | 10.306 | 1.00 | 21.52 | A | C |
| ATOM | 574 | O | HIS | A | 74 | -2.757 | -18.435 | 11.003 | 1.00 | 21.20 | A | O |
| ATOM | 575 | N | ARG | A | 75 | -4.502 | -18.231 | 9.694 | 1.00 | 21.50 | A | N |
| ATOM | 576 | CA | ARG | A | 75 | -4.653 | -16.795 | 9.915 | 1.00 | 22.33 | A | C |
| ATOM | 577 | CB | ARG | A | 75 | -5.450 | -16.180 | 8.769 | 1.00 | 22.31 | A | C |
| ATOM | 578 | CG | ARG | A | 75 | -6.043 | -14.849 | 9.140 | 1.00 | 22.69 | A | C |
| ATOM | 579 | CD | ARG | A | 75 | -6.460 | -14.042 | 7.949 | 1.00 | 21.24 | A | C |
| ATOM | 580 | NE | ARG | A | 75 | -6.703 | -12.682 | 8.377 | 1.00 | 22.56 | A | N |
| ATOM | 581 | CZ | ARG | A | 75 | -7.319 | -11.749 | 7.665 | 1.00 | 20.85 | A | C |
| ATOM | 582 | NH1 | ARG | A | 75 | -7.727 | -11.987 | 6.437 | 1.00 | 20.39 | A | N |
| ATOM | 583 | NH2 | ARG | A | 75 | -7.473 | -10.554 | 8.187 | 1.00 | 20.76 | A | N |
| ATOM | 584 | C | ARG | A | 75 | -5.327 | -16.464 | 11.265 | 1.00 | 21.79 | A | C |
| ATOM | 585 | O | ARG | A | 75 | -4.933 | -15.502 | 11.947 | 1.00 | 21.64 | A | O |
| ATOM | 586 | N | PHE | A | 76 | -6.331 | -17.275 | 11.620 | 1.00 | 20.73 | A | N |
| ATOM | 587 | CA | PHE | A | 76 | -7.072 | -17.142 | 12.853 | 1.00 | 19.96 | A | C |
| ATOM | 588 | CB | PHE | A | 76 | -8.539 | -17.227 | 12.544 | 1.00 | 19.36 | A | C |
| ATOM | 589 | CG | PHE | A | 76 | -8.984 | -16.151 | 11.630 | 1.00 | 19.43 | A | C |
| ATOM | 590 | CD1 | PHE | A | 76 | -9.156 | -14.874 | 12.108 | 1.00 | 17.29 | A | C |
| ATOM | 591 | CE1 | PHE | A | 76 | -9.549 | -13.897 | 11.273 | 1.00 | 18.02 | A | C |
| ATOM | 592 | CZ | PHE | A | 76 | -9.699 | -14.147 | 9.960 | 1.00 | 16.62 | A | C |
| ATOM | 593 | CE2 | PHE | A | 76 | -9.507 | -15.392 | 9.471 | 1.00 | 17.48 | A | C |
| ATOM | 594 | CD2 | PHE | A | 76 | -9.145 | -16.390 | 10.284 | 1.00 | 15.87 | A | C |
| ATOM | 595 | C | PHE | A | 76 | -6.752 | -18.191 | 13.890 | 1.00 | 20.94 | A | C |
| ATOM | 596 | O | PHE | A | 76 | -6.583 | -19.374 | 13.560 | 1.00 | 21.39 | A | O |
| ATOM | 597 | N | GLU | A | 77 | -6.618 | -17.727 | 15.137 | 1.00 | 21.91 | A | N |
| ATOM | 598 | CA | GLU | A | 77 | -6.633 | -18.584 | 16.312 | 1.00 | 22.56 | A | C |
| ATOM | 599 | CB | GLU | A | 77 | -5.908 | -17.926 | 17.491 | 1.00 | 24.24 | A | C |
| ATOM | 600 | CG | GLU | A | 77 | -5.729 | -18.834 | 18.705 | 1.00 | 26.42 | A | C |
| ATOM | 601 | CD | GLU | A | 77 | -4.756 | -19.978 | 18.430 | 1.00 | 30.22 | A | C |
| ATOM | 602 | OE1 | GLU | A | 77 | -5.206 | -21.124 | 18.406 | 1.00 | 31.63 | A | O |
| ATOM | 603 | OE2 | GLU | A | 77 | -3.552 | -19.738 | 18.202 | 1.00 | 31.88 | A | O |
| ATOM | 604 | C | GLU | A | 77 | -8.102 | -18.715 | 16.650 | 1.00 | 21.64 | A | C |
| ATOM | 605 | O | GLU | A | 77 | -8.823 | -17.732 | 16.647 | 1.00 | 21.72 | A | O |
| ATOM | 606 | N | ILE | A | 78 | -8.558 | -19.925 | 16.906 | 1.00 | 21.21 | A | N |
| ATOM | 607 | CA | ILE | A | 78 | -9.928 | -20.126 | 17.216 | 1.00 | 20.18 | A | C |
| ATOM | 608 | CB | ILE | A | 78 | -10.510 | -21.255 | 16.434 | 1.00 | 19.64 | A | C |
| ATOM | 609 | CG1 | ILE | A | 78 | -10.391 | -20.885 | 14.944 | 1.00 | 21.24 | A | C |
| ATOM | 610 | CD1 | ILE | A | 78 | -11.000 | -21.853 | 13.936 | 1.00 | 19.74 | A | C |
| ATOM | 611 | CG2 | ILE | A | 78 | -11.950 | -21.442 | 16.840 | 1.00 | 18.74 | A | C |
| ATOM | 612 | C | ILE | A | 78 | -10.017 | -20.332 | 18.692 | 1.00 | 20.84 | A | C |
| ATOM | 613 | O | ILE | A | 78 | -9.512 | -21.303 | 19.244 | 1.00 | 22.65 | A | O |
| ATOM | 614 | N | ILE | A | 79 | -10.648 | -19.365 | 19.332 | 1.00 | 20.69 | A | N |
| ATOM | 615 | CA | ILE | A | 79 | -10.717 | -19.308 | 20.744 | 1.00 | 20.49 | A | C |
| ATOM | 616 | CB | ILE | A | 79 | -10.499 | -17.831 | 21.182 | 1.00 | 22.28 | A | C |
| ATOM | 617 | CG1 | ILE | A | 79 | -9.000 | -17.525 | 21.056 | 1.00 | 22.60 | A | C |
| ATOM | 618 | CD1 | ILE | A | 79 | -8.683 | -16.112 | 20.954 | 1.00 | 25.33 | A | C |
| ATOM | 619 | CG2 | ILE | A | 79 | -10.990 | -17.572 | 22.645 | 1.00 | 22.37 | A | C |
| ATOM | 620 | C | ILE | A | 79 | -11.993 | -19.931 | 21.248 | 1.00 | 19.31 | A | C |
| ATOM | 621 | O | ILE | A | 79 | -11.981 | -20.617 | 22.240 | 1.00 | 19.59 | A | O |

FIG. 2-14

| | | | | | | | | | | | | |
|---|---|---|---|---|---|---|---|---|---|---|---|---|
| ATOM | 622 | N | GLU | A | 80 | -13.101 | -19.702 | 20.559 | 1.00 | 18.55 | A | N |
| ATOM | 623 | CA | GLU | A | 80 | -14.381 | -20.338 | 20.905 | 1.00 | 17.71 | A | C |
| ATOM | 624 | CB | GLU | A | 80 | -15.449 | -19.912 | 19.891 | 1.00 | 17.46 | A | C |
| ATOM | 625 | CG | GLU | A | 80 | -16.834 | -20.518 | 20.077 | 1.00 | 17.47 | A | C |
| ATOM | 626 | CD | GLU | A | 80 | -17.323 | -20.267 | 21.447 | 1.00 | 18.77 | A | C |
| ATOM | 627 | OE1 | GLU | A | 80 | -18.077 | -19.282 | 21.682 | 1.00 | 20.03 | A | O |
| ATOM | 628 | OE2 | GLU | A | 80 | -16.879 | -21.023 | 22.314 | 1.00 | 20.21 | A | O |
| ATOM | 629 | C | GLU | A | 80 | -14.160 | -21.813 | 20.796 | 1.00 | 16.77 | A | C |
| ATOM | 630 | O | GLU | A | 80 | -13.317 | -22.234 | 20.002 | 1.00 | 18.28 | A | O |
| ATOM | 631 | N | GLY | A | 81 | -14.923 | -22.610 | 21.527 | 1.00 | 16.42 | A | N |
| ATOM | 632 | CA | GLY | A | 81 | -14.783 | -24.090 | 21.495 | 1.00 | 15.55 | A | C |
| ATOM | 633 | C | GLY | A | 81 | -13.843 | -24.656 | 22.577 | 1.00 | 16.45 | A | C |
| ATOM | 634 | O | GLY | A | 81 | -14.004 | -25.781 | 23.006 | 1.00 | 15.16 | A | O |
| ATOM | 635 | N | ARG | A | 82 | -12.840 | -23.896 | 23.016 | 1.00 | 16.78 | A | N |
| ATOM | 636 | CA | ARG | A | 82 | -11.977 | -24.394 | 24.083 | 1.00 | 18.58 | A | C |
| ATOM | 637 | CB | ARG | A | 82 | -10.622 | -23.738 | 24.022 | 1.00 | 19.00 | A | C |
| ATOM | 638 | CG | ARG | A | 82 | -10.049 | -23.729 | 22.614 | 1.00 | 19.26 | A | C |
| ATOM | 639 | CD | ARG | A | 82 | -8.529 | -23.885 | 22.602 | 1.00 | 22.10 | A | C |
| ATOM | 640 | NE | ARG | A | 82 | -8.005 | -22.974 | 21.612 | 1.00 | 25.14 | A | N |
| ATOM | 641 | CZ | ARG | A | 82 | -6.847 | -23.067 | 20.983 | 1.00 | 26.07 | A | C |
| ATOM | 642 | NH1 | ARG | A | 82 | -5.999 | -24.041 | 21.196 | 1.00 | 27.20 | A | N |
| ATOM | 643 | NH2 | ARG | A | 82 | -6.553 | -22.143 | 20.102 | 1.00 | 30.40 | A | N |
| ATOM | 644 | C | ARG | A | 82 | -12.616 | -24.133 | 25.422 | 1.00 | 19.88 | A | C |
| ATOM | 645 | O | ARG | A | 82 | -13.398 | -23.203 | 25.550 | 1.00 | 19.50 | A | O |
| ATOM | 646 | N | ASP | A | 83 | -12.275 | -24.921 | 26.433 | 1.00 | 21.92 | A | N |
| ATOM | 647 | CA | ASP | A | 83 | -12.786 | -24.616 | 27.761 | 1.00 | 24.32 | A | C |
| ATOM | 648 | CB | ASP | A | 83 | -12.585 | -25.758 | 28.765 | 1.00 | 26.49 | A | C |
| ATOM | 649 | CG | ASP | A | 83 | -11.182 | -25.822 | 29.354 | 1.00 | 31.14 | A | C |
| ATOM | 650 | OD1 | ASP | A | 83 | -10.667 | -24.822 | 29.928 | 1.00 | 33.34 | A | O |
| ATOM | 651 | OD2 | ASP | A | 83 | -10.611 | -26.931 | 29.282 | 1.00 | 36.31 | A | O |
| ATOM | 652 | C | ASP | A | 83 | -12.254 | -23.284 | 28.253 | 1.00 | 24.76 | A | C |
| ATOM | 653 | O | ASP | A | 83 | -11.265 | -22.766 | 27.757 | 1.00 | 25.46 | A | O |
| ATOM | 654 | N | ARG | A | 84 | -12.946 | -22.719 | 29.229 | 1.00 | 25.80 | A | N |
| ATOM | 655 | CA | ARG | A | 84 | -12.758 | -21.329 | 29.595 | 1.00 | 25.68 | A | C |
| ATOM | 656 | CB | ARG | A | 84 | -13.786 | -21.013 | 30.654 | 1.00 | 26.96 | A | C |
| ATOM | 657 | CG | ARG | A | 84 | -14.026 | -19.572 | 30.952 | 1.00 | 26.70 | A | C |
| ATOM | 658 | CD | ARG | A | 84 | -14.977 | -19.507 | 32.125 | 1.00 | 27.20 | A | C |
| ATOM | 659 | NE | ARG | A | 84 | -15.605 | -18.207 | 32.234 | 1.00 | 28.48 | A | N |
| ATOM | 660 | CZ | ARG | A | 84 | -16.536 | -17.884 | 33.131 | 1.00 | 29.36 | A | C |
| ATOM | 661 | NH1 | ARG | A | 84 | -16.944 | -18.771 | 34.030 | 1.00 | 32.29 | A | N |
| ATOM | 662 | NH2 | ARG | A | 84 | -17.047 | -16.654 | 33.141 | 1.00 | 27.99 | A | N |
| ATOM | 663 | C | ARG | A | 84 | -11.321 | -20.999 | 30.053 | 1.00 | 26.98 | A | C |
| ATOM | 664 | O | ARG | A | 84 | -10.717 | -20.042 | 29.585 | 1.00 | 26.80 | A | O |
| ATOM | 665 | N | ILE | A | 85 | -10.753 | -21.804 | 30.931 | 1.00 | 28.79 | A | N |
| ATOM | 666 | CA | ILE | A | 85 | -9.381 | -21.570 | 31.389 | 1.00 | 30.65 | A | C |
| ATOM | 667 | CB | ILE | A | 85 | -8.975 | -22.501 | 32.572 | 1.00 | 33.18 | A | C |
| ATOM | 668 | CG1 | ILE | A | 85 | -9.972 | -22.386 | 33.742 | 1.00 | 34.22 | A | C |
| ATOM | 669 | CD1 | ILE | A | 85 | -10.276 | -20.971 | 34.143 | 1.00 | 36.07 | A | C |
| ATOM | 670 | CG2 | ILE | A | 85 | -7.536 | -22.207 | 33.036 | 1.00 | 33.46 | A | C |
| ATOM | 671 | C | ILE | A | 85 | -8.362 | -21.729 | 30.248 | 1.00 | 30.41 | A | C |
| ATOM | 672 | O | ILE | A | 85 | -7.439 | -20.926 | 30.107 | 1.00 | 30.66 | A | O |
| ATOM | 673 | N | MET | A | 86 | -8.516 | -22.757 | 29.429 | 1.00 | 30.29 | A | N |
| ATOM | 674 | CA | MET | A | 86 | -7.646 | -22.911 | 28.260 | 1.00 | 30.11 | A | C |
| ATOM | 675 | CB | MET | A | 86 | -8.004 | -24.163 | 27.482 | 1.00 | 30.47 | A | C |
| ATOM | 676 | CG | MET | A | 86 | -7.168 | -24.362 | 26.203 | 1.00 | 34.57 | A | C |
| ATOM | 677 | SD | MET | A | 86 | -5.456 | -24.872 | 26.581 | 1.00 | 47.42 | A | S |
| ATOM | 678 | CE | MET | A | 86 | -5.822 | -26.631 | 26.898 | 1.00 | 46.36 | A | C |
| ATOM | 679 | C | MET | A | 86 | -7.825 | -21.735 | 27.348 | 1.00 | 27.47 | A | C |
| ATOM | 680 | O | MET | A | 86 | -6.861 | -21.180 | 26.817 | 1.00 | 27.61 | A | O |
| ATOM | 681 | N | ALA | A | 87 | -9.070 | -21.336 | 27.172 | 1.00 | 25.40 | A | N |
| ATOM | 682 | CA | ALA | A | 87 | -9.361 | -20.172 | 26.327 | 1.00 | 24.02 | A | C |
| ATOM | 683 | CB | ALA | A | 87 | -10.873 | -19.921 | 26.269 | 1.00 | 22.34 | A | C |
| ATOM | 684 | C | ALA | A | 87 | -8.607 | -18.914 | 26.793 | 1.00 | 24.83 | A | C |

FIG. 2-15

| | | | | | | | | | | | | |
|---|---|---|---|---|---|---|---|---|---|---|---|---|
| ATOM | 685 | O | ALA | A | 87 | -7.987 | -18.218 | 26.014 | 1.00 | 23.73 | A | O |
| ATOM | 686 | N | TRP | A | 88 | -8.647 | -18.625 | 28.085 | 1.00 | 27.46 | A | N |
| ATOM | 687 | CA | TRP | A | 88 | -7.946 | -17.454 | 28.569 | 1.00 | 29.09 | A | C |
| ATOM | 688 | CB | TRP | A | 88 | -8.407 | -17.101 | 29.971 | 1.00 | 31.42 | A | C |
| ATOM | 689 | CG | TRP | A | 88 | -9.623 | -16.265 | 29.969 | 1.00 | 32.23 | A | C |
| ATOM | 690 | CD1 | TRP | A | 88 | -10.857 | -16.633 | 30.385 | 1.00 | 33.83 | A | C |
| ATOM | 691 | NE1 | TRP | A | 88 | -11.745 | -15.602 | 30.219 | 1.00 | 32.94 | A | N |
| ATOM | 692 | CE2 | TRP | A | 88 | -11.083 | -14.529 | 29.688 | 1.00 | 33.49 | A | C |
| ATOM | 693 | CD2 | TRP | A | 88 | -9.741 | -14.913 | 29.508 | 1.00 | 34.13 | A | C |
| ATOM | 694 | CE3 | TRP | A | 88 | -8.839 | -13.980 | 28.978 | 1.00 | 35.66 | A | C |
| ATOM | 695 | CZ3 | TRP | A | 88 | -9.316 | -12.705 | 28.639 | 1.00 | 35.71 | A | C |
| ATOM | 696 | CH2 | TRP | A | 88 | -10.660 | -12.365 | 28.823 | 1.00 | 33.86 | A | C |
| ATOM | 697 | CZ2 | TRP | A | 88 | -11.554 | -13.253 | 29.348 | 1.00 | 33.51 | A | C |
| ATOM | 698 | C | TRP | A | 88 | -6.409 | -17.585 | 28.478 | 1.00 | 30.02 | A | C |
| ATOM | 699 | O | TRP | A | 88 | -5.725 | -16.568 | 28.292 | 1.00 | 30.77 | A | O |
| ATOM | 700 | N | THR | A | 89 | -5.870 | -18.801 | 28.592 | 1.00 | 29.92 | A | N |
| ATOM | 701 | CA | THR | A | 89 | -4.419 | -18.982 | 28.499 | 1.00 | 31.72 | A | C |
| ATOM | 702 | CB | THR | A | 89 | -3.922 | -20.431 | 28.725 | 1.00 | 32.18 | A | C |
| ATOM | 703 | OG1 | THR | A | 89 | -4.511 | -20.990 | 29.897 | 1.00 | 34.56 | A | O |
| ATOM | 704 | CG2 | THR | A | 89 | -2.441 | -20.421 | 28.932 | 1.00 | 33.82 | A | C |
| ATOM | 705 | C | THR | A | 89 | -3.976 | -18.587 | 27.112 | 1.00 | 30.66 | A | C |
| ATOM | 706 | O | THR | A | 89 | -3.028 | -17.815 | 26.947 | 1.00 | 31.67 | A | O |
| ATOM | 707 | N | VAL | A | 90 | -4.688 | -19.094 | 26.113 | 1.00 | 28.11 | A | N |
| ATOM | 708 | CA | VAL | A | 90 | -4.388 | -18.728 | 24.754 | 1.00 | 26.92 | A | C |
| ATOM | 709 | CB | VAL | A | 90 | -5.294 | -19.455 | 23.731 | 1.00 | 24.83 | A | C |
| ATOM | 710 | CG1 | VAL | A | 90 | -5.039 | -18.911 | 22.355 | 1.00 | 23.93 | A | C |
| ATOM | 711 | CG2 | VAL | A | 90 | -5.008 | -20.967 | 23.732 | 1.00 | 22.64 | A | C |
| ATOM | 712 | C | VAL | A | 90 | -4.487 | -17.233 | 24.571 | 1.00 | 27.87 | A | C |
| ATOM | 713 | O | VAL | A | 90 | -3.602 | -16.610 | 23.989 | 1.00 | 28.85 | A | O |
| ATOM | 714 | N | VAL | A | 91 | -5.544 | -16.640 | 25.110 | 1.00 | 28.70 | A | N |
| ATOM | 715 | CA | VAL | A | 91 | -5.738 | -15.192 | 24.986 | 1.00 | 29.04 | A | C |
| ATOM | 716 | CB | VAL | A | 91 | -7.113 | -14.736 | 25.578 | 1.00 | 28.96 | A | C |
| ATOM | 717 | CG1 | VAL | A | 91 | -7.179 | -13.211 | 25.701 | 1.00 | 29.25 | A | C |
| ATOM | 718 | CG2 | VAL | A | 91 | -8.253 | -15.289 | 24.744 | 1.00 | 23.50 | A | C |
| ATOM | 719 | C | VAL | A | 91 | -4.578 | -14.460 | 25.646 | 1.00 | 31.68 | A | C |
| ATOM | 720 | O | VAL | A | 91 | -3.904 | -13.687 | 25.012 | 1.00 | 32.87 | A | O |
| ATOM | 721 | N | ASN | A | 92 | -4.312 | -14.717 | 26.906 | 1.00 | 33.65 | A | N |
| ATOM | 722 | CA | ASN | A | 92 | -3.200 | -14.029 | 27.542 | 1.00 | 36.86 | A | C |
| ATOM | 723 | CB | ASN | A | 92 | -3.006 | -14.539 | 28.970 | 1.00 | 38.97 | A | C |
| ATOM | 724 | CG | ASN | A | 92 | -4.119 | -14.106 | 29.903 | 1.00 | 39.87 | A | C |
| ATOM | 725 | OD1 | ASN | A | 92 | -4.844 | -13.152 | 29.628 | 1.00 | 39.13 | A | O |
| ATOM | 726 | ND2 | ASN | A | 92 | -4.251 | -14.814 | 31.030 | 1.00 | 42.69 | A | N |
| ATOM | 727 | C | ASN | A | 92 | -1.881 | -14.130 | 26.760 | 1.00 | 37.28 | A | C |
| ATOM | 728 | O | ASN | A | 92 | -1.149 | -13.159 | 26.606 | 1.00 | 38.40 | A | O |
| ATOM | 729 | N | SER | A | 93 | -1.588 | -15.307 | 26.247 | 1.00 | 36.94 | A | N |
| ATOM | 730 | CA | SER | A | 93 | -0.337 | -15.503 | 25.521 | 1.00 | 38.34 | A | C |
| ATOM | 731 | CB | SER | A | 93 | -0.124 | -16.968 | 25.192 | 1.00 | 37.18 | A | C |
| ATOM | 732 | OG | SER | A | 93 | 0.898 | -17.026 | 24.224 | 1.00 | 40.28 | A | O |
| ATOM | 733 | C | SER | A | 93 | -0.206 | -14.687 | 24.223 | 1.00 | 37.33 | A | C |
| ATOM | 734 | O | SER | A | 93 | 0.896 | -14.256 | 23.872 | 1.00 | 39.36 | A | O |
| ATOM | 735 | N | ILE | A | 94 | -1.320 | -14.509 | 23.522 | 1.00 | 34.69 | A | N |
| ATOM | 736 | CA | ILE | A | 94 | -1.373 | -13.709 | 22.305 | 1.00 | 33.75 | A | C |
| ATOM | 737 | CB | ILE | A | 94 | -2.770 | -13.817 | 21.632 | 1.00 | 31.25 | A | C |
| ATOM | 738 | CG1 | ILE | A | 94 | -2.839 | -15.093 | 20.798 | 1.00 | 27.80 | A | C |
| ATOM | 739 | CD1 | ILE | A | 94 | -4.235 | -15.666 | 20.631 | 1.00 | 21.21 | A | C |
| ATOM | 740 | CG2 | ILE | A | 94 | -3.058 | -12.605 | 20.773 | 1.00 | 32.33 | A | C |
| ATOM | 741 | C | ILE | A | 94 | -1.081 | -12.275 | 22.647 | 1.00 | 35.87 | A | C |
| ATOM | 742 | O | ILE | A | 94 | -0.264 | -11.609 | 22.000 | 1.00 | 37.38 | A | O |
| ATOM | 743 | N | CYS | A | 95 | -1.739 | -11.799 | 23.688 | 1.00 | 36.60 | A | N |
| ATOM | 744 | CA | CYS | A | 95 | -1.440 | -10.478 | 24.220 | 1.00 | 39.22 | A | C |
| ATOM | 745 | CB | CYS | A | 95 | -2.417 | -10.153 | 25.342 | 1.00 | 39.48 | A | C |
| ATOM | 746 | SG | CYS | A | 95 | -4.117 | -10.039 | 24.773 | 1.00 | 36.90 | A | S |
| ATOM | 747 | C | CYS | A | 95 | 0.006 | -10.357 | 24.717 | 1.00 | 42.33 | A | C |

FIG. 2-16

| | | | | | | | | | | | | |
|---|---|---|---|---|---|---|---|---|---|---|---|---|
| ATOM | 748 | O | CYS | A | 95 | 0.619 | -9.297 | 24.611 | 1.00 | 44.48 | A | O |
| ATOM | 749 | N | ASN | A | 96 | 0.547 | -11.433 | 25.273 | 1.00 | 43.48 | A | N |
| ATOM | 750 | CA | ASN | A | 96 | 1.951 | -11.440 | 25.730 | 1.00 | 46.80 | A | C |
| ATOM | 751 | CB | ASN | A | 96 | 2.222 | -12.687 | 26.595 | 1.00 | 47.81 | A | C |
| ATOM | 752 | CG | ASN | A | 96 | 3.569 | -13.345 | 26.293 | 1.00 | 50.31 | A | C |
| ATOM | 753 | OD1 | ASN | A | 96 | 4.614 | -12.854 | 26.714 | 1.00 | 53.01 | A | O |
| ATOM | 754 | ND2 | ASN | A | 96 | 3.541 | -14.465 | 25.552 | 1.00 | 50.84 | A | N |
| ATOM | 755 | C | ASN | A | 96 | 2.908 | -11.383 | 24.539 | 1.00 | 46.83 | A | C |
| ATOM | 756 | O | ASN | A | 96 | 3.914 | -10.667 | 24.543 | 1.00 | 47.99 | A | O |
| ATOM | 757 | N | THR | A | 97 | 2.566 | -12.151 | 23.512 | 1.00 | 44.55 | A | N |
| ATOM | 758 | CA | THR | A | 97 | 3.365 | -12.206 | 22.307 | 1.00 | 44.73 | A | C |
| ATOM | 759 | CB | THR | A | 97 | 2.979 | -13.441 | 21.449 | 1.00 | 42.72 | A | C |
| ATOM | 760 | OG1 | THR | A | 97 | 3.603 | -14.611 | 21.987 | 1.00 | 43.16 | A | O |
| ATOM | 761 | CG2 | THR | A | 97 | 3.409 | -13.268 | 19.979 | 1.00 | 43.11 | A | C |
| ATOM | 762 | C | THR | A | 97 | 3.229 | -10.954 | 21.442 | 1.00 | 44.68 | A | C |
| ATOM | 763 | O | THR | A | 97 | 4.108 | -10.694 | 20.634 | 1.00 | 46.45 | A | O |
| ATOM | 764 | N | THR | A | 98 | 2.138 | -10.197 | 21.557 | 1.00 | 43.17 | A | N |
| ATOM | 765 | CA | THR | A | 98 | 1.885 | -9.140 | 20.559 | 1.00 | 42.50 | A | C |
| ATOM | 766 | CB | THR | A | 98 | 0.774 | -9.528 | 19.530 | 1.00 | 40.02 | A | C |
| ATOM | 767 | OG1 | THR | A | 98 | -0.519 | -9.388 | 20.127 | 1.00 | 39.65 | A | O |
| ATOM | 768 | CG2 | THR | A | 98 | 0.928 | -10.950 | 19.005 | 1.00 | 38.10 | A | C |
| ATOM | 769 | C | THR | A | 98 | 1.486 | -7.800 | 21.107 | 1.00 | 43.20 | A | C |
| ATOM | 770 | O | THR | A | 98 | 1.238 | -6.912 | 20.329 | 1.00 | 43.28 | A | O |
| ATOM | 771 | N | GLY | A | 99 | 1.389 | -7.637 | 22.418 | 1.00 | 44.05 | A | N |
| ATOM | 772 | CA | GLY | A | 99 | 1.029 | -6.339 | 22.989 | 1.00 | 45.96 | A | C |
| ATOM | 773 | C | GLY | A | 99 | -0.395 | -5.842 | 22.772 | 1.00 | 44.86 | A | C |
| ATOM | 774 | O | GLY | A | 99 | -0.725 | -4.728 | 23.166 | 1.00 | 46.20 | A | O |
| ATOM | 775 | N | VAL | A | 100 | -1.249 | -6.637 | 22.134 | 1.00 | 42.66 | A | N |
| ATOM | 776 | CA | VAL | A | 100 | -2.643 | -6.255 | 22.034 | 1.00 | 42.24 | A | C |
| ATOM | 777 | CB | VAL | A | 100 | -3.438 | -7.106 | 21.022 | 1.00 | 39.82 | A | C |
| ATOM | 778 | CG1 | VAL | A | 100 | -2.855 | -8.495 | 20.861 | 1.00 | 39.65 | A | C |
| ATOM | 779 | CG2 | VAL | A | 100 | -4.899 | -7.208 | 21.447 | 1.00 | 38.69 | A | C |
| ATOM | 780 | C | VAL | A | 100 | -3.235 | -6.366 | 23.438 | 1.00 | 43.13 | A | C |
| ATOM | 781 | O | VAL | A | 100 | -2.872 | -7.245 | 24.213 | 1.00 | 42.09 | A | O |
| ATOM | 782 | N | GLU | A | 101 | -4.123 | -5.448 | 23.782 | 1.00 | 44.88 | A | N |
| ATOM | 783 | CA | GLU | A | 101 | -4.626 | -5.412 | 25.143 | 1.00 | 46.74 | A | C |
| ATOM | 784 | CB | GLU | A | 101 | -5.175 | -4.039 | 25.489 | 1.00 | 49.49 | A | C |
| ATOM | 785 | CG | GLU | A | 101 | -4.014 | -3.037 | 25.794 | 1.00 | 54.31 | A | C |
| ATOM | 786 | CD | GLU | A | 101 | -4.266 | -1.646 | 25.254 | 1.00 | 57.93 | A | C |
| ATOM | 787 | OE1 | GLU | A | 101 | -5.005 | -1.523 | 24.244 | 1.00 | 57.00 | A | O |
| ATOM | 788 | OE2 | GLU | A | 101 | -3.716 | -0.677 | 25.837 | 1.00 | 62.35 | A | O |
| ATOM | 789 | C | GLU | A | 101 | -5.652 | -6.488 | 25.328 | 1.00 | 44.56 | A | C |
| ATOM | 790 | O | GLU | A | 101 | -6.359 | -6.857 | 24.382 | 1.00 | 42.09 | A | O |
| ATOM | 791 | N | LYS | A | 102 | -5.682 | -7.027 | 26.543 | 1.00 | 45.57 | A | N |
| ATOM | 792 | CA | LYS | A | 102 | -6.553 | -8.133 | 26.874 | 1.00 | 43.83 | A | C |
| ATOM | 793 | CB | LYS | A | 102 | -6.235 | -8.668 | 28.282 | 1.00 | 45.87 | A | C |
| ATOM | 794 | CG | LYS | A | 102 | -4.899 | -9.419 | 28.386 | 1.00 | 48.08 | A | C |
| ATOM | 795 | CD | LYS | A | 102 | -4.396 | -9.528 | 29.870 | 1.00 | 53.47 | A | C |
| ATOM | 796 | CE | LYS | A | 102 | -3.050 | -10.282 | 29.960 | 1.00 | 54.41 | A | C |
| ATOM | 797 | NZ | LYS | A | 102 | -2.405 | -10.204 | 31.304 | 1.00 | 58.67 | A | N |
| ATOM | 798 | C | LYS | A | 102 | -7.998 | -7.644 | 26.787 | 1.00 | 42.94 | A | C |
| ATOM | 799 | O | LYS | A | 102 | -8.318 | -6.529 | 27.206 | 1.00 | 44.44 | A | O |
| ATOM | 800 | N | PRO | A | 103 | -8.867 | -8.451 | 26.179 | 1.00 | 40.32 | A | N |
| ATOM | 801 | CA | PRO | A | 103 | -10.274 | -8.104 | 26.212 | 1.00 | 40.13 | A | C |
| ATOM | 802 | CB | PRO | A | 103 | -10.868 | -9.008 | 25.150 | 1.00 | 37.14 | A | C |
| ATOM | 803 | CG | PRO | A | 103 | -9.912 | -10.159 | 25.048 | 1.00 | 35.56 | A | C |
| ATOM | 804 | CD | PRO | A | 103 | -8.594 | -9.592 | 25.285 | 1.00 | 37.55 | A | C |
| ATOM | 805 | C | PRO | A | 103 | -10.846 | -8.406 | 27.590 | 1.00 | 41.44 | A | C |
| ATOM | 806 | O | PRO | A | 103 | -10.265 | -9.206 | 28.325 | 1.00 | 41.12 | A | O |
| ATOM | 807 | N | LYS | A | 104 | -11.945 | -7.741 | 27.949 | 1.00 | 42.91 | A | N |
| ATOM | 808 | CA | LYS | A | 104 | -12.576 | -7.967 | 29.253 | 1.00 | 44.59 | A | C |
| ATOM | 809 | CB | LYS | A | 104 | -13.456 | -6.777 | 29.690 | 1.00 | 47.61 | A | C |
| ATOM | 810 | CG | LYS | A | 104 | -12.841 | -5.357 | 29.568 | 1.00 | 50.39 | A | C |

FIG. 2-17

| | | | | | | | | | | | | |
|---|---|---|---|---|---|---|---|---|---|---|---|---|
| ATOM | 811 | CD | LYS | A | 104 | -11.857 | -5.015 | 30.699 | 1.00 | 54.21 | A | C |
| ATOM | 812 | CE | LYS | A | 104 | -11.561 | -3.510 | 30.765 | 1.00 | 57.22 | A | C |
| ATOM | 813 | NZ | LYS | A | 104 | -11.294 | -3.031 | 32.157 | 1.00 | 60.01 | A | N |
| ATOM | 814 | C | LYS | A | 104 | -13.412 | -9.259 | 29.189 | 1.00 | 42.20 | A | C |
| ATOM | 815 | O | LYS | A | 104 | -13.539 | -9.955 | 30.193 | 1.00 | 42.76 | A | O |
| ATOM | 816 | N | PHE | A | 105 | -13.931 | -9.590 | 27.999 | 1.00 | 39.21 | A | N |
| ATOM | 817 | CA | PHE | A | 105 | -14.756 | -10.787 | 27.779 | 1.00 | 36.79 | A | C |
| ATOM | 818 | CB | PHE | A | 105 | -16.162 | -10.349 | 27.320 | 1.00 | 36.78 | A | C |
| ATOM | 819 | CG | PHE | A | 105 | -16.887 | -9.470 | 28.335 | 1.00 | 40.39 | A | C |
| ATOM | 820 | CD1 | PHE | A | 105 | -16.614 | -8.096 | 28.421 | 1.00 | 44.91 | A | C |
| ATOM | 821 | CE1 | PHE | A | 105 | -17.246 | -7.272 | 29.373 | 1.00 | 46.44 | A | C |
| ATOM | 822 | CZ | PHE | A | 105 | -18.166 | -7.831 | 30.239 | 1.00 | 48.49 | A | C |
| ATOM | 823 | CE2 | PHE | A | 105 | -18.455 | -9.211 | 30.158 | 1.00 | 46.08 | A | C |
| ATOM | 824 | CD2 | PHE | A | 105 | -17.809 | -10.014 | 29.221 | 1.00 | 41.49 | A | C |
| ATOM | 825 | C | PHE | A | 105 | -14.095 | -11.734 | 26.748 | 1.00 | 33.83 | A | C |
| ATOM | 826 | O | PHE | A | 105 | -13.360 | -11.287 | 25.888 | 1.00 | 33.24 | A | O |
| ATOM | 827 | N | LEU | A | 106 | -14.347 | -13.038 | 26.822 | 1.00 | 31.90 | A | N |
| ATOM | 828 | CA | LEU | A | 106 | -13.744 | -13.971 | 25.863 | 1.00 | 29.47 | A | C |
| ATOM | 829 | CB | LEU | A | 106 | -14.042 | -15.425 | 26.188 | 1.00 | 28.98 | A | C |
| ATOM | 830 | CG | LEU | A | 106 | -13.058 | -16.172 | 27.051 | 1.00 | 31.59 | A | C |
| ATOM | 831 | CD1 | LEU | A | 106 | -13.528 | -17.616 | 27.085 | 1.00 | 31.44 | A | C |
| ATOM | 832 | CD2 | LEU | A | 106 | -11.653 | -16.028 | 26.468 | 1.00 | 32.35 | A | C |
| ATOM | 833 | C | LEU | A | 106 | -14.282 | -13.777 | 24.473 | 1.00 | 27.08 | A | C |
| ATOM | 834 | O | LEU | A | 106 | -15.483 | -13.754 | 24.300 | 1.00 | 26.62 | A | O |
| ATOM | 835 | N | PRO | A | 107 | -13.394 | -13.686 | 23.471 | 1.00 | 25.12 | A | N |
| ATOM | 836 | CA | PRO | A | 107 | -13.859 | -13.629 | 22.115 | 1.00 | 23.06 | A | C |
| ATOM | 837 | CB | PRO | A | 107 | -12.793 | -12.792 | 21.395 | 1.00 | 23.11 | A | C |
| ATOM | 838 | CG | PRO | A | 107 | -11.723 | -12.584 | 22.338 | 1.00 | 25.26 | A | C |
| ATOM | 839 | CD | PRO | A | 107 | -11.973 | -13.328 | 23.581 | 1.00 | 25.96 | A | C |
| ATOM | 840 | C | PRO | A | 107 | -13.938 | -15.002 | 21.507 | 1.00 | 21.48 | A | C |
| ATOM | 841 | O | PRO | A | 107 | -13.809 | -16.013 | 22.183 | 1.00 | 21.22 | A | O |
| ATOM | 842 | N | ASP | A | 108 | -14.123 | -15.023 | 20.204 | 1.00 | 20.33 | A | N |
| ATOM | 843 | CA | ASP | A | 108 | -14.236 | -16.238 | 19.495 | 1.00 | 19.01 | A | C |
| ATOM | 844 | CB | ASP | A | 108 | -15.438 | -16.120 | 18.591 | 1.00 | 18.62 | A | C |
| ATOM | 845 | CG | ASP | A | 108 | -16.728 | -16.017 | 19.366 | 1.00 | 19.88 | A | C |
| ATOM | 846 | OD1 | ASP | A | 108 | -16.888 | -16.782 | 20.339 | 1.00 | 18.38 | A | O |
| ATOM | 847 | OD2 | ASP | A | 108 | -17.604 | -15.211 | 18.966 | 1.00 | 24.12 | A | O |
| ATOM | 848 | C | ASP | A | 108 | -12.983 | -16.537 | 18.696 | 1.00 | 19.17 | A | C |
| ATOM | 849 | O | ASP | A | 108 | -12.559 | -17.702 | 18.649 | 1.00 | 19.01 | A | O |
| ATOM | 850 | N | LEU | A | 109 | -12.424 | -15.498 | 18.052 | 1.00 | 19.50 | A | N |
| ATOM | 851 | CA | LEU | A | 109 | -11.235 | -15.604 | 17.208 | 1.00 | 19.30 | A | C |
| ATOM | 852 | CB | LEU | A | 109 | -11.620 | -15.460 | 15.746 | 1.00 | 19.03 | A | C |
| ATOM | 853 | CG | LEU | A | 109 | -12.797 | -16.288 | 15.245 | 1.00 | 18.60 | A | C |
| ATOM | 854 | CD1 | LEU | A | 109 | -13.247 | -15.809 | 13.877 | 1.00 | 17.11 | A | C |
| ATOM | 855 | CD2 | LEU | A | 109 | -12.423 | -17.774 | 15.181 | 1.00 | 16.39 | A | C |
| ATOM | 856 | C | LEU | A | 109 | -10.172 | -14.527 | 17.507 | 1.00 | 20.42 | A | C |
| ATOM | 857 | O | LEU | A | 109 | -10.419 | -13.529 | 18.150 | 1.00 | 20.87 | A | O |
| ATOM | 858 | N | TYR | A | 110 | -8.971 | -14.772 | 17.024 | 1.00 | 21.17 | A | N |
| ATOM | 859 | CA | TYR | A | 110 | -7.913 | -13.768 | 17.009 | 1.00 | 23.18 | A | C |
| ATOM | 860 | CB | TYR | A | 110 | -6.738 | -14.110 | 17.960 | 1.00 | 23.21 | A | C |
| ATOM | 861 | CG | TYR | A | 110 | -5.687 | -13.026 | 17.906 | 1.00 | 24.16 | A | C |
| ATOM | 862 | CD1 | TYR | A | 110 | -5.849 | -11.845 | 18.609 | 1.00 | 23.79 | A | C |
| ATOM | 863 | CE1 | TYR | A | 110 | -4.906 | -10.826 | 18.532 | 1.00 | 26.68 | A | C |
| ATOM | 864 | CZ | TYR | A | 110 | -3.776 | -10.973 | 17.733 | 1.00 | 27.84 | A | C |
| ATOM | 865 | OH | TYR | A | 110 | -2.839 | -9.941 | 17.665 | 1.00 | 31.95 | A | O |
| ATOM | 866 | CE2 | TYR | A | 110 | -3.591 | -12.146 | 17.017 | 1.00 | 25.34 | A | C |
| ATOM | 867 | CD2 | TYR | A | 110 | -4.546 | -13.162 | 17.105 | 1.00 | 24.55 | A | C |
| ATOM | 868 | C | TYR | A | 110 | -7.424 | -13.740 | 15.567 | 1.00 | 23.58 | A | C |
| ATOM | 869 | O | TYR | A | 110 | -7.307 | -14.798 | 14.936 | 1.00 | 23.79 | A | O |
| ATOM | 870 | N | ASP | A | 111 | -7.129 | -12.552 | 15.057 | 1.00 | 24.83 | A | N |
| ATOM | 871 | CA | ASP | A | 111 | -6.707 | -12.396 | 13.663 | 1.00 | 25.09 | A | C |
| ATOM | 872 | CB | ASP | A | 111 | -7.500 | -11.282 | 12.952 | 1.00 | 24.86 | A | C |
| ATOM | 873 | CG | ASP | A | 111 | -7.183 | -11.204 | 11.449 | 1.00 | 27.30 | A | C |

FIG. 2-18

| | | | | | | | | | | | | |
|---|---|---|---|---|---|---|---|---|---|---|---|---|
| ATOM | 874 | OD1 | ASP | A | 111 | -6.028 | -11.502 | 11.071 | 1.00 | 29.01 | A | O |
| ATOM | 875 | OD2 | ASP | A | 111 | -8.060 | -10.821 | 10.634 | 1.00 | 26.97 | A | O |
| ATOM | 876 | C | ASP | A | 111 | -5.228 | -12.097 | 13.679 | 1.00 | 25.63 | A | C |
| ATOM | 877 | O | ASP | A | 111 | -4.824 | -11.018 | 14.063 | 1.00 | 27.34 | A | O |
| ATOM | 878 | N | TYR | A | 112 | -4.411 | -13.044 | 13.259 | 1.00 | 25.27 | A | N |
| ATOM | 879 | CA | TYR | A | 112 | -2.948 | -12.830 | 13.295 | 1.00 | 26.62 | A | C |
| ATOM | 880 | CB | TYR | A | 112 | -2.197 | -14.151 | 13.144 | 1.00 | 25.93 | A | C |
| ATOM | 881 | CG | TYR | A | 112 | -2.257 | -15.085 | 14.339 | 1.00 | 23.97 | A | C |
| ATOM | 882 | CD1 | TYR | A | 112 | -2.984 | -16.261 | 14.283 | 1.00 | 22.17 | A | C |
| ATOM | 883 | CE1 | TYR | A | 112 | -3.018 | -17.121 | 15.342 | 1.00 | 20.62 | A | C |
| ATOM | 884 | CZ | TYR | A | 112 | -2.325 | -16.820 | 16.473 | 1.00 | 21.62 | A | C |
| ATOM | 885 | OH | TYR | A | 112 | -2.389 | -17.695 | 17.511 | 1.00 | 22.57 | A | O |
| ATOM | 886 | CE2 | TYR | A | 112 | -1.596 | -15.676 | 16.569 | 1.00 | 22.89 | A | C |
| ATOM | 887 | CD2 | TYR | A | 112 | -1.558 | -14.815 | 15.505 | 1.00 | 24.02 | A | C |
| ATOM | 888 | C | TYR | A | 112 | -2.437 | -11.792 | 12.266 | 1.00 | 28.99 | A | C |
| ATOM | 889 | O | TYR | A | 112 | -1.330 | -11.242 | 12.444 | 1.00 | 31.17 | A | O |
| ATOM | 890 | N | LYS | A | 113 | -3.238 | -11.515 | 11.226 | 1.00 | 28.59 | A | N |
| ATOM | 891 | CA | LYS | A | 113 | -2.947 | -10.439 | 10.271 | 1.00 | 30.80 | A | C |
| ATOM | 892 | CB | LYS | A | 113 | -3.686 | -10.624 | 8.939 | 1.00 | 30.21 | A | C |
| ATOM | 893 | CG | LYS | A | 113 | -3.282 | -9.610 | 7.850 | 1.00 | 33.82 | A | C |
| ATOM | 894 | CD | LYS | A | 113 | -4.537 | -8.999 | 7.173 | 1.00 | 35.86 | A | C |
| ATOM | 895 | CE | LYS | A | 113 | -4.288 | -8.270 | 5.800 | 1.00 | 38.22 | A | C |
| ATOM | 896 | NZ | LYS | A | 113 | -5.496 | -8.425 | 4.841 | 1.00 | 36.89 | A | N |
| ATOM | 897 | C | LYS | A | 113 | -3.273 | -9.053 | 10.824 | 1.00 | 31.90 | A | C |
| ATOM | 898 | O | LYS | A | 113 | -2.399 | -8.180 | 10.816 | 1.00 | 34.68 | A | O |
| ATOM | 899 | N | GLU | A | 114 | -4.513 | -8.831 | 11.276 | 1.00 | 30.94 | A | N |
| ATOM | 900 | CA | GLU | A | 114 | -4.925 | -7.508 | 11.744 | 1.00 | 31.98 | A | C |
| ATOM | 901 | CB | GLU | A | 114 | -6.413 | -7.294 | 11.580 | 1.00 | 31.77 | A | C |
| ATOM | 902 | CG | GLU | A | 114 | -6.916 | -7.307 | 10.146 | 1.00 | 34.31 | A | C |
| ATOM | 903 | CD | GLU | A | 114 | -6.555 | -6.075 | 9.344 | 1.00 | 39.25 | A | C |
| ATOM | 904 | OE1 | GLU | A | 114 | -5.598 | -5.336 | 9.680 | 1.00 | 43.46 | A | O |
| ATOM | 905 | OE2 | GLU | A | 114 | -7.240 | -5.858 | 8.331 | 1.00 | 44.48 | A | O |
| ATOM | 906 | C | GLU | A | 114 | -4.606 | -7.285 | 13.188 | 1.00 | 32.10 | A | C |
| ATOM | 907 | O | GLU | A | 114 | -4.784 | -6.180 | 13.686 | 1.00 | 34.06 | A | O |
| ATOM | 908 | N | ASN | A | 115 | -4.130 | -8.322 | 13.863 | 1.00 | 30.43 | A | N |
| ATOM | 909 | CA | ASN | A | 115 | -3.846 | -8.254 | 15.264 | 1.00 | 30.57 | A | C |
| ATOM | 910 | CB | ASN | A | 115 | -2.616 | -7.395 | 15.519 | 1.00 | 33.23 | A | C |
| ATOM | 911 | CG | ASN | A | 115 | -1.344 | -8.024 | 14.985 | 1.00 | 34.24 | A | C |
| ATOM | 912 | OD1 | ASN | A | 115 | -0.663 | -7.433 | 14.140 | 1.00 | 33.21 | A | O |
| ATOM | 913 | ND2 | ASN | A | 115 | -0.995 | -9.215 | 15.505 | 1.00 | 31.29 | A | N |
| ATOM | 914 | C | ASN | A | 115 | -5.047 | -7.743 | 16.062 | 1.00 | 29.97 | A | C |
| ATOM | 915 | O | ASN | A | 115 | -4.970 | -6.708 | 16.720 | 1.00 | 31.48 | A | O |
| ATOM | 916 | N | ARG | A | 116 | -6.159 | -8.468 | 16.000 | 1.00 | 27.44 | A | N |
| ATOM | 917 | CA | ARG | A | 116 | -7.314 | -8.126 | 16.829 | 1.00 | 27.17 | A | C |
| ATOM | 918 | CB | ARG | A | 116 | -8.155 | -7.025 | 16.188 | 1.00 | 27.75 | A | C |
| ATOM | 919 | CG | ARG | A | 116 | -8.476 | -7.291 | 14.774 | 1.00 | 27.44 | A | C |
| ATOM | 920 | CD | ARG | A | 116 | -9.170 | -6.152 | 14.091 | 1.00 | 30.15 | A | C |
| ATOM | 921 | NE | ARG | A | 116 | -9.810 | -6.632 | 12.870 | 1.00 | 29.20 | A | N |
| ATOM | 922 | CZ | ARG | A | 116 | -10.027 | -5.896 | 11.790 | 1.00 | 31.42 | A | C |
| ATOM | 923 | NH1 | ARG | A | 116 | -9.663 | -4.630 | 11.758 | 1.00 | 33.58 | A | N |
| ATOM | 924 | NH2 | ARG | A | 116 | -10.612 | -6.445 | 10.728 | 1.00 | 31.88 | A | N |
| ATOM | 925 | C | ARG | A | 116 | -8.162 | -9.331 | 17.129 | 1.00 | 24.70 | A | C |
| ATOM | 926 | O | ARG | A | 116 | -8.163 | -10.278 | 16.391 | 1.00 | 23.44 | A | O |
| ATOM | 927 | N | PHE | A | 117 | -8.857 | -9.295 | 18.255 | 1.00 | 24.79 | A | N |
| ATOM | 928 | CA | PHE | A | 117 | -9.746 | -10.369 | 18.621 | 1.00 | 22.59 | A | C |
| ATOM | 929 | CB | PHE | A | 117 | -9.951 | -10.402 | 20.131 | 1.00 | 23.08 | A | C |
| ATOM | 930 | CG | PHE | A | 117 | -8.780 | -10.915 | 20.873 | 1.00 | 21.97 | A | C |
| ATOM | 931 | CD1 | PHE | A | 117 | -8.537 | -12.266 | 20.941 | 1.00 | 21.70 | A | C |
| ATOM | 932 | CE1 | PHE | A | 117 | -7.421 | -12.756 | 21.606 | 1.00 | 21.64 | A | C |
| ATOM | 933 | CZ | PHE | A | 117 | -6.547 | -11.891 | 22.193 | 1.00 | 22.64 | A | C |
| ATOM | 934 | CE2 | PHE | A | 117 | -6.756 | -10.536 | 22.104 | 1.00 | 23.09 | A | C |
| ATOM | 935 | CD2 | PHE | A | 117 | -7.861 | -10.056 | 21.431 | 1.00 | 24.35 | A | C |
| ATOM | 936 | C | PHE | A | 117 | -11.015 | -10.067 | 17.950 | 1.00 | 22.46 | A | C |

FIG. 2-19

| | | | | | | | | | | | | |
|---|---|---|---|---|---|---|---|---|---|---|---|---|
| ATOM | 937 | O | PHE | A | 117 | -11.314 | -8.915 | 17.702 | 1.00 | 24.46 | A | O |
| ATOM | 938 | N | ILE | A | 118 | -11.785 | -11.093 | 17.665 | 1.00 | 21.99 | A | N |
| ATOM | 939 | CA | ILE | A | 118 | -13.081 | -10.925 | 17.000 | 1.00 | 21.97 | A | C |
| ATOM | 940 | CB | ILE | A | 118 | -13.107 | -11.586 | 15.575 | 1.00 | 20.98 | A | C |
| ATOM | 941 | CG1 | ILE | A | 118 | -11.979 | -11.073 | 14.702 | 1.00 | 22.82 | A | C |
| ATOM | 942 | CD1 | ILE | A | 118 | -11.952 | -11.700 | 13.359 | 1.00 | 22.50 | A | C |
| ATOM | 943 | CG2 | ILE | A | 118 | -14.426 | -11.316 | 14.873 | 1.00 | 21.92 | A | C |
| ATOM | 944 | C | ILE | A | 118 | -14.124 | -11.637 | 17.833 | 1.00 | 21.02 | A | C |
| ATOM | 945 | O | ILE | A | 118 | -13.886 | -12.749 | 18.283 | 1.00 | 19.24 | A | O |
| ATOM | 946 | N | GLU | A | 119 | -15.269 | -10.987 | 18.028 | 1.00 | 22.25 | A | N |
| ATOM | 947 | CA | GLU | A | 119 | -16.474 | -11.626 | 18.595 | 1.00 | 22.01 | A | C |
| ATOM | 948 | CB | GLU | A | 119 | -17.155 | -10.674 | 19.607 | 1.00 | 24.47 | A | C |
| ATOM | 949 | CG | GLU | A | 119 | -18.537 | -11.103 | 20.127 | 1.00 | 25.86 | A | C |
| ATOM | 950 | CD | GLU | A | 119 | -18.518 | -12.466 | 20.786 | 1.00 | 27.75 | A | C |
| ATOM | 951 | OE1 | GLU | A | 119 | -17.833 | -12.584 | 21.810 | 1.00 | 31.85 | A | O |
| ATOM | 952 | OE2 | GLU | A | 119 | -19.191 | -13.409 | 20.311 | 1.00 | 28.17 | A | O |
| ATOM | 953 | C | GLU | A | 119 | -17.424 | -11.954 | 17.445 | 1.00 | 20.38 | A | C |
| ATOM | 954 | O | GLU | A | 119 | -17.764 | -11.065 | 16.633 | 1.00 | 20.55 | A | O |
| ATOM | 955 | N | ILE | A | 120 | -17.830 | -13.222 | 17.338 | 1.00 | 18.50 | A | N |
| ATOM | 956 | CA | ILE | A | 120 | -18.763 | -13.625 | 16.277 | 1.00 | 17.22 | A | C |
| ATOM | 957 | CB | ILE | A | 120 | -18.403 | -14.968 | 15.633 | 1.00 | 15.29 | A | C |
| ATOM | 958 | CG1 | ILE | A | 120 | -17.023 | -14.936 | 14.951 | 1.00 | 14.77 | A | C |
| ATOM | 959 | CD1 | ILE | A | 120 | -16.962 | -14.259 | 13.705 | 1.00 | 14.15 | A | C |
| ATOM | 960 | CG2 | ILE | A | 120 | -19.444 | -15.378 | 14.609 | 1.00 | 13.20 | A | C |
| ATOM | 961 | C | ILE | A | 120 | -20.147 | -13.733 | 16.862 | 1.00 | 17.93 | A | C |
| ATOM | 962 | O | ILE | A | 120 | -20.367 | -14.459 | 17.816 | 1.00 | 18.28 | A | O |
| ATOM | 963 | N | GLY | A | 121 | -21.076 | -12.999 | 16.289 | 1.00 | 19.46 | A | N |
| ATOM | 964 | CA | GLY | A | 121 | -22.500 | -13.163 | 16.588 | 1.00 | 21.04 | A | C |
| ATOM | 965 | C | GLY | A | 121 | -23.265 | -13.921 | 15.507 | 1.00 | 21.01 | A | C |
| ATOM | 966 | O | GLY | A | 121 | -23.040 | -13.718 | 14.329 | 1.00 | 19.79 | A | O |
| ATOM | 967 | N | VAL | A | 122 | -24.136 | -14.835 | 15.942 | 1.00 | 22.40 | A | N |
| ATOM | 968 | CA | VAL | A | 122 | -25.161 | -15.416 | 15.092 | 1.00 | 23.38 | A | C |
| ATOM | 969 | CB | VAL | A | 122 | -24.883 | -16.900 | 14.793 | 1.00 | 22.81 | A | C |
| ATOM | 970 | CG1 | VAL | A | 122 | -25.964 | -17.442 | 13.871 | 1.00 | 23.86 | A | C |
| ATOM | 971 | CG2 | VAL | A | 122 | -23.449 | -17.119 | 14.174 | 1.00 | 18.25 | A | C |
| ATOM | 972 | C | VAL | A | 122 | -26.488 | -15.262 | 15.820 | 1.00 | 25.57 | A | C |
| ATOM | 973 | O | VAL | A | 122 | -26.645 | -15.798 | 16.910 | 1.00 | 26.52 | A | O |
| ATOM | 974 | N | THR | A | 123 | -27.423 | -14.514 | 15.226 | 1.00 | 27.67 | A | N |
| ATOM | 975 | CA | THR | A | 123 | -28.718 | -14.194 | 15.833 | 1.00 | 29.23 | A | C |
| ATOM | 976 | CB | THR | A | 123 | -28.847 | -12.652 | 16.054 | 1.00 | 31.50 | A | C |
| ATOM | 977 | OG1 | THR | A | 123 | -30.020 | -12.357 | 16.811 | 1.00 | 31.34 | A | O |
| ATOM | 978 | CG2 | THR | A | 123 | -28.867 | -11.877 | 14.715 | 1.00 | 30.26 | A | C |
| ATOM | 979 | C | THR | A | 123 | -29.918 | -14.655 | 14.992 | 1.00 | 31.33 | A | C |
| ATOM | 980 | O | THR | A | 123 | -29.984 | -14.442 | 13.779 | 1.00 | 31.78 | A | O |
| ATOM | 981 | N | ARG | A | 124 | -30.882 | -15.274 | 15.659 | 1.00 | 33.15 | A | N |
| ATOM | 982 | CA | ARG | A | 124 | -32.177 | -15.560 | 15.080 | 1.00 | 35.18 | A | C |
| ATOM | 983 | CB | ARG | A | 124 | -32.967 | -16.550 | 15.942 | 1.00 | 36.29 | A | C |
| ATOM | 984 | CG | ARG | A | 124 | -32.343 | -17.936 | 16.226 | 1.00 | 37.15 | A | C |
| ATOM | 985 | CD | ARG | A | 124 | -31.628 | -17.978 | 17.599 | 1.00 | 41.14 | A | C |
| ATOM | 986 | NE | ARG | A | 124 | -32.035 | -19.077 | 18.492 | 1.00 | 43.21 | A | N |
| ATOM | 987 | CZ | ARG | A | 124 | -31.433 | -19.385 | 19.645 | 1.00 | 41.99 | A | C |
| ATOM | 988 | NH1 | ARG | A | 124 | -30.369 | -18.711 | 20.062 | 1.00 | 40.67 | A | N |
| ATOM | 989 | NH2 | ARG | A | 124 | -31.894 | -20.386 | 20.385 | 1.00 | 43.27 | A | N |
| ATOM | 990 | C | ARG | A | 124 | -32.992 | -14.271 | 14.962 | 1.00 | 37.37 | A | C |
| ATOM | 991 | O | ARG | A | 124 | -34.028 | -14.246 | 14.289 | 1.00 | 38.57 | A | O |
| ATOM | 992 | N | ARG | A | 125 | -32.532 | -13.201 | 15.602 | 1.00 | 38.17 | A | N |
| ATOM | 993 | CA | ARG | A | 125 | -33.250 | -11.912 | 15.562 | 1.00 | 41.22 | A | C |
| ATOM | 994 | CB | ARG | A | 125 | -33.016 | -11.156 | 16.881 | 1.00 | 42.21 | A | C |
| ATOM | 995 | CG | ARG | A | 125 | -33.484 | -11.919 | 18.115 | 1.00 | 42.07 | A | C |
| ATOM | 996 | CD | ARG | A | 125 | -33.430 | -11.057 | 19.354 | 1.00 | 41.85 | A | C |
| ATOM | 997 | NE | ARG | A | 125 | -32.101 | -11.061 | 19.940 | 1.00 | 39.46 | A | N |
| ATOM | 998 | CZ | ARG | A | 125 | -31.717 | -10.316 | 20.975 | 1.00 | 40.24 | A | C |
| ATOM | 999 | NH1 | ARG | A | 125 | -32.553 | -9.477 | 21.576 | 1.00 | 41.40 | A | N |

FIG. 2-20

| | | | | | | | | | | | | |
|---|---|---|---|---|---|---|---|---|---|---|---|---|
| ATOM | 1000 | NH2 | ARG | A | 125 | -30.471 | -10.416 | 21.416 | 1.00 | 39.37 | A | N |
| ATOM | 1001 | C | ARG | A | 125 | -32.890 | -11.034 | 14.344 | 1.00 | 41.74 | A | C |
| ATOM | 1002 | O | ARG | A | 125 | -32.536 | -11.537 | 13.279 | 1.00 | 41.77 | A | O |
| ATOM | 1003 | N | GLU | A | 126 | -33.043 | -9.726 | 14.478 | 1.00 | 43.70 | A | N |
| ATOM | 1004 | CA | GLU | A | 126 | -32.568 | -8.784 | 13.477 | 1.00 | 44.15 | A | C |
| ATOM | 1005 | CB | GLU | A | 126 | -33.614 | -7.682 | 13.251 | 1.00 | 47.73 | A | C |
| ATOM | 1006 | CG | GLU | A | 126 | -34.960 | -8.194 | 12.678 | 1.00 | 50.38 | A | C |
| ATOM | 1007 | CD | GLU | A | 126 | -36.171 | -7.860 | 13.566 | 1.00 | 54.94 | A | C |
| ATOM | 1008 | OE1 | GLU | A | 126 | -37.209 | -7.382 | 13.042 | 1.00 | 56.33 | A | O |
| ATOM | 1009 | OE2 | GLU | A | 126 | -36.080 | -8.084 | 14.796 | 1.00 | 55.82 | A | O |
| ATOM | 1010 | C | GLU | A | 126 | -31.270 | -8.217 | 14.007 | 1.00 | 42.39 | A | C |
| ATOM | 1011 | O | GLU | A | 126 | -31.133 | -7.997 | 15.203 | 1.00 | 42.57 | A | O |
| ATOM | 1012 | N | VAL | A | 127 | -30.320 | -7.974 | 13.119 | 1.00 | 40.95 | A | N |
| ATOM | 1013 | CA | VAL | A | 127 | -28.908 | -7.865 | 13.506 | 1.00 | 38.67 | A | C |
| ATOM | 1014 | CB | VAL | A | 127 | -28.023 | -8.137 | 12.283 | 1.00 | 37.45 | A | C |
| ATOM | 1015 | CG1 | VAL | A | 127 | -26.599 | -8.400 | 12.690 | 1.00 | 36.34 | A | C |
| ATOM | 1016 | CG2 | VAL | A | 127 | -28.501 | -9.351 | 11.567 | 1.00 | 37.25 | A | C |
| ATOM | 1017 | C | VAL | A | 127 | -28.456 | -6.546 | 14.155 | 1.00 | 39.69 | A | C |
| ATOM | 1018 | O | VAL | A | 127 | -27.370 | -6.476 | 14.724 | 1.00 | 38.67 | A | O |
| ATOM | 1019 | N | HIS | A | 128 | -29.246 | -5.487 | 14.077 | 1.00 | 41.75 | A | N |
| ATOM | 1020 | CA | HIS | A | 128 | -28.804 | -4.238 | 14.686 | 1.00 | 43.30 | A | C |
| ATOM | 1021 | CB | HIS | A | 128 | -29.461 | -3.024 | 14.044 | 1.00 | 46.76 | A | C |
| ATOM | 1022 | CG | HIS | A | 128 | -29.172 | -2.870 | 12.586 | 1.00 | 49.58 | A | C |
| ATOM | 1023 | ND1 | HIS | A | 128 | -27.886 | -2.823 | 12.078 | 1.00 | 50.91 | A | N |
| ATOM | 1024 | CE1 | HIS | A | 128 | -27.947 | -2.669 | 10.764 | 1.00 | 52.55 | A | C |
| ATOM | 1025 | NE2 | HIS | A | 128 | -29.219 | -2.606 | 10.407 | 1.00 | 52.49 | A | N |
| ATOM | 1026 | CD2 | HIS | A | 128 | -30.005 | -2.719 | 11.526 | 1.00 | 51.47 | A | C |
| ATOM | 1027 | C | HIS | A | 128 | -29.102 | -4.272 | 16.175 | 1.00 | 42.90 | A | C |
| ATOM | 1028 | O | HIS | A | 128 | -28.302 | -3.779 | 16.976 | 1.00 | 42.72 | A | O |
| ATOM | 1029 | N | ILE | A | 129 | -30.265 | -4.831 | 16.526 | 1.00 | 42.28 | A | N |
| ATOM | 1030 | CA | ILE | A | 129 | -30.622 | -5.086 | 17.910 | 1.00 | 42.49 | A | C |
| ATOM | 1031 | CB | ILE | A | 129 | -31.942 | -5.844 | 18.030 | 1.00 | 42.88 | A | C |
| ATOM | 1032 | CG1 | ILE | A | 129 | -33.113 | -4.987 | 17.541 | 1.00 | 45.10 | A | C |
| ATOM | 1033 | CD1 | ILE | A | 129 | -34.357 | -5.759 | 17.263 | 1.00 | 43.33 | A | C |
| ATOM | 1034 | CG2 | ILE | A | 129 | -32.214 | -6.231 | 19.484 | 1.00 | 42.58 | A | C |
| ATOM | 1035 | C | ILE | A | 129 | -29.554 | -5.914 | 18.614 | 1.00 | 40.65 | A | C |
| ATOM | 1036 | O | ILE | A | 129 | -29.225 | -5.642 | 19.755 | 1.00 | 41.71 | A | O |
| ATOM | 1037 | N | TYR | A | 130 | -29.009 | -6.911 | 17.925 | 1.00 | 38.48 | A | N |
| ATOM | 1038 | CA | TYR | A | 130 | -28.003 | -7.757 | 18.481 | 1.00 | 36.89 | A | C |
| ATOM | 1039 | CB | TYR | A | 130 | -27.874 | -9.022 | 17.646 | 1.00 | 34.64 | A | C |
| ATOM | 1040 | CG | TYR | A | 130 | -27.085 | -10.161 | 18.286 | 1.00 | 33.81 | A | C |
| ATOM | 1041 | CD1 | TYR | A | 130 | -27.724 | -11.168 | 18.999 | 1.00 | 34.44 | A | C |
| ATOM | 1042 | CE1 | TYR | A | 130 | -26.983 | -12.229 | 19.580 | 1.00 | 33.80 | A | C |
| ATOM | 1043 | CZ | TYR | A | 130 | -25.602 | -12.273 | 19.435 | 1.00 | 31.71 | A | C |
| ATOM | 1044 | OH | TYR | A | 130 | -24.883 | -13.300 | 20.008 | 1.00 | 34.72 | A | O |
| ATOM | 1045 | CE2 | TYR | A | 130 | -24.945 | -11.296 | 18.738 | 1.00 | 30.52 | A | C |
| ATOM | 1046 | CD2 | TYR | A | 130 | -25.683 | -10.239 | 18.161 | 1.00 | 33.43 | A | C |
| ATOM | 1047 | C | TYR | A | 130 | -26.689 | -6.982 | 18.554 | 1.00 | 37.66 | A | C |
| ATOM | 1048 | O | TYR | A | 130 | -26.065 | -6.922 | 19.609 | 1.00 | 37.62 | A | O |
| ATOM | 1049 | N | TYR | A | 131 | -26.283 | -6.362 | 17.449 | 1.00 | 38.85 | A | N |
| ATOM | 1050 | CA | TYR | A | 131 | -25.057 | -5.536 | 17.428 | 1.00 | 39.75 | A | C |
| ATOM | 1051 | CB | TYR | A | 131 | -24.949 | -4.739 | 16.125 | 1.00 | 40.66 | A | C |
| ATOM | 1052 | CG | TYR | A | 131 | -23.663 | -3.937 | 15.975 | 1.00 | 41.87 | A | C |
| ATOM | 1053 | CD1 | TYR | A | 131 | -22.590 | -4.462 | 15.294 | 1.00 | 41.42 | A | C |
| ATOM | 1054 | CE1 | TYR | A | 131 | -21.422 | -3.749 | 15.131 | 1.00 | 42.24 | A | C |
| ATOM | 1055 | CZ | TYR | A | 131 | -21.305 | -2.482 | 15.642 | 1.00 | 45.27 | A | C |
| ATOM | 1056 | OH | TYR | A | 131 | -20.104 | -1.845 | 15.437 | 1.00 | 48.27 | A | O |
| ATOM | 1057 | CE2 | TYR | A | 131 | -22.352 | -1.901 | 16.328 | 1.00 | 46.24 | A | C |
| ATOM | 1058 | CD2 | TYR | A | 131 | -23.535 | -2.633 | 16.489 | 1.00 | 47.24 | A | C |
| ATOM | 1059 | C | TYR | A | 131 | -25.030 | -4.556 | 18.583 | 1.00 | 42.12 | A | C |
| ATOM | 1060 | O | TYR | A | 131 | -24.006 | -4.341 | 19.191 | 1.00 | 42.27 | A | O |
| ATOM | 1061 | N | LEU | A | 132 | -26.173 | -3.965 | 18.871 | 1.00 | 44.85 | A | N |
| ATOM | 1062 | CA | LEU | A | 132 | -26.271 | -2.966 | 19.915 | 1.00 | 47.90 | A | C |

FIG. 2-21

| | | | | | | | | | | | | |
|---|---|---|---|---|---|---|---|---|---|---|---|---|
| ATOM | 1063 | CB | LEU | A | 132 | -27.627 | -2.268 | 19.808 | 1.00 | 49.90 | A | C |
| ATOM | 1064 | CG | LEU | A | 132 | -27.693 | -0.843 | 20.312 | 1.00 | 51.56 | A | C |
| ATOM | 1065 | CD1 | LEU | A | 132 | -26.648 | -0.015 | 19.587 | 1.00 | 49.52 | A | C |
| ATOM | 1066 | CD2 | LEU | A | 132 | -29.101 | -0.304 | 20.116 | 1.00 | 50.10 | A | C |
| ATOM | 1067 | C | LEU | A | 132 | -26.056 | -3.567 | 21.318 | 1.00 | 48.76 | A | C |
| ATOM | 1068 | O | LEU | A | 132 | -25.314 | -3.020 | 22.128 | 1.00 | 49.84 | A | O |
| ATOM | 1069 | N | GLU | A | 133 | -26.692 | -4.694 | 21.601 | 1.00 | 48.84 | A | N |
| ATOM | 1070 | CA | GLU | A | 133 | -26.417 | -5.423 | 22.836 | 1.00 | 49.90 | A | C |
| ATOM | 1071 | CB | GLU | A | 133 | -27.192 | -6.722 | 22.873 | 1.00 | 48.99 | A | C |
| ATOM | 1072 | CG | GLU | A | 133 | -28.610 | -6.601 | 23.299 | 1.00 | 51.22 | A | C |
| ATOM | 1073 | CD | GLU | A | 133 | -29.343 | -7.876 | 23.013 | 1.00 | 52.45 | A | C |
| ATOM | 1074 | OE1 | GLU | A | 133 | -28.665 | -8.899 | 22.723 | 1.00 | 49.60 | A | O |
| ATOM | 1075 | OE2 | GLU | A | 133 | -30.598 | -7.868 | 23.056 | 1.00 | 57.45 | A | O |
| ATOM | 1076 | C | GLU | A | 133 | -24.955 | -5.813 | 23.018 | 1.00 | 49.20 | A | C |
| ATOM | 1077 | O | GLU | A | 133 | -24.449 | -5.734 | 24.127 | 1.00 | 50.95 | A | O |
| ATOM | 1078 | N | LYS | A | 134 | -24.297 | -6.267 | 21.954 | 1.00 | 47.52 | A | N |
| ATOM | 1079 | CA | LYS | A | 134 | -22.918 | -6.716 | 22.056 | 1.00 | 47.13 | A | C |
| ATOM | 1080 | CB | LYS | A | 134 | -22.558 | -7.669 | 20.891 | 1.00 | 44.61 | A | C |
| ATOM | 1081 | CG | LYS | A | 134 | -22.998 | -9.141 | 21.101 | 1.00 | 43.57 | A | C |
| ATOM | 1082 | CD | LYS | A | 134 | -21.871 | -10.003 | 21.754 | 1.00 | 45.33 | A | C |
| ATOM | 1083 | CE | LYS | A | 134 | -22.122 | -11.557 | 21.705 | 1.00 | 45.28 | A | C |
| ATOM | 1084 | NZ | LYS | A | 134 | -22.353 | -12.203 | 23.073 | 1.00 | 45.74 | A | N |
| ATOM | 1085 | C | LYS | A | 134 | -21.950 | -5.537 | 22.122 | 1.00 | 49.73 | A | C |
| ATOM | 1086 | O | LYS | A | 134 | -21.005 | -5.538 | 22.921 | 1.00 | 50.25 | A | O |
| ATOM | 1087 | N | ALA | A | 135 | -22.182 | -4.530 | 21.283 | 1.00 | 52.31 | A | N |
| ATOM | 1088 | CA | ALA | A | 135 | -21.353 | -3.310 | 21.276 | 1.00 | 54.81 | A | C |
| ATOM | 1089 | CB | ALA | A | 135 | -21.736 | -2.399 | 20.115 | 1.00 | 55.85 | A | C |
| ATOM | 1090 | C | ALA | A | 135 | -21.457 | -2.556 | 22.588 | 1.00 | 58.36 | A | C |
| ATOM | 1091 | O | ALA | A | 135 | -20.439 | -2.167 | 23.167 | 1.00 | 59.43 | A | O |
| ATOM | 1092 | N | ASN | A | 136 | -22.685 | -2.378 | 23.070 | 1.00 | 61.08 | A | N |
| ATOM | 1093 | CA | ASN | A | 136 | -22.929 | -1.712 | 24.364 | 1.00 | 64.99 | A | C |
| ATOM | 1094 | CB | ASN | A | 136 | -24.377 | -1.159 | 24.420 | 1.00 | 67.57 | A | C |
| ATOM | 1095 | CG | ASN | A | 136 | -24.486 | 0.173 | 25.172 | 1.00 | 71.94 | A | C |
| ATOM | 1096 | OD1 | ASN | A | 136 | -23.947 | 0.334 | 26.267 | 1.00 | 73.57 | A | O |
| ATOM | 1097 | ND2 | ASN | A | 136 | -25.205 | 1.124 | 24.584 | 1.00 | 74.29 | A | N |
| ATOM | 1098 | C | ASN | A | 136 | -22.626 | -2.663 | 25.547 | 1.00 | 64.83 | A | C |
| ATOM | 1099 | O | ASN | A | 136 | -23.192 | -2.523 | 26.637 | 1.00 | 66.98 | A | O |
| ATOM | 1100 | N | LYS | A | 137 | -21.753 | -3.642 | 25.287 | 1.00 | 62.92 | A | N |
| ATOM | 1101 | CA | LYS | A | 137 | -21.091 | -4.487 | 26.291 | 1.00 | 62.98 | A | C |
| ATOM | 1102 | CB | LYS | A | 137 | -21.868 | -5.794 | 26.524 | 1.00 | 61.42 | A | C |
| ATOM | 1103 | CG | LYS | A | 137 | -20.983 | -7.050 | 26.706 | 1.00 | 60.28 | A | C |
| ATOM | 1104 | CD | LYS | A | 137 | -21.811 | -8.308 | 27.033 | 1.00 | 61.08 | A | C |
| ATOM | 1105 | CE | LYS | A | 137 | -20.950 | -9.431 | 27.631 | 1.00 | 60.58 | A | C |
| ATOM | 1106 | NZ | LYS | A | 137 | -21.576 | -10.052 | 28.854 | 1.00 | 62.60 | A | N |
| ATOM | 1107 | C | LYS | A | 137 | -19.678 | -4.792 | 25.772 | 1.00 | 61.38 | A | C |
| ATOM | 1108 | O | LYS | A | 137 | -18.679 | -4.392 | 26.375 | 1.00 | 63.57 | A | O |
| ATOM | 1109 | N | LYS | A | 142 | -11.808 | -2.879 | 22.186 | 1.00 | 43.60 | A | N |
| ATOM | 1110 | CA | LYS | A | 142 | -11.035 | -2.973 | 20.927 | 1.00 | 43.07 | A | C |
| ATOM | 1111 | CB | LYS | A | 142 | -9.535 | -2.721 | 21.167 | 1.00 | 44.52 | A | C |
| ATOM | 1112 | CG | LYS | A | 142 | -9.273 | -1.639 | 22.197 | 1.00 | 50.43 | A | C |
| ATOM | 1113 | CD | LYS | A | 142 | -7.911 | -0.934 | 22.018 | 1.00 | 54.90 | A | C |
| ATOM | 1114 | CE | LYS | A | 142 | -7.775 | 0.176 | 23.065 | 1.00 | 59.58 | A | C |
| ATOM | 1115 | NZ | LYS | A | 142 | -6.575 | 1.060 | 22.900 | 1.00 | 65.00 | A | N |
| ATOM | 1116 | C | LYS | A | 142 | -11.199 | -4.308 | 20.200 | 1.00 | 39.25 | A | C |
| ATOM | 1117 | O | LYS | A | 142 | -10.560 | -4.536 | 19.177 | 1.00 | 37.65 | A | O |
| ATOM | 1118 | N | THR | A | 143 | -12.028 | -5.189 | 20.752 | 1.00 | 37.84 | A | N |
| ATOM | 1119 | CA | THR | A | 143 | -12.468 | -6.430 | 20.084 | 1.00 | 34.92 | A | C |
| ATOM | 1120 | CB | THR | A | 143 | -13.329 | -7.261 | 21.015 | 1.00 | 34.29 | A | C |
| ATOM | 1121 | OG1 | THR | A | 143 | -12.507 | -7.867 | 22.019 | 1.00 | 36.56 | A | O |
| ATOM | 1122 | CG2 | THR | A | 143 | -14.084 | -8.332 | 20.238 | 1.00 | 32.44 | A | C |
| ATOM | 1123 | C | THR | A | 143 | -13.379 | -6.123 | 18.937 | 1.00 | 33.76 | A | C |
| ATOM | 1124 | O | THR | A | 143 | -14.347 | -5.412 | 19.119 | 1.00 | 35.42 | A | O |
| ATOM | 1125 | N | HIS | A | 144 | -13.103 | -6.683 | 17.768 | 1.00 | 31.58 | A | N |

FIG. 2-22

| | | | | | | | | | | | | |
|---|---|---|---|---|---|---|---|---|---|---|---|---|
| ATOM | 1126 | CA | HIS | A | 144 | -13.879 | -6.389 | 16.570 | 1.00 | 30.64 | A | C |
| ATOM | 1127 | CB | HIS | A | 144 | -13.013 | -6.690 | 15.353 | 1.00 | 30.26 | A | C |
| ATOM | 1128 | CG | HIS | A | 144 | -13.421 | -5.965 | 14.116 | 1.00 | 31.02 | A | C |
| ATOM | 1129 | ND1 | HIS | A | 144 | -12.924 | -4.723 | 13.789 | 1.00 | 33.31 | A | N |
| ATOM | 1130 | CE1 | HIS | A | 144 | -13.450 | -4.331 | 12.645 | 1.00 | 35.40 | A | C |
| ATOM | 1131 | NE2 | HIS | A | 144 | -14.265 | -5.278 | 12.215 | 1.00 | 34.11 | A | N |
| ATOM | 1132 | CD2 | HIS | A | 144 | -14.258 | -6.314 | 13.115 | 1.00 | 30.72 | A | C |
| ATOM | 1133 | C | HIS | A | 144 | -15.124 | -7.274 | 16.582 | 1.00 | 28.60 | A | C |
| ATOM | 1134 | O | HIS | A | 144 | -15.026 | -8.452 | 16.869 | 1.00 | 27.93 | A | O |
| ATOM | 1135 | N | ILE | A | 145 | -16.295 | -6.707 | 16.316 | 1.00 | 29.03 | A | N |
| ATOM | 1136 | CA | ILE | A | 145 | -17.565 | -7.456 | 16.324 | 1.00 | 27.56 | A | C |
| ATOM | 1137 | CB | ILE | A | 145 | -18.682 | -6.671 | 17.081 | 1.00 | 29.24 | A | C |
| ATOM | 1138 | CG1 | ILE | A | 145 | -18.243 | -6.290 | 18.498 | 1.00 | 30.10 | A | C |
| ATOM | 1139 | CD1 | ILE | A | 145 | -19.218 | -5.350 | 19.228 | 1.00 | 31.54 | A | C |
| ATOM | 1140 | CG2 | ILE | A | 145 | -19.970 | -7.472 | 17.144 | 1.00 | 28.53 | A | C |
| ATOM | 1141 | C | ILE | A | 145 | -18.030 | -7.718 | 14.877 | 1.00 | 27.06 | A | C |
| ATOM | 1142 | O | ILE | A | 145 | -18.013 | -6.809 | 14.037 | 1.00 | 29.01 | A | O |
| ATOM | 1143 | N | HIS | A | 146 | -18.444 | -8.949 | 14.591 | 1.00 | 24.85 | A | N |
| ATOM | 1144 | CA | HIS | A | 146 | -19.029 | -9.311 | 13.301 | 1.00 | 23.84 | A | C |
| ATOM | 1145 | CB | HIS | A | 146 | -17.994 | -10.107 | 12.522 | 1.00 | 22.81 | A | C |
| ATOM | 1146 | CG | HIS | A | 146 | -18.276 | -10.241 | 11.063 | 1.00 | 23.36 | A | C |
| ATOM | 1147 | ND1 | HIS | A | 146 | -17.269 | -10.235 | 10.117 | 1.00 | 24.62 | A | N |
| ATOM | 1148 | CE1 | HIS | A | 146 | -17.794 | -10.383 | 8.918 | 1.00 | 24.66 | A | C |
| ATOM | 1149 | NE2 | HIS | A | 146 | -19.104 | -10.480 | 9.049 | 1.00 | 25.22 | A | N |
| ATOM | 1150 | CD2 | HIS | A | 146 | -19.431 | -10.402 | 10.383 | 1.00 | 23.16 | A | C |
| ATOM | 1151 | C | HIS | A | 146 | -20.263 | -10.181 | 13.583 | 1.00 | 22.82 | A | C |
| ATOM | 1152 | O | HIS | A | 146 | -20.167 | -11.214 | 14.220 | 1.00 | 21.58 | A | O |
| ATOM | 1153 | N | ILE | A | 147 | -21.403 | -9.755 | 13.078 | 1.00 | 23.29 | A | N |
| ATOM | 1154 | CA | ILE | A | 147 | -22.685 | -10.383 | 13.305 | 1.00 | 22.31 | A | C |
| ATOM | 1155 | CB | ILE | A | 147 | -23.736 | -9.332 | 13.702 | 1.00 | 24.10 | A | C |
| ATOM | 1156 | CG1 | ILE | A | 147 | -23.437 | -8.797 | 15.093 | 1.00 | 25.27 | A | C |
| ATOM | 1157 | CD1 | ILE | A | 147 | -22.925 | -9.868 | 16.011 | 1.00 | 22.49 | A | C |
| ATOM | 1158 | CG2 | ILE | A | 147 | -25.135 | -9.925 | 13.604 | 1.00 | 24.13 | A | C |
| ATOM | 1159 | C | ILE | A | 147 | -23.234 | -10.928 | 12.029 | 1.00 | 22.12 | A | C |
| ATOM | 1160 | O | ILE | A | 147 | -23.261 | -10.211 | 11.034 | 1.00 | 22.47 | A | O |
| ATOM | 1161 | N | PHE | A | 148 | -23.741 | -12.165 | 12.087 | 1.00 | 21.33 | A | N |
| ATOM | 1162 | CA | PHE | A | 148 | -24.475 | -12.782 | 10.996 | 1.00 | 21.67 | A | C |
| ATOM | 1163 | CB | PHE | A | 148 | -23.814 | -14.079 | 10.669 | 1.00 | 19.74 | A | C |
| ATOM | 1164 | CG | PHE | A | 148 | -22.506 | -13.942 | 9.994 | 1.00 | 20.45 | A | C |
| ATOM | 1165 | CD1 | PHE | A | 148 | -22.446 | -13.717 | 8.628 | 1.00 | 20.06 | A | C |
| ATOM | 1166 | CE1 | PHE | A | 148 | -21.248 | -13.646 | 7.974 | 1.00 | 18.84 | A | C |
| ATOM | 1167 | CZ | PHE | A | 148 | -20.100 | -13.800 | 8.653 | 1.00 | 19.15 | A | C |
| ATOM | 1168 | CE2 | PHE | A | 148 | -20.122 | -14.040 | 10.047 | 1.00 | 18.95 | A | C |
| ATOM | 1169 | CD2 | PHE | A | 148 | -21.312 | -14.120 | 10.705 | 1.00 | 19.37 | A | C |
| ATOM | 1170 | C | PHE | A | 148 | -25.892 | -13.119 | 11.417 | 1.00 | 22.61 | A | C |
| ATOM | 1171 | O | PHE | A | 148 | -26.097 | -13.387 | 12.577 | 1.00 | 23.73 | A | O |
| ATOM | 1172 | N | SER | A | 149 | -26.854 | -13.137 | 10.496 | 1.00 | 24.41 | A | N |
| ATOM | 1173 | CA | SER | A | 149 | -28.223 | -13.595 | 10.804 | 1.00 | 26.40 | A | C |
| ATOM | 1174 | CB | SER | A | 149 | -29.250 | -12.547 | 10.442 | 1.00 | 28.65 | A | C |
| ATOM | 1175 | OG | SER | A | 149 | -29.568 | -12.615 | 9.073 | 1.00 | 31.05 | A | O |
| ATOM | 1176 | C | SER | A | 149 | -28.569 | -14.877 | 10.062 | 1.00 | 26.57 | A | C |
| ATOM | 1177 | O | SER | A | 149 | -27.817 | -15.306 | 9.191 | 1.00 | 27.76 | A | O |
| ATOM | 1178 | N | PHE | A | 150 | -29.694 | -15.502 | 10.418 | 1.00 | 27.04 | A | N |
| ATOM | 1179 | CA | PHE | A | 150 | -30.184 | -16.660 | 9.682 | 1.00 | 26.50 | A | C |
| ATOM | 1180 | CB | PHE | A | 150 | -31.136 | -17.518 | 10.528 | 1.00 | 26.32 | A | C |
| ATOM | 1181 | CG | PHE | A | 150 | -30.440 | -18.335 | 11.527 | 1.00 | 23.45 | A | C |
| ATOM | 1182 | CD1 | PHE | A | 150 | -30.021 | -19.627 | 11.220 | 1.00 | 21.13 | A | C |
| ATOM | 1183 | CE1 | PHE | A | 150 | -29.343 | -20.366 | 12.119 | 1.00 | 16.81 | A | C |
| ATOM | 1184 | CZ | PHE | A | 150 | -28.995 | -19.828 | 13.358 | 1.00 | 19.31 | A | C |
| ATOM | 1185 | CE2 | PHE | A | 150 | -29.371 | -18.548 | 13.692 | 1.00 | 20.69 | A | C |
| ATOM | 1186 | CD2 | PHE | A | 150 | -30.111 | -17.802 | 12.762 | 1.00 | 24.45 | A | C |
| ATOM | 1187 | C | PHE | A | 150 | -30.879 | -16.220 | 8.395 | 1.00 | 28.91 | A | C |
| ATOM | 1188 | O | PHE | A | 150 | -31.139 | -17.065 | 7.529 | 1.00 | 29.34 | A | O |

FIG. 2-23

| | | | | | | | | | | | | |
|---|---|---|---|---|---|---|---|---|---|---|---|---|
| ATOM | 1189 | N | THR | A | 151 | -31.211 | -14.928 | 8.278 | 1.00 | 30.40 | A | N |
| ATOM | 1190 | CA | THR | A | 151 | -31.908 | -14.417 | 7.104 | 1.00 | 32.32 | A | C |
| ATOM | 1191 | CB | THR | A | 151 | -33.014 | -13.405 | 7.505 | 1.00 | 34.26 | A | C |
| ATOM | 1192 | OG1 | THR | A | 151 | -32.547 | -12.574 | 8.564 | 1.00 | 33.56 | A | O |
| ATOM | 1193 | CG2 | THR | A | 151 | -34.259 | -14.132 | 7.964 | 1.00 | 34.11 | A | C |
| ATOM | 1194 | C | THR | A | 151 | -30.993 | -13.796 | 6.056 | 1.00 | 33.29 | A | C |
| ATOM | 1195 | O | THR | A | 151 | -31.453 | -13.156 | 5.135 | 1.00 | 36.54 | A | O |
| ATOM | 1196 | N | GLY | A | 152 | -29.695 | -13.973 | 6.181 | 1.00 | 32.92 | A | N |
| ATOM | 1197 | CA | GLY | A | 152 | -28.760 | -13.482 | 5.169 | 1.00 | 33.43 | A | C |
| ATOM | 1198 | C | GLY | A | 152 | -28.133 | -12.114 | 5.396 | 1.00 | 34.12 | A | C |
| ATOM | 1199 | O | GLY | A | 152 | -27.382 | -11.663 | 4.543 | 1.00 | 35.73 | A | O |
| ATOM | 1200 | N | GLU | A | 153 | -28.431 | -11.442 | 6.507 | 1.00 | 33.78 | A | N |
| ATOM | 1201 | CA | GLU | A | 153 | -27.876 | -10.114 | 6.768 | 1.00 | 34.81 | A | C |
| ATOM | 1202 | CB | GLU | A | 153 | -28.876 | -9.227 | 7.503 | 1.00 | 36.84 | A | C |
| ATOM | 1203 | CG | GLU | A | 153 | -30.088 | -8.814 | 6.698 | 1.00 | 40.70 | A | C |
| ATOM | 1204 | CD | GLU | A | 153 | -31.271 | -8.468 | 7.591 | 1.00 | 45.04 | A | C |
| ATOM | 1205 | OE1 | GLU | A | 153 | -31.626 | -9.335 | 8.431 | 1.00 | 42.84 | A | O |
| ATOM | 1206 | OE2 | GLU | A | 153 | -31.849 | -7.338 | 7.450 | 1.00 | 49.64 | A | O |
| ATOM | 1207 | C | GLU | A | 153 | -26.615 | -10.218 | 7.613 | 1.00 | 32.76 | A | C |
| ATOM | 1208 | O | GLU | A | 153 | -26.390 | -11.227 | 8.288 | 1.00 | 30.70 | A | O |
| ATOM | 1209 | N | GLU | A | 154 | -25.785 | -9.178 | 7.574 | 1.00 | 33.09 | A | N |
| ATOM | 1210 | CA | GLU | A | 154 | -24.577 | -9.155 | 8.394 | 1.00 | 31.82 | A | C |
| ATOM | 1211 | CB | GLU | A | 154 | -23.393 | -9.824 | 7.671 | 1.00 | 30.31 | A | C |
| ATOM | 1212 | CG | GLU | A | 154 | -22.914 | -9.031 | 6.469 | 1.00 | 33.94 | A | C |
| ATOM | 1213 | CD | GLU | A | 154 | -21.598 | -9.499 | 5.860 | 1.00 | 35.24 | A | C |
| ATOM | 1214 | OE1 | GLU | A | 154 | -20.734 | -10.113 | 6.543 | 1.00 | 33.20 | A | O |
| ATOM | 1215 | OE2 | GLU | A | 154 | -21.429 | -9.195 | 4.666 | 1.00 | 38.99 | A | O |
| ATOM | 1216 | C | GLU | A | 154 | -24.219 | -7.737 | 8.780 | 1.00 | 32.97 | A | C |
| ATOM | 1217 | O | GLU | A | 154 | -24.552 | -6.800 | 8.070 | 1.00 | 34.72 | A | O |
| ATOM | 1218 | N | MET | A | 155 | -23.545 | -7.575 | 9.915 | 1.00 | 32.59 | A | N |
| ATOM | 1219 | CA | MET | A | 155 | -22.881 | -6.303 | 10.196 | 1.00 | 34.59 | A | C |
| ATOM | 1220 | CB | MET | A | 155 | -23.861 | -5.263 | 10.735 | 1.00 | 37.18 | A | C |
| ATOM | 1221 | CG | MET | A | 155 | -24.313 | -5.424 | 12.146 | 1.00 | 39.53 | A | C |
| ATOM | 1222 | SD | MET | A | 155 | -25.553 | -4.136 | 12.466 | 1.00 | 50.66 | A | S |
| ATOM | 1223 | CE | MET | A | 155 | -26.996 | -4.967 | 11.774 | 1.00 | 46.78 | A | C |
| ATOM | 1224 | C | MET | A | 155 | -21.626 | -6.435 | 11.063 | 1.00 | 32.52 | A | C |
| ATOM | 1225 | O | MET | A | 155 | -21.516 | -7.341 | 11.854 | 1.00 | 29.62 | A | O |
| ATOM | 1226 | N | ALA | A | 156 | -20.694 | -5.502 | 10.885 | 1.00 | 33.66 | A | N |
| ATOM | 1227 | CA | ALA | A | 156 | -19.379 | -5.591 | 11.500 | 1.00 | 32.99 | A | C |
| ATOM | 1228 | CB | ALA | A | 156 | -18.440 | -6.221 | 10.549 | 1.00 | 31.69 | A | C |
| ATOM | 1229 | C | ALA | A | 156 | -18.843 | -4.229 | 11.958 | 1.00 | 35.67 | A | C |
| ATOM | 1230 | O | ALA | A | 156 | -19.040 | -3.223 | 11.280 | 1.00 | 38.97 | A | O |
| ATOM | 1231 | N | THR | A | 157 | -18.163 | -4.197 | 13.106 | 1.00 | 35.16 | A | N |
| ATOM | 1232 | CA | THR | A | 157 | -17.575 | -2.967 | 13.600 | 1.00 | 37.13 | A | C |
| ATOM | 1233 | CB | THR | A | 157 | -16.562 | -3.220 | 14.764 | 1.00 | 36.63 | A | C |
| ATOM | 1234 | OG1 | THR | A | 157 | -17.229 | -3.077 | 16.026 | 1.00 | 39.19 | A | O |
| ATOM | 1235 | CG2 | THR | A | 157 | -15.445 | -2.196 | 14.763 | 1.00 | 38.72 | A | C |
| ATOM | 1236 | C | THR | A | 157 | -16.884 | -2.237 | 12.468 | 1.00 | 38.18 | A | C |
| ATOM | 1237 | O | THR | A | 157 | -16.137 | -2.844 | 11.730 | 1.00 | 36.37 | A | O |
| ATOM | 1238 | N | LYS | A | 158 | -17.158 | -0.933 | 12.348 | 1.00 | 41.09 | A | N |
| ATOM | 1239 | CA | LYS | A | 158 | -16.553 | -0.062 | 11.354 | 1.00 | 43.23 | A | C |
| ATOM | 1240 | CB | LYS | A | 158 | -15.025 | -0.009 | 11.536 | 1.00 | 43.59 | A | C |
| ATOM | 1241 | CG | LYS | A | 158 | -14.535 | 0.841 | 12.715 | 1.00 | 47.25 | A | C |
| ATOM | 1242 | CD | LYS | A | 158 | -13.015 | 0.665 | 12.924 | 1.00 | 49.55 | A | C |
| ATOM | 1243 | CE | LYS | A | 158 | -12.343 | 1.858 | 13.643 | 1.00 | 53.50 | A | C |
| ATOM | 1244 | NZ | LYS | A | 158 | -12.056 | 1.562 | 15.084 | 1.00 | 52.93 | A | N |
| ATOM | 1245 | C | LYS | A | 158 | -16.883 | -0.409 | 9.905 | 1.00 | 42.65 | A | C |
| ATOM | 1246 | O | LYS | A | 158 | -16.308 | 0.167 | 8.998 | 1.00 | 45.29 | A | O |
| ATOM | 1247 | N | ALA | A | 159 | -17.805 | -1.328 | 9.674 | 1.00 | 40.71 | A | N |
| ATOM | 1248 | CA | ALA | A | 159 | -18.094 | -1.836 | 8.312 | 1.00 | 40.55 | A | C |
| ATOM | 1249 | CB | ALA | A | 159 | -18.549 | -0.720 | 7.402 | 1.00 | 42.47 | A | C |
| ATOM | 1250 | C | ALA | A | 159 | -16.900 | -2.619 | 7.699 | 1.00 | 39.14 | A | C |
| ATOM | 1251 | O | ALA | A | 159 | -16.752 | -2.729 | 6.466 | 1.00 | 39.69 | A | O |

FIG. 2-24

| | | | | | | | | | | | | |
|---|---|---|---|---|---|---|---|---|---|---|---|---|
| ATOM | 1252 | N | ASP | A | 160 | -16.077 | -3.173 | 8.587 | 1.00 | 37.02 | A | N |
| ATOM | 1253 | CA | ASP | A | 160 | -14.924 | -3.970 | 8.218 | 1.00 | 35.61 | A | C |
| ATOM | 1254 | CB | ASP | A | 160 | -13.694 | -3.549 | 9.046 | 1.00 | 35.96 | A | C |
| ATOM | 1255 | CG | ASP | A | 160 | -12.406 | -4.237 | 8.608 | 1.00 | 34.75 | A | C |
| ATOM | 1256 | OD1 | ASP | A | 160 | -12.434 | -5.102 | 7.716 | 1.00 | 32.77 | A | O |
| ATOM | 1257 | OD2 | ASP | A | 160 | -11.341 | -3.907 | 9.175 | 1.00 | 37.58 | A | O |
| ATOM | 1258 | C | ASP | A | 160 | -15.259 | -5.438 | 8.450 | 1.00 | 33.02 | A | C |
| ATOM | 1259 | O | ASP | A | 160 | -15.233 | -5.937 | 9.596 | 1.00 | 30.79 | A | O |
| ATOM | 1260 | N | TYR | A | 161 | -15.542 | -6.139 | 7.355 | 1.00 | 32.31 | A | N |
| ATOM | 1261 | CA | TYR | A | 161 | -16.011 | -7.499 | 7.467 | 1.00 | 30.28 | A | C |
| ATOM | 1262 | CB | TYR | A | 161 | -17.033 | -7.779 | 6.381 | 1.00 | 30.73 | A | C |
| ATOM | 1263 | CG | TYR | A | 161 | -18.186 | -6.817 | 6.446 | 1.00 | 34.16 | A | C |
| ATOM | 1264 | CD1 | TYR | A | 161 | -19.245 | -7.035 | 7.322 | 1.00 | 34.14 | A | C |
| ATOM | 1265 | CE1 | TYR | A | 161 | -20.320 | -6.158 | 7.390 | 1.00 | 36.01 | A | C |
| ATOM | 1266 | CZ | TYR | A | 161 | -20.338 | -5.032 | 6.595 | 1.00 | 40.45 | A | C |
| ATOM | 1267 | OH | TYR | A | 161 | -21.402 | -4.162 | 6.699 | 1.00 | 45.76 | A | O |
| ATOM | 1268 | CE2 | TYR | A | 161 | -19.291 | -4.770 | 5.712 | 1.00 | 41.25 | A | C |
| ATOM | 1269 | CD2 | TYR | A | 161 | -18.215 | -5.665 | 5.645 | 1.00 | 39.08 | A | C |
| ATOM | 1270 | C | TYR | A | 161 | -14.869 | -8.494 | 7.451 | 1.00 | 28.89 | A | C |
| ATOM | 1271 | O | TYR | A | 161 | -15.106 | -9.712 | 7.375 | 1.00 | 26.31 | A | O |
| ATOM | 1272 | N | THR | A | 162 | -13.639 | -7.975 | 7.557 | 1.00 | 29.48 | A | N |
| ATOM | 1273 | CA | THR | A | 162 | -12.439 | -8.801 | 7.625 | 1.00 | 29.16 | A | C |
| ATOM | 1274 | CB | THR | A | 162 | -12.433 | -9.684 | 8.868 | 1.00 | 26.95 | A | C |
| ATOM | 1275 | OG1 | THR | A | 162 | -12.638 | -8.877 | 10.017 | 1.00 | 27.65 | A | O |
| ATOM | 1276 | CG2 | THR | A | 162 | -11.095 | -10.413 | 9.014 | 1.00 | 27.47 | A | C |
| ATOM | 1277 | C | THR | A | 162 | -12.217 | -9.696 | 6.403 | 1.00 | 29.42 | A | C |
| ATOM | 1278 | O | THR | A | 162 | -11.279 | -9.486 | 5.663 | 1.00 | 31.31 | A | O |
| ATOM | 1279 | N | LEU | A | 163 | -13.067 | -10.705 | 6.215 | 1.00 | 29.00 | A | N |
| ATOM | 1280 | CA | LEU | A | 163 | -12.918 | -11.681 | 5.124 | 1.00 | 28.99 | A | C |
| ATOM | 1281 | CB | LEU | A | 163 | -13.864 | -12.867 | 5.305 | 1.00 | 26.83 | A | C |
| ATOM | 1282 | CG | LEU | A | 163 | -13.694 | -13.727 | 6.560 | 1.00 | 24.81 | A | C |
| ATOM | 1283 | CD1 | LEU | A | 163 | -14.813 | -14.756 | 6.672 | 1.00 | 17.75 | A | C |
| ATOM | 1284 | CD2 | LEU | A | 163 | -12.293 | -14.373 | 6.544 | 1.00 | 24.21 | A | C |
| ATOM | 1285 | C | LEU | A | 163 | -13.271 | -11.053 | 3.814 | 1.00 | 31.29 | A | C |
| ATOM | 1286 | O | LEU | A | 163 | -13.794 | -9.958 | 3.782 | 1.00 | 34.30 | A | O |
| ATOM | 1287 | N | ASP | A | 164 | -13.000 | -11.774 | 2.738 | 1.00 | 31.82 | A | N |
| ATOM | 1288 | CA | ASP | A | 164 | -13.570 | -11.497 | 1.415 | 1.00 | 33.23 | A | C |
| ATOM | 1289 | CB | ASP | A | 164 | -12.836 | -12.353 | 0.375 | 1.00 | 33.86 | A | C |
| ATOM | 1290 | CG | ASP | A | 164 | -12.879 | -13.837 | 0.723 | 1.00 | 31.15 | A | C |
| ATOM | 1291 | OD1 | ASP | A | 164 | -12.646 | -14.181 | 1.920 | 1.00 | 22.95 | A | O |
| ATOM | 1292 | OD2 | ASP | A | 164 | -13.190 | -14.635 | -0.192 | 1.00 | 30.23 | A | O |
| ATOM | 1293 | C | ASP | A | 164 | -15.059 | -11.840 | 1.351 | 1.00 | 32.77 | A | C |
| ATOM | 1294 | O | ASP | A | 164 | -15.611 | -12.492 | 2.244 | 1.00 | 30.52 | A | O |
| ATOM | 1295 | N | GLU | A | 165 | -15.687 | -11.452 | 0.245 | 1.00 | 35.33 | A | N |
| ATOM | 1296 | CA | GLU | A | 165 | -17.135 | -11.620 | 0.060 | 1.00 | 35.80 | A | C |
| ATOM | 1297 | CB | GLU | A | 165 | -17.621 | -10.754 | -1.098 | 1.00 | 39.00 | A | C |
| ATOM | 1298 | CG | GLU | A | 165 | -17.718 | -9.290 | -0.680 | 1.00 | 42.20 | A | C |
| ATOM | 1299 | CD | GLU | A | 165 | -17.909 | -8.328 | -1.841 | 1.00 | 47.50 | A | C |
| ATOM | 1300 | OE1 | GLU | A | 165 | -19.041 | -8.247 | -2.387 | 1.00 | 51.13 | A | O |
| ATOM | 1301 | OE2 | GLU | A | 165 | -16.929 | -7.628 | -2.177 | 1.00 | 47.82 | A | O |
| ATOM | 1302 | C | GLU | A | 165 | -17.584 | -13.082 | -0.086 | 1.00 | 34.46 | A | C |
| ATOM | 1303 | O | GLU | A | 165 | -18.644 | -13.461 | 0.441 | 1.00 | 33.54 | A | O |
| ATOM | 1304 | N | GLU | A | 166 | -16.778 | -13.904 | -0.758 | 1.00 | 33.94 | A | N |
| ATOM | 1305 | CA | GLU | A | 166 | -17.147 | -15.309 | -0.988 | 1.00 | 32.81 | A | C |
| ATOM | 1306 | CB | GLU | A | 166 | -16.138 | -15.997 | -1.909 | 1.00 | 33.94 | A | C |
| ATOM | 1307 | CG | GLU | A | 166 | -16.477 | -15.868 | -3.354 | 1.00 | 40.06 | A | C |
| ATOM | 1308 | CD | GLU | A | 166 | -17.695 | -16.674 | -3.717 | 1.00 | 42.03 | A | C |
| ATOM | 1309 | OE1 | GLU | A | 166 | -18.699 | -16.036 | -4.118 | 1.00 | 43.59 | A | O |
| ATOM | 1310 | OE2 | GLU | A | 166 | -17.654 | -17.930 | -3.578 | 1.00 | 40.54 | A | O |
| ATOM | 1311 | C | GLU | A | 166 | -17.236 | -16.105 | 0.302 | 1.00 | 29.15 | A | C |
| ATOM | 1312 | O | GLU | A | 166 | -18.157 | -16.895 | 0.491 | 1.00 | 27.59 | A | O |
| ATOM | 1313 | N | SER | A | 167 | -16.234 | -15.926 | 1.152 | 1.00 | 27.33 | A | N |
| ATOM | 1314 | CA | SER | A | 167 | -16.229 | -16.533 | 2.450 | 1.00 | 25.51 | A | C |

FIG. 2-25

| | | | | | | | | | | | | |
|---|---|---|---|---|---|---|---|---|---|---|---|---|
| ATOM | 1315 | CB | SER | A | 167 | -14.930 | -16.159 | 3.196 | 1.00 | 25.59 | A | C |
| ATOM | 1316 | OG | SER | A | 167 | -13.773 | -16.490 | 2.425 | 1.00 | 26.87 | A | O |
| ATOM | 1317 | C | SER | A | 167 | -17.481 | -16.111 | 3.241 | 1.00 | 24.17 | A | C |
| ATOM | 1318 | O | SER | A | 167 | -18.175 | -16.931 | 3.813 | 1.00 | 22.43 | A | O |
| ATOM | 1319 | N | ARG | A | 168 | -17.816 | -14.830 | 3.199 | 1.00 | 25.85 | A | N |
| ATOM | 1320 | CA | ARG | A | 168 | -19.049 | -14.335 | 3.861 | 1.00 | 25.35 | A | C |
| ATOM | 1321 | CB | ARG | A | 168 | -19.076 | -12.826 | 3.853 | 1.00 | 26.28 | A | C |
| ATOM | 1322 | CG | ARG | A | 168 | -17.933 | -12.273 | 4.684 | 1.00 | 27.62 | A | C |
| ATOM | 1323 | CD | ARG | A | 168 | -18.113 | -10.808 | 4.963 | 1.00 | 30.07 | A | C |
| ATOM | 1324 | NE | ARG | A | 168 | -17.401 | -9.988 | 4.007 | 1.00 | 33.04 | A | N |
| ATOM | 1325 | CZ | ARG | A | 168 | -17.931 | -8.996 | 3.302 | 1.00 | 36.55 | A | C |
| ATOM | 1326 | NH1 | ARG | A | 168 | -19.205 | -8.665 | 3.410 | 1.00 | 34.96 | A | N |
| ATOM | 1327 | NH2 | ARG | A | 168 | -17.148 | -8.314 | 2.483 | 1.00 | 40.96 | A | N |
| ATOM | 1328 | C | ARG | A | 168 | -20.346 | -14.895 | 3.293 | 1.00 | 25.33 | A | C |
| ATOM | 1329 | O | ARG | A | 168 | -21.255 | -15.244 | 4.039 | 1.00 | 24.28 | A | O |
| ATOM | 1330 | N | ALA | A | 169 | -20.419 | -14.997 | 1.983 | 1.00 | 26.69 | A | N |
| ATOM | 1331 | CA | ALA | A | 169 | -21.601 | -15.479 | 1.328 | 1.00 | 27.83 | A | C |
| ATOM | 1332 | CB | ALA | A | 169 | -21.462 | -15.252 | -0.141 | 1.00 | 30.58 | A | C |
| ATOM | 1333 | C | ALA | A | 169 | -21.770 | -16.952 | 1.608 | 1.00 | 27.84 | A | C |
| ATOM | 1334 | O | ALA | A | 169 | -22.874 | -17.450 | 1.708 | 1.00 | 27.83 | A | O |
| ATOM | 1335 | N | ARG | A | 170 | -20.649 | -17.659 | 1.686 | 1.00 | 27.97 | A | N |
| ATOM | 1336 | CA | ARG | A | 170 | -20.652 | -19.049 | 2.079 | 1.00 | 27.76 | A | C |
| ATOM | 1337 | CB | ARG | A | 170 | -19.208 | -19.559 | 2.086 | 1.00 | 27.38 | A | C |
| ATOM | 1338 | CG | ARG | A | 170 | -18.994 | -20.951 | 2.580 | 1.00 | 29.26 | A | C |
| ATOM | 1339 | CD | ARG | A | 170 | -17.511 | -21.395 | 2.298 | 1.00 | 35.19 | A | C |
| ATOM | 1340 | NE | ARG | A | 170 | -17.249 | -22.811 | 2.599 | 1.00 | 36.75 | A | N |
| ATOM | 1341 | CZ | ARG | A | 170 | -16.789 | -23.292 | 3.757 | 1.00 | 38.06 | A | C |
| ATOM | 1342 | NH1 | ARG | A | 170 | -16.502 | -22.488 | 4.783 | 1.00 | 36.34 | A | N |
| ATOM | 1343 | NH2 | ARG | A | 170 | -16.611 | -24.609 | 3.888 | 1.00 | 39.67 | A | N |
| ATOM | 1344 | C | ARG | A | 170 | -21.321 | -19.263 | 3.462 | 1.00 | 25.65 | A | C |
| ATOM | 1345 | O | ARG | A | 170 | -22.153 | -20.168 | 3.610 | 1.00 | 26.74 | A | O |
| ATOM | 1346 | N | ILE | A | 171 | -20.959 | -18.453 | 4.454 | 1.00 | 23.34 | A | N |
| ATOM | 1347 | CA | ILE | A | 171 | -21.528 | -18.581 | 5.815 | 1.00 | 21.38 | A | C |
| ATOM | 1348 | CB | ILE | A | 171 | -20.724 | -17.757 | 6.872 | 1.00 | 20.28 | A | C |
| ATOM | 1349 | CG1 | ILE | A | 171 | -19.253 | -18.186 | 6.935 | 1.00 | 20.15 | A | C |
| ATOM | 1350 | CD1 | ILE | A | 171 | -18.357 | -17.285 | 7.730 | 1.00 | 19.43 | A | C |
| ATOM | 1351 | CG2 | ILE | A | 171 | -21.302 | -17.951 | 8.245 | 1.00 | 19.43 | A | C |
| ATOM | 1352 | C | ILE | A | 171 | -23.017 | -18.141 | 5.869 | 1.00 | 21.64 | A | C |
| ATOM | 1353 | O | ILE | A | 171 | -23.864 | -18.852 | 6.423 | 1.00 | 20.45 | A | O |
| ATOM | 1354 | N | LYS | A | 172 | -23.316 | -16.980 | 5.288 | 1.00 | 21.99 | A | N |
| ATOM | 1355 | CA | LYS | A | 172 | -24.699 | -16.519 | 5.112 | 1.00 | 23.19 | A | C |
| ATOM | 1356 | CB | LYS | A | 172 | -24.717 | -15.260 | 4.268 | 1.00 | 25.29 | A | C |
| ATOM | 1357 | CG | LYS | A | 172 | -24.311 | -13.997 | 5.005 | 1.00 | 26.28 | A | C |
| ATOM | 1358 | CD | LYS | A | 172 | -24.515 | -12.763 | 4.124 | 1.00 | 29.81 | A | C |
| ATOM | 1359 | CE | LYS | A | 172 | -23.230 | -12.281 | 3.458 | 1.00 | 30.35 | A | C |
| ATOM | 1360 | NZ | LYS | A | 172 | -23.272 | -10.797 | 3.295 | 1.00 | 34.17 | A | N |
| ATOM | 1361 | C | LYS | A | 172 | -25.619 | -17.547 | 4.436 | 1.00 | 23.68 | A | C |
| ATOM | 1362 | O | LYS | A | 172 | -26.742 | -17.750 | 4.851 | 1.00 | 23.47 | A | O |
| ATOM | 1363 | N | THR | A | 173 | -25.133 | -18.165 | 3.372 | 1.00 | 24.52 | A | N |
| ATOM | 1364 | CA | THR | A | 173 | -25.788 | -19.315 | 2.754 | 1.00 | 25.18 | A | C |
| ATOM | 1365 | CB | THR | A | 173 | -25.002 | -19.806 | 1.553 | 1.00 | 26.05 | A | C |
| ATOM | 1366 | OG1 | THR | A | 173 | -25.177 | -18.867 | 0.500 | 1.00 | 25.67 | A | O |
| ATOM | 1367 | CG2 | THR | A | 173 | -25.501 | -21.177 | 1.095 | 1.00 | 27.22 | A | C |
| ATOM | 1368 | C | THR | A | 173 | -25.999 | -20.487 | 3.707 | 1.00 | 23.67 | A | C |
| ATOM | 1369 | O | THR | A | 173 | -27.134 | -20.937 | 3.915 | 1.00 | 23.84 | A | O |
| ATOM | 1370 | N | ARG | A | 174 | -24.927 | -20.987 | 4.292 | 1.00 | 22.32 | A | N |
| ATOM | 1371 | CA | ARG | A | 174 | -25.076 | -22.077 | 5.292 | 1.00 | 21.02 | A | C |
| ATOM | 1372 | CB | ARG | A | 174 | -23.743 | -22.347 | 5.954 | 1.00 | 19.66 | A | C |
| ATOM | 1373 | CG | ARG | A | 174 | -23.755 | -23.374 | 7.102 | 1.00 | 19.80 | A | C |
| ATOM | 1374 | CD | ARG | A | 174 | -24.160 | -24.739 | 6.651 | 1.00 | 19.79 | A | C |
| ATOM | 1375 | NE | ARG | A | 174 | -23.943 | -25.723 | 7.712 | 1.00 | 20.94 | A | N |
| ATOM | 1376 | CZ | ARG | A | 174 | -24.575 | -26.887 | 7.812 | 1.00 | 21.39 | A | C |
| ATOM | 1377 | NH1 | ARG | A | 174 | -25.469 | -27.228 | 6.914 | 1.00 | 24.70 | A | N |

FIG. 2-26

| | | | | | | | | | | | | |
|---|---|---|---|---|---|---|---|---|---|---|---|---|
| ATOM | 1378 | NH2 | ARG | A | 174 | -24.338 | -27.697 | 8.830 | 1.00 | 21.74 | A | N |
| ATOM | 1379 | C | ARG | A | 174 | -26.159 | -21.801 | 6.364 | 1.00 | 20.47 | A | C |
| ATOM | 1380 | O | ARG | A | 174 | -26.930 | -22.688 | 6.717 | 1.00 | 22.09 | A | O |
| ATOM | 1381 | N | LEU | A | 175 | -26.230 | -20.572 | 6.860 | 1.00 | 19.74 | A | N |
| ATOM | 1382 | CA | LEU | A | 175 | -27.168 | -20.197 | 7.923 | 1.00 | 18.80 | A | C |
| ATOM | 1383 | CB | LEU | A | 175 | -26.799 | -18.832 | 8.467 | 1.00 | 18.24 | A | C |
| ATOM | 1384 | CG | LEU | A | 175 | -25.526 | -18.838 | 9.316 | 1.00 | 16.34 | A | C |
| ATOM | 1385 | CD1 | LEU | A | 175 | -25.099 | -17.421 | 9.637 | 1.00 | 15.42 | A | C |
| ATOM | 1386 | CD2 | LEU | A | 175 | -25.756 | -19.624 | 10.574 | 1.00 | 11.76 | A | C |
| ATOM | 1387 | C | LEU | A | 175 | -28.596 | -20.173 | 7.409 | 1.00 | 20.46 | A | C |
| ATOM | 1388 | O | LEU | A | 175 | -29.533 | -20.652 | 8.063 | 1.00 | 20.52 | A | O |
| ATOM | 1389 | N | PHE | A | 176 | -28.754 | -19.600 | 6.227 | 1.00 | 21.77 | A | N |
| ATOM | 1390 | CA | PHE | A | 176 | -30.021 | -19.600 | 5.549 | 1.00 | 23.48 | A | C |
| ATOM | 1391 | CB | PHE | A | 176 | -29.906 | -18.837 | 4.240 | 1.00 | 25.28 | A | C |
| ATOM | 1392 | CG | PHE | A | 176 | -31.208 | -18.645 | 3.558 | 1.00 | 26.90 | A | C |
| ATOM | 1393 | CD1 | PHE | A | 176 | -31.952 | -17.509 | 3.783 | 1.00 | 28.37 | A | C |
| ATOM | 1394 | CE1 | PHE | A | 176 | -33.206 | -17.345 | 3.166 | 1.00 | 31.59 | A | C |
| ATOM | 1395 | CZ | PHE | A | 176 | -33.697 | -18.328 | 2.334 | 1.00 | 31.69 | A | C |
| ATOM | 1396 | CE2 | PHE | A | 176 | -32.946 | -19.476 | 2.110 | 1.00 | 30.52 | A | C |
| ATOM | 1397 | CD2 | PHE | A | 176 | -31.722 | -19.633 | 2.730 | 1.00 | 27.45 | A | C |
| ATOM | 1398 | C | PHE | A | 176 | -30.513 | -21.035 | 5.323 | 1.00 | 23.97 | A | C |
| ATOM | 1399 | O | PHE | A | 176 | -31.675 | -21.334 | 5.533 | 1.00 | 24.81 | A | O |
| ATOM | 1400 | N | THR | A | 177 | -29.617 | -21.929 | 4.940 | 1.00 | 23.73 | A | N |
| ATOM | 1401 | CA | THR | A | 177 | -29.978 | -23.323 | 4.688 | 1.00 | 24.64 | A | C |
| ATOM | 1402 | CB | THR | A | 177 | -28.798 | -24.073 | 4.026 | 1.00 | 24.41 | A | C |
| ATOM | 1403 | OG1 | THR | A | 177 | -28.493 | -23.455 | 2.773 | 1.00 | 27.31 | A | O |
| ATOM | 1404 | CG2 | THR | A | 177 | -29.122 | -25.522 | 3.789 | 1.00 | 24.94 | A | C |
| ATOM | 1405 | C | THR | A | 177 | -30.381 | -24.014 | 5.991 | 1.00 | 24.04 | A | C |
| ATOM | 1406 | O | THR | A | 177 | -31.293 | -24.814 | 6.010 | 1.00 | 24.79 | A | O |
| ATOM | 1407 | N | ILE | A | 178 | -29.689 | -23.706 | 7.089 | 1.00 | 22.92 | A | N |
| ATOM | 1408 | CA | ILE | A | 178 | -30.005 | -24.332 | 8.367 | 1.00 | 21.84 | A | C |
| ATOM | 1409 | CB | ILE | A | 178 | -29.032 | -23.921 | 9.493 | 1.00 | 20.44 | A | C |
| ATOM | 1410 | CG1 | ILE | A | 178 | -27.674 | -24.610 | 9.258 | 1.00 | 20.61 | A | C |
| ATOM | 1411 | CD1 | ILE | A | 178 | -26.467 | -24.066 | 10.079 | 1.00 | 19.02 | A | C |
| ATOM | 1412 | CG2 | ILE | A | 178 | -29.610 | -24.329 | 10.830 | 1.00 | 17.28 | A | C |
| ATOM | 1413 | C | ILE | A | 178 | -31.407 | -23.974 | 8.746 | 1.00 | 23.42 | A | C |
| ATOM | 1414 | O | ILE | A | 178 | -32.105 | -24.773 | 9.346 | 1.00 | 23.94 | A | O |
| ATOM | 1415 | N | ARG | A | 179 | -31.831 | -22.772 | 8.346 | 1.00 | 24.37 | A | N |
| ATOM | 1416 | CA | ARG | A | 179 | -33.143 | -22.284 | 8.686 | 1.00 | 25.71 | A | C |
| ATOM | 1417 | CB | ARG | A | 179 | -33.206 | -20.771 | 8.492 | 1.00 | 26.10 | A | C |
| ATOM | 1418 | CG | ARG | A | 179 | -34.586 | -20.143 | 8.572 | 1.00 | 26.15 | A | C |
| ATOM | 1419 | CD | ARG | A | 179 | -34.391 | -18.643 | 8.699 | 1.00 | 25.26 | A | C |
| ATOM | 1420 | NE | ARG | A | 179 | -35.601 | -17.834 | 8.687 | 1.00 | 27.38 | A | N |
| ATOM | 1421 | CZ | ARG | A | 179 | -36.290 | -17.499 | 7.589 | 1.00 | 28.24 | A | C |
| ATOM | 1422 | NH1 | ARG | A | 179 | -35.918 | -17.966 | 6.401 | 1.00 | 27.05 | A | N |
| ATOM | 1423 | NH2 | ARG | A | 179 | -37.359 | -16.695 | 7.682 | 1.00 | 28.26 | A | N |
| ATOM | 1424 | C | ARG | A | 179 | -34.232 | -22.999 | 7.901 | 1.00 | 27.95 | A | C |
| ATOM | 1425 | O | ARG | A | 179 | -35.230 | -23.401 | 8.488 | 1.00 | 28.79 | A | O |
| ATOM | 1426 | N | GLN | A | 180 | -34.035 | -23.139 | 6.592 | 1.00 | 29.37 | A | N |
| ATOM | 1427 | CA | GLN | A | 180 | -34.993 | -23.845 | 5.723 | 1.00 | 32.45 | A | C |
| ATOM | 1428 | CB | GLN | A | 180 | -34.444 | -24.033 | 4.301 | 1.00 | 33.31 | A | C |
| ATOM | 1429 | CG | GLN | A | 180 | -34.436 | -22.794 | 3.393 | 1.00 | 35.31 | A | C |
| ATOM | 1430 | CD | GLN | A | 180 | -34.070 | -23.140 | 1.895 | 1.00 | 38.64 | A | C |
| ATOM | 1431 | OE1 | GLN | A | 180 | -33.029 | -23.787 | 1.631 | 1.00 | 36.28 | A | O |
| ATOM | 1432 | NE2 | GLN | A | 180 | -34.917 | -22.690 | 0.934 | 1.00 | 33.57 | A | N |
| ATOM | 1433 | C | GLN | A | 180 | -35.241 | -25.219 | 6.295 | 1.00 | 32.96 | A | C |
| ATOM | 1434 | O | GLN | A | 180 | -36.373 | -25.620 | 6.512 | 1.00 | 33.91 | A | O |
| ATOM | 1435 | N | GLU | A | 181 | -34.145 | -25.924 | 6.565 | 1.00 | 32.68 | A | N |
| ATOM | 1436 | CA | GLU | A | 181 | -34.206 | -27.318 | 6.994 | 1.00 | 33.70 | A | C |
| ATOM | 1437 | CB | GLU | A | 181 | -32.813 | -27.901 | 7.128 | 1.00 | 32.17 | A | C |
| ATOM | 1438 | CG | GLU | A | 181 | -31.988 | -27.873 | 5.832 | 1.00 | 34.86 | A | C |
| ATOM | 1439 | CD | GLU | A | 181 | -32.544 | -28.754 | 4.719 | 1.00 | 41.94 | A | C |
| ATOM | 1440 | OE1 | GLU | A | 181 | -33.685 | -29.295 | 4.852 | 1.00 | 42.23 | A | O |

FIG. 2-27

| | | | | | | | | | | | | |
|---|---|---|---|---|---|---|---|---|---|---|---|---|
| ATOM | 1441 | OE2 | GLU | A | 181 | -31.820 | -28.884 | 3.689 | 1.00 | 45.95 | A | O |
| ATOM | 1442 | C | GLU | A | 181 | -34.966 | -27.485 | 8.299 | 1.00 | 33.82 | A | C |
| ATOM | 1443 | O | GLU | A | 181 | -35.753 | -28.421 | 8.444 | 1.00 | 35.45 | A | O |
| ATOM | 1444 | N | MET | A | 182 | -34.737 | -26.564 | 9.232 | 1.00 | 31.80 | A | N |
| ATOM | 1445 | CA | MET | A | 182 | -35.500 | -26.543 | 10.455 | 1.00 | 31.53 | A | C |
| ATOM | 1446 | CB | MET | A | 182 | -34.948 | -25.490 | 11.412 | 1.00 | 30.23 | A | C |
| ATOM | 1447 | CG | MET | A | 182 | -33.702 | -25.929 | 12.115 | 1.00 | 26.42 | A | C |
| ATOM | 1448 | SD | MET | A | 182 | -33.111 | -24.639 | 13.192 | 1.00 | 26.48 | A | S |
| ATOM | 1449 | CE | MET | A | 182 | -31.606 | -25.384 | 13.838 | 1.00 | 19.66 | A | C |
| ATOM | 1450 | C | MET | A | 182 | -36.956 | -26.261 | 10.181 | 1.00 | 33.86 | A | C |
| ATOM | 1451 | O | MET | A | 182 | -37.825 | -26.948 | 10.709 | 1.00 | 35.48 | A | O |
| ATOM | 1452 | N | ALA | A | 183 | -37.223 | -25.233 | 9.380 | 1.00 | 34.28 | A | N |
| ATOM | 1453 | CA | ALA | A | 183 | -38.584 | -24.850 | 9.071 | 1.00 | 36.44 | A | C |
| ATOM | 1454 | CB | ALA | A | 183 | -38.602 | -23.665 | 8.145 | 1.00 | 36.72 | A | C |
| ATOM | 1455 | C | ALA | A | 183 | -39.331 | -26.046 | 8.471 | 1.00 | 38.62 | A | C |
| ATOM | 1456 | O | ALA | A | 183 | -40.399 | -26.393 | 8.949 | 1.00 | 40.80 | A | O |
| ATOM | 1457 | N | SER | A | 184 | -38.748 | -26.689 | 7.457 | 1.00 | 38.62 | A | N |
| ATOM | 1458 | CA | SER | A | 184 | -39.262 | -27.958 | 6.867 | 1.00 | 40.39 | A | C |
| ATOM | 1459 | CB | SER | A | 184 | -38.225 | -28.565 | 5.919 | 1.00 | 39.77 | A | C |
| ATOM | 1460 | OG | SER | A | 184 | -38.112 | -27.806 | 4.727 | 1.00 | 42.27 | A | O |
| ATOM | 1461 | C | SER | A | 184 | -39.602 | -29.046 | 7.868 | 1.00 | 40.03 | A | C |
| ATOM | 1462 | O | SER | A | 184 | -40.507 | -29.828 | 7.668 | 1.00 | 41.57 | A | O |
| ATOM | 1463 | N | ARG | A | 185 | -38.827 | -29.117 | 8.925 | 1.00 | 38.25 | A | N |
| ATOM | 1464 | CA | ARG | A | 185 | -38.988 | -30.148 | 9.937 | 1.00 | 38.93 | A | C |
| ATOM | 1465 | CB | ARG | A | 185 | -37.600 | -30.608 | 10.376 | 1.00 | 37.10 | A | C |
| ATOM | 1466 | CG | ARG | A | 185 | -36.863 | -31.340 | 9.246 | 1.00 | 38.89 | A | C |
| ATOM | 1467 | CD | ARG | A | 185 | -35.378 | -31.600 | 9.541 | 1.00 | 39.89 | A | C |
| ATOM | 1468 | NE | ARG | A | 185 | -34.823 | -32.547 | 8.571 | 1.00 | 43.99 | A | N |
| ATOM | 1469 | CZ | ARG | A | 185 | -34.592 | -32.289 | 7.275 | 1.00 | 46.58 | A | C |
| ATOM | 1470 | NH1 | ARG | A | 185 | -34.817 | -31.080 | 6.741 | 1.00 | 46.22 | A | N |
| ATOM | 1471 | NH2 | ARG | A | 185 | -34.114 | -33.257 | 6.499 | 1.00 | 47.51 | A | N |
| ATOM | 1472 | C | ARG | A | 185 | -39.851 | -29.644 | 11.112 | 1.00 | 39.09 | A | C |
| ATOM | 1473 | O | ARG | A | 185 | -39.839 | -30.216 | 12.220 | 1.00 | 38.87 | A | O |
| ATOM | 1474 | N | SER | A | 186 | -40.617 | -28.589 | 10.814 | 1.00 | 38.98 | A | N |
| ATOM | 1475 | CA | SER | A | 186 | -41.364 | -27.775 | 11.774 | 1.00 | 39.02 | A | C |
| ATOM | 1476 | CB | SER | A | 186 | -42.787 | -28.318 | 11.970 | 1.00 | 42.25 | A | C |
| ATOM | 1477 | OG | SER | A | 186 | -42.858 | -29.255 | 13.014 | 1.00 | 43.17 | A | O |
| ATOM | 1478 | C | SER | A | 186 | -40.638 | -27.562 | 13.087 | 1.00 | 36.41 | A | C |
| ATOM | 1479 | O | SER | A | 186 | -41.217 | -27.708 | 14.141 | 1.00 | 37.30 | A | O |
| ATOM | 1480 | N | LEU | A | 187 | -39.369 | -27.185 | 12.993 | 1.00 | 33.31 | A | N |
| ATOM | 1481 | CA | LEU | A | 187 | -38.513 | -26.960 | 14.150 | 1.00 | 31.65 | A | C |
| ATOM | 1482 | CB | LEU | A | 187 | -37.232 | -27.804 | 14.027 | 1.00 | 29.58 | A | C |
| ATOM | 1483 | CG | LEU | A | 187 | -37.318 | -29.320 | 14.224 | 1.00 | 31.16 | A | C |
| ATOM | 1484 | CD1 | LEU | A | 187 | -35.913 | -29.921 | 14.157 | 1.00 | 26.69 | A | C |
| ATOM | 1485 | CD2 | LEU | A | 187 | -38.056 | -29.719 | 15.547 | 1.00 | 31.38 | A | C |
| ATOM | 1486 | C | LEU | A | 187 | -38.081 | -25.506 | 14.335 | 1.00 | 30.61 | A | C |
| ATOM | 1487 | O | LEU | A | 187 | -37.476 | -25.176 | 15.341 | 1.00 | 28.40 | A | O |
| ATOM | 1488 | N | TRP | A | 188 | -38.383 | -24.641 | 13.374 | 1.00 | 32.06 | A | N |
| ATOM | 1489 | CA | TRP | A | 188 | -37.838 | -23.293 | 13.380 | 1.00 | 32.09 | A | C |
| ATOM | 1490 | CB | TRP | A | 188 | -37.803 | -22.720 | 11.964 | 1.00 | 32.52 | A | C |
| ATOM | 1491 | CG | TRP | A | 188 | -37.354 | -21.281 | 11.890 | 1.00 | 32.48 | A | C |
| ATOM | 1492 | CD1 | TRP | A | 188 | -38.137 | -20.203 | 11.622 | 1.00 | 33.85 | A | C |
| ATOM | 1493 | NE1 | TRP | A | 188 | -37.378 | -19.054 | 11.638 | 1.00 | 34.60 | A | N |
| ATOM | 1494 | CE2 | TRP | A | 188 | -36.080 | -19.384 | 11.910 | 1.00 | 30.05 | A | C |
| ATOM | 1495 | CD2 | TRP | A | 188 | -36.024 | -20.775 | 12.069 | 1.00 | 30.38 | A | C |
| ATOM | 1496 | CE3 | TRP | A | 188 | -34.789 | -21.363 | 12.359 | 1.00 | 31.15 | A | C |
| ATOM | 1497 | CZ3 | TRP | A | 188 | -33.659 | -20.545 | 12.464 | 1.00 | 26.54 | A | C |
| ATOM | 1498 | CH2 | TRP | A | 188 | -33.761 | -19.174 | 12.298 | 1.00 | 27.22 | A | C |
| ATOM | 1499 | CZ2 | TRP | A | 188 | -34.963 | -18.576 | 12.035 | 1.00 | 29.26 | A | C |
| ATOM | 1500 | C | TRP | A | 188 | -38.592 | -22.381 | 14.351 | 1.00 | 33.95 | A | C |
| ATOM | 1501 | O | TRP | A | 188 | -37.981 | -21.702 | 15.167 | 1.00 | 34.22 | A | O |
| ATOM | 1502 | N | ASP | A | 189 | -39.905 | -22.378 | 14.297 | 1.00 | 36.86 | A | N |
| ATOM | 1503 | CA | ASP | A | 189 | -40.679 | -21.561 | 15.217 | 1.00 | 39.20 | A | C |

FIG. 2-28

| | | | | | | | | | | | | |
|---|---|---|---|---|---|---|---|---|---|---|---|---|
| ATOM | 1504 | CB | ASP | A | 189 | -42.171 | -21.874 | 15.115 | 1.00 | 42.44 | A | C |
| ATOM | 1505 | CG | ASP | A | 189 | -42.760 | -21.466 | 13.773 | 1.00 | 43.79 | A | C |
| ATOM | 1506 | OD1 | ASP | A | 189 | -42.109 | -20.684 | 13.047 | 1.00 | 43.56 | A | O |
| ATOM | 1507 | OD2 | ASP | A | 189 | -43.866 | -21.932 | 13.438 | 1.00 | 46.72 | A | O |
| ATOM | 1508 | C | ASP | A | 189 | -40.181 | -21.706 | 16.642 | 1.00 | 39.03 | A | C |
| ATOM | 1509 | O | ASP | A | 189 | -39.831 | -20.714 | 17.255 | 1.00 | 39.50 | A | O |
| ATOM | 1510 | N | SER | A | 190 | -40.099 | -22.928 | 17.158 | 1.00 | 39.41 | A | N |
| ATOM | 1511 | CA | SER | A | 190 | -39.605 | -23.130 | 18.516 | 1.00 | 39.55 | A | C |
| ATOM | 1512 | CB | SER | A | 190 | -39.674 | -24.615 | 18.903 | 1.00 | 39.97 | A | C |
| ATOM | 1513 | OG | SER | A | 190 | -38.850 | -24.924 | 20.035 | 1.00 | 39.28 | A | O |
| ATOM | 1514 | C | SER | A | 190 | -38.180 | -22.573 | 18.712 | 1.00 | 37.78 | A | C |
| ATOM | 1515 | O | SER | A | 190 | -37.877 | -22.011 | 19.766 | 1.00 | 38.13 | A | O |
| ATOM | 1516 | N | PHE | A | 191 | -37.323 | -22.707 | 17.704 | 1.00 | 36.14 | A | N |
| ATOM | 1517 | CA | PHE | A | 191 | -35.919 | -22.295 | 17.825 | 1.00 | 34.76 | A | C |
| ATOM | 1518 | CB | PHE | A | 191 | -35.126 | -22.858 | 16.649 | 1.00 | 32.56 | A | C |
| ATOM | 1519 | CG | PHE | A | 191 | -33.655 | -22.577 | 16.699 | 1.00 | 28.05 | A | C |
| ATOM | 1520 | CD1 | PHE | A | 191 | -32.859 | -23.145 | 17.673 | 1.00 | 26.10 | A | C |
| ATOM | 1521 | CE1 | PHE | A | 191 | -31.509 | -22.927 | 17.724 | 1.00 | 22.35 | A | C |
| ATOM | 1522 | CZ | PHE | A | 191 | -30.897 | -22.142 | 16.782 | 1.00 | 23.35 | A | C |
| ATOM | 1523 | CE2 | PHE | A | 191 | -31.668 | -21.568 | 15.776 | 1.00 | 27.43 | A | C |
| ATOM | 1524 | CD2 | PHE | A | 191 | -33.055 | -21.800 | 15.742 | 1.00 | 27.43 | A | C |
| ATOM | 1525 | C | PHE | A | 191 | -35.752 | -20.780 | 17.869 | 1.00 | 36.67 | A | C |
| ATOM | 1526 | O | PHE | A | 191 | -34.854 | -20.263 | 18.533 | 1.00 | 36.41 | A | O |
| ATOM | 1527 | N | ARG | A | 192 | -36.633 | -20.090 | 17.157 | 1.00 | 39.71 | A | N |
| ATOM | 1528 | CA | ARG | A | 192 | -36.670 | -18.634 | 17.075 | 1.00 | 41.72 | A | C |
| ATOM | 1529 | CB | ARG | A | 192 | -37.507 | -18.260 | 15.838 | 1.00 | 43.43 | A | C |
| ATOM | 1530 | CG | ARG | A | 192 | -37.926 | -16.796 | 15.732 | 1.00 | 46.86 | A | C |
| ATOM | 1531 | CD | ARG | A | 192 | -36.756 | -15.946 | 15.341 | 1.00 | 46.92 | A | C |
| ATOM | 1532 | NE | ARG | A | 192 | -37.181 | -14.578 | 15.048 | 1.00 | 51.32 | A | N |
| ATOM | 1533 | CZ | ARG | A | 192 | -37.150 | -13.558 | 15.906 | 1.00 | 53.74 | A | C |
| ATOM | 1534 | NH1 | ARG | A | 192 | -36.720 | -13.721 | 17.156 | 1.00 | 54.57 | A | N |
| ATOM | 1535 | NH2 | ARG | A | 192 | -37.564 | -12.358 | 15.508 | 1.00 | 56.15 | A | N |
| ATOM | 1536 | C | ARG | A | 192 | -37.283 | -17.993 | 18.339 | 1.00 | 44.52 | A | C |
| ATOM | 1537 | O | ARG | A | 192 | -36.831 | -16.940 | 18.808 | 1.00 | 44.73 | A | O |
| ATOM | 1538 | N | GLN | A | 193 | -38.349 | -18.607 | 18.847 | 1.00 | 46.67 | A | N |
| ATOM | 1539 | CA | GLN | A | 193 | -38.993 | -18.146 | 20.062 | 1.00 | 49.61 | A | C |
| ATOM | 1540 | CB | GLN | A | 193 | -40.376 | -18.822 | 20.220 | 1.00 | 53.00 | A | C |
| ATOM | 1541 | CG | GLN | A | 193 | -41.410 | -18.323 | 19.172 | 1.00 | 56.38 | A | C |
| ATOM | 1542 | CD | GLN | A | 193 | -42.784 | -18.976 | 19.287 | 1.00 | 63.04 | A | C |
| ATOM | 1543 | OE1 | GLN | A | 193 | -43.723 | -18.396 | 19.867 | 1.00 | 69.39 | A | O |
| ATOM | 1544 | NE2 | GLN | A | 193 | -42.922 | -20.177 | 18.716 | 1.00 | 63.68 | A | N |
| ATOM | 1545 | C | GLN | A | 193 | -38.107 | -18.317 | 21.310 | 1.00 | 48.43 | A | C |
| ATOM | 1546 | O | GLN | A | 193 | -38.182 | -17.532 | 22.240 | 1.00 | 49.72 | A | O |
| ATOM | 1547 | N | SER | A | 194 | -37.237 | -19.316 | 21.319 | 1.00 | 46.39 | A | N |
| ATOM | 1548 | CA | SER | A | 194 | -36.257 | -19.433 | 22.392 | 1.00 | 45.38 | A | C |
| ATOM | 1549 | CB | SER | A | 194 | -35.786 | -20.875 | 22.548 | 1.00 | 44.24 | A | C |
| ATOM | 1550 | OG | SER | A | 194 | -34.552 | -21.076 | 21.874 | 1.00 | 41.52 | A | O |
| ATOM | 1551 | C | SER | A | 194 | -35.082 | -18.537 | 22.058 | 1.00 | 43.11 | A | C |
| ATOM | 1552 | O | SER | A | 194 | -34.156 | -18.430 | 22.842 | 1.00 | 42.28 | A | O |
| ATOM | 1553 | MN | MN | A | 901 | -19.730 | -15.353 | 19.652 | 1.00 | 24.66 | A | MN |
| ATOM | 1554 | MN | MN | A | 902 | -17.636 | -17.125 | 22.275 | 1.00 | 27.74 | A | MN |
| ATOM | 1555 | S | SO4 | A | 401 | -16.315 | -14.270 | 29.711 | 1.00 | 49.62 | A | S |
| ATOM | 1556 | O1 | SO4 | A | 401 | -16.679 | -14.563 | 28.329 | 1.00 | 47.34 | A | O |
| ATOM | 1557 | O2 | SO4 | A | 401 | -15.179 | -13.353 | 29.695 | 1.00 | 50.25 | A | O |
| ATOM | 1558 | O3 | SO4 | A | 401 | -15.826 | -15.471 | 30.411 | 1.00 | 48.00 | A | O |
| ATOM | 1559 | O4 | SO4 | A | 401 | -17.503 | -13.682 | 30.326 | 1.00 | 48.14 | A | O |
| ATOM | 1560 | S | SO4 | A | 402 | -37.933 | -15.252 | 10.914 | 1.00 | 51.77 | A | S |
| ATOM | 1561 | O1 | SO4 | A | 402 | -36.726 | -15.591 | 10.198 | 1.00 | 48.67 | A | O |
| ATOM | 1562 | O2 | SO4 | A | 402 | -37.598 | -14.973 | 12.305 | 1.00 | 52.29 | A | O |
| ATOM | 1563 | O3 | SO4 | A | 402 | -38.880 | -16.367 | 10.883 | 1.00 | 54.48 | A | O |
| ATOM | 1564 | O4 | SO4 | A | 402 | -38.557 | -14.070 | 10.323 | 1.00 | 54.14 | A | O |
| ATOM | 1565 | S | SO4 | A | 403 | -34.546 | -25.119 | 24.645 | 1.00 | 54.24 | A | S |
| ATOM | 1566 | O1 | SO4 | A | 403 | -33.134 | -24.717 | 24.606 | 1.00 | 44.33 | A | O |

FIG. 2-29

```
ATOM   1567  O2  SO4 A 403     -34.970 -25.344  26.041  1.00 57.26       A    O
ATOM   1568  O3  SO4 A 403     -34.671 -26.397  23.918  1.00 53.36       A    O
ATOM   1569  O4  SO4 A 403     -35.509 -24.120  24.115  1.00 53.43       A    O
ATOM   1570  S   SO4 A 404     -30.517 -14.816  19.351  1.00 49.29       A    S
ATOM   1571  O1  SO4 A 404     -30.690 -15.206  17.973  1.00 46.82       A    O
ATOM   1572  O2  SO4 A 404     -29.139 -15.139  19.746  1.00 46.81       A    O
ATOM   1573  O3  SO4 A 404     -31.523 -15.523  20.160  1.00 50.01       A    O
ATOM   1574  O4  SO4 A 404     -30.727 -13.368  19.479  1.00 51.58       A    O
ATOM   1575 CL   ci3 A 801     -25.090 -19.946  21.321  1.00 48.41       A   CL
ATOM   1576  CZB ci3 A 801     -23.772 -19.842  22.519  1.00 35.75       A    C
ATOM   1577  CEB ci3 A 801     -22.456 -19.789  22.057  1.00 31.41       A    C
ATOM   1578  CDB ci3 A 801     -21.432 -19.704  22.992  1.00 29.45       A    C
ATOM   1579  CEA ci3 A 801     -24.083 -19.829  23.882  1.00 34.17       A    C
ATOM   1580  CDA ci3 A 801     -23.041 -19.743  24.796  1.00 31.84       A    C
ATOM   1581  CGA ci3 A 801     -21.728 -19.682  24.352  1.00 29.22       A    C
ATOM   1582  CO  ci3 A 801     -20.601 -19.560  25.340  1.00 30.06       A    C
ATOM   1583  CF  ci3 A 801     -20.221 -18.093  25.621  1.00 30.88       A    C
ATOM   1584  CB  ci3 A 801     -19.972 -17.347  24.313  1.00 28.20       A    C
ATOM   1585  CM  ci3 A 801     -21.054 -16.681  23.533  1.00 27.21       A    C
ATOM   1586  CA  ci3 A 801     -20.840 -16.187  22.287  1.00 26.30       A    C
ATOM   1587  CE  ci3 A 801     -21.950 -15.566  21.577  1.00 27.57       A    C
ATOM   1588  OAO ci3 A 801     -21.803 -15.292  20.358  1.00 26.92       A    O
ATOM   1589  OAN ci3 A 801     -23.004 -15.296  22.220  1.00 30.71       A    O
ATOM   1590  O14 ci3 A 801     -19.652 -16.189  21.691  1.00 22.31       A    O
ATOM   1591  O13 ci3 A 801     -18.834 -17.336  23.871  1.00 25.98       A    O
ATOM   1592  CG  ci3 A 801     -21.392 -17.444  26.404  1.00 30.85       A    C
ATOM   1593  CK  ci3 A 801     -21.031 -16.189  27.199  1.00 33.96       A    C
ATOM   1594  CI  ci3 A 801     -19.573 -16.130  27.627  1.00 35.23       A    C
ATOM   1595  NJ  ci3 A 801     -19.034 -17.502  27.735  1.00 35.00       A    N
ATOM   1596  CH  ci3 A 801     -18.884 -18.064  26.396  1.00 30.47       A    C
ATOM   1597  CP  ci3 A 801     -17.731 -17.546  28.491  1.00 38.12       A    C
ATOM   1598  CGB ci3 A 801     -17.631 -18.891  29.181  1.00 38.25       A    C
ATOM   1599  CD1 ci3 A 801     -16.977 -19.953  28.555  1.00 36.44       A    C
ATOM   1600  CE1 ci3 A 801     -16.943 -21.187  29.173  1.00 36.89       A    C
ATOM   1601  CZ  ci3 A 801     -17.557 -21.372  30.401  1.00 37.89       A    C
ATOM   1602  CE2 ci3 A 801     -18.218 -20.318  31.023  1.00 41.22       A    C
ATOM   1603  CD2 ci3 A 801     -18.257 -19.072  30.405  1.00 40.70       A    C
ATOM   6409  OH2 WAT A 903     -10.601  -9.091  11.772  1.00 32.57       A    O
ATOM   6410  OH2 WAT A 904     -14.901  -8.548  10.607  1.00 16.35       A    O
ATOM   6412  OH2 WAT A 905     -17.002 -19.982  -5.112  1.00 42.22       A    O
ATOM   6414  OH2 WAT A 906     -17.378 -15.047  22.418  1.00 22.40       A    O
ATOM   6416  OH2 WAT A 907     -18.289 -26.989   9.464  1.00 32.93       A    O
ATOM   6417  OH2 WAT A 908      -6.835 -22.198  16.683  1.00 23.51       A    O
ATOM   6418  OH2 WAT A 909     -18.589 -34.825  23.372  1.00 31.96       A    O
ATOM   6420  OH2 WAT A 910     -14.376 -25.985   8.906  1.00 29.63       A    O
ATOM   6421  OH2 WAT A 911     -37.599 -11.578  18.813  1.00 42.67       A    O
ATOM   6422  OH2 WAT A 912     -15.925 -27.185  26.775  1.00 29.68       A    O
ATOM   6423  OH2 WAT A 913     -25.317 -39.185  20.346  1.00 31.82       A    O
END
```

FIG.3-1

Figure 3: H1N1 polypeptide fragment (Chain D) with bound EMBL-R05-3

```
HEADER    ----                                   XX-XXX-9-   xxxx
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.50
REMARK   3   RESOLUTION RANGE LOW  (ANGSTROMS) :  89.10
REMARK   3   DATA CUTOFF            (SIGMA(F)) : NONE
REMARK   3   COMPLETENESS FOR RANGE        (%) :  99.04
REMARK   3   NUMBER OF REFLECTIONS             :   28997
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.20822
REMARK   3   R VALUE            (WORKING SET) :  0.20459
REMARK   3   FREE R VALUE                     :  0.27625
REMARK   3   FREE R VALUE TEST SET SIZE   (%) :  5.1
REMARK   3   FREE R VALUE TEST SET COUNT      :  1545
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    2.502
REMARK   3   BIN RESOLUTION RANGE LOW            :    2.567
REMARK   3   REFLECTION IN BIN     (WORKING SET) :     1968
REMARK   3   BIN COMPLETENESS (WORKING+TEST) (%) :    93.65
REMARK   3   BIN R VALUE           (WORKING SET) :    0.268
REMARK   3   BIN FREE R VALUE SET COUNT          :      113
REMARK   3   BIN FREE R VALUE                    :    0.378
REMARK   3
REMARK   3  NUMBER OF NON-HYDROGEN ATOMS USED IN REFINEMENT.
REMARK   3   ALL ATOMS                :     6523
REMARK   3
REMARK   3  B VALUES.
REMARK   3   FROM WILSON PLOT           (A**2) : NULL
REMARK   3   MEAN B VALUE      (OVERALL, A**2) :  29.083
REMARK   3   OVERALL ANISOTROPIC B VALUE.
REMARK   3    B11 (A**2) :     0.24
REMARK   3    B22 (A**2) :    -0.24
REMARK   3    B33 (A**2) :     0.00
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.783
REMARK   3   ESU BASED ON FREE R VALUE                       (A):   0.335
REMARK   3   ESU BASED ON MAXIMUM LIKELIHOOD                 (A):   0.240
REMARK   3   ESU FOR B VALUES BASED ON MAXIMUM LIKELIHOOD (A**2):  23.556
REMARK   3
REMARK   3 CORRELATION COEFFICIENTS.
REMARK   3   CORRELATION COEFFICIENT FO-FC      :   0.937
REMARK   3   CORRELATION COEFFICIENT FO-FC FREE :   0.891
REMARK   3
```

FIG.3-2

```
REMARK   3  RMS DEVIATIONS FROM IDEAL VALUES        COUNT    RMS    WEIGHT
REMARK   3   BOND LENGTHS REFINED ATOMS        (A):  6520 ; 0.016 ; 0.022
REMARK   3   BOND LENGTHS OTHERS               (A):  4574 ; 0.001 ; 0.020
REMARK   3   BOND ANGLES REFINED ATOMS   (DEGREES):  8769 ; 1.513 ; 1.974
REMARK   3   BOND ANGLES OTHERS          (DEGREES): 11027 ; 0.893 ; 3.000
REMARK   3   TORSION ANGLES, PERIOD 1    (DEGREES):   741 ; 6.052 ; 5.000
REMARK   3   TORSION ANGLES, PERIOD 2    (DEGREES):   332 ;35.152 ;23.373
REMARK   3   TORSION ANGLES, PERIOD 3    (DEGREES):  1193 ;19.051 ;15.000
REMARK   3   TORSION ANGLES, PERIOD 4    (DEGREES):    55 ;19.093 ;15.000
REMARK   3   CHIRAL-CENTER RESTRAINTS       (A**3):   920 ; 0.086 ; 0.200
REMARK   3   GENERAL PLANES REFINED ATOMS      (A):  7058 ; 0.006 ; 0.020
REMARK   3   GENERAL PLANES OTHERS             (A):  1441 ; 0.001 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):  3740 ; 0.632 ; 1.500
REMARK   3   MAIN-CHAIN BOND OTHER ATOMS    (A**2):  1503 ; 0.123 ; 1.500
REMARK   3   MAIN-CHAIN ANGLE REFINED ATOMS (A**2):  6055 ; 1.173 ; 2.000
REMARK   3   SIDE-CHAIN BOND REFINED ATOMS  (A**2):  2780 ; 1.839 ; 3.000
REMARK   3   SIDE-CHAIN ANGLE REFINED ATOMS (A**2):  2714 ; 2.962 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  :    4
REMARK   3   ATOM RECORD CONTAINS SUM OF TLS AND RESIDUAL B FACTORS
REMARK   3
REMARK   3   TLS GROUP :     1
REMARK   3    NUMBER OF COMPONENTS GROUP :    4
REMARK   3    COMPONENTS        C SSSEQI   TO  C SSSEQI
REMARK   3    RESIDUE RANGE :   A    -2        A   194
REMARK   3    RESIDUE RANGE :   A   901        A   902
REMARK   3    RESIDUE RANGE :   A   401        A   404
REMARK   3    RESIDUE RANGE :   A   801        A   801
REMARK   3    ORIGIN FOR THE GROUP (A): -18.7820 -18.3467  15.6409
REMARK   3    T TENSOR
REMARK   3      T11:   0.0626 T22:   0.0601
REMARK   3      T33:   0.0370 T12:   0.0477
REMARK   3      T13:   0.0061 T23:  -0.0096
REMARK   3    L TENSOR
REMARK   3      L11:   3.8491 L22:   3.1615
REMARK   3      L33:   2.2199 L12:   0.4794
REMARK   3      L13:   0.2562 L23:  -0.2521
REMARK   3    S TENSOR
REMARK   3      S11:   0.0271 S12:  -0.0426 S13:   0.3012
REMARK   3      S21:   0.1037 S22:   0.0068 S23:   0.2311
REMARK   3      S31:  -0.2046 S32:   0.0173 S33:  -0.0339
REMARK   3
REMARK   3   TLS GROUP :     2
REMARK   3    NUMBER OF COMPONENTS GROUP :    4
REMARK   3    COMPONENTS        C SSSEQI   TO  C SSSEQI
REMARK   3    RESIDUE RANGE :   B    -2        B   193
REMARK   3    RESIDUE RANGE :   B   901        B   902
REMARK   3    RESIDUE RANGE :   B   401        B   404
REMARK   3    RESIDUE RANGE :   B   801        B   801
REMARK   3    ORIGIN FOR THE GROUP (A):  -9.5592 -43.9684  15.4406
REMARK   3    T TENSOR
REMARK   3      T11:   0.0655 T22:   0.0616
REMARK   3      T33:   0.0284 T12:   0.0424
```

FIG.3-3

```
REMARK   3      T13:  -0.0096 T23:   0.0116
REMARK   3    L TENSOR
REMARK   3      L11:   3.5209 L22:   2.7524
REMARK   3      L33:   2.1675 L12:   0.0213
REMARK   3      L13:  -0.8001 L23:   0.2855
REMARK   3    S TENSOR
REMARK   3      S11:   0.0173 S12:  -0.0992 S13:  -0.2131
REMARK   3      S21:   0.1239 S22:  -0.0222 S23:  -0.2049
REMARK   3      S31:   0.2223 S32:  -0.0015 S33:   0.0049
REMARK   3
REMARK   3   TLS GROUP :     3
REMARK   3    NUMBER OF COMPONENTS GROUP :    4
REMARK   3    COMPONENTS          C SSSEQI   TO  C SSSEQI
REMARK   3    RESIDUE RANGE :   C      0         C   195
REMARK   3    RESIDUE RANGE :   C    901         C   902
REMARK   3    RESIDUE RANGE :   C    401         C   403
REMARK   3    RESIDUE RANGE :   C    801         C   801
REMARK   3    ORIGIN FOR THE GROUP (A):  -4.3952 -15.1378  52.3445
REMARK   3    T TENSOR
REMARK   3      T11:   0.0906 T22:   0.0725
REMARK   3      T33:   0.0515 T12:  -0.0225
REMARK   3      T13:  -0.0351 T23:  -0.0026
REMARK   3    L TENSOR
REMARK   3      L11:   3.4910 L22:   2.7740
REMARK   3      L33:   2.4480 L12:   1.0609
REMARK   3      L13:  -0.2109 L23:  -1.3961
REMARK   3    S TENSOR
REMARK   3      S11:  -0.0152 S12:   0.1383 S13:  -0.1047
REMARK   3      S21:  -0.2065 S22:  -0.0565 S23:  -0.0793
REMARK   3      S31:   0.1206 S32:   0.1449 S33:   0.0717
REMARK   3
REMARK   3   TLS GROUP :     4
REMARK   3    NUMBER OF COMPONENTS GROUP :    4
REMARK   3    COMPONENTS          C SSSEQI   TO  C SSSEQI
REMARK   3    RESIDUE RANGE :   D      0         D   195
REMARK   3    RESIDUE RANGE :   D    901         D   902
REMARK   3    RESIDUE RANGE :   D    401         D   403
REMARK   3    RESIDUE RANGE :   D    801         D   801
REMARK   3    ORIGIN FOR THE GROUP (A): -21.2945 -45.7592  51.4140
REMARK   3    T TENSOR
REMARK   3      T11:   0.1308 T22:   0.1190
REMARK   3      T33:   0.0216 T12:  -0.0416
REMARK   3      T13:  -0.0097 T23:   0.0186
REMARK   3    L TENSOR
REMARK   3      L11:   3.6692 L22:   2.1484
REMARK   3      L33:   2.5225 L12:  -0.2058
REMARK   3      L13:  -0.3579 L23:   1.1039
REMARK   3    S TENSOR
REMARK   3      S11:   0.0541 S12:   0.3685 S13:  -0.0165
REMARK   3      S21:  -0.1313 S22:  -0.0722 S23:   0.0569
REMARK   3      S31:   0.0558 S32:  -0.2205 S33:   0.0181
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : WITH TLS ADDED
```

FIG.3-4

```
REMARK   3
LINKR             GLU A  64                             LEU A  71              gap
LINKR             LYS A 137                             LYS A 142              gap
LINKR             GLU B  64                             LEU B  71              gap
LINKR             PHE D  51                             LEU D  72              gap
CRYST1   54.570  122.540  129.780  90.00  90.00  90.00 P 21 21 21
SCALE1      0.018325  0.000000  0.000000        0.00000
SCALE2      0.000000  0.008161  0.000000        0.00000
SCALE3      0.000000  0.000000  0.007705        0.00000
ATOM   9666  N   ALA D   0     -43.744 -40.288  53.969  1.00 42.23           N
ATOM   9667  CA  ALA D   0     -43.826 -41.746  53.723  1.00 42.48           C
ATOM   9669  CB  ALA D   0     -44.635 -42.041  52.466  1.00 44.64           C
ATOM   9673  C   ALA D   0     -42.411 -42.327  53.631  1.00 39.94           C
ATOM   9674  O   ALA D   0     -42.069 -43.247  54.364  1.00 38.22           O
ATOM   9678  N   MET D   1     -41.574 -41.775  52.762  1.00 39.94           N
ATOM   9679  CA  MET D   1     -40.208 -42.297  52.608  1.00 38.00           C
ATOM   9681  CB  MET D   1     -39.385 -41.479  51.609  1.00 37.81           C
ATOM   9684  CG  MET D   1     -37.883 -41.908  51.505  1.00 36.08           C
ATOM   9687  SD  MET D   1     -37.557 -43.690  51.304  1.00 35.33           S
ATOM   9688  CE  MET D   1     -37.104 -43.712  49.542  1.00 33.59           C
ATOM   9692  C   MET D   1     -39.499 -42.281  53.930  1.00 36.72           C
ATOM   9693  O   MET D   1     -38.809 -43.255  54.296  1.00 34.99           O
ATOM   9695  N   GLU D   2     -39.684 -41.184  54.655  1.00 37.51           N
ATOM   9696  CA  GLU D   2     -39.021 -41.017  55.936  1.00 37.19           C
ATOM   9698  CB  GLU D   2     -39.021 -39.545  56.373  1.00 37.65           C
ATOM   9701  CG  GLU D   2     -40.358 -38.993  56.715  1.00 42.68           C
ATOM   9704  CD  GLU D   2     -40.452 -37.507  56.461  1.00 48.57           C
ATOM   9705  OE1 GLU D   2     -39.625 -36.753  57.036  1.00 48.70           O
ATOM   9706  OE2 GLU D   2     -41.364 -37.102  55.684  1.00 52.95           O
ATOM   9707  C   GLU D   2     -39.638 -41.929  56.992  1.00 38.02           C
ATOM   9708  O   GLU D   2     -38.994 -42.264  57.988  1.00 36.83           O
ATOM   9710  N   ASP D   3     -40.875 -42.351  56.777  1.00 40.21           N
ATOM   9711  CA  ASP D   3     -41.445 -43.362  57.652  1.00 42.06           C
ATOM   9713  CB  ASP D   3     -42.955 -43.488  57.446  1.00 45.00           C
ATOM   9716  CG  ASP D   3     -43.727 -42.487  58.282  1.00 47.81           C
ATOM   9717  OD1 ASP D   3     -44.705 -42.891  58.951  1.00 52.73           O
ATOM   9718  OD2 ASP D   3     -43.329 -41.299  58.308  1.00 49.71           O
ATOM   9719  C   ASP D   3     -40.740 -44.703  57.451  1.00 41.14           C
ATOM   9720  O   ASP D   3     -40.297 -45.335  58.401  1.00 40.50           O
ATOM   9722  N   PHE D   4     -40.629 -45.111  56.198  1.00 41.26           N
ATOM   9723  CA  PHE D   4     -39.893 -46.304  55.833  1.00 40.45           C
ATOM   9725  CB  PHE D   4     -39.854 -46.397  54.306  1.00 41.06           C
ATOM   9728  CG  PHE D   4     -39.038 -47.530  53.785  1.00 40.10           C
ATOM   9729  CD1 PHE D   4     -39.498 -48.817  53.876  1.00 42.36           C
ATOM   9731  CE1 PHE D   4     -38.755 -49.853  53.391  1.00 42.25           C
ATOM   9733  CZ  PHE D   4     -37.537 -49.606  52.790  1.00 39.59           C
ATOM   9735  CE2 PHE D   4     -37.081 -48.333  52.693  1.00 37.73           C
ATOM   9737  CD2 PHE D   4     -37.822 -47.301  53.194  1.00 38.13           C
ATOM   9739  C   PHE D   4     -38.470 -46.315  56.422  1.00 37.45           C
ATOM   9740  O   PHE D   4     -38.050 -47.289  57.045  1.00 37.05           O
ATOM   9742  N   VAL D   5     -37.735 -45.233  56.236  1.00 35.56           N
ATOM   9743  CA  VAL D   5     -36.353 -45.167  56.743  1.00 32.58           C
ATOM   9745  CB  VAL D   5     -35.720 -43.789  56.472  1.00 31.10           C
ATOM   9747  CG1 VAL D   5     -34.368 -43.645  57.192  1.00 26.65           C
ATOM   9751  CG2 VAL D   5     -35.563 -43.593  54.986  1.00 29.67           C
ATOM   9755  C   VAL D   5     -36.279 -45.502  58.238  1.00 32.77           C
ATOM   9756  O   VAL D   5     -35.536 -46.386  58.650  1.00 30.97           O
ATOM   9758  N   ARG D   6     -37.078 -44.802  59.025  1.00 34.64           N
ATOM   9759  CA  ARG D   6     -37.118 -44.976  60.476  1.00 36.17           C
ATOM   9761  CB  ARG D   6     -38.070 -43.960  61.098  1.00 37.98           C
ATOM   9764  CG  ARG D   6     -37.498 -42.587  61.222  1.00 37.05           C
ATOM   9767  CD  ARG D   6     -38.492 -41.688  61.893  1.00 41.18           C
ATOM   9770  NE  ARG D   6     -38.293 -40.344  61.389  1.00 43.18           N
```

FIG.3-5

| | | | | | | | | | | | |
|---|---|---|---|---|---|---|---|---|---|---|---|
| ATOM | 9772 | CZ | ARG | D | 6 | -39.242 | -39.439 | 61.206 | 1.00 | 45.47 | C |
| ATOM | 9773 | NH1 | ARG | D | 6 | -40.521 | -39.687 | 61.506 | 1.00 | 46.55 | N |
| ATOM | 9776 | NH2 | ARG | D | 6 | -38.881 | -38.264 | 60.705 | 1.00 | 47.08 | N |
| ATOM | 9779 | C | ARG | D | 6 | -37.577 | -46.329 | 60.974 | 1.00 | 37.73 | C |
| ATOM | 9780 | O | ARG | D | 6 | -37.069 | -46.825 | 61.964 | 1.00 | 37.69 | O |
| ATOM | 9782 | N | GLN | D | 7 | -38.554 | -46.910 | 60.312 | 1.00 | 39.94 | N |
| ATOM | 9783 | CA | GLN | D | 7 | -39.108 | -48.160 | 60.775 | 1.00 | 42.97 | C |
| ATOM | 9785 | CB | GLN | D | 7 | -40.601 | -48.276 | 60.363 | 1.00 | 45.71 | C |
| ATOM | 9788 | CG | GLN | D | 7 | -41.532 | -47.252 | 61.074 | 1.00 | 47.44 | C |
| ATOM | 9791 | CD | GLN | D | 7 | -42.881 | -47.051 | 60.382 | 1.00 | 50.85 | C |
| ATOM | 9792 | OE1 | GLN | D | 7 | -43.048 | -47.342 | 59.187 | 1.00 | 51.31 | O |
| ATOM | 9793 | NE2 | GLN | D | 7 | -43.855 | -46.557 | 61.144 | 1.00 | 52.57 | N |
| ATOM | 9796 | C | GLN | D | 7 | -38.283 | -49.373 | 60.290 | 1.00 | 42.96 | C |
| ATOM | 9797 | O | GLN | D | 7 | -38.309 | -50.430 | 60.930 | 1.00 | 44.30 | O |
| ATOM | 9799 | N | CYS | D | 8 | -37.524 | -49.212 | 59.201 | 1.00 | 41.61 | N |
| ATOM | 9800 | CA | CYS | D | 8 | -36.845 | -50.356 | 58.550 | 1.00 | 41.17 | C |
| ATOM | 9802 | CB | CYS | D | 8 | -37.336 | -50.455 | 57.106 | 1.00 | 42.02 | C |
| ATOM | 9805 | SG | CYS | D | 8 | -39.125 | -51.002 | 57.072 | 1.00 | 49.42 | S |
| ATOM | 9807 | C | CYS | D | 8 | -35.289 | -50.444 | 58.667 | 1.00 | 37.81 | C |
| ATOM | 9808 | O | CYS | D | 8 | -34.747 | -51.549 | 58.799 | 1.00 | 38.30 | O |
| ATOM | 9810 | N | PHE | D | 9 | -34.586 | -49.309 | 58.670 | 1.00 | 34.43 | N |
| ATOM | 9811 | CA | PHE | D | 9 | -33.153 | -49.292 | 58.933 | 1.00 | 31.22 | C |
| ATOM | 9813 | CB | PHE | D | 9 | -32.532 | -47.993 | 58.442 | 1.00 | 29.82 | C |
| ATOM | 9816 | CG | PHE | D | 9 | -32.317 | -47.945 | 56.971 | 1.00 | 30.28 | C |
| ATOM | 9817 | CD1 | PHE | D | 9 | -31.160 | -48.507 | 56.406 | 1.00 | 29.51 | C |
| ATOM | 9819 | CE1 | PHE | D | 9 | -30.955 | -48.468 | 55.052 | 1.00 | 29.38 | C |
| ATOM | 9821 | CZ | PHE | D | 9 | -31.885 | -47.848 | 54.240 | 1.00 | 30.60 | C |
| ATOM | 9823 | CE2 | PHE | D | 9 | -33.036 | -47.274 | 54.796 | 1.00 | 31.63 | C |
| ATOM | 9825 | CD2 | PHE | D | 9 | -33.240 | -47.322 | 56.148 | 1.00 | 30.27 | C |
| ATOM | 9827 | C | PHE | D | 9 | -32.868 | -49.358 | 60.415 | 1.00 | 30.46 | C |
| ATOM | 9828 | O | PHE | D | 9 | -33.641 | -48.830 | 61.199 | 1.00 | 29.72 | O |
| ATOM | 9830 | N | ASN | D | 10 | -31.711 | -49.919 | 60.783 | 1.00 | 29.56 | N |
| ATOM | 9831 | CA | ASN | D | 10 | -31.223 | -49.875 | 62.181 | 1.00 | 29.84 | C |
| ATOM | 9833 | CB | ASN | D | 10 | -29.789 | -50.423 | 62.334 | 1.00 | 29.38 | C |
| ATOM | 9836 | CG | ASN | D | 10 | -29.417 | -50.679 | 63.808 | 1.00 | 32.78 | C |
| ATOM | 9837 | OD1 | ASN | D | 10 | -28.584 | -49.985 | 64.391 | 1.00 | 33.24 | O |
| ATOM | 9838 | ND2 | ASN | D | 10 | -30.092 | -51.642 | 64.426 | 1.00 | 37.50 | N |
| ATOM | 9841 | C | ASN | D | 10 | -31.259 | -48.452 | 62.736 | 1.00 | 28.42 | C |
| ATOM | 9842 | O | ASN | D | 10 | -30.713 | -47.556 | 62.145 | 1.00 | 26.91 | O |
| ATOM | 9844 | N | PRO | D | 11 | -31.894 | -48.248 | 63.893 | 1.00 | 29.78 | N |
| ATOM | 9845 | CA | PRO | D | 11 | -32.022 | -46.899 | 64.426 | 1.00 | 29.42 | C |
| ATOM | 9847 | CB | PRO | D | 11 | -32.778 | -47.109 | 65.735 | 1.00 | 31.22 | C |
| ATOM | 9850 | CG | PRO | D | 11 | -32.696 | -48.551 | 66.006 | 1.00 | 32.47 | C |
| ATOM | 9853 | CD | PRO | D | 11 | -32.683 | -49.204 | 64.682 | 1.00 | 31.29 | C |
| ATOM | 9856 | C | PRO | D | 11 | -30.721 | -46.161 | 64.698 | 1.00 | 28.64 | C |
| ATOM | 9857 | O | PRO | D | 11 | -30.733 | -44.934 | 64.695 | 1.00 | 28.47 | O |
| ATOM | 9858 | N | MET | D | 12 | -29.613 | -46.864 | 64.938 | 1.00 | 28.31 | N |
| ATOM | 9859 | CA | MET | D | 12 | -28.340 | -46.174 | 65.046 | 1.00 | 27.14 | C |
| ATOM | 9861 | CB | MET | D | 12 | -27.211 | -47.052 | 65.620 | 1.00 | 28.43 | C |
| ATOM | 9864 | CG | MET | D | 12 | -25.942 | -46.240 | 66.000 | 1.00 | 30.14 | C |
| ATOM | 9867 | SD | MET | D | 12 | -24.670 | -47.181 | 66.898 | 1.00 | 39.52 | S |
| ATOM | 9868 | CE | MET | D | 12 | -24.080 | -48.285 | 65.615 | 1.00 | 33.57 | C |
| ATOM | 9872 | C | MET | D | 12 | -27.954 | -45.600 | 63.685 | 1.00 | 24.11 | C |
| ATOM | 9873 | O | MET | D | 12 | -27.434 | -44.483 | 63.592 | 1.00 | 22.48 | O |
| ATOM | 9875 | N | ILE | D | 13 | -28.217 | -46.340 | 62.623 | 1.00 | 22.82 | N |
| ATOM | 9876 | CA | ILE | D | 13 | -27.957 | -45.798 | 61.277 | 1.00 | 21.13 | C |
| ATOM | 9878 | CB | ILE | D | 13 | -28.282 | -46.818 | 60.180 | 1.00 | 21.15 | C |
| ATOM | 9880 | CG1 | ILE | D | 13 | -27.559 | -48.164 | 60.439 | 1.00 | 22.92 | C |
| ATOM | 9883 | CD1 | ILE | D | 13 | -26.162 | -48.280 | 59.976 | 1.00 | 22.54 | C |
| ATOM | 9887 | CG2 | ILE | D | 13 | -27.908 | -46.264 | 58.834 | 1.00 | 21.35 | C |
| ATOM | 9891 | C | ILE | D | 13 | -28.780 | -44.493 | 61.069 | 1.00 | 20.44 | C |
| ATOM | 9892 | O | ILE | D | 13 | -28.261 | -43.449 | 60.691 | 1.00 | 18.18 | O |
| ATOM | 9894 | N | VAL | D | 14 | -30.059 | -44.530 | 61.409 | 1.00 | 21.13 | N |

FIG.3-6

| | | | | | | | | | | | |
|---|---|---|---|---|---|---|---|---|---|---|---|
| ATOM | 9895 | CA | VAL | D | 14 | -30.915 | -43.373 | 61.162 | 1.00 | 21.32 | C |
| ATOM | 9897 | CB | VAL | D | 14 | -32.383 | -43.744 | 61.439 | 1.00 | 22.38 | C |
| ATOM | 9899 | CG1 | VAL | D | 14 | -33.291 | -42.582 | 61.199 | 1.00 | 22.67 | C |
| ATOM | 9903 | CG2 | VAL | D | 14 | -32.770 | -44.906 | 60.544 | 1.00 | 22.26 | C |
| ATOM | 9907 | C | VAL | D | 14 | -30.424 | -42.122 | 61.940 | 1.00 | 21.19 | C |
| ATOM | 9908 | O | VAL | D | 14 | -30.270 | -41.032 | 61.358 | 1.00 | 21.33 | O |
| ATOM | 9910 | N | GLU | D | 15 | -30.120 | -42.295 | 63.219 | 1.00 | 20.98 | N |
| ATOM | 9911 | CA | GLU | D | 15 | -29.554 | -41.196 | 64.023 | 1.00 | 21.19 | C |
| ATOM | 9913 | CB | GLU | D | 15 | -29.379 | -41.592 | 65.488 | 1.00 | 21.42 | C |
| ATOM | 9916 | CG | GLU | D | 15 | -30.688 | -41.998 | 66.134 | 1.00 | 22.70 | C |
| ATOM | 9919 | CD | GLU | D | 15 | -30.697 | -41.975 | 67.651 | 1.00 | 23.66 | C |
| ATOM | 9920 | OE1 | GLU | D | 15 | -29.608 | -41.922 | 68.247 | 1.00 | 23.41 | O |
| ATOM | 9921 | OE2 | GLU | D | 15 | -31.818 | -41.979 | 68.240 | 1.00 | 24.95 | O |
| ATOM | 9922 | C | GLU | D | 15 | -28.229 | -40.679 | 63.457 | 1.00 | 20.49 | C |
| ATOM | 9923 | O | GLU | D | 15 | -28.042 | -39.487 | 63.309 | 1.00 | 20.63 | O |
| ATOM | 9925 | N | LEU | D | 16 | -27.324 | -41.572 | 63.092 | 1.00 | 20.12 | N |
| ATOM | 9926 | CA | LEU | D | 16 | -26.090 | -41.128 | 62.498 | 1.00 | 19.69 | C |
| ATOM | 9928 | CB | LEU | D | 16 | -25.121 | -42.306 | 62.234 | 1.00 | 18.98 | C |
| ATOM | 9931 | CG | LEU | D | 16 | -24.589 | -43.000 | 63.499 | 1.00 | 20.75 | C |
| ATOM | 9933 | CD1 | LEU | D | 16 | -23.898 | -44.384 | 63.221 | 1.00 | 19.34 | C |
| ATOM | 9937 | CD2 | LEU | D | 16 | -23.664 | -42.088 | 64.271 | 1.00 | 18.92 | C |
| ATOM | 9941 | C | LEU | D | 16 | -26.394 | -40.349 | 61.218 | 1.00 | 19.34 | C |
| ATOM | 9942 | O | LEU | D | 16 | -25.783 | -39.320 | 60.959 | 1.00 | 20.59 | O |
| ATOM | 9944 | N | ALA | D | 17 | -27.331 | -40.825 | 60.413 | 1.00 | 19.68 | N |
| ATOM | 9945 | CA | ALA | D | 17 | -27.665 | -40.117 | 59.176 | 1.00 | 19.28 | C |
| ATOM | 9947 | CB | ALA | D | 17 | -28.687 | -40.846 | 58.422 | 1.00 | 19.11 | C |
| ATOM | 9951 | C | ALA | D | 17 | -28.141 | -38.702 | 59.515 | 1.00 | 20.15 | C |
| ATOM | 9952 | O | ALA | D | 17 | -27.655 | -37.747 | 58.933 | 1.00 | 20.22 | O |
| ATOM | 9954 | N | GLU | D | 18 | -29.044 | -38.580 | 60.495 | 1.00 | 20.95 | N |
| ATOM | 9955 | CA | GLU | D | 18 | -29.559 | -37.270 | 60.937 | 1.00 | 22.10 | C |
| ATOM | 9957 | CB | GLU | D | 18 | -30.542 | -37.451 | 62.089 | 1.00 | 22.35 | C |
| ATOM | 9960 | CG | GLU | D | 18 | -31.852 | -37.995 | 61.539 | 1.00 | 23.65 | C |
| ATOM | 9963 | CD | GLU | D | 18 | -32.872 | -38.424 | 62.579 | 1.00 | 23.56 | C |
| ATOM | 9964 | OE1 | GLU | D | 18 | -32.635 | -38.282 | 63.816 | 1.00 | 22.31 | O |
| ATOM | 9965 | OE2 | GLU | D | 18 | -33.921 | -38.927 | 62.120 | 1.00 | 22.14 | O |
| ATOM | 9966 | C | GLU | D | 18 | -28.479 | -36.281 | 61.339 | 1.00 | 22.50 | C |
| ATOM | 9967 | O | GLU | D | 18 | -28.573 | -35.090 | 61.117 | 1.00 | 23.22 | O |
| ATOM | 9969 | N | LYS | D | 19 | -27.449 | -36.815 | 61.944 | 1.00 | 22.77 | N |
| ATOM | 9970 | CA | LYS | D | 19 | -26.388 | -36.040 | 62.512 | 1.00 | 23.69 | C |
| ATOM | 9972 | CB | LYS | D | 19 | -25.739 | -36.864 | 63.640 | 1.00 | 23.72 | C |
| ATOM | 9975 | CG | LYS | D | 19 | -24.295 | -36.630 | 63.926 | 1.00 | 26.03 | C |
| ATOM | 9978 | CD | LYS | D | 19 | -23.485 | -37.830 | 63.387 | 1.00 | 31.54 | C |
| ATOM | 9981 | CE | LYS | D | 19 | -22.122 | -37.897 | 64.017 | 1.00 | 30.79 | C |
| ATOM | 9984 | NZ | LYS | D | 19 | -22.425 | -37.752 | 65.450 | 1.00 | 34.24 | N |
| ATOM | 9988 | C | LYS | D | 19 | -25.442 | -35.568 | 61.392 | 1.00 | 23.07 | C |
| ATOM | 9989 | O | LYS | D | 19 | -25.033 | -34.394 | 61.393 | 1.00 | 23.91 | O |
| ATOM | 9991 | N | ALA | D | 20 | -25.173 | -36.432 | 60.405 | 1.00 | 21.96 | N |
| ATOM | 9992 | CA | ALA | D | 20 | -24.408 | -36.023 | 59.199 | 1.00 | 21.27 | C |
| ATOM | 9994 | CB | ALA | D | 20 | -24.177 | -37.195 | 58.261 | 1.00 | 19.62 | C |
| ATOM | 9998 | C | ALA | D | 20 | -25.145 | -34.932 | 58.459 | 1.00 | 22.50 | C |
| ATOM | 9999 | O | ALA | D | 20 | -24.530 | -33.945 | 58.057 | 1.00 | 23.54 | O |
| ATOM | 10001 | N | MET | D | 21 | -26.454 | -35.078 | 58.287 | 1.00 | 22.08 | N |
| ATOM | 10002 | CA | MET | D | 21 | -27.139 | -34.153 | 57.419 | 1.00 | 23.85 | C |
| ATOM | 10004 | CB | MET | D | 21 | -28.550 | -34.648 | 57.081 | 1.00 | 24.83 | C |
| ATOM | 10007 | CG | MET | D | 21 | -28.562 | -35.883 | 56.178 | 1.00 | 23.06 | C |
| ATOM | 10010 | SD | MET | D | 21 | -30.208 | -36.181 | 55.543 | 1.00 | 25.52 | S |
| ATOM | 10011 | CE | MET | D | 21 | -30.405 | -34.936 | 54.278 | 1.00 | 23.85 | C |
| ATOM | 10015 | C | MET | D | 21 | -27.151 | -32.759 | 58.072 | 1.00 | 25.63 | C |
| ATOM | 10016 | O | MET | D | 21 | -26.965 | -31.709 | 57.414 | 1.00 | 24.63 | O |
| ATOM | 10018 | N | LYS | D | 22 | -27.315 | -32.764 | 59.384 | 1.00 | 26.67 | N |
| ATOM | 10019 | CA | LYS | D | 22 | -27.262 | -31.533 | 60.125 | 1.00 | 29.19 | C |
| ATOM | 10021 | CB | LYS | D | 22 | -27.631 | -31.763 | 61.581 | 1.00 | 29.37 | C |
| ATOM | 10024 | CG | LYS | D | 22 | -27.945 | -30.463 | 62.321 | 1.00 | 32.41 | C |

FIG.3-7

| | | | | | | | | | | | |
|---|---|---|---|---|---|---|---|---|---|---|---|
| ATOM | 10027 | CD | LYS | D | 22 | -27.654 | -30.623 | 63.809 | 1.00 | 34.28 | C |
| ATOM | 10030 | CE | LYS | D | 22 | -28.397 | -29.596 | 64.657 | 1.00 | 37.41 | C |
| ATOM | 10033 | NZ | LYS | D | 22 | -28.723 | -30.168 | 66.029 | 1.00 | 38.83 | N |
| ATOM | 10037 | C | LYS | D | 22 | -25.847 | -30.929 | 59.999 | 1.00 | 29.62 | C |
| ATOM | 10038 | O | LYS | D | 22 | -25.714 | -29.723 | 59.864 | 1.00 | 30.17 | O |
| ATOM | 10040 | N | GLU | D | 23 | -24.810 | -31.769 | 60.010 | 1.00 | 28.79 | N |
| ATOM | 10041 | CA | GLU | D | 23 | -23.445 | -31.255 | 59.948 | 1.00 | 29.93 | C |
| ATOM | 10043 | CB | GLU | D | 23 | -22.383 | -32.306 | 60.318 | 1.00 | 27.88 | C |
| ATOM | 10046 | CG | GLU | D | 23 | -21.000 | -31.683 | 60.382 | 1.00 | 28.69 | C |
| ATOM | 10049 | CD | GLU | D | 23 | -19.856 | -32.640 | 60.726 | 1.00 | 28.62 | C |
| ATOM | 10050 | OE1 | GLU | D | 23 | -20.069 | -33.857 | 60.801 | 1.00 | 27.71 | O |
| ATOM | 10051 | OE2 | GLU | D | 23 | -18.713 | -32.153 | 60.915 | 1.00 | 30.05 | O |
| ATOM | 10052 | C | GLU | D | 23 | -23.158 | -30.661 | 58.568 | 1.00 | 31.93 | C |
| ATOM | 10053 | O | GLU | D | 23 | -22.455 | -29.652 | 58.463 | 1.00 | 33.71 | O |
| ATOM | 10055 | N | TYR | D | 24 | -23.689 | -31.287 | 57.521 | 1.00 | 32.32 | N |
| ATOM | 10056 | CA | TYR | D | 24 | -23.511 | -30.802 | 56.156 | 1.00 | 34.10 | C |
| ATOM | 10058 | CB | TYR | D | 24 | -23.915 | -31.911 | 55.182 | 1.00 | 34.13 | C |
| ATOM | 10061 | CG | TYR | D | 24 | -23.264 | -31.887 | 53.817 | 1.00 | 37.55 | C |
| ATOM | 10062 | CD1 | TYR | D | 24 | -21.901 | -32.077 | 53.674 | 1.00 | 39.42 | C |
| ATOM | 10064 | CE1 | TYR | D | 24 | -21.291 | -32.071 | 52.413 | 1.00 | 42.57 | C |
| ATOM | 10066 | CZ | TYR | D | 24 | -22.067 | -31.890 | 51.263 | 1.00 | 45.24 | C |
| ATOM | 10067 | OH | TYR | D | 24 | -21.483 | -31.874 | 50.005 | 1.00 | 45.86 | O |
| ATOM | 10069 | CE2 | TYR | D | 24 | -23.442 | -31.704 | 51.382 | 1.00 | 45.57 | C |
| ATOM | 10071 | CD2 | TYR | D | 24 | -24.032 | -31.707 | 52.660 | 1.00 | 42.99 | C |
| ATOM | 10073 | C | TYR | D | 24 | -24.353 | -29.534 | 55.934 | 1.00 | 35.56 | C |
| ATOM | 10074 | O | TYR | D | 24 | -23.924 | -28.601 | 55.276 | 1.00 | 37.31 | O |
| ATOM | 10076 | N | GLY | D | 25 | -25.528 | -29.483 | 56.531 | 1.00 | 35.78 | N |
| ATOM | 10077 | CA | GLY | D | 25 | -26.395 | -28.286 | 56.459 | 1.00 | 37.89 | C |
| ATOM | 10080 | C | GLY | D | 25 | -27.640 | -28.642 | 55.691 | 1.00 | 38.22 | C |
| ATOM | 10081 | O | GLY | D | 25 | -28.171 | -27.865 | 54.923 | 1.00 | 40.85 | O |
| ATOM | 10083 | N | GLU | D | 26 | -28.100 | -29.860 | 55.889 | 1.00 | 36.62 | N |
| ATOM | 10084 | CA | GLU | D | 26 | -29.216 | -30.368 | 55.147 | 1.00 | 36.54 | C |
| ATOM | 10086 | CB | GLU | D | 26 | -28.728 | -31.297 | 54.037 | 1.00 | 35.78 | C |
| ATOM | 10089 | CG | GLU | D | 26 | -28.267 | -30.507 | 52.806 | 1.00 | 39.21 | C |
| ATOM | 10092 | CD | GLU | D | 26 | -27.755 | -31.388 | 51.661 | 1.00 | 42.65 | C |
| ATOM | 10093 | OE1 | GLU | D | 26 | -27.414 | -32.574 | 51.914 | 1.00 | 42.60 | O |
| ATOM | 10094 | OE2 | GLU | D | 26 | -27.671 | -30.886 | 50.504 | 1.00 | 44.18 | O |
| ATOM | 10095 | C | GLU | D | 26 | -30.176 | -31.030 | 56.102 | 1.00 | 34.71 | C |
| ATOM | 10096 | O | GLU | D | 26 | -29.799 | -31.550 | 57.155 | 1.00 | 33.55 | O |
| ATOM | 10098 | N | ASP | D | 27 | -31.436 | -30.972 | 55.718 | 1.00 | 34.93 | N |
| ATOM | 10099 | CA | ASP | D | 27 | -32.533 | -31.242 | 56.617 | 1.00 | 34.36 | C |
| ATOM | 10101 | CB | ASP | D | 27 | -33.468 | -30.046 | 56.599 | 1.00 | 36.60 | C |
| ATOM | 10104 | CG | ASP | D | 27 | -34.666 | -30.235 | 57.465 | 1.00 | 37.11 | C |
| ATOM | 10105 | OD1 | ASP | D | 27 | -34.719 | -31.229 | 58.237 | 1.00 | 33.25 | O |
| ATOM | 10106 | OD2 | ASP | D | 27 | -35.568 | -29.380 | 57.339 | 1.00 | 38.21 | O |
| ATOM | 10107 | C | ASP | D | 27 | -33.260 | -32.520 | 56.195 | 1.00 | 32.76 | C |
| ATOM | 10108 | O | ASP | D | 27 | -33.975 | -32.514 | 55.192 | 1.00 | 33.20 | O |
| ATOM | 10110 | N | PRO | D | 28 | -33.097 | -33.613 | 56.979 | 1.00 | 30.71 | N |
| ATOM | 10111 | CA | PRO | D | 28 | -33.693 | -34.964 | 56.762 | 1.00 | 29.60 | C |
| ATOM | 10113 | CB | PRO | D | 28 | -33.410 | -35.671 | 58.072 | 1.00 | 28.32 | C |
| ATOM | 10116 | CG | PRO | D | 28 | -32.216 | -35.031 | 58.588 | 1.00 | 28.02 | C |
| ATOM | 10119 | CD | PRO | D | 28 | -32.369 | -33.572 | 58.256 | 1.00 | 29.71 | C |
| ATOM | 10122 | C | PRO | D | 28 | -35.201 | -34.995 | 56.518 | 1.00 | 31.33 | C |
| ATOM | 10123 | O | PRO | D | 28 | -35.720 | -35.992 | 56.050 | 1.00 | 30.93 | O |
| ATOM | 10124 | N | LYS | D | 29 | -35.885 | -33.910 | 56.861 | 1.00 | 33.67 | N |
| ATOM | 10125 | CA | LYS | D | 29 | -37.317 | -33.805 | 56.717 | 1.00 | 36.61 | C |
| ATOM | 10127 | CB | LYS | D | 29 | -37.895 | -32.820 | 57.771 | 1.00 | 38.38 | C |
| ATOM | 10130 | CG | LYS | D | 29 | -37.638 | -33.247 | 59.255 | 1.00 | 38.09 | C |
| ATOM | 10133 | CD | LYS | D | 29 | -38.534 | -32.522 | 60.257 | 1.00 | 42.26 | C |
| ATOM | 10136 | CE | LYS | D | 29 | -38.149 | -31.035 | 60.476 | 1.00 | 44.88 | C |
| ATOM | 10139 | NZ | LYS | D | 29 | -39.205 | -30.289 | 61.265 | 1.00 | 46.07 | N |
| ATOM | 10143 | C | LYS | D | 29 | -37.697 | -33.376 | 55.302 | 1.00 | 38.14 | C |
| ATOM | 10144 | O | LYS | D | 29 | -38.811 | -33.656 | 54.857 | 1.00 | 40.07 | O |

FIG.3-8

| | | | | | | | | | | | |
|---|---|---|---|---|---|---|---|---|---|---|---|
| ATOM | 10146 | N | ILE | D | 30 | -36.776 | -32.711 | 54.605 | 1.00 | 38.09 | N |
| ATOM | 10147 | CA | ILE | D | 30 | -37.045 | -32.136 | 53.276 | 1.00 | 39.99 | C |
| ATOM | 10149 | CB | ILE | D | 30 | -36.452 | -30.689 | 53.091 | 1.00 | 41.14 | C |
| ATOM | 10151 | CG1 | ILE | D | 30 | -36.755 | -29.803 | 54.323 | 1.00 | 41.83 | C |
| ATOM | 10154 | CD1 | ILE | D | 30 | -36.556 | -28.257 | 54.131 | 1.00 | 41.98 | C |
| ATOM | 10158 | CG2 | ILE | D | 30 | -36.977 | -30.055 | 51.811 | 1.00 | 42.65 | C |
| ATOM | 10162 | C | ILE | D | 30 | -36.482 | -33.062 | 52.215 | 1.00 | 38.96 | C |
| ATOM | 10163 | O | ILE | D | 30 | -37.216 | -33.486 | 51.355 | 1.00 | 40.45 | O |
| ATOM | 10165 | N | GLU | D | 31 | -35.193 | -33.391 | 52.276 | 1.00 | 37.35 | N |
| ATOM | 10166 | CA | GLU | D | 31 | -34.630 | -34.347 | 51.314 | 1.00 | 37.00 | C |
| ATOM | 10168 | CB | GLU | D | 31 | -33.268 | -33.937 | 50.740 | 1.00 | 36.92 | C |
| ATOM | 10171 | CG | GLU | D | 31 | -32.339 | -33.221 | 51.659 | 1.00 | 38.57 | C |
| ATOM | 10174 | CD | GLU | D | 31 | -32.386 | -31.714 | 51.462 | 1.00 | 43.67 | C |
| ATOM | 10175 | OE1 | GLU | D | 31 | -32.638 | -31.297 | 50.303 | 1.00 | 44.42 | O |
| ATOM | 10176 | OE2 | GLU | D | 31 | -32.146 | -30.960 | 52.454 | 1.00 | 46.22 | O |
| ATOM | 10177 | C | GLU | D | 31 | -34.588 | -35.756 | 51.871 | 1.00 | 34.98 | C |
| ATOM | 10178 | O | GLU | D | 31 | -33.546 | -36.283 | 52.277 | 1.00 | 33.32 | O |
| ATOM | 10180 | N | THR | D | 32 | -35.758 | -36.371 | 51.833 | 1.00 | 35.60 | N |
| ATOM | 10181 | CA | THR | D | 32 | -35.983 | -37.656 | 52.449 | 1.00 | 34.06 | C |
| ATOM | 10183 | CB | THR | D | 32 | -37.495 | -37.919 | 52.629 | 1.00 | 35.97 | C |
| ATOM | 10185 | OG1 | THR | D | 32 | -38.114 | -38.072 | 51.351 | 1.00 | 37.69 | O |
| ATOM | 10187 | CG2 | THR | D | 32 | -38.164 | -36.762 | 53.366 | 1.00 | 37.68 | C |
| ATOM | 10191 | C | THR | D | 32 | -35.349 | -38.792 | 51.650 | 1.00 | 32.30 | C |
| ATOM | 10192 | O | THR | D | 32 | -34.923 | -39.782 | 52.240 | 1.00 | 30.42 | O |
| ATOM | 10194 | N | ASN | D | 33 | -35.301 | -38.676 | 50.319 | 1.00 | 32.61 | N |
| ATOM | 10195 | CA | ASN | D | 33 | -34.591 | -39.666 | 49.519 | 1.00 | 31.15 | C |
| ATOM | 10197 | CB | ASN | D | 33 | -34.827 | -39.467 | 48.040 | 1.00 | 33.44 | C |
| ATOM | 10200 | CG | ASN | D | 33 | -36.189 | -39.899 | 47.608 | 1.00 | 34.80 | C |
| ATOM | 10201 | OD1 | ASN | D | 33 | -36.819 | -39.228 | 46.799 | 1.00 | 39.60 | O |
| ATOM | 10202 | ND2 | ASN | D | 33 | -36.658 | -41.026 | 48.136 | 1.00 | 33.49 | N |
| ATOM | 10205 | C | ASN | D | 33 | -33.115 | -39.624 | 49.769 | 1.00 | 29.11 | C |
| ATOM | 10206 | O | ASN | D | 33 | -32.489 | -40.655 | 49.935 | 1.00 | 27.88 | O |
| ATOM | 10208 | N | LYS | D | 34 | -32.547 | -38.430 | 49.813 | 1.00 | 29.41 | N |
| ATOM | 10209 | CA | LYS | D | 34 | -31.142 | -38.308 | 50.129 | 1.00 | 28.21 | C |
| ATOM | 10211 | CB | LYS | D | 34 | -30.685 | -36.841 | 50.113 | 1.00 | 28.89 | C |
| ATOM | 10214 | CG | LYS | D | 34 | -29.159 | -36.732 | 50.245 | 1.00 | 30.84 | C |
| ATOM | 10217 | CD | LYS | D | 34 | -28.664 | -35.330 | 50.430 | 1.00 | 35.84 | C |
| ATOM | 10220 | CE | LYS | D | 34 | -28.678 | -34.517 | 49.139 | 1.00 | 39.72 | C |
| ATOM | 10223 | NZ | LYS | D | 34 | -28.615 | -33.039 | 49.462 | 1.00 | 42.40 | N |
| ATOM | 10227 | C | LYS | D | 34 | -30.853 | -38.954 | 51.496 | 1.00 | 26.41 | C |
| ATOM | 10228 | O | LYS | D | 34 | -29.826 | -39.616 | 51.681 | 1.00 | 24.92 | O |
| ATOM | 10230 | N | PHE | D | 35 | -31.773 | -38.754 | 52.433 | 1.00 | 27.00 | N |
| ATOM | 10231 | CA | PHE | D | 35 | -31.710 | -39.310 | 53.794 | 1.00 | 26.20 | C |
| ATOM | 10233 | CB | PHE | D | 35 | -32.997 | -38.912 | 54.530 | 1.00 | 27.70 | C |
| ATOM | 10236 | CG | PHE | D | 35 | -33.103 | -39.356 | 55.973 | 1.00 | 27.64 | C |
| ATOM | 10237 | CD1 | PHE | D | 35 | -32.016 | -39.362 | 56.825 | 1.00 | 28.06 | C |
| ATOM | 10239 | CE1 | PHE | D | 35 | -32.162 | -39.707 | 58.160 | 1.00 | 28.17 | C |
| ATOM | 10241 | CZ | PHE | D | 35 | -33.412 | -40.027 | 58.668 | 1.00 | 29.11 | C |
| ATOM | 10243 | CE2 | PHE | D | 35 | -34.497 | -40.000 | 57.850 | 1.00 | 30.48 | C |
| ATOM | 10245 | CD2 | PHE | D | 35 | -34.347 | -39.651 | 56.504 | 1.00 | 30.63 | C |
| ATOM | 10247 | C | PHE | D | 35 | -31.613 | -40.801 | 53.742 | 1.00 | 25.62 | C |
| ATOM | 10248 | O | PHE | D | 35 | -30.766 | -41.401 | 54.404 | 1.00 | 24.89 | O |
| ATOM | 10250 | N | ALA | D | 36 | -32.489 | -41.403 | 52.941 | 1.00 | 26.66 | N |
| ATOM | 10251 | CA | ALA | D | 36 | -32.503 | -42.855 | 52.776 | 1.00 | 26.23 | C |
| ATOM | 10253 | CB | ALA | D | 36 | -33.708 | -43.277 | 51.909 | 1.00 | 27.86 | C |
| ATOM | 10257 | C | ALA | D | 36 | -31.202 | -43.356 | 52.156 | 1.00 | 24.54 | C |
| ATOM | 10258 | O | ALA | D | 36 | -30.794 | -44.490 | 52.374 | 1.00 | 23.31 | O |
| ATOM | 10260 | N | ALA | D | 37 | -30.574 | -42.504 | 51.362 | 1.00 | 24.52 | N |
| ATOM | 10261 | CA | ALA | D | 37 | -29.330 | -42.846 | 50.686 | 1.00 | 23.98 | C |
| ATOM | 10263 | CB | ALA | D | 37 | -29.086 | -41.896 | 49.513 | 1.00 | 25.43 | C |
| ATOM | 10267 | C | ALA | D | 37 | -28.148 | -42.820 | 51.646 | 1.00 | 22.17 | C |
| ATOM | 10268 | O | ALA | D | 37 | -27.306 | -43.741 | 51.620 | 1.00 | 21.11 | O |
| ATOM | 10270 | N | ILE | D | 38 | -28.078 | -41.781 | 52.489 | 1.00 | 21.44 | N |

FIG.3-9

| | | | | | | | | | | | |
|---|---|---|---|---|---|---|---|---|---|---|---|
| ATOM | 10271 | CA | ILE | D | 38 | -26.988 | -41.695 | 53.486 | 1.00 | 19.80 | C |
| ATOM | 10273 | CB | ILE | D | 38 | -27.074 | -40.459 | 54.436 | 1.00 | 20.43 | C |
| ATOM | 10275 | CG1 | ILE | D | 38 | -27.497 | -39.173 | 53.694 | 1.00 | 22.08 | C |
| ATOM | 10278 | CD1 | ILE | D | 38 | -26.572 | -38.696 | 52.677 | 1.00 | 19.46 | C |
| ATOM | 10282 | CG2 | ILE | D | 38 | -25.730 | -40.183 | 55.094 | 1.00 | 18.32 | C |
| ATOM | 10286 | C | ILE | D | 38 | -27.060 | -42.979 | 54.330 | 1.00 | 18.70 | C |
| ATOM | 10287 | O | ILE | D | 38 | -26.034 | -43.648 | 54.553 | 1.00 | 17.98 | O |
| ATOM | 10289 | N | CYS | D | 39 | -28.281 | -43.322 | 54.756 | 1.00 | 18.57 | N |
| ATOM | 10290 | CA | CYS | D | 39 | -28.554 | -44.527 | 55.519 | 1.00 | 18.83 | C |
| ATOM | 10292 | CB | CYS | D | 39 | -30.055 | -44.670 | 55.812 | 1.00 | 20.70 | C |
| ATOM | 10295 | SG | CYS | D | 39 | -30.745 | -43.590 | 57.057 | 1.00 | 21.43 | S |
| ATOM | 10297 | C | CYS | D | 39 | -28.085 | -45.808 | 54.854 | 1.00 | 18.65 | C |
| ATOM | 10298 | O | CYS | D | 39 | -27.428 | -46.631 | 55.472 | 1.00 | 18.45 | O |
| ATOM | 10300 | N | THR | D | 40 | -28.470 | -46.001 | 53.607 | 1.00 | 19.58 | N |
| ATOM | 10301 | CA | THR | D | 40 | -28.016 | -47.158 | 52.836 | 1.00 | 19.90 | C |
| ATOM | 10303 | CB | THR | D | 40 | -28.596 | -47.114 | 51.402 | 1.00 | 20.83 | C |
| ATOM | 10305 | OG1 | THR | D | 40 | -30.003 | -47.226 | 51.483 | 1.00 | 21.62 | O |
| ATOM | 10307 | CG2 | THR | D | 40 | -28.081 | -48.251 | 50.572 | 1.00 | 22.06 | C |
| ATOM | 10311 | C | THR | D | 40 | -26.516 | -47.169 | 52.728 | 1.00 | 18.58 | C |
| ATOM | 10312 | O | THR | D | 40 | -25.867 | -48.184 | 52.954 | 1.00 | 18.19 | O |
| ATOM | 10314 | N | HIS | D | 41 | -25.972 | -46.022 | 52.383 | 1.00 | 18.27 | N |
| ATOM | 10315 | CA | HIS | D | 41 | -24.535 | -45.919 | 52.216 | 1.00 | 18.96 | C |
| ATOM | 10317 | CB | HIS | D | 41 | -24.162 | -44.509 | 51.727 | 1.00 | 18.85 | C |
| ATOM | 10320 | CG | HIS | D | 41 | -22.694 | -44.302 | 51.546 | 1.00 | 19.60 | C |
| ATOM | 10321 | ND1 | HIS | D | 41 | -21.892 | -43.818 | 52.549 | 1.00 | 20.02 | N |
| ATOM | 10323 | CE1 | HIS | D | 41 | -20.650 | -43.719 | 52.105 | 1.00 | 19.91 | C |
| ATOM | 10325 | NE2 | HIS | D | 41 | -20.616 | -44.137 | 50.854 | 1.00 | 17.66 | N |
| ATOM | 10327 | CD2 | HIS | D | 41 | -21.880 | -44.515 | 50.482 | 1.00 | 20.23 | C |
| ATOM | 10329 | C | HIS | D | 41 | -23.796 | -46.287 | 53.513 | 1.00 | 18.49 | C |
| ATOM | 10330 | O | HIS | D | 41 | -22.793 | -47.038 | 53.512 | 1.00 | 17.36 | O |
| ATOM | 10332 | N | LEU | D | 42 | -24.315 | -45.764 | 54.617 | 1.00 | 18.90 | N |
| ATOM | 10333 | CA | LEU | D | 42 | -23.714 | -46.022 | 55.901 | 1.00 | 19.08 | C |
| ATOM | 10335 | CB | LEU | D | 42 | -24.482 | -45.275 | 56.976 | 1.00 | 19.96 | C |
| ATOM | 10338 | CG | LEU | D | 42 | -23.787 | -44.208 | 57.816 | 1.00 | 19.37 | C |
| ATOM | 10340 | CD1 | LEU | D | 42 | -24.802 | -43.486 | 58.707 | 1.00 | 20.36 | C |
| ATOM | 10344 | CD2 | LEU | D | 42 | -22.770 | -44.860 | 58.655 | 1.00 | 16.31 | C |
| ATOM | 10348 | C | LEU | D | 42 | -23.769 | -47.522 | 56.157 | 1.00 | 19.94 | C |
| ATOM | 10349 | O | LEU | D | 42 | -22.758 | -48.181 | 56.493 | 1.00 | 19.58 | O |
| ATOM | 10351 | N | GLU | D | 43 | -24.964 | -48.064 | 55.978 | 1.00 | 21.11 | N |
| ATOM | 10352 | CA | GLU | D | 43 | -25.174 | -49.489 | 56.197 | 1.00 | 22.45 | C |
| ATOM | 10354 | CB | GLU | D | 43 | -26.585 | -49.907 | 55.788 | 1.00 | 23.52 | C |
| ATOM | 10357 | CG | GLU | D | 43 | -26.990 | -51.187 | 56.491 | 1.00 | 25.98 | C |
| ATOM | 10360 | CD | GLU | D | 43 | -28.452 | -51.501 | 56.433 | 1.00 | 27.97 | C |
| ATOM | 10361 | OE1 | GLU | D | 43 | -29.112 | -51.234 | 55.406 | 1.00 | 26.25 | O |
| ATOM | 10362 | OE2 | GLU | D | 43 | -28.939 | -52.063 | 57.436 | 1.00 | 33.45 | O |
| ATOM | 10363 | C | GLU | D | 43 | -24.109 | -50.353 | 55.495 | 1.00 | 22.17 | C |
| ATOM | 10364 | O | GLU | D | 43 | -23.495 | -51.220 | 56.129 | 1.00 | 23.22 | O |
| ATOM | 10366 | N | VAL | D | 44 | -23.845 | -50.059 | 54.225 | 1.00 | 20.97 | N |
| ATOM | 10367 | CA | VAL | D | 44 | -22.829 | -50.767 | 53.455 | 1.00 | 20.76 | C |
| ATOM | 10369 | CB | VAL | D | 44 | -22.747 | -50.236 | 52.001 | 1.00 | 21.10 | C |
| ATOM | 10371 | CG1 | VAL | D | 44 | -21.596 | -50.880 | 51.261 | 1.00 | 19.31 | C |
| ATOM | 10375 | CG2 | VAL | D | 44 | -24.083 | -50.463 | 51.276 | 1.00 | 20.55 | C |
| ATOM | 10379 | C | VAL | D | 44 | -21.441 | -50.623 | 54.049 | 1.00 | 20.53 | C |
| ATOM | 10380 | O | VAL | D | 44 | -20.686 | -51.583 | 54.193 | 1.00 | 20.00 | O |
| ATOM | 10382 | N | CYS | D | 45 | -21.099 | -49.395 | 54.382 | 1.00 | 21.02 | N |
| ATOM | 10383 | CA | CYS | D | 45 | -19.834 | -49.130 | 55.042 | 1.00 | 20.47 | C |
| ATOM | 10385 | CB | CYS | D | 45 | -19.735 | -47.663 | 55.360 | 1.00 | 19.81 | C |
| ATOM | 10388 | SG | CYS | D | 45 | -19.327 | -46.656 | 53.924 | 1.00 | 21.21 | S |
| ATOM | 10390 | C | CYS | D | 45 | -19.700 | -49.991 | 56.289 | 1.00 | 21.62 | C |
| ATOM | 10391 | O | CYS | D | 45 | -18.667 | -50.628 | 56.486 | 1.00 | 21.60 | O |
| ATOM | 10393 | N | PHE | D | 46 | -20.761 | -50.085 | 57.100 | 1.00 | 23.35 | N |
| ATOM | 10394 | CA | PHE | D | 46 | -20.687 | -50.910 | 58.331 | 1.00 | 24.64 | C |
| ATOM | 10396 | CB | PHE | D | 46 | -21.878 | -50.685 | 59.269 | 1.00 | 25.68 | C |

FIG.3-10

| | | | | | | | | | | | |
|---|---|---|---|---|---|---|---|---|---|---|---|
| ATOM | 10399 | CG | PHE | D | 46 | -21.906 | -49.321 | 59.949 | 1.00 | 25.78 | C |
| ATOM | 10400 | CD1 | PHE | D | 46 | -20.901 | -48.370 | 59.754 | 1.00 | 26.01 | C |
| ATOM | 10402 | CE1 | PHE | D | 46 | -20.942 | -47.123 | 60.374 | 1.00 | 24.14 | C |
| ATOM | 10404 | CZ | PHE | D | 46 | -21.975 | -46.826 | 61.219 | 1.00 | 27.52 | C |
| ATOM | 10406 | CE2 | PHE | D | 46 | -22.993 | -47.768 | 61.440 | 1.00 | 28.91 | C |
| ATOM | 10408 | CD2 | PHE | D | 46 | -22.946 | -49.005 | 60.802 | 1.00 | 28.79 | C |
| ATOM | 10410 | C | PHE | D | 46 | -20.599 | -52.378 | 58.016 | 1.00 | 25.86 | C |
| ATOM | 10411 | O | PHE | D | 46 | -19.946 | -53.116 | 58.729 | 1.00 | 27.29 | O |
| ATOM | 10413 | N | MET | D | 47 | -21.259 | -52.820 | 56.953 | 1.00 | 26.86 | N |
| ATOM | 10414 | CA | MET | D | 47 | -21.237 | -54.239 | 56.605 | 1.00 | 27.62 | C |
| ATOM | 10416 | CB | MET | D | 47 | -22.374 | -54.557 | 55.656 | 1.00 | 27.79 | C |
| ATOM | 10419 | CG | MET | D | 47 | -23.783 | -54.442 | 56.256 | 1.00 | 27.80 | C |
| ATOM | 10422 | SD | MET | D | 47 | -25.051 | -54.624 | 54.977 | 1.00 | 28.52 | S |
| ATOM | 10423 | CE | MET | D | 47 | -25.144 | -56.385 | 54.790 | 1.00 | 26.66 | C |
| ATOM | 10427 | C | MET | D | 47 | -19.872 | -54.607 | 56.001 | 1.00 | 28.44 | C |
| ATOM | 10428 | O | MET | D | 47 | -19.314 | -55.665 | 56.270 | 1.00 | 30.45 | O |
| ATOM | 10430 | N | TYR | D | 48 | -19.316 | -53.716 | 55.209 | 1.00 | 27.99 | N |
| ATOM | 10431 | CA | TYR | D | 48 | -18.041 | -53.979 | 54.548 | 1.00 | 28.75 | C |
| ATOM | 10433 | CB | TYR | D | 48 | -17.686 | -52.763 | 53.698 | 1.00 | 26.89 | C |
| ATOM | 10436 | CG | TYR | D | 48 | -16.758 | -52.996 | 52.536 | 1.00 | 25.04 | C |
| ATOM | 10437 | CD1 | TYR | D | 48 | -17.229 | -52.955 | 51.233 | 1.00 | 22.51 | C |
| ATOM | 10439 | CE1 | TYR | D | 48 | -16.374 | -53.117 | 50.174 | 1.00 | 22.19 | C |
| ATOM | 10441 | CZ | TYR | D | 48 | -15.017 | -53.284 | 50.406 | 1.00 | 22.27 | C |
| ATOM | 10442 | OH | TYR | D | 48 | -14.123 | -53.423 | 49.359 | 1.00 | 20.04 | O |
| ATOM | 10444 | CE2 | TYR | D | 48 | -14.537 | -53.312 | 51.696 | 1.00 | 22.33 | C |
| ATOM | 10446 | CD2 | TYR | D | 48 | -15.390 | -53.142 | 52.736 | 1.00 | 22.26 | C |
| ATOM | 10448 | C | TYR | D | 48 | -16.923 | -54.267 | 55.564 | 1.00 | 30.28 | C |
| ATOM | 10449 | O | TYR | D | 48 | -16.102 | -55.148 | 55.359 | 1.00 | 30.57 | O |
| ATOM | 10451 | N | SER | D | 49 | -16.940 | -53.520 | 56.665 | 1.00 | 32.17 | N |
| ATOM | 10452 | CA | SER | D | 49 | -15.913 | -53.570 | 57.701 | 1.00 | 33.79 | C |
| ATOM | 10454 | CB | SER | D | 49 | -15.547 | -52.156 | 58.126 | 1.00 | 32.57 | C |
| ATOM | 10457 | OG | SER | D | 49 | -16.671 | -51.468 | 58.644 | 1.00 | 33.19 | O |
| ATOM | 10459 | C | SER | D | 49 | -16.277 | -54.362 | 58.936 | 1.00 | 36.43 | C |
| ATOM | 10460 | O | SER | D | 49 | -15.519 | -54.341 | 59.887 | 1.00 | 37.68 | O |
| ATOM | 10462 | N | ASP | D | 50 | -17.373 | -55.108 | 58.909 | 1.00 | 39.33 | N |
| ATOM | 10463 | CA | ASP | D | 50 | -17.880 | -55.781 | 60.113 | 1.00 | 43.16 | C |
| ATOM | 10465 | CB | ASP | D | 50 | -16.997 | -56.959 | 60.564 | 1.00 | 45.40 | C |
| ATOM | 10468 | CG | ASP | D | 50 | -17.060 | -58.140 | 59.652 | 1.00 | 48.53 | C |
| ATOM | 10469 | OD1 | ASP | D | 50 | -17.132 | -57.970 | 58.406 | 1.00 | 50.84 | O |
| ATOM | 10470 | OD2 | ASP | D | 50 | -16.997 | -59.256 | 60.209 | 1.00 | 52.08 | O |
| ATOM | 10471 | C | ASP | D | 50 | -17.928 | -54.809 | 61.294 | 1.00 | 44.06 | C |
| ATOM | 10472 | O | ASP | D | 50 | -17.318 | -55.083 | 62.341 | 1.00 | 45.39 | O |
| ATOM | 10474 | N | PHE | D | 51 | -18.596 | -53.672 | 61.140 | 1.00 | 44.11 | N |
| ATOM | 10475 | CA | PHE | D | 51 | -18.733 | -52.774 | 62.265 | 1.00 | 45.34 | C |
| ATOM | 10477 | CB | PHE | D | 51 | -19.413 | -51.465 | 61.880 | 1.00 | 44.40 | C |
| ATOM | 10480 | CG | PHE | D | 51 | -19.350 | -50.415 | 62.961 | 1.00 | 45.30 | C |
| ATOM | 10481 | CD1 | PHE | D | 51 | -18.210 | -49.654 | 63.126 | 1.00 | 45.52 | C |
| ATOM | 10483 | CE1 | PHE | D | 51 | -18.129 | -48.671 | 64.109 | 1.00 | 46.41 | C |
| ATOM | 10485 | CZ | PHE | D | 51 | -19.185 | -48.445 | 64.930 | 1.00 | 47.67 | C |
| ATOM | 10487 | CE2 | PHE | D | 51 | -20.361 | -49.214 | 64.792 | 1.00 | 48.92 | C |
| ATOM | 10489 | CD2 | PHE | D | 51 | -20.428 | -50.194 | 63.810 | 1.00 | 48.18 | C |
| ATOM | 10491 | C | PHE | D | 51 | -19.529 | -53.458 | 63.369 | 1.00 | 47.33 | C |
| ATOM | 10492 | O | PHE | D | 51 | -19.133 | -53.403 | 64.534 | 1.00 | 49.18 | O |
| ATOM | 10494 | N | LEU | D | 72 | -8.988 | -59.570 | 68.353 | 1.00 | 62.22 | N |
| ATOM | 10495 | CA | LEU | D | 72 | -7.685 | -59.041 | 67.935 | 1.00 | 61.49 | C |
| ATOM | 10497 | CB | LEU | D | 72 | -6.727 | -60.192 | 67.578 | 1.00 | 63.65 | C |
| ATOM | 10503 | C | LEU | D | 72 | -7.868 | -58.041 | 66.775 | 1.00 | 57.74 | C |
| ATOM | 10504 | O | LEU | D | 72 | -8.975 | -57.563 | 66.543 | 1.00 | 55.53 | O |
| ATOM | 10506 | N | LYS | D | 73 | -6.786 | -57.733 | 66.057 | 1.00 | 57.15 | N |
| ATOM | 10507 | CA | LYS | D | 73 | -6.736 | -56.583 | 65.121 | 1.00 | 53.86 | C |
| ATOM | 10509 | CB | LYS | D | 73 | -5.376 | -56.532 | 64.419 | 1.00 | 54.25 | C |
| ATOM | 10516 | C | LYS | D | 73 | -7.845 | -56.542 | 64.052 | 1.00 | 51.43 | C |
| ATOM | 10517 | O | LYS | D | 73 | -7.982 | -57.483 | 63.247 | 1.00 | 52.46 | O |

FIG.3-11

| | | | | | | | | | | | |
|---|---|---|---|---|---|---|---|---|---|---|---|
| ATOM | 10519 | N | HIS | D | 74 | -8.613 | -55.445 | 64.058 | 1.00 | 48.14 | N |
| ATOM | 10520 | CA | HIS | D | 74 | -9.609 | -55.141 | 63.024 | 1.00 | 45.20 | C |
| ATOM | 10522 | CB | HIS | D | 74 | -10.452 | -53.911 | 63.423 | 1.00 | 44.05 | C |
| ATOM | 10525 | CG | HIS | D | 74 | -11.816 | -54.246 | 63.931 | 1.00 | 46.72 | C |
| ATOM | 10526 | ND1 | HIS | D | 74 | -12.961 | -53.969 | 63.211 | 1.00 | 48.52 | N |
| ATOM | 10528 | CE1 | HIS | D | 74 | -14.017 | -54.392 | 63.890 | 1.00 | 50.46 | C |
| ATOM | 10530 | NE2 | HIS | D | 74 | -13.599 | -54.911 | 65.036 | 1.00 | 50.71 | N |
| ATOM | 10532 | CD2 | HIS | D | 74 | -12.227 | -54.832 | 65.086 | 1.00 | 50.66 | C |
| ATOM | 10534 | C | HIS | D | 74 | -8.909 | -54.831 | 61.704 | 1.00 | 42.43 | C |
| ATOM | 10535 | O | HIS | D | 74 | -7.868 | -54.168 | 61.688 | 1.00 | 42.74 | O |
| ATOM | 10537 | N | ARG | D | 75 | -9.504 | -55.274 | 60.600 | 1.00 | 39.37 | N |
| ATOM | 10538 | CA | ARG | D | 75 | -8.914 | -55.112 | 59.267 | 1.00 | 36.90 | C |
| ATOM | 10540 | CB | ARG | D | 75 | -9.436 | -56.203 | 58.324 | 1.00 | 37.10 | C |
| ATOM | 10543 | CG | ARG | D | 75 | -8.603 | -56.342 | 57.055 | 1.00 | 37.23 | C |
| ATOM | 10546 | CD | ARG | D | 75 | -9.457 | -56.636 | 55.837 | 1.00 | 36.66 | C |
| ATOM | 10549 | NE | ARG | D | 75 | -8.772 | -56.330 | 54.579 | 1.00 | 35.46 | N |
| ATOM | 10551 | CZ | ARG | D | 75 | -8.711 | -57.130 | 53.530 | 1.00 | 35.68 | C |
| ATOM | 10552 | NH1 | ARG | D | 75 | -9.288 | -58.308 | 53.557 | 1.00 | 39.50 | N |
| ATOM | 10555 | NH2 | ARG | D | 75 | -8.075 | -56.748 | 52.435 | 1.00 | 36.83 | N |
| ATOM | 10558 | C | ARG | D | 75 | -9.201 | -53.748 | 58.635 | 1.00 | 33.06 | C |
| ATOM | 10559 | O | ARG | D | 75 | -8.428 | -53.250 | 57.839 | 1.00 | 32.65 | O |
| ATOM | 10561 | N | PHE | D | 76 | -10.342 | -53.179 | 58.968 | 1.00 | 30.04 | N |
| ATOM | 10562 | CA | PHE | D | 76 | -10.749 | -51.923 | 58.418 | 1.00 | 27.04 | C |
| ATOM | 10564 | CB | PHE | D | 76 | -12.051 | -52.065 | 57.653 | 1.00 | 25.51 | C |
| ATOM | 10567 | CG | PHE | D | 76 | -11.973 | -52.997 | 56.503 | 1.00 | 26.10 | C |
| ATOM | 10568 | CD1 | PHE | D | 76 | -11.380 | -52.598 | 55.315 | 1.00 | 27.18 | C |
| ATOM | 10570 | CE1 | PHE | D | 76 | -11.297 | -53.457 | 54.243 | 1.00 | 27.93 | C |
| ATOM | 10572 | CZ | PHE | D | 76 | -11.850 | -54.733 | 54.349 | 1.00 | 29.41 | C |
| ATOM | 10574 | CE2 | PHE | D | 76 | -12.459 | -55.132 | 55.539 | 1.00 | 27.69 | C |
| ATOM | 10576 | CD2 | PHE | D | 76 | -12.522 | -54.275 | 56.589 | 1.00 | 27.12 | C |
| ATOM | 10578 | C | PHE | D | 76 | -10.954 | -50.896 | 59.514 | 1.00 | 25.51 | C |
| ATOM | 10579 | O | PHE | D | 76 | -11.418 | -51.203 | 60.603 | 1.00 | 25.09 | O |
| ATOM | 10581 | N | GLU | D | 77 | -10.637 | -49.658 | 59.177 | 1.00 | 23.99 | N |
| ATOM | 10582 | CA | GLU | D | 77 | -11.040 | -48.536 | 59.984 | 1.00 | 22.86 | C |
| ATOM | 10584 | CB | GLU | D | 77 | -9.923 | -47.533 | 60.100 | 1.00 | 22.90 | C |
| ATOM | 10587 | CG | GLU | D | 77 | -10.155 | -46.566 | 61.199 | 1.00 | 24.13 | C |
| ATOM | 10590 | CD | GLU | D | 77 | -10.005 | -47.194 | 62.564 | 1.00 | 24.46 | C |
| ATOM | 10591 | OE1 | GLU | D | 77 | -10.944 | -47.054 | 63.363 | 1.00 | 24.01 | O |
| ATOM | 10592 | OE2 | GLU | D | 77 | -8.951 | -47.818 | 62.818 | 1.00 | 24.25 | O |
| ATOM | 10593 | C | GLU | D | 77 | -12.195 | -47.861 | 59.327 | 1.00 | 21.32 | C |
| ATOM | 10594 | O | GLU | D | 77 | -12.161 | -47.520 | 58.140 | 1.00 | 20.30 | O |
| ATOM | 10596 | N | ILE | D | 78 | -13.221 | -47.629 | 60.106 | 1.00 | 21.06 | N |
| ATOM | 10597 | CA | ILE | D | 78 | -14.332 | -46.868 | 59.608 | 1.00 | 20.39 | C |
| ATOM | 10599 | CB | ILE | D | 78 | -15.625 | -47.313 | 60.225 | 1.00 | 20.73 | C |
| ATOM | 10601 | CG1 | ILE | D | 78 | -16.764 | -46.594 | 59.514 | 1.00 | 20.45 | C |
| ATOM | 10604 | CD1 | ILE | D | 78 | -18.005 | -47.339 | 59.587 | 1.00 | 23.42 | C |
| ATOM | 10608 | CG2 | ILE | D | 78 | -15.625 | -47.074 | 61.765 | 1.00 | 22.46 | C |
| ATOM | 10612 | C | ILE | D | 78 | -14.160 | -45.366 | 59.809 | 1.00 | 20.01 | C |
| ATOM | 10613 | O | ILE | D | 78 | -13.989 | -44.868 | 60.935 | 1.00 | 21.07 | O |
| ATOM | 10615 | N | ILE | D | 79 | -14.248 | -44.659 | 58.690 | 1.00 | 19.15 | N |
| ATOM | 10616 | CA | ILE | D | 79 | -14.168 | -43.205 | 58.622 | 1.00 | 19.24 | C |
| ATOM | 10618 | CB | ILE | D | 79 | -13.202 | -42.819 | 57.517 | 1.00 | 19.30 | C |
| ATOM | 10620 | CG1 | ILE | D | 79 | -11.923 | -43.646 | 57.696 | 1.00 | 19.42 | C |
| ATOM | 10623 | CD1 | ILE | D | 79 | -10.818 | -43.290 | 56.753 | 1.00 | 20.67 | C |
| ATOM | 10627 | CG2 | ILE | D | 79 | -12.971 | -41.316 | 57.501 | 1.00 | 18.20 | C |
| ATOM | 10631 | C | ILE | D | 79 | -15.549 | -42.574 | 58.354 | 1.00 | 19.33 | C |
| ATOM | 10632 | O | ILE | D | 79 | -15.887 | -41.600 | 58.954 | 1.00 | 19.03 | O |
| ATOM | 10634 | N | GLU | D | 80 | -16.356 | -43.149 | 57.461 | 1.00 | 19.90 | N |
| ATOM | 10635 | CA | GLU | D | 80 | -17.688 | -42.609 | 57.226 | 1.00 | 20.03 | C |
| ATOM | 10637 | CB | GLU | D | 80 | -18.371 | -43.365 | 56.112 | 1.00 | 20.46 | C |
| ATOM | 10640 | CG | GLU | D | 80 | -19.783 | -42.877 | 55.740 | 1.00 | 22.53 | C |
| ATOM | 10643 | CD | GLU | D | 80 | -19.834 | -41.429 | 55.297 | 1.00 | 24.88 | C |
| ATOM | 10644 | OE1 | GLU | D | 80 | -19.476 | -41.133 | 54.134 | 1.00 | 25.39 | O |

FIG.3-12

| | | | | | | | | | | | |
|---|---|---|---|---|---|---|---|---|---|---|---|
| ATOM | 10645 | OE2 | GLU | D | 80 | -20.263 | -40.589 | 56.121 | 1.00 | 28.04 | O |
| ATOM | 10646 | C | GLU | D | 80 | -18.547 | -42.701 | 58.474 | 1.00 | 20.31 | C |
| ATOM | 10647 | O | GLU | D | 80 | -18.439 | -43.671 | 59.272 | 1.00 | 19.98 | O |
| ATOM | 10649 | N | GLY | D | 81 | -19.433 | -41.719 | 58.639 | 1.00 | 19.99 | N |
| ATOM | 10650 | CA | GLY | D | 81 | -20.310 | -41.684 | 59.847 | 1.00 | 20.15 | C |
| ATOM | 10653 | C | GLY | D | 81 | -19.778 | -40.859 | 61.010 | 1.00 | 19.72 | C |
| ATOM | 10654 | O | GLY | D | 81 | -20.521 | -40.465 | 61.894 | 1.00 | 19.53 | O |
| ATOM | 10656 | N | ARG | D | 82 | -18.476 | -40.593 | 61.008 | 1.00 | 19.30 | N |
| ATOM | 10657 | CA | ARG | D | 82 | -17.893 | -39.720 | 61.984 | 1.00 | 19.10 | C |
| ATOM | 10659 | CB | ARG | D | 82 | -16.391 | -39.967 | 62.067 | 1.00 | 19.08 | C |
| ATOM | 10662 | CG | ARG | D | 82 | -16.014 | -41.396 | 62.380 | 1.00 | 17.27 | C |
| ATOM | 10665 | CD | ARG | D | 82 | -14.519 | -41.518 | 62.552 | 1.00 | 14.54 | C |
| ATOM | 10668 | NE | ARG | D | 82 | -14.086 | -42.877 | 62.911 | 1.00 | 14.56 | N |
| ATOM | 10670 | CZ | ARG | D | 82 | -13.823 | -43.303 | 64.148 | 1.00 | 13.61 | C |
| ATOM | 10671 | NH1 | ARG | D | 82 | -13.948 | -42.519 | 65.204 | 1.00 | 15.62 | N |
| ATOM | 10674 | NH2 | ARG | D | 82 | -13.405 | -44.526 | 64.340 | 1.00 | 12.88 | N |
| ATOM | 10677 | C | ARG | D | 82 | -18.192 | -38.308 | 61.500 | 1.00 | 19.49 | C |
| ATOM | 10678 | O | ARG | D | 82 | -18.533 | -38.138 | 60.332 | 1.00 | 19.61 | O |
| ATOM | 10680 | N | ASP | D | 83 | -18.071 | -37.314 | 62.384 | 1.00 | 19.86 | N |
| ATOM | 10681 | CA | ASP | D | 83 | -18.101 | -35.904 | 61.974 | 1.00 | 20.68 | C |
| ATOM | 10683 | CB | ASP | D | 83 | -18.485 | -34.971 | 63.140 | 1.00 | 21.42 | C |
| ATOM | 10686 | CG | ASP | D | 83 | -17.410 | -34.885 | 64.211 | 1.00 | 24.02 | C |
| ATOM | 10687 | OD1 | ASP | D | 83 | -16.378 | -35.559 | 64.132 | 1.00 | 23.95 | O |
| ATOM | 10688 | OD2 | ASP | D | 83 | -17.600 | -34.115 | 65.164 | 1.00 | 31.98 | O |
| ATOM | 10689 | C | ASP | D | 83 | -16.762 | -35.510 | 61.352 | 1.00 | 20.10 | C |
| ATOM | 10690 | O | ASP | D | 83 | -15.842 | -36.299 | 61.338 | 1.00 | 19.28 | O |
| ATOM | 10692 | N | ARG | D | 84 | -16.667 | -34.305 | 60.805 | 1.00 | 21.08 | N |
| ATOM | 10693 | CA | ARG | D | 84 | -15.442 | -33.924 | 60.105 | 1.00 | 22.29 | C |
| ATOM | 10695 | CB | ARG | D | 84 | -15.539 | -32.562 | 59.426 | 1.00 | 23.52 | C |
| ATOM | 10698 | CG | ARG | D | 84 | -16.045 | -32.627 | 58.025 | 1.00 | 24.81 | C |
| ATOM | 10701 | CD | ARG | D | 84 | -15.979 | -31.268 | 57.376 | 1.00 | 28.72 | C |
| ATOM | 10704 | NE | ARG | D | 84 | -16.599 | -31.255 | 56.049 | 1.00 | 29.44 | N |
| ATOM | 10706 | CZ | ARG | D | 84 | -17.745 | -30.644 | 55.749 | 1.00 | 34.75 | C |
| ATOM | 10707 | NH1 | ARG | D | 84 | -18.437 | -29.962 | 56.664 | 1.00 | 35.56 | N |
| ATOM | 10710 | NH2 | ARG | D | 84 | -18.219 | -30.712 | 54.508 | 1.00 | 38.55 | N |
| ATOM | 10713 | C | ARG | D | 84 | -14.217 | -33.954 | 61.023 | 1.00 | 23.32 | C |
| ATOM | 10714 | O | ARG | D | 84 | -13.200 | -34.470 | 60.592 | 1.00 | 22.67 | O |
| ATOM | 10716 | N | ILE | D | 85 | -14.331 | -33.411 | 62.256 | 1.00 | 24.56 | N |
| ATOM | 10717 | CA | ILE | D | 85 | -13.209 | -33.378 | 63.193 | 1.00 | 25.89 | C |
| ATOM | 10719 | CB | ILE | D | 85 | -13.525 | -32.829 | 64.645 | 1.00 | 27.33 | C |
| ATOM | 10721 | CG1 | ILE | D | 85 | -14.337 | -31.515 | 64.671 | 1.00 | 28.71 | C |
| ATOM | 10724 | CD1 | ILE | D | 85 | -13.825 | -30.448 | 63.852 | 1.00 | 30.00 | C |
| ATOM | 10728 | CG2 | ILE | D | 85 | -12.250 | -32.574 | 65.397 | 1.00 | 27.41 | C |
| ATOM | 10732 | C | ILE | D | 85 | -12.639 | -34.789 | 63.354 | 1.00 | 24.91 | C |
| ATOM | 10733 | O | ILE | D | 85 | -11.464 | -35.009 | 63.114 | 1.00 | 24.68 | O |
| ATOM | 10735 | N | MET | D | 86 | -13.488 | -35.746 | 63.708 | 1.00 | 24.04 | N |
| ATOM | 10736 | CA | MET | D | 86 | -13.014 | -37.100 | 64.055 | 1.00 | 23.40 | C |
| ATOM | 10738 | CB | MET | D | 86 | -14.109 | -37.901 | 64.751 | 1.00 | 23.09 | C |
| ATOM | 10741 | CG | MET | D | 86 | -14.446 | -37.396 | 66.160 | 1.00 | 25.62 | C |
| ATOM | 10744 | SD | MET | D | 86 | -13.047 | -37.633 | 67.305 | 1.00 | 33.11 | S |
| ATOM | 10745 | CE | MET | D | 86 | -12.658 | -35.921 | 67.695 | 1.00 | 33.18 | C |
| ATOM | 10749 | C | MET | D | 86 | -12.518 | -37.836 | 62.845 | 1.00 | 22.08 | C |
| ATOM | 10750 | O | MET | D | 86 | -11.575 | -38.617 | 62.911 | 1.00 | 23.02 | O |
| ATOM | 10752 | N | ALA | D | 87 | -13.144 | -37.555 | 61.728 | 1.00 | 21.02 | N |
| ATOM | 10753 | CA | ALA | D | 87 | -12.770 | -38.159 | 60.481 | 1.00 | 20.27 | C |
| ATOM | 10755 | CB | ALA | D | 87 | -13.755 | -37.749 | 59.381 | 1.00 | 20.12 | C |
| ATOM | 10759 | C | ALA | D | 87 | -11.375 | -37.725 | 60.121 | 1.00 | 20.58 | C |
| ATOM | 10760 | O | ALA | D | 87 | -10.568 | -38.536 | 59.689 | 1.00 | 20.94 | O |
| ATOM | 10762 | N | TRP | D | 88 | -11.080 | -36.444 | 60.293 | 1.00 | 20.70 | N |
| ATOM | 10763 | CA | TRP | D | 88 | -9.729 | -35.967 | 60.022 | 1.00 | 21.71 | C |
| ATOM | 10765 | CB | TRP | D | 88 | -9.714 | -34.447 | 59.754 | 1.00 | 22.79 | C |
| ATOM | 10768 | CG | TRP | D | 88 | -10.114 | -34.159 | 58.336 | 1.00 | 25.39 | C |
| ATOM | 10769 | CD1 | TRP | D | 88 | -11.238 | -33.502 | 57.883 | 1.00 | 25.70 | C |

FIG.3-13

| | | | | | | | | | | | |
|---|---|---|---|---|---|---|---|---|---|---|---|
| ATOM | 10771 | NE1 | TRP | D | 88 | -11.249 | -33.475 | 56.503 | 1.00 | 25.62 | N |
| ATOM | 10773 | CE2 | TRP | D | 88 | -10.141 | -34.138 | 56.048 | 1.00 | 29.04 | C |
| ATOM | 10774 | CD2 | TRP | D | 88 | -9.410 | -34.584 | 57.171 | 1.00 | 27.97 | C |
| ATOM | 10775 | CE3 | TRP | D | 88 | -8.252 | -35.321 | 56.968 | 1.00 | 28.64 | C |
| ATOM | 10777 | CZ3 | TRP | D | 88 | -7.853 | -35.581 | 55.679 | 1.00 | 30.95 | C |
| ATOM | 10779 | CH2 | TRP | D | 88 | -8.589 | -35.129 | 54.588 | 1.00 | 29.78 | C |
| ATOM | 10781 | CZ2 | TRP | D | 88 | -9.734 | -34.406 | 54.751 | 1.00 | 31.24 | C |
| ATOM | 10783 | C | TRP | D | 88 | -8.699 | -36.410 | 61.099 | 1.00 | 21.12 | C |
| ATOM | 10784 | O | TRP | D | 88 | -7.528 | -36.681 | 60.783 | 1.00 | 21.20 | O |
| ATOM | 10786 | N | THR | D | 89 | -9.145 | -36.494 | 62.342 | 1.00 | 19.96 | N |
| ATOM | 10787 | CA | THR | D | 89 | -8.341 | -37.070 | 63.389 | 1.00 | 20.95 | C |
| ATOM | 10789 | CB | THR | D | 89 | -9.075 | -37.070 | 64.748 | 1.00 | 21.64 | C |
| ATOM | 10791 | OG1 | THR | D | 89 | -9.567 | -35.747 | 65.050 | 1.00 | 21.71 | O |
| ATOM | 10793 | CG2 | THR | D | 89 | -8.128 | -37.555 | 65.842 | 1.00 | 18.21 | C |
| ATOM | 10797 | C | THR | D | 89 | -7.936 | -38.515 | 63.015 | 1.00 | 20.70 | C |
| ATOM | 10798 | O | THR | D | 89 | -6.748 | -38.846 | 63.018 | 1.00 | 21.58 | O |
| ATOM | 10800 | N | VAL | D | 90 | -8.905 | -39.356 | 62.651 | 1.00 | 18.90 | N |
| ATOM | 10801 | CA | VAL | D | 90 | -8.575 | -40.751 | 62.300 | 1.00 | 18.68 | C |
| ATOM | 10803 | CB | VAL | D | 90 | -9.819 | -41.654 | 62.157 | 1.00 | 17.20 | C |
| ATOM | 10805 | CG1 | VAL | D | 90 | -9.392 | -43.035 | 61.644 | 1.00 | 16.28 | C |
| ATOM | 10809 | CG2 | VAL | D | 90 | -10.556 | -41.763 | 63.533 | 1.00 | 17.37 | C |
| ATOM | 10813 | C | VAL | D | 90 | -7.723 | -40.901 | 61.045 | 1.00 | 18.56 | C |
| ATOM | 10814 | O | VAL | D | 90 | -6.818 | -41.728 | 61.018 | 1.00 | 20.06 | O |
| ATOM | 10816 | N | VAL | D | 91 | -8.012 | -40.135 | 59.999 | 1.00 | 18.11 | N |
| ATOM | 10817 | CA | VAL | D | 91 | -7.185 | -40.195 | 58.801 | 1.00 | 18.28 | C |
| ATOM | 10819 | CB | VAL | D | 91 | -7.840 | -39.460 | 57.632 | 1.00 | 17.88 | C |
| ATOM | 10821 | CG1 | VAL | D | 91 | -6.850 | -39.230 | 56.491 | 1.00 | 18.37 | C |
| ATOM | 10825 | CG2 | VAL | D | 91 | -9.047 | -40.250 | 57.133 | 1.00 | 16.26 | C |
| ATOM | 10829 | C | VAL | D | 91 | -5.761 | -39.677 | 59.076 | 1.00 | 20.42 | C |
| ATOM | 10830 | O | VAL | D | 91 | -4.800 | -40.221 | 58.558 | 1.00 | 21.57 | O |
| ATOM | 10832 | N | ASN | D | 92 | -5.620 | -38.655 | 59.910 | 1.00 | 21.56 | N |
| ATOM | 10833 | CA | ASN | D | 92 | -4.294 | -38.161 | 60.254 | 1.00 | 23.76 | C |
| ATOM | 10835 | CB | ASN | D | 92 | -4.374 | -36.861 | 61.085 | 1.00 | 24.40 | C |
| ATOM | 10838 | CG | ASN | D | 92 | -4.752 | -35.655 | 60.246 | 1.00 | 23.60 | C |
| ATOM | 10839 | OD1 | ASN | D | 92 | -4.652 | -35.695 | 59.022 | 1.00 | 23.35 | O |
| ATOM | 10840 | ND2 | ASN | D | 92 | -5.182 | -34.580 | 60.893 | 1.00 | 20.20 | N |
| ATOM | 10843 | C | ASN | D | 92 | -3.456 | -39.205 | 60.995 | 1.00 | 24.53 | C |
| ATOM | 10844 | O | ASN | D | 92 | -2.258 | -39.351 | 60.731 | 1.00 | 25.65 | O |
| ATOM | 10846 | N | SER | D | 93 | -4.091 | -39.916 | 61.918 | 1.00 | 23.92 | N |
| ATOM | 10847 | CA | SER | D | 93 | -3.397 | -40.927 | 62.700 | 1.00 | 25.43 | C |
| ATOM | 10849 | CB | SER | D | 93 | -4.262 | -41.322 | 63.899 | 1.00 | 25.34 | C |
| ATOM | 10852 | OG | SER | D | 93 | -4.094 | -42.677 | 64.262 | 1.00 | 27.29 | O |
| ATOM | 10854 | C | SER | D | 93 | -2.976 | -42.152 | 61.844 | 1.00 | 25.59 | C |
| ATOM | 10855 | O | SER | D | 93 | -1.891 | -42.666 | 61.994 | 1.00 | 27.01 | O |
| ATOM | 10857 | N | ILE | D | 94 | -3.829 | -42.604 | 60.940 | 1.00 | 24.37 | N |
| ATOM | 10858 | CA | ILE | D | 94 | -3.470 | -43.674 | 60.013 | 1.00 | 24.56 | C |
| ATOM | 10860 | CB | ILE | D | 94 | -4.665 | -44.037 | 59.110 | 1.00 | 23.03 | C |
| ATOM | 10862 | CG1 | ILE | D | 94 | -5.766 | -44.709 | 59.916 | 1.00 | 21.15 | C |
| ATOM | 10865 | CD1 | ILE | D | 94 | -7.088 | -44.664 | 59.194 | 1.00 | 22.77 | C |
| ATOM | 10869 | CG2 | ILE | D | 94 | -4.246 | -44.899 | 58.001 | 1.00 | 20.27 | C |
| ATOM | 10873 | C | ILE | D | 94 | -2.319 | -43.268 | 59.094 | 1.00 | 26.61 | C |
| ATOM | 10874 | O | ILE | D | 94 | -1.409 | -44.082 | 58.777 | 1.00 | 26.98 | O |
| ATOM | 10876 | N | CYS | D | 95 | -2.351 | -42.015 | 58.654 | 1.00 | 27.05 | N |
| ATOM | 10877 | CA | CYS | D | 95 | -1.315 | -41.541 | 57.743 | 1.00 | 28.72 | C |
| ATOM | 10879 | CB | CYS | D | 95 | -1.733 | -40.233 | 57.066 | 1.00 | 28.26 | C |
| ATOM | 10882 | SG | CYS | D | 95 | -3.036 | -40.558 | 55.823 | 1.00 | 29.35 | S |
| ATOM | 10884 | C | CYS | D | 95 | 0.047 | -41.465 | 58.430 | 1.00 | 30.59 | C |
| ATOM | 10885 | O | CYS | D | 95 | 1.036 | -41.931 | 57.884 | 1.00 | 31.72 | O |
| ATOM | 10887 | N | ASN | D | 96 | 0.095 | -40.899 | 59.630 | 1.00 | 32.04 | N |
| ATOM | 10888 | CA | ASN | D | 96 | 1.373 | -40.730 | 60.360 | 1.00 | 34.51 | C |
| ATOM | 10890 | CB | ASN | D | 96 | 1.190 | -39.935 | 61.652 | 1.00 | 35.40 | C |
| ATOM | 10893 | CG | ASN | D | 96 | 0.683 | -38.513 | 61.430 | 1.00 | 35.47 | C |
| ATOM | 10894 | OD1 | ASN | D | 96 | 1.257 | -37.749 | 60.662 | 1.00 | 36.94 | O |

FIG.3-14

| | | | | | | | | | | | |
|---|---|---|---|---|---|---|---|---|---|---|---|
| ATOM | 10895 | ND2 | ASN | D | 96 | -0.367 | -38.144 | 62.158 | 1.00 | 31.66 | N |
| ATOM | 10898 | C | ASN | D | 96 | 1.979 | -42.084 | 60.744 | 1.00 | 35.23 | C |
| ATOM | 10899 | O | ASN | D | 96 | 3.201 | -42.216 | 60.885 | 1.00 | 37.25 | O |
| ATOM | 10901 | N | THR | D | 97 | 1.098 | -43.074 | 60.879 | 1.00 | 33.72 | N |
| ATOM | 10902 | CA | THR | D | 97 | 1.429 | -44.410 | 61.351 | 1.00 | 34.39 | C |
| ATOM | 10904 | CB | THR | D | 97 | 0.212 | -45.029 | 62.077 | 1.00 | 32.39 | C |
| ATOM | 10906 | OG1 | THR | D | 97 | 0.184 | -44.535 | 63.412 | 1.00 | 34.63 | O |
| ATOM | 10908 | CG2 | THR | D | 97 | 0.316 | -46.501 | 62.150 | 1.00 | 33.78 | C |
| ATOM | 10912 | C | THR | D | 97 | 1.898 | -45.352 | 60.241 | 1.00 | 34.38 | C |
| ATOM | 10913 | O | THR | D | 97 | 2.930 | -45.982 | 60.378 | 1.00 | 36.17 | O |
| ATOM | 10915 | N | THR | D | 98 | 1.113 | -45.477 | 59.174 | 1.00 | 32.90 | N |
| ATOM | 10916 | CA | THR | D | 98 | 1.442 | -46.372 | 58.079 | 1.00 | 33.46 | C |
| ATOM | 10918 | CB | THR | D | 98 | 0.196 | -46.880 | 57.315 | 1.00 | 31.74 | C |
| ATOM | 10920 | OG1 | THR | D | 98 | -0.621 | -45.767 | 56.926 | 1.00 | 33.13 | O |
| ATOM | 10922 | CG2 | THR | D | 98 | -0.632 | -47.860 | 58.190 | 1.00 | 31.22 | C |
| ATOM | 10926 | C | THR | D | 98 | 2.344 | -45.678 | 57.097 | 1.00 | 34.36 | C |
| ATOM | 10927 | O | THR | D | 98 | 3.120 | -46.332 | 56.437 | 1.00 | 35.52 | O |
| ATOM | 10929 | N | GLY | D | 99 | 2.254 | -44.353 | 57.007 | 1.00 | 34.38 | N |
| ATOM | 10930 | CA | GLY | D | 99 | 3.077 | -43.598 | 56.082 | 1.00 | 35.61 | C |
| ATOM | 10933 | C | GLY | D | 99 | 2.447 | -43.529 | 54.709 | 1.00 | 35.08 | C |
| ATOM | 10934 | O | GLY | D | 99 | 3.098 | -43.099 | 53.774 | 1.00 | 36.15 | O |
| ATOM | 10936 | N | VAL | D | 100 | 1.181 | -43.940 | 54.578 | 1.00 | 33.53 | N |
| ATOM | 10937 | CA | VAL | D | 100 | 0.446 | -43.707 | 53.338 | 1.00 | 33.15 | C |
| ATOM | 10939 | CB | VAL | D | 100 | -0.897 | -44.437 | 53.297 | 1.00 | 31.43 | C |
| ATOM | 10941 | CG1 | VAL | D | 100 | -1.698 | -43.934 | 52.103 | 1.00 | 31.38 | C |
| ATOM | 10945 | CG2 | VAL | D | 100 | -0.684 | -45.952 | 53.178 | 1.00 | 32.18 | C |
| ATOM | 10949 | C | VAL | D | 100 | 0.153 | -42.229 | 53.108 | 1.00 | 33.44 | C |
| ATOM | 10950 | O | VAL | D | 100 | -0.201 | -41.489 | 54.032 | 1.00 | 33.23 | O |
| ATOM | 10952 | N | GLU | D | 101 | 0.305 | -41.815 | 51.860 | 1.00 | 34.85 | N |
| ATOM | 10953 | CA | GLU | D | 101 | -0.086 | -40.489 | 51.389 | 1.00 | 35.66 | C |
| ATOM | 10955 | CB | GLU | D | 101 | -0.106 | -40.511 | 49.840 | 1.00 | 37.08 | C |
| ATOM | 10958 | CG | GLU | D | 101 | -0.914 | -39.393 | 49.144 | 1.00 | 39.86 | C |
| ATOM | 10961 | CD | GLU | D | 101 | -0.412 | -39.071 | 47.734 | 1.00 | 44.29 | C |
| ATOM | 10962 | OE1 | GLU | D | 101 | -1.173 | -38.473 | 46.951 | 1.00 | 46.95 | O |
| ATOM | 10963 | OE2 | GLU | D | 101 | 0.747 | -39.395 | 47.404 | 1.00 | 48.84 | O |
| ATOM | 10964 | C | GLU | D | 101 | -1.435 | -40.057 | 51.975 | 1.00 | 33.15 | C |
| ATOM | 10965 | O | GLU | D | 101 | -2.332 | -40.858 | 52.193 | 1.00 | 31.25 | O |
| ATOM | 10967 | N | LYS | D | 102 | -1.577 | -38.783 | 52.272 | 1.00 | 33.92 | N |
| ATOM | 10968 | CA | LYS | D | 102 | -2.842 | -38.311 | 52.856 | 1.00 | 32.27 | C |
| ATOM | 10970 | CB | LYS | D | 102 | -2.650 | -37.072 | 53.743 | 1.00 | 32.89 | C |
| ATOM | 10973 | CG | LYS | D | 102 | -3.710 | -36.947 | 54.865 | 1.00 | 30.89 | C |
| ATOM | 10976 | CD | LYS | D | 102 | -3.414 | -35.816 | 55.873 | 1.00 | 31.22 | C |
| ATOM | 10979 | CE | LYS | D | 102 | -2.233 | -36.142 | 56.783 | 1.00 | 32.10 | C |
| ATOM | 10982 | NZ | LYS | D | 102 | -2.088 | -35.330 | 58.041 | 1.00 | 31.25 | N |
| ATOM | 10986 | C | LYS | D | 102 | -3.802 | -38.016 | 51.723 | 1.00 | 31.74 | C |
| ATOM | 10987 | O | LYS | D | 102 | -3.455 | -37.334 | 50.775 | 1.00 | 32.47 | O |
| ATOM | 10989 | N | PRO | D | 103 | -5.007 | -38.572 | 51.799 | 1.00 | 30.57 | N |
| ATOM | 10990 | CA | PRO | D | 103 | -5.992 | -38.255 | 50.801 | 1.00 | 30.52 | C |
| ATOM | 10992 | CB | PRO | D | 103 | -7.100 | -39.262 | 51.080 | 1.00 | 28.44 | C |
| ATOM | 10995 | CG | PRO | D | 103 | -6.982 | -39.583 | 52.491 | 1.00 | 27.57 | C |
| ATOM | 10998 | CD | PRO | D | 103 | -5.582 | -39.356 | 52.903 | 1.00 | 29.57 | C |
| ATOM | 11001 | C | PRO | D | 103 | -6.455 | -36.820 | 50.996 | 1.00 | 31.35 | C |
| ATOM | 11002 | O | PRO | D | 103 | -6.427 | -36.328 | 52.118 | 1.00 | 30.64 | O |
| ATOM | 11003 | N | LYS | D | 104 | -6.837 | -36.154 | 49.905 | 1.00 | 33.01 | N |
| ATOM | 11004 | CA | LYS | D | 104 | -7.235 | -34.730 | 49.952 | 1.00 | 34.29 | C |
| ATOM | 11006 | CB | LYS | D | 104 | -6.745 | -33.978 | 48.702 | 1.00 | 36.54 | C |
| ATOM | 11009 | CG | LYS | D | 104 | -5.224 | -34.077 | 48.450 | 1.00 | 38.95 | C |
| ATOM | 11012 | CD | LYS | D | 104 | -4.859 | -33.499 | 47.086 | 1.00 | 41.60 | C |
| ATOM | 11015 | CE | LYS | D | 104 | -3.634 | -34.185 | 46.474 | 1.00 | 43.82 | C |
| ATOM | 11018 | NZ | LYS | D | 104 | -3.371 | -33.689 | 45.065 | 1.00 | 45.63 | N |
| ATOM | 11022 | C | LYS | D | 104 | -8.757 | -34.561 | 50.121 | 1.00 | 32.74 | C |
| ATOM | 11023 | O | LYS | D | 104 | -9.277 | -33.458 | 50.014 | 1.00 | 34.40 | O |
| ATOM | 11025 | N | PHE | D | 105 | -9.449 | -35.661 | 50.381 | 1.00 | 30.39 | N |

FIG.3-15

| | | | | | | | | | | | |
|---|---|---|---|---|---|---|---|---|---|---|---|
| ATOM | 11026 | CA | PHE | D | 105 | -10.880 | -35.666 | 50.700 | 1.00 | 29.29 | C |
| ATOM | 11028 | CB | PHE | D | 105 | -11.697 | -36.031 | 49.455 | 1.00 | 29.63 | C |
| ATOM | 11031 | CG | PHE | D | 105 | -11.755 | -37.523 | 49.184 | 1.00 | 31.64 | C |
| ATOM | 11032 | CD1 | PHE | D | 105 | -12.926 | -38.259 | 49.447 | 1.00 | 33.99 | C |
| ATOM | 11034 | CE1 | PHE | D | 105 | -12.991 | -39.670 | 49.202 | 1.00 | 31.96 | C |
| ATOM | 11036 | CZ | PHE | D | 105 | -11.869 | -40.337 | 48.715 | 1.00 | 31.31 | C |
| ATOM | 11038 | CE2 | PHE | D | 105 | -10.695 | -39.608 | 48.440 | 1.00 | 32.98 | C |
| ATOM | 11040 | CD2 | PHE | D | 105 | -10.640 | -38.211 | 48.684 | 1.00 | 33.57 | C |
| ATOM | 11042 | C | PHE | D | 105 | -11.081 | -36.740 | 51.769 | 1.00 | 26.05 | C |
| ATOM | 11043 | O | PHE | D | 105 | -10.225 | -37.590 | 51.932 | 1.00 | 24.89 | O |
| ATOM | 11045 | N | LEU | D | 106 | -12.192 | -36.736 | 52.489 | 1.00 | 24.17 | N |
| ATOM | 11046 | CA | LEU | D | 106 | -12.481 | -37.890 | 53.384 | 1.00 | 22.29 | C |
| ATOM | 11048 | CB | LEU | D | 106 | -13.461 | -37.503 | 54.469 | 1.00 | 20.83 | C |
| ATOM | 11051 | CG | LEU | D | 106 | -12.891 | -36.516 | 55.478 | 1.00 | 21.62 | C |
| ATOM | 11053 | CD1 | LEU | D | 106 | -14.026 | -36.112 | 56.402 | 1.00 | 20.23 | C |
| ATOM | 11057 | CD2 | LEU | D | 106 | -11.704 | -37.104 | 56.260 | 1.00 | 20.68 | C |
| ATOM | 11061 | C | LEU | D | 106 | -13.007 | -39.151 | 52.657 | 1.00 | 21.28 | C |
| ATOM | 11062 | O | LEU | D | 106 | -14.085 | -39.106 | 52.103 | 1.00 | 21.19 | O |
| ATOM | 11064 | N | PRO | D | 107 | -12.254 | -40.281 | 52.685 | 1.00 | 21.24 | N |
| ATOM | 11065 | CA | PRO | D | 107 | -12.745 | -41.625 | 52.272 | 1.00 | 20.47 | C |
| ATOM | 11067 | CB | PRO | D | 107 | -11.494 | -42.507 | 52.344 | 1.00 | 20.82 | C |
| ATOM | 11070 | CG | PRO | D | 107 | -10.355 | -41.601 | 52.365 | 1.00 | 22.49 | C |
| ATOM | 11073 | CD | PRO | D | 107 | -10.811 | -40.316 | 52.990 | 1.00 | 22.15 | C |
| ATOM | 11076 | C | PRO | D | 107 | -13.778 | -42.225 | 53.215 | 1.00 | 19.49 | C |
| ATOM | 11077 | O | PRO | D | 107 | -14.140 | -41.620 | 54.189 | 1.00 | 19.91 | O |
| ATOM | 11078 | N | ASP | D | 108 | -14.210 | -43.444 | 52.956 | 1.00 | 19.04 | N |
| ATOM | 11079 | CA | ASP | D | 108 | -15.120 | -44.105 | 53.873 | 1.00 | 18.39 | C |
| ATOM | 11081 | CB | ASP | D | 108 | -16.179 | -44.797 | 53.063 | 1.00 | 18.10 | C |
| ATOM | 11084 | CG | ASP | D | 108 | -16.958 | -43.811 | 52.180 | 1.00 | 17.67 | C |
| ATOM | 11085 | OD1 | ASP | D | 108 | -17.461 | -42.812 | 52.747 | 1.00 | 12.43 | O |
| ATOM | 11086 | OD2 | ASP | D | 108 | -17.082 | -44.059 | 50.948 | 1.00 | 15.59 | O |
| ATOM | 11087 | C | ASP | D | 108 | -14.459 | -45.090 | 54.849 | 1.00 | 18.94 | C |
| ATOM | 11088 | O | ASP | D | 108 | -14.894 | -45.163 | 56.000 | 1.00 | 18.33 | O |
| ATOM | 11090 | N | LEU | D | 109 | -13.419 | -45.799 | 54.379 | 1.00 | 19.03 | N |
| ATOM | 11091 | CA | LEU | D | 109 | -12.735 | -46.843 | 55.105 | 1.00 | 19.62 | C |
| ATOM | 11093 | CB | LEU | D | 109 | -13.223 | -48.210 | 54.645 | 1.00 | 20.13 | C |
| ATOM | 11096 | CG | LEU | D | 109 | -14.645 | -48.661 | 54.995 | 1.00 | 22.03 | C |
| ATOM | 11098 | CD1 | LEU | D | 109 | -14.814 | -50.120 | 54.632 | 1.00 | 23.58 | C |
| ATOM | 11102 | CD2 | LEU | D | 109 | -15.000 | -48.417 | 56.472 | 1.00 | 21.73 | C |
| ATOM | 11106 | C | LEU | D | 109 | -11.243 | -46.820 | 54.823 | 1.00 | 20.51 | C |
| ATOM | 11107 | O | LEU | D | 109 | -10.836 | -46.332 | 53.758 | 1.00 | 20.97 | O |
| ATOM | 11109 | N | TYR | D | 110 | -10.452 | -47.322 | 55.788 | 1.00 | 20.70 | N |
| ATOM | 11110 | CA | TYR | D | 110 | -9.052 | -47.655 | 55.604 | 1.00 | 22.01 | C |
| ATOM | 11112 | CB | TYR | D | 110 | -8.138 | -46.893 | 56.586 | 1.00 | 22.47 | C |
| ATOM | 11115 | CG | TYR | D | 110 | -6.704 | -47.186 | 56.285 | 1.00 | 21.12 | C |
| ATOM | 11116 | CD1 | TYR | D | 110 | -6.098 | -46.644 | 55.163 | 1.00 | 20.26 | C |
| ATOM | 11118 | CE1 | TYR | D | 110 | -4.802 | -46.948 | 54.836 | 1.00 | 22.71 | C |
| ATOM | 11120 | CZ | TYR | D | 110 | -4.054 | -47.811 | 55.645 | 1.00 | 23.66 | C |
| ATOM | 11121 | OH | TYR | D | 110 | -2.751 | -48.111 | 55.294 | 1.00 | 26.81 | O |
| ATOM | 11123 | CE2 | TYR | D | 110 | -4.623 | -48.366 | 56.755 | 1.00 | 22.33 | C |
| ATOM | 11125 | CD2 | TYR | D | 110 | -5.974 | -48.061 | 57.060 | 1.00 | 22.26 | C |
| ATOM | 11127 | C | TYR | D | 110 | -8.840 | -49.177 | 55.803 | 1.00 | 24.15 | C |
| ATOM | 11128 | O | TYR | D | 110 | -9.313 | -49.743 | 56.807 | 1.00 | 23.87 | O |
| ATOM | 11130 | N | ASP | D | 111 | -8.119 | -49.806 | 54.860 | 1.00 | 25.63 | N |
| ATOM | 11131 | CA | ASP | D | 111 | -7.811 | -51.247 | 54.881 | 1.00 | 27.51 | C |
| ATOM | 11133 | CB | ASP | D | 111 | -7.919 | -51.810 | 53.474 | 1.00 | 28.12 | C |
| ATOM | 11136 | CG | ASP | D | 111 | -7.706 | -53.315 | 53.415 | 1.00 | 30.82 | C |
| ATOM | 11137 | OD1 | ASP | D | 111 | -7.171 | -53.906 | 54.379 | 1.00 | 34.77 | O |
| ATOM | 11138 | OD2 | ASP | D | 111 | -8.074 | -53.920 | 52.383 | 1.00 | 31.66 | O |
| ATOM | 11139 | C | ASP | D | 111 | -6.390 | -51.502 | 55.353 | 1.00 | 29.31 | C |
| ATOM | 11140 | O | ASP | D | 111 | -5.446 | -51.110 | 54.686 | 1.00 | 29.40 | O |
| ATOM | 11142 | N | TYR | D | 112 | -6.234 | -52.194 | 56.474 | 1.00 | 30.68 | N |
| ATOM | 11143 | CA | TYR | D | 112 | -4.904 | -52.410 | 57.049 | 1.00 | 32.66 | C |

FIG.3-16

| | | | | | | | | | | | |
|---|---|---|---|---|---|---|---|---|---|---|---|
| ATOM | 11145 | CB | TYR | D | 112 | -4.993 | -52.715 | 58.546 | 1.00 | 33.52 | C |
| ATOM | 11148 | CG | TYR | D | 112 | -5.365 | -51.527 | 59.389 | 1.00 | 34.28 | C |
| ATOM | 11149 | CD1 | TYR | D | 112 | -6.594 | -51.485 | 60.059 | 1.00 | 35.69 | C |
| ATOM | 11151 | CE1 | TYR | D | 112 | -6.955 | -50.373 | 60.857 | 1.00 | 35.35 | C |
| ATOM | 11153 | CZ | TYR | D | 112 | -6.066 | -49.301 | 61.000 | 1.00 | 37.04 | C |
| ATOM | 11154 | OH | TYR | D | 112 | -6.441 | -48.225 | 61.804 | 1.00 | 38.71 | O |
| ATOM | 11156 | CE2 | TYR | D | 112 | -4.817 | -49.329 | 60.354 | 1.00 | 35.88 | C |
| ATOM | 11158 | CD2 | TYR | D | 112 | -4.479 | -50.447 | 59.553 | 1.00 | 36.05 | C |
| ATOM | 11160 | C | TYR | D | 112 | -4.101 | -53.511 | 56.361 | 1.00 | 33.66 | C |
| ATOM | 11161 | O | TYR | D | 112 | -2.872 | -53.497 | 56.395 | 1.00 | 34.40 | O |
| ATOM | 11163 | N | LYS | D | 113 | -4.789 | -54.474 | 55.759 | 1.00 | 33.94 | N |
| ATOM | 11164 | CA | LYS | D | 113 | -4.108 | -55.570 | 55.065 | 1.00 | 35.12 | C |
| ATOM | 11166 | CB | LYS | D | 113 | -5.068 | -56.728 | 54.794 | 1.00 | 35.57 | C |
| ATOM | 11169 | CG | LYS | D | 113 | -4.367 | -58.023 | 54.310 | 1.00 | 39.16 | C |
| ATOM | 11172 | CD | LYS | D | 113 | -5.202 | -58.748 | 53.260 | 1.00 | 41.19 | C |
| ATOM | 11175 | CE | LYS | D | 113 | -4.423 | -59.843 | 52.580 | 1.00 | 44.54 | C |
| ATOM | 11178 | NZ | LYS | D | 113 | -4.163 | -60.984 | 53.505 | 1.00 | 47.74 | N |
| ATOM | 11182 | C | LYS | D | 113 | -3.490 | -55.077 | 53.758 | 1.00 | 34.66 | C |
| ATOM | 11183 | O | LYS | D | 113 | -2.354 | -55.437 | 53.450 | 1.00 | 36.20 | O |
| ATOM | 11185 | N | GLU | D | 114 | -4.232 | -54.254 | 53.013 | 1.00 | 32.70 | N |
| ATOM | 11186 | CA | GLU | D | 114 | -3.830 | -53.798 | 51.669 | 1.00 | 33.14 | C |
| ATOM | 11188 | CB | GLU | D | 114 | -5.057 | -53.764 | 50.742 | 1.00 | 32.77 | C |
| ATOM | 11191 | CG | GLU | D | 114 | -5.564 | -55.147 | 50.299 | 1.00 | 34.95 | C |
| ATOM | 11194 | CD | GLU | D | 114 | -4.604 | -55.862 | 49.358 | 1.00 | 39.59 | C |
| ATOM | 11195 | OE1 | GLU | D | 114 | -3.997 | -55.162 | 48.498 | 1.00 | 42.17 | O |
| ATOM | 11196 | OE2 | GLU | D | 114 | -4.466 | -57.111 | 49.471 | 1.00 | 40.13 | O |
| ATOM | 11197 | C | GLU | D | 114 | -3.164 | -52.423 | 51.689 | 1.00 | 32.17 | C |
| ATOM | 11198 | O | GLU | D | 114 | -2.580 | -51.978 | 50.701 | 1.00 | 31.87 | O |
| ATOM | 11200 | N | ASN | D | 115 | -3.268 | -51.776 | 52.841 | 1.00 | 31.58 | N |
| ATOM | 11201 | CA | ASN | D | 115 | -2.694 | -50.464 | 53.133 | 1.00 | 31.82 | C |
| ATOM | 11203 | CB | ASN | D | 115 | -1.173 | -50.546 | 53.354 | 1.00 | 33.95 | C |
| ATOM | 11206 | CG | ASN | D | 115 | -0.818 | -50.884 | 54.821 | 1.00 | 36.60 | C |
| ATOM | 11207 | OD1 | ASN | D | 115 | 0.074 | -51.697 | 55.063 | 1.00 | 40.72 | O |
| ATOM | 11208 | ND2 | ASN | D | 115 | -1.534 | -50.273 | 55.799 | 1.00 | 32.45 | N |
| ATOM | 11211 | C | ASN | D | 115 | -3.095 | -49.327 | 52.204 | 1.00 | 30.47 | C |
| ATOM | 11212 | O | ASN | D | 115 | -2.262 | -48.590 | 51.665 | 1.00 | 31.43 | O |
| ATOM | 11214 | N | ARG | D | 116 | -4.396 | -49.152 | 52.100 | 1.00 | 28.23 | N |
| ATOM | 11215 | CA | ARG | D | 116 | -4.973 | -48.147 | 51.227 | 1.00 | 27.72 | C |
| ATOM | 11217 | CB | ARG | D | 116 | -5.085 | -48.730 | 49.824 | 1.00 | 27.48 | C |
| ATOM | 11220 | CG | ARG | D | 116 | -6.036 | -49.926 | 49.729 | 1.00 | 27.69 | C |
| ATOM | 11223 | CD | ARG | D | 116 | -5.969 | -50.567 | 48.377 | 1.00 | 28.30 | C |
| ATOM | 11226 | NE | ARG | D | 116 | -6.766 | -51.783 | 48.296 | 1.00 | 28.86 | N |
| ATOM | 11228 | CZ | ARG | D | 116 | -6.607 | -52.743 | 47.380 | 1.00 | 29.74 | C |
| ATOM | 11229 | NH1 | ARG | D | 116 | -5.662 | -52.658 | 46.449 | 1.00 | 29.18 | N |
| ATOM | 11232 | NH2 | ARG | D | 116 | -7.380 | -53.822 | 47.422 | 1.00 | 30.56 | N |
| ATOM | 11235 | C | ARG | D | 116 | -6.352 | -47.732 | 51.756 | 1.00 | 25.96 | C |
| ATOM | 11236 | O | ARG | D | 116 | -7.055 | -48.528 | 52.357 | 1.00 | 26.03 | O |
| ATOM | 11238 | N | PHE | D | 117 | -6.736 | -46.492 | 51.555 | 1.00 | 25.82 | N |
| ATOM | 11239 | CA | PHE | D | 117 | -8.116 | -46.094 | 51.840 | 1.00 | 24.79 | C |
| ATOM | 11241 | CB | PHE | D | 117 | -8.251 | -44.574 | 51.892 | 1.00 | 25.21 | C |
| ATOM | 11244 | CG | PHE | D | 117 | -7.588 | -43.959 | 53.084 | 1.00 | 26.40 | C |
| ATOM | 11245 | CD1 | PHE | D | 117 | -8.269 | -43.860 | 54.293 | 1.00 | 25.80 | C |
| ATOM | 11247 | CE1 | PHE | D | 117 | -7.655 | -43.305 | 55.397 | 1.00 | 28.23 | C |
| ATOM | 11249 | CZ | PHE | D | 117 | -6.325 | -42.848 | 55.302 | 1.00 | 30.05 | C |
| ATOM | 11251 | CE2 | PHE | D | 117 | -5.637 | -42.944 | 54.103 | 1.00 | 29.22 | C |
| ATOM | 11253 | CD2 | PHE | D | 117 | -6.268 | -43.508 | 53.000 | 1.00 | 28.74 | C |
| ATOM | 11255 | C | PHE | D | 117 | -9.040 | -46.617 | 50.760 | 1.00 | 24.69 | C |
| ATOM | 11256 | O | PHE | D | 117 | -8.602 | -46.928 | 49.643 | 1.00 | 24.86 | O |
| ATOM | 11258 | N | ILE | D | 118 | -10.322 | -46.706 | 51.114 | 1.00 | 23.62 | N |
| ATOM | 11259 | CA | ILE | D | 118 | -11.383 | -47.101 | 50.188 | 1.00 | 23.01 | C |
| ATOM | 11261 | CB | ILE | D | 118 | -12.052 | -48.393 | 50.629 | 1.00 | 22.85 | C |
| ATOM | 11263 | CG1 | ILE | D | 118 | -11.035 | -49.514 | 50.753 | 1.00 | 24.26 | C |
| ATOM | 11266 | CD1 | ILE | D | 118 | -11.595 | -50.697 | 51.505 | 1.00 | 26.62 | C |

FIG.3-17

| | | | | | | | | | | | |
|---|---|---|---|---|---|---|---|---|---|---|---|
| ATOM | 11270 | CG2 | ILE | D | 118 | -13.117 | -48.790 | 49.662 | 1.00 | 21.80 | C |
| ATOM | 11274 | C | ILE | D | 118 | -12.490 | -46.062 | 50.143 | 1.00 | 22.17 | C |
| ATOM | 11275 | O | ILE | D | 118 | -12.931 | -45.573 | 51.194 | 1.00 | 20.78 | O |
| ATOM | 11277 | N | GLU | D | 119 | -12.925 | -45.733 | 48.922 | 1.00 | 22.67 | N |
| ATOM | 11278 | CA | GLU | D | 119 | -14.179 | -45.016 | 48.696 | 1.00 | 22.16 | C |
| ATOM | 11280 | CB | GLU | D | 119 | -13.965 | -43.863 | 47.709 | 1.00 | 22.98 | C |
| ATOM | 11283 | CG | GLU | D | 119 | -15.186 | -42.998 | 47.364 | 1.00 | 24.76 | C |
| ATOM | 11286 | CD | GLU | D | 119 | -15.959 | -42.482 | 48.562 | 1.00 | 26.12 | C |
| ATOM | 11287 | OE1 | GLU | D | 119 | -15.316 | -42.302 | 49.598 | 1.00 | 29.20 | O |
| ATOM | 11288 | OE2 | GLU | D | 119 | -17.200 | -42.236 | 48.484 | 1.00 | 27.45 | O |
| ATOM | 11289 | C | GLU | D | 119 | -15.235 | -46.008 | 48.205 | 1.00 | 21.91 | C |
| ATOM | 11290 | O | GLU | D | 119 | -15.050 | -46.661 | 47.158 | 1.00 | 22.57 | O |
| ATOM | 11292 | N | ILE | D | 120 | -16.304 | -46.132 | 48.999 | 1.00 | 20.63 | N |
| ATOM | 11293 | CA | ILE | D | 120 | -17.486 | -46.922 | 48.699 | 1.00 | 20.54 | C |
| ATOM | 11295 | CB | ILE | D | 120 | -18.163 | -47.392 | 49.967 | 1.00 | 20.44 | C |
| ATOM | 11297 | CG1 | ILE | D | 120 | -17.237 | -48.288 | 50.814 | 1.00 | 21.06 | C |
| ATOM | 11300 | CD1 | ILE | D | 120 | -17.494 | -49.775 | 50.641 | 1.00 | 20.07 | C |
| ATOM | 11304 | CG2 | ILE | D | 120 | -19.440 | -48.140 | 49.641 | 1.00 | 20.24 | C |
| ATOM | 11308 | C | ILE | D | 120 | -18.519 | -46.080 | 47.980 | 1.00 | 21.10 | C |
| ATOM | 11309 | O | ILE | D | 120 | -18.717 | -44.922 | 48.305 | 1.00 | 21.73 | O |
| ATOM | 11311 | N | GLY | D | 121 | -19.175 | -46.668 | 46.992 | 1.00 | 22.15 | N |
| ATOM | 11312 | CA | GLY | D | 121 | -20.267 | -46.021 | 46.258 | 1.00 | 22.76 | C |
| ATOM | 11315 | C | GLY | D | 121 | -21.515 | -46.901 | 46.236 | 1.00 | 22.95 | C |
| ATOM | 11316 | O | GLY | D | 121 | -21.410 | -48.124 | 46.174 | 1.00 | 23.35 | O |
| ATOM | 11318 | N | VAL | D | 122 | -22.685 | -46.276 | 46.337 | 1.00 | 22.92 | N |
| ATOM | 11319 | CA | VAL | D | 122 | -23.966 | -46.955 | 46.221 | 1.00 | 23.71 | C |
| ATOM | 11321 | CB | VAL | D | 122 | -24.682 | -47.087 | 47.573 | 1.00 | 22.99 | C |
| ATOM | 11323 | CG1 | VAL | D | 122 | -25.852 | -48.092 | 47.449 | 1.00 | 25.65 | C |
| ATOM | 11327 | CG2 | VAL | D | 122 | -23.737 | -47.507 | 48.633 | 1.00 | 20.66 | C |
| ATOM | 11331 | C | VAL | D | 122 | -24.851 | -46.186 | 45.264 | 1.00 | 25.15 | C |
| ATOM | 11332 | O | VAL | D | 122 | -25.250 | -45.081 | 45.547 | 1.00 | 25.16 | O |
| ATOM | 11334 | N | THR | D | 123 | -25.138 | -46.772 | 44.115 | 1.00 | 27.83 | N |
| ATOM | 11335 | CA | THR | D | 123 | -25.885 | -46.091 | 43.046 | 1.00 | 29.95 | C |
| ATOM | 11337 | CB | THR | D | 123 | -24.998 | -45.920 | 41.763 | 1.00 | 31.02 | C |
| ATOM | 11339 | OG1 | THR | D | 123 | -25.690 | -45.154 | 40.762 | 1.00 | 32.09 | O |
| ATOM | 11341 | CG2 | THR | D | 123 | -24.587 | -47.255 | 41.193 | 1.00 | 30.85 | C |
| ATOM | 11345 | C | THR | D | 123 | -27.182 | -46.844 | 42.701 | 1.00 | 32.09 | C |
| ATOM | 11346 | O | THR | D | 123 | -27.222 | -48.060 | 42.638 | 1.00 | 31.54 | O |
| ATOM | 11348 | N | ARG | D | 124 | -28.239 | -46.090 | 42.473 | 1.00 | 34.91 | N |
| ATOM | 11349 | CA | ARG | D | 124 | -29.484 | -46.633 | 41.967 | 1.00 | 38.00 | C |
| ATOM | 11351 | CB | ARG | D | 124 | -30.655 | -45.745 | 42.412 | 1.00 | 39.13 | C |
| ATOM | 11354 | CG | ARG | D | 124 | -30.968 | -45.808 | 43.917 | 1.00 | 38.96 | C |
| ATOM | 11357 | CD | ARG | D | 124 | -30.222 | -44.751 | 44.710 | 1.00 | 39.84 | C |
| ATOM | 11360 | NE | ARG | D | 124 | -30.923 | -43.475 | 44.825 | 1.00 | 42.41 | N |
| ATOM | 11362 | CZ | ARG | D | 124 | -30.373 | -42.346 | 45.288 | 1.00 | 45.57 | C |
| ATOM | 11363 | NH1 | ARG | D | 124 | -29.096 | -42.307 | 45.684 | 1.00 | 45.12 | N |
| ATOM | 11366 | NH2 | ARG | D | 124 | -31.105 | -41.232 | 45.360 | 1.00 | 48.31 | N |
| ATOM | 11369 | C | ARG | D | 124 | -29.454 | -46.736 | 40.438 | 1.00 | 40.77 | C |
| ATOM | 11370 | O | ARG | D | 124 | -30.433 | -47.186 | 39.816 | 1.00 | 42.13 | O |
| ATOM | 11372 | N | ARG | D | 125 | -28.335 | -46.314 | 39.847 | 1.00 | 41.57 | N |
| ATOM | 11373 | CA | ARG | D | 125 | -28.208 | -46.174 | 38.395 | 1.00 | 45.03 | C |
| ATOM | 11375 | CB | ARG | D | 125 | -27.855 | -44.719 | 38.005 | 1.00 | 46.02 | C |
| ATOM | 11378 | CG | ARG | D | 125 | -28.510 | -43.614 | 38.832 | 1.00 | 48.87 | C |
| ATOM | 11381 | CD | ARG | D | 125 | -28.243 | -42.204 | 38.247 | 1.00 | 53.76 | C |
| ATOM | 11384 | NE | ARG | D | 125 | -29.113 | -41.923 | 37.088 | 1.00 | 60.75 | N |
| ATOM | 11386 | CZ | ARG | D | 125 | -28.865 | -41.024 | 36.129 | 1.00 | 64.34 | C |
| ATOM | 11387 | NH1 | ARG | D | 125 | -27.764 | -40.268 | 36.175 | 1.00 | 65.11 | N |
| ATOM | 11390 | NH2 | ARG | D | 125 | -29.722 | -40.884 | 35.116 | 1.00 | 65.65 | N |
| ATOM | 11393 | C | ARG | D | 125 | -27.124 | -47.151 | 37.894 | 1.00 | 44.97 | C |
| ATOM | 11394 | O | ARG | D | 125 | -26.933 | -48.222 | 38.473 | 1.00 | 44.28 | O |
| ATOM | 11396 | N | GLU | D | 126 | -26.406 | -46.786 | 36.831 | 1.00 | 46.10 | N |
| ATOM | 11397 | CA | GLU | D | 126 | -25.518 | -47.722 | 36.180 | 1.00 | 46.17 | C |
| ATOM | 11399 | CB | GLU | D | 126 | -25.428 | -47.422 | 34.691 | 1.00 | 49.13 | C |

FIG.3-18

| | | | | | | | | | | | |
|---|---|---|---|---|---|---|---|---|---|---|---|
| ATOM | 11402 | CG | GLU | D | 126 | -24.992 | -48.616 | 33.849 | 1.00 | 51.00 | C |
| ATOM | 11405 | CD | GLU | D | 126 | -23.490 | -48.805 | 33.849 | 1.00 | 50.01 | C |
| ATOM | 11406 | OE1 | GLU | D | 126 | -22.998 | -49.964 | 33.883 | 1.00 | 50.63 | O |
| ATOM | 11407 | OE2 | GLU | D | 126 | -22.803 | -47.774 | 33.843 | 1.00 | 47.97 | O |
| ATOM | 11408 | C | GLU | D | 126 | -24.158 | -47.682 | 36.864 | 1.00 | 43.96 | C |
| ATOM | 11409 | O | GLU | D | 126 | -23.516 | -46.618 | 36.986 | 1.00 | 43.49 | O |
| ATOM | 11411 | N | VAL | D | 127 | -23.726 | -48.870 | 37.290 | 1.00 | 42.11 | N |
| ATOM | 11412 | CA | VAL | D | 127 | -22.574 | -49.031 | 38.166 | 1.00 | 39.12 | C |
| ATOM | 11414 | CB | VAL | D | 127 | -22.497 | -50.506 | 38.648 | 1.00 | 38.93 | C |
| ATOM | 11416 | CG1 | VAL | D | 127 | -21.698 | -51.387 | 37.667 | 1.00 | 40.52 | C |
| ATOM | 11420 | CG2 | VAL | D | 127 | -21.964 | -50.603 | 40.064 | 1.00 | 36.45 | C |
| ATOM | 11424 | C | VAL | D | 127 | -21.266 | -48.577 | 37.499 | 1.00 | 38.61 | C |
| ATOM | 11425 | O | VAL | D | 127 | -20.306 | -48.303 | 38.167 | 1.00 | 37.48 | O |
| ATOM | 11427 | N | HIS | D | 128 | -21.242 | -48.461 | 36.186 | 1.00 | 39.10 | N |
| ATOM | 11428 | CA | HIS | D | 128 | -20.037 | -48.056 | 35.492 | 1.00 | 39.49 | C |
| ATOM | 11430 | CB | HIS | D | 128 | -20.093 | -48.585 | 34.040 | 1.00 | 42.49 | C |
| ATOM | 11433 | CG | HIS | D | 128 | -18.768 | -48.912 | 33.446 | 1.00 | 42.48 | C |
| ATOM | 11434 | ND1 | HIS | D | 128 | -18.624 | -49.851 | 32.449 | 1.00 | 45.75 | N |
| ATOM | 11436 | CE1 | HIS | D | 128 | -17.355 | -49.922 | 32.090 | 1.00 | 46.12 | C |
| ATOM | 11438 | NE2 | HIS | D | 128 | -16.665 | -49.074 | 32.834 | 1.00 | 45.23 | N |
| ATOM | 11440 | CD2 | HIS | D | 128 | -17.528 | -48.427 | 33.689 | 1.00 | 42.92 | C |
| ATOM | 11442 | C | HIS | D | 128 | -19.835 | -46.522 | 35.502 | 1.00 | 38.84 | C |
| ATOM | 11443 | O | HIS | D | 128 | -18.779 | -46.043 | 35.854 | 1.00 | 37.66 | O |
| ATOM | 11445 | N | ILE | D | 129 | -20.836 | -45.745 | 35.102 | 1.00 | 39.76 | N |
| ATOM | 11446 | CA | ILE | D | 129 | -20.624 | -44.305 | 34.995 | 1.00 | 39.99 | C |
| ATOM | 11448 | CB | ILE | D | 129 | -21.637 | -43.549 | 34.038 | 1.00 | 42.72 | C |
| ATOM | 11450 | CG1 | ILE | D | 129 | -22.787 | -42.906 | 34.785 | 1.00 | 42.83 | C |
| ATOM | 11453 | CD1 | ILE | D | 129 | -23.882 | -42.403 | 33.834 | 1.00 | 47.90 | C |
| ATOM | 11457 | CG2 | ILE | D | 129 | -22.180 | -44.452 | 32.918 | 1.00 | 44.46 | C |
| ATOM | 11461 | C | ILE | D | 129 | -20.539 | -43.701 | 36.390 | 1.00 | 37.06 | C |
| ATOM | 11462 | O | ILE | D | 129 | -19.853 | -42.703 | 36.588 | 1.00 | 37.31 | O |
| ATOM | 11464 | N | TYR | D | 130 | -21.191 | -44.327 | 37.364 | 1.00 | 34.61 | N |
| ATOM | 11465 | CA | TYR | D | 130 | -21.031 | -43.926 | 38.737 | 1.00 | 31.96 | C |
| ATOM | 11467 | CB | TYR | D | 130 | -22.055 | -44.615 | 39.650 | 1.00 | 31.69 | C |
| ATOM | 11470 | CG | TYR | D | 130 | -22.158 | -43.979 | 41.017 | 1.00 | 28.18 | C |
| ATOM | 11471 | CD1 | TYR | D | 130 | -22.982 | -42.892 | 41.235 | 1.00 | 30.14 | C |
| ATOM | 11473 | CE1 | TYR | D | 130 | -23.097 | -42.296 | 42.509 | 1.00 | 31.16 | C |
| ATOM | 11475 | CZ | TYR | D | 130 | -22.359 | -42.797 | 43.562 | 1.00 | 29.86 | C |
| ATOM | 11476 | OH | TYR | D | 130 | -22.439 | -42.223 | 44.797 | 1.00 | 31.44 | O |
| ATOM | 11478 | CE2 | TYR | D | 130 | -21.530 | -43.882 | 43.367 | 1.00 | 29.97 | C |
| ATOM | 11480 | CD2 | TYR | D | 130 | -21.431 | -44.467 | 42.078 | 1.00 | 29.02 | C |
| ATOM | 11482 | C | TYR | D | 130 | -19.644 | -44.194 | 39.260 | 1.00 | 30.26 | C |
| ATOM | 11483 | O | TYR | D | 130 | -19.095 | -43.342 | 39.896 | 1.00 | 30.16 | O |
| ATOM | 11485 | N | TYR | D | 131 | -19.062 | -45.362 | 39.028 | 1.00 | 30.19 | N |
| ATOM | 11486 | CA | TYR | D | 131 | -17.605 | -45.521 | 39.293 | 1.00 | 29.83 | C |
| ATOM | 11488 | CB | TYR | D | 131 | -17.011 | -46.781 | 38.667 | 1.00 | 31.00 | C |
| ATOM | 11491 | CG | TYR | D | 131 | -15.520 | -47.025 | 38.964 | 1.00 | 30.49 | C |
| ATOM | 11492 | CD1 | TYR | D | 131 | -15.123 | -47.845 | 40.001 | 1.00 | 29.21 | C |
| ATOM | 11494 | CE1 | TYR | D | 131 | -13.787 | -48.093 | 40.250 | 1.00 | 28.88 | C |
| ATOM | 11496 | CZ | TYR | D | 131 | -12.829 | -47.526 | 39.450 | 1.00 | 30.39 | C |
| ATOM | 11497 | OH | TYR | D | 131 | -11.494 | -47.764 | 39.703 | 1.00 | 32.25 | O |
| ATOM | 11499 | CE2 | TYR | D | 131 | -13.192 | -46.721 | 38.414 | 1.00 | 30.93 | C |
| ATOM | 11501 | CD2 | TYR | D | 131 | -14.524 | -46.480 | 38.170 | 1.00 | 32.61 | C |
| ATOM | 11503 | C | TYR | D | 131 | -16.809 | -44.378 | 38.745 | 1.00 | 31.10 | C |
| ATOM | 11504 | O | TYR | D | 131 | -15.954 | -43.877 | 39.423 | 1.00 | 30.80 | O |
| ATOM | 11506 | N | LEU | D | 132 | -17.052 | -44.002 | 37.495 | 1.00 | 34.01 | N |
| ATOM | 11507 | CA | LEU | D | 132 | -16.241 | -42.985 | 36.851 | 1.00 | 36.05 | C |
| ATOM | 11509 | CB | LEU | D | 132 | -16.518 | -42.969 | 35.353 | 1.00 | 38.96 | C |
| ATOM | 11512 | CG | LEU | D | 132 | -16.149 | -44.222 | 34.546 | 1.00 | 40.94 | C |
| ATOM | 11514 | CD1 | LEU | D | 132 | -16.564 | -44.059 | 33.102 | 1.00 | 43.11 | C |
| ATOM | 11518 | CD2 | LEU | D | 132 | -14.660 | -44.537 | 34.600 | 1.00 | 42.31 | C |
| ATOM | 11522 | C | LEU | D | 132 | -16.472 | -41.602 | 37.468 | 1.00 | 36.06 | C |
| ATOM | 11523 | O | LEU | D | 132 | -15.515 | -40.839 | 37.641 | 1.00 | 35.93 | O |

FIG.3-19

| | | | | | | | | | | | |
|---|---|---|---|---|---|---|---|---|---|---|---|
| ATOM | 11525 | N | GLU | D | 133 | -17.722 | -41.294 | 37.820 | 1.00 | 36.17 | N |
| ATOM | 11526 | CA | GLU | D | 133 | -18.037 | -40.016 | 38.447 | 1.00 | 36.93 | C |
| ATOM | 11528 | CB | GLU | D | 133 | -19.534 | -39.861 | 38.735 | 1.00 | 36.22 | C |
| ATOM | 11531 | CG | GLU | D | 133 | -20.284 | -39.334 | 37.514 | 1.00 | 39.74 | C |
| ATOM | 11534 | CD | GLU | D | 133 | -21.813 | -39.546 | 37.514 | 1.00 | 42.20 | C |
| ATOM | 11535 | OE1 | GLU | D | 133 | -22.374 | -40.317 | 38.341 | 1.00 | 43.64 | O |
| ATOM | 11536 | OE2 | GLU | D | 133 | -22.468 | -38.930 | 36.646 | 1.00 | 44.27 | O |
| ATOM | 11537 | C | GLU | D | 133 | -17.234 | -39.931 | 39.710 | 1.00 | 35.85 | C |
| ATOM | 11538 | O | GLU | D | 133 | -16.646 | -38.914 | 40.034 | 1.00 | 36.14 | O |
| ATOM | 11540 | N | LYS | D | 134 | -17.157 | -41.042 | 40.402 | 1.00 | 35.38 | N |
| ATOM | 11541 | CA | LYS | D | 134 | -16.385 | -41.078 | 41.609 | 1.00 | 34.94 | C |
| ATOM | 11543 | CB | LYS | D | 134 | -16.693 | -42.358 | 42.375 | 1.00 | 33.62 | C |
| ATOM | 11546 | CG | LYS | D | 134 | -17.970 | -42.261 | 43.165 | 1.00 | 33.21 | C |
| ATOM | 11549 | CD | LYS | D | 134 | -17.774 | -41.405 | 44.446 | 1.00 | 32.64 | C |
| ATOM | 11552 | CE | LYS | D | 134 | -18.893 | -41.629 | 45.489 | 1.00 | 31.69 | C |
| ATOM | 11555 | NZ | LYS | D | 134 | -20.059 | -40.724 | 45.291 | 1.00 | 32.12 | N |
| ATOM | 11559 | C | LYS | D | 134 | -14.905 | -40.931 | 41.346 | 1.00 | 36.35 | C |
| ATOM | 11560 | O | LYS | D | 134 | -14.268 | -40.107 | 41.971 | 1.00 | 35.94 | O |
| ATOM | 11562 | N | ALA | D | 135 | -14.357 | -41.708 | 40.416 | 1.00 | 38.90 | N |
| ATOM | 11563 | CA | ALA | D | 135 | -12.962 | -41.529 | 40.015 | 1.00 | 41.34 | C |
| ATOM | 11565 | CB | ALA | D | 135 | -12.616 | -42.413 | 38.834 | 1.00 | 42.63 | C |
| ATOM | 11569 | C | ALA | D | 135 | -12.726 | -40.056 | 39.683 | 1.00 | 44.50 | C |
| ATOM | 11570 | O | ALA | D | 135 | -11.825 | -39.431 | 40.239 | 1.00 | 45.52 | O |
| ATOM | 11572 | N | ASN | D | 136 | -13.561 | -39.493 | 38.812 | 1.00 | 47.13 | N |
| ATOM | 11573 | CA | ASN | D | 136 | -13.468 | -38.066 | 38.459 | 1.00 | 49.96 | C |
| ATOM | 11575 | CB | ASN | D | 136 | -14.446 | -37.761 | 37.310 | 1.00 | 52.17 | C |
| ATOM | 11578 | CG | ASN | D | 136 | -14.197 | -36.428 | 36.664 | 1.00 | 54.64 | C |
| ATOM | 11579 | OD1 | ASN | D | 136 | -14.484 | -35.376 | 37.234 | 1.00 | 55.02 | O |
| ATOM | 11580 | ND2 | ASN | D | 136 | -13.693 | -36.463 | 35.447 | 1.00 | 58.23 | N |
| ATOM | 11583 | C | ASN | D | 136 | -13.689 | -37.074 | 39.637 | 1.00 | 49.63 | C |
| ATOM | 11584 | O | ASN | D | 136 | -13.053 | -36.020 | 39.670 | 1.00 | 50.64 | O |
| ATOM | 11586 | N | LYS | D | 137 | -14.578 | -37.392 | 40.582 | 1.00 | 48.40 | N |
| ATOM | 11587 | CA | LYS | D | 137 | -14.800 | -36.505 | 41.741 | 1.00 | 48.61 | C |
| ATOM | 11589 | CB | LYS | D | 137 | -16.046 | -36.882 | 42.570 | 1.00 | 47.09 | C |
| ATOM | 11592 | CG | LYS | D | 137 | -17.384 | -36.410 | 42.011 | 1.00 | 49.77 | C |
| ATOM | 11595 | CD | LYS | D | 137 | -18.519 | -36.729 | 42.986 | 1.00 | 50.24 | C |
| ATOM | 11598 | CE | LYS | D | 137 | -19.838 | -37.158 | 42.292 | 1.00 | 52.04 | C |
| ATOM | 11601 | NZ | LYS | D | 137 | -20.535 | -38.202 | 43.127 | 1.00 | 49.80 | N |
| ATOM | 11605 | C | LYS | D | 137 | -13.594 | -36.581 | 42.645 | 1.00 | 47.94 | C |
| ATOM | 11606 | O | LYS | D | 137 | -12.992 | -35.566 | 42.967 | 1.00 | 48.99 | O |
| ATOM | 11608 | N | ILE | D | 138 | -13.283 | -37.817 | 43.038 | 1.00 | 46.97 | N |
| ATOM | 11609 | CA | ILE | D | 138 | -12.137 | -38.207 | 43.882 | 1.00 | 46.02 | C |
| ATOM | 11611 | CB | ILE | D | 138 | -11.884 | -39.782 | 43.782 | 1.00 | 45.48 | C |
| ATOM | 11613 | CG1 | ILE | D | 138 | -11.407 | -40.362 | 45.098 | 1.00 | 43.83 | C |
| ATOM | 11616 | CD1 | ILE | D | 138 | -10.806 | -41.741 | 44.940 | 1.00 | 44.28 | C |
| ATOM | 11620 | CG2 | ILE | D | 138 | -10.864 | -40.175 | 42.636 | 1.00 | 46.83 | C |
| ATOM | 11624 | C | ILE | D | 138 | -10.819 | -37.539 | 43.533 | 1.00 | 47.32 | C |
| ATOM | 11625 | O | ILE | D | 138 | -10.232 | -36.854 | 44.355 | 1.00 | 46.85 | O |
| ATOM | 11627 | N | LYS | D | 139 | -10.370 | -37.773 | 42.300 | 1.00 | 49.38 | N |
| ATOM | 11628 | CA | LYS | D | 139 | -8.969 | -37.566 | 41.858 | 1.00 | 51.15 | C |
| ATOM | 11630 | CB | LYS | D | 139 | -8.797 | -36.150 | 41.274 | 1.00 | 53.55 | C |
| ATOM | 11633 | CG | LYS | D | 139 | -9.849 | -35.824 | 40.186 | 1.00 | 55.21 | C |
| ATOM | 11636 | CD | LYS | D | 139 | -9.567 | -34.523 | 39.410 | 1.00 | 59.03 | C |
| ATOM | 11639 | CE | LYS | D | 139 | -10.178 | -34.545 | 37.977 | 1.00 | 61.27 | C |
| ATOM | 11642 | NZ | LYS | D | 139 | -9.700 | -33.421 | 37.089 | 1.00 | 62.12 | N |
| ATOM | 11646 | C | LYS | D | 139 | -7.875 | -37.929 | 42.907 | 1.00 | 50.02 | C |
| ATOM | 11647 | O | LYS | D | 139 | -6.806 | -37.343 | 42.928 | 1.00 | 51.38 | O |
| ATOM | 11649 | N | SER | D | 140 | -8.153 | -38.900 | 43.772 | 1.00 | 47.96 | N |
| ATOM | 11650 | CA | SER | D | 140 | -7.090 | -39.597 | 44.478 | 1.00 | 47.54 | C |
| ATOM | 11652 | CB | SER | D | 140 | -7.418 | -39.879 | 45.952 | 1.00 | 45.45 | C |
| ATOM | 11655 | OG | SER | D | 140 | -6.869 | -38.866 | 46.802 | 1.00 | 47.29 | O |
| ATOM | 11657 | C | SER | D | 140 | -6.888 | -40.872 | 43.697 | 1.00 | 47.59 | C |
| ATOM | 11658 | O | SER | D | 140 | -7.683 | -41.827 | 43.758 | 1.00 | 46.48 | O |

FIG.3-20

| | | | | | | | | | | | |
|---|---|---|---|---|---|---|---|---|---|---|---|
| ATOM | 11660 | N | GLU | D | 141 | -5.812 | -40.878 | 42.935 | 1.00 | 49.10 | N |
| ATOM | 11661 | CA | GLU | D | 141 | -5.473 | -42.033 | 42.145 | 1.00 | 49.51 | C |
| ATOM | 11663 | CB | GLU | D | 141 | -4.329 | -41.686 | 41.188 | 1.00 | 52.84 | C |
| ATOM | 11666 | CG | GLU | D | 141 | -4.623 | -40.504 | 40.223 | 1.00 | 55.81 | C |
| ATOM | 11669 | CD | GLU | D | 141 | -3.350 | -39.799 | 39.748 | 1.00 | 60.59 | C |
| ATOM | 11670 | OE1 | GLU | D | 141 | -2.370 | -39.703 | 40.541 | 1.00 | 59.44 | O |
| ATOM | 11671 | OE2 | GLU | D | 141 | -3.338 | -39.331 | 38.577 | 1.00 | 64.77 | O |
| ATOM | 11672 | C | GLU | D | 141 | -5.096 | -43.228 | 43.038 | 1.00 | 47.18 | C |
| ATOM | 11673 | O | GLU | D | 141 | -5.123 | -44.369 | 42.561 | 1.00 | 47.70 | O |
| ATOM | 11675 | N | LYS | D | 142 | -4.748 | -42.953 | 44.310 | 1.00 | 44.44 | N |
| ATOM | 11676 | CA | LYS | D | 142 | -4.318 | -43.960 | 45.287 | 1.00 | 41.79 | C |
| ATOM | 11678 | CB | LYS | D | 142 | -3.197 | -43.400 | 46.174 | 1.00 | 42.46 | C |
| ATOM | 11681 | CG | LYS | D | 142 | -1.833 | -43.467 | 45.558 | 1.00 | 45.67 | C |
| ATOM | 11684 | CD | LYS | D | 142 | -0.773 | -42.972 | 46.526 | 1.00 | 48.23 | C |
| ATOM | 11687 | CE | LYS | D | 142 | 0.471 | -42.481 | 45.782 | 1.00 | 52.26 | C |
| ATOM | 11690 | NZ | LYS | D | 142 | 1.619 | -42.223 | 46.691 | 1.00 | 54.00 | N |
| ATOM | 11694 | C | LYS | D | 142 | -5.439 | -44.408 | 46.210 | 1.00 | 38.54 | C |
| ATOM | 11695 | O | LYS | D | 142 | -5.199 | -45.189 | 47.155 | 1.00 | 38.05 | O |
| ATOM | 11697 | N | THR | D | 143 | -6.653 | -43.914 | 45.998 | 1.00 | 35.44 | N |
| ATOM | 11698 | CA | THR | D | 143 | -7.769 | -44.426 | 46.790 | 1.00 | 32.64 | C |
| ATOM | 11700 | CB | THR | D | 143 | -8.637 | -43.276 | 47.372 | 1.00 | 31.53 | C |
| ATOM | 11702 | OG1 | THR | D | 143 | -7.937 | -42.683 | 48.477 | 1.00 | 32.38 | O |
| ATOM | 11704 | CG2 | THR | D | 143 | -9.957 | -43.761 | 47.873 | 1.00 | 29.73 | C |
| ATOM | 11708 | C | THR | D | 143 | -8.549 | -45.499 | 45.999 | 1.00 | 31.14 | C |
| ATOM | 11709 | O | THR | D | 143 | -8.950 | -45.289 | 44.877 | 1.00 | 32.45 | O |
| ATOM | 11711 | N | HIS | D | 144 | -8.725 | -46.665 | 46.603 | 1.00 | 29.03 | N |
| ATOM | 11712 | CA | HIS | D | 144 | -9.411 | -47.770 | 45.983 | 1.00 | 28.06 | C |
| ATOM | 11714 | CB | HIS | D | 144 | -9.064 | -49.078 | 46.713 | 1.00 | 28.24 | C |
| ATOM | 11717 | CG | HIS | D | 144 | -9.145 | -50.287 | 45.836 | 1.00 | 31.06 | C |
| ATOM | 11718 | ND1 | HIS | D | 144 | -8.135 | -50.636 | 44.957 | 1.00 | 33.84 | N |
| ATOM | 11720 | CE1 | HIS | D | 144 | -8.503 | -51.716 | 44.286 | 1.00 | 35.06 | C |
| ATOM | 11722 | NE2 | HIS | D | 144 | -9.711 | -52.075 | 44.695 | 1.00 | 33.08 | N |
| ATOM | 11724 | CD2 | HIS | D | 144 | -10.140 | -51.189 | 45.652 | 1.00 | 30.89 | C |
| ATOM | 11726 | C | HIS | D | 144 | -10.907 | -47.467 | 46.043 | 1.00 | 26.18 | C |
| ATOM | 11727 | O | HIS | D | 144 | -11.419 | -47.074 | 47.086 | 1.00 | 24.25 | O |
| ATOM | 11729 | N | ILE | D | 145 | -11.572 | -47.594 | 44.897 | 1.00 | 25.76 | N |
| ATOM | 11730 | CA | ILE | D | 145 | -12.998 | -47.343 | 44.750 | 1.00 | 24.45 | C |
| ATOM | 11732 | CB | ILE | D | 145 | -13.258 | -46.514 | 43.496 | 1.00 | 26.08 | C |
| ATOM | 11734 | CG1 | ILE | D | 145 | -12.229 | -45.400 | 43.356 | 1.00 | 25.87 | C |
| ATOM | 11737 | CD1 | ILE | D | 145 | -12.577 | -44.397 | 42.255 | 1.00 | 25.33 | C |
| ATOM | 11741 | CG2 | ILE | D | 145 | -14.708 | -45.949 | 43.488 | 1.00 | 26.68 | C |
| ATOM | 11745 | C | ILE | D | 145 | -13.778 | -48.666 | 44.591 | 1.00 | 24.08 | C |
| ATOM | 11746 | O | ILE | D | 145 | -13.437 | -49.479 | 43.740 | 1.00 | 23.81 | O |
| ATOM | 11748 | N | HIS | D | 146 | -14.789 | -48.889 | 45.444 | 1.00 | 23.05 | N |
| ATOM | 11749 | CA | HIS | D | 146 | -15.740 | -50.013 | 45.295 | 1.00 | 22.78 | C |
| ATOM | 11751 | CB | HIS | D | 146 | -15.656 | -50.947 | 46.495 | 1.00 | 22.61 | C |
| ATOM | 11754 | CG | HIS | D | 146 | -16.166 | -52.328 | 46.222 | 1.00 | 23.08 | C |
| ATOM | 11755 | ND1 | HIS | D | 146 | -15.623 | -53.444 | 46.814 | 1.00 | 21.87 | N |
| ATOM | 11757 | CE1 | HIS | D | 146 | -16.245 | -54.521 | 46.356 | 1.00 | 26.01 | C |
| ATOM | 11759 | NE2 | HIS | D | 146 | -17.165 | -54.144 | 45.491 | 1.00 | 23.82 | N |
| ATOM | 11761 | CD2 | HIS | D | 146 | -17.127 | -52.776 | 45.379 | 1.00 | 25.01 | C |
| ATOM | 11763 | C | HIS | D | 146 | -17.170 | -49.487 | 45.202 | 1.00 | 21.76 | C |
| ATOM | 11764 | O | HIS | D | 146 | -17.636 | -48.842 | 46.124 | 1.00 | 18.96 | O |
| ATOM | 11766 | N | ILE | D | 147 | -17.849 | -49.762 | 44.086 | 1.00 | 23.08 | N |
| ATOM | 11767 | CA | ILE | D | 147 | -19.234 | -49.308 | 43.860 | 1.00 | 23.28 | C |
| ATOM | 11769 | CB | ILE | D | 147 | -19.415 | -48.614 | 42.478 | 1.00 | 24.67 | C |
| ATOM | 11771 | CG1 | ILE | D | 147 | -18.401 | -47.489 | 42.263 | 1.00 | 24.03 | C |
| ATOM | 11774 | CD1 | ILE | D | 147 | -18.472 | -46.342 | 43.263 | 1.00 | 19.12 | C |
| ATOM | 11778 | CG2 | ILE | D | 147 | -20.857 | -48.076 | 42.297 | 1.00 | 24.14 | C |
| ATOM | 11782 | C | ILE | D | 147 | -20.165 | -50.505 | 43.830 | 1.00 | 24.12 | C |
| ATOM | 11783 | O | ILE | D | 147 | -19.914 | -51.444 | 43.083 | 1.00 | 25.47 | O |
| ATOM | 11785 | N | PHE | D | 148 | -21.241 | -50.454 | 44.606 | 1.00 | 23.56 | N |
| ATOM | 11786 | CA | PHE | D | 148 | -22.360 | -51.407 | 44.483 | 1.00 | 24.84 | C |

FIG.3-21

| | | | | | | | | | | | |
|---|---|---|---|---|---|---|---|---|---|---|---|
| ATOM | 11788 | CB | PHE | D | 148 | -22.716 | -51.970 | 45.864 | 1.00 | 23.78 | C |
| ATOM | 11791 | CG | PHE | D | 148 | -21.571 | -52.676 | 46.594 | 1.00 | 22.59 | C |
| ATOM | 11792 | CD1 | PHE | D | 148 | -21.463 | -54.076 | 46.574 | 1.00 | 22.09 | C |
| ATOM | 11794 | CE1 | PHE | D | 148 | -20.453 | -54.719 | 47.262 | 1.00 | 21.46 | C |
| ATOM | 11796 | CZ | PHE | D | 148 | -19.549 | -53.993 | 48.016 | 1.00 | 20.38 | C |
| ATOM | 11798 | CE2 | PHE | D | 148 | -19.640 | -52.618 | 48.051 | 1.00 | 20.15 | C |
| ATOM | 11800 | CD2 | PHE | D | 148 | -20.664 | -51.963 | 47.358 | 1.00 | 20.22 | C |
| ATOM | 11802 | C | PHE | D | 148 | -23.656 | -50.753 | 43.900 | 1.00 | 26.39 | C |
| ATOM | 11803 | O | PHE | D | 148 | -23.899 | -49.553 | 44.096 | 1.00 | 25.58 | O |
| ATOM | 11805 | N | SER | D | 149 | -24.478 | -51.535 | 43.181 | 1.00 | 28.44 | N |
| ATOM | 11806 | CA | SER | D | 149 | -25.842 | -51.116 | 42.828 | 1.00 | 30.01 | C |
| ATOM | 11808 | CB | SER | D | 149 | -26.071 | -51.275 | 41.343 | 1.00 | 32.27 | C |
| ATOM | 11811 | OG | SER | D | 149 | -26.391 | -52.618 | 41.063 | 1.00 | 33.41 | O |
| ATOM | 11813 | C | SER | D | 149 | -26.932 | -51.918 | 43.537 | 1.00 | 31.21 | C |
| ATOM | 11814 | O | SER | D | 149 | -26.674 | -52.961 | 44.154 | 1.00 | 31.25 | O |
| ATOM | 11816 | N | PHE | D | 150 | -28.174 | -51.453 | 43.413 | 1.00 | 33.01 | N |
| ATOM | 11817 | CA | PHE | D | 150 | -29.310 | -52.140 | 44.055 | 1.00 | 34.21 | C |
| ATOM | 11819 | CB | PHE | D | 150 | -30.490 | -51.192 | 44.299 | 1.00 | 34.37 | C |
| ATOM | 11822 | CG | PHE | D | 150 | -30.293 | -50.220 | 45.430 | 1.00 | 32.20 | C |
| ATOM | 11823 | CD1 | PHE | D | 150 | -30.872 | -50.447 | 46.678 | 1.00 | 33.43 | C |
| ATOM | 11825 | CE1 | PHE | D | 150 | -30.707 | -49.527 | 47.736 | 1.00 | 31.51 | C |
| ATOM | 11827 | CZ | PHE | D | 150 | -29.985 | -48.355 | 47.520 | 1.00 | 29.65 | C |
| ATOM | 11829 | CE2 | PHE | D | 150 | -29.435 | -48.122 | 46.270 | 1.00 | 29.66 | C |
| ATOM | 11831 | CD2 | PHE | D | 150 | -29.598 | -49.043 | 45.237 | 1.00 | 30.34 | C |
| ATOM | 11833 | C | PHE | D | 150 | -29.733 | -53.318 | 43.172 | 1.00 | 37.08 | C |
| ATOM | 11834 | O | PHE | D | 150 | -30.488 | -54.203 | 43.597 | 1.00 | 39.31 | O |
| ATOM | 11836 | N | THR | D | 151 | -29.237 | -53.316 | 41.944 | 1.00 | 37.93 | N |
| ATOM | 11837 | CA | THR | D | 151 | -29.475 | -54.382 | 40.987 | 1.00 | 40.29 | C |
| ATOM | 11839 | CB | THR | D | 151 | -29.445 | -53.790 | 39.592 | 1.00 | 41.72 | C |
| ATOM | 11841 | OG1 | THR | D | 151 | -30.615 | -52.988 | 39.432 | 1.00 | 44.28 | O |
| ATOM | 11843 | CG2 | THR | D | 151 | -29.450 | -54.850 | 38.538 | 1.00 | 45.90 | C |
| ATOM | 11847 | C | THR | D | 151 | -28.453 | -55.509 | 41.088 | 1.00 | 39.97 | C |
| ATOM | 11848 | O | THR | D | 151 | -28.538 | -56.471 | 40.342 | 1.00 | 41.39 | O |
| ATOM | 11850 | N | GLY | D | 152 | -27.475 | -55.389 | 41.994 | 1.00 | 37.82 | N |
| ATOM | 11851 | CA | GLY | D | 152 | -26.586 | -56.510 | 42.304 | 1.00 | 37.91 | C |
| ATOM | 11854 | C | GLY | D | 152 | -25.234 | -56.528 | 41.602 | 1.00 | 38.15 | C |
| ATOM | 11855 | O | GLY | D | 152 | -24.396 | -57.391 | 41.888 | 1.00 | 38.24 | O |
| ATOM | 11857 | N | GLU | D | 153 | -25.000 | -55.593 | 40.683 | 1.00 | 38.24 | N |
| ATOM | 11858 | CA | GLU | D | 153 | -23.694 | -55.481 | 40.052 | 1.00 | 37.93 | C |
| ATOM | 11860 | CB | GLU | D | 153 | -23.787 | -54.776 | 38.705 | 1.00 | 39.85 | C |
| ATOM | 11863 | CG | GLU | D | 153 | -24.753 | -55.455 | 37.727 | 1.00 | 44.05 | C |
| ATOM | 11866 | CD | GLU | D | 153 | -26.037 | -54.678 | 37.487 | 1.00 | 46.05 | C |
| ATOM | 11867 | OE1 | GLU | D | 153 | -26.495 | -54.637 | 36.320 | 1.00 | 50.88 | O |
| ATOM | 11868 | OE2 | GLU | D | 153 | -26.588 | -54.102 | 38.449 | 1.00 | 47.02 | O |
| ATOM | 11869 | C | GLU | D | 153 | -22.757 | -54.734 | 40.975 | 1.00 | 35.05 | C |
| ATOM | 11870 | O | GLU | D | 153 | -23.154 | -54.237 | 42.028 | 1.00 | 33.81 | O |
| ATOM | 11872 | N | GLU | D | 154 | -21.489 | -54.690 | 40.595 | 1.00 | 34.47 | N |
| ATOM | 11873 | CA | GLU | D | 154 | -20.494 | -54.026 | 41.392 | 1.00 | 31.77 | C |
| ATOM | 11875 | CB | GLU | D | 154 | -20.081 | -54.860 | 42.616 | 1.00 | 30.63 | C |
| ATOM | 11878 | CG | GLU | D | 154 | -19.738 | -56.313 | 42.287 | 1.00 | 32.09 | C |
| ATOM | 11881 | CD | GLU | D | 154 | -18.984 | -57.063 | 43.387 | 1.00 | 31.57 | C |
| ATOM | 11882 | OE1 | GLU | D | 154 | -18.518 | -56.458 | 44.358 | 1.00 | 29.03 | O |
| ATOM | 11883 | OE2 | GLU | D | 154 | -18.856 | -58.300 | 43.279 | 1.00 | 35.08 | O |
| ATOM | 11884 | C | GLU | D | 154 | -19.317 | -53.779 | 40.515 | 1.00 | 32.16 | C |
| ATOM | 11885 | O | GLU | D | 154 | -19.078 | -54.510 | 39.565 | 1.00 | 33.55 | O |
| ATOM | 11887 | N | MET | D | 155 | -18.585 | -52.730 | 40.846 | 1.00 | 30.95 | N |
| ATOM | 11888 | CA | MET | D | 155 | -17.350 | -52.436 | 40.183 | 1.00 | 31.44 | C |
| ATOM | 11890 | CB | MET | D | 155 | -17.578 | -51.383 | 39.109 | 1.00 | 32.43 | C |
| ATOM | 11893 | CG | MET | D | 155 | -16.393 | -51.223 | 38.197 | 1.00 | 35.00 | C |
| ATOM | 11896 | SD | MET | D | 155 | -16.867 | -50.320 | 36.753 | 1.00 | 40.80 | S |
| ATOM | 11897 | CE | MET | D | 155 | -17.791 | -51.525 | 35.789 | 1.00 | 42.22 | C |
| ATOM | 11901 | C | MET | D | 155 | -16.342 | -51.935 | 41.195 | 1.00 | 29.60 | C |
| ATOM | 11902 | O | MET | D | 155 | -16.703 | -51.211 | 42.099 | 1.00 | 27.86 | O |

FIG.3-22

| | | | | | | | | | | | |
|---|---|---|---|---|---|---|---|---|---|---|---|
| ATOM | 11904 | N | ALA | D | 156 | -15.078 | -52.315 | 40.997 | 1.00 | 30.56 | N |
| ATOM | 11905 | CA | ALA | D | 156 | -13.969 | -51.891 | 41.826 | 1.00 | 29.48 | C |
| ATOM | 11907 | CB | ALA | D | 156 | -13.675 | -52.944 | 42.876 | 1.00 | 29.13 | C |
| ATOM | 11911 | C | ALA | D | 156 | -12.708 | -51.611 | 41.016 | 1.00 | 31.16 | C |
| ATOM | 11912 | O | ALA | D | 156 | -12.519 | -52.122 | 39.910 | 1.00 | 31.47 | O |
| ATOM | 11914 | N | THR | D | 157 | -11.839 | -50.796 | 41.617 | 1.00 | 31.56 | N |
| ATOM | 11915 | CA | THR | D | 157 | -10.532 | -50.468 | 41.045 | 1.00 | 33.49 | C |
| ATOM | 11917 | CB | THR | D | 157 | -9.737 | -49.560 | 41.981 | 1.00 | 32.23 | C |
| ATOM | 11919 | OG1 | THR | D | 157 | -10.409 | -48.315 | 42.028 | 1.00 | 30.99 | O |
| ATOM | 11921 | CG2 | THR | D | 157 | -8.301 | -49.306 | 41.483 | 1.00 | 32.10 | C |
| ATOM | 11925 | C | THR | D | 157 | -9.719 | -51.701 | 40.677 | 1.00 | 35.89 | C |
| ATOM | 11926 | O | THR | D | 157 | -9.507 | -52.605 | 41.490 | 1.00 | 36.07 | O |
| ATOM | 11928 | N | LYS | D | 158 | -9.316 | -51.728 | 39.414 | 1.00 | 38.94 | N |
| ATOM | 11929 | CA | LYS | D | 158 | -8.505 | -52.802 | 38.848 | 1.00 | 41.36 | C |
| ATOM | 11931 | CB | LYS | D | 158 | -7.070 | -52.708 | 39.414 | 1.00 | 41.62 | C |
| ATOM | 11934 | CG | LYS | D | 158 | -6.554 | -51.241 | 39.333 | 1.00 | 43.71 | C |
| ATOM | 11937 | CD | LYS | D | 158 | -5.045 | -50.999 | 39.535 | 1.00 | 46.85 | C |
| ATOM | 11940 | CE | LYS | D | 158 | -4.748 | -49.470 | 39.465 | 1.00 | 47.67 | C |
| ATOM | 11943 | NZ | LYS | D | 158 | -3.283 | -49.088 | 39.519 | 1.00 | 50.10 | N |
| ATOM | 11947 | C | LYS | D | 158 | -9.160 | -54.158 | 39.062 | 1.00 | 41.16 | C |
| ATOM | 11948 | O | LYS | D | 158 | -8.485 | -55.151 | 39.158 | 1.00 | 43.22 | O |
| ATOM | 11950 | N | ALA | D | 159 | -10.486 | -54.189 | 39.108 | 1.00 | 40.46 | N |
| ATOM | 11951 | CA | ALA | D | 159 | -11.268 | -55.416 | 39.361 | 1.00 | 40.58 | C |
| ATOM | 11953 | CB | ALA | D | 159 | -11.213 | -56.348 | 38.173 | 1.00 | 42.48 | C |
| ATOM | 11957 | C | ALA | D | 159 | -10.873 | -56.156 | 40.647 | 1.00 | 39.88 | C |
| ATOM | 11958 | O | ALA | D | 159 | -11.089 | -57.364 | 40.768 | 1.00 | 40.90 | O |
| ATOM | 11960 | N | ASP | D | 160 | -10.336 | -55.407 | 41.610 | 1.00 | 38.43 | N |
| ATOM | 11961 | CA | ASP | D | 160 | -9.890 | -55.944 | 42.873 | 1.00 | 37.41 | C |
| ATOM | 11963 | CB | ASP | D | 160 | -8.547 | -55.312 | 43.223 | 1.00 | 37.65 | C |
| ATOM | 11966 | CG | ASP | D | 160 | -8.065 | -55.705 | 44.585 | 1.00 | 38.77 | C |
| ATOM | 11967 | OD1 | ASP | D | 160 | -8.821 | -56.408 | 45.306 | 1.00 | 40.38 | O |
| ATOM | 11968 | OD2 | ASP | D | 160 | -6.931 | -55.309 | 44.931 | 1.00 | 41.04 | O |
| ATOM | 11969 | C | ASP | D | 160 | -10.955 | -55.596 | 43.902 | 1.00 | 35.17 | C |
| ATOM | 11970 | O | ASP | D | 160 | -11.085 | -54.445 | 44.328 | 1.00 | 34.28 | O |
| ATOM | 11972 | N | TYR | D | 161 | -11.730 | -56.592 | 44.302 | 1.00 | 35.04 | N |
| ATOM | 11973 | CA | TYR | D | 161 | -12.921 | -56.359 | 45.111 | 1.00 | 32.90 | C |
| ATOM | 11975 | CB | TYR | D | 161 | -14.026 | -57.334 | 44.746 | 1.00 | 33.82 | C |
| ATOM | 11978 | CG | TYR | D | 161 | -14.434 | -57.273 | 43.317 | 1.00 | 33.31 | C |
| ATOM | 11979 | CD1 | TYR | D | 161 | -15.229 | -56.236 | 42.853 | 1.00 | 31.18 | C |
| ATOM | 11981 | CE1 | TYR | D | 161 | -15.625 | -56.178 | 41.540 | 1.00 | 32.44 | C |
| ATOM | 11983 | CZ | TYR | D | 161 | -15.229 | -57.176 | 40.677 | 1.00 | 33.70 | C |
| ATOM | 11984 | OH | TYR | D | 161 | -15.612 | -57.130 | 39.382 | 1.00 | 35.47 | O |
| ATOM | 11986 | CE2 | TYR | D | 161 | -14.455 | -58.224 | 41.112 | 1.00 | 34.45 | C |
| ATOM | 11988 | CD2 | TYR | D | 161 | -14.057 | -58.266 | 42.432 | 1.00 | 34.07 | C |
| ATOM | 11990 | C | TYR | D | 161 | -12.662 | -56.503 | 46.566 | 1.00 | 31.85 | C |
| ATOM | 11991 | O | TYR | D | 161 | -13.606 | -56.565 | 47.346 | 1.00 | 30.83 | O |
| ATOM | 11993 | N | THR | D | 162 | -11.390 | -56.591 | 46.933 | 1.00 | 32.70 | N |
| ATOM | 11994 | CA | THR | D | 162 | -10.966 | -56.531 | 48.344 | 1.00 | 32.03 | C |
| ATOM | 11996 | CB | THR | D | 162 | -11.282 | -55.156 | 49.000 | 1.00 | 29.88 | C |
| ATOM | 11998 | OG1 | THR | D | 162 | -10.363 | -54.165 | 48.511 | 1.00 | 28.97 | O |
| ATOM | 12000 | CG2 | THR | D | 162 | -11.161 | -55.228 | 50.511 | 1.00 | 29.13 | C |
| ATOM | 12004 | C | THR | D | 162 | -11.586 | -57.653 | 49.151 | 1.00 | 32.99 | C |
| ATOM | 12005 | O | THR | D | 162 | -10.868 | -58.530 | 49.620 | 1.00 | 34.69 | O |
| ATOM | 12007 | N | LEU | D | 163 | -12.905 | -57.629 | 49.327 | 1.00 | 32.51 | N |
| ATOM | 12008 | CA | LEU | D | 163 | -13.568 | -58.687 | 50.077 | 1.00 | 33.68 | C |
| ATOM | 12010 | CB | LEU | D | 163 | -14.964 | -58.261 | 50.535 | 1.00 | 32.44 | C |
| ATOM | 12013 | CG | LEU | D | 163 | -15.030 | -57.082 | 51.492 | 1.00 | 30.24 | C |
| ATOM | 12015 | CD1 | LEU | D | 163 | -16.449 | -56.801 | 51.991 | 1.00 | 25.53 | C |
| ATOM | 12019 | CD2 | LEU | D | 163 | -14.106 | -57.371 | 52.667 | 1.00 | 31.84 | C |
| ATOM | 12023 | C | LEU | D | 163 | -13.672 | -60.008 | 49.301 | 1.00 | 36.23 | C |
| ATOM | 12024 | O | LEU | D | 163 | -13.398 | -60.094 | 48.098 | 1.00 | 36.84 | O |
| ATOM | 12026 | N | ASP | D | 164 | -14.059 | -61.038 | 50.041 | 1.00 | 37.83 | N |
| ATOM | 12027 | CA | ASP | D | 164 | -14.443 | -62.316 | 49.471 | 1.00 | 40.28 | C |

FIG.3-23

| | | | | | | | | | | | |
|---|---|---|---|---|---|---|---|---|---|---|---|
| ATOM | 12029 | CB | ASP | D | 164 | -14.249 | -63.472 | 50.467 | 1.00 | 42.34 | C |
| ATOM | 12032 | CG | ASP | D | 164 | -14.901 | -63.212 | 51.811 | 1.00 | 42.62 | C |
| ATOM | 12033 | OD1 | ASP | D | 164 | -15.120 | -62.040 | 52.192 | 1.00 | 44.72 | O |
| ATOM | 12034 | OD2 | ASP | D | 164 | -15.165 | -64.194 | 52.509 | 1.00 | 46.90 | O |
| ATOM | 12035 | C | ASP | D | 164 | -15.885 | -62.221 | 49.044 | 1.00 | 39.83 | C |
| ATOM | 12036 | O | ASP | D | 164 | -16.593 | -61.273 | 49.416 | 1.00 | 38.82 | O |
| ATOM | 12038 | N | GLU | D | 165 | -16.311 | -63.212 | 48.263 | 1.00 | 41.32 | N |
| ATOM | 12039 | CA | GLU | D | 165 | -17.567 | -63.140 | 47.544 | 1.00 | 40.77 | C |
| ATOM | 12041 | CB | GLU | D | 165 | -17.654 | -64.257 | 46.506 | 1.00 | 43.41 | C |
| ATOM | 12044 | CG | GLU | D | 165 | -18.683 | -64.001 | 45.418 | 1.00 | 44.17 | C |
| ATOM | 12047 | CD | GLU | D | 165 | -18.903 | -65.185 | 44.510 | 1.00 | 46.19 | C |
| ATOM | 12048 | OE1 | GLU | D | 165 | -19.776 | -65.094 | 43.633 | 1.00 | 47.41 | O |
| ATOM | 12049 | OE2 | GLU | D | 165 | -18.216 | -66.204 | 44.670 | 1.00 | 48.74 | O |
| ATOM | 12050 | C | GLU | D | 165 | -18.747 | -63.177 | 48.495 | 1.00 | 40.26 | C |
| ATOM | 12051 | O | GLU | D | 165 | -19.741 | -62.489 | 48.270 | 1.00 | 39.60 | O |
| ATOM | 12053 | N | GLU | D | 166 | -18.653 | -63.942 | 49.573 | 1.00 | 40.83 | N |
| ATOM | 12054 | CA | GLU | D | 166 | -19.790 | -64.022 | 50.485 | 1.00 | 40.94 | C |
| ATOM | 12056 | CB | GLU | D | 166 | -19.599 | -65.125 | 51.529 | 1.00 | 43.13 | C |
| ATOM | 12059 | CG | GLU | D | 166 | -20.791 | -65.319 | 52.506 | 1.00 | 45.95 | C |
| ATOM | 12062 | CD | GLU | D | 166 | -22.078 | -65.877 | 51.858 | 1.00 | 50.29 | C |
| ATOM | 12063 | OE1 | GLU | D | 166 | -22.171 | -66.009 | 50.606 | 1.00 | 50.97 | O |
| ATOM | 12064 | OE2 | GLU | D | 166 | -23.010 | -66.205 | 52.626 | 1.00 | 51.77 | O |
| ATOM | 12065 | C | GLU | D | 166 | -20.091 | -62.675 | 51.140 | 1.00 | 37.79 | C |
| ATOM | 12066 | O | GLU | D | 166 | -21.250 | -62.254 | 51.215 | 1.00 | 37.49 | O |
| ATOM | 12068 | N | SER | D | 167 | -19.056 | -61.985 | 51.593 | 1.00 | 35.47 | N |
| ATOM | 12069 | CA | SER | D | 167 | -19.264 | -60.717 | 52.288 | 1.00 | 32.81 | C |
| ATOM | 12071 | CB | SER | D | 167 | -17.928 | -60.183 | 52.787 | 1.00 | 31.40 | C |
| ATOM | 12074 | OG | SER | D | 167 | -17.219 | -61.233 | 53.390 | 1.00 | 33.27 | O |
| ATOM | 12076 | C | SER | D | 167 | -19.944 | -59.713 | 51.359 | 1.00 | 30.85 | C |
| ATOM | 12077 | O | SER | D | 167 | -20.846 | -58.998 | 51.746 | 1.00 | 29.35 | O |
| ATOM | 12079 | N | ARG | D | 168 | -19.489 | -59.702 | 50.121 | 1.00 | 30.86 | N |
| ATOM | 12080 | CA | ARG | D | 168 | -20.066 | -58.886 | 49.062 | 1.00 | 30.41 | C |
| ATOM | 12082 | CB | ARG | D | 168 | -19.164 | -58.963 | 47.825 | 1.00 | 31.30 | C |
| ATOM | 12085 | CG | ARG | D | 168 | -17.836 | -58.296 | 48.081 | 1.00 | 32.31 | C |
| ATOM | 12088 | CD | ARG | D | 168 | -17.017 | -58.318 | 46.847 | 1.00 | 35.25 | C |
| ATOM | 12091 | NE | ARG | D | 168 | -16.365 | -59.603 | 46.702 | 1.00 | 37.68 | N |
| ATOM | 12093 | CZ | ARG | D | 168 | -16.173 | -60.231 | 45.554 | 1.00 | 39.01 | C |
| ATOM | 12094 | NH1 | ARG | D | 168 | -16.605 | -59.722 | 44.405 | 1.00 | 39.11 | N |
| ATOM | 12097 | NH2 | ARG | D | 168 | -15.549 | -61.387 | 45.571 | 1.00 | 40.93 | N |
| ATOM | 12100 | C | ARG | D | 168 | -21.453 | -59.339 | 48.669 | 1.00 | 30.59 | C |
| ATOM | 12101 | O | ARG | D | 168 | -22.302 | -58.531 | 48.329 | 1.00 | 29.77 | O |
| ATOM | 12103 | N | ALA | D | 169 | -21.663 | -60.645 | 48.676 | 1.00 | 31.96 | N |
| ATOM | 12104 | CA | ALA | D | 169 | -22.969 | -61.179 | 48.373 | 1.00 | 33.14 | C |
| ATOM | 12106 | CB | ALA | D | 169 | -22.915 | -62.688 | 48.264 | 1.00 | 35.23 | C |
| ATOM | 12110 | C | ALA | D | 169 | -23.929 | -60.724 | 49.466 | 1.00 | 32.14 | C |
| ATOM | 12111 | O | ALA | D | 169 | -25.034 | -60.291 | 49.188 | 1.00 | 31.42 | O |
| ATOM | 12113 | N | ARG | D | 170 | -23.459 | -60.826 | 50.707 | 1.00 | 32.02 | N |
| ATOM | 12114 | CA | ARG | D | 170 | -24.132 | -60.280 | 51.876 | 1.00 | 31.46 | C |
| ATOM | 12116 | CB | ARG | D | 170 | -23.161 | -60.383 | 53.070 | 1.00 | 31.70 | C |
| ATOM | 12119 | CG | ARG | D | 170 | -23.797 | -60.563 | 54.447 | 1.00 | 35.80 | C |
| ATOM | 12122 | CD | ARG | D | 170 | -22.767 | -60.868 | 55.577 | 1.00 | 40.47 | C |
| ATOM | 12125 | NE | ARG | D | 170 | -23.113 | -60.108 | 56.800 | 1.00 | 43.77 | N |
| ATOM | 12127 | CZ | ARG | D | 170 | -22.692 | -58.866 | 57.092 | 1.00 | 43.38 | C |
| ATOM | 12128 | NH1 | ARG | D | 170 | -21.856 | -58.206 | 56.291 | 1.00 | 42.86 | N |
| ATOM | 12131 | NH2 | ARG | D | 170 | -23.111 | -58.266 | 58.208 | 1.00 | 43.95 | N |
| ATOM | 12134 | C | ARG | D | 170 | -24.631 | -58.816 | 51.617 | 1.00 | 29.01 | C |
| ATOM | 12135 | O | ARG | D | 170 | -25.827 | -58.536 | 51.758 | 1.00 | 28.41 | O |
| ATOM | 12137 | N | ILE | D | 171 | -23.720 | -57.919 | 51.195 | 1.00 | 26.61 | N |
| ATOM | 12138 | CA | ILE | D | 171 | -24.065 | -56.524 | 50.845 | 1.00 | 24.48 | C |
| ATOM | 12140 | CB | ILE | D | 171 | -22.804 | -55.702 | 50.470 | 1.00 | 23.29 | C |
| ATOM | 12142 | CG1 | ILE | D | 171 | -21.945 | -55.422 | 51.718 | 1.00 | 22.42 | C |
| ATOM | 12145 | CD1 | ILE | D | 171 | -20.487 | -55.094 | 51.434 | 1.00 | 20.75 | C |
| ATOM | 12149 | CG2 | ILE | D | 171 | -23.196 | -54.388 | 49.761 | 1.00 | 19.72 | C |

FIG.3-24

| | | | | | | | | | | | |
|---|---|---|---|---|---|---|---|---|---|---|---|
| ATOM | 12153 | C | ILE | D | 171 | -25.014 | -56.426 | 49.658 | 1.00 | 25.42 | C |
| ATOM | 12154 | O | ILE | D | 171 | -25.955 | -55.624 | 49.676 | 1.00 | 24.89 | O |
| ATOM | 12156 | N | LYS | D | 172 | -24.750 | -57.210 | 48.608 | 1.00 | 26.05 | N |
| ATOM | 12157 | CA | LYS | D | 172 | -25.603 | -57.169 | 47.405 | 1.00 | 26.90 | C |
| ATOM | 12159 | CB | LYS | D | 172 | -25.069 | -58.090 | 46.321 | 1.00 | 27.55 | C |
| ATOM | 12162 | CG | LYS | D | 172 | -23.887 | -57.524 | 45.619 | 1.00 | 25.13 | C |
| ATOM | 12165 | CD | LYS | D | 172 | -23.084 | -58.574 | 44.968 | 1.00 | 24.07 | C |
| ATOM | 12168 | CE | LYS | D | 172 | -21.815 | -58.049 | 44.332 | 1.00 | 21.74 | C |
| ATOM | 12171 | NZ | LYS | D | 172 | -20.948 | -59.188 | 43.839 | 1.00 | 23.23 | N |
| ATOM | 12175 | C | LYS | D | 172 | -27.062 | -57.514 | 47.702 | 1.00 | 28.33 | C |
| ATOM | 12176 | O | LYS | D | 172 | -27.975 | -56.849 | 47.220 | 1.00 | 28.52 | O |
| ATOM | 12178 | N | THR | D | 173 | -27.257 | -58.552 | 48.496 | 1.00 | 29.69 | N |
| ATOM | 12179 | CA | THR | D | 173 | -28.576 | -58.968 | 48.956 | 1.00 | 31.84 | C |
| ATOM | 12181 | CB | THR | D | 173 | -28.464 | -60.226 | 49.823 | 1.00 | 33.15 | C |
| ATOM | 12183 | OG1 | THR | D | 173 | -27.880 | -61.258 | 49.032 | 1.00 | 34.28 | O |
| ATOM | 12185 | CG2 | THR | D | 173 | -29.843 | -60.669 | 50.345 | 1.00 | 33.68 | C |
| ATOM | 12189 | C | THR | D | 173 | -29.289 | -57.907 | 49.782 | 1.00 | 31.15 | C |
| ATOM | 12190 | O | THR | D | 173 | -30.498 | -57.705 | 49.654 | 1.00 | 32.04 | O |
| ATOM | 12192 | N | ARG | D | 174 | -28.544 | -57.256 | 50.649 | 1.00 | 30.04 | N |
| ATOM | 12193 | CA | ARG | D | 174 | -29.115 | -56.194 | 51.437 | 1.00 | 30.11 | C |
| ATOM | 12195 | CB | ARG | D | 174 | -28.042 | -55.625 | 52.370 | 1.00 | 28.34 | C |
| ATOM | 12198 | CG | ARG | D | 174 | -28.506 | -54.573 | 53.312 | 1.00 | 29.41 | C |
| ATOM | 12201 | CD | ARG | D | 174 | -29.703 | -55.049 | 54.057 | 1.00 | 35.70 | C |
| ATOM | 12204 | NE | ARG | D | 174 | -29.949 | -54.288 | 55.282 | 1.00 | 40.26 | N |
| ATOM | 12206 | CZ | ARG | D | 174 | -31.112 | -53.730 | 55.618 | 1.00 | 44.12 | C |
| ATOM | 12207 | NH1 | ARG | D | 174 | -32.169 | -53.849 | 54.822 | 1.00 | 48.17 | N |
| ATOM | 12210 | NH2 | ARG | D | 174 | -31.235 | -53.063 | 56.766 | 1.00 | 43.20 | N |
| ATOM | 12213 | C | ARG | D | 174 | -29.722 | -55.115 | 50.507 | 1.00 | 30.42 | C |
| ATOM | 12214 | O | ARG | D | 174 | -30.853 | -54.703 | 50.709 | 1.00 | 31.19 | O |
| ATOM | 12216 | N | LEU | D | 175 | -28.992 | -54.687 | 49.472 | 1.00 | 30.45 | N |
| ATOM | 12217 | CA | LEU | D | 175 | -29.503 | -53.639 | 48.567 | 1.00 | 31.20 | C |
| ATOM | 12219 | CB | LEU | D | 175 | -28.390 | -53.039 | 47.693 | 1.00 | 29.88 | C |
| ATOM | 12222 | CG | LEU | D | 175 | -27.208 | -52.478 | 48.499 | 1.00 | 27.58 | C |
| ATOM | 12224 | CD1 | LEU | D | 175 | -25.939 | -52.327 | 47.659 | 1.00 | 26.06 | C |
| ATOM | 12228 | CD2 | LEU | D | 175 | -27.591 | -51.180 | 49.173 | 1.00 | 23.45 | C |
| ATOM | 12232 | C | LEU | D | 175 | -30.640 | -54.205 | 47.715 | 1.00 | 34.22 | C |
| ATOM | 12233 | O | LEU | D | 175 | -31.663 | -53.547 | 47.485 | 1.00 | 34.49 | O |
| ATOM | 12235 | N | PHE | D | 176 | -30.458 | -55.450 | 47.301 | 1.00 | 36.30 | N |
| ATOM | 12236 | CA | PHE | D | 176 | -31.491 | -56.191 | 46.646 | 1.00 | 39.61 | C |
| ATOM | 12238 | CB | PHE | D | 176 | -31.066 | -57.664 | 46.476 | 1.00 | 41.55 | C |
| ATOM | 12241 | CG | PHE | D | 176 | -31.824 | -58.402 | 45.399 | 1.00 | 44.53 | C |
| ATOM | 12242 | CD1 | PHE | D | 176 | -31.396 | -58.351 | 44.082 | 1.00 | 46.61 | C |
| ATOM | 12244 | CE1 | PHE | D | 176 | -32.089 | -59.032 | 43.068 | 1.00 | 49.41 | C |
| ATOM | 12246 | CZ | PHE | D | 176 | -33.222 | -59.778 | 43.387 | 1.00 | 51.85 | C |
| ATOM | 12248 | CE2 | PHE | D | 176 | -33.662 | -59.831 | 44.716 | 1.00 | 50.56 | C |
| ATOM | 12250 | CD2 | PHE | D | 176 | -32.956 | -59.143 | 45.709 | 1.00 | 47.43 | C |
| ATOM | 12252 | C | PHE | D | 176 | -32.765 | -56.063 | 47.470 | 1.00 | 40.89 | C |
| ATOM | 12253 | O | PHE | D | 176 | -33.791 | -55.556 | 46.972 | 1.00 | 42.53 | O |
| ATOM | 12255 | N | THR | D | 177 | -32.691 | -56.486 | 48.734 | 1.00 | 40.51 | N |
| ATOM | 12256 | CA | THR | D | 177 | -33.829 | -56.398 | 49.651 | 1.00 | 40.93 | C |
| ATOM | 12258 | CB | THR | D | 177 | -33.437 | -56.873 | 51.089 | 1.00 | 40.82 | C |
| ATOM | 12260 | OG1 | THR | D | 177 | -33.513 | -58.302 | 51.144 | 1.00 | 43.04 | O |
| ATOM | 12262 | CG2 | THR | D | 177 | -34.361 | -56.310 | 52.154 | 1.00 | 41.08 | C |
| ATOM | 12266 | C | THR | D | 177 | -34.415 | -54.985 | 49.687 | 1.00 | 39.49 | C |
| ATOM | 12267 | O | THR | D | 177 | -35.598 | -54.814 | 49.442 | 1.00 | 41.04 | O |
| ATOM | 12269 | N | ILE | D | 178 | -33.591 | -53.977 | 49.964 | 1.00 | 36.71 | N |
| ATOM | 12270 | CA | ILE | D | 178 | -34.092 | -52.598 | 50.165 | 1.00 | 35.43 | C |
| ATOM | 12272 | CB | ILE | D | 178 | -32.947 | -51.593 | 50.459 | 1.00 | 32.62 | C |
| ATOM | 12274 | CG1 | ILE | D | 178 | -32.364 | -51.798 | 51.861 | 1.00 | 31.58 | C |
| ATOM | 12277 | CD1 | ILE | D | 178 | -30.876 | -51.395 | 52.009 | 1.00 | 27.36 | C |
| ATOM | 12281 | CG2 | ILE | D | 178 | -33.426 | -50.201 | 50.367 | 1.00 | 31.39 | C |
| ATOM | 12285 | C | ILE | D | 178 | -34.928 | -52.103 | 48.978 | 1.00 | 37.06 | C |
| ATOM | 12286 | O | ILE | D | 178 | -35.981 | -51.521 | 49.163 | 1.00 | 38.29 | O |

FIG.3-25

| | | | | | | | | | | | |
|---|---|---|---|---|---|---|---|---|---|---|---|
| ATOM | 12288 | N | ARG | D | 179 | -34.465 | -52.362 | 47.764 | 1.00 | 37.72 | N |
| ATOM | 12289 | CA | ARG | D | 179 | -35.134 | -51.888 | 46.552 | 1.00 | 39.49 | C |
| ATOM | 12291 | CB | ARG | D | 179 | -34.224 | -52.137 | 45.326 | 1.00 | 39.85 | C |
| ATOM | 12294 | CG | ARG | D | 179 | -34.933 | -52.378 | 43.996 | 1.00 | 43.52 | C |
| ATOM | 12297 | CD | ARG | D | 179 | -33.963 | -52.193 | 42.820 | 1.00 | 46.15 | C |
| ATOM | 12300 | NE | ARG | D | 179 | -34.013 | -53.225 | 41.789 | 1.00 | 48.57 | N |
| ATOM | 12302 | CZ | ARG | D | 179 | -35.036 | -53.443 | 40.964 | 1.00 | 53.40 | C |
| ATOM | 12303 | NH1 | ARG | D | 179 | -36.163 | -52.737 | 41.050 | 1.00 | 54.73 | N |
| ATOM | 12306 | NH2 | ARG | D | 179 | -34.940 | -54.399 | 40.047 | 1.00 | 55.92 | N |
| ATOM | 12309 | C | ARG | D | 179 | -36.472 | -52.582 | 46.357 | 1.00 | 41.99 | C |
| ATOM | 12310 | O | ARG | D | 179 | -37.454 | -51.963 | 45.953 | 1.00 | 43.26 | O |
| ATOM | 12312 | N | GLN | D | 180 | -36.486 | -53.886 | 46.615 | 1.00 | 42.75 | N |
| ATOM | 12313 | CA | GLN | D | 180 | -37.699 | -54.661 | 46.512 | 1.00 | 45.40 | C |
| ATOM | 12315 | CB | GLN | D | 180 | -37.391 | -56.167 | 46.567 | 1.00 | 46.64 | C |
| ATOM | 12318 | CG | GLN | D | 180 | -36.582 | -56.600 | 45.324 | 1.00 | 48.36 | C |
| ATOM | 12321 | CD | GLN | D | 180 | -36.702 | -58.061 | 44.959 | 1.00 | 51.64 | C |
| ATOM | 12322 | OE1 | GLN | D | 180 | -36.816 | -58.917 | 45.830 | 1.00 | 54.29 | O |
| ATOM | 12323 | NE2 | GLN | D | 180 | -36.638 | -58.357 | 43.658 | 1.00 | 52.43 | N |
| ATOM | 12326 | C | GLN | D | 180 | -38.722 | -54.231 | 47.551 | 1.00 | 45.54 | C |
| ATOM | 12327 | O | GLN | D | 180 | -39.897 | -54.173 | 47.248 | 1.00 | 47.32 | O |
| ATOM | 12329 | N | GLU | D | 181 | -38.281 | -53.890 | 48.751 | 1.00 | 44.02 | N |
| ATOM | 12330 | CA | GLU | D | 181 | -39.214 | -53.434 | 49.762 | 1.00 | 45.40 | C |
| ATOM | 12332 | CB | GLU | D | 181 | -38.611 | -53.525 | 51.167 | 1.00 | 44.53 | C |
| ATOM | 12335 | CG | GLU | D | 181 | -38.563 | -54.951 | 51.731 | 1.00 | 47.63 | C |
| ATOM | 12338 | CD | GLU | D | 181 | -39.835 | -55.755 | 51.459 | 1.00 | 53.66 | C |
| ATOM | 12339 | OE1 | GLU | D | 181 | -40.837 | -55.553 | 52.194 | 1.00 | 57.27 | O |
| ATOM | 12340 | OE2 | GLU | D | 181 | -39.835 | -56.577 | 50.504 | 1.00 | 56.33 | O |
| ATOM | 12341 | C | GLU | D | 181 | -39.727 | -52.029 | 49.464 | 1.00 | 44.92 | C |
| ATOM | 12342 | O | GLU | D | 181 | -40.911 | -51.768 | 49.636 | 1.00 | 46.40 | O |
| ATOM | 12344 | N | MET | D | 182 | -38.847 | -51.147 | 49.001 | 1.00 | 43.02 | N |
| ATOM | 12345 | CA | MET | D | 182 | -39.246 | -49.807 | 48.527 | 1.00 | 43.23 | C |
| ATOM | 12347 | CB | MET | D | 182 | -38.039 | -48.995 | 48.052 | 1.00 | 41.07 | C |
| ATOM | 12350 | CG | MET | D | 182 | -37.247 | -48.310 | 49.111 | 1.00 | 38.22 | C |
| ATOM | 12353 | SD | MET | D | 182 | -35.864 | -47.434 | 48.358 | 1.00 | 37.92 | S |
| ATOM | 12354 | CE | MET | D | 182 | -35.329 | -46.346 | 49.672 | 1.00 | 39.82 | C |
| ATOM | 12358 | C | MET | D | 182 | -40.222 | -49.913 | 47.360 | 1.00 | 46.23 | C |
| ATOM | 12359 | O | MET | D | 182 | -41.181 | -49.138 | 47.281 | 1.00 | 47.86 | O |
| ATOM | 12361 | N | ALA | D | 183 | -39.959 | -50.850 | 46.447 | 1.00 | 46.98 | N |
| ATOM | 12362 | CA | ALA | D | 183 | -40.876 | -51.133 | 45.364 | 1.00 | 50.19 | C |
| ATOM | 12364 | CB | ALA | D | 183 | -40.294 | -52.210 | 44.447 | 1.00 | 50.69 | C |
| ATOM | 12368 | C | ALA | D | 183 | -42.259 | -51.556 | 45.914 | 1.00 | 52.99 | C |
| ATOM | 12369 | O | ALA | D | 183 | -43.299 | -51.073 | 45.450 | 1.00 | 55.13 | O |
| ATOM | 12371 | N | SER | D | 184 | -42.262 | -52.416 | 46.933 | 1.00 | 52.96 | N |
| ATOM | 12372 | CA | SER | D | 184 | -43.499 | -52.938 | 47.521 | 1.00 | 55.63 | C |
| ATOM | 12374 | CB | SER | D | 184 | -43.193 | -54.013 | 48.584 | 1.00 | 55.48 | C |
| ATOM | 12377 | OG | SER | D | 184 | -42.547 | -55.152 | 48.004 | 1.00 | 56.61 | O |
| ATOM | 12379 | C | SER | D | 184 | -44.380 | -51.846 | 48.119 | 1.00 | 55.96 | C |
| ATOM | 12380 | O | SER | D | 184 | -45.520 | -52.095 | 48.476 | 1.00 | 58.00 | O |
| ATOM | 12382 | N | ARG | D | 185 | -43.839 | -50.638 | 48.238 | 1.00 | 54.34 | N |
| ATOM | 12383 | CA | ARG | D | 185 | -44.605 | -49.485 | 48.690 | 1.00 | 54.82 | C |
| ATOM | 12385 | CB | ARG | D | 185 | -44.085 | -49.027 | 50.032 | 1.00 | 53.02 | C |
| ATOM | 12388 | CG | ARG | D | 185 | -44.408 | -49.994 | 51.138 | 1.00 | 56.42 | C |
| ATOM | 12391 | CD | ARG | D | 185 | -43.287 | -50.982 | 51.402 | 1.00 | 57.87 | C |
| ATOM | 12394 | NE | ARG | D | 185 | -43.227 | -51.331 | 52.818 | 1.00 | 61.18 | N |
| ATOM | 12396 | CZ | ARG | D | 185 | -42.389 | -52.213 | 53.364 | 1.00 | 62.75 | C |
| ATOM | 12397 | NH1 | ARG | D | 185 | -41.510 | -52.894 | 52.611 | 1.00 | 61.78 | N |
| ATOM | 12400 | NH2 | ARG | D | 185 | -42.442 | -52.414 | 54.687 | 1.00 | 63.46 | N |
| ATOM | 12403 | C | ARG | D | 185 | -44.523 | -48.342 | 47.717 | 1.00 | 54.23 | C |
| ATOM | 12404 | O | ARG | D | 185 | -44.808 | -47.210 | 48.079 | 1.00 | 53.61 | O |
| ATOM | 12406 | N | SER | D | 186 | -44.142 | -48.650 | 46.479 | 1.00 | 54.48 | N |
| ATOM | 12407 | CA | SER | D | 186 | -43.914 | -47.647 | 45.437 | 1.00 | 54.60 | C |
| ATOM | 12409 | CB | SER | D | 186 | -45.242 | -47.355 | 44.712 | 1.00 | 58.29 | C |
| ATOM | 12412 | OG | SER | D | 186 | -46.327 | -47.327 | 45.620 | 1.00 | 59.32 | O |

FIG.3-26

| | | | | | | | | | | | |
|---|---|---|---|---|---|---|---|---|---|---|---|
| ATOM | 12414 | C | SER | D | 186 | -43.221 | -46.354 | 45.933 | 1.00 | 52.16 | C |
| ATOM | 12415 | O | SER | D | 186 | -43.622 | -45.242 | 45.592 | 1.00 | 52.94 | O |
| ATOM | 12417 | N | LEU | D | 187 | -42.183 | -46.516 | 46.745 | 1.00 | 49.04 | N |
| ATOM | 12418 | CA | LEU | D | 187 | -41.310 | -45.408 | 47.108 | 1.00 | 47.26 | C |
| ATOM | 12420 | CB | LEU | D | 187 | -40.807 | -45.581 | 48.556 | 1.00 | 45.01 | C |
| ATOM | 12423 | CG | LEU | D | 187 | -41.824 | -45.524 | 49.702 | 1.00 | 44.89 | C |
| ATOM | 12425 | CD1 | LEU | D | 187 | -41.312 | -46.318 | 50.907 | 1.00 | 41.69 | C |
| ATOM | 12429 | CD2 | LEU | D | 187 | -42.142 | -44.076 | 50.072 | 1.00 | 43.58 | C |
| ATOM | 12433 | C | LEU | D | 187 | -40.098 | -45.340 | 46.148 | 1.00 | 46.50 | C |
| ATOM | 12434 | O | LEU | D | 187 | -39.372 | -44.318 | 46.097 | 1.00 | 45.52 | O |
| ATOM | 12436 | N | TRP | D | 188 | -39.895 | -46.429 | 45.403 | 1.00 | 46.79 | N |
| ATOM | 12437 | CA | TRP | D | 188 | -38.670 | -46.662 | 44.648 | 1.00 | 46.35 | C |
| ATOM | 12439 | CB | TRP | D | 188 | -38.595 | -48.134 | 44.219 | 1.00 | 46.60 | C |
| ATOM | 12442 | CG | TRP | D | 188 | -37.524 | -48.411 | 43.236 | 1.00 | 44.64 | C |
| ATOM | 12443 | CD1 | TRP | D | 188 | -37.670 | -48.633 | 41.909 | 1.00 | 45.46 | C |
| ATOM | 12445 | NE1 | TRP | D | 188 | -36.449 | -48.864 | 41.319 | 1.00 | 43.84 | N |
| ATOM | 12447 | CE2 | TRP | D | 188 | -35.477 | -48.781 | 42.279 | 1.00 | 43.71 | C |
| ATOM | 12448 | CD2 | TRP | D | 188 | -36.125 | -48.484 | 43.505 | 1.00 | 43.13 | C |
| ATOM | 12449 | CE3 | TRP | D | 188 | -35.352 | -48.352 | 44.664 | 1.00 | 38.00 | C |
| ATOM | 12451 | CZ3 | TRP | D | 188 | -33.974 | -48.502 | 44.564 | 1.00 | 38.57 | C |
| ATOM | 12453 | CH2 | TRP | D | 188 | -33.347 | -48.788 | 43.328 | 1.00 | 37.48 | C |
| ATOM | 12455 | CZ2 | TRP | D | 188 | -34.076 | -48.921 | 42.178 | 1.00 | 41.08 | C |
| ATOM | 12457 | C | TRP | D | 188 | -38.505 | -45.769 | 43.411 | 1.00 | 48.51 | C |
| ATOM | 12458 | O | TRP | D | 188 | -37.491 | -45.093 | 43.241 | 1.00 | 47.29 | O |
| ATOM | 12460 | N | ASP | D | 189 | -39.491 | -45.785 | 42.530 | 1.00 | 52.50 | N |
| ATOM | 12461 | CA | ASP | D | 189 | -39.354 | -45.062 | 41.291 | 1.00 | 55.01 | C |
| ATOM | 12463 | CB | ASP | D | 189 | -40.665 | -45.133 | 40.491 | 1.00 | 58.57 | C |
| ATOM | 12466 | CG | ASP | D | 189 | -40.778 | -46.429 | 39.657 | 1.00 | 61.60 | C |
| ATOM | 12467 | OD1 | ASP | D | 189 | -41.897 | -46.992 | 39.549 | 1.00 | 64.37 | O |
| ATOM | 12468 | OD2 | ASP | D | 189 | -39.744 | -46.885 | 39.099 | 1.00 | 62.98 | O |
| ATOM | 12469 | C | ASP | D | 189 | -38.828 | -43.629 | 41.558 | 1.00 | 54.43 | C |
| ATOM | 12470 | O | ASP | D | 189 | -37.881 | -43.184 | 40.912 | 1.00 | 54.40 | O |
| ATOM | 12472 | N | SER | D | 190 | -39.388 | -42.954 | 42.557 | 1.00 | 54.60 | N |
| ATOM | 12473 | CA | SER | D | 190 | -38.973 | -41.596 | 42.941 | 1.00 | 54.39 | C |
| ATOM | 12475 | CB | SER | D | 190 | -39.994 | -41.040 | 43.952 | 1.00 | 54.76 | C |
| ATOM | 12478 | OG | SER | D | 190 | -39.508 | -39.894 | 44.627 | 1.00 | 54.38 | O |
| ATOM | 12480 | C | SER | D | 190 | -37.524 | -41.552 | 43.510 | 1.00 | 51.92 | C |
| ATOM | 12481 | O | SER | D | 190 | -36.734 | -40.639 | 43.207 | 1.00 | 51.62 | O |
| ATOM | 12483 | N | PHE | D | 191 | -37.204 | -42.541 | 44.341 | 1.00 | 50.22 | N |
| ATOM | 12484 | CA | PHE | D | 191 | -35.854 | -42.756 | 44.860 | 1.00 | 48.23 | C |
| ATOM | 12486 | CB | PHE | D | 191 | -35.847 | -44.033 | 45.717 | 1.00 | 46.68 | C |
| ATOM | 12489 | CG | PHE | D | 191 | -34.596 | -44.245 | 46.522 | 1.00 | 43.90 | C |
| ATOM | 12490 | CD1 | PHE | D | 191 | -34.231 | -43.357 | 47.530 | 1.00 | 43.04 | C |
| ATOM | 12492 | CE1 | PHE | D | 191 | -33.093 | -43.575 | 48.302 | 1.00 | 39.26 | C |
| ATOM | 12494 | CZ | PHE | D | 191 | -32.314 | -44.701 | 48.076 | 1.00 | 38.81 | C |
| ATOM | 12496 | CE2 | PHE | D | 191 | -32.664 | -45.597 | 47.081 | 1.00 | 40.47 | C |
| ATOM | 12498 | CD2 | PHE | D | 191 | -33.806 | -45.376 | 46.316 | 1.00 | 43.34 | C |
| ATOM | 12500 | C | PHE | D | 191 | -34.831 | -42.881 | 43.715 | 1.00 | 48.87 | C |
| ATOM | 12501 | O | PHE | D | 191 | -33.759 | -42.277 | 43.774 | 1.00 | 47.49 | O |
| ATOM | 12503 | N | ARG | D | 192 | -35.170 | -43.663 | 42.684 | 1.00 | 50.96 | N |
| ATOM | 12504 | CA | ARG | D | 192 | -34.286 | -43.844 | 41.533 | 1.00 | 51.76 | C |
| ATOM | 12506 | CB | ARG | D | 192 | -34.829 | -44.929 | 40.592 | 1.00 | 53.96 | C |
| ATOM | 12509 | CG | ARG | D | 192 | -34.006 | -45.207 | 39.298 | 1.00 | 55.98 | C |
| ATOM | 12512 | CD | ARG | D | 192 | -34.956 | -45.213 | 38.047 | 1.00 | 61.20 | C |
| ATOM | 12515 | NE | ARG | D | 192 | -34.263 | -45.335 | 36.761 | 1.00 | 63.86 | N |
| ATOM | 12517 | CZ | ARG | D | 192 | -34.812 | -45.098 | 35.566 | 1.00 | 68.34 | C |
| ATOM | 12518 | NH1 | ARG | D | 192 | -36.079 | -44.704 | 35.452 | 1.00 | 72.04 | N |
| ATOM | 12521 | NH2 | ARG | D | 192 | -34.085 | -45.246 | 34.463 | 1.00 | 69.34 | N |
| ATOM | 12524 | C | ARG | D | 192 | -34.138 | -42.515 | 40.817 | 1.00 | 52.89 | C |
| ATOM | 12525 | O | ARG | D | 192 | -33.030 | -42.076 | 40.537 | 1.00 | 51.34 | O |
| ATOM | 12527 | N | GLN | D | 193 | -35.259 | -41.854 | 40.561 | 1.00 | 55.49 | N |
| ATOM | 12528 | CA | GLN | D | 193 | -35.243 | -40.655 | 39.736 | 1.00 | 58.03 | C |
| ATOM | 12530 | CB | GLN | D | 193 | -36.667 | -40.178 | 39.419 | 1.00 | 60.99 | C |

FIG.3-27

| | | | | | | | | | | | |
|---|---|---|---|---|---|---|---|---|---|---|---|
| ATOM | 12533 | CG | GLN | D | 193 | -37.538 | -41.162 | 38.574 | 1.00 | 64.09 | C |
| ATOM | 12536 | CD | GLN | D | 193 | -36.980 | -41.497 | 37.178 | 1.00 | 67.02 | C |
| ATOM | 12537 | OE1 | GLN | D | 193 | -35.836 | -41.171 | 36.836 | 1.00 | 67.05 | O |
| ATOM | 12538 | NE2 | GLN | D | 193 | -37.804 | -42.162 | 36.368 | 1.00 | 70.31 | N |
| ATOM | 12541 | C | GLN | D | 193 | -34.431 | -39.508 | 40.329 | 1.00 | 57.02 | C |
| ATOM | 12542 | O | GLN | D | 193 | -34.048 | -38.602 | 39.593 | 1.00 | 59.00 | O |
| ATOM | 12544 | N | SER | D | 194 | -34.135 | -39.551 | 41.628 | 1.00 | 54.66 | N |
| ATOM | 12545 | CA | SER | D | 194 | -33.509 | -38.399 | 42.304 | 1.00 | 53.79 | C |
| ATOM | 12547 | CB | SER | D | 194 | -34.262 | -38.101 | 43.609 | 1.00 | 52.88 | C |
| ATOM | 12550 | OG | SER | D | 194 | -34.037 | -39.109 | 44.572 | 1.00 | 50.44 | O |
| ATOM | 12552 | C | SER | D | 194 | -31.981 | -38.449 | 42.575 | 1.00 | 51.71 | C |
| ATOM | 12553 | O | SER | D | 194 | -31.426 | -37.492 | 43.110 | 1.00 | 51.24 | O |
| ATOM | 12555 | N | GLU | D | 195 | -31.288 | -39.526 | 42.219 | 1.00 | 51.03 | N |
| ATOM | 12556 | CA | GLU | D | 195 | -29.820 | -39.502 | 42.293 | 1.00 | 49.61 | C |
| ATOM | 12558 | CB | GLU | D | 195 | -29.223 | -40.869 | 41.978 | 1.00 | 48.86 | C |
| ATOM | 12561 | CG | GLU | D | 195 | -27.737 | -40.968 | 42.412 | 1.00 | 47.74 | C |
| ATOM | 12564 | CD | GLU | D | 195 | -27.161 | -42.354 | 42.238 | 1.00 | 47.16 | C |
| ATOM | 12565 | OE1 | GLU | D | 195 | -27.716 | -43.298 | 42.831 | 1.00 | 46.61 | O |
| ATOM | 12566 | OE2 | GLU | D | 195 | -26.154 | -42.499 | 41.509 | 1.00 | 49.24 | O |
| ATOM | 12567 | C | GLU | D | 195 | -29.199 | -38.442 | 41.365 | 1.00 | 51.23 | C |
| ATOM | 12568 | O | GLU | D | 195 | -29.595 | -38.298 | 40.196 | 1.00 | 53.99 | O |
| ATOM | 12570 | MN | MN | D | 901 | -18.745 | -43.295 | 49.760 | 1.00 | 26.31 | MN |
| ATOM | 12571 | MN | MN | D | 902 | -17.803 | -40.957 | 52.434 | 1.00 | 34.52 | MN |
| ATOM | 12572 | CL | ci3 | D | 801 | -25.956 | -34.127 | 53.753 | 1.00 | 54.96 | CL |
| ATOM | 12573 | CZB | ci3 | D | 801 | -24.690 | -35.342 | 53.444 | 1.00 | 43.18 | C |
| ATOM | 12574 | CEB | ci3 | D | 801 | -24.448 | -35.727 | 52.134 | 1.00 | 40.81 | C |
| ATOM | 12576 | CDB | ci3 | D | 801 | -23.468 | -36.666 | 51.878 | 1.00 | 39.27 | C |
| ATOM | 12578 | CEA | ci3 | D | 801 | -23.981 | -35.856 | 54.527 | 1.00 | 40.07 | C |
| ATOM | 12580 | CDA | ci3 | D | 801 | -22.996 | -36.797 | 54.275 | 1.00 | 39.18 | C |
| ATOM | 12582 | CGA | ci3 | D | 801 | -22.734 | -37.200 | 52.949 | 1.00 | 38.70 | C |
| ATOM | 12583 | CO | ci3 | D | 801 | -21.646 | -38.221 | 52.689 | 1.00 | 35.86 | C |
| ATOM | 12586 | CF | ci3 | D | 801 | -20.316 | -37.614 | 52.180 | 1.00 | 33.98 | C |
| ATOM | 12587 | CB | ci3 | D | 801 | -19.651 | -38.848 | 51.627 | 1.00 | 29.61 | C |
| ATOM | 12588 | CM | ci3 | D | 801 | -20.220 | -39.457 | 50.399 | 1.00 | 26.51 | C |
| ATOM | 12590 | CA | ci3 | D | 801 | -19.959 | -40.717 | 49.992 | 1.00 | 25.57 | C |
| ATOM | 12591 | CE | ci3 | D | 801 | -20.655 | -41.205 | 48.791 | 1.00 | 25.30 | C |
| ATOM | 12592 | OAO | ci3 | D | 801 | -20.599 | -42.397 | 48.496 | 1.00 | 25.52 | O |
| ATOM | 12593 | OAN | ci3 | D | 801 | -21.313 | -40.438 | 48.064 | 1.00 | 27.12 | O |
| ATOM | 12594 | O14 | ci3 | D | 801 | -19.090 | -41.503 | 50.630 | 1.00 | 22.81 | O |
| ATOM | 12596 | O13 | ci3 | D | 801 | -18.745 | -39.389 | 52.269 | 1.00 | 30.18 | O |
| ATOM | 12597 | CG | ci3 | D | 801 | -20.543 | -36.526 | 51.115 | 1.00 | 36.49 | C |
| ATOM | 12600 | CK | ci3 | D | 801 | -19.310 | -35.745 | 50.632 | 1.00 | 37.77 | C |
| ATOM | 12603 | CI | ci3 | D | 801 | -18.302 | -35.444 | 51.736 | 1.00 | 36.98 | C |
| ATOM | 12606 | NJ | ci3 | D | 801 | -18.837 | -35.721 | 53.085 | 1.00 | 38.68 | N |
| ATOM | 12608 | CH | ci3 | D | 801 | -19.477 | -37.051 | 53.325 | 1.00 | 35.02 | C |
| ATOM | 12611 | CP | ci3 | D | 801 | -17.773 | -35.502 | 54.121 | 1.00 | 40.12 | C |
| ATOM | 12614 | CGB | ci3 | D | 801 | -18.471 | -35.119 | 55.413 | 1.00 | 42.33 | C |
| ATOM | 12615 | CD1 | ci3 | D | 801 | -18.172 | -35.778 | 56.596 | 1.00 | 42.90 | C |
| ATOM | 12617 | CE1 | ci3 | D | 801 | -18.862 | -35.438 | 57.757 | 1.00 | 44.15 | C |
| ATOM | 12619 | CZ | ci3 | D | 801 | -19.840 | -34.427 | 57.731 | 1.00 | 46.06 | C |
| ATOM | 12621 | CE2 | ci3 | D | 801 | -20.145 | -33.764 | 56.556 | 1.00 | 44.97 | C |
| ATOM | 12623 | CD2 | ci3 | D | 801 | -19.452 | -34.112 | 55.402 | 1.00 | 44.58 | C |
| ATOM | 12625 | S | SO4 | D | 401 | -14.624 | -34.192 | 52.148 | 1.00 | 66.16 | S |
| ATOM | 12626 | O1 | SO4 | D | 401 | -15.155 | -35.548 | 52.307 | 1.00 | 64.30 | O |
| ATOM | 12627 | O2 | SO4 | D | 401 | -13.212 | -34.208 | 52.533 | 1.00 | 66.20 | O |
| ATOM | 12628 | O3 | SO4 | D | 401 | -15.314 | -33.237 | 53.026 | 1.00 | 65.34 | O |
| ATOM | 12629 | O4 | SO4 | D | 401 | -14.788 | -33.791 | 50.731 | 1.00 | 67.19 | O |
| ATOM | 12630 | S | SO4 | D | 402 | -34.392 | -49.793 | 38.082 | 1.00 | 77.20 | S |
| ATOM | 12631 | O1 | SO4 | D | 402 | -33.781 | -48.467 | 38.166 | 1.00 | 76.12 | O |
| ATOM | 12632 | O2 | SO4 | D | 402 | -35.849 | -49.595 | 38.009 | 1.00 | 78.54 | O |
| ATOM | 12633 | O3 | SO4 | D | 402 | -34.050 | -50.591 | 39.265 | 1.00 | 74.06 | O |
| ATOM | 12634 | O4 | SO4 | D | 402 | -33.880 | -50.461 | 36.875 | 1.00 | 77.77 | O |
| ATOM | 12635 | S | SO4 | D | 403 | -34.859 | -35.764 | 47.792 | 1.00 | 71.04 | S |

FIG.3-28

```
ATOM  12636  O1   SO4 D 403      -33.707 -36.216  48.593  1.00 64.37           O
ATOM  12637  O2   SO4 D 403      -34.918 -34.295  47.851  1.00 72.70           O
ATOM  12638  O3   SO4 D 403      -36.136 -36.311  48.281  1.00 70.86           O
ATOM  12639  O4   SO4 D 403      -34.737 -36.186  46.387  1.00 71.30           O
ATOM   6464  OH2  WAT D 903      -12.713 -53.361  46.394  1.00 18.08       D   O
ATOM   6466  OH2  WAT D 904      -23.583 -42.624  54.397  1.00 21.49       D   O
ATOM   6469  OH2  WAT D 905      -16.273 -40.780  51.257  1.00 25.68       D   O
ATOM   6470  OH2  WAT D 906      -17.996 -39.513  48.206  1.00 59.37       D   O
ATOM   6473  OH2  WAT D 907      -36.072 -38.721  60.846  1.00 29.20       D   O
ATOM   6474  OH2  WAT D 908      -13.932 -51.948  62.527  1.00 59.26       D   O
ATOM   6476  OH2  WAT D 909      -13.424 -32.315  54.842  1.00 28.40       D   O
ATOM   6477  OH2  WAT D 910      -16.728 -40.455  54.280  1.00 20.53       D   O
ATOM   6479  OH2  WAT D 911      -21.321 -49.827  31.532  1.00 61.32       D   O
END
```

FIG.4-1

Figure 4: H1N1 polypeptide fragment (Chain A) with bound EMBL-R05-2

```
HEADER    ----                                  XX-XXX-XX   xxxx
COMPND    ---
REMARK   3
REMARK   3 REFINEMENT.
REMARK   3  PROGRAM     : REFMAC 5.5.0102
REMARK   3  AUTHORS     : MURSHUDOV,VAGIN,DODSON
REMARK   3
REMARK   3   REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.07
REMARK   3   RESOLUTION RANGE LOW  (ANGSTROMS) :  43.96
REMARK   3   DATA CUTOFF            (SIGMA(F)) : NONE
REMARK   3   COMPLETENESS FOR RANGE        (%) :  83.72
REMARK   3   NUMBER OF REFLECTIONS             :   42925
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.20756
REMARK   3   R VALUE            (WORKING SET) :  0.20470
REMARK   3   FREE R VALUE                     :  0.25936
REMARK   3   FREE R VALUE TEST SET SIZE   (%) :  5.2
REMARK   3   FREE R VALUE TEST SET COUNT      :  2363
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    2.074
REMARK   3   BIN RESOLUTION RANGE LOW            :    2.128
REMARK   3   REFLECTION IN BIN     (WORKING SET) :        0
REMARK   3   BIN COMPLETENESS (WORKING+TEST) (%) :     0.00
REMARK   3   BIN R VALUE           (WORKING SET) :    0.000
REMARK   3   BIN FREE R VALUE SET COUNT          :        0
REMARK   3   BIN FREE R VALUE                    :    0.000
REMARK   3
REMARK   3  NUMBER OF NON-HYDROGEN ATOMS USED IN REFINEMENT.
REMARK   3   ALL ATOMS                 :     6854
REMARK   3
REMARK   3  B VALUES.
REMARK   3   FROM WILSON PLOT           (A**2) : NULL
REMARK   3   MEAN B VALUE      (OVERALL, A**2) :  27.640
REMARK   3   OVERALL ANISOTROPIC B VALUE.
REMARK   3    B11 (A**2) :     0.78
REMARK   3    B22 (A**2) :   -14.79
REMARK   3    B33 (A**2) :    14.01
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.065
REMARK   3   ESU BASED ON FREE R VALUE                       (A):   0.049
REMARK   3   ESU BASED ON MAXIMUM LIKELIHOOD                 (A):   0.145
REMARK   3   ESU FOR B VALUES BASED ON MAXIMUM LIKELIHOOD (A**2):   5.932
REMARK   3
REMARK   3 CORRELATION COEFFICIENTS.
REMARK   3   CORRELATION COEFFICIENT FO-FC      :   0.938
REMARK   3   CORRELATION COEFFICIENT FO-FC FREE :   0.910
REMARK   3
```

FIG.4-2

```
REMARK   3  RMS DEVIATIONS FROM IDEAL VALUES        COUNT    RMS    WEIGHT
REMARK   3   BOND LENGTHS REFINED ATOMS        (A):  6698 ; 0.022 ; 0.022
REMARK   3   BOND LENGTHS OTHERS               (A):  4778 ; 0.001 ; 0.020
REMARK   3   BOND ANGLES REFINED ATOMS   (DEGREES):  8994 ; 1.850 ; 1.963
REMARK   3   BOND ANGLES OTHERS          (DEGREES): 11525 ; 1.010 ; 3.000
REMARK   3   TORSION ANGLES, PERIOD 1    (DEGREES):   766 ; 6.495 ; 5.000
REMARK   3   TORSION ANGLES, PERIOD 2    (DEGREES):   349 ;35.595 ;23.352
REMARK   3   TORSION ANGLES, PERIOD 3    (DEGREES):  1240 ;18.483 ;15.000
REMARK   3   TORSION ANGLES, PERIOD 4    (DEGREES):    60 ;18.609 ;15.000
REMARK   3   CHIRAL-CENTER RESTRAINTS       (A**3):   956 ; 0.112 ; 0.200
REMARK   3   GENERAL PLANES REFINED ATOMS      (A):  7283 ; 0.008 ; 0.020
REMARK   3   GENERAL PLANES OTHERS             (A):  1473 ; 0.001 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):  3872 ; 1.139 ; 1.500
REMARK   3   MAIN-CHAIN BOND OTHER ATOMS    (A**2):  1558 ; 0.276 ; 1.500
REMARK   3   MAIN-CHAIN ANGLE REFINED ATOMS (A**2):  6267 ; 2.034 ; 2.000
REMARK   3   SIDE-CHAIN BOND REFINED ATOMS  (A**2):  2826 ; 3.019 ; 3.000
REMARK   3   SIDE-CHAIN ANGLE REFINED ATOMS (A**2):  2727 ; 4.650 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  :    2
REMARK   3      TWIN DOMAIN   :    1
REMARK   3      TWIN OPERATOR :  H,  K,  L
REMARK   3      TWIN FRACTION : 0.945
REMARK   3      TWIN DOMAIN   :    2
REMARK   3      TWIN OPERATOR : -H,  L,  K
REMARK   3      TWIN FRACTION : 0.055
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
LINKR           GLU A  64                      ASN A  69                gap
LINKR           LYS A 139                      GLU A 141                gap
LINKR           GLY B  66                      PRO B  68                gap
LINKR           ILE B 138                      GLU B 141                gap
LINKR           ILE C 138                      GLU C 141                gap
LINKR           GLU D  64                      ASN D  69                gap
CRYST1   56.590  120.810  128.200  90.00  90.00  90.00 P 21 21 21
SCALE1      0.017671  0.000000  0.000000        0.00000
SCALE2      0.000000  0.008277  0.000000        0.00000
SCALE3      0.000000  0.000000  0.007800        0.00000
ATOM      1  N   ALA A   0      15.963 -18.335 -14.296  1.00 30.50           N
ATOM      2  CA  ALA A   0      14.952 -19.442 -14.473  1.00 30.30           C
ATOM      4  CB  ALA A   0      15.422 -20.671 -13.830  1.00 29.96           C
ATOM      8  C   ALA A   0      13.538 -19.079 -13.941  1.00 29.59           C
ATOM      9  O   ALA A   0      13.372 -18.413 -12.924  1.00 30.09           O
```

FIG.4-3

| | | | | | | | | | | | |
|---|---|---|---|---|---|---|---|---|---|---|---|
| ATOM | 13 | N | MET | A | 1 | 12.518 | -19.561 | -14.619 | 1.00 | 29.48 | N |
| ATOM | 14 | CA | MET | A | 1 | 11.155 | -19.136 | -14.334 | 1.00 | 28.52 | C |
| ATOM | 16 | CB | MET | A | 1 | 10.237 | -19.764 | -15.358 | 1.00 | 27.94 | C |
| ATOM | 19 | CG | MET | A | 1 | 8.765 | -19.272 | -15.196 | 1.00 | 26.77 | C |
| ATOM | 22 | SD | MET | A | 1 | 8.519 | -17.513 | -15.422 | 1.00 | 27.05 | S |
| ATOM | 23 | CE | MET | A | 1 | 8.337 | -17.593 | -17.243 | 1.00 | 26.50 | C |
| ATOM | 27 | C | MET | A | 1 | 10.626 | -19.394 | -12.868 | 1.00 | 28.59 | C |
| ATOM | 28 | O | MET | A | 1 | 9.933 | -18.569 | -12.293 | 1.00 | 27.16 | O |
| ATOM | 30 | N | GLU | A | 2 | 10.950 | -20.533 | -12.294 | 1.00 | 29.03 | N |
| ATOM | 31 | CA | GLU | A | 2 | 10.517 | -20.864 | -10.922 | 1.00 | 30.60 | C |
| ATOM | 33 | CB | GLU | A | 2 | 11.001 | -22.260 | -10.531 | 1.00 | 31.63 | C |
| ATOM | 36 | CG | GLU | A | 2 | 10.547 | -22.757 | -9.123 | 1.00 | 34.24 | C |
| ATOM | 39 | CD | GLU | A | 2 | 11.264 | -24.025 | -8.697 | 1.00 | 36.34 | C |
| ATOM | 40 | OE1 | GLU | A | 2 | 11.848 | -24.675 | -9.596 | 1.00 | 45.20 | O |
| ATOM | 41 | OE2 | GLU | A | 2 | 11.260 | -24.386 | -7.486 | 1.00 | 37.19 | O |
| ATOM | 42 | C | GLU | A | 2 | 11.006 | -19.834 | -9.935 | 1.00 | 29.96 | C |
| ATOM | 43 | O | GLU | A | 2 | 10.207 | -19.319 | -9.169 | 1.00 | 31.97 | O |
| ATOM | 45 | N | ASP | A | 3 | 12.278 | -19.449 | -9.991 | 1.00 | 30.03 | N |
| ATOM | 46 | CA | ASP | A | 3 | 12.747 | -18.326 | -9.148 | 1.00 | 30.22 | C |
| ATOM | 48 | CB | ASP | A | 3 | 14.259 | -18.093 | -9.235 | 1.00 | 31.49 | C |
| ATOM | 51 | CG | ASP | A | 3 | 15.114 | -19.239 | -8.654 | 1.00 | 35.34 | C |
| ATOM | 52 | OD1 | ASP | A | 3 | 14.590 | -20.236 | -8.135 | 1.00 | 37.70 | O |
| ATOM | 53 | OD2 | ASP | A | 3 | 16.358 | -19.105 | -8.749 | 1.00 | 40.48 | O |
| ATOM | 54 | C | ASP | A | 3 | 12.111 | -16.969 | -9.536 | 1.00 | 28.85 | C |
| ATOM | 55 | O | ASP | A | 3 | 11.971 | -16.100 | -8.682 | 1.00 | 28.74 | O |
| ATOM | 57 | N | PHE | A | 4 | 11.858 | -16.743 | -10.826 | 1.00 | 25.92 | N |
| ATOM | 58 | CA | PHE | A | 4 | 11.240 | -15.514 | -11.231 | 1.00 | 25.14 | C |
| ATOM | 60 | CB | PHE | A | 4 | 10.940 | -15.516 | -12.720 | 1.00 | 26.12 | C |
| ATOM | 63 | CG | PHE | A | 4 | 10.199 | -14.303 | -13.176 | 1.00 | 25.82 | C |
| ATOM | 64 | CD1 | PHE | A | 4 | 10.855 | -13.109 | -13.350 | 1.00 | 31.54 | C |
| ATOM | 66 | CE1 | PHE | A | 4 | 10.157 | -11.973 | -13.740 | 1.00 | 31.11 | C |
| ATOM | 68 | CZ | PHE | A | 4 | 8.812 | -12.050 | -13.953 | 1.00 | 28.26 | C |
| ATOM | 70 | CE2 | PHE | A | 4 | 8.162 | -13.233 | -13.770 | 1.00 | 23.22 | C |
| ATOM | 72 | CD2 | PHE | A | 4 | 8.850 | -14.346 | -13.394 | 1.00 | 26.07 | C |
| ATOM | 74 | C | PHE | A | 4 | 9.891 | -15.372 | -10.514 | 1.00 | 24.20 | C |
| ATOM | 75 | O | PHE | A | 4 | 9.533 | -14.318 | -10.059 | 1.00 | 21.92 | O |
| ATOM | 77 | N | VAL | A | 5 | 9.136 | -16.461 | -10.509 | 1.00 | 24.87 | N |
| ATOM | 78 | CA | VAL | A | 5 | 7.761 | -16.494 | -9.947 | 1.00 | 24.17 | C |
| ATOM | 80 | CB | VAL | A | 5 | 7.008 | -17.814 | -10.302 | 1.00 | 23.63 | C |
| ATOM | 82 | CG1 | VAL | A | 5 | 5.663 | -17.929 | -9.575 | 1.00 | 23.20 | C |
| ATOM | 86 | CG2 | VAL | A | 5 | 6.735 | -17.799 | -11.792 | 1.00 | 21.82 | C |
| ATOM | 90 | C | VAL | A | 5 | 7.864 | -16.229 | -8.510 | 1.00 | 23.21 | C |
| ATOM | 91 | O | VAL | A | 5 | 7.154 | -15.412 | -7.992 | 1.00 | 23.26 | O |
| ATOM | 93 | N | ARG | A | 6 | 8.818 | -16.835 | -7.861 | 1.00 | 25.02 | N |
| ATOM | 94 | CA | ARG | A | 6 | 8.922 | -16.611 | -6.423 | 1.00 | 26.02 | C |
| ATOM | 96 | CB | ARG | A | 6 | 9.688 | -17.753 | -5.745 | 1.00 | 26.67 | C |
| ATOM | 99 | CG | ARG | A | 6 | 8.864 | -18.980 | -5.620 | 1.00 | 30.23 | C |
| ATOM | 102 | CD | ARG | A | 6 | 9.219 | -19.915 | -4.467 | 1.00 | 35.47 | C |
| ATOM | 105 | NE | ARG | A | 6 | 9.975 | -20.992 | -5.049 | 1.00 | 37.99 | N |
| ATOM | 107 | CZ | ARG | A | 6 | 9.522 | -22.173 | -5.425 | 1.00 | 34.04 | C |
| ATOM | 108 | NH1 | ARG | A | 6 | 8.282 | -22.582 | -5.180 | 1.00 | 32.65 | N |
| ATOM | 111 | NH2 | ARG | A | 6 | 10.395 | -22.984 | -5.996 | 1.00 | 32.12 | N |
| ATOM | 114 | C | ARG | A | 6 | 9.446 | -15.228 | -6.012 | 1.00 | 25.83 | C |
| ATOM | 115 | O | ARG | A | 6 | 9.177 | -14.769 | -4.860 | 1.00 | 26.33 | O |
| ATOM | 117 | N | GLN | A | 7 | 10.141 | -14.526 | -6.899 | 1.00 | 23.76 | N |
| ATOM | 118 | CA | GLN | A | 7 | 10.517 | -13.140 | -6.602 | 1.00 | 24.38 | C |
| ATOM | 120 | CB | GLN | A | 7 | 11.882 | -12.791 | -7.229 | 1.00 | 25.78 | C |
| ATOM | 123 | CG | GLN | A | 7 | 12.479 | -11.400 | -6.824 | 1.00 | 26.59 | C |
| ATOM | 126 | CD | GLN | A | 7 | 14.014 | -11.233 | -7.185 | 1.00 | 30.80 | C |
| ATOM | 127 | OE1 | GLN | A | 7 | 14.741 | -12.195 | -7.386 | 1.00 | 34.92 | O |
| ATOM | 128 | NE2 | GLN | A | 7 | 14.459 | -9.986 | -7.298 | 1.00 | 35.42 | N |
| ATOM | 131 | C | GLN | A | 7 | 9.474 | -12.173 | -7.147 | 1.00 | 23.65 | C |
| ATOM | 132 | O | GLN | A | 7 | 9.284 | -11.078 | -6.628 | 1.00 | 23.50 | O |

FIG.4-4

| | | | | | | | | | | | |
|---|---|---|---|---|---|---|---|---|---|---|---|
| ATOM | 134 | N | CYS | A | 8 | 8.780 | -12.560 | -8.203 | 1.00 | 22.57 | N |
| ATOM | 135 | CA | CYS | A | 8 | 7.796 | -11.650 | -8.814 | 1.00 | 23.37 | C |
| ATOM | 137 | CB | CYS | A | 8 | 7.479 | -12.116 | -10.255 | 1.00 | 24.09 | C |
| ATOM | 140 | SG | CYS | A | 8 | 6.220 | -11.130 | -11.142 | 1.00 | 27.30 | S |
| ATOM | 142 | C | CYS | A | 8 | 6.500 | -11.537 | -7.998 | 1.00 | 22.00 | C |
| ATOM | 143 | O | CYS | A | 8 | 5.918 | -10.447 | -7.846 | 1.00 | 23.07 | O |
| ATOM | 145 | N | PHE | A | 9 | 6.028 | -12.639 | -7.447 | 1.00 | 21.92 | N |
| ATOM | 146 | CA | PHE | A | 9 | 4.689 | -12.596 | -6.875 | 1.00 | 21.00 | C |
| ATOM | 148 | CB | PHE | A | 9 | 3.886 | -13.712 | -7.416 | 1.00 | 21.08 | C |
| ATOM | 151 | CG | PHE | A | 9 | 3.607 | -13.610 | -8.851 | 1.00 | 17.90 | C |
| ATOM | 152 | CD1 | PHE | A | 9 | 2.545 | -12.874 | -9.297 | 1.00 | 18.87 | C |
| ATOM | 154 | CE1 | PHE | A | 9 | 2.245 | -12.799 | -10.672 | 1.00 | 18.19 | C |
| ATOM | 156 | CZ | PHE | A | 9 | 2.940 | -13.523 | -11.520 | 1.00 | 15.03 | C |
| ATOM | 158 | CE2 | PHE | A | 9 | 4.006 | -14.302 | -11.070 | 1.00 | 15.44 | C |
| ATOM | 160 | CD2 | PHE | A | 9 | 4.321 | -14.334 | -9.747 | 1.00 | 15.21 | C |
| ATOM | 162 | C | PHE | A | 9 | 4.693 | -12.688 | -5.361 | 1.00 | 21.04 | C |
| ATOM | 163 | O | PHE | A | 9 | 5.569 | -13.276 | -4.744 | 1.00 | 21.34 | O |
| ATOM | 165 | N | ASN | A | 10 | 3.707 | -12.099 | -4.743 | 1.00 | 21.70 | N |
| ATOM | 166 | CA | ASN | A | 10 | 3.634 | -12.130 | -3.299 | 1.00 | 22.00 | C |
| ATOM | 168 | CB | ASN | A | 10 | 2.566 | -11.109 | -2.839 | 1.00 | 23.91 | C |
| ATOM | 171 | CG | ASN | A | 10 | 1.908 | -11.475 | -1.549 | 1.00 | 30.75 | C |
| ATOM | 172 | OD1 | ASN | A | 10 | 1.257 | -12.491 | -1.470 | 1.00 | 37.96 | O |
| ATOM | 173 | ND2 | ASN | A | 10 | 2.097 | -10.641 | -0.502 | 1.00 | 37.10 | N |
| ATOM | 176 | C | ASN | A | 10 | 3.517 | -13.585 | -2.766 | 1.00 | 21.84 | C |
| ATOM | 177 | O | ASN | A | 10 | 2.930 | -14.486 | -3.428 | 1.00 | 22.22 | O |
| ATOM | 179 | N | PRO | A | 11 | 4.136 | -13.866 | -1.599 | 1.00 | 20.03 | N |
| ATOM | 180 | CA | PRO | A | 11 | 4.201 | -15.225 | -1.070 | 1.00 | 20.02 | C |
| ATOM | 182 | CB | PRO | A | 11 | 4.963 | -15.068 | 0.275 | 1.00 | 21.83 | C |
| ATOM | 185 | CG | PRO | A | 11 | 5.196 | -13.582 | 0.501 | 1.00 | 21.21 | C |
| ATOM | 188 | CD | PRO | A | 11 | 4.829 | -12.857 | -0.762 | 1.00 | 21.14 | C |
| ATOM | 191 | C | PRO | A | 11 | 2.847 | -15.966 | -0.856 | 1.00 | 18.60 | C |
| ATOM | 192 | O | PRO | A | 11 | 2.763 | -17.208 | -0.994 | 1.00 | 17.01 | O |
| ATOM | 193 | N | MET | A | 12 | 1.785 | -15.228 | -0.565 | 1.00 | 16.84 | N |
| ATOM | 194 | CA | MET | A | 12 | 0.486 | -15.852 | -0.393 | 1.00 | 18.09 | C |
| ATOM | 196 | CB | MET | A | 12 | -0.513 | -14.835 | 0.188 | 1.00 | 18.65 | C |
| ATOM | 199 | CG | MET | A | 12 | -1.898 | -15.447 | 0.458 | 1.00 | 23.68 | C |
| ATOM | 202 | SD | MET | A | 12 | -2.937 | -14.278 | 1.382 | 1.00 | 36.48 | S |
| ATOM | 203 | CE | MET | A | 12 | -3.437 | -13.193 | 0.081 | 1.00 | 33.14 | C |
| ATOM | 207 | C | MET | A | 12 | -0.029 | -16.421 | -1.720 | 1.00 | 15.53 | C |
| ATOM | 208 | O | MET | A | 12 | -0.432 | -17.563 | -1.765 | 1.00 | 14.91 | O |
| ATOM | 210 | N | ILE | A | 13 | 0.112 | -15.639 | -2.800 | 1.00 | 15.96 | N |
| ATOM | 211 | CA | ILE | A | 13 | -0.230 | -16.078 | -4.170 | 1.00 | 15.35 | C |
| ATOM | 213 | CB | ILE | A | 13 | -0.047 | -14.949 | -5.174 | 1.00 | 16.08 | C |
| ATOM | 215 | CG1 | ILE | A | 13 | -1.072 | -13.902 | -4.833 | 1.00 | 17.49 | C |
| ATOM | 218 | CD1 | ILE | A | 13 | -0.931 | -12.604 | -5.521 | 1.00 | 19.74 | C |
| ATOM | 222 | CG2 | ILE | A | 13 | -0.243 | -15.506 | -6.689 | 1.00 | 17.69 | C |
| ATOM | 226 | C | ILE | A | 13 | 0.572 | -17.309 | -4.520 | 1.00 | 14.39 | C |
| ATOM | 227 | O | ILE | A | 13 | 0.006 | -18.360 | -4.810 | 1.00 | 15.26 | O |
| ATOM | 229 | N | VAL | A | 14 | 1.886 | -17.278 | -4.309 | 1.00 | 14.68 | N |
| ATOM | 230 | CA | VAL | A | 14 | 2.727 | -18.390 | -4.684 | 1.00 | 13.57 | C |
| ATOM | 232 | CB | VAL | A | 14 | 4.237 | -18.043 | -4.472 | 1.00 | 15.21 | C |
| ATOM | 234 | CG1 | VAL | A | 14 | 5.095 | -19.212 | -4.794 | 1.00 | 8.84 | C |
| ATOM | 238 | CG2 | VAL | A | 14 | 4.665 | -16.779 | -5.309 | 1.00 | 13.78 | C |
| ATOM | 242 | C | VAL | A | 14 | 2.377 | -19.664 | -3.884 | 1.00 | 15.27 | C |
| ATOM | 243 | O | VAL | A | 14 | 2.302 | -20.753 | -4.454 | 1.00 | 12.96 | O |
| ATOM | 245 | N | GLU | A | 15 | 2.122 | -19.526 | -2.565 | 1.00 | 15.49 | N |
| ATOM | 246 | CA | GLU | A | 15 | 1.706 | -20.650 | -1.766 | 1.00 | 14.48 | C |
| ATOM | 248 | CB | GLU | A | 15 | 1.616 | -20.326 | -0.250 | 1.00 | 14.05 | C |
| ATOM | 251 | CG | GLU | A | 15 | 2.960 | -20.368 | 0.476 | 1.00 | 19.20 | C |
| ATOM | 254 | CD | GLU | A | 15 | 2.886 | -20.021 | 1.993 | 1.00 | 21.09 | C |
| ATOM | 255 | OE1 | GLU | A | 15 | 3.961 | -19.852 | 2.610 | 1.00 | 15.17 | O |
| ATOM | 256 | OE2 | GLU | A | 15 | 1.770 | -20.029 | 2.554 | 1.00 | 21.26 | O |
| ATOM | 257 | C | GLU | A | 15 | 0.389 | -21.260 | -2.228 | 1.00 | 14.35 | C |

FIG.4-5

| | | | | | | | | | | | |
|---|---|---|---|---|---|---|---|---|---|---|---|
| ATOM | 258 | O | GLU | A | 15 | 0.237 | -22.465 | -2.210 | 1.00 | 16.19 | O |
| ATOM | 260 | N | LEU | A | 16 | -0.572 | -20.456 | -2.601 | 1.00 | 14.17 | N |
| ATOM | 261 | CA | LEU | A | 16 | -1.826 | -20.994 | -3.128 | 1.00 | 13.85 | C |
| ATOM | 263 | CB | LEU | A | 16 | -2.839 | -19.882 | -3.277 | 1.00 | 13.31 | C |
| ATOM | 266 | CG | LEU | A | 16 | -3.389 | -19.207 | -1.980 | 1.00 | 14.08 | C |
| ATOM | 268 | CD1 | LEU | A | 16 | -4.060 | -17.913 | -2.331 | 1.00 | 13.26 | C |
| ATOM | 272 | CD2 | LEU | A | 16 | -4.383 | -20.157 | -1.260 | 1.00 | 15.28 | C |
| ATOM | 276 | C | LEU | A | 16 | -1.598 | -21.713 | -4.456 | 1.00 | 15.22 | C |
| ATOM | 277 | O | LEU | A | 16 | -2.117 | -22.822 | -4.694 | 1.00 | 15.20 | O |
| ATOM | 279 | N | ALA | A | 17 | -0.757 | -21.116 | -5.292 | 1.00 | 16.69 | N |
| ATOM | 280 | CA | ALA | A | 17 | -0.555 | -21.666 | -6.630 | 1.00 | 18.69 | C |
| ATOM | 282 | CB | ALA | A | 17 | 0.212 | -20.598 | -7.558 | 1.00 | 19.05 | C |
| ATOM | 286 | C | ALA | A | 17 | 0.181 | -23.025 | -6.513 | 1.00 | 18.76 | C |
| ATOM | 287 | O | ALA | A | 17 | -0.225 | -24.027 | -7.189 | 1.00 | 18.40 | O |
| ATOM | 289 | N | GLU | A | 18 | 1.121 | -23.120 | -5.558 | 1.00 | 17.99 | N |
| ATOM | 290 | CA | GLU | A | 18 | 1.886 | -24.363 | -5.325 | 1.00 | 18.12 | C |
| ATOM | 292 | CB | GLU | A | 18 | 2.985 | -24.281 | -4.223 | 1.00 | 17.68 | C |
| ATOM | 295 | CG | GLU | A | 18 | 4.225 | -23.578 | -4.596 | 1.00 | 19.29 | C |
| ATOM | 298 | CD | GLU | A | 18 | 5.052 | -23.100 | -3.420 | 1.00 | 20.38 | C |
| ATOM | 299 | OE1 | GLU | A | 18 | 4.592 | -23.126 | -2.244 | 1.00 | 23.14 | O |
| ATOM | 300 | OE2 | GLU | A | 18 | 6.155 | -22.587 | -3.655 | 1.00 | 19.15 | O |
| ATOM | 301 | C | GLU | A | 18 | 1.007 | -25.519 | -4.926 | 1.00 | 17.38 | C |
| ATOM | 302 | O | GLU | A | 18 | 1.116 | -26.598 | -5.483 | 1.00 | 16.57 | O |
| ATOM | 304 | N | LYS | A | 19 | 0.167 | -25.278 | -3.938 | 1.00 | 17.85 | N |
| ATOM | 305 | CA | LYS | A | 19 | -0.759 | -26.288 | -3.498 | 1.00 | 18.53 | C |
| ATOM | 307 | CB | LYS | A | 19 | -1.541 | -25.834 | -2.284 | 1.00 | 17.80 | C |
| ATOM | 310 | CG | LYS | A | 19 | -0.670 | -25.718 | -1.056 | 1.00 | 20.23 | C |
| ATOM | 313 | CD | LYS | A | 19 | -1.572 | -25.295 | 0.179 | 1.00 | 15.69 | C |
| ATOM | 316 | CE | LYS | A | 19 | -0.769 | -24.910 | 1.388 | 1.00 | 13.48 | C |
| ATOM | 319 | NZ | LYS | A | 19 | 0.134 | -26.026 | 1.972 | 1.00 | 10.75 | N |
| ATOM | 323 | C | LYS | A | 19 | -1.736 | -26.729 | -4.586 | 1.00 | 18.63 | C |
| ATOM | 324 | O | LYS | A | 19 | -2.098 | -27.881 | -4.626 | 1.00 | 18.44 | O |
| ATOM | 326 | N | ALA | A | 20 | -2.217 | -25.786 | -5.392 | 1.00 | 18.75 | N |
| ATOM | 327 | CA | ALA | A | 20 | -3.192 | -26.100 | -6.404 | 1.00 | 17.98 | C |
| ATOM | 329 | CB | ALA | A | 20 | -3.642 | -24.858 | -7.067 | 1.00 | 15.83 | C |
| ATOM | 333 | C | ALA | A | 20 | -2.556 | -27.061 | -7.417 | 1.00 | 18.39 | C |
| ATOM | 334 | O | ALA | A | 20 | -3.141 | -28.112 | -7.800 | 1.00 | 18.30 | O |
| ATOM | 336 | N | MET | A | 21 | -1.322 | -26.771 | -7.772 | 1.00 | 19.18 | N |
| ATOM | 337 | CA | MET | A | 21 | -0.586 | -27.606 | -8.701 | 1.00 | 20.29 | C |
| ATOM | 339 | CB | MET | A | 21 | 0.697 | -26.909 | -9.160 | 1.00 | 19.78 | C |
| ATOM | 342 | CG | MET | A | 21 | 0.450 | -25.855 | -10.135 | 1.00 | 20.69 | C |
| ATOM | 345 | SD | MET | A | 21 | 1.970 | -24.975 | -10.717 | 1.00 | 22.66 | S |
| ATOM | 346 | CE | MET | A | 21 | 2.404 | -26.127 | -12.032 | 1.00 | 19.16 | C |
| ATOM | 350 | C | MET | A | 21 | -0.351 | -29.008 | -8.138 | 1.00 | 21.58 | C |
| ATOM | 351 | O | MET | A | 21 | -0.736 | -30.040 | -8.751 | 1.00 | 21.61 | O |
| ATOM | 353 | N | LYS | A | 22 | 0.199 | -29.097 | -6.945 | 1.00 | 23.10 | N |
| ATOM | 354 | CA | LYS | A | 22 | 0.494 | -30.405 | -6.400 | 1.00 | 22.72 | C |
| ATOM | 356 | CB | LYS | A | 22 | 1.209 | -30.264 | -5.088 | 1.00 | 24.05 | C |
| ATOM | 359 | CG | LYS | A | 22 | 2.676 | -29.875 | -5.156 | 1.00 | 29.28 | C |
| ATOM | 362 | CD | LYS | A | 22 | 3.453 | -31.198 | -5.148 | 1.00 | 35.51 | C |
| ATOM | 365 | CE | LYS | A | 22 | 4.970 | -31.082 | -5.288 | 1.00 | 38.58 | C |
| ATOM | 368 | NZ | LYS | A | 22 | 5.474 | -32.448 | -5.775 | 1.00 | 41.37 | N |
| ATOM | 372 | C | LYS | A | 22 | -0.781 | -31.220 | -6.216 | 1.00 | 23.34 | C |
| ATOM | 373 | O | LYS | A | 22 | -0.823 | -32.425 | -6.486 | 1.00 | 22.04 | O |
| ATOM | 375 | N | GLU | A | 23 | -1.837 | -30.586 | -5.748 | 1.00 | 22.65 | N |
| ATOM | 376 | CA | GLU | A | 23 | -3.014 | -31.344 | -5.458 | 1.00 | 23.24 | C |
| ATOM | 378 | CB | GLU | A | 23 | -3.973 | -30.500 | -4.634 | 1.00 | 23.90 | C |
| ATOM | 381 | CG | GLU | A | 23 | -3.500 | -30.170 | -3.160 | 1.00 | 26.16 | C |
| ATOM | 384 | CD | GLU | A | 23 | -4.359 | -29.026 | -2.569 | 1.00 | 29.31 | C |
| ATOM | 385 | OE1 | GLU | A | 23 | -4.044 | -28.459 | -1.484 | 1.00 | 32.31 | O |
| ATOM | 386 | OE2 | GLU | A | 23 | -5.347 | -28.699 | -3.248 | 1.00 | 29.57 | O |
| ATOM | 387 | C | GLU | A | 23 | -3.683 | -31.902 | -6.729 | 1.00 | 23.54 | C |
| ATOM | 388 | O | GLU | A | 23 | -4.340 | -32.940 | -6.676 | 1.00 | 22.41 | O |

FIG.4-6

| | | | | | | | | | | | |
|---|---|---|---|---|---|---|---|---|---|---|---|
| ATOM | 390 | N | TYR | A | 24 | -3.470 | -31.237 | -7.864 | 1.00 | 24.01 | N |
| ATOM | 391 | CA | TYR | A | 24 | -3.936 | -31.723 | -9.126 | 1.00 | 24.70 | C |
| ATOM | 393 | CB | TYR | A | 24 | -4.410 | -30.569 | -10.016 | 1.00 | 24.71 | C |
| ATOM | 396 | CG | TYR | A | 24 | -5.791 | -30.035 | -9.623 | 1.00 | 25.44 | C |
| ATOM | 397 | CD1 | TYR | A | 24 | -5.929 | -29.075 | -8.642 | 1.00 | 23.12 | C |
| ATOM | 399 | CE1 | TYR | A | 24 | -7.149 | -28.592 | -8.292 | 1.00 | 26.13 | C |
| ATOM | 401 | CZ | TYR | A | 24 | -8.289 | -29.081 | -8.898 | 1.00 | 27.35 | C |
| ATOM | 402 | OH | TYR | A | 24 | -9.483 | -28.561 | -8.531 | 1.00 | 31.77 | O |
| ATOM | 404 | CE2 | TYR | A | 24 | -8.206 | -30.051 | -9.853 | 1.00 | 28.19 | C |
| ATOM | 406 | CD2 | TYR | A | 24 | -6.955 | -30.535 | -10.215 | 1.00 | 26.70 | C |
| ATOM | 408 | C | TYR | A | 24 | -2.927 | -32.564 | -9.858 | 1.00 | 25.45 | C |
| ATOM | 409 | O | TYR | A | 24 | -3.130 | -32.862 | -11.042 | 1.00 | 25.67 | O |
| ATOM | 411 | N | GLY | A | 25 | -1.864 | -32.973 | -9.169 | 1.00 | 26.36 | N |
| ATOM | 412 | CA | GLY | A | 25 | -0.879 | -33.817 | -9.751 | 1.00 | 27.66 | C |
| ATOM | 415 | C | GLY | A | 25 | 0.226 | -33.141 | -10.533 | 1.00 | 29.55 | C |
| ATOM | 416 | O | GLY | A | 25 | 0.979 | -33.849 | -11.198 | 1.00 | 30.50 | O |
| ATOM | 418 | N | GLU | A | 26 | 0.356 | -31.807 | -10.486 | 1.00 | 30.09 | N |
| ATOM | 419 | CA | GLU | A | 26 | 1.419 | -31.129 | -11.219 | 1.00 | 30.84 | C |
| ATOM | 421 | CB | GLU | A | 26 | 0.841 | -29.965 | -12.030 | 1.00 | 31.77 | C |
| ATOM | 424 | CG | GLU | A | 26 | -0.240 | -30.318 | -13.001 | 1.00 | 34.86 | C |
| ATOM | 427 | CD | GLU | A | 26 | -1.061 | -29.103 | -13.387 | 1.00 | 39.14 | C |
| ATOM | 428 | OE1 | GLU | A | 26 | -0.696 | -27.991 | -12.961 | 1.00 | 43.75 | O |
| ATOM | 429 | OE2 | GLU | A | 26 | -2.087 | -29.249 | -14.078 | 1.00 | 42.46 | O |
| ATOM | 430 | C | GLU | A | 26 | 2.515 | -30.541 | -10.315 | 1.00 | 30.90 | C |
| ATOM | 431 | O | GLU | A | 26 | 2.301 | -30.132 | -9.163 | 1.00 | 31.68 | O |
| ATOM | 433 | N | ASP | A | 27 | 3.691 | -30.446 | -10.870 | 1.00 | 29.80 | N |
| ATOM | 434 | CA | ASP | A | 27 | 4.805 | -29.937 | -10.148 | 1.00 | 29.02 | C |
| ATOM | 436 | CB | ASP | A | 27 | 5.978 | -30.882 | -10.304 | 1.00 | 29.29 | C |
| ATOM | 439 | CG | ASP | A | 27 | 7.109 | -30.501 | -9.393 | 1.00 | 33.70 | C |
| ATOM | 440 | OD1 | ASP | A | 27 | 7.678 | -29.403 | -9.568 | 1.00 | 36.24 | O |
| ATOM | 441 | OD2 | ASP | A | 27 | 7.399 | -31.272 | -8.469 | 1.00 | 42.25 | O |
| ATOM | 442 | C | ASP | A | 27 | 5.192 | -28.541 | -10.664 | 1.00 | 27.83 | C |
| ATOM | 443 | O | ASP | A | 27 | 5.462 | -28.378 | -11.856 | 1.00 | 26.63 | O |
| ATOM | 445 | N | PRO | A | 28 | 5.218 | -27.549 | -9.778 | 1.00 | 26.63 | N |
| ATOM | 446 | CA | PRO | A | 28 | 5.559 | -26.203 | -10.233 | 1.00 | 27.90 | C |
| ATOM | 448 | CB | PRO | A | 28 | 5.303 | -25.341 | -9.001 | 1.00 | 26.61 | C |
| ATOM | 451 | CG | PRO | A | 28 | 5.227 | -26.272 | -7.879 | 1.00 | 27.36 | C |
| ATOM | 454 | CD | PRO | A | 28 | 4.734 | -27.546 | -8.384 | 1.00 | 26.55 | C |
| ATOM | 457 | C | PRO | A | 28 | 7.022 | -26.035 | -10.712 | 1.00 | 28.98 | C |
| ATOM | 458 | O | PRO | A | 28 | 7.316 | -25.137 | -11.518 | 1.00 | 28.72 | O |
| ATOM | 459 | N | LYS | A | 29 | 7.898 | -26.895 | -10.206 | 1.00 | 30.22 | N |
| ATOM | 460 | CA | LYS | A | 29 | 9.298 | -26.962 | -10.607 | 1.00 | 32.09 | C |
| ATOM | 462 | CB | LYS | A | 29 | 10.078 | -27.837 | -9.606 | 1.00 | 32.86 | C |
| ATOM | 465 | CG | LYS | A | 29 | 11.406 | -28.413 | -10.105 | 1.00 | 36.73 | C |
| ATOM | 468 | CD | LYS | A | 29 | 12.332 | -28.853 | -8.910 | 1.00 | 40.09 | C |
| ATOM | 471 | CE | LYS | A | 29 | 12.943 | -27.692 | -8.123 | 1.00 | 42.70 | C |
| ATOM | 474 | NZ | LYS | A | 29 | 12.991 | -28.049 | -6.652 | 1.00 | 44.13 | N |
| ATOM | 478 | C | LYS | A | 29 | 9.445 | -27.486 | -12.055 | 1.00 | 33.14 | C |
| ATOM | 479 | O | LYS | A | 29 | 10.377 | -27.108 | -12.754 | 1.00 | 33.57 | O |
| ATOM | 481 | N | ILE | A | 30 | 8.488 | -28.302 | -12.509 | 1.00 | 33.67 | N |
| ATOM | 482 | CA | ILE | A | 30 | 8.451 | -28.810 | -13.866 | 1.00 | 33.42 | C |
| ATOM | 484 | CB | ILE | A | 30 | 7.975 | -30.286 | -13.837 | 1.00 | 33.81 | C |
| ATOM | 486 | CG1 | ILE | A | 30 | 8.980 | -31.147 | -13.057 | 1.00 | 35.38 | C |
| ATOM | 489 | CD1 | ILE | A | 30 | 8.594 | -32.629 | -12.901 | 1.00 | 31.76 | C |
| ATOM | 493 | CG2 | ILE | A | 30 | 7.769 | -30.831 | -15.251 | 1.00 | 36.17 | C |
| ATOM | 497 | C | ILE | A | 30 | 7.564 | -27.943 | -14.798 | 1.00 | 32.85 | C |
| ATOM | 498 | O | ILE | A | 30 | 7.999 | -27.482 | -15.864 | 1.00 | 33.05 | O |
| ATOM | 500 | N | GLU | A | 31 | 6.332 | -27.659 | -14.410 | 1.00 | 31.24 | N |
| ATOM | 501 | CA | GLU | A | 31 | 5.496 | -26.840 | -15.278 | 1.00 | 30.25 | C |
| ATOM | 503 | CB | GLU | A | 31 | 4.063 | -27.280 | -15.207 | 1.00 | 30.90 | C |
| ATOM | 506 | CG | GLU | A | 31 | 3.864 | -28.748 | -15.091 | 1.00 | 34.36 | C |
| ATOM | 509 | CD | GLU | A | 31 | 2.908 | -29.213 | -16.150 | 1.00 | 40.95 | C |
| ATOM | 510 | OE1 | GLU | A | 31 | 3.323 | -29.141 | -17.335 | 1.00 | 41.41 | O |

FIG.4-7

| | | | | | | | | | | | |
|---|---|---|---|---|---|---|---|---|---|---|---|
| ATOM | 511 | OE2 | GLU | A | 31 | 1.766 | -29.608 | -15.801 | 1.00 | 42.33 | O |
| ATOM | 512 | C | GLU | A | 31 | 5.567 | -25.402 | -14.858 | 1.00 | 28.18 | C |
| ATOM | 513 | O | GLU | A | 31 | 4.597 | -24.870 | -14.297 | 1.00 | 28.99 | O |
| ATOM | 515 | N | THR | A | 32 | 6.676 | -24.749 | -15.155 | 1.00 | 25.71 | N |
| ATOM | 516 | CA | THR | A | 32 | 6.956 | -23.398 | -14.638 | 1.00 | 25.35 | C |
| ATOM | 518 | CB | THR | A | 32 | 8.492 | -23.076 | -14.720 | 1.00 | 24.96 | C |
| ATOM | 520 | OG1 | THR | A | 32 | 8.961 | -23.182 | -16.086 | 1.00 | 31.47 | O |
| ATOM | 522 | CG2 | THR | A | 32 | 9.204 | -24.048 | -13.930 | 1.00 | 27.43 | C |
| ATOM | 526 | C | THR | A | 32 | 6.181 | -22.258 | -15.245 | 1.00 | 23.24 | C |
| ATOM | 527 | O | THR | A | 32 | 5.908 | -21.258 | -14.593 | 1.00 | 22.09 | O |
| ATOM | 529 | N | ASN | A | 33 | 5.899 | -22.351 | -16.521 | 1.00 | 23.72 | N |
| ATOM | 530 | CA | ASN | A | 33 | 5.052 | -21.370 | -17.207 | 1.00 | 23.16 | C |
| ATOM | 532 | CB | ASN | A | 33 | 5.071 | -21.580 | -18.735 | 1.00 | 22.31 | C |
| ATOM | 535 | CG | ASN | A | 33 | 6.425 | -21.261 | -19.351 | 1.00 | 25.75 | C |
| ATOM | 536 | OD1 | ASN | A | 33 | 7.084 | -20.270 | -18.997 | 1.00 | 24.11 | O |
| ATOM | 537 | ND2 | ASN | A | 33 | 6.875 | -22.132 | -20.270 | 1.00 | 26.78 | N |
| ATOM | 540 | C | ASN | A | 33 | 3.634 | -21.468 | -16.658 | 1.00 | 22.02 | C |
| ATOM | 541 | O | ASN | A | 33 | 2.970 | -20.450 | -16.488 | 1.00 | 21.98 | O |
| ATOM | 543 | N | LYS | A | 34 | 3.173 | -22.691 | -16.395 | 1.00 | 22.17 | N |
| ATOM | 544 | CA | LYS | A | 34 | 1.847 | -22.873 | -15.826 | 1.00 | 21.65 | C |
| ATOM | 546 | CB | LYS | A | 34 | 1.473 | -24.323 | -15.817 | 1.00 | 22.10 | C |
| ATOM | 549 | CG | LYS | A | 34 | -0.025 | -24.621 | -15.808 | 1.00 | 27.83 | C |
| ATOM | 552 | CD | LYS | A | 34 | -0.241 | -26.144 | -16.124 | 1.00 | 32.95 | C |
| ATOM | 555 | CE | LYS | A | 34 | -1.387 | -26.441 | -17.048 | 1.00 | 36.23 | C |
| ATOM | 558 | NZ | LYS | A | 34 | -1.246 | -27.808 | -17.750 | 1.00 | 39.17 | N |
| ATOM | 562 | C | LYS | A | 34 | 1.841 | -22.274 | -14.401 | 1.00 | 20.72 | C |
| ATOM | 563 | O | LYS | A | 34 | 0.930 | -21.565 | -14.056 | 1.00 | 19.72 | O |
| ATOM | 565 | N | PHE | A | 35 | 2.899 | -22.526 | -13.622 | 1.00 | 20.54 | N |
| ATOM | 566 | CA | PHE | A | 35 | 3.101 | -21.895 | -12.316 | 1.00 | 20.15 | C |
| ATOM | 568 | CB | PHE | A | 35 | 4.448 | -22.357 | -11.805 | 1.00 | 20.75 | C |
| ATOM | 571 | CG | PHE | A | 35 | 4.814 | -21.957 | -10.417 | 1.00 | 20.43 | C |
| ATOM | 572 | CD1 | PHE | A | 35 | 6.149 | -21.716 | -10.134 | 1.00 | 16.84 | C |
| ATOM | 574 | CE1 | PHE | A | 35 | 6.594 | -21.428 | -8.813 | 1.00 | 20.67 | C |
| ATOM | 576 | CZ | PHE | A | 35 | 5.690 | -21.356 | -7.767 | 1.00 | 18.61 | C |
| ATOM | 578 | CE2 | PHE | A | 35 | 4.325 | -21.604 | -8.017 | 1.00 | 15.74 | C |
| ATOM | 580 | CD2 | PHE | A | 35 | 3.888 | -21.950 | -9.354 | 1.00 | 19.43 | C |
| ATOM | 582 | C | PHE | A | 35 | 2.914 | -20.377 | -12.367 | 1.00 | 21.24 | C |
| ATOM | 583 | O | PHE | A | 35 | 2.133 | -19.809 | -11.592 | 1.00 | 18.39 | O |
| ATOM | 585 | N | ALA | A | 36 | 3.574 | -19.720 | -13.340 | 1.00 | 21.28 | N |
| ATOM | 586 | CA | ALA | A | 36 | 3.533 | -18.267 | -13.504 | 1.00 | 19.46 | C |
| ATOM | 588 | CB | ALA | A | 36 | 4.616 | -17.811 | -14.518 | 1.00 | 19.96 | C |
| ATOM | 592 | C | ALA | A | 36 | 2.159 | -17.788 | -14.006 | 1.00 | 19.48 | C |
| ATOM | 593 | O | ALA | A | 36 | 1.692 | -16.693 | -13.644 | 1.00 | 17.95 | O |
| ATOM | 595 | N | ALA | A | 37 | 1.520 | -18.613 | -14.813 | 1.00 | 16.92 | N |
| ATOM | 596 | CA | ALA | A | 37 | 0.172 | -18.304 | -15.269 | 1.00 | 18.30 | C |
| ATOM | 598 | CB | ALA | A | 37 | -0.241 | -19.183 | -16.477 | 1.00 | 15.61 | C |
| ATOM | 602 | C | ALA | A | 37 | -0.885 | -18.397 | -14.134 | 1.00 | 17.24 | C |
| ATOM | 603 | O | ALA | A | 37 | -1.848 | -17.624 | -14.127 | 1.00 | 19.08 | O |
| ATOM | 605 | N | ILE | A | 38 | -0.749 | -19.384 | -13.271 | 1.00 | 17.39 | N |
| ATOM | 606 | CA | ILE | A | 38 | -1.649 | -19.549 | -12.145 | 1.00 | 17.68 | C |
| ATOM | 608 | CB | ILE | A | 38 | -1.476 | -20.891 | -11.443 | 1.00 | 19.04 | C |
| ATOM | 610 | CG1 | ILE | A | 38 | -2.016 | -21.972 | -12.357 | 1.00 | 20.82 | C |
| ATOM | 613 | CD1 | ILE | A | 38 | -1.258 | -23.262 | -12.299 | 1.00 | 24.99 | C |
| ATOM | 617 | CG2 | ILE | A | 38 | -2.228 | -20.960 | -10.079 | 1.00 | 15.86 | C |
| ATOM | 621 | C | ILE | A | 38 | -1.483 | -18.377 | -11.205 | 1.00 | 17.31 | C |
| ATOM | 622 | O | ILE | A | 38 | -2.482 | -17.778 | -10.805 | 1.00 | 16.97 | O |
| ATOM | 624 | N | CYS | A | 39 | -0.253 | -17.965 | -10.948 | 1.00 | 16.99 | N |
| ATOM | 625 | CA | CYS | A | 39 | 0.008 | -16.819 | -10.052 | 1.00 | 15.61 | C |
| ATOM | 627 | CB | CYS | A | 39 | 1.494 | -16.653 | -9.761 | 1.00 | 15.70 | C |
| ATOM | 630 | SG | CYS | A | 39 | 2.197 | -17.917 | -8.780 | 1.00 | 19.73 | S |
| ATOM | 632 | C | CYS | A | 39 | -0.515 | -15.557 | -10.589 | 1.00 | 15.45 | C |
| ATOM | 633 | O | CYS | A | 39 | -1.049 | -14.745 | -9.846 | 1.00 | 14.82 | O |
| ATOM | 635 | N | THR | A | 40 | -0.380 | -15.360 | -11.912 | 1.00 | 16.20 | N |

FIG.4-8

| | | | | | | | | | | | |
|---|---|---|---|---|---|---|---|---|---|---|---|
| ATOM | 636 | CA | THR | A | 40 | -0.825 | -14.165 | -12.577 | 1.00 | 13.99 | C |
| ATOM | 638 | CB | THR | A | 40 | -0.433 | -14.203 | -14.065 | 1.00 | 13.35 | C |
| ATOM | 640 | OG1 | THR | A | 40 | 0.951 | -14.263 | -14.179 | 1.00 | 16.39 | O |
| ATOM | 642 | CG2 | THR | A | 40 | -0.833 | -12.979 | -14.746 | 1.00 | 12.50 | C |
| ATOM | 646 | C | THR | A | 40 | -2.332 | -13.992 | -12.586 | 1.00 | 13.71 | C |
| ATOM | 647 | O | THR | A | 40 | -2.821 | -12.903 | -12.367 | 1.00 | 13.31 | O |
| ATOM | 649 | N | HIS | A | 41 | -3.047 | -15.069 | -12.867 | 1.00 | 14.67 | N |
| ATOM | 650 | CA | HIS | A | 41 | -4.516 | -15.058 | -12.866 | 1.00 | 14.29 | C |
| ATOM | 652 | CB | HIS | A | 41 | -5.064 | -16.389 | -13.362 | 1.00 | 12.92 | C |
| ATOM | 655 | CG | HIS | A | 41 | -6.557 | -16.530 | -13.256 | 1.00 | 17.06 | C |
| ATOM | 656 | ND1 | HIS | A | 41 | -7.164 | -17.161 | -12.193 | 1.00 | 12.13 | N |
| ATOM | 658 | CE1 | HIS | A | 41 | -8.474 | -17.135 | -12.361 | 1.00 | 19.25 | C |
| ATOM | 660 | NE2 | HIS | A | 41 | -8.741 | -16.538 | -13.508 | 1.00 | 18.10 | N |
| ATOM | 662 | CD2 | HIS | A | 41 | -7.560 | -16.144 | -14.087 | 1.00 | 18.11 | C |
| ATOM | 664 | C | HIS | A | 41 | -4.990 | -14.752 | -11.440 | 1.00 | 15.56 | C |
| ATOM | 665 | O | HIS | A | 41 | -5.877 | -13.883 | -11.229 | 1.00 | 15.77 | O |
| ATOM | 667 | N | LEU | A | 42 | -4.462 | -15.486 | -10.475 | 1.00 | 15.04 | N |
| ATOM | 668 | CA | LEU | A | 42 | -4.766 | -15.193 | -9.073 | 1.00 | 16.63 | C |
| ATOM | 670 | CB | LEU | A | 42 | -3.878 | -16.077 | -8.182 | 1.00 | 17.22 | C |
| ATOM | 673 | CG | LEU | A | 42 | -4.357 | -16.984 | -7.049 | 1.00 | 22.42 | C |
| ATOM | 675 | CD1 | LEU | A | 42 | -5.839 | -17.309 | -6.971 | 1.00 | 25.30 | C |
| ATOM | 679 | CD2 | LEU | A | 42 | -3.511 | -18.291 | -7.104 | 1.00 | 26.49 | C |
| ATOM | 683 | C | LEU | A | 42 | -4.493 | -13.743 | -8.695 | 1.00 | 15.22 | C |
| ATOM | 684 | O | LEU | A | 42 | -5.318 | -13.055 | -8.065 | 1.00 | 14.84 | O |
| ATOM | 686 | N | GLU | A | 43 | -3.300 | -13.263 | -9.011 | 1.00 | 14.76 | N |
| ATOM | 687 | CA | GLU | A | 43 | -3.040 | -11.869 | -8.782 | 1.00 | 15.62 | C |
| ATOM | 689 | CB | GLU | A | 43 | -1.707 | -11.496 | -9.298 | 1.00 | 16.05 | C |
| ATOM | 692 | CG | GLU | A | 43 | -1.282 | -10.105 | -8.900 | 1.00 | 24.48 | C |
| ATOM | 695 | CD | GLU | A | 43 | 0.165 | -9.855 | -9.234 | 1.00 | 31.12 | C |
| ATOM | 696 | OE1 | GLU | A | 43 | 0.956 | -9.726 | -8.311 | 1.00 | 32.89 | O |
| ATOM | 697 | OE2 | GLU | A | 43 | 0.501 | -9.820 | -10.448 | 1.00 | 36.99 | O |
| ATOM | 698 | C | GLU | A | 43 | -4.023 | -10.894 | -9.393 | 1.00 | 15.59 | C |
| ATOM | 699 | O | GLU | A | 43 | -4.269 | -9.880 | -8.807 | 1.00 | 14.48 | O |
| ATOM | 701 | N | VAL | A | 44 | -4.520 | -11.156 | -10.603 | 1.00 | 15.61 | N |
| ATOM | 702 | CA | VAL | A | 44 | -5.430 | -10.180 | -11.261 | 1.00 | 15.94 | C |
| ATOM | 704 | CB | VAL | A | 44 | -5.615 | -10.527 | -12.794 | 1.00 | 15.90 | C |
| ATOM | 706 | CG1 | VAL | A | 44 | -6.797 | -9.766 | -13.426 | 1.00 | 12.56 | C |
| ATOM | 710 | CG2 | VAL | A | 44 | -4.286 | -10.170 | -13.496 | 1.00 | 17.14 | C |
| ATOM | 714 | C | VAL | A | 44 | -6.778 | -10.239 | -10.596 | 1.00 | 15.13 | C |
| ATOM | 715 | O | VAL | A | 44 | -7.419 | -9.227 | -10.476 | 1.00 | 17.66 | O |
| ATOM | 717 | N | CYS | A | 45 | -7.203 | -11.412 | -10.177 | 1.00 | 15.15 | N |
| ATOM | 718 | CA | CYS | A | 45 | -8.476 | -11.540 | -9.456 | 1.00 | 16.24 | C |
| ATOM | 720 | CB | CYS | A | 45 | -8.797 | -12.980 | -9.152 | 1.00 | 14.89 | C |
| ATOM | 723 | SG | CYS | A | 45 | -9.209 | -14.110 | -10.579 | 1.00 | 18.03 | S |
| ATOM | 725 | C | CYS | A | 45 | -8.456 | -10.752 | -8.124 | 1.00 | 17.43 | C |
| ATOM | 726 | O | CYS | A | 45 | -9.463 | -10.120 | -7.775 | 1.00 | 18.28 | O |
| ATOM | 728 | N | PHE | A | 46 | -7.334 | -10.841 | -7.394 | 1.00 | 16.26 | N |
| ATOM | 729 | CA | PHE | A | 46 | -7.170 | -10.063 | -6.204 | 1.00 | 17.98 | C |
| ATOM | 731 | CB | PHE | A | 46 | -5.942 | -10.518 | -5.389 | 1.00 | 17.25 | C |
| ATOM | 734 | CG | PHE | A | 46 | -5.992 | -11.947 | -4.921 | 1.00 | 18.26 | C |
| ATOM | 735 | CD1 | PHE | A | 46 | -7.115 | -12.735 | -5.072 | 1.00 | 22.19 | C |
| ATOM | 737 | CE1 | PHE | A | 46 | -7.146 | -14.026 | -4.628 | 1.00 | 20.50 | C |
| ATOM | 739 | CZ | PHE | A | 46 | -6.053 | -14.544 | -3.978 | 1.00 | 20.22 | C |
| ATOM | 741 | CE2 | PHE | A | 46 | -4.942 | -13.796 | -3.856 | 1.00 | 21.94 | C |
| ATOM | 743 | CD2 | PHE | A | 46 | -4.916 | -12.492 | -4.334 | 1.00 | 19.78 | C |
| ATOM | 745 | C | PHE | A | 46 | -7.065 | -8.567 | -6.525 | 1.00 | 18.86 | C |
| ATOM | 746 | O | PHE | A | 46 | -7.673 | -7.745 | -5.856 | 1.00 | 19.42 | O |
| ATOM | 748 | N | MET | A | 47 | -6.302 | -8.204 | -7.555 | 1.00 | 19.81 | N |
| ATOM | 749 | CA | MET | A | 47 | -6.217 | -6.789 | -7.951 | 1.00 | 19.89 | C |
| ATOM | 751 | CB | MET | A | 47 | -5.219 | -6.492 | -9.058 | 1.00 | 19.83 | C |
| ATOM | 754 | CG | MET | A | 47 | -3.771 | -6.811 | -8.755 | 1.00 | 23.47 | C |
| ATOM | 757 | SD | MET | A | 47 | -2.626 | -6.263 | -10.034 | 1.00 | 24.82 | S |
| ATOM | 758 | CE | MET | A | 47 | -2.935 | -4.506 | -9.996 | 1.00 | 21.80 | C |

FIG.4-9

| | | | | | | | | | | | |
|---|---|---|---|---|---|---|---|---|---|---|---|
| ATOM | 762 | C | MET | A | 47 | -7.577 | -6.288 | -8.369 | 1.00 | 19.33 | C |
| ATOM | 763 | O | MET | A | 47 | -7.919 | -5.136 | -8.070 | 1.00 | 19.94 | O |
| ATOM | 765 | N | TYR | A | 48 | -8.354 | -7.123 | -9.027 | 1.00 | 19.10 | N |
| ATOM | 766 | CA | TYR | A | 48 | -9.680 | -6.725 | -9.488 | 1.00 | 20.16 | C |
| ATOM | 768 | CB | TYR | A | 48 | -10.330 | -7.853 | -10.304 | 1.00 | 19.64 | C |
| ATOM | 771 | CG | TYR | A | 48 | -11.384 | -7.475 | -11.329 | 1.00 | 18.21 | C |
| ATOM | 772 | CD1 | TYR | A | 48 | -11.117 | -7.558 | -12.693 | 1.00 | 15.64 | C |
| ATOM | 774 | CE1 | TYR | A | 48 | -12.080 | -7.229 | -13.631 | 1.00 | 14.20 | C |
| ATOM | 776 | CZ | TYR | A | 48 | -13.294 | -6.843 | -13.250 | 1.00 | 17.43 | C |
| ATOM | 777 | OH | TYR | A | 48 | -14.243 | -6.489 | -14.259 | 1.00 | 17.51 | O |
| ATOM | 779 | CE2 | TYR | A | 48 | -13.589 | -6.701 | -11.847 | 1.00 | 12.11 | C |
| ATOM | 781 | CD2 | TYR | A | 48 | -12.657 | -7.074 | -10.943 | 1.00 | 18.69 | C |
| ATOM | 783 | C | TYR | A | 48 | -10.572 | -6.350 | -8.282 | 1.00 | 22.24 | C |
| ATOM | 784 | O | TYR | A | 48 | -11.295 | -5.349 | -8.336 | 1.00 | 23.14 | O |
| ATOM | 786 | N | SER | A | 49 | -10.539 | -7.112 | -7.201 | 1.00 | 24.64 | N |
| ATOM | 787 | CA | SER | A | 49 | -11.342 | -6.715 | -5.981 | 1.00 | 28.17 | C |
| ATOM | 789 | CB | SER | A | 49 | -11.687 | -7.886 | -5.049 | 1.00 | 26.81 | C |
| ATOM | 792 | OG | SER | A | 49 | -10.691 | -8.878 | -5.111 | 1.00 | 33.40 | O |
| ATOM | 794 | C | SER | A | 49 | -10.751 | -5.588 | -5.144 | 1.00 | 30.07 | C |
| ATOM | 795 | O | SER | A | 49 | -11.500 | -4.830 | -4.544 | 1.00 | 31.68 | O |
| ATOM | 797 | N | ASP | A | 50 | -9.427 | -5.448 | -5.126 | 1.00 | 33.58 | N |
| ATOM | 798 | CA | ASP | A | 50 | -8.745 | -4.559 | -4.172 | 1.00 | 35.29 | C |
| ATOM | 800 | CB | ASP | A | 50 | -7.207 | -4.647 | -4.351 | 1.00 | 36.94 | C |
| ATOM | 803 | CG | ASP | A | 50 | -6.591 | -5.777 | -3.513 | 1.00 | 38.10 | C |
| ATOM | 804 | OD1 | ASP | A | 50 | -7.324 | -6.461 | -2.764 | 1.00 | 41.46 | O |
| ATOM | 805 | OD2 | ASP | A | 50 | -5.370 | -5.988 | -3.608 | 1.00 | 44.96 | O |
| ATOM | 806 | C | ASP | A | 50 | -9.215 | -3.122 | -4.220 | 1.00 | 35.74 | C |
| ATOM | 807 | O | ASP | A | 50 | -9.446 | -2.576 | -5.278 | 1.00 | 36.08 | O |
| ATOM | 809 | N | PHE | A | 51 | -9.375 | -2.518 | -3.036 | 1.00 | 36.46 | N |
| ATOM | 810 | CA | PHE | A | 51 | -9.741 | -1.093 | -2.893 | 1.00 | 35.69 | C |
| ATOM | 812 | CB | PHE | A | 51 | -8.895 | -0.148 | -3.771 | 1.00 | 36.43 | C |
| ATOM | 815 | CG | PHE | A | 51 | -7.434 | -0.370 | -3.703 | 1.00 | 39.21 | C |
| ATOM | 816 | CD1 | PHE | A | 51 | -6.775 | -0.514 | -2.469 | 1.00 | 42.51 | C |
| ATOM | 818 | CE1 | PHE | A | 51 | -5.383 | -0.694 | -2.415 | 1.00 | 42.42 | C |
| ATOM | 820 | CZ | PHE | A | 51 | -4.666 | -0.716 | -3.575 | 1.00 | 44.11 | C |
| ATOM | 822 | CE2 | PHE | A | 51 | -5.318 | -0.547 | -4.817 | 1.00 | 42.67 | C |
| ATOM | 824 | CD2 | PHE | A | 51 | -6.681 | -0.365 | -4.872 | 1.00 | 40.16 | C |
| ATOM | 826 | C | PHE | A | 51 | -11.165 | -0.748 | -3.233 | 1.00 | 34.79 | C |
| ATOM | 827 | O | PHE | A | 51 | -11.519 | 0.430 | -3.153 | 1.00 | 35.95 | O |
| ATOM | 829 | N | HIS | A | 52 | -11.987 | -1.720 | -3.616 | 1.00 | 33.61 | N |
| ATOM | 830 | CA | HIS | A | 52 | -13.339 | -1.425 | -4.090 | 1.00 | 32.70 | C |
| ATOM | 832 | CB | HIS | A | 52 | -13.633 | -2.213 | -5.382 | 1.00 | 32.49 | C |
| ATOM | 835 | CG | HIS | A | 52 | -12.716 | -1.820 | -6.477 | 1.00 | 35.73 | C |
| ATOM | 836 | ND1 | HIS | A | 52 | -11.546 | -2.495 | -6.737 | 1.00 | 39.01 | N |
| ATOM | 838 | CE1 | HIS | A | 52 | -10.877 | -1.860 | -7.692 | 1.00 | 39.74 | C |
| ATOM | 840 | NE2 | HIS | A | 52 | -11.563 | -0.788 | -8.042 | 1.00 | 37.46 | N |
| ATOM | 842 | CD2 | HIS | A | 52 | -12.706 | -0.723 | -7.277 | 1.00 | 38.30 | C |
| ATOM | 844 | C | HIS | A | 52 | -14.353 | -1.722 | -3.014 | 1.00 | 30.80 | C |
| ATOM | 845 | O | HIS | A | 52 | -14.510 | -2.844 | -2.597 | 1.00 | 28.92 | O |
| ATOM | 847 | N | PHE | A | 53 | -15.072 | -0.699 | -2.598 | 1.00 | 29.95 | N |
| ATOM | 848 | CA | PHE | A | 53 | -16.109 | -0.874 | -1.601 | 1.00 | 29.74 | C |
| ATOM | 850 | CB | PHE | A | 53 | -15.641 | -0.239 | -0.292 | 1.00 | 29.37 | C |
| ATOM | 853 | CG | PHE | A | 53 | -14.370 | -0.825 | 0.197 | 1.00 | 29.01 | C |
| ATOM | 854 | CD1 | PHE | A | 53 | -14.367 | -1.960 | 0.969 | 1.00 | 31.98 | C |
| ATOM | 856 | CE1 | PHE | A | 53 | -13.172 | -2.517 | 1.404 | 1.00 | 32.29 | C |
| ATOM | 858 | CZ | PHE | A | 53 | -11.985 | -1.975 | 1.048 | 1.00 | 31.74 | C |
| ATOM | 860 | CE2 | PHE | A | 53 | -11.983 | -0.860 | 0.243 | 1.00 | 35.12 | C |
| ATOM | 862 | CD2 | PHE | A | 53 | -13.185 | -0.295 | -0.178 | 1.00 | 31.45 | C |
| ATOM | 864 | C | PHE | A | 53 | -17.396 | -0.294 | -2.086 | 1.00 | 29.76 | C |
| ATOM | 865 | O | PHE | A | 53 | -17.477 | 0.178 | -3.197 | 1.00 | 28.42 | O |
| ATOM | 867 | N | ILE | A | 54 | -18.406 | -0.342 | -1.232 | 1.00 | 30.62 | N |
| ATOM | 868 | CA | ILE | A | 54 | -19.725 | 0.193 | -1.550 | 1.00 | 30.36 | C |
| ATOM | 870 | CB | ILE | A | 54 | -20.850 | -0.879 | -1.489 | 1.00 | 29.74 | C |

FIG.4-10

| | | | | | | | | | | | |
|---|---|---|---|---|---|---|---|---|---|---|---|
| ATOM | 872 | CG1 | ILE | A | 54 | -20.465 | -2.125 | -2.288 | 1.00 | 29.55 | C |
| ATOM | 875 | CD1 | ILE | A | 54 | -20.790 | -2.049 | -3.677 | 1.00 | 31.07 | C |
| ATOM | 879 | CG2 | ILE | A | 54 | -22.222 | -0.272 | -1.953 | 1.00 | 29.02 | C |
| ATOM | 883 | C | ILE | A | 54 | -19.983 | 1.158 | -0.422 | 1.00 | 31.02 | C |
| ATOM | 884 | O | ILE | A | 54 | -19.790 | 0.764 | 0.724 | 1.00 | 29.51 | O |
| ATOM | 886 | N | ASP | A | 55 | -20.389 | 2.399 | -0.753 | 1.00 | 32.46 | N |
| ATOM | 887 | CA | ASP | A | 55 | -20.611 | 3.461 | 0.252 | 1.00 | 33.38 | C |
| ATOM | 889 | CB | ASP | A | 55 | -20.168 | 4.839 | -0.264 | 1.00 | 33.28 | C |
| ATOM | 892 | CG | ASP | A | 55 | -21.113 | 5.438 | -1.328 | 1.00 | 35.07 | C |
| ATOM | 893 | OD1 | ASP | A | 55 | -22.137 | 4.800 | -1.699 | 1.00 | 34.63 | O |
| ATOM | 894 | OD2 | ASP | A | 55 | -20.811 | 6.570 | -1.810 | 1.00 | 34.87 | O |
| ATOM | 895 | C | ASP | A | 55 | -22.063 | 3.485 | 0.674 | 1.00 | 34.60 | C |
| ATOM | 896 | O | ASP | A | 55 | -22.862 | 2.633 | 0.286 | 1.00 | 32.29 | O |
| ATOM | 898 | N | GLU | A | 56 | -22.396 | 4.473 | 1.490 | 1.00 | 36.97 | N |
| ATOM | 899 | CA | GLU | A | 56 | -23.736 | 4.560 | 2.064 | 1.00 | 39.09 | C |
| ATOM | 901 | CB | GLU | A | 56 | -23.792 | 5.715 | 3.084 | 1.00 | 39.40 | C |
| ATOM | 904 | CG | GLU | A | 56 | -23.009 | 5.340 | 4.371 | 1.00 | 41.09 | C |
| ATOM | 907 | CD | GLU | A | 56 | -22.944 | 6.455 | 5.397 | 1.00 | 42.83 | C |
| ATOM | 908 | OE1 | GLU | A | 56 | -22.309 | 7.461 | 5.099 | 1.00 | 46.74 | O |
| ATOM | 909 | OE2 | GLU | A | 56 | -23.531 | 6.332 | 6.501 | 1.00 | 45.11 | O |
| ATOM | 910 | C | GLU | A | 56 | -24.833 | 4.630 | 0.974 | 1.00 | 39.80 | C |
| ATOM | 911 | O | GLU | A | 56 | -25.883 | 4.044 | 1.144 | 1.00 | 40.55 | O |
| ATOM | 913 | N | ARG | A | 57 | -24.538 | 5.260 | -0.168 | 1.00 | 40.80 | N |
| ATOM | 914 | CA | ARG | A | 57 | -25.448 | 5.318 | -1.327 | 1.00 | 40.68 | C |
| ATOM | 916 | CB | ARG | A | 57 | -24.983 | 6.410 | -2.303 | 1.00 | 40.79 | C |
| ATOM | 919 | CG | ARG | A | 57 | -24.801 | 7.815 | -1.758 | 1.00 | 39.77 | C |
| ATOM | 922 | CD | ARG | A | 57 | -24.097 | 8.679 | -2.807 | 1.00 | 38.90 | C |
| ATOM | 925 | NE | ARG | A | 57 | -22.697 | 8.302 | -2.948 | 1.00 | 38.83 | N |
| ATOM | 927 | CZ | ARG | A | 57 | -21.917 | 8.583 | -3.997 | 1.00 | 40.06 | C |
| ATOM | 928 | NH1 | ARG | A | 57 | -22.360 | 9.261 | -5.042 | 1.00 | 38.85 | N |
| ATOM | 931 | NH2 | ARG | A | 57 | -20.665 | 8.163 | -4.011 | 1.00 | 40.10 | N |
| ATOM | 934 | C | ARG | A | 57 | -25.562 | 4.031 | -2.174 | 1.00 | 41.31 | C |
| ATOM | 935 | O | ARG | A | 57 | -26.278 | 4.025 | -3.184 | 1.00 | 42.62 | O |
| ATOM | 937 | N | GLY | A | 58 | -24.848 | 2.957 | -1.862 | 1.00 | 40.49 | N |
| ATOM | 938 | CA | GLY | A | 58 | -24.848 | 1.810 | -2.812 | 1.00 | 39.29 | C |
| ATOM | 941 | C | GLY | A | 58 | -23.957 | 2.045 | -4.030 | 1.00 | 37.83 | C |
| ATOM | 942 | O | GLY | A | 58 | -23.980 | 1.276 | -4.989 | 1.00 | 36.76 | O |
| ATOM | 944 | N | GLU | A | 59 | -23.160 | 3.114 | -3.997 | 1.00 | 37.02 | N |
| ATOM | 945 | CA | GLU | A | 59 | -22.234 | 3.423 | -5.093 | 1.00 | 36.11 | C |
| ATOM | 947 | CB | GLU | A | 59 | -22.101 | 4.939 | -5.263 | 1.00 | 36.60 | C |
| ATOM | 950 | CG | GLU | A | 59 | -23.368 | 5.649 | -5.722 | 1.00 | 37.72 | C |
| ATOM | 953 | CD | GLU | A | 59 | -23.748 | 5.344 | -7.188 | 1.00 | 42.53 | C |
| ATOM | 954 | OE1 | GLU | A | 59 | -22.836 | 5.093 | -8.022 | 1.00 | 38.87 | O |
| ATOM | 955 | OE2 | GLU | A | 59 | -24.963 | 5.347 | -7.480 | 1.00 | 44.08 | O |
| ATOM | 956 | C | GLU | A | 59 | -20.841 | 2.792 | -4.886 | 1.00 | 36.10 | C |
| ATOM | 957 | O | GLU | A | 59 | -20.432 | 2.514 | -3.741 | 1.00 | 34.00 | O |
| ATOM | 959 | N | SER | A | 60 | -20.133 | 2.555 | -6.008 | 1.00 | 36.08 | N |
| ATOM | 960 | CA | SER | A | 60 | -18.803 | 1.965 | -5.997 | 1.00 | 36.64 | C |
| ATOM | 962 | CB | SER | A | 60 | -18.379 | 1.429 | -7.374 | 1.00 | 36.60 | C |
| ATOM | 965 | OG | SER | A | 60 | -17.185 | 0.633 | -7.259 | 1.00 | 38.00 | O |
| ATOM | 967 | C | SER | A | 60 | -17.877 | 3.062 | -5.593 | 1.00 | 37.06 | C |
| ATOM | 968 | O | SER | A | 60 | -17.976 | 4.156 | -6.126 | 1.00 | 39.81 | O |
| ATOM | 970 | N | ILE | A | 61 | -16.982 | 2.804 | -4.660 | 1.00 | 36.48 | N |
| ATOM | 971 | CA | ILE | A | 61 | -15.957 | 3.792 | -4.334 | 1.00 | 36.52 | C |
| ATOM | 973 | CB | ILE | A | 61 | -16.244 | 4.524 | -2.960 | 1.00 | 36.18 | C |
| ATOM | 975 | CG1 | ILE | A | 61 | -16.331 | 3.515 | -1.803 | 1.00 | 35.09 | C |
| ATOM | 978 | CD1 | ILE | A | 61 | -16.023 | 4.122 | -0.441 | 1.00 | 37.25 | C |
| ATOM | 982 | CG2 | ILE | A | 61 | -17.505 | 5.320 | -3.041 | 1.00 | 36.52 | C |
| ATOM | 986 | C | ILE | A | 61 | -14.652 | 3.045 | -4.254 | 1.00 | 36.45 | C |
| ATOM | 987 | O | ILE | A | 61 | -14.641 | 1.824 | -4.157 | 1.00 | 36.79 | O |
| ATOM | 989 | N | ILE | A | 62 | -13.561 | 3.796 | -4.301 | 1.00 | 38.15 | N |
| ATOM | 990 | CA | ILE | A | 62 | -12.195 | 3.285 | -4.169 | 1.00 | 38.42 | C |
| ATOM | 992 | CB | ILE | A | 62 | -11.327 | 3.686 | -5.393 | 1.00 | 38.22 | C |

FIG.4-11

| | | | | | | | | | | | |
|---|---|---|---|---|---|---|---|---|---|---|---|
| ATOM | 994 | CG1 | ILE | A | 62 | -11.674 | 2.834 | -6.617 | 1.00 | 39.63 | C |
| ATOM | 997 | CD1 | ILE | A | 62 | -11.127 | 3.420 | -7.948 | 1.00 | 39.20 | C |
| ATOM | 1001 | CG2 | ILE | A | 62 | -9.827 | 3.502 | -5.116 | 1.00 | 37.26 | C |
| ATOM | 1005 | C | ILE | A | 62 | -11.573 | 3.836 | -2.866 | 1.00 | 38.94 | C |
| ATOM | 1006 | O | ILE | A | 62 | -11.695 | 5.027 | -2.561 | 1.00 | 38.86 | O |
| ATOM | 1008 | N | VAL | A | 63 | -10.944 | 2.960 | -2.096 | 1.00 | 39.30 | N |
| ATOM | 1009 | CA | VAL | A | 63 | -10.259 | 3.371 | -0.885 | 1.00 | 40.85 | C |
| ATOM | 1011 | CB | VAL | A | 63 | -11.128 | 3.252 | 0.397 | 1.00 | 40.45 | C |
| ATOM | 1013 | CG1 | VAL | A | 63 | -10.287 | 3.695 | 1.603 | 1.00 | 40.89 | C |
| ATOM | 1017 | CG2 | VAL | A | 63 | -12.362 | 4.110 | 0.291 | 1.00 | 41.72 | C |
| ATOM | 1021 | C | VAL | A | 63 | -8.994 | 2.558 | -0.643 | 1.00 | 41.66 | C |
| ATOM | 1022 | O | VAL | A | 63 | -9.044 | 1.352 | -0.400 | 1.00 | 40.46 | O |
| ATOM | 1024 | N | GLU | A | 64 | -7.864 | 3.247 | -0.664 | 1.00 | 44.26 | N |
| ATOM | 1025 | CA | GLU | A | 64 | -6.581 | 2.589 | -0.586 | 1.00 | 46.11 | C |
| ATOM | 1027 | CB | GLU | A | 64 | -5.793 | 2.808 | -1.878 | 1.00 | 46.95 | C |
| ATOM | 1030 | CG | GLU | A | 64 | -5.387 | 4.252 | -2.157 | 1.00 | 50.19 | C |
| ATOM | 1033 | CD | GLU | A | 64 | -4.832 | 4.421 | -3.555 | 1.00 | 55.07 | C |
| ATOM | 1034 | OE1 | GLU | A | 64 | -5.160 | 3.568 | -4.422 | 1.00 | 58.64 | O |
| ATOM | 1035 | OE2 | GLU | A | 64 | -4.068 | 5.396 | -3.791 | 1.00 | 56.49 | O |
| ATOM | 1036 | C | GLU | A | 64 | -5.817 | 3.089 | 0.605 | 1.00 | 46.65 | C |
| ATOM | 1037 | O | GLU | A | 64 | -4.871 | 2.416 | 1.025 | 1.00 | 48.61 | O |
| ATOM | 1039 | N | ASN | A | 69 | -9.699 | -5.137 | 4.836 | 1.00 | 50.30 | N |
| ATOM | 1040 | CA | ASN | A | 69 | -9.802 | -5.461 | 6.261 | 1.00 | 50.93 | C |
| ATOM | 1042 | CB | ASN | A | 69 | -8.423 | -5.348 | 6.949 | 1.00 | 51.20 | C |
| ATOM | 1045 | CG | ASN | A | 69 | -7.534 | -6.523 | 6.676 | 1.00 | 53.81 | C |
| ATOM | 1046 | OD1 | ASN | A | 69 | -7.366 | -6.926 | 5.520 | 1.00 | 56.28 | O |
| ATOM | 1047 | ND2 | ASN | A | 69 | -6.929 | -7.086 | 7.744 | 1.00 | 55.89 | N |
| ATOM | 1050 | C | ASN | A | 69 | -10.804 | -4.548 | 6.991 | 1.00 | 49.52 | C |
| ATOM | 1051 | O | ASN | A | 69 | -12.024 | -4.770 | 6.940 | 1.00 | 50.35 | O |
| ATOM | 1053 | N | ALA | A | 70 | -10.273 | -3.493 | 7.610 | 1.00 | 47.79 | N |
| ATOM | 1054 | CA | ALA | A | 70 | -11.027 | -2.551 | 8.482 | 1.00 | 46.02 | C |
| ATOM | 1056 | CB | ALA | A | 70 | -10.095 | -1.393 | 8.917 | 1.00 | 45.20 | C |
| ATOM | 1060 | C | ALA | A | 70 | -12.329 | -1.993 | 7.853 | 1.00 | 43.84 | C |
| ATOM | 1061 | O | ALA | A | 70 | -13.152 | -1.387 | 8.550 | 1.00 | 45.49 | O |
| ATOM | 1063 | N | LEU | A | 71 | -12.506 | -2.208 | 6.553 | 1.00 | 40.70 | N |
| ATOM | 1064 | CA | LEU | A | 71 | -13.664 | -1.724 | 5.808 | 1.00 | 38.26 | C |
| ATOM | 1066 | CB | LEU | A | 71 | -13.178 | -0.799 | 4.679 | 1.00 | 37.81 | C |
| ATOM | 1069 | CG | LEU | A | 71 | -14.076 | 0.322 | 4.165 | 1.00 | 35.97 | C |
| ATOM | 1071 | CD1 | LEU | A | 71 | -14.811 | 1.089 | 5.312 | 1.00 | 30.90 | C |
| ATOM | 1075 | CD2 | LEU | A | 71 | -13.167 | 1.269 | 3.355 | 1.00 | 31.34 | C |
| ATOM | 1079 | C | LEU | A | 71 | -14.414 | -2.950 | 5.275 | 1.00 | 36.69 | C |
| ATOM | 1080 | O | LEU | A | 71 | -13.859 | -3.751 | 4.506 | 1.00 | 36.93 | O |
| ATOM | 1082 | N | LEU | A | 72 | -15.655 | -3.107 | 5.706 | 1.00 | 34.62 | N |
| ATOM | 1083 | CA | LEU | A | 72 | -16.363 | -4.380 | 5.567 | 1.00 | 33.79 | C |
| ATOM | 1085 | CB | LEU | A | 72 | -17.089 | -4.697 | 6.873 | 1.00 | 34.75 | C |
| ATOM | 1088 | CG | LEU | A | 72 | -16.263 | -4.782 | 8.171 | 1.00 | 36.57 | C |
| ATOM | 1090 | CD1 | LEU | A | 72 | -17.229 | -5.172 | 9.290 | 1.00 | 36.78 | C |
| ATOM | 1094 | CD2 | LEU | A | 72 | -15.123 | -5.823 | 8.033 | 1.00 | 34.27 | C |
| ATOM | 1098 | C | LEU | A | 72 | -17.374 | -4.392 | 4.398 | 1.00 | 31.42 | C |
| ATOM | 1099 | O | LEU | A | 72 | -17.904 | -5.442 | 4.051 | 1.00 | 30.18 | O |
| ATOM | 1101 | N | LYS | A | 73 | -17.659 | -3.246 | 3.810 | 1.00 | 29.50 | N |
| ATOM | 1102 | CA | LYS | A | 73 | -18.592 | -3.226 | 2.651 | 1.00 | 29.77 | C |
| ATOM | 1104 | CB | LYS | A | 73 | -19.534 | -2.034 | 2.709 | 1.00 | 30.39 | C |
| ATOM | 1107 | CG | LYS | A | 73 | -20.853 | -2.377 | 3.466 | 1.00 | 32.55 | C |
| ATOM | 1110 | CD | LYS | A | 73 | -21.774 | -3.200 | 2.533 | 1.00 | 38.94 | C |
| ATOM | 1113 | CE | LYS | A | 73 | -23.291 | -2.935 | 2.766 | 1.00 | 44.43 | C |
| ATOM | 1116 | NZ | LYS | A | 73 | -24.173 | -3.378 | 1.609 | 1.00 | 47.06 | N |
| ATOM | 1120 | C | LYS | A | 73 | -17.902 | -3.396 | 1.284 | 1.00 | 27.45 | C |
| ATOM | 1121 | O | LYS | A | 73 | -17.762 | -2.455 | 0.523 | 1.00 | 27.16 | O |
| ATOM | 1123 | N | HIS | A | 74 | -17.478 | -4.624 | 1.032 | 1.00 | 25.84 | N |
| ATOM | 1124 | CA | HIS | A | 74 | -16.683 | -5.005 | -0.157 | 1.00 | 26.65 | C |
| ATOM | 1126 | CB | HIS | A | 74 | -16.084 | -6.403 | 0.045 | 1.00 | 26.92 | C |
| ATOM | 1129 | CG | HIS | A | 74 | -15.125 | -6.465 | 1.176 | 1.00 | 31.99 | C |

FIG.4-12

| | | | | | | | | | | | |
|---|---|---|---|---|---|---|---|---|---|---|---|
| ATOM | 1130 | ND1 | HIS | A | 74 | -14.808 | -7.627 | 1.840 | 1.00 | 34.39 | N |
| ATOM | 1132 | CE1 | HIS | A | 74 | -13.914 | -7.366 | 2.780 | 1.00 | 35.49 | C |
| ATOM | 1134 | NE2 | HIS | A | 74 | -13.646 | -6.076 | 2.754 | 1.00 | 35.02 | N |
| ATOM | 1136 | CD2 | HIS | A | 74 | -14.395 | -5.492 | 1.761 | 1.00 | 35.96 | C |
| ATOM | 1138 | C | HIS | A | 74 | -17.525 | -5.072 | -1.391 | 1.00 | 23.93 | C |
| ATOM | 1139 | O | HIS | A | 74 | -18.553 | -5.692 | -1.375 | 1.00 | 24.65 | O |
| ATOM | 1141 | N | ARG | A | 75 | -17.074 | -4.493 | -2.480 | 1.00 | 23.49 | N |
| ATOM | 1142 | CA | ARG | A | 75 | -17.809 | -4.603 | -3.765 | 1.00 | 22.29 | C |
| ATOM | 1144 | CB | ARG | A | 75 | -17.343 | -3.542 | -4.803 | 1.00 | 22.01 | C |
| ATOM | 1147 | CG | ARG | A | 75 | -18.051 | -3.752 | -6.184 | 1.00 | 23.60 | C |
| ATOM | 1150 | CD | ARG | A | 75 | -17.769 | -2.714 | -7.198 | 1.00 | 24.27 | C |
| ATOM | 1153 | NE | ARG | A | 75 | -18.534 | -2.960 | -8.405 | 1.00 | 27.56 | N |
| ATOM | 1155 | CZ | ARG | A | 75 | -18.511 | -2.213 | -9.502 | 1.00 | 24.04 | C |
| ATOM | 1156 | NH1 | ARG | A | 75 | -17.780 | -1.126 | -9.587 | 1.00 | 28.81 | N |
| ATOM | 1159 | NH2 | ARG | A | 75 | -19.259 | -2.557 | -10.496 | 1.00 | 27.51 | N |
| ATOM | 1162 | C | ARG | A | 75 | -17.779 | -6.002 | -4.362 | 1.00 | 21.43 | C |
| ATOM | 1163 | O | ARG | A | 75 | -18.765 | -6.429 | -4.938 | 1.00 | 23.45 | O |
| ATOM | 1165 | N | PHE | A | 76 | -16.651 | -6.709 | -4.270 | 1.00 | 21.36 | N |
| ATOM | 1166 | CA | PHE | A | 76 | -16.536 | -8.069 | -4.821 | 1.00 | 21.10 | C |
| ATOM | 1168 | CB | PHE | A | 76 | -15.330 | -8.131 | -5.771 | 1.00 | 19.96 | C |
| ATOM | 1171 | CG | PHE | A | 76 | -15.412 | -7.153 | -6.852 | 1.00 | 21.31 | C |
| ATOM | 1172 | CD1 | PHE | A | 76 | -16.231 | -7.399 | -7.962 | 1.00 | 19.74 | C |
| ATOM | 1174 | CE1 | PHE | A | 76 | -16.364 | -6.446 | -8.985 | 1.00 | 19.45 | C |
| ATOM | 1176 | CZ | PHE | A | 76 | -15.753 | -5.300 | -8.906 | 1.00 | 16.56 | C |
| ATOM | 1178 | CE2 | PHE | A | 76 | -14.922 | -5.017 | -7.808 | 1.00 | 18.83 | C |
| ATOM | 1180 | CD2 | PHE | A | 76 | -14.791 | -5.939 | -6.751 | 1.00 | 19.24 | C |
| ATOM | 1182 | C | PHE | A | 76 | -16.338 | -9.143 | -3.748 | 1.00 | 20.61 | C |
| ATOM | 1183 | O | PHE | A | 76 | -15.537 | -8.934 | -2.848 | 1.00 | 20.88 | O |
| ATOM | 1185 | N | GLU | A | 77 | -17.030 | -10.273 | -3.877 | 1.00 | 20.45 | N |
| ATOM | 1186 | CA | GLU | A | 77 | -16.632 | -11.489 | -3.184 | 1.00 | 20.69 | C |
| ATOM | 1188 | CB | GLU | A | 77 | -17.797 | -12.436 | -2.940 | 1.00 | 21.46 | C |
| ATOM | 1191 | CG | GLU | A | 77 | -17.538 | -13.402 | -1.730 | 1.00 | 23.66 | C |
| ATOM | 1194 | CD | GLU | A | 77 | -17.471 | -12.674 | -0.396 | 1.00 | 26.23 | C |
| ATOM | 1195 | OE1 | GLU | A | 77 | -18.410 | -11.952 | -0.052 | 1.00 | 34.43 | O |
| ATOM | 1196 | OE2 | GLU | A | 77 | -16.479 | -12.817 | 0.329 | 1.00 | 31.80 | O |
| ATOM | 1197 | C | GLU | A | 77 | -15.590 | -12.208 | -4.015 | 1.00 | 21.50 | C |
| ATOM | 1198 | O | GLU | A | 77 | -15.820 | -12.502 | -5.177 | 1.00 | 20.48 | O |
| ATOM | 1200 | N | ILE | A | 78 | -14.468 | -12.538 | -3.392 | 1.00 | 21.53 | N |
| ATOM | 1201 | CA | ILE | A | 78 | -13.438 | -13.321 | -4.057 | 1.00 | 22.68 | C |
| ATOM | 1203 | CB | ILE | A | 78 | -12.091 | -13.044 | -3.458 | 1.00 | 23.45 | C |
| ATOM | 1205 | CG1 | ILE | A | 78 | -10.991 | -13.951 | -4.034 | 1.00 | 24.51 | C |
| ATOM | 1208 | CD1 | ILE | A | 78 | -10.754 | -13.790 | -5.423 | 1.00 | 24.46 | C |
| ATOM | 1212 | CG2 | ILE | A | 78 | -12.092 | -13.324 | -1.879 | 1.00 | 24.26 | C |
| ATOM | 1216 | C | ILE | A | 78 | -13.740 | -14.805 | -3.933 | 1.00 | 22.92 | C |
| ATOM | 1217 | O | ILE | A | 78 | -13.859 | -15.293 | -2.811 | 1.00 | 23.85 | O |
| ATOM | 1219 | N | ILE | A | 79 | -13.931 | -15.494 | -5.085 | 1.00 | 21.80 | N |
| ATOM | 1220 | CA | ILE | A | 79 | -14.250 | -16.923 | -5.158 | 1.00 | 19.88 | C |
| ATOM | 1222 | CB | ILE | A | 79 | -15.485 | -17.209 | -6.069 | 1.00 | 20.09 | C |
| ATOM | 1224 | CG1 | ILE | A | 79 | -16.745 | -16.541 | -5.481 | 1.00 | 20.63 | C |
| ATOM | 1227 | CD1 | ILE | A | 79 | -17.744 | -16.082 | -6.465 | 1.00 | 23.17 | C |
| ATOM | 1231 | CG2 | ILE | A | 79 | -15.783 | -18.773 | -6.198 | 1.00 | 16.69 | C |
| ATOM | 1235 | C | ILE | A | 79 | -12.981 | -17.745 | -5.550 | 1.00 | 20.44 | C |
| ATOM | 1236 | O | ILE | A | 79 | -12.751 | -18.790 | -4.980 | 1.00 | 19.75 | O |
| ATOM | 1238 | N | GLU | A | 80 | -12.139 | -17.242 | -6.450 | 1.00 | 19.89 | N |
| ATOM | 1239 | CA | GLU | A | 80 | -10.868 | -17.885 | -6.810 | 1.00 | 20.47 | C |
| ATOM | 1241 | CB | GLU | A | 80 | -10.116 | -17.073 | -7.936 | 1.00 | 21.83 | C |
| ATOM | 1244 | CG | GLU | A | 80 | -8.984 | -17.851 | -8.730 | 1.00 | 22.70 | C |
| ATOM | 1247 | CD | GLU | A | 80 | -9.368 | -19.280 | -9.169 | 1.00 | 26.61 | C |
| ATOM | 1248 | OE1 | GLU | A | 80 | -9.892 | -19.522 | -10.337 | 1.00 | 26.94 | O |
| ATOM | 1249 | OE2 | GLU | A | 80 | -9.164 | -20.176 | -8.333 | 1.00 | 25.79 | O |
| ATOM | 1250 | C | GLU | A | 80 | -9.957 | -17.918 | -5.642 | 1.00 | 20.93 | C |
| ATOM | 1251 | O | GLU | A | 80 | -9.918 | -16.978 | -4.850 | 1.00 | 20.60 | O |
| ATOM | 1253 | N | GLY | A | 81 | -9.226 | -19.011 | -5.523 | 1.00 | 19.93 | N |

FIG.4-13

| | | | | | | | | | | | |
|---|---|---|---|---|---|---|---|---|---|---|---|
| ATOM | 1254 | CA | GLY | A | 81 | -8.220 | -19.122 | -4.550 | 1.00 | 19.78 | C |
| ATOM | 1257 | C | GLY | A | 81 | -8.748 | -20.015 | -3.479 | 1.00 | 20.64 | C |
| ATOM | 1258 | O | GLY | A | 81 | -7.981 | -20.616 | -2.795 | 1.00 | 21.05 | O |
| ATOM | 1260 | N | ARG | A | 82 | -10.073 | -20.103 | -3.309 | 1.00 | 21.77 | N |
| ATOM | 1261 | CA | ARG | A | 82 | -10.638 | -21.006 | -2.275 | 1.00 | 21.34 | C |
| ATOM | 1263 | CB | ARG | A | 82 | -12.043 | -20.525 | -1.906 | 1.00 | 21.09 | C |
| ATOM | 1266 | CG | ARG | A | 82 | -12.135 | -19.091 | -1.313 | 1.00 | 19.98 | C |
| ATOM | 1269 | CD | ARG | A | 82 | -13.552 | -18.784 | -1.148 | 1.00 | 20.28 | C |
| ATOM | 1272 | NE | ARG | A | 82 | -13.925 | -17.401 | -0.934 | 1.00 | 21.64 | N |
| ATOM | 1274 | CZ | ARG | A | 82 | -14.331 | -16.883 | 0.224 | 1.00 | 19.55 | C |
| ATOM | 1275 | NH1 | ARG | A | 82 | -14.271 | -17.565 | 1.337 | 1.00 | 17.21 | N |
| ATOM | 1278 | NH2 | ARG | A | 82 | -14.665 | -15.624 | 0.284 | 1.00 | 22.68 | N |
| ATOM | 1281 | C | ARG | A | 82 | -10.690 | -22.443 | -2.762 | 1.00 | 21.95 | C |
| ATOM | 1282 | O | ARG | A | 82 | -10.862 | -22.668 | -3.956 | 1.00 | 21.32 | O |
| ATOM | 1284 | N | ASP | A | 83 | -10.566 | -23.444 | -1.868 | 1.00 | 22.70 | N |
| ATOM | 1285 | CA | ASP | A | 83 | -11.013 | -24.810 | -2.189 | 1.00 | 22.14 | C |
| ATOM | 1287 | CB | ASP | A | 83 | -10.708 | -25.780 | -1.053 | 1.00 | 24.64 | C |
| ATOM | 1290 | CG | ASP | A | 83 | -11.499 | -25.490 | 0.220 | 1.00 | 29.11 | C |
| ATOM | 1291 | OD1 | ASP | A | 83 | -12.691 | -25.853 | 0.285 | 1.00 | 34.82 | O |
| ATOM | 1292 | OD2 | ASP | A | 83 | -10.905 | -24.912 | 1.183 | 1.00 | 38.03 | O |
| ATOM | 1293 | C | ASP | A | 83 | -12.501 | -24.887 | -2.650 | 1.00 | 22.32 | C |
| ATOM | 1294 | O | ASP | A | 83 | -13.264 | -23.926 | -2.433 | 1.00 | 21.71 | O |
| ATOM | 1296 | N | ARG | A | 84 | -12.847 | -25.968 | -3.402 | 1.00 | 21.87 | N |
| ATOM | 1297 | CA | ARG | A | 84 | -14.170 | -26.164 | -3.982 | 1.00 | 21.71 | C |
| ATOM | 1299 | CB | ARG | A | 84 | -14.200 | -27.352 | -4.958 | 1.00 | 22.42 | C |
| ATOM | 1302 | CG | ARG | A | 84 | -13.356 | -27.108 | -6.234 | 1.00 | 24.99 | C |
| ATOM | 1305 | CD | ARG | A | 84 | -13.705 | -27.915 | -7.495 | 1.00 | 33.08 | C |
| ATOM | 1308 | NE | ARG | A | 84 | -12.898 | -29.121 | -7.539 | 1.00 | 37.24 | N |
| ATOM | 1310 | CZ | ARG | A | 84 | -12.403 | -29.720 | -8.617 | 1.00 | 35.66 | C |
| ATOM | 1311 | NH1 | ARG | A | 84 | -12.622 | -29.278 | -9.868 | 1.00 | 39.32 | N |
| ATOM | 1314 | NH2 | ARG | A | 84 | -11.718 | -30.840 | -8.426 | 1.00 | 35.09 | N |
| ATOM | 1317 | C | ARG | A | 84 | -15.340 | -26.231 | -2.959 | 1.00 | 21.04 | C |
| ATOM | 1318 | O | ARG | A | 84 | -16.415 | -25.747 | -3.240 | 1.00 | 20.23 | O |
| ATOM | 1320 | N | ILE | A | 85 | -15.085 | -26.730 | -1.768 | 1.00 | 20.61 | N |
| ATOM | 1321 | CA | ILE | A | 85 | -16.091 | -26.779 | -0.717 | 1.00 | 21.35 | C |
| ATOM | 1323 | CB | ILE | A | 85 | -15.551 | -27.556 | 0.555 | 1.00 | 22.56 | C |
| ATOM | 1325 | CG1 | ILE | A | 85 | -15.196 | -28.982 | 0.166 | 1.00 | 20.56 | C |
| ATOM | 1328 | CD1 | ILE | A | 85 | -14.091 | -29.593 | 1.026 | 1.00 | 21.78 | C |
| ATOM | 1332 | CG2 | ILE | A | 85 | -16.544 | -27.523 | 1.708 | 1.00 | 22.29 | C |
| ATOM | 1336 | C | ILE | A | 85 | -16.507 | -25.396 | -0.344 | 1.00 | 20.16 | C |
| ATOM | 1337 | O | ILE | A | 85 | -17.699 | -25.074 | -0.351 | 1.00 | 20.10 | O |
| ATOM | 1339 | N | MET | A | 86 | -15.515 | -24.553 | -0.062 | 1.00 | 19.64 | N |
| ATOM | 1340 | CA | MET | A | 86 | -15.770 | -23.208 | 0.368 | 1.00 | 18.69 | C |
| ATOM | 1342 | CB | MET | A | 86 | -14.548 | -22.623 | 1.097 | 1.00 | 19.83 | C |
| ATOM | 1345 | CG | MET | A | 86 | -14.434 | -23.111 | 2.573 | 1.00 | 22.33 | C |
| ATOM | 1348 | SD | MET | A | 86 | -15.951 | -22.818 | 3.515 | 1.00 | 36.97 | S |
| ATOM | 1349 | CE | MET | A | 86 | -16.285 | -21.118 | 3.278 | 1.00 | 16.27 | C |
| ATOM | 1353 | C | MET | A | 86 | -16.172 | -22.311 | -0.785 | 1.00 | 18.74 | C |
| ATOM | 1354 | O | MET | A | 86 | -16.992 | -21.401 | -0.584 | 1.00 | 16.67 | O |
| ATOM | 1356 | N | ALA | A | 87 | -15.593 | -22.548 | -1.984 | 1.00 | 17.76 | N |
| ATOM | 1357 | CA | ALA | A | 87 | -16.033 | -21.848 | -3.153 | 1.00 | 17.60 | C |
| ATOM | 1359 | CB | ALA | A | 87 | -15.181 | -22.271 | -4.417 | 1.00 | 18.74 | C |
| ATOM | 1363 | C | ALA | A | 87 | -17.522 | -22.070 | -3.388 | 1.00 | 17.40 | C |
| ATOM | 1364 | O | ALA | A | 87 | -18.247 | -21.106 | -3.619 | 1.00 | 18.53 | O |
| ATOM | 1366 | N | TRP | A | 88 | -17.977 | -23.312 | -3.360 | 1.00 | 18.16 | N |
| ATOM | 1367 | CA | TRP | A | 88 | -19.399 | -23.592 | -3.573 | 1.00 | 19.10 | C |
| ATOM | 1369 | CB | TRP | A | 88 | -19.647 | -25.082 | -3.898 | 1.00 | 18.82 | C |
| ATOM | 1372 | CG | TRP | A | 88 | -19.387 | -25.425 | -5.278 | 1.00 | 16.31 | C |
| ATOM | 1373 | CD1 | TRP | A | 88 | -18.378 | -26.203 | -5.776 | 1.00 | 13.37 | C |
| ATOM | 1375 | NE1 | TRP | A | 88 | -18.462 | -26.239 | -7.146 | 1.00 | 16.31 | N |
| ATOM | 1377 | CE2 | TRP | A | 88 | -19.468 | -25.428 | -7.552 | 1.00 | 14.82 | C |
| ATOM | 1378 | CD2 | TRP | A | 88 | -20.065 | -24.891 | -6.391 | 1.00 | 16.25 | C |
| ATOM | 1379 | CE3 | TRP | A | 88 | -21.130 | -24.021 | -6.531 | 1.00 | 16.53 | C |

FIG.4-14

| | | | | | | | | | | | |
|---|---|---|---|---|---|---|---|---|---|---|---|
| ATOM | 1381 | CZ3 | TRP | A | 88 | -21.587 | -23.720 | -7.816 | 1.00 | 16.31 | C |
| ATOM | 1383 | CH2 | TRP | A | 88 | -20.966 | -24.246 | -8.942 | 1.00 | 14.98 | C |
| ATOM | 1385 | CZ2 | TRP | A | 88 | -19.890 | -25.095 | -8.831 | 1.00 | 17.58 | C |
| ATOM | 1387 | C | TRP | A | 88 | -20.282 | -23.149 | -2.407 | 1.00 | 18.61 | C |
| ATOM | 1388 | O | TRP | A | 88 | -21.392 | -22.765 | -2.629 | 1.00 | 20.91 | O |
| ATOM | 1390 | N | THR | A | 89 | -19.783 | -23.213 | -1.180 | 1.00 | 18.27 | N |
| ATOM | 1391 | CA | THR | A | 89 | -20.462 | -22.627 | -0.029 | 1.00 | 18.10 | C |
| ATOM | 1393 | CB | THR | A | 89 | -19.672 | -22.939 | 1.273 | 1.00 | 18.78 | C |
| ATOM | 1395 | OG1 | THR | A | 89 | -19.491 | -24.336 | 1.411 | 1.00 | 15.81 | O |
| ATOM | 1397 | CG2 | THR | A | 89 | -20.341 | -22.403 | 2.572 | 1.00 | 19.57 | C |
| ATOM | 1401 | C | THR | A | 89 | -20.706 | -21.117 | -0.207 | 1.00 | 18.81 | C |
| ATOM | 1402 | O | THR | A | 89 | -21.814 | -20.596 | 0.097 | 1.00 | 19.84 | O |
| ATOM | 1404 | N | VAL | A | 90 | -19.698 | -20.391 | -0.685 | 1.00 | 19.00 | N |
| ATOM | 1405 | CA | VAL | A | 90 | -19.826 | -18.964 | -0.906 | 1.00 | 18.31 | C |
| ATOM | 1407 | CB | VAL | A | 90 | -18.449 | -18.241 | -1.155 | 1.00 | 19.43 | C |
| ATOM | 1409 | CG1 | VAL | A | 90 | -18.661 | -16.721 | -1.475 | 1.00 | 17.31 | C |
| ATOM | 1413 | CG2 | VAL | A | 90 | -17.618 | -18.314 | 0.069 | 1.00 | 20.21 | C |
| ATOM | 1417 | C | VAL | A | 90 | -20.799 | -18.688 | -2.006 | 1.00 | 17.64 | C |
| ATOM | 1418 | O | VAL | A | 90 | -21.691 | -17.879 | -1.803 | 1.00 | 17.18 | O |
| ATOM | 1420 | N | VAL | A | 91 | -20.690 | -19.387 | -3.152 | 1.00 | 18.06 | N |
| ATOM | 1421 | CA | VAL | A | 91 | -21.669 | -19.218 | -4.258 | 1.00 | 17.21 | C |
| ATOM | 1423 | CB | VAL | A | 91 | -21.376 | -20.129 | -5.440 | 1.00 | 17.76 | C |
| ATOM | 1425 | CG1 | VAL | A | 91 | -22.589 | -20.184 | -6.384 | 1.00 | 16.67 | C |
| ATOM | 1429 | CG2 | VAL | A | 91 | -20.145 | -19.600 | -6.162 | 1.00 | 16.76 | C |
| ATOM | 1433 | C | VAL | A | 91 | -23.143 | -19.449 | -3.790 | 1.00 | 18.15 | C |
| ATOM | 1434 | O | VAL | A | 91 | -24.033 | -18.671 | -4.096 | 1.00 | 14.83 | O |
| ATOM | 1436 | N | ASN | A | 92 | -23.350 | -20.517 | -3.036 | 1.00 | 19.48 | N |
| ATOM | 1437 | CA | ASN | A | 92 | -24.653 | -20.841 | -2.514 | 1.00 | 21.21 | C |
| ATOM | 1439 | CB | ASN | A | 92 | -24.562 | -22.133 | -1.722 | 1.00 | 21.93 | C |
| ATOM | 1442 | CG | ASN | A | 92 | -24.618 | -23.354 | -2.612 | 1.00 | 28.79 | C |
| ATOM | 1443 | OD1 | ASN | A | 92 | -24.601 | -23.238 | -3.860 | 1.00 | 36.94 | O |
| ATOM | 1444 | ND2 | ASN | A | 92 | -24.680 | -24.544 | -1.995 | 1.00 | 31.11 | N |
| ATOM | 1447 | C | ASN | A | 92 | -25.250 | -19.799 | -1.608 | 1.00 | 20.96 | C |
| ATOM | 1448 | O | ASN | A | 92 | -26.395 | -19.438 | -1.726 | 1.00 | 20.73 | O |
| ATOM | 1450 | N | SER | A | 93 | -24.468 | -19.335 | -0.662 | 1.00 | 22.18 | N |
| ATOM | 1451 | CA | SER | A | 93 | -24.883 | -18.242 | 0.235 | 1.00 | 22.20 | C |
| ATOM | 1453 | CB | SER | A | 93 | -23.823 | -18.090 | 1.320 | 1.00 | 21.57 | C |
| ATOM | 1456 | OG | SER | A | 93 | -23.813 | -16.817 | 1.872 | 1.00 | 27.30 | O |
| ATOM | 1458 | C | SER | A | 93 | -25.207 | -16.908 | -0.529 | 1.00 | 22.52 | C |
| ATOM | 1459 | O | SER | A | 93 | -26.212 | -16.213 | -0.235 | 1.00 | 19.76 | O |
| ATOM | 1461 | N | ILE | A | 94 | -24.400 | -16.569 | -1.527 | 1.00 | 22.32 | N |
| ATOM | 1462 | CA | ILE | A | 94 | -24.707 | -15.425 | -2.362 | 1.00 | 22.22 | C |
| ATOM | 1464 | CB | ILE | A | 94 | -23.553 | -15.081 | -3.388 | 1.00 | 22.50 | C |
| ATOM | 1466 | CG1 | ILE | A | 94 | -22.321 | -14.560 | -2.680 | 1.00 | 22.23 | C |
| ATOM | 1469 | CD1 | ILE | A | 94 | -21.084 | -14.589 | -3.556 | 1.00 | 19.61 | C |
| ATOM | 1473 | CG2 | ILE | A | 94 | -24.011 | -14.069 | -4.435 | 1.00 | 20.41 | C |
| ATOM | 1477 | C | ILE | A | 94 | -26.002 | -15.660 | -3.143 | 1.00 | 22.46 | C |
| ATOM | 1478 | O | ILE | A | 94 | -26.846 | -14.817 | -3.164 | 1.00 | 22.87 | O |
| ATOM | 1480 | N | CYS | A | 95 | -26.160 | -16.762 | -3.836 | 1.00 | 24.44 | N |
| ATOM | 1481 | CA | CYS | A | 95 | -27.452 | -17.048 | -4.483 | 1.00 | 26.05 | C |
| ATOM | 1483 | CB | CYS | A | 95 | -27.415 | -18.426 | -5.131 | 1.00 | 26.83 | C |
| ATOM | 1486 | SG | CYS | A | 95 | -26.204 | -18.541 | -6.527 | 1.00 | 28.09 | S |
| ATOM | 1488 | C | CYS | A | 95 | -28.679 | -16.925 | -3.462 | 1.00 | 26.95 | C |
| ATOM | 1489 | O | CYS | A | 95 | -29.652 | -16.193 | -3.689 | 1.00 | 25.51 | O |
| ATOM | 1491 | N | ASN | A | 96 | -28.550 | -17.605 | -2.337 | 1.00 | 27.06 | N |
| ATOM | 1492 | CA | ASN | A | 96 | -29.481 | -17.488 | -1.228 | 1.00 | 27.69 | C |
| ATOM | 1494 | CB | ASN | A | 96 | -28.972 | -18.174 | 0.062 | 1.00 | 26.25 | C |
| ATOM | 1497 | CG | ASN | A | 96 | -29.018 | -19.689 | -0.008 | 1.00 | 26.75 | C |
| ATOM | 1498 | OD1 | ASN | A | 96 | -29.531 | -20.260 | -0.973 | 1.00 | 27.85 | O |
| ATOM | 1499 | ND2 | ASN | A | 96 | -28.442 | -20.362 | 1.010 | 1.00 | 22.79 | N |
| ATOM | 1502 | C | ASN | A | 96 | -29.851 | -16.062 | -0.942 | 1.00 | 28.01 | C |
| ATOM | 1503 | O | ASN | A | 96 | -31.032 | -15.800 | -0.825 | 1.00 | 28.33 | O |
| ATOM | 1505 | N | THR | A | 97 | -28.889 | -15.138 | -0.907 | 1.00 | 28.06 | N |

FIG.4-15

| | | | | | | | | | | | |
|---|---|---|---|---|---|---|---|---|---|---|---|
| ATOM | 1506 | CA | THR | A | 97 | -29.174 | -13.806 | -0.423 | 1.00 | 27.85 | C |
| ATOM | 1508 | CB | THR | A | 97 | -28.054 | -13.215 | 0.562 | 1.00 | 28.24 | C |
| ATOM | 1510 | OG1 | THR | A | 97 | -27.298 | -12.176 | -0.069 | 1.00 | 32.96 | O |
| ATOM | 1512 | CG2 | THR | A | 97 | -27.163 | -14.189 | 1.054 | 1.00 | 23.90 | C |
| ATOM | 1516 | C | THR | A | 97 | -29.471 | -12.749 | -1.475 | 1.00 | 27.72 | C |
| ATOM | 1517 | O | THR | A | 97 | -30.047 | -11.754 | -1.146 | 1.00 | 29.22 | O |
| ATOM | 1519 | N | THR | A | 98 | -29.021 | -12.896 | -2.704 | 1.00 | 27.28 | N |
| ATOM | 1520 | CA | THR | A | 98 | -29.289 | -11.899 | -3.744 | 1.00 | 26.68 | C |
| ATOM | 1522 | CB | THR | A | 98 | -28.001 | -11.558 | -4.526 | 1.00 | 26.80 | C |
| ATOM | 1524 | OG1 | THR | A | 98 | -27.577 | -12.711 | -5.266 | 1.00 | 24.60 | O |
| ATOM | 1526 | CG2 | THR | A | 98 | -26.870 | -11.158 | -3.537 | 1.00 | 26.11 | C |
| ATOM | 1530 | C | THR | A | 98 | -30.290 | -12.425 | -4.719 | 1.00 | 26.65 | C |
| ATOM | 1531 | O | THR | A | 98 | -30.740 | -11.703 | -5.557 | 1.00 | 27.58 | O |
| ATOM | 1533 | N | GLY | A | 99 | -30.630 | -13.699 | -4.627 | 1.00 | 27.19 | N |
| ATOM | 1534 | CA | GLY | A | 99 | -31.450 | -14.312 | -5.636 | 1.00 | 27.70 | C |
| ATOM | 1537 | C | GLY | A | 99 | -30.864 | -14.417 | -7.041 | 1.00 | 28.93 | C |
| ATOM | 1538 | O | GLY | A | 99 | -31.576 | -14.865 | -7.924 | 1.00 | 27.61 | O |
| ATOM | 1540 | N | VAL | A | 100 | -29.581 | -14.105 | -7.301 | 1.00 | 29.69 | N |
| ATOM | 1541 | CA | VAL | A | 100 | -29.070 | -14.467 | -8.651 | 1.00 | 29.83 | C |
| ATOM | 1543 | CB | VAL | A | 100 | -27.649 | -13.943 | -8.974 | 1.00 | 30.24 | C |
| ATOM | 1545 | CG1 | VAL | A | 100 | -27.638 | -12.444 | -9.003 | 1.00 | 33.39 | C |
| ATOM | 1549 | CG2 | VAL | A | 100 | -26.661 | -14.494 | -7.998 | 1.00 | 28.50 | C |
| ATOM | 1553 | C | VAL | A | 100 | -29.013 | -15.968 | -8.833 | 1.00 | 29.97 | C |
| ATOM | 1554 | O | VAL | A | 100 | -28.908 | -16.747 | -7.893 | 1.00 | 28.90 | O |
| ATOM | 1556 | N | GLU | A | 101 | -29.022 | -16.347 | -10.098 | 1.00 | 31.73 | N |
| ATOM | 1557 | CA | GLU | A | 101 | -29.019 | -17.731 | -10.575 | 1.00 | 32.51 | C |
| ATOM | 1559 | CB | GLU | A | 101 | -29.275 | -17.620 | -12.082 | 1.00 | 34.61 | C |
| ATOM | 1562 | CG | GLU | A | 101 | -29.647 | -18.878 | -12.833 | 1.00 | 40.79 | C |
| ATOM | 1565 | CD | GLU | A | 101 | -29.851 | -18.595 | -14.350 | 1.00 | 44.48 | C |
| ATOM | 1566 | OE1 | GLU | A | 101 | -29.096 | -19.175 | -15.161 | 1.00 | 48.94 | O |
| ATOM | 1567 | OE2 | GLU | A | 101 | -30.724 | -17.765 | -14.714 | 1.00 | 47.68 | O |
| ATOM | 1568 | C | GLU | A | 101 | -27.678 | -18.410 | -10.315 | 1.00 | 31.48 | C |
| ATOM | 1569 | O | GLU | A | 101 | -26.634 | -17.788 | -10.445 | 1.00 | 31.03 | O |
| ATOM | 1571 | N | LYS | A | 102 | -27.714 | -19.675 | -9.931 | 1.00 | 31.74 | N |
| ATOM | 1572 | CA | LYS | A | 102 | -26.538 | -20.434 | -9.531 | 1.00 | 32.82 | C |
| ATOM | 1574 | CB | LYS | A | 102 | -26.958 | -21.667 | -8.721 | 1.00 | 32.25 | C |
| ATOM | 1577 | CG | LYS | A | 102 | -25.854 | -22.316 | -7.911 | 1.00 | 33.10 | C |
| ATOM | 1580 | CD | LYS | A | 102 | -26.308 | -23.663 | -7.265 | 1.00 | 34.79 | C |
| ATOM | 1583 | CE | LYS | A | 102 | -27.071 | -23.472 | -5.945 | 1.00 | 36.05 | C |
| ATOM | 1586 | NZ | LYS | A | 102 | -27.818 | -24.722 | -5.568 | 1.00 | 35.64 | N |
| ATOM | 1590 | C | LYS | A | 102 | -25.798 | -20.870 | -10.779 | 1.00 | 33.19 | C |
| ATOM | 1591 | O | LYS | A | 102 | -26.340 | -21.613 | -11.581 | 1.00 | 35.22 | O |
| ATOM | 1593 | N | PRO | A | 103 | -24.558 | -20.411 | -10.963 | 1.00 | 33.42 | N |
| ATOM | 1594 | CA | PRO | A | 103 | -23.861 | -20.827 | -12.199 | 1.00 | 33.38 | C |
| ATOM | 1596 | CB | PRO | A | 103 | -22.579 | -19.991 | -12.170 | 1.00 | 33.40 | C |
| ATOM | 1599 | CG | PRO | A | 103 | -22.256 | -19.841 | -10.665 | 1.00 | 32.31 | C |
| ATOM | 1602 | CD | PRO | A | 103 | -23.619 | -19.918 | -9.929 | 1.00 | 33.43 | C |
| ATOM | 1605 | C | PRO | A | 103 | -23.543 | -22.320 | -12.143 | 1.00 | 33.18 | C |
| ATOM | 1606 | O | PRO | A | 103 | -23.588 | -22.919 | -11.078 | 1.00 | 32.89 | O |
| ATOM | 1607 | N | LYS | A | 104 | -23.242 | -22.954 | -13.267 | 1.00 | 33.97 | N |
| ATOM | 1608 | CA | LYS | A | 104 | -22.902 | -24.390 | -13.177 | 1.00 | 34.76 | C |
| ATOM | 1610 | CB | LYS | A | 104 | -23.428 | -25.172 | -14.359 | 1.00 | 35.87 | C |
| ATOM | 1613 | CG | LYS | A | 104 | -24.969 | -25.171 | -14.468 | 1.00 | 39.54 | C |
| ATOM | 1616 | CD | LYS | A | 104 | -25.631 | -26.419 | -13.849 | 1.00 | 41.86 | C |
| ATOM | 1619 | CE | LYS | A | 104 | -27.006 | -26.709 | -14.510 | 1.00 | 45.68 | C |
| ATOM | 1622 | NZ | LYS | A | 104 | -27.195 | -28.167 | -14.830 | 1.00 | 48.38 | N |
| ATOM | 1626 | C | LYS | A | 104 | -21.411 | -24.609 | -13.008 | 1.00 | 33.55 | C |
| ATOM | 1627 | O | LYS | A | 104 | -21.025 | -25.616 | -12.423 | 1.00 | 34.79 | O |
| ATOM | 1629 | N | PHE | A | 105 | -20.572 | -23.682 | -13.481 | 1.00 | 32.04 | N |
| ATOM | 1630 | CA | PHE | A | 105 | -19.128 | -23.710 | -13.095 | 1.00 | 31.60 | C |
| ATOM | 1632 | CB | PHE | A | 105 | -18.265 | -23.565 | -14.343 | 1.00 | 33.09 | C |
| ATOM | 1635 | CG | PHE | A | 105 | -18.624 | -24.511 | -15.427 | 1.00 | 35.88 | C |
| ATOM | 1636 | CD1 | PHE | A | 105 | -18.454 | -25.869 | -15.257 | 1.00 | 40.92 | C |

FIG.4-16

| | | | | | | | | | | | |
|---|---|---|---|---|---|---|---|---|---|---|---|
| ATOM | 1638 | CE1 | PHE | A | 105 | -18.801 | -26.753 | -16.258 | 1.00 | 41.97 | C |
| ATOM | 1640 | CZ | PHE | A | 105 | -19.309 | -26.308 | -17.431 | 1.00 | 39.96 | C |
| ATOM | 1642 | CE2 | PHE | A | 105 | -19.511 | -24.967 | -17.617 | 1.00 | 42.33 | C |
| ATOM | 1644 | CD2 | PHE | A | 105 | -19.159 | -24.059 | -16.613 | 1.00 | 40.48 | C |
| ATOM | 1646 | C | PHE | A | 105 | -18.725 | -22.579 | -12.097 | 1.00 | 28.22 | C |
| ATOM | 1647 | O | PHE | A | 105 | -19.356 | -21.501 | -12.064 | 1.00 | 27.52 | O |
| ATOM | 1649 | N | LEU | A | 106 | -17.663 | -22.788 | -11.334 | 1.00 | 24.93 | N |
| ATOM | 1650 | CA | LEU | A | 106 | -17.241 | -21.751 | -10.371 | 1.00 | 23.49 | C |
| ATOM | 1652 | CB | LEU | A | 106 | -16.153 | -22.262 | -9.438 | 1.00 | 23.80 | C |
| ATOM | 1655 | CG | LEU | A | 106 | -16.607 | -23.265 | -8.425 | 1.00 | 22.14 | C |
| ATOM | 1657 | CD1 | LEU | A | 106 | -15.361 | -23.908 | -7.734 | 1.00 | 18.98 | C |
| ATOM | 1661 | CD2 | LEU | A | 106 | -17.485 | -22.415 | -7.457 | 1.00 | 16.61 | C |
| ATOM | 1665 | C | LEU | A | 106 | -16.688 | -20.544 | -11.061 | 1.00 | 22.77 | C |
| ATOM | 1666 | O | LEU | A | 106 | -15.827 | -20.685 | -11.904 | 1.00 | 21.46 | O |
| ATOM | 1668 | N | PRO | A | 107 | -17.208 | -19.340 | -10.716 | 1.00 | 22.55 | N |
| ATOM | 1669 | CA | PRO | A | 107 | -16.619 | -18.120 | -11.178 | 1.00 | 20.85 | C |
| ATOM | 1671 | CB | PRO | A | 107 | -17.789 | -17.133 | -11.147 | 1.00 | 20.47 | C |
| ATOM | 1674 | CG | PRO | A | 107 | -18.621 | -17.581 | -10.120 | 1.00 | 22.95 | C |
| ATOM | 1677 | CD | PRO | A | 107 | -18.456 | -19.074 | -9.979 | 1.00 | 23.33 | C |
| ATOM | 1680 | C | PRO | A | 107 | -15.489 | -17.684 | -10.294 | 1.00 | 18.23 | C |
| ATOM | 1681 | O | PRO | A | 107 | -15.055 | -18.381 | -9.418 | 1.00 | 17.05 | O |
| ATOM | 1682 | N | ASP | A | 108 | -14.997 | -16.504 | -10.583 | 1.00 | 18.35 | N |
| ATOM | 1683 | CA | ASP | A | 108 | -13.814 | -16.028 | -9.984 | 1.00 | 16.38 | C |
| ATOM | 1685 | CB | ASP | A | 108 | -12.964 | -15.326 | -11.003 | 1.00 | 14.64 | C |
| ATOM | 1688 | CG | ASP | A | 108 | -12.096 | -16.272 | -11.866 | 1.00 | 14.48 | C |
| ATOM | 1689 | OD1 | ASP | A | 108 | -11.953 | -15.977 | -13.050 | 1.00 | 16.75 | O |
| ATOM | 1690 | OD2 | ASP | A | 108 | -11.510 | -17.237 | -11.408 | 1.00 | 14.43 | O |
| ATOM | 1691 | C | ASP | A | 108 | -14.189 | -15.040 | -8.894 | 1.00 | 16.04 | C |
| ATOM | 1692 | O | ASP | A | 108 | -13.495 | -15.007 | -7.857 | 1.00 | 15.86 | O |
| ATOM | 1694 | N | LEU | A | 109 | -15.173 | -14.191 | -9.213 | 1.00 | 16.67 | N |
| ATOM | 1695 | CA | LEU | A | 109 | -15.614 | -13.070 | -8.357 | 1.00 | 16.75 | C |
| ATOM | 1697 | CB | LEU | A | 109 | -15.039 | -11.759 | -8.805 | 1.00 | 17.47 | C |
| ATOM | 1700 | CG | LEU | A | 109 | -13.511 | -11.535 | -8.861 | 1.00 | 17.53 | C |
| ATOM | 1702 | CD1 | LEU | A | 109 | -13.197 | -10.316 | -9.670 | 1.00 | 21.08 | C |
| ATOM | 1706 | CD2 | LEU | A | 109 | -12.987 | -11.405 | -7.452 | 1.00 | 19.67 | C |
| ATOM | 1710 | C | LEU | A | 109 | -17.164 | -12.956 | -8.360 | 1.00 | 17.15 | C |
| ATOM | 1711 | O | LEU | A | 109 | -17.817 | -13.467 | -9.222 | 1.00 | 18.18 | O |
| ATOM | 1713 | N | TYR | A | 110 | -17.739 | -12.296 | -7.348 | 1.00 | 19.32 | N |
| ATOM | 1714 | CA | TYR | A | 110 | -19.106 | -11.836 | -7.371 | 1.00 | 18.38 | C |
| ATOM | 1716 | CB | TYR | A | 110 | -20.010 | -12.574 | -6.329 | 1.00 | 19.15 | C |
| ATOM | 1719 | CG | TYR | A | 110 | -21.457 | -12.104 | -6.434 | 1.00 | 19.24 | C |
| ATOM | 1720 | CD1 | TYR | A | 110 | -22.249 | -12.529 | -7.483 | 1.00 | 20.32 | C |
| ATOM | 1722 | CE1 | TYR | A | 110 | -23.551 | -12.125 | -7.630 | 1.00 | 15.06 | C |
| ATOM | 1724 | CZ | TYR | A | 110 | -24.080 | -11.225 | -6.751 | 1.00 | 21.81 | C |
| ATOM | 1725 | OH | TYR | A | 110 | -25.374 | -10.866 | -6.953 | 1.00 | 21.28 | O |
| ATOM | 1727 | CE2 | TYR | A | 110 | -23.334 | -10.742 | -5.664 | 1.00 | 17.41 | C |
| ATOM | 1729 | CD2 | TYR | A | 110 | -21.995 | -11.163 | -5.543 | 1.00 | 21.83 | C |
| ATOM | 1731 | C | TYR | A | 110 | -19.113 | -10.349 | -7.147 | 1.00 | 18.92 | C |
| ATOM | 1732 | O | TYR | A | 110 | -18.457 | -9.833 | -6.246 | 1.00 | 18.02 | O |
| ATOM | 1734 | N | ASP | A | 111 | -19.885 | -9.646 | -7.970 | 1.00 | 20.94 | N |
| ATOM | 1735 | CA | ASP | A | 111 | -19.949 | -8.185 | -7.962 | 1.00 | 22.09 | C |
| ATOM | 1737 | CB | ASP | A | 111 | -19.850 | -7.650 | -9.396 | 1.00 | 22.02 | C |
| ATOM | 1740 | CG | ASP | A | 111 | -20.084 | -6.162 | -9.519 | 1.00 | 23.79 | C |
| ATOM | 1741 | OD1 | ASP | A | 111 | -20.492 | -5.449 | -8.554 | 1.00 | 22.21 | O |
| ATOM | 1742 | OD2 | ASP | A | 111 | -19.910 | -5.689 | -10.637 | 1.00 | 24.62 | O |
| ATOM | 1743 | C | ASP | A | 111 | -21.279 | -7.833 | -7.349 | 1.00 | 24.14 | C |
| ATOM | 1744 | O | ASP | A | 111 | -22.315 | -8.026 | -7.999 | 1.00 | 24.35 | O |
| ATOM | 1746 | N | TYR | A | 112 | -21.249 | -7.403 | -6.080 | 1.00 | 25.61 | N |
| ATOM | 1747 | CA | TYR | A | 112 | -22.462 | -6.953 | -5.363 | 1.00 | 26.29 | C |
| ATOM | 1749 | CB | TYR | A | 112 | -22.150 | -6.732 | -3.859 | 1.00 | 25.98 | C |
| ATOM | 1752 | CG | TYR | A | 112 | -21.866 | -7.964 | -3.050 | 1.00 | 27.30 | C |
| ATOM | 1753 | CD1 | TYR | A | 112 | -20.550 | -8.363 | -2.758 | 1.00 | 26.81 | C |
| ATOM | 1755 | CE1 | TYR | A | 112 | -20.299 | -9.484 | -2.008 | 1.00 | 27.21 | C |

FIG.4-17

| | | | | | | | | | | | |
|---|---|---|---|---|---|---|---|---|---|---|---|
| ATOM | 1757 | CZ | TYR | A | 112 | -21.366 | -10.237 | -1.550 | 1.00 | 28.73 | C |
| ATOM | 1758 | OH | TYR | A | 112 | -21.130 | -11.370 | -0.831 | 1.00 | 31.55 | O |
| ATOM | 1760 | CE2 | TYR | A | 112 | -22.657 | -9.869 | -1.823 | 1.00 | 27.89 | C |
| ATOM | 1762 | CD2 | TYR | A | 112 | -22.906 | -8.744 | -2.558 | 1.00 | 28.83 | C |
| ATOM | 1764 | C | TYR | A | 112 | -23.057 | -5.645 | -5.930 | 1.00 | 27.21 | C |
| ATOM | 1765 | O | TYR | A | 112 | -24.160 | -5.274 | -5.532 | 1.00 | 27.86 | O |
| ATOM | 1767 | N | LYS | A | 113 | -22.358 | -4.884 | -6.791 | 1.00 | 28.62 | N |
| ATOM | 1768 | CA | LYS | A | 113 | -23.036 | -3.703 | -7.406 | 1.00 | 28.75 | C |
| ATOM | 1770 | CB | LYS | A | 113 | -22.103 | -2.530 | -7.793 | 1.00 | 29.51 | C |
| ATOM | 1773 | CG | LYS | A | 113 | -22.911 | -1.285 | -8.187 | 1.00 | 29.92 | C |
| ATOM | 1776 | CD | LYS | A | 113 | -22.077 | -0.013 | -8.355 | 1.00 | 34.77 | C |
| ATOM | 1779 | CE | LYS | A | 113 | -22.549 | 0.884 | -9.559 | 1.00 | 35.34 | C |
| ATOM | 1782 | NZ | LYS | A | 113 | -21.356 | 1.197 | -10.524 | 1.00 | 37.61 | N |
| ATOM | 1786 | C | LYS | A | 113 | -23.889 | -4.014 | -8.599 | 1.00 | 29.07 | C |
| ATOM | 1787 | O | LYS | A | 113 | -24.989 | -3.468 | -8.726 | 1.00 | 29.19 | O |
| ATOM | 1789 | N | GLU | A | 114 | -23.408 | -4.859 | -9.505 | 1.00 | 29.27 | N |
| ATOM | 1790 | CA | GLU | A | 114 | -24.210 | -5.278 | -10.662 | 1.00 | 28.26 | C |
| ATOM | 1792 | CB | GLU | A | 114 | -23.294 | -5.453 | -11.843 | 1.00 | 29.03 | C |
| ATOM | 1795 | CG | GLU | A | 114 | -22.385 | -4.270 | -12.059 | 1.00 | 30.44 | C |
| ATOM | 1798 | CD | GLU | A | 114 | -23.092 | -3.092 | -12.681 | 1.00 | 37.26 | C |
| ATOM | 1799 | OE1 | GLU | A | 114 | -24.235 | -3.278 | -13.193 | 1.00 | 38.37 | O |
| ATOM | 1800 | OE2 | GLU | A | 114 | -22.496 | -1.978 | -12.620 | 1.00 | 40.87 | O |
| ATOM | 1801 | C | GLU | A | 114 | -24.999 | -6.557 | -10.480 | 1.00 | 28.88 | C |
| ATOM | 1802 | O | GLU | A | 114 | -25.766 | -6.975 | -11.373 | 1.00 | 28.68 | O |
| ATOM | 1804 | N | ASN | A | 115 | -24.774 | -7.219 | -9.343 | 1.00 | 29.17 | N |
| ATOM | 1805 | CA | ASN | A | 115 | -25.381 | -8.506 | -9.006 | 1.00 | 28.97 | C |
| ATOM | 1807 | CB | ASN | A | 115 | -26.877 | -8.350 | -8.587 | 1.00 | 29.39 | C |
| ATOM | 1810 | CG | ASN | A | 115 | -27.003 | -7.869 | -7.171 | 1.00 | 32.64 | C |
| ATOM | 1811 | OD1 | ASN | A | 115 | -27.393 | -6.719 | -6.926 | 1.00 | 36.46 | O |
| ATOM | 1812 | ND2 | ASN | A | 115 | -26.550 | -8.702 | -6.216 | 1.00 | 30.25 | N |
| ATOM | 1815 | C | ASN | A | 115 | -25.171 | -9.577 | -10.048 | 1.00 | 27.50 | C |
| ATOM | 1816 | O | ASN | A | 115 | -26.110 | -10.227 | -10.527 | 1.00 | 27.57 | O |
| ATOM | 1818 | N | ARG | A | 116 | -23.900 | -9.795 | -10.349 | 1.00 | 26.76 | N |
| ATOM | 1819 | CA | ARG | A | 116 | -23.485 | -10.851 | -11.260 | 1.00 | 24.38 | C |
| ATOM | 1821 | CB | ARG | A | 116 | -23.465 | -10.333 | -12.691 | 1.00 | 24.02 | C |
| ATOM | 1824 | CG | ARG | A | 116 | -22.458 | -9.243 | -12.891 | 1.00 | 24.22 | C |
| ATOM | 1827 | CD | ARG | A | 116 | -22.724 | -8.473 | -14.123 | 1.00 | 24.86 | C |
| ATOM | 1830 | NE | ARG | A | 116 | -21.691 | -7.456 | -14.356 | 1.00 | 27.78 | N |
| ATOM | 1832 | CZ | ARG | A | 116 | -21.816 | -6.451 | -15.231 | 1.00 | 28.23 | C |
| ATOM | 1833 | NH1 | ARG | A | 116 | -22.943 | -6.289 | -15.954 | 1.00 | 27.75 | N |
| ATOM | 1836 | NH2 | ARG | A | 116 | -20.842 | -5.579 | -15.348 | 1.00 | 24.86 | N |
| ATOM | 1839 | C | ARG | A | 116 | -22.117 | -11.426 | -10.905 | 1.00 | 21.72 | C |
| ATOM | 1840 | O | ARG | A | 116 | -21.272 | -10.766 | -10.368 | 1.00 | 20.29 | O |
| ATOM | 1842 | N | PHE | A | 117 | -21.945 | -12.691 | -11.233 | 1.00 | 20.91 | N |
| ATOM | 1843 | CA | PHE | A | 117 | -20.654 | -13.338 | -11.202 | 1.00 | 19.71 | C |
| ATOM | 1845 | CB | PHE | A | 117 | -20.829 | -14.805 | -11.225 | 1.00 | 18.91 | C |
| ATOM | 1848 | CG | PHE | A | 117 | -21.511 | -15.335 | -10.028 | 1.00 | 20.54 | C |
| ATOM | 1849 | CD1 | PHE | A | 117 | -20.823 | -15.466 | -8.819 | 1.00 | 24.79 | C |
| ATOM | 1851 | CE1 | PHE | A | 117 | -21.439 | -15.936 | -7.686 | 1.00 | 23.52 | C |
| ATOM | 1853 | CZ | PHE | A | 117 | -22.741 | -16.334 | -7.749 | 1.00 | 25.41 | C |
| ATOM | 1855 | CE2 | PHE | A | 117 | -23.449 | -16.234 | -8.937 | 1.00 | 25.83 | C |
| ATOM | 1857 | CD2 | PHE | A | 117 | -22.827 | -15.738 | -10.087 | 1.00 | 23.53 | C |
| ATOM | 1859 | C | PHE | A | 117 | -19.796 | -12.914 | -12.366 | 1.00 | 19.90 | C |
| ATOM | 1860 | O | PHE | A | 117 | -20.316 | -12.421 | -13.353 | 1.00 | 18.65 | O |
| ATOM | 1862 | N | ILE | A | 118 | -18.477 | -13.097 | -12.200 | 1.00 | 18.22 | N |
| ATOM | 1863 | CA | ILE | A | 118 | -17.502 | -12.619 | -13.138 | 1.00 | 18.37 | C |
| ATOM | 1865 | CB | ILE | A | 118 | -16.708 | -11.373 | -12.601 | 1.00 | 17.99 | C |
| ATOM | 1867 | CG1 | ILE | A | 118 | -17.622 | -10.220 | -12.350 | 1.00 | 18.21 | C |
| ATOM | 1870 | CD1 | ILE | A | 118 | -16.994 | -9.029 | -11.736 | 1.00 | 16.51 | C |
| ATOM | 1874 | CG2 | ILE | A | 118 | -15.682 | -10.949 | -13.592 | 1.00 | 19.63 | C |
| ATOM | 1878 | C | ILE | A | 118 | -16.478 | -13.681 | -13.331 | 1.00 | 17.25 | C |
| ATOM | 1879 | O | ILE | A | 118 | -16.003 | -14.271 | -12.365 | 1.00 | 17.71 | O |
| ATOM | 1881 | N | GLU | A | 119 | -16.146 | -13.944 | -14.581 | 1.00 | 17.50 | N |

FIG.4-18

| | | | | | | | | | | | |
|---|---|---|---|---|---|---|---|---|---|---|---|
| ATOM | 1882 | CA | GLU | A | 119 | -15.076 | -14.847 | -14.880 | 1.00 | 18.83 | C |
| ATOM | 1884 | CB | GLU | A | 119 | -15.582 | -15.938 | -15.835 | 1.00 | 19.64 | C |
| ATOM | 1887 | CG | GLU | A | 119 | -14.423 | -16.668 | -16.517 | 1.00 | 21.62 | C |
| ATOM | 1890 | CD | GLU | A | 119 | -13.691 | -17.560 | -15.560 | 1.00 | 27.20 | C |
| ATOM | 1891 | OE1 | GLU | A | 119 | -14.396 | -18.319 | -14.810 | 1.00 | 26.78 | O |
| ATOM | 1892 | OE2 | GLU | A | 119 | -12.415 | -17.489 | -15.556 | 1.00 | 29.28 | O |
| ATOM | 1893 | C | GLU | A | 119 | -13.938 | -14.023 | -15.504 | 1.00 | 17.40 | C |
| ATOM | 1894 | O | GLU | A | 119 | -14.151 | -13.323 | -16.505 | 1.00 | 16.54 | O |
| ATOM | 1896 | N | ILE | A | 120 | -12.738 | -14.153 | -14.922 | 1.00 | 16.83 | N |
| ATOM | 1897 | CA | ILE | A | 120 | -11.570 | -13.406 | -15.342 | 1.00 | 16.12 | C |
| ATOM | 1899 | CB | ILE | A | 120 | -10.760 | -12.847 | -14.160 | 1.00 | 16.33 | C |
| ATOM | 1901 | CG1 | ILE | A | 120 | -11.573 | -11.819 | -13.361 | 1.00 | 17.76 | C |
| ATOM | 1904 | CD1 | ILE | A | 120 | -12.263 | -10.786 | -14.228 | 1.00 | 27.36 | C |
| ATOM | 1908 | CG2 | ILE | A | 120 | -9.446 | -12.146 | -14.581 | 1.00 | 13.88 | C |
| ATOM | 1912 | C | ILE | A | 120 | -10.658 | -14.381 | -16.053 | 1.00 | 15.76 | C |
| ATOM | 1913 | O | ILE | A | 120 | -10.410 | -15.463 | -15.565 | 1.00 | 13.37 | O |
| ATOM | 1915 | N | GLY | A | 121 | -10.068 | -13.902 | -17.139 | 1.00 | 15.55 | N |
| ATOM | 1916 | CA | GLY | A | 121 | -9.004 | -14.619 | -17.879 | 1.00 | 14.19 | C |
| ATOM | 1919 | C | GLY | A | 121 | -7.871 | -13.662 | -18.171 | 1.00 | 13.81 | C |
| ATOM | 1920 | O | GLY | A | 121 | -8.075 | -12.459 | -18.299 | 1.00 | 13.14 | O |
| ATOM | 1922 | N | VAL | A | 122 | -6.651 | -14.190 | -18.201 | 1.00 | 14.17 | N |
| ATOM | 1923 | CA | VAL | A | 122 | -5.510 | -13.370 | -18.488 | 1.00 | 14.51 | C |
| ATOM | 1925 | CB | VAL | A | 122 | -4.570 | -13.211 | -17.237 | 1.00 | 14.04 | C |
| ATOM | 1927 | CG1 | VAL | A | 122 | -3.317 | -12.479 | -17.552 | 1.00 | 13.22 | C |
| ATOM | 1931 | CG2 | VAL | A | 122 | -5.291 | -12.518 | -16.063 | 1.00 | 15.86 | C |
| ATOM | 1935 | C | VAL | A | 122 | -4.811 | -14.164 | -19.565 | 1.00 | 16.23 | C |
| ATOM | 1936 | O | VAL | A | 122 | -4.467 | -15.282 | -19.309 | 1.00 | 14.98 | O |
| ATOM | 1938 | N | THR | A | 123 | -4.605 | -13.595 | -20.770 | 1.00 | 17.75 | N |
| ATOM | 1939 | CA | THR | A | 123 | -4.065 | -14.381 | -21.872 | 1.00 | 18.91 | C |
| ATOM | 1941 | CB | THR | A | 123 | -5.123 | -14.590 | -23.041 | 1.00 | 17.81 | C |
| ATOM | 1943 | OG1 | THR | A | 123 | -4.618 | -15.580 | -23.949 | 1.00 | 22.42 | O |
| ATOM | 1945 | CG2 | THR | A | 123 | -5.441 | -13.327 | -23.772 | 1.00 | 18.47 | C |
| ATOM | 1949 | C | THR | A | 123 | -2.787 | -13.805 | -22.487 | 1.00 | 19.65 | C |
| ATOM | 1950 | O | THR | A | 123 | -2.577 | -12.642 | -22.453 | 1.00 | 21.50 | O |
| ATOM | 1952 | N | ARG | A | 124 | -1.984 | -14.641 | -23.095 | 1.00 | 22.23 | N |
| ATOM | 1953 | CA | ARG | A | 124 | -0.904 | -14.190 | -23.959 | 1.00 | 25.61 | C |
| ATOM | 1955 | CB | ARG | A | 124 | 0.480 | -14.652 | -23.417 | 1.00 | 26.74 | C |
| ATOM | 1958 | CG | ARG | A | 124 | 0.532 | -16.005 | -22.949 | 1.00 | 30.80 | C |
| ATOM | 1961 | CD | ARG | A | 124 | 1.086 | -16.246 | -21.527 | 1.00 | 29.87 | C |
| ATOM | 1964 | NE | ARG | A | 124 | 0.205 | -17.242 | -20.884 | 1.00 | 28.22 | N |
| ATOM | 1966 | CZ | ARG | A | 124 | 0.467 | -18.494 | -20.529 | 1.00 | 27.99 | C |
| ATOM | 1967 | NH1 | ARG | A | 124 | 1.648 | -19.122 | -20.695 | 1.00 | 29.17 | N |
| ATOM | 1970 | NH2 | ARG | A | 124 | -0.515 | -19.148 | -19.966 | 1.00 | 28.47 | N |
| ATOM | 1973 | C | ARG | A | 124 | -1.145 | -14.530 | -25.479 | 1.00 | 26.60 | C |
| ATOM | 1974 | O | ARG | A | 124 | -0.254 | -14.329 | -26.297 | 1.00 | 25.75 | O |
| ATOM | 1976 | N | ARG | A | 125 | -2.382 | -14.968 | -25.793 | 1.00 | 27.09 | N |
| ATOM | 1977 | CA | ARG | A | 125 | -2.911 | -15.193 | -27.136 | 1.00 | 26.52 | C |
| ATOM | 1979 | CB | ARG | A | 125 | -3.541 | -16.555 | -27.256 | 1.00 | 26.05 | C |
| ATOM | 1982 | CG | ARG | A | 125 | -2.623 | -17.769 | -27.241 | 1.00 | 27.91 | C |
| ATOM | 1985 | CD | ARG | A | 125 | -3.468 | -19.012 | -27.295 | 1.00 | 29.20 | C |
| ATOM | 1988 | NE | ARG | A | 125 | -4.248 | -19.132 | -26.075 | 1.00 | 34.62 | N |
| ATOM | 1990 | CZ | ARG | A | 125 | -5.215 | -20.023 | -25.832 | 1.00 | 37.80 | C |
| ATOM | 1991 | NH1 | ARG | A | 125 | -5.569 | -20.963 | -26.732 | 1.00 | 38.27 | N |
| ATOM | 1994 | NH2 | ARG | A | 125 | -5.823 | -19.973 | -24.639 | 1.00 | 38.09 | N |
| ATOM | 1997 | C | ARG | A | 125 | -3.969 | -14.101 | -27.457 | 1.00 | 26.64 | C |
| ATOM | 1998 | O | ARG | A | 125 | -4.356 | -13.300 | -26.620 | 1.00 | 27.37 | O |
| ATOM | 2000 | N | GLU | A | 126 | -4.388 | -14.029 | -28.708 | 1.00 | 26.40 | N |
| ATOM | 2001 | CA | GLU | A | 126 | -5.385 | -13.067 | -29.129 | 1.00 | 25.30 | C |
| ATOM | 2003 | CB | GLU | A | 126 | -5.936 | -13.469 | -30.532 | 1.00 | 24.50 | C |
| ATOM | 2006 | CG | GLU | A | 126 | -7.479 | -13.282 | -30.656 | 1.00 | 23.62 | C |
| ATOM | 2009 | CD | GLU | A | 126 | -7.684 | -11.957 | -30.933 | 1.00 | 24.93 | C |
| ATOM | 2010 | OE1 | GLU | A | 126 | -6.622 | -11.430 | -31.048 | 1.00 | 29.31 | O |
| ATOM | 2011 | OE2 | GLU | A | 126 | -8.780 | -11.393 | -31.035 | 1.00 | 28.68 | O |

FIG.4-19

| | | | | | | | | | | | |
|---|---|---|---|---|---|---|---|---|---|---|---|
| ATOM | 2012 | C | GLU | A | 126 | -6.514 | -13.156 | -28.109 | 1.00 | 24.21 | C |
| ATOM | 2013 | O | GLU | A | 126 | -6.951 | -14.256 | -27.854 | 1.00 | 24.01 | O |
| ATOM | 2015 | N | VAL | A | 127 | -7.063 | -12.024 | -27.664 | 1.00 | 24.98 | N |
| ATOM | 2016 | CA | VAL | A | 127 | -8.099 | -11.982 | -26.580 | 1.00 | 26.27 | C |
| ATOM | 2018 | CB | VAL | A | 127 | -8.417 | -10.519 | -26.115 | 1.00 | 27.43 | C |
| ATOM | 2020 | CG1 | VAL | A | 127 | -7.293 | -9.961 | -25.368 | 1.00 | 27.23 | C |
| ATOM | 2024 | CG2 | VAL | A | 127 | -8.762 | -9.559 | -27.338 | 1.00 | 28.59 | C |
| ATOM | 2028 | C | VAL | A | 127 | -9.445 | -12.655 | -26.865 | 1.00 | 25.98 | C |
| ATOM | 2029 | O | VAL | A | 127 | -10.172 | -13.036 | -25.916 | 1.00 | 25.27 | O |
| ATOM | 2031 | N | HIS | A | 128 | -9.828 | -12.763 | -28.150 | 1.00 | 24.52 | N |
| ATOM | 2032 | CA | HIS | A | 128 | -11.054 | -13.426 | -28.473 | 1.00 | 23.35 | C |
| ATOM | 2034 | CB | HIS | A | 128 | -11.414 | -13.288 | -29.971 | 1.00 | 25.33 | C |
| ATOM | 2037 | CG | HIS | A | 128 | -11.856 | -11.914 | -30.322 | 1.00 | 19.06 | C |
| ATOM | 2038 | ND1 | HIS | A | 128 | -10.958 | -10.907 | -30.575 | 1.00 | 18.80 | N |
| ATOM | 2040 | CE1 | HIS | A | 128 | -11.611 | -9.781 | -30.798 | 1.00 | 20.84 | C |
| ATOM | 2042 | NE2 | HIS | A | 128 | -12.912 | -10.024 | -30.667 | 1.00 | 19.44 | N |
| ATOM | 2044 | CD2 | HIS | A | 128 | -13.089 | -11.352 | -30.359 | 1.00 | 19.96 | C |
| ATOM | 2046 | C | HIS | A | 128 | -10.983 | -14.851 | -28.132 | 1.00 | 22.89 | C |
| ATOM | 2047 | O | HIS | A | 128 | -11.983 | -15.442 | -27.833 | 1.00 | 22.14 | O |
| ATOM | 2049 | N | ILE | A | 129 | -9.787 | -15.411 | -28.132 | 1.00 | 23.38 | N |
| ATOM | 2050 | CA | ILE | A | 129 | -9.648 | -16.819 | -27.902 | 1.00 | 23.32 | C |
| ATOM | 2052 | CB | ILE | A | 129 | -8.255 | -17.309 | -28.283 | 1.00 | 22.59 | C |
| ATOM | 2054 | CG1 | ILE | A | 129 | -8.059 | -17.188 | -29.808 | 1.00 | 22.07 | C |
| ATOM | 2057 | CD1 | ILE | A | 129 | -6.676 | -17.757 | -30.271 | 1.00 | 22.28 | C |
| ATOM | 2061 | CG2 | ILE | A | 129 | -8.104 | -18.755 | -27.806 | 1.00 | 23.75 | C |
| ATOM | 2065 | C | ILE | A | 129 | -10.005 | -17.231 | -26.471 | 1.00 | 24.22 | C |
| ATOM | 2066 | O | ILE | A | 129 | -10.868 | -18.100 | -26.265 | 1.00 | 24.33 | O |
| ATOM | 2068 | N | TYR | A | 130 | -9.359 | -16.633 | -25.472 | 1.00 | 24.98 | N |
| ATOM | 2069 | CA | TYR | A | 130 | -9.770 | -16.956 | -24.077 | 1.00 | 26.34 | C |
| ATOM | 2071 | CB | TYR | A | 130 | -8.910 | -16.194 | -23.090 | 1.00 | 26.88 | C |
| ATOM | 2074 | CG | TYR | A | 130 | -8.737 | -16.845 | -21.740 | 1.00 | 32.11 | C |
| ATOM | 2075 | CD1 | TYR | A | 130 | -7.494 | -17.325 | -21.336 | 1.00 | 34.68 | C |
| ATOM | 2077 | CE1 | TYR | A | 130 | -7.323 | -17.891 | -20.115 | 1.00 | 35.80 | C |
| ATOM | 2079 | CZ | TYR | A | 130 | -8.379 | -17.955 | -19.235 | 1.00 | 36.03 | C |
| ATOM | 2080 | OH | TYR | A | 130 | -8.189 | -18.527 | -18.005 | 1.00 | 41.73 | O |
| ATOM | 2082 | CE2 | TYR | A | 130 | -9.621 | -17.465 | -19.572 | 1.00 | 35.71 | C |
| ATOM | 2084 | CD2 | TYR | A | 130 | -9.795 | -16.896 | -20.811 | 1.00 | 35.79 | C |
| ATOM | 2086 | C | TYR | A | 130 | -11.258 | -16.648 | -23.880 | 1.00 | 25.18 | C |
| ATOM | 2087 | O | TYR | A | 130 | -11.986 | -17.447 | -23.289 | 1.00 | 24.90 | O |
| ATOM | 2089 | N | TYR | A | 131 | -11.723 | -15.510 | -24.404 | 1.00 | 25.15 | N |
| ATOM | 2090 | CA | TYR | A | 131 | -13.136 | -15.160 | -24.341 | 1.00 | 24.93 | C |
| ATOM | 2092 | CB | TYR | A | 131 | -13.427 | -13.860 | -25.084 | 1.00 | 24.59 | C |
| ATOM | 2095 | CG | TYR | A | 131 | -14.808 | -13.403 | -24.819 | 1.00 | 24.95 | C |
| ATOM | 2096 | CD1 | TYR | A | 131 | -15.065 | -12.450 | -23.856 | 1.00 | 24.13 | C |
| ATOM | 2098 | CE1 | TYR | A | 131 | -16.305 | -12.076 | -23.546 | 1.00 | 23.50 | C |
| ATOM | 2100 | CZ | TYR | A | 131 | -17.395 | -12.653 | -24.173 | 1.00 | 28.67 | C |
| ATOM | 2101 | OH | TYR | A | 131 | -18.690 | -12.187 | -23.856 | 1.00 | 27.17 | O |
| ATOM | 2103 | CE2 | TYR | A | 131 | -17.193 | -13.588 | -25.164 | 1.00 | 30.09 | C |
| ATOM | 2105 | CD2 | TYR | A | 131 | -15.897 | -13.975 | -25.478 | 1.00 | 30.21 | C |
| ATOM | 2107 | C | TYR | A | 131 | -14.038 | -16.269 | -24.892 | 1.00 | 26.90 | C |
| ATOM | 2108 | O | TYR | A | 131 | -15.006 | -16.614 | -24.240 | 1.00 | 25.95 | O |
| ATOM | 2110 | N | LEU | A | 132 | -13.713 | -16.839 | -26.076 | 1.00 | 28.42 | N |
| ATOM | 2111 | CA | LEU | A | 132 | -14.509 | -17.966 | -26.664 | 1.00 | 28.97 | C |
| ATOM | 2113 | CB | LEU | A | 132 | -13.956 | -18.362 | -28.056 | 1.00 | 29.43 | C |
| ATOM | 2116 | CG | LEU | A | 132 | -14.117 | -17.291 | -29.136 | 1.00 | 31.58 | C |
| ATOM | 2118 | CD1 | LEU | A | 132 | -13.623 | -17.752 | -30.546 | 1.00 | 27.53 | C |
| ATOM | 2122 | CD2 | LEU | A | 132 | -15.575 | -16.857 | -29.145 | 1.00 | 25.39 | C |
| ATOM | 2126 | C | LEU | A | 132 | -14.449 | -19.211 | -25.822 | 1.00 | 29.28 | C |
| ATOM | 2127 | O | LEU | A | 132 | -15.463 | -19.895 | -25.573 | 1.00 | 27.68 | O |
| ATOM | 2129 | N | GLU | A | 133 | -13.249 | -19.553 | -25.390 | 1.00 | 31.42 | N |
| ATOM | 2130 | CA | GLU | A | 133 | -13.129 | -20.787 | -24.589 | 1.00 | 33.34 | C |
| ATOM | 2132 | CB | GLU | A | 133 | -11.704 | -21.086 | -24.169 | 1.00 | 33.37 | C |
| ATOM | 2135 | CG | GLU | A | 133 | -10.854 | -21.366 | -25.370 | 1.00 | 38.04 | C |

FIG.4-20

| | | | | | | | | | | | |
|---|---|---|---|---|---|---|---|---|---|---|---|
| ATOM | 2138 | CD | GLU | A | 133 | -9.387 | -21.656 | -25.073 | 1.00 | 42.78 | C |
| ATOM | 2139 | OE1 | GLU | A | 133 | -8.977 | -21.697 | -23.880 | 1.00 | 45.36 | O |
| ATOM | 2140 | OE2 | GLU | A | 133 | -8.651 | -21.867 | -26.072 | 1.00 | 47.10 | O |
| ATOM | 2141 | C | GLU | A | 133 | -14.031 | -20.721 | -23.402 | 1.00 | 33.96 | C |
| ATOM | 2142 | O | GLU | A | 133 | -14.672 | -21.716 | -23.062 | 1.00 | 35.17 | O |
| ATOM | 2144 | N | LYS | A | 134 | -14.129 | -19.553 | -22.792 | 1.00 | 34.78 | N |
| ATOM | 2145 | CA | LYS | A | 134 | -14.964 | -19.403 | -21.631 | 1.00 | 36.41 | C |
| ATOM | 2147 | CB | LYS | A | 134 | -14.381 | -18.372 | -20.614 | 1.00 | 36.53 | C |
| ATOM | 2150 | CG | LYS | A | 134 | -13.061 | -18.869 | -19.908 | 1.00 | 38.50 | C |
| ATOM | 2153 | CD | LYS | A | 134 | -13.230 | -20.269 | -19.209 | 1.00 | 43.08 | C |
| ATOM | 2156 | CE | LYS | A | 134 | -11.924 | -21.067 | -18.997 | 1.00 | 44.84 | C |
| ATOM | 2159 | NZ | LYS | A | 134 | -12.187 | -22.562 | -18.962 | 1.00 | 48.99 | N |
| ATOM | 2163 | C | LYS | A | 134 | -16.443 | -19.181 | -21.924 | 1.00 | 37.46 | C |
| ATOM | 2164 | O | LYS | A | 134 | -17.277 | -19.657 | -21.144 | 1.00 | 36.37 | O |
| ATOM | 2166 | N | ALA | A | 135 | -16.788 | -18.470 | -23.004 | 1.00 | 38.60 | N |
| ATOM | 2167 | CA | ALA | A | 135 | -18.215 | -18.370 | -23.414 | 1.00 | 39.74 | C |
| ATOM | 2169 | CB | ALA | A | 135 | -18.416 | -17.303 | -24.520 | 1.00 | 39.13 | C |
| ATOM | 2173 | C | ALA | A | 135 | -18.811 | -19.733 | -23.862 | 1.00 | 41.19 | C |
| ATOM | 2174 | O | ALA | A | 135 | -20.034 | -19.971 | -23.749 | 1.00 | 40.43 | O |
| ATOM | 2176 | N | ASN | A | 136 | -17.954 | -20.617 | -24.367 | 1.00 | 43.50 | N |
| ATOM | 2177 | CA | ASN | A | 136 | -18.398 | -21.936 | -24.833 | 1.00 | 46.08 | C |
| ATOM | 2179 | CB | ASN | A | 136 | -17.261 | -22.693 | -25.550 | 1.00 | 46.15 | C |
| ATOM | 2182 | CG | ASN | A | 136 | -17.037 | -22.200 | -26.993 | 1.00 | 48.34 | C |
| ATOM | 2183 | OD1 | ASN | A | 136 | -17.824 | -21.402 | -27.523 | 1.00 | 49.55 | O |
| ATOM | 2184 | ND2 | ASN | A | 136 | -15.932 | -22.672 | -27.635 | 1.00 | 50.97 | N |
| ATOM | 2187 | C | ASN | A | 136 | -19.022 | -22.784 | -23.722 | 1.00 | 47.77 | C |
| ATOM | 2188 | O | ASN | A | 136 | -20.081 | -23.375 | -23.923 | 1.00 | 48.03 | O |
| ATOM | 2190 | N | LYS | A | 137 | -18.381 | -22.809 | -22.555 | 1.00 | 50.42 | N |
| ATOM | 2191 | CA | LYS | A | 137 | -18.894 | -23.517 | -21.371 | 1.00 | 52.35 | C |
| ATOM | 2193 | CB | LYS | A | 137 | -17.724 | -23.793 | -20.423 | 1.00 | 53.15 | C |
| ATOM | 2196 | CG | LYS | A | 137 | -16.865 | -25.004 | -20.836 | 1.00 | 55.37 | C |
| ATOM | 2199 | CD | LYS | A | 137 | -15.544 | -24.603 | -21.505 | 1.00 | 57.57 | C |
| ATOM | 2202 | CE | LYS | A | 137 | -14.875 | -25.810 | -22.180 | 1.00 | 60.15 | C |
| ATOM | 2205 | NZ | LYS | A | 137 | -13.428 | -25.568 | -22.481 | 1.00 | 62.86 | N |
| ATOM | 2209 | C | LYS | A | 137 | -20.031 | -22.798 | -20.608 | 1.00 | 53.64 | C |
| ATOM | 2210 | O | LYS | A | 137 | -20.954 | -23.434 | -20.087 | 1.00 | 53.80 | O |
| ATOM | 2212 | N | ILE | A | 138 | -19.960 | -21.476 | -20.554 | 1.00 | 54.94 | N |
| ATOM | 2213 | CA | ILE | A | 138 | -20.962 | -20.644 | -19.882 | 1.00 | 56.34 | C |
| ATOM | 2215 | CB | ILE | A | 138 | -20.400 | -19.202 | -19.722 | 1.00 | 56.27 | C |
| ATOM | 2217 | CG1 | ILE | A | 138 | -19.567 | -19.117 | -18.442 | 1.00 | 56.21 | C |
| ATOM | 2220 | CD1 | ILE | A | 138 | -18.643 | -17.902 | -18.383 | 1.00 | 55.28 | C |
| ATOM | 2224 | CG2 | ILE | A | 138 | -21.502 | -18.147 | -19.754 | 1.00 | 57.01 | C |
| ATOM | 2228 | C | ILE | A | 138 | -22.342 | -20.603 | -20.563 | 1.00 | 57.52 | C |
| ATOM | 2229 | O | ILE | A | 138 | -23.352 | -20.244 | -19.919 | 1.00 | 58.75 | O |
| ATOM | 2231 | N | LYS | A | 139 | -22.384 | -20.972 | -21.843 | 1.00 | 58.47 | N |
| ATOM | 2232 | CA | LYS | A | 139 | -23.606 | -20.937 | -22.677 | 1.00 | 59.03 | C |
| ATOM | 2234 | CB | LYS | A | 139 | -24.283 | -22.314 | -22.714 | 1.00 | 59.40 | C |
| ATOM | 2237 | CG | LYS | A | 139 | -23.567 | -23.375 | -23.583 | 1.00 | 61.60 | C |
| ATOM | 2240 | CD | LYS | A | 139 | -23.664 | -23.086 | -25.117 | 1.00 | 63.74 | C |
| ATOM | 2243 | CE | LYS | A | 139 | -23.146 | -24.277 | -25.948 | 1.00 | 65.00 | C |
| ATOM | 2246 | NZ | LYS | A | 139 | -22.573 | -23.906 | -27.284 | 1.00 | 66.48 | N |
| ATOM | 2250 | C | LYS | A | 139 | -24.616 | -19.863 | -22.259 | 1.00 | 58.99 | C |
| ATOM | 2251 | O | LYS | A | 139 | -25.540 | -20.123 | -21.483 | 1.00 | 58.89 | O |
| ATOM | 2253 | N | GLU | A | 141 | -25.979 | -18.214 | -19.379 | 1.00 | 50.86 | N |
| ATOM | 2254 | CA | GLU | A | 141 | -24.832 | -17.298 | -19.464 | 1.00 | 50.54 | C |
| ATOM | 2256 | CB | GLU | A | 141 | -24.517 | -16.940 | -20.936 | 1.00 | 51.64 | C |
| ATOM | 2259 | CG | GLU | A | 141 | -25.745 | -16.809 | -21.884 | 1.00 | 54.93 | C |
| ATOM | 2262 | CD | GLU | A | 141 | -26.562 | -15.516 | -21.730 | 1.00 | 58.27 | C |
| ATOM | 2263 | OE1 | GLU | A | 141 | -26.960 | -14.961 | -22.789 | 1.00 | 60.97 | O |
| ATOM | 2264 | OE2 | GLU | A | 141 | -26.847 | -15.077 | -20.585 | 1.00 | 60.03 | O |
| ATOM | 2265 | C | GLU | A | 141 | -24.989 | -16.005 | -18.666 | 1.00 | 48.69 | C |
| ATOM | 2266 | O | GLU | A | 141 | -24.764 | -14.905 | -19.184 | 1.00 | 49.48 | O |
| ATOM | 2268 | N | LYS | A | 142 | -25.337 | -16.107 | -17.396 | 1.00 | 46.08 | N |

FIG.4-21

| | | | | | | | | | | | |
|---|---|---|---|---|---|---|---|---|---|---|---|
| ATOM | 2269 | CA | LYS | A | 142 | -25.369 | -14.877 | -16.589 | 1.00 | 43.51 | C |
| ATOM | 2271 | CB | LYS | A | 142 | -26.465 | -15.005 | -15.535 | 1.00 | 43.94 | C |
| ATOM | 2274 | CG | LYS | A | 142 | -27.855 | -15.247 | -16.199 | 1.00 | 46.65 | C |
| ATOM | 2277 | CD | LYS | A | 142 | -28.984 | -14.426 | -15.531 | 1.00 | 51.06 | C |
| ATOM | 2280 | CE | LYS | A | 142 | -29.126 | -12.991 | -16.116 | 1.00 | 52.66 | C |
| ATOM | 2283 | NZ | LYS | A | 142 | -30.332 | -12.857 | -17.031 | 1.00 | 51.94 | N |
| ATOM | 2287 | C | LYS | A | 142 | -23.992 | -14.478 | -16.003 | 1.00 | 39.86 | C |
| ATOM | 2288 | O | LYS | A | 142 | -23.857 | -13.490 | -15.238 | 1.00 | 38.77 | O |
| ATOM | 2290 | N | THR | A | 143 | -22.963 | -15.244 | -16.348 | 1.00 | 35.54 | N |
| ATOM | 2291 | CA | THR | A | 143 | -21.640 | -14.964 | -15.787 | 1.00 | 32.29 | C |
| ATOM | 2293 | CB | THR | A | 143 | -20.855 | -16.223 | -15.534 | 1.00 | 31.98 | C |
| ATOM | 2295 | OG1 | THR | A | 143 | -21.482 | -16.936 | -14.461 | 1.00 | 32.43 | O |
| ATOM | 2297 | CG2 | THR | A | 143 | -19.436 | -15.916 | -15.122 | 1.00 | 30.99 | C |
| ATOM | 2301 | C | THR | A | 143 | -20.965 | -13.970 | -16.736 | 1.00 | 30.44 | C |
| ATOM | 2302 | O | THR | A | 143 | -20.903 | -14.187 | -17.952 | 1.00 | 30.80 | O |
| ATOM | 2304 | N | HIS | A | 144 | -20.548 | -12.835 | -16.192 | 1.00 | 27.71 | N |
| ATOM | 2305 | CA | HIS | A | 144 | -19.849 | -11.816 | -16.974 | 1.00 | 26.31 | C |
| ATOM | 2307 | CB | HIS | A | 144 | -19.872 | -10.499 | -16.220 | 1.00 | 25.89 | C |
| ATOM | 2310 | CG | HIS | A | 144 | -19.848 | -9.292 | -17.110 | 1.00 | 25.95 | C |
| ATOM | 2311 | ND1 | HIS | A | 144 | -20.985 | -8.781 | -17.691 | 1.00 | 23.29 | N |
| ATOM | 2313 | CE1 | HIS | A | 144 | -20.674 | -7.684 | -18.363 | 1.00 | 25.31 | C |
| ATOM | 2315 | NE2 | HIS | A | 144 | -19.381 | -7.455 | -18.224 | 1.00 | 20.55 | N |
| ATOM | 2317 | CD2 | HIS | A | 144 | -18.837 | -8.462 | -17.464 | 1.00 | 24.29 | C |
| ATOM | 2319 | C | HIS | A | 144 | -18.401 | -12.215 | -17.187 | 1.00 | 25.34 | C |
| ATOM | 2320 | O | HIS | A | 144 | -17.779 | -12.650 | -16.225 | 1.00 | 24.19 | O |
| ATOM | 2322 | N | ILE | A | 145 | -17.866 | -12.048 | -18.417 | 1.00 | 22.58 | N |
| ATOM | 2323 | CA | ILE | A | 145 | -16.508 | -12.466 | -18.758 | 1.00 | 20.97 | C |
| ATOM | 2325 | CB | ILE | A | 145 | -16.464 | -13.312 | -20.082 | 1.00 | 21.27 | C |
| ATOM | 2327 | CG1 | ILE | A | 145 | -17.378 | -14.497 | -20.022 | 1.00 | 21.49 | C |
| ATOM | 2330 | CD1 | ILE | A | 145 | -17.419 | -15.334 | -21.374 | 1.00 | 17.19 | C |
| ATOM | 2334 | CG2 | ILE | A | 145 | -15.143 | -13.876 | -20.357 | 1.00 | 20.45 | C |
| ATOM | 2338 | C | ILE | A | 145 | -15.684 | -11.219 | -18.985 | 1.00 | 21.22 | C |
| ATOM | 2339 | O | ILE | A | 145 | -16.163 | -10.323 | -19.651 | 1.00 | 21.63 | O |
| ATOM | 2341 | N | HIS | A | 146 | -14.454 | -11.149 | -18.426 | 1.00 | 20.18 | N |
| ATOM | 2342 | CA | HIS | A | 146 | -13.550 | -10.070 | -18.670 | 1.00 | 19.45 | C |
| ATOM | 2344 | CB | HIS | A | 146 | -13.495 | -9.132 | -17.464 | 1.00 | 20.53 | C |
| ATOM | 2347 | CG | HIS | A | 146 | -12.856 | -7.807 | -17.730 | 1.00 | 19.65 | C |
| ATOM | 2348 | ND1 | HIS | A | 146 | -13.235 | -6.663 | -17.065 | 1.00 | 19.96 | N |
| ATOM | 2350 | CE1 | HIS | A | 146 | -12.503 | -5.646 | -17.489 | 1.00 | 21.90 | C |
| ATOM | 2352 | NE2 | HIS | A | 146 | -11.643 | -6.098 | -18.385 | 1.00 | 18.30 | N |
| ATOM | 2354 | CD2 | HIS | A | 146 | -11.837 | -7.446 | -18.544 | 1.00 | 20.67 | C |
| ATOM | 2356 | C | HIS | A | 146 | -12.208 | -10.672 | -18.859 | 1.00 | 20.19 | C |
| ATOM | 2357 | O | HIS | A | 146 | -11.674 | -11.322 | -17.921 | 1.00 | 19.48 | O |
| ATOM | 2359 | N | ILE | A | 147 | -11.620 | -10.424 | -20.035 | 1.00 | 19.77 | N |
| ATOM | 2360 | CA | ILE | A | 147 | -10.316 | -10.989 | -20.380 | 1.00 | 20.64 | C |
| ATOM | 2362 | CB | ILE | A | 147 | -10.316 | -11.676 | -21.781 | 1.00 | 22.08 | C |
| ATOM | 2364 | CG1 | ILE | A | 147 | -11.479 | -12.695 | -21.908 | 1.00 | 23.83 | C |
| ATOM | 2367 | CD1 | ILE | A | 147 | -11.275 | -13.963 | -21.095 | 1.00 | 28.34 | C |
| ATOM | 2371 | CG2 | ILE | A | 147 | -8.954 | -12.269 | -22.059 | 1.00 | 18.00 | C |
| ATOM | 2375 | C | ILE | A | 147 | -9.322 | -9.854 | -20.438 | 1.00 | 20.39 | C |
| ATOM | 2376 | O | ILE | A | 147 | -9.612 | -8.776 | -20.940 | 1.00 | 19.54 | O |
| ATOM | 2378 | N | PHE | A | 148 | -8.139 | -10.087 | -19.914 | 1.00 | 20.81 | N |
| ATOM | 2379 | CA | PHE | A | 148 | -7.089 | -9.101 | -20.027 | 1.00 | 21.42 | C |
| ATOM | 2381 | CB | PHE | A | 148 | -6.520 | -8.725 | -18.647 | 1.00 | 20.44 | C |
| ATOM | 2384 | CG | PHE | A | 148 | -7.475 | -7.995 | -17.759 | 1.00 | 18.59 | C |
| ATOM | 2385 | CD1 | PHE | A | 148 | -7.427 | -6.623 | -17.675 | 1.00 | 16.88 | C |
| ATOM | 2387 | CE1 | PHE | A | 148 | -8.293 | -5.907 | -16.816 | 1.00 | 18.61 | C |
| ATOM | 2389 | CZ | PHE | A | 148 | -9.150 | -6.574 | -16.009 | 1.00 | 15.82 | C |
| ATOM | 2391 | CE2 | PHE | A | 148 | -9.199 | -7.949 | -16.053 | 1.00 | 16.39 | C |
| ATOM | 2393 | CD2 | PHE | A | 148 | -8.384 | -8.673 | -16.947 | 1.00 | 14.33 | C |
| ATOM | 2395 | C | PHE | A | 148 | -5.962 | -9.766 | -20.820 | 1.00 | 22.77 | C |
| ATOM | 2396 | O | PHE | A | 148 | -5.827 | -10.947 | -20.774 | 1.00 | 24.80 | O |
| ATOM | 2398 | N | SER | A | 149 | -5.094 | -8.997 | -21.441 | 1.00 | 25.54 | N |

FIG.4-22

| | | | | | | | | | | | |
|---|---|---|---|---|---|---|---|---|---|---|---|
| ATOM | 2399 | CA | SER | A | 149 | -4.004 | -9.551 | -22.218 | 1.00 | 27.57 | C |
| ATOM | 2401 | CB | SER | A | 149 | -4.324 | -9.418 | -23.730 | 1.00 | 28.36 | C |
| ATOM | 2404 | OG | SER | A | 149 | -3.237 | -8.851 | -24.430 | 1.00 | 31.65 | O |
| ATOM | 2406 | C | SER | A | 149 | -2.750 | -8.815 | -21.846 | 1.00 | 28.12 | C |
| ATOM | 2407 | O | SER | A | 149 | -2.798 | -7.814 | -21.170 | 1.00 | 29.37 | O |
| ATOM | 2409 | N | PHE | A | 150 | -1.613 | -9.341 | -22.242 | 1.00 | 29.44 | N |
| ATOM | 2410 | CA | PHE | A | 150 | -0.349 | -8.768 | -21.859 | 1.00 | 29.97 | C |
| ATOM | 2412 | CB | PHE | A | 150 | 0.774 | -9.853 | -21.787 | 1.00 | 30.15 | C |
| ATOM | 2415 | CG | PHE | A | 150 | 0.776 | -10.720 | -20.553 | 1.00 | 26.32 | C |
| ATOM | 2416 | CD1 | PHE | A | 150 | 1.529 | -10.388 | -19.475 | 1.00 | 25.66 | C |
| ATOM | 2418 | CE1 | PHE | A | 150 | 1.567 | -11.161 | -18.360 | 1.00 | 22.39 | C |
| ATOM | 2420 | CZ | PHE | A | 150 | 0.849 | -12.358 | -18.302 | 1.00 | 23.54 | C |
| ATOM | 2422 | CE2 | PHE | A | 150 | 0.092 | -12.712 | -19.353 | 1.00 | 20.62 | C |
| ATOM | 2424 | CD2 | PHE | A | 150 | 0.065 | -11.898 | -20.495 | 1.00 | 26.99 | C |
| ATOM | 2426 | C | PHE | A | 150 | -0.005 | -7.694 | -22.910 | 1.00 | 31.85 | C |
| ATOM | 2427 | O | PHE | A | 150 | 1.103 | -7.209 | -22.930 | 1.00 | 33.22 | O |
| ATOM | 2429 | N | THR | A | 151 | -0.943 | -7.326 | -23.783 | 1.00 | 32.17 | N |
| ATOM | 2430 | CA | THR | A | 151 | -0.667 | -6.333 | -24.841 | 1.00 | 32.67 | C |
| ATOM | 2432 | CB | THR | A | 151 | -1.199 | -6.748 | -26.287 | 1.00 | 32.13 | C |
| ATOM | 2434 | OG1 | THR | A | 151 | -2.642 | -6.863 | -26.288 | 1.00 | 33.12 | O |
| ATOM | 2436 | CG2 | THR | A | 151 | -0.640 | -8.025 | -26.738 | 1.00 | 31.02 | C |
| ATOM | 2440 | C | THR | A | 151 | -1.404 | -5.062 | -24.556 | 1.00 | 32.44 | C |
| ATOM | 2441 | O | THR | A | 151 | -1.257 | -4.109 | -25.292 | 1.00 | 32.41 | O |
| ATOM | 2443 | N | GLY | A | 152 | -2.246 | -5.070 | -23.526 | 1.00 | 32.32 | N |
| ATOM | 2444 | CA | GLY | A | 152 | -3.124 | -3.936 | -23.280 | 1.00 | 31.84 | C |
| ATOM | 2447 | C | GLY | A | 152 | -4.561 | -4.041 | -23.735 | 1.00 | 30.62 | C |
| ATOM | 2448 | O | GLY | A | 152 | -5.388 | -3.226 | -23.314 | 1.00 | 32.36 | O |
| ATOM | 2450 | N | GLU | A | 153 | -4.878 | -4.990 | -24.597 | 1.00 | 29.33 | N |
| ATOM | 2451 | CA | GLU | A | 153 | -6.244 | -5.239 | -25.050 | 1.00 | 28.81 | C |
| ATOM | 2453 | CB | GLU | A | 153 | -6.294 | -6.144 | -26.311 | 1.00 | 29.16 | C |
| ATOM | 2456 | CG | GLU | A | 153 | -5.528 | -5.593 | -27.515 | 1.00 | 34.39 | C |
| ATOM | 2459 | CD | GLU | A | 153 | -5.423 | -6.598 | -28.624 | 1.00 | 37.09 | C |
| ATOM | 2460 | OE1 | GLU | A | 153 | -4.267 | -6.948 | -28.983 | 1.00 | 43.50 | O |
| ATOM | 2461 | OE2 | GLU | A | 153 | -6.493 | -7.050 | -29.081 | 1.00 | 33.81 | O |
| ATOM | 2462 | C | GLU | A | 153 | -7.060 | -5.928 | -23.951 | 1.00 | 27.34 | C |
| ATOM | 2463 | O | GLU | A | 153 | -6.520 | -6.690 | -23.180 | 1.00 | 26.85 | O |
| ATOM | 2465 | N | GLU | A | 154 | -8.346 | -5.624 | -23.893 | 1.00 | 26.64 | N |
| ATOM | 2466 | CA | GLU | A | 154 | -9.294 | -6.317 | -23.056 | 1.00 | 28.17 | C |
| ATOM | 2468 | CB | GLU | A | 154 | -9.787 | -5.434 | -21.919 | 1.00 | 28.44 | C |
| ATOM | 2471 | CG | GLU | A | 154 | -8.784 | -4.778 | -21.031 | 1.00 | 29.35 | C |
| ATOM | 2474 | CD | GLU | A | 154 | -9.443 | -3.680 | -20.206 | 1.00 | 31.99 | C |
| ATOM | 2475 | OE1 | GLU | A | 154 | -10.224 | -4.006 | -19.260 | 1.00 | 27.59 | O |
| ATOM | 2476 | OE2 | GLU | A | 154 | -9.199 | -2.480 | -20.536 | 1.00 | 33.26 | O |
| ATOM | 2477 | C | GLU | A | 154 | -10.533 | -6.690 | -23.877 | 1.00 | 28.57 | C |
| ATOM | 2478 | O | GLU | A | 154 | -10.837 | -6.067 | -24.898 | 1.00 | 29.85 | O |
| ATOM | 2480 | N | MET | A | 155 | -11.249 | -7.697 | -23.416 | 1.00 | 28.27 | N |
| ATOM | 2481 | CA | MET | A | 155 | -12.542 | -8.016 | -23.954 | 1.00 | 27.95 | C |
| ATOM | 2483 | CB | MET | A | 155 | -12.397 | -9.086 | -25.045 | 1.00 | 28.61 | C |
| ATOM | 2486 | CG | MET | A | 155 | -13.695 | -9.578 | -25.605 | 1.00 | 29.85 | C |
| ATOM | 2489 | SD | MET | A | 155 | -13.473 | -10.569 | -27.093 | 1.00 | 32.63 | S |
| ATOM | 2490 | CE | MET | A | 155 | -13.281 | -9.059 | -28.068 | 1.00 | 35.44 | C |
| ATOM | 2494 | C | MET | A | 155 | -13.497 | -8.465 | -22.837 | 1.00 | 27.07 | C |
| ATOM | 2495 | O | MET | A | 155 | -13.233 | -9.409 | -22.106 | 1.00 | 25.23 | O |
| ATOM | 2497 | N | ALA | A | 156 | -14.594 | -7.744 | -22.720 | 1.00 | 27.17 | N |
| ATOM | 2498 | CA | ALA | A | 156 | -15.584 | -7.970 | -21.682 | 1.00 | 28.43 | C |
| ATOM | 2500 | CB | ALA | A | 156 | -15.657 | -6.774 | -20.687 | 1.00 | 27.43 | C |
| ATOM | 2504 | C | ALA | A | 156 | -16.906 | -8.133 | -22.356 | 1.00 | 28.18 | C |
| ATOM | 2505 | O | ALA | A | 156 | -17.134 | -7.517 | -23.406 | 1.00 | 28.26 | O |
| ATOM | 2507 | N | THR | A | 157 | -17.773 | -8.963 | -21.777 | 1.00 | 28.86 | N |
| ATOM | 2508 | CA | THR | A | 157 | -19.119 | -9.076 | -22.313 | 1.00 | 28.83 | C |
| ATOM | 2510 | CB | THR | A | 157 | -19.910 | -10.291 | -21.749 | 1.00 | 30.26 | C |
| ATOM | 2512 | OG1 | THR | A | 157 | -21.272 | -9.948 | -21.377 | 1.00 | 32.79 | O |
| ATOM | 2514 | CG2 | THR | A | 157 | -19.173 | -10.901 | -20.657 | 1.00 | 22.57 | C |

FIG.4-23

| | | | | | | | | | | | |
|---|---|---|---|---|---|---|---|---|---|---|---|
| ATOM | 2518 | C | THR | A | 157 | -19.902 | -7.743 | -22.383 | 1.00 | 29.08 | C |
| ATOM | 2519 | O | THR | A | 157 | -19.809 | -6.874 | -21.491 | 1.00 | 27.35 | O |
| ATOM | 2521 | N | LYS | A | 158 | -20.601 | -7.606 | -23.540 | 1.00 | 29.75 | N |
| ATOM | 2522 | CA | LYS | A | 158 | -21.300 | -6.405 | -23.979 | 1.00 | 29.46 | C |
| ATOM | 2524 | CB | LYS | A | 158 | -22.543 | -6.143 | -23.124 | 1.00 | 30.88 | C |
| ATOM | 2527 | CG | LYS | A | 158 | -23.664 | -7.067 | -23.399 | 1.00 | 33.93 | C |
| ATOM | 2530 | CD | LYS | A | 158 | -24.908 | -6.587 | -22.636 | 1.00 | 37.97 | C |
| ATOM | 2533 | CE | LYS | A | 158 | -25.731 | -7.723 | -22.036 | 1.00 | 38.89 | C |
| ATOM | 2536 | NZ | LYS | A | 158 | -26.962 | -7.133 | -21.386 | 1.00 | 44.09 | N |
| ATOM | 2540 | C | LYS | A | 158 | -20.439 | -5.191 | -23.925 | 1.00 | 29.29 | C |
| ATOM | 2541 | O | LYS | A | 158 | -20.965 | -4.094 | -23.775 | 1.00 | 29.22 | O |
| ATOM | 2543 | N | ALA | A | 159 | -19.124 | -5.363 | -24.025 | 1.00 | 28.23 | N |
| ATOM | 2544 | CA | ALA | A | 159 | -18.214 | -4.246 | -23.875 | 1.00 | 27.72 | C |
| ATOM | 2546 | CB | ALA | A | 159 | -18.268 | -3.339 | -25.125 | 1.00 | 27.45 | C |
| ATOM | 2550 | C | ALA | A | 159 | -18.417 | -3.449 | -22.575 | 1.00 | 26.99 | C |
| ATOM | 2551 | O | ALA | A | 159 | -18.112 | -2.280 | -22.480 | 1.00 | 26.15 | O |
| ATOM | 2553 | N | ASP | A | 160 | -18.892 | -4.113 | -21.539 | 1.00 | 27.50 | N |
| ATOM | 2554 | CA | ASP | A | 160 | -19.009 | -3.534 | -20.201 | 1.00 | 26.58 | C |
| ATOM | 2556 | CB | ASP | A | 160 | -20.297 | -4.092 | -19.616 | 1.00 | 28.34 | C |
| ATOM | 2559 | CG | ASP | A | 160 | -20.612 | -3.593 | -18.226 | 1.00 | 28.80 | C |
| ATOM | 2560 | OD1 | ASP | A | 160 | -19.747 | -2.968 | -17.562 | 1.00 | 28.49 | O |
| ATOM | 2561 | OD2 | ASP | A | 160 | -21.779 | -3.854 | -17.820 | 1.00 | 31.47 | O |
| ATOM | 2562 | C | ASP | A | 160 | -17.766 | -3.973 | -19.379 | 1.00 | 26.86 | C |
| ATOM | 2563 | O | ASP | A | 160 | -17.569 | -5.139 | -19.037 | 1.00 | 25.77 | O |
| ATOM | 2565 | N | TYR | A | 161 | -16.913 | -3.019 | -19.048 | 1.00 | 26.95 | N |
| ATOM | 2566 | CA | TYR | A | 161 | -15.658 | -3.349 | -18.414 | 1.00 | 27.50 | C |
| ATOM | 2568 | CB | TYR | A | 161 | -14.587 | -2.461 | -19.006 | 1.00 | 26.48 | C |
| ATOM | 2571 | CG | TYR | A | 161 | -14.366 | -2.732 | -20.454 | 1.00 | 30.05 | C |
| ATOM | 2572 | CD1 | TYR | A | 161 | -13.636 | -3.830 | -20.871 | 1.00 | 31.06 | C |
| ATOM | 2574 | CE1 | TYR | A | 161 | -13.416 | -4.067 | -22.232 | 1.00 | 36.48 | C |
| ATOM | 2576 | CZ | TYR | A | 161 | -13.941 | -3.164 | -23.197 | 1.00 | 36.01 | C |
| ATOM | 2577 | OH | TYR | A | 161 | -13.731 | -3.378 | -24.524 | 1.00 | 36.30 | O |
| ATOM | 2579 | CE2 | TYR | A | 161 | -14.682 | -2.079 | -22.805 | 1.00 | 33.71 | C |
| ATOM | 2581 | CD2 | TYR | A | 161 | -14.876 | -1.849 | -21.440 | 1.00 | 36.04 | C |
| ATOM | 2583 | C | TYR | A | 161 | -15.665 | -3.310 | -16.860 | 1.00 | 26.13 | C |
| ATOM | 2584 | O | TYR | A | 161 | -14.651 | -3.519 | -16.222 | 1.00 | 26.59 | O |
| ATOM | 2586 | N | THR | A | 162 | -16.833 | -3.103 | -16.284 | 1.00 | 26.72 | N |
| ATOM | 2587 | CA | THR | A | 162 | -17.093 | -3.127 | -14.814 | 1.00 | 25.55 | C |
| ATOM | 2589 | CB | THR | A | 162 | -16.799 | -4.515 | -14.188 | 1.00 | 26.01 | C |
| ATOM | 2591 | OG1 | THR | A | 162 | -17.667 | -5.503 | -14.752 | 1.00 | 24.29 | O |
| ATOM | 2593 | CG2 | THR | A | 162 | -17.003 | -4.499 | -12.642 | 1.00 | 24.98 | C |
| ATOM | 2597 | C | THR | A | 162 | -16.362 | -2.064 | -14.018 | 1.00 | 25.32 | C |
| ATOM | 2598 | O | THR | A | 162 | -16.975 | -1.217 | -13.407 | 1.00 | 24.39 | O |
| ATOM | 2600 | N | LEU | A | 163 | -15.037 | -2.137 | -13.988 | 1.00 | 25.35 | N |
| ATOM | 2601 | CA | LEU | A | 163 | -14.223 | -1.227 | -13.180 | 1.00 | 24.16 | C |
| ATOM | 2603 | CB | LEU | A | 163 | -12.871 | -1.884 | -12.978 | 1.00 | 23.47 | C |
| ATOM | 2606 | CG | LEU | A | 163 | -12.849 | -3.199 | -12.193 | 1.00 | 20.40 | C |
| ATOM | 2608 | CD1 | LEU | A | 163 | -11.417 | -3.756 | -12.243 | 1.00 | 19.33 | C |
| ATOM | 2612 | CD2 | LEU | A | 163 | -13.268 | -2.932 | -10.827 | 1.00 | 16.61 | C |
| ATOM | 2616 | C | LEU | A | 163 | -13.998 | 0.119 | -13.867 | 1.00 | 25.44 | C |
| ATOM | 2617 | O | LEU | A | 163 | -14.137 | 0.228 | -15.113 | 1.00 | 26.02 | O |
| ATOM | 2619 | N | ASP | A | 164 | -13.612 | 1.122 | -13.078 | 1.00 | 25.92 | N |
| ATOM | 2620 | CA | ASP | A | 164 | -13.156 | 2.411 | -13.611 | 1.00 | 27.67 | C |
| ATOM | 2622 | CB | ASP | A | 164 | -12.812 | 3.383 | -12.487 | 1.00 | 28.55 | C |
| ATOM | 2625 | CG | ASP | A | 164 | -11.681 | 2.869 | -11.595 | 1.00 | 32.34 | C |
| ATOM | 2626 | OD1 | ASP | A | 164 | -11.986 | 2.073 | -10.684 | 1.00 | 36.78 | O |
| ATOM | 2627 | OD2 | ASP | A | 164 | -10.483 | 3.228 | -11.801 | 1.00 | 38.62 | O |
| ATOM | 2628 | C | ASP | A | 164 | -11.889 | 2.283 | -14.446 | 1.00 | 26.93 | C |
| ATOM | 2629 | O | ASP | A | 164 | -11.105 | 1.342 | -14.270 | 1.00 | 26.55 | O |
| ATOM | 2631 | N | GLU | A | 165 | -11.655 | 3.277 | -15.284 | 1.00 | 26.54 | N |
| ATOM | 2632 | CA | GLU | A | 165 | -10.460 | 3.300 | -16.110 | 1.00 | 27.41 | C |
| ATOM | 2634 | CB | GLU | A | 165 | -10.345 | 4.579 | -16.974 | 1.00 | 27.87 | C |
| ATOM | 2637 | CG | GLU | A | 165 | -9.794 | 4.249 | -18.441 | 1.00 | 32.49 | C |

FIG.4-24

| | | | | | | | | | | | |
|---|---|---|---|---|---|---|---|---|---|---|---|
| ATOM | 2640 | CD | GLU | A | 165 | -9.346 | 5.481 | -19.287 | 1.00 | 38.18 | C |
| ATOM | 2641 | OE1 | GLU | A | 165 | -10.068 | 6.515 | -19.249 | 1.00 | 40.83 | O |
| ATOM | 2642 | OE2 | GLU | A | 165 | -8.269 | 5.404 | -19.972 | 1.00 | 39.28 | O |
| ATOM | 2643 | C | GLU | A | 165 | -9.176 | 3.123 | -15.309 | 1.00 | 26.49 | C |
| ATOM | 2644 | O | GLU | A | 165 | -8.269 | 2.385 | -15.750 | 1.00 | 26.51 | O |
| ATOM | 2646 | N | GLU | A | 166 | -9.086 | 3.780 | -14.144 | 1.00 | 25.65 | N |
| ATOM | 2647 | CA | GLU | A | 166 | -7.831 | 3.759 | -13.367 | 1.00 | 24.90 | C |
| ATOM | 2649 | CB | GLU | A | 166 | -7.766 | 4.893 | -12.308 | 1.00 | 25.89 | C |
| ATOM | 2652 | CG | GLU | A | 166 | -6.557 | 4.845 | -11.256 | 1.00 | 27.20 | C |
| ATOM | 2655 | CD | GLU | A | 166 | -5.207 | 5.176 | -11.884 | 1.00 | 31.46 | C |
| ATOM | 2656 | OE1 | GLU | A | 166 | -5.196 | 5.320 | -13.104 | 1.00 | 36.92 | O |
| ATOM | 2657 | OE2 | GLU | A | 166 | -4.179 | 5.346 | -11.188 | 1.00 | 33.28 | O |
| ATOM | 2658 | C | GLU | A | 166 | -7.513 | 2.366 | -12.796 | 1.00 | 23.39 | C |
| ATOM | 2659 | O | GLU | A | 166 | -6.384 | 1.985 | -12.800 | 1.00 | 23.57 | O |
| ATOM | 2661 | N | SER | A | 167 | -8.485 | 1.581 | -12.362 | 1.00 | 21.96 | N |
| ATOM | 2662 | CA | SER | A | 167 | -8.196 | 0.262 | -11.855 | 1.00 | 21.28 | C |
| ATOM | 2664 | CB | SER | A | 167 | -9.382 | -0.289 | -11.108 | 1.00 | 21.54 | C |
| ATOM | 2667 | OG | SER | A | 167 | -9.873 | 0.607 | -10.137 | 1.00 | 23.03 | O |
| ATOM | 2669 | C | SER | A | 167 | -7.831 | -0.732 | -12.968 | 1.00 | 22.43 | C |
| ATOM | 2670 | O | SER | A | 167 | -7.006 | -1.656 | -12.776 | 1.00 | 20.55 | O |
| ATOM | 2672 | N | ARG | A | 168 | -8.438 | -0.544 | -14.146 | 1.00 | 22.10 | N |
| ATOM | 2673 | CA | ARG | A | 168 | -8.072 | -1.372 | -15.270 | 1.00 | 22.84 | C |
| ATOM | 2675 | CB | ARG | A | 168 | -9.055 | -1.204 | -16.427 | 1.00 | 22.98 | C |
| ATOM | 2678 | CG | ARG | A | 168 | -10.480 | -1.746 | -16.146 | 1.00 | 24.56 | C |
| ATOM | 2681 | CD | ARG | A | 168 | -11.169 | -1.910 | -17.448 | 1.00 | 29.37 | C |
| ATOM | 2684 | NE | ARG | A | 168 | -11.740 | -0.691 | -17.957 | 1.00 | 31.84 | N |
| ATOM | 2686 | CZ | ARG | A | 168 | -11.753 | -0.301 | -19.225 | 1.00 | 30.69 | C |
| ATOM | 2687 | NH1 | ARG | A | 168 | -11.167 | -0.969 | -20.196 | 1.00 | 33.79 | N |
| ATOM | 2690 | NH2 | ARG | A | 168 | -12.352 | 0.805 | -19.514 | 1.00 | 29.78 | N |
| ATOM | 2693 | C | ARG | A | 168 | -6.627 | -1.068 | -15.710 | 1.00 | 21.35 | C |
| ATOM | 2694 | O | ARG | A | 168 | -5.887 | -1.974 | -16.070 | 1.00 | 19.69 | O |
| ATOM | 2696 | N | ALA | A | 169 | -6.240 | 0.196 | -15.667 | 1.00 | 21.39 | N |
| ATOM | 2697 | CA | ALA | A | 169 | -4.874 | 0.579 | -16.055 | 1.00 | 22.12 | C |
| ATOM | 2699 | CB | ALA | A | 169 | -4.806 | 2.114 | -16.246 | 1.00 | 22.67 | C |
| ATOM | 2703 | C | ALA | A | 169 | -3.805 | 0.078 | -15.052 | 1.00 | 21.58 | C |
| ATOM | 2704 | O | ALA | A | 169 | -2.678 | -0.196 | -15.400 | 1.00 | 22.14 | O |
| ATOM | 2706 | N | ARG | A | 170 | -4.197 | -0.058 | -13.805 | 1.00 | 22.87 | N |
| ATOM | 2707 | CA | ARG | A | 170 | -3.356 | -0.591 | -12.767 | 1.00 | 23.19 | C |
| ATOM | 2709 | CB | ARG | A | 170 | -4.077 | -0.343 | -11.469 | 1.00 | 25.00 | C |
| ATOM | 2712 | CG | ARG | A | 170 | -3.231 | -0.432 | -10.239 | 1.00 | 30.84 | C |
| ATOM | 2715 | CD | ARG | A | 170 | -3.998 | -0.081 | -8.958 | 1.00 | 37.81 | C |
| ATOM | 2718 | NE | ARG | A | 170 | -3.160 | -0.405 | -7.783 | 1.00 | 43.54 | N |
| ATOM | 2720 | CZ | ARG | A | 170 | -2.454 | 0.484 | -7.052 | 1.00 | 47.99 | C |
| ATOM | 2721 | NH1 | ARG | A | 170 | -2.485 | 1.793 | -7.330 | 1.00 | 48.50 | N |
| ATOM | 2724 | NH2 | ARG | A | 170 | -1.726 | 0.070 | -6.002 | 1.00 | 47.36 | N |
| ATOM | 2727 | C | ARG | A | 170 | -3.065 | -2.090 | -12.998 | 1.00 | 22.30 | C |
| ATOM | 2728 | O | ARG | A | 170 | -1.890 | -2.497 | -13.034 | 1.00 | 22.41 | O |
| ATOM | 2730 | N | ILE | A | 171 | -4.115 | -2.872 | -13.257 | 1.00 | 21.20 | N |
| ATOM | 2731 | CA | ILE | A | 171 | -3.998 | -4.261 | -13.719 | 1.00 | 21.18 | C |
| ATOM | 2733 | CB | ILE | A | 171 | -5.406 | -4.868 | -14.032 | 1.00 | 21.39 | C |
| ATOM | 2735 | CG1 | ILE | A | 171 | -6.249 | -4.835 | -12.743 | 1.00 | 21.48 | C |
| ATOM | 2738 | CD1 | ILE | A | 171 | -7.609 | -5.381 | -12.762 | 1.00 | 21.47 | C |
| ATOM | 2742 | CG2 | ILE | A | 171 | -5.268 | -6.273 | -14.685 | 1.00 | 19.89 | C |
| ATOM | 2746 | C | ILE | A | 171 | -3.131 | -4.314 | -14.962 | 1.00 | 22.08 | C |
| ATOM | 2747 | O | ILE | A | 171 | -2.183 | -5.076 | -15.048 | 1.00 | 22.01 | O |
| ATOM | 2749 | N | LYS | A | 172 | -3.426 | -3.492 | -15.953 | 1.00 | 23.68 | N |
| ATOM | 2750 | CA | LYS | A | 172 | -2.645 | -3.570 | -17.198 | 1.00 | 23.86 | C |
| ATOM | 2752 | CB | LYS | A | 172 | -3.266 | -2.680 | -18.237 | 1.00 | 24.88 | C |
| ATOM | 2755 | CG | LYS | A | 172 | -4.632 | -3.113 | -18.725 | 1.00 | 25.07 | C |
| ATOM | 2758 | CD | LYS | A | 172 | -5.317 | -1.857 | -19.226 | 1.00 | 25.86 | C |
| ATOM | 2761 | CE | LYS | A | 172 | -6.336 | -2.104 | -20.216 | 1.00 | 29.35 | C |
| ATOM | 2764 | NZ | LYS | A | 172 | -7.284 | -0.864 | -20.262 | 1.00 | 35.34 | N |
| ATOM | 2768 | C | LYS | A | 172 | -1.198 | -3.144 | -16.986 | 1.00 | 22.74 | C |

FIG.4-25

| | | | | | | | | | | | |
|---|---|---|---|---|---|---|---|---|---|---|---|
| ATOM | 2769 | O | LYS | A | 172 | -0.274 | -3.716 | -17.558 | 1.00 | 22.06 | O |
| ATOM | 2771 | N | THR | A | 173 | -0.982 | -2.167 | -16.112 | 1.00 | 22.31 | N |
| ATOM | 2772 | CA | THR | A | 173 | 0.395 | -1.877 | -15.732 | 1.00 | 21.79 | C |
| ATOM | 2774 | CB | THR | A | 173 | 0.510 | -0.647 | -14.861 | 1.00 | 22.72 | C |
| ATOM | 2776 | OG1 | THR | A | 173 | -0.118 | 0.445 | -15.546 | 1.00 | 24.08 | O |
| ATOM | 2778 | CG2 | THR | A | 173 | 1.945 | -0.338 | -14.663 | 1.00 | 21.78 | C |
| ATOM | 2782 | C | THR | A | 173 | 1.067 | -3.004 | -15.064 | 1.00 | 20.73 | C |
| ATOM | 2783 | O | THR | A | 173 | 2.243 | -3.241 | -15.300 | 1.00 | 23.71 | O |
| ATOM | 2785 | N | ARG | A | 174 | 0.332 | -3.797 | -14.288 | 1.00 | 20.12 | N |
| ATOM | 2786 | CA | ARG | A | 174 | 0.965 | -4.886 | -13.618 | 1.00 | 19.03 | C |
| ATOM | 2788 | CB | ARG | A | 174 | 0.071 | -5.428 | -12.516 | 1.00 | 18.29 | C |
| ATOM | 2791 | CG | ARG | A | 174 | 0.575 | -6.661 | -11.863 | 1.00 | 17.17 | C |
| ATOM | 2794 | CD | ARG | A | 174 | 2.015 | -6.519 | -11.337 | 1.00 | 22.49 | C |
| ATOM | 2797 | NE | ARG | A | 174 | 2.322 | -7.691 | -10.547 | 1.00 | 20.97 | N |
| ATOM | 2799 | CZ | ARG | A | 174 | 3.509 | -8.016 | -10.083 | 1.00 | 20.69 | C |
| ATOM | 2800 | NH1 | ARG | A | 174 | 4.603 | -7.305 | -10.326 | 1.00 | 21.42 | N |
| ATOM | 2803 | NH2 | ARG | A | 174 | 3.586 | -9.114 | -9.400 | 1.00 | 24.76 | N |
| ATOM | 2806 | C | ARG | A | 174 | 1.361 | -5.935 | -14.650 | 1.00 | 18.32 | C |
| ATOM | 2807 | O | ARG | A | 174 | 2.474 | -6.451 | -14.641 | 1.00 | 14.85 | O |
| ATOM | 2809 | N | LEU | A | 175 | 0.468 | -6.217 | -15.588 | 1.00 | 19.56 | N |
| ATOM | 2810 | CA | LEU | A | 175 | 0.826 | -7.165 | -16.676 | 1.00 | 19.33 | C |
| ATOM | 2812 | CB | LEU | A | 175 | -0.431 | -7.415 | -17.508 | 1.00 | 19.46 | C |
| ATOM | 2815 | CG | LEU | A | 175 | -1.606 | -7.965 | -16.724 | 1.00 | 18.04 | C |
| ATOM | 2817 | CD1 | LEU | A | 175 | -2.977 | -7.864 | -17.474 | 1.00 | 16.10 | C |
| ATOM | 2821 | CD2 | LEU | A | 175 | -1.314 | -9.363 | -16.265 | 1.00 | 13.78 | C |
| ATOM | 2825 | C | LEU | A | 175 | 1.980 | -6.656 | -17.585 | 1.00 | 21.22 | C |
| ATOM | 2826 | O | LEU | A | 175 | 2.829 | -7.429 | -17.989 | 1.00 | 22.40 | O |
| ATOM | 2828 | N | PHE | A | 176 | 2.005 | -5.365 | -17.911 | 1.00 | 23.21 | N |
| ATOM | 2829 | CA | PHE | A | 176 | 3.109 | -4.762 | -18.729 | 1.00 | 24.74 | C |
| ATOM | 2831 | CB | PHE | A | 176 | 2.841 | -3.242 | -18.909 | 1.00 | 26.23 | C |
| ATOM | 2834 | CG | PHE | A | 176 | 3.946 | -2.464 | -19.651 | 1.00 | 29.22 | C |
| ATOM | 2835 | CD1 | PHE | A | 176 | 3.856 | -2.248 | -21.038 | 1.00 | 32.47 | C |
| ATOM | 2837 | CE1 | PHE | A | 176 | 4.887 | -1.517 | -21.726 | 1.00 | 33.44 | C |
| ATOM | 2839 | CZ | PHE | A | 176 | 5.958 | -0.986 | -21.015 | 1.00 | 30.76 | C |
| ATOM | 2841 | CE2 | PHE | A | 176 | 6.031 | -1.164 | -19.646 | 1.00 | 30.78 | C |
| ATOM | 2843 | CD2 | PHE | A | 176 | 5.019 | -1.891 | -18.958 | 1.00 | 29.87 | C |
| ATOM | 2845 | C | PHE | A | 176 | 4.484 | -5.017 | -18.072 | 1.00 | 24.93 | C |
| ATOM | 2846 | O | PHE | A | 176 | 5.428 | -5.441 | -18.731 | 1.00 | 24.99 | O |
| ATOM | 2848 | N | THR | A | 177 | 4.548 | -4.831 | -16.753 | 1.00 | 24.79 | N |
| ATOM | 2849 | CA | THR | A | 177 | 5.743 | -5.023 | -15.952 | 1.00 | 24.17 | C |
| ATOM | 2851 | CB | THR | A | 177 | 5.527 | -4.549 | -14.470 | 1.00 | 23.86 | C |
| ATOM | 2853 | OG1 | THR | A | 177 | 4.972 | -3.251 | -14.459 | 1.00 | 27.31 | O |
| ATOM | 2855 | CG2 | THR | A | 177 | 6.839 | -4.507 | -13.715 | 1.00 | 27.23 | C |
| ATOM | 2859 | C | THR | A | 177 | 6.112 | -6.453 | -15.911 | 1.00 | 23.54 | C |
| ATOM | 2860 | O | THR | A | 177 | 7.288 | -6.806 | -15.969 | 1.00 | 23.20 | O |
| ATOM | 2862 | N | ILE | A | 178 | 5.114 | -7.318 | -15.738 | 1.00 | 23.34 | N |
| ATOM | 2863 | CA | ILE | A | 178 | 5.418 | -8.741 | -15.709 | 1.00 | 21.32 | C |
| ATOM | 2865 | CB | ILE | A | 178 | 4.185 | -9.596 | -15.446 | 1.00 | 20.37 | C |
| ATOM | 2867 | CG1 | ILE | A | 178 | 3.808 | -9.591 | -13.955 | 1.00 | 20.95 | C |
| ATOM | 2870 | CD1 | ILE | A | 178 | 2.363 | -10.058 | -13.752 | 1.00 | 16.61 | C |
| ATOM | 2874 | CG2 | ILE | A | 178 | 4.423 | -11.014 | -15.846 | 1.00 | 14.36 | C |
| ATOM | 2878 | C | ILE | A | 178 | 6.052 | -9.161 | -17.063 | 1.00 | 22.00 | C |
| ATOM | 2879 | O | ILE | A | 178 | 7.019 | -9.928 | -17.099 | 1.00 | 19.45 | O |
| ATOM | 2881 | N | ARG | A | 179 | 5.506 | -8.644 | -18.151 | 1.00 | 23.00 | N |
| ATOM | 2882 | CA | ARG | A | 179 | 6.051 | -8.975 | -19.500 | 1.00 | 25.50 | C |
| ATOM | 2884 | CB | ARG | A | 179 | 5.155 | -8.435 | -20.612 | 1.00 | 25.34 | C |
| ATOM | 2887 | CG | ARG | A | 179 | 5.608 | -8.760 | -21.993 | 1.00 | 30.92 | C |
| ATOM | 2890 | CD | ARG | A | 179 | 4.982 | -7.913 | -23.090 | 1.00 | 37.60 | C |
| ATOM | 2893 | NE | ARG | A | 179 | 5.477 | -8.339 | -24.410 | 1.00 | 45.25 | N |
| ATOM | 2895 | CZ | ARG | A | 179 | 6.670 | -8.027 | -24.958 | 1.00 | 52.11 | C |
| ATOM | 2896 | NH1 | ARG | A | 179 | 7.564 | -7.254 | -24.333 | 1.00 | 54.21 | N |
| ATOM | 2899 | NH2 | ARG | A | 179 | 6.996 | -8.512 | -26.165 | 1.00 | 56.15 | N |
| ATOM | 2902 | C | ARG | A | 179 | 7.467 | -8.390 | -19.651 | 1.00 | 25.34 | C |

FIG.4-26

| | | | | | | | | | | | |
|---|---|---|---|---|---|---|---|---|---|---|---|
| ATOM | 2903 | O | ARG | A | 179 | 8.403 | -9.136 | -19.995 | 1.00 | 24.83 | O |
| ATOM | 2905 | N | GLN | A | 180 | 7.623 | -7.095 | -19.381 | 1.00 | 25.95 | N |
| ATOM | 2906 | CA | GLN | A | 180 | 8.966 | -6.439 | -19.529 | 1.00 | 27.74 | C |
| ATOM | 2908 | CB | GLN | A | 180 | 8.948 | -4.991 | -19.121 | 1.00 | 27.52 | C |
| ATOM | 2911 | CG | GLN | A | 180 | 8.009 | -4.054 | -19.876 | 1.00 | 32.54 | C |
| ATOM | 2914 | CD | GLN | A | 180 | 8.425 | -3.792 | -21.318 | 1.00 | 35.49 | C |
| ATOM | 2915 | OE1 | GLN | A | 180 | 8.133 | -4.597 | -22.223 | 1.00 | 39.28 | O |
| ATOM | 2916 | NE2 | GLN | A | 180 | 9.108 | -2.669 | -21.540 | 1.00 | 36.58 | N |
| ATOM | 2919 | C | GLN | A | 180 | 10.089 | -7.159 | -18.730 | 1.00 | 28.07 | C |
| ATOM | 2920 | O | GLN | A | 180 | 11.188 | -7.365 | -19.227 | 1.00 | 29.14 | O |
| ATOM | 2922 | N | GLU | A | 181 | 9.799 | -7.554 | -17.501 | 1.00 | 28.48 | N |
| ATOM | 2923 | CA | GLU | A | 181 | 10.764 | -8.268 | -16.657 | 1.00 | 28.66 | C |
| ATOM | 2925 | CB | GLU | A | 181 | 10.322 | -8.241 | -15.190 | 1.00 | 28.88 | C |
| ATOM | 2928 | CG | GLU | A | 181 | 10.140 | -6.835 | -14.600 | 1.00 | 28.54 | C |
| ATOM | 2931 | CD | GLU | A | 181 | 11.495 | -6.148 | -14.269 | 1.00 | 31.19 | C |
| ATOM | 2932 | OE1 | GLU | A | 181 | 12.579 | -6.734 | -14.494 | 1.00 | 30.46 | O |
| ATOM | 2933 | OE2 | GLU | A | 181 | 11.465 | -5.019 | -13.813 | 1.00 | 33.08 | O |
| ATOM | 2934 | C | GLU | A | 181 | 11.021 | -9.694 | -17.084 | 1.00 | 29.47 | C |
| ATOM | 2935 | O | GLU | A | 181 | 12.150 | -10.208 | -16.930 | 1.00 | 31.66 | O |
| ATOM | 2937 | N | MET | A | 182 | 10.019 | -10.385 | -17.603 | 1.00 | 29.58 | N |
| ATOM | 2938 | CA | MET | A | 182 | 10.302 | -11.692 | -18.138 | 1.00 | 29.45 | C |
| ATOM | 2940 | CB | MET | A | 182 | 9.044 | -12.439 | -18.547 | 1.00 | 29.37 | C |
| ATOM | 2943 | CG | MET | A | 182 | 8.165 | -13.014 | -17.415 | 1.00 | 28.62 | C |
| ATOM | 2946 | SD | MET | A | 182 | 6.731 | -13.920 | -18.081 | 1.00 | 24.07 | S |
| ATOM | 2947 | CE | MET | A | 182 | 6.068 | -14.615 | -16.554 | 1.00 | 20.99 | C |
| ATOM | 2951 | C | MET | A | 182 | 11.197 | -11.537 | -19.400 | 1.00 | 30.74 | C |
| ATOM | 2952 | O | MET | A | 182 | 12.159 | -12.315 | -19.594 | 1.00 | 28.90 | O |
| ATOM | 2954 | N | ALA | A | 183 | 10.851 | -10.568 | -20.255 | 1.00 | 31.32 | N |
| ATOM | 2955 | CA | ALA | A | 183 | 11.575 | -10.343 | -21.553 | 1.00 | 33.08 | C |
| ATOM | 2957 | CB | ALA | A | 183 | 10.921 | -9.259 | -22.386 | 1.00 | 31.94 | C |
| ATOM | 2961 | C | ALA | A | 183 | 13.066 | -10.017 | -21.382 | 1.00 | 34.03 | C |
| ATOM | 2962 | O | ALA | A | 183 | 13.913 | -10.521 | -22.110 | 1.00 | 35.32 | O |
| ATOM | 2964 | N | SER | A | 184 | 13.379 | -9.177 | -20.412 | 1.00 | 35.01 | N |
| ATOM | 2965 | CA | SER | A | 184 | 14.744 | -8.819 | -20.150 | 1.00 | 35.34 | C |
| ATOM | 2967 | CB | SER | A | 184 | 14.781 | -7.640 | -19.219 | 1.00 | 35.27 | C |
| ATOM | 2970 | OG | SER | A | 184 | 14.628 | -8.162 | -17.920 | 1.00 | 37.79 | O |
| ATOM | 2972 | C | SER | A | 184 | 15.512 | -9.973 | -19.517 | 1.00 | 35.94 | C |
| ATOM | 2973 | O | SER | A | 184 | 16.717 | -9.861 | -19.336 | 1.00 | 38.09 | O |
| ATOM | 2975 | N | ARG | A | 185 | 14.833 | -11.066 | -19.165 | 1.00 | 34.89 | N |
| ATOM | 2976 | CA | ARG | A | 185 | 15.495 | -12.258 | -18.676 | 1.00 | 34.32 | C |
| ATOM | 2978 | CB | ARG | A | 185 | 14.947 | -12.633 | -17.295 | 1.00 | 34.77 | C |
| ATOM | 2981 | CG | ARG | A | 185 | 15.251 | -11.591 | -16.255 | 1.00 | 36.90 | C |
| ATOM | 2984 | CD | ARG | A | 185 | 14.500 | -11.881 | -14.962 | 1.00 | 39.45 | C |
| ATOM | 2987 | NE | ARG | A | 185 | 14.853 | -10.927 | -13.907 | 1.00 | 41.21 | N |
| ATOM | 2989 | CZ | ARG | A | 185 | 14.448 | -9.653 | -13.843 | 1.00 | 44.40 | C |
| ATOM | 2990 | NH1 | ARG | A | 185 | 13.659 | -9.121 | -14.769 | 1.00 | 45.96 | N |
| ATOM | 2993 | NH2 | ARG | A | 185 | 14.835 | -8.892 | -12.834 | 1.00 | 45.86 | N |
| ATOM | 2996 | C | ARG | A | 185 | 15.377 | -13.437 | -19.617 | 1.00 | 33.06 | C |
| ATOM | 2997 | O | ARG | A | 185 | 15.808 | -14.504 | -19.269 | 1.00 | 32.13 | O |
| ATOM | 2999 | N | SER | A | 186 | 14.842 | -13.221 | -20.824 | 1.00 | 32.75 | N |
| ATOM | 3000 | CA | SER | A | 186 | 14.653 | -14.272 | -21.833 | 1.00 | 33.07 | C |
| ATOM | 3002 | CB | SER | A | 186 | 16.007 | -14.899 | -22.287 | 1.00 | 33.90 | C |
| ATOM | 3005 | OG | SER | A | 186 | 16.829 | -13.897 | -22.872 | 1.00 | 36.07 | O |
| ATOM | 3007 | C | SER | A | 186 | 13.668 | -15.344 | -21.441 | 1.00 | 32.43 | C |
| ATOM | 3008 | O | SER | A | 186 | 13.792 | -16.500 | -21.888 | 1.00 | 32.01 | O |
| ATOM | 3010 | N | LEU | A | 187 | 12.656 | -14.955 | -20.648 | 1.00 | 31.80 | N |
| ATOM | 3011 | CA | LEU | A | 187 | 11.615 | -15.867 | -20.212 | 1.00 | 30.00 | C |
| ATOM | 3013 | CB | LEU | A | 187 | 11.396 | -15.692 | -18.705 | 1.00 | 30.36 | C |
| ATOM | 3016 | CG | LEU | A | 187 | 12.502 | -16.242 | -17.793 | 1.00 | 27.61 | C |
| ATOM | 3018 | CD1 | LEU | A | 187 | 12.357 | -15.696 | -16.463 | 1.00 | 29.76 | C |
| ATOM | 3022 | CD2 | LEU | A | 187 | 12.512 | -17.744 | -17.696 | 1.00 | 25.51 | C |
| ATOM | 3026 | C | LEU | A | 187 | 10.305 | -15.665 | -20.987 | 1.00 | 29.92 | C |
| ATOM | 3027 | O | LEU | A | 187 | 9.444 | -16.570 | -21.034 | 1.00 | 28.42 | O |

FIG.4-27

| | | | | | | | | | | | |
|---|---|---|---|---|---|---|---|---|---|---|---|
| ATOM | 3029 | N | TRP | A | 188 | 10.172 | -14.516 | -21.651 | 1.00 | 29.73 | N |
| ATOM | 3030 | CA | TRP | A | 188 | 8.915 | -14.160 | -22.285 | 1.00 | 30.61 | C |
| ATOM | 3032 | CB | TRP | A | 188 | 8.923 | -12.731 | -22.771 | 1.00 | 30.55 | C |
| ATOM | 3035 | CG | TRP | A | 188 | 7.662 | -12.343 | -23.429 | 1.00 | 31.02 | C |
| ATOM | 3036 | CD1 | TRP | A | 188 | 7.506 | -11.975 | -24.743 | 1.00 | 28.67 | C |
| ATOM | 3038 | NE1 | TRP | A | 188 | 6.175 | -11.658 | -24.987 | 1.00 | 33.73 | N |
| ATOM | 3040 | CE2 | TRP | A | 188 | 5.436 | -11.818 | -23.833 | 1.00 | 31.22 | C |
| ATOM | 3041 | CD2 | TRP | A | 188 | 6.335 | -12.251 | -22.816 | 1.00 | 32.14 | C |
| ATOM | 3042 | CE3 | TRP | A | 188 | 5.842 | -12.446 | -21.516 | 1.00 | 31.23 | C |
| ATOM | 3044 | CZ3 | TRP | A | 188 | 4.452 | -12.222 | -21.274 | 1.00 | 32.46 | C |
| ATOM | 3046 | CH2 | TRP | A | 188 | 3.593 | -11.807 | -22.333 | 1.00 | 33.56 | C |
| ATOM | 3048 | CZ2 | TRP | A | 188 | 4.074 | -11.598 | -23.598 | 1.00 | 32.56 | C |
| ATOM | 3050 | C | TRP | A | 188 | 8.501 | -15.061 | -23.431 | 1.00 | 31.67 | C |
| ATOM | 3051 | O | TRP | A | 188 | 7.333 | -15.477 | -23.501 | 1.00 | 30.66 | O |
| ATOM | 3053 | N | ASP | A | 189 | 9.445 | -15.358 | -24.330 | 1.00 | 32.87 | N |
| ATOM | 3054 | CA | ASP | A | 189 | 9.135 | -16.154 | -25.546 | 1.00 | 33.62 | C |
| ATOM | 3056 | CB | ASP | A | 189 | 10.389 | -16.351 | -26.430 | 1.00 | 34.77 | C |
| ATOM | 3059 | CG | ASP | A | 189 | 10.723 | -15.112 | -27.250 | 1.00 | 39.04 | C |
| ATOM | 3060 | OD1 | ASP | A | 189 | 9.783 | -14.367 | -27.643 | 1.00 | 43.38 | O |
| ATOM | 3061 | OD2 | ASP | A | 189 | 11.933 | -14.897 | -27.516 | 1.00 | 45.77 | O |
| ATOM | 3062 | C | ASP | A | 189 | 8.574 | -17.515 | -25.176 | 1.00 | 31.81 | C |
| ATOM | 3063 | O | ASP | A | 189 | 7.530 | -17.934 | -25.671 | 1.00 | 32.23 | O |
| ATOM | 3065 | N | SER | A | 190 | 9.265 | -18.221 | -24.309 | 1.00 | 29.34 | N |
| ATOM | 3066 | CA | SER | A | 190 | 8.765 | -19.516 | -23.889 | 1.00 | 28.80 | C |
| ATOM | 3068 | CB | SER | A | 190 | 9.840 | -20.207 | -23.033 | 1.00 | 28.07 | C |
| ATOM | 3071 | OG | SER | A | 190 | 9.290 | -21.332 | -22.363 | 1.00 | 28.32 | O |
| ATOM | 3073 | C | SER | A | 190 | 7.364 | -19.383 | -23.150 | 1.00 | 27.84 | C |
| ATOM | 3074 | O | SER | A | 190 | 6.430 | -20.169 | -23.351 | 1.00 | 28.28 | O |
| ATOM | 3076 | N | PHE | A | 191 | 7.206 | -18.349 | -22.336 | 1.00 | 27.26 | N |
| ATOM | 3077 | CA | PHE | A | 191 | 5.949 | -18.163 | -21.590 | 1.00 | 26.62 | C |
| ATOM | 3079 | CB | PHE | A | 191 | 6.080 | -17.053 | -20.524 | 1.00 | 24.94 | C |
| ATOM | 3082 | CG | PHE | A | 191 | 4.796 | -16.797 | -19.719 | 1.00 | 19.84 | C |
| ATOM | 3083 | CD1 | PHE | A | 191 | 4.352 | -17.700 | -18.808 | 1.00 | 19.79 | C |
| ATOM | 3085 | CE1 | PHE | A | 191 | 3.164 | -17.486 | -18.091 | 1.00 | 18.95 | C |
| ATOM | 3087 | CZ | PHE | A | 191 | 2.470 | -16.327 | -18.247 | 1.00 | 16.44 | C |
| ATOM | 3089 | CE2 | PHE | A | 191 | 2.912 | -15.381 | -19.121 | 1.00 | 16.60 | C |
| ATOM | 3091 | CD2 | PHE | A | 191 | 4.100 | -15.634 | -19.855 | 1.00 | 19.93 | C |
| ATOM | 3093 | C | PHE | A | 191 | 4.847 | -17.843 | -22.575 | 1.00 | 27.88 | C |
| ATOM | 3094 | O | PHE | A | 191 | 3.790 | -18.415 | -22.497 | 1.00 | 27.55 | O |
| ATOM | 3096 | N | ARG | A | 192 | 5.112 | -16.921 | -23.492 | 1.00 | 30.82 | N |
| ATOM | 3097 | CA | ARG | A | 192 | 4.123 | -16.494 | -24.525 | 1.00 | 33.38 | C |
| ATOM | 3099 | CB | ARG | A | 192 | 4.678 | -15.286 | -25.356 | 1.00 | 35.13 | C |
| ATOM | 3102 | CG | ARG | A | 192 | 4.043 | -15.010 | -26.770 | 1.00 | 38.94 | C |
| ATOM | 3105 | CD | ARG | A | 192 | 4.669 | -13.773 | -27.530 | 1.00 | 45.61 | C |
| ATOM | 3108 | NE | ARG | A | 192 | 3.897 | -12.521 | -27.314 | 1.00 | 52.10 | N |
| ATOM | 3110 | CZ | ARG | A | 192 | 4.110 | -11.329 | -27.896 | 1.00 | 54.81 | C |
| ATOM | 3111 | NH1 | ARG | A | 192 | 5.099 | -11.149 | -28.776 | 1.00 | 57.29 | N |
| ATOM | 3114 | NH2 | ARG | A | 192 | 3.312 | -10.303 | -27.596 | 1.00 | 54.94 | N |
| ATOM | 3117 | C | ARG | A | 192 | 3.668 | -17.641 | -25.439 | 1.00 | 33.69 | C |
| ATOM | 3118 | O | ARG | A | 192 | 2.586 | -17.587 | -25.991 | 1.00 | 35.29 | O |
| ATOM | 3120 | N | GLN | A | 193 | 4.468 | -18.685 | -25.589 | 1.00 | 34.34 | N |
| ATOM | 3121 | CA | GLN | A | 193 | 4.113 | -19.776 | -26.504 | 1.00 | 35.14 | C |
| ATOM | 3123 | CB | GLN | A | 193 | 5.358 | -20.234 | -27.285 | 1.00 | 36.40 | C |
| ATOM | 3126 | CG | GLN | A | 193 | 5.895 | -19.133 | -28.248 | 1.00 | 38.81 | C |
| ATOM | 3129 | CD | GLN | A | 193 | 7.264 | -19.466 | -28.862 | 1.00 | 44.26 | C |
| ATOM | 3130 | OE1 | GLN | A | 193 | 7.508 | -20.604 | -29.285 | 1.00 | 49.54 | O |
| ATOM | 3131 | NE2 | GLN | A | 193 | 8.154 | -18.471 | -28.920 | 1.00 | 45.12 | N |
| ATOM | 3134 | C | GLN | A | 193 | 3.446 | -20.936 | -25.815 | 1.00 | 33.94 | C |
| ATOM | 3135 | O | GLN | A | 193 | 2.791 | -21.724 | -26.472 | 1.00 | 32.24 | O |
| ATOM | 3137 | N | SER | A | 194 | 3.529 | -20.980 | -24.482 | 1.00 | 33.88 | N |
| ATOM | 3138 | CA | SER | A | 194 | 3.085 | -22.143 | -23.697 | 1.00 | 33.50 | C |
| ATOM | 3140 | CB | SER | A | 194 | 3.872 | -22.234 | -22.378 | 1.00 | 34.18 | C |
| ATOM | 3143 | OG | SER | A | 194 | 3.782 | -21.015 | -21.644 | 1.00 | 36.26 | O |

FIG.4-28

| | | | | | | | | | | | | |
|---|---|---|---|---|---|---|---|---|---|---|---|---|
| ATOM | 3145 | C | SER | A | 194 | 1.598 | -22.204 | -23.359 | 1.00 | 33.28 | | C |
| ATOM | 3146 | O | SER | A | 194 | 1.142 | -23.247 | -22.895 | 1.00 | 32.79 | | O |
| ATOM | 3148 | N | GLU | A | 195 | 0.833 | -21.130 | -23.564 | 1.00 | 33.76 | | N |
| ATOM | 3149 | CA | GLU | A | 195 | -0.606 | -21.179 | -23.200 | 1.00 | 35.56 | | C |
| ATOM | 3151 | CB | GLU | A | 195 | -1.192 | -19.783 | -23.254 | 1.00 | 34.42 | | C |
| ATOM | 3154 | CG | GLU | A | 195 | -2.669 | -19.666 | -22.814 | 1.00 | 31.19 | | C |
| ATOM | 3157 | CD | GLU | A | 195 | -3.133 | -18.225 | -22.769 | 1.00 | 28.91 | | C |
| ATOM | 3158 | OE1 | GLU | A | 195 | -2.342 | -17.330 | -22.397 | 1.00 | 27.02 | | O |
| ATOM | 3159 | OE2 | GLU | A | 195 | -4.272 | -17.934 | -23.186 | 1.00 | 34.26 | | O |
| ATOM | 3160 | C | GLU | A | 195 | -1.407 | -22.098 | -24.152 | 1.00 | 37.98 | | C |
| ATOM | 3161 | O | GLU | A | 195 | -1.192 | -22.064 | -25.351 | 1.00 | 37.85 | | O |
| ATOM | 3163 | N | ARG | A | 196 | -2.340 | -22.897 | -23.653 | 1.00 | 41.27 | | N |
| ATOM | 3164 | CA | ARG | A | 196 | -3.202 | -23.691 | -24.598 | 1.00 | 44.13 | | C |
| ATOM | 3166 | CB | ARG | A | 196 | -2.632 | -25.092 | -24.924 | 1.00 | 44.56 | | C |
| ATOM | 3169 | CG | ARG | A | 196 | -1.340 | -25.090 | -25.665 | 1.00 | 46.98 | | C |
| ATOM | 3172 | CD | ARG | A | 196 | -0.396 | -26.126 | -25.115 | 1.00 | 51.59 | | C |
| ATOM | 3175 | NE | ARG | A | 196 | 0.901 | -26.111 | -25.824 | 1.00 | 56.06 | | N |
| ATOM | 3177 | CZ | ARG | A | 196 | 1.977 | -26.853 | -25.504 | 1.00 | 58.69 | | C |
| ATOM | 3178 | NH1 | ARG | A | 196 | 1.959 | -27.695 | -24.456 | 1.00 | 59.44 | | N |
| ATOM | 3181 | NH2 | ARG | A | 196 | 3.097 | -26.749 | -26.238 | 1.00 | 58.42 | | N |
| ATOM | 3184 | C | ARG | A | 196 | -4.655 | -23.839 | -24.121 | 1.00 | 44.90 | | C |
| ATOM | 3185 | O | ARG | A | 196 | -4.994 | -23.523 | -22.960 | 1.00 | 43.59 | | O |
| ATOM | 3187 | N | GLY | A | 197 | -5.499 | -24.327 | -25.034 | 1.00 | 45.89 | | N |
| ATOM | 3188 | CA | GLY | A | 197 | -6.918 | -24.546 | -24.725 | 1.00 | 47.04 | | C |
| ATOM | 3191 | C | GLY | A | 197 | -7.382 | -25.915 | -25.169 | 1.00 | 47.97 | | C |
| ATOM | 3192 | O | GLY | A | 197 | -8.522 | -26.060 | -25.651 | 1.00 | 49.87 | | O |
| ATOM | 3194 | CL | CI2 | A | 801 | -15.728 | -22.157 | -18.301 | 1.00 | 59.92 | | CL |
| ATOM | 3195 | CZB | CI2 | A | 801 | -14.908 | -22.736 | -16.812 | 1.00 | 55.31 | | C |
| ATOM | 3196 | CEB | CI2 | A | 801 | -14.510 | -24.060 | -16.666 | 1.00 | 53.54 | | C |
| ATOM | 3198 | CDB | CI2 | A | 801 | -13.900 | -24.462 | -15.490 | 1.00 | 51.40 | | C |
| ATOM | 3200 | CEA | CI2 | A | 801 | -14.701 | -21.812 | -15.796 | 1.00 | 53.54 | | C |
| ATOM | 3202 | CDA | CI2 | A | 801 | -14.109 | -22.226 | -14.621 | 1.00 | 53.52 | | C |
| ATOM | 3204 | CGA | CI2 | A | 801 | -13.681 | -23.532 | -14.477 | 1.00 | 49.32 | | C |
| ATOM | 3205 | CO | CI2 | A | 801 | -13.076 | -23.937 | -13.177 | 1.00 | 45.66 | | C |
| ATOM | 3208 | CF | CI2 | A | 801 | -11.643 | -23.539 | -12.821 | 1.00 | 43.95 | | C |
| ATOM | 3209 | CB | CI2 | A | 801 | -11.425 | -22.038 | -12.875 | 1.00 | 35.87 | | C |
| ATOM | 3210 | CM | CI2 | A | 801 | -10.757 | -21.464 | -14.059 | 1.00 | 30.39 | | C |
| ATOM | 3212 | CA | CI2 | A | 801 | -10.456 | -20.174 | -14.315 | 1.00 | 30.57 | | C |
| ATOM | 3213 | CE | CI2 | A | 801 | -9.778 | -19.854 | -15.595 | 1.00 | 31.60 | | C |
| ATOM | 3214 | OAO | CI2 | A | 801 | -9.659 | -18.665 | -15.946 | 1.00 | 30.40 | | O |
| ATOM | 3215 | OAN | CI2 | A | 801 | -9.354 | -20.807 | -16.303 | 1.00 | 33.34 | | O |
| ATOM | 3216 | O14 | CI2 | A | 801 | -10.714 | -19.173 | -13.533 | 1.00 | 22.32 | | O |
| ATOM | 3218 | O13 | CI2 | A | 801 | -11.767 | -21.343 | -11.934 | 1.00 | 35.37 | | O |
| ATOM | 3219 | CH | CI2 | A | 801 | -10.664 | -24.334 | -13.706 | 1.00 | 43.59 | | C |
| ATOM | 3222 | CI | CI2 | A | 801 | -9.513 | -24.981 | -12.927 | 1.00 | 43.92 | | C |
| ATOM | 3225 | NJ | CI2 | A | 801 | -9.064 | -24.273 | -11.717 | 1.00 | 44.89 | | N |
| ATOM | 3227 | CK | CI2 | A | 801 | -10.133 | -23.961 | -10.754 | 1.00 | 43.72 | | C |
| ATOM | 3230 | CG | CI2 | A | 801 | -11.516 | -24.037 | -11.361 | 1.00 | 44.45 | | C |
| ATOM | 3233 | CP | CI2 | A | 801 | -8.057 | -25.042 | -10.938 | 1.00 | 43.40 | | C |
| ATOM | 3236 | CGB | CI2 | A | 801 | -6.786 | -25.369 | -11.720 | 1.00 | 42.05 | | C |
| ATOM | 3238 | CD1 | CI2 | A | 801 | -5.548 | -24.981 | -10.878 | 1.00 | 41.01 | | C |
| ATOM | 3241 | CE1 | CI2 | A | 801 | -4.249 | -25.642 | -11.354 | 1.00 | 40.36 | | C |
| ATOM | 3244 | CZ | CI2 | A | 801 | -4.382 | -27.124 | -11.626 | 1.00 | 39.96 | | C |
| ATOM | 3247 | CE2 | CI2 | A | 801 | -5.490 | -27.358 | -12.644 | 1.00 | 40.19 | | C |
| ATOM | 3250 | CD2 | CI2 | A | 801 | -6.820 | -26.867 | -12.069 | 1.00 | 40.71 | | C |
| ATOM | 3253 | MN | MN | A | 901 | -10.703 | -17.245 | -14.404 | 1.00 | 24.64 | | MN |
| ATOM | 3254 | MN | MN | A | 902 | -11.701 | -19.336 | -11.518 | 1.00 | 32.43 | | MN |
| ATOM | 6571 | O20 | WAT | A | 910 | -16.355 | -6.528 | -16.875 | 1.00 | 21.81 | A | O |
| ATOM | 6572 | O21 | WAT | A | 910 | -19.399 | -7.074 | -12.901 | 0.01 | 27.10 | A | O |
| ATOM | 6573 | O50 | WAT | A | 911 | 2.434 | -24.032 | -0.834 | 1.00 | 25.92 | A | O |
| ATOM | 3255 | OH2 | WAT | A | 912 | -12.701 | -19.641 | -9.315 | 1.00 | 21.06 | A | O |
| ATOM | 3258 | OH2 | WAT | A | 913 | -13.728 | -19.144 | -12.466 | 1.00 | 20.27 | A | O |
| ATOM | 6574 | OH2 | WAT | A | 914 | 2.063 | -10.125 | -6.063 | 1.00 | 23.18 | A | O |

FIG.4- 29

| | | | | | | | | | | | | | |
|---|---|---|---|---|---|---|---|---|---|---|---|---|---|
| ATOM | 6575 | OH2 | WAT | A | 915 | -19.399 | -7.074 | -12.901 | 1.00 | 27.10 | A | O |
| ATOM | 6576 | OH2 | WAT | A | 916 | -5.118 | -18.786 | -10.812 | 1.00 | 25.47 | A | O |
| ATOM | 6578 | OH2 | WAT | A | 917 | -19.803 | -1.210 | -12.980 | 1.00 | 26.51 | A | O |
| ATOM | 6580 | OH2 | WAT | A | 918 | -12.079 | -19.380 | 2.248 | 1.00 | 31.24 | A | O |
| ATOM | 6582 | OH2 | WAT | A | 919 | -25.501 | -7.311 | -15.726 | 1.00 | 41.38 | A | O |
| ATOM | 6583 | OH2 | WAT | A | 920 | -13.635 | 1.322 | -17.485 | 1.00 | 30.53 | A | O |
| ATOM | 6584 | OH2 | WAT | A | 921 | -8.119 | -21.447 | -11.560 | 1.00 | 40.66 | A | O |
| ATOM | 6585 | OH2 | WAT | A | 922 | -13.999 | -12.156 | -0.739 | 1.00 | 26.43 | A | O |
| ATOM | 6586 | OH2 | WAT | A | 923 | -16.887 | -19.453 | -14.787 | 1.00 | 25.99 | A | O |
| ATOM | 6587 | OH2 | WAT | A | 924 | -23.343 | -9.865 | -17.567 | 1.00 | 38.22 | A | O |
| ATOM | 6588 | OH2 | WAT | A | 925 | -23.435 | -4.842 | -19.324 | 1.00 | 39.09 | A | O |
| ATOM | 6589 | OH2 | WAT | A | 925 | -20.248 | -1.299 | -15.398 | 1.00 | 37.28 | A | O |
| ATOM | 6590 | OH2 | WAT | A | 926 | -26.917 | -23.079 | -1.691 | 1.00 | 37.24 | A | O |
| ATOM | 6591 | OH2 | WAT | A | 927 | 9.381 | -19.345 | -19.330 | 1.00 | 36.94 | A | O |
| ATOM | 6592 | OH2 | WAT | A | 928 | -10.762 | -27.509 | -10.825 | 1.00 | 35.37 | A | O |
| ATOM | 6593 | OH2 | WAT | A | 929 | -3.662 | -8.088 | -4.503 | 1.00 | 42.30 | A | O |
| ATOM | 6594 | OH2 | WAT | A | 930 | -6.176 | -26.098 | -4.456 | 1.00 | 40.14 | A | O |
| ATOM | 6595 | OH2 | WAT | A | 931 | 12.331 | -25.605 | -11.961 | 1.00 | 45.87 | A | O |
| ATOM | 6596 | OH2 | WAT | A | 932 | -7.467 | -1.794 | -22.654 | 1.00 | 31.36 | A | O |
| END | | | | | | | | | | | | |

FIG.5-1

Figure 5: H1N1 polypeptide fragment (Chain A) with bound rUMP

```
HEADER    INFLUENZA POLYMERASE H1N1/2009 PA with bound rUMP
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.05
REMARK   3   RESOLUTION RANGE LOW  (ANGSTROMS) :  41.70
REMARK   3   DATA CUTOFF            (SIGMA(F)) : NONE
REMARK   3   COMPLETENESS FOR RANGE        (%) :  99.70
REMARK   3   NUMBER OF REFLECTIONS             :   51176
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.20823
REMARK   3   R VALUE            (WORKING SET) :  0.20611
REMARK   3   FREE R VALUE                     :  0.24659
REMARK   3   FREE R VALUE TEST SET SIZE   (%) :  5.1
REMARK   3   FREE R VALUE TEST SET COUNT      :  2750
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    2.049
REMARK   3   BIN RESOLUTION RANGE LOW            :    2.102
REMARK   3   REFLECTION IN BIN     (WORKING SET) :     3657
REMARK   3   BIN COMPLETENESS (WORKING+TEST) (%) :    98.37
REMARK   3   BIN R VALUE           (WORKING SET) :    0.266
REMARK   3   BIN FREE R VALUE SET COUNT          :      202
REMARK   3   BIN FREE R VALUE                    :    0.342
REMARK   3
REMARK   3  NUMBER OF NON-HYDROGEN ATOMS USED IN REFINEMENT.
REMARK   3   ALL ATOMS                :     6703
REMARK   3
REMARK   3  B VALUES.
REMARK   3   FROM WILSON PLOT           (A**2) : NULL
REMARK   3   MEAN B VALUE      (OVERALL, A**2) :  32.525
REMARK   3   OVERALL ANISOTROPIC B VALUE.
REMARK   3    B11 (A**2) :     1.67
REMARK   3    B22 (A**2) :    -4.82
REMARK   3    B33 (A**2) :     3.15
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.048
REMARK   3   ESU BASED ON FREE R VALUE                       (A):   0.039
REMARK   3   ESU BASED ON MAXIMUM LIKELIHOOD                 (A):   0.112
REMARK   3   ESU FOR B VALUES BASED ON MAXIMUM LIKELIHOOD (A**2):   4.400
REMARK   3
REMARK   3 CORRELATION COEFFICIENTS.
REMARK   3   CORRELATION COEFFICIENT FO-FC      :   0.950
REMARK   3   CORRELATION COEFFICIENT FO-FC FREE :   0.933
REMARK   3
REMARK   3  RMS DEVIATIONS FROM IDEAL VALUES        COUNT    RMS    WEIGHT
```

FIG.5-2

```
REMARK   3   BOND LENGTHS REFINED ATOMS        (A):  6607 ; 0.022 ; 0.022
REMARK   3   BOND LENGTHS OTHERS               (A):  4665 ; 0.001 ; 0.020
REMARK   3   BOND ANGLES REFINED ATOMS   (DEGREES):  8878 ; 1.802 ; 1.958
REMARK   3   BOND ANGLES OTHERS          (DEGREES): 11258 ; 0.969 ; 3.000
REMARK   3   TORSION ANGLES, PERIOD 1    (DEGREES):   761 ; 6.279 ; 5.000
REMARK   3   TORSION ANGLES, PERIOD 2    (DEGREES):   343 ;34.946 ;23.353
REMARK   3   TORSION ANGLES, PERIOD 3    (DEGREES):  1239 ;16.895 ;15.000
REMARK   3   TORSION ANGLES, PERIOD 4    (DEGREES):    58 ;19.417 ;15.000
REMARK   3   CHIRAL-CENTER RESTRAINTS       (A**3):   953 ; 0.109 ; 0.200
REMARK   3   GENERAL PLANES REFINED ATOMS      (A):  7174 ; 0.008 ; 0.020
REMARK   3   GENERAL PLANES OTHERS             (A):  1448 ; 0.001 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):  3827 ; 1.188 ; 1.500
REMARK   3   MAIN-CHAIN BOND OTHER ATOMS    (A**2):  1544 ; 0.279 ; 1.500
REMARK   3   MAIN-CHAIN ANGLE REFINED ATOMS (A**2):  6207 ; 2.129 ; 2.000
REMARK   3   SIDE-CHAIN BOND REFINED ATOMS  (A**2):  2780 ; 3.015 ; 3.000
REMARK   3   SIDE-CHAIN ANGLE REFINED ATOMS (A**2):  2671 ; 4.741 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
CRYST1   54.940  120.110  128.050  90.00  90.00  90.00 P 21 21 21
SCALE1      0.018202  0.000000  0.000000        0.00000
SCALE2      0.000000  0.008326  0.000000        0.00000
SCALE3      0.000000  0.000000  0.007809        0.00000
ATOM   3300  N   MET A  -1      44.698  17.489   9.099  1.00 40.91           N
ATOM   3301  CA  MET A  -1      44.458  17.093  10.548  1.00 40.32           C
ATOM   3303  CB  MET A  -1      45.798  17.161  11.322  1.00 41.66           C
ATOM   3306  CG  MET A  -1      46.997  16.546  10.564  1.00 45.78           C
ATOM   3309  SD  MET A  -1      46.893  14.753  10.413  1.00 52.82           S
ATOM   3310  CE  MET A  -1      46.688  14.411   8.644  1.00 50.00           C
ATOM   3314  C   MET A  -1      43.379  17.909  11.321  1.00 38.01           C
ATOM   3315  O   MET A  -1      43.065  17.622  12.493  1.00 36.72           O
ATOM   3319  N   ALA A   0      42.842  18.953  10.706  1.00 34.89           N
ATOM   3320  CA  ALA A   0      41.910  19.785  11.419  1.00 33.46           C
ATOM   3322  CB  ALA A   0      41.918  21.220  10.891  1.00 32.88           C
ATOM   3326  C   ALA A   0      40.508  19.114  11.302  1.00 31.89           C
ATOM   3327  O   ALA A   0      40.300  18.100  10.623  1.00 30.47           O
ATOM   3329  N   MET A   1      39.583  19.632  12.066  1.00 30.44           N
ATOM   3330  CA  MET A   1      38.245  19.059  12.085  1.00 29.55           C
ATOM   3332  CB  MET A   1      37.342  19.793  13.103  1.00 28.89           C
ATOM   3335  CG  MET A   1      35.880  19.186  13.136  1.00 24.61           C
ATOM   3338  SD  MET A   1      35.730  17.443  13.354  1.00 27.64           S
```

FIG.5-3

| | | | | | | | | | | | |
|---|---|---|---|---|---|---|---|---|---|---|---|
| ATOM | 3339 | CE | MET | A | 1 | 35.644 | 17.550 | 15.168 | 1.00 | 25.29 | C |
| ATOM | 3343 | C | MET | A | 1 | 37.646 | 19.099 | 10.659 | 1.00 | 29.07 | C |
| ATOM | 3344 | O | MET | A | 1 | 37.026 | 18.115 | 10.219 | 1.00 | 27.82 | O |
| ATOM | 3346 | N | GLU | A | 2 | 37.894 | 20.196 | 9.952 | 1.00 | 30.15 | N |
| ATOM | 3347 | CA | GLU | A | 2 | 37.405 | 20.362 | 8.585 | 1.00 | 31.45 | C |
| ATOM | 3349 | CB | GLU | A | 2 | 37.594 | 21.798 | 8.043 | 1.00 | 32.75 | C |
| ATOM | 3352 | CG | GLU | A | 2 | 39.027 | 22.336 | 7.945 | 1.00 | 37.90 | C |
| ATOM | 3355 | CD | GLU | A | 2 | 39.480 | 23.058 | 9.209 | 1.00 | 42.36 | C |
| ATOM | 3356 | OE1 | GLU | A | 2 | 39.147 | 22.631 | 10.342 | 1.00 | 41.20 | O |
| ATOM | 3357 | OE2 | GLU | A | 2 | 40.191 | 24.066 | 9.052 | 1.00 | 52.40 | O |
| ATOM | 3358 | C | GLU | A | 2 | 37.921 | 19.311 | 7.632 | 1.00 | 31.57 | C |
| ATOM | 3359 | O | GLU | A | 2 | 37.179 | 18.819 | 6.770 | 1.00 | 30.37 | O |
| ATOM | 3361 | N | ASP | A | 3 | 39.172 | 18.903 | 7.789 | 1.00 | 31.04 | N |
| ATOM | 3362 | CA | ASP | A | 3 | 39.704 | 17.947 | 6.872 | 1.00 | 29.76 | C |
| ATOM | 3364 | CB | ASP | A | 3 | 41.220 | 17.882 | 6.994 | 1.00 | 31.29 | C |
| ATOM | 3367 | CG | ASP | A | 3 | 41.842 | 19.240 | 6.902 | 1.00 | 33.01 | C |
| ATOM | 3368 | OD1 | ASP | A | 3 | 41.648 | 19.925 | 5.866 | 1.00 | 38.27 | O |
| ATOM | 3369 | OD2 | ASP | A | 3 | 42.456 | 19.657 | 7.896 | 1.00 | 36.12 | O |
| ATOM | 3370 | C | ASP | A | 3 | 39.070 | 16.612 | 7.203 | 1.00 | 29.57 | C |
| ATOM | 3371 | O | ASP | A | 3 | 38.671 | 15.872 | 6.321 | 1.00 | 30.25 | O |
| ATOM | 3373 | N | PHE | A | 4 | 38.972 | 16.293 | 8.474 | 1.00 | 28.06 | N |
| ATOM | 3374 | CA | PHE | A | 4 | 38.319 | 15.085 | 8.873 | 1.00 | 29.20 | C |
| ATOM | 3376 | CB | PHE | A | 4 | 38.271 | 15.021 | 10.382 | 1.00 | 29.95 | C |
| ATOM | 3379 | CG | PHE | A | 4 | 37.421 | 13.905 | 10.886 | 1.00 | 32.18 | C |
| ATOM | 3380 | CD1 | PHE | A | 4 | 37.762 | 12.583 | 10.604 | 1.00 | 38.76 | C |
| ATOM | 3382 | CE1 | PHE | A | 4 | 36.948 | 11.514 | 11.072 | 1.00 | 41.89 | C |
| ATOM | 3384 | CZ | PHE | A | 4 | 35.798 | 11.798 | 11.841 | 1.00 | 40.09 | C |
| ATOM | 3386 | CE2 | PHE | A | 4 | 35.480 | 13.120 | 12.115 | 1.00 | 37.85 | C |
| ATOM | 3388 | CD2 | PHE | A | 4 | 36.297 | 14.160 | 11.640 | 1.00 | 37.54 | C |
| ATOM | 3390 | C | PHE | A | 4 | 36.836 | 14.976 | 8.374 | 1.00 | 26.94 | C |
| ATOM | 3391 | O | PHE | A | 4 | 36.433 | 13.973 | 7.834 | 1.00 | 27.50 | O |
| ATOM | 3393 | N | VAL | A | 5 | 36.061 | 16.017 | 8.567 | 1.00 | 26.36 | N |
| ATOM | 3394 | CA | VAL | A | 5 | 34.659 | 16.030 | 8.029 | 1.00 | 25.59 | C |
| ATOM | 3396 | CB | VAL | A | 5 | 33.979 | 17.380 | 8.226 | 1.00 | 24.18 | C |
| ATOM | 3398 | CG1 | VAL | A | 5 | 32.585 | 17.500 | 7.406 | 1.00 | 24.01 | C |
| ATOM | 3402 | CG2 | VAL | A | 5 | 33.790 | 17.633 | 9.695 | 1.00 | 24.93 | C |
| ATOM | 3406 | C | VAL | A | 5 | 34.704 | 15.719 | 6.543 | 1.00 | 27.22 | C |
| ATOM | 3407 | O | VAL | A | 5 | 34.049 | 14.761 | 6.093 | 1.00 | 25.52 | O |
| ATOM | 3409 | N | ARG | A | 6 | 35.531 | 16.453 | 5.798 | 1.00 | 29.68 | N |
| ATOM | 3410 | CA | ARG | A | 6 | 35.568 | 16.304 | 4.336 | 1.00 | 33.09 | C |
| ATOM | 3412 | CB | ARG | A | 6 | 36.413 | 17.400 | 3.660 | 1.00 | 33.40 | C |
| ATOM | 3415 | CG | ARG | A | 6 | 35.813 | 18.727 | 3.765 | 1.00 | 36.20 | C |
| ATOM | 3418 | CD | ARG | A | 6 | 36.406 | 19.649 | 2.717 | 1.00 | 43.32 | C |
| ATOM | 3421 | NE | ARG | A | 6 | 37.721 | 20.133 | 3.111 | 1.00 | 45.97 | N |
| ATOM | 3423 | CZ | ARG | A | 6 | 37.937 | 21.249 | 3.807 | 1.00 | 50.61 | C |
| ATOM | 3424 | NH1 | ARG | A | 6 | 36.916 | 22.020 | 4.212 | 1.00 | 50.28 | N |
| ATOM | 3427 | NH2 | ARG | A | 6 | 39.195 | 21.599 | 4.104 | 1.00 | 49.54 | N |
| ATOM | 3430 | C | ARG | A | 6 | 36.035 | 14.980 | 3.811 | 1.00 | 34.75 | C |
| ATOM | 3431 | O | ARG | A | 6 | 35.563 | 14.527 | 2.754 | 1.00 | 35.03 | O |
| ATOM | 3433 | N | GLN | A | 7 | 36.953 | 14.345 | 4.527 | 1.00 | 37.42 | N |
| ATOM | 3434 | CA | GLN | A | 7 | 37.582 | 13.126 | 4.022 | 1.00 | 39.14 | C |
| ATOM | 3436 | CB | GLN | A | 7 | 38.833 | 12.780 | 4.862 | 1.00 | 40.63 | C |
| ATOM | 3439 | CG | GLN | A | 7 | 39.987 | 13.751 | 4.663 | 1.00 | 44.77 | C |
| ATOM | 3442 | CD | GLN | A | 7 | 41.119 | 13.532 | 5.640 | 1.00 | 49.32 | C |
| ATOM | 3443 | OE1 | GLN | A | 7 | 40.976 | 12.828 | 6.650 | 1.00 | 53.38 | O |
| ATOM | 3444 | NE2 | GLN | A | 7 | 42.262 | 14.134 | 5.340 | 1.00 | 49.61 | N |
| ATOM | 3447 | C | GLN | A | 7 | 36.659 | 11.958 | 4.147 | 1.00 | 39.73 | C |
| ATOM | 3448 | O | GLN | A | 7 | 36.621 | 11.078 | 3.240 | 1.00 | 41.23 | O |
| ATOM | 3450 | N | CYS | A | 8 | 35.963 | 11.957 | 5.304 | 1.00 | 38.83 | N |
| ATOM | 3451 | CA | CYS | A | 8 | 35.250 | 10.834 | 5.846 | 1.00 | 38.15 | C |
| ATOM | 3453 | CB | CYS | A | 8 | 35.656 | 10.617 | 7.296 | 1.00 | 38.88 | C |
| ATOM | 3456 | SG | CYS | A | 8 | 37.448 | 10.236 | 7.355 | 1.00 | 41.26 | S |
| ATOM | 3458 | C | CYS | A | 8 | 33.715 | 10.870 | 5.761 | 1.00 | 36.31 | C |

FIG.5-4

| | | | | | | | | | | | |
|---|---|---|---|---|---|---|---|---|---|---|---|
| ATOM | 3459 | O | CYS | A | 8 | 33.128 | 9.806 | 5.630 | 1.00 | 36.01 | O |
| ATOM | 3461 | N | PHE | A | 9 | 33.063 | 12.025 | 5.763 | 1.00 | 33.35 | N |
| ATOM | 3462 | CA | PHE | A | 9 | 31.625 | 11.977 | 5.490 | 1.00 | 31.75 | C |
| ATOM | 3464 | CB | PHE | A | 9 | 30.914 | 13.198 | 6.020 | 1.00 | 31.67 | C |
| ATOM | 3467 | CG | PHE | A | 9 | 30.676 | 13.159 | 7.483 | 1.00 | 33.12 | C |
| ATOM | 3468 | CD1 | PHE | A | 9 | 29.559 | 12.548 | 7.999 | 1.00 | 34.29 | C |
| ATOM | 3470 | CE1 | PHE | A | 9 | 29.337 | 12.520 | 9.358 | 1.00 | 35.00 | C |
| ATOM | 3472 | CZ | PHE | A | 9 | 30.249 | 13.097 | 10.205 | 1.00 | 36.38 | C |
| ATOM | 3474 | CE2 | PHE | A | 9 | 31.349 | 13.720 | 9.713 | 1.00 | 34.45 | C |
| ATOM | 3476 | CD2 | PHE | A | 9 | 31.586 | 13.723 | 8.355 | 1.00 | 35.44 | C |
| ATOM | 3478 | C | PHE | A | 9 | 31.406 | 11.848 | 4.003 | 1.00 | 30.09 | C |
| ATOM | 3479 | O | PHE | A | 9 | 32.194 | 12.313 | 3.202 | 1.00 | 28.69 | O |
| ATOM | 3481 | N | ASN | A | 10 | 30.297 | 11.233 | 3.625 | 1.00 | 29.73 | N |
| ATOM | 3482 | CA | ASN | A | 10 | 29.898 | 11.173 | 2.227 | 1.00 | 29.38 | C |
| ATOM | 3484 | CB | ASN | A | 10 | 28.549 | 10.477 | 2.109 | 1.00 | 31.02 | C |
| ATOM | 3487 | CG | ASN | A | 10 | 27.999 | 10.502 | 0.708 | 1.00 | 33.11 | C |
| ATOM | 3488 | OD1 | ASN | A | 10 | 27.393 | 11.479 | 0.271 | 1.00 | 39.21 | O |
| ATOM | 3489 | ND2 | ASN | A | 10 | 28.205 | 9.421 | -0.006 | 1.00 | 42.47 | N |
| ATOM | 3492 | C | ASN | A | 10 | 29.855 | 12.596 | 1.614 | 1.00 | 26.54 | C |
| ATOM | 3493 | O | ASN | A | 10 | 29.391 | 13.563 | 2.236 | 1.00 | 25.97 | O |
| ATOM | 3495 | N | PRO | A | 11 | 30.400 | 12.746 | 0.411 | 1.00 | 26.89 | N |
| ATOM | 3496 | CA | PRO | A | 11 | 30.528 | 14.097 | -0.108 | 1.00 | 24.69 | C |
| ATOM | 3498 | CB | PRO | A | 11 | 31.265 | 13.922 | -1.423 | 1.00 | 26.82 | C |
| ATOM | 3501 | CG | PRO | A | 11 | 31.376 | 12.415 | -1.663 | 1.00 | 29.01 | C |
| ATOM | 3504 | CD | PRO | A | 11 | 31.108 | 11.724 | -0.400 | 1.00 | 27.04 | C |
| ATOM | 3507 | C | PRO | A | 11 | 29.149 | 14.758 | -0.319 | 1.00 | 23.39 | C |
| ATOM | 3508 | O | PRO | A | 11 | 29.058 | 15.951 | -0.196 | 1.00 | 20.17 | O |
| ATOM | 3509 | N | MET | A | 12 | 28.077 | 14.008 | -0.611 | 1.00 | 21.62 | N |
| ATOM | 3510 | CA | MET | A | 12 | 26.791 | 14.707 | -0.761 | 1.00 | 22.43 | C |
| ATOM | 3512 | CB | MET | A | 12 | 25.593 | 13.910 | -1.314 | 1.00 | 23.96 | C |
| ATOM | 3515 | CG | MET | A | 12 | 24.357 | 14.976 | -1.680 | 1.00 | 24.53 | C |
| ATOM | 3518 | SD | MET | A | 12 | 23.021 | 14.070 | -2.475 | 1.00 | 42.59 | S |
| ATOM | 3519 | CE | MET | A | 12 | 22.353 | 13.024 | -1.154 | 1.00 | 34.73 | C |
| ATOM | 3523 | C | MET | A | 12 | 26.397 | 15.303 | 0.580 | 1.00 | 20.83 | C |
| ATOM | 3524 | O | MET | A | 12 | 25.914 | 16.411 | 0.619 | 1.00 | 21.28 | O |
| ATOM | 3526 | N | ILE | A | 13 | 26.654 | 14.580 | 1.655 | 1.00 | 21.51 | N |
| ATOM | 3527 | CA | ILE | A | 13 | 26.329 | 15.064 | 2.986 | 1.00 | 21.30 | C |
| ATOM | 3529 | CB | ILE | A | 13 | 26.543 | 13.963 | 4.053 | 1.00 | 22.14 | C |
| ATOM | 3531 | CG1 | ILE | A | 13 | 25.321 | 13.012 | 4.020 | 1.00 | 27.29 | C |
| ATOM | 3534 | CD1 | ILE | A | 13 | 25.638 | 11.704 | 4.445 | 1.00 | 26.10 | C |
| ATOM | 3538 | CG2 | ILE | A | 13 | 26.685 | 14.650 | 5.457 | 1.00 | 21.85 | C |
| ATOM | 3542 | C | ILE | A | 13 | 27.105 | 16.341 | 3.315 | 1.00 | 18.76 | C |
| ATOM | 3543 | O | ILE | A | 13 | 26.524 | 17.342 | 3.823 | 1.00 | 20.01 | O |
| ATOM | 3545 | N | VAL | A | 14 | 28.439 | 16.341 | 3.086 | 1.00 | 17.20 | N |
| ATOM | 3546 | CA | VAL | A | 14 | 29.228 | 17.535 | 3.294 | 1.00 | 15.09 | C |
| ATOM | 3548 | CB | VAL | A | 14 | 30.818 | 17.223 | 3.070 | 1.00 | 17.03 | C |
| ATOM | 3550 | CG1 | VAL | A | 14 | 31.559 | 18.390 | 3.439 | 1.00 | 17.67 | C |
| ATOM | 3554 | CG2 | VAL | A | 14 | 31.244 | 16.046 | 3.961 | 1.00 | 14.52 | C |
| ATOM | 3558 | C | VAL | A | 14 | 28.777 | 18.766 | 2.484 | 1.00 | 16.48 | C |
| ATOM | 3559 | O | VAL | A | 14 | 28.769 | 19.876 | 3.012 | 1.00 | 17.36 | O |
| ATOM | 3561 | N | GLU | A | 15 | 28.399 | 18.605 | 1.225 | 1.00 | 17.56 | N |
| ATOM | 3562 | CA | GLU | A | 15 | 27.882 | 19.711 | 0.381 | 1.00 | 17.94 | C |
| ATOM | 3564 | CB | GLU | A | 15 | 27.723 | 19.312 | -1.078 | 1.00 | 18.26 | C |
| ATOM | 3567 | CG | GLU | A | 15 | 29.068 | 19.087 | -1.759 | 1.00 | 23.15 | C |
| ATOM | 3570 | CD | GLU | A | 15 | 29.034 | 19.173 | -3.277 | 1.00 | 21.40 | C |
| ATOM | 3571 | OE1 | GLU | A | 15 | 27.972 | 19.446 | -3.898 | 1.00 | 24.67 | O |
| ATOM | 3572 | OE2 | GLU | A | 15 | 30.090 | 18.923 | -3.860 | 1.00 | 21.37 | O |
| ATOM | 3573 | C | GLU | A | 15 | 26.548 | 20.273 | 0.864 | 1.00 | 17.81 | C |
| ATOM | 3574 | O | GLU | A | 15 | 26.362 | 21.474 | 0.832 | 1.00 | 15.92 | O |
| ATOM | 3576 | N | LEU | A | 16 | 25.722 | 19.397 | 1.430 | 1.00 | 18.53 | N |
| ATOM | 3577 | CA | LEU | A | 16 | 24.393 | 19.784 | 2.036 | 1.00 | 18.74 | C |
| ATOM | 3579 | CB | LEU | A | 16 | 23.550 | 18.549 | 2.208 | 1.00 | 18.19 | C |
| ATOM | 3582 | CG | LEU | A | 16 | 23.052 | 17.889 | 0.914 | 1.00 | 20.78 | C |

FIG.5-5

| | | | | | | | | | | | |
|---|---|---|---|---|---|---|---|---|---|---|---|
| ATOM | 3584 | CD1 | LEU | A | 16 | 22.321 | 16.580 | 1.330 | 1.00 | 14.91 | C |
| ATOM | 3588 | CD2 | LEU | A | 16 | 22.126 | 18.762 | 0.088 | 1.00 | 21.73 | C |
| ATOM | 3592 | C | LEU | A | 16 | 24.577 | 20.464 | 3.354 | 1.00 | 17.59 | C |
| ATOM | 3593 | O | LEU | A | 16 | 23.927 | 21.448 | 3.644 | 1.00 | 17.80 | O |
| ATOM | 3595 | N | ALA | A | 17 | 25.628 | 20.091 | 4.081 | 1.00 | 19.85 | N |
| ATOM | 3596 | CA | ALA | A | 17 | 26.025 | 20.809 | 5.292 | 1.00 | 17.75 | C |
| ATOM | 3598 | CB | ALA | A | 17 | 27.082 | 19.961 | 6.124 | 1.00 | 17.76 | C |
| ATOM | 3602 | C | ALA | A | 17 | 26.531 | 22.196 | 5.031 | 1.00 | 19.62 | C |
| ATOM | 3603 | O | ALA | A | 17 | 26.177 | 23.152 | 5.736 | 1.00 | 22.29 | O |
| ATOM | 3605 | N | GLU | A | 18 | 27.376 | 22.330 | 4.011 | 1.00 | 20.93 | N |
| ATOM | 3606 | CA | GLU | A | 18 | 27.886 | 23.589 | 3.573 | 1.00 | 20.59 | C |
| ATOM | 3608 | CB | GLU | A | 18 | 28.936 | 23.434 | 2.482 | 1.00 | 19.91 | C |
| ATOM | 3611 | CG | GLU | A | 18 | 30.189 | 22.772 | 3.004 | 1.00 | 20.80 | C |
| ATOM | 3614 | CD | GLU | A | 18 | 31.204 | 22.356 | 1.896 | 1.00 | 28.00 | C |
| ATOM | 3615 | OE1 | GLU | A | 18 | 30.975 | 22.621 | 0.691 | 1.00 | 27.49 | O |
| ATOM | 3616 | OE2 | GLU | A | 18 | 32.296 | 21.882 | 2.257 | 1.00 | 27.65 | O |
| ATOM | 3617 | C | GLU | A | 18 | 26.752 | 24.462 | 3.092 | 1.00 | 20.21 | C |
| ATOM | 3618 | O | GLU | A | 18 | 26.683 | 25.614 | 3.479 | 1.00 | 20.68 | O |
| ATOM | 3620 | N | LYS | A | 19 | 25.853 | 23.885 | 2.329 | 1.00 | 19.70 | N |
| ATOM | 3621 | CA | LYS | A | 19 | 24.613 | 24.618 | 1.859 | 1.00 | 20.49 | C |
| ATOM | 3623 | CB | LYS | A | 19 | 23.751 | 23.671 | 1.019 | 1.00 | 19.55 | C |
| ATOM | 3626 | CG | LYS | A | 19 | 22.479 | 24.247 | 0.396 | 1.00 | 19.45 | C |
| ATOM | 3629 | CD | LYS | A | 19 | 21.637 | 23.165 | -0.383 | 1.00 | 24.26 | C |
| ATOM | 3632 | CE | LYS | A | 19 | 20.832 | 22.282 | 0.535 | 1.00 | 25.00 | C |
| ATOM | 3635 | NZ | LYS | A | 19 | 19.611 | 22.966 | 1.177 | 1.00 | 26.59 | N |
| ATOM | 3639 | C | LYS | A | 19 | 23.800 | 25.134 | 3.018 | 1.00 | 21.30 | C |
| ATOM | 3640 | O | LYS | A | 19 | 23.421 | 26.310 | 3.040 | 1.00 | 23.58 | O |
| ATOM | 3642 | N | ALA | A | 20 | 23.520 | 24.273 | 3.995 | 1.00 | 22.46 | N |
| ATOM | 3643 | CA | ALA | A | 20 | 22.776 | 24.699 | 5.191 | 1.00 | 23.28 | C |
| ATOM | 3645 | CB | ALA | A | 20 | 22.424 | 23.437 | 6.066 | 1.00 | 22.23 | C |
| ATOM | 3649 | C | ALA | A | 20 | 23.476 | 25.829 | 6.025 | 1.00 | 24.91 | C |
| ATOM | 3650 | O | ALA | A | 20 | 22.866 | 26.876 | 6.421 | 1.00 | 22.86 | O |
| ATOM | 3652 | N | MET | A | 21 | 24.789 | 25.674 | 6.238 | 1.00 | 23.58 | N |
| ATOM | 3653 | CA | MET | A | 21 | 25.557 | 26.691 | 6.943 | 1.00 | 23.67 | C |
| ATOM | 3655 | CB | MET | A | 21 | 26.965 | 26.176 | 7.239 | 1.00 | 23.36 | C |
| ATOM | 3658 | CG | MET | A | 21 | 26.950 | 25.095 | 8.265 | 1.00 | 24.99 | C |
| ATOM | 3661 | SD | MET | A | 21 | 28.628 | 24.595 | 8.865 | 1.00 | 27.42 | S |
| ATOM | 3662 | CE | MET | A | 21 | 28.928 | 25.886 | 10.026 | 1.00 | 27.71 | C |
| ATOM | 3666 | C | MET | A | 21 | 25.630 | 28.009 | 6.174 | 1.00 | 24.25 | C |
| ATOM | 3667 | O | MET | A | 21 | 25.441 | 29.063 | 6.757 | 1.00 | 24.07 | O |
| ATOM | 3669 | N | LYS | A | 22 | 25.805 | 27.967 | 4.872 | 1.00 | 24.70 | N |
| ATOM | 3670 | CA | LYS | A | 22 | 25.623 | 29.171 | 4.088 | 1.00 | 26.29 | C |
| ATOM | 3672 | CB | LYS | A | 22 | 25.970 | 28.918 | 2.652 | 1.00 | 26.62 | C |
| ATOM | 3675 | CG | LYS | A | 22 | 25.948 | 30.174 | 1.832 | 1.00 | 31.39 | C |
| ATOM | 3678 | CD | LYS | A | 22 | 26.633 | 29.962 | 0.506 | 1.00 | 38.31 | C |
| ATOM | 3681 | CE | LYS | A | 22 | 26.536 | 31.214 | -0.492 | 1.00 | 40.15 | C |
| ATOM | 3684 | NZ | LYS | A | 22 | 26.927 | 30.772 | -1.912 | 1.00 | 39.47 | N |
| ATOM | 3688 | C | LYS | A | 22 | 24.167 | 29.753 | 4.159 | 1.00 | 26.21 | C |
| ATOM | 3689 | O | LYS | A | 22 | 23.988 | 30.954 | 4.160 | 1.00 | 25.40 | O |
| ATOM | 3691 | N | GLU | A | 23 | 23.137 | 28.929 | 4.212 | 1.00 | 25.78 | N |
| ATOM | 3692 | CA | GLU | A | 23 | 21.777 | 29.511 | 4.336 | 1.00 | 26.23 | C |
| ATOM | 3694 | CB | GLU | A | 23 | 20.709 | 28.430 | 4.187 | 1.00 | 25.11 | C |
| ATOM | 3697 | CG | GLU | A | 23 | 19.290 | 29.003 | 4.192 | 1.00 | 26.74 | C |
| ATOM | 3700 | CD | GLU | A | 23 | 18.256 | 27.915 | 4.191 | 1.00 | 29.44 | C |
| ATOM | 3701 | OE1 | GLU | A | 23 | 18.675 | 26.735 | 4.300 | 1.00 | 27.51 | O |
| ATOM | 3702 | OE2 | GLU | A | 23 | 17.047 | 28.250 | 4.089 | 1.00 | 28.84 | O |
| ATOM | 3703 | C | GLU | A | 23 | 21.634 | 30.231 | 5.687 | 1.00 | 27.52 | C |
| ATOM | 3704 | O | GLU | A | 23 | 21.062 | 31.319 | 5.788 | 1.00 | 26.79 | O |
| ATOM | 3706 | N | TYR | A | 24 | 22.247 | 29.649 | 6.706 | 1.00 | 29.75 | N |
| ATOM | 3707 | CA | TYR | A | 24 | 22.252 | 30.245 | 8.010 | 1.00 | 32.46 | C |
| ATOM | 3709 | CB | TYR | A | 24 | 22.547 | 29.192 | 9.064 | 1.00 | 32.16 | C |
| ATOM | 3712 | CG | TYR | A | 24 | 21.595 | 28.024 | 9.080 | 1.00 | 34.64 | C |
| ATOM | 3713 | CD1 | TYR | A | 24 | 22.029 | 26.756 | 9.471 | 1.00 | 36.69 | C |

FIG.5-6

| | | | | | | | | | | | |
|---|---|---|---|---|---|---|---|---|---|---|---|
| ATOM | 3715 | CE1 | TYR | A | 24 | 21.140 | 25.650 | 9.508 | 1.00 | 39.66 | C |
| ATOM | 3717 | CZ | TYR | A | 24 | 19.812 | 25.840 | 9.151 | 1.00 | 40.75 | C |
| ATOM | 3718 | OH | TYR | A | 24 | 18.907 | 24.789 | 9.163 | 1.00 | 44.75 | O |
| ATOM | 3720 | CE2 | TYR | A | 24 | 19.368 | 27.100 | 8.752 | 1.00 | 40.65 | C |
| ATOM | 3722 | CD2 | TYR | A | 24 | 20.251 | 28.186 | 8.732 | 1.00 | 36.13 | C |
| ATOM | 3724 | C | TYR | A | 24 | 23.200 | 31.414 | 8.188 | 1.00 | 33.98 | C |
| ATOM | 3725 | O | TYR | A | 24 | 23.116 | 32.079 | 9.175 | 1.00 | 35.27 | O |
| ATOM | 3727 | N | GLY | A | 25 | 24.089 | 31.678 | 7.241 | 1.00 | 35.71 | N |
| ATOM | 3728 | CA | GLY | A | 25 | 25.142 | 32.658 | 7.467 | 1.00 | 35.78 | C |
| ATOM | 3731 | C | GLY | A | 25 | 26.261 | 32.239 | 8.429 | 1.00 | 37.15 | C |
| ATOM | 3732 | O | GLY | A | 25 | 26.957 | 33.101 | 8.959 | 1.00 | 37.79 | O |
| ATOM | 3734 | N | GLU | A | 26 | 26.475 | 30.934 | 8.634 | 1.00 | 36.80 | N |
| ATOM | 3735 | CA | GLU | A | 26 | 27.603 | 30.429 | 9.451 | 1.00 | 35.63 | C |
| ATOM | 3737 | CB | GLU | A | 26 | 27.072 | 29.339 | 10.397 | 1.00 | 37.55 | C |
| ATOM | 3740 | CG | GLU | A | 26 | 25.916 | 29.751 | 11.422 | 1.00 | 42.61 | C |
| ATOM | 3743 | CD | GLU | A | 26 | 24.872 | 28.631 | 11.728 | 1.00 | 51.24 | C |
| ATOM | 3744 | OE1 | GLU | A | 26 | 23.713 | 28.968 | 12.174 | 1.00 | 56.20 | O |
| ATOM | 3745 | OE2 | GLU | A | 26 | 25.173 | 27.405 | 11.509 | 1.00 | 55.98 | O |
| ATOM | 3746 | C | GLU | A | 26 | 28.672 | 29.843 | 8.493 | 1.00 | 33.96 | C |
| ATOM | 3747 | O | GLU | A | 26 | 28.330 | 29.224 | 7.478 | 1.00 | 31.11 | O |
| ATOM | 3749 | N | ASP | A | 27 | 29.956 | 29.987 | 8.819 | 1.00 | 32.67 | N |
| ATOM | 3750 | CA | ASP | A | 27 | 31.067 | 29.607 | 7.921 | 1.00 | 32.26 | C |
| ATOM | 3752 | CB | ASP | A | 27 | 32.161 | 30.683 | 8.023 | 1.00 | 33.82 | C |
| ATOM | 3755 | CG | ASP | A | 27 | 33.281 | 30.502 | 6.985 | 1.00 | 31.25 | C |
| ATOM | 3756 | OD1 | ASP | A | 27 | 33.499 | 29.386 | 6.502 | 1.00 | 31.52 | O |
| ATOM | 3757 | OD2 | ASP | A | 27 | 33.918 | 31.480 | 6.644 | 1.00 | 32.07 | O |
| ATOM | 3758 | C | ASP | A | 27 | 31.654 | 28.230 | 8.300 | 1.00 | 31.93 | C |
| ATOM | 3759 | O | ASP | A | 27 | 32.133 | 28.078 | 9.400 | 1.00 | 30.37 | O |
| ATOM | 3761 | N | PRO | A | 28 | 31.613 | 27.221 | 7.386 | 1.00 | 31.08 | N |
| ATOM | 3762 | CA | PRO | A | 28 | 32.150 | 25.910 | 7.664 | 1.00 | 32.11 | C |
| ATOM | 3764 | CB | PRO | A | 28 | 31.898 | 25.126 | 6.378 | 1.00 | 32.10 | C |
| ATOM | 3767 | CG | PRO | A | 28 | 30.760 | 25.807 | 5.785 | 1.00 | 33.26 | C |
| ATOM | 3770 | CD | PRO | A | 28 | 30.899 | 27.238 | 6.107 | 1.00 | 32.15 | C |
| ATOM | 3773 | C | PRO | A | 28 | 33.660 | 25.961 | 7.961 | 1.00 | 32.67 | C |
| ATOM | 3774 | O | PRO | A | 28 | 34.142 | 25.132 | 8.674 | 1.00 | 32.31 | O |
| ATOM | 3775 | N | LYS | A | 29 | 34.335 | 26.995 | 7.486 | 1.00 | 33.37 | N |
| ATOM | 3776 | CA | LYS | A | 29 | 35.787 | 27.156 | 7.747 | 1.00 | 35.20 | C |
| ATOM | 3778 | CB | LYS | A | 29 | 36.360 | 28.112 | 6.709 | 1.00 | 34.94 | C |
| ATOM | 3781 | CG | LYS | A | 29 | 36.020 | 27.628 | 5.262 | 1.00 | 37.58 | C |
| ATOM | 3784 | CD | LYS | A | 29 | 36.363 | 28.657 | 4.136 | 1.00 | 38.64 | C |
| ATOM | 3787 | CE | LYS | A | 29 | 37.801 | 29.104 | 4.268 | 1.00 | 40.39 | C |
| ATOM | 3790 | NZ | LYS | A | 29 | 38.400 | 29.308 | 2.978 | 1.00 | 37.87 | N |
| ATOM | 3794 | C | LYS | A | 29 | 36.072 | 27.617 | 9.186 | 1.00 | 34.80 | C |
| ATOM | 3795 | O | LYS | A | 29 | 37.108 | 27.305 | 9.732 | 1.00 | 35.64 | O |
| ATOM | 3797 | N | ILE | A | 30 | 35.112 | 28.303 | 9.819 | 1.00 | 35.20 | N |
| ATOM | 3798 | CA | ILE | A | 30 | 35.270 | 28.815 | 11.182 | 1.00 | 34.52 | C |
| ATOM | 3800 | CB | ILE | A | 30 | 34.716 | 30.220 | 11.318 | 1.00 | 35.55 | C |
| ATOM | 3802 | CG1 | ILE | A | 30 | 35.493 | 31.164 | 10.393 | 1.00 | 37.16 | C |
| ATOM | 3805 | CD1 | ILE | A | 30 | 34.949 | 32.583 | 10.305 | 1.00 | 40.89 | C |
| ATOM | 3809 | CG2 | ILE | A | 30 | 34.808 | 30.728 | 12.753 | 1.00 | 36.66 | C |
| ATOM | 3813 | C | ILE | A | 30 | 34.622 | 27.878 | 12.173 | 1.00 | 34.34 | C |
| ATOM | 3814 | O | ILE | A | 30 | 35.297 | 27.361 | 13.079 | 1.00 | 32.95 | O |
| ATOM | 3816 | N | GLU | A | 31 | 33.317 | 27.615 | 11.985 | 1.00 | 32.99 | N |
| ATOM | 3817 | CA | GLU | A | 31 | 32.569 | 26.844 | 12.960 | 1.00 | 32.08 | C |
| ATOM | 3819 | CB | GLU | A | 31 | 31.121 | 27.392 | 13.011 | 1.00 | 32.50 | C |
| ATOM | 3822 | CG | GLU | A | 31 | 30.975 | 28.714 | 13.857 | 1.00 | 36.73 | C |
| ATOM | 3825 | CD | GLU | A | 31 | 29.506 | 29.249 | 13.897 | 1.00 | 46.12 | C |
| ATOM | 3826 | OE1 | GLU | A | 31 | 28.783 | 29.008 | 14.908 | 1.00 | 49.86 | O |
| ATOM | 3827 | OE2 | GLU | A | 31 | 29.053 | 29.893 | 12.898 | 1.00 | 50.48 | O |
| ATOM | 3828 | C | GLU | A | 31 | 32.672 | 25.375 | 12.604 | 1.00 | 31.19 | C |
| ATOM | 3829 | O | GLU | A | 31 | 31.688 | 24.743 | 12.099 | 1.00 | 30.07 | O |
| ATOM | 3831 | N | THR | A | 32 | 33.864 | 24.820 | 12.855 | 1.00 | 28.87 | N |
| ATOM | 3832 | CA | THR | A | 32 | 34.233 | 23.553 | 12.306 | 1.00 | 28.77 | C |

FIG.5-7

| | | | | | | | | | | | |
|---|---|---|---|---|---|---|---|---|---|---|---|
| ATOM | 3834 | CB | THR | A | 32 | 35.810 | 23.390 | 12.218 | 1.00 | 29.05 | C |
| ATOM | 3836 | OG1 | THR | A | 32 | 36.345 | 23.501 | 13.517 | 1.00 | 30.38 | O |
| ATOM | 3838 | CG2 | THR | A | 32 | 36.368 | 24.474 | 11.355 | 1.00 | 28.51 | C |
| ATOM | 3842 | C | THR | A | 32 | 33.635 | 22.443 | 13.073 | 1.00 | 27.91 | C |
| ATOM | 3843 | O | THR | A | 32 | 33.340 | 21.383 | 12.503 | 1.00 | 28.55 | O |
| ATOM | 3845 | N | ASN | A | 33 | 33.471 | 22.632 | 14.362 | 1.00 | 26.97 | N |
| ATOM | 3846 | CA | ASN | A | 33 | 32.753 | 21.647 | 15.167 | 1.00 | 27.78 | C |
| ATOM | 3848 | CB | ASN | A | 33 | 32.901 | 21.951 | 16.651 | 1.00 | 27.61 | C |
| ATOM | 3851 | CG | ASN | A | 33 | 34.220 | 21.427 | 17.205 | 1.00 | 34.08 | C |
| ATOM | 3852 | OD1 | ASN | A | 33 | 34.773 | 20.410 | 16.718 | 1.00 | 33.29 | O |
| ATOM | 3853 | ND2 | ASN | A | 33 | 34.761 | 22.142 | 18.169 | 1.00 | 31.62 | N |
| ATOM | 3856 | C | ASN | A | 33 | 31.243 | 21.559 | 14.798 | 1.00 | 27.02 | C |
| ATOM | 3857 | O | ASN | A | 33 | 30.725 | 20.482 | 14.721 | 1.00 | 29.90 | O |
| ATOM | 3859 | N | LYS | A | 34 | 30.594 | 22.686 | 14.587 | 1.00 | 26.67 | N |
| ATOM | 3860 | CA | LYS | A | 34 | 29.164 | 22.748 | 14.188 | 1.00 | 27.48 | C |
| ATOM | 3862 | CB | LYS | A | 34 | 28.771 | 24.219 | 14.154 | 1.00 | 28.16 | C |
| ATOM | 3865 | CG | LYS | A | 34 | 27.391 | 24.511 | 13.601 | 1.00 | 30.94 | C |
| ATOM | 3868 | CD | LYS | A | 34 | 26.279 | 24.037 | 14.609 | 1.00 | 36.57 | C |
| ATOM | 3871 | CE | LYS | A | 34 | 25.549 | 25.212 | 15.353 | 1.00 | 35.99 | C |
| ATOM | 3874 | NZ | LYS | A | 34 | 25.371 | 26.473 | 14.534 | 1.00 | 37.66 | N |
| ATOM | 3878 | C | LYS | A | 34 | 28.989 | 22.054 | 12.809 | 1.00 | 25.55 | C |
| ATOM | 3879 | O | LYS | A | 34 | 28.154 | 21.184 | 12.622 | 1.00 | 25.90 | O |
| ATOM | 3881 | N | PHE | A | 35 | 29.917 | 22.356 | 11.911 | 1.00 | 25.88 | N |
| ATOM | 3882 | CA | PHE | A | 35 | 30.084 | 21.660 | 10.646 | 1.00 | 24.88 | C |
| ATOM | 3884 | CB | PHE | A | 35 | 31.337 | 22.189 | 9.977 | 1.00 | 25.57 | C |
| ATOM | 3887 | CG | PHE | A | 35 | 31.576 | 21.715 | 8.565 | 1.00 | 26.65 | C |
| ATOM | 3888 | CD1 | PHE | A | 35 | 30.509 | 21.442 | 7.670 | 1.00 | 25.74 | C |
| ATOM | 3890 | CE1 | PHE | A | 35 | 30.770 | 21.053 | 6.365 | 1.00 | 20.88 | C |
| ATOM | 3892 | CZ | PHE | A | 35 | 32.106 | 20.952 | 5.929 | 1.00 | 24.97 | C |
| ATOM | 3894 | CE2 | PHE | A | 35 | 33.176 | 21.171 | 6.825 | 1.00 | 21.40 | C |
| ATOM | 3896 | CD2 | PHE | A | 35 | 32.918 | 21.528 | 8.120 | 1.00 | 24.71 | C |
| ATOM | 3898 | C | PHE | A | 35 | 30.050 | 20.178 | 10.778 | 1.00 | 24.09 | C |
| ATOM | 3899 | O | PHE | A | 35 | 29.175 | 19.546 | 10.170 | 1.00 | 23.97 | O |
| ATOM | 3901 | N | ALA | A | 36 | 30.909 | 19.588 | 11.611 | 1.00 | 23.22 | N |
| ATOM | 3902 | CA | ALA | A | 36 | 30.815 | 18.185 | 11.907 | 1.00 | 23.31 | C |
| ATOM | 3904 | CB | ALA | A | 36 | 31.894 | 17.752 | 12.953 | 1.00 | 23.98 | C |
| ATOM | 3908 | C | ALA | A | 36 | 29.461 | 17.760 | 12.465 | 1.00 | 21.84 | C |
| ATOM | 3909 | O | ALA | A | 36 | 29.005 | 16.666 | 12.203 | 1.00 | 21.60 | O |
| ATOM | 3911 | N | ALA | A | 37 | 28.887 | 18.561 | 13.336 | 1.00 | 21.88 | N |
| ATOM | 3912 | CA | ALA | A | 37 | 27.649 | 18.133 | 13.999 | 1.00 | 21.44 | C |
| ATOM | 3914 | CB | ALA | A | 37 | 27.350 | 19.027 | 15.213 | 1.00 | 20.06 | C |
| ATOM | 3918 | C | ALA | A | 37 | 26.493 | 18.183 | 12.966 | 1.00 | 19.17 | C |
| ATOM | 3919 | O | ALA | A | 37 | 25.615 | 17.369 | 12.978 | 1.00 | 21.53 | O |
| ATOM | 3921 | N | ILE | A | 38 | 26.522 | 19.156 | 12.093 | 1.00 | 20.44 | N |
| ATOM | 3922 | CA | ILE | A | 38 | 25.508 | 19.254 | 11.009 | 1.00 | 19.29 | C |
| ATOM | 3924 | CB | ILE | A | 38 | 25.626 | 20.564 | 10.260 | 1.00 | 18.50 | C |
| ATOM | 3926 | CG1 | ILE | A | 38 | 25.142 | 21.636 | 11.216 | 1.00 | 20.39 | C |
| ATOM | 3929 | CD1 | ILE | A | 38 | 25.427 | 23.045 | 10.873 | 1.00 | 25.17 | C |
| ATOM | 3933 | CG2 | ILE | A | 38 | 24.808 | 20.544 | 8.898 | 1.00 | 18.73 | C |
| ATOM | 3937 | C | ILE | A | 38 | 25.634 | 18.084 | 10.136 | 1.00 | 19.70 | C |
| ATOM | 3938 | O | ILE | A | 38 | 24.640 | 17.422 | 9.856 | 1.00 | 17.66 | O |
| ATOM | 3940 | N | CYS | A | 39 | 26.880 | 17.717 | 9.771 | 1.00 | 18.67 | N |
| ATOM | 3941 | CA | CYS | A | 39 | 27.049 | 16.524 | 8.938 | 1.00 | 18.32 | C |
| ATOM | 3943 | CB | CYS | A | 39 | 28.559 | 16.305 | 8.470 | 1.00 | 18.20 | C |
| ATOM | 3946 | SG | CYS | A | 39 | 29.211 | 17.518 | 7.360 | 1.00 | 23.17 | S |
| ATOM | 3948 | C | CYS | A | 39 | 26.525 | 15.264 | 9.605 | 1.00 | 17.79 | C |
| ATOM | 3949 | O | CYS | A | 39 | 25.835 | 14.456 | 8.981 | 1.00 | 18.02 | O |
| ATOM | 3951 | N | THR | A | 40 | 26.865 | 15.082 | 10.884 | 1.00 | 17.25 | N |
| ATOM | 3952 | CA | THR | A | 40 | 26.475 | 13.945 | 11.640 | 1.00 | 18.06 | C |
| ATOM | 3954 | CB | THR | A | 40 | 27.049 | 14.050 | 13.007 | 1.00 | 20.01 | C |
| ATOM | 3956 | OG1 | THR | A | 40 | 28.484 | 14.100 | 12.864 | 1.00 | 23.15 | O |
| ATOM | 3958 | CG2 | THR | A | 40 | 26.685 | 12.824 | 13.845 | 1.00 | 19.86 | C |
| ATOM | 3962 | C | THR | A | 40 | 24.938 | 13.819 | 11.761 | 1.00 | 17.94 | C |

FIG.5-8

| | | | | | | | | | | | |
|---|---|---|---|---|---|---|---|---|---|---|---|
| ATOM | 3963 | O | THR | A | 40 | 24.439 | 12.774 | 11.588 | 1.00 | 17.27 | O |
| ATOM | 3965 | N | HIS | A | 41 | 24.292 | 14.931 | 12.077 | 1.00 | 19.50 | N |
| ATOM | 3966 | CA | HIS | A | 41 | 22.842 | 15.007 | 12.276 | 1.00 | 19.81 | C |
| ATOM | 3968 | CB | HIS | A | 41 | 22.432 | 16.388 | 12.814 | 1.00 | 19.82 | C |
| ATOM | 3971 | CG | HIS | A | 41 | 20.952 | 16.664 | 12.758 | 1.00 | 20.37 | C |
| ATOM | 3972 | ND1 | HIS | A | 41 | 20.339 | 17.302 | 11.700 | 1.00 | 21.48 | N |
| ATOM | 3974 | CE1 | HIS | A | 41 | 19.041 | 17.429 | 11.962 | 1.00 | 22.42 | C |
| ATOM | 3976 | NE2 | HIS | A | 41 | 18.805 | 16.912 | 13.150 | 1.00 | 23.82 | N |
| ATOM | 3978 | CD2 | HIS | A | 41 | 19.989 | 16.484 | 13.690 | 1.00 | 18.08 | C |
| ATOM | 3980 | C | HIS | A | 41 | 22.224 | 14.710 | 10.937 | 1.00 | 18.88 | C |
| ATOM | 3981 | O | HIS | A | 41 | 21.294 | 13.919 | 10.903 | 1.00 | 19.64 | O |
| ATOM | 3983 | N | LEU | A | 42 | 22.761 | 15.283 | 9.831 | 1.00 | 18.01 | N |
| ATOM | 3984 | CA | LEU | A | 42 | 22.189 | 14.974 | 8.517 | 1.00 | 18.86 | C |
| ATOM | 3986 | CB | LEU | A | 42 | 22.807 | 15.848 | 7.376 | 1.00 | 20.46 | C |
| ATOM | 3989 | CG | LEU | A | 42 | 22.161 | 15.809 | 5.987 | 1.00 | 24.61 | C |
| ATOM | 3991 | CD1 | LEU | A | 42 | 20.616 | 16.114 | 6.039 | 1.00 | 25.14 | C |
| ATOM | 3995 | CD2 | LEU | A | 42 | 22.827 | 16.886 | 5.102 | 1.00 | 31.06 | C |
| ATOM | 3999 | C | LEU | A | 42 | 22.347 | 13.512 | 8.210 | 1.00 | 19.21 | C |
| ATOM | 4000 | O | LEU | A | 42 | 21.405 | 12.844 | 7.701 | 1.00 | 19.82 | O |
| ATOM | 4002 | N | GLU | A | 43 | 23.540 | 12.984 | 8.467 | 1.00 | 19.50 | N |
| ATOM | 4003 | CA | GLU | A | 43 | 23.734 | 11.592 | 8.266 | 1.00 | 20.69 | C |
| ATOM | 4005 | CB | GLU | A | 43 | 25.223 | 11.209 | 8.489 | 1.00 | 22.31 | C |
| ATOM | 4008 | CG | GLU | A | 43 | 25.350 | 9.825 | 7.982 | 1.00 | 27.94 | C |
| ATOM | 4011 | CD | GLU | A | 43 | 26.715 | 9.334 | 7.937 | 1.00 | 30.82 | C |
| ATOM | 4012 | OE1 | GLU | A | 43 | 26.925 | 8.463 | 7.114 | 1.00 | 43.59 | O |
| ATOM | 4013 | OE2 | GLU | A | 43 | 27.560 | 9.792 | 8.675 | 1.00 | 33.88 | O |
| ATOM | 4014 | C | GLU | A | 43 | 22.781 | 10.741 | 9.124 | 1.00 | 20.20 | C |
| ATOM | 4015 | O | GLU | A | 43 | 22.208 | 9.800 | 8.621 | 1.00 | 18.66 | O |
| ATOM | 4017 | N | VAL | A | 44 | 22.488 | 11.131 | 10.371 | 1.00 | 19.84 | N |
| ATOM | 4018 | CA | VAL | A | 44 | 21.521 | 10.329 | 11.153 | 1.00 | 20.97 | C |
| ATOM | 4020 | CB | VAL | A | 44 | 21.570 | 10.698 | 12.675 | 1.00 | 21.29 | C |
| ATOM | 4022 | CG1 | VAL | A | 44 | 20.456 | 10.080 | 13.447 | 1.00 | 21.90 | C |
| ATOM | 4026 | CG2 | VAL | A | 44 | 22.984 | 10.268 | 13.386 | 1.00 | 24.03 | C |
| ATOM | 4030 | C | VAL | A | 44 | 20.068 | 10.409 | 10.585 | 1.00 | 21.37 | C |
| ATOM | 4031 | O | VAL | A | 44 | 19.314 | 9.403 | 10.565 | 1.00 | 21.88 | O |
| ATOM | 4033 | N | CYS | A | 45 | 19.646 | 11.606 | 10.174 | 1.00 | 21.03 | N |
| ATOM | 4034 | CA | CYS | A | 45 | 18.296 | 11.785 | 9.544 | 1.00 | 21.16 | C |
| ATOM | 4036 | CB | CYS | A | 45 | 18.088 | 13.231 | 9.152 | 1.00 | 18.88 | C |
| ATOM | 4039 | SG | CYS | A | 45 | 17.930 | 14.217 | 10.522 | 1.00 | 20.57 | S |
| ATOM | 4041 | C | CYS | A | 45 | 18.157 | 10.855 | 8.323 | 1.00 | 22.81 | C |
| ATOM | 4042 | O | CYS | A | 45 | 17.151 | 10.092 | 8.203 | 1.00 | 23.44 | O |
| ATOM | 4044 | N | PHE | A | 46 | 19.194 | 10.836 | 7.483 | 1.00 | 22.85 | N |
| ATOM | 4045 | CA | PHE | A | 46 | 19.223 | 9.915 | 6.361 | 1.00 | 26.26 | C |
| ATOM | 4047 | CB | PHE | A | 46 | 20.445 | 10.179 | 5.493 | 1.00 | 26.97 | C |
| ATOM | 4050 | CG | PHE | A | 46 | 20.397 | 11.481 | 4.689 | 1.00 | 27.31 | C |
| ATOM | 4051 | CD1 | PHE | A | 46 | 19.450 | 12.456 | 4.902 | 1.00 | 27.51 | C |
| ATOM | 4053 | CE1 | PHE | A | 46 | 19.449 | 13.626 | 4.142 | 1.00 | 30.33 | C |
| ATOM | 4055 | CZ | PHE | A | 46 | 20.401 | 13.827 | 3.186 | 1.00 | 27.29 | C |
| ATOM | 4057 | CE2 | PHE | A | 46 | 21.352 | 12.926 | 2.996 | 1.00 | 29.34 | C |
| ATOM | 4059 | CD2 | PHE | A | 46 | 21.347 | 11.715 | 3.736 | 1.00 | 29.82 | C |
| ATOM | 4061 | C | PHE | A | 46 | 19.195 | 8.414 | 6.763 | 1.00 | 26.98 | C |
| ATOM | 4062 | O | PHE | A | 46 | 18.445 | 7.634 | 6.142 | 1.00 | 28.73 | O |
| ATOM | 4064 | N | MET | A | 47 | 19.990 | 7.997 | 7.765 | 1.00 | 26.04 | N |
| ATOM | 4065 | CA | MET | A | 47 | 19.944 | 6.582 | 8.216 | 1.00 | 27.74 | C |
| ATOM | 4067 | CB | MET | A | 47 | 21.066 | 6.272 | 9.205 | 1.00 | 28.12 | C |
| ATOM | 4070 | CG | MET | A | 47 | 22.453 | 6.608 | 8.674 | 1.00 | 29.74 | C |
| ATOM | 4073 | SD | MET | A | 47 | 23.783 | 6.300 | 9.814 | 1.00 | 34.67 | S |
| ATOM | 4074 | CE | MET | A | 47 | 23.511 | 4.549 | 10.197 | 1.00 | 27.14 | C |
| ATOM | 4078 | C | MET | A | 47 | 18.608 | 6.268 | 8.849 | 1.00 | 28.19 | C |
| ATOM | 4079 | O | MET | A | 47 | 18.052 | 5.162 | 8.703 | 1.00 | 29.11 | O |
| ATOM | 4081 | N | TYR | A | 48 | 18.059 | 7.247 | 9.549 | 1.00 | 27.66 | N |
| ATOM | 4082 | CA | TYR | A | 48 | 16.780 | 7.030 | 10.187 | 1.00 | 27.82 | C |
| ATOM | 4084 | CB | TYR | A | 48 | 16.401 | 8.265 | 10.959 | 1.00 | 25.59 | C |

FIG.5-9

| | | | | | | | | | | | |
|---|---|---|---|---|---|---|---|---|---|---|---|
| ATOM | 4087 | CG | TYR | A | 48 | 15.429 | 8.073 | 12.090 | 1.00 | 25.74 | C |
| ATOM | 4088 | CD1 | TYR | A | 48 | 15.833 | 8.175 | 13.405 | 1.00 | 22.42 | C |
| ATOM | 4090 | CE1 | TYR | A | 48 | 14.938 | 8.030 | 14.445 | 1.00 | 24.87 | C |
| ATOM | 4092 | CZ | TYR | A | 48 | 13.596 | 7.800 | 14.216 | 1.00 | 26.71 | C |
| ATOM | 4093 | OH | TYR | A | 48 | 12.717 | 7.671 | 15.318 | 1.00 | 24.81 | O |
| ATOM | 4095 | CE2 | TYR | A | 48 | 13.155 | 7.668 | 12.933 | 1.00 | 27.06 | C |
| ATOM | 4097 | CD2 | TYR | A | 48 | 14.075 | 7.810 | 11.856 | 1.00 | 26.71 | C |
| ATOM | 4099 | C | TYR | A | 48 | 15.696 | 6.670 | 9.165 | 1.00 | 29.27 | C |
| ATOM | 4100 | O | TYR | A | 48 | 14.869 | 5.790 | 9.378 | 1.00 | 26.64 | O |
| ATOM | 4102 | N | SER | A | 49 | 15.736 | 7.339 | 8.030 | 1.00 | 32.83 | N |
| ATOM | 4103 | CA | SER | A | 49 | 14.783 | 7.093 | 6.948 | 1.00 | 35.43 | C |
| ATOM | 4105 | CB | SER | A | 49 | 14.690 | 8.314 | 6.035 | 1.00 | 35.64 | C |
| ATOM | 4108 | OG | SER | A | 49 | 13.905 | 7.940 | 4.900 | 1.00 | 36.39 | O |
| ATOM | 4110 | C | SER | A | 49 | 15.091 | 5.876 | 6.073 | 1.00 | 37.95 | C |
| ATOM | 4111 | O | SER | A | 49 | 14.155 | 5.202 | 5.581 | 1.00 | 40.05 | O |
| ATOM | 4113 | N | ASP | A | 50 | 16.367 | 5.581 | 5.874 | 1.00 | 40.93 | N |
| ATOM | 4114 | CA | ASP | A | 50 | 16.801 | 4.547 | 4.909 | 1.00 | 44.18 | C |
| ATOM | 4116 | CB | ASP | A | 50 | 18.353 | 4.437 | 4.799 | 1.00 | 44.74 | C |
| ATOM | 4119 | CG | ASP | A | 50 | 18.963 | 5.590 | 3.997 | 1.00 | 46.66 | C |
| ATOM | 4120 | OD1 | ASP | A | 50 | 20.206 | 5.775 | 4.030 | 1.00 | 51.65 | O |
| ATOM | 4121 | OD2 | ASP | A | 50 | 18.182 | 6.351 | 3.358 | 1.00 | 50.32 | O |
| ATOM | 4122 | C | ASP | A | 50 | 16.230 | 3.184 | 5.192 | 1.00 | 45.66 | C |
| ATOM | 4123 | O | ASP | A | 50 | 16.137 | 2.758 | 6.351 | 1.00 | 47.11 | O |
| ATOM | 4125 | N | PHE | A | 51 | 15.823 | 2.521 | 4.117 | 1.00 | 47.20 | N |
| ATOM | 4126 | CA | PHE | A | 51 | 15.291 | 1.168 | 4.160 | 1.00 | 48.87 | C |
| ATOM | 4128 | CB | PHE | A | 51 | 16.265 | 0.175 | 4.872 | 1.00 | 48.96 | C |
| ATOM | 4131 | CG | PHE | A | 51 | 17.707 | 0.312 | 4.467 | 1.00 | 52.30 | C |
| ATOM | 4132 | CD1 | PHE | A | 51 | 18.081 | 0.217 | 3.117 | 1.00 | 55.97 | C |
| ATOM | 4134 | CE1 | PHE | A | 51 | 19.425 | 0.343 | 2.737 | 1.00 | 57.47 | C |
| ATOM | 4136 | CZ | PHE | A | 51 | 20.407 | 0.582 | 3.733 | 1.00 | 58.95 | C |
| ATOM | 4138 | CE2 | PHE | A | 51 | 20.030 | 0.662 | 5.089 | 1.00 | 55.32 | C |
| ATOM | 4140 | CD2 | PHE | A | 51 | 18.703 | 0.519 | 5.443 | 1.00 | 53.55 | C |
| ATOM | 4142 | C | PHE | A | 51 | 13.899 | 1.030 | 4.796 | 1.00 | 49.11 | C |
| ATOM | 4143 | O | PHE | A | 51 | 13.422 | -0.077 | 4.888 | 1.00 | 49.98 | O |
| ATOM | 4145 | N | HIS | A | 52 | 13.238 | 2.104 | 5.225 | 1.00 | 49.71 | N |
| ATOM | 4146 | CA | HIS | A | 52 | 11.891 | 1.980 | 5.787 | 1.00 | 49.81 | C |
| ATOM | 4148 | CB | HIS | A | 52 | 11.780 | 2.734 | 7.099 | 1.00 | 50.49 | C |
| ATOM | 4151 | CG | HIS | A | 52 | 12.629 | 2.144 | 8.177 | 1.00 | 51.72 | C |
| ATOM | 4152 | ND1 | HIS | A | 52 | 13.791 | 2.742 | 8.617 | 1.00 | 53.36 | N |
| ATOM | 4154 | CE1 | HIS | A | 52 | 14.350 | 1.973 | 9.537 | 1.00 | 54.13 | C |
| ATOM | 4156 | NE2 | HIS | A | 52 | 13.605 | 0.893 | 9.694 | 1.00 | 53.31 | N |
| ATOM | 4158 | CD2 | HIS | A | 52 | 12.527 | 0.971 | 8.846 | 1.00 | 52.73 | C |
| ATOM | 4160 | C | HIS | A | 52 | 10.790 | 2.384 | 4.838 | 1.00 | 50.48 | C |
| ATOM | 4161 | O | HIS | A | 52 | 10.791 | 3.486 | 4.284 | 1.00 | 49.74 | O |
| ATOM | 4163 | N | PHE | A | 53 | 9.847 | 1.462 | 4.651 | 1.00 | 51.60 | N |
| ATOM | 4164 | CA | PHE | A | 53 | 8.869 | 1.556 | 3.590 | 1.00 | 53.19 | C |
| ATOM | 4166 | CB | PHE | A | 53 | 9.300 | 0.668 | 2.425 | 1.00 | 53.76 | C |
| ATOM | 4169 | CG | PHE | A | 53 | 10.480 | 1.201 | 1.643 | 1.00 | 53.69 | C |
| ATOM | 4170 | CD1 | PHE | A | 53 | 10.307 | 2.155 | 0.679 | 1.00 | 53.29 | C |
| ATOM | 4172 | CE1 | PHE | A | 53 | 11.377 | 2.639 | -0.042 | 1.00 | 55.70 | C |
| ATOM | 4174 | CZ | PHE | A | 53 | 12.652 | 2.162 | 0.196 | 1.00 | 56.82 | C |
| ATOM | 4176 | CE2 | PHE | A | 53 | 12.836 | 1.188 | 1.148 | 1.00 | 56.35 | C |
| ATOM | 4178 | CD2 | PHE | A | 53 | 11.754 | 0.715 | 1.867 | 1.00 | 55.39 | C |
| ATOM | 4180 | C | PHE | A | 53 | 7.503 | 1.153 | 4.108 | 1.00 | 54.70 | C |
| ATOM | 4181 | O | PHE | A | 53 | 7.398 | 0.526 | 5.142 | 1.00 | 53.81 | O |
| ATOM | 4183 | N | ILE | A | 54 | 6.444 | 1.562 | 3.419 | 1.00 | 57.24 | N |
| ATOM | 4184 | CA | ILE | A | 54 | 5.089 | 1.171 | 3.818 | 1.00 | 58.97 | C |
| ATOM | 4186 | CB | ILE | A | 54 | 4.281 | 2.349 | 4.455 | 1.00 | 58.93 | C |
| ATOM | 4188 | CG1 | ILE | A | 54 | 4.550 | 3.674 | 3.743 | 1.00 | 58.38 | C |
| ATOM | 4191 | CD1 | ILE | A | 54 | 3.806 | 4.853 | 4.359 | 1.00 | 56.17 | C |
| ATOM | 4195 | CG2 | ILE | A | 54 | 4.614 | 2.476 | 5.934 | 1.00 | 59.10 | C |
| ATOM | 4199 | C | ILE | A | 54 | 4.331 | 0.556 | 2.636 | 1.00 | 61.05 | C |
| ATOM | 4200 | O | ILE | A | 54 | 4.235 | 1.163 | 1.564 | 1.00 | 60.93 | O |

FIG.5-10

| | | | | | | | | | | | |
|---|---|---|---|---|---|---|---|---|---|---|---|
| ATOM | 4202 | N | ASP | A | 55 | 3.796 | -0.649 | 2.849 | 1.00 | 63.73 | N |
| ATOM | 4203 | CA | ASP | A | 55 | 3.250 | -1.472 | 1.758 | 1.00 | 65.98 | C |
| ATOM | 4205 | CB | ASP | A | 55 | 3.105 | -2.958 | 2.172 | 1.00 | 66.36 | C |
| ATOM | 4208 | CG | ASP | A | 55 | 2.077 | -3.188 | 3.269 | 1.00 | 67.76 | C |
| ATOM | 4209 | OD1 | ASP | A | 55 | 2.250 | -4.178 | 4.015 | 1.00 | 71.29 | O |
| ATOM | 4210 | OD2 | ASP | A | 55 | 1.103 | -2.408 | 3.396 | 1.00 | 70.42 | O |
| ATOM | 4211 | C | ASP | A | 55 | 1.949 | -0.933 | 1.132 | 1.00 | 67.80 | C |
| ATOM | 4212 | O | ASP | A | 55 | 1.460 | -1.492 | 0.132 | 1.00 | 68.87 | O |
| ATOM | 4214 | N | ASP | A | 56 | 1.390 | 0.128 | 1.719 | 1.00 | 69.38 | N |
| ATOM | 4215 | CA | ASP | A | 56 | 0.330 | 0.915 | 1.074 | 1.00 | 70.37 | C |
| ATOM | 4217 | CB | ASP | A | 56 | -1.024 | 0.187 | 1.157 | 1.00 | 70.91 | C |
| ATOM | 4220 | CG | ASP | A | 56 | -2.058 | 0.742 | 0.178 | 1.00 | 72.59 | C |
| ATOM | 4221 | OD1 | ASP | A | 56 | -1.944 | 1.917 | -0.257 | 1.00 | 74.34 | O |
| ATOM | 4222 | OD2 | ASP | A | 56 | -3.003 | -0.008 | -0.155 | 1.00 | 76.69 | O |
| ATOM | 4223 | C | ASP | A | 56 | 0.231 | 2.295 | 1.730 | 1.00 | 70.77 | C |
| ATOM | 4224 | O | ASP | A | 56 | 0.004 | 2.402 | 2.943 | 1.00 | 71.00 | O |
| ATOM | 4226 | N | GLY | A | 58 | 0.587 | -1.157 | 6.263 | 1.00 | 81.38 | N |
| ATOM | 4227 | CA | GLY | A | 58 | 1.600 | -1.539 | 7.247 | 1.00 | 81.46 | C |
| ATOM | 4230 | C | GLY | A | 58 | 2.991 | -1.331 | 6.679 | 1.00 | 81.74 | C |
| ATOM | 4231 | O | GLY | A | 58 | 3.138 | -1.095 | 5.472 | 1.00 | 81.77 | O |
| ATOM | 4233 | N | GLU | A | 59 | 4.019 | -1.422 | 7.527 | 1.00 | 81.75 | N |
| ATOM | 4234 | CA | GLU | A | 59 | 5.391 | -1.072 | 7.101 | 1.00 | 81.67 | C |
| ATOM | 4236 | CB | GLU | A | 59 | 6.076 | -0.095 | 8.085 | 1.00 | 81.61 | C |
| ATOM | 4239 | CG | GLU | A | 59 | 6.951 | -0.720 | 9.176 | 1.00 | 81.33 | C |
| ATOM | 4242 | CD | GLU | A | 59 | 6.136 | -1.423 | 10.247 | 1.00 | 80.59 | C |
| ATOM | 4243 | OE1 | GLU | A | 59 | 5.322 | -2.303 | 9.900 | 1.00 | 81.03 | O |
| ATOM | 4244 | OE2 | GLU | A | 59 | 6.301 | -1.093 | 11.440 | 1.00 | 77.96 | O |
| ATOM | 4245 | C | GLU | A | 59 | 6.264 | -2.289 | 6.848 | 1.00 | 81.47 | C |
| ATOM | 4246 | O | GLU | A | 59 | 5.885 | -3.414 | 7.152 | 1.00 | 81.51 | O |
| ATOM | 4248 | N | SER | A | 60 | 7.436 | -2.032 | 6.279 | 1.00 | 81.57 | N |
| ATOM | 4249 | CA | SER | A | 60 | 8.369 | -3.072 | 5.890 | 1.00 | 81.64 | C |
| ATOM | 4251 | CB | SER | A | 60 | 7.881 | -3.798 | 4.634 | 1.00 | 81.53 | C |
| ATOM | 4254 | OG | SER | A | 60 | 7.444 | -2.889 | 3.646 | 1.00 | 80.41 | O |
| ATOM | 4256 | C | SER | A | 60 | 9.759 | -2.492 | 5.657 | 1.00 | 82.25 | C |
| ATOM | 4257 | O | SER | A | 60 | 9.920 | -1.312 | 5.327 | 1.00 | 81.91 | O |
| ATOM | 4259 | N | ILE | A | 61 | 10.746 | -3.365 | 5.820 | 1.00 | 83.15 | N |
| ATOM | 4260 | CA | ILE | A | 61 | 12.172 | -3.035 | 5.807 | 1.00 | 83.98 | C |
| ATOM | 4262 | CB | ILE | A | 61 | 12.824 | -3.573 | 7.126 | 1.00 | 84.00 | C |
| ATOM | 4264 | CG1 | ILE | A | 61 | 11.974 | -3.152 | 8.347 | 1.00 | 84.28 | C |
| ATOM | 4267 | CD1 | ILE | A | 61 | 12.623 | -3.382 | 9.701 | 1.00 | 83.44 | C |
| ATOM | 4271 | CG2 | ILE | A | 61 | 14.255 | -3.105 | 7.253 | 1.00 | 83.90 | C |
| ATOM | 4275 | C | ILE | A | 61 | 12.838 | -3.678 | 4.563 | 1.00 | 84.60 | C |
| ATOM | 4276 | O | ILE | A | 61 | 12.521 | -4.827 | 4.229 | 1.00 | 85.06 | O |
| ATOM | 4278 | N | ILE | A | 62 | 13.729 | -2.950 | 3.871 | 1.00 | 85.09 | N |
| ATOM | 4279 | CA | ILE | A | 62 | 14.450 | -3.481 | 2.676 | 1.00 | 85.39 | C |
| ATOM | 4281 | CB | ILE | A | 62 | 14.074 | -2.722 | 1.367 | 1.00 | 85.47 | C |
| ATOM | 4283 | CG1 | ILE | A | 62 | 12.570 | -2.830 | 1.082 | 1.00 | 85.98 | C |
| ATOM | 4286 | CD1 | ILE | A | 62 | 12.129 | -2.183 | -0.273 | 1.00 | 85.70 | C |
| ATOM | 4290 | CG2 | ILE | A | 62 | 14.839 | -3.290 | 0.169 | 1.00 | 85.59 | C |
| ATOM | 4294 | C | ILE | A | 62 | 15.983 | -3.474 | 2.872 | 1.00 | 85.49 | C |
| ATOM | 4295 | O | ILE | A | 62 | 16.765 | -3.150 | 1.962 | 1.00 | 85.65 | O |
| ATOM | 4297 | N | LYS | A | 73 | 6.938 | 2.964 | -1.660 | 1.00 | 48.05 | N |
| ATOM | 4298 | CA | LYS | A | 73 | 6.539 | 4.123 | -0.839 | 1.00 | 48.25 | C |
| ATOM | 4300 | CB | LYS | A | 73 | 5.067 | 3.954 | -0.459 | 1.00 | 49.02 | C |
| ATOM | 4303 | CG | LYS | A | 73 | 4.385 | 5.133 | 0.229 | 1.00 | 53.20 | C |
| ATOM | 4306 | CD | LYS | A | 73 | 2.844 | 4.863 | 0.197 | 1.00 | 56.19 | C |
| ATOM | 4309 | CE | LYS | A | 73 | 1.921 | 6.006 | 0.697 | 1.00 | 57.81 | C |
| ATOM | 4312 | NZ | LYS | A | 73 | 0.509 | 5.455 | 0.873 | 1.00 | 56.71 | N |
| ATOM | 4316 | C | LYS | A | 73 | 7.395 | 4.315 | 0.444 | 1.00 | 46.21 | C |
| ATOM | 4317 | O | LYS | A | 73 | 7.399 | 3.441 | 1.331 | 1.00 | 45.27 | O |
| ATOM | 4319 | N | HIS | A | 74 | 8.047 | 5.478 | 0.570 | 1.00 | 42.54 | N |
| ATOM | 4320 | CA | HIS | A | 74 | 8.901 | 5.755 | 1.732 | 1.00 | 41.51 | C |
| ATOM | 4322 | CB | HIS | A | 74 | 9.773 | 7.001 | 1.502 | 1.00 | 41.99 | C |

FIG.5-11

| | | | | | | | | | | | |
|---|---|---|---|---|---|---|---|---|---|---|---|
| ATOM | 4325 | CG | HIS | A | 74 | 10.794 | 6.828 | 0.424 | 1.00 | 45.77 | C |
| ATOM | 4326 | ND1 | HIS | A | 74 | 11.882 | 7.666 | 0.278 | 1.00 | 51.13 | N |
| ATOM | 4328 | CE1 | HIS | A | 74 | 12.613 | 7.272 | -0.747 | 1.00 | 50.19 | C |
| ATOM | 4330 | NE2 | HIS | A | 74 | 12.053 | 6.192 | -1.257 | 1.00 | 49.77 | N |
| ATOM | 4332 | CD2 | HIS | A | 74 | 10.909 | 5.900 | -0.551 | 1.00 | 48.34 | C |
| ATOM | 4334 | C | HIS | A | 74 | 8.053 | 5.945 | 2.990 | 1.00 | 38.11 | C |
| ATOM | 4335 | O | HIS | A | 74 | 7.068 | 6.687 | 2.971 | 1.00 | 39.13 | O |
| ATOM | 4337 | N | ARG | A | 75 | 8.432 | 5.286 | 4.078 | 1.00 | 33.28 | N |
| ATOM | 4338 | CA | ARG | A | 75 | 7.790 | 5.529 | 5.383 | 1.00 | 31.40 | C |
| ATOM | 4340 | CB | ARG | A | 75 | 8.310 | 4.536 | 6.419 | 1.00 | 30.88 | C |
| ATOM | 4343 | CG | ARG | A | 75 | 7.838 | 4.843 | 7.806 | 1.00 | 32.49 | C |
| ATOM | 4346 | CD | ARG | A | 75 | 8.088 | 3.752 | 8.788 | 1.00 | 29.37 | C |
| ATOM | 4349 | NE | ARG | A | 75 | 7.641 | 4.211 | 10.076 | 1.00 | 32.59 | N |
| ATOM | 4351 | CZ | ARG | A | 75 | 7.726 | 3.528 | 11.208 | 1.00 | 35.96 | C |
| ATOM | 4352 | NH1 | ARG | A | 75 | 8.254 | 2.326 | 11.229 | 1.00 | 40.55 | N |
| ATOM | 4355 | NH2 | ARG | A | 75 | 7.309 | 4.078 | 12.327 | 1.00 | 38.41 | N |
| ATOM | 4358 | C | ARG | A | 75 | 7.998 | 6.972 | 5.893 | 1.00 | 29.60 | C |
| ATOM | 4359 | O | ARG | A | 75 | 7.136 | 7.555 | 6.553 | 1.00 | 29.98 | O |
| ATOM | 4361 | N | PHE | A | 76 | 9.131 | 7.552 | 5.569 | 1.00 | 27.87 | N |
| ATOM | 4362 | CA | PHE | A | 76 | 9.510 | 8.814 | 6.132 | 1.00 | 27.42 | C |
| ATOM | 4364 | CB | PHE | A | 76 | 10.811 | 8.665 | 6.904 | 1.00 | 27.96 | C |
| ATOM | 4367 | CG | PHE | A | 76 | 10.705 | 7.775 | 8.089 | 1.00 | 25.71 | C |
| ATOM | 4368 | CD1 | PHE | A | 76 | 10.062 | 8.207 | 9.226 | 1.00 | 24.03 | C |
| ATOM | 4370 | CE1 | PHE | A | 76 | 9.966 | 7.392 | 10.311 | 1.00 | 26.98 | C |
| ATOM | 4372 | CZ | PHE | A | 76 | 10.511 | 6.175 | 10.276 | 1.00 | 24.68 | C |
| ATOM | 4374 | CE2 | PHE | A | 76 | 11.176 | 5.725 | 9.176 | 1.00 | 26.92 | C |
| ATOM | 4376 | CD2 | PHE | A | 76 | 11.281 | 6.528 | 8.084 | 1.00 | 29.01 | C |
| ATOM | 4378 | C | PHE | A | 76 | 9.738 | 9.838 | 5.041 | 1.00 | 26.82 | C |
| ATOM | 4379 | O | PHE | A | 76 | 10.435 | 9.552 | 4.078 | 1.00 | 28.59 | O |
| ATOM | 4381 | N | GLU | A | 77 | 9.205 | 11.041 | 5.206 | 1.00 | 25.46 | N |
| ATOM | 4382 | CA | GLU | A | 77 | 9.584 | 12.135 | 4.363 | 1.00 | 24.88 | C |
| ATOM | 4384 | CB | GLU | A | 77 | 8.437 | 13.136 | 4.297 | 1.00 | 26.37 | C |
| ATOM | 4387 | CG | GLU | A | 77 | 8.775 | 14.311 | 3.354 | 1.00 | 29.27 | C |
| ATOM | 4390 | CD | GLU | A | 77 | 8.802 | 13.849 | 1.933 | 1.00 | 30.94 | C |
| ATOM | 4391 | OE1 | GLU | A | 77 | 9.772 | 14.104 | 1.188 | 1.00 | 38.76 | O |
| ATOM | 4392 | OE2 | GLU | A | 77 | 7.870 | 13.122 | 1.617 | 1.00 | 33.73 | O |
| ATOM | 4393 | C | GLU | A | 77 | 10.833 | 12.818 | 4.985 | 1.00 | 25.17 | C |
| ATOM | 4394 | O | GLU | A | 77 | 10.836 | 13.070 | 6.172 | 1.00 | 25.52 | O |
| ATOM | 4396 | N | ILE | A | 78 | 11.868 | 13.153 | 4.212 | 1.00 | 23.90 | N |
| ATOM | 4397 | CA | ILE | A | 78 | 13.028 | 13.832 | 4.801 | 1.00 | 24.27 | C |
| ATOM | 4399 | CB | ILE | A | 78 | 14.384 | 13.395 | 4.193 | 1.00 | 26.03 | C |
| ATOM | 4401 | CG1 | ILE | A | 78 | 14.548 | 11.854 | 4.322 | 1.00 | 28.41 | C |
| ATOM | 4404 | CD1 | ILE | A | 78 | 15.529 | 11.142 | 3.285 | 1.00 | 29.47 | C |
| ATOM | 4408 | CG2 | ILE | A | 78 | 15.522 | 14.075 | 4.953 | 1.00 | 25.15 | C |
| ATOM | 4412 | C | ILE | A | 78 | 12.861 | 15.359 | 4.682 | 1.00 | 22.51 | C |
| ATOM | 4413 | O | ILE | A | 78 | 12.699 | 15.869 | 3.638 | 1.00 | 23.77 | O |
| ATOM | 4415 | N | ILE | A | 79 | 12.775 | 16.053 | 5.791 | 1.00 | 21.51 | N |
| ATOM | 4416 | CA | ILE | A | 79 | 12.680 | 17.524 | 5.836 | 1.00 | 20.74 | C |
| ATOM | 4418 | CB | ILE | A | 79 | 11.719 | 17.834 | 6.936 | 1.00 | 20.06 | C |
| ATOM | 4420 | CG1 | ILE | A | 79 | 10.335 | 17.217 | 6.505 | 1.00 | 23.77 | C |
| ATOM | 4423 | CD1 | ILE | A | 79 | 9.431 | 17.082 | 7.599 | 1.00 | 25.23 | C |
| ATOM | 4427 | CG2 | ILE | A | 79 | 11.557 | 19.343 | 7.135 | 1.00 | 18.11 | C |
| ATOM | 4431 | C | ILE | A | 79 | 14.063 | 18.196 | 5.974 | 1.00 | 19.32 | C |
| ATOM | 4432 | O | ILE | A | 79 | 14.410 | 19.151 | 5.254 | 1.00 | 18.63 | O |
| ATOM | 4434 | N | GLU | A | 80 | 14.873 | 17.649 | 6.850 | 1.00 | 18.99 | N |
| ATOM | 4435 | CA | GLU | A | 80 | 16.261 | 18.154 | 7.077 | 1.00 | 19.21 | C |
| ATOM | 4437 | CB | GLU | A | 80 | 16.902 | 17.361 | 8.223 | 1.00 | 19.58 | C |
| ATOM | 4440 | CG | GLU | A | 80 | 18.266 | 17.872 | 8.736 | 1.00 | 21.39 | C |
| ATOM | 4443 | CD | GLU | A | 80 | 18.271 | 19.248 | 9.206 | 1.00 | 21.69 | C |
| ATOM | 4444 | OE1 | GLU | A | 80 | 17.943 | 19.564 | 10.330 | 1.00 | 27.20 | O |
| ATOM | 4445 | OE2 | GLU | A | 80 | 18.622 | 20.130 | 8.457 | 1.00 | 26.69 | O |
| ATOM | 4446 | C | GLU | A | 80 | 17.038 | 17.953 | 5.817 | 1.00 | 18.98 | C |
| ATOM | 4447 | O | GLU | A | 80 | 16.826 | 16.974 | 5.126 | 1.00 | 19.55 | O |

FIG.5-12

| | | | | | | | | | | | |
|---|---|---|---|---|---|---|---|---|---|---|---|
| ATOM | 4449 | N | GLY | A | 81 | 17.961 | 18.865 | 5.521 | 1.00 | 21.49 | N |
| ATOM | 4450 | CA | GLY | A | 81 | 18.735 | 18.863 | 4.276 | 1.00 | 20.61 | C |
| ATOM | 4453 | C | GLY | A | 81 | 18.147 | 19.780 | 3.223 | 1.00 | 21.59 | C |
| ATOM | 4454 | O | GLY | A | 81 | 18.865 | 20.256 | 2.335 | 1.00 | 20.89 | O |
| ATOM | 4456 | N | ARG | A | 82 | 16.841 | 20.039 | 3.318 | 1.00 | 21.56 | N |
| ATOM | 4457 | CA | ARG | A | 82 | 16.174 | 20.983 | 2.435 | 1.00 | 22.08 | C |
| ATOM | 4459 | CB | ARG | A | 82 | 14.643 | 20.698 | 2.362 | 1.00 | 22.60 | C |
| ATOM | 4462 | CG | ARG | A | 82 | 14.384 | 19.272 | 1.930 | 1.00 | 21.62 | C |
| ATOM | 4465 | CD | ARG | A | 82 | 13.003 | 18.619 | 2.219 | 1.00 | 31.85 | C |
| ATOM | 4468 | NE | ARG | A | 82 | 12.520 | 18.520 | 0.905 | 1.00 | 35.87 | N |
| ATOM | 4470 | CZ | ARG | A | 82 | 12.224 | 17.517 | 0.130 | 1.00 | 27.09 | C |
| ATOM | 4471 | NH1 | ARG | A | 82 | 11.988 | 16.259 | 0.455 | 1.00 | 27.90 | N |
| ATOM | 4474 | NH2 | ARG | A | 82 | 12.075 | 17.918 | -1.087 | 1.00 | 29.02 | N |
| ATOM | 4477 | C | ARG | A | 82 | 16.454 | 22.385 | 2.890 | 1.00 | 21.61 | C |
| ATOM | 4478 | O | ARG | A | 82 | 16.526 | 22.619 | 4.030 | 1.00 | 21.64 | O |
| ATOM | 4480 | N | ASP | A | 83 | 16.529 | 23.362 | 1.993 | 1.00 | 23.18 | N |
| ATOM | 4481 | CA | ASP | A | 83 | 16.443 | 24.742 | 2.466 | 1.00 | 24.33 | C |
| ATOM | 4483 | CB | ASP | A | 83 | 16.859 | 25.761 | 1.367 | 1.00 | 25.29 | C |
| ATOM | 4486 | CG | ASP | A | 83 | 15.830 | 25.943 | 0.262 | 1.00 | 29.71 | C |
| ATOM | 4487 | OD1 | ASP | A | 83 | 14.707 | 25.406 | 0.276 | 1.00 | 33.99 | O |
| ATOM | 4488 | OD2 | ASP | A | 83 | 16.167 | 26.685 | -0.640 | 1.00 | 39.38 | O |
| ATOM | 4489 | C | ASP | A | 83 | 15.048 | 25.062 | 3.081 | 1.00 | 23.94 | C |
| ATOM | 4490 | O | ASP | A | 83 | 14.131 | 24.238 | 3.020 | 1.00 | 22.18 | O |
| ATOM | 4492 | N | ARG | A | 84 | 14.921 | 26.239 | 3.678 | 1.00 | 23.12 | N |
| ATOM | 4493 | CA | ARG | A | 84 | 13.766 | 26.490 | 4.515 | 1.00 | 23.78 | C |
| ATOM | 4495 | CB | ARG | A | 84 | 13.879 | 27.780 | 5.304 | 1.00 | 23.86 | C |
| ATOM | 4498 | CG | ARG | A | 84 | 14.665 | 27.726 | 6.571 | 1.00 | 25.58 | C |
| ATOM | 4501 | CD | ARG | A | 84 | 14.592 | 29.049 | 7.254 | 1.00 | 25.51 | C |
| ATOM | 4504 | NE | ARG | A | 84 | 15.303 | 29.032 | 8.540 | 1.00 | 30.29 | N |
| ATOM | 4506 | CZ | ARG | A | 84 | 16.408 | 29.722 | 8.799 | 1.00 | 32.03 | C |
| ATOM | 4507 | NH1 | ARG | A | 84 | 16.949 | 30.502 | 7.870 | 1.00 | 31.92 | N |
| ATOM | 4510 | NH2 | ARG | A | 84 | 16.991 | 29.639 | 9.994 | 1.00 | 35.49 | N |
| ATOM | 4513 | C | ARG | A | 84 | 12.546 | 26.540 | 3.617 | 1.00 | 24.57 | C |
| ATOM | 4514 | O | ARG | A | 84 | 11.480 | 26.093 | 4.009 | 1.00 | 24.75 | O |
| ATOM | 4516 | N | ILE | A | 85 | 12.706 | 27.115 | 2.433 | 1.00 | 23.26 | N |
| ATOM | 4517 | CA | ILE | A | 85 | 11.607 | 27.261 | 1.537 | 1.00 | 23.31 | C |
| ATOM | 4519 | CB | ILE | A | 85 | 11.979 | 28.167 | 0.400 | 1.00 | 24.01 | C |
| ATOM | 4521 | CG1 | ILE | A | 85 | 12.224 | 29.574 | 0.954 | 1.00 | 25.10 | C |
| ATOM | 4524 | CD1 | ILE | A | 85 | 13.111 | 30.416 | -0.093 | 1.00 | 33.55 | C |
| ATOM | 4528 | CG2 | ILE | A | 85 | 10.892 | 28.156 | -0.692 | 1.00 | 23.45 | C |
| ATOM | 4532 | C | ILE | A | 85 | 11.032 | 25.951 | 1.080 | 1.00 | 23.83 | C |
| ATOM | 4533 | O | ILE | A | 85 | 9.799 | 25.728 | 1.232 | 1.00 | 23.01 | O |
| ATOM | 4535 | N | MET | A | 86 | 11.880 | 25.047 | 0.594 | 1.00 | 23.70 | N |
| ATOM | 4536 | CA | MET | A | 86 | 11.453 | 23.706 | 0.240 | 1.00 | 24.04 | C |
| ATOM | 4538 | CB | MET | A | 86 | 12.552 | 22.913 | -0.480 | 1.00 | 25.61 | C |
| ATOM | 4541 | CG | MET | A | 86 | 12.822 | 23.410 | -1.922 | 1.00 | 29.68 | C |
| ATOM | 4544 | SD | MET | A | 86 | 11.329 | 23.275 | -2.901 | 1.00 | 38.30 | S |
| ATOM | 4545 | CE | MET | A | 86 | 11.932 | 24.152 | -4.366 | 1.00 | 44.18 | C |
| ATOM | 4549 | C | MET | A | 86 | 10.973 | 22.895 | 1.436 | 1.00 | 23.56 | C |
| ATOM | 4550 | O | MET | A | 86 | 9.939 | 22.184 | 1.343 | 1.00 | 22.21 | O |
| ATOM | 4552 | N | ALA | A | 87 | 11.647 | 23.030 | 2.569 | 1.00 | 20.43 | N |
| ATOM | 4553 | CA | ALA | A | 87 | 11.207 | 22.367 | 3.790 | 1.00 | 20.21 | C |
| ATOM | 4555 | CB | ALA | A | 87 | 12.126 | 22.651 | 4.934 | 1.00 | 19.24 | C |
| ATOM | 4559 | C | ALA | A | 87 | 9.730 | 22.784 | 4.199 | 1.00 | 19.78 | C |
| ATOM | 4560 | O | ALA | A | 87 | 8.900 | 21.935 | 4.518 | 1.00 | 18.95 | O |
| ATOM | 4562 | N | TRP | A | 88 | 9.447 | 24.054 | 4.200 | 1.00 | 20.65 | N |
| ATOM | 4563 | CA | TRP | A | 88 | 8.053 | 24.500 | 4.559 | 1.00 | 21.04 | C |
| ATOM | 4565 | CB | TRP | A | 88 | 8.023 | 25.960 | 4.796 | 1.00 | 21.58 | C |
| ATOM | 4568 | CG | TRP | A | 88 | 8.508 | 26.312 | 6.146 | 1.00 | 18.17 | C |
| ATOM | 4569 | CD1 | TRP | A | 88 | 9.592 | 27.069 | 6.449 | 1.00 | 20.94 | C |
| ATOM | 4571 | NE1 | TRP | A | 88 | 9.730 | 27.182 | 7.781 | 1.00 | 24.67 | N |
| ATOM | 4573 | CE2 | TRP | A | 88 | 8.689 | 26.540 | 8.395 | 1.00 | 23.58 | C |
| ATOM | 4574 | CD2 | TRP | A | 88 | 7.883 | 25.997 | 7.378 | 1.00 | 18.52 | C |

FIG.5-13

| | | | | | | | | | | | |
|---|---|---|---|---|---|---|---|---|---|---|---|
| ATOM | 4575 | CE3 | TRP | A | 88 | 6.746 | 25.251 | 7.733 | 1.00 | 20.25 | C |
| ATOM | 4577 | CZ3 | TRP | A | 88 | 6.448 | 25.093 | 9.039 | 1.00 | 22.47 | C |
| ATOM | 4579 | CH2 | TRP | A | 88 | 7.274 | 25.653 | 10.060 | 1.00 | 26.37 | C |
| ATOM | 4581 | CZ2 | TRP | A | 88 | 8.402 | 26.373 | 9.750 | 1.00 | 26.62 | C |
| ATOM | 4583 | C | TRP | A | 88 | 7.069 | 24.096 | 3.498 | 1.00 | 21.67 | C |
| ATOM | 4584 | O | TRP | A | 88 | 5.957 | 23.688 | 3.812 | 1.00 | 22.18 | O |
| ATOM | 4586 | N | THR | A | 89 | 7.535 | 24.024 | 2.254 | 1.00 | 21.88 | N |
| ATOM | 4587 | CA | THR | A | 89 | 6.691 | 23.547 | 1.176 | 1.00 | 22.15 | C |
| ATOM | 4589 | CB | THR | A | 89 | 7.405 | 23.610 | -0.167 | 1.00 | 21.30 | C |
| ATOM | 4591 | OG1 | THR | A | 89 | 7.803 | 24.932 | -0.361 | 1.00 | 21.89 | O |
| ATOM | 4593 | CG2 | THR | A | 89 | 6.491 | 23.236 | -1.421 | 1.00 | 25.31 | C |
| ATOM | 4597 | C | THR | A | 89 | 6.247 | 22.158 | 1.508 | 1.00 | 22.56 | C |
| ATOM | 4598 | O | THR | A | 89 | 5.039 | 21.808 | 1.356 | 1.00 | 19.63 | O |
| ATOM | 4600 | N | VAL | A | 90 | 7.219 | 21.327 | 1.925 | 1.00 | 22.06 | N |
| ATOM | 4601 | CA | VAL | A | 90 | 6.956 | 19.943 | 2.169 | 1.00 | 22.93 | C |
| ATOM | 4603 | CB | VAL | A | 90 | 8.279 | 19.123 | 2.270 | 1.00 | 24.11 | C |
| ATOM | 4605 | CG1 | VAL | A | 90 | 8.045 | 17.790 | 2.870 | 1.00 | 25.20 | C |
| ATOM | 4609 | CG2 | VAL | A | 90 | 8.902 | 18.931 | 0.886 | 1.00 | 27.88 | C |
| ATOM | 4613 | C | VAL | A | 90 | 6.080 | 19.790 | 3.427 | 1.00 | 21.81 | C |
| ATOM | 4614 | O | VAL | A | 90 | 5.127 | 19.031 | 3.408 | 1.00 | 20.95 | O |
| ATOM | 4616 | N | VAL | A | 91 | 6.400 | 20.533 | 4.486 | 1.00 | 20.25 | N |
| ATOM | 4617 | CA | VAL | A | 91 | 5.663 | 20.469 | 5.719 | 1.00 | 19.92 | C |
| ATOM | 4619 | CB | VAL | A | 91 | 6.315 | 21.321 | 6.791 | 1.00 | 20.85 | C |
| ATOM | 4621 | CG1 | VAL | A | 91 | 5.403 | 21.463 | 8.018 | 1.00 | 17.94 | C |
| ATOM | 4625 | CG2 | VAL | A | 91 | 7.751 | 20.664 | 7.174 | 1.00 | 20.42 | C |
| ATOM | 4629 | C | VAL | A | 91 | 4.193 | 20.917 | 5.464 | 1.00 | 20.56 | C |
| ATOM | 4630 | O | VAL | A | 91 | 3.262 | 20.259 | 5.914 | 1.00 | 19.15 | O |
| ATOM | 4632 | N | ASN | A | 92 | 4.029 | 21.980 | 4.706 | 1.00 | 21.42 | N |
| ATOM | 4633 | CA | ASN | A | 92 | 2.711 | 22.489 | 4.435 | 1.00 | 23.06 | C |
| ATOM | 4635 | CB | ASN | A | 92 | 2.824 | 23.766 | 3.639 | 1.00 | 23.94 | C |
| ATOM | 4638 | CG | ASN | A | 92 | 3.210 | 24.892 | 4.454 | 1.00 | 25.31 | C |
| ATOM | 4639 | OD1 | ASN | A | 92 | 3.365 | 24.790 | 5.696 | 1.00 | 26.26 | O |
| ATOM | 4640 | ND2 | ASN | A | 92 | 3.312 | 26.060 | 3.795 | 1.00 | 31.85 | N |
| ATOM | 4643 | C | ASN | A | 92 | 1.864 | 21.506 | 3.694 | 1.00 | 23.30 | C |
| ATOM | 4644 | O | ASN | A | 92 | 0.733 | 21.255 | 4.085 | 1.00 | 23.77 | O |
| ATOM | 4646 | N | SER | A | 93 | 2.439 | 20.884 | 2.672 | 1.00 | 23.36 | N |
| ATOM | 4647 | CA | SER | A | 93 | 1.746 | 19.906 | 1.866 | 1.00 | 23.47 | C |
| ATOM | 4649 | CB | SER | A | 93 | 2.687 | 19.507 | 0.737 | 1.00 | 23.42 | C |
| ATOM | 4652 | OG | SER | A | 93 | 2.219 | 18.458 | -0.044 | 1.00 | 26.35 | O |
| ATOM | 4654 | C | SER | A | 93 | 1.285 | 18.677 | 2.697 | 1.00 | 25.02 | C |
| ATOM | 4655 | O | SER | A | 93 | 0.131 | 18.189 | 2.604 | 1.00 | 22.83 | O |
| ATOM | 4657 | N | ILE | A | 94 | 2.179 | 18.198 | 3.559 | 1.00 | 24.78 | N |
| ATOM | 4658 | CA | ILE | A | 94 | 1.880 | 17.107 | 4.421 | 1.00 | 23.76 | C |
| ATOM | 4660 | CB | ILE | A | 94 | 3.130 | 16.675 | 5.220 | 1.00 | 24.01 | C |
| ATOM | 4662 | CG1 | ILE | A | 94 | 4.079 | 15.862 | 4.356 | 1.00 | 24.64 | C |
| ATOM | 4665 | CD1 | ILE | A | 94 | 5.475 | 15.728 | 5.021 | 1.00 | 21.78 | C |
| ATOM | 4669 | CG2 | ILE | A | 94 | 2.731 | 15.884 | 6.456 | 1.00 | 20.87 | C |
| ATOM | 4673 | C | ILE | A | 94 | 0.737 | 17.460 | 5.426 | 1.00 | 24.70 | C |
| ATOM | 4674 | O | ILE | A | 94 | -0.172 | 16.623 | 5.618 | 1.00 | 24.12 | O |
| ATOM | 4676 | N | CYS | A | 95 | 0.819 | 18.629 | 6.074 | 1.00 | 22.49 | N |
| ATOM | 4677 | CA | CYS | A | 95 | -0.214 | 19.057 | 6.999 | 1.00 | 24.70 | C |
| ATOM | 4679 | CB | CYS | A | 95 | 0.165 | 20.366 | 7.692 | 1.00 | 23.51 | C |
| ATOM | 4682 | SG | CYS | A | 95 | 1.627 | 20.123 | 8.837 | 1.00 | 26.20 | S |
| ATOM | 4684 | C | CYS | A | 95 | -1.584 | 19.178 | 6.317 | 1.00 | 25.37 | C |
| ATOM | 4685 | O | CYS | A | 95 | -2.582 | 18.683 | 6.860 | 1.00 | 27.30 | O |
| ATOM | 4687 | N | ASN | A | 96 | -1.589 | 19.743 | 5.115 | 1.00 | 25.91 | N |
| ATOM | 4688 | CA | ASN | A | 96 | -2.819 | 19.958 | 4.350 | 1.00 | 27.86 | C |
| ATOM | 4690 | CB | ASN | A | 96 | -2.520 | 20.768 | 3.075 | 1.00 | 27.67 | C |
| ATOM | 4693 | CG | ASN | A | 96 | -2.179 | 22.197 | 3.357 | 1.00 | 31.54 | C |
| ATOM | 4694 | OD1 | ASN | A | 96 | -2.443 | 22.722 | 4.457 | 1.00 | 36.77 | O |
| ATOM | 4695 | ND2 | ASN | A | 96 | -1.603 | 22.877 | 2.341 | 1.00 | 32.47 | N |
| ATOM | 4698 | C | ASN | A | 96 | -3.476 | 18.633 | 4.003 | 1.00 | 28.53 | C |
| ATOM | 4699 | O | ASN | A | 96 | -4.684 | 18.421 | 4.140 | 1.00 | 26.67 | O |

FIG.5-14

| | | | | | | | | | | | |
|---|---|---|---|---|---|---|---|---|---|---|---|
| ATOM | 4701 | N | THR | A | 97 | -2.625 | 17.725 | 3.578 | 1.00 | 29.23 | N |
| ATOM | 4702 | CA | THR | A | 97 | -2.958 | 16.414 | 3.104 | 1.00 | 31.24 | C |
| ATOM | 4704 | CB | THR | A | 97 | -1.773 | 16.031 | 2.220 | 1.00 | 32.02 | C |
| ATOM | 4706 | OG1 | THR | A | 97 | -1.988 | 16.668 | 0.933 | 1.00 | 38.24 | O |
| ATOM | 4708 | CG2 | THR | A | 97 | -1.551 | 14.653 | 2.113 | 1.00 | 33.72 | C |
| ATOM | 4712 | C | THR | A | 97 | -3.277 | 15.324 | 4.165 | 1.00 | 31.50 | C |
| ATOM | 4713 | O | THR | A | 97 | -4.028 | 14.426 | 3.876 | 1.00 | 31.45 | O |
| ATOM | 4715 | N | THR | A | 98 | -2.746 | 15.425 | 5.380 | 1.00 | 30.49 | N |
| ATOM | 4716 | CA | THR | A | 98 | -2.925 | 14.408 | 6.412 | 1.00 | 30.11 | C |
| ATOM | 4718 | CB | THR | A | 98 | -1.563 | 13.981 | 7.029 | 1.00 | 29.99 | C |
| ATOM | 4720 | OG1 | THR | A | 98 | -0.999 | 15.135 | 7.642 | 1.00 | 25.52 | O |
| ATOM | 4722 | CG2 | THR | A | 98 | -0.642 | 13.365 | 5.996 | 1.00 | 29.30 | C |
| ATOM | 4726 | C | THR | A | 98 | -3.737 | 14.879 | 7.583 | 1.00 | 31.24 | C |
| ATOM | 4727 | O | THR | A | 98 | -4.207 | 14.054 | 8.359 | 1.00 | 31.90 | O |
| ATOM | 4729 | N | GLY | A | 99 | -3.864 | 16.186 | 7.741 | 1.00 | 32.43 | N |
| ATOM | 4730 | CA | GLY | A | 99 | -4.546 | 16.782 | 8.879 | 1.00 | 33.28 | C |
| ATOM | 4733 | C | GLY | A | 99 | -3.662 | 16.923 | 10.121 | 1.00 | 33.98 | C |
| ATOM | 4734 | O | GLY | A | 99 | -4.112 | 17.455 | 11.117 | 1.00 | 35.59 | O |
| ATOM | 4736 | N | VAL | A | 100 | -2.413 | 16.455 | 10.095 | 1.00 | 33.92 | N |
| ATOM | 4737 | CA | VAL | A | 100 | -1.538 | 16.717 | 11.259 | 1.00 | 33.90 | C |
| ATOM | 4739 | CB | VAL | A | 100 | -0.118 | 16.037 | 11.163 | 1.00 | 33.99 | C |
| ATOM | 4741 | CG1 | VAL | A | 100 | -0.297 | 14.580 | 11.342 | 1.00 | 33.72 | C |
| ATOM | 4745 | CG2 | VAL | A | 100 | 0.618 | 16.372 | 9.801 | 1.00 | 32.56 | C |
| ATOM | 4749 | C | VAL | A | 100 | -1.357 | 18.182 | 11.504 | 1.00 | 33.22 | C |
| ATOM | 4750 | O | VAL | A | 100 | -1.251 | 18.974 | 10.596 | 1.00 | 32.99 | O |
| ATOM | 4752 | N | GLU | A | 101 | -1.331 | 18.510 | 12.776 | 1.00 | 34.14 | N |
| ATOM | 4753 | CA | GLU | A | 101 | -1.006 | 19.834 | 13.309 | 1.00 | 35.00 | C |
| ATOM | 4755 | CB | GLU | A | 101 | -0.882 | 19.699 | 14.859 | 1.00 | 36.13 | C |
| ATOM | 4758 | CG | GLU | A | 101 | -0.204 | 20.878 | 15.637 | 1.00 | 40.70 | C |
| ATOM | 4761 | CD | GLU | A | 101 | -0.190 | 20.628 | 17.154 | 1.00 | 48.59 | C |
| ATOM | 4762 | OE1 | GLU | A | 101 | -1.295 | 20.645 | 17.806 | 1.00 | 51.01 | O |
| ATOM | 4763 | OE2 | GLU | A | 101 | 0.928 | 20.390 | 17.694 | 1.00 | 53.90 | O |
| ATOM | 4764 | C | GLU | A | 101 | 0.293 | 20.398 | 12.716 | 1.00 | 33.10 | C |
| ATOM | 4765 | O | GLU | A | 101 | 1.286 | 19.684 | 12.550 | 1.00 | 32.12 | O |
| ATOM | 4767 | N | LYS | A | 102 | 0.261 | 21.665 | 12.351 | 1.00 | 32.11 | N |
| ATOM | 4768 | CA | LYS | A | 102 | 1.386 | 22.248 | 11.710 | 1.00 | 31.98 | C |
| ATOM | 4770 | CB | LYS | A | 102 | 0.959 | 23.431 | 10.909 | 1.00 | 32.96 | C |
| ATOM | 4773 | CG | LYS | A | 102 | 2.188 | 24.058 | 10.219 | 1.00 | 33.83 | C |
| ATOM | 4776 | CD | LYS | A | 102 | 1.787 | 25.023 | 9.206 | 1.00 | 36.21 | C |
| ATOM | 4779 | CE | LYS | A | 102 | 0.973 | 24.404 | 8.111 | 1.00 | 32.75 | C |
| ATOM | 4782 | NZ | LYS | A | 102 | 0.724 | 25.545 | 7.167 | 1.00 | 29.74 | N |
| ATOM | 4786 | C | LYS | A | 102 | 2.425 | 22.663 | 12.725 | 1.00 | 30.91 | C |
| ATOM | 4787 | O | LYS | A | 102 | 2.139 | 23.447 | 13.601 | 1.00 | 30.99 | O |
| ATOM | 4789 | N | PRO | A | 103 | 3.645 | 22.148 | 12.615 | 1.00 | 30.60 | N |
| ATOM | 4790 | CA | PRO | A | 103 | 4.657 | 22.542 | 13.633 | 1.00 | 30.96 | C |
| ATOM | 4792 | CB | PRO | A | 103 | 5.916 | 21.724 | 13.264 | 1.00 | 31.44 | C |
| ATOM | 4795 | CG | PRO | A | 103 | 5.696 | 21.202 | 11.868 | 1.00 | 31.26 | C |
| ATOM | 4798 | CD | PRO | A | 103 | 4.189 | 21.301 | 11.552 | 1.00 | 31.28 | C |
| ATOM | 4801 | C | PRO | A | 103 | 4.969 | 24.028 | 13.550 | 1.00 | 30.24 | C |
| ATOM | 4802 | O | PRO | A | 103 | 4.737 | 24.626 | 12.516 | 1.00 | 29.18 | O |
| ATOM | 4803 | N | LYS | A | 104 | 5.461 | 24.607 | 14.642 | 1.00 | 30.63 | N |
| ATOM | 4804 | CA | LYS | A | 104 | 5.923 | 26.017 | 14.646 | 1.00 | 31.79 | C |
| ATOM | 4806 | CB | LYS | A | 104 | 5.792 | 26.637 | 16.037 | 1.00 | 33.81 | C |
| ATOM | 4809 | CG | LYS | A | 104 | 4.372 | 26.720 | 16.545 | 1.00 | 38.65 | C |
| ATOM | 4812 | CD | LYS | A | 104 | 3.581 | 27.852 | 15.799 | 1.00 | 42.44 | C |
| ATOM | 4815 | CE | LYS | A | 104 | 2.159 | 27.987 | 16.401 | 1.00 | 46.56 | C |
| ATOM | 4818 | NZ | LYS | A | 104 | 2.184 | 28.941 | 17.582 | 1.00 | 47.58 | N |
| ATOM | 4822 | C | LYS | A | 104 | 7.385 | 26.136 | 14.192 | 1.00 | 30.83 | C |
| ATOM | 4823 | O | LYS | A | 104 | 7.790 | 27.188 | 13.734 | 1.00 | 29.36 | O |
| ATOM | 4825 | N | PHE | A | 105 | 8.144 | 25.040 | 14.272 | 1.00 | 29.59 | N |
| ATOM | 4826 | CA | PHE | A | 105 | 9.482 | 24.994 | 13.736 | 1.00 | 29.63 | C |
| ATOM | 4828 | CB | PHE | A | 105 | 10.501 | 24.953 | 14.899 | 1.00 | 31.16 | C |
| ATOM | 4831 | CG | PHE | A | 105 | 10.191 | 25.941 | 16.009 | 1.00 | 33.67 | C |

FIG.5-15

| | | | | | | | | | | | |
|---|---|---|---|---|---|---|---|---|---|---|---|
| ATOM | 4832 | CD1 | PHE | A | 105 | 10.709 | 27.232 | 15.972 | 1.00 | 37.41 | C |
| ATOM | 4834 | CE1 | PHE | A | 105 | 10.372 | 28.145 | 16.966 | 1.00 | 38.82 | C |
| ATOM | 4836 | CZ | PHE | A | 105 | 9.495 | 27.770 | 18.002 | 1.00 | 36.70 | C |
| ATOM | 4838 | CE2 | PHE | A | 105 | 8.965 | 26.517 | 18.026 | 1.00 | 36.76 | C |
| ATOM | 4840 | CD2 | PHE | A | 105 | 9.304 | 25.601 | 17.039 | 1.00 | 34.31 | C |
| ATOM | 4842 | C | PHE | A | 105 | 9.636 | 23.750 | 12.843 | 1.00 | 27.42 | C |
| ATOM | 4843 | O | PHE | A | 105 | 8.995 | 22.711 | 13.063 | 1.00 | 29.07 | O |
| ATOM | 4845 | N | LEU | A | 106 | 10.543 | 23.855 | 11.909 | 1.00 | 25.19 | N |
| ATOM | 4846 | CA | LEU | A | 106 | 10.824 | 22.816 | 10.977 | 1.00 | 25.00 | C |
| ATOM | 4848 | CB | LEU | A | 106 | 11.827 | 23.279 | 9.936 | 1.00 | 25.27 | C |
| ATOM | 4851 | CG | LEU | A | 106 | 11.338 | 24.314 | 8.903 | 1.00 | 24.10 | C |
| ATOM | 4853 | CD1 | LEU | A | 106 | 12.616 | 24.876 | 8.179 | 1.00 | 22.92 | C |
| ATOM | 4857 | CD2 | LEU | A | 106 | 10.362 | 23.685 | 7.888 | 1.00 | 20.32 | C |
| ATOM | 4861 | C | LEU | A | 106 | 11.361 | 21.596 | 11.725 | 1.00 | 24.06 | C |
| ATOM | 4862 | O | LEU | A | 106 | 12.305 | 21.692 | 12.484 | 1.00 | 23.08 | O |
| ATOM | 4864 | N | PRO | A | 107 | 10.719 | 20.441 | 11.524 | 1.00 | 23.01 | N |
| ATOM | 4865 | CA | PRO | A | 107 | 11.221 | 19.229 | 12.105 | 1.00 | 21.52 | C |
| ATOM | 4867 | CB | PRO | A | 107 | 9.976 | 18.354 | 12.238 | 1.00 | 21.18 | C |
| ATOM | 4870 | CG | PRO | A | 107 | 9.005 | 18.884 | 11.261 | 1.00 | 24.05 | C |
| ATOM | 4873 | CD | PRO | A | 107 | 9.438 | 20.241 | 10.824 | 1.00 | 23.47 | C |
| ATOM | 4876 | C | PRO | A | 107 | 12.160 | 18.624 | 11.123 | 1.00 | 20.29 | C |
| ATOM | 4877 | O | PRO | A | 107 | 12.350 | 19.163 | 10.011 | 1.00 | 19.85 | O |
| ATOM | 4878 | N | ASP | A | 108 | 12.616 | 17.430 | 11.450 | 1.00 | 19.68 | N |
| ATOM | 4879 | CA | ASP | A | 108 | 13.500 | 16.725 | 10.564 | 1.00 | 19.49 | C |
| ATOM | 4881 | CB | ASP | A | 108 | 14.489 | 16.014 | 11.446 | 1.00 | 19.69 | C |
| ATOM | 4884 | CG | ASP | A | 108 | 15.403 | 16.964 | 12.116 | 1.00 | 19.29 | C |
| ATOM | 4885 | OD1 | ASP | A | 108 | 15.795 | 18.026 | 11.495 | 1.00 | 18.08 | O |
| ATOM | 4886 | OD2 | ASP | A | 108 | 15.687 | 16.644 | 13.284 | 1.00 | 14.86 | O |
| ATOM | 4887 | C | ASP | A | 108 | 12.965 | 15.691 | 9.621 | 1.00 | 18.52 | C |
| ATOM | 4888 | O | ASP | A | 108 | 13.547 | 15.523 | 8.551 | 1.00 | 17.83 | O |
| ATOM | 4890 | N | LEU | A | 109 | 11.916 | 14.961 | 10.082 | 1.00 | 19.44 | N |
| ATOM | 4891 | CA | LEU | A | 109 | 11.272 | 13.891 | 9.386 | 1.00 | 18.77 | C |
| ATOM | 4893 | CB | LEU | A | 109 | 11.781 | 12.534 | 9.873 | 1.00 | 18.44 | C |
| ATOM | 4896 | CG | LEU | A | 109 | 13.263 | 12.120 | 9.679 | 1.00 | 17.95 | C |
| ATOM | 4898 | CD1 | LEU | A | 109 | 13.491 | 10.795 | 10.239 | 1.00 | 25.66 | C |
| ATOM | 4902 | CD2 | LEU | A | 109 | 13.695 | 12.110 | 8.230 | 1.00 | 14.62 | C |
| ATOM | 4906 | C | LEU | A | 109 | 9.753 | 13.971 | 9.602 | 1.00 | 18.72 | C |
| ATOM | 4907 | O | LEU | A | 109 | 9.298 | 14.650 | 10.518 | 1.00 | 18.75 | O |
| ATOM | 4909 | N | TYR | A | 110 | 9.031 | 13.346 | 8.690 | 1.00 | 19.56 | N |
| ATOM | 4910 | CA | TYR | A | 110 | 7.621 | 12.948 | 8.872 | 1.00 | 20.42 | C |
| ATOM | 4912 | CB | TYR | A | 110 | 6.705 | 13.767 | 7.964 | 1.00 | 21.85 | C |
| ATOM | 4915 | CG | TYR | A | 110 | 5.235 | 13.432 | 8.170 | 1.00 | 22.08 | C |
| ATOM | 4916 | CD1 | TYR | A | 110 | 4.529 | 13.962 | 9.272 | 1.00 | 23.99 | C |
| ATOM | 4918 | CE1 | TYR | A | 110 | 3.191 | 13.642 | 9.493 | 1.00 | 24.06 | C |
| ATOM | 4920 | CZ | TYR | A | 110 | 2.550 | 12.774 | 8.601 | 1.00 | 22.57 | C |
| ATOM | 4921 | OH | TYR | A | 110 | 1.234 | 12.512 | 8.805 | 1.00 | 25.86 | O |
| ATOM | 4923 | CE2 | TYR | A | 110 | 3.203 | 12.255 | 7.526 | 1.00 | 24.34 | C |
| ATOM | 4925 | CD2 | TYR | A | 110 | 4.587 | 12.576 | 7.316 | 1.00 | 17.59 | C |
| ATOM | 4927 | C | TYR | A | 110 | 7.435 | 11.452 | 8.629 | 1.00 | 21.88 | C |
| ATOM | 4928 | O | TYR | A | 110 | 7.881 | 10.892 | 7.643 | 1.00 | 24.70 | O |
| ATOM | 4930 | N | ASP | A | 111 | 6.771 | 10.823 | 9.571 | 1.00 | 22.57 | N |
| ATOM | 4931 | CA | ASP | A | 111 | 6.555 | 9.412 | 9.647 | 1.00 | 24.85 | C |
| ATOM | 4933 | CB | ASP | A | 111 | 6.730 | 8.999 | 11.109 | 1.00 | 22.59 | C |
| ATOM | 4936 | CG | ASP | A | 111 | 6.476 | 7.507 | 11.343 | 1.00 | 28.35 | C |
| ATOM | 4937 | OD1 | ASP | A | 111 | 5.940 | 6.820 | 10.436 | 1.00 | 29.11 | O |
| ATOM | 4938 | OD2 | ASP | A | 111 | 6.872 | 7.017 | 12.428 | 1.00 | 25.75 | O |
| ATOM | 4939 | C | ASP | A | 111 | 5.108 | 9.171 | 9.176 | 1.00 | 25.94 | C |
| ATOM | 4940 | O | ASP | A | 111 | 4.141 | 9.533 | 9.872 | 1.00 | 24.93 | O |
| ATOM | 4942 | N | TYR | A | 112 | 4.973 | 8.699 | 7.958 | 1.00 | 29.67 | N |
| ATOM | 4943 | CA | TYR | A | 112 | 3.642 | 8.476 | 7.400 | 1.00 | 32.79 | C |
| ATOM | 4945 | CB | TYR | A | 112 | 3.649 | 8.215 | 5.880 | 1.00 | 33.41 | C |
| ATOM | 4948 | CG | TYR | A | 112 | 3.973 | 9.441 | 5.010 | 1.00 | 33.52 | C |
| ATOM | 4949 | CD1 | TYR | A | 112 | 3.015 | 10.366 | 4.627 | 1.00 | 34.66 | C |

FIG.5-16

| | | | | | | | | | | | |
|---|---|---|---|---|---|---|---|---|---|---|---|
| ATOM | 4951 | CE1 | TYR | A | 112 | 3.373 | 11.469 | 3.804 | 1.00 | 34.31 | C |
| ATOM | 4953 | CZ | TYR | A | 112 | 4.717 | 11.591 | 3.438 | 1.00 | 36.36 | C |
| ATOM | 4954 | OH | TYR | A | 112 | 5.277 | 12.534 | 2.633 | 1.00 | 34.77 | O |
| ATOM | 4956 | CE2 | TYR | A | 112 | 5.614 | 10.664 | 3.838 | 1.00 | 36.92 | C |
| ATOM | 4958 | CD2 | TYR | A | 112 | 5.233 | 9.617 | 4.572 | 1.00 | 33.66 | C |
| ATOM | 4960 | C | TYR | A | 112 | 2.997 | 7.280 | 8.083 | 1.00 | 35.76 | C |
| ATOM | 4961 | O | TYR | A | 112 | 1.817 | 7.103 | 7.925 | 1.00 | 36.77 | O |
| ATOM | 4963 | N | LYS | A | 113 | 3.751 | 6.414 | 8.778 | 1.00 | 37.26 | N |
| ATOM | 4964 | CA | LYS | A | 113 | 3.103 | 5.277 | 9.437 | 1.00 | 38.17 | C |
| ATOM | 4966 | CB | LYS | A | 113 | 4.066 | 4.140 | 9.704 | 1.00 | 38.53 | C |
| ATOM | 4969 | CG | LYS | A | 113 | 3.447 | 2.932 | 10.408 | 1.00 | 41.42 | C |
| ATOM | 4972 | CD | LYS | A | 113 | 4.520 | 2.151 | 11.195 | 1.00 | 44.74 | C |
| ATOM | 4975 | CE | LYS | A | 113 | 3.970 | 0.799 | 11.740 | 1.00 | 48.17 | C |
| ATOM | 4978 | NZ | LYS | A | 113 | 3.745 | -0.277 | 10.637 | 1.00 | 46.49 | N |
| ATOM | 4982 | C | LYS | A | 113 | 2.469 | 5.769 | 10.707 | 1.00 | 38.53 | C |
| ATOM | 4983 | O | LYS | A | 113 | 1.315 | 5.465 | 10.998 | 1.00 | 40.27 | O |
| ATOM | 4985 | N | GLU | A | 114 | 3.184 | 6.568 | 11.471 | 1.00 | 37.48 | N |
| ATOM | 4986 | CA | GLU | A | 114 | 2.637 | 7.026 | 12.734 | 1.00 | 36.27 | C |
| ATOM | 4988 | CB | GLU | A | 114 | 3.759 | 7.201 | 13.732 | 1.00 | 36.48 | C |
| ATOM | 4991 | CG | GLU | A | 114 | 4.431 | 5.914 | 14.134 | 1.00 | 39.44 | C |
| ATOM | 4994 | CD | GLU | A | 114 | 3.696 | 5.136 | 15.241 | 1.00 | 43.74 | C |
| ATOM | 4995 | OE1 | GLU | A | 114 | 2.798 | 5.703 | 15.895 | 1.00 | 44.63 | O |
| ATOM | 4996 | OE2 | GLU | A | 114 | 4.043 | 3.945 | 15.446 | 1.00 | 47.49 | O |
| ATOM | 4997 | C | GLU | A | 114 | 1.867 | 8.316 | 12.578 | 1.00 | 34.69 | C |
| ATOM | 4998 | O | GLU | A | 114 | 1.199 | 8.758 | 13.478 | 1.00 | 33.45 | O |
| ATOM | 5000 | N | ASN | A | 115 | 1.982 | 8.929 | 11.414 | 1.00 | 34.33 | N |
| ATOM | 5001 | CA | ASN | A | 115 | 1.404 | 10.244 | 11.156 | 1.00 | 33.81 | C |
| ATOM | 5003 | CB | ASN | A | 115 | -0.107 | 10.163 | 10.908 | 1.00 | 35.90 | C |
| ATOM | 5006 | CG | ASN | A | 115 | -0.405 | 9.640 | 9.501 | 1.00 | 39.18 | C |
| ATOM | 5007 | OD1 | ASN | A | 115 | -0.881 | 8.528 | 9.395 | 1.00 | 42.57 | O |
| ATOM | 5008 | ND2 | ASN | A | 115 | -0.020 | 10.405 | 8.408 | 1.00 | 37.31 | N |
| ATOM | 5011 | C | ASN | A | 115 | 1.821 | 11.294 | 12.163 | 1.00 | 31.77 | C |
| ATOM | 5012 | O | ASN | A | 115 | 0.995 | 11.947 | 12.814 | 1.00 | 30.79 | O |
| ATOM | 5014 | N | ARG | A | 116 | 3.154 | 11.515 | 12.199 | 1.00 | 29.00 | N |
| ATOM | 5015 | CA | ARG | A | 116 | 3.729 | 12.517 | 13.060 | 1.00 | 26.39 | C |
| ATOM | 5017 | CB | ARG | A | 116 | 3.853 | 11.991 | 14.457 | 1.00 | 27.63 | C |
| ATOM | 5020 | CG | ARG | A | 116 | 4.810 | 10.866 | 14.648 | 1.00 | 28.83 | C |
| ATOM | 5023 | CD | ARG | A | 116 | 4.485 | 10.128 | 15.957 | 1.00 | 29.50 | C |
| ATOM | 5026 | NE | ARG | A | 116 | 5.452 | 9.033 | 16.179 | 1.00 | 31.02 | N |
| ATOM | 5028 | CZ | ARG | A | 116 | 5.386 | 8.136 | 17.181 | 1.00 | 33.08 | C |
| ATOM | 5029 | NH1 | ARG | A | 116 | 4.393 | 8.174 | 18.064 | 1.00 | 34.43 | N |
| ATOM | 5032 | NH2 | ARG | A | 116 | 6.335 | 7.195 | 17.322 | 1.00 | 29.98 | N |
| ATOM | 5035 | C | ARG | A | 116 | 5.085 | 12.974 | 12.582 | 1.00 | 24.57 | C |
| ATOM | 5036 | O | ARG | A | 116 | 5.819 | 12.227 | 11.942 | 1.00 | 22.78 | O |
| ATOM | 5038 | N | PHE | A | 117 | 5.385 | 14.218 | 12.898 | 1.00 | 22.64 | N |
| ATOM | 5039 | CA | PHE | A | 117 | 6.705 | 14.750 | 12.590 | 1.00 | 22.98 | C |
| ATOM | 5041 | CB | PHE | A | 117 | 6.659 | 16.257 | 12.563 | 1.00 | 21.78 | C |
| ATOM | 5044 | CG | PHE | A | 117 | 5.946 | 16.794 | 11.385 | 1.00 | 22.84 | C |
| ATOM | 5045 | CD1 | PHE | A | 117 | 6.548 | 16.822 | 10.186 | 1.00 | 20.76 | C |
| ATOM | 5047 | CE1 | PHE | A | 117 | 5.860 | 17.320 | 9.030 | 1.00 | 21.40 | C |
| ATOM | 5049 | CZ | PHE | A | 117 | 4.564 | 17.707 | 9.145 | 1.00 | 23.52 | C |
| ATOM | 5051 | CE2 | PHE | A | 117 | 3.927 | 17.649 | 10.412 | 1.00 | 22.69 | C |
| ATOM | 5053 | CD2 | PHE | A | 117 | 4.618 | 17.224 | 11.502 | 1.00 | 20.29 | C |
| ATOM | 5055 | C | PHE | A | 117 | 7.665 | 14.267 | 13.661 | 1.00 | 22.43 | C |
| ATOM | 5056 | O | PHE | A | 117 | 7.226 | 13.905 | 14.783 | 1.00 | 23.34 | O |
| ATOM | 5058 | N | ILE | A | 118 | 8.960 | 14.280 | 13.320 | 1.00 | 22.57 | N |
| ATOM | 5059 | CA | ILE | A | 118 | 10.012 | 13.863 | 14.258 | 1.00 | 21.68 | C |
| ATOM | 5061 | CB | ILE | A | 118 | 10.638 | 12.501 | 13.857 | 1.00 | 22.40 | C |
| ATOM | 5063 | CG1 | ILE | A | 118 | 9.600 | 11.453 | 13.660 | 1.00 | 24.98 | C |
| ATOM | 5066 | CD1 | ILE | A | 118 | 10.183 | 10.160 | 13.058 | 1.00 | 23.03 | C |
| ATOM | 5070 | CG2 | ILE | A | 118 | 11.684 | 12.014 | 14.939 | 1.00 | 21.73 | C |
| ATOM | 5074 | C | ILE | A | 118 | 11.096 | 14.882 | 14.188 | 1.00 | 20.97 | C |
| ATOM | 5075 | O | ILE | A | 118 | 11.529 | 15.308 | 13.074 | 1.00 | 20.64 | O |

FIG.5-17

| | | | | | | | | | | | |
|---|---|---|---|---|---|---|---|---|---|---|---|
| ATOM | 5077 | N | GLU | A | 119 | 11.562 | 15.230 | 15.386 | 1.00 | 20.99 | N |
| ATOM | 5078 | CA | GLU | A | 119 | 12.715 | 16.021 | 15.620 | 1.00 | 20.79 | C |
| ATOM | 5080 | CB | GLU | A | 119 | 12.433 | 17.127 | 16.674 | 1.00 | 20.86 | C |
| ATOM | 5083 | CG | GLU | A | 119 | 13.679 | 17.989 | 17.035 | 1.00 | 23.81 | C |
| ATOM | 5086 | CD | GLU | A | 119 | 14.379 | 18.631 | 15.829 | 1.00 | 28.19 | C |
| ATOM | 5087 | OE1 | GLU | A | 119 | 13.661 | 19.191 | 14.981 | 1.00 | 28.89 | O |
| ATOM | 5088 | OE2 | GLU | A | 119 | 15.637 | 18.571 | 15.732 | 1.00 | 31.88 | O |
| ATOM | 5089 | C | GLU | A | 119 | 13.807 | 15.104 | 16.131 | 1.00 | 21.33 | C |
| ATOM | 5090 | O | GLU | A | 119 | 13.647 | 14.420 | 17.143 | 1.00 | 22.44 | O |
| ATOM | 5092 | N | ILE | A | 120 | 14.901 | 15.049 | 15.379 | 1.00 | 21.35 | N |
| ATOM | 5093 | CA | ILE | A | 120 | 16.000 | 14.171 | 15.679 | 1.00 | 19.98 | C |
| ATOM | 5095 | CB | ILE | A | 120 | 16.636 | 13.623 | 14.409 | 1.00 | 21.39 | C |
| ATOM | 5097 | CG1 | ILE | A | 120 | 15.683 | 12.670 | 13.677 | 1.00 | 20.96 | C |
| ATOM | 5100 | CD1 | ILE | A | 120 | 15.279 | 11.486 | 14.397 | 1.00 | 26.55 | C |
| ATOM | 5104 | CG2 | ILE | A | 120 | 17.943 | 12.912 | 14.706 | 1.00 | 20.43 | C |
| ATOM | 5108 | C | ILE | A | 120 | 17.012 | 15.012 | 16.354 | 1.00 | 20.11 | C |
| ATOM | 5109 | O | ILE | A | 120 | 17.336 | 16.107 | 15.887 | 1.00 | 19.50 | O |
| ATOM | 5111 | N | GLY | A | 121 | 17.556 | 14.527 | 17.454 | 1.00 | 20.99 | N |
| ATOM | 5112 | CA | GLY | A | 121 | 18.675 | 15.210 | 18.076 | 1.00 | 20.91 | C |
| ATOM | 5115 | C | GLY | A | 121 | 19.884 | 14.315 | 18.144 | 1.00 | 20.94 | C |
| ATOM | 5116 | O | GLY | A | 121 | 19.739 | 13.120 | 18.384 | 1.00 | 20.56 | O |
| ATOM | 5118 | N | VAL | A | 122 | 21.074 | 14.880 | 17.934 | 1.00 | 21.69 | N |
| ATOM | 5119 | CA | VAL | A | 122 | 22.308 | 14.072 | 18.065 | 1.00 | 23.58 | C |
| ATOM | 5121 | CB | VAL | A | 122 | 23.055 | 13.779 | 16.772 | 1.00 | 25.29 | C |
| ATOM | 5123 | CG1 | VAL | A | 122 | 24.420 | 13.036 | 17.114 | 1.00 | 23.52 | C |
| ATOM | 5127 | CG2 | VAL | A | 122 | 22.312 | 12.875 | 15.858 | 1.00 | 22.13 | C |
| ATOM | 5131 | C | VAL | A | 122 | 23.236 | 14.871 | 19.017 | 1.00 | 23.55 | C |
| ATOM | 5132 | O | VAL | A | 122 | 23.485 | 16.010 | 18.792 | 1.00 | 22.71 | O |
| ATOM | 5134 | N | THR | A | 123 | 23.536 | 14.268 | 20.154 | 1.00 | 24.16 | N |
| ATOM | 5135 | CA | THR | A | 123 | 24.111 | 14.971 | 21.284 | 1.00 | 26.23 | C |
| ATOM | 5137 | CB | THR | A | 123 | 23.125 | 15.206 | 22.463 | 1.00 | 25.44 | C |
| ATOM | 5139 | OG1 | THR | A | 123 | 23.761 | 16.103 | 23.393 | 1.00 | 25.14 | O |
| ATOM | 5141 | CG2 | THR | A | 123 | 22.757 | 13.968 | 23.147 | 1.00 | 26.59 | C |
| ATOM | 5145 | C | THR | A | 123 | 25.359 | 14.317 | 21.863 | 1.00 | 27.75 | C |
| ATOM | 5146 | O | THR | A | 123 | 25.461 | 13.086 | 21.927 | 1.00 | 27.75 | O |
| ATOM | 5148 | N | ARG | A | 124 | 26.285 | 15.191 | 22.238 | 1.00 | 30.85 | N |
| ATOM | 5149 | CA | ARG | A | 124 | 27.501 | 14.861 | 22.983 | 1.00 | 32.89 | C |
| ATOM | 5151 | CB | ARG | A | 124 | 28.606 | 15.773 | 22.454 | 1.00 | 33.22 | C |
| ATOM | 5154 | CG | ARG | A | 124 | 28.831 | 15.761 | 20.939 | 1.00 | 35.45 | C |
| ATOM | 5157 | CD | ARG | A | 124 | 29.434 | 17.052 | 20.435 | 1.00 | 37.68 | C |
| ATOM | 5160 | NE | ARG | A | 124 | 28.434 | 17.724 | 19.671 | 1.00 | 38.87 | N |
| ATOM | 5162 | CZ | ARG | A | 124 | 28.509 | 18.929 | 19.134 | 1.00 | 37.32 | C |
| ATOM | 5163 | NH1 | ARG | A | 124 | 29.571 | 19.738 | 19.271 | 1.00 | 36.52 | N |
| ATOM | 5166 | NH2 | ARG | A | 124 | 27.455 | 19.316 | 18.457 | 1.00 | 34.67 | N |
| ATOM | 5169 | C | ARG | A | 124 | 27.324 | 15.188 | 24.485 | 1.00 | 34.45 | C |
| ATOM | 5170 | O | ARG | A | 124 | 28.273 | 15.086 | 25.231 | 1.00 | 35.66 | O |
| ATOM | 5172 | N | ARG | A | 125 | 26.178 | 15.752 | 24.870 | 1.00 | 35.36 | N |
| ATOM | 5173 | CA | ARG | A | 125 | 25.840 | 16.009 | 26.273 | 1.00 | 35.64 | C |
| ATOM | 5175 | CB | ARG | A | 125 | 25.160 | 17.381 | 26.433 | 1.00 | 35.56 | C |
| ATOM | 5178 | CG | ARG | A | 125 | 26.059 | 18.578 | 26.306 | 1.00 | 35.38 | C |
| ATOM | 5181 | CD | ARG | A | 125 | 25.271 | 19.859 | 26.363 | 1.00 | 37.73 | C |
| ATOM | 5184 | NE | ARG | A | 125 | 24.263 | 19.915 | 25.294 | 1.00 | 38.35 | N |
| ATOM | 5186 | CZ | ARG | A | 125 | 23.242 | 20.769 | 25.208 | 1.00 | 42.26 | C |
| ATOM | 5187 | NH1 | ARG | A | 125 | 23.032 | 21.704 | 26.127 | 1.00 | 42.33 | N |
| ATOM | 5190 | NH2 | ARG | A | 125 | 22.415 | 20.687 | 24.160 | 1.00 | 43.26 | N |
| ATOM | 5193 | C | ARG | A | 125 | 24.908 | 14.935 | 26.790 | 1.00 | 35.73 | C |
| ATOM | 5194 | O | ARG | A | 125 | 24.482 | 14.009 | 26.070 | 1.00 | 36.31 | O |
| ATOM | 5196 | N | GLU | A | 126 | 24.582 | 15.027 | 28.065 | 1.00 | 36.52 | N |
| ATOM | 5197 | CA | GLU | A | 126 | 23.645 | 14.080 | 28.655 | 1.00 | 36.81 | C |
| ATOM | 5199 | CB | GLU | A | 126 | 23.424 | 14.460 | 30.138 | 1.00 | 37.31 | C |
| ATOM | 5202 | CG | GLU | A | 126 | 23.034 | 13.241 | 30.999 | 1.00 | 39.80 | C |
| ATOM | 5205 | CD | GLU | A | 126 | 21.622 | 12.866 | 30.788 | 1.00 | 35.83 | C |
| ATOM | 5206 | OE1 | GLU | A | 126 | 20.868 | 13.816 | 30.553 | 1.00 | 41.69 | O |

FIG.5-18

| | | | | | | | | | | | |
|---|---|---|---|---|---|---|---|---|---|---|---|
| ATOM | 5207 | OE2 | GLU | A | 126 | 21.265 | 11.686 | 30.835 | 1.00 | 33.68 | O |
| ATOM | 5208 | C | GLU | A | 126 | 22.324 | 14.036 | 27.814 | 1.00 | 35.45 | C |
| ATOM | 5209 | O | GLU | A | 126 | 21.724 | 15.068 | 27.511 | 1.00 | 35.89 | O |
| ATOM | 5211 | N | VAL | A | 127 | 21.877 | 12.837 | 27.463 | 1.00 | 35.07 | N |
| ATOM | 5212 | CA | VAL | A | 127 | 20.745 | 12.630 | 26.561 | 1.00 | 33.41 | C |
| ATOM | 5214 | CB | VAL | A | 127 | 20.515 | 11.111 | 26.306 | 1.00 | 34.98 | C |
| ATOM | 5216 | CG1 | VAL | A | 127 | 19.572 | 10.410 | 27.370 | 1.00 | 30.93 | C |
| ATOM | 5220 | CG2 | VAL | A | 127 | 20.028 | 10.851 | 24.856 | 1.00 | 33.48 | C |
| ATOM | 5224 | C | VAL | A | 127 | 19.436 | 13.337 | 26.962 | 1.00 | 34.24 | C |
| ATOM | 5225 | O | VAL | A | 127 | 18.696 | 13.779 | 26.070 | 1.00 | 32.79 | O |
| ATOM | 5227 | N | HIS | A | 128 | 19.142 | 13.469 | 28.266 | 1.00 | 32.85 | N |
| ATOM | 5228 | CA | HIS | A | 128 | 17.899 | 14.203 | 28.675 | 1.00 | 33.05 | C |
| ATOM | 5230 | CB | HIS | A | 128 | 17.558 | 14.043 | 30.177 | 1.00 | 32.76 | C |
| ATOM | 5233 | CG | HIS | A | 128 | 17.185 | 12.655 | 30.563 | 1.00 | 31.31 | C |
| ATOM | 5234 | ND1 | HIS | A | 128 | 18.122 | 11.702 | 30.874 | 1.00 | 36.05 | N |
| ATOM | 5236 | CE1 | HIS | A | 128 | 17.510 | 10.567 | 31.143 | 1.00 | 37.04 | C |
| ATOM | 5238 | NE2 | HIS | A | 128 | 16.208 | 10.756 | 31.022 | 1.00 | 35.99 | N |
| ATOM | 5240 | CD2 | HIS | A | 128 | 15.984 | 12.045 | 30.628 | 1.00 | 35.98 | C |
| ATOM | 5242 | C | HIS | A | 128 | 17.974 | 15.689 | 28.375 | 1.00 | 32.21 | C |
| ATOM | 5243 | O | HIS | A | 128 | 16.969 | 16.273 | 28.175 | 1.00 | 32.13 | O |
| ATOM | 5245 | N | ILE | A | 129 | 19.163 | 16.279 | 28.352 | 1.00 | 32.38 | N |
| ATOM | 5246 | CA | ILE | A | 129 | 19.314 | 17.721 | 28.164 | 1.00 | 33.03 | C |
| ATOM | 5248 | CB | ILE | A | 129 | 20.796 | 18.156 | 28.389 | 1.00 | 34.00 | C |
| ATOM | 5250 | CG1 | ILE | A | 129 | 21.149 | 18.025 | 29.884 | 1.00 | 33.95 | C |
| ATOM | 5253 | CD1 | ILE | A | 129 | 22.553 | 18.290 | 30.237 | 1.00 | 34.74 | C |
| ATOM | 5257 | CG2 | ILE | A | 129 | 21.100 | 19.562 | 27.866 | 1.00 | 32.34 | C |
| ATOM | 5261 | C | ILE | A | 129 | 18.798 | 18.161 | 26.802 | 1.00 | 33.61 | C |
| ATOM | 5262 | O | ILE | A | 129 | 17.950 | 19.077 | 26.675 | 1.00 | 34.12 | O |
| ATOM | 5264 | N | TYR | A | 130 | 19.220 | 17.455 | 25.771 | 1.00 | 32.85 | N |
| ATOM | 5265 | CA | TYR | A | 130 | 18.885 | 17.883 | 24.457 | 1.00 | 32.65 | C |
| ATOM | 5267 | CB | TYR | A | 130 | 19.769 | 17.159 | 23.431 | 1.00 | 34.68 | C |
| ATOM | 5270 | CG | TYR | A | 130 | 19.979 | 17.920 | 22.150 | 1.00 | 37.22 | C |
| ATOM | 5271 | CD1 | TYR | A | 130 | 20.188 | 19.300 | 22.136 | 1.00 | 44.34 | C |
| ATOM | 5273 | CE1 | TYR | A | 130 | 20.382 | 19.981 | 20.918 | 1.00 | 46.32 | C |
| ATOM | 5275 | CZ | TYR | A | 130 | 20.373 | 19.237 | 19.717 | 1.00 | 43.87 | C |
| ATOM | 5276 | OH | TYR | A | 130 | 20.526 | 19.808 | 18.456 | 1.00 | 44.04 | O |
| ATOM | 5278 | CE2 | TYR | A | 130 | 20.184 | 17.922 | 19.764 | 1.00 | 42.09 | C |
| ATOM | 5280 | CD2 | TYR | A | 130 | 19.976 | 17.269 | 20.960 | 1.00 | 41.85 | C |
| ATOM | 5282 | C | TYR | A | 130 | 17.414 | 17.620 | 24.242 | 1.00 | 31.94 | C |
| ATOM | 5283 | O | TYR | A | 130 | 16.733 | 18.382 | 23.535 | 1.00 | 28.25 | O |
| ATOM | 5285 | N | TYR | A | 131 | 16.913 | 16.588 | 24.942 | 1.00 | 30.99 | N |
| ATOM | 5286 | CA | TYR | A | 131 | 15.552 | 16.181 | 24.782 | 1.00 | 31.03 | C |
| ATOM | 5288 | CB | TYR | A | 131 | 15.210 | 14.896 | 25.581 | 1.00 | 30.32 | C |
| ATOM | 5291 | CG | TYR | A | 131 | 13.724 | 14.596 | 25.493 | 1.00 | 30.23 | C |
| ATOM | 5292 | CD1 | TYR | A | 131 | 13.237 | 13.728 | 24.542 | 1.00 | 30.44 | C |
| ATOM | 5294 | CE1 | TYR | A | 131 | 11.914 | 13.511 | 24.390 | 1.00 | 35.11 | C |
| ATOM | 5296 | CZ | TYR | A | 131 | 10.999 | 14.141 | 25.202 | 1.00 | 37.00 | C |
| ATOM | 5297 | OH | TYR | A | 131 | 9.662 | 13.845 | 25.026 | 1.00 | 42.43 | O |
| ATOM | 5299 | CE2 | TYR | A | 131 | 11.424 | 15.008 | 26.175 | 1.00 | 32.98 | C |
| ATOM | 5301 | CD2 | TYR | A | 131 | 12.794 | 15.241 | 26.315 | 1.00 | 34.17 | C |
| ATOM | 5303 | C | TYR | A | 131 | 14.747 | 17.354 | 25.292 | 1.00 | 30.93 | C |
| ATOM | 5304 | O | TYR | A | 131 | 13.775 | 17.730 | 24.714 | 1.00 | 31.34 | O |
| ATOM | 5306 | N | LEU | A | 132 | 15.197 | 17.935 | 26.395 | 1.00 | 32.82 | N |
| ATOM | 5307 | CA | LEU | A | 132 | 14.443 | 18.962 | 27.097 | 1.00 | 32.46 | C |
| ATOM | 5309 | CB | LEU | A | 132 | 14.950 | 19.076 | 28.544 | 1.00 | 32.00 | C |
| ATOM | 5312 | CG | LEU | A | 132 | 14.423 | 18.024 | 29.520 | 1.00 | 31.87 | C |
| ATOM | 5314 | CD1 | LEU | A | 132 | 15.403 | 17.900 | 30.669 | 1.00 | 27.92 | C |
| ATOM | 5318 | CD2 | LEU | A | 132 | 12.966 | 18.327 | 30.013 | 1.00 | 31.96 | C |
| ATOM | 5322 | C | LEU | A | 132 | 14.516 | 20.314 | 26.388 | 1.00 | 33.12 | C |
| ATOM | 5323 | O | LEU | A | 132 | 13.491 | 21.014 | 26.271 | 1.00 | 32.87 | O |
| ATOM | 5325 | N | GLU | A | 133 | 15.691 | 20.675 | 25.880 | 1.00 | 34.26 | N |
| ATOM | 5326 | CA | GLU | A | 133 | 15.813 | 21.873 | 24.990 | 1.00 | 35.13 | C |
| ATOM | 5328 | CB | GLU | A | 133 | 17.220 | 22.011 | 24.434 | 1.00 | 35.77 | C |

FIG.5-19

| | | | | | | | | | | | |
|---|---|---|---|---|---|---|---|---|---|---|---|
| ATOM | 5331 | CG | GLU | A | 133 | 18.329 | 22.032 | 25.512 | 1.00 | 38.71 | C |
| ATOM | 5334 | CD | GLU | A | 133 | 19.701 | 22.450 | 24.973 | 1.00 | 42.35 | C |
| ATOM | 5335 | OE1 | GLU | A | 133 | 20.114 | 22.044 | 23.851 | 1.00 | 46.63 | O |
| ATOM | 5336 | OE2 | GLU | A | 133 | 20.396 | 23.179 | 25.689 | 1.00 | 41.91 | O |
| ATOM | 5337 | C | GLU | A | 133 | 14.853 | 21.791 | 23.796 | 1.00 | 35.24 | C |
| ATOM | 5338 | O | GLU | A | 133 | 14.162 | 22.736 | 23.477 | 1.00 | 34.78 | O |
| ATOM | 5340 | N | LYS | A | 134 | 14.811 | 20.633 | 23.150 | 1.00 | 36.33 | N |
| ATOM | 5341 | CA | LYS | A | 134 | 13.904 | 20.433 | 22.050 | 1.00 | 36.65 | C |
| ATOM | 5343 | CB | LYS | A | 134 | 14.105 | 19.081 | 21.371 | 1.00 | 37.06 | C |
| ATOM | 5346 | CG | LYS | A | 134 | 15.492 | 18.851 | 20.740 | 1.00 | 38.38 | C |
| ATOM | 5349 | CD | LYS | A | 134 | 15.709 | 19.662 | 19.463 | 1.00 | 38.57 | C |
| ATOM | 5352 | CE | LYS | A | 134 | 17.012 | 19.227 | 18.717 | 1.00 | 36.39 | C |
| ATOM | 5355 | NZ | LYS | A | 134 | 17.241 | 20.091 | 17.562 | 1.00 | 34.31 | N |
| ATOM | 5359 | C | LYS | A | 134 | 12.491 | 20.533 | 22.543 | 1.00 | 37.39 | C |
| ATOM | 5360 | O | LYS | A | 134 | 11.732 | 21.289 | 21.960 | 1.00 | 37.59 | O |
| ATOM | 5362 | N | ALA | A | 135 | 12.130 | 19.775 | 23.594 | 1.00 | 37.71 | N |
| ATOM | 5363 | CA | ALA | A | 135 | 10.733 | 19.804 | 24.080 | 1.00 | 39.89 | C |
| ATOM | 5365 | CB | ALA | A | 135 | 10.451 | 18.788 | 25.239 | 1.00 | 38.29 | C |
| ATOM | 5369 | C | ALA | A | 135 | 10.374 | 21.194 | 24.538 | 1.00 | 41.41 | C |
| ATOM | 5370 | O | ALA | A | 135 | 9.273 | 21.627 | 24.347 | 1.00 | 41.30 | O |
| ATOM | 5372 | N | ASN | A | 136 | 11.300 | 21.896 | 25.158 | 1.00 | 45.15 | N |
| ATOM | 5373 | CA | ASN | A | 136 | 10.964 | 23.237 | 25.514 | 1.00 | 48.79 | C |
| ATOM | 5375 | CB | ASN | A | 136 | 11.907 | 23.813 | 26.550 | 1.00 | 49.28 | C |
| ATOM | 5378 | CG | ASN | A | 136 | 11.394 | 25.138 | 27.082 | 1.00 | 52.63 | C |
| ATOM | 5379 | OD1 | ASN | A | 136 | 11.519 | 26.154 | 26.396 | 1.00 | 55.30 | O |
| ATOM | 5380 | ND2 | ASN | A | 136 | 10.767 | 25.131 | 28.286 | 1.00 | 53.15 | N |
| ATOM | 5383 | C | ASN | A | 136 | 10.881 | 24.124 | 24.265 | 1.00 | 51.27 | C |
| ATOM | 5384 | O | ASN | A | 136 | 9.877 | 24.796 | 24.077 | 1.00 | 51.97 | O |
| ATOM | 5386 | N | LYS | A | 137 | 11.904 | 24.090 | 23.403 | 1.00 | 54.54 | N |
| ATOM | 5387 | CA | LYS | A | 137 | 11.915 | 24.940 | 22.197 | 1.00 | 56.62 | C |
| ATOM | 5389 | CB | LYS | A | 137 | 13.105 | 24.672 | 21.271 | 1.00 | 56.82 | C |
| ATOM | 5392 | CG | LYS | A | 137 | 12.842 | 25.253 | 19.864 | 1.00 | 57.48 | C |
| ATOM | 5395 | CD | LYS | A | 137 | 14.030 | 25.240 | 18.949 | 1.00 | 59.50 | C |
| ATOM | 5398 | CE | LYS | A | 137 | 13.750 | 26.048 | 17.679 | 1.00 | 60.50 | C |
| ATOM | 5401 | NZ | LYS | A | 137 | 13.229 | 27.441 | 17.992 | 1.00 | 60.93 | N |
| ATOM | 5405 | C | LYS | A | 137 | 10.637 | 24.740 | 21.416 | 1.00 | 58.12 | C |
| ATOM | 5406 | O | LYS | A | 137 | 9.942 | 25.701 | 21.138 | 1.00 | 59.00 | O |
| ATOM | 5408 | N | ILE | A | 138 | 10.348 | 23.498 | 21.031 | 1.00 | 60.12 | N |
| ATOM | 5409 | CA | ILE | A | 138 | 9.099 | 23.224 | 20.328 | 1.00 | 61.65 | C |
| ATOM | 5411 | CB | ILE | A | 138 | 9.139 | 21.967 | 19.338 | 1.00 | 61.70 | C |
| ATOM | 5413 | CG1 | ILE | A | 138 | 9.009 | 20.611 | 20.060 | 1.00 | 61.14 | C |
| ATOM | 5416 | CD1 | ILE | A | 138 | 7.583 | 20.106 | 20.169 | 1.00 | 59.21 | C |
| ATOM | 5420 | CG2 | ILE | A | 138 | 10.376 | 22.005 | 18.459 | 1.00 | 61.29 | C |
| ATOM | 5424 | C | ILE | A | 138 | 8.089 | 23.021 | 21.402 | 1.00 | 63.14 | C |
| ATOM | 5425 | O | ILE | A | 138 | 8.441 | 22.845 | 22.559 | 1.00 | 64.78 | O |
| ATOM | 5460 | N | GLU | A | 141 | 3.876 | 19.557 | 21.554 | 1.00 | 59.21 | N |
| ATOM | 5461 | CA | GLU | A | 141 | 3.782 | 18.176 | 21.160 | 1.00 | 57.45 | C |
| ATOM | 5463 | CB | GLU | A | 141 | 3.028 | 17.314 | 22.216 | 1.00 | 57.96 | C |
| ATOM | 5466 | CG | GLU | A | 141 | 1.473 | 17.202 | 22.034 | 1.00 | 59.82 | C |
| ATOM | 5469 | CD | GLU | A | 141 | 0.681 | 17.478 | 23.312 | 1.00 | 63.12 | C |
| ATOM | 5470 | OE1 | GLU | A | 141 | -0.228 | 16.672 | 23.606 | 1.00 | 64.80 | O |
| ATOM | 5471 | OE2 | GLU | A | 141 | 0.957 | 18.492 | 24.013 | 1.00 | 64.58 | O |
| ATOM | 5472 | C | GLU | A | 141 | 3.181 | 18.029 | 19.770 | 1.00 | 54.78 | C |
| ATOM | 5473 | O | GLU | A | 141 | 3.192 | 18.958 | 18.942 | 1.00 | 54.77 | O |
| ATOM | 5475 | N | LYS | A | 142 | 2.667 | 16.826 | 19.544 | 1.00 | 50.93 | N |
| ATOM | 5476 | CA | LYS | A | 142 | 2.484 | 16.289 | 18.244 | 1.00 | 48.09 | C |
| ATOM | 5478 | CB | LYS | A | 142 | 1.578 | 17.164 | 17.381 | 1.00 | 48.08 | C |
| ATOM | 5481 | CG | LYS | A | 142 | 0.237 | 17.433 | 18.087 | 1.00 | 50.33 | C |
| ATOM | 5484 | CD | LYS | A | 142 | -0.578 | 16.144 | 18.293 | 1.00 | 53.05 | C |
| ATOM | 5487 | CE | LYS | A | 142 | -2.094 | 16.429 | 18.369 | 1.00 | 55.73 | C |
| ATOM | 5490 | NZ | LYS | A | 142 | -2.617 | 16.712 | 19.746 | 1.00 | 56.54 | N |
| ATOM | 5494 | C | LYS | A | 142 | 3.887 | 15.996 | 17.697 | 1.00 | 43.19 | C |
| ATOM | 5495 | O | LYS | A | 142 | 4.136 | 14.868 | 17.407 | 1.00 | 43.47 | O |

FIG.5-20

| | | | | | | | | | | | |
|---|---|---|---|---|---|---|---|---|---|---|---|
| ATOM | 5497 | N | THR | A | 143 | 4.816 | 16.943 | 17.652 | 1.00 | 39.10 | N |
| ATOM | 5498 | CA | THR | A | 143 | 6.159 | 16.569 | 17.163 | 1.00 | 35.58 | C |
| ATOM | 5500 | CB | THR | A | 143 | 7.045 | 17.742 | 16.865 | 1.00 | 35.34 | C |
| ATOM | 5502 | OG1 | THR | A | 143 | 6.364 | 18.615 | 15.975 | 1.00 | 34.89 | O |
| ATOM | 5504 | CG2 | THR | A | 143 | 8.424 | 17.267 | 16.225 | 1.00 | 33.54 | C |
| ATOM | 5508 | C | THR | A | 143 | 6.856 | 15.617 | 18.128 | 1.00 | 32.81 | C |
| ATOM | 5509 | O | THR | A | 143 | 7.194 | 15.973 | 19.256 | 1.00 | 32.08 | O |
| ATOM | 5511 | N | HIS | A | 144 | 7.104 | 14.412 | 17.646 | 1.00 | 30.83 | N |
| ATOM | 5512 | CA | HIS | A | 144 | 7.873 | 13.396 | 18.380 | 1.00 | 29.52 | C |
| ATOM | 5514 | CB | HIS | A | 144 | 7.661 | 12.082 | 17.674 | 1.00 | 28.83 | C |
| ATOM | 5517 | CG | HIS | A | 144 | 7.736 | 10.904 | 18.577 | 1.00 | 29.31 | C |
| ATOM | 5518 | ND1 | HIS | A | 144 | 6.681 | 10.521 | 19.389 | 1.00 | 26.72 | N |
| ATOM | 5520 | CE1 | HIS | A | 144 | 7.032 | 9.446 | 20.061 | 1.00 | 30.35 | C |
| ATOM | 5522 | NE2 | HIS | A | 144 | 8.263 | 9.116 | 19.708 | 1.00 | 32.52 | N |
| ATOM | 5524 | CD2 | HIS | A | 144 | 8.714 | 10.005 | 18.771 | 1.00 | 29.00 | C |
| ATOM | 5526 | C | HIS | A | 144 | 9.381 | 13.696 | 18.436 | 1.00 | 28.96 | C |
| ATOM | 5527 | O | HIS | A | 144 | 9.951 | 14.079 | 17.444 | 1.00 | 30.10 | O |
| ATOM | 5529 | N | ILE | A | 145 | 10.034 | 13.539 | 19.584 | 1.00 | 27.20 | N |
| ATOM | 5530 | CA | ILE | A | 145 | 11.453 | 13.833 | 19.700 | 1.00 | 25.64 | C |
| ATOM | 5532 | CB | ILE | A | 145 | 11.755 | 14.734 | 20.888 | 1.00 | 26.53 | C |
| ATOM | 5534 | CG1 | ILE | A | 145 | 11.049 | 16.080 | 20.720 | 1.00 | 28.31 | C |
| ATOM | 5537 | CD1 | ILE | A | 145 | 10.803 | 16.793 | 22.041 | 1.00 | 29.05 | C |
| ATOM | 5541 | CG2 | ILE | A | 145 | 13.254 | 14.968 | 21.086 | 1.00 | 21.92 | C |
| ATOM | 5545 | C | ILE | A | 145 | 12.197 | 12.521 | 19.866 | 1.00 | 26.87 | C |
| ATOM | 5546 | O | ILE | A | 145 | 11.795 | 11.665 | 20.685 | 1.00 | 28.32 | O |
| ATOM | 5548 | N | HIS | A | 146 | 13.294 | 12.336 | 19.127 | 1.00 | 24.40 | N |
| ATOM | 5549 | CA | HIS | A | 146 | 14.166 | 11.171 | 19.313 | 1.00 | 23.21 | C |
| ATOM | 5551 | CB | HIS | A | 146 | 13.917 | 10.157 | 18.188 | 1.00 | 23.84 | C |
| ATOM | 5554 | CG | HIS | A | 146 | 14.520 | 8.782 | 18.403 | 1.00 | 21.72 | C |
| ATOM | 5555 | ND1 | HIS | A | 146 | 14.045 | 7.666 | 17.746 | 1.00 | 24.44 | N |
| ATOM | 5557 | CE1 | HIS | A | 146 | 14.742 | 6.607 | 18.102 | 1.00 | 25.79 | C |
| ATOM | 5559 | NE2 | HIS | A | 146 | 15.694 | 6.993 | 18.941 | 1.00 | 26.04 | N |
| ATOM | 5561 | CD2 | HIS | A | 146 | 15.575 | 8.350 | 19.141 | 1.00 | 27.26 | C |
| ATOM | 5563 | C | HIS | A | 146 | 15.595 | 11.668 | 19.301 | 1.00 | 23.84 | C |
| ATOM | 5564 | O | HIS | A | 146 | 16.060 | 12.294 | 18.290 | 1.00 | 21.67 | O |
| ATOM | 5566 | N | ILE | A | 147 | 16.280 | 11.437 | 20.427 | 1.00 | 23.11 | N |
| ATOM | 5567 | CA | ILE | A | 147 | 17.584 | 11.931 | 20.679 | 1.00 | 22.94 | C |
| ATOM | 5569 | CB | ILE | A | 147 | 17.690 | 12.630 | 22.000 | 1.00 | 22.97 | C |
| ATOM | 5571 | CG1 | ILE | A | 147 | 16.688 | 13.772 | 22.162 | 1.00 | 22.95 | C |
| ATOM | 5574 | CD1 | ILE | A | 147 | 16.835 | 14.950 | 21.198 | 1.00 | 21.64 | C |
| ATOM | 5578 | CG2 | ILE | A | 147 | 19.164 | 13.019 | 22.253 | 1.00 | 20.59 | C |
| ATOM | 5582 | C | ILE | A | 147 | 18.546 | 10.755 | 20.752 | 1.00 | 25.00 | C |
| ATOM | 5583 | O | ILE | A | 147 | 18.223 | 9.719 | 21.373 | 1.00 | 26.02 | O |
| ATOM | 5585 | N | PHE | A | 148 | 19.704 | 10.886 | 20.127 | 1.00 | 24.41 | N |
| ATOM | 5586 | CA | PHE | A | 148 | 20.727 | 9.841 | 20.143 | 1.00 | 26.58 | C |
| ATOM | 5588 | CB | PHE | A | 148 | 21.107 | 9.331 | 18.768 | 1.00 | 25.84 | C |
| ATOM | 5591 | CG | PHE | A | 148 | 20.027 | 8.628 | 18.052 | 1.00 | 24.60 | C |
| ATOM | 5592 | CD1 | PHE | A | 148 | 19.916 | 7.252 | 18.128 | 1.00 | 25.26 | C |
| ATOM | 5594 | CE1 | PHE | A | 148 | 18.912 | 6.544 | 17.449 | 1.00 | 24.20 | C |
| ATOM | 5596 | CZ | PHE | A | 148 | 18.014 | 7.212 | 16.690 | 1.00 | 26.92 | C |
| ATOM | 5598 | CE2 | PHE | A | 148 | 18.104 | 8.616 | 16.601 | 1.00 | 25.66 | C |
| ATOM | 5600 | CD2 | PHE | A | 148 | 19.109 | 9.310 | 17.305 | 1.00 | 23.77 | C |
| ATOM | 5602 | C | PHE | A | 148 | 21.965 | 10.524 | 20.679 | 1.00 | 27.81 | C |
| ATOM | 5603 | O | PHE | A | 148 | 22.230 | 11.650 | 20.326 | 1.00 | 27.99 | O |
| ATOM | 5605 | N | SER | A | 149 | 22.701 | 9.870 | 21.562 | 1.00 | 28.62 | N |
| ATOM | 5606 | CA | SER | A | 149 | 23.991 | 10.413 | 21.944 | 1.00 | 30.88 | C |
| ATOM | 5608 | CB | SER | A | 149 | 24.177 | 10.469 | 23.452 | 1.00 | 31.17 | C |
| ATOM | 5611 | OG | SER | A | 149 | 24.505 | 9.186 | 23.871 | 1.00 | 34.53 | O |
| ATOM | 5613 | C | SER | A | 149 | 25.101 | 9.570 | 21.377 | 1.00 | 31.23 | C |
| ATOM | 5614 | O | SER | A | 149 | 24.887 | 8.434 | 20.985 | 1.00 | 33.07 | O |
| ATOM | 5616 | N | PHE | A | 150 | 26.286 | 10.138 | 21.365 | 1.00 | 32.55 | N |
| ATOM | 5617 | CA | PHE | A | 150 | 27.466 | 9.400 | 20.978 | 1.00 | 34.57 | C |
| ATOM | 5619 | CB | PHE | A | 150 | 28.663 | 10.325 | 20.745 | 1.00 | 33.55 | C |

FIG.5-21

| | | | | | | | | | | | |
|---|---|---|---|---|---|---|---|---|---|---|---|
| ATOM | 5622 | CG | PHE | A | 150 | 28.524 | 11.219 | 19.550 | 1.00 | 31.30 | C |
| ATOM | 5623 | CD1 | PHE | A | 150 | 27.896 | 12.435 | 19.667 | 1.00 | 28.52 | C |
| ATOM | 5625 | CE1 | PHE | A | 150 | 27.790 | 13.275 | 18.600 | 1.00 | 29.60 | C |
| ATOM | 5627 | CZ | PHE | A | 150 | 28.285 | 12.888 | 17.354 | 1.00 | 33.22 | C |
| ATOM | 5629 | CE2 | PHE | A | 150 | 28.932 | 11.662 | 17.214 | 1.00 | 29.70 | C |
| ATOM | 5631 | CD2 | PHE | A | 150 | 29.033 | 10.843 | 18.297 | 1.00 | 31.31 | C |
| ATOM | 5633 | C | PHE | A | 150 | 27.814 | 8.317 | 22.005 | 1.00 | 37.59 | C |
| ATOM | 5634 | O | PHE | A | 150 | 28.628 | 7.464 | 21.697 | 1.00 | 38.78 | O |
| ATOM | 5636 | N | THR | A | 151 | 27.187 | 8.310 | 23.189 | 1.00 | 39.50 | N |
| ATOM | 5637 | CA | THR | A | 151 | 27.470 | 7.257 | 24.166 | 1.00 | 41.17 | C |
| ATOM | 5639 | CB | THR | A | 151 | 27.163 | 7.680 | 25.603 | 1.00 | 42.21 | C |
| ATOM | 5641 | OG1 | THR | A | 151 | 25.735 | 7.694 | 25.763 | 1.00 | 44.81 | O |
| ATOM | 5643 | CG2 | THR | A | 151 | 27.744 | 9.026 | 25.920 | 1.00 | 42.12 | C |
| ATOM | 5647 | C | THR | A | 151 | 26.594 | 6.049 | 23.950 | 1.00 | 41.24 | C |
| ATOM | 5648 | O | THR | A | 151 | 26.752 | 5.071 | 24.655 | 1.00 | 43.10 | O |
| ATOM | 5650 | N | GLY | A | 152 | 25.635 | 6.113 | 23.029 | 1.00 | 39.78 | N |
| ATOM | 5651 | CA | GLY | A | 152 | 24.809 | 4.965 | 22.707 | 1.00 | 37.64 | C |
| ATOM | 5654 | C | GLY | A | 152 | 23.445 | 5.034 | 23.337 | 1.00 | 36.58 | C |
| ATOM | 5655 | O | GLY | A | 152 | 22.608 | 4.175 | 23.113 | 1.00 | 37.39 | O |
| ATOM | 5657 | N | GLU | A | 153 | 23.217 | 6.038 | 24.155 | 1.00 | 35.57 | N |
| ATOM | 5658 | CA | GLU | A | 153 | 21.942 | 6.177 | 24.852 | 1.00 | 35.12 | C |
| ATOM | 5660 | CB | GLU | A | 153 | 22.137 | 7.014 | 26.105 | 1.00 | 35.59 | C |
| ATOM | 5663 | CG | GLU | A | 153 | 23.104 | 6.361 | 27.126 | 1.00 | 40.05 | C |
| ATOM | 5666 | CD | GLU | A | 153 | 22.996 | 6.976 | 28.550 | 1.00 | 43.31 | C |
| ATOM | 5667 | OE1 | GLU | A | 153 | 22.432 | 8.055 | 28.711 | 1.00 | 44.86 | O |
| ATOM | 5668 | OE2 | GLU | A | 153 | 23.438 | 6.338 | 29.537 | 1.00 | 50.12 | O |
| ATOM | 5669 | C | GLU | A | 153 | 20.968 | 6.844 | 23.892 | 1.00 | 33.92 | C |
| ATOM | 5670 | O | GLU | A | 153 | 21.381 | 7.468 | 22.915 | 1.00 | 31.33 | O |
| ATOM | 5672 | N | GLU | A | 154 | 19.681 | 6.680 | 24.137 | 1.00 | 33.73 | N |
| ATOM | 5673 | CA | GLU | A | 154 | 18.690 | 7.350 | 23.334 | 1.00 | 33.95 | C |
| ATOM | 5675 | CB | GLU | A | 154 | 18.290 | 6.555 | 22.051 | 1.00 | 34.14 | C |
| ATOM | 5678 | CG | GLU | A | 154 | 17.675 | 5.218 | 22.304 | 1.00 | 36.12 | C |
| ATOM | 5681 | CD | GLU | A | 154 | 17.436 | 4.373 | 21.068 | 1.00 | 36.61 | C |
| ATOM | 5682 | OE1 | GLU | A | 154 | 17.069 | 4.856 | 19.973 | 1.00 | 30.15 | O |
| ATOM | 5683 | OE2 | GLU | A | 154 | 17.600 | 3.155 | 21.225 | 1.00 | 37.95 | O |
| ATOM | 5684 | C | GLU | A | 154 | 17.541 | 7.681 | 24.272 | 1.00 | 35.16 | C |
| ATOM | 5685 | O | GLU | A | 154 | 17.394 | 7.092 | 25.337 | 1.00 | 34.87 | O |
| ATOM | 5687 | N | MET | A | 155 | 16.813 | 8.721 | 23.926 | 1.00 | 34.53 | N |
| ATOM | 5688 | CA | MET | A | 155 | 15.613 | 9.063 | 24.583 | 1.00 | 34.55 | C |
| ATOM | 5690 | CB | MET | A | 155 | 15.898 | 10.173 | 25.528 | 1.00 | 35.98 | C |
| ATOM | 5693 | CG | MET | A | 155 | 14.684 | 10.641 | 26.185 | 1.00 | 40.29 | C |
| ATOM | 5696 | SD | MET | A | 155 | 15.144 | 11.635 | 27.551 | 1.00 | 48.65 | S |
| ATOM | 5697 | CE | MET | A | 155 | 13.454 | 11.711 | 28.268 | 1.00 | 47.98 | C |
| ATOM | 5701 | C | MET | A | 155 | 14.668 | 9.577 | 23.518 | 1.00 | 33.54 | C |
| ATOM | 5702 | O | MET | A | 155 | 15.088 | 10.320 | 22.603 | 1.00 | 32.14 | O |
| ATOM | 5704 | N | ALA | A | 156 | 13.412 | 9.191 | 23.651 | 1.00 | 31.53 | N |
| ATOM | 5705 | CA | ALA | A | 156 | 12.383 | 9.514 | 22.721 | 1.00 | 31.19 | C |
| ATOM | 5707 | CB | ALA | A | 156 | 12.239 | 8.383 | 21.741 | 1.00 | 29.85 | C |
| ATOM | 5711 | C | ALA | A | 156 | 11.053 | 9.764 | 23.483 | 1.00 | 32.17 | C |
| ATOM | 5712 | O | ALA | A | 156 | 10.808 | 9.181 | 24.550 | 1.00 | 32.09 | O |
| ATOM | 5714 | N | THR | A | 157 | 10.228 | 10.637 | 22.934 | 1.00 | 31.32 | N |
| ATOM | 5715 | CA | THR | A | 157 | 8.879 | 10.907 | 23.437 | 1.00 | 33.56 | C |
| ATOM | 5717 | CB | THR | A | 157 | 8.101 | 11.753 | 22.388 | 1.00 | 32.63 | C |
| ATOM | 5719 | OG1 | THR | A | 157 | 8.845 | 12.937 | 22.118 | 1.00 | 31.49 | O |
| ATOM | 5721 | CG2 | THR | A | 157 | 6.707 | 12.151 | 22.838 | 1.00 | 35.00 | C |
| ATOM | 5725 | C | THR | A | 157 | 8.172 | 9.606 | 23.824 | 1.00 | 33.29 | C |
| ATOM | 5726 | O | THR | A | 157 | 8.106 | 8.634 | 23.056 | 1.00 | 34.08 | O |
| ATOM | 5728 | N | LYS | A | 158 | 7.752 | 9.567 | 25.077 | 1.00 | 36.21 | N |
| ATOM | 5729 | CA | LYS | A | 158 | 7.024 | 8.410 | 25.655 | 1.00 | 36.17 | C |
| ATOM | 5731 | CB | LYS | A | 158 | 5.719 | 8.258 | 24.934 | 1.00 | 36.36 | C |
| ATOM | 5734 | CG | LYS | A | 158 | 4.851 | 9.513 | 25.033 | 1.00 | 38.77 | C |
| ATOM | 5737 | CD | LYS | A | 158 | 3.633 | 9.378 | 24.118 | 1.00 | 41.45 | C |
| ATOM | 5740 | CE | LYS | A | 158 | 2.366 | 9.796 | 24.825 | 1.00 | 45.12 | C |

FIG.5-22

| | | | | | | | | | | | |
|---|---|---|---|---|---|---|---|---|---|---|---|
| ATOM | 5743 | NZ | LYS | A | 158 | 2.412 | 11.238 | 25.121 | 1.00 | 46.77 | N |
| ATOM | 5747 | C | LYS | A | 158 | 7.753 | 7.129 | 25.511 | 1.00 | 36.28 | C |
| ATOM | 5748 | O | LYS | A | 158 | 7.123 | 6.112 | 25.271 | 1.00 | 37.46 | O |
| ATOM | 5750 | N | ALA | A | 159 | 9.081 | 7.161 | 25.582 | 1.00 | 36.45 | N |
| ATOM | 5751 | CA | ALA | A | 159 | 9.905 | 5.962 | 25.305 | 1.00 | 35.35 | C |
| ATOM | 5753 | CB | ALA | A | 159 | 10.007 | 5.044 | 26.560 | 1.00 | 36.36 | C |
| ATOM | 5757 | C | ALA | A | 159 | 9.404 | 5.181 | 24.090 | 1.00 | 35.52 | C |
| ATOM | 5758 | O | ALA | A | 159 | 9.529 | 3.949 | 24.038 | 1.00 | 33.91 | O |
| ATOM | 5760 | N | ASP | A | 160 | 8.890 | 5.918 | 23.074 | 1.00 | 35.12 | N |
| ATOM | 5761 | CA | ASP | A | 160 | 8.504 | 5.331 | 21.801 | 1.00 | 33.93 | C |
| ATOM | 5763 | CB | ASP | A | 160 | 7.116 | 5.860 | 21.447 | 1.00 | 34.67 | C |
| ATOM | 5766 | CG | ASP | A | 160 | 6.644 | 5.427 | 20.129 | 1.00 | 34.90 | C |
| ATOM | 5767 | OD1 | ASP | A | 160 | 7.329 | 4.661 | 19.439 | 1.00 | 36.96 | O |
| ATOM | 5768 | OD2 | ASP | A | 160 | 5.544 | 5.861 | 19.745 | 1.00 | 37.75 | O |
| ATOM | 5769 | C | ASP | A | 160 | 9.611 | 5.701 | 20.785 | 1.00 | 34.19 | C |
| ATOM | 5770 | O | ASP | A | 160 | 9.741 | 6.889 | 20.315 | 1.00 | 32.67 | O |
| ATOM | 5772 | N | TYR | A | 161 | 10.416 | 4.685 | 20.458 | 1.00 | 32.93 | N |
| ATOM | 5773 | CA | TYR | A | 161 | 11.664 | 4.863 | 19.684 | 1.00 | 32.18 | C |
| ATOM | 5775 | CB | TYR | A | 161 | 12.738 | 3.875 | 20.196 | 1.00 | 32.82 | C |
| ATOM | 5778 | CG | TYR | A | 161 | 13.091 | 4.101 | 21.663 | 1.00 | 32.93 | C |
| ATOM | 5779 | CD1 | TYR | A | 161 | 13.825 | 5.186 | 22.040 | 1.00 | 31.88 | C |
| ATOM | 5781 | CE1 | TYR | A | 161 | 14.101 | 5.442 | 23.336 | 1.00 | 38.00 | C |
| ATOM | 5783 | CZ | TYR | A | 161 | 13.671 | 4.553 | 24.314 | 1.00 | 42.38 | C |
| ATOM | 5784 | OH | TYR | A | 161 | 13.999 | 4.788 | 25.598 | 1.00 | 44.08 | O |
| ATOM | 5786 | CE2 | TYR | A | 161 | 12.959 | 3.434 | 23.970 | 1.00 | 42.24 | C |
| ATOM | 5788 | CD2 | TYR | A | 161 | 12.667 | 3.214 | 22.640 | 1.00 | 37.73 | C |
| ATOM | 5790 | C | TYR | A | 161 | 11.421 | 4.696 | 18.168 | 1.00 | 31.18 | C |
| ATOM | 5791 | O | TYR | A | 161 | 12.372 | 4.731 | 17.357 | 1.00 | 27.16 | O |
| ATOM | 5793 | N | THR | A | 162 | 10.129 | 4.485 | 17.813 | 1.00 | 29.57 | N |
| ATOM | 5794 | CA | THR | A | 162 | 9.659 | 4.426 | 16.452 | 1.00 | 29.27 | C |
| ATOM | 5796 | CB | THR | A | 162 | 10.002 | 5.748 | 15.633 | 1.00 | 28.80 | C |
| ATOM | 5798 | OG1 | THR | A | 162 | 9.498 | 6.881 | 16.307 | 1.00 | 26.38 | O |
| ATOM | 5800 | CG2 | THR | A | 162 | 9.413 | 5.750 | 14.310 | 1.00 | 28.12 | C |
| ATOM | 5804 | C | THR | A | 162 | 10.218 | 3.296 | 15.661 | 1.00 | 29.90 | C |
| ATOM | 5805 | O | THR | A | 162 | 9.474 | 2.561 | 14.981 | 1.00 | 29.65 | O |
| ATOM | 5807 | N | LEU | A | 163 | 11.545 | 3.233 | 15.610 | 1.00 | 30.60 | N |
| ATOM | 5808 | CA | LEU | A | 163 | 12.189 | 2.292 | 14.761 | 1.00 | 31.31 | C |
| ATOM | 5810 | CB | LEU | A | 163 | 13.541 | 2.829 | 14.343 | 1.00 | 30.83 | C |
| ATOM | 5813 | CG | LEU | A | 163 | 13.591 | 4.104 | 13.492 | 1.00 | 31.84 | C |
| ATOM | 5815 | CD1 | LEU | A | 163 | 15.033 | 4.384 | 13.159 | 1.00 | 31.55 | C |
| ATOM | 5819 | CD2 | LEU | A | 163 | 12.743 | 4.007 | 12.212 | 1.00 | 29.01 | C |
| ATOM | 5823 | C | LEU | A | 163 | 12.394 | 0.960 | 15.520 | 1.00 | 32.80 | C |
| ATOM | 5824 | O | LEU | A | 163 | 12.337 | 0.940 | 16.753 | 1.00 | 32.75 | O |
| ATOM | 5826 | N | ASP | A | 164 | 12.664 | -0.099 | 14.754 | 1.00 | 34.26 | N |
| ATOM | 5827 | CA | ASP | A | 164 | 13.129 | -1.384 | 15.243 | 1.00 | 36.76 | C |
| ATOM | 5829 | CB | ASP | A | 164 | 13.276 | -2.390 | 14.089 | 1.00 | 37.95 | C |
| ATOM | 5832 | CG | ASP | A | 164 | 14.189 | -1.884 | 12.975 | 1.00 | 42.05 | C |
| ATOM | 5833 | OD1 | ASP | A | 164 | 13.788 | -0.942 | 12.214 | 1.00 | 49.39 | O |
| ATOM | 5834 | OD2 | ASP | A | 164 | 15.330 | -2.370 | 12.858 | 1.00 | 47.06 | O |
| ATOM | 5835 | C | ASP | A | 164 | 14.511 | -1.193 | 15.875 | 1.00 | 37.68 | C |
| ATOM | 5836 | O | ASP | A | 164 | 15.244 | -0.243 | 15.547 | 1.00 | 35.84 | O |
| ATOM | 5838 | N | GLU | A | 165 | 14.892 | -2.146 | 16.717 | 1.00 | 37.68 | N |
| ATOM | 5839 | CA | GLU | A | 165 | 16.167 | -2.082 | 17.428 | 1.00 | 38.72 | C |
| ATOM | 5841 | CB | GLU | A | 165 | 16.216 | -3.208 | 18.495 | 1.00 | 39.95 | C |
| ATOM | 5844 | CG | GLU | A | 165 | 17.138 | -2.904 | 19.703 | 1.00 | 43.37 | C |
| ATOM | 5847 | CD | GLU | A | 165 | 17.045 | -3.968 | 20.802 | 1.00 | 50.02 | C |
| ATOM | 5848 | OE1 | GLU | A | 165 | 15.915 | -4.436 | 21.077 | 1.00 | 51.72 | O |
| ATOM | 5849 | OE2 | GLU | A | 165 | 18.097 | -4.305 | 21.405 | 1.00 | 55.03 | O |
| ATOM | 5850 | C | GLU | A | 165 | 17.400 | -2.114 | 16.492 | 1.00 | 38.14 | C |
| ATOM | 5851 | O | GLU | A | 165 | 18.398 | -1.440 | 16.743 | 1.00 | 38.13 | O |
| ATOM | 5853 | N | GLU | A | 166 | 17.323 | -2.850 | 15.390 | 1.00 | 37.57 | N |
| ATOM | 5854 | CA | GLU | A | 166 | 18.460 | -2.963 | 14.486 | 1.00 | 37.34 | C |
| ATOM | 5856 | CB | GLU | A | 166 | 18.258 | -4.102 | 13.473 | 1.00 | 37.68 | C |

FIG.5-23

| | | | | | | | | | | | |
|---|---|---|---|---|---|---|---|---|---|---|---|
| ATOM | 5859 | CG | GLU | A | 166 | 19.312 | -4.182 | 12.324 | 1.00 | 39.46 | C |
| ATOM | 5862 | CD | GLU | A | 166 | 20.695 | -4.674 | 12.773 | 1.00 | 42.44 | C |
| ATOM | 5863 | OE1 | GLU | A | 166 | 20.955 | -4.769 | 13.978 | 1.00 | 46.71 | O |
| ATOM | 5864 | OE2 | GLU | A | 166 | 21.542 | -4.978 | 11.915 | 1.00 | 45.64 | O |
| ATOM | 5865 | C | GLU | A | 166 | 18.674 | -1.641 | 13.760 | 1.00 | 36.13 | C |
| ATOM | 5866 | O | GLU | A | 166 | 19.796 | -1.184 | 13.659 | 1.00 | 38.21 | O |
| ATOM | 5868 | N | SER | A | 167 | 17.599 | -1.005 | 13.318 | 1.00 | 34.14 | N |
| ATOM | 5869 | CA | SER | A | 167 | 17.720 | 0.303 | 12.650 | 1.00 | 33.30 | C |
| ATOM | 5871 | CB | SER | A | 167 | 16.374 | 0.828 | 12.222 | 1.00 | 32.17 | C |
| ATOM | 5874 | OG | SER | A | 167 | 15.715 | -0.099 | 11.377 | 1.00 | 34.51 | O |
| ATOM | 5876 | C | SER | A | 167 | 18.393 | 1.283 | 13.571 | 1.00 | 30.87 | C |
| ATOM | 5877 | O | SER | A | 167 | 19.278 | 1.992 | 13.134 | 1.00 | 31.49 | O |
| ATOM | 5879 | N | ARG | A | 168 | 18.004 | 1.292 | 14.850 | 1.00 | 29.38 | N |
| ATOM | 5880 | CA | ARG | A | 168 | 18.639 | 2.157 | 15.836 | 1.00 | 28.56 | C |
| ATOM | 5882 | CB | ARG | A | 168 | 17.878 | 2.150 | 17.117 | 1.00 | 29.48 | C |
| ATOM | 5885 | CG | ARG | A | 168 | 16.554 | 2.835 | 16.999 | 1.00 | 32.07 | C |
| ATOM | 5888 | CD | ARG | A | 168 | 15.965 | 2.874 | 18.359 | 1.00 | 35.95 | C |
| ATOM | 5891 | NE | ARG | A | 168 | 14.991 | 1.874 | 18.490 | 1.00 | 35.74 | N |
| ATOM | 5893 | CZ | ARG | A | 168 | 14.726 | 1.168 | 19.590 | 1.00 | 36.73 | C |
| ATOM | 5894 | NH1 | ARG | A | 168 | 15.316 | 1.352 | 20.776 | 1.00 | 36.99 | N |
| ATOM | 5897 | NH2 | ARG | A | 168 | 13.784 | 0.300 | 19.477 | 1.00 | 34.77 | N |
| ATOM | 5900 | C | ARG | A | 168 | 20.080 | 1.827 | 16.140 | 1.00 | 27.43 | C |
| ATOM | 5901 | O | ARG | A | 168 | 20.873 | 2.702 | 16.442 | 1.00 | 23.27 | O |
| ATOM | 5903 | N | ALA | A | 169 | 20.387 | 0.539 | 16.103 | 1.00 | 28.70 | N |
| ATOM | 5904 | CA | ALA | A | 169 | 21.760 | 0.054 | 16.309 | 1.00 | 28.58 | C |
| ATOM | 5906 | CB | ALA | A | 169 | 21.742 | -1.535 | 16.398 | 1.00 | 29.63 | C |
| ATOM | 5910 | C | ALA | A | 169 | 22.629 | 0.488 | 15.165 | 1.00 | 28.42 | C |
| ATOM | 5911 | O | ALA | A | 169 | 23.743 | 0.765 | 15.365 | 1.00 | 27.79 | O |
| ATOM | 5913 | N | ARG | A | 170 | 22.113 | 0.467 | 13.938 | 1.00 | 30.11 | N |
| ATOM | 5914 | CA | ARG | A | 170 | 22.866 | 0.994 | 12.794 | 1.00 | 31.58 | C |
| ATOM | 5916 | CB | ARG | A | 170 | 22.006 | 0.931 | 11.532 | 1.00 | 32.82 | C |
| ATOM | 5919 | CG | ARG | A | 170 | 22.751 | 1.149 | 10.228 | 1.00 | 40.04 | C |
| ATOM | 5922 | CD | ARG | A | 170 | 21.770 | 1.308 | 9.040 | 1.00 | 48.48 | C |
| ATOM | 5925 | NE | ARG | A | 170 | 21.170 | 0.011 | 8.738 | 1.00 | 55.58 | N |
| ATOM | 5927 | CZ | ARG | A | 170 | 21.846 | -1.004 | 8.190 | 1.00 | 61.84 | C |
| ATOM | 5928 | NH1 | ARG | A | 170 | 23.139 | -0.858 | 7.859 | 1.00 | 63.30 | N |
| ATOM | 5931 | NH2 | ARG | A | 170 | 21.237 | -2.177 | 7.957 | 1.00 | 62.81 | N |
| ATOM | 5934 | C | ARG | A | 170 | 23.353 | 2.424 | 13.076 | 1.00 | 30.18 | C |
| ATOM | 5935 | O | ARG | A | 170 | 24.553 | 2.747 | 12.979 | 1.00 | 28.40 | O |
| ATOM | 5937 | N | ILE | A | 171 | 22.420 | 3.279 | 13.497 | 1.00 | 29.52 | N |
| ATOM | 5938 | CA | ILE | A | 171 | 22.735 | 4.681 | 13.852 | 1.00 | 28.02 | C |
| ATOM | 5940 | CB | ILE | A | 171 | 21.440 | 5.476 | 14.225 | 1.00 | 28.40 | C |
| ATOM | 5942 | CG1 | ILE | A | 171 | 20.586 | 5.674 | 12.978 | 1.00 | 27.25 | C |
| ATOM | 5945 | CD1 | ILE | A | 171 | 18.989 | 6.056 | 13.237 | 1.00 | 25.06 | C |
| ATOM | 5949 | CG2 | ILE | A | 171 | 21.804 | 6.871 | 14.938 | 1.00 | 28.73 | C |
| ATOM | 5953 | C | ILE | A | 171 | 23.719 | 4.780 | 15.001 | 1.00 | 28.08 | C |
| ATOM | 5954 | O | ILE | A | 171 | 24.734 | 5.492 | 14.934 | 1.00 | 26.21 | O |
| ATOM | 5956 | N | LYS | A | 172 | 23.448 | 4.064 | 16.078 | 1.00 | 28.36 | N |
| ATOM | 5957 | CA | LYS | A | 172 | 24.382 | 4.088 | 17.208 | 1.00 | 29.21 | C |
| ATOM | 5959 | CB | LYS | A | 172 | 23.871 | 3.176 | 18.319 | 1.00 | 29.60 | C |
| ATOM | 5962 | CG | LYS | A | 172 | 22.531 | 3.591 | 18.882 | 1.00 | 32.46 | C |
| ATOM | 5965 | CD | LYS | A | 172 | 22.010 | 2.576 | 19.817 | 1.00 | 34.70 | C |
| ATOM | 5968 | CE | LYS | A | 172 | 20.754 | 3.100 | 20.479 | 1.00 | 37.65 | C |
| ATOM | 5971 | NZ | LYS | A | 172 | 19.894 | 1.954 | 21.015 | 1.00 | 33.76 | N |
| ATOM | 5975 | C | LYS | A | 172 | 25.776 | 3.586 | 16.781 | 1.00 | 27.84 | C |
| ATOM | 5976 | O | LYS | A | 172 | 26.796 | 4.046 | 17.279 | 1.00 | 29.48 | O |
| ATOM | 5978 | N | THR | A | 173 | 25.823 | 2.614 | 15.893 | 1.00 | 27.57 | N |
| ATOM | 5979 | CA | THR | A | 173 | 27.105 | 2.097 | 15.452 | 1.00 | 28.51 | C |
| ATOM | 5981 | CB | THR | A | 173 | 26.963 | 0.785 | 14.599 | 1.00 | 29.22 | C |
| ATOM | 5983 | OG1 | THR | A | 173 | 26.463 | -0.272 | 15.431 | 1.00 | 34.02 | O |
| ATOM | 5985 | CG2 | THR | A | 173 | 28.321 | 0.268 | 14.032 | 1.00 | 28.21 | C |
| ATOM | 5989 | C | THR | A | 173 | 27.792 | 3.227 | 14.704 | 1.00 | 28.01 | C |
| ATOM | 5990 | O | THR | A | 173 | 28.975 | 3.501 | 14.887 | 1.00 | 28.49 | O |

FIG.5-24

| | | | | | | | | | | | |
|---|---|---|---|---|---|---|---|---|---|---|---|
| ATOM | 5992 | N | ARG | A | 174 | 27.023 | 3.969 | 13.897 | 1.00 | 27.44 | N |
| ATOM | 5993 | CA | ARG | A | 174 | 27.637 | 5.090 | 13.182 | 1.00 | 27.11 | C |
| ATOM | 5995 | CB | ARG | A | 174 | 26.650 | 5.785 | 12.238 | 1.00 | 27.58 | C |
| ATOM | 5998 | CG | ARG | A | 174 | 27.241 | 6.903 | 11.457 | 1.00 | 29.58 | C |
| ATOM | 6001 | CD | ARG | A | 174 | 28.232 | 6.266 | 10.520 | 1.00 | 35.38 | C |
| ATOM | 6004 | NE | ARG | A | 174 | 28.827 | 7.248 | 9.661 | 1.00 | 41.14 | N |
| ATOM | 6006 | CZ | ARG | A | 174 | 29.542 | 6.955 | 8.585 | 1.00 | 47.71 | C |
| ATOM | 6007 | NH1 | ARG | A | 174 | 29.761 | 5.678 | 8.237 | 1.00 | 48.98 | N |
| ATOM | 6010 | NH2 | ARG | A | 174 | 30.059 | 7.944 | 7.867 | 1.00 | 50.34 | N |
| ATOM | 6013 | C | ARG | A | 174 | 28.237 | 6.067 | 14.114 | 1.00 | 25.23 | C |
| ATOM | 6014 | O | ARG | A | 174 | 29.363 | 6.523 | 13.875 | 1.00 | 22.94 | O |
| ATOM | 6016 | N | LEU | A | 175 | 27.486 | 6.425 | 15.157 | 1.00 | 24.54 | N |
| ATOM | 6017 | CA | LEU | A | 175 | 27.963 | 7.440 | 16.133 | 1.00 | 24.11 | C |
| ATOM | 6019 | CB | LEU | A | 175 | 26.851 | 7.857 | 17.074 | 1.00 | 23.47 | C |
| ATOM | 6022 | CG | LEU | A | 175 | 25.529 | 8.406 | 16.403 | 1.00 | 24.12 | C |
| ATOM | 6024 | CD1 | LEU | A | 175 | 24.436 | 8.769 | 17.378 | 1.00 | 23.42 | C |
| ATOM | 6028 | CD2 | LEU | A | 175 | 25.861 | 9.611 | 15.603 | 1.00 | 19.70 | C |
| ATOM | 6032 | C | LEU | A | 175 | 29.152 | 6.967 | 16.977 | 1.00 | 26.04 | C |
| ATOM | 6033 | O | LEU | A | 175 | 29.996 | 7.739 | 17.316 | 1.00 | 25.79 | O |
| ATOM | 6035 | N | PHE | A | 176 | 29.159 | 5.707 | 17.358 | 1.00 | 28.13 | N |
| ATOM | 6036 | CA | PHE | A | 176 | 30.308 | 5.113 | 18.090 | 1.00 | 30.90 | C |
| ATOM | 6038 | CB | PHE | A | 176 | 29.962 | 3.653 | 18.364 | 1.00 | 31.38 | C |
| ATOM | 6041 | CG | PHE | A | 176 | 31.038 | 2.854 | 19.041 | 1.00 | 37.70 | C |
| ATOM | 6042 | CD1 | PHE | A | 176 | 32.010 | 2.187 | 18.286 | 1.00 | 39.42 | C |
| ATOM | 6044 | CE1 | PHE | A | 176 | 33.007 | 1.437 | 18.911 | 1.00 | 40.80 | C |
| ATOM | 6046 | CZ | PHE | A | 176 | 33.012 | 1.313 | 20.305 | 1.00 | 41.87 | C |
| ATOM | 6048 | CE2 | PHE | A | 176 | 32.038 | 1.931 | 21.066 | 1.00 | 43.88 | C |
| ATOM | 6050 | CD2 | PHE | A | 176 | 31.038 | 2.701 | 20.428 | 1.00 | 42.08 | C |
| ATOM | 6052 | C | PHE | A | 176 | 31.568 | 5.251 | 17.219 | 1.00 | 31.17 | C |
| ATOM | 6053 | O | PHE | A | 176 | 32.597 | 5.670 | 17.679 | 1.00 | 29.60 | O |
| ATOM | 6055 | N | THR | A | 177 | 31.417 | 4.946 | 15.931 | 1.00 | 32.23 | N |
| ATOM | 6056 | CA | THR | A | 177 | 32.519 | 4.966 | 14.983 | 1.00 | 32.30 | C |
| ATOM | 6058 | CB | THR | A | 177 | 32.060 | 4.444 | 13.655 | 1.00 | 32.56 | C |
| ATOM | 6060 | OG1 | THR | A | 177 | 31.573 | 3.110 | 13.823 | 1.00 | 33.77 | O |
| ATOM | 6062 | CG2 | THR | A | 177 | 33.180 | 4.420 | 12.683 | 1.00 | 34.29 | C |
| ATOM | 6066 | C | THR | A | 177 | 33.050 | 6.329 | 14.762 | 1.00 | 31.78 | C |
| ATOM | 6067 | O | THR | A | 177 | 34.257 | 6.513 | 14.645 | 1.00 | 30.06 | O |
| ATOM | 6069 | N | ILE | A | 178 | 32.146 | 7.319 | 14.694 | 1.00 | 31.31 | N |
| ATOM | 6070 | CA | ILE | A | 178 | 32.555 | 8.683 | 14.494 | 1.00 | 29.31 | C |
| ATOM | 6072 | CB | ILE | A | 178 | 31.349 | 9.587 | 14.228 | 1.00 | 31.07 | C |
| ATOM | 6074 | CG1 | ILE | A | 178 | 30.870 | 9.441 | 12.748 | 1.00 | 28.43 | C |
| ATOM | 6077 | CD1 | ILE | A | 178 | 29.386 | 10.059 | 12.500 | 1.00 | 28.35 | C |
| ATOM | 6081 | CG2 | ILE | A | 178 | 31.701 | 10.989 | 14.602 | 1.00 | 27.52 | C |
| ATOM | 6085 | C | ILE | A | 178 | 33.306 | 9.190 | 15.713 | 1.00 | 31.15 | C |
| ATOM | 6086 | O | ILE | A | 178 | 34.316 | 9.908 | 15.590 | 1.00 | 28.66 | O |
| ATOM | 6088 | N | ARG | A | 179 | 32.817 | 8.863 | 16.900 | 1.00 | 30.03 | N |
| ATOM | 6089 | CA | ARG | A | 179 | 33.498 | 9.271 | 18.083 | 1.00 | 31.68 | C |
| ATOM | 6091 | CB | ARG | A | 179 | 32.663 | 8.898 | 19.291 | 1.00 | 32.08 | C |
| ATOM | 6094 | CG | ARG | A | 179 | 33.357 | 8.981 | 20.664 | 1.00 | 35.09 | C |
| ATOM | 6097 | CD | ARG | A | 179 | 32.474 | 8.196 | 21.636 | 1.00 | 42.45 | C |
| ATOM | 6100 | NE | ARG | A | 179 | 32.544 | 8.615 | 23.039 | 1.00 | 50.82 | N |
| ATOM | 6102 | CZ | ARG | A | 179 | 33.293 | 8.037 | 23.995 | 1.00 | 57.90 | C |
| ATOM | 6103 | NH1 | ARG | A | 179 | 34.115 | 7.004 | 23.739 | 1.00 | 58.57 | N |
| ATOM | 6106 | NH2 | ARG | A | 179 | 33.238 | 8.514 | 25.238 | 1.00 | 61.33 | N |
| ATOM | 6109 | C | ARG | A | 179 | 34.898 | 8.553 | 18.176 | 1.00 | 33.24 | C |
| ATOM | 6110 | O | ARG | A | 179 | 35.878 | 9.180 | 18.448 | 1.00 | 30.58 | O |
| ATOM | 6112 | N | GLN | A | 180 | 34.959 | 7.255 | 17.969 | 1.00 | 36.01 | N |
| ATOM | 6113 | CA | GLN | A | 180 | 36.294 | 6.597 | 18.031 | 1.00 | 39.30 | C |
| ATOM | 6115 | CB | GLN | A | 180 | 36.150 | 5.101 | 17.822 | 1.00 | 39.90 | C |
| ATOM | 6118 | CG | GLN | A | 180 | 35.443 | 4.390 | 19.003 | 1.00 | 46.03 | C |
| ATOM | 6121 | CD | GLN | A | 180 | 36.186 | 4.482 | 20.354 | 1.00 | 52.50 | C |
| ATOM | 6122 | OE1 | GLN | A | 180 | 37.398 | 4.785 | 20.399 | 1.00 | 56.81 | O |
| ATOM | 6123 | NE2 | GLN | A | 180 | 35.454 | 4.203 | 21.469 | 1.00 | 54.63 | N |

FIG.5-25

| | | | | | | | | | | | | |
|---|---|---|---|---|---|---|---|---|---|---|---|---|
| ATOM | 6126 | C | GLN | A | 180 | 37.306 | 7.275 | 17.077 | 1.00 | 39.85 | C |
| ATOM | 6127 | O | GLN | A | 180 | 38.433 | 7.669 | 17.483 | 1.00 | 41.27 | O |
| ATOM | 6129 | N | GLU | A | 181 | 36.879 | 7.516 | 15.831 | 1.00 | 40.96 | N |
| ATOM | 6130 | CA | GLU | A | 181 | 37.761 | 8.110 | 14.826 | 1.00 | 39.80 | C |
| ATOM | 6132 | CB | GLU | A | 181 | 37.119 | 8.145 | 13.460 | 1.00 | 40.41 | C |
| ATOM | 6135 | CG | GLU | A | 181 | 36.979 | 6.829 | 12.791 | 1.00 | 41.90 | C |
| ATOM | 6138 | CD | GLU | A | 181 | 38.322 | 6.124 | 12.546 | 1.00 | 45.90 | C |
| ATOM | 6139 | OE1 | GLU | A | 181 | 39.341 | 6.806 | 12.241 | 1.00 | 46.42 | O |
| ATOM | 6140 | OE2 | GLU | A | 181 | 38.324 | 4.879 | 12.692 | 1.00 | 49.22 | O |
| ATOM | 6141 | C | GLU | A | 181 | 38.160 | 9.503 | 15.187 | 1.00 | 40.61 | C |
| ATOM | 6142 | O | GLU | A | 181 | 39.278 | 9.956 | 14.826 | 1.00 | 39.32 | O |
| ATOM | 6144 | N | MET | A | 182 | 37.266 | 10.245 | 15.851 | 1.00 | 39.52 | N |
| ATOM | 6145 | CA | MET | A | 182 | 37.613 | 11.608 | 16.256 | 1.00 | 38.77 | C |
| ATOM | 6147 | CB | MET | A | 182 | 36.389 | 12.354 | 16.759 | 1.00 | 37.91 | C |
| ATOM | 6150 | CG | MET | A | 182 | 35.416 | 12.823 | 15.688 | 1.00 | 37.77 | C |
| ATOM | 6153 | SD | MET | A | 182 | 34.183 | 13.936 | 16.362 | 1.00 | 35.31 | S |
| ATOM | 6154 | CE | MET | A | 182 | 33.315 | 14.409 | 14.804 | 1.00 | 34.42 | C |
| ATOM | 6158 | C | MET | A | 182 | 38.675 | 11.566 | 17.383 | 1.00 | 39.15 | C |
| ATOM | 6159 | O | MET | A | 182 | 39.660 | 12.326 | 17.380 | 1.00 | 38.70 | O |
| ATOM | 6161 | N | ALA | A | 183 | 38.418 | 10.697 | 18.342 | 1.00 | 39.85 | N |
| ATOM | 6162 | CA | ALA | A | 183 | 39.359 | 10.386 | 19.434 | 1.00 | 41.20 | C |
| ATOM | 6164 | CB | ALA | A | 183 | 38.798 | 9.292 | 20.328 | 1.00 | 40.66 | C |
| ATOM | 6168 | C | ALA | A | 183 | 40.740 | 10.022 | 18.879 | 1.00 | 41.54 | C |
| ATOM | 6169 | O | ALA | A | 183 | 41.685 | 10.691 | 19.171 | 1.00 | 42.10 | O |
| ATOM | 6171 | N | SER | A | 184 | 40.810 | 9.050 | 17.978 | 1.00 | 43.07 | N |
| ATOM | 6172 | CA | SER | A | 184 | 42.041 | 8.737 | 17.237 | 1.00 | 43.27 | C |
| ATOM | 6174 | CB | SER | A | 184 | 41.755 | 7.761 | 16.096 | 1.00 | 43.55 | C |
| ATOM | 6177 | OG | SER | A | 184 | 41.410 | 6.515 | 16.639 | 1.00 | 47.00 | O |
| ATOM | 6179 | C | SER | A | 184 | 42.769 | 9.882 | 16.592 | 1.00 | 43.28 | C |
| ATOM | 6180 | O | SER | A | 184 | 43.941 | 9.719 | 16.261 | 1.00 | 41.85 | O |
| ATOM | 6182 | N | ARG | A | 185 | 42.091 | 11.006 | 16.330 | 1.00 | 42.56 | N |
| ATOM | 6183 | CA | ARG | A | 185 | 42.778 | 12.132 | 15.684 | 1.00 | 41.98 | C |
| ATOM | 6185 | CB | ARG | A | 185 | 42.035 | 12.541 | 14.427 | 1.00 | 42.71 | C |
| ATOM | 6188 | CG | ARG | A | 185 | 42.112 | 11.513 | 13.286 | 1.00 | 44.32 | C |
| ATOM | 6191 | CD | ARG | A | 185 | 40.772 | 11.375 | 12.601 | 1.00 | 46.31 | C |
| ATOM | 6194 | NE | ARG | A | 185 | 40.841 | 11.600 | 11.167 | 1.00 | 48.70 | N |
| ATOM | 6196 | CZ | ARG | A | 185 | 40.855 | 10.662 | 10.232 | 1.00 | 50.47 | C |
| ATOM | 6197 | NH1 | ARG | A | 185 | 40.810 | 9.367 | 10.552 | 1.00 | 54.56 | N |
| ATOM | 6200 | NH2 | ARG | A | 185 | 40.915 | 11.028 | 8.954 | 1.00 | 51.36 | N |
| ATOM | 6203 | C | ARG | A | 185 | 42.921 | 13.280 | 16.643 | 1.00 | 41.46 | C |
| ATOM | 6204 | O | ARG | A | 185 | 43.389 | 14.357 | 16.255 | 1.00 | 42.04 | O |
| ATOM | 6206 | N | SER | A | 186 | 42.559 | 13.049 | 17.907 | 1.00 | 40.15 | N |
| ATOM | 6207 | CA | SER | A | 186 | 42.690 | 14.080 | 18.895 | 1.00 | 40.46 | C |
| ATOM | 6209 | CB | SER | A | 186 | 44.168 | 14.565 | 18.967 | 1.00 | 41.03 | C |
| ATOM | 6212 | OG | SER | A | 186 | 45.057 | 13.465 | 18.793 | 1.00 | 41.70 | O |
| ATOM | 6214 | C | SER | A | 186 | 41.722 | 15.225 | 18.625 | 1.00 | 40.66 | C |
| ATOM | 6215 | O | SER | A | 186 | 42.049 | 16.387 | 18.830 | 1.00 | 41.52 | O |
| ATOM | 6217 | N | LEU | A | 187 | 40.516 | 14.903 | 18.137 | 1.00 | 40.17 | N |
| ATOM | 6218 | CA | LEU | A | 187 | 39.545 | 15.937 | 17.811 | 1.00 | 39.38 | C |
| ATOM | 6220 | CB | LEU | A | 187 | 39.071 | 15.792 | 16.342 | 1.00 | 37.70 | C |
| ATOM | 6223 | CG | LEU | A | 187 | 40.052 | 16.060 | 15.231 | 1.00 | 35.50 | C |
| ATOM | 6225 | CD1 | LEU | A | 187 | 39.533 | 15.545 | 13.893 | 1.00 | 37.73 | C |
| ATOM | 6229 | CD2 | LEU | A | 187 | 40.413 | 17.519 | 15.118 | 1.00 | 34.91 | C |
| ATOM | 6233 | C | LEU | A | 187 | 38.335 | 15.825 | 18.718 | 1.00 | 40.04 | C |
| ATOM | 6234 | O | LEU | A | 187 | 37.467 | 16.714 | 18.680 | 1.00 | 40.14 | O |
| ATOM | 6236 | N | TRP | A | 188 | 38.254 | 14.728 | 19.485 | 1.00 | 40.63 | N |
| ATOM | 6237 | CA | TRP | A | 188 | 37.047 | 14.372 | 20.247 | 1.00 | 41.70 | C |
| ATOM | 6239 | CB | TRP | A | 188 | 37.019 | 12.876 | 20.680 | 1.00 | 41.23 | C |
| ATOM | 6242 | CG | TRP | A | 188 | 35.865 | 12.590 | 21.612 | 1.00 | 42.78 | C |
| ATOM | 6243 | CD1 | TRP | A | 188 | 35.933 | 12.377 | 22.974 | 1.00 | 43.61 | C |
| ATOM | 6245 | NE1 | TRP | A | 188 | 34.664 | 12.209 | 23.495 | 1.00 | 41.33 | N |
| ATOM | 6247 | CE2 | TRP | A | 188 | 33.745 | 12.333 | 22.489 | 1.00 | 43.56 | C |
| ATOM | 6248 | CD2 | TRP | A | 188 | 34.458 | 12.603 | 21.287 | 1.00 | 41.64 | C |

FIG.5-26

| | | | | | | | | | | | |
|---|---|---|---|---|---|---|---|---|---|---|---|
| ATOM | 6249 | CE3 | TRP | A | 188 | 33.738 | 12.766 | 20.097 | 1.00 | 38.96 | C |
| ATOM | 6251 | CZ3 | TRP | A | 188 | 32.347 | 12.690 | 20.142 | 1.00 | 38.37 | C |
| ATOM | 6253 | CH2 | TRP | A | 188 | 31.658 | 12.452 | 21.351 | 1.00 | 40.60 | C |
| ATOM | 6255 | CZ2 | TRP | A | 188 | 32.331 | 12.261 | 22.533 | 1.00 | 42.31 | C |
| ATOM | 6257 | C | TRP | A | 188 | 36.821 | 15.323 | 21.417 | 1.00 | 42.95 | C |
| ATOM | 6258 | O | TRP | A | 188 | 35.773 | 15.966 | 21.514 | 1.00 | 42.21 | O |
| ATOM | 6260 | N | ASP | A | 189 | 37.832 | 15.487 | 22.267 | 1.00 | 44.68 | N |
| ATOM | 6261 | CA | ASP | A | 189 | 37.728 | 16.438 | 23.387 | 1.00 | 45.62 | C |
| ATOM | 6263 | CB | ASP | A | 189 | 39.089 | 16.690 | 24.078 | 1.00 | 46.90 | C |
| ATOM | 6266 | CG | ASP | A | 189 | 39.618 | 15.458 | 24.792 | 1.00 | 50.88 | C |
| ATOM | 6267 | OD1 | ASP | A | 189 | 38.856 | 14.464 | 24.951 | 1.00 | 57.27 | O |
| ATOM | 6268 | OD2 | ASP | A | 189 | 40.813 | 15.474 | 25.177 | 1.00 | 58.02 | O |
| ATOM | 6269 | C | ASP | A | 189 | 37.125 | 17.765 | 22.978 | 1.00 | 44.63 | C |
| ATOM | 6270 | O | ASP | A | 189 | 36.178 | 18.228 | 23.623 | 1.00 | 44.50 | O |
| ATOM | 6272 | N | SER | A | 190 | 37.629 | 18.368 | 21.909 | 1.00 | 43.98 | N |
| ATOM | 6273 | CA | SER | A | 190 | 37.135 | 19.698 | 21.536 | 1.00 | 43.64 | C |
| ATOM | 6275 | CB | SER | A | 190 | 38.034 | 20.373 | 20.535 | 1.00 | 44.12 | C |
| ATOM | 6278 | OG | SER | A | 190 | 37.320 | 21.490 | 19.984 | 1.00 | 42.51 | O |
| ATOM | 6280 | C | SER | A | 190 | 35.721 | 19.664 | 20.921 | 1.00 | 43.14 | C |
| ATOM | 6281 | O | SER | A | 190 | 34.929 | 20.549 | 21.165 | 1.00 | 44.73 | O |
| ATOM | 6283 | N | PHE | A | 191 | 35.449 | 18.659 | 20.092 | 1.00 | 42.12 | N |
| ATOM | 6284 | CA | PHE | A | 191 | 34.103 | 18.405 | 19.586 | 1.00 | 40.48 | C |
| ATOM | 6286 | CB | PHE | A | 191 | 34.103 | 17.229 | 18.602 | 1.00 | 38.37 | C |
| ATOM | 6289 | CG | PHE | A | 191 | 32.735 | 16.951 | 17.994 | 1.00 | 35.18 | C |
| ATOM | 6290 | CD1 | PHE | A | 191 | 32.162 | 17.840 | 17.115 | 1.00 | 31.73 | C |
| ATOM | 6292 | CE1 | PHE | A | 191 | 30.916 | 17.572 | 16.525 | 1.00 | 28.61 | C |
| ATOM | 6294 | CZ | PHE | A | 191 | 30.249 | 16.436 | 16.850 | 1.00 | 28.17 | C |
| ATOM | 6296 | CE2 | PHE | A | 191 | 30.790 | 15.514 | 17.715 | 1.00 | 30.21 | C |
| ATOM | 6298 | CD2 | PHE | A | 191 | 32.039 | 15.784 | 18.293 | 1.00 | 34.28 | C |
| ATOM | 6300 | C | PHE | A | 191 | 33.120 | 18.178 | 20.758 | 1.00 | 40.75 | C |
| ATOM | 6301 | O | PHE | A | 191 | 32.107 | 18.871 | 20.872 | 1.00 | 41.14 | O |
| ATOM | 6303 | N | ARG | A | 192 | 33.456 | 17.282 | 21.662 | 1.00 | 42.35 | N |
| ATOM | 6304 | CA | ARG | A | 192 | 32.569 | 17.012 | 22.783 | 1.00 | 44.44 | C |
| ATOM | 6306 | CB | ARG | A | 192 | 33.051 | 15.841 | 23.662 | 1.00 | 44.72 | C |
| ATOM | 6309 | CG | ARG | A | 192 | 32.136 | 15.580 | 24.891 | 1.00 | 49.27 | C |
| ATOM | 6312 | CD | ARG | A | 192 | 32.653 | 14.523 | 25.877 | 1.00 | 55.19 | C |
| ATOM | 6315 | NE | ARG | A | 192 | 34.062 | 14.741 | 26.241 | 1.00 | 60.10 | N |
| ATOM | 6317 | CZ | ARG | A | 192 | 34.508 | 15.720 | 27.034 | 1.00 | 64.70 | C |
| ATOM | 6318 | NH1 | ARG | A | 192 | 33.664 | 16.614 | 27.576 | 1.00 | 65.66 | N |
| ATOM | 6321 | NH2 | ARG | A | 192 | 35.817 | 15.824 | 27.271 | 1.00 | 64.46 | N |
| ATOM | 6324 | C | ARG | A | 192 | 32.302 | 18.237 | 23.622 | 1.00 | 44.96 | C |
| ATOM | 6325 | O | ARG | A | 192 | 31.224 | 18.349 | 24.187 | 1.00 | 45.11 | O |
| ATOM | 6327 | N | GLN | A | 193 | 33.238 | 19.169 | 23.691 | 1.00 | 46.51 | N |
| ATOM | 6328 | CA | GLN | A | 193 | 33.043 | 20.382 | 24.510 | 1.00 | 47.96 | C |
| ATOM | 6330 | CB | GLN | A | 193 | 34.407 | 20.906 | 25.012 | 1.00 | 48.06 | C |
| ATOM | 6333 | CG | GLN | A | 193 | 35.007 | 20.014 | 26.104 | 1.00 | 51.75 | C |
| ATOM | 6336 | CD | GLN | A | 193 | 36.350 | 20.516 | 26.638 | 1.00 | 54.61 | C |
| ATOM | 6337 | OE1 | GLN | A | 193 | 37.410 | 19.937 | 26.341 | 1.00 | 56.62 | O |
| ATOM | 6338 | NE2 | GLN | A | 193 | 36.311 | 21.594 | 27.434 | 1.00 | 55.66 | N |
| ATOM | 6341 | C | GLN | A | 193 | 32.253 | 21.552 | 23.879 | 1.00 | 48.24 | C |
| ATOM | 6342 | O | GLN | A | 193 | 31.846 | 22.474 | 24.583 | 1.00 | 48.42 | O |
| ATOM | 6344 | N | SER | A | 194 | 32.052 | 21.546 | 22.569 | 1.00 | 48.36 | N |
| ATOM | 6345 | CA | SER | A | 194 | 31.495 | 22.723 | 21.896 | 1.00 | 48.16 | C |
| ATOM | 6347 | CB | SER | A | 194 | 32.097 | 22.849 | 20.484 | 1.00 | 48.00 | C |
| ATOM | 6350 | OG | SER | A | 194 | 32.187 | 21.578 | 19.842 | 1.00 | 48.78 | O |
| ATOM | 6352 | C | SER | A | 194 | 29.972 | 22.751 | 21.789 | 1.00 | 47.98 | C |
| ATOM | 6353 | O | SER | A | 194 | 29.428 | 23.698 | 21.243 | 1.00 | 48.12 | O |
| ATOM | 6355 | N | GLU | A | 195 | 29.270 | 21.739 | 22.270 | 1.00 | 48.15 | N |
| ATOM | 6356 | CA | GLU | A | 195 | 27.818 | 21.734 | 22.083 | 1.00 | 49.04 | C |
| ATOM | 6358 | CB | GLU | A | 195 | 27.248 | 20.337 | 22.246 | 1.00 | 47.73 | C |
| ATOM | 6361 | CG | GLU | A | 195 | 25.708 | 20.275 | 21.988 | 1.00 | 47.51 | C |
| ATOM | 6364 | CD | GLU | A | 195 | 25.184 | 18.866 | 21.954 | 1.00 | 40.56 | C |
| ATOM | 6365 | OE1 | GLU | A | 195 | 25.951 | 17.957 | 21.535 | 1.00 | 38.62 | O |

FIG.5-27

| | | | | | | | | | | | | |
|---|---|---|---|---|---|---|---|---|---|---|---|---|
| ATOM | 6366 | OE2 | GLU | A | 195 | 24.018 | 18.661 | 22.355 | 1.00 | 41.85 | | O |
| ATOM | 6367 | C | GLU | A | 195 | 27.106 | 22.774 | 23.002 | 1.00 | 50.42 | | C |
| ATOM | 6368 | O | GLU | A | 195 | 27.407 | 22.858 | 24.191 | 1.00 | 50.12 | | O |
| ATOM | 6370 | N | ARG | A | 196 | 26.208 | 23.572 | 22.413 | 1.00 | 52.14 | | N |
| ATOM | 6371 | CA | ARG | A | 196 | 25.535 | 24.719 | 23.085 | 1.00 | 54.22 | | C |
| ATOM | 6373 | CB | ARG | A | 196 | 25.553 | 25.970 | 22.178 | 1.00 | 54.91 | | C |
| ATOM | 6376 | CG | ARG | A | 196 | 26.913 | 26.280 | 21.555 | 1.00 | 58.70 | | C |
| ATOM | 6379 | CD | ARG | A | 196 | 27.193 | 27.801 | 21.309 | 1.00 | 63.36 | | C |
| ATOM | 6382 | NE | ARG | A | 196 | 28.625 | 28.093 | 21.546 | 1.00 | 67.68 | | N |
| ATOM | 6384 | CZ | ARG | A | 196 | 29.219 | 29.289 | 21.466 | 1.00 | 69.92 | | C |
| ATOM | 6385 | NH1 | ARG | A | 196 | 28.536 | 30.386 | 21.126 | 1.00 | 70.56 | | N |
| ATOM | 6388 | NH2 | ARG | A | 196 | 30.526 | 29.380 | 21.728 | 1.00 | 70.21 | | N |
| ATOM | 6391 | C | ARG | A | 196 | 24.073 | 24.422 | 23.392 | 1.00 | 53.67 | | C |
| ATOM | 6392 | O | ARG | A | 196 | 23.387 | 23.853 | 22.541 | 1.00 | 53.86 | | O |
| ATOM | 6394 | MN | MN | A | 495 | 17.177 | 17.733 | 14.554 | 1.00 | 27.34 | | MN |
| ATOM | 6395 | MN | MN | A | 496 | 16.334 | 20.007 | 11.605 | 1.00 | 25.22 | | MN |
| ATOM | 6396 | P | U | A | 910 | 18.219 | 20.415 | 14.571 | 1.00 | 27.05 | | P |
| ATOM | 6397 | O1P | U | A | 910 | 17.604 | 21.673 | 15.082 | 1.00 | 23.04 | | O |
| ATOM | 6398 | O2P | U | A | 910 | 18.577 | 19.263 | 15.469 | 1.00 | 31.98 | | O |
| ATOM | 6399 | O5* | U | A | 910 | 19.574 | 21.020 | 13.967 | 1.00 | 23.57 | | O |
| ATOM | 6400 | C5* | U | A | 910 | 20.367 | 20.247 | 13.117 | 1.00 | 24.39 | | C |
| ATOM | 6403 | C4* | U | A | 910 | 21.784 | 20.705 | 13.215 | 1.00 | 28.06 | | C |
| ATOM | 6405 | O4* | U | A | 910 | 21.815 | 21.996 | 12.589 | 1.00 | 26.37 | | O |
| ATOM | 6406 | C1* | U | A | 910 | 22.248 | 22.933 | 13.474 | 1.00 | 30.01 | | C |
| ATOM | 6408 | N1 | U | A | 910 | 21.536 | 24.181 | 13.181 | 1.00 | 32.01 | | N |
| ATOM | 6409 | C2 | U | A | 910 | 22.256 | 25.356 | 12.994 | 1.00 | 32.20 | | C |
| ATOM | 6410 | O2 | U | A | 910 | 23.483 | 25.405 | 12.991 | 1.00 | 34.28 | | O |
| ATOM | 6411 | N3 | U | A | 910 | 21.467 | 26.454 | 12.746 | 1.00 | 28.48 | | N |
| ATOM | 6413 | C4 | U | A | 910 | 20.056 | 26.518 | 12.730 | 1.00 | 33.14 | | C |
| ATOM | 6414 | O4 | U | A | 910 | 19.445 | 27.586 | 12.504 | 1.00 | 34.24 | | O |
| ATOM | 6415 | C5 | U | A | 910 | 19.400 | 25.246 | 12.961 | 1.00 | 30.32 | | C |
| ATOM | 6417 | C6 | U | A | 910 | 20.134 | 24.159 | 13.139 | 1.00 | 31.66 | | C |
| ATOM | 6419 | C2* | U | A | 910 | 22.008 | 22.384 | 14.874 | 1.00 | 31.55 | | C |
| ATOM | 6421 | O2* | U | A | 910 | 22.837 | 23.039 | 15.841 | 1.00 | 37.61 | | O |
| ATOM | 6423 | C3* | U | A | 910 | 22.338 | 20.935 | 14.627 | 1.00 | 30.46 | | C |
| ATOM | 6425 | O3* | U | A | 910 | 23.743 | 20.749 | 14.670 | 1.00 | 31.33 | | O |
| ATOM | 6426 | O3P | U | A | 910 | 17.461 | 19.664 | 13.515 | 1.00 | 23.08 | | O |
| ATOM | 1588 | OH2 | WAT | A | 1 | 14.505 | 20.354 | 12.931 | 1.00 | 21.34 | A | O |
| ATOM | 1589 | OH2 | WAT | A | 2 | 14.846 | 20.240 | 9.761 | 1.00 | 23.05 | A | O |
| ATOM | 1591 | OH2 | WAT | A | 3 | 18.587 | 22.283 | 9.729 | 1.00 | 43.33 | A | O |
| ATOM | 1592 | OH2 | WAT | A | 4 | 16.862 | 22.040 | 11.589 | 1.00 | 22.93 | A | O |
| ATOM | 1593 | OH2 | WAT | A | 5 | 21.286 | 20.252 | 8.173 | 1.00 | 26.14 | A | O |
| ATOM | 1594 | OH2 | WAT | A | 6 | 27.845 | 21.922 | 17.662 | 1.00 | 36.53 | A | O |
| ATOM | 1595 | OH2 | WAT | A | 7 | 29.576 | 24.494 | -0.774 | 1.00 | 26.71 | A | O |
| ATOM | 1597 | OH2 | WAT | A | 8 | 20.137 | 24.907 | 2.814 | 1.00 | 35.50 | A | O |
| ATOM | 1598 | OH2 | WAT | A | 9 | 16.624 | 30.565 | 4.822 | 1.00 | 24.94 | A | O |
| ATOM | 1599 | OH2 | WAT | A | 10 | 11.003 | 7.856 | 18.224 | 1.00 | 25.82 | A | O |
| ATOM | 1600 | OH2 | WAT | A | 11 | 21.990 | 18.523 | 10.066 | 1.00 | 21.07 | A | O |
| ATOM | 1601 | OH2 | WAT | A | 12 | 34.615 | 22.163 | 3.521 | 1.00 | 31.63 | A | O |
| ATOM | 1602 | OH2 | WAT | A | 13 | 3.807 | 28.657 | 3.719 | 1.00 | 24.89 | A | O |
| ATOM | 1603 | OH2 | WAT | A | 14 | 3.370 | 27.070 | 7.393 | 1.00 | 29.15 | A | O |
| ATOM | 1604 | OH2 | WAT | A | 15 | 7.739 | 8.326 | 14.326 | 1.00 | 33.16 | A | O |
| ATOM | 1605 | OH2 | WAT | A | 16 | 11.825 | 12.412 | 1.504 | 1.00 | 39.80 | A | O |

END

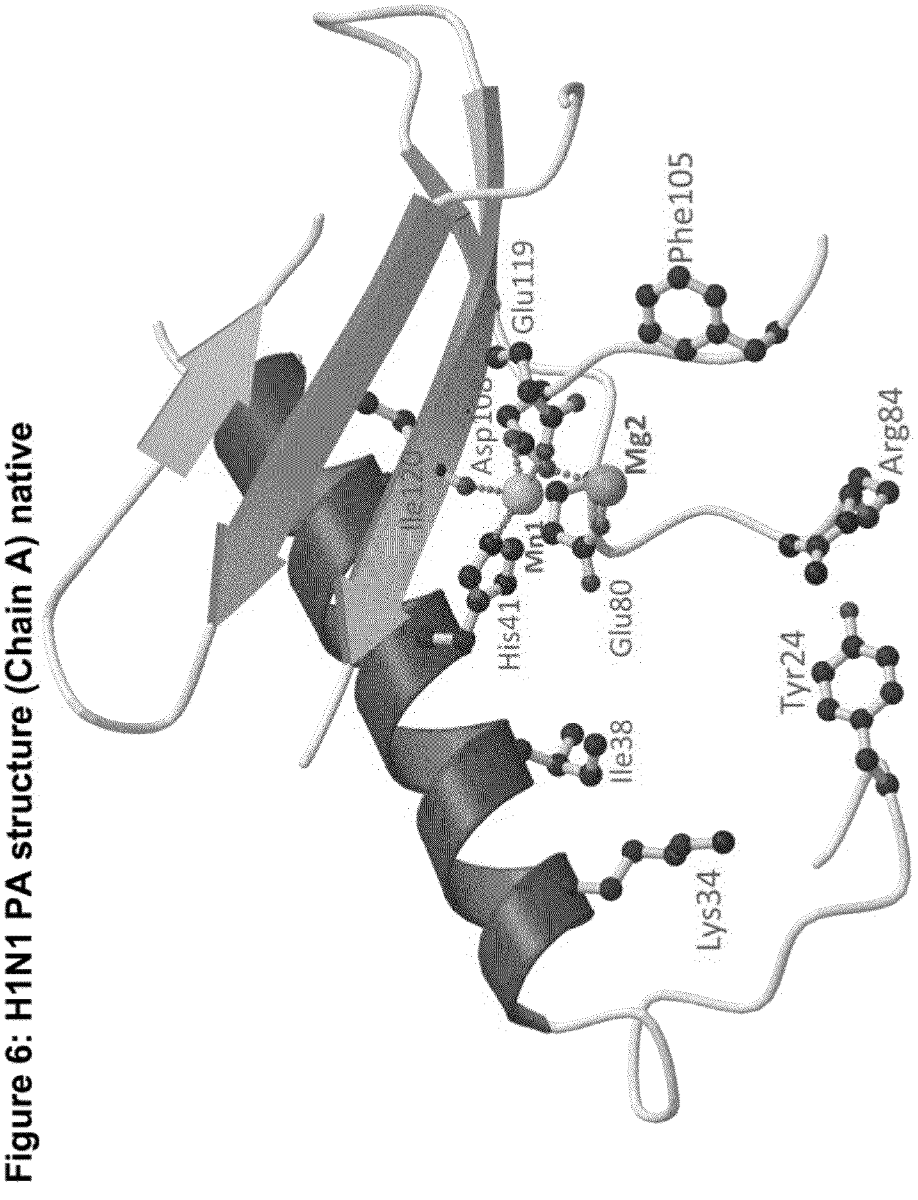
Figure 6: H1N1 PA structure (Chain A) native

Figure 7A: H1N1 PA structure (Chain A) with EMBL-R05-3
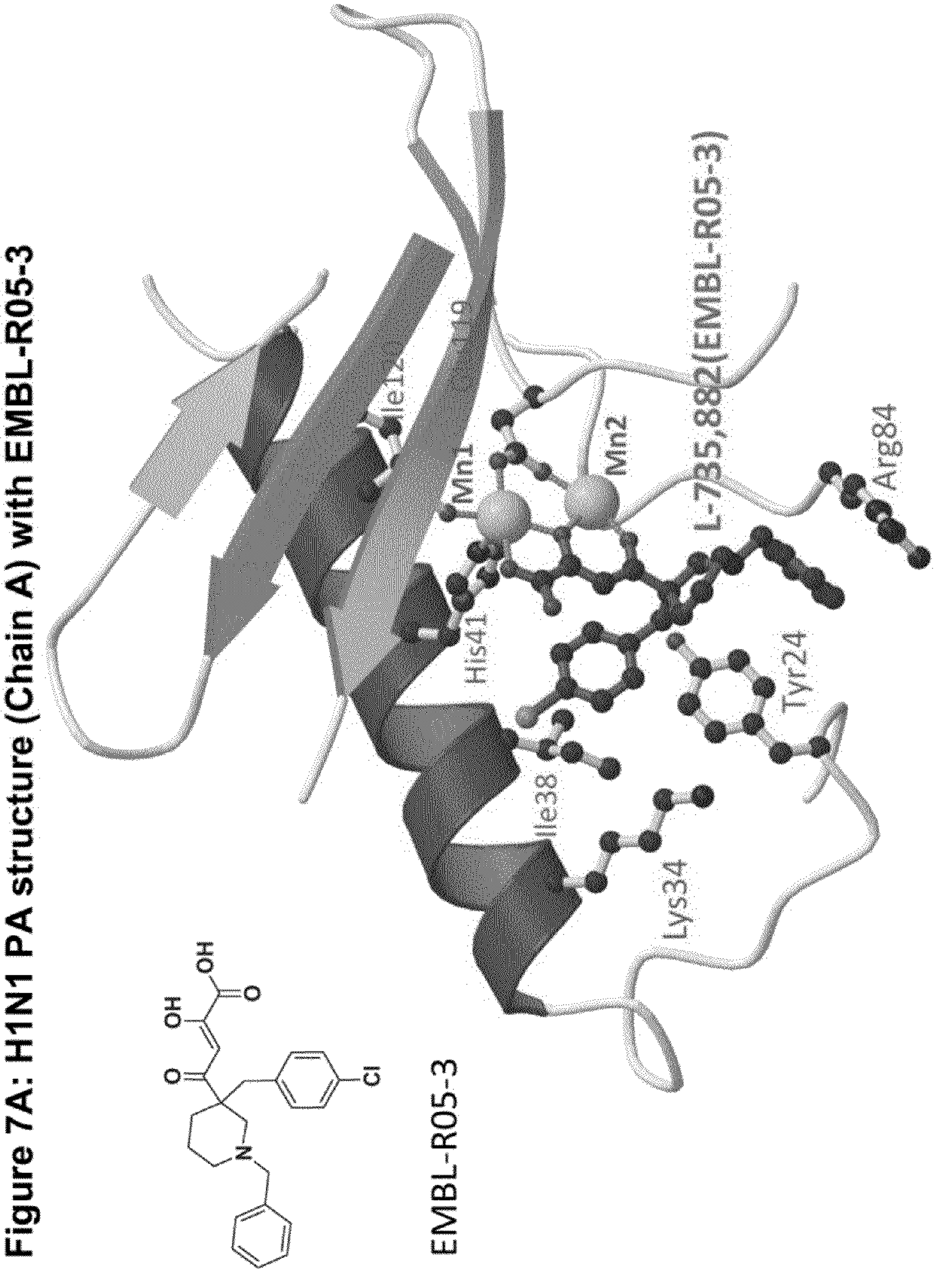

Figure 7B: H1N1 PA structure (Chain A) with EMBL-R05-3
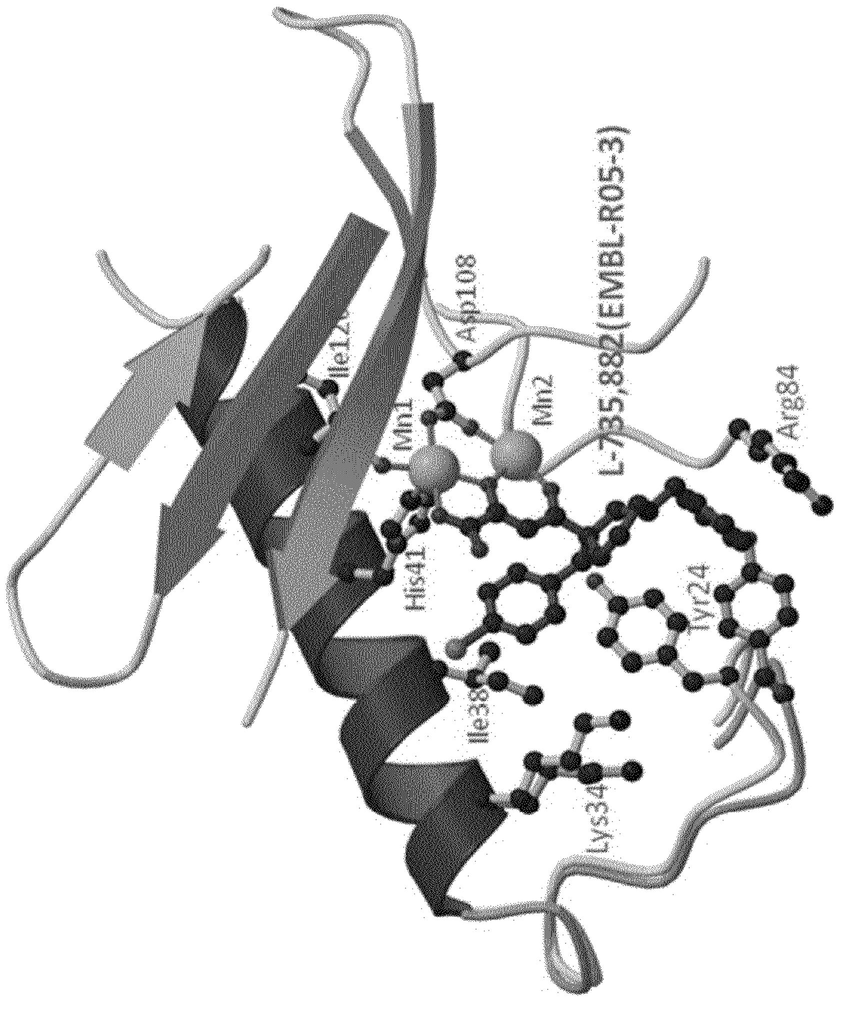

Figure 8: H1N1 PA structure (Chain D) with EMBL-R05-3
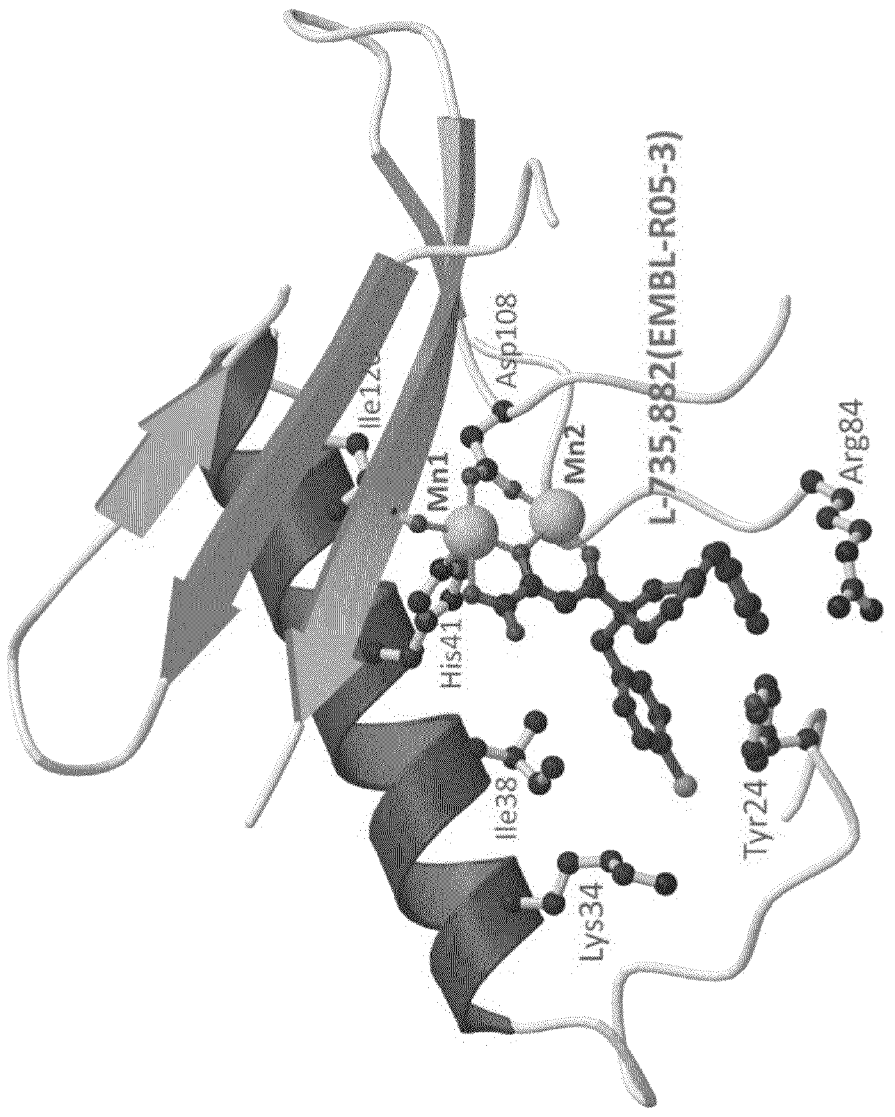

Figure 9: H1N1 PA structure (Chain A) with EMBL-R05-2
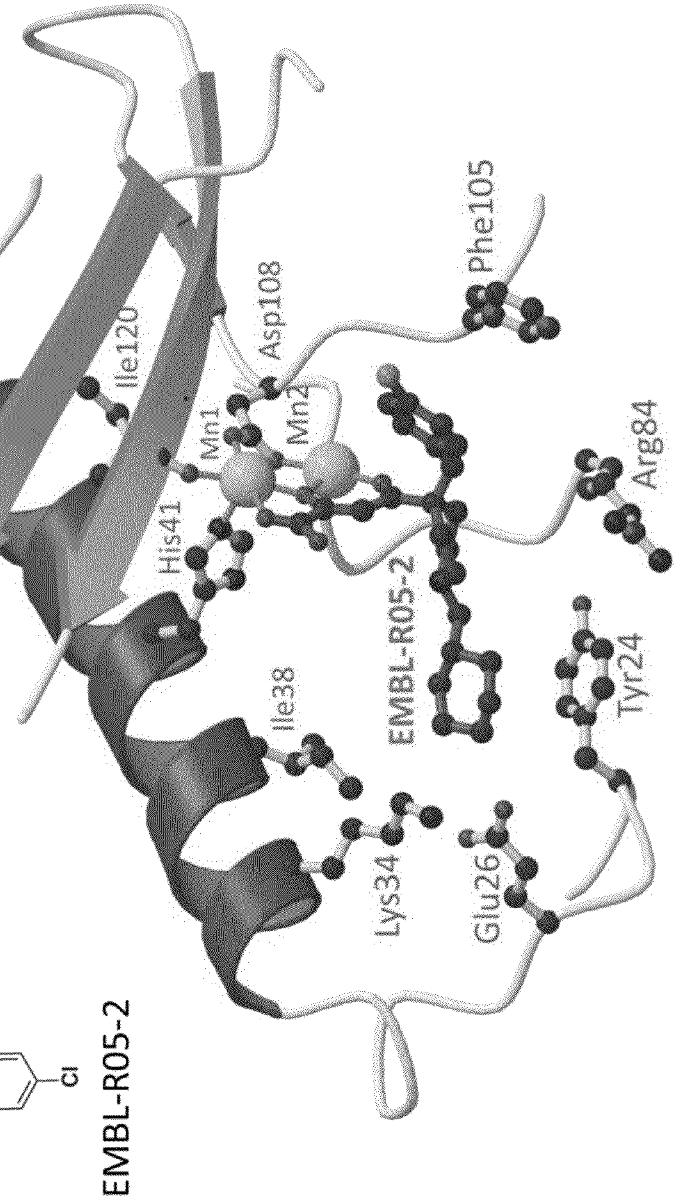
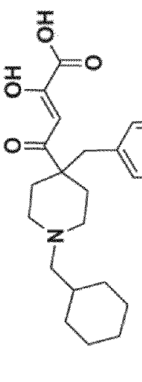
EMBL-R05-2

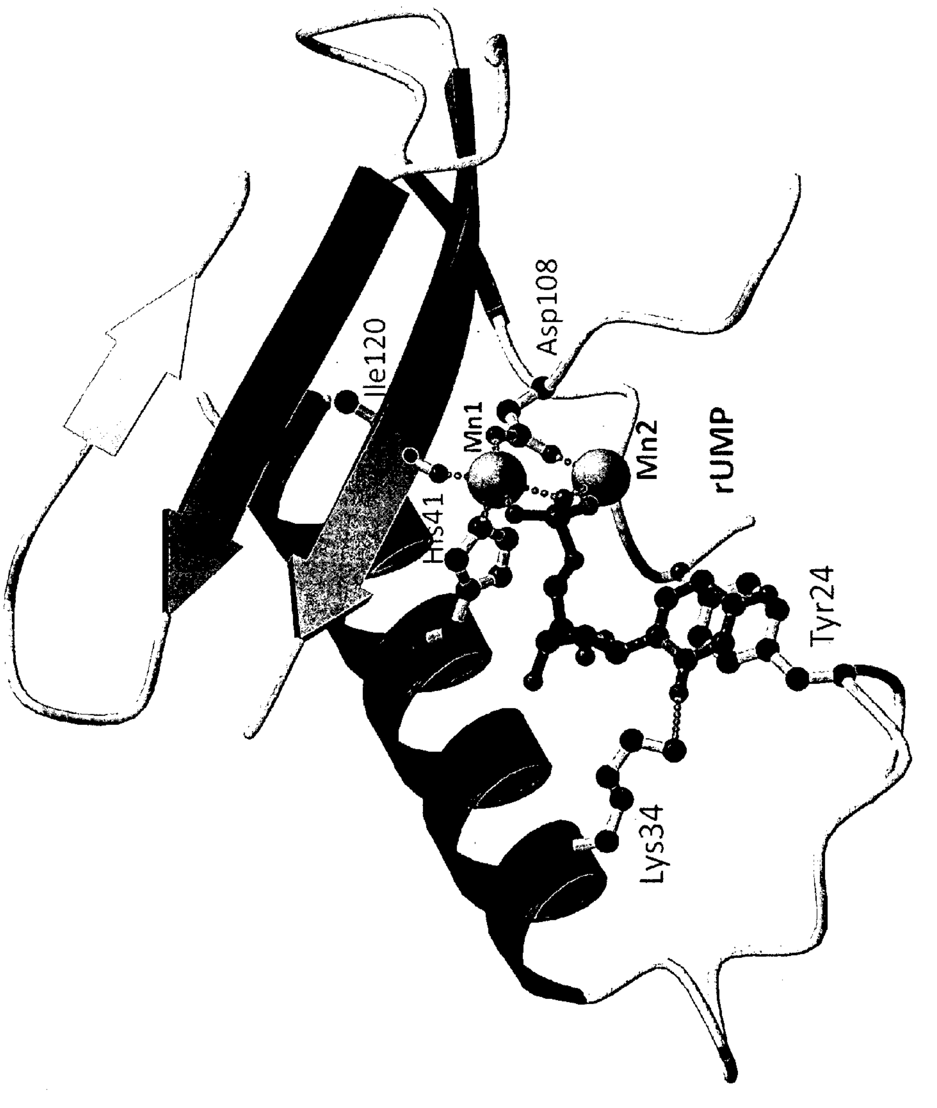
Figure 10: H1N1 PA structure (Chain A) with ribo-Uridine Monophosphate

Figure 11
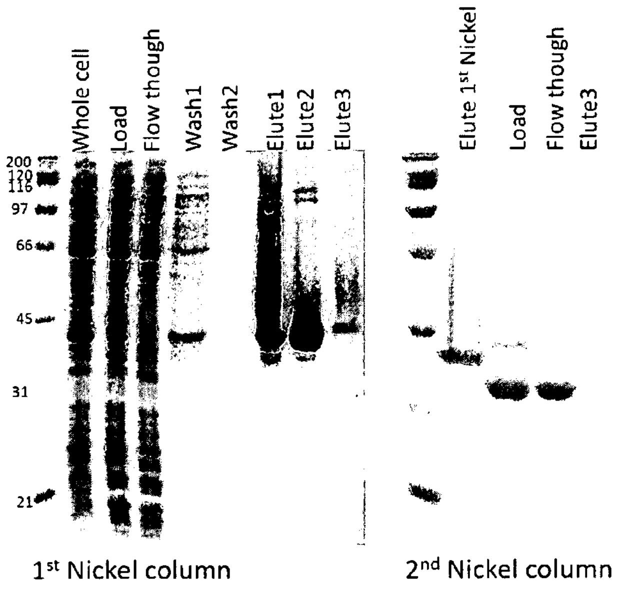
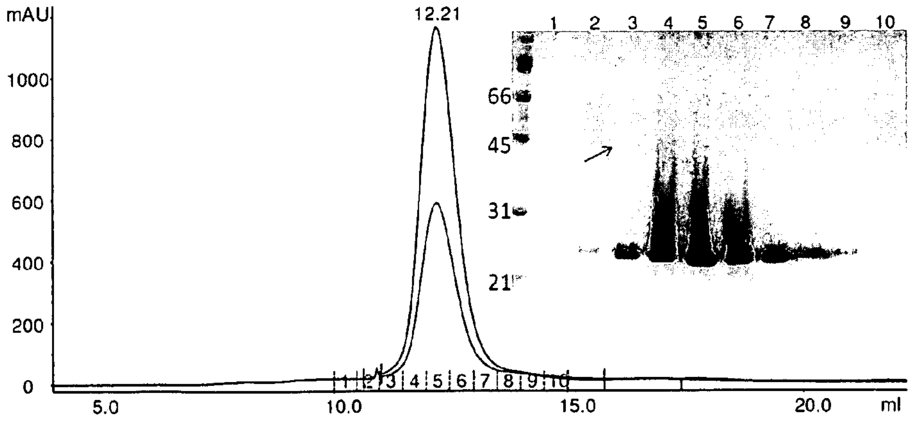

FIG.15-1

Figure 15: H1N1 polypeptide fragment (chain A) with bound EMBL-R05-1

```
HEADER    ----                                   XX-XXX-XX   xxxx
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   1.90
REMARK   3   RESOLUTION RANGE LOW  (ANGSTROMS) :  65.01
REMARK   3   DATA CUTOFF            (SIGMA(F)) : NONE
REMARK   3   COMPLETENESS FOR RANGE        (%) :  99.79
REMARK   3   NUMBER OF REFLECTIONS             :   15580
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.20827
REMARK   3   R VALUE            (WORKING SET) :  0.20610
REMARK   3   FREE R VALUE                     :  0.25114
REMARK   3   FREE R VALUE TEST SET SIZE   (%) :  5.1
REMARK   3   FREE R VALUE TEST SET COUNT      :   830
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    1.899
REMARK   3   BIN RESOLUTION RANGE LOW            :    1.949
REMARK   3   REFLECTION IN BIN     (WORKING SET) :     1092
REMARK   3   BIN COMPLETENESS (WORKING+TEST) (%) :    98.15
REMARK   3   BIN R VALUE           (WORKING SET) :    0.317
REMARK   3   BIN FREE R VALUE SET COUNT          :       77
REMARK   3   BIN FREE R VALUE                    :    0.355
REMARK   3
REMARK   3  NUMBER OF NON-HYDROGEN ATOMS USED IN REFINEMENT.
REMARK   3   ALL ATOMS                 :     1592
REMARK   3
REMARK   3  B VALUES.
REMARK   3   FROM WILSON PLOT           (A**2) : NULL
REMARK   3   MEAN B VALUE      (OVERALL, A**2) :  30.699
REMARK   3   OVERALL ANISOTROPIC B VALUE.
REMARK   3    B11 (A**2) :     2.00
REMARK   3    B22 (A**2) :     2.00
REMARK   3    B33 (A**2) :    -4.00
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.035
REMARK   3   ESU BASED ON FREE R VALUE                       (A):   0.033
REMARK   3   ESU BASED ON MAXIMUM LIKELIHOOD                 (A):   0.084
REMARK   3   ESU FOR B VALUES BASED ON MAXIMUM LIKELIHOOD (A**2):   3.129
REMARK   3
REMARK   3 CORRELATION COEFFICIENTS.
REMARK   3   CORRELATION COEFFICIENT FO-FC      :   0.952
REMARK   3   CORRELATION COEFFICIENT FO-FC FREE :   0.939
REMARK   3
```

FIG.15-2

```
REMARK   3  RMS DEVIATIONS FROM IDEAL VALUES        COUNT    RMS    WEIGHT
REMARK   3   BOND LENGTHS REFINED ATOMS        (A):  1522 ; 0.022 ; 0.022
REMARK   3   BOND LENGTHS OTHERS               (A):  1075 ; 0.002 ; 0.020
REMARK   3   BOND ANGLES REFINED ATOMS   (DEGREES):  2045 ; 1.843 ; 1.966
REMARK   3   BOND ANGLES OTHERS          (DEGREES):  2588 ; 1.007 ; 3.000
REMARK   3   TORSION ANGLES, PERIOD 1    (DEGREES):   173 ; 5.556 ; 5.000
REMARK   3   TORSION ANGLES, PERIOD 2    (DEGREES):    78 ;34.734 ;23.333
REMARK   3   TORSION ANGLES, PERIOD 3    (DEGREES):   279 ;14.663 ;15.000
REMARK   3   TORSION ANGLES, PERIOD 4    (DEGREES):    13 ;17.969 ;15.000
REMARK   3   CHIRAL-CENTER RESTRAINTS       (A**3):   215 ; 0.111 ; 0.200
REMARK   3   GENERAL PLANES REFINED ATOMS      (A):  1658 ; 0.010 ; 0.020
REMARK   3   GENERAL PLANES OTHERS             (A):   340 ; 0.004 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):   878 ; 1.390 ; 1.500
REMARK   3   MAIN-CHAIN BOND OTHER ATOMS    (A**2):   353 ; 0.396 ; 1.500
REMARK   3   MAIN-CHAIN ANGLE REFINED ATOMS (A**2):  1418 ; 2.403 ; 2.000
REMARK   3   SIDE-CHAIN BOND REFINED ATOMS  (A**2):   644 ; 3.554 ; 3.000
REMARK   3   SIDE-CHAIN ANGLE REFINED ATOMS (A**2):   627 ; 5.783 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
LINKR            GLY A  52                      LYS A  73               gap
LINKR            LYS A 139                      GLU A 141               gap
CRYST1   75.060   75.060  120.050  90.00  90.00 120.00 P 62 2 2
SCALE1      0.013323  0.007692  0.000000        0.00000
SCALE2      0.000000  0.015384  0.000000        0.00000
SCALE3      0.000000  0.000000  0.008330        0.00000
ATOM      1  N   ALA A   0      32.705   9.904  20.915  1.00 46.80           N
ATOM      2  CA  ALA A   0      34.010  10.013  21.658  1.00 46.90           C
ATOM      4  CB  ALA A   0      34.129   8.971  22.756  1.00 46.72           C
ATOM      8  C   ALA A   0      35.274   9.961  20.738  1.00 45.78           C
ATOM      9  O   ALA A   0      35.571   8.954  20.084  1.00 48.51           O
ATOM     13  N   MET A   1      36.021  11.036  20.730  1.00 45.20           N
ATOM     14  CA  MET A   1      37.196  11.143  19.801  1.00 44.87           C
ATOM     16  CB  MET A   1      37.842  12.491  19.948  1.00 43.94           C
ATOM     19  CG  MET A   1      39.041  12.697  19.045  1.00 43.15           C
ATOM     22  SD  MET A   1      38.629  12.410  17.284  1.00 38.41           S
ATOM     23  CE  MET A   1      38.364  14.091  17.050  1.00 30.85           C
ATOM     27  C   MET A   1      38.222  10.049  20.005  1.00 44.30           C
ATOM     28  O   MET A   1      38.737   9.461  19.057  1.00 43.72           O
ATOM     30  N   GLU A   2      38.510   9.716  21.259  1.00 45.08           N
ATOM     31  CA  GLU A   2      39.458   8.627  21.499  1.00 45.07           C
```

FIG.15-3

| | | | | | | | | | | | |
|---|---|---|---|---|---|---|---|---|---|---|---|
| ATOM | 33 | CB | GLU | A | 2 | 39.699 | 8.426 | 23.013 | 1.00 | 46.79 | C |
| ATOM | 36 | CG | GLU | A | 2 | 40.839 | 7.490 | 23.302 | 1.00 | 48.28 | C |
| ATOM | 39 | CD | GLU | A | 2 | 40.849 | 6.940 | 24.750 | 1.00 | 51.47 | C |
| ATOM | 40 | OE1 | GLU | A | 2 | 40.318 | 7.609 | 25.663 | 1.00 | 51.73 | O |
| ATOM | 41 | OE2 | GLU | A | 2 | 41.412 | 5.837 | 24.937 | 1.00 | 53.93 | O |
| ATOM | 42 | C | GLU | A | 2 | 39.015 | 7.339 | 20.841 | 1.00 | 44.15 | C |
| ATOM | 43 | O | GLU | A | 2 | 39.817 | 6.682 | 20.212 | 1.00 | 44.18 | O |
| ATOM | 45 | N | ASP | A | 3 | 37.736 | 6.958 | 20.961 | 1.00 | 43.00 | N |
| ATOM | 46 | CA | ASP | A | 3 | 37.230 | 5.748 | 20.260 | 1.00 | 42.31 | C |
| ATOM | 48 | CB | ASP | A | 3 | 35.831 | 5.336 | 20.768 | 1.00 | 43.36 | C |
| ATOM | 51 | CG | ASP | A | 3 | 35.898 | 4.734 | 22.204 | 1.00 | 46.34 | C |
| ATOM | 52 | OD1 | ASP | A | 3 | 36.548 | 3.673 | 22.411 | 1.00 | 45.20 | O |
| ATOM | 53 | OD2 | ASP | A | 3 | 35.375 | 5.402 | 23.096 | 1.00 | 51.42 | O |
| ATOM | 54 | C | ASP | A | 3 | 37.187 | 5.895 | 18.727 | 1.00 | 39.54 | C |
| ATOM | 55 | O | ASP | A | 3 | 37.526 | 5.003 | 18.015 | 1.00 | 36.33 | O |
| ATOM | 57 | N | PHE | A | 4 | 36.740 | 7.029 | 18.230 | 1.00 | 40.01 | N |
| ATOM | 58 | CA | PHE | A | 4 | 37.014 | 7.336 | 16.828 | 1.00 | 39.34 | C |
| ATOM | 60 | CB | PHE | A | 4 | 36.748 | 8.784 | 16.542 | 1.00 | 39.01 | C |
| ATOM | 63 | CG | PHE | A | 4 | 37.007 | 9.100 | 15.139 | 1.00 | 40.24 | C |
| ATOM | 64 | CD1 | PHE | A | 4 | 36.113 | 8.658 | 14.181 | 1.00 | 42.88 | C |
| ATOM | 66 | CE1 | PHE | A | 4 | 36.362 | 8.860 | 12.834 | 1.00 | 43.41 | C |
| ATOM | 68 | CZ | PHE | A | 4 | 37.548 | 9.481 | 12.450 | 1.00 | 40.84 | C |
| ATOM | 70 | CE2 | PHE | A | 4 | 38.445 | 9.923 | 13.390 | 1.00 | 39.99 | C |
| ATOM | 72 | CD2 | PHE | A | 4 | 38.206 | 9.697 | 14.741 | 1.00 | 38.67 | C |
| ATOM | 74 | C | PHE | A | 4 | 38.447 | 6.982 | 16.287 | 1.00 | 38.41 | C |
| ATOM | 75 | O | PHE | A | 4 | 38.632 | 6.188 | 15.326 | 1.00 | 37.84 | O |
| ATOM | 77 | N | VAL | A | 5 | 39.459 | 7.552 | 16.929 | 1.00 | 39.80 | N |
| ATOM | 78 | CA | VAL | A | 5 | 40.863 | 7.302 | 16.532 | 1.00 | 39.12 | C |
| ATOM | 80 | CB | VAL | A | 5 | 41.832 | 7.994 | 17.471 | 1.00 | 40.00 | C |
| ATOM | 82 | CG1 | VAL | A | 5 | 43.292 | 7.610 | 17.120 | 1.00 | 34.65 | C |
| ATOM | 86 | CG2 | VAL | A | 5 | 41.597 | 9.515 | 17.449 | 1.00 | 36.50 | C |
| ATOM | 90 | C | VAL | A | 5 | 41.203 | 5.854 | 16.534 | 1.00 | 40.24 | C |
| ATOM | 91 | O | VAL | A | 5 | 41.846 | 5.337 | 15.614 | 1.00 | 39.45 | O |
| ATOM | 93 | N | ARG | A | 6 | 40.734 | 5.130 | 17.555 | 1.00 | 41.95 | N |
| ATOM | 94 | CA | ARG | A | 6 | 40.971 | 3.692 | 17.573 | 1.00 | 42.22 | C |
| ATOM | 96 | CB | ARG | A | 6 | 40.695 | 3.128 | 18.979 | 1.00 | 42.67 | C |
| ATOM | 99 | CG | ARG | A | 6 | 41.687 | 3.685 | 19.986 | 1.00 | 45.01 | C |
| ATOM | 102 | CD | ARG | A | 6 | 41.385 | 3.360 | 21.445 | 1.00 | 46.86 | C |
| ATOM | 105 | NE | ARG | A | 6 | 42.179 | 4.217 | 22.335 | 1.00 | 46.22 | N |
| ATOM | 107 | CZ | ARG | A | 6 | 43.471 | 4.043 | 22.607 | 1.00 | 43.79 | C |
| ATOM | 108 | NH1 | ARG | A | 6 | 44.140 | 3.040 | 22.057 | 1.00 | 44.27 | N |
| ATOM | 111 | NH2 | ARG | A | 6 | 44.098 | 4.892 | 23.461 | 1.00 | 49.15 | N |
| ATOM | 114 | C | ARG | A | 6 | 40.257 | 2.919 | 16.459 | 1.00 | 42.70 | C |
| ATOM | 115 | O | ARG | A | 6 | 40.715 | 1.864 | 16.046 | 1.00 | 43.47 | O |
| ATOM | 117 | N | GLN | A | 7 | 39.157 | 3.442 | 15.934 | 1.00 | 43.72 | N |
| ATOM | 118 | CA | GLN | A | 7 | 38.462 | 2.741 | 14.826 | 1.00 | 43.50 | C |
| ATOM | 120 | CB | GLN | A | 7 | 36.942 | 2.884 | 14.934 | 1.00 | 44.41 | C |
| ATOM | 123 | CG | GLN | A | 7 | 36.334 | 4.286 | 14.587 | 1.00 | 49.44 | C |
| ATOM | 126 | CD | GLN | A | 7 | 35.161 | 4.240 | 13.571 | 1.00 | 56.61 | C |
| ATOM | 127 | OE1 | GLN | A | 7 | 34.923 | 3.214 | 12.911 | 1.00 | 62.15 | O |
| ATOM | 128 | NE2 | GLN | A | 7 | 34.412 | 5.350 | 13.459 | 1.00 | 62.20 | N |
| ATOM | 131 | C | GLN | A | 7 | 38.908 | 3.198 | 13.416 | 1.00 | 42.71 | C |
| ATOM | 132 | O | GLN | A | 7 | 38.763 | 2.473 | 12.455 | 1.00 | 41.90 | O |
| ATOM | 134 | N | CYS | A | 8 | 39.418 | 4.408 | 13.322 | 1.00 | 41.81 | N |
| ATOM | 135 | CA | CYS | A | 8 | 39.768 | 5.063 | 12.016 | 1.00 | 40.76 | C |
| ATOM | 137 | CB | CYS | A | 8 | 39.578 | 6.568 | 12.224 | 1.00 | 40.40 | C |
| ATOM | 140 | SG | CYS | A | 8 | 40.073 | 7.732 | 10.854 | 1.00 | 42.15 | S |
| ATOM | 142 | C | CYS | A | 8 | 41.186 | 4.710 | 11.485 | 1.00 | 39.98 | C |
| ATOM | 143 | O | CYS | A | 8 | 41.409 | 4.496 | 10.282 | 1.00 | 40.49 | O |
| ATOM | 145 | N | PHE | A | 9 | 42.141 | 4.563 | 12.396 | 1.00 | 39.04 | N |
| ATOM | 146 | CA | PHE | A | 9 | 43.501 | 4.272 | 12.052 | 1.00 | 37.93 | C |
| ATOM | 148 | CB | PHE | A | 9 | 44.375 | 5.256 | 12.812 | 1.00 | 38.19 | C |
| ATOM | 151 | CG | PHE | A | 9 | 44.104 | 6.657 | 12.432 | 1.00 | 31.90 | C |

FIG.15-4

| | | | | | | | | | | | |
|---|---|---|---|---|---|---|---|---|---|---|---|
| ATOM | 152 | CD1 | PHE | A | 9 | 44.692 | 7.190 | 11.317 | 1.00 | 32.40 | C |
| ATOM | 154 | CE1 | PHE | A | 9 | 44.454 | 8.473 | 10.986 | 1.00 | 27.02 | C |
| ATOM | 156 | CZ | PHE | A | 9 | 43.652 | 9.216 | 11.685 | 1.00 | 32.18 | C |
| ATOM | 158 | CE2 | PHE | A | 9 | 43.036 | 8.710 | 12.814 | 1.00 | 32.36 | C |
| ATOM | 160 | CD2 | PHE | A | 9 | 43.299 | 7.436 | 13.182 | 1.00 | 30.81 | C |
| ATOM | 162 | C | PHE | A | 9 | 43.937 | 2.872 | 12.361 | 1.00 | 40.11 | C |
| ATOM | 163 | O | PHE | A | 9 | 43.472 | 2.232 | 13.305 | 1.00 | 38.23 | O |
| ATOM | 165 | N | ASN | A | 10 | 44.867 | 2.401 | 11.579 | 1.00 | 41.36 | N |
| ATOM | 166 | CA | ASN | A | 10 | 45.299 | 1.074 | 11.753 | 1.00 | 43.17 | C |
| ATOM | 168 | CB | ASN | A | 10 | 46.002 | 0.568 | 10.504 | 1.00 | 45.30 | C |
| ATOM | 171 | CG | ASN | A | 10 | 47.485 | 0.770 | 10.490 | 1.00 | 49.13 | C |
| ATOM | 172 | OD1 | ASN | A | 10 | 48.109 | 1.231 | 11.457 | 1.00 | 55.05 | O |
| ATOM | 173 | ND2 | ASN | A | 10 | 48.086 | 0.394 | 9.355 | 1.00 | 56.56 | N |
| ATOM | 176 | C | ASN | A | 10 | 46.059 | 0.920 | 13.068 | 1.00 | 43.49 | C |
| ATOM | 177 | O | ASN | A | 10 | 46.443 | 1.924 | 13.716 | 1.00 | 41.30 | O |
| ATOM | 179 | N | PRO | A | 11 | 46.174 | -0.332 | 13.524 | 1.00 | 43.22 | N |
| ATOM | 180 | CA | PRO | A | 11 | 46.665 | -0.469 | 14.876 | 1.00 | 42.66 | C |
| ATOM | 182 | CB | PRO | A | 11 | 46.538 | -1.983 | 15.155 | 1.00 | 43.18 | C |
| ATOM | 185 | CG | PRO | A | 11 | 45.578 | -2.512 | 14.138 | 1.00 | 44.32 | C |
| ATOM | 188 | CD | PRO | A | 11 | 45.433 | -1.529 | 13.059 | 1.00 | 43.91 | C |
| ATOM | 191 | C | PRO | A | 11 | 48.094 | -0.021 | 15.037 | 1.00 | 40.71 | C |
| ATOM | 192 | O | PRO | A | 11 | 48.399 | 0.518 | 16.080 | 1.00 | 40.83 | O |
| ATOM | 193 | N | MET | A | 12 | 48.949 | -0.280 | 14.039 | 1.00 | 39.97 | N |
| ATOM | 194 | CA | MET | A | 12 | 50.332 | 0.177 | 14.063 | 1.00 | 39.17 | C |
| ATOM | 196 | CB | MET | A | 12 | 51.046 | -0.192 | 12.782 | 1.00 | 40.79 | C |
| ATOM | 199 | CG | MET | A | 12 | 52.432 | 0.498 | 12.579 | 1.00 | 46.56 | C |
| ATOM | 202 | SD | MET | A | 12 | 53.061 | 0.207 | 10.883 | 1.00 | 62.60 | S |
| ATOM | 203 | CE | MET | A | 12 | 51.840 | 1.130 | 9.888 | 1.00 | 60.09 | C |
| ATOM | 207 | C | MET | A | 12 | 50.401 | 1.686 | 14.309 | 1.00 | 37.46 | C |
| ATOM | 208 | O | MET | A | 12 | 51.213 | 2.141 | 15.092 | 1.00 | 35.55 | O |
| ATOM | 210 | N | ILE | A | 13 | 49.532 | 2.436 | 13.634 | 1.00 | 35.53 | N |
| ATOM | 211 | CA | ILE | A | 13 | 49.544 | 3.896 | 13.670 | 1.00 | 35.50 | C |
| ATOM | 213 | CB | ILE | A | 13 | 48.616 | 4.513 | 12.594 | 1.00 | 33.84 | C |
| ATOM | 215 | CG1 | ILE | A | 13 | 49.112 | 4.292 | 11.162 | 1.00 | 36.54 | C |
| ATOM | 218 | CD1 | ILE | A | 13 | 50.209 | 5.154 | 10.801 | 1.00 | 40.55 | C |
| ATOM | 222 | CG2 | ILE | A | 13 | 48.304 | 6.056 | 12.857 | 1.00 | 33.81 | C |
| ATOM | 226 | C | ILE | A | 13 | 49.114 | 4.326 | 15.061 | 1.00 | 34.57 | C |
| ATOM | 227 | O | ILE | A | 13 | 49.746 | 5.203 | 15.694 | 1.00 | 34.50 | O |
| ATOM | 229 | N | VAL | A | 14 | 48.037 | 3.727 | 15.564 | 1.00 | 33.15 | N |
| ATOM | 230 | CA | VAL | A | 14 | 47.560 | 4.085 | 16.871 | 1.00 | 34.21 | C |
| ATOM | 232 | CB | VAL | A | 14 | 46.238 | 3.382 | 17.252 | 1.00 | 34.30 | C |
| ATOM | 234 | CG1 | VAL | A | 14 | 45.764 | 3.804 | 18.648 | 1.00 | 33.03 | C |
| ATOM | 238 | CG2 | VAL | A | 14 | 45.143 | 3.737 | 16.259 | 1.00 | 35.73 | C |
| ATOM | 242 | C | VAL | A | 14 | 48.637 | 3.828 | 17.927 | 1.00 | 35.71 | C |
| ATOM | 243 | O | VAL | A | 14 | 48.869 | 4.682 | 18.779 | 1.00 | 36.45 | O |
| ATOM | 245 | N | GLU | A | 15 | 49.309 | 2.691 | 17.838 | 1.00 | 37.13 | N |
| ATOM | 246 | CA | GLU | A | 15 | 50.369 | 2.354 | 18.800 | 1.00 | 39.91 | C |
| ATOM | 248 | CB | GLU | A | 15 | 51.026 | 0.998 | 18.463 | 1.00 | 40.71 | C |
| ATOM | 251 | CG | GLU | A | 15 | 50.412 | -0.243 | 19.100 | 1.00 | 48.93 | C |
| ATOM | 254 | CD | GLU | A | 15 | 51.305 | -1.515 | 18.976 | 1.00 | 55.78 | C |
| ATOM | 255 | OE1 | GLU | A | 15 | 52.425 | -1.469 | 18.368 | 1.00 | 57.79 | O |
| ATOM | 256 | OE2 | GLU | A | 15 | 50.855 | -2.578 | 19.489 | 1.00 | 60.50 | O |
| ATOM | 257 | C | GLU | A | 15 | 51.471 | 3.447 | 18.744 | 1.00 | 39.79 | C |
| ATOM | 258 | O | GLU | A | 15 | 51.893 | 3.961 | 19.781 | 1.00 | 38.30 | O |
| ATOM | 260 | N | LEU | A | 16 | 51.949 | 3.743 | 17.527 | 1.00 | 40.41 | N |
| ATOM | 261 | CA | LEU | A | 16 | 53.006 | 4.748 | 17.359 | 1.00 | 40.78 | C |
| ATOM | 263 | CB | LEU | A | 16 | 53.446 | 4.889 | 15.911 | 1.00 | 41.25 | C |
| ATOM | 266 | CG | LEU | A | 16 | 54.075 | 3.611 | 15.380 | 1.00 | 42.02 | C |
| ATOM | 268 | CD1 | LEU | A | 16 | 54.294 | 3.737 | 13.894 | 1.00 | 41.89 | C |
| ATOM | 272 | CD2 | LEU | A | 16 | 55.363 | 3.242 | 16.153 | 1.00 | 42.80 | C |
| ATOM | 276 | C | LEU | A | 16 | 52.596 | 6.085 | 17.905 | 1.00 | 40.38 | C |
| ATOM | 277 | O | LEU | A | 16 | 53.429 | 6.760 | 18.567 | 1.00 | 39.11 | O |
| ATOM | 279 | N | ALA | A | 17 | 51.343 | 6.469 | 17.669 | 1.00 | 38.39 | N |

FIG.15-5

| | | | | | | | | | | | |
|---|---|---|---|---|---|---|---|---|---|---|---|
| ATOM | 280 | CA | ALA | A | 17 | 50.814 | 7.733 | 18.214 | 1.00 | 39.46 | C |
| ATOM | 282 | CB | ALA | A | 17 | 49.439 | 8.076 | 17.652 | 1.00 | 38.01 | C |
| ATOM | 286 | C | ALA | A | 17 | 50.776 | 7.753 | 19.760 | 1.00 | 40.24 | C |
| ATOM | 287 | O | ALA | A | 17 | 51.120 | 8.751 | 20.408 | 1.00 | 38.60 | O |
| ATOM | 289 | N | GLU | A | 18 | 50.360 | 6.646 | 20.349 | 1.00 | 42.22 | N |
| ATOM | 290 | CA | GLU | A | 18 | 50.302 | 6.592 | 21.813 | 1.00 | 43.95 | C |
| ATOM | 292 | CB | GLU | A | 18 | 49.642 | 5.305 | 22.265 | 1.00 | 44.73 | C |
| ATOM | 295 | CG | GLU | A | 18 | 48.140 | 5.305 | 22.036 | 1.00 | 46.92 | C |
| ATOM | 298 | CD | GLU | A | 18 | 47.446 | 4.139 | 22.729 | 1.00 | 48.80 | C |
| ATOM | 299 | OE1 | GLU | A | 18 | 47.661 | 3.013 | 22.289 | 1.00 | 49.43 | O |
| ATOM | 300 | OE2 | GLU | A | 18 | 46.703 | 4.360 | 23.721 | 1.00 | 53.91 | O |
| ATOM | 301 | C | GLU | A | 18 | 51.716 | 6.727 | 22.394 | 1.00 | 44.65 | C |
| ATOM | 302 | O | GLU | A | 18 | 51.903 | 7.477 | 23.336 | 1.00 | 44.11 | O |
| ATOM | 304 | N | LYS | A | 19 | 52.680 | 6.030 | 21.794 | 1.00 | 46.00 | N |
| ATOM | 305 | CA | LYS | A | 19 | 54.089 | 6.073 | 22.208 | 1.00 | 47.58 | C |
| ATOM | 307 | CB | LYS | A | 19 | 54.899 | 5.094 | 21.380 | 1.00 | 48.56 | C |
| ATOM | 310 | CG | LYS | A | 19 | 54.717 | 3.593 | 21.687 | 1.00 | 51.09 | C |
| ATOM | 313 | CD | LYS | A | 19 | 55.743 | 2.795 | 20.830 | 1.00 | 55.89 | C |
| ATOM | 316 | CE | LYS | A | 19 | 55.447 | 1.282 | 20.716 | 1.00 | 59.14 | C |
| ATOM | 319 | NZ | LYS | A | 19 | 56.675 | 0.552 | 20.235 | 1.00 | 59.08 | N |
| ATOM | 323 | C | LYS | A | 19 | 54.721 | 7.477 | 22.045 | 1.00 | 48.06 | C |
| ATOM | 324 | O | LYS | A | 19 | 55.474 | 7.937 | 22.906 | 1.00 | 47.61 | O |
| ATOM | 326 | N | ALA | A | 20 | 54.436 | 8.136 | 20.930 | 1.00 | 46.96 | N |
| ATOM | 327 | CA | ALA | A | 20 | 54.903 | 9.479 | 20.695 | 1.00 | 48.49 | C |
| ATOM | 329 | CB | ALA | A | 20 | 54.526 | 9.998 | 19.225 | 1.00 | 47.84 | C |
| ATOM | 333 | C | ALA | A | 20 | 54.338 | 10.402 | 21.752 | 1.00 | 49.19 | C |
| ATOM | 334 | O | ALA | A | 20 | 55.038 | 11.276 | 22.241 | 1.00 | 49.21 | O |
| ATOM | 336 | N | MET | A | 21 | 53.084 | 10.198 | 22.131 | 1.00 | 50.73 | N |
| ATOM | 337 | CA | MET | A | 21 | 52.445 | 11.108 | 23.057 | 1.00 | 52.02 | C |
| ATOM | 339 | CB | MET | A | 21 | 50.950 | 10.867 | 23.139 | 1.00 | 51.42 | C |
| ATOM | 342 | CG | MET | A | 21 | 50.267 | 11.467 | 21.923 | 1.00 | 49.73 | C |
| ATOM | 345 | SD | MET | A | 21 | 48.495 | 11.479 | 21.966 | 1.00 | 44.10 | S |
| ATOM | 346 | CE | MET | A | 21 | 48.082 | 13.087 | 22.545 | 1.00 | 41.49 | C |
| ATOM | 350 | C | MET | A | 21 | 53.126 | 11.039 | 24.413 | 1.00 | 54.84 | C |
| ATOM | 351 | O | MET | A | 21 | 53.518 | 12.079 | 24.964 | 1.00 | 55.52 | O |
| ATOM | 353 | N | LYS | A | 22 | 53.354 | 9.824 | 24.890 | 1.00 | 57.57 | N |
| ATOM | 354 | CA | LYS | A | 22 | 53.987 | 9.630 | 26.193 | 1.00 | 59.31 | C |
| ATOM | 356 | CB | LYS | A | 22 | 53.859 | 8.177 | 26.603 | 1.00 | 60.30 | C |
| ATOM | 359 | CG | LYS | A | 22 | 52.368 | 7.746 | 26.726 | 1.00 | 63.31 | C |
| ATOM | 362 | CD | LYS | A | 22 | 52.229 | 6.314 | 27.283 | 1.00 | 67.07 | C |
| ATOM | 365 | CE | LYS | A | 22 | 50.800 | 5.752 | 27.151 | 1.00 | 68.81 | C |
| ATOM | 368 | NZ | LYS | A | 22 | 50.629 | 4.591 | 28.075 | 1.00 | 70.93 | N |
| ATOM | 372 | C | LYS | A | 22 | 55.440 | 10.148 | 26.216 | 1.00 | 59.45 | C |
| ATOM | 373 | O | LYS | A | 22 | 55.781 | 10.969 | 27.083 | 1.00 | 59.33 | O |
| ATOM | 375 | N | GLU | A | 23 | 56.245 | 9.735 | 25.223 | 1.00 | 59.22 | N |
| ATOM | 376 | CA | GLU | A | 23 | 57.616 | 10.256 | 24.998 | 1.00 | 59.66 | C |
| ATOM | 378 | CB | GLU | A | 23 | 58.186 | 9.782 | 23.618 | 1.00 | 59.02 | C |
| ATOM | 381 | CG | GLU | A | 23 | 59.705 | 9.948 | 23.441 | 1.00 | 60.52 | C |
| ATOM | 384 | CD | GLU | A | 23 | 60.265 | 9.386 | 22.104 | 1.00 | 61.02 | C |
| ATOM | 385 | OE1 | GLU | A | 23 | 59.536 | 9.342 | 21.091 | 1.00 | 63.65 | O |
| ATOM | 386 | OE2 | GLU | A | 23 | 61.447 | 9.008 | 22.063 | 1.00 | 61.08 | O |
| ATOM | 387 | C | GLU | A | 23 | 57.679 | 11.781 | 25.099 | 1.00 | 59.34 | C |
| ATOM | 388 | O | GLU | A | 23 | 58.688 | 12.358 | 25.503 | 1.00 | 59.71 | O |
| ATOM | 390 | N | TYR | A | 24 | 56.583 | 12.429 | 24.748 | 1.00 | 59.76 | N |
| ATOM | 391 | CA | TYR | A | 24 | 56.513 | 13.871 | 24.706 | 1.00 | 59.92 | C |
| ATOM | 393 | CB | TYR | A | 24 | 56.107 | 14.290 | 23.290 | 1.00 | 60.13 | C |
| ATOM | 396 | CG | TYR | A | 24 | 56.570 | 15.662 | 22.869 | 1.00 | 61.52 | C |
| ATOM | 397 | CD1 | TYR | A | 24 | 57.901 | 15.900 | 22.553 | 1.00 | 62.62 | C |
| ATOM | 399 | CE1 | TYR | A | 24 | 58.332 | 17.177 | 22.150 | 1.00 | 64.21 | C |
| ATOM | 401 | CZ | TYR | A | 24 | 57.416 | 18.225 | 22.052 | 1.00 | 63.87 | C |
| ATOM | 402 | OH | TYR | A | 24 | 57.846 | 19.480 | 21.655 | 1.00 | 65.64 | O |
| ATOM | 404 | CE2 | TYR | A | 24 | 56.082 | 18.010 | 22.357 | 1.00 | 63.99 | C |
| ATOM | 406 | CD2 | TYR | A | 24 | 55.662 | 16.726 | 22.756 | 1.00 | 63.49 | C |

FIG.15-6

| | | | | | | | | | | | |
|---|---|---|---|---|---|---|---|---|---|---|---|
| ATOM | 408 | C | TYR | A | 24 | 55.545 | 14.403 | 25.765 | 1.00 | 59.58 | C |
| ATOM | 409 | O | TYR | A | 24 | 55.087 | 15.534 | 25.666 | 1.00 | 59.96 | O |
| ATOM | 411 | N | GLY | A | 25 | 55.242 | 13.571 | 26.764 | 1.00 | 59.90 | N |
| ATOM | 412 | CA | GLY | A | 25 | 54.493 | 13.986 | 27.971 | 1.00 | 59.81 | C |
| ATOM | 415 | C | GLY | A | 25 | 52.975 | 13.809 | 28.081 | 1.00 | 59.97 | C |
| ATOM | 416 | O | GLY | A | 25 | 52.454 | 13.843 | 29.209 | 1.00 | 60.51 | O |
| ATOM | 418 | N | GLU | A | 26 | 52.282 | 13.554 | 26.952 | 1.00 | 59.10 | N |
| ATOM | 419 | CA | GLU | A | 26 | 50.803 | 13.738 | 26.812 | 1.00 | 58.30 | C |
| ATOM | 421 | CB | GLU | A | 26 | 50.511 | 14.338 | 25.424 | 1.00 | 58.29 | C |
| ATOM | 424 | CG | GLU | A | 26 | 51.224 | 15.617 | 25.096 | 1.00 | 58.31 | C |
| ATOM | 427 | CD | GLU | A | 26 | 50.792 | 16.726 | 25.993 | 1.00 | 59.07 | C |
| ATOM | 428 | OE1 | GLU | A | 26 | 49.566 | 16.850 | 26.204 | 1.00 | 62.18 | O |
| ATOM | 429 | OE2 | GLU | A | 26 | 51.666 | 17.476 | 26.481 | 1.00 | 59.44 | O |
| ATOM | 430 | C | GLU | A | 26 | 49.911 | 12.484 | 26.935 | 1.00 | 58.16 | C |
| ATOM | 431 | O | GLU | A | 26 | 50.320 | 11.351 | 26.616 | 1.00 | 58.80 | O |
| ATOM | 433 | N | ASP | A | 27 | 48.659 | 12.703 | 27.329 | 1.00 | 57.04 | N |
| ATOM | 434 | CA | ASP | A | 27 | 47.728 | 11.607 | 27.544 | 1.00 | 56.23 | C |
| ATOM | 436 | CB | ASP | A | 27 | 46.989 | 11.777 | 28.873 | 1.00 | 56.36 | C |
| ATOM | 439 | CG | ASP | A | 27 | 45.982 | 10.649 | 29.149 | 1.00 | 58.44 | C |
| ATOM | 440 | OD1 | ASP | A | 27 | 45.917 | 9.653 | 28.376 | 1.00 | 59.06 | O |
| ATOM | 441 | OD2 | ASP | A | 27 | 45.240 | 10.742 | 30.157 | 1.00 | 62.08 | O |
| ATOM | 442 | C | ASP | A | 27 | 46.696 | 11.564 | 26.402 | 1.00 | 54.78 | C |
| ATOM | 443 | O | ASP | A | 27 | 45.894 | 12.491 | 26.277 | 1.00 | 53.52 | O |
| ATOM | 445 | N | PRO | A | 28 | 46.676 | 10.462 | 25.627 | 1.00 | 53.87 | N |
| ATOM | 446 | CA | PRO | A | 28 | 45.700 | 10.276 | 24.528 | 1.00 | 53.60 | C |
| ATOM | 448 | CB | PRO | A | 28 | 46.037 | 8.879 | 23.983 | 1.00 | 53.21 | C |
| ATOM | 451 | CG | PRO | A | 28 | 46.822 | 8.218 | 25.035 | 1.00 | 54.25 | C |
| ATOM | 454 | CD | PRO | A | 28 | 47.586 | 9.300 | 25.725 | 1.00 | 53.63 | C |
| ATOM | 457 | C | PRO | A | 28 | 44.264 | 10.261 | 24.976 | 1.00 | 53.18 | C |
| ATOM | 458 | O | PRO | A | 28 | 43.363 | 10.578 | 24.198 | 1.00 | 52.05 | O |
| ATOM | 459 | N | LYS | A | 29 | 44.048 | 9.894 | 26.238 | 1.00 | 53.31 | N |
| ATOM | 460 | CA | LYS | A | 29 | 42.709 | 9.864 | 26.790 | 1.00 | 53.08 | C |
| ATOM | 462 | CB | LYS | A | 29 | 42.678 | 8.987 | 28.050 | 1.00 | 53.95 | C |
| ATOM | 465 | CG | LYS | A | 29 | 42.953 | 7.491 | 27.783 | 1.00 | 57.43 | C |
| ATOM | 468 | CD | LYS | A | 29 | 42.406 | 6.593 | 28.927 | 1.00 | 62.00 | C |
| ATOM | 471 | CE | LYS | A | 29 | 41.955 | 5.187 | 28.437 | 1.00 | 62.89 | C |
| ATOM | 474 | NZ | LYS | A | 29 | 41.360 | 4.375 | 29.540 | 1.00 | 61.45 | N |
| ATOM | 478 | C | LYS | A | 29 | 42.165 | 11.277 | 27.056 | 1.00 | 51.76 | C |
| ATOM | 479 | O | LYS | A | 29 | 40.972 | 11.479 | 27.102 | 1.00 | 51.40 | O |
| ATOM | 481 | N | ILE | A | 30 | 43.035 | 12.262 | 27.187 | 1.00 | 50.90 | N |
| ATOM | 482 | CA | ILE | A | 30 | 42.615 | 13.618 | 27.477 | 1.00 | 50.42 | C |
| ATOM | 484 | CB | ILE | A | 30 | 43.505 | 14.239 | 28.616 | 1.00 | 51.21 | C |
| ATOM | 486 | CG1 | ILE | A | 30 | 43.253 | 13.532 | 29.953 | 1.00 | 53.48 | C |
| ATOM | 489 | CD1 | ILE | A | 30 | 43.921 | 14.213 | 31.165 | 1.00 | 55.34 | C |
| ATOM | 493 | CG2 | ILE | A | 30 | 43.261 | 15.776 | 28.768 | 1.00 | 51.82 | C |
| ATOM | 497 | C | ILE | A | 30 | 42.713 | 14.501 | 26.246 | 1.00 | 48.45 | C |
| ATOM | 498 | O | ILE | A | 30 | 41.763 | 15.195 | 25.886 | 1.00 | 48.91 | O |
| ATOM | 500 | N | GLU | A | 31 | 43.887 | 14.489 | 25.619 | 1.00 | 46.18 | N |
| ATOM | 501 | CA | GLU | A | 31 | 44.183 | 15.345 | 24.505 | 1.00 | 44.26 | C |
| ATOM | 503 | CB | GLU | A | 31 | 45.683 | 15.708 | 24.473 | 1.00 | 45.81 | C |
| ATOM | 506 | CG | GLU | A | 31 | 46.152 | 16.676 | 25.618 | 1.00 | 48.19 | C |
| ATOM | 509 | CD | GLU | A | 31 | 45.103 | 17.734 | 25.877 | 1.00 | 52.01 | C |
| ATOM | 510 | OE1 | GLU | A | 31 | 44.886 | 18.554 | 24.952 | 1.00 | 51.03 | O |
| ATOM | 511 | OE2 | GLU | A | 31 | 44.449 | 17.713 | 26.959 | 1.00 | 53.86 | O |
| ATOM | 512 | C | GLU | A | 31 | 43.769 | 14.468 | 23.314 | 1.00 | 42.26 | C |
| ATOM | 513 | O | GLU | A | 31 | 44.612 | 13.862 | 22.649 | 1.00 | 40.25 | O |
| ATOM | 515 | N | THR | A | 32 | 42.467 | 14.347 | 23.109 | 1.00 | 39.04 | N |
| ATOM | 516 | CA | THR | A | 32 | 41.988 | 13.407 | 22.131 | 1.00 | 37.70 | C |
| ATOM | 518 | CB | THR | A | 32 | 40.578 | 12.869 | 22.416 | 1.00 | 38.00 | C |
| ATOM | 520 | OG1 | THR | A | 32 | 39.651 | 13.931 | 22.420 | 1.00 | 39.31 | O |
| ATOM | 522 | CG2 | THR | A | 32 | 40.544 | 12.091 | 23.782 | 1.00 | 39.07 | C |
| ATOM | 526 | C | THR | A | 32 | 42.119 | 14.005 | 20.747 | 1.00 | 35.54 | C |
| ATOM | 527 | O | THR | A | 32 | 42.374 | 13.291 | 19.814 | 1.00 | 34.64 | O |

FIG.15-7

| | | | | | | | | | | | |
|---|---|---|---|---|---|---|---|---|---|---|---|
| ATOM | 529 | N | ASN | A | 33 | 42.047 | 15.311 | 20.619 | 1.00 | 34.52 | N |
| ATOM | 530 | CA | ASN | A | 33 | 42.145 | 15.911 | 19.313 | 1.00 | 33.77 | C |
| ATOM | 532 | CB | ASN | A | 33 | 41.674 | 17.313 | 19.304 | 1.00 | 33.95 | C |
| ATOM | 535 | CG | ASN | A | 33 | 40.179 | 17.452 | 19.360 | 1.00 | 35.32 | C |
| ATOM | 536 | OD1 | ASN | A | 33 | 39.715 | 18.561 | 19.587 | 1.00 | 38.41 | O |
| ATOM | 537 | ND2 | ASN | A | 33 | 39.418 | 16.381 | 19.074 | 1.00 | 32.64 | N |
| ATOM | 540 | C | ASN | A | 33 | 43.580 | 15.840 | 18.857 | 1.00 | 34.12 | C |
| ATOM | 541 | O | ASN | A | 33 | 43.853 | 15.485 | 17.733 | 1.00 | 32.00 | O |
| ATOM | 543 | N | LYS | A | 34 | 44.500 | 16.115 | 19.765 | 1.00 | 34.79 | N |
| ATOM | 544 | CA | LYS | A | 34 | 45.919 | 15.927 | 19.490 | 1.00 | 34.89 | C |
| ATOM | 546 | CB | LYS | A | 34 | 46.721 | 16.362 | 20.702 | 1.00 | 36.54 | C |
| ATOM | 549 | CG | LYS | A | 34 | 48.206 | 16.161 | 20.584 | 1.00 | 39.36 | C |
| ATOM | 552 | CD | LYS | A | 34 | 48.870 | 16.791 | 21.860 | 1.00 | 47.58 | C |
| ATOM | 555 | CE | LYS | A | 34 | 48.868 | 18.335 | 21.853 | 1.00 | 50.27 | C |
| ATOM | 558 | NZ | LYS | A | 34 | 48.393 | 18.882 | 23.193 | 1.00 | 55.33 | N |
| ATOM | 562 | C | LYS | A | 34 | 46.265 | 14.502 | 19.096 | 1.00 | 33.45 | C |
| ATOM | 563 | O | LYS | A | 34 | 46.964 | 14.323 | 18.101 | 1.00 | 31.93 | O |
| ATOM | 565 | N | PHE | A | 35 | 45.730 | 13.501 | 19.826 | 1.00 | 32.58 | N |
| ATOM | 566 | CA | PHE | A | 35 | 45.875 | 12.063 | 19.493 | 1.00 | 32.48 | C |
| ATOM | 568 | CB | PHE | A | 35 | 44.996 | 11.244 | 20.484 | 1.00 | 31.76 | C |
| ATOM | 571 | CG | PHE | A | 35 | 45.077 | 9.740 | 20.379 | 1.00 | 31.60 | C |
| ATOM | 572 | CD1 | PHE | A | 35 | 46.201 | 9.067 | 19.980 | 1.00 | 30.51 | C |
| ATOM | 574 | CE1 | PHE | A | 35 | 46.237 | 7.661 | 19.937 | 1.00 | 32.27 | C |
| ATOM | 576 | CZ | PHE | A | 35 | 45.177 | 6.935 | 20.348 | 1.00 | 37.25 | C |
| ATOM | 578 | CE2 | PHE | A | 35 | 44.039 | 7.583 | 20.762 | 1.00 | 35.15 | C |
| ATOM | 580 | CD2 | PHE | A | 35 | 44.009 | 8.981 | 20.824 | 1.00 | 36.86 | C |
| ATOM | 582 | C | PHE | A | 35 | 45.411 | 11.797 | 18.025 | 1.00 | 31.14 | C |
| ATOM | 583 | O | PHE | A | 35 | 46.058 | 11.081 | 17.267 | 1.00 | 30.28 | O |
| ATOM | 585 | N | ALA | A | 36 | 44.271 | 12.387 | 17.665 | 1.00 | 31.50 | N |
| ATOM | 586 | CA | ALA | A | 36 | 43.759 | 12.234 | 16.292 | 1.00 | 30.02 | C |
| ATOM | 588 | CB | ALA | A | 36 | 42.380 | 12.805 | 16.164 | 1.00 | 29.01 | C |
| ATOM | 592 | C | ALA | A | 36 | 44.697 | 12.898 | 15.276 | 1.00 | 29.95 | C |
| ATOM | 593 | O | ALA | A | 36 | 44.958 | 12.329 | 14.209 | 1.00 | 29.06 | O |
| ATOM | 595 | N | ALA | A | 37 | 45.231 | 14.082 | 15.617 | 1.00 | 27.72 | N |
| ATOM | 596 | CA | ALA | A | 37 | 46.127 | 14.794 | 14.720 | 1.00 | 27.19 | C |
| ATOM | 598 | CB | ALA | A | 37 | 46.406 | 16.237 | 15.252 | 1.00 | 26.52 | C |
| ATOM | 602 | C | ALA | A | 37 | 47.420 | 14.046 | 14.511 | 1.00 | 27.00 | C |
| ATOM | 603 | O | ALA | A | 37 | 47.950 | 14.030 | 13.399 | 1.00 | 27.38 | O |
| ATOM | 605 | N | ILE | A | 38 | 47.954 | 13.461 | 15.573 | 1.00 | 27.10 | N |
| ATOM | 606 | CA | ILE | A | 38 | 49.239 | 12.726 | 15.521 | 1.00 | 28.20 | C |
| ATOM | 608 | CB | ILE | A | 38 | 49.710 | 12.324 | 16.925 | 1.00 | 30.03 | C |
| ATOM | 610 | CG1 | ILE | A | 38 | 50.129 | 13.588 | 17.683 | 1.00 | 31.11 | C |
| ATOM | 613 | CD1 | ILE | A | 38 | 50.240 | 13.306 | 19.252 | 1.00 | 33.33 | C |
| ATOM | 617 | CG2 | ILE | A | 38 | 50.866 | 11.234 | 16.864 | 1.00 | 26.80 | C |
| ATOM | 621 | C | ILE | A | 38 | 49.068 | 11.492 | 14.675 | 1.00 | 28.32 | C |
| ATOM | 622 | O | ILE | A | 38 | 49.911 | 11.222 | 13.811 | 1.00 | 27.19 | O |
| ATOM | 624 | N | CYS | A | 39 | 47.929 | 10.791 | 14.825 | 1.00 | 26.33 | N |
| ATOM | 625 | CA | CYS | A | 39 | 47.654 | 9.640 | 13.946 | 1.00 | 27.24 | C |
| ATOM | 627 | CB | CYS | A | 39 | 46.325 | 8.957 | 14.327 | 1.00 | 28.57 | C |
| ATOM | 630 | SG | CYS | A | 39 | 46.482 | 8.073 | 15.870 | 1.00 | 32.84 | S |
| ATOM | 632 | C | CYS | A | 39 | 47.574 | 10.045 | 12.485 | 1.00 | 24.91 | C |
| ATOM | 633 | O | CYS | A | 39 | 48.128 | 9.399 | 11.634 | 1.00 | 25.54 | O |
| ATOM | 635 | N | THR | A | 40 | 46.834 | 11.091 | 12.214 | 1.00 | 25.66 | N |
| ATOM | 636 | CA | THR | A | 40 | 46.624 | 11.561 | 10.853 | 1.00 | 25.89 | C |
| ATOM | 638 | CB | THR | A | 40 | 45.742 | 12.791 | 10.851 | 1.00 | 26.03 | C |
| ATOM | 640 | OG1 | THR | A | 40 | 44.458 | 12.490 | 11.452 | 1.00 | 26.97 | O |
| ATOM | 642 | CG2 | THR | A | 40 | 45.513 | 13.288 | 9.457 | 1.00 | 25.07 | C |
| ATOM | 646 | C | THR | A | 40 | 47.987 | 11.888 | 10.237 | 1.00 | 25.84 | C |
| ATOM | 647 | O | THR | A | 40 | 48.301 | 11.509 | 9.111 | 1.00 | 26.38 | O |
| ATOM | 649 | N | HIS | A | 41 | 48.749 | 12.681 | 10.943 | 1.00 | 24.88 | N |
| ATOM | 650 | CA | HIS | A | 41 | 50.096 | 13.100 | 10.454 | 1.00 | 25.98 | C |
| ATOM | 652 | CB | HIS | A | 41 | 50.710 | 14.208 | 11.363 | 1.00 | 26.34 | C |
| ATOM | 655 | CG | HIS | A | 41 | 52.135 | 14.537 | 11.071 | 1.00 | 24.61 | C |

FIG.15-8

| | | | | | | | | | | | |
|---|---|---|---|---|---|---|---|---|---|---|---|
| ATOM | 656 | ND1 | HIS | A | 41 | 53.166 | 13.780 | 11.564 | 1.00 | 24.99 | N |
| ATOM | 658 | CE1 | HIS | A | 41 | 54.313 | 14.295 | 11.172 | 1.00 | 27.54 | C |
| ATOM | 660 | NE2 | HIS | A | 41 | 54.069 | 15.346 | 10.413 | 1.00 | 22.92 | N |
| ATOM | 662 | CD2 | HIS | A | 41 | 52.714 | 15.546 | 10.361 | 1.00 | 26.94 | C |
| ATOM | 664 | C | HIS | A | 41 | 51.027 | 11.898 | 10.262 | 1.00 | 25.39 | C |
| ATOM | 665 | O | HIS | A | 41 | 51.700 | 11.744 | 9.231 | 1.00 | 24.47 | O |
| ATOM | 667 | N | LEU | A | 42 | 51.033 | 10.999 | 11.214 | 1.00 | 25.11 | N |
| ATOM | 668 | CA | LEU | A | 42 | 51.739 | 9.740 | 10.958 | 1.00 | 27.52 | C |
| ATOM | 670 | CB | LEU | A | 42 | 51.675 | 8.772 | 12.137 | 1.00 | 27.69 | C |
| ATOM | 673 | CG | LEU | A | 42 | 52.538 | 8.928 | 13.366 | 1.00 | 31.80 | C |
| ATOM | 675 | CD1 | LEU | A | 42 | 51.909 | 8.078 | 14.530 | 1.00 | 34.67 | C |
| ATOM | 679 | CD2 | LEU | A | 42 | 53.984 | 8.476 | 13.059 | 1.00 | 34.51 | C |
| ATOM | 683 | C | LEU | A | 42 | 51.287 | 9.045 | 9.702 | 1.00 | 26.25 | C |
| ATOM | 684 | O | LEU | A | 42 | 52.099 | 8.585 | 8.909 | 1.00 | 27.53 | O |
| ATOM | 686 | N | GLU | A | 43 | 49.985 | 8.943 | 9.477 | 1.00 | 26.61 | N |
| ATOM | 687 | CA | GLU | A | 43 | 49.543 | 8.160 | 8.321 | 1.00 | 26.85 | C |
| ATOM | 689 | CB | GLU | A | 43 | 47.996 | 7.994 | 8.340 | 1.00 | 28.03 | C |
| ATOM | 692 | CG | GLU | A | 43 | 47.566 | 7.084 | 7.311 | 1.00 | 32.44 | C |
| ATOM | 695 | CD | GLU | A | 43 | 46.169 | 6.480 | 7.510 | 1.00 | 39.32 | C |
| ATOM | 696 | OE1 | GLU | A | 43 | 45.851 | 5.546 | 6.765 | 1.00 | 43.40 | O |
| ATOM | 697 | OE2 | GLU | A | 43 | 45.385 | 6.966 | 8.312 | 1.00 | 43.91 | O |
| ATOM | 698 | C | GLU | A | 43 | 49.955 | 8.865 | 7.033 | 1.00 | 26.06 | C |
| ATOM | 699 | O | GLU | A | 43 | 50.295 | 8.232 | 6.029 | 1.00 | 26.34 | O |
| ATOM | 701 | N | VAL | A | 44 | 49.909 | 10.185 | 7.020 | 1.00 | 23.78 | N |
| ATOM | 702 | CA | VAL | A | 44 | 50.323 | 10.911 | 5.811 | 1.00 | 21.96 | C |
| ATOM | 704 | CB | VAL | A | 44 | 49.966 | 12.383 | 5.908 | 1.00 | 22.48 | C |
| ATOM | 706 | CG1 | VAL | A | 44 | 50.695 | 13.245 | 4.839 | 1.00 | 22.23 | C |
| ATOM | 710 | CG2 | VAL | A | 44 | 48.441 | 12.534 | 5.884 | 1.00 | 23.28 | C |
| ATOM | 714 | C | VAL | A | 44 | 51.794 | 10.701 | 5.538 | 1.00 | 22.90 | C |
| ATOM | 715 | O | VAL | A | 44 | 52.186 | 10.414 | 4.392 | 1.00 | 23.74 | O |
| ATOM | 717 | N | CYS | A | 45 | 52.595 | 10.761 | 6.581 | 1.00 | 22.26 | N |
| ATOM | 718 | CA | CYS | A | 45 | 54.021 | 10.450 | 6.426 | 1.00 | 23.67 | C |
| ATOM | 720 | CB | CYS | A | 45 | 54.761 | 10.631 | 7.732 | 1.00 | 23.37 | C |
| ATOM | 723 | SG | CYS | A | 45 | 54.877 | 12.405 | 8.328 | 1.00 | 25.99 | S |
| ATOM | 725 | C | CYS | A | 45 | 54.280 | 9.033 | 5.830 | 1.00 | 23.51 | C |
| ATOM | 726 | O | CYS | A | 45 | 55.125 | 8.860 | 4.964 | 1.00 | 23.06 | O |
| ATOM | 728 | N | PHE | A | 46 | 53.627 | 8.026 | 6.362 | 1.00 | 25.19 | N |
| ATOM | 729 | CA | PHE | A | 46 | 53.761 | 6.714 | 5.852 | 1.00 | 26.03 | C |
| ATOM | 731 | CB | PHE | A | 46 | 53.050 | 5.689 | 6.734 | 1.00 | 27.99 | C |
| ATOM | 734 | CG | PHE | A | 46 | 53.596 | 5.627 | 8.169 | 1.00 | 31.74 | C |
| ATOM | 735 | CD1 | PHE | A | 46 | 52.924 | 4.903 | 9.133 | 1.00 | 42.03 | C |
| ATOM | 737 | CE1 | PHE | A | 46 | 53.407 | 4.838 | 10.463 | 1.00 | 42.43 | C |
| ATOM | 739 | CZ | PHE | A | 46 | 54.558 | 5.469 | 10.790 | 1.00 | 43.17 | C |
| ATOM | 741 | CE2 | PHE | A | 46 | 55.220 | 6.209 | 9.834 | 1.00 | 41.76 | C |
| ATOM | 743 | CD2 | PHE | A | 46 | 54.740 | 6.269 | 8.538 | 1.00 | 37.20 | C |
| ATOM | 745 | C | PHE | A | 46 | 53.252 | 6.601 | 4.434 | 1.00 | 27.54 | C |
| ATOM | 746 | O | PHE | A | 46 | 53.902 | 5.987 | 3.603 | 1.00 | 27.30 | O |
| ATOM | 748 | N | MET | A | 47 | 52.127 | 7.221 | 4.119 | 1.00 | 28.70 | N |
| ATOM | 749 | CA | MET | A | 47 | 51.658 | 7.197 | 2.735 | 1.00 | 28.78 | C |
| ATOM | 751 | CB | MET | A | 47 | 50.304 | 7.827 | 2.597 | 1.00 | 28.05 | C |
| ATOM | 754 | CG | MET | A | 47 | 49.155 | 7.042 | 3.260 | 1.00 | 30.76 | C |
| ATOM | 757 | SD | MET | A | 47 | 47.646 | 8.044 | 3.112 | 1.00 | 31.27 | S |
| ATOM | 758 | CE | MET | A | 47 | 47.341 | 7.951 | 1.406 | 1.00 | 30.23 | C |
| ATOM | 762 | C | MET | A | 47 | 52.602 | 7.921 | 1.775 | 1.00 | 29.96 | C |
| ATOM | 763 | O | MET | A | 47 | 52.790 | 7.463 | 0.631 | 1.00 | 31.63 | O |
| ATOM | 765 | N | TYR | A | 48 | 53.183 | 9.028 | 2.226 | 1.00 | 28.93 | N |
| ATOM | 766 | CA | TYR | A | 48 | 54.063 | 9.828 | 1.433 | 1.00 | 28.12 | C |
| ATOM | 768 | CB | TYR | A | 48 | 54.509 | 11.043 | 2.218 | 1.00 | 26.67 | C |
| ATOM | 771 | CG | TYR | A | 48 | 54.988 | 12.219 | 1.405 | 1.00 | 26.63 | C |
| ATOM | 772 | CD1 | TYR | A | 48 | 54.207 | 13.365 | 1.308 | 1.00 | 25.62 | C |
| ATOM | 774 | CE1 | TYR | A | 48 | 54.660 | 14.471 | 0.711 | 1.00 | 20.45 | C |
| ATOM | 776 | CZ | TYR | A | 48 | 55.859 | 14.446 | 0.020 | 1.00 | 24.91 | C |
| ATOM | 777 | OH | TYR | A | 48 | 56.264 | 15.598 | -0.589 | 1.00 | 26.73 | O |

FIG.15-9

| | | | | | | | | | | | |
|---|---|---|---|---|---|---|---|---|---|---|---|
| ATOM | 779 | CE2 | TYR | A | 48 | 56.652 | 13.337 | 0.068 | 1.00 | 24.50 | C |
| ATOM | 781 | CD2 | TYR | A | 48 | 56.230 | 12.242 | 0.801 | 1.00 | 23.89 | C |
| ATOM | 783 | C | TYR | A | 48 | 55.235 | 8.951 | 1.073 | 1.00 | 28.14 | C |
| ATOM | 784 | O | TYR | A | 48 | 55.702 | 8.943 | -0.033 | 1.00 | 28.09 | O |
| ATOM | 786 | N | SER | A | 49 | 55.713 | 8.283 | 2.074 | 1.00 | 31.34 | N |
| ATOM | 787 | CA | SER | A | 49 | 56.873 | 7.448 | 1.973 | 1.00 | 35.16 | C |
| ATOM | 789 | CB | SER | A | 49 | 57.364 | 7.048 | 3.319 | 1.00 | 34.36 | C |
| ATOM | 792 | OG | SER | A | 49 | 58.502 | 6.211 | 3.091 | 1.00 | 40.09 | O |
| ATOM | 794 | C | SER | A | 49 | 56.597 | 6.197 | 1.167 | 1.00 | 37.53 | C |
| ATOM | 795 | O | SER | A | 49 | 57.432 | 5.810 | 0.383 | 1.00 | 38.85 | O |
| ATOM | 797 | N | ASP | A | 50 | 55.415 | 5.611 | 1.302 | 1.00 | 41.01 | N |
| ATOM | 798 | CA | ASP | A | 50 | 55.086 | 4.387 | 0.521 | 1.00 | 44.36 | C |
| ATOM | 800 | CB | ASP | A | 50 | 53.871 | 3.670 | 1.158 | 1.00 | 44.72 | C |
| ATOM | 803 | CG | ASP | A | 50 | 54.263 | 2.996 | 2.523 | 1.00 | 48.52 | C |
| ATOM | 804 | OD1 | ASP | A | 50 | 53.394 | 2.439 | 3.225 | 1.00 | 53.16 | O |
| ATOM | 805 | OD2 | ASP | A | 50 | 55.482 | 3.045 | 2.902 | 1.00 | 51.41 | O |
| ATOM | 806 | C | ASP | A | 50 | 54.938 | 4.657 | -0.978 | 1.00 | 46.30 | C |
| ATOM | 807 | O | ASP | A | 50 | 55.223 | 3.805 | -1.817 | 1.00 | 46.29 | O |
| ATOM | 809 | N | PHE | A | 51 | 54.579 | 5.882 | -1.314 | 1.00 | 49.65 | N |
| ATOM | 810 | CA | PHE | A | 51 | 54.555 | 6.340 | -2.711 | 1.00 | 52.45 | C |
| ATOM | 812 | CB | PHE | A | 51 | 53.730 | 7.647 | -2.795 | 1.00 | 51.92 | C |
| ATOM | 815 | CG | PHE | A | 51 | 52.269 | 7.456 | -2.432 | 1.00 | 53.76 | C |
| ATOM | 816 | CD1 | PHE | A | 51 | 51.590 | 8.378 | -1.627 | 1.00 | 56.10 | C |
| ATOM | 818 | CE1 | PHE | A | 51 | 50.252 | 8.187 | -1.302 | 1.00 | 52.71 | C |
| ATOM | 820 | CZ | PHE | A | 51 | 49.579 | 7.085 | -1.769 | 1.00 | 56.18 | C |
| ATOM | 822 | CE2 | PHE | A | 51 | 50.234 | 6.158 | -2.596 | 1.00 | 56.57 | C |
| ATOM | 824 | CD2 | PHE | A | 51 | 51.567 | 6.345 | -2.906 | 1.00 | 55.25 | C |
| ATOM | 826 | C | PHE | A | 51 | 55.948 | 6.567 | -3.310 | 1.00 | 53.76 | C |
| ATOM | 827 | O | PHE | A | 51 | 56.169 | 7.579 | -3.945 | 1.00 | 54.84 | O |
| ATOM | 829 | N | GLY | A | 52 | 56.882 | 5.627 | -3.135 | 1.00 | 55.39 | N |
| ATOM | 830 | CA | GLY | A | 52 | 58.270 | 5.824 | -3.623 | 1.00 | 55.86 | C |
| ATOM | 833 | C | GLY | A | 52 | 59.124 | 4.584 | -3.436 | 1.00 | 56.18 | C |
| ATOM | 834 | O | GLY | A | 52 | 58.612 | 3.530 | -3.011 | 1.00 | 57.12 | O |
| ATOM | 836 | N | LYS | A | 73 | 63.661 | 2.892 | -6.173 | 1.00 | 55.58 | N |
| ATOM | 837 | CA | LYS | A | 73 | 63.127 | 1.698 | -5.471 | 1.00 | 55.21 | C |
| ATOM | 839 | CB | LYS | A | 73 | 64.266 | 0.696 | -5.157 | 1.00 | 55.05 | C |
| ATOM | 846 | C | LYS | A | 73 | 62.439 | 2.121 | -4.171 | 1.00 | 54.02 | C |
| ATOM | 847 | O | LYS | A | 73 | 61.217 | 1.927 | -3.973 | 1.00 | 56.31 | O |
| ATOM | 849 | N | HIS | A | 74 | 63.257 | 2.727 | -3.306 | 1.00 | 51.19 | N |
| ATOM | 850 | CA | HIS | A | 74 | 62.878 | 3.239 | -2.005 | 1.00 | 48.42 | C |
| ATOM | 852 | CB | HIS | A | 74 | 63.526 | 2.328 | -0.948 | 1.00 | 48.86 | C |
| ATOM | 855 | CG | HIS | A | 74 | 63.718 | 2.923 | 0.430 | 1.00 | 53.09 | C |
| ATOM | 856 | ND1 | HIS | A | 74 | 62.684 | 3.094 | 1.342 | 1.00 | 58.57 | N |
| ATOM | 858 | CE1 | HIS | A | 74 | 63.171 | 3.574 | 2.481 | 1.00 | 54.31 | C |
| ATOM | 860 | NE2 | HIS | A | 74 | 64.479 | 3.719 | 2.348 | 1.00 | 50.07 | N |
| ATOM | 862 | CD2 | HIS | A | 74 | 64.852 | 3.297 | 1.087 | 1.00 | 54.26 | C |
| ATOM | 864 | C | HIS | A | 74 | 63.400 | 4.698 | -2.015 | 1.00 | 44.69 | C |
| ATOM | 865 | O | HIS | A | 74 | 64.551 | 4.967 | -1.689 | 1.00 | 45.18 | O |
| ATOM | 867 | N | ARG | A | 75 | 62.556 | 5.614 | -2.489 | 1.00 | 39.40 | N |
| ATOM | 868 | CA | ARG | A | 75 | 62.892 | 7.037 | -2.567 | 1.00 | 35.64 | C |
| ATOM | 870 | CB | ARG | A | 75 | 61.858 | 7.781 | -3.390 | 1.00 | 34.06 | C |
| ATOM | 873 | CG | ARG | A | 75 | 62.093 | 9.252 | -3.420 | 1.00 | 33.10 | C |
| ATOM | 876 | CD | ARG | A | 75 | 61.336 | 9.942 | -4.532 | 1.00 | 30.93 | C |
| ATOM | 879 | NE | ARG | A | 75 | 61.583 | 11.378 | -4.556 | 1.00 | 29.38 | N |
| ATOM | 881 | CZ | ARG | A | 75 | 61.059 | 12.226 | -5.408 | 1.00 | 32.69 | C |
| ATOM | 882 | NH1 | ARG | A | 75 | 60.260 | 11.798 | -6.389 | 1.00 | 38.25 | N |
| ATOM | 885 | NH2 | ARG | A | 75 | 61.328 | 13.504 | -5.306 | 1.00 | 35.66 | N |
| ATOM | 888 | C | ARG | A | 75 | 62.981 | 7.704 | -1.191 | 1.00 | 31.56 | C |
| ATOM | 889 | O | ARG | A | 75 | 63.714 | 8.681 | -1.027 | 1.00 | 32.55 | O |
| ATOM | 891 | N | PHE | A | 76 | 62.206 | 7.269 | -0.210 | 1.00 | 30.32 | N |
| ATOM | 892 | CA | PHE | A | 76 | 62.102 | 8.029 | 1.018 | 1.00 | 28.41 | C |
| ATOM | 894 | CB | PHE | A | 76 | 60.675 | 8.503 | 1.272 | 1.00 | 28.48 | C |
| ATOM | 897 | CG | PHE | A | 76 | 60.187 | 9.447 | 0.246 | 1.00 | 26.94 | C |

FIG.15-10

| | | | | | | | | | | | |
|---|---|---|---|---|---|---|---|---|---|---|---|
| ATOM | 898 | CD1 | PHE | A | 76 | 60.621 | 10.781 | 0.228 | 1.00 | 27.25 | C |
| ATOM | 900 | CE1 | PHE | A | 76 | 60.212 | 11.599 | -0.762 | 1.00 | 26.70 | C |
| ATOM | 902 | CZ | PHE | A | 76 | 59.388 | 11.142 | -1.733 | 1.00 | 27.76 | C |
| ATOM | 904 | CE2 | PHE | A | 76 | 58.973 | 9.864 | -1.711 | 1.00 | 27.83 | C |
| ATOM | 906 | CD2 | PHE | A | 76 | 59.379 | 9.023 | -0.747 | 1.00 | 27.10 | C |
| ATOM | 908 | C | PHE | A | 76 | 62.583 | 7.249 | 2.208 | 1.00 | 30.06 | C |
| ATOM | 909 | O | PHE | A | 76 | 62.446 | 6.030 | 2.237 | 1.00 | 31.26 | O |
| ATOM | 911 | N | GLU | A | 77 | 63.162 | 7.959 | 3.164 | 1.00 | 27.71 | N |
| ATOM | 912 | CA | GLU | A | 77 | 63.458 | 7.371 | 4.502 | 1.00 | 28.00 | C |
| ATOM | 914 | CB | GLU | A | 77 | 64.846 | 7.740 | 4.961 | 1.00 | 26.44 | C |
| ATOM | 917 | CG | GLU | A | 77 | 65.305 | 7.028 | 6.186 | 1.00 | 28.16 | C |
| ATOM | 920 | CD | GLU | A | 77 | 65.654 | 5.584 | 5.872 | 1.00 | 32.53 | C |
| ATOM | 921 | OE1 | GLU | A | 77 | 65.139 | 4.762 | 6.621 | 1.00 | 38.28 | O |
| ATOM | 922 | OE2 | GLU | A | 77 | 66.367 | 5.286 | 4.831 | 1.00 | 36.50 | O |
| ATOM | 923 | C | GLU | A | 77 | 62.463 | 7.980 | 5.402 | 1.00 | 27.97 | C |
| ATOM | 924 | O | GLU | A | 77 | 62.321 | 9.206 | 5.371 | 1.00 | 29.70 | O |
| ATOM | 926 | N | ILE | A | 78 | 61.772 | 7.176 | 6.201 | 1.00 | 27.77 | N |
| ATOM | 927 | CA | ILE | A | 78 | 60.738 | 7.699 | 7.101 | 1.00 | 28.41 | C |
| ATOM | 929 | CB | ILE | A | 78 | 59.628 | 6.703 | 7.395 | 1.00 | 29.44 | C |
| ATOM | 931 | CG1 | ILE | A | 78 | 58.998 | 6.205 | 6.100 | 1.00 | 33.21 | C |
| ATOM | 934 | CD1 | ILE | A | 78 | 57.800 | 5.243 | 6.268 | 1.00 | 39.92 | C |
| ATOM | 938 | CG2 | ILE | A | 78 | 58.498 | 7.366 | 8.216 | 1.00 | 32.00 | C |
| ATOM | 942 | C | ILE | A | 78 | 61.444 | 8.020 | 8.373 | 1.00 | 28.76 | C |
| ATOM | 943 | O | ILE | A | 78 | 62.180 | 7.175 | 8.910 | 1.00 | 31.57 | O |
| ATOM | 945 | N | ILE | A | 79 | 61.284 | 9.241 | 8.857 | 1.00 | 26.91 | N |
| ATOM | 946 | CA | ILE | A | 79 | 61.910 | 9.628 | 10.085 | 1.00 | 26.42 | C |
| ATOM | 948 | CB | ILE | A | 79 | 62.714 | 10.984 | 9.908 | 1.00 | 27.71 | C |
| ATOM | 950 | CG1 | ILE | A | 79 | 63.917 | 10.703 | 8.990 | 1.00 | 30.83 | C |
| ATOM | 953 | CD1 | ILE | A | 79 | 64.427 | 11.895 | 8.278 | 1.00 | 36.25 | C |
| ATOM | 957 | CG2 | ILE | A | 79 | 63.219 | 11.472 | 11.308 | 1.00 | 24.00 | C |
| ATOM | 961 | C | ILE | A | 79 | 60.882 | 9.715 | 11.214 | 1.00 | 27.24 | C |
| ATOM | 962 | O | ILE | A | 79 | 61.122 | 9.223 | 12.364 | 1.00 | 26.71 | O |
| ATOM | 964 | N | GLU | A | 80 | 59.745 | 10.309 | 10.872 | 1.00 | 26.46 | N |
| ATOM | 965 | CA | GLU | A | 80 | 58.575 | 10.339 | 11.707 | 1.00 | 28.25 | C |
| ATOM | 967 | CB | GLU | A | 80 | 57.421 | 11.028 | 10.971 | 1.00 | 27.80 | C |
| ATOM | 970 | CG | GLU | A | 80 | 56.166 | 11.382 | 11.846 | 1.00 | 32.66 | C |
| ATOM | 973 | CD | GLU | A | 80 | 56.536 | 12.175 | 13.090 | 1.00 | 31.24 | C |
| ATOM | 974 | OE1 | GLU | A | 80 | 56.533 | 13.481 | 13.122 | 1.00 | 29.45 | O |
| ATOM | 975 | OE2 | GLU | A | 80 | 56.898 | 11.496 | 14.046 | 1.00 | 39.19 | O |
| ATOM | 976 | C | GLU | A | 80 | 58.177 | 8.906 | 12.167 | 1.00 | 28.75 | C |
| ATOM | 977 | O | GLU | A | 80 | 58.308 | 7.949 | 11.446 | 1.00 | 29.51 | O |
| ATOM | 979 | N | GLY | A | 81 | 57.710 | 8.762 | 13.380 | 1.00 | 31.70 | N |
| ATOM | 980 | CA | GLY | A | 81 | 57.310 | 7.417 | 13.827 | 1.00 | 32.58 | C |
| ATOM | 983 | C | GLY | A | 81 | 58.398 | 6.644 | 14.534 | 1.00 | 33.97 | C |
| ATOM | 984 | O | GLY | A | 81 | 58.123 | 5.643 | 15.231 | 1.00 | 37.29 | O |
| ATOM | 986 | N | ARG | A | 82 | 59.638 | 7.060 | 14.383 | 1.00 | 33.41 | N |
| ATOM | 987 | CA | ARG | A | 82 | 60.701 | 6.441 | 15.138 | 1.00 | 33.70 | C |
| ATOM | 989 | CB | ARG | A | 82 | 61.994 | 6.577 | 14.372 | 1.00 | 33.53 | C |
| ATOM | 992 | CG | ARG | A | 82 | 61.953 | 5.965 | 12.977 | 1.00 | 35.61 | C |
| ATOM | 995 | CD | ARG | A | 82 | 63.226 | 6.193 | 12.351 | 1.00 | 37.85 | C |
| ATOM | 998 | NE | ARG | A | 82 | 63.309 | 5.799 | 10.935 | 1.00 | 36.78 | N |
| ATOM | 1000 | CZ | ARG | A | 82 | 63.724 | 4.627 | 10.493 | 1.00 | 42.41 | C |
| ATOM | 1001 | NH1 | ARG | A | 82 | 64.055 | 3.665 | 11.349 | 1.00 | 43.93 | N |
| ATOM | 1004 | NH2 | ARG | A | 82 | 63.808 | 4.421 | 9.185 | 1.00 | 45.62 | N |
| ATOM | 1007 | C | ARG | A | 82 | 60.797 | 7.107 | 16.528 | 1.00 | 33.23 | C |
| ATOM | 1008 | O | ARG | A | 82 | 60.483 | 8.284 | 16.685 | 1.00 | 33.61 | O |
| ATOM | 1010 | N | ASP | A | 83 | 61.234 | 6.375 | 17.544 | 1.00 | 34.42 | N |
| ATOM | 1011 | CA | ASP | A | 83 | 61.584 | 7.033 | 18.795 | 1.00 | 34.75 | C |
| ATOM | 1013 | CB | ASP | A | 83 | 61.906 | 6.032 | 19.933 | 1.00 | 37.10 | C |
| ATOM | 1016 | CG | ASP | A | 83 | 63.228 | 5.255 | 19.760 | 1.00 | 41.05 | C |
| ATOM | 1017 | OD1 | ASP | A | 83 | 64.295 | 5.849 | 19.496 | 1.00 | 42.23 | O |
| ATOM | 1018 | OD2 | ASP | A | 83 | 63.221 | 4.014 | 20.011 | 1.00 | 51.05 | O |
| ATOM | 1019 | C | ASP | A | 83 | 62.722 | 8.029 | 18.544 | 1.00 | 34.57 | C |

FIG.15-11

| | | | | | | | | | | | |
|---|---|---|---|---|---|---|---|---|---|---|---|
| ATOM | 1020 | O | ASP | A | 83 | 63.490 | 7.899 | 17.579 | 1.00 | 33.96 | O |
| ATOM | 1022 | N | ARG | A | 84 | 62.864 | 8.971 | 19.445 | 1.00 | 35.28 | N |
| ATOM | 1023 | CA | ARG | A | 84 | 63.754 | 10.123 | 19.275 | 1.00 | 35.45 | C |
| ATOM | 1025 | CB | ARG | A | 84 | 63.729 | 10.987 | 20.547 | 1.00 | 36.54 | C |
| ATOM | 1028 | CG | ARG | A | 84 | 63.558 | 12.438 | 20.330 | 1.00 | 39.98 | C |
| ATOM | 1031 | CD | ARG | A | 84 | 63.533 | 13.125 | 21.692 | 1.00 | 41.59 | C |
| ATOM | 1034 | NE | ARG | A | 84 | 62.870 | 14.417 | 21.723 | 1.00 | 47.97 | N |
| ATOM | 1036 | CZ | ARG | A | 84 | 61.914 | 14.784 | 22.578 | 1.00 | 52.02 | C |
| ATOM | 1037 | NH1 | ARG | A | 84 | 61.460 | 13.970 | 23.520 | 1.00 | 55.25 | N |
| ATOM | 1040 | NH2 | ARG | A | 84 | 61.437 | 16.015 | 22.519 | 1.00 | 55.87 | N |
| ATOM | 1043 | C | ARG | A | 84 | 65.179 | 9.761 | 18.939 | 1.00 | 34.18 | C |
| ATOM | 1044 | O | ARG | A | 84 | 65.787 | 10.360 | 18.019 | 1.00 | 33.81 | O |
| ATOM | 1046 | N | ILE | A | 85 | 65.724 | 8.763 | 19.630 | 1.00 | 32.73 | N |
| ATOM | 1047 | CA | ILE | A | 85 | 67.098 | 8.353 | 19.418 | 1.00 | 31.80 | C |
| ATOM | 1049 | CB | ILE | A | 85 | 67.539 | 7.375 | 20.510 | 1.00 | 34.16 | C |
| ATOM | 1051 | CG1 | ILE | A | 85 | 67.603 | 8.142 | 21.850 | 1.00 | 34.27 | C |
| ATOM | 1054 | CD1 | ILE | A | 85 | 67.623 | 7.273 | 23.022 | 1.00 | 38.78 | C |
| ATOM | 1058 | CG2 | ILE | A | 85 | 68.878 | 6.662 | 20.105 | 1.00 | 32.58 | C |
| ATOM | 1062 | C | ILE | A | 85 | 67.337 | 7.729 | 18.065 | 1.00 | 32.35 | C |
| ATOM | 1063 | O | ILE | A | 85 | 68.304 | 8.059 | 17.361 | 1.00 | 27.06 | O |
| ATOM | 1065 | N | MET | A | 86 | 66.413 | 6.851 | 17.674 | 1.00 | 30.51 | N |
| ATOM | 1066 | CA | MET | A | 86 | 66.456 | 6.287 | 16.346 | 1.00 | 32.48 | C |
| ATOM | 1068 | CB | MET | A | 86 | 65.445 | 5.157 | 16.199 | 1.00 | 33.04 | C |
| ATOM | 1071 | CG | MET | A | 86 | 65.931 | 3.934 | 16.997 | 1.00 | 40.81 | C |
| ATOM | 1074 | SD | MET | A | 86 | 67.681 | 3.564 | 16.685 | 1.00 | 51.34 | S |
| ATOM | 1075 | CE | MET | A | 86 | 67.698 | 3.446 | 14.868 | 1.00 | 41.58 | C |
| ATOM | 1079 | C | MET | A | 86 | 66.295 | 7.308 | 15.258 | 1.00 | 29.80 | C |
| ATOM | 1080 | O | MET | A | 86 | 66.954 | 7.182 | 14.234 | 1.00 | 29.70 | O |
| ATOM | 1082 | N | ALA | A | 87 | 65.434 | 8.270 | 15.480 | 1.00 | 28.27 | N |
| ATOM | 1083 | CA | ALA | A | 87 | 65.167 | 9.291 | 14.519 | 1.00 | 28.84 | C |
| ATOM | 1085 | CB | ALA | A | 87 | 64.007 | 10.201 | 14.949 | 1.00 | 27.51 | C |
| ATOM | 1089 | C | ALA | A | 87 | 66.464 | 10.077 | 14.243 | 1.00 | 29.11 | C |
| ATOM | 1090 | O | ALA | A | 87 | 66.852 | 10.258 | 13.085 | 1.00 | 27.10 | O |
| ATOM | 1092 | N | TRP | A | 88 | 67.120 | 10.512 | 15.311 | 1.00 | 28.23 | N |
| ATOM | 1093 | CA | TRP | A | 88 | 68.350 | 11.231 | 15.181 | 1.00 | 28.62 | C |
| ATOM | 1095 | CB | TRP | A | 88 | 68.699 | 11.958 | 16.481 | 1.00 | 28.73 | C |
| ATOM | 1098 | CG | TRP | A | 88 | 67.926 | 13.220 | 16.669 | 1.00 | 27.17 | C |
| ATOM | 1099 | CD1 | TRP | A | 88 | 67.025 | 13.495 | 17.686 | 1.00 | 29.81 | C |
| ATOM | 1101 | NE1 | TRP | A | 88 | 66.504 | 14.751 | 17.531 | 1.00 | 29.27 | N |
| ATOM | 1103 | CE2 | TRP | A | 88 | 67.065 | 15.335 | 16.426 | 1.00 | 30.57 | C |
| ATOM | 1104 | CD2 | TRP | A | 88 | 67.975 | 14.398 | 15.861 | 1.00 | 28.98 | C |
| ATOM | 1105 | CE3 | TRP | A | 88 | 68.679 | 14.755 | 14.702 | 1.00 | 31.11 | C |
| ATOM | 1107 | CZ3 | TRP | A | 88 | 68.491 | 16.039 | 14.153 | 1.00 | 30.88 | C |
| ATOM | 1109 | CH2 | TRP | A | 88 | 67.568 | 16.952 | 14.743 | 1.00 | 32.87 | C |
| ATOM | 1111 | CZ2 | TRP | A | 88 | 66.871 | 16.617 | 15.891 | 1.00 | 32.84 | C |
| ATOM | 1113 | C | TRP | A | 88 | 69.496 | 10.341 | 14.669 | 1.00 | 29.09 | C |
| ATOM | 1114 | O | TRP | A | 88 | 70.376 | 10.844 | 13.988 | 1.00 | 29.20 | O |
| ATOM | 1116 | N | THR | A | 89 | 69.513 | 9.051 | 14.992 | 1.00 | 28.39 | N |
| ATOM | 1117 | CA | THR | A | 89 | 70.511 | 8.203 | 14.458 | 1.00 | 28.07 | C |
| ATOM | 1119 | CB | THR | A | 89 | 70.351 | 6.780 | 15.025 | 1.00 | 30.45 | C |
| ATOM | 1121 | OG1 | THR | A | 89 | 70.403 | 6.829 | 16.472 | 1.00 | 30.47 | O |
| ATOM | 1123 | CG2 | THR | A | 89 | 71.375 | 5.852 | 14.445 | 1.00 | 27.45 | C |
| ATOM | 1127 | C | THR | A | 89 | 70.363 | 8.163 | 12.951 | 1.00 | 27.73 | C |
| ATOM | 1128 | O | THR | A | 89 | 71.364 | 8.202 | 12.254 | 1.00 | 29.24 | O |
| ATOM | 1130 | N | VAL | A | 90 | 69.128 | 7.984 | 12.455 | 1.00 | 26.04 | N |
| ATOM | 1131 | CA | VAL | A | 90 | 68.880 | 7.973 | 11.025 | 1.00 | 28.17 | C |
| ATOM | 1133 | CB | VAL | A | 90 | 67.392 | 7.630 | 10.747 | 1.00 | 28.09 | C |
| ATOM | 1135 | CG1 | VAL | A | 90 | 67.116 | 7.760 | 9.270 | 1.00 | 32.79 | C |
| ATOM | 1139 | CG2 | VAL | A | 90 | 67.117 | 6.165 | 11.183 | 1.00 | 33.06 | C |
| ATOM | 1143 | C | VAL | A | 90 | 69.294 | 9.304 | 10.332 | 1.00 | 25.29 | C |
| ATOM | 1144 | O | VAL | A | 90 | 69.917 | 9.313 | 9.281 | 1.00 | 26.94 | O |
| ATOM | 1146 | N | VAL | A | 91 | 68.920 | 10.413 | 10.941 | 1.00 | 24.78 | N |
| ATOM | 1147 | CA | VAL | A | 91 | 69.194 | 11.703 | 10.388 | 1.00 | 26.03 | C |

FIG.15-12

| | | | | | | | | | | | |
|---|---|---|---|---|---|---|---|---|---|---|---|
| ATOM | 1149 | CB | VAL | A | 91 | 68.555 | 12.844 | 11.211 | 1.00 | 26.73 | C |
| ATOM | 1151 | CG1 | VAL | A | 91 | 69.226 | 14.161 | 10.901 | 1.00 | 24.74 | C |
| ATOM | 1155 | CG2 | VAL | A | 91 | 67.028 | 12.902 | 11.061 | 1.00 | 26.13 | C |
| ATOM | 1159 | C | VAL | A | 91 | 70.698 | 11.864 | 10.345 | 1.00 | 26.72 | C |
| ATOM | 1160 | O | VAL | A | 91 | 71.220 | 12.272 | 9.344 | 1.00 | 25.76 | O |
| ATOM | 1162 | N | ASN | A | 92 | 71.363 | 11.530 | 11.440 | 1.00 | 28.74 | N |
| ATOM | 1163 | CA | ASN | A | 92 | 72.821 | 11.583 | 11.468 | 1.00 | 29.66 | C |
| ATOM | 1165 | CB | ASN | A | 92 | 73.295 | 11.150 | 12.829 | 1.00 | 31.16 | C |
| ATOM | 1168 | CG | ASN | A | 92 | 73.037 | 12.204 | 13.841 | 1.00 | 38.36 | C |
| ATOM | 1169 | OD1 | ASN | A | 92 | 72.486 | 13.261 | 13.498 | 1.00 | 40.90 | O |
| ATOM | 1170 | ND2 | ASN | A | 92 | 73.409 | 11.946 | 15.108 | 1.00 | 46.19 | N |
| ATOM | 1173 | C | ASN | A | 92 | 73.514 | 10.765 | 10.410 | 1.00 | 29.41 | C |
| ATOM | 1174 | O | ASN | A | 92 | 74.465 | 11.238 | 9.759 | 1.00 | 29.52 | O |
| ATOM | 1176 | N | SER | A | 93 | 73.027 | 9.559 | 10.243 | 1.00 | 28.39 | N |
| ATOM | 1177 | CA | SER | A | 93 | 73.528 | 8.654 | 9.251 | 1.00 | 29.99 | C |
| ATOM | 1179 | CB | SER | A | 93 | 72.762 | 7.340 | 9.352 | 1.00 | 30.93 | C |
| ATOM | 1182 | OG | SER | A | 93 | 73.330 | 6.429 | 8.454 | 1.00 | 38.77 | O |
| ATOM | 1184 | C | SER | A | 93 | 73.381 | 9.231 | 7.849 | 1.00 | 28.47 | C |
| ATOM | 1185 | O | SER | A | 93 | 74.335 | 9.186 | 7.015 | 1.00 | 28.29 | O |
| ATOM | 1187 | N | ILE | A | 94 | 72.231 | 9.843 | 7.598 | 1.00 | 25.74 | N |
| ATOM | 1188 | CA | ILE | A | 94 | 72.003 | 10.410 | 6.313 | 1.00 | 26.38 | C |
| ATOM | 1190 | CB | ILE | A | 94 | 70.526 | 10.827 | 6.109 | 1.00 | 25.00 | C |
| ATOM | 1192 | CG1 | ILE | A | 94 | 69.641 | 9.573 | 5.895 | 1.00 | 27.06 | C |
| ATOM | 1195 | CD1 | ILE | A | 94 | 68.146 | 9.944 | 6.065 | 1.00 | 27.94 | C |
| ATOM | 1199 | CG2 | ILE | A | 94 | 70.440 | 11.755 | 4.881 | 1.00 | 23.67 | C |
| ATOM | 1203 | C | ILE | A | 94 | 72.946 | 11.607 | 6.118 | 1.00 | 26.78 | C |
| ATOM | 1204 | O | ILE | A | 94 | 73.590 | 11.779 | 5.052 | 1.00 | 28.05 | O |
| ATOM | 1206 | N | CYS | A | 95 | 73.071 | 12.431 | 7.121 | 1.00 | 28.08 | N |
| ATOM | 1207 | CA | CYS | A | 95 | 73.914 | 13.621 | 6.966 | 1.00 | 27.76 | C |
| ATOM | 1209 | CB | CYS | A | 95 | 73.825 | 14.514 | 8.170 | 1.00 | 28.99 | C |
| ATOM | 1212 | SG | CYS | A | 95 | 72.182 | 15.295 | 8.255 | 1.00 | 30.96 | S |
| ATOM | 1214 | C | CYS | A | 95 | 75.391 | 13.222 | 6.771 | 1.00 | 28.81 | C |
| ATOM | 1215 | O | CYS | A | 95 | 76.076 | 13.847 | 6.000 | 1.00 | 30.43 | O |
| ATOM | 1217 | N | ASN | A | 96 | 75.805 | 12.165 | 7.428 | 1.00 | 30.19 | N |
| ATOM | 1218 | CA | ASN | A | 96 | 77.155 | 11.638 | 7.326 | 1.00 | 30.99 | C |
| ATOM | 1220 | CB | ASN | A | 96 | 77.390 | 10.648 | 8.409 | 1.00 | 31.98 | C |
| ATOM | 1223 | CG | ASN | A | 96 | 77.529 | 11.285 | 9.703 | 1.00 | 34.09 | C |
| ATOM | 1224 | OD1 | ASN | A | 96 | 77.785 | 12.471 | 9.760 | 1.00 | 38.12 | O |
| ATOM | 1225 | ND2 | ASN | A | 96 | 77.443 | 10.505 | 10.777 | 1.00 | 37.79 | N |
| ATOM | 1228 | C | ASN | A | 96 | 77.469 | 10.997 | 5.990 | 1.00 | 30.99 | C |
| ATOM | 1229 | O | ASN | A | 96 | 78.632 | 10.916 | 5.608 | 1.00 | 32.53 | O |
| ATOM | 1231 | N | THR | A | 97 | 76.458 | 10.584 | 5.241 | 1.00 | 31.87 | N |
| ATOM | 1232 | CA | THR | A | 97 | 76.677 | 9.940 | 3.958 | 1.00 | 31.89 | C |
| ATOM | 1234 | CB | THR | A | 97 | 75.918 | 8.581 | 3.922 | 1.00 | 33.06 | C |
| ATOM | 1236 | OG1 | THR | A | 97 | 74.547 | 8.804 | 4.168 | 1.00 | 30.94 | O |
| ATOM | 1238 | CG2 | THR | A | 97 | 76.432 | 7.624 | 4.993 | 1.00 | 37.08 | C |
| ATOM | 1242 | C | THR | A | 97 | 76.274 | 10.796 | 2.784 | 1.00 | 32.52 | C |
| ATOM | 1243 | O | THR | A | 97 | 76.406 | 10.371 | 1.632 | 1.00 | 34.10 | O |
| ATOM | 1245 | N | THR | A | 98 | 75.752 | 11.999 | 3.017 | 1.00 | 32.16 | N |
| ATOM | 1246 | CA | THR | A | 98 | 75.389 | 12.895 | 1.956 | 1.00 | 30.79 | C |
| ATOM | 1248 | CB | THR | A | 98 | 73.850 | 13.080 | 1.925 | 1.00 | 31.93 | C |
| ATOM | 1250 | OG1 | THR | A | 98 | 73.465 | 13.807 | 3.105 | 1.00 | 28.31 | O |
| ATOM | 1252 | CG2 | THR | A | 98 | 73.141 | 11.726 | 1.783 | 1.00 | 28.96 | C |
| ATOM | 1256 | C | THR | A | 98 | 75.966 | 14.277 | 2.059 | 1.00 | 32.23 | C |
| ATOM | 1257 | O | THR | A | 98 | 75.926 | 15.075 | 1.083 | 1.00 | 33.52 | O |
| ATOM | 1259 | N | GLY | A | 99 | 76.450 | 14.600 | 3.238 | 1.00 | 32.13 | N |
| ATOM | 1260 | CA | GLY | A | 99 | 76.811 | 15.938 | 3.594 | 1.00 | 35.19 | C |
| ATOM | 1263 | C | GLY | A | 99 | 75.688 | 16.961 | 3.648 | 1.00 | 35.47 | C |
| ATOM | 1264 | O | GLY | A | 99 | 75.954 | 18.163 | 3.863 | 1.00 | 37.28 | O |
| ATOM | 1266 | N | VAL | A | 100 | 74.436 | 16.554 | 3.397 | 1.00 | 34.98 | N |
| ATOM | 1267 | CA | VAL | A | 100 | 73.326 | 17.477 | 3.629 | 1.00 | 34.52 | C |
| ATOM | 1269 | CB | VAL | A | 100 | 71.940 | 16.785 | 3.368 | 1.00 | 33.48 | C |
| ATOM | 1271 | CG1 | VAL | A | 100 | 70.760 | 17.662 | 3.875 | 1.00 | 34.09 | C |

FIG.15-13

| | | | | | | | | | | | |
|---|---|---|---|---|---|---|---|---|---|---|---|
| ATOM | 1275 | CG2 | VAL | A | 100 | 71.806 | 16.509 | 1.922 | 1.00 | 34.00 | C |
| ATOM | 1279 | C | VAL | A | 100 | 73.455 | 17.959 | 5.053 | 1.00 | 34.99 | C |
| ATOM | 1280 | O | VAL | A | 100 | 73.786 | 17.220 | 5.937 | 1.00 | 35.13 | O |
| ATOM | 1282 | N | GLU | A | 101 | 73.228 | 19.227 | 5.245 | 1.00 | 38.67 | N |
| ATOM | 1283 | CA | GLU | A | 101 | 73.307 | 19.882 | 6.541 | 1.00 | 40.23 | C |
| ATOM | 1285 | CB | GLU | A | 101 | 72.974 | 21.356 | 6.298 | 1.00 | 41.73 | C |
| ATOM | 1288 | CG | GLU | A | 101 | 72.946 | 22.267 | 7.549 | 1.00 | 49.25 | C |
| ATOM | 1291 | CD | GLU | A | 101 | 72.581 | 23.732 | 7.225 | 1.00 | 55.29 | C |
| ATOM | 1292 | OE1 | GLU | A | 101 | 72.233 | 24.471 | 8.179 | 1.00 | 57.93 | O |
| ATOM | 1293 | OE2 | GLU | A | 101 | 72.626 | 24.125 | 6.024 | 1.00 | 59.90 | O |
| ATOM | 1294 | C | GLU | A | 101 | 72.313 | 19.279 | 7.592 | 1.00 | 39.87 | C |
| ATOM | 1295 | O | GLU | A | 101 | 71.163 | 18.964 | 7.245 | 1.00 | 36.74 | O |
| ATOM | 1297 | N | LYS | A | 102 | 72.755 | 19.161 | 8.851 | 1.00 | 40.02 | N |
| ATOM | 1298 | CA | LYS | A | 102 | 71.892 | 18.586 | 9.906 | 1.00 | 40.48 | C |
| ATOM | 1300 | CB | LYS | A | 102 | 72.636 | 18.175 | 11.173 | 1.00 | 42.28 | C |
| ATOM | 1303 | CG | LYS | A | 102 | 72.525 | 16.685 | 11.437 | 1.00 | 46.45 | C |
| ATOM | 1306 | CD | LYS | A | 102 | 73.005 | 16.258 | 12.827 | 1.00 | 50.39 | C |
| ATOM | 1309 | CE | LYS | A | 102 | 74.493 | 16.040 | 12.865 | 1.00 | 51.80 | C |
| ATOM | 1312 | NZ | LYS | A | 102 | 74.829 | 15.096 | 13.928 | 1.00 | 52.68 | N |
| ATOM | 1316 | C | LYS | A | 102 | 70.808 | 19.553 | 10.275 | 1.00 | 38.78 | C |
| ATOM | 1317 | O | LYS | A | 102 | 71.093 | 20.702 | 10.549 | 1.00 | 38.04 | O |
| ATOM | 1319 | N | PRO | A | 103 | 69.549 | 19.092 | 10.274 | 1.00 | 36.34 | N |
| ATOM | 1320 | CA | PRO | A | 103 | 68.519 | 20.053 | 10.566 | 1.00 | 34.63 | C |
| ATOM | 1322 | CB | PRO | A | 103 | 67.227 | 19.361 | 10.090 | 1.00 | 35.11 | C |
| ATOM | 1325 | CG | PRO | A | 103 | 67.552 | 17.966 | 10.133 | 1.00 | 34.09 | C |
| ATOM | 1328 | CD | PRO | A | 103 | 68.992 | 17.865 | 9.710 | 1.00 | 35.93 | C |
| ATOM | 1331 | C | PRO | A | 103 | 68.510 | 20.316 | 12.058 | 1.00 | 33.46 | C |
| ATOM | 1332 | O | PRO | A | 103 | 68.935 | 19.464 | 12.829 | 1.00 | 31.01 | O |
| ATOM | 1333 | N | LYS | A | 104 | 68.059 | 21.514 | 12.418 | 1.00 | 32.72 | N |
| ATOM | 1334 | CA | LYS | A | 104 | 67.884 | 21.946 | 13.803 | 1.00 | 35.25 | C |
| ATOM | 1336 | CB | LYS | A | 104 | 67.467 | 23.424 | 13.835 | 1.00 | 36.22 | C |
| ATOM | 1339 | CG | LYS | A | 104 | 68.572 | 24.305 | 13.322 | 1.00 | 42.91 | C |
| ATOM | 1342 | CD | LYS | A | 104 | 68.375 | 25.787 | 13.693 | 1.00 | 49.19 | C |
| ATOM | 1345 | CE | LYS | A | 104 | 69.093 | 26.641 | 12.663 | 1.00 | 54.36 | C |
| ATOM | 1348 | NZ | LYS | A | 104 | 69.130 | 28.087 | 13.047 | 1.00 | 60.95 | N |
| ATOM | 1352 | C | LYS | A | 104 | 66.802 | 21.156 | 14.492 | 1.00 | 34.59 | C |
| ATOM | 1353 | O | LYS | A | 104 | 66.902 | 20.889 | 15.686 | 1.00 | 34.61 | O |
| ATOM | 1355 | N | PHE | A | 105 | 65.760 | 20.802 | 13.724 | 1.00 | 33.69 | N |
| ATOM | 1356 | CA | PHE | A | 105 | 64.588 | 20.072 | 14.280 | 1.00 | 32.73 | C |
| ATOM | 1358 | CB | PHE | A | 105 | 63.377 | 20.941 | 14.096 | 1.00 | 33.45 | C |
| ATOM | 1361 | CG | PHE | A | 105 | 63.479 | 22.256 | 14.838 | 1.00 | 38.65 | C |
| ATOM | 1362 | CD1 | PHE | A | 105 | 63.467 | 22.272 | 16.239 | 1.00 | 44.18 | C |
| ATOM | 1364 | CE1 | PHE | A | 105 | 63.573 | 23.510 | 16.927 | 1.00 | 47.09 | C |
| ATOM | 1366 | CZ | PHE | A | 105 | 63.683 | 24.702 | 16.211 | 1.00 | 43.63 | C |
| ATOM | 1368 | CE2 | PHE | A | 105 | 63.704 | 24.675 | 14.830 | 1.00 | 43.54 | C |
| ATOM | 1370 | CD2 | PHE | A | 105 | 63.619 | 23.463 | 14.150 | 1.00 | 40.08 | C |
| ATOM | 1372 | C | PHE | A | 105 | 64.395 | 18.757 | 13.518 | 1.00 | 31.55 | C |
| ATOM | 1373 | O | PHE | A | 105 | 64.729 | 18.701 | 12.357 | 1.00 | 29.93 | O |
| ATOM | 1375 | N | LEU | A | 106 | 63.901 | 17.723 | 14.160 | 1.00 | 28.75 | N |
| ATOM | 1376 | CA | LEU | A | 106 | 63.668 | 16.474 | 13.437 | 1.00 | 28.86 | C |
| ATOM | 1378 | CB | LEU | A | 106 | 63.049 | 15.409 | 14.367 | 1.00 | 29.42 | C |
| ATOM | 1381 | CG | LEU | A | 106 | 63.864 | 14.395 | 15.129 | 1.00 | 34.72 | C |
| ATOM | 1383 | CD1 | LEU | A | 106 | 62.880 | 13.291 | 15.671 | 1.00 | 34.63 | C |
| ATOM | 1387 | CD2 | LEU | A | 106 | 64.900 | 13.789 | 14.279 | 1.00 | 26.80 | C |
| ATOM | 1391 | C | LEU | A | 106 | 62.705 | 16.690 | 12.294 | 1.00 | 26.40 | C |
| ATOM | 1392 | O | LEU | A | 106 | 61.663 | 17.245 | 12.485 | 1.00 | 25.36 | O |
| ATOM | 1394 | N | PRO | A | 107 | 63.028 | 16.276 | 11.079 | 1.00 | 25.21 | N |
| ATOM | 1395 | CA | PRO | A | 107 | 62.022 | 16.372 | 10.006 | 1.00 | 24.80 | C |
| ATOM | 1397 | CB | PRO | A | 107 | 62.916 | 16.504 | 8.771 | 1.00 | 26.70 | C |
| ATOM | 1400 | CG | PRO | A | 107 | 64.078 | 15.644 | 9.118 | 1.00 | 27.32 | C |
| ATOM | 1403 | CD | PRO | A | 107 | 64.334 | 15.842 | 10.564 | 1.00 | 27.04 | C |
| ATOM | 1406 | C | PRO | A | 107 | 61.257 | 15.059 | 9.938 | 1.00 | 25.01 | C |
| ATOM | 1407 | O | PRO | A | 107 | 61.460 | 14.178 | 10.812 | 1.00 | 25.42 | O |

FIG.15-14

| | | | | | | | | | | | |
|---|---|---|---|---|---|---|---|---|---|---|---|
| ATOM | 1408 | N | ASP | A | 108 | 60.466 | 14.890 | 8.893 | 1.00 | 23.40 | N |
| ATOM | 1409 | CA | ASP | A | 108 | 59.559 | 13.751 | 8.794 | 1.00 | 24.79 | C |
| ATOM | 1411 | CB | ASP | A | 108 | 58.193 | 14.244 | 8.337 | 1.00 | 23.28 | C |
| ATOM | 1414 | CG | ASP | A | 108 | 57.524 | 15.051 | 9.405 | 1.00 | 23.89 | C |
| ATOM | 1415 | OD1 | ASP | A | 108 | 57.552 | 14.593 | 10.575 | 1.00 | 23.84 | O |
| ATOM | 1416 | OD2 | ASP | A | 108 | 56.930 | 16.083 | 9.088 | 1.00 | 27.89 | O |
| ATOM | 1417 | C | ASP | A | 108 | 60.067 | 12.661 | 7.891 | 1.00 | 24.46 | C |
| ATOM | 1418 | O | ASP | A | 108 | 59.785 | 11.513 | 8.193 | 1.00 | 25.25 | O |
| ATOM | 1420 | N | LEU | A | 109 | 60.705 | 13.049 | 6.774 | 1.00 | 23.26 | N |
| ATOM | 1421 | CA | LEU | A | 109 | 61.250 | 12.171 | 5.748 | 1.00 | 23.65 | C |
| ATOM | 1423 | CB | LEU | A | 109 | 60.318 | 12.051 | 4.527 | 1.00 | 24.18 | C |
| ATOM | 1426 | CG | LEU | A | 109 | 58.818 | 11.678 | 4.749 | 1.00 | 27.31 | C |
| ATOM | 1428 | CD1 | LEU | A | 109 | 58.000 | 11.950 | 3.517 | 1.00 | 30.45 | C |
| ATOM | 1432 | CD2 | LEU | A | 109 | 58.641 | 10.255 | 5.224 | 1.00 | 27.38 | C |
| ATOM | 1436 | C | LEU | A | 109 | 62.597 | 12.680 | 5.223 | 1.00 | 23.28 | C |
| ATOM | 1437 | O | LEU | A | 109 | 62.890 | 13.883 | 5.336 | 1.00 | 24.26 | O |
| ATOM | 1439 | N | TYR | A | 110 | 63.329 | 11.800 | 4.547 | 1.00 | 22.76 | N |
| ATOM | 1440 | CA | TYR | A | 110 | 64.429 | 12.229 | 3.656 | 1.00 | 23.81 | C |
| ATOM | 1442 | CB | TYR | A | 110 | 65.803 | 11.706 | 4.129 | 1.00 | 24.70 | C |
| ATOM | 1445 | CG | TYR | A | 110 | 66.980 | 12.214 | 3.313 | 1.00 | 23.87 | C |
| ATOM | 1446 | CD1 | TYR | A | 110 | 67.413 | 13.498 | 3.439 | 1.00 | 26.85 | C |
| ATOM | 1448 | CE1 | TYR | A | 110 | 68.436 | 13.961 | 2.692 | 1.00 | 28.71 | C |
| ATOM | 1450 | CZ | TYR | A | 110 | 69.049 | 13.150 | 1.805 | 1.00 | 26.47 | C |
| ATOM | 1451 | OH | TYR | A | 110 | 70.128 | 13.601 | 1.049 | 1.00 | 29.18 | O |
| ATOM | 1453 | CE2 | TYR | A | 110 | 68.618 | 11.870 | 1.634 | 1.00 | 26.21 | C |
| ATOM | 1455 | CD2 | TYR | A | 110 | 67.593 | 11.413 | 2.387 | 1.00 | 24.74 | C |
| ATOM | 1457 | C | TYR | A | 110 | 64.119 | 11.708 | 2.277 | 1.00 | 25.22 | C |
| ATOM | 1458 | O | TYR | A | 110 | 63.721 | 10.539 | 2.101 | 1.00 | 26.47 | O |
| ATOM | 1460 | N | ASP | A | 111 | 64.304 | 12.577 | 1.304 | 1.00 | 23.71 | N |
| ATOM | 1461 | CA | ASP | A | 111 | 64.098 | 12.272 | -0.086 | 1.00 | 23.95 | C |
| ATOM | 1463 | CB | ASP | A | 111 | 63.483 | 13.478 | -0.715 | 1.00 | 23.51 | C |
| ATOM | 1466 | CG | ASP | A | 111 | 63.150 | 13.295 | -2.204 | 1.00 | 26.19 | C |
| ATOM | 1467 | OD1 | ASP | A | 111 | 63.722 | 12.431 | -2.905 | 1.00 | 24.46 | O |
| ATOM | 1468 | OD2 | ASP | A | 111 | 62.289 | 14.049 | -2.662 | 1.00 | 24.83 | O |
| ATOM | 1469 | C | ASP | A | 111 | 65.507 | 11.982 | -0.670 | 1.00 | 26.57 | C |
| ATOM | 1470 | O | ASP | A | 111 | 66.307 | 12.900 | -0.806 | 1.00 | 23.25 | O |
| ATOM | 1472 | N | TYR | A | 112 | 65.732 | 10.710 | -0.974 | 1.00 | 26.78 | N |
| ATOM | 1473 | CA | TYR | A | 112 | 67.010 | 10.213 | -1.566 | 1.00 | 29.95 | C |
| ATOM | 1475 | CB | TYR | A | 112 | 67.105 | 8.681 | -1.458 | 1.00 | 28.48 | C |
| ATOM | 1478 | CG | TYR | A | 112 | 67.357 | 8.175 | -0.088 | 1.00 | 32.03 | C |
| ATOM | 1479 | CD1 | TYR | A | 112 | 68.546 | 8.448 | 0.552 | 1.00 | 30.80 | C |
| ATOM | 1481 | CE1 | TYR | A | 112 | 68.783 | 8.007 | 1.833 | 1.00 | 30.92 | C |
| ATOM | 1483 | CZ | TYR | A | 112 | 67.865 | 7.231 | 2.485 | 1.00 | 32.17 | C |
| ATOM | 1484 | OH | TYR | A | 112 | 68.134 | 6.827 | 3.780 | 1.00 | 32.83 | O |
| ATOM | 1486 | CE2 | TYR | A | 112 | 66.665 | 6.929 | 1.887 | 1.00 | 32.64 | C |
| ATOM | 1488 | CD2 | TYR | A | 112 | 66.416 | 7.428 | 0.588 | 1.00 | 34.95 | C |
| ATOM | 1490 | C | TYR | A | 112 | 67.120 | 10.605 | -3.017 | 1.00 | 31.55 | C |
| ATOM | 1491 | O | TYR | A | 112 | 68.229 | 10.662 | -3.560 | 1.00 | 34.48 | O |
| ATOM | 1493 | N | LYS | A | 113 | 66.021 | 10.955 | -3.649 | 1.00 | 31.03 | N |
| ATOM | 1494 | CA | LYS | A | 113 | 66.136 | 11.436 | -5.022 | 1.00 | 32.58 | C |
| ATOM | 1496 | CB | LYS | A | 113 | 64.861 | 11.173 | -5.826 | 1.00 | 32.76 | C |
| ATOM | 1499 | CG | LYS | A | 113 | 64.985 | 11.582 | -7.320 | 1.00 | 36.49 | C |
| ATOM | 1502 | CD | LYS | A | 113 | 63.685 | 11.401 | -7.983 | 1.00 | 44.02 | C |
| ATOM | 1505 | CE | LYS | A | 113 | 63.790 | 11.452 | -9.517 | 1.00 | 47.29 | C |
| ATOM | 1508 | NZ | LYS | A | 113 | 62.618 | 10.654 | -10.007 | 1.00 | 52.44 | N |
| ATOM | 1512 | C | LYS | A | 113 | 66.528 | 12.874 | -5.113 | 1.00 | 32.02 | C |
| ATOM | 1513 | O | LYS | A | 113 | 67.505 | 13.200 | -5.798 | 1.00 | 31.77 | O |
| ATOM | 1515 | N | GLU | A | 114 | 65.843 | 13.749 | -4.396 | 1.00 | 29.70 | N |
| ATOM | 1516 | CA | GLU | A | 114 | 66.268 | 15.163 | -4.318 | 1.00 | 30.53 | C |
| ATOM | 1518 | CB | GLU | A | 114 | 65.061 | 16.089 | -4.047 | 1.00 | 31.86 | C |
| ATOM | 1521 | CG | GLU | A | 114 | 64.012 | 15.925 | -5.044 | 1.00 | 33.89 | C |
| ATOM | 1524 | CD | GLU | A | 114 | 64.247 | 16.698 | -6.340 | 1.00 | 40.59 | C |
| ATOM | 1525 | OE1 | GLU | A | 114 | 65.163 | 17.578 | -6.395 | 1.00 | 35.62 | O |

FIG.15-15

| | | | | | | | | | | | |
|---|---|---|---|---|---|---|---|---|---|---|---|
| ATOM | 1526 | OE2 | GLU | A | 114 | 63.476 | 16.385 | -7.296 | 1.00 | 43.51 | O |
| ATOM | 1527 | C | GLU | A | 114 | 67.323 | 15.477 | -3.304 | 1.00 | 29.79 | C |
| ATOM | 1528 | O | GLU | A | 114 | 67.813 | 16.593 | -3.281 | 1.00 | 32.38 | O |
| ATOM | 1530 | N | ASN | A | 115 | 67.699 | 14.512 | -2.485 | 1.00 | 29.15 | N |
| ATOM | 1531 | CA | ASN | A | 115 | 68.634 | 14.708 | -1.367 | 1.00 | 29.75 | C |
| ATOM | 1533 | CB | ASN | A | 115 | 70.072 | 14.728 | -1.936 | 1.00 | 30.28 | C |
| ATOM | 1536 | CG | ASN | A | 115 | 70.553 | 13.324 | -2.317 | 1.00 | 30.10 | C |
| ATOM | 1537 | OD1 | ASN | A | 115 | 70.645 | 12.971 | -3.492 | 1.00 | 34.49 | O |
| ATOM | 1538 | ND2 | ASN | A | 115 | 70.713 | 12.501 | -1.337 | 1.00 | 27.64 | N |
| ATOM | 1541 | C | ASN | A | 115 | 68.323 | 15.896 | -0.517 | 1.00 | 28.87 | C |
| ATOM | 1542 | O | ASN | A | 115 | 69.133 | 16.839 | -0.311 | 1.00 | 27.25 | O |
| ATOM | 1544 | N | ARG | A | 116 | 67.094 | 15.871 | 0.044 | 1.00 | 28.59 | N |
| ATOM | 1545 | CA | ARG | A | 116 | 66.681 | 16.835 | 0.994 | 1.00 | 25.83 | C |
| ATOM | 1547 | CB | ARG | A | 116 | 66.001 | 17.985 | 0.311 | 1.00 | 27.04 | C |
| ATOM | 1550 | CG | ARG | A | 116 | 64.665 | 17.601 | -0.372 | 1.00 | 26.90 | C |
| ATOM | 1553 | CD | ARG | A | 116 | 64.373 | 18.665 | -1.444 | 1.00 | 29.00 | C |
| ATOM | 1556 | NE | ARG | A | 116 | 63.155 | 18.330 | -2.105 | 1.00 | 28.73 | N |
| ATOM | 1558 | CZ | ARG | A | 116 | 62.725 | 18.858 | -3.256 | 1.00 | 29.84 | C |
| ATOM | 1559 | NH1 | ARG | A | 116 | 63.390 | 19.844 | -3.811 | 1.00 | 33.24 | N |
| ATOM | 1562 | NH2 | ARG | A | 116 | 61.565 | 18.440 | -3.768 | 1.00 | 30.97 | N |
| ATOM | 1565 | C | ARG | A | 116 | 65.722 | 16.258 | 2.024 | 1.00 | 25.38 | C |
| ATOM | 1566 | O | ARG | A | 116 | 65.030 | 15.281 | 1.755 | 1.00 | 24.92 | O |
| ATOM | 1568 | N | PHE | A | 117 | 65.772 | 16.789 | 3.213 | 1.00 | 24.74 | N |
| ATOM | 1569 | CA | PHE | A | 117 | 64.812 | 16.401 | 4.246 | 1.00 | 25.21 | C |
| ATOM | 1571 | CB | PHE | A | 117 | 65.299 | 16.777 | 5.616 | 1.00 | 24.84 | C |
| ATOM | 1574 | CG | PHE | A | 117 | 66.385 | 15.919 | 6.121 | 1.00 | 26.07 | C |
| ATOM | 1575 | CD1 | PHE | A | 117 | 66.112 | 14.682 | 6.606 | 1.00 | 25.75 | C |
| ATOM | 1577 | CE1 | PHE | A | 117 | 67.112 | 13.877 | 7.105 | 1.00 | 30.03 | C |
| ATOM | 1579 | CZ | PHE | A | 117 | 68.442 | 14.304 | 7.092 | 1.00 | 26.03 | C |
| ATOM | 1581 | CE2 | PHE | A | 117 | 68.736 | 15.523 | 6.581 | 1.00 | 27.23 | C |
| ATOM | 1583 | CD2 | PHE | A | 117 | 67.708 | 16.360 | 6.142 | 1.00 | 24.45 | C |
| ATOM | 1585 | C | PHE | A | 117 | 63.497 | 17.086 | 3.926 | 1.00 | 24.15 | C |
| ATOM | 1586 | O | PHE | A | 117 | 63.437 | 18.159 | 3.275 | 1.00 | 25.20 | O |
| ATOM | 1588 | N | ILE | A | 118 | 62.418 | 16.449 | 4.364 | 1.00 | 24.50 | N |
| ATOM | 1589 | CA | ILE | A | 118 | 61.081 | 16.993 | 4.177 | 1.00 | 24.40 | C |
| ATOM | 1591 | CB | ILE | A | 118 | 60.220 | 16.073 | 3.318 | 1.00 | 24.41 | C |
| ATOM | 1593 | CG1 | ILE | A | 118 | 60.801 | 15.888 | 1.924 | 1.00 | 27.44 | C |
| ATOM | 1596 | CD1 | ILE | A | 118 | 60.182 | 14.688 | 1.242 | 1.00 | 30.22 | C |
| ATOM | 1600 | CG2 | ILE | A | 118 | 58.808 | 16.625 | 3.101 | 1.00 | 22.98 | C |
| ATOM | 1604 | C | ILE | A | 118 | 60.342 | 17.124 | 5.514 | 1.00 | 23.65 | C |
| ATOM | 1605 | O | ILE | A | 118 | 60.311 | 16.195 | 6.326 | 1.00 | 24.27 | O |
| ATOM | 1607 | N | GLU | A | 119 | 59.668 | 18.249 | 5.675 | 1.00 | 24.65 | N |
| ATOM | 1608 | CA | GLU | A | 119 | 58.798 | 18.522 | 6.792 | 1.00 | 25.58 | C |
| ATOM | 1610 | CB | GLU | A | 119 | 59.029 | 19.893 | 7.475 | 1.00 | 25.17 | C |
| ATOM | 1613 | CG | GLU | A | 119 | 57.961 | 20.192 | 8.529 | 1.00 | 29.34 | C |
| ATOM | 1616 | CD | GLU | A | 119 | 57.827 | 19.121 | 9.619 | 1.00 | 29.67 | C |
| ATOM | 1617 | OE1 | GLU | A | 119 | 58.861 | 18.599 | 10.094 | 1.00 | 26.90 | O |
| ATOM | 1618 | OE2 | GLU | A | 119 | 56.688 | 18.876 | 10.074 | 1.00 | 27.14 | O |
| ATOM | 1619 | C | GLU | A | 119 | 57.360 | 18.457 | 6.214 | 1.00 | 25.13 | C |
| ATOM | 1620 | O | GLU | A | 119 | 57.036 | 19.157 | 5.294 | 1.00 | 24.01 | O |
| ATOM | 1622 | N | ILE | A | 120 | 56.588 | 17.522 | 6.729 | 1.00 | 23.31 | N |
| ATOM | 1623 | CA | ILE | A | 120 | 55.195 | 17.327 | 6.363 | 1.00 | 25.06 | C |
| ATOM | 1625 | CB | ILE | A | 120 | 54.854 | 15.838 | 6.355 | 1.00 | 24.51 | C |
| ATOM | 1627 | CG1 | ILE | A | 120 | 55.653 | 15.156 | 5.290 | 1.00 | 25.83 | C |
| ATOM | 1630 | CD1 | ILE | A | 120 | 55.366 | 15.654 | 4.029 | 1.00 | 25.16 | C |
| ATOM | 1634 | CG2 | ILE | A | 120 | 53.302 | 15.602 | 6.164 | 1.00 | 26.01 | C |
| ATOM | 1638 | C | ILE | A | 120 | 54.311 | 18.004 | 7.404 | 1.00 | 24.05 | C |
| ATOM | 1639 | O | ILE | A | 120 | 54.449 | 17.712 | 8.639 | 1.00 | 25.86 | O |
| ATOM | 1641 | N | GLY | A | 121 | 53.382 | 18.804 | 6.867 | 1.00 | 26.74 | N |
| ATOM | 1642 | CA | GLY | A | 121 | 52.413 | 19.536 | 7.659 | 1.00 | 25.86 | C |
| ATOM | 1645 | C | GLY | A | 121 | 51.010 | 19.088 | 7.280 | 1.00 | 25.17 | C |
| ATOM | 1646 | O | GLY | A | 121 | 50.707 | 18.934 | 6.118 | 1.00 | 24.93 | O |
| ATOM | 1648 | N | VAL | A | 122 | 50.192 | 18.836 | 8.280 | 1.00 | 23.76 | N |

FIG.15-16

| | | | | | | | | | | | |
|---|---|---|---|---|---|---|---|---|---|---|---|
| ATOM | 1649 | CA | VAL | A | 122 | 48.749 | 18.577 | 8.099 | 1.00 | 23.87 | C |
| ATOM | 1651 | CB | VAL | A | 122 | 48.341 | 17.149 | 8.504 | 1.00 | 25.39 | C |
| ATOM | 1653 | CG1 | VAL | A | 122 | 46.777 | 16.950 | 8.262 | 1.00 | 22.76 | C |
| ATOM | 1657 | CG2 | VAL | A | 122 | 49.165 | 16.116 | 7.717 | 1.00 | 24.40 | C |
| ATOM | 1661 | C | VAL | A | 122 | 47.943 | 19.558 | 8.917 | 1.00 | 25.55 | C |
| ATOM | 1662 | O | VAL | A | 122 | 48.085 | 19.597 | 10.138 | 1.00 | 27.28 | O |
| ATOM | 1664 | N | THR | A | 123 | 47.110 | 20.361 | 8.278 | 1.00 | 27.69 | N |
| ATOM | 1665 | CA | THR | A | 123 | 46.442 | 21.458 | 8.985 | 1.00 | 29.10 | C |
| ATOM | 1667 | CB | THR | A | 123 | 46.983 | 22.854 | 8.510 | 1.00 | 30.55 | C |
| ATOM | 1669 | OG1 | THR | A | 123 | 46.353 | 23.946 | 9.208 | 1.00 | 32.05 | O |
| ATOM | 1671 | CG2 | THR | A | 123 | 46.716 | 23.090 | 7.018 | 1.00 | 29.90 | C |
| ATOM | 1675 | C | THR | A | 123 | 44.938 | 21.435 | 8.745 | 1.00 | 29.70 | C |
| ATOM | 1676 | O | THR | A | 123 | 44.500 | 21.161 | 7.678 | 1.00 | 25.46 | O |
| ATOM | 1678 | N | ARG | A | 124 | 44.206 | 21.897 | 9.748 | 1.00 | 29.79 | N |
| ATOM | 1679 | CA | ARG | A | 124 | 42.798 | 22.154 | 9.611 | 1.00 | 32.70 | C |
| ATOM | 1681 | CB | ARG | A | 124 | 42.125 | 21.846 | 10.929 | 1.00 | 32.34 | C |
| ATOM | 1684 | CG | ARG | A | 124 | 42.049 | 20.403 | 11.359 | 1.00 | 35.33 | C |
| ATOM | 1687 | CD | ARG | A | 124 | 42.241 | 20.320 | 12.915 | 1.00 | 39.10 | C |
| ATOM | 1690 | NE | ARG | A | 124 | 43.567 | 19.998 | 13.192 | 1.00 | 38.12 | N |
| ATOM | 1692 | CZ | ARG | A | 124 | 44.110 | 19.738 | 14.364 | 1.00 | 37.82 | C |
| ATOM | 1693 | NH1 | ARG | A | 124 | 43.484 | 19.846 | 15.540 | 1.00 | 35.25 | N |
| ATOM | 1696 | NH2 | ARG | A | 124 | 45.367 | 19.427 | 14.324 | 1.00 | 35.38 | N |
| ATOM | 1699 | C | ARG | A | 124 | 42.507 | 23.600 | 9.259 | 1.00 | 34.47 | C |
| ATOM | 1700 | O | ARG | A | 124 | 41.348 | 23.974 | 9.180 | 1.00 | 36.83 | O |
| ATOM | 1702 | N | ARG | A | 125 | 43.546 | 24.423 | 9.183 | 1.00 | 34.59 | N |
| ATOM | 1703 | CA | ARG | A | 125 | 43.473 | 25.784 | 8.783 | 1.00 | 36.06 | C |
| ATOM | 1705 | CB | ARG | A | 125 | 44.406 | 26.606 | 9.671 | 1.00 | 35.43 | C |
| ATOM | 1708 | CG | ARG | A | 125 | 43.949 | 26.637 | 11.120 | 1.00 | 38.75 | C |
| ATOM | 1711 | CD | ARG | A | 125 | 44.967 | 27.396 | 11.978 | 1.00 | 40.42 | C |
| ATOM | 1714 | NE | ARG | A | 125 | 46.138 | 26.564 | 12.276 | 1.00 | 39.65 | N |
| ATOM | 1716 | CZ | ARG | A | 125 | 47.320 | 27.021 | 12.674 | 1.00 | 45.69 | C |
| ATOM | 1717 | NH1 | ARG | A | 125 | 47.564 | 28.325 | 12.786 | 1.00 | 49.63 | N |
| ATOM | 1720 | NH2 | ARG | A | 125 | 48.291 | 26.161 | 12.940 | 1.00 | 49.30 | N |
| ATOM | 1723 | C | ARG | A | 125 | 43.903 | 25.892 | 7.315 | 1.00 | 36.89 | C |
| ATOM | 1724 | O | ARG | A | 125 | 44.077 | 24.878 | 6.617 | 1.00 | 37.27 | O |
| ATOM | 1726 | N | GLU | A | 126 | 44.104 | 27.111 | 6.867 | 1.00 | 36.51 | N |
| ATOM | 1727 | CA | GLU | A | 126 | 44.486 | 27.390 | 5.480 | 1.00 | 37.82 | C |
| ATOM | 1729 | CB | GLU | A | 126 | 44.384 | 28.897 | 5.230 | 1.00 | 40.38 | C |
| ATOM | 1732 | CG | GLU | A | 126 | 42.990 | 29.535 | 5.450 | 1.00 | 46.89 | C |
| ATOM | 1735 | CD | GLU | A | 126 | 42.287 | 29.740 | 4.130 | 1.00 | 53.98 | C |
| ATOM | 1736 | OE1 | GLU | A | 126 | 41.958 | 28.703 | 3.509 | 1.00 | 54.03 | O |
| ATOM | 1737 | OE2 | GLU | A | 126 | 42.116 | 30.919 | 3.693 | 1.00 | 58.25 | O |
| ATOM | 1738 | C | GLU | A | 126 | 45.952 | 26.978 | 5.315 | 1.00 | 36.18 | C |
| ATOM | 1739 | O | GLU | A | 126 | 46.763 | 27.271 | 6.183 | 1.00 | 35.97 | O |
| ATOM | 1741 | N | VAL | A | 127 | 46.269 | 26.287 | 4.229 | 1.00 | 34.74 | N |
| ATOM | 1742 | CA | VAL | A | 127 | 47.626 | 25.793 | 3.986 | 1.00 | 34.58 | C |
| ATOM | 1744 | CB | VAL | A | 127 | 47.730 | 24.908 | 2.713 | 1.00 | 32.34 | C |
| ATOM | 1746 | CG1 | VAL | A | 127 | 46.776 | 23.713 | 2.864 | 1.00 | 32.03 | C |
| ATOM | 1750 | CG2 | VAL | A | 127 | 47.458 | 25.708 | 1.360 | 1.00 | 33.77 | C |
| ATOM | 1754 | C | VAL | A | 127 | 48.663 | 26.885 | 3.957 | 1.00 | 35.18 | C |
| ATOM | 1755 | O | VAL | A | 127 | 49.707 | 26.707 | 4.522 | 1.00 | 35.08 | O |
| ATOM | 1757 | N | HIS | A | 128 | 48.364 | 28.050 | 3.386 | 1.00 | 37.46 | N |
| ATOM | 1758 | CA | HIS | A | 128 | 49.400 | 29.132 | 3.346 | 1.00 | 39.07 | C |
| ATOM | 1760 | CB | HIS | A | 128 | 48.992 | 30.293 | 2.444 | 1.00 | 40.36 | C |
| ATOM | 1763 | CG | HIS | A | 128 | 47.761 | 31.010 | 2.910 | 1.00 | 46.62 | C |
| ATOM | 1764 | ND1 | HIS | A | 128 | 46.524 | 30.837 | 2.319 | 1.00 | 53.49 | N |
| ATOM | 1766 | CE1 | HIS | A | 128 | 45.626 | 31.582 | 2.943 | 1.00 | 54.15 | C |
| ATOM | 1768 | NE2 | HIS | A | 128 | 46.235 | 32.225 | 3.928 | 1.00 | 53.93 | N |
| ATOM | 1770 | CD2 | HIS | A | 128 | 47.569 | 31.883 | 3.928 | 1.00 | 52.74 | C |
| ATOM | 1772 | C | HIS | A | 128 | 49.758 | 29.606 | 4.734 | 1.00 | 38.82 | C |
| ATOM | 1773 | O | HIS | A | 128 | 50.907 | 29.903 | 4.962 | 1.00 | 41.18 | O |
| ATOM | 1775 | N | ILE | A | 129 | 48.786 | 29.629 | 5.649 | 1.00 | 38.08 | N |
| ATOM | 1776 | CA | ILE | A | 129 | 48.950 | 29.995 | 7.056 | 1.00 | 38.75 | C |

FIG.15-17

| | | | | | | | | | | | |
|---|---|---|---|---|---|---|---|---|---|---|---|
| ATOM | 1778 | CB | ILE | A | 129 | 47.513 | 30.106 | 7.719 | 1.00 | 40.14 | C |
| ATOM | 1780 | CG1 | ILE | A | 129 | 46.770 | 31.305 | 7.116 | 1.00 | 45.03 | C |
| ATOM | 1783 | CD1 | ILE | A | 129 | 45.423 | 31.608 | 7.784 | 1.00 | 50.51 | C |
| ATOM | 1787 | CG2 | ILE | A | 129 | 47.514 | 30.187 | 9.211 | 1.00 | 41.78 | C |
| ATOM | 1791 | C | ILE | A | 129 | 49.854 | 29.019 | 7.813 | 1.00 | 36.91 | C |
| ATOM | 1792 | O | ILE | A | 129 | 50.829 | 29.383 | 8.527 | 1.00 | 35.23 | O |
| ATOM | 1794 | N | TYR | A | 130 | 49.519 | 27.738 | 7.679 | 1.00 | 34.42 | N |
| ATOM | 1795 | CA | TYR | A | 130 | 50.326 | 26.744 | 8.319 | 1.00 | 32.26 | C |
| ATOM | 1797 | CB | TYR | A | 130 | 49.571 | 25.424 | 8.285 | 1.00 | 33.12 | C |
| ATOM | 1800 | CG | TYR | A | 130 | 50.105 | 24.423 | 9.227 | 1.00 | 29.16 | C |
| ATOM | 1801 | CD1 | TYR | A | 130 | 50.162 | 24.672 | 10.574 | 1.00 | 34.13 | C |
| ATOM | 1803 | CE1 | TYR | A | 130 | 50.665 | 23.754 | 11.457 | 1.00 | 34.09 | C |
| ATOM | 1805 | CZ | TYR | A | 130 | 51.046 | 22.500 | 10.972 | 1.00 | 32.73 | C |
| ATOM | 1806 | OH | TYR | A | 130 | 51.505 | 21.529 | 11.773 | 1.00 | 33.99 | O |
| ATOM | 1808 | CE2 | TYR | A | 130 | 50.999 | 22.244 | 9.650 | 1.00 | 31.35 | C |
| ATOM | 1810 | CD2 | TYR | A | 130 | 50.560 | 23.225 | 8.773 | 1.00 | 32.28 | C |
| ATOM | 1812 | C | TYR | A | 130 | 51.714 | 26.640 | 7.665 | 1.00 | 30.92 | C |
| ATOM | 1813 | O | TYR | A | 130 | 52.659 | 26.402 | 8.365 | 1.00 | 31.54 | O |
| ATOM | 1815 | N | TYR | A | 131 | 51.819 | 26.837 | 6.364 | 1.00 | 31.50 | N |
| ATOM | 1816 | CA | TYR | A | 131 | 53.103 | 26.832 | 5.673 | 1.00 | 32.79 | C |
| ATOM | 1818 | CB | TYR | A | 131 | 52.966 | 27.138 | 4.179 | 1.00 | 32.33 | C |
| ATOM | 1821 | CG | TYR | A | 131 | 54.325 | 27.104 | 3.461 | 1.00 | 35.34 | C |
| ATOM | 1822 | CD1 | TYR | A | 131 | 54.779 | 25.939 | 2.846 | 1.00 | 38.30 | C |
| ATOM | 1824 | CE1 | TYR | A | 131 | 56.009 | 25.877 | 2.217 | 1.00 | 37.73 | C |
| ATOM | 1826 | CZ | TYR | A | 131 | 56.810 | 27.009 | 2.181 | 1.00 | 40.99 | C |
| ATOM | 1827 | OH | TYR | A | 131 | 58.005 | 26.936 | 1.576 | 1.00 | 44.82 | O |
| ATOM | 1829 | CE2 | TYR | A | 131 | 56.410 | 28.182 | 2.789 | 1.00 | 40.13 | C |
| ATOM | 1831 | CD2 | TYR | A | 131 | 55.164 | 28.230 | 3.416 | 1.00 | 38.86 | C |
| ATOM | 1833 | C | TYR | A | 131 | 54.035 | 27.861 | 6.321 | 1.00 | 33.95 | C |
| ATOM | 1834 | O | TYR | A | 131 | 55.210 | 27.593 | 6.630 | 1.00 | 32.72 | O |
| ATOM | 1836 | N | LEU | A | 132 | 53.481 | 29.059 | 6.533 | 1.00 | 35.56 | N |
| ATOM | 1837 | CA | LEU | A | 132 | 54.252 | 30.196 | 7.096 | 1.00 | 37.00 | C |
| ATOM | 1839 | CB | LEU | A | 132 | 53.369 | 31.476 | 7.106 | 1.00 | 37.41 | C |
| ATOM | 1842 | CG | LEU | A | 132 | 53.206 | 32.108 | 5.722 | 1.00 | 40.82 | C |
| ATOM | 1844 | CD1 | LEU | A | 132 | 52.087 | 33.123 | 5.661 | 1.00 | 43.05 | C |
| ATOM | 1848 | CD2 | LEU | A | 132 | 54.485 | 32.793 | 5.376 | 1.00 | 42.60 | C |
| ATOM | 1852 | C | LEU | A | 132 | 54.687 | 29.888 | 8.477 | 1.00 | 36.29 | C |
| ATOM | 1853 | O | LEU | A | 132 | 55.849 | 30.096 | 8.852 | 1.00 | 38.30 | O |
| ATOM | 1855 | N | GLU | A | 133 | 53.767 | 29.361 | 9.243 | 1.00 | 35.44 | N |
| ATOM | 1856 | CA | GLU | A | 133 | 54.051 | 28.949 | 10.587 | 1.00 | 36.86 | C |
| ATOM | 1858 | CB | GLU | A | 133 | 52.783 | 28.433 | 11.272 | 1.00 | 36.73 | C |
| ATOM | 1861 | CG | GLU | A | 133 | 53.010 | 27.900 | 12.640 | 1.00 | 43.86 | C |
| ATOM | 1864 | CD | GLU | A | 133 | 51.843 | 27.101 | 13.209 | 1.00 | 50.30 | C |
| ATOM | 1865 | OE1 | GLU | A | 133 | 50.686 | 27.594 | 13.126 | 1.00 | 55.46 | O |
| ATOM | 1866 | OE2 | GLU | A | 133 | 52.107 | 25.985 | 13.740 | 1.00 | 53.00 | O |
| ATOM | 1867 | C | GLU | A | 133 | 55.180 | 27.913 | 10.659 | 1.00 | 35.70 | C |
| ATOM | 1868 | O | GLU | A | 133 | 56.075 | 28.002 | 11.515 | 1.00 | 35.52 | O |
| ATOM | 1870 | N | LYS | A | 134 | 55.173 | 26.950 | 9.743 | 1.00 | 36.10 | N |
| ATOM | 1871 | CA | LYS | A | 134 | 56.178 | 25.919 | 9.742 | 1.00 | 36.22 | C |
| ATOM | 1873 | CB | LYS | A | 134 | 55.813 | 24.780 | 8.769 | 1.00 | 36.51 | C |
| ATOM | 1876 | CG | LYS | A | 134 | 54.829 | 23.807 | 9.356 | 1.00 | 40.26 | C |
| ATOM | 1879 | CD | LYS | A | 134 | 55.496 | 22.994 | 10.439 | 1.00 | 43.13 | C |
| ATOM | 1882 | CE | LYS | A | 134 | 54.779 | 21.666 | 10.663 | 1.00 | 43.25 | C |
| ATOM | 1885 | NZ | LYS | A | 134 | 54.946 | 21.318 | 12.058 | 1.00 | 45.22 | N |
| ATOM | 1889 | C | LYS | A | 134 | 57.520 | 26.480 | 9.314 | 1.00 | 35.70 | C |
| ATOM | 1890 | O | LYS | A | 134 | 58.534 | 26.195 | 9.941 | 1.00 | 33.54 | O |
| ATOM | 1892 | N | ALA | A | 135 | 57.515 | 27.165 | 8.168 | 1.00 | 37.54 | N |
| ATOM | 1893 | CA | ALA | A | 135 | 58.702 | 27.714 | 7.566 | 1.00 | 37.54 | C |
| ATOM | 1895 | CB | ALA | A | 135 | 58.335 | 28.490 | 6.291 | 1.00 | 38.38 | C |
| ATOM | 1899 | C | ALA | A | 135 | 59.384 | 28.649 | 8.539 | 1.00 | 39.49 | C |
| ATOM | 1900 | O | ALA | A | 135 | 60.618 | 28.638 | 8.660 | 1.00 | 37.56 | O |
| ATOM | 1902 | N | ASN | A | 136 | 58.577 | 29.449 | 9.219 | 1.00 | 41.06 | N |
| ATOM | 1903 | CA | ASN | A | 136 | 59.086 | 30.369 | 10.272 | 1.00 | 43.97 | C |

FIG.15-18

| | | | | | | | | | | | |
|---|---|---|---|---|---|---|---|---|---|---|---|
| ATOM | 1905 | CB | ASN | A | 136 | 57.975 | 31.265 | 10.849 | 1.00 | 42.31 | C |
| ATOM | 1908 | CG | ASN | A | 136 | 58.525 | 32.236 | 11.892 | 1.00 | 44.84 | C |
| ATOM | 1909 | OD1 | ASN | A | 136 | 59.404 | 33.042 | 11.561 | 1.00 | 42.30 | O |
| ATOM | 1910 | ND2 | ASN | A | 136 | 58.043 | 32.152 | 13.147 | 1.00 | 39.73 | N |
| ATOM | 1913 | C | ASN | A | 136 | 59.710 | 29.582 | 11.410 | 1.00 | 47.15 | C |
| ATOM | 1914 | O | ASN | A | 136 | 60.811 | 29.920 | 11.915 | 1.00 | 47.98 | O |
| ATOM | 1916 | N | LYS | A | 137 | 59.021 | 28.514 | 11.801 | 1.00 | 50.42 | N |
| ATOM | 1917 | CA | LYS | A | 137 | 59.456 | 27.724 | 12.929 | 1.00 | 53.76 | C |
| ATOM | 1919 | CB | LYS | A | 137 | 58.399 | 26.703 | 13.328 | 1.00 | 55.00 | C |
| ATOM | 1922 | CG | LYS | A | 137 | 58.931 | 25.484 | 14.114 | 1.00 | 58.80 | C |
| ATOM | 1925 | CD | LYS | A | 137 | 59.354 | 25.799 | 15.557 | 1.00 | 61.04 | C |
| ATOM | 1928 | CE | LYS | A | 137 | 59.777 | 24.511 | 16.260 | 1.00 | 64.10 | C |
| ATOM | 1931 | NZ | LYS | A | 137 | 59.915 | 24.664 | 17.745 | 1.00 | 65.54 | N |
| ATOM | 1935 | C | LYS | A | 137 | 60.750 | 27.016 | 12.650 | 1.00 | 55.16 | C |
| ATOM | 1936 | O | LYS | A | 137 | 61.562 | 26.898 | 13.552 | 1.00 | 55.31 | O |
| ATOM | 1938 | N | ILE | A | 138 | 60.951 | 26.510 | 11.430 | 1.00 | 57.26 | N |
| ATOM | 1939 | CA | ILE | A | 138 | 62.014 | 25.514 | 11.246 | 1.00 | 58.82 | C |
| ATOM | 1941 | CB | ILE | A | 138 | 61.638 | 24.265 | 10.364 | 1.00 | 58.37 | C |
| ATOM | 1943 | CG1 | ILE | A | 138 | 61.470 | 24.598 | 8.891 | 1.00 | 57.40 | C |
| ATOM | 1946 | CD1 | ILE | A | 138 | 61.075 | 23.331 | 8.097 | 1.00 | 53.52 | C |
| ATOM | 1950 | CG2 | ILE | A | 138 | 60.398 | 23.521 | 10.909 | 1.00 | 59.17 | C |
| ATOM | 1954 | C | ILE | A | 138 | 63.298 | 26.119 | 10.751 | 1.00 | 60.85 | C |
| ATOM | 1955 | O | ILE | A | 138 | 64.373 | 25.690 | 11.188 | 1.00 | 62.53 | O |
| ATOM | 1957 | N | LYS | A | 139 | 63.179 | 27.082 | 9.842 | 1.00 | 62.69 | N |
| ATOM | 1958 | CA | LYS | A | 139 | 64.296 | 27.681 | 9.097 | 1.00 | 64.44 | C |
| ATOM | 1960 | CB | LYS | A | 139 | 64.722 | 29.007 | 9.754 | 1.00 | 65.41 | C |
| ATOM | 1963 | CG | LYS | A | 139 | 63.656 | 30.089 | 9.672 | 1.00 | 67.28 | C |
| ATOM | 1966 | CD | LYS | A | 139 | 63.710 | 30.729 | 8.289 | 1.00 | 71.31 | C |
| ATOM | 1969 | CE | LYS | A | 139 | 62.621 | 31.773 | 8.128 | 1.00 | 72.84 | C |
| ATOM | 1972 | NZ | LYS | A | 139 | 62.877 | 33.018 | 8.930 | 1.00 | 73.64 | N |
| ATOM | 1976 | C | LYS | A | 139 | 65.504 | 26.773 | 8.904 | 1.00 | 64.77 | C |
| ATOM | 1977 | O | LYS | A | 139 | 66.589 | 27.072 | 9.406 | 1.00 | 65.82 | O |
| ATOM | 1979 | N | GLU | A | 141 | 66.252 | 26.330 | 6.007 | 1.00 | 54.19 | N |
| ATOM | 1980 | CA | GLU | A | 141 | 65.971 | 26.468 | 4.553 | 1.00 | 54.93 | C |
| ATOM | 1982 | CB | GLU | A | 141 | 66.633 | 27.733 | 3.955 | 1.00 | 56.54 | C |
| ATOM | 1985 | CG | GLU | A | 141 | 65.680 | 28.870 | 3.689 | 1.00 | 60.97 | C |
| ATOM | 1988 | CD | GLU | A | 141 | 66.254 | 29.946 | 2.789 | 1.00 | 66.63 | C |
| ATOM | 1989 | OE1 | GLU | A | 141 | 67.437 | 29.847 | 2.350 | 1.00 | 70.47 | O |
| ATOM | 1990 | OE2 | GLU | A | 141 | 65.497 | 30.914 | 2.526 | 1.00 | 71.07 | O |
| ATOM | 1991 | C | GLU | A | 141 | 66.455 | 25.315 | 3.660 | 1.00 | 52.30 | C |
| ATOM | 1992 | O | GLU | A | 141 | 66.354 | 25.412 | 2.432 | 1.00 | 53.22 | O |
| ATOM | 1994 | N | LYS | A | 142 | 67.056 | 24.268 | 4.208 | 1.00 | 48.76 | N |
| ATOM | 1995 | CA | LYS | A | 142 | 67.351 | 23.156 | 3.312 | 1.00 | 45.83 | C |
| ATOM | 1997 | CB | LYS | A | 142 | 68.699 | 22.518 | 3.630 | 1.00 | 46.92 | C |
| ATOM | 2000 | CG | LYS | A | 142 | 69.914 | 23.416 | 3.212 | 1.00 | 48.41 | C |
| ATOM | 2003 | CD | LYS | A | 142 | 69.975 | 23.689 | 1.694 | 1.00 | 49.50 | C |
| ATOM | 2006 | CE | LYS | A | 142 | 71.273 | 24.477 | 1.335 | 1.00 | 52.43 | C |
| ATOM | 2009 | NZ | LYS | A | 142 | 71.287 | 25.053 | -0.054 | 1.00 | 54.98 | N |
| ATOM | 2013 | C | LYS | A | 142 | 66.161 | 22.174 | 3.366 | 1.00 | 41.85 | C |
| ATOM | 2014 | O | LYS | A | 142 | 65.904 | 21.483 | 2.391 | 1.00 | 42.59 | O |
| ATOM | 2016 | N | THR | A | 143 | 65.424 | 22.204 | 4.466 | 1.00 | 37.79 | N |
| ATOM | 2017 | CA | THR | A | 143 | 64.265 | 21.330 | 4.686 | 1.00 | 36.03 | C |
| ATOM | 2019 | CB | THR | A | 143 | 63.871 | 21.227 | 6.185 | 1.00 | 35.63 | C |
| ATOM | 2021 | OG1 | THR | A | 143 | 64.958 | 20.676 | 6.941 | 1.00 | 36.26 | O |
| ATOM | 2023 | CG2 | THR | A | 143 | 62.639 | 20.237 | 6.370 | 1.00 | 34.75 | C |
| ATOM | 2027 | C | THR | A | 143 | 63.078 | 21.784 | 3.858 | 1.00 | 34.21 | C |
| ATOM | 2028 | O | THR | A | 143 | 62.558 | 22.884 | 4.067 | 1.00 | 34.89 | O |
| ATOM | 2030 | N | HIS | A | 144 | 62.714 | 20.931 | 2.897 | 1.00 | 31.61 | N |
| ATOM | 2031 | CA | HIS | A | 144 | 61.557 | 21.048 | 2.101 | 1.00 | 29.62 | C |
| ATOM | 2033 | CB | HIS | A | 144 | 61.573 | 20.060 | 0.969 | 1.00 | 29.61 | C |
| ATOM | 2036 | CG | HIS | A | 144 | 60.901 | 20.538 | -0.260 | 1.00 | 31.00 | C |
| ATOM | 2037 | ND1 | HIS | A | 144 | 61.530 | 21.406 | -1.146 | 1.00 | 30.50 | N |
| ATOM | 2039 | CE1 | HIS | A | 144 | 60.698 | 21.661 | -2.148 | 1.00 | 32.11 | C |

FIG.15-19

| | | | | | | | | | | | |
|---|---|---|---|---|---|---|---|---|---|---|---|
| ATOM | 2041 | NE2 | HIS | A | 144 | 59.582 | 20.965 | -1.968 | 1.00 | 31.10 | N |
| ATOM | 2043 | CD2 | HIS | A | 144 | 59.685 | 20.247 | -0.805 | 1.00 | 26.87 | C |
| ATOM | 2045 | C | HIS | A | 144 | 60.291 | 20.879 | 2.888 | 1.00 | 28.47 | C |
| ATOM | 2046 | O | HIS | A | 144 | 60.116 | 19.879 | 3.541 | 1.00 | 27.79 | O |
| ATOM | 2048 | N | ILE | A | 145 | 59.381 | 21.841 | 2.748 | 1.00 | 27.56 | N |
| ATOM | 2049 | CA | ILE | A | 145 | 58.080 | 21.792 | 3.438 | 1.00 | 27.91 | C |
| ATOM | 2051 | CB | ILE | A | 145 | 57.761 | 23.115 | 4.109 | 1.00 | 28.32 | C |
| ATOM | 2053 | CG1 | ILE | A | 145 | 58.790 | 23.402 | 5.167 | 1.00 | 28.36 | C |
| ATOM | 2056 | CD1 | ILE | A | 145 | 58.893 | 24.933 | 5.450 | 1.00 | 29.89 | C |
| ATOM | 2060 | CG2 | ILE | A | 145 | 56.325 | 23.070 | 4.881 | 1.00 | 27.62 | C |
| ATOM | 2064 | C | ILE | A | 145 | 56.975 | 21.421 | 2.522 | 1.00 | 27.68 | C |
| ATOM | 2065 | O | ILE | A | 145 | 56.886 | 21.927 | 1.415 | 1.00 | 28.64 | O |
| ATOM | 2067 | N | HIS | A | 146 | 56.111 | 20.518 | 2.971 | 1.00 | 26.16 | N |
| ATOM | 2068 | CA | HIS | A | 146 | 54.929 | 20.144 | 2.201 | 1.00 | 24.73 | C |
| ATOM | 2070 | CB | HIS | A | 146 | 55.136 | 18.818 | 1.472 | 1.00 | 24.51 | C |
| ATOM | 2073 | CG | HIS | A | 146 | 54.169 | 18.565 | 0.349 | 1.00 | 24.21 | C |
| ATOM | 2074 | ND1 | HIS | A | 146 | 54.447 | 17.723 | -0.705 | 1.00 | 24.83 | N |
| ATOM | 2076 | CE1 | HIS | A | 146 | 53.403 | 17.658 | -1.495 | 1.00 | 26.04 | C |
| ATOM | 2078 | NE2 | HIS | A | 146 | 52.438 | 18.410 | -0.980 | 1.00 | 26.01 | N |
| ATOM | 2080 | CD2 | HIS | A | 146 | 52.892 | 18.996 | 0.161 | 1.00 | 23.03 | C |
| ATOM | 2082 | C | HIS | A | 146 | 53.743 | 20.098 | 3.168 | 1.00 | 24.70 | C |
| ATOM | 2083 | O | HIS | A | 146 | 53.741 | 19.318 | 4.118 | 1.00 | 25.50 | O |
| ATOM | 2085 | N | ILE | A | 147 | 52.733 | 20.918 | 2.879 | 1.00 | 25.24 | N |
| ATOM | 2086 | CA | ILE | A | 147 | 51.561 | 21.095 | 3.697 | 1.00 | 25.32 | C |
| ATOM | 2088 | CB | ILE | A | 147 | 51.276 | 22.604 | 4.068 | 1.00 | 27.36 | C |
| ATOM | 2090 | CG1 | ILE | A | 147 | 52.496 | 23.287 | 4.709 | 1.00 | 24.22 | C |
| ATOM | 2093 | CD1 | ILE | A | 147 | 53.108 | 22.684 | 5.995 | 1.00 | 25.83 | C |
| ATOM | 2097 | CG2 | ILE | A | 147 | 50.020 | 22.683 | 4.958 | 1.00 | 24.95 | C |
| ATOM | 2101 | C | ILE | A | 147 | 50.321 | 20.586 | 2.971 | 1.00 | 24.52 | C |
| ATOM | 2102 | O | ILE | A | 147 | 50.121 | 20.813 | 1.767 | 1.00 | 26.06 | O |
| ATOM | 2104 | N | PHE | A | 148 | 49.511 | 19.799 | 3.700 | 1.00 | 23.79 | N |
| ATOM | 2105 | CA | PHE | A | 148 | 48.264 | 19.311 | 3.214 | 1.00 | 24.52 | C |
| ATOM | 2107 | CB | PHE | A | 148 | 48.246 | 17.752 | 3.251 | 1.00 | 22.62 | C |
| ATOM | 2110 | CG | PHE | A | 148 | 49.172 | 17.107 | 2.331 | 1.00 | 23.94 | C |
| ATOM | 2111 | CD1 | PHE | A | 148 | 48.826 | 16.863 | 1.009 | 1.00 | 24.02 | C |
| ATOM | 2113 | CE1 | PHE | A | 148 | 49.719 | 16.254 | 0.125 | 1.00 | 26.48 | C |
| ATOM | 2115 | CZ | PHE | A | 148 | 50.943 | 15.861 | 0.585 | 1.00 | 24.27 | C |
| ATOM | 2117 | CE2 | PHE | A | 148 | 51.291 | 16.076 | 1.927 | 1.00 | 23.44 | C |
| ATOM | 2119 | CD2 | PHE | A | 148 | 50.429 | 16.705 | 2.787 | 1.00 | 23.79 | C |
| ATOM | 2121 | C | PHE | A | 148 | 47.144 | 19.791 | 4.126 | 1.00 | 24.42 | C |
| ATOM | 2122 | O | PHE | A | 148 | 47.348 | 19.816 | 5.362 | 1.00 | 25.05 | O |
| ATOM | 2124 | N | SER | A | 149 | 45.977 | 20.084 | 3.547 | 1.00 | 25.10 | N |
| ATOM | 2125 | CA | SER | A | 149 | 44.806 | 20.383 | 4.306 | 1.00 | 25.50 | C |
| ATOM | 2127 | CB | SER | A | 149 | 44.099 | 21.644 | 3.774 | 1.00 | 26.08 | C |
| ATOM | 2130 | OG | SER | A | 149 | 43.483 | 21.414 | 2.506 | 1.00 | 28.35 | O |
| ATOM | 2132 | C | SER | A | 149 | 43.839 | 19.204 | 4.272 | 1.00 | 26.70 | C |
| ATOM | 2133 | O | SER | A | 149 | 44.091 | 18.235 | 3.586 | 1.00 | 26.61 | O |
| ATOM | 2135 | N | PHE | A | 150 | 42.741 | 19.313 | 5.008 | 1.00 | 26.45 | N |
| ATOM | 2136 | CA | PHE | A | 150 | 41.639 | 18.391 | 4.875 | 1.00 | 27.80 | C |
| ATOM | 2138 | CB | PHE | A | 150 | 40.931 | 18.288 | 6.218 | 1.00 | 28.57 | C |
| ATOM | 2141 | CG | PHE | A | 150 | 41.767 | 17.653 | 7.309 | 1.00 | 26.93 | C |
| ATOM | 2142 | CD1 | PHE | A | 150 | 41.667 | 16.303 | 7.599 | 1.00 | 23.08 | C |
| ATOM | 2144 | CE1 | PHE | A | 150 | 42.369 | 15.751 | 8.576 | 1.00 | 24.02 | C |
| ATOM | 2146 | CZ | PHE | A | 150 | 43.297 | 16.513 | 9.298 | 1.00 | 26.68 | C |
| ATOM | 2148 | CE2 | PHE | A | 150 | 43.443 | 17.857 | 9.016 | 1.00 | 28.79 | C |
| ATOM | 2150 | CD2 | PHE | A | 150 | 42.691 | 18.412 | 8.009 | 1.00 | 27.83 | C |
| ATOM | 2152 | C | PHE | A | 150 | 40.650 | 18.836 | 3.765 | 1.00 | 29.06 | C |
| ATOM | 2153 | O | PHE | A | 150 | 39.548 | 18.367 | 3.719 | 1.00 | 30.35 | O |
| ATOM | 2155 | N | THR | A | 151 | 41.041 | 19.811 | 2.936 | 1.00 | 30.82 | N |
| ATOM | 2156 | CA | THR | A | 151 | 40.217 | 20.378 | 1.901 | 1.00 | 31.77 | C |
| ATOM | 2158 | CB | THR | A | 151 | 40.138 | 21.930 | 2.053 | 1.00 | 32.21 | C |
| ATOM | 2160 | OG1 | THR | A | 151 | 41.463 | 22.507 | 1.760 | 1.00 | 35.79 | O |
| ATOM | 2162 | CG2 | THR | A | 151 | 39.645 | 22.290 | 3.432 | 1.00 | 32.61 | C |

FIG.15-20

| | | | | | | | | | | | |
|---|---|---|---|---|---|---|---|---|---|---|---|
| ATOM | 2166 | C | THR | A | 151 | 40.809 | 20.046 | 0.507 | 1.00 | 31.31 | C |
| ATOM | 2167 | O | THR | A | 151 | 40.309 | 20.571 | -0.475 | 1.00 | 31.21 | O |
| ATOM | 2169 | N | GLY | A | 152 | 41.920 | 19.284 | 0.438 | 1.00 | 29.28 | N |
| ATOM | 2170 | CA | GLY | A | 152 | 42.507 | 18.954 | -0.837 | 1.00 | 30.05 | C |
| ATOM | 2173 | C | GLY | A | 152 | 43.457 | 19.992 | -1.298 | 1.00 | 30.16 | C |
| ATOM | 2174 | O | GLY | A | 152 | 43.849 | 19.994 | -2.482 | 1.00 | 28.81 | O |
| ATOM | 2176 | N | GLU | A | 153 | 43.789 | 20.913 | -0.395 | 1.00 | 28.76 | N |
| ATOM | 2177 | CA | GLU | A | 153 | 44.788 | 21.894 | -0.724 | 1.00 | 30.94 | C |
| ATOM | 2179 | CB | GLU | A | 153 | 44.422 | 23.209 | -0.098 | 1.00 | 30.70 | C |
| ATOM | 2182 | CG | GLU | A | 153 | 43.191 | 23.755 | -0.720 | 1.00 | 37.46 | C |
| ATOM | 2185 | CD | GLU | A | 153 | 43.467 | 24.156 | -2.172 | 1.00 | 48.47 | C |
| ATOM | 2186 | OE1 | GLU | A | 153 | 44.252 | 25.126 | -2.392 | 1.00 | 55.74 | O |
| ATOM | 2187 | OE2 | GLU | A | 153 | 42.952 | 23.478 | -3.098 | 1.00 | 55.29 | O |
| ATOM | 2188 | C | GLU | A | 153 | 46.196 | 21.426 | -0.313 | 1.00 | 29.71 | C |
| ATOM | 2189 | O | GLU | A | 153 | 46.354 | 20.673 | 0.639 | 1.00 | 27.76 | O |
| ATOM | 2191 | N | GLU | A | 154 | 47.198 | 21.945 | -0.991 | 1.00 | 29.46 | N |
| ATOM | 2192 | CA | GLU | A | 154 | 48.562 | 21.730 | -0.576 | 1.00 | 30.45 | C |
| ATOM | 2194 | CB | GLU | A | 154 | 49.126 | 20.443 | -1.232 | 1.00 | 30.39 | C |
| ATOM | 2197 | CG | GLU | A | 154 | 49.029 | 20.438 | -2.711 | 1.00 | 30.47 | C |
| ATOM | 2200 | CD | GLU | A | 154 | 49.543 | 19.158 | -3.375 | 1.00 | 32.96 | C |
| ATOM | 2201 | OE1 | GLU | A | 154 | 49.165 | 18.974 | -4.568 | 1.00 | 31.61 | O |
| ATOM | 2202 | OE2 | GLU | A | 154 | 50.338 | 18.351 | -2.753 | 1.00 | 29.73 | O |
| ATOM | 2203 | C | GLU | A | 154 | 49.358 | 22.958 | -0.921 | 1.00 | 29.77 | C |
| ATOM | 2204 | O | GLU | A | 154 | 48.999 | 23.718 | -1.838 | 1.00 | 31.37 | O |
| ATOM | 2206 | N | MET | A | 155 | 50.431 | 23.118 | -0.202 | 1.00 | 29.24 | N |
| ATOM | 2207 | CA | MET | A | 155 | 51.468 | 24.115 | -0.452 | 1.00 | 30.22 | C |
| ATOM | 2209 | CB | MET | A | 155 | 51.227 | 25.396 | 0.327 | 1.00 | 26.93 | C |
| ATOM | 2212 | CG | MET | A | 155 | 52.217 | 26.532 | 0.009 | 1.00 | 32.34 | C |
| ATOM | 2215 | SD | MET | A | 155 | 51.787 | 28.035 | 0.881 | 1.00 | 36.87 | S |
| ATOM | 2216 | CE | MET | A | 155 | 50.684 | 28.665 | -0.426 | 1.00 | 41.93 | C |
| ATOM | 2220 | C | MET | A | 155 | 52.827 | 23.509 | -0.074 | 1.00 | 29.88 | C |
| ATOM | 2221 | O | MET | A | 155 | 52.967 | 22.893 | 0.970 | 1.00 | 30.17 | O |
| ATOM | 2223 | N | ALA | A | 156 | 53.813 | 23.732 | -0.939 | 1.00 | 31.46 | N |
| ATOM | 2224 | CA | ALA | A | 156 | 55.135 | 23.141 | -0.788 | 1.00 | 31.35 | C |
| ATOM | 2226 | CB | ALA | A | 156 | 55.209 | 21.891 | -1.695 | 1.00 | 31.85 | C |
| ATOM | 2230 | C | ALA | A | 156 | 56.190 | 24.165 | -1.143 | 1.00 | 32.96 | C |
| ATOM | 2231 | O | ALA | A | 156 | 55.946 | 25.051 | -2.001 | 1.00 | 32.16 | O |
| ATOM | 2233 | N | THR | A | 157 | 57.344 | 24.081 | -0.481 | 1.00 | 31.90 | N |
| ATOM | 2234 | CA | THR | A | 157 | 58.473 | 24.916 | -0.848 | 1.00 | 32.63 | C |
| ATOM | 2236 | CB | THR | A | 157 | 59.719 | 24.392 | -0.261 | 1.00 | 31.33 | C |
| ATOM | 2238 | OG1 | THR | A | 157 | 59.526 | 24.218 | 1.131 | 1.00 | 30.59 | O |
| ATOM | 2240 | CG2 | THR | A | 157 | 60.969 | 25.400 | -0.589 | 1.00 | 33.92 | C |
| ATOM | 2244 | C | THR | A | 157 | 58.627 | 24.965 | -2.356 | 1.00 | 33.71 | C |
| ATOM | 2245 | O | THR | A | 157 | 58.709 | 23.939 | -2.983 | 1.00 | 33.41 | O |
| ATOM | 2247 | N | LYS | A | 158 | 58.684 | 26.178 | -2.926 | 1.00 | 35.63 | N |
| ATOM | 2248 | CA | LYS | A | 158 | 59.037 | 26.426 | -4.345 | 1.00 | 38.06 | C |
| ATOM | 2250 | CB | LYS | A | 158 | 60.440 | 25.881 | -4.720 | 1.00 | 38.52 | C |
| ATOM | 2253 | CG | LYS | A | 158 | 61.548 | 26.813 | -4.287 | 1.00 | 43.77 | C |
| ATOM | 2256 | CD | LYS | A | 158 | 62.920 | 26.176 | -4.451 | 1.00 | 50.12 | C |
| ATOM | 2259 | CE | LYS | A | 158 | 63.968 | 26.696 | -3.419 | 1.00 | 51.94 | C |
| ATOM | 2262 | NZ | LYS | A | 158 | 65.303 | 25.978 | -3.569 | 1.00 | 54.48 | N |
| ATOM | 2266 | C | LYS | A | 158 | 57.947 | 25.882 | -5.222 | 1.00 | 36.66 | C |
| ATOM | 2267 | O | LYS | A | 158 | 58.120 | 25.633 | -6.409 | 1.00 | 37.81 | O |
| ATOM | 2269 | N | ALA | A | 159 | 56.778 | 25.672 | -4.620 | 1.00 | 36.78 | N |
| ATOM | 2270 | CA | ALA | A | 159 | 55.736 | 24.921 | -5.290 | 1.00 | 35.33 | C |
| ATOM | 2272 | CB | ALA | A | 159 | 54.976 | 25.840 | -6.328 | 1.00 | 35.78 | C |
| ATOM | 2276 | C | ALA | A | 159 | 56.247 | 23.630 | -5.941 | 1.00 | 34.36 | C |
| ATOM | 2277 | O | ALA | A | 159 | 55.789 | 23.215 | -6.989 | 1.00 | 35.50 | O |
| ATOM | 2279 | N | ASP | A | 160 | 57.194 | 22.962 | -5.276 | 1.00 | 33.74 | N |
| ATOM | 2280 | CA | ASP | A | 160 | 57.680 | 21.695 | -5.702 | 1.00 | 32.65 | C |
| ATOM | 2282 | CB | ASP | A | 160 | 59.195 | 21.657 | -5.490 | 1.00 | 33.13 | C |
| ATOM | 2285 | CG | ASP | A | 160 | 59.807 | 20.348 | -5.880 | 1.00 | 33.72 | C |
| ATOM | 2286 | OD1 | ASP | A | 160 | 59.094 | 19.340 | -6.149 | 1.00 | 37.99 | O |

FIG.15-21

| | | | | | | | | | | | |
|---|---|---|---|---|---|---|---|---|---|---|---|
| ATOM | 2287 | OD2 | ASP | A | 160 | 61.050 | 20.297 | -5.922 | 1.00 | 36.13 | O |
| ATOM | 2288 | C | ASP | A | 160 | 56.994 | 20.667 | -4.813 | 1.00 | 31.04 | C |
| ATOM | 2289 | O | ASP | A | 160 | 57.323 | 20.583 | -3.656 | 1.00 | 30.14 | O |
| ATOM | 2291 | N | TYR | A | 161 | 55.990 | 19.993 | -5.356 | 1.00 | 31.54 | N |
| ATOM | 2292 | CA | TYR | A | 161 | 55.150 | 19.039 | -4.597 | 1.00 | 30.31 | C |
| ATOM | 2294 | CB | TYR | A | 161 | 53.761 | 18.992 | -5.205 | 1.00 | 31.64 | C |
| ATOM | 2297 | CG | TYR | A | 161 | 53.080 | 20.350 | -5.121 | 1.00 | 31.18 | C |
| ATOM | 2298 | CD1 | TYR | A | 161 | 52.722 | 20.893 | -3.914 | 1.00 | 30.44 | C |
| ATOM | 2300 | CE1 | TYR | A | 161 | 52.067 | 22.143 | -3.845 | 1.00 | 32.44 | C |
| ATOM | 2302 | CZ | TYR | A | 161 | 51.843 | 22.853 | -5.036 | 1.00 | 38.20 | C |
| ATOM | 2303 | OH | TYR | A | 161 | 51.207 | 24.078 | -5.056 | 1.00 | 39.66 | O |
| ATOM | 2305 | CE2 | TYR | A | 161 | 52.215 | 22.326 | -6.234 | 1.00 | 34.66 | C |
| ATOM | 2307 | CD2 | TYR | A | 161 | 52.842 | 21.088 | -6.278 | 1.00 | 37.13 | C |
| ATOM | 2309 | C | TYR | A | 161 | 55.754 | 17.607 | -4.494 | 1.00 | 29.93 | C |
| ATOM | 2310 | O | TYR | A | 161 | 55.142 | 16.694 | -3.932 | 1.00 | 26.52 | O |
| ATOM | 2312 | N | THR | A | 162 | 56.976 | 17.440 | -5.018 | 1.00 | 31.04 | N |
| ATOM | 2313 | CA | THR | A | 162 | 57.783 | 16.227 | -4.830 | 1.00 | 29.62 | C |
| ATOM | 2315 | CB | THR | A | 162 | 58.114 | 15.930 | -3.310 | 1.00 | 28.53 | C |
| ATOM | 2317 | OG1 | THR | A | 162 | 58.865 | 16.995 | -2.757 | 1.00 | 27.24 | O |
| ATOM | 2319 | CG2 | THR | A | 162 | 58.884 | 14.666 | -3.140 | 1.00 | 26.62 | C |
| ATOM | 2323 | C | THR | A | 162 | 57.168 | 15.000 | -5.450 | 1.00 | 30.35 | C |
| ATOM | 2324 | O | THR | A | 162 | 57.798 | 14.372 | -6.306 | 1.00 | 31.59 | O |
| ATOM | 2326 | N | LEU | A | 163 | 55.952 | 14.588 | -5.027 | 1.00 | 29.24 | N |
| ATOM | 2327 | CA | LEU | A | 163 | 55.304 | 13.380 | -5.504 | 1.00 | 28.46 | C |
| ATOM | 2329 | CB | LEU | A | 163 | 54.302 | 12.829 | -4.464 | 1.00 | 29.74 | C |
| ATOM | 2332 | CG | LEU | A | 163 | 54.888 | 12.473 | -3.103 | 1.00 | 30.65 | C |
| ATOM | 2334 | CD1 | LEU | A | 163 | 53.824 | 12.209 | -2.055 | 1.00 | 30.87 | C |
| ATOM | 2338 | CD2 | LEU | A | 163 | 55.757 | 11.188 | -3.301 | 1.00 | 27.81 | C |
| ATOM | 2342 | C | LEU | A | 163 | 54.540 | 13.647 | -6.821 | 1.00 | 29.29 | C |
| ATOM | 2343 | O | LEU | A | 163 | 54.259 | 14.767 | -7.177 | 1.00 | 30.11 | O |
| ATOM | 2345 | N | ASP | A | 164 | 54.200 | 12.596 | -7.508 | 1.00 | 30.22 | N |
| ATOM | 2346 | CA | ASP | A | 164 | 53.320 | 12.707 | -8.701 | 1.00 | 32.33 | C |
| ATOM | 2348 | CB | ASP | A | 164 | 53.387 | 11.478 | -9.605 | 1.00 | 32.82 | C |
| ATOM | 2351 | CG | ASP | A | 164 | 52.827 | 10.191 | -8.939 | 1.00 | 39.74 | C |
| ATOM | 2352 | OD1 | ASP | A | 164 | 52.212 | 10.249 | -7.832 | 1.00 | 42.97 | O |
| ATOM | 2353 | OD2 | ASP | A | 164 | 53.018 | 9.089 | -9.527 | 1.00 | 43.10 | O |
| ATOM | 2354 | C | ASP | A | 164 | 51.889 | 12.990 | -8.219 | 1.00 | 33.00 | C |
| ATOM | 2355 | O | ASP | A | 164 | 51.568 | 12.945 | -7.005 | 1.00 | 30.46 | O |
| ATOM | 2357 | N | GLU | A | 165 | 51.038 | 13.304 | -9.181 | 1.00 | 33.85 | N |
| ATOM | 2358 | CA | GLU | A | 165 | 49.652 | 13.749 | -8.914 | 1.00 | 35.10 | C |
| ATOM | 2360 | CB | GLU | A | 165 | 48.959 | 14.137 | -10.215 | 1.00 | 35.75 | C |
| ATOM | 2363 | CG | GLU | A | 165 | 49.597 | 15.382 | -10.844 | 1.00 | 38.75 | C |
| ATOM | 2366 | CD | GLU | A | 165 | 49.198 | 16.668 | -10.160 | 1.00 | 46.27 | C |
| ATOM | 2367 | OE1 | GLU | A | 165 | 48.227 | 16.711 | -9.322 | 1.00 | 49.58 | O |
| ATOM | 2368 | OE2 | GLU | A | 165 | 49.853 | 17.682 | -10.467 | 1.00 | 50.07 | O |
| ATOM | 2369 | C | GLU | A | 165 | 48.836 | 12.687 | -8.195 | 1.00 | 33.48 | C |
| ATOM | 2370 | O | GLU | A | 165 | 48.088 | 13.029 | -7.260 | 1.00 | 32.20 | O |
| ATOM | 2372 | N | GLU | A | 166 | 49.008 | 11.434 | -8.622 | 1.00 | 31.26 | N |
| ATOM | 2373 | CA | GLU | A | 166 | 48.276 | 10.347 | -8.047 | 1.00 | 32.53 | C |
| ATOM | 2375 | CB | GLU | A | 166 | 48.427 | 9.052 | -8.797 | 1.00 | 33.11 | C |
| ATOM | 2378 | CG | GLU | A | 166 | 47.620 | 7.961 | -8.149 | 1.00 | 38.83 | C |
| ATOM | 2381 | CD | GLU | A | 166 | 47.435 | 6.732 | -8.966 | 1.00 | 47.82 | C |
| ATOM | 2382 | OE1 | GLU | A | 166 | 47.707 | 6.766 | -10.189 | 1.00 | 54.26 | O |
| ATOM | 2383 | OE2 | GLU | A | 166 | 46.991 | 5.718 | -8.381 | 1.00 | 53.70 | O |
| ATOM | 2384 | C | GLU | A | 166 | 48.597 | 10.128 | -6.572 | 1.00 | 31.20 | C |
| ATOM | 2385 | O | GLU | A | 166 | 47.704 | 9.799 | -5.780 | 1.00 | 27.69 | O |
| ATOM | 2387 | N | SER | A | 167 | 49.858 | 10.360 | -6.200 | 1.00 | 30.33 | N |
| ATOM | 2388 | CA | SER | A | 167 | 50.253 | 10.084 | -4.831 | 1.00 | 30.62 | C |
| ATOM | 2390 | CB | SER | A | 167 | 51.768 | 10.001 | -4.697 | 1.00 | 31.04 | C |
| ATOM | 2393 | OG | SER | A | 167 | 52.236 | 8.805 | -5.296 | 1.00 | 32.02 | O |
| ATOM | 2395 | C | SER | A | 167 | 49.643 | 11.154 | -3.972 | 1.00 | 29.54 | C |
| ATOM | 2396 | O | SER | A | 167 | 49.121 | 10.861 | -2.878 | 1.00 | 28.16 | O |
| ATOM | 2398 | N | ARG | A | 168 | 49.680 | 12.390 | -4.468 | 1.00 | 27.80 | N |

FIG.15-22

| | | | | | | | | | | | |
|---|---|---|---|---|---|---|---|---|---|---|---|
| ATOM | 2399 | CA | ARG | A | 168 | 49.181 | 13.483 | -3.676 | 1.00 | 27.94 | C |
| ATOM | 2401 | CB | ARG | A | 168 | 49.602 | 14.756 | -4.289 | 1.00 | 27.61 | C |
| ATOM | 2404 | CG | ARG | A | 168 | 51.052 | 15.132 | -3.932 | 1.00 | 30.40 | C |
| ATOM | 2407 | CD | ARG | A | 168 | 51.303 | 16.482 | -4.557 | 1.00 | 40.05 | C |
| ATOM | 2410 | NE | ARG | A | 168 | 51.643 | 16.311 | -5.894 | 1.00 | 41.57 | N |
| ATOM | 2412 | CZ | ARG | A | 168 | 51.408 | 17.095 | -6.946 | 1.00 | 40.06 | C |
| ATOM | 2413 | NH1 | ARG | A | 168 | 50.701 | 18.206 | -6.942 | 1.00 | 41.33 | N |
| ATOM | 2416 | NH2 | ARG | A | 168 | 51.920 | 16.648 | -8.076 | 1.00 | 39.18 | N |
| ATOM | 2419 | C | ARG | A | 168 | 47.650 | 13.374 | -3.584 | 1.00 | 28.20 | C |
| ATOM | 2420 | O | ARG | A | 168 | 47.074 | 13.630 | -2.527 | 1.00 | 27.76 | O |
| ATOM | 2422 | N | ALA | A | 169 | 47.032 | 13.007 | -4.692 | 1.00 | 27.81 | N |
| ATOM | 2423 | CA | ALA | A | 169 | 45.548 | 12.764 | -4.693 | 1.00 | 28.27 | C |
| ATOM | 2425 | CB | ALA | A | 169 | 45.087 | 12.409 | -6.075 | 1.00 | 27.69 | C |
| ATOM | 2429 | C | ALA | A | 169 | 45.112 | 11.696 | -3.665 | 1.00 | 27.68 | C |
| ATOM | 2430 | O | ALA | A | 169 | 44.105 | 11.874 | -2.985 | 1.00 | 27.14 | O |
| ATOM | 2432 | N | ARG | A | 170 | 45.856 | 10.605 | -3.508 | 1.00 | 28.18 | N |
| ATOM | 2433 | CA | ARG | A | 170 | 45.515 | 9.601 | -2.535 | 1.00 | 28.85 | C |
| ATOM | 2435 | CB | ARG | A | 170 | 46.323 | 8.331 | -2.663 | 1.00 | 30.37 | C |
| ATOM | 2438 | CG | ARG | A | 170 | 46.175 | 7.629 | -4.044 | 1.00 | 38.79 | C |
| ATOM | 2441 | CD | ARG | A | 170 | 46.727 | 6.173 | -3.939 | 1.00 | 46.28 | C |
| ATOM | 2444 | NE | ARG | A | 170 | 46.438 | 5.369 | -5.143 | 1.00 | 56.73 | N |
| ATOM | 2446 | CZ | ARG | A | 170 | 46.761 | 4.074 | -5.288 | 1.00 | 61.83 | C |
| ATOM | 2447 | NH1 | ARG | A | 170 | 47.389 | 3.410 | -4.301 | 1.00 | 61.96 | N |
| ATOM | 2450 | NH2 | ARG | A | 170 | 46.462 | 3.435 | -6.426 | 1.00 | 63.35 | N |
| ATOM | 2453 | C | ARG | A | 170 | 45.673 | 10.124 | -1.113 | 1.00 | 27.52 | C |
| ATOM | 2454 | O | ARG | A | 170 | 44.894 | 9.782 | -0.225 | 1.00 | 25.16 | O |
| ATOM | 2456 | N | ILE | A | 171 | 46.695 | 10.922 | -0.882 | 1.00 | 24.59 | N |
| ATOM | 2457 | CA | ILE | A | 171 | 46.852 | 11.521 | 0.453 | 1.00 | 23.95 | C |
| ATOM | 2459 | CB | ILE | A | 171 | 48.202 | 12.243 | 0.559 | 1.00 | 22.75 | C |
| ATOM | 2461 | CG1 | ILE | A | 171 | 49.324 | 11.240 | 0.584 | 1.00 | 25.81 | C |
| ATOM | 2464 | CD1 | ILE | A | 171 | 50.712 | 11.862 | 0.201 | 1.00 | 27.61 | C |
| ATOM | 2468 | CG2 | ILE | A | 171 | 48.280 | 13.221 | 1.786 | 1.00 | 22.81 | C |
| ATOM | 2472 | C | ILE | A | 171 | 45.669 | 12.493 | 0.739 | 1.00 | 23.85 | C |
| ATOM | 2473 | O | ILE | A | 171 | 45.043 | 12.455 | 1.813 | 1.00 | 21.70 | O |
| ATOM | 2475 | N | LYS | A | 172 | 45.352 | 13.311 | -0.244 | 1.00 | 23.48 | N |
| ATOM | 2476 | CA | LYS | A | 172 | 44.295 | 14.270 | -0.114 | 1.00 | 23.54 | C |
| ATOM | 2478 | CB | LYS | A | 172 | 44.202 | 15.135 | -1.376 | 1.00 | 22.27 | C |
| ATOM | 2481 | CG | LYS | A | 172 | 45.327 | 16.113 | -1.474 | 1.00 | 24.79 | C |
| ATOM | 2484 | CD | LYS | A | 172 | 45.367 | 16.711 | -2.930 | 1.00 | 25.26 | C |
| ATOM | 2487 | CE | LYS | A | 172 | 46.374 | 17.801 | -3.082 | 1.00 | 28.91 | C |
| ATOM | 2490 | NZ | LYS | A | 172 | 46.554 | 18.236 | -4.533 | 1.00 | 29.28 | N |
| ATOM | 2494 | C | LYS | A | 172 | 42.971 | 13.542 | 0.173 | 1.00 | 23.88 | C |
| ATOM | 2495 | O | LYS | A | 172 | 42.165 | 14.030 | 1.010 | 1.00 | 22.00 | O |
| ATOM | 2497 | N | THR | A | 173 | 42.757 | 12.416 | -0.514 | 1.00 | 22.09 | N |
| ATOM | 2498 | CA | THR | A | 173 | 41.527 | 11.632 | -0.363 | 1.00 | 23.82 | C |
| ATOM | 2500 | CB | THR | A | 173 | 41.394 | 10.515 | -1.407 | 1.00 | 24.34 | C |
| ATOM | 2502 | OG1 | THR | A | 173 | 41.422 | 11.125 | -2.696 | 1.00 | 23.99 | O |
| ATOM | 2504 | CG2 | THR | A | 173 | 40.096 | 9.695 | -1.190 | 1.00 | 22.42 | C |
| ATOM | 2508 | C | THR | A | 173 | 41.439 | 11.057 | 1.030 | 1.00 | 23.63 | C |
| ATOM | 2509 | O | THR | A | 173 | 40.400 | 11.143 | 1.690 | 1.00 | 23.28 | O |
| ATOM | 2511 | N | ARG | A | 174 | 42.540 | 10.554 | 1.524 | 1.00 | 23.86 | N |
| ATOM | 2512 | CA | ARG | A | 174 | 42.509 | 9.975 | 2.870 | 1.00 | 23.67 | C |
| ATOM | 2514 | CB | ARG | A | 174 | 43.814 | 9.284 | 3.146 | 1.00 | 23.50 | C |
| ATOM | 2517 | CG | ARG | A | 174 | 43.920 | 8.746 | 4.577 | 1.00 | 24.93 | C |
| ATOM | 2520 | CD | ARG | A | 174 | 42.896 | 7.651 | 4.897 | 1.00 | 26.22 | C |
| ATOM | 2523 | NE | ARG | A | 174 | 43.107 | 7.214 | 6.290 | 1.00 | 28.64 | N |
| ATOM | 2525 | CZ | ARG | A | 174 | 42.196 | 6.719 | 7.111 | 1.00 | 34.36 | C |
| ATOM | 2526 | NH1 | ARG | A | 174 | 40.900 | 6.626 | 6.767 | 1.00 | 32.44 | N |
| ATOM | 2529 | NH2 | ARG | A | 174 | 42.594 | 6.367 | 8.317 | 1.00 | 33.99 | N |
| ATOM | 2532 | C | ARG | A | 174 | 42.214 | 11.052 | 3.922 | 1.00 | 23.15 | C |
| ATOM | 2533 | O | ARG | A | 174 | 41.442 | 10.781 | 4.858 | 1.00 | 23.23 | O |
| ATOM | 2535 | N | LEU | A | 175 | 42.907 | 12.223 | 3.853 | 1.00 | 22.25 | N |
| ATOM | 2536 | CA | LEU | A | 175 | 42.683 | 13.315 | 4.791 | 1.00 | 22.73 | C |

FIG.15-23

| | | | | | | | | | | | |
|---|---|---|---|---|---|---|---|---|---|---|---|
| ATOM | 2538 | CB | LEU | A | 175 | 43.562 | 14.486 | 4.428 | 1.00 | 23.20 | C |
| ATOM | 2541 | CG | LEU | A | 175 | 45.052 | 14.243 | 4.736 | 1.00 | 21.29 | C |
| ATOM | 2543 | CD1 | LEU | A | 175 | 45.978 | 15.356 | 4.264 | 1.00 | 22.48 | C |
| ATOM | 2547 | CD2 | LEU | A | 175 | 45.154 | 14.117 | 6.277 | 1.00 | 20.52 | C |
| ATOM | 2551 | C | LEU | A | 175 | 41.191 | 13.719 | 4.774 | 1.00 | 24.51 | C |
| ATOM | 2552 | O | LEU | A | 175 | 40.549 | 13.806 | 5.814 | 1.00 | 23.15 | O |
| ATOM | 2554 | N | PHE | A | 176 | 40.646 | 13.897 | 3.560 | 1.00 | 24.68 | N |
| ATOM | 2555 | CA | PHE | A | 176 | 39.267 | 14.332 | 3.426 | 1.00 | 24.62 | C |
| ATOM | 2557 | CB | PHE | A | 176 | 38.960 | 14.629 | 1.959 | 1.00 | 25.01 | C |
| ATOM | 2560 | CG | PHE | A | 176 | 37.599 | 15.275 | 1.727 | 1.00 | 20.36 | C |
| ATOM | 2561 | CD1 | PHE | A | 176 | 37.441 | 16.648 | 1.745 | 1.00 | 28.35 | C |
| ATOM | 2563 | CE1 | PHE | A | 176 | 36.194 | 17.214 | 1.532 | 1.00 | 28.96 | C |
| ATOM | 2565 | CZ | PHE | A | 176 | 35.148 | 16.389 | 1.345 | 1.00 | 26.10 | C |
| ATOM | 2567 | CE2 | PHE | A | 176 | 35.295 | 15.084 | 1.376 | 1.00 | 23.03 | C |
| ATOM | 2569 | CD2 | PHE | A | 176 | 36.503 | 14.497 | 1.593 | 1.00 | 24.15 | C |
| ATOM | 2571 | C | PHE | A | 176 | 38.334 | 13.253 | 3.974 | 1.00 | 23.43 | C |
| ATOM | 2572 | O | PHE | A | 176 | 37.286 | 13.587 | 4.580 | 1.00 | 24.90 | O |
| ATOM | 2574 | N | THR | A | 177 | 38.669 | 12.001 | 3.790 | 1.00 | 24.64 | N |
| ATOM | 2575 | CA | THR | A | 177 | 37.884 | 10.928 | 4.311 | 1.00 | 24.07 | C |
| ATOM | 2577 | CB | THR | A | 177 | 38.364 | 9.607 | 3.764 | 1.00 | 26.26 | C |
| ATOM | 2579 | OG1 | THR | A | 177 | 38.215 | 9.651 | 2.345 | 1.00 | 26.99 | O |
| ATOM | 2581 | CG2 | THR | A | 177 | 37.616 | 8.416 | 4.360 | 1.00 | 27.14 | C |
| ATOM | 2585 | C | THR | A | 177 | 37.876 | 10.951 | 5.852 | 1.00 | 26.03 | C |
| ATOM | 2586 | O | THR | A | 177 | 36.823 | 10.815 | 6.481 | 1.00 | 24.89 | O |
| ATOM | 2588 | N | ILE | A | 178 | 39.041 | 11.144 | 6.462 | 1.00 | 25.83 | N |
| ATOM | 2589 | CA | ILE | A | 178 | 39.119 | 11.251 | 7.945 | 1.00 | 24.22 | C |
| ATOM | 2591 | CB | ILE | A | 178 | 40.548 | 11.538 | 8.404 | 1.00 | 24.87 | C |
| ATOM | 2593 | CG1 | ILE | A | 178 | 41.441 | 10.290 | 8.145 | 1.00 | 21.54 | C |
| ATOM | 2596 | CD1 | ILE | A | 178 | 42.964 | 10.562 | 8.107 | 1.00 | 24.20 | C |
| ATOM | 2600 | CG2 | ILE | A | 178 | 40.539 | 12.106 | 9.885 | 1.00 | 25.42 | C |
| ATOM | 2604 | C | ILE | A | 178 | 38.199 | 12.381 | 8.379 | 1.00 | 25.55 | C |
| ATOM | 2605 | O | ILE | A | 178 | 37.462 | 12.227 | 9.347 | 1.00 | 28.89 | O |
| ATOM | 2607 | N | ARG | A | 179 | 38.279 | 13.542 | 7.747 | 1.00 | 25.10 | N |
| ATOM | 2608 | CA | ARG | A | 179 | 37.461 | 14.672 | 8.099 | 1.00 | 25.30 | C |
| ATOM | 2610 | CB | ARG | A | 179 | 37.755 | 15.812 | 7.115 | 1.00 | 26.41 | C |
| ATOM | 2613 | CG | ARG | A | 179 | 36.779 | 16.943 | 7.113 | 1.00 | 26.34 | C |
| ATOM | 2616 | CD | ARG | A | 179 | 37.121 | 18.019 | 6.100 | 1.00 | 31.57 | C |
| ATOM | 2619 | NE | ARG | A | 179 | 35.931 | 18.813 | 5.749 | 1.00 | 32.67 | N |
| ATOM | 2621 | CZ | ARG | A | 179 | 35.889 | 19.741 | 4.834 | 1.00 | 36.55 | C |
| ATOM | 2622 | NH1 | ARG | A | 179 | 36.985 | 20.033 | 4.106 | 1.00 | 38.00 | N |
| ATOM | 2625 | NH2 | ARG | A | 179 | 34.744 | 20.380 | 4.606 | 1.00 | 39.70 | N |
| ATOM | 2628 | C | ARG | A | 179 | 35.983 | 14.288 | 8.070 | 1.00 | 26.17 | C |
| ATOM | 2629 | O | ARG | A | 179 | 35.218 | 14.604 | 8.998 | 1.00 | 25.08 | O |
| ATOM | 2631 | N | GLN | A | 180 | 35.572 | 13.655 | 6.962 | 1.00 | 26.58 | N |
| ATOM | 2632 | CA | GLN | A | 180 | 34.154 | 13.298 | 6.825 | 1.00 | 27.17 | C |
| ATOM | 2634 | CB | GLN | A | 180 | 33.885 | 12.855 | 5.390 | 1.00 | 26.73 | C |
| ATOM | 2637 | CG | GLN | A | 180 | 34.018 | 13.994 | 4.390 | 1.00 | 23.51 | C |
| ATOM | 2640 | CD | GLN | A | 180 | 33.116 | 15.130 | 4.695 | 1.00 | 24.73 | C |
| ATOM | 2641 | OE1 | GLN | A | 180 | 31.982 | 14.953 | 5.153 | 1.00 | 26.56 | O |
| ATOM | 2642 | NE2 | GLN | A | 180 | 33.573 | 16.305 | 4.450 | 1.00 | 24.59 | N |
| ATOM | 2645 | C | GLN | A | 180 | 33.730 | 12.203 | 7.835 | 1.00 | 28.34 | C |
| ATOM | 2646 | O | GLN | A | 180 | 32.531 | 12.191 | 8.265 | 1.00 | 31.72 | O |
| ATOM | 2648 | N | GLU | A | 181 | 34.614 | 11.263 | 8.183 | 1.00 | 27.65 | N |
| ATOM | 2649 | CA | GLU | A | 181 | 34.296 | 10.254 | 9.194 | 1.00 | 29.16 | C |
| ATOM | 2651 | CB | GLU | A | 181 | 35.316 | 9.122 | 9.257 | 1.00 | 28.63 | C |
| ATOM | 2654 | CG | GLU | A | 181 | 35.324 | 8.306 | 7.968 | 1.00 | 33.56 | C |
| ATOM | 2657 | CD | GLU | A | 181 | 36.360 | 7.231 | 7.983 | 1.00 | 37.89 | C |
| ATOM | 2658 | OE1 | GLU | A | 181 | 37.231 | 7.237 | 8.889 | 1.00 | 43.00 | O |
| ATOM | 2659 | OE2 | GLU | A | 181 | 36.346 | 6.376 | 7.073 | 1.00 | 45.13 | O |
| ATOM | 2660 | C | GLU | A | 181 | 34.160 | 10.935 | 10.531 | 1.00 | 29.30 | C |
| ATOM | 2661 | O | GLU | A | 181 | 33.228 | 10.619 | 11.313 | 1.00 | 29.71 | O |
| ATOM | 2663 | N | MET | A | 182 | 34.974 | 11.960 | 10.774 | 1.00 | 28.89 | N |
| ATOM | 2664 | CA | MET | A | 182 | 34.773 | 12.791 | 11.978 | 1.00 | 27.59 | C |

FIG.15-24

| | | | | | | | | | | | |
|---|---|---|---|---|---|---|---|---|---|---|---|
| ATOM | 2666 | CB | MET | A | 182 | 35.909 | 13.781 | 12.237 | 1.00 | 26.73 | C |
| ATOM | 2669 | CG | MET | A | 182 | 37.272 | 13.095 | 12.513 | 1.00 | 26.59 | C |
| ATOM | 2672 | SD | MET | A | 182 | 38.431 | 14.392 | 12.816 | 1.00 | 30.86 | S |
| ATOM | 2673 | CE | MET | A | 182 | 39.752 | 13.396 | 13.318 | 1.00 | 29.47 | C |
| ATOM | 2677 | C | MET | A | 182 | 33.476 | 13.551 | 11.903 | 1.00 | 29.37 | C |
| ATOM | 2678 | O | MET | A | 182 | 32.724 | 13.602 | 12.893 | 1.00 | 30.90 | O |
| ATOM | 2680 | N | ALA | A | 183 | 33.170 | 14.128 | 10.732 | 1.00 | 29.41 | N |
| ATOM | 2681 | CA | ALA | A | 183 | 31.936 | 14.879 | 10.585 | 1.00 | 29.66 | C |
| ATOM | 2683 | CB | ALA | A | 183 | 31.840 | 15.655 | 9.208 | 1.00 | 28.42 | C |
| ATOM | 2687 | C | ALA | A | 183 | 30.739 | 13.951 | 10.774 | 1.00 | 30.31 | C |
| ATOM | 2688 | O | ALA | A | 183 | 29.721 | 14.382 | 11.300 | 1.00 | 32.63 | O |
| ATOM | 2690 | N | SER | A | 184 | 30.857 | 12.711 | 10.379 | 1.00 | 33.09 | N |
| ATOM | 2691 | CA | SER | A | 184 | 29.799 | 11.758 | 10.550 | 1.00 | 34.98 | C |
| ATOM | 2693 | CB | SER | A | 184 | 30.210 | 10.395 | 10.093 | 1.00 | 34.44 | C |
| ATOM | 2696 | OG | SER | A | 184 | 30.307 | 10.394 | 8.685 | 1.00 | 40.38 | O |
| ATOM | 2698 | C | SER | A | 184 | 29.431 | 11.622 | 12.015 | 1.00 | 37.48 | C |
| ATOM | 2699 | O | SER | A | 184 | 28.245 | 11.442 | 12.315 | 1.00 | 36.22 | O |
| ATOM | 2701 | N | ARG | A | 185 | 30.460 | 11.607 | 12.867 | 1.00 | 38.38 | N |
| ATOM | 2702 | CA | ARG | A | 185 | 30.344 | 11.463 | 14.314 | 1.00 | 40.16 | C |
| ATOM | 2704 | CB | ARG | A | 185 | 31.492 | 10.558 | 14.820 | 1.00 | 41.09 | C |
| ATOM | 2707 | CG | ARG | A | 185 | 31.447 | 9.154 | 14.176 | 1.00 | 45.67 | C |
| ATOM | 2710 | CD | ARG | A | 185 | 32.420 | 8.085 | 14.767 | 1.00 | 53.28 | C |
| ATOM | 2713 | NE | ARG | A | 185 | 32.377 | 8.033 | 16.256 | 1.00 | 59.10 | N |
| ATOM | 2715 | CZ | ARG | A | 185 | 33.014 | 7.155 | 17.043 | 1.00 | 54.68 | C |
| ATOM | 2716 | NH1 | ARG | A | 185 | 33.727 | 6.155 | 16.537 | 1.00 | 55.85 | N |
| ATOM | 2719 | NH2 | ARG | A | 185 | 32.878 | 7.272 | 18.350 | 1.00 | 57.19 | N |
| ATOM | 2722 | C | ARG | A | 185 | 30.252 | 12.759 | 15.082 | 1.00 | 39.45 | C |
| ATOM | 2723 | O | ARG | A | 185 | 30.312 | 12.734 | 16.279 | 1.00 | 40.69 | O |
| ATOM | 2725 | N | SER | A | 186 | 30.043 | 13.886 | 14.404 | 1.00 | 39.19 | N |
| ATOM | 2726 | CA | SER | A | 186 | 29.988 | 15.215 | 14.994 | 1.00 | 39.62 | C |
| ATOM | 2728 | CB | SER | A | 186 | 28.676 | 15.387 | 15.824 | 1.00 | 41.74 | C |
| ATOM | 2731 | OG | SER | A | 186 | 27.524 | 15.263 | 14.982 | 1.00 | 41.75 | O |
| ATOM | 2733 | C | SER | A | 186 | 31.236 | 15.598 | 15.809 | 1.00 | 39.62 | C |
| ATOM | 2734 | O | SER | A | 186 | 31.153 | 16.349 | 16.794 | 1.00 | 39.05 | O |
| ATOM | 2736 | N | LEU | A | 187 | 32.401 | 15.096 | 15.370 | 1.00 | 38.55 | N |
| ATOM | 2737 | CA | LEU | A | 187 | 33.700 | 15.343 | 16.016 | 1.00 | 36.62 | C |
| ATOM | 2739 | CB | LEU | A | 187 | 34.441 | 14.052 | 16.203 | 1.00 | 37.57 | C |
| ATOM | 2742 | CG | LEU | A | 187 | 33.783 | 12.907 | 16.973 | 1.00 | 37.85 | C |
| ATOM | 2744 | CD1 | LEU | A | 187 | 34.698 | 11.790 | 16.843 | 1.00 | 34.83 | C |
| ATOM | 2748 | CD2 | LEU | A | 187 | 33.520 | 13.383 | 18.393 | 1.00 | 41.06 | C |
| ATOM | 2752 | C | LEU | A | 187 | 34.606 | 16.302 | 15.239 | 1.00 | 36.62 | C |
| ATOM | 2753 | O | LEU | A | 187 | 35.654 | 16.715 | 15.784 | 1.00 | 37.11 | O |
| ATOM | 2755 | N | TRP | A | 188 | 34.238 | 16.642 | 13.988 | 1.00 | 35.45 | N |
| ATOM | 2756 | CA | TRP | A | 188 | 35.060 | 17.477 | 13.113 | 1.00 | 35.47 | C |
| ATOM | 2758 | CB | TRP | A | 188 | 34.489 | 17.537 | 11.668 | 1.00 | 35.76 | C |
| ATOM | 2761 | CG | TRP | A | 188 | 35.171 | 18.570 | 10.882 | 1.00 | 31.25 | C |
| ATOM | 2762 | CD1 | TRP | A | 188 | 34.667 | 19.785 | 10.506 | 1.00 | 32.35 | C |
| ATOM | 2764 | NE1 | TRP | A | 188 | 35.623 | 20.513 | 9.849 | 1.00 | 32.61 | N |
| ATOM | 2766 | CE2 | TRP | A | 188 | 36.795 | 19.794 | 9.837 | 1.00 | 28.06 | C |
| ATOM | 2767 | CD2 | TRP | A | 188 | 36.545 | 18.568 | 10.487 | 1.00 | 28.00 | C |
| ATOM | 2768 | CE3 | TRP | A | 188 | 37.573 | 17.637 | 10.593 | 1.00 | 29.17 | C |
| ATOM | 2770 | CZ3 | TRP | A | 188 | 38.797 | 17.942 | 10.023 | 1.00 | 26.69 | C |
| ATOM | 2772 | CH2 | TRP | A | 188 | 39.019 | 19.174 | 9.408 | 1.00 | 23.86 | C |
| ATOM | 2774 | CZ2 | TRP | A | 188 | 38.014 | 20.111 | 9.302 | 1.00 | 26.86 | C |
| ATOM | 2776 | C | TRP | A | 188 | 35.192 | 18.928 | 13.646 | 1.00 | 36.29 | C |
| ATOM | 2777 | O | TRP | A | 188 | 36.256 | 19.491 | 13.693 | 1.00 | 35.22 | O |
| ATOM | 2779 | N | ASP | A | 189 | 34.084 | 19.538 | 14.029 | 1.00 | 36.39 | N |
| ATOM | 2780 | CA | ASP | A | 189 | 34.147 | 20.903 | 14.454 | 1.00 | 37.65 | C |
| ATOM | 2782 | CB | ASP | A | 189 | 32.734 | 21.378 | 14.778 | 1.00 | 38.87 | C |
| ATOM | 2785 | CG | ASP | A | 189 | 32.691 | 22.838 | 15.076 | 1.00 | 43.69 | C |
| ATOM | 2786 | OD1 | ASP | A | 189 | 32.547 | 23.642 | 14.113 | 1.00 | 51.93 | O |
| ATOM | 2787 | OD2 | ASP | A | 189 | 32.773 | 23.173 | 16.270 | 1.00 | 48.12 | O |
| ATOM | 2788 | C | ASP | A | 189 | 35.131 | 21.123 | 15.650 | 1.00 | 36.44 | C |

FIG.15-25

| | | | | | | | | | | | |
|---|---|---|---|---|---|---|---|---|---|---|---|
| ATOM | 2789 | O | ASP | A | 189 | 35.949 | 22.046 | 15.628 | 1.00 | 37.05 | O |
| ATOM | 2791 | N | SER | A | 190 | 35.075 | 20.237 | 16.630 | 1.00 | 35.71 | N |
| ATOM | 2792 | CA | SER | A | 190 | 35.958 | 20.251 | 17.781 | 1.00 | 36.18 | C |
| ATOM | 2794 | CB | SER | A | 190 | 35.649 | 19.078 | 18.701 | 1.00 | 35.90 | C |
| ATOM | 2797 | OG | SER | A | 190 | 36.657 | 18.917 | 19.700 | 1.00 | 36.76 | O |
| ATOM | 2799 | C | SER | A | 190 | 37.396 | 20.128 | 17.297 | 1.00 | 36.17 | C |
| ATOM | 2800 | O | SER | A | 190 | 38.274 | 20.997 | 17.564 | 1.00 | 35.59 | O |
| ATOM | 2802 | N | PHE | A | 191 | 37.609 | 19.077 | 16.508 | 1.00 | 35.68 | N |
| ATOM | 2803 | CA | PHE | A | 191 | 38.964 | 18.783 | 15.974 | 1.00 | 34.86 | C |
| ATOM | 2805 | CB | PHE | A | 191 | 38.941 | 17.520 | 15.120 | 1.00 | 34.80 | C |
| ATOM | 2808 | CG | PHE | A | 191 | 40.256 | 17.159 | 14.536 | 1.00 | 29.83 | C |
| ATOM | 2809 | CD1 | PHE | A | 191 | 41.267 | 16.608 | 15.319 | 1.00 | 27.51 | C |
| ATOM | 2811 | CE1 | PHE | A | 191 | 42.483 | 16.243 | 14.715 | 1.00 | 28.12 | C |
| ATOM | 2813 | CZ | PHE | A | 191 | 42.660 | 16.403 | 13.371 | 1.00 | 28.30 | C |
| ATOM | 2815 | CE2 | PHE | A | 191 | 41.662 | 16.899 | 12.606 | 1.00 | 31.17 | C |
| ATOM | 2817 | CD2 | PHE | A | 191 | 40.469 | 17.308 | 13.186 | 1.00 | 30.35 | C |
| ATOM | 2819 | C | PHE | A | 191 | 39.484 | 19.953 | 15.240 | 1.00 | 35.81 | C |
| ATOM | 2820 | O | PHE | A | 191 | 40.635 | 20.377 | 15.468 | 1.00 | 39.04 | O |
| ATOM | 2822 | N | ARG | A | 192 | 38.681 | 20.510 | 14.364 | 1.00 | 37.44 | N |
| ATOM | 2823 | CA | ARG | A | 192 | 39.101 | 21.661 | 13.596 | 1.00 | 40.73 | C |
| ATOM | 2825 | CB | ARG | A | 192 | 38.016 | 22.101 | 12.627 | 1.00 | 40.97 | C |
| ATOM | 2828 | CG | ARG | A | 192 | 38.410 | 23.310 | 11.820 | 1.00 | 45.51 | C |
| ATOM | 2831 | CD | ARG | A | 192 | 37.284 | 23.911 | 11.063 | 1.00 | 47.51 | C |
| ATOM | 2834 | NE | ARG | A | 192 | 36.085 | 24.046 | 11.889 | 1.00 | 52.34 | N |
| ATOM | 2836 | CZ | ARG | A | 192 | 35.718 | 25.145 | 12.543 | 1.00 | 55.03 | C |
| ATOM | 2837 | NH1 | ARG | A | 192 | 36.460 | 26.233 | 12.528 | 1.00 | 56.77 | N |
| ATOM | 2840 | NH2 | ARG | A | 192 | 34.594 | 25.149 | 13.239 | 1.00 | 57.12 | N |
| ATOM | 2843 | C | ARG | A | 192 | 39.465 | 22.872 | 14.471 | 1.00 | 42.53 | C |
| ATOM | 2844 | O | ARG | A | 192 | 40.391 | 23.620 | 14.168 | 1.00 | 42.73 | O |
| ATOM | 2846 | N | GLN | A | 193 | 38.718 | 23.101 | 15.540 | 1.00 | 42.64 | N |
| ATOM | 2847 | CA | GLN | A | 193 | 39.006 | 24.286 | 16.361 | 1.00 | 42.84 | C |
| ATOM | 2849 | CB | GLN | A | 193 | 37.741 | 24.763 | 17.083 | 1.00 | 42.89 | C |
| ATOM | 2852 | CG | GLN | A | 193 | 36.664 | 25.313 | 16.209 | 1.00 | 41.61 | C |
| ATOM | 2855 | CD | GLN | A | 193 | 35.556 | 25.994 | 17.016 | 1.00 | 44.64 | C |
| ATOM | 2856 | OE1 | GLN | A | 193 | 35.743 | 27.085 | 17.557 | 1.00 | 39.07 | O |
| ATOM | 2857 | NE2 | GLN | A | 193 | 34.384 | 25.349 | 17.081 | 1.00 | 45.01 | N |
| ATOM | 2860 | C | GLN | A | 193 | 40.210 | 24.107 | 17.307 | 1.00 | 44.01 | C |
| ATOM | 2861 | O | GLN | A | 193 | 40.785 | 25.124 | 17.712 | 1.00 | 45.48 | O |
| ATOM | 2863 | N | SER | A | 194 | 40.663 | 22.886 | 17.593 | 1.00 | 44.02 | N |
| ATOM | 2864 | CA | SER | A | 194 | 41.803 | 22.698 | 18.519 | 1.00 | 45.95 | C |
| ATOM | 2866 | CB | SER | A | 194 | 41.708 | 21.356 | 19.167 | 1.00 | 45.22 | C |
| ATOM | 2869 | OG | SER | A | 194 | 41.505 | 20.452 | 18.153 | 1.00 | 49.40 | O |
| ATOM | 2871 | C | SER | A | 194 | 43.218 | 22.837 | 17.948 | 1.00 | 47.09 | C |
| ATOM | 2872 | O | SER | A | 194 | 44.201 | 22.407 | 18.561 | 1.00 | 48.16 | O |
| ATOM | 2874 | N | GLU | A | 195 | 43.351 | 23.392 | 16.763 | 1.00 | 47.27 | N |
| ATOM | 2875 | CA | GLU | A | 195 | 44.713 | 23.569 | 16.211 | 1.00 | 47.89 | C |
| ATOM | 2877 | CB | GLU | A | 195 | 44.749 | 23.242 | 14.698 | 1.00 | 46.47 | C |
| ATOM | 2880 | CG | GLU | A | 195 | 46.171 | 23.343 | 14.088 | 1.00 | 46.49 | C |
| ATOM | 2883 | CD | GLU | A | 195 | 46.208 | 23.019 | 12.592 | 1.00 | 42.09 | C |
| ATOM | 2884 | OE1 | GLU | A | 195 | 45.667 | 21.977 | 12.213 | 1.00 | 39.80 | O |
| ATOM | 2885 | OE2 | GLU | A | 195 | 46.695 | 23.836 | 11.817 | 1.00 | 37.52 | O |
| ATOM | 2886 | C | GLU | A | 195 | 45.098 | 25.032 | 16.431 | 1.00 | 48.18 | C |
| ATOM | 2887 | O | GLU | A | 195 | 44.312 | 25.890 | 16.106 | 1.00 | 48.18 | O |
| ATOM | 2889 | N | ARG | A | 196 | 46.316 | 25.274 | 16.904 | 1.00 | 50.67 | N |
| ATOM | 2890 | CA | ARG | A | 196 | 46.898 | 26.649 | 17.239 | 1.00 | 52.34 | C |
| ATOM | 2892 | CB | ARG | A | 196 | 48.434 | 26.548 | 17.169 | 1.00 | 51.78 | C |
| ATOM | 2901 | C | ARG | A | 196 | 46.510 | 27.934 | 16.445 | 1.00 | 52.74 | C |
| ATOM | 2902 | O | ARG | A | 196 | 45.357 | 28.154 | 16.021 | 1.00 | 55.25 | O |
| ATOM | 2904 | O32 | ci1 | A | 801 | 61.053 | 17.166 | 17.336 | 0.60 | 57.73 | O |
| ATOM | 2905 | S30 | ci1 | A | 801 | 60.183 | 16.043 | 17.508 | 0.60 | 56.27 | S |
| ATOM | 2906 | O31 | ci1 | A | 801 | 60.426 | 15.130 | 16.424 | 0.60 | 57.38 | O |
| ATOM | 2907 | CP | ci1 | A | 801 | 60.634 | 15.277 | 18.941 | 1.00 | 56.91 | C |
| ATOM | 2910 | CGB | ci1 | A | 801 | 59.951 | 13.939 | 19.141 | 1.00 | 57.03 | C |

FIG.15-26

| | | | | | | | | | | | |
|---|---|---|---|---|---|---|---|---|---|---|---|
| ATOM | 2911 | CD2 | ci1 | A | 801 | 58.907 | 13.839 | 20.061 | 1.00 | 58.23 | C |
| ATOM | 2913 | CE2 | ci1 | A | 801 | 58.254 | 12.616 | 20.248 | 1.00 | 60.31 | C |
| ATOM | 2915 | CZ | ci1 | A | 801 | 58.665 | 11.481 | 19.524 | 1.00 | 60.85 | C |
| ATOM | 2917 | CE1 | ci1 | A | 801 | 59.720 | 11.576 | 18.615 | 1.00 | 59.94 | C |
| ATOM | 2919 | CD1 | ci1 | A | 801 | 60.356 | 12.805 | 18.419 | 1.00 | 56.93 | C |
| ATOM | 2921 | NJ | ci1 | A | 801 | 58.703 | 16.509 | 17.539 | 1.00 | 52.53 | N |
| ATOM | 2922 | CI | ci1 | A | 801 | 58.427 | 17.933 | 17.855 | 1.00 | 51.58 | C |
| ATOM | 2925 | CK | ci1 | A | 801 | 57.175 | 18.469 | 17.184 | 1.00 | 49.24 | C |
| ATOM | 2928 | CG | ci1 | A | 801 | 56.064 | 17.431 | 17.352 | 1.00 | 48.54 | C |
| ATOM | 2931 | CH | ci1 | A | 801 | 57.642 | 15.516 | 17.314 | 1.00 | 46.73 | C |
| ATOM | 2934 | CF | ci1 | A | 801 | 56.410 | 16.120 | 16.631 | 1.00 | 45.93 | C |
| ATOM | 2935 | CB | ci1 | A | 801 | 56.698 | 16.366 | 15.149 | 1.00 | 36.01 | C |
| ATOM | 2936 | O13 | ci1 | A | 801 | 57.678 | 15.835 | 14.580 | 1.00 | 32.50 | O |
| ATOM | 2937 | CM | ci1 | A | 801 | 55.730 | 17.248 | 14.445 | 1.00 | 32.79 | C |
| ATOM | 2939 | CA | ci1 | A | 801 | 55.509 | 17.325 | 13.110 | 1.00 | 32.20 | C |
| ATOM | 2940 | O14 | ci1 | A | 801 | 56.235 | 16.638 | 12.291 | 1.00 | 25.87 | O |
| ATOM | 2942 | CE | ci1 | A | 801 | 54.451 | 18.222 | 12.629 | 1.00 | 33.27 | C |
| ATOM | 2943 | OAN | ci1 | A | 801 | 54.043 | 19.050 | 13.478 | 1.00 | 35.33 | O |
| ATOM | 2944 | OAO | ci1 | A | 801 | 54.071 | 18.295 | 11.450 | 1.00 | 30.90 | O |
| ATOM | 2945 | CO | ci1 | A | 801 | 55.258 | 15.099 | 16.672 | 1.00 | 50.17 | C |
| ATOM | 2948 | CGA | ci1 | A | 801 | 54.568 | 15.044 | 18.019 | 1.00 | 53.47 | C |
| ATOM | 2949 | CDB | ci1 | A | 801 | 53.630 | 16.024 | 18.401 | 1.00 | 55.14 | C |
| ATOM | 2951 | CEB | ci1 | A | 801 | 53.018 | 15.968 | 19.658 | 1.00 | 57.71 | C |
| ATOM | 2953 | CDA | ci1 | A | 801 | 54.895 | 13.997 | 18.886 | 1.00 | 56.23 | C |
| ATOM | 2955 | CEA | ci1 | A | 801 | 54.261 | 13.934 | 20.128 | 1.00 | 58.00 | C |
| ATOM | 2957 | CZB | ci1 | A | 801 | 53.342 | 14.916 | 20.500 | 1.00 | 57.45 | C |
| ATOM | 2958 | CL | ci1 | A | 801 | 52.552 | 14.795 | 22.088 | 1.00 | 65.61 | CL |
| ATOM | 2959 | MN | MN | A | 901 | 55.441 | 17.121 | 10.259 | 1.00 | 26.23 | MN |
| ATOM | 2960 | MN | MN | A | 902 | 57.695 | 15.256 | 12.553 | 1.00 | 32.69 | MN |
| ATOM | 2961 | OH2 | WAT | A | 903 | 59.083 | 16.811 | 11.845 | 1.00 | 30.18 | O |
| ATOM | 2964 | OH2 | WAT | A | 904 | 59.506 | 13.985 | 12.897 | 1.00 | 34.20 | O |
| ATOM | 2967 | OH2 | WAT | Z | 1 | 57.073 | 18.744 | -1.578 | 1.00 | 27.97 | O |
| ATOM | 2970 | OH2 | WAT | Z | 2 | 61.259 | 16.436 | -1.670 | 1.00 | 28.42 | O |
| ATOM | 2973 | OH2 | WAT | Z | 3 | 38.704 | 21.743 | 20.181 | 0.50 | 24.92 | O |
| ATOM | 2976 | OH2 | WAT | Z | 4 | 51.566 | 18.952 | 10.933 | 1.00 | 24.92 | O |
| ATOM | 2979 | OH2 | WAT | Z | 5 | 64.685 | 16.407 | 19.443 | 1.00 | 34.57 | O |
| ATOM | 2982 | OH2 | WAT | Z | 6 | 40.128 | 6.104 | 4.054 | 1.00 | 35.98 | O |
| ATOM | 2985 | OH2 | WAT | Z | 7 | 67.540 | 19.096 | 3.287 | 1.00 | 28.22 | O |
| ATOM | 2988 | OH2 | WAT | Z | 8 | 41.923 | 21.652 | 6.410 | 1.00 | 31.66 | O |
| ATOM | 2991 | OH2 | WAT | Z | 9 | 46.140 | 18.576 | 11.562 | 1.00 | 29.29 | O |
| ATOM | 2994 | OH2 | WAT | Z | 10 | 52.050 | 13.557 | -11.851 | 1.00 | 42.71 | O |
| ATOM | 2997 | OH2 | WAT | Z | 11 | 30.038 | 16.498 | 6.206 | 1.00 | 30.20 | O |
| ATOM | 3000 | OH2 | WAT | Z | 12 | 47.655 | 16.197 | 11.836 | 1.00 | 29.72 | O |
| ATOM | 3003 | OH2 | WAT | Z | 13 | 55.304 | 9.756 | -6.788 | 1.00 | 41.79 | O |
| ATOM | 3006 | OH2 | WAT | Z | 14 | 42.495 | 16.851 | 1.694 | 1.00 | 28.06 | O |
| ATOM | 3009 | OH2 | WAT | Z | 15 | 50.309 | 10.910 | -11.312 | 1.00 | 42.43 | O |
| ATOM | 3012 | OH2 | WAT | Z | 16 | 45.497 | 3.737 | 9.204 | 1.00 | 37.30 | O |
| ATOM | 3015 | OH2 | WAT | Z | 18 | 65.343 | 22.138 | 10.865 | 1.00 | 36.86 | O |
| ATOM | 3018 | OH2 | WAT | Z | 19 | 59.976 | 5.414 | -0.644 | 1.00 | 40.92 | O |
| ATOM | 3021 | OH2 | WAT | Z | 20 | 43.941 | 25.422 | 2.549 | 1.00 | 40.75 | O |
| ATOM | 3024 | OH2 | WAT | Z | 21 | 49.956 | 17.533 | 12.556 | 1.00 | 34.74 | O |
| ATOM | 3027 | OH2 | WAT | Z | 22 | 31.343 | 18.235 | 13.530 | 1.00 | 38.23 | O |
| ATOM | 3030 | OH2 | WAT | Z | 23 | 69.121 | 19.282 | 1.068 | 1.00 | 34.73 | O |
| ATOM | 3033 | OH2 | WAT | Z | 24 | 42.744 | 19.068 | -4.776 | 1.00 | 32.18 | O |
| ATOM | 3036 | OH2 | WAT | Z | 25 | 71.088 | 5.741 | 6.557 | 1.00 | 42.30 | O |
| ATOM | 3039 | OH2 | WAT | Z | 26 | 40.961 | 7.159 | 1.472 | 1.00 | 41.68 | O |
| ATOM | 3042 | OH2 | WAT | Z | 27 | 73.968 | 7.591 | 13.017 | 1.00 | 38.60 | O |
| ATOM | 3045 | OH2 | WAT | Z | 29 | 60.643 | 15.295 | -7.290 | 1.00 | 34.95 | O |
| ATOM | 3048 | OH2 | WAT | Z | 30 | 71.852 | 14.259 | 15.848 | 1.00 | 48.93 | O |
| ATOM | 3051 | OH2 | WAT | Z | 31 | 38.051 | 21.616 | -1.639 | 1.00 | 42.27 | O |
| ATOM | 3054 | OH2 | WAT | Z | 32 | 55.765 | 19.517 | -8.142 | 1.00 | 39.74 | O |
| ATOM | 3057 | OH2 | WAT | Z | 33 | 61.902 | 3.640 | 17.023 | 1.00 | 43.42 | O |
| ATOM | 3060 | OH2 | WAT | Z | 34 | 45.519 | 20.703 | -4.713 | 1.00 | 44.57 | O |

FIG.15-27

| | | | | | | | | | | | |
|---|---|---|---|---|---|---|---|---|---|---|---|
| ATOM | 3063 | OH2 | WAT | Z | 35 | 38.985 | 5.470 | 8.431 | 1.00 | 38.90 | O |
| ATOM | 3066 | OH2 | WAT | Z | 36 | 59.427 | 12.749 | 15.253 | 1.00 | 39.92 | O |
| ATOM | 3069 | OH2 | WAT | Z | 37 | 60.472 | 10.440 | 14.876 | 1.00 | 35.27 | O |
| ATOM | 3072 | OH2 | WAT | Z | 38 | 52.941 | 25.345 | -3.209 | 1.00 | 36.14 | O |
| ATOM | 3075 | OH2 | WAT | Z | 39 | 32.646 | 18.717 | 17.216 | 1.00 | 38.32 | O |
| ATOM | 3078 | OH2 | WAT | Z | 40 | 48.706 | 23.747 | -4.804 | 1.00 | 34.97 | O |
| ATOM | 3081 | OH2 | WAT | Z | 43 | 63.902 | 22.703 | -1.026 | 1.00 | 39.80 | O |
| ATOM | 3084 | OH2 | WAT | Z | 44 | 47.086 | 15.488 | -7.245 | 1.00 | 41.14 | O |
| ATOM | 3087 | OH2 | WAT | Z | 45 | 37.348 | 29.035 | 17.843 | 1.00 | 37.75 | O |
| ATOM | 3090 | OH2 | WAT | Z | 46 | 43.518 | 7.443 | -0.088 | 1.00 | 41.34 | O |
| ATOM | 3093 | OH2 | WAT | Z | 47 | 35.474 | 23.141 | 8.204 | 1.00 | 43.91 | O |
| ATOM | 3096 | OH2 | WAT | Z | 48 | 62.625 | 4.491 | 6.219 | 1.00 | 46.42 | O |
| ATOM | 3099 | OH2 | WAT | Z | 49 | 55.363 | 3.527 | 4.813 | 1.00 | 53.74 | O |
| ATOM | 3102 | OH2 | WAT | Z | 50 | 29.097 | 17.237 | 11.257 | 1.00 | 40.71 | O |
| ATOM | 3105 | OH2 | WAT | Z | 52 | 46.450 | 23.495 | -3.357 | 1.00 | 36.42 | O |
| ATOM | 3108 | OH2 | WAT | Z | 53 | 39.816 | 22.566 | 7.787 | 1.00 | 44.23 | O |
| ATOM | 3111 | OH2 | WAT | Z | 54 | 50.790 | 25.296 | -7.626 | 1.00 | 47.59 | O |
| ATOM | 3114 | OH2 | WAT | Z | 55 | 33.752 | 18.740 | 7.662 | 1.00 | 38.93 | O |
| ATOM | 3117 | OH2 | WAT | Z | 56 | 54.946 | 28.181 | -2.378 | 1.00 | 56.22 | O |
| ATOM | 3120 | OH2 | WAT | Z | 57 | 59.397 | 28.744 | -1.513 | 1.00 | 44.95 | O |
| ATOM | 3123 | OH2 | WAT | Z | 58 | 37.750 | 23.261 | 6.502 | 1.00 | 48.53 | O |
| ATOM | 3126 | OH2 | WAT | Z | 59 | 35.300 | 12.965 | 21.863 | 1.00 | 57.82 | O |
| ATOM | 3129 | OH2 | WAT | Z | 60 | 37.614 | 7.381 | 1.350 | 1.00 | 36.73 | O |
| ATOM | 3132 | OH2 | WAT | Z | 61 | 63.498 | 3.175 | 14.610 | 1.00 | 53.27 | O |
| ATOM | 3135 | OH2 | WAT | Z | 62 | 42.301 | 24.286 | 4.864 | 1.00 | 42.97 | O |
| ATOM | 3138 | OH2 | WAT | Z | 63 | 63.366 | 18.279 | 16.941 | 1.00 | 39.55 | O |
| ATOM | 3141 | OH2 | WAT | Z | 64 | 31.100 | 18.979 | 7.375 | 1.00 | 44.42 | O |
| ATOM | 3144 | OH2 | WAT | Z | 65 | 45.337 | 18.138 | 1.047 | 1.00 | 40.67 | O |
| ATOM | 3147 | OH2 | WAT | Z | 66 | 52.657 | 12.351 | 13.992 | 1.00 | 35.16 | O |
| ATOM | 3150 | OH2 | WAT | Z | 67 | 42.874 | 29.165 | 8.279 | 1.00 | 45.65 | O |
| ATOM | 3153 | OH2 | WAT | Z | 68 | 56.220 | 29.847 | 13.406 | 1.00 | 45.04 | O |
| ATOM | 3156 | OH2 | WAT | Z | 69 | 62.411 | 22.567 | -5.362 | 1.00 | 45.81 | O |
| ATOM | 3159 | OH2 | WAT | Z | 70 | 70.451 | 9.758 | -2.164 | 1.00 | 39.56 | O |
| ATOM | 3162 | OH2 | WAT | Z | 71 | 66.063 | 3.607 | -9.354 | 1.00 | 58.02 | O |
| ATOM | 3165 | OH2 | WAT | Z | 72 | 68.977 | 20.053 | 5.572 | 1.00 | 50.52 | O |
| ATOM | 3168 | OH2 | WAT | Z | 73 | 43.220 | 1.110 | 20.549 | 1.00 | 57.38 | O |
| ATOM | 3171 | OH2 | WAT | Z | 74 | 60.177 | 18.447 | 15.195 | 1.00 | 63.23 | O |
| ATOM | 3174 | OH2 | WAT | Z | 75 | 47.048 | -0.137 | 18.643 | 1.00 | 41.49 | O |
| ATOM | 3177 | OH2 | WAT | Z | 76 | 30.889 | 18.926 | 11.147 | 1.00 | 49.30 | O |
| ATOM | 3180 | OH2 | WAT | Z | 77 | 35.546 | 5.848 | 2.440 | 1.00 | 51.27 | O |
| ATOM | 3183 | OH2 | WAT | Z | 78 | 42.310 | 8.977 | -4.655 | 1.00 | 44.90 | O |
| ATOM | 3186 | OH2 | WAT | Z | 79 | 29.515 | 19.108 | 15.277 | 1.00 | 52.98 | O |
| ATOM | 3189 | OH2 | WAT | Z | 80 | 65.972 | 21.567 | -0.154 | 1.00 | 54.82 | O |
| ATOM | 3192 | OH2 | WAT | Z | 81 | 63.611 | 19.972 | 10.280 | 1.00 | 34.36 | O |
| ATOM | 3195 | OH2 | WAT | Z | 84 | 70.312 | 14.978 | -5.408 | 1.00 | 46.49 | O |
| ATOM | 3198 | OH2 | WAT | Z | 85 | 59.075 | 17.120 | -8.006 | 1.00 | 36.47 | O |
| ATOM | 3201 | OH2 | WAT | Z | 86 | 61.218 | 19.761 | 10.732 | 1.00 | 35.24 | O |
| ATOM | 3204 | OH2 | WAT | Z | 87 | 34.505 | 22.643 | 2.888 | 1.00 | 43.76 | O |
| ATOM | 3207 | OH2 | WAT | Z | 88 | 70.603 | 23.278 | 9.934 | 1.00 | 58.37 | O |
| ATOM | 3210 | OH2 | WAT | Z | 89 | 42.605 | 6.965 | -2.891 | 1.00 | 51.64 | O |
| ATOM | 3213 | OH2 | WAT | Z | 90 | 32.745 | 7.515 | 11.255 | 1.00 | 53.65 | O |
| ATOM | 3216 | OH2 | WAT | Z | 91 | 76.625 | 8.103 | 10.968 | 1.00 | 49.14 | O |
| ATOM | 3219 | OH2 | WAT | Z | 92 | 70.296 | 18.337 | -2.321 | 1.00 | 43.04 | O |
| ATOM | 3222 | OH2 | WAT | Z | 93 | 51.113 | 31.653 | 10.198 | 1.00 | 45.47 | O |
| ATOM | 3225 | OH2 | WAT | Z | 94 | 35.555 | 17.473 | 21.332 | 1.00 | 46.53 | O |
| ATOM | 3228 | OH2 | WAT | Z | 95 | 45.909 | 28.788 | 1.826 | 1.00 | 40.43 | O |
| ATOM | 3231 | OH2 | WAT | Z | 96 | 69.218 | 11.585 | -7.075 | 1.00 | 42.48 | O |
| ATOM | 3234 | OH2 | WAT | Z | 100 | 53.881 | 27.018 | 15.702 | 1.00 | 61.65 | O |
| ATOM | 3237 | OH2 | WAT | Z | 101 | 58.547 | 4.831 | 11.123 | 1.00 | 54.10 | O |
| ATOM | 3240 | OH2 | WAT | Z | 102 | 28.101 | 8.109 | 12.728 | 1.00 | 57.92 | O |
| ATOM | 3243 | OH2 | WAT | Z | 103 | 54.197 | 23.707 | -9.308 | 1.00 | 51.65 | O |
| ATOM | 3246 | OH2 | WAT | Z | 104 | 44.604 | -0.043 | 17.825 | 1.00 | 40.83 | O |
| ATOM | 3249 | OH2 | WAT | Z | 106 | 67.152 | 23.413 | 10.396 | 1.00 | 53.36 | O |

FIG.15-28

```
ATOM   3252  OH2 WAT Z 107      47.292  19.642  16.716  1.00 59.73           O
ATOM   3255  OH2 WAT Z 111      50.477   6.557  -6.233  1.00 49.13           O
END
```

FIG.16-1

Figure 16: H1N1 polypeptide fragment (chain A) with bound EGCG

```
HEADER    ----                                  XX-XXX-XX   xxxx
COMPND    ---
REMARK   3
REMARK   3 REFINEMENT.
REMARK   3   PROGRAM     : REFMAC 5.5.0102
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.60
REMARK   3   RESOLUTION RANGE LOW  (ANGSTROMS) :  42.78
REMARK   3   DATA CUTOFF            (SIGMA(F)) : NONE
REMARK   3   COMPLETENESS FOR RANGE        (%) :  98.48
REMARK   3   NUMBER OF REFLECTIONS             :    7434
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE     (WORKING + TEST SET) : 0.25191
REMARK   3   R VALUE            (WORKING SET) :  0.24948
REMARK   3   FREE R VALUE                     :  0.30415
REMARK   3   FREE R VALUE TEST SET SIZE   (%) :  4.7
REMARK   3   FREE R VALUE TEST SET COUNT      :   363
REMARK   3
REMARK   3  FIT IN THE HIGHEST RESOLUTION BIN.
REMARK   3   TOTAL NUMBER OF BINS USED           :      20
REMARK   3   BIN RESOLUTION RANGE HIGH           :    2.602
REMARK   3   BIN RESOLUTION RANGE LOW            :    2.669
REMARK   3   REFLECTION IN BIN     (WORKING SET) :      523
REMARK   3   BIN COMPLETENESS (WORKING+TEST) (%) :    97.35
REMARK   3   BIN R VALUE           (WORKING SET) :    0.340
REMARK   3   BIN FREE R VALUE SET COUNT          :       27
REMARK   3   BIN FREE R VALUE                    :    0.559
REMARK   3
REMARK   3  NUMBER OF NON-HYDROGEN ATOMS USED IN REFINEMENT.
REMARK   3   ALL ATOMS                :     1557
REMARK   3
REMARK   3  B VALUES.
REMARK   3   FROM WILSON PLOT           (A**2) : NULL
REMARK   3   MEAN B VALUE      (OVERALL, A**2) :  34.202
REMARK   3   OVERALL ANISOTROPIC B VALUE.
REMARK   3    B11 (A**2) :     9.15
REMARK   3    B22 (A**2) :     9.15
REMARK   3    B33 (A**2) :   -18.30
REMARK   3    B12 (A**2) :     0.00
REMARK   3    B13 (A**2) :     0.00
REMARK   3    B23 (A**2) :     0.00
REMARK   3
REMARK   3  ESTIMATED OVERALL COORDINATE ERROR.
REMARK   3   ESU BASED ON R VALUE                            (A):   0.160
REMARK   3   ESU BASED ON FREE R VALUE                       (A):   0.078
REMARK   3   ESU BASED ON MAXIMUM LIKELIHOOD                 (A):   0.257
REMARK   3   ESU FOR B VALUES BASED ON MAXIMUM LIKELIHOOD (A**2):  13.175
REMARK   3
REMARK   3 CORRELATION COEFFICIENTS.
REMARK   3   CORRELATION COEFFICIENT FO-FC      :   0.902
REMARK   3   CORRELATION COEFFICIENT FO-FC FREE :   0.868
REMARK   3
REMARK   3  RMS DEVIATIONS FROM IDEAL VALUES        COUNT    RMS    WEIGHT
```

FIG.16-2

```
REMARK   3   BOND LENGTHS REFINED ATOMS        (A):  1554 ; 0.009 ; 0.022
REMARK   3   BOND LENGTHS OTHERS               (A):  1094 ; 0.001 ; 0.020
REMARK   3   BOND ANGLES REFINED ATOMS   (DEGREES):  2088 ; 1.201 ; 1.973
REMARK   3   BOND ANGLES OTHERS          (DEGREES):  2634 ; 0.789 ; 3.000
REMARK   3   TORSION ANGLES, PERIOD 1    (DEGREES):   176 ; 5.150 ; 5.000
REMARK   3   TORSION ANGLES, PERIOD 2    (DEGREES):    79 ;35.593 ;23.165
REMARK   3   TORSION ANGLES, PERIOD 3    (DEGREES):   290 ;16.970 ;15.000
REMARK   3   TORSION ANGLES, PERIOD 4    (DEGREES):    14 ;18.333 ;15.000
REMARK   3   CHIRAL-CENTER RESTRAINTS       (A**3):   219 ; 0.058 ; 0.200
REMARK   3   GENERAL PLANES REFINED ATOMS      (A):  1686 ; 0.004 ; 0.020
REMARK   3   GENERAL PLANES OTHERS             (A):   342 ; 0.001 ; 0.020
REMARK   3
REMARK   3  ISOTROPIC THERMAL FACTOR RESTRAINTS.     COUNT   RMS    WEIGHT
REMARK   3   MAIN-CHAIN BOND REFINED ATOMS  (A**2):   889 ; 0.548 ; 1.500
REMARK   3   MAIN-CHAIN BOND OTHER ATOMS    (A**2):   359 ; 0.069 ; 1.500
REMARK   3   MAIN-CHAIN ANGLE REFINED ATOMS (A**2):  1438 ; 1.057 ; 2.000
REMARK   3   SIDE-CHAIN BOND REFINED ATOMS  (A**2):   665 ; 1.403 ; 3.000
REMARK   3   SIDE-CHAIN ANGLE REFINED ATOMS (A**2):   650 ; 2.392 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS  : NULL
REMARK   3
REMARK   3
REMARK   3  BULK SOLVENT MODELLING.
REMARK   3   METHOD USED :  MASK
REMARK   3   PARAMETERS FOR MASK CALCULATION
REMARK   3   VDW PROBE RADIUS   :   1.40
REMARK   3   ION PROBE RADIUS   :   0.80
REMARK   3   SHRINKAGE RADIUS   :   0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
LINKR            GLY A  52                      ALA A  70                gap
LINKR            LYS A 139                      GLU A 141                gap
CRYST1   99.940   99.940   82.730  90.00  90.00 120.00 P 64 2 2
SCALE1      0.010006  0.005777  0.000000        0.00000
SCALE2      0.000000  0.011554  0.000000        0.00000
SCALE3      0.000000  0.000000  0.012088        0.00000
ATOM      2  CA  ALA A   0      -2.958 -50.956  20.866  1.00 38.32           C
ATOM      4  CB  ALA A   0      -4.292 -50.809  20.158  1.00 38.65           C
ATOM      8  C   ALA A   0      -1.914 -50.172  20.100  1.00 38.49           C
ATOM      9  O   ALA A   0      -1.251 -50.707  19.213  1.00 38.54           O
ATOM     10  N   MET A   1      -1.797 -48.886  20.419  1.00 38.55           N
ATOM     11  CA  MET A   1      -0.896 -47.991  19.693  1.00 38.41           C
ATOM     13  CB  MET A   1      -1.116 -46.540  20.118  1.00 38.56           C
ATOM     16  CG  MET A   1      -0.069 -45.553  19.591  1.00 38.72           C
ATOM     19  SD  MET A   1      -0.064 -45.442  17.800  1.00 38.46           S
ATOM     20  CE  MET A   1      -1.234 -44.111  17.543  1.00 38.94           C
ATOM     24  C   MET A   1       0.562 -48.381  19.889  1.00 38.50           C
ATOM     25  O   MET A   1       1.389 -48.168  19.005  1.00 38.18           O
ATOM     27  N   GLU A   2       0.888 -48.956  21.038  1.00 38.78           N
ATOM     28  CA  GLU A   2       2.254 -49.380  21.251  1.00 39.20           C
ATOM     30  CB  GLU A   2       2.473 -49.950  22.654  1.00 39.51           C
ATOM     33  CG  GLU A   2       3.962 -50.141  22.975  1.00 39.86           C
```

FIG.16-3

| | | | | | | | | | | | |
|---|---|---|---|---|---|---|---|---|---|---|---|
| ATOM | 36 | CD | GLU | A | 2 | 4.244 | -50.723 | 24.351 | 1.00 | 41.32 | C |
| ATOM | 37 | OE1 | GLU | A | 2 | 3.315 | -51.206 | 25.047 | 1.00 | 42.21 | O |
| ATOM | 38 | OE2 | GLU | A | 2 | 5.430 | -50.700 | 24.736 | 1.00 | 43.38 | O |
| ATOM | 39 | C | GLU | A | 2 | 2.616 | -50.410 | 20.205 | 1.00 | 39.33 | C |
| ATOM | 40 | O | GLU | A | 2 | 3.656 | -50.312 | 19.575 | 1.00 | 39.67 | O |
| ATOM | 42 | N | ASP | A | 3 | 1.742 | -51.387 | 20.001 | 1.00 | 39.74 | N |
| ATOM | 43 | CA | ASP | A | 3 | 2.044 | -52.518 | 19.106 | 1.00 | 39.73 | C |
| ATOM | 45 | CB | ASP | A | 3 | 1.003 | -53.621 | 19.292 | 1.00 | 40.00 | C |
| ATOM | 48 | CG | ASP | A | 3 | 1.006 | -54.180 | 20.706 | 1.00 | 42.56 | C |
| ATOM | 49 | OD1 | ASP | A | 3 | 2.114 | -54.449 | 21.244 | 1.00 | 46.13 | O |
| ATOM | 50 | OD2 | ASP | A | 3 | -0.091 | -54.336 | 21.290 | 1.00 | 45.10 | O |
| ATOM | 51 | C | ASP | A | 3 | 2.141 | -52.096 | 17.642 | 1.00 | 38.69 | C |
| ATOM | 52 | O | ASP | A | 3 | 2.936 | -52.639 | 16.870 | 1.00 | 38.86 | O |
| ATOM | 54 | N | PHE | A | 4 | 1.340 | -51.115 | 17.268 | 1.00 | 37.65 | N |
| ATOM | 55 | CA | PHE | A | 4 | 1.449 | -50.531 | 15.946 | 1.00 | 37.05 | C |
| ATOM | 57 | CB | PHE | A | 4 | 0.439 | -49.408 | 15.769 | 1.00 | 36.69 | C |
| ATOM | 60 | CG | PHE | A | 4 | 0.588 | -48.694 | 14.481 | 1.00 | 37.32 | C |
| ATOM | 61 | CD1 | PHE | A | 4 | 0.130 | -49.271 | 13.311 | 1.00 | 37.67 | C |
| ATOM | 63 | CE1 | PHE | A | 4 | 0.277 | -48.622 | 12.103 | 1.00 | 37.71 | C |
| ATOM | 65 | CZ | PHE | A | 4 | 0.897 | -47.386 | 12.057 | 1.00 | 38.26 | C |
| ATOM | 67 | CE2 | PHE | A | 4 | 1.376 | -46.800 | 13.224 | 1.00 | 36.88 | C |
| ATOM | 69 | CD2 | PHE | A | 4 | 1.226 | -47.455 | 14.421 | 1.00 | 37.64 | C |
| ATOM | 71 | C | PHE | A | 4 | 2.861 | -49.989 | 15.721 | 1.00 | 36.40 | C |
| ATOM | 72 | O | PHE | A | 4 | 3.539 | -50.387 | 14.773 | 1.00 | 36.25 | O |
| ATOM | 74 | N | VAL | A | 5 | 3.297 | -49.098 | 16.607 | 1.00 | 35.59 | N |
| ATOM | 75 | CA | VAL | A | 5 | 4.622 | -48.513 | 16.507 | 1.00 | 35.33 | C |
| ATOM | 77 | CB | VAL | A | 5 | 4.990 | -47.674 | 17.758 | 1.00 | 35.58 | C |
| ATOM | 79 | CG1 | VAL | A | 5 | 6.443 | -47.169 | 17.646 | 1.00 | 35.49 | C |
| ATOM | 83 | CG2 | VAL | A | 5 | 4.017 | -46.485 | 17.951 | 1.00 | 34.00 | C |
| ATOM | 87 | C | VAL | A | 5 | 5.697 | -49.586 | 16.253 | 1.00 | 35.25 | C |
| ATOM | 88 | O | VAL | A | 5 | 6.487 | -49.448 | 15.320 | 1.00 | 34.86 | O |
| ATOM | 90 | N | ARG | A | 6 | 5.678 | -50.673 | 17.025 | 1.00 | 34.99 | N |
| ATOM | 91 | CA | ARG | A | 6 | 6.731 | -51.687 | 16.946 | 1.00 | 35.30 | C |
| ATOM | 93 | CB | ARG | A | 6 | 6.811 | -52.561 | 18.219 | 1.00 | 35.55 | C |
| ATOM | 96 | CG | ARG | A | 6 | 6.306 | -51.916 | 19.512 | 1.00 | 36.75 | C |
| ATOM | 99 | CD | ARG | A | 6 | 6.714 | -52.703 | 20.745 | 1.00 | 37.93 | C |
| ATOM | 102 | NE | ARG | A | 6 | 8.038 | -52.291 | 21.188 | 1.00 | 40.77 | N |
| ATOM | 104 | CZ | ARG | A | 6 | 8.297 | -51.363 | 22.108 | 1.00 | 41.42 | C |
| ATOM | 105 | NH1 | ARG | A | 6 | 7.325 | -50.737 | 22.757 | 1.00 | 42.21 | N |
| ATOM | 108 | NH2 | ARG | A | 6 | 9.554 | -51.069 | 22.396 | 1.00 | 42.13 | N |
| ATOM | 111 | C | ARG | A | 6 | 6.579 | -52.605 | 15.735 | 1.00 | 35.22 | C |
| ATOM | 112 | O | ARG | A | 6 | 7.390 | -53.511 | 15.533 | 1.00 | 35.54 | O |
| ATOM | 114 | N | GLN | A | 7 | 5.520 | -52.421 | 14.961 | 1.00 | 34.97 | N |
| ATOM | 115 | CA | GLN | A | 7 | 5.358 | -53.141 | 13.697 | 1.00 | 34.58 | C |
| ATOM | 117 | CB | GLN | A | 7 | 3.942 | -53.733 | 13.586 | 1.00 | 35.12 | C |
| ATOM | 120 | CG | GLN | A | 7 | 3.617 | -54.842 | 14.604 | 1.00 | 36.29 | C |
| ATOM | 123 | CD | GLN | A | 7 | 2.111 | -54.980 | 14.879 | 1.00 | 38.16 | C |
| ATOM | 124 | OE1 | GLN | A | 7 | 1.284 | -54.470 | 14.121 | 1.00 | 40.59 | O |
| ATOM | 125 | NE2 | GLN | A | 7 | 1.758 | -55.653 | 15.974 | 1.00 | 36.63 | N |
| ATOM | 128 | C | GLN | A | 7 | 5.594 | -52.176 | 12.557 | 1.00 | 33.63 | C |
| ATOM | 129 | O | GLN | A | 7 | 6.157 | -52.545 | 11.545 | 1.00 | 33.98 | O |
| ATOM | 131 | N | CYS | A | 8 | 5.154 | -50.932 | 12.719 | 1.00 | 32.58 | N |
| ATOM | 132 | CA | CYS | A | 8 | 5.220 | -49.952 | 11.641 | 1.00 | 32.10 | C |
| ATOM | 134 | CB | CYS | A | 8 | 4.286 | -48.791 | 11.956 | 1.00 | 31.88 | C |
| ATOM | 137 | SG | CYS | A | 8 | 4.508 | -47.419 | 10.843 | 1.00 | 33.87 | S |
| ATOM | 139 | C | CYS | A | 8 | 6.636 | -49.414 | 11.372 | 1.00 | 31.12 | C |
| ATOM | 140 | O | CYS | A | 8 | 6.987 | -49.056 | 10.243 | 1.00 | 30.42 | O |
| ATOM | 142 | N | PHE | A | 9 | 7.434 | -49.342 | 12.426 | 1.00 | 30.32 | N |
| ATOM | 143 | CA | PHE | A | 9 | 8.717 | -48.676 | 12.363 | 1.00 | 29.67 | C |
| ATOM | 145 | CB | PHE | A | 9 | 8.768 | -47.548 | 13.405 | 1.00 | 29.41 | C |
| ATOM | 148 | CG | PHE | A | 9 | 7.812 | -46.413 | 13.114 | 1.00 | 28.23 | C |
| ATOM | 149 | CD1 | PHE | A | 9 | 8.093 | -45.501 | 12.095 | 1.00 | 28.80 | C |
| ATOM | 151 | CE1 | PHE | A | 9 | 7.223 | -44.444 | 11.809 | 1.00 | 28.14 | C |

FIG.16-4

| | | | | | | | | | | | |
|---|---|---|---|---|---|---|---|---|---|---|---|
| ATOM | 153 | CZ | PHE | A | 9 | 6.052 | -44.311 | 12.549 | 1.00 | 27.84 | C |
| ATOM | 155 | CE2 | PHE | A | 9 | 5.764 | -45.224 | 13.571 | 1.00 | 26.77 | C |
| ATOM | 157 | CD2 | PHE | A | 9 | 6.639 | -46.262 | 13.840 | 1.00 | 26.84 | C |
| ATOM | 159 | C | PHE | A | 9 | 9.813 | -49.690 | 12.583 | 1.00 | 29.45 | C |
| ATOM | 160 | O | PHE | A | 9 | 9.621 | -50.671 | 13.298 | 1.00 | 29.14 | O |
| ATOM | 162 | N | ASN | A | 10 | 10.962 | -49.463 | 11.953 | 1.00 | 29.40 | N |
| ATOM | 163 | CA | ASN | A | 10 | 12.074 | -50.379 | 12.116 | 1.00 | 29.32 | C |
| ATOM | 165 | CB | ASN | A | 10 | 13.155 | -50.136 | 11.048 | 1.00 | 29.60 | C |
| ATOM | 168 | CG | ASN | A | 10 | 14.130 | -49.044 | 11.425 | 1.00 | 30.88 | C |
| ATOM | 169 | OD1 | ASN | A | 10 | 14.838 | -49.152 | 12.422 | 1.00 | 34.37 | O |
| ATOM | 170 | ND2 | ASN | A | 10 | 14.204 | -48.003 | 10.611 | 1.00 | 31.40 | N |
| ATOM | 173 | C | ASN | A | 10 | 12.601 | -50.288 | 13.561 | 1.00 | 28.82 | C |
| ATOM | 174 | O | ASN | A | 10 | 12.433 | -49.262 | 14.234 | 1.00 | 28.98 | O |
| ATOM | 176 | N | PRO | A | 11 | 13.210 | -51.366 | 14.054 | 1.00 | 27.98 | N |
| ATOM | 177 | CA | PRO | A | 11 | 13.616 | -51.390 | 15.452 | 1.00 | 28.02 | C |
| ATOM | 179 | CB | PRO | A | 11 | 14.245 | -52.786 | 15.602 | 1.00 | 28.00 | C |
| ATOM | 182 | CG | PRO | A | 11 | 13.689 | -53.585 | 14.484 | 1.00 | 27.59 | C |
| ATOM | 185 | CD | PRO | A | 11 | 13.491 | -52.638 | 13.370 | 1.00 | 27.90 | C |
| ATOM | 188 | C | PRO | A | 11 | 14.603 | -50.282 | 15.908 | 1.00 | 28.28 | C |
| ATOM | 189 | O | PRO | A | 11 | 14.509 | -49.839 | 17.057 | 1.00 | 27.65 | O |
| ATOM | 190 | N | MET | A | 12 | 15.522 | -49.847 | 15.037 | 1.00 | 28.46 | N |
| ATOM | 191 | CA | MET | A | 12 | 16.458 | -48.764 | 15.370 | 1.00 | 29.11 | C |
| ATOM | 193 | CB | MET | A | 12 | 17.460 | -48.497 | 14.214 | 1.00 | 30.11 | C |
| ATOM | 196 | CG | MET | A | 12 | 18.237 | -47.137 | 14.301 | 1.00 | 34.75 | C |
| ATOM | 199 | SD | MET | A | 12 | 19.622 | -46.832 | 13.106 | 1.00 | 45.22 | S |
| ATOM | 200 | CE | MET | A | 12 | 18.752 | -45.924 | 11.808 | 1.00 | 42.93 | C |
| ATOM | 204 | C | MET | A | 12 | 15.676 | -47.504 | 15.727 | 1.00 | 28.27 | C |
| ATOM | 205 | O | MET | A | 12 | 15.883 | -46.915 | 16.791 | 1.00 | 27.82 | O |
| ATOM | 207 | N | ILE | A | 13 | 14.777 | -47.107 | 14.831 | 1.00 | 27.74 | N |
| ATOM | 208 | CA | ILE | A | 13 | 13.888 | -45.963 | 15.043 | 1.00 | 27.50 | C |
| ATOM | 210 | CB | ILE | A | 13 | 12.812 | -45.867 | 13.916 | 1.00 | 27.79 | C |
| ATOM | 212 | CG1 | ILE | A | 13 | 13.453 | -45.462 | 12.590 | 1.00 | 28.46 | C |
| ATOM | 215 | CD1 | ILE | A | 13 | 14.177 | -44.171 | 12.667 | 1.00 | 31.66 | C |
| ATOM | 219 | CG2 | ILE | A | 13 | 11.711 | -44.885 | 14.272 | 1.00 | 26.30 | C |
| ATOM | 223 | C | ILE | A | 13 | 13.158 | -46.090 | 16.377 | 1.00 | 27.31 | C |
| ATOM | 224 | O | ILE | A | 13 | 13.194 | -45.183 | 17.218 | 1.00 | 27.14 | O |
| ATOM | 226 | N | VAL | A | 14 | 12.486 | -47.220 | 16.568 | 1.00 | 26.83 | N |
| ATOM | 227 | CA | VAL | A | 14 | 11.727 | -47.422 | 17.790 | 1.00 | 26.51 | C |
| ATOM | 229 | CB | VAL | A | 14 | 11.073 | -48.826 | 17.851 | 1.00 | 26.30 | C |
| ATOM | 231 | CG1 | VAL | A | 14 | 10.888 | -49.271 | 19.269 | 1.00 | 25.54 | C |
| ATOM | 235 | CG2 | VAL | A | 14 | 9.747 | -48.811 | 17.135 | 1.00 | 25.28 | C |
| ATOM | 239 | C | VAL | A | 14 | 12.655 | -47.199 | 18.966 | 1.00 | 26.65 | C |
| ATOM | 240 | O | VAL | A | 14 | 12.350 | -46.410 | 19.841 | 1.00 | 27.21 | O |
| ATOM | 242 | N | GLU | A | 15 | 13.806 | -47.860 | 18.956 | 1.00 | 26.55 | N |
| ATOM | 243 | CA | GLU | A | 15 | 14.763 | -47.767 | 20.057 | 1.00 | 26.50 | C |
| ATOM | 245 | CB | GLU | A | 15 | 15.994 | -48.643 | 19.759 | 1.00 | 26.92 | C |
| ATOM | 248 | CG | GLU | A | 15 | 17.055 | -48.645 | 20.831 | 1.00 | 28.10 | C |
| ATOM | 251 | CD | GLU | A | 15 | 16.546 | -49.161 | 22.138 | 1.00 | 30.86 | C |
| ATOM | 252 | OE1 | GLU | A | 15 | 15.821 | -50.179 | 22.118 | 1.00 | 32.95 | O |
| ATOM | 253 | OE2 | GLU | A | 15 | 16.870 | -48.560 | 23.187 | 1.00 | 33.11 | O |
| ATOM | 254 | C | GLU | A | 15 | 15.170 | -46.321 | 20.324 | 1.00 | 25.96 | C |
| ATOM | 255 | O | GLU | A | 15 | 15.196 | -45.888 | 21.470 | 1.00 | 26.34 | O |
| ATOM | 257 | N | LEU | A | 16 | 15.463 | -45.567 | 19.276 | 1.00 | 25.16 | N |
| ATOM | 258 | CA | LEU | A | 16 | 15.798 | -44.165 | 19.443 | 1.00 | 24.97 | C |
| ATOM | 260 | CB | LEU | A | 16 | 16.244 | -43.535 | 18.108 | 1.00 | 24.92 | C |
| ATOM | 263 | CG | LEU | A | 16 | 17.655 | -43.892 | 17.596 | 1.00 | 24.76 | C |
| ATOM | 265 | CD1 | LEU | A | 16 | 17.995 | -43.157 | 16.316 | 1.00 | 24.82 | C |
| ATOM | 269 | CD2 | LEU | A | 16 | 18.706 | -43.597 | 18.648 | 1.00 | 23.94 | C |
| ATOM | 273 | C | LEU | A | 16 | 14.629 | -43.377 | 20.041 | 1.00 | 25.24 | C |
| ATOM | 274 | O | LEU | A | 16 | 14.831 | -42.437 | 20.833 | 1.00 | 25.65 | O |
| ATOM | 276 | N | ALA | A | 17 | 13.408 | -43.744 | 19.669 | 1.00 | 25.24 | N |
| ATOM | 277 | CA | ALA | A | 17 | 12.228 | -43.077 | 20.214 | 1.00 | 25.17 | C |
| ATOM | 279 | CB | ALA | A | 17 | 10.972 | -43.559 | 19.525 | 1.00 | 24.97 | C |

FIG.16-5

| | | | | | | | | | | | |
|---|---|---|---|---|---|---|---|---|---|---|---|
| ATOM | 283 | C | ALA | A | 17 | 12.132 | -43.298 | 21.718 | 1.00 | 25.19 | C |
| ATOM | 284 | O | ALA | A | 17 | 11.855 | -42.361 | 22.464 | 1.00 | 24.69 | O |
| ATOM | 286 | N | GLU | A | 18 | 12.384 | -44.526 | 22.163 | 1.00 | 25.61 | N |
| ATOM | 287 | CA | GLU | A | 18 | 12.268 | -44.852 | 23.582 | 1.00 | 26.54 | C |
| ATOM | 289 | CB | GLU | A | 18 | 12.446 | -46.343 | 23.831 | 1.00 | 26.75 | C |
| ATOM | 292 | CG | GLU | A | 18 | 11.279 | -47.172 | 23.345 | 1.00 | 28.90 | C |
| ATOM | 295 | CD | GLU | A | 18 | 11.627 | -48.644 | 23.197 | 1.00 | 30.85 | C |
| ATOM | 296 | OE1 | GLU | A | 18 | 12.348 | -49.014 | 22.244 | 1.00 | 35.60 | O |
| ATOM | 297 | OE2 | GLU | A | 18 | 11.176 | -49.439 | 24.025 | 1.00 | 30.02 | O |
| ATOM | 298 | C | GLU | A | 18 | 13.280 | -44.081 | 24.406 | 1.00 | 26.76 | C |
| ATOM | 299 | O | GLU | A | 18 | 12.914 | -43.368 | 25.333 | 1.00 | 26.80 | O |
| ATOM | 301 | N | LYS | A | 19 | 14.553 | -44.221 | 24.062 | 1.00 | 27.19 | N |
| ATOM | 302 | CA | LYS | A | 19 | 15.599 | -43.493 | 24.761 | 1.00 | 27.72 | C |
| ATOM | 304 | CB | LYS | A | 19 | 16.943 | -43.745 | 24.075 | 1.00 | 28.13 | C |
| ATOM | 307 | CG | LYS | A | 19 | 18.075 | -42.844 | 24.515 | 1.00 | 30.88 | C |
| ATOM | 310 | CD | LYS | A | 19 | 19.393 | -43.274 | 23.846 | 1.00 | 35.40 | C |
| ATOM | 313 | CE | LYS | A | 19 | 20.548 | -42.341 | 24.229 | 1.00 | 38.04 | C |
| ATOM | 316 | NZ | LYS | A | 19 | 21.565 | -42.290 | 23.135 | 1.00 | 40.40 | N |
| ATOM | 320 | C | LYS | A | 19 | 15.255 | -41.991 | 24.838 | 1.00 | 27.32 | C |
| ATOM | 321 | O | LYS | A | 19 | 15.385 | -41.377 | 25.883 | 1.00 | 27.25 | O |
| ATOM | 323 | N | ALA | A | 20 | 14.788 | -41.417 | 23.738 | 1.00 | 27.29 | N |
| ATOM | 324 | CA | ALA | A | 20 | 14.406 | -40.008 | 23.712 | 1.00 | 27.47 | C |
| ATOM | 326 | CB | ALA | A | 20 | 14.017 | -39.594 | 22.305 | 1.00 | 27.28 | C |
| ATOM | 330 | C | ALA | A | 20 | 13.271 | -39.704 | 24.692 | 1.00 | 27.79 | C |
| ATOM | 331 | O | ALA | A | 20 | 13.338 | -38.729 | 25.440 | 1.00 | 28.10 | O |
| ATOM | 333 | N | MET | A | 21 | 12.235 | -40.541 | 24.704 | 1.00 | 28.05 | N |
| ATOM | 334 | CA | MET | A | 21 | 11.116 | -40.328 | 25.625 | 1.00 | 27.93 | C |
| ATOM | 336 | CB | MET | A | 21 | 9.982 | -41.310 | 25.361 | 1.00 | 27.92 | C |
| ATOM | 339 | CG | MET | A | 21 | 9.211 | -41.021 | 24.095 | 1.00 | 27.92 | C |
| ATOM | 342 | SD | MET | A | 21 | 7.753 | -42.077 | 23.918 | 1.00 | 27.49 | S |
| ATOM | 343 | CE | MET | A | 21 | 6.684 | -41.421 | 25.202 | 1.00 | 24.54 | C |
| ATOM | 347 | C | MET | A | 21 | 11.578 | -40.463 | 27.052 | 1.00 | 27.87 | C |
| ATOM | 348 | O | MET | A | 21 | 11.203 | -39.661 | 27.898 | 1.00 | 27.95 | O |
| ATOM | 350 | N | LYS | A | 22 | 12.395 | -41.476 | 27.319 | 1.00 | 27.99 | N |
| ATOM | 351 | CA | LYS | A | 22 | 12.909 | -41.696 | 28.668 | 1.00 | 28.41 | C |
| ATOM | 353 | CB | LYS | A | 22 | 13.624 | -43.047 | 28.768 | 1.00 | 28.43 | C |
| ATOM | 356 | CG | LYS | A | 22 | 12.701 | -44.266 | 28.780 | 1.00 | 28.34 | C |
| ATOM | 359 | CD | LYS | A | 22 | 13.443 | -45.537 | 29.204 | 1.00 | 28.21 | C |
| ATOM | 362 | CE | LYS | A | 22 | 12.817 | -46.786 | 28.586 | 1.00 | 28.68 | C |
| ATOM | 365 | NZ | LYS | A | 22 | 13.112 | -48.026 | 29.373 | 1.00 | 29.07 | N |
| ATOM | 369 | C | LYS | A | 22 | 13.847 | -40.569 | 29.145 | 1.00 | 28.80 | C |
| ATOM | 370 | O | LYS | A | 22 | 13.923 | -40.278 | 30.336 | 1.00 | 28.62 | O |
| ATOM | 372 | N | GLU | A | 23 | 14.564 | -39.931 | 28.230 | 1.00 | 29.39 | N |
| ATOM | 373 | CA | GLU | A | 23 | 15.401 | -38.805 | 28.624 | 1.00 | 30.07 | C |
| ATOM | 375 | CB | GLU | A | 23 | 16.215 | -38.281 | 27.453 | 1.00 | 30.38 | C |
| ATOM | 378 | CG | GLU | A | 23 | 17.462 | -39.073 | 27.187 | 1.00 | 31.17 | C |
| ATOM | 381 | CD | GLU | A | 23 | 18.211 | -38.579 | 25.977 | 1.00 | 32.82 | C |
| ATOM | 382 | OE1 | GLU | A | 23 | 18.295 | -37.344 | 25.781 | 1.00 | 33.58 | O |
| ATOM | 383 | OE2 | GLU | A | 23 | 18.724 | -39.441 | 25.227 | 1.00 | 35.98 | O |
| ATOM | 384 | C | GLU | A | 23 | 14.551 | -37.692 | 29.184 | 1.00 | 30.41 | C |
| ATOM | 385 | O | GLU | A | 23 | 14.984 | -36.954 | 30.063 | 1.00 | 29.86 | O |
| ATOM | 387 | N | TYR | A | 24 | 13.326 | -37.591 | 28.684 | 1.00 | 31.29 | N |
| ATOM | 388 | CA | TYR | A | 24 | 12.436 | -36.506 | 29.058 | 1.00 | 32.01 | C |
| ATOM | 390 | CB | TYR | A | 24 | 11.680 | -35.998 | 27.823 | 1.00 | 32.57 | C |
| ATOM | 393 | CG | TYR | A | 24 | 12.421 | -34.885 | 27.141 | 1.00 | 34.05 | C |
| ATOM | 394 | CD1 | TYR | A | 24 | 13.112 | -35.091 | 25.952 | 1.00 | 35.94 | C |
| ATOM | 396 | CE1 | TYR | A | 24 | 13.811 | -34.047 | 25.349 | 1.00 | 38.48 | C |
| ATOM | 398 | CZ | TYR | A | 24 | 13.823 | -32.794 | 25.964 | 1.00 | 39.58 | C |
| ATOM | 399 | OH | TYR | A | 24 | 14.491 | -31.727 | 25.425 | 1.00 | 43.50 | O |
| ATOM | 401 | CE2 | TYR | A | 24 | 13.159 | -32.586 | 27.145 | 1.00 | 38.47 | C |
| ATOM | 403 | CD2 | TYR | A | 24 | 12.469 | -33.625 | 27.726 | 1.00 | 36.71 | C |
| ATOM | 405 | C | TYR | A | 24 | 11.485 | -36.887 | 30.161 | 1.00 | 32.07 | C |
| ATOM | 406 | O | TYR | A | 24 | 10.630 | -36.093 | 30.535 | 1.00 | 32.09 | O |

FIG.16-6

| | | | | | | | | | | | |
|---|---|---|---|---|---|---|---|---|---|---|---|
| ATOM | 408 | N | GLY | A | 25 | 11.645 | -38.096 | 30.692 | 1.00 | 32.53 | N |
| ATOM | 409 | CA | GLY | A | 25 | 10.838 | -38.559 | 31.818 | 1.00 | 32.86 | C |
| ATOM | 412 | C | GLY | A | 25 | 9.575 | -39.324 | 31.463 | 1.00 | 33.29 | C |
| ATOM | 413 | O | GLY | A | 25 | 8.864 | -39.762 | 32.355 | 1.00 | 33.72 | O |
| ATOM | 415 | N | GLU | A | 26 | 9.325 | -39.532 | 30.174 | 1.00 | 33.69 | N |
| ATOM | 416 | CA | GLU | A | 26 | 8.064 | -40.092 | 29.697 | 1.00 | 34.32 | C |
| ATOM | 418 | CB | GLU | A | 26 | 7.618 | -39.372 | 28.423 | 1.00 | 34.42 | C |
| ATOM | 421 | CG | GLU | A | 26 | 7.417 | -37.866 | 28.630 | 1.00 | 34.93 | C |
| ATOM | 424 | CD | GLU | A | 26 | 7.632 | -37.040 | 27.379 | 1.00 | 36.22 | C |
| ATOM | 425 | OE1 | GLU | A | 26 | 7.048 | -35.939 | 27.323 | 1.00 | 39.27 | O |
| ATOM | 426 | OE2 | GLU | A | 26 | 8.369 | -37.460 | 26.454 | 1.00 | 36.41 | O |
| ATOM | 427 | C | GLU | A | 26 | 8.172 | -41.576 | 29.425 | 1.00 | 34.69 | C |
| ATOM | 428 | O | GLU | A | 26 | 9.215 | -42.067 | 29.009 | 1.00 | 35.07 | O |
| ATOM | 430 | N | ASP | A | 27 | 7.076 | -42.285 | 29.655 | 1.00 | 35.11 | N |
| ATOM | 431 | CA | ASP | A | 27 | 7.045 | -43.723 | 29.502 | 1.00 | 35.48 | C |
| ATOM | 433 | CB | ASP | A | 27 | 6.205 | -44.352 | 30.610 | 1.00 | 35.66 | C |
| ATOM | 436 | CG | ASP | A | 27 | 6.389 | -45.850 | 30.709 | 1.00 | 36.28 | C |
| ATOM | 437 | OD1 | ASP | A | 27 | 6.685 | -46.510 | 29.686 | 1.00 | 36.77 | O |
| ATOM | 438 | OD2 | ASP | A | 27 | 6.221 | -46.368 | 31.829 | 1.00 | 38.44 | O |
| ATOM | 439 | C | ASP | A | 27 | 6.445 | -44.053 | 28.153 | 1.00 | 35.74 | C |
| ATOM | 440 | O | ASP | A | 27 | 5.270 | -43.758 | 27.895 | 1.00 | 35.78 | O |
| ATOM | 442 | N | PRO | A | 28 | 7.240 | -44.675 | 27.277 | 1.00 | 36.14 | N |
| ATOM | 443 | CA | PRO | A | 28 | 6.687 | -45.024 | 25.970 | 1.00 | 36.38 | C |
| ATOM | 445 | CB | PRO | A | 28 | 7.853 | -45.751 | 25.265 | 1.00 | 36.24 | C |
| ATOM | 448 | CG | PRO | A | 28 | 8.907 | -45.959 | 26.290 | 1.00 | 36.08 | C |
| ATOM | 451 | CD | PRO | A | 28 | 8.680 | -44.975 | 27.379 | 1.00 | 36.08 | C |
| ATOM | 454 | C | PRO | A | 28 | 5.408 | -45.905 | 26.023 | 1.00 | 36.68 | C |
| ATOM | 455 | O | PRO | A | 28 | 4.645 | -45.909 | 25.052 | 1.00 | 36.76 | O |
| ATOM | 456 | N | LYS | A | 29 | 5.194 | -46.625 | 27.130 | 1.00 | 36.79 | N |
| ATOM | 457 | CA | LYS | A | 29 | 4.002 | -47.472 | 27.333 | 1.00 | 37.06 | C |
| ATOM | 459 | CB | LYS | A | 29 | 4.247 | -48.522 | 28.427 | 1.00 | 37.41 | C |
| ATOM | 462 | CG | LYS | A | 29 | 5.280 | -49.560 | 28.071 | 1.00 | 39.12 | C |
| ATOM | 465 | CD | LYS | A | 29 | 5.366 | -50.612 | 29.151 | 1.00 | 42.04 | C |
| ATOM | 468 | CE | LYS | A | 29 | 6.753 | -51.290 | 29.199 | 1.00 | 43.90 | C |
| ATOM | 471 | NZ | LYS | A | 29 | 6.861 | -52.266 | 30.348 | 1.00 | 45.30 | N |
| ATOM | 475 | C | LYS | A | 29 | 2.737 | -46.732 | 27.722 | 1.00 | 36.64 | C |
| ATOM | 476 | O | LYS | A | 29 | 1.658 | -47.291 | 27.606 | 1.00 | 37.00 | O |
| ATOM | 478 | N | ILE | A | 30 | 2.852 | -45.506 | 28.222 | 1.00 | 36.45 | N |
| ATOM | 479 | CA | ILE | A | 30 | 1.667 | -44.721 | 28.562 | 1.00 | 36.02 | C |
| ATOM | 481 | CB | ILE | A | 30 | 1.803 | -44.030 | 29.927 | 1.00 | 36.25 | C |
| ATOM | 483 | CG1 | ILE | A | 30 | 2.287 | -45.018 | 31.003 | 1.00 | 36.11 | C |
| ATOM | 486 | CD1 | ILE | A | 30 | 1.499 | -46.310 | 31.080 | 1.00 | 36.55 | C |
| ATOM | 490 | CG2 | ILE | A | 30 | 0.473 | -43.339 | 30.317 | 1.00 | 35.94 | C |
| ATOM | 494 | C | ILE | A | 30 | 1.403 | -43.650 | 27.522 | 1.00 | 35.72 | C |
| ATOM | 495 | O | ILE | A | 30 | 0.269 | -43.449 | 27.115 | 1.00 | 36.26 | O |
| ATOM | 497 | N | GLU | A | 31 | 2.441 | -42.940 | 27.109 | 1.00 | 35.26 | N |
| ATOM | 498 | CA | GLU | A | 31 | 2.273 | -41.871 | 26.138 | 1.00 | 34.97 | C |
| ATOM | 500 | CB | GLU | A | 31 | 3.210 | -40.720 | 26.446 | 1.00 | 35.31 | C |
| ATOM | 503 | CG | GLU | A | 31 | 2.981 | -40.100 | 27.798 | 1.00 | 36.95 | C |
| ATOM | 506 | CD | GLU | A | 31 | 2.764 | -38.617 | 27.680 | 1.00 | 40.75 | C |
| ATOM | 507 | OE1 | GLU | A | 31 | 1.617 | -38.238 | 27.320 | 1.00 | 43.96 | O |
| ATOM | 508 | OE2 | GLU | A | 31 | 3.730 | -37.840 | 27.917 | 1.00 | 41.59 | O |
| ATOM | 509 | C | GLU | A | 31 | 2.531 | -42.417 | 24.746 | 1.00 | 34.31 | C |
| ATOM | 510 | O | GLU | A | 31 | 3.514 | -42.068 | 24.080 | 1.00 | 33.82 | O |
| ATOM | 512 | N | THR | A | 32 | 1.605 | -43.266 | 24.312 | 1.00 | 33.64 | N |
| ATOM | 513 | CA | THR | A | 32 | 1.749 | -44.027 | 23.082 | 1.00 | 32.92 | C |
| ATOM | 515 | CB | THR | A | 32 | 0.766 | -45.203 | 23.074 | 1.00 | 32.98 | C |
| ATOM | 517 | OG1 | THR | A | 32 | -0.558 | -44.717 | 23.315 | 1.00 | 32.87 | O |
| ATOM | 519 | CG2 | THR | A | 32 | 1.138 | -46.200 | 24.170 | 1.00 | 32.57 | C |
| ATOM | 523 | C | THR | A | 32 | 1.564 | -43.165 | 21.835 | 1.00 | 32.43 | C |
| ATOM | 524 | O | THR | A | 32 | 2.176 | -43.427 | 20.800 | 1.00 | 31.95 | O |
| ATOM | 526 | N | ASN | A | 33 | 0.740 | -42.129 | 21.917 | 1.00 | 32.03 | N |
| ATOM | 527 | CA | ASN | A | 33 | 0.617 | -41.239 | 20.772 | 1.00 | 32.16 | C |

FIG.16-7

| | | | | | | | | | | | |
|---|---|---|---|---|---|---|---|---|---|---|---|
| ATOM | 529 | CB | ASN | A | 33 | -0.532 | -40.248 | 20.949 | 1.00 | 32.51 | C |
| ATOM | 532 | CG | ASN | A | 33 | -1.905 | -40.919 | 20.849 | 1.00 | 34.05 | C |
| ATOM | 533 | OD1 | ASN | A | 33 | -2.073 | -41.913 | 20.141 | 1.00 | 36.33 | O |
| ATOM | 534 | ND2 | ASN | A | 33 | -2.886 | -40.378 | 21.563 | 1.00 | 34.87 | N |
| ATOM | 537 | C | ASN | A | 33 | 1.939 | -40.523 | 20.516 | 1.00 | 31.51 | C |
| ATOM | 538 | O | ASN | A | 33 | 2.489 | -40.610 | 19.414 | 1.00 | 32.10 | O |
| ATOM | 540 | N | LYS | A | 34 | 2.454 | -39.849 | 21.546 | 1.00 | 30.49 | N |
| ATOM | 541 | CA | LYS | A | 34 | 3.769 | -39.209 | 21.499 | 1.00 | 29.32 | C |
| ATOM | 543 | CB | LYS | A | 34 | 4.112 | -38.635 | 22.870 | 1.00 | 29.26 | C |
| ATOM | 546 | CG | LYS | A | 34 | 5.512 | -38.037 | 22.957 | 1.00 | 30.64 | C |
| ATOM | 549 | CD | LYS | A | 34 | 5.696 | -37.126 | 24.195 | 1.00 | 31.23 | C |
| ATOM | 552 | CE | LYS | A | 34 | 5.585 | -35.640 | 23.859 | 1.00 | 32.05 | C |
| ATOM | 555 | NZ | LYS | A | 34 | 6.238 | -34.764 | 24.901 | 1.00 | 33.88 | N |
| ATOM | 559 | C | LYS | A | 34 | 4.863 | -40.180 | 21.021 | 1.00 | 28.15 | C |
| ATOM | 560 | O | LYS | A | 34 | 5.655 | -39.838 | 20.148 | 1.00 | 27.91 | O |
| ATOM | 562 | N | PHE | A | 35 | 4.879 | -41.395 | 21.568 | 1.00 | 26.76 | N |
| ATOM | 563 | CA | PHE | A | 35 | 5.828 | -42.434 | 21.143 | 1.00 | 26.05 | C |
| ATOM | 565 | CB | PHE | A | 35 | 5.447 | -43.793 | 21.778 | 1.00 | 25.73 | C |
| ATOM | 568 | CG | PHE | A | 35 | 6.429 | -44.926 | 21.528 | 1.00 | 24.67 | C |
| ATOM | 569 | CD1 | PHE | A | 35 | 6.014 | -46.240 | 21.708 | 1.00 | 24.64 | C |
| ATOM | 571 | CE1 | PHE | A | 35 | 6.880 | -47.318 | 21.516 | 1.00 | 24.84 | C |
| ATOM | 573 | CZ | PHE | A | 35 | 8.200 | -47.096 | 21.127 | 1.00 | 25.53 | C |
| ATOM | 575 | CE2 | PHE | A | 35 | 8.645 | -45.788 | 20.949 | 1.00 | 25.67 | C |
| ATOM | 577 | CD2 | PHE | A | 35 | 7.753 | -44.703 | 21.156 | 1.00 | 25.59 | C |
| ATOM | 579 | C | PHE | A | 35 | 5.872 | -42.524 | 19.627 | 1.00 | 25.88 | C |
| ATOM | 580 | O | PHE | A | 35 | 6.952 | -42.475 | 19.034 | 1.00 | 26.20 | O |
| ATOM | 582 | N | ALA | A | 36 | 4.685 | -42.630 | 19.021 | 1.00 | 25.55 | N |
| ATOM | 583 | CA | ALA | A | 36 | 4.513 | -42.758 | 17.578 | 1.00 | 25.05 | C |
| ATOM | 585 | CB | ALA | A | 36 | 3.101 | -43.221 | 17.272 | 1.00 | 25.33 | C |
| ATOM | 589 | C | ALA | A | 36 | 4.782 | -41.450 | 16.848 | 1.00 | 24.97 | C |
| ATOM | 590 | O | ALA | A | 36 | 5.292 | -41.448 | 15.720 | 1.00 | 24.71 | O |
| ATOM | 592 | N | ALA | A | 37 | 4.409 | -40.330 | 17.460 | 1.00 | 24.56 | N |
| ATOM | 593 | CA | ALA | A | 37 | 4.827 | -39.039 | 16.916 | 1.00 | 24.55 | C |
| ATOM | 595 | CB | ALA | A | 37 | 4.384 | -37.869 | 17.824 | 1.00 | 24.00 | C |
| ATOM | 599 | C | ALA | A | 37 | 6.356 | -39.043 | 16.751 | 1.00 | 24.28 | C |
| ATOM | 600 | O | ALA | A | 37 | 6.866 | -38.683 | 15.703 | 1.00 | 24.04 | O |
| ATOM | 602 | N | ILE | A | 38 | 7.068 | -39.492 | 17.784 | 1.00 | 24.05 | N |
| ATOM | 603 | CA | ILE | A | 38 | 8.517 | -39.364 | 17.814 | 1.00 | 24.02 | C |
| ATOM | 605 | CB | ILE | A | 38 | 9.095 | -39.711 | 19.211 | 1.00 | 24.10 | C |
| ATOM | 607 | CG1 | ILE | A | 38 | 8.771 | -38.580 | 20.198 | 1.00 | 22.62 | C |
| ATOM | 610 | CD1 | ILE | A | 38 | 8.897 | -38.962 | 21.658 | 1.00 | 20.65 | C |
| ATOM | 614 | CG2 | ILE | A | 38 | 10.620 | -39.909 | 19.133 | 1.00 | 24.14 | C |
| ATOM | 618 | C | ILE | A | 38 | 9.146 | -40.221 | 16.733 | 1.00 | 24.02 | C |
| ATOM | 619 | O | ILE | A | 38 | 10.007 | -39.750 | 15.998 | 1.00 | 23.57 | O |
| ATOM | 621 | N | CYS | A | 39 | 8.695 | -41.469 | 16.631 | 1.00 | 24.20 | N |
| ATOM | 622 | CA | CYS | A | 39 | 9.126 | -42.363 | 15.551 | 1.00 | 24.21 | C |
| ATOM | 624 | CB | CYS | A | 39 | 8.363 | -43.683 | 15.603 | 1.00 | 24.23 | C |
| ATOM | 627 | SG | CYS | A | 39 | 8.741 | -44.707 | 17.021 | 1.00 | 23.25 | S |
| ATOM | 629 | C | CYS | A | 39 | 8.925 | -41.755 | 14.167 | 1.00 | 24.60 | C |
| ATOM | 630 | O | CYS | A | 39 | 9.740 | -41.993 | 13.265 | 1.00 | 25.04 | O |
| ATOM | 632 | N | THR | A | 40 | 7.842 | -40.995 | 13.985 | 1.00 | 24.47 | N |
| ATOM | 633 | CA | THR | A | 40 | 7.545 | -40.399 | 12.675 | 1.00 | 24.55 | C |
| ATOM | 635 | CB | THR | A | 40 | 6.078 | -39.851 | 12.581 | 1.00 | 24.67 | C |
| ATOM | 637 | OG1 | THR | A | 40 | 5.141 | -40.934 | 12.550 | 1.00 | 24.71 | O |
| ATOM | 639 | CG2 | THR | A | 40 | 5.882 | -39.021 | 11.335 | 1.00 | 24.61 | C |
| ATOM | 643 | C | THR | A | 40 | 8.525 | -39.278 | 12.340 | 1.00 | 24.61 | C |
| ATOM | 644 | O | THR | A | 40 | 8.996 | -39.191 | 11.203 | 1.00 | 24.74 | O |
| ATOM | 646 | N | HIS | A | 41 | 8.800 | -38.407 | 13.310 | 1.00 | 24.80 | N |
| ATOM | 647 | CA | HIS | A | 41 | 9.762 | -37.318 | 13.123 | 1.00 | 25.34 | C |
| ATOM | 649 | CB | HIS | A | 41 | 9.794 | -36.393 | 14.350 | 1.00 | 25.49 | C |
| ATOM | 652 | CG | HIS | A | 41 | 10.878 | -35.346 | 14.317 | 1.00 | 27.04 | C |
| ATOM | 653 | ND1 | HIS | A | 41 | 12.215 | -35.646 | 14.493 | 1.00 | 28.09 | N |
| ATOM | 655 | CE1 | HIS | A | 41 | 12.923 | -34.529 | 14.434 | 1.00 | 27.73 | C |

FIG.16-8

| | | | | | | | | | | | |
|---|---|---|---|---|---|---|---|---|---|---|---|
| ATOM | 657 | NE2 | HIS | A | 41 | 12.095 | -33.515 | 14.262 | 1.00 | 26.35 | N |
| ATOM | 659 | CD2 | HIS | A | 41 | 10.811 | -33.996 | 14.191 | 1.00 | 26.13 | C |
| ATOM | 661 | C | HIS | A | 41 | 11.129 | -37.940 | 12.859 | 1.00 | 25.49 | C |
| ATOM | 662 | O | HIS | A | 41 | 11.822 | -37.551 | 11.933 | 1.00 | 25.38 | O |
| ATOM | 664 | N | LEU | A | 42 | 11.492 | -38.928 | 13.666 | 1.00 | 25.95 | N |
| ATOM | 665 | CA | LEU | A | 42 | 12.727 | -39.667 | 13.460 | 1.00 | 26.48 | C |
| ATOM | 667 | CB | LEU | A | 42 | 12.858 | -40.826 | 14.465 | 1.00 | 26.51 | C |
| ATOM | 670 | CG | LEU | A | 42 | 13.836 | -40.745 | 15.658 | 1.00 | 26.43 | C |
| ATOM | 672 | CD1 | LEU | A | 42 | 14.571 | -39.408 | 15.828 | 1.00 | 25.29 | C |
| ATOM | 676 | CD2 | LEU | A | 42 | 13.123 | -41.119 | 16.939 | 1.00 | 26.61 | C |
| ATOM | 680 | C | LEU | A | 42 | 12.819 | -40.187 | 12.034 | 1.00 | 27.21 | C |
| ATOM | 681 | O | LEU | A | 42 | 13.809 | -39.915 | 11.350 | 1.00 | 27.76 | O |
| ATOM | 683 | N | GLU | A | 43 | 11.804 | -40.917 | 11.565 | 1.00 | 27.88 | N |
| ATOM | 684 | CA | GLU | A | 43 | 11.883 | -41.507 | 10.210 | 1.00 | 28.30 | C |
| ATOM | 686 | CB | GLU | A | 43 | 10.735 | -42.478 | 9.913 | 1.00 | 28.63 | C |
| ATOM | 689 | CG | GLU | A | 43 | 10.925 | -43.232 | 8.584 | 1.00 | 30.06 | C |
| ATOM | 692 | CD | GLU | A | 43 | 10.083 | -44.492 | 8.456 | 1.00 | 33.14 | C |
| ATOM | 693 | OE1 | GLU | A | 43 | 10.294 | -45.275 | 7.495 | 1.00 | 35.19 | O |
| ATOM | 694 | OE2 | GLU | A | 43 | 9.197 | -44.709 | 9.307 | 1.00 | 35.59 | O |
| ATOM | 695 | C | GLU | A | 43 | 11.940 | -40.461 | 9.103 | 1.00 | 28.09 | C |
| ATOM | 696 | O | GLU | A | 43 | 12.699 | -40.628 | 8.149 | 1.00 | 28.64 | O |
| ATOM | 698 | N | VAL | A | 44 | 11.148 | -39.396 | 9.202 | 1.00 | 27.56 | N |
| ATOM | 699 | CA | VAL | A | 44 | 11.221 | -38.348 | 8.188 | 1.00 | 27.48 | C |
| ATOM | 701 | CB | VAL | A | 44 | 10.156 | -37.241 | 8.381 | 1.00 | 27.51 | C |
| ATOM | 703 | CG1 | VAL | A | 44 | 10.482 | -36.018 | 7.545 | 1.00 | 26.93 | C |
| ATOM | 707 | CG2 | VAL | A | 44 | 8.798 | -37.763 | 7.983 | 1.00 | 28.07 | C |
| ATOM | 711 | C | VAL | A | 44 | 12.620 | -37.750 | 8.130 | 1.00 | 27.30 | C |
| ATOM | 712 | O | VAL | A | 44 | 13.127 | -37.529 | 7.062 | 1.00 | 27.85 | O |
| ATOM | 714 | N | CYS | A | 45 | 13.248 | -37.501 | 9.270 | 1.00 | 27.56 | N |
| ATOM | 715 | CA | CYS | A | 45 | 14.614 | -36.979 | 9.287 | 1.00 | 27.71 | C |
| ATOM | 717 | CB | CYS | A | 45 | 15.094 | -36.735 | 10.715 | 1.00 | 27.72 | C |
| ATOM | 720 | SG | CYS | A | 45 | 14.293 | -35.368 | 11.552 | 1.00 | 27.67 | S |
| ATOM | 722 | C | CYS | A | 45 | 15.595 | -37.897 | 8.575 | 1.00 | 28.00 | C |
| ATOM | 723 | O | CYS | A | 45 | 16.425 | -37.432 | 7.808 | 1.00 | 27.62 | O |
| ATOM | 725 | N | PHE | A | 46 | 15.498 | -39.198 | 8.819 | 1.00 | 28.77 | N |
| ATOM | 726 | CA | PHE | A | 46 | 16.415 | -40.127 | 8.179 | 1.00 | 29.80 | C |
| ATOM | 728 | CB | PHE | A | 46 | 16.412 | -41.496 | 8.852 | 1.00 | 29.70 | C |
| ATOM | 731 | CG | PHE | A | 46 | 16.831 | -41.489 | 10.309 | 1.00 | 30.79 | C |
| ATOM | 732 | CD1 | PHE | A | 46 | 17.366 | -40.365 | 10.922 | 1.00 | 32.94 | C |
| ATOM | 734 | CE1 | PHE | A | 46 | 17.739 | -40.398 | 12.267 | 1.00 | 33.58 | C |
| ATOM | 736 | CZ | PHE | A | 46 | 17.602 | -41.562 | 12.991 | 1.00 | 33.59 | C |
| ATOM | 738 | CE2 | PHE | A | 46 | 17.075 | -42.677 | 12.392 | 1.00 | 33.18 | C |
| ATOM | 740 | CD2 | PHE | A | 46 | 16.703 | -42.644 | 11.066 | 1.00 | 32.37 | C |
| ATOM | 742 | C | PHE | A | 46 | 16.108 | -40.283 | 6.696 | 1.00 | 30.78 | C |
| ATOM | 743 | O | PHE | A | 46 | 17.011 | -40.524 | 5.900 | 1.00 | 31.29 | O |
| ATOM | 745 | N | MET | A | 47 | 14.847 | -40.156 | 6.307 | 1.00 | 31.99 | N |
| ATOM | 746 | CA | MET | A | 47 | 14.514 | -40.254 | 4.889 | 1.00 | 33.04 | C |
| ATOM | 748 | CB | MET | A | 47 | 13.002 | -40.321 | 4.667 | 1.00 | 33.38 | C |
| ATOM | 751 | CG | MET | A | 47 | 12.404 | -41.707 | 4.804 | 1.00 | 34.59 | C |
| ATOM | 754 | SD | MET | A | 47 | 10.606 | -41.610 | 4.589 | 1.00 | 38.97 | S |
| ATOM | 755 | CE | MET | A | 47 | 10.524 | -41.399 | 2.805 | 1.00 | 37.18 | C |
| ATOM | 759 | C | MET | A | 47 | 15.079 | -39.044 | 4.177 | 1.00 | 33.39 | C |
| ATOM | 760 | O | MET | A | 47 | 15.726 | -39.168 | 3.144 | 1.00 | 33.49 | O |
| ATOM | 762 | N | TYR | A | 48 | 14.810 | -37.877 | 4.754 | 1.00 | 33.98 | N |
| ATOM | 763 | CA | TYR | A | 48 | 15.295 | -36.599 | 4.251 | 1.00 | 34.87 | C |
| ATOM | 765 | CB | TYR | A | 48 | 14.890 | -35.497 | 5.234 | 1.00 | 34.73 | C |
| ATOM | 768 | CG | TYR | A | 48 | 14.804 | -34.073 | 4.699 | 1.00 | 34.60 | C |
| ATOM | 769 | CD1 | TYR | A | 48 | 13.603 | -33.363 | 4.742 | 1.00 | 34.57 | C |
| ATOM | 771 | CE1 | TYR | A | 48 | 13.528 | -32.057 | 4.295 | 1.00 | 34.17 | C |
| ATOM | 773 | CZ | TYR | A | 48 | 14.673 | -31.443 | 3.804 | 1.00 | 34.27 | C |
| ATOM | 774 | OH | TYR | A | 48 | 14.635 | -30.137 | 3.349 | 1.00 | 34.35 | O |
| ATOM | 776 | CE2 | TYR | A | 48 | 15.863 | -32.121 | 3.773 | 1.00 | 32.97 | C |
| ATOM | 778 | CD2 | TYR | A | 48 | 15.929 | -33.415 | 4.224 | 1.00 | 34.11 | C |

FIG.16-9

| | | | | | | | | | | | |
|---|---|---|---|---|---|---|---|---|---|---|---|
| ATOM | 780 | C | TYR | A | 48 | 16.817 | -36.658 | 4.081 | 1.00 | 35.92 | C |
| ATOM | 781 | O | TYR | A | 48 | 17.354 | -36.181 | 3.085 | 1.00 | 35.93 | O |
| ATOM | 783 | N | SER | A | 49 | 17.492 | -37.266 | 5.059 | 1.00 | 37.24 | N |
| ATOM | 784 | CA | SER | A | 49 | 18.933 | -37.492 | 5.011 | 1.00 | 38.34 | C |
| ATOM | 786 | CB | SER | A | 49 | 19.410 | -38.209 | 6.284 | 1.00 | 38.66 | C |
| ATOM | 789 | OG | SER | A | 49 | 20.564 | -39.016 | 6.046 | 1.00 | 38.81 | O |
| ATOM | 791 | C | SER | A | 49 | 19.343 | -38.315 | 3.804 | 1.00 | 39.36 | C |
| ATOM | 792 | O | SER | A | 49 | 20.182 | -37.871 | 3.015 | 1.00 | 39.83 | O |
| ATOM | 794 | N | ASP | A | 50 | 18.743 | -39.500 | 3.663 | 1.00 | 40.23 | N |
| ATOM | 795 | CA | ASP | A | 50 | 19.183 | -40.483 | 2.665 | 1.00 | 41.03 | C |
| ATOM | 797 | CB | ASP | A | 50 | 18.439 | -41.811 | 2.825 | 1.00 | 41.26 | C |
| ATOM | 800 | CG | ASP | A | 50 | 19.245 | -42.842 | 3.613 | 1.00 | 42.74 | C |
| ATOM | 801 | OD1 | ASP | A | 50 | 20.087 | -43.543 | 2.994 | 1.00 | 44.74 | O |
| ATOM | 802 | OD2 | ASP | A | 50 | 19.037 | -42.959 | 4.845 | 1.00 | 44.45 | O |
| ATOM | 803 | C | ASP | A | 50 | 19.103 | -40.002 | 1.214 | 1.00 | 41.46 | C |
| ATOM | 804 | O | ASP | A | 50 | 19.787 | -40.555 | 0.352 | 1.00 | 41.38 | O |
| ATOM | 806 | N | PHE | A | 51 | 18.282 | -38.987 | 0.940 | 1.00 | 41.96 | N |
| ATOM | 807 | CA | PHE | A | 51 | 18.325 | -38.316 | -0.363 | 1.00 | 42.54 | C |
| ATOM | 809 | CB | PHE | A | 51 | 17.059 | -37.472 | -0.605 | 1.00 | 42.51 | C |
| ATOM | 812 | CG | PHE | A | 51 | 15.766 | -38.256 | -0.491 | 1.00 | 41.89 | C |
| ATOM | 813 | CD1 | PHE | A | 51 | 14.701 | -37.761 | 0.261 | 1.00 | 41.74 | C |
| ATOM | 815 | CE1 | PHE | A | 51 | 13.506 | -38.478 | 0.376 | 1.00 | 41.45 | C |
| ATOM | 817 | CZ | PHE | A | 51 | 13.370 | -39.715 | -0.256 | 1.00 | 41.44 | C |
| ATOM | 819 | CE2 | PHE | A | 51 | 14.427 | -40.226 | -0.999 | 1.00 | 41.90 | C |
| ATOM | 821 | CD2 | PHE | A | 51 | 15.621 | -39.495 | -1.114 | 1.00 | 41.38 | C |
| ATOM | 823 | C | PHE | A | 51 | 19.590 | -37.449 | -0.417 | 1.00 | 43.16 | C |
| ATOM | 824 | O | PHE | A | 51 | 19.659 | -36.397 | 0.215 | 1.00 | 43.67 | O |
| ATOM | 826 | N | GLY | A | 52 | 20.598 | -37.914 | -1.151 | 1.00 | 43.59 | N |
| ATOM | 827 | CA | GLY | A | 52 | 21.914 | -37.265 | -1.174 | 1.00 | 43.70 | C |
| ATOM | 830 | C | GLY | A | 52 | 23.017 | -38.301 | -1.175 | 1.00 | 43.78 | C |
| ATOM | 831 | O | GLY | A | 52 | 22.773 | -39.472 | -1.481 | 1.00 | 43.78 | O |
| ATOM | 833 | N | ALA | A | 70 | 24.774 | -33.472 | -7.196 | 1.00 | 61.12 | N |
| ATOM | 834 | CA | ALA | A | 70 | 25.654 | -34.263 | -8.043 | 1.00 | 61.17 | C |
| ATOM | 836 | CB | ALA | A | 70 | 25.413 | -33.925 | -9.517 | 1.00 | 61.15 | C |
| ATOM | 840 | C | ALA | A | 70 | 27.133 | -34.073 | -7.668 | 1.00 | 61.08 | C |
| ATOM | 841 | O | ALA | A | 70 | 27.929 | -35.001 | -7.808 | 1.00 | 61.30 | O |
| ATOM | 843 | N | LEU | A | 71 | 27.497 | -32.883 | -7.185 | 1.00 | 60.92 | N |
| ATOM | 844 | CA | LEU | A | 71 | 28.890 | -32.597 | -6.793 | 1.00 | 60.78 | C |
| ATOM | 846 | CB | LEU | A | 71 | 29.097 | -31.087 | -6.586 | 1.00 | 60.80 | C |
| ATOM | 849 | CG | LEU | A | 71 | 30.547 | -30.618 | -6.387 | 1.00 | 61.38 | C |
| ATOM | 851 | CD1 | LEU | A | 71 | 31.433 | -31.044 | -7.561 | 1.00 | 61.28 | C |
| ATOM | 855 | CD2 | LEU | A | 71 | 30.602 | -29.107 | -6.191 | 1.00 | 61.40 | C |
| ATOM | 859 | C | LEU | A | 71 | 29.308 | -33.366 | -5.527 | 1.00 | 60.34 | C |
| ATOM | 860 | O | LEU | A | 71 | 30.232 | -34.188 | -5.563 | 1.00 | 60.62 | O |
| ATOM | 862 | N | LEU | A | 72 | 28.607 | -33.102 | -4.425 | 1.00 | 59.64 | N |
| ATOM | 863 | CA | LEU | A | 72 | 28.912 | -33.695 | -3.115 | 1.00 | 58.90 | C |
| ATOM | 865 | CB | LEU | A | 72 | 28.115 | -32.971 | -2.023 | 1.00 | 58.84 | C |
| ATOM | 868 | CG | LEU | A | 72 | 28.349 | -31.460 | -1.881 | 1.00 | 58.58 | C |
| ATOM | 870 | CD1 | LEU | A | 72 | 27.079 | -30.733 | -1.437 | 1.00 | 57.55 | C |
| ATOM | 874 | CD2 | LEU | A | 72 | 29.518 | -31.186 | -0.930 | 1.00 | 58.09 | C |
| ATOM | 878 | C | LEU | A | 72 | 28.581 | -35.197 | -3.080 | 1.00 | 58.23 | C |
| ATOM | 879 | O | LEU | A | 72 | 27.828 | -35.692 | -3.933 | 1.00 | 58.38 | O |
| ATOM | 881 | N | LYS | A | 73 | 29.141 | -35.910 | -2.096 | 1.00 | 57.05 | N |
| ATOM | 882 | CA | LYS | A | 73 | 28.864 | -37.351 | -1.913 | 1.00 | 55.92 | C |
| ATOM | 884 | CB | LYS | A | 73 | 30.087 | -38.087 | -1.350 | 1.00 | 56.13 | C |
| ATOM | 887 | CG | LYS | A | 73 | 31.279 | -38.109 | -2.332 | 1.00 | 57.08 | C |
| ATOM | 890 | CD | LYS | A | 73 | 32.401 | -39.076 | -1.906 | 1.00 | 58.07 | C |
| ATOM | 893 | CE | LYS | A | 73 | 33.716 | -38.794 | -2.659 | 1.00 | 58.09 | C |
| ATOM | 896 | NZ | LYS | A | 73 | 34.612 | -39.985 | -2.737 | 1.00 | 57.03 | N |
| ATOM | 900 | C | LYS | A | 73 | 27.635 | -37.558 | -1.029 | 1.00 | 54.30 | C |
| ATOM | 901 | O | LYS | A | 73 | 26.687 | -38.236 | -1.431 | 1.00 | 54.49 | O |
| ATOM | 903 | N | HIS | A | 74 | 27.657 | -36.965 | 0.163 | 1.00 | 52.21 | N |
| ATOM | 904 | CA | HIS | A | 74 | 26.484 | -36.901 | 1.036 | 1.00 | 50.51 | C |

FIG.16-10

| | | | | | | | | | | | |
|---|---|---|---|---|---|---|---|---|---|---|---|
| ATOM | 906 | CB | HIS | A | 74 | 26.787 | -37.469 | 2.426 | 1.00 | 50.51 | C |
| ATOM | 909 | CG | HIS | A | 74 | 27.450 | -38.810 | 2.412 | 1.00 | 52.26 | C |
| ATOM | 910 | ND1 | HIS | A | 74 | 26.741 | -39.995 | 2.460 | 1.00 | 54.03 | N |
| ATOM | 912 | CE1 | HIS | A | 74 | 27.587 | -41.011 | 2.446 | 1.00 | 54.64 | C |
| ATOM | 914 | NE2 | HIS | A | 74 | 28.818 | -40.531 | 2.392 | 1.00 | 54.70 | N |
| ATOM | 916 | CD2 | HIS | A | 74 | 28.761 | -39.156 | 2.375 | 1.00 | 53.75 | C |
| ATOM | 918 | C | HIS | A | 74 | 26.107 | -35.437 | 1.173 | 1.00 | 48.59 | C |
| ATOM | 919 | O | HIS | A | 74 | 26.887 | -34.655 | 1.718 | 1.00 | 48.33 | O |
| ATOM | 921 | N | ARG | A | 75 | 24.928 | -35.055 | 0.684 | 1.00 | 46.50 | N |
| ATOM | 922 | CA | ARG | A | 75 | 24.495 | -33.655 | 0.792 | 1.00 | 44.90 | C |
| ATOM | 924 | CB | ARG | A | 75 | 23.347 | -33.327 | -0.168 | 1.00 | 44.90 | C |
| ATOM | 927 | CG | ARG | A | 75 | 22.869 | -31.875 | -0.037 | 1.00 | 44.48 | C |
| ATOM | 930 | CD | ARG | A | 75 | 21.760 | -31.521 | -0.991 | 1.00 | 44.37 | C |
| ATOM | 933 | NE | ARG | A | 75 | 21.202 | -30.227 | -0.627 | 1.00 | 44.87 | N |
| ATOM | 935 | CZ | ARG | A | 75 | 20.268 | -29.579 | -1.319 | 1.00 | 45.23 | C |
| ATOM | 936 | NH1 | ARG | A | 75 | 19.779 | -30.101 | -2.439 | 1.00 | 44.86 | N |
| ATOM | 939 | NH2 | ARG | A | 75 | 19.829 | -28.393 | -0.891 | 1.00 | 44.76 | N |
| ATOM | 942 | C | ARG | A | 75 | 24.081 | -33.283 | 2.215 | 1.00 | 43.31 | C |
| ATOM | 943 | O | ARG | A | 75 | 24.117 | -32.104 | 2.589 | 1.00 | 42.93 | O |
| ATOM | 945 | N | PHE | A | 76 | 23.691 | -34.278 | 3.007 | 1.00 | 41.50 | N |
| ATOM | 946 | CA | PHE | A | 76 | 23.236 | -34.002 | 4.362 | 1.00 | 40.11 | C |
| ATOM | 948 | CB | PHE | A | 76 | 21.762 | -34.350 | 4.493 | 1.00 | 39.96 | C |
| ATOM | 951 | CG | PHE | A | 76 | 20.891 | -33.560 | 3.571 | 1.00 | 39.79 | C |
| ATOM | 952 | CD1 | PHE | A | 76 | 20.608 | -32.224 | 3.841 | 1.00 | 40.41 | C |
| ATOM | 954 | CE1 | PHE | A | 76 | 19.804 | -31.475 | 2.983 | 1.00 | 39.78 | C |
| ATOM | 956 | CZ | PHE | A | 76 | 19.288 | -32.070 | 1.842 | 1.00 | 40.19 | C |
| ATOM | 958 | CE2 | PHE | A | 76 | 19.574 | -33.406 | 1.565 | 1.00 | 39.39 | C |
| ATOM | 960 | CD2 | PHE | A | 76 | 20.375 | -34.135 | 2.424 | 1.00 | 39.30 | C |
| ATOM | 962 | C | PHE | A | 76 | 24.062 | -34.698 | 5.426 | 1.00 | 38.82 | C |
| ATOM | 963 | O | PHE | A | 76 | 24.587 | -35.786 | 5.210 | 1.00 | 38.78 | O |
| ATOM | 965 | N | GLU | A | 77 | 24.209 | -34.033 | 6.565 | 1.00 | 37.43 | N |
| ATOM | 966 | CA | GLU | A | 77 | 24.704 | -34.679 | 7.762 | 1.00 | 36.49 | C |
| ATOM | 968 | CB | GLU | A | 77 | 25.830 | -33.856 | 8.406 | 1.00 | 36.48 | C |
| ATOM | 971 | CG | GLU | A | 77 | 26.439 | -34.455 | 9.679 | 1.00 | 37.14 | C |
| ATOM | 974 | CD | GLU | A | 77 | 26.757 | -35.947 | 9.578 | 1.00 | 39.38 | C |
| ATOM | 975 | OE1 | GLU | A | 77 | 27.526 | -36.348 | 8.677 | 1.00 | 39.72 | O |
| ATOM | 976 | OE2 | GLU | A | 77 | 26.231 | -36.730 | 10.408 | 1.00 | 41.46 | O |
| ATOM | 977 | C | GLU | A | 77 | 23.506 | -34.819 | 8.693 | 1.00 | 35.48 | C |
| ATOM | 978 | O | GLU | A | 77 | 22.754 | -33.856 | 8.880 | 1.00 | 35.25 | O |
| ATOM | 980 | N | ILE | A | 78 | 23.329 | -36.016 | 9.253 | 1.00 | 34.19 | N |
| ATOM | 981 | CA | ILE | A | 78 | 22.249 | -36.286 | 10.197 | 1.00 | 33.34 | C |
| ATOM | 983 | CB | ILE | A | 78 | 21.824 | -37.792 | 10.252 | 1.00 | 33.41 | C |
| ATOM | 985 | CG1 | ILE | A | 78 | 21.965 | -38.479 | 8.894 | 1.00 | 34.00 | C |
| ATOM | 988 | CD1 | ILE | A | 78 | 21.409 | -39.916 | 8.851 | 1.00 | 35.88 | C |
| ATOM | 992 | CG2 | ILE | A | 78 | 20.376 | -37.908 | 10.758 | 1.00 | 33.46 | C |
| ATOM | 996 | C | ILE | A | 78 | 22.702 | -35.884 | 11.597 | 1.00 | 32.35 | C |
| ATOM | 997 | O | ILE | A | 78 | 23.801 | -36.242 | 12.028 | 1.00 | 32.27 | O |
| ATOM | 999 | N | ILE | A | 79 | 21.840 | -35.155 | 12.299 | 1.00 | 31.20 | N |
| ATOM | 1000 | CA | ILE | A | 79 | 22.112 | -34.670 | 13.646 | 1.00 | 30.26 | C |
| ATOM | 1002 | CB | ILE | A | 79 | 22.172 | -33.131 | 13.641 | 1.00 | 30.23 | C |
| ATOM | 1004 | CG1 | ILE | A | 79 | 23.380 | -32.676 | 12.801 | 1.00 | 29.79 | C |
| ATOM | 1007 | CD1 | ILE | A | 79 | 23.128 | -31.486 | 11.982 | 1.00 | 29.52 | C |
| ATOM | 1011 | CG2 | ILE | A | 79 | 22.277 | -32.579 | 15.054 | 1.00 | 29.14 | C |
| ATOM | 1015 | C | ILE | A | 79 | 21.061 | -35.198 | 14.635 | 1.00 | 30.14 | C |
| ATOM | 1016 | O | ILE | A | 79 | 21.383 | -35.563 | 15.778 | 1.00 | 30.11 | O |
| ATOM | 1018 | N | GLU | A | 80 | 19.807 | -35.267 | 14.196 | 1.00 | 29.68 | N |
| ATOM | 1019 | CA | GLU | A | 80 | 18.777 | -35.948 | 14.978 | 1.00 | 29.13 | C |
| ATOM | 1021 | CB | GLU | A | 80 | 17.404 | -35.750 | 14.338 | 1.00 | 28.67 | C |
| ATOM | 1024 | CG | GLU | A | 80 | 16.227 | -36.286 | 15.152 | 1.00 | 27.69 | C |
| ATOM | 1027 | CD | GLU | A | 80 | 16.084 | -35.673 | 16.522 | 1.00 | 24.21 | C |
| ATOM | 1028 | OE1 | GLU | A | 80 | 15.340 | -34.696 | 16.655 | 1.00 | 19.59 | O |
| ATOM | 1029 | OE2 | GLU | A | 80 | 16.716 | -36.180 | 17.465 | 1.00 | 24.81 | O |
| ATOM | 1030 | C | GLU | A | 80 | 19.122 | -37.431 | 15.081 | 1.00 | 28.93 | C |

FIG.16-11

| | | | | | | | | | | | |
|---|---|---|---|---|---|---|---|---|---|---|---|
| ATOM | 1031 | O | GLU | A | 80 | 19.790 | -37.978 | 14.206 | 1.00 | 28.88 | O |
| ATOM | 1033 | N | GLY | A | 81 | 18.702 | -38.071 | 16.165 | 1.00 | 28.61 | N |
| ATOM | 1034 | CA | GLY | A | 81 | 18.942 | -39.506 | 16.328 | 1.00 | 28.77 | C |
| ATOM | 1037 | C | GLY | A | 81 | 20.350 | -39.872 | 16.766 | 1.00 | 28.87 | C |
| ATOM | 1038 | O | GLY | A | 81 | 20.805 | -41.004 | 16.587 | 1.00 | 29.88 | O |
| ATOM | 1040 | N | ARG | A | 82 | 21.055 | -38.918 | 17.351 | 1.00 | 28.47 | N |
| ATOM | 1041 | CA | ARG | A | 82 | 22.362 | -39.182 | 17.897 | 1.00 | 27.66 | C |
| ATOM | 1043 | CB | ARG | A | 82 | 23.391 | -38.304 | 17.208 | 1.00 | 27.67 | C |
| ATOM | 1046 | CG | ARG | A | 82 | 23.679 | -38.639 | 15.772 | 1.00 | 27.21 | C |
| ATOM | 1049 | CD | ARG | A | 82 | 24.752 | -37.707 | 15.303 | 1.00 | 27.78 | C |
| ATOM | 1052 | NE | ARG | A | 82 | 25.171 | -37.915 | 13.923 | 1.00 | 28.81 | N |
| ATOM | 1054 | CZ | ARG | A | 82 | 26.069 | -38.808 | 13.520 | 1.00 | 28.31 | C |
| ATOM | 1055 | NH1 | ARG | A | 82 | 26.654 | -39.633 | 14.388 | 1.00 | 28.57 | N |
| ATOM | 1058 | NH2 | ARG | A | 82 | 26.370 | -38.883 | 12.230 | 1.00 | 27.26 | N |
| ATOM | 1061 | C | ARG | A | 82 | 22.286 | -38.815 | 19.362 | 1.00 | 27.49 | C |
| ATOM | 1062 | O | ARG | A | 82 | 21.506 | -37.927 | 19.728 | 1.00 | 27.56 | O |
| ATOM | 1064 | N | ASP | A | 83 | 23.081 | -39.478 | 20.199 | 1.00 | 27.02 | N |
| ATOM | 1065 | CA | ASP | A | 83 | 23.251 | -39.025 | 21.569 | 1.00 | 27.25 | C |
| ATOM | 1067 | CB | ASP | A | 83 | 24.171 | -39.952 | 22.387 | 1.00 | 27.27 | C |
| ATOM | 1070 | CG | ASP | A | 83 | 25.654 | -39.734 | 22.089 | 1.00 | 30.15 | C |
| ATOM | 1071 | OD1 | ASP | A | 83 | 26.160 | -40.198 | 21.032 | 1.00 | 29.66 | O |
| ATOM | 1072 | OD2 | ASP | A | 83 | 26.326 | -39.101 | 22.944 | 1.00 | 35.18 | O |
| ATOM | 1073 | C | ASP | A | 83 | 23.774 | -37.594 | 21.522 | 1.00 | 26.74 | C |
| ATOM | 1074 | O | ASP | A | 83 | 24.328 | -37.146 | 20.512 | 1.00 | 26.66 | O |
| ATOM | 1076 | N | ARG | A | 84 | 23.566 | -36.860 | 22.602 | 1.00 | 26.74 | N |
| ATOM | 1077 | CA | ARG | A | 84 | 23.844 | -35.429 | 22.599 | 1.00 | 26.67 | C |
| ATOM | 1079 | CB | ARG | A | 84 | 23.255 | -34.777 | 23.826 | 1.00 | 27.25 | C |
| ATOM | 1082 | CG | ARG | A | 84 | 21.765 | -34.602 | 23.719 | 1.00 | 30.70 | C |
| ATOM | 1085 | CD | ARG | A | 84 | 21.118 | -34.753 | 25.075 | 1.00 | 35.33 | C |
| ATOM | 1088 | NE | ARG | A | 84 | 21.055 | -33.482 | 25.773 | 1.00 | 39.75 | N |
| ATOM | 1090 | CZ | ARG | A | 84 | 19.926 | -32.872 | 26.131 | 1.00 | 45.20 | C |
| ATOM | 1091 | NH1 | ARG | A | 84 | 18.735 | -33.430 | 25.862 | 1.00 | 47.41 | N |
| ATOM | 1094 | NH2 | ARG | A | 84 | 19.983 | -31.702 | 26.771 | 1.00 | 45.45 | N |
| ATOM | 1097 | C | ARG | A | 84 | 25.313 | -35.077 | 22.488 | 1.00 | 25.43 | C |
| ATOM | 1098 | O | ARG | A | 84 | 25.639 | -34.085 | 21.851 | 1.00 | 24.47 | O |
| ATOM | 1100 | N | ILE | A | 85 | 26.179 | -35.886 | 23.098 | 1.00 | 24.95 | N |
| ATOM | 1101 | CA | ILE | A | 85 | 27.620 | -35.670 | 23.018 | 1.00 | 24.78 | C |
| ATOM | 1103 | CB | ILE | A | 85 | 28.438 | -36.749 | 23.793 | 1.00 | 24.78 | C |
| ATOM | 1105 | CG1 | ILE | A | 85 | 28.068 | -36.800 | 25.286 | 1.00 | 24.24 | C |
| ATOM | 1108 | CD1 | ILE | A | 85 | 27.601 | -35.517 | 25.840 | 1.00 | 23.47 | C |
| ATOM | 1112 | CG2 | ILE | A | 85 | 29.928 | -36.513 | 23.642 | 1.00 | 24.54 | C |
| ATOM | 1116 | C | ILE | A | 85 | 28.053 | -35.653 | 21.553 | 1.00 | 24.93 | C |
| ATOM | 1117 | O | ILE | A | 85 | 28.682 | -34.702 | 21.099 | 1.00 | 24.65 | O |
| ATOM | 1119 | N | MET | A | 86 | 27.678 | -36.688 | 20.811 | 1.00 | 25.38 | N |
| ATOM | 1120 | CA | MET | A | 86 | 28.030 | -36.785 | 19.387 | 1.00 | 26.03 | C |
| ATOM | 1122 | CB | MET | A | 86 | 27.744 | -38.194 | 18.837 | 1.00 | 26.65 | C |
| ATOM | 1125 | CG | MET | A | 86 | 28.900 | -39.200 | 19.039 | 1.00 | 29.33 | C |
| ATOM | 1128 | SD | MET | A | 86 | 30.372 | -38.922 | 17.989 | 1.00 | 35.60 | S |
| ATOM | 1129 | CE | MET | A | 86 | 29.696 | -38.027 | 16.600 | 1.00 | 33.20 | C |
| ATOM | 1133 | C | MET | A | 86 | 27.320 | -35.753 | 18.524 | 1.00 | 25.32 | C |
| ATOM | 1134 | O | MET | A | 86 | 27.883 | -35.270 | 17.546 | 1.00 | 26.22 | O |
| ATOM | 1136 | N | ALA | A | 87 | 26.078 | -35.438 | 18.850 | 1.00 | 24.52 | N |
| ATOM | 1137 | CA | ALA | A | 87 | 25.333 | -34.462 | 18.074 | 1.00 | 23.76 | C |
| ATOM | 1139 | CB | ALA | A | 87 | 23.909 | -34.284 | 18.641 | 1.00 | 23.37 | C |
| ATOM | 1143 | C | ALA | A | 87 | 26.093 | -33.142 | 18.073 | 1.00 | 23.09 | C |
| ATOM | 1144 | O | ALA | A | 87 | 26.356 | -32.564 | 17.018 | 1.00 | 23.05 | O |
| ATOM | 1146 | N | TRP | A | 88 | 26.466 | -32.678 | 19.255 | 1.00 | 22.72 | N |
| ATOM | 1147 | CA | TRP | A | 88 | 27.188 | -31.422 | 19.361 | 1.00 | 22.83 | C |
| ATOM | 1149 | CB | TRP | A | 88 | 27.214 | -30.939 | 20.792 | 1.00 | 22.74 | C |
| ATOM | 1152 | CG | TRP | A | 88 | 25.943 | -30.321 | 21.220 | 1.00 | 21.88 | C |
| ATOM | 1153 | CD1 | TRP | A | 88 | 25.040 | -30.838 | 22.084 | 1.00 | 21.81 | C |
| ATOM | 1155 | NE1 | TRP | A | 88 | 23.990 | -29.968 | 22.252 | 1.00 | 21.74 | N |
| ATOM | 1157 | CE2 | TRP | A | 88 | 24.203 | -28.866 | 21.472 | 1.00 | 22.00 | C |

FIG.16-12

| | | | | | | | | | | | |
|---|---|---|---|---|---|---|---|---|---|---|---|
| ATOM | 1158 | CD2 | TRP | A | 88 | 25.438 | -29.050 | 20.819 | 1.00 | 22.37 | C |
| ATOM | 1159 | CE3 | TRP | A | 88 | 25.900 | -28.049 | 19.957 | 1.00 | 23.06 | C |
| ATOM | 1161 | CZ3 | TRP | A | 88 | 25.120 | -26.905 | 19.779 | 1.00 | 22.32 | C |
| ATOM | 1163 | CH2 | TRP | A | 88 | 23.898 | -26.747 | 20.457 | 1.00 | 22.11 | C |
| ATOM | 1165 | CZ2 | TRP | A | 88 | 23.422 | -27.713 | 21.300 | 1.00 | 22.43 | C |
| ATOM | 1167 | C | TRP | A | 88 | 28.612 | -31.517 | 18.800 | 1.00 | 23.30 | C |
| ATOM | 1168 | O | TRP | A | 88 | 29.142 | -30.535 | 18.274 | 1.00 | 22.77 | O |
| ATOM | 1170 | N | THR | A | 89 | 29.217 | -32.701 | 18.882 | 1.00 | 23.62 | N |
| ATOM | 1171 | CA | THR | A | 89 | 30.522 | -32.913 | 18.266 | 1.00 | 23.72 | C |
| ATOM | 1173 | CB | THR | A | 89 | 31.094 | -34.322 | 18.532 | 1.00 | 23.67 | C |
| ATOM | 1175 | OG1 | THR | A | 89 | 31.402 | -34.456 | 19.920 | 1.00 | 22.95 | O |
| ATOM | 1177 | CG2 | THR | A | 89 | 32.357 | -34.557 | 17.692 | 1.00 | 22.34 | C |
| ATOM | 1181 | C | THR | A | 89 | 30.398 | -32.713 | 16.779 | 1.00 | 24.28 | C |
| ATOM | 1182 | O | THR | A | 89 | 31.201 | -31.987 | 16.192 | 1.00 | 24.53 | O |
| ATOM | 1184 | N | VAL | A | 90 | 29.396 | -33.350 | 16.172 | 1.00 | 24.74 | N |
| ATOM | 1185 | CA | VAL | A | 90 | 29.158 | -33.191 | 14.734 | 1.00 | 25.32 | C |
| ATOM | 1187 | CB | VAL | A | 90 | 28.055 | -34.146 | 14.209 | 1.00 | 25.51 | C |
| ATOM | 1189 | CG1 | VAL | A | 90 | 27.830 | -33.943 | 12.730 | 1.00 | 24.97 | C |
| ATOM | 1193 | CG2 | VAL | A | 90 | 28.428 | -35.604 | 14.462 | 1.00 | 25.28 | C |
| ATOM | 1197 | C | VAL | A | 90 | 28.803 | -31.731 | 14.406 | 1.00 | 25.79 | C |
| ATOM | 1198 | O | VAL | A | 90 | 29.408 | -31.114 | 13.537 | 1.00 | 25.15 | O |
| ATOM | 1200 | N | VAL | A | 91 | 27.853 | -31.164 | 15.131 | 1.00 | 26.67 | N |
| ATOM | 1201 | CA | VAL | A | 91 | 27.490 | -29.761 | 14.919 | 1.00 | 27.54 | C |
| ATOM | 1203 | CB | VAL | A | 91 | 26.332 | -29.343 | 15.852 | 1.00 | 27.45 | C |
| ATOM | 1205 | CG1 | VAL | A | 91 | 26.090 | -27.856 | 15.796 | 1.00 | 27.80 | C |
| ATOM | 1209 | CG2 | VAL | A | 91 | 25.082 | -30.077 | 15.459 | 1.00 | 27.65 | C |
| ATOM | 1213 | C | VAL | A | 91 | 28.676 | -28.788 | 15.069 | 1.00 | 28.44 | C |
| ATOM | 1214 | O | VAL | A | 91 | 28.792 | -27.852 | 14.293 | 1.00 | 28.27 | O |
| ATOM | 1216 | N | ASN | A | 92 | 29.544 | -29.006 | 16.057 | 1.00 | 29.67 | N |
| ATOM | 1217 | CA | ASN | A | 92 | 30.720 | -28.135 | 16.276 | 1.00 | 30.42 | C |
| ATOM | 1219 | CB | ASN | A | 92 | 31.376 | -28.387 | 17.641 | 1.00 | 30.16 | C |
| ATOM | 1222 | CG | ASN | A | 92 | 30.654 | -27.711 | 18.782 | 1.00 | 29.62 | C |
| ATOM | 1223 | OD1 | ASN | A | 92 | 30.317 | -26.531 | 18.706 | 1.00 | 29.36 | O |
| ATOM | 1224 | ND2 | ASN | A | 92 | 30.434 | -28.453 | 19.868 | 1.00 | 29.77 | N |
| ATOM | 1227 | C | ASN | A | 92 | 31.774 | -28.338 | 15.205 | 1.00 | 31.86 | C |
| ATOM | 1228 | O | ASN | A | 92 | 32.441 | -27.389 | 14.805 | 1.00 | 32.25 | O |
| ATOM | 1230 | N | SER | A | 93 | 31.941 | -29.585 | 14.767 | 1.00 | 33.42 | N |
| ATOM | 1231 | CA | SER | A | 93 | 32.839 | -29.910 | 13.656 | 1.00 | 34.58 | C |
| ATOM | 1233 | CB | SER | A | 93 | 32.772 | -31.417 | 13.354 | 1.00 | 34.62 | C |
| ATOM | 1236 | OG | SER | A | 93 | 33.711 | -31.839 | 12.387 | 1.00 | 34.43 | O |
| ATOM | 1238 | C | SER | A | 93 | 32.444 | -29.080 | 12.428 | 1.00 | 35.88 | C |
| ATOM | 1239 | O | SER | A | 93 | 33.268 | -28.339 | 11.890 | 1.00 | 36.78 | O |
| ATOM | 1241 | N | ILE | A | 94 | 31.177 | -29.194 | 12.016 | 1.00 | 36.99 | N |
| ATOM | 1242 | CA | ILE | A | 94 | 30.605 | -28.432 | 10.896 | 1.00 | 37.62 | C |
| ATOM | 1244 | CB | ILE | A | 94 | 29.074 | -28.692 | 10.772 | 1.00 | 37.60 | C |
| ATOM | 1246 | CG1 | ILE | A | 94 | 28.798 | -30.044 | 10.096 | 1.00 | 38.01 | C |
| ATOM | 1249 | CD1 | ILE | A | 94 | 27.445 | -30.681 | 10.487 | 1.00 | 37.00 | C |
| ATOM | 1253 | CG2 | ILE | A | 94 | 28.379 | -27.570 | 9.998 | 1.00 | 37.52 | C |
| ATOM | 1257 | C | ILE | A | 94 | 30.826 | -26.921 | 11.039 | 1.00 | 38.56 | C |
| ATOM | 1258 | O | ILE | A | 94 | 31.247 | -26.250 | 10.099 | 1.00 | 38.63 | O |
| ATOM | 1260 | N | CYS | A | 95 | 30.529 | -26.384 | 12.214 | 1.00 | 39.56 | N |
| ATOM | 1261 | CA | CYS | A | 95 | 30.689 | -24.957 | 12.447 | 1.00 | 40.38 | C |
| ATOM | 1263 | CB | CYS | A | 95 | 30.092 | -24.571 | 13.790 | 1.00 | 40.24 | C |
| ATOM | 1266 | SG | CYS | A | 95 | 28.303 | -24.673 | 13.828 | 1.00 | 39.52 | S |
| ATOM | 1268 | C | CYS | A | 95 | 32.156 | -24.548 | 12.397 | 1.00 | 41.75 | C |
| ATOM | 1269 | O | CYS | A | 95 | 32.508 | -23.560 | 11.767 | 1.00 | 42.30 | O |
| ATOM | 1271 | N | ASN | A | 96 | 33.016 | -25.320 | 13.048 | 1.00 | 43.14 | N |
| ATOM | 1272 | CA | ASN | A | 96 | 34.429 | -24.979 | 13.111 | 1.00 | 44.09 | C |
| ATOM | 1274 | CB | ASN | A | 96 | 35.157 | -25.860 | 14.145 | 1.00 | 44.46 | C |
| ATOM | 1277 | CG | ASN | A | 96 | 34.629 | -25.659 | 15.596 | 1.00 | 46.19 | C |
| ATOM | 1278 | OD1 | ASN | A | 96 | 33.702 | -24.871 | 15.851 | 1.00 | 48.05 | O |
| ATOM | 1279 | ND2 | ASN | A | 96 | 35.218 | -26.396 | 16.540 | 1.00 | 47.62 | N |
| ATOM | 1282 | C | ASN | A | 96 | 35.130 | -25.059 | 11.751 | 1.00 | 44.38 | C |

FIG.16-13

| | | | | | | | | | | | |
|---|---|---|---|---|---|---|---|---|---|---|---|
| ATOM | 1283 | O | ASN | A | 96 | 36.153 | -24.416 | 11.568 | 1.00 | 44.60 | O |
| ATOM | 1285 | N | THR | A | 97 | 34.585 | -25.828 | 10.806 | 1.00 | 44.78 | N |
| ATOM | 1286 | CA | THR | A | 97 | 35.242 | -26.052 | 9.511 | 1.00 | 45.13 | C |
| ATOM | 1288 | CB | THR | A | 97 | 35.372 | -27.552 | 9.207 | 1.00 | 45.22 | C |
| ATOM | 1290 | OG1 | THR | A | 97 | 34.096 | -28.063 | 8.822 | 1.00 | 45.02 | O |
| ATOM | 1292 | CG2 | THR | A | 97 | 35.900 | -28.321 | 10.414 | 1.00 | 45.09 | C |
| ATOM | 1296 | C | THR | A | 97 | 34.538 | -25.435 | 8.295 | 1.00 | 45.62 | C |
| ATOM | 1297 | O | THR | A | 97 | 35.025 | -25.576 | 7.168 | 1.00 | 46.04 | O |
| ATOM | 1299 | N | THR | A | 98 | 33.380 | -24.812 | 8.510 | 1.00 | 45.85 | N |
| ATOM | 1300 | CA | THR | A | 98 | 32.670 | -24.063 | 7.465 | 1.00 | 45.77 | C |
| ATOM | 1302 | CB | THR | A | 98 | 31.306 | -24.703 | 7.122 | 1.00 | 45.97 | C |
| ATOM | 1304 | OG1 | THR | A | 98 | 30.401 | -24.547 | 8.233 | 1.00 | 45.21 | O |
| ATOM | 1306 | CG2 | THR | A | 98 | 31.459 | -26.185 | 6.750 | 1.00 | 45.92 | C |
| ATOM | 1310 | C | THR | A | 98 | 32.372 | -22.622 | 7.892 | 1.00 | 45.89 | C |
| ATOM | 1311 | O | THR | A | 98 | 31.915 | -21.822 | 7.073 | 1.00 | 46.24 | O |
| ATOM | 1313 | N | GLY | A | 99 | 32.575 | -22.308 | 9.170 | 1.00 | 45.62 | N |
| ATOM | 1314 | CA | GLY | A | 99 | 32.351 | -20.964 | 9.692 | 1.00 | 45.67 | C |
| ATOM | 1317 | C | GLY | A | 99 | 30.921 | -20.499 | 9.918 | 1.00 | 45.69 | C |
| ATOM | 1318 | O | GLY | A | 99 | 30.715 | -19.363 | 10.356 | 1.00 | 45.73 | O |
| ATOM | 1320 | N | VAL | A | 100 | 29.927 | -21.343 | 9.639 | 1.00 | 45.65 | N |
| ATOM | 1321 | CA | VAL | A | 100 | 28.529 | -20.953 | 9.871 | 1.00 | 45.60 | C |
| ATOM | 1323 | CB | VAL | A | 100 | 27.510 | -21.958 | 9.252 | 1.00 | 45.73 | C |
| ATOM | 1325 | CG1 | VAL | A | 100 | 27.853 | -22.242 | 7.780 | 1.00 | 45.96 | C |
| ATOM | 1329 | CG2 | VAL | A | 100 | 27.461 | -23.248 | 10.044 | 1.00 | 45.34 | C |
| ATOM | 1333 | C | VAL | A | 100 | 28.279 | -20.793 | 11.373 | 1.00 | 45.62 | C |
| ATOM | 1334 | O | VAL | A | 100 | 28.953 | -21.416 | 12.192 | 1.00 | 45.43 | O |
| ATOM | 1336 | N | GLU | A | 101 | 27.321 | -19.943 | 11.728 | 1.00 | 45.76 | N |
| ATOM | 1337 | CA | GLU | A | 101 | 27.008 | -19.676 | 13.135 | 1.00 | 45.87 | C |
| ATOM | 1339 | CB | GLU | A | 101 | 26.001 | -18.526 | 13.244 | 1.00 | 45.97 | C |
| ATOM | 1342 | CG | GLU | A | 101 | 25.934 | -17.911 | 14.649 | 1.00 | 47.57 | C |
| ATOM | 1345 | CD | GLU | A | 101 | 24.684 | -17.059 | 14.901 | 1.00 | 49.41 | C |
| ATOM | 1346 | OE1 | GLU | A | 101 | 23.724 | -17.112 | 14.096 | 1.00 | 50.37 | O |
| ATOM | 1347 | OE2 | GLU | A | 101 | 24.661 | -16.345 | 15.930 | 1.00 | 50.00 | O |
| ATOM | 1348 | C | GLU | A | 101 | 26.467 | -20.930 | 13.868 | 1.00 | 45.61 | C |
| ATOM | 1349 | O | GLU | A | 101 | 25.748 | -21.748 | 13.280 | 1.00 | 45.51 | O |
| ATOM | 1351 | N | LYS | A | 102 | 26.818 | -21.049 | 15.150 | 1.00 | 45.19 | N |
| ATOM | 1352 | CA | LYS | A | 102 | 26.495 | -22.207 | 15.974 | 1.00 | 44.90 | C |
| ATOM | 1354 | CB | LYS | A | 102 | 27.503 | -22.327 | 17.119 | 1.00 | 44.92 | C |
| ATOM | 1357 | CG | LYS | A | 102 | 27.167 | -23.380 | 18.177 | 1.00 | 45.81 | C |
| ATOM | 1360 | CD | LYS | A | 102 | 28.370 | -23.672 | 19.077 | 1.00 | 47.07 | C |
| ATOM | 1363 | CE | LYS | A | 102 | 28.056 | -24.760 | 20.101 | 1.00 | 48.07 | C |
| ATOM | 1366 | NZ | LYS | A | 102 | 29.283 | -25.225 | 20.821 | 1.00 | 48.42 | N |
| ATOM | 1370 | C | LYS | A | 102 | 25.078 | -22.093 | 16.535 | 1.00 | 44.59 | C |
| ATOM | 1371 | O | LYS | A | 102 | 24.739 | -21.084 | 17.145 | 1.00 | 44.77 | O |
| ATOM | 1373 | N | PRO | A | 103 | 24.247 | -23.132 | 16.339 | 1.00 | 44.06 | N |
| ATOM | 1374 | CA | PRO | A | 103 | 22.878 | -23.088 | 16.847 | 1.00 | 43.66 | C |
| ATOM | 1376 | CB | PRO | A | 103 | 22.261 | -24.400 | 16.336 | 1.00 | 43.85 | C |
| ATOM | 1379 | CG | PRO | A | 103 | 23.186 | -24.915 | 15.299 | 1.00 | 44.09 | C |
| ATOM | 1382 | CD | PRO | A | 103 | 24.533 | -24.390 | 15.624 | 1.00 | 44.10 | C |
| ATOM | 1385 | C | PRO | A | 103 | 22.832 | -23.066 | 18.367 | 1.00 | 43.12 | C |
| ATOM | 1386 | O | PRO | A | 103 | 23.731 | -23.611 | 19.002 | 1.00 | 42.87 | O |
| ATOM | 1387 | N | LYS | A | 104 | 21.796 | -22.439 | 18.931 | 1.00 | 42.34 | N |
| ATOM | 1388 | CA | LYS | A | 104 | 21.566 | -22.469 | 20.373 | 1.00 | 41.95 | C |
| ATOM | 1390 | CB | LYS | A | 104 | 20.646 | -21.326 | 20.804 | 1.00 | 42.29 | C |
| ATOM | 1393 | CG | LYS | A | 104 | 21.334 | -19.969 | 20.845 | 1.00 | 44.73 | C |
| ATOM | 1396 | CD | LYS | A | 104 | 20.385 | -18.854 | 21.320 | 1.00 | 47.70 | C |
| ATOM | 1399 | CE | LYS | A | 104 | 21.032 | -17.459 | 21.175 | 1.00 | 49.06 | C |
| ATOM | 1402 | NZ | LYS | A | 104 | 20.091 | -16.354 | 21.565 | 1.00 | 49.81 | N |
| ATOM | 1406 | C | LYS | A | 104 | 20.976 | -23.815 | 20.814 | 1.00 | 40.95 | C |
| ATOM | 1407 | O | LYS | A | 104 | 21.213 | -24.265 | 21.932 | 1.00 | 40.78 | O |
| ATOM | 1409 | N | PHE | A | 105 | 20.196 | -24.437 | 19.933 | 1.00 | 39.87 | N |
| ATOM | 1410 | CA | PHE | A | 105 | 19.614 | -25.754 | 20.182 | 1.00 | 39.25 | C |
| ATOM | 1412 | CB | PHE | A | 105 | 18.093 | -25.633 | 20.319 | 1.00 | 39.72 | C |

FIG.16-14

| | | | | | | | | | | | |
|---|---|---|---|---|---|---|---|---|---|---|---|
| ATOM | 1415 | CG | PHE | A | 105 | 17.647 | -24.831 | 21.528 | 1.00 | 41.82 | C |
| ATOM | 1416 | CD1 | PHE | A | 105 | 17.921 | -25.279 | 22.820 | 1.00 | 43.75 | C |
| ATOM | 1418 | CE1 | PHE | A | 105 | 17.513 | -24.545 | 23.940 | 1.00 | 44.10 | C |
| ATOM | 1420 | CZ | PHE | A | 105 | 16.813 | -23.361 | 23.769 | 1.00 | 43.68 | C |
| ATOM | 1422 | CE2 | PHE | A | 105 | 16.523 | -22.908 | 22.485 | 1.00 | 43.88 | C |
| ATOM | 1424 | CD2 | PHE | A | 105 | 16.939 | -23.640 | 21.374 | 1.00 | 43.40 | C |
| ATOM | 1426 | C | PHE | A | 105 | 19.976 | -26.714 | 19.038 | 1.00 | 37.58 | C |
| ATOM | 1427 | O | PHE | A | 105 | 20.211 | -26.271 | 17.916 | 1.00 | 37.07 | O |
| ATOM | 1429 | N | LEU | A | 106 | 20.028 | -28.017 | 19.322 | 1.00 | 35.46 | N |
| ATOM | 1430 | CA | LEU | A | 106 | 20.329 | -28.997 | 18.280 | 1.00 | 34.09 | C |
| ATOM | 1432 | CB | LEU | A | 106 | 20.461 | -30.413 | 18.851 | 1.00 | 34.01 | C |
| ATOM | 1435 | CG | LEU | A | 106 | 21.754 | -30.873 | 19.528 | 1.00 | 33.36 | C |
| ATOM | 1437 | CD1 | LEU | A | 106 | 21.567 | -32.315 | 19.959 | 1.00 | 32.09 | C |
| ATOM | 1441 | CD2 | LEU | A | 106 | 22.967 | -30.742 | 18.619 | 1.00 | 31.50 | C |
| ATOM | 1445 | C | LEU | A | 106 | 19.235 | -29.020 | 17.226 | 1.00 | 32.92 | C |
| ATOM | 1446 | O | LEU | A | 106 | 18.078 | -29.165 | 17.561 | 1.00 | 32.71 | O |
| ATOM | 1448 | N | PRO | A | 107 | 19.598 | -28.895 | 15.944 | 1.00 | 32.17 | N |
| ATOM | 1449 | CA | PRO | A | 107 | 18.626 | -29.063 | 14.885 | 1.00 | 31.74 | C |
| ATOM | 1451 | CB | PRO | A | 107 | 19.138 | -28.097 | 13.816 | 1.00 | 31.71 | C |
| ATOM | 1454 | CG | PRO | A | 107 | 20.610 | -28.086 | 14.005 | 1.00 | 31.66 | C |
| ATOM | 1457 | CD | PRO | A | 107 | 20.924 | -28.587 | 15.381 | 1.00 | 32.17 | C |
| ATOM | 1460 | C | PRO | A | 107 | 18.629 | -30.521 | 14.417 | 1.00 | 31.09 | C |
| ATOM | 1461 | O | PRO | A | 107 | 19.133 | -31.374 | 15.139 | 1.00 | 30.98 | O |
| ATOM | 1462 | N | ASP | A | 108 | 18.078 | -30.803 | 13.237 | 1.00 | 30.62 | N |
| ATOM | 1463 | CA | ASP | A | 108 | 17.933 | -32.179 | 12.749 | 1.00 | 30.37 | C |
| ATOM | 1465 | CB | ASP | A | 108 | 16.505 | -32.388 | 12.239 | 1.00 | 30.40 | C |
| ATOM | 1468 | CG | ASP | A | 108 | 15.449 | -32.136 | 13.322 | 1.00 | 30.54 | C |
| ATOM | 1469 | OD1 | ASP | A | 108 | 15.634 | -32.602 | 14.477 | 1.00 | 27.46 | O |
| ATOM | 1470 | OD2 | ASP | A | 108 | 14.439 | -31.465 | 13.005 | 1.00 | 30.39 | O |
| ATOM | 1471 | C | ASP | A | 108 | 18.934 | -32.569 | 11.656 | 1.00 | 30.46 | C |
| ATOM | 1472 | O | ASP | A | 108 | 19.354 | -33.714 | 11.595 | 1.00 | 30.14 | O |
| ATOM | 1474 | N | LEU | A | 109 | 19.302 | -31.624 | 10.790 | 1.00 | 30.79 | N |
| ATOM | 1475 | CA | LEU | A | 109 | 20.242 | -31.887 | 9.691 | 1.00 | 30.85 | C |
| ATOM | 1477 | CB | LEU | A | 109 | 19.475 | -32.231 | 8.415 | 1.00 | 30.72 | C |
| ATOM | 1480 | CG | LEU | A | 109 | 18.466 | -33.377 | 8.371 | 1.00 | 30.21 | C |
| ATOM | 1482 | CD1 | LEU | A | 109 | 17.591 | -33.139 | 7.173 | 1.00 | 30.04 | C |
| ATOM | 1486 | CD2 | LEU | A | 109 | 19.121 | -34.764 | 8.281 | 1.00 | 29.17 | C |
| ATOM | 1490 | C | LEU | A | 109 | 21.152 | -30.691 | 9.376 | 1.00 | 31.31 | C |
| ATOM | 1491 | O | LEU | A | 109 | 20.917 | -29.577 | 9.818 | 1.00 | 31.04 | O |
| ATOM | 1493 | N | TYR | A | 110 | 22.197 | -30.942 | 8.602 | 1.00 | 32.34 | N |
| ATOM | 1494 | CA | TYR | A | 110 | 22.981 | -29.870 | 7.989 | 1.00 | 33.22 | C |
| ATOM | 1496 | CB | TYR | A | 110 | 24.423 | -29.826 | 8.523 | 1.00 | 33.33 | C |
| ATOM | 1499 | CG | TYR | A | 110 | 25.215 | -28.662 | 7.954 | 1.00 | 33.07 | C |
| ATOM | 1500 | CD1 | TYR | A | 110 | 24.932 | -27.359 | 8.333 | 1.00 | 33.36 | C |
| ATOM | 1502 | CE1 | TYR | A | 110 | 25.643 | -26.278 | 7.809 | 1.00 | 34.08 | C |
| ATOM | 1504 | CZ | TYR | A | 110 | 26.648 | -26.495 | 6.898 | 1.00 | 34.55 | C |
| ATOM | 1505 | OH | TYR | A | 110 | 27.344 | -25.421 | 6.388 | 1.00 | 36.03 | O |
| ATOM | 1507 | CE2 | TYR | A | 110 | 26.951 | -27.782 | 6.491 | 1.00 | 35.02 | C |
| ATOM | 1509 | CD2 | TYR | A | 110 | 26.227 | -28.864 | 7.021 | 1.00 | 34.78 | C |
| ATOM | 1511 | C | TYR | A | 110 | 23.032 | -30.095 | 6.496 | 1.00 | 33.87 | C |
| ATOM | 1512 | O | TYR | A | 110 | 23.252 | -31.215 | 6.047 | 1.00 | 33.49 | O |
| ATOM | 1514 | N | ASP | A | 111 | 22.842 | -29.022 | 5.737 | 1.00 | 35.09 | N |
| ATOM | 1515 | CA | ASP | A | 111 | 22.890 | -29.087 | 4.284 | 1.00 | 36.18 | C |
| ATOM | 1517 | CB | ASP | A | 111 | 21.758 | -28.230 | 3.705 | 1.00 | 36.30 | C |
| ATOM | 1520 | CG | ASP | A | 111 | 21.542 | -28.465 | 2.219 | 1.00 | 36.33 | C |
| ATOM | 1521 | OD1 | ASP | A | 111 | 22.409 | -29.106 | 1.577 | 1.00 | 35.59 | O |
| ATOM | 1522 | OD2 | ASP | A | 111 | 20.492 | -28.013 | 1.696 | 1.00 | 35.58 | O |
| ATOM | 1523 | C | ASP | A | 111 | 24.244 | -28.580 | 3.781 | 1.00 | 37.05 | C |
| ATOM | 1524 | O | ASP | A | 111 | 24.540 | -27.387 | 3.862 | 1.00 | 36.92 | O |
| ATOM | 1526 | N | TYR | A | 112 | 25.059 | -29.482 | 3.250 | 1.00 | 38.34 | N |
| ATOM | 1527 | CA | TYR | A | 112 | 26.397 | -29.104 | 2.782 | 1.00 | 39.58 | C |
| ATOM | 1529 | CB | TYR | A | 112 | 27.258 | -30.343 | 2.538 | 1.00 | 39.64 | C |
| ATOM | 1532 | CG | TYR | A | 112 | 27.802 | -30.984 | 3.798 | 1.00 | 39.90 | C |

FIG.16-15

| | | | | | | | | | | | |
|---|---|---|---|---|---|---|---|---|---|---|---|
| ATOM | 1533 | CD1 | TYR | A | 112 | 27.340 | -32.223 | 4.222 | 1.00 | 40.91 | C |
| ATOM | 1535 | CE1 | TYR | A | 112 | 27.839 | -32.825 | 5.374 | 1.00 | 41.15 | C |
| ATOM | 1537 | CZ | TYR | A | 112 | 28.806 | -32.181 | 6.111 | 1.00 | 40.99 | C |
| ATOM | 1538 | OH | TYR | A | 112 | 29.284 | -32.781 | 7.246 | 1.00 | 41.18 | O |
| ATOM | 1540 | CE2 | TYR | A | 112 | 29.287 | -30.946 | 5.708 | 1.00 | 40.68 | C |
| ATOM | 1542 | CD2 | TYR | A | 112 | 28.785 | -30.358 | 4.555 | 1.00 | 40.03 | C |
| ATOM | 1544 | C | TYR | A | 112 | 26.401 | -28.224 | 1.521 | 1.00 | 40.71 | C |
| ATOM | 1545 | O | TYR | A | 112 | 27.384 | -27.536 | 1.243 | 1.00 | 41.24 | O |
| ATOM | 1547 | N | LYS | A | 113 | 25.316 | -28.260 | 0.753 | 1.00 | 41.88 | N |
| ATOM | 1548 | CA | LYS | A | 113 | 25.241 | -27.532 | -0.508 | 1.00 | 42.22 | C |
| ATOM | 1550 | CB | LYS | A | 113 | 24.270 | -28.237 | -1.471 | 1.00 | 42.45 | C |
| ATOM | 1553 | CG | LYS | A | 113 | 23.912 | -27.443 | -2.738 | 1.00 | 43.40 | C |
| ATOM | 1556 | CD | LYS | A | 113 | 23.015 | -28.238 | -3.687 | 1.00 | 43.70 | C |
| ATOM | 1559 | CE | LYS | A | 113 | 22.563 | -27.374 | -4.874 | 1.00 | 44.50 | C |
| ATOM | 1562 | NZ | LYS | A | 113 | 21.360 | -27.929 | -5.585 | 1.00 | 44.53 | N |
| ATOM | 1566 | C | LYS | A | 113 | 24.825 | -26.088 | -0.245 | 1.00 | 42.47 | C |
| ATOM | 1567 | O | LYS | A | 113 | 25.389 | -25.166 | -0.833 | 1.00 | 43.03 | O |
| ATOM | 1569 | N | GLU | A | 114 | 23.850 | -25.893 | 0.640 | 1.00 | 42.38 | N |
| ATOM | 1570 | CA | GLU | A | 114 | 23.326 | -24.566 | 0.925 | 1.00 | 42.25 | C |
| ATOM | 1572 | CB | GLU | A | 114 | 21.804 | -24.625 | 1.045 | 1.00 | 42.48 | C |
| ATOM | 1575 | CG | GLU | A | 114 | 21.101 | -25.211 | -0.177 | 1.00 | 43.12 | C |
| ATOM | 1578 | CD | GLU | A | 114 | 20.972 | -24.245 | -1.341 | 1.00 | 44.54 | C |
| ATOM | 1579 | OE1 | GLU | A | 114 | 21.635 | -23.182 | -1.349 | 1.00 | 45.47 | O |
| ATOM | 1580 | OE2 | GLU | A | 114 | 20.187 | -24.558 | -2.267 | 1.00 | 46.87 | O |
| ATOM | 1581 | C | GLU | A | 114 | 23.918 | -24.018 | 2.210 | 1.00 | 42.27 | C |
| ATOM | 1582 | O | GLU | A | 114 | 23.530 | -22.937 | 2.672 | 1.00 | 42.36 | O |
| ATOM | 1584 | N | ASN | A | 115 | 24.841 | -24.781 | 2.793 | 1.00 | 42.24 | N |
| ATOM | 1585 | CA | ASN | A | 115 | 25.518 | -24.420 | 4.037 | 1.00 | 42.33 | C |
| ATOM | 1587 | CB | ASN | A | 115 | 26.706 | -23.506 | 3.747 | 1.00 | 42.54 | C |
| ATOM | 1590 | CG | ASN | A | 115 | 27.775 | -24.201 | 2.913 | 1.00 | 44.14 | C |
| ATOM | 1591 | OD1 | ASN | A | 115 | 28.134 | -23.730 | 1.822 | 1.00 | 47.65 | O |
| ATOM | 1592 | ND2 | ASN | A | 115 | 28.266 | -25.345 | 3.403 | 1.00 | 43.77 | N |
| ATOM | 1595 | C | ASN | A | 115 | 24.611 | -23.819 | 5.102 | 1.00 | 41.99 | C |
| ATOM | 1596 | O | ASN | A | 115 | 24.735 | -22.644 | 5.468 | 1.00 | 42.22 | O |
| ATOM | 1598 | N | ARG | A | 116 | 23.702 | -24.649 | 5.601 | 1.00 | 41.33 | N |
| ATOM | 1599 | CA | ARG | A | 116 | 22.796 | -24.242 | 6.657 | 1.00 | 40.59 | C |
| ATOM | 1601 | CB | ARG | A | 116 | 21.693 | -23.370 | 6.084 | 1.00 | 40.85 | C |
| ATOM | 1604 | CG | ARG | A | 116 | 20.850 | -24.073 | 5.049 | 1.00 | 42.04 | C |
| ATOM | 1607 | CD | ARG | A | 116 | 19.894 | -23.108 | 4.403 | 1.00 | 43.56 | C |
| ATOM | 1610 | NE | ARG | A | 116 | 19.078 | -23.770 | 3.396 | 1.00 | 45.04 | N |
| ATOM | 1612 | CZ | ARG | A | 116 | 18.320 | -23.134 | 2.508 | 1.00 | 46.12 | C |
| ATOM | 1613 | NH1 | ARG | A | 116 | 18.263 | -21.805 | 2.498 | 1.00 | 45.63 | N |
| ATOM | 1616 | NH2 | ARG | A | 116 | 17.611 | -23.835 | 1.629 | 1.00 | 46.47 | N |
| ATOM | 1619 | C | ARG | A | 116 | 22.169 | -25.444 | 7.336 | 1.00 | 39.65 | C |
| ATOM | 1620 | O | ARG | A | 116 | 22.084 | -26.537 | 6.746 | 1.00 | 39.49 | O |
| ATOM | 1622 | N | PHE | A | 117 | 21.720 | -25.216 | 8.570 | 1.00 | 38.46 | N |
| ATOM | 1623 | CA | PHE | A | 117 | 21.048 | -26.229 | 9.365 | 1.00 | 37.48 | C |
| ATOM | 1625 | CB | PHE | A | 117 | 21.268 | -25.985 | 10.851 | 1.00 | 37.18 | C |
| ATOM | 1628 | CG | PHE | A | 117 | 22.660 | -26.297 | 11.303 | 1.00 | 36.90 | C |
| ATOM | 1629 | CD1 | PHE | A | 117 | 23.060 | -27.612 | 11.488 | 1.00 | 35.87 | C |
| ATOM | 1631 | CE1 | PHE | A | 117 | 24.342 | -27.908 | 11.891 | 1.00 | 35.89 | C |
| ATOM | 1633 | CZ | PHE | A | 117 | 25.245 | -26.886 | 12.122 | 1.00 | 35.53 | C |
| ATOM | 1635 | CE2 | PHE | A | 117 | 24.856 | -25.569 | 11.939 | 1.00 | 36.00 | C |
| ATOM | 1637 | CD2 | PHE | A | 117 | 23.577 | -25.279 | 11.533 | 1.00 | 36.26 | C |
| ATOM | 1639 | C | PHE | A | 117 | 19.570 | -26.245 | 9.060 | 1.00 | 37.05 | C |
| ATOM | 1640 | O | PHE | A | 117 | 18.997 | -25.225 | 8.649 | 1.00 | 36.82 | O |
| ATOM | 1642 | N | ILE | A | 118 | 18.967 | -27.419 | 9.253 | 1.00 | 36.44 | N |
| ATOM | 1643 | CA | ILE | A | 118 | 17.545 | -27.641 | 8.960 | 1.00 | 35.88 | C |
| ATOM | 1645 | CB | ILE | A | 118 | 17.348 | -28.632 | 7.801 | 1.00 | 35.62 | C |
| ATOM | 1647 | CG1 | ILE | A | 118 | 18.150 | -28.199 | 6.567 | 1.00 | 35.28 | C |
| ATOM | 1650 | CD1 | ILE | A | 118 | 18.272 | -29.271 | 5.489 | 1.00 | 33.61 | C |
| ATOM | 1654 | CG2 | ILE | A | 118 | 15.871 | -28.765 | 7.470 | 1.00 | 35.12 | C |
| ATOM | 1658 | C | ILE | A | 118 | 16.820 | -28.200 | 10.185 | 1.00 | 35.61 | C |

FIG.16-16

| | | | | | | | | | | | |
|---|---|---|---|---|---|---|---|---|---|---|---|
| ATOM | 1659 | O | ILE | A | 118 | 17.305 | -29.147 | 10.836 | 1.00 | 35.73 | O |
| ATOM | 1661 | N | GLU | A | 119 | 15.672 | -27.607 | 10.499 | 1.00 | 34.98 | N |
| ATOM | 1662 | CA | GLU | A | 119 | 14.801 | -28.113 | 11.547 | 1.00 | 35.00 | C |
| ATOM | 1664 | CB | GLU | A | 119 | 14.467 | -27.017 | 12.570 | 1.00 | 35.24 | C |
| ATOM | 1667 | CG | GLU | A | 119 | 13.432 | -27.405 | 13.641 | 1.00 | 35.49 | C |
| ATOM | 1670 | CD | GLU | A | 119 | 13.728 | -28.715 | 14.333 | 1.00 | 35.78 | C |
| ATOM | 1671 | OE1 | GLU | A | 119 | 12.765 | -29.474 | 14.574 | 1.00 | 37.24 | O |
| ATOM | 1672 | OE2 | GLU | A | 119 | 14.910 | -28.990 | 14.629 | 1.00 | 35.45 | O |
| ATOM | 1673 | C | GLU | A | 119 | 13.537 | -28.664 | 10.898 | 1.00 | 34.57 | C |
| ATOM | 1674 | O | GLU | A | 119 | 12.692 | -27.901 | 10.431 | 1.00 | 34.20 | O |
| ATOM | 1676 | N | ILE | A | 120 | 13.453 | -29.996 | 10.854 | 1.00 | 34.05 | N |
| ATOM | 1677 | CA | ILE | A | 120 | 12.318 | -30.709 | 10.307 | 1.00 | 33.58 | C |
| ATOM | 1679 | CB | ILE | A | 120 | 12.673 | -32.156 | 9.965 | 1.00 | 33.46 | C |
| ATOM | 1681 | CG1 | ILE | A | 120 | 13.751 | -32.220 | 8.883 | 1.00 | 34.02 | C |
| ATOM | 1684 | CD1 | ILE | A | 120 | 13.395 | -31.531 | 7.587 | 1.00 | 34.17 | C |
| ATOM | 1688 | CG2 | ILE | A | 120 | 11.436 | -32.925 | 9.549 | 1.00 | 33.36 | C |
| ATOM | 1692 | C | ILE | A | 120 | 11.219 | -30.752 | 11.357 | 1.00 | 33.80 | C |
| ATOM | 1693 | O | ILE | A | 120 | 11.450 | -31.129 | 12.506 | 1.00 | 33.34 | O |
| ATOM | 1695 | N | GLY | A | 121 | 10.026 | -30.344 | 10.950 | 1.00 | 34.18 | N |
| ATOM | 1696 | CA | GLY | A | 121 | 8.836 | -30.476 | 11.770 | 1.00 | 34.33 | C |
| ATOM | 1699 | C | GLY | A | 121 | 7.862 | -31.419 | 11.099 | 1.00 | 34.42 | C |
| ATOM | 1700 | O | GLY | A | 121 | 7.762 | -31.454 | 9.878 | 1.00 | 33.90 | O |
| ATOM | 1702 | N | VAL | A | 122 | 7.170 | -32.207 | 11.909 | 1.00 | 35.16 | N |
| ATOM | 1703 | CA | VAL | A | 122 | 6.058 | -33.020 | 11.451 | 1.00 | 35.47 | C |
| ATOM | 1705 | CB | VAL | A | 122 | 6.397 | -34.497 | 11.474 | 1.00 | 35.31 | C |
| ATOM | 1707 | CG1 | VAL | A | 122 | 5.261 | -35.292 | 10.848 | 1.00 | 34.65 | C |
| ATOM | 1711 | CG2 | VAL | A | 122 | 7.716 | -34.744 | 10.750 | 1.00 | 34.22 | C |
| ATOM | 1715 | C | VAL | A | 122 | 4.887 | -32.752 | 12.376 | 1.00 | 36.49 | C |
| ATOM | 1716 | O | VAL | A | 122 | 5.006 | -32.889 | 13.580 | 1.00 | 36.06 | O |
| ATOM | 1718 | N | THR | A | 123 | 3.763 | -32.334 | 11.812 | 1.00 | 38.25 | N |
| ATOM | 1719 | CA | THR | A | 123 | 2.579 | -32.030 | 12.606 | 1.00 | 39.75 | C |
| ATOM | 1721 | CB | THR | A | 123 | 2.302 | -30.519 | 12.644 | 1.00 | 39.76 | C |
| ATOM | 1723 | OG1 | THR | A | 123 | 1.369 | -30.240 | 13.688 | 1.00 | 40.75 | O |
| ATOM | 1725 | CG2 | THR | A | 123 | 1.740 | -30.008 | 11.307 | 1.00 | 39.49 | C |
| ATOM | 1729 | C | THR | A | 123 | 1.388 | -32.736 | 12.011 | 1.00 | 40.95 | C |
| ATOM | 1730 | O | THR | A | 123 | 1.397 | -33.051 | 10.833 | 1.00 | 40.89 | O |
| ATOM | 1732 | N | ARG | A | 124 | 0.369 | -32.991 | 12.820 | 1.00 | 42.67 | N |
| ATOM | 1733 | CA | ARG | A | 124 | -0.873 | -33.583 | 12.300 | 1.00 | 44.25 | C |
| ATOM | 1735 | CB | ARG | A | 124 | -1.262 | -34.879 | 13.053 | 1.00 | 44.20 | C |
| ATOM | 1738 | CG | ARG | A | 124 | -1.043 | -34.891 | 14.572 | 1.00 | 43.73 | C |
| ATOM | 1741 | CD | ARG | A | 124 | -0.181 | -36.060 | 15.073 | 1.00 | 42.41 | C |
| ATOM | 1744 | NE | ARG | A | 124 | 0.776 | -35.603 | 16.085 | 1.00 | 42.71 | N |
| ATOM | 1746 | CZ | ARG | A | 124 | 0.789 | -35.911 | 17.387 | 1.00 | 42.89 | C |
| ATOM | 1747 | NH1 | ARG | A | 124 | -0.099 | -36.727 | 17.936 | 1.00 | 43.49 | N |
| ATOM | 1750 | NH2 | ARG | A | 124 | 1.736 | -35.394 | 18.162 | 1.00 | 43.09 | N |
| ATOM | 1753 | C | ARG | A | 124 | -1.993 | -32.520 | 12.239 | 1.00 | 45.93 | C |
| ATOM | 1754 | O | ARG | A | 124 | -3.164 | -32.819 | 11.957 | 1.00 | 45.97 | O |
| ATOM | 1756 | N | ARG | A | 125 | -1.585 | -31.271 | 12.463 | 1.00 | 47.69 | N |
| ATOM | 1757 | CA | ARG | A | 125 | -2.415 | -30.106 | 12.229 | 1.00 | 49.21 | C |
| ATOM | 1759 | CB | ARG | A | 125 | -2.260 | -29.132 | 13.397 | 1.00 | 49.39 | C |
| ATOM | 1762 | CG | ARG | A | 125 | -2.830 | -29.639 | 14.696 | 1.00 | 50.37 | C |
| ATOM | 1765 | CD | ARG | A | 125 | -2.641 | -28.591 | 15.785 | 1.00 | 52.42 | C |
| ATOM | 1768 | NE | ARG | A | 125 | -1.401 | -28.782 | 16.544 | 1.00 | 53.57 | N |
| ATOM | 1770 | CZ | ARG | A | 125 | -0.676 | -27.807 | 17.098 | 1.00 | 53.86 | C |
| ATOM | 1771 | NH1 | ARG | A | 125 | -1.030 | -26.533 | 16.976 | 1.00 | 53.62 | N |
| ATOM | 1774 | NH2 | ARG | A | 125 | 0.433 | -28.113 | 17.768 | 1.00 | 54.17 | N |
| ATOM | 1777 | C | ARG | A | 125 | -2.031 | -29.439 | 10.890 | 1.00 | 50.38 | C |
| ATOM | 1778 | O | ARG | A | 125 | -1.513 | -30.102 | 9.977 | 1.00 | 50.26 | O |
| ATOM | 1780 | N | GLU | A | 126 | -2.299 | -28.135 | 10.776 | 1.00 | 51.87 | N |
| ATOM | 1781 | CA | GLU | A | 126 | -2.062 | -27.375 | 9.544 | 1.00 | 52.89 | C |
| ATOM | 1783 | CB | GLU | A | 126 | -3.159 | -26.323 | 9.357 | 1.00 | 53.10 | C |
| ATOM | 1786 | CG | GLU | A | 126 | -4.582 | -26.846 | 9.556 | 1.00 | 54.37 | C |
| ATOM | 1789 | CD | GLU | A | 126 | -5.549 | -25.734 | 9.907 | 1.00 | 56.25 | C |

FIG.16-17

| | | | | | | | | | | | |
|---|---|---|---|---|---|---|---|---|---|---|---|
| ATOM | 1790 | OE1 | GLU | A | 126 | -5.627 | -24.762 | 9.129 | 1.00 | 57.91 | O |
| ATOM | 1791 | OE2 | GLU | A | 126 | -6.222 | -25.819 | 10.959 | 1.00 | 57.22 | O |
| ATOM | 1792 | C | GLU | A | 126 | -0.687 | -26.694 | 9.589 | 1.00 | 53.27 | C |
| ATOM | 1793 | O | GLU | A | 126 | -0.390 | -25.930 | 10.518 | 1.00 | 53.08 | O |
| ATOM | 1795 | N | VAL | A | 127 | 0.140 | -26.997 | 8.587 | 1.00 | 53.87 | N |
| ATOM | 1796 | CA | VAL | A | 127 | 1.521 | -26.509 | 8.517 | 1.00 | 54.32 | C |
| ATOM | 1798 | CB | VAL | A | 127 | 2.066 | -26.550 | 7.065 | 1.00 | 54.30 | C |
| ATOM | 1800 | CG1 | VAL | A | 127 | 2.669 | -27.906 | 6.752 | 1.00 | 54.92 | C |
| ATOM | 1804 | CG2 | VAL | A | 127 | 0.972 | -26.217 | 6.056 | 1.00 | 54.54 | C |
| ATOM | 1808 | C | VAL | A | 127 | 1.710 | -25.096 | 9.072 | 1.00 | 54.78 | C |
| ATOM | 1809 | O | VAL | A | 127 | 2.426 | -24.906 | 10.053 | 1.00 | 54.69 | O |
| ATOM | 1811 | N | HIS | A | 128 | 1.041 | -24.122 | 8.459 | 1.00 | 55.54 | N |
| ATOM | 1812 | CA | HIS | A | 128 | 1.350 | -22.702 | 8.676 | 1.00 | 56.24 | C |
| ATOM | 1814 | CB | HIS | A | 128 | 0.349 | -21.774 | 7.955 | 1.00 | 56.67 | C |
| ATOM | 1817 | CG | HIS | A | 128 | -1.060 | -21.872 | 8.463 | 1.00 | 58.76 | C |
| ATOM | 1818 | ND1 | HIS | A | 128 | -1.852 | -22.986 | 8.264 | 1.00 | 60.13 | N |
| ATOM | 1820 | CE1 | HIS | A | 128 | -3.036 | -22.786 | 8.815 | 1.00 | 60.50 | C |
| ATOM | 1822 | NE2 | HIS | A | 128 | -3.048 | -21.579 | 9.354 | 1.00 | 60.99 | N |
| ATOM | 1824 | CD2 | HIS | A | 128 | -1.826 | -20.985 | 9.145 | 1.00 | 60.28 | C |
| ATOM | 1826 | C | HIS | A | 128 | 1.472 | -22.326 | 10.146 | 1.00 | 56.07 | C |
| ATOM | 1827 | O | HIS | A | 128 | 2.369 | -21.566 | 10.506 | 1.00 | 56.30 | O |
| ATOM | 1829 | N | ILE | A | 129 | 0.608 | -22.881 | 10.994 | 1.00 | 55.81 | N |
| ATOM | 1830 | CA | ILE | A | 129 | 0.647 | -22.555 | 12.428 | 1.00 | 55.67 | C |
| ATOM | 1832 | CB | ILE | A | 129 | -0.656 | -22.934 | 13.180 | 1.00 | 55.88 | C |
| ATOM | 1834 | CG1 | ILE | A | 129 | -1.900 | -22.732 | 12.290 | 1.00 | 56.67 | C |
| ATOM | 1837 | CD1 | ILE | A | 129 | -3.237 | -22.828 | 13.032 | 1.00 | 57.10 | C |
| ATOM | 1841 | CG2 | ILE | A | 129 | -0.749 | -22.119 | 14.478 | 1.00 | 55.39 | C |
| ATOM | 1845 | C | ILE | A | 129 | 1.821 | -23.238 | 13.135 | 1.00 | 55.29 | C |
| ATOM | 1846 | O | ILE | A | 129 | 2.501 | -22.619 | 13.952 | 1.00 | 55.20 | O |
| ATOM | 1848 | N | TYR | A | 130 | 2.046 | -24.516 | 12.830 | 1.00 | 55.01 | N |
| ATOM | 1849 | CA | TYR | A | 130 | 3.141 | -25.268 | 13.453 | 1.00 | 54.74 | C |
| ATOM | 1851 | CB | TYR | A | 130 | 3.120 | -26.749 | 13.053 | 1.00 | 54.46 | C |
| ATOM | 1854 | CG | TYR | A | 130 | 4.114 | -27.608 | 13.822 | 1.00 | 53.54 | C |
| ATOM | 1855 | CD1 | TYR | A | 130 | 3.840 | -28.040 | 15.119 | 1.00 | 52.88 | C |
| ATOM | 1857 | CE1 | TYR | A | 130 | 4.748 | -28.833 | 15.828 | 1.00 | 51.74 | C |
| ATOM | 1859 | CZ | TYR | A | 130 | 5.941 | -29.207 | 15.235 | 1.00 | 50.71 | C |
| ATOM | 1860 | OH | TYR | A | 130 | 6.837 | -29.994 | 15.923 | 1.00 | 47.79 | O |
| ATOM | 1862 | CE2 | TYR | A | 130 | 6.227 | -28.799 | 13.948 | 1.00 | 50.99 | C |
| ATOM | 1864 | CD2 | TYR | A | 130 | 5.319 | -28.003 | 13.249 | 1.00 | 52.18 | C |
| ATOM | 1866 | C | TYR | A | 130 | 4.471 | -24.642 | 13.078 | 1.00 | 54.65 | C |
| ATOM | 1867 | O | TYR | A | 130 | 5.349 | -24.505 | 13.915 | 1.00 | 54.47 | O |
| ATOM | 1869 | N | TYR | A | 131 | 4.602 | -24.255 | 11.817 | 1.00 | 54.85 | N |
| ATOM | 1870 | CA | TYR | A | 131 | 5.757 | -23.507 | 11.367 | 1.00 | 55.14 | C |
| ATOM | 1872 | CB | TYR | A | 131 | 5.542 | -23.029 | 9.932 | 1.00 | 54.97 | C |
| ATOM | 1875 | CG | TYR | A | 131 | 6.691 | -22.227 | 9.373 | 1.00 | 53.88 | C |
| ATOM | 1876 | CD1 | TYR | A | 131 | 7.614 | -22.808 | 8.519 | 1.00 | 52.45 | C |
| ATOM | 1878 | CE1 | TYR | A | 131 | 8.668 | -22.082 | 8.008 | 1.00 | 52.73 | C |
| ATOM | 1880 | CZ | TYR | A | 131 | 8.811 | -20.751 | 8.353 | 1.00 | 53.28 | C |
| ATOM | 1881 | OH | TYR | A | 131 | 9.856 | -20.015 | 7.849 | 1.00 | 53.98 | O |
| ATOM | 1883 | CE2 | TYR | A | 131 | 7.904 | -20.147 | 9.202 | 1.00 | 53.18 | C |
| ATOM | 1885 | CD2 | TYR | A | 131 | 6.856 | -20.883 | 9.709 | 1.00 | 53.29 | C |
| ATOM | 1887 | C | TYR | A | 131 | 6.019 | -22.316 | 12.292 | 1.00 | 55.97 | C |
| ATOM | 1888 | O | TYR | A | 131 | 7.136 | -22.126 | 12.772 | 1.00 | 55.86 | O |
| ATOM | 1890 | N | LEU | A | 132 | 4.985 | -21.520 | 12.546 | 1.00 | 57.03 | N |
| ATOM | 1891 | CA | LEU | A | 132 | 5.140 | -20.327 | 13.369 | 1.00 | 58.04 | C |
| ATOM | 1893 | CB | LEU | A | 132 | 3.872 | -19.464 | 13.343 | 1.00 | 58.13 | C |
| ATOM | 1896 | CG | LEU | A | 132 | 3.549 | -18.730 | 12.033 | 1.00 | 58.50 | C |
| ATOM | 1898 | CD1 | LEU | A | 132 | 2.332 | -17.827 | 12.236 | 1.00 | 58.65 | C |
| ATOM | 1902 | CD2 | LEU | A | 132 | 4.739 | -17.923 | 11.512 | 1.00 | 58.44 | C |
| ATOM | 1906 | C | LEU | A | 132 | 5.523 | -20.654 | 14.811 | 1.00 | 58.85 | C |
| ATOM | 1907 | O | LEU | A | 132 | 6.281 | -19.910 | 15.430 | 1.00 | 59.31 | O |
| ATOM | 1909 | N | GLU | A | 133 | 5.005 | -21.756 | 15.351 | 1.00 | 59.71 | N |
| ATOM | 1910 | CA | GLU | A | 133 | 5.376 | -22.181 | 16.705 | 1.00 | 60.14 | C |

FIG.16-18

| | | | | | | | | | | | |
|---|---|---|---|---|---|---|---|---|---|---|---|
| ATOM | 1912 | CB | GLU | A | 133 | 4.385 | -23.218 | 17.251 | 1.00 | 60.24 | C |
| ATOM | 1915 | CG | GLU | A | 133 | 2.961 | -22.659 | 17.466 | 1.00 | 60.87 | C |
| ATOM | 1918 | CD | GLU | A | 133 | 1.961 | -23.690 | 18.018 | 1.00 | 61.61 | C |
| ATOM | 1919 | OE1 | GLU | A | 133 | 2.344 | -24.858 | 18.247 | 1.00 | 62.42 | O |
| ATOM | 1920 | OE2 | GLU | A | 133 | 0.779 | -23.331 | 18.219 | 1.00 | 61.07 | O |
| ATOM | 1921 | C | GLU | A | 133 | 6.814 | -22.710 | 16.729 | 1.00 | 60.43 | C |
| ATOM | 1922 | O | GLU | A | 133 | 7.506 | -22.592 | 17.742 | 1.00 | 60.50 | O |
| ATOM | 1924 | N | LYS | A | 134 | 7.264 | -23.272 | 15.607 | 1.00 | 60.82 | N |
| ATOM | 1925 | CA | LYS | A | 134 | 8.660 | -23.692 | 15.472 | 1.00 | 61.22 | C |
| ATOM | 1927 | CB | LYS | A | 134 | 8.894 | -24.505 | 14.192 | 1.00 | 61.09 | C |
| ATOM | 1930 | CG | LYS | A | 134 | 8.749 | -26.001 | 14.367 | 1.00 | 60.85 | C |
| ATOM | 1933 | CD | LYS | A | 134 | 9.906 | -26.617 | 15.147 | 1.00 | 59.97 | C |
| ATOM | 1936 | CE | LYS | A | 134 | 9.756 | -28.123 | 15.233 | 1.00 | 59.41 | C |
| ATOM | 1939 | NZ | LYS | A | 134 | 10.467 | -28.695 | 16.401 | 1.00 | 59.78 | N |
| ATOM | 1943 | C | LYS | A | 134 | 9.575 | -22.485 | 15.465 | 1.00 | 61.76 | C |
| ATOM | 1944 | O | LYS | A | 134 | 10.472 | -22.388 | 16.297 | 1.00 | 61.78 | O |
| ATOM | 1946 | N | ALA | A | 135 | 9.337 | -21.579 | 14.520 | 1.00 | 62.52 | N |
| ATOM | 1947 | CA | ALA | A | 135 | 10.149 | -20.370 | 14.353 | 1.00 | 63.28 | C |
| ATOM | 1949 | CB | ALA | A | 135 | 9.513 | -19.446 | 13.327 | 1.00 | 63.27 | C |
| ATOM | 1953 | C | ALA | A | 135 | 10.376 | -19.617 | 15.664 | 1.00 | 64.11 | C |
| ATOM | 1954 | O | ALA | A | 135 | 11.512 | -19.266 | 15.990 | 1.00 | 64.12 | O |
| ATOM | 1956 | N | ASN | A | 136 | 9.303 | -19.378 | 16.413 | 1.00 | 65.15 | N |
| ATOM | 1957 | CA | ASN | A | 136 | 9.408 | -18.693 | 17.708 | 1.00 | 66.21 | C |
| ATOM | 1959 | CB | ASN | A | 136 | 8.048 | -18.649 | 18.414 | 1.00 | 66.23 | C |
| ATOM | 1962 | CG | ASN | A | 136 | 7.113 | -17.611 | 17.820 | 1.00 | 66.63 | C |
| ATOM | 1963 | OD1 | ASN | A | 136 | 7.328 | -17.108 | 16.711 | 1.00 | 66.81 | O |
| ATOM | 1964 | ND2 | ASN | A | 136 | 6.059 | -17.285 | 18.561 | 1.00 | 67.06 | N |
| ATOM | 1967 | C | ASN | A | 136 | 10.453 | -19.304 | 18.650 | 1.00 | 66.97 | C |
| ATOM | 1968 | O | ASN | A | 136 | 11.259 | -18.583 | 19.232 | 1.00 | 67.21 | O |
| ATOM | 1970 | N | LYS | A | 137 | 10.430 | -20.627 | 18.791 | 1.00 | 67.87 | N |
| ATOM | 1971 | CA | LYS | A | 137 | 11.375 | -21.335 | 19.656 | 1.00 | 68.71 | C |
| ATOM | 1973 | CB | LYS | A | 137 | 10.977 | -22.815 | 19.765 | 1.00 | 68.85 | C |
| ATOM | 1976 | CG | LYS | A | 137 | 12.044 | -23.707 | 20.395 | 1.00 | 69.45 | C |
| ATOM | 1979 | CD | LYS | A | 137 | 11.492 | -25.045 | 20.875 | 1.00 | 70.12 | C |
| ATOM | 1982 | CE | LYS | A | 137 | 12.631 | -25.968 | 21.308 | 1.00 | 70.41 | C |
| ATOM | 1985 | NZ | LYS | A | 137 | 12.148 | -27.131 | 22.094 | 1.00 | 70.63 | N |
| ATOM | 1989 | C | LYS | A | 137 | 12.841 | -21.220 | 19.203 | 1.00 | 69.26 | C |
| ATOM | 1990 | O | LYS | A | 137 | 13.752 | -21.252 | 20.032 | 1.00 | 69.34 | O |
| ATOM | 1992 | N | ILE | A | 138 | 13.059 | -21.077 | 17.897 | 1.00 | 70.01 | N |
| ATOM | 1993 | CA | ILE | A | 138 | 14.401 | -21.134 | 17.302 | 1.00 | 70.47 | C |
| ATOM | 1995 | CB | ILE | A | 138 | 14.391 | -22.020 | 16.031 | 1.00 | 70.45 | C |
| ATOM | 1997 | CG1 | ILE | A | 138 | 13.905 | -23.429 | 16.357 | 1.00 | 70.76 | C |
| ATOM | 2000 | CD1 | ILE | A | 138 | 13.693 | -24.266 | 15.127 | 1.00 | 71.11 | C |
| ATOM | 2004 | CG2 | ILE | A | 138 | 15.764 | -22.103 | 15.413 | 1.00 | 70.41 | C |
| ATOM | 2008 | C | ILE | A | 138 | 14.930 | -19.756 | 16.900 | 1.00 | 70.95 | C |
| ATOM | 2009 | O | ILE | A | 138 | 14.448 | -19.153 | 15.933 | 1.00 | 71.13 | O |
| ATOM | 2011 | N | LYS | A | 139 | 15.925 | -19.262 | 17.633 | 1.00 | 71.34 | N |
| ATOM | 2012 | CA | LYS | A | 139 | 16.692 | -18.093 | 17.195 | 1.00 | 71.67 | C |
| ATOM | 2014 | CB | LYS | A | 139 | 16.520 | -16.908 | 18.153 | 1.00 | 71.72 | C |
| ATOM | 2017 | CG | LYS | A | 139 | 15.622 | -15.804 | 17.599 | 1.00 | 71.82 | C |
| ATOM | 2020 | CD | LYS | A | 139 | 15.766 | -14.502 | 18.380 | 1.00 | 71.87 | C |
| ATOM | 2023 | CE | LYS | A | 139 | 15.252 | -13.315 | 17.575 | 1.00 | 71.74 | C |
| ATOM | 2026 | NZ | LYS | A | 139 | 15.132 | -12.089 | 18.406 | 1.00 | 71.74 | N |
| ATOM | 2030 | C | LYS | A | 139 | 18.171 | -18.446 | 17.030 | 1.00 | 71.93 | C |
| ATOM | 2031 | O | LYS | A | 139 | 18.667 | -18.556 | 15.903 | 1.00 | 72.13 | O |
| ATOM | 2033 | N | GLU | A | 141 | 17.092 | -18.759 | 14.096 | 1.00 | 56.22 | N |
| ATOM | 2034 | CA | GLU | A | 141 | 16.583 | -17.809 | 13.106 | 1.00 | 56.40 | C |
| ATOM | 2036 | CB | GLU | A | 141 | 16.762 | -16.357 | 13.579 | 1.00 | 56.67 | C |
| ATOM | 2039 | CG | GLU | A | 141 | 16.675 | -15.319 | 12.435 | 1.00 | 58.19 | C |
| ATOM | 2042 | CD | GLU | A | 141 | 16.506 | -13.876 | 12.902 | 1.00 | 59.66 | C |
| ATOM | 2043 | OE1 | GLU | A | 141 | 16.120 | -13.641 | 14.073 | 1.00 | 60.52 | O |
| ATOM | 2044 | OE2 | GLU | A | 141 | 16.754 | -12.974 | 12.070 | 1.00 | 60.27 | O |
| ATOM | 2045 | C | GLU | A | 141 | 17.268 | -17.997 | 11.761 | 1.00 | 55.75 | C |

FIG.16-19

| | | | | | | | | | | | |
|---|---|---|---|---|---|---|---|---|---|---|---|
| ATOM | 2046 | O | GLU | A | 141 | 16.683 | -17.703 | 10.718 | 1.00 | 55.89 | O |
| ATOM | 2048 | N | LYS | A | 142 | 18.515 | -18.459 | 11.798 | 1.00 | 54.98 | N |
| ATOM | 2049 | CA | LYS | A | 142 | 19.285 | -18.717 | 10.585 | 1.00 | 54.31 | C |
| ATOM | 2051 | CB | LYS | A | 142 | 20.736 | -18.286 | 10.791 | 1.00 | 54.42 | C |
| ATOM | 2054 | CG | LYS | A | 142 | 20.869 | -16.843 | 11.297 | 1.00 | 54.96 | C |
| ATOM | 2057 | CD | LYS | A | 142 | 22.329 | -16.434 | 11.466 | 1.00 | 55.72 | C |
| ATOM | 2060 | CE | LYS | A | 142 | 22.990 | -16.006 | 10.154 | 1.00 | 55.44 | C |
| ATOM | 2063 | NZ | LYS | A | 142 | 24.472 | -16.091 | 10.270 | 1.00 | 54.93 | N |
| ATOM | 2067 | C | LYS | A | 142 | 19.194 | -20.192 | 10.195 | 1.00 | 53.35 | C |
| ATOM | 2068 | O | LYS | A | 142 | 19.723 | -20.604 | 9.158 | 1.00 | 52.94 | O |
| ATOM | 2070 | N | THR | A | 143 | 18.510 | -20.972 | 11.033 | 1.00 | 52.37 | N |
| ATOM | 2071 | CA | THR | A | 143 | 18.187 | -22.366 | 10.738 | 1.00 | 51.54 | C |
| ATOM | 2073 | CB | THR | A | 143 | 17.780 | -23.128 | 12.012 | 1.00 | 51.60 | C |
| ATOM | 2075 | OG1 | THR | A | 143 | 18.867 | -23.128 | 12.945 | 1.00 | 52.12 | O |
| ATOM | 2077 | CG2 | THR | A | 143 | 17.403 | -24.560 | 11.684 | 1.00 | 51.66 | C |
| ATOM | 2081 | C | THR | A | 143 | 17.009 | -22.437 | 9.781 | 1.00 | 50.61 | C |
| ATOM | 2082 | O | THR | A | 143 | 15.972 | -21.839 | 10.030 | 1.00 | 50.42 | O |
| ATOM | 2084 | N | HIS | A | 144 | 17.168 | -23.185 | 8.700 | 1.00 | 49.59 | N |
| ATOM | 2085 | CA | HIS | A | 144 | 16.083 | -23.397 | 7.751 | 1.00 | 49.04 | C |
| ATOM | 2087 | CB | HIS | A | 144 | 16.656 | -23.927 | 6.434 | 1.00 | 49.09 | C |
| ATOM | 2090 | CG | HIS | A | 144 | 15.766 | -23.705 | 5.253 | 1.00 | 49.77 | C |
| ATOM | 2091 | ND1 | HIS | A | 144 | 15.778 | -22.535 | 4.525 | 1.00 | 49.98 | N |
| ATOM | 2093 | CE1 | HIS | A | 144 | 14.906 | -22.629 | 3.538 | 1.00 | 50.58 | C |
| ATOM | 2095 | NE2 | HIS | A | 144 | 14.328 | -23.817 | 3.601 | 1.00 | 50.51 | N |
| ATOM | 2097 | CD2 | HIS | A | 144 | 14.852 | -24.511 | 4.663 | 1.00 | 50.38 | C |
| ATOM | 2099 | C | HIS | A | 144 | 15.049 | -24.384 | 8.334 | 1.00 | 48.04 | C |
| ATOM | 2100 | O | HIS | A | 144 | 15.405 | -25.444 | 8.815 | 1.00 | 47.85 | O |
| ATOM | 2102 | N | ILE | A | 145 | 13.776 | -24.014 | 8.293 | 1.00 | 47.07 | N |
| ATOM | 2103 | CA | ILE | A | 145 | 12.697 | -24.836 | 8.836 | 1.00 | 46.29 | C |
| ATOM | 2105 | CB | ILE | A | 145 | 11.751 | -23.994 | 9.720 | 1.00 | 46.08 | C |
| ATOM | 2107 | CG1 | ILE | A | 145 | 12.510 | -23.454 | 10.938 | 1.00 | 45.79 | C |
| ATOM | 2110 | CD1 | ILE | A | 145 | 11.753 | -22.421 | 11.752 | 1.00 | 45.49 | C |
| ATOM | 2114 | CG2 | ILE | A | 145 | 10.546 | -24.812 | 10.159 | 1.00 | 45.29 | C |
| ATOM | 2118 | C | ILE | A | 145 | 11.896 | -25.478 | 7.708 | 1.00 | 45.92 | C |
| ATOM | 2119 | O | ILE | A | 145 | 11.712 | -24.880 | 6.660 | 1.00 | 45.65 | O |
| ATOM | 2121 | N | HIS | A | 146 | 11.429 | -26.701 | 7.934 | 1.00 | 45.79 | N |
| ATOM | 2122 | CA | HIS | A | 146 | 10.636 | -27.439 | 6.946 | 1.00 | 45.53 | C |
| ATOM | 2124 | CB | HIS | A | 146 | 11.562 | -28.322 | 6.107 | 1.00 | 45.36 | C |
| ATOM | 2127 | CG | HIS | A | 146 | 10.961 | -28.786 | 4.819 | 1.00 | 44.92 | C |
| ATOM | 2128 | ND1 | HIS | A | 146 | 11.679 | -28.837 | 3.644 | 1.00 | 44.45 | N |
| ATOM | 2130 | CE1 | HIS | A | 146 | 10.904 | -29.296 | 2.678 | 1.00 | 44.56 | C |
| ATOM | 2132 | NE2 | HIS | A | 146 | 9.707 | -29.535 | 3.181 | 1.00 | 44.13 | N |
| ATOM | 2134 | CD2 | HIS | A | 146 | 9.715 | -29.224 | 4.519 | 1.00 | 44.35 | C |
| ATOM | 2136 | C | HIS | A | 146 | 9.575 | -28.296 | 7.653 | 1.00 | 45.49 | C |
| ATOM | 2137 | O | HIS | A | 146 | 9.905 | -29.269 | 8.325 | 1.00 | 45.24 | O |
| ATOM | 2139 | N | ILE | A | 147 | 8.307 | -27.916 | 7.521 | 1.00 | 45.44 | N |
| ATOM | 2140 | CA | ILE | A | 147 | 7.223 | -28.662 | 8.149 | 1.00 | 45.52 | C |
| ATOM | 2142 | CB | ILE | A | 147 | 6.155 | -27.735 | 8.758 | 1.00 | 45.50 | C |
| ATOM | 2144 | CG1 | ILE | A | 147 | 6.813 | -26.626 | 9.580 | 1.00 | 46.11 | C |
| ATOM | 2147 | CD1 | ILE | A | 147 | 7.783 | -27.133 | 10.634 | 1.00 | 45.97 | C |
| ATOM | 2151 | CG2 | ILE | A | 147 | 5.213 | -28.515 | 9.646 | 1.00 | 44.84 | C |
| ATOM | 2155 | C | ILE | A | 147 | 6.566 | -29.590 | 7.130 | 1.00 | 45.87 | C |
| ATOM | 2156 | O | ILE | A | 147 | 6.449 | -29.259 | 5.949 | 1.00 | 45.65 | O |
| ATOM | 2158 | N | PHE | A | 148 | 6.195 | -30.778 | 7.592 | 1.00 | 46.20 | N |
| ATOM | 2159 | CA | PHE | A | 148 | 5.323 | -31.671 | 6.848 | 1.00 | 46.38 | C |
| ATOM | 2161 | CB | PHE | A | 148 | 5.989 | -33.014 | 6.596 | 1.00 | 46.34 | C |
| ATOM | 2164 | CG | PHE | A | 148 | 7.155 | -32.939 | 5.686 | 1.00 | 46.66 | C |
| ATOM | 2165 | CD1 | PHE | A | 148 | 7.001 | -33.146 | 4.328 | 1.00 | 47.50 | C |
| ATOM | 2167 | CE1 | PHE | A | 148 | 8.095 | -33.074 | 3.469 | 1.00 | 47.74 | C |
| ATOM | 2169 | CZ | PHE | A | 148 | 9.354 | -32.795 | 3.977 | 1.00 | 47.54 | C |
| ATOM | 2171 | CE2 | PHE | A | 148 | 9.514 | -32.589 | 5.335 | 1.00 | 47.37 | C |
| ATOM | 2173 | CD2 | PHE | A | 148 | 8.416 | -32.660 | 6.181 | 1.00 | 47.27 | C |
| ATOM | 2175 | C | PHE | A | 148 | 4.106 | -31.890 | 7.705 | 1.00 | 46.56 | C |

FIG.16-20

| | | | | | | | | | | | |
|---|---|---|---|---|---|---|---|---|---|---|---|
| ATOM | 2176 | O | PHE | A | 148 | 4.142 | -31.666 | 8.910 | 1.00 | 46.65 | O |
| ATOM | 2178 | N | SER | A | 149 | 3.022 | -32.324 | 7.084 | 1.00 | 46.95 | N |
| ATOM | 2179 | CA | SER | A | 149 | 1.815 | -32.649 | 7.827 | 1.00 | 47.08 | C |
| ATOM | 2181 | CB | SER | A | 149 | 0.825 | -31.489 | 7.772 | 1.00 | 47.20 | C |
| ATOM | 2184 | OG | SER | A | 149 | 0.524 | -31.175 | 6.421 | 1.00 | 48.80 | O |
| ATOM | 2186 | C | SER | A | 149 | 1.195 | -33.903 | 7.254 | 1.00 | 46.81 | C |
| ATOM | 2187 | O | SER | A | 149 | 1.487 | -34.285 | 6.119 | 1.00 | 46.80 | O |
| ATOM | 2189 | N | PHE | A | 150 | 0.348 | -34.545 | 8.050 | 1.00 | 46.57 | N |
| ATOM | 2190 | CA | PHE | A | 150 | -0.388 | -35.712 | 7.587 | 1.00 | 46.60 | C |
| ATOM | 2192 | CB | PHE | A | 150 | -0.882 | -36.538 | 8.775 | 1.00 | 46.47 | C |
| ATOM | 2195 | CG | PHE | A | 150 | 0.192 | -37.368 | 9.436 | 1.00 | 45.05 | C |
| ATOM | 2196 | CD1 | PHE | A | 150 | 0.402 | -38.682 | 9.054 | 1.00 | 43.86 | C |
| ATOM | 2198 | CE1 | PHE | A | 150 | 1.378 | -39.454 | 9.672 | 1.00 | 43.74 | C |
| ATOM | 2200 | CZ | PHE | A | 150 | 2.153 | -38.908 | 10.686 | 1.00 | 43.47 | C |
| ATOM | 2202 | CE2 | PHE | A | 150 | 1.952 | -37.602 | 11.081 | 1.00 | 43.34 | C |
| ATOM | 2204 | CD2 | PHE | A | 150 | 0.975 | -36.838 | 10.459 | 1.00 | 44.17 | C |
| ATOM | 2206 | C | PHE | A | 150 | -1.559 | -35.319 | 6.666 | 1.00 | 46.94 | C |
| ATOM | 2207 | O | PHE | A | 150 | -2.227 | -36.187 | 6.101 | 1.00 | 46.82 | O |
| ATOM | 2209 | N | THR | A | 151 | -1.800 | -34.017 | 6.513 | 1.00 | 47.15 | N |
| ATOM | 2210 | CA | THR | A | 151 | -2.744 | -33.520 | 5.515 | 1.00 | 47.38 | C |
| ATOM | 2212 | CB | THR | A | 151 | -3.248 | -32.091 | 5.868 | 1.00 | 47.52 | C |
| ATOM | 2214 | OG1 | THR | A | 151 | -2.190 | -31.136 | 5.694 | 1.00 | 48.54 | O |
| ATOM | 2216 | CG2 | THR | A | 151 | -3.769 | -32.022 | 7.314 | 1.00 | 47.41 | C |
| ATOM | 2220 | C | THR | A | 151 | -2.133 | -33.505 | 4.108 | 1.00 | 47.33 | C |
| ATOM | 2221 | O | THR | A | 151 | -2.806 | -33.147 | 3.143 | 1.00 | 47.31 | O |
| ATOM | 2223 | N | GLY | A | 152 | -0.855 | -33.870 | 4.002 | 1.00 | 47.40 | N |
| ATOM | 2224 | CA | GLY | A | 152 | -0.158 | -33.967 | 2.717 | 1.00 | 47.31 | C |
| ATOM | 2227 | C | GLY | A | 152 | 0.576 | -32.690 | 2.351 | 1.00 | 47.49 | C |
| ATOM | 2228 | O | GLY | A | 152 | 1.300 | -32.636 | 1.342 | 1.00 | 47.67 | O |
| ATOM | 2230 | N | GLU | A | 153 | 0.392 | -31.659 | 3.171 | 1.00 | 47.43 | N |
| ATOM | 2231 | CA | GLU | A | 153 | 0.999 | -30.359 | 2.924 | 1.00 | 47.61 | C |
| ATOM | 2233 | CB | GLU | A | 153 | 0.218 | -29.279 | 3.682 | 1.00 | 47.73 | C |
| ATOM | 2236 | CG | GLU | A | 153 | -1.084 | -28.906 | 3.025 | 1.00 | 48.08 | C |
| ATOM | 2239 | CD | GLU | A | 153 | -2.110 | -28.339 | 3.987 | 1.00 | 48.76 | C |
| ATOM | 2240 | OE1 | GLU | A | 153 | -1.735 | -27.840 | 5.079 | 1.00 | 47.98 | O |
| ATOM | 2241 | OE2 | GLU | A | 153 | -3.307 | -28.402 | 3.625 | 1.00 | 49.67 | O |
| ATOM | 2242 | C | GLU | A | 153 | 2.476 | -30.295 | 3.335 | 1.00 | 47.64 | C |
| ATOM | 2243 | O | GLU | A | 153 | 3.029 | -31.243 | 3.910 | 1.00 | 47.48 | O |
| ATOM | 2245 | N | GLU | A | 154 | 3.097 | -29.158 | 3.022 | 1.00 | 47.60 | N |
| ATOM | 2246 | CA | GLU | A | 154 | 4.407 | -28.822 | 3.534 | 1.00 | 47.64 | C |
| ATOM | 2248 | CB | GLU | A | 154 | 5.488 | -29.464 | 2.684 | 1.00 | 47.55 | C |
| ATOM | 2251 | CG | GLU | A | 154 | 5.330 | -29.254 | 1.195 | 1.00 | 47.62 | C |
| ATOM | 2254 | CD | GLU | A | 154 | 6.524 | -29.753 | 0.415 | 1.00 | 46.94 | C |
| ATOM | 2255 | OE1 | GLU | A | 154 | 7.470 | -30.256 | 1.049 | 1.00 | 46.23 | O |
| ATOM | 2256 | OE2 | GLU | A | 154 | 6.523 | -29.634 | -0.829 | 1.00 | 47.81 | O |
| ATOM | 2257 | C | GLU | A | 154 | 4.600 | -27.314 | 3.607 | 1.00 | 47.99 | C |
| ATOM | 2258 | O | GLU | A | 154 | 3.764 | -26.559 | 3.135 | 1.00 | 48.24 | O |
| ATOM | 2260 | N | MET | A | 155 | 5.692 | -26.888 | 4.235 | 1.00 | 48.34 | N |
| ATOM | 2261 | CA | MET | A | 155 | 6.029 | -25.477 | 4.356 | 1.00 | 48.49 | C |
| ATOM | 2263 | CB | MET | A | 155 | 5.088 | -24.775 | 5.336 | 1.00 | 48.57 | C |
| ATOM | 2266 | CG | MET | A | 155 | 5.554 | -23.365 | 5.694 | 1.00 | 49.76 | C |
| ATOM | 2269 | SD | MET | A | 155 | 4.258 | -22.235 | 6.206 | 1.00 | 51.85 | S |
| ATOM | 2270 | CE | MET | A | 155 | 3.416 | -21.995 | 4.633 | 1.00 | 51.21 | C |
| ATOM | 2274 | C | MET | A | 155 | 7.477 | -25.310 | 4.819 | 1.00 | 48.63 | C |
| ATOM | 2275 | O | MET | A | 155 | 7.881 | -25.926 | 5.803 | 1.00 | 48.67 | O |
| ATOM | 2277 | N | ALA | A | 156 | 8.229 | -24.454 | 4.115 | 1.00 | 48.88 | N |
| ATOM | 2278 | CA | ALA | A | 156 | 9.649 | -24.181 | 4.388 | 1.00 | 48.84 | C |
| ATOM | 2280 | CB | ALA | A | 156 | 10.505 | -24.910 | 3.391 | 1.00 | 48.79 | C |
| ATOM | 2284 | C | ALA | A | 156 | 9.963 | -22.680 | 4.342 | 1.00 | 49.16 | C |
| ATOM | 2285 | O | ALA | A | 156 | 9.288 | -21.925 | 3.639 | 1.00 | 49.18 | O |
| ATOM | 2287 | N | THR | A | 157 | 10.988 | -22.242 | 5.080 | 1.00 | 49.43 | N |
| ATOM | 2288 | CA | THR | A | 157 | 11.311 | -20.812 | 5.148 | 1.00 | 49.65 | C |
| ATOM | 2290 | CB | THR | A | 157 | 12.572 | -20.500 | 5.986 | 1.00 | 49.80 | C |

FIG.16-21

| | | | | | | | | | | | |
|---|---|---|---|---|---|---|---|---|---|---|---|
| ATOM | 2292 | OG1 | THR | A | 157 | 13.675 | -21.279 | 5.505 | 1.00 | 51.08 | O |
| ATOM | 2294 | CG2 | THR | A | 157 | 12.354 | -20.799 | 7.452 | 1.00 | 50.12 | C |
| ATOM | 2298 | C | THR | A | 157 | 11.554 | -20.280 | 3.752 | 1.00 | 49.49 | C |
| ATOM | 2299 | O | THR | A | 157 | 12.238 | -20.925 | 2.956 | 1.00 | 49.49 | O |
| ATOM | 2301 | N | LYS | A | 158 | 10.980 | -19.108 | 3.465 | 1.00 | 49.50 | N |
| ATOM | 2302 | CA | LYS | A | 158 | 11.108 | -18.449 | 2.163 | 1.00 | 49.29 | C |
| ATOM | 2304 | CB | LYS | A | 158 | 12.537 | -17.920 | 1.977 | 1.00 | 49.40 | C |
| ATOM | 2307 | CG | LYS | A | 158 | 12.979 | -16.904 | 3.032 | 1.00 | 50.03 | C |
| ATOM | 2310 | CD | LYS | A | 158 | 14.455 | -16.535 | 2.862 | 1.00 | 51.02 | C |
| ATOM | 2313 | CE | LYS | A | 158 | 15.089 | -16.043 | 4.165 | 1.00 | 52.04 | C |
| ATOM | 2316 | NZ | LYS | A | 158 | 16.567 | -16.317 | 4.217 | 1.00 | 52.29 | N |
| ATOM | 2320 | C | LYS | A | 158 | 10.724 | -19.373 | 0.998 | 1.00 | 48.93 | C |
| ATOM | 2321 | O | LYS | A | 158 | 11.213 | -19.203 | -0.120 | 1.00 | 49.33 | O |
| ATOM | 2323 | N | ALA | A | 159 | 9.852 | -20.345 | 1.269 | 1.00 | 48.23 | N |
| ATOM | 2324 | CA | ALA | A | 159 | 9.461 | -21.358 | 0.295 | 1.00 | 47.78 | C |
| ATOM | 2326 | CB | ALA | A | 159 | 8.446 | -20.785 | -0.684 | 1.00 | 47.65 | C |
| ATOM | 2330 | C | ALA | A | 159 | 10.630 | -21.984 | -0.466 | 1.00 | 47.54 | C |
| ATOM | 2331 | O | ALA | A | 159 | 10.533 | -22.191 | -1.673 | 1.00 | 48.06 | O |
| ATOM | 2333 | N | ASP | A | 160 | 11.729 | -22.273 | 0.227 | 1.00 | 46.99 | N |
| ATOM | 2334 | CA | ASP | A | 160 | 12.820 | -23.067 | -0.349 | 1.00 | 46.60 | C |
| ATOM | 2336 | CB | ASP | A | 160 | 14.176 | -22.426 | -0.042 | 1.00 | 46.49 | C |
| ATOM | 2339 | CG | ASP | A | 160 | 15.346 | -23.127 | -0.743 | 1.00 | 46.39 | C |
| ATOM | 2340 | OD1 | ASP | A | 160 | 15.222 | -24.300 | -1.170 | 1.00 | 45.22 | O |
| ATOM | 2341 | OD2 | ASP | A | 160 | 16.413 | -22.488 | -0.851 | 1.00 | 46.18 | O |
| ATOM | 2342 | C | ASP | A | 160 | 12.723 | -24.463 | 0.271 | 1.00 | 46.37 | C |
| ATOM | 2343 | O | ASP | A | 160 | 12.914 | -24.619 | 1.482 | 1.00 | 46.41 | O |
| ATOM | 2345 | N | TYR | A | 161 | 12.399 | -25.466 | -0.548 | 1.00 | 45.83 | N |
| ATOM | 2346 | CA | TYR | A | 161 | 12.113 | -26.810 | -0.040 | 1.00 | 45.28 | C |
| ATOM | 2348 | CB | TYR | A | 161 | 10.901 | -27.411 | -0.755 | 1.00 | 45.45 | C |
| ATOM | 2351 | CG | TYR | A | 161 | 9.655 | -26.583 | -0.557 | 1.00 | 46.81 | C |
| ATOM | 2352 | CD1 | TYR | A | 161 | 9.106 | -26.420 | 0.711 | 1.00 | 48.02 | C |
| ATOM | 2354 | CE1 | TYR | A | 161 | 7.976 | -25.645 | 0.912 | 1.00 | 48.30 | C |
| ATOM | 2356 | CZ | TYR | A | 161 | 7.369 | -25.027 | -0.158 | 1.00 | 48.63 | C |
| ATOM | 2357 | OH | TYR | A | 161 | 6.243 | -24.266 | 0.050 | 1.00 | 48.24 | O |
| ATOM | 2359 | CE2 | TYR | A | 161 | 7.891 | -25.174 | -1.433 | 1.00 | 48.64 | C |
| ATOM | 2361 | CD2 | TYR | A | 161 | 9.035 | -25.946 | -1.625 | 1.00 | 48.02 | C |
| ATOM | 2363 | C | TYR | A | 161 | 13.322 | -27.725 | -0.149 | 1.00 | 44.58 | C |
| ATOM | 2364 | O | TYR | A | 161 | 13.221 | -28.929 | 0.114 | 1.00 | 44.46 | O |
| ATOM | 2366 | N | THR | A | 162 | 14.469 | -27.158 | -0.525 | 1.00 | 43.50 | N |
| ATOM | 2367 | CA | THR | A | 162 | 15.734 | -27.875 | -0.479 | 1.00 | 42.55 | C |
| ATOM | 2369 | CB | THR | A | 162 | 16.044 | -28.359 | 0.958 | 1.00 | 42.54 | C |
| ATOM | 2371 | OG1 | THR | A | 162 | 16.154 | -27.227 | 1.825 | 1.00 | 41.69 | O |
| ATOM | 2373 | CG2 | THR | A | 162 | 17.322 | -29.204 | 1.002 | 1.00 | 41.51 | C |
| ATOM | 2377 | C | THR | A | 162 | 15.712 | -29.071 | -1.400 | 1.00 | 42.09 | C |
| ATOM | 2378 | O | THR | A | 162 | 16.518 | -29.172 | -2.327 | 1.00 | 42.35 | O |
| ATOM | 2380 | N | LEU | A | 163 | 14.797 | -29.992 | -1.122 | 1.00 | 41.33 | N |
| ATOM | 2381 | CA | LEU | A | 163 | 14.695 | -31.226 | -1.881 | 1.00 | 40.86 | C |
| ATOM | 2383 | CB | LEU | A | 163 | 13.922 | -32.265 | -1.073 | 1.00 | 40.74 | C |
| ATOM | 2386 | CG | LEU | A | 163 | 14.601 | -32.768 | 0.202 | 1.00 | 40.22 | C |
| ATOM | 2388 | CD1 | LEU | A | 163 | 13.633 | -33.659 | 0.988 | 1.00 | 39.56 | C |
| ATOM | 2392 | CD2 | LEU | A | 163 | 15.895 | -33.504 | -0.127 | 1.00 | 38.43 | C |
| ATOM | 2396 | C | LEU | A | 163 | 13.994 | -30.990 | -3.207 | 1.00 | 40.47 | C |
| ATOM | 2397 | O | LEU | A | 163 | 13.321 | -29.968 | -3.401 | 1.00 | 40.41 | O |
| ATOM | 2399 | N | ASP | A | 164 | 14.158 | -31.941 | -4.120 | 1.00 | 39.93 | N |
| ATOM | 2400 | CA | ASP | A | 164 | 13.407 | -31.922 | -5.363 | 1.00 | 39.57 | C |
| ATOM | 2402 | CB | ASP | A | 164 | 14.114 | -32.769 | -6.435 | 1.00 | 39.32 | C |
| ATOM | 2405 | CG | ASP | A | 164 | 14.104 | -34.257 | -6.130 | 1.00 | 39.41 | C |
| ATOM | 2406 | OD1 | ASP | A | 164 | 13.323 | -34.691 | -5.272 | 1.00 | 40.02 | O |
| ATOM | 2407 | OD2 | ASP | A | 164 | 14.869 | -35.010 | -6.768 | 1.00 | 39.21 | O |
| ATOM | 2408 | C | ASP | A | 164 | 11.960 | -32.375 | -5.065 | 1.00 | 39.44 | C |
| ATOM | 2409 | O | ASP | A | 164 | 11.632 | -32.706 | -3.925 | 1.00 | 39.11 | O |
| ATOM | 2411 | N | GLU | A | 165 | 11.089 | -32.358 | -6.073 | 1.00 | 39.55 | N |
| ATOM | 2412 | CA | GLU | A | 165 | 9.694 | -32.802 | -5.888 | 1.00 | 39.27 | C |

FIG.16-22

| | | | | | | | | | | | |
|---|---|---|---|---|---|---|---|---|---|---|---|
| ATOM | 2414 | CB | GLU | A | 165 | 8.822 | -32.354 | -7.069 | 1.00 | 39.27 | C |
| ATOM | 2417 | CG | GLU | A | 165 | 7.307 | -32.480 | -6.836 | 1.00 | 39.15 | C |
| ATOM | 2420 | CD | GLU | A | 165 | 6.769 | -33.907 | -7.054 | 1.00 | 39.46 | C |
| ATOM | 2421 | OE1 | GLU | A | 165 | 7.393 | -34.708 | -7.794 | 1.00 | 36.27 | O |
| ATOM | 2422 | OE2 | GLU | A | 165 | 5.707 | -34.226 | -6.477 | 1.00 | 38.42 | O |
| ATOM | 2423 | C | GLU | A | 165 | 9.630 | -34.320 | -5.707 | 1.00 | 39.07 | C |
| ATOM | 2424 | O | GLU | A | 165 | 8.838 | -34.818 | -4.923 | 1.00 | 38.30 | O |
| ATOM | 2426 | N | GLU | A | 166 | 10.486 | -35.040 | -6.431 | 1.00 | 39.48 | N |
| ATOM | 2427 | CA | GLU | A | 166 | 10.538 | -36.504 | -6.359 | 1.00 | 39.85 | C |
| ATOM | 2429 | CB | GLU | A | 166 | 11.716 | -37.053 | -7.184 | 1.00 | 40.16 | C |
| ATOM | 2432 | CG | GLU | A | 166 | 11.431 | -38.312 | -8.024 | 1.00 | 41.37 | C |
| ATOM | 2435 | CD | GLU | A | 166 | 10.428 | -39.254 | -7.402 | 1.00 | 43.24 | C |
| ATOM | 2436 | OE1 | GLU | A | 166 | 10.741 | -39.852 | -6.356 | 1.00 | 45.39 | O |
| ATOM | 2437 | OE2 | GLU | A | 166 | 9.322 | -39.405 | -7.967 | 1.00 | 45.28 | O |
| ATOM | 2438 | C | GLU | A | 166 | 10.685 | -36.964 | -4.910 | 1.00 | 39.58 | C |
| ATOM | 2439 | O | GLU | A | 166 | 9.953 | -37.839 | -4.456 | 1.00 | 40.05 | O |
| ATOM | 2441 | N | SER | A | 167 | 11.628 | -36.351 | -4.198 | 1.00 | 39.07 | N |
| ATOM | 2442 | CA | SER | A | 167 | 12.011 | -36.761 | -2.847 | 1.00 | 38.68 | C |
| ATOM | 2444 | CB | SER | A | 167 | 13.306 | -36.047 | -2.440 | 1.00 | 38.68 | C |
| ATOM | 2447 | OG | SER | A | 167 | 14.400 | -36.472 | -3.242 | 1.00 | 38.61 | O |
| ATOM | 2449 | C | SER | A | 167 | 10.922 | -36.466 | -1.824 | 1.00 | 38.49 | C |
| ATOM | 2450 | O | SER | A | 167 | 10.638 | -37.276 | -0.951 | 1.00 | 38.05 | O |
| ATOM | 2452 | N | ARG | A | 168 | 10.328 | -35.286 | -1.941 | 1.00 | 38.56 | N |
| ATOM | 2453 | CA | ARG | A | 168 | 9.246 | -34.868 | -1.074 | 1.00 | 38.63 | C |
| ATOM | 2455 | CB | ARG | A | 168 | 8.887 | -33.428 | -1.377 | 1.00 | 39.02 | C |
| ATOM | 2458 | CG | ARG | A | 168 | 9.941 | -32.454 | -0.910 | 1.00 | 41.33 | C |
| ATOM | 2461 | CD | ARG | A | 168 | 9.551 | -31.031 | -1.250 | 1.00 | 44.07 | C |
| ATOM | 2464 | NE | ARG | A | 168 | 10.124 | -30.579 | -2.517 | 1.00 | 46.13 | N |
| ATOM | 2466 | CZ | ARG | A | 168 | 9.627 | -29.587 | -3.254 | 1.00 | 48.23 | C |
| ATOM | 2467 | NH1 | ARG | A | 168 | 8.520 | -28.935 | -2.875 | 1.00 | 47.89 | N |
| ATOM | 2470 | NH2 | ARG | A | 168 | 10.238 | -29.249 | -4.387 | 1.00 | 49.04 | N |
| ATOM | 2473 | C | ARG | A | 168 | 7.992 | -35.732 | -1.196 | 1.00 | 38.13 | C |
| ATOM | 2474 | O | ARG | A | 168 | 7.341 | -36.032 | -0.195 | 1.00 | 38.30 | O |
| ATOM | 2476 | N | ALA | A | 169 | 7.649 | -36.130 | -2.413 | 1.00 | 37.40 | N |
| ATOM | 2477 | CA | ALA | A | 169 | 6.492 | -36.984 | -2.605 | 1.00 | 36.97 | C |
| ATOM | 2479 | CB | ALA | A | 169 | 6.211 | -37.180 | -4.082 | 1.00 | 36.88 | C |
| ATOM | 2483 | C | ALA | A | 169 | 6.688 | -38.328 | -1.909 | 1.00 | 36.77 | C |
| ATOM | 2484 | O | ALA | A | 169 | 5.715 | -38.956 | -1.498 | 1.00 | 36.91 | O |
| ATOM | 2486 | N | ARG | A | 170 | 7.938 | -38.771 | -1.778 | 1.00 | 36.50 | N |
| ATOM | 2487 | CA | ARG | A | 170 | 8.230 | -40.028 | -1.086 | 1.00 | 36.39 | C |
| ATOM | 2489 | CB | ARG | A | 170 | 9.653 | -40.512 | -1.369 | 1.00 | 36.90 | C |
| ATOM | 2492 | CG | ARG | A | 170 | 9.822 | -41.048 | -2.772 | 1.00 | 39.59 | C |
| ATOM | 2495 | CD | ARG | A | 170 | 11.186 | -41.654 | -3.012 | 1.00 | 43.56 | C |
| ATOM | 2498 | NE | ARG | A | 170 | 11.427 | -41.820 | -4.450 | 1.00 | 47.71 | N |
| ATOM | 2500 | CZ | ARG | A | 170 | 12.598 | -42.155 | -5.000 | 1.00 | 50.88 | C |
| ATOM | 2501 | NH1 | ARG | A | 170 | 13.675 | -42.371 | -4.236 | 1.00 | 52.20 | N |
| ATOM | 2504 | NH2 | ARG | A | 170 | 12.698 | -42.269 | -6.328 | 1.00 | 51.43 | N |
| ATOM | 2507 | C | ARG | A | 170 | 8.016 | -39.879 | 0.401 | 1.00 | 35.26 | C |
| ATOM | 2508 | O | ARG | A | 170 | 7.486 | -40.784 | 1.040 | 1.00 | 35.00 | O |
| ATOM | 2510 | N | ILE | A | 171 | 8.432 | -38.737 | 0.944 | 1.00 | 34.26 | N |
| ATOM | 2511 | CA | ILE | A | 171 | 8.190 | -38.421 | 2.354 | 1.00 | 33.56 | C |
| ATOM | 2513 | CB | ILE | A | 171 | 8.914 | -37.113 | 2.806 | 1.00 | 33.43 | C |
| ATOM | 2515 | CG1 | ILE | A | 171 | 10.422 | -37.362 | 2.944 | 1.00 | 33.13 | C |
| ATOM | 2518 | CD1 | ILE | A | 171 | 11.238 | -36.091 | 3.066 | 1.00 | 32.34 | C |
| ATOM | 2522 | CG2 | ILE | A | 171 | 8.347 | -36.595 | 4.142 | 1.00 | 32.80 | C |
| ATOM | 2526 | C | ILE | A | 171 | 6.687 | -38.312 | 2.602 | 1.00 | 33.02 | C |
| ATOM | 2527 | O | ILE | A | 171 | 6.183 | -38.805 | 3.613 | 1.00 | 32.73 | O |
| ATOM | 2529 | N | LYS | A | 172 | 5.982 | -37.676 | 1.671 | 1.00 | 32.37 | N |
| ATOM | 2530 | CA | LYS | A | 172 | 4.546 | -37.475 | 1.806 | 1.00 | 32.17 | C |
| ATOM | 2532 | CB | LYS | A | 172 | 4.036 | -36.486 | 0.774 | 1.00 | 32.34 | C |
| ATOM | 2535 | CG | LYS | A | 172 | 4.276 | -35.045 | 1.144 | 1.00 | 33.47 | C |
| ATOM | 2538 | CD | LYS | A | 172 | 4.162 | -34.168 | -0.082 | 1.00 | 35.92 | C |
| ATOM | 2541 | CE | LYS | A | 172 | 4.518 | -32.727 | 0.228 | 1.00 | 38.04 | C |

FIG.16-23

| | | | | | | | | | | | |
|---|---|---|---|---|---|---|---|---|---|---|---|
| ATOM | 2544 | NZ | LYS | A | 172 | 4.926 | -31.994 | -1.022 | 1.00 | 39.72 | N |
| ATOM | 2548 | C | LYS | A | 172 | 3.776 | -38.776 | 1.683 | 1.00 | 31.57 | C |
| ATOM | 2549 | O | LYS | A | 172 | 2.800 | -38.985 | 2.407 | 1.00 | 31.40 | O |
| ATOM | 2551 | N | THR | A | 173 | 4.204 | -39.650 | 0.775 | 1.00 | 31.01 | N |
| ATOM | 2552 | CA | THR | A | 173 | 3.568 | -40.956 | 0.646 | 1.00 | 30.66 | C |
| ATOM | 2554 | CB | THR | A | 173 | 4.229 | -41.808 | -0.408 | 1.00 | 30.42 | C |
| ATOM | 2556 | OG1 | THR | A | 173 | 4.246 | -41.075 | -1.630 | 1.00 | 31.59 | O |
| ATOM | 2558 | CG2 | THR | A | 173 | 3.478 | -43.112 | -0.604 | 1.00 | 28.72 | C |
| ATOM | 2562 | C | THR | A | 173 | 3.655 | -41.691 | 1.956 | 1.00 | 30.79 | C |
| ATOM | 2563 | O | THR | A | 173 | 2.643 | -42.172 | 2.465 | 1.00 | 31.04 | O |
| ATOM | 2565 | N | ARG | A | 174 | 4.868 | -41.747 | 2.504 | 1.00 | 30.80 | N |
| ATOM | 2566 | CA | ARG | A | 174 | 5.139 | -42.462 | 3.750 | 1.00 | 30.82 | C |
| ATOM | 2568 | CB | ARG | A | 174 | 6.624 | -42.342 | 4.121 | 1.00 | 30.93 | C |
| ATOM | 2571 | CG | ARG | A | 174 | 7.042 | -43.028 | 5.408 | 1.00 | 30.30 | C |
| ATOM | 2574 | CD | ARG | A | 174 | 6.820 | -44.537 | 5.399 | 1.00 | 30.20 | C |
| ATOM | 2577 | NE | ARG | A | 174 | 7.206 | -45.090 | 6.700 | 1.00 | 30.59 | N |
| ATOM | 2579 | CZ | ARG | A | 174 | 6.703 | -46.192 | 7.256 | 1.00 | 30.17 | C |
| ATOM | 2580 | NH1 | ARG | A | 174 | 5.775 | -46.917 | 6.637 | 1.00 | 30.61 | N |
| ATOM | 2583 | NH2 | ARG | A | 174 | 7.132 | -46.571 | 8.454 | 1.00 | 29.36 | N |
| ATOM | 2586 | C | ARG | A | 174 | 4.268 | -41.956 | 4.886 | 1.00 | 30.81 | C |
| ATOM | 2587 | O | ARG | A | 174 | 3.783 | -42.739 | 5.670 | 1.00 | 30.61 | O |
| ATOM | 2589 | N | LEU | A | 175 | 4.075 | -40.647 | 4.977 | 1.00 | 31.27 | N |
| ATOM | 2590 | CA | LEU | A | 175 | 3.181 | -40.092 | 5.991 | 1.00 | 31.49 | C |
| ATOM | 2592 | CB | LEU | A | 175 | 3.164 | -38.566 | 5.943 | 1.00 | 31.29 | C |
| ATOM | 2595 | CG | LEU | A | 175 | 4.406 | -37.866 | 6.486 | 1.00 | 32.29 | C |
| ATOM | 2597 | CD1 | LEU | A | 175 | 4.250 | -36.336 | 6.439 | 1.00 | 33.56 | C |
| ATOM | 2601 | CD2 | LEU | A | 175 | 4.686 | -38.311 | 7.914 | 1.00 | 33.38 | C |
| ATOM | 2605 | C | LEU | A | 175 | 1.774 | -40.631 | 5.795 | 1.00 | 31.82 | C |
| ATOM | 2606 | O | LEU | A | 175 | 1.184 | -41.170 | 6.734 | 1.00 | 32.27 | O |
| ATOM | 2608 | N | PHE | A | 176 | 1.241 | -40.499 | 4.578 | 1.00 | 32.00 | N |
| ATOM | 2609 | CA | PHE | A | 176 | -0.103 | -40.994 | 4.274 | 1.00 | 32.00 | C |
| ATOM | 2611 | CB | PHE | A | 176 | -0.541 | -40.649 | 2.846 | 1.00 | 32.08 | C |
| ATOM | 2614 | CG | PHE | A | 176 | -1.094 | -39.252 | 2.691 | 1.00 | 31.82 | C |
| ATOM | 2615 | CD1 | PHE | A | 176 | -0.532 | -38.359 | 1.786 | 1.00 | 32.96 | C |
| ATOM | 2617 | CE1 | PHE | A | 176 | -1.048 | -37.070 | 1.643 | 1.00 | 32.60 | C |
| ATOM | 2619 | CZ | PHE | A | 176 | -2.128 | -36.674 | 2.415 | 1.00 | 31.47 | C |
| ATOM | 2621 | CE2 | PHE | A | 176 | -2.691 | -37.562 | 3.306 | 1.00 | 30.41 | C |
| ATOM | 2623 | CD2 | PHE | A | 176 | -2.176 | -38.834 | 3.440 | 1.00 | 30.66 | C |
| ATOM | 2625 | C | PHE | A | 176 | -0.187 | -42.499 | 4.486 | 1.00 | 32.30 | C |
| ATOM | 2626 | O | PHE | A | 176 | -1.203 | -42.995 | 4.982 | 1.00 | 32.74 | O |
| ATOM | 2628 | N | THR | A | 177 | 0.871 | -43.229 | 4.133 | 1.00 | 32.09 | N |
| ATOM | 2629 | CA | THR | A | 177 | 0.898 | -44.660 | 4.405 | 1.00 | 32.03 | C |
| ATOM | 2631 | CB | THR | A | 177 | 2.165 | -45.330 | 3.867 | 1.00 | 32.06 | C |
| ATOM | 2633 | OG1 | THR | A | 177 | 2.290 | -45.084 | 2.455 | 1.00 | 30.50 | O |
| ATOM | 2635 | CG2 | THR | A | 177 | 2.123 | -46.826 | 4.138 | 1.00 | 30.92 | C |
| ATOM | 2639 | C | THR | A | 177 | 0.770 | -44.943 | 5.911 | 1.00 | 32.84 | C |
| ATOM | 2640 | O | THR | A | 177 | 0.081 | -45.881 | 6.304 | 1.00 | 33.30 | O |
| ATOM | 2642 | N | ILE | A | 178 | 1.414 | -44.133 | 6.752 | 1.00 | 33.26 | N |
| ATOM | 2643 | CA | ILE | A | 178 | 1.328 | -44.321 | 8.196 | 1.00 | 33.71 | C |
| ATOM | 2645 | CB | ILE | A | 178 | 2.301 | -43.404 | 8.977 | 1.00 | 33.68 | C |
| ATOM | 2647 | CG1 | ILE | A | 178 | 3.758 | -43.806 | 8.729 | 1.00 | 33.87 | C |
| ATOM | 2650 | CD1 | ILE | A | 178 | 4.770 | -42.747 | 9.141 | 1.00 | 31.58 | C |
| ATOM | 2654 | CG2 | ILE | A | 178 | 2.017 | -43.475 | 10.472 | 1.00 | 33.34 | C |
| ATOM | 2658 | C | ILE | A | 178 | -0.088 | -44.000 | 8.648 | 1.00 | 34.49 | C |
| ATOM | 2659 | O | ILE | A | 178 | -0.646 | -44.678 | 9.510 | 1.00 | 34.24 | O |
| ATOM | 2661 | N | ARG | A | 179 | -0.645 | -42.951 | 8.049 | 1.00 | 35.35 | N |
| ATOM | 2662 | CA | ARG | A | 179 | -1.970 | -42.468 | 8.380 | 1.00 | 35.92 | C |
| ATOM | 2664 | CB | ARG | A | 179 | -2.264 | -41.190 | 7.608 | 1.00 | 35.74 | C |
| ATOM | 2667 | CG | ARG | A | 179 | -3.700 | -40.757 | 7.715 | 1.00 | 35.42 | C |
| ATOM | 2670 | CD | ARG | A | 179 | -3.938 | -39.436 | 7.075 | 1.00 | 34.74 | C |
| ATOM | 2673 | NE | ARG | A | 179 | -5.224 | -38.921 | 7.504 | 1.00 | 35.39 | N |
| ATOM | 2675 | CZ | ARG | A | 179 | -5.571 | -37.641 | 7.498 | 1.00 | 36.51 | C |
| ATOM | 2676 | NH1 | ARG | A | 179 | -4.725 | -36.708 | 7.076 | 1.00 | 37.51 | N |

FIG.16-24

| | | | | | | | | | | | |
|---|---|---|---|---|---|---|---|---|---|---|---|
| ATOM | 2679 | NH2 | ARG | A | 179 | -6.775 | -37.293 | 7.925 | 1.00 | 36.68 | N |
| ATOM | 2682 | C | ARG | A | 179 | -3.070 | -43.480 | 8.093 | 1.00 | 36.92 | C |
| ATOM | 2683 | O | ARG | A | 179 | -3.978 | -43.642 | 8.906 | 1.00 | 37.30 | O |
| ATOM | 2685 | N | GLN | A | 180 | -3.020 | -44.135 | 6.935 | 1.00 | 38.06 | N |
| ATOM | 2686 | CA | GLN | A | 180 | -4.070 | -45.107 | 6.586 | 1.00 | 38.99 | C |
| ATOM | 2688 | CB | GLN | A | 180 | -4.068 | -45.449 | 5.087 | 1.00 | 39.16 | C |
| ATOM | 2691 | CG | GLN | A | 180 | -3.512 | -46.837 | 4.735 | 1.00 | 40.72 | C |
| ATOM | 2694 | CD | GLN | A | 180 | -3.364 | -47.050 | 3.241 | 1.00 | 42.02 | C |
| ATOM | 2695 | OE1 | GLN | A | 180 | -4.150 | -46.524 | 2.449 | 1.00 | 42.40 | O |
| ATOM | 2696 | NE2 | GLN | A | 180 | -2.345 | -47.823 | 2.846 | 1.00 | 42.09 | N |
| ATOM | 2699 | C | GLN | A | 180 | -3.904 | -46.361 | 7.446 | 1.00 | 39.24 | C |
| ATOM | 2700 | O | GLN | A | 180 | -4.879 | -46.978 | 7.864 | 1.00 | 39.17 | O |
| ATOM | 2702 | N | GLU | A | 181 | -2.656 | -46.718 | 7.721 | 1.00 | 39.78 | N |
| ATOM | 2703 | CA | GLU | A | 181 | -2.358 | -47.867 | 8.577 | 1.00 | 40.30 | C |
| ATOM | 2705 | CB | GLU | A | 181 | -0.867 | -48.178 | 8.522 | 1.00 | 40.73 | C |
| ATOM | 2708 | CG | GLU | A | 181 | -0.387 | -48.673 | 7.157 | 1.00 | 42.79 | C |
| ATOM | 2711 | CD | GLU | A | 181 | -0.770 | -50.112 | 6.871 | 1.00 | 46.05 | C |
| ATOM | 2712 | OE1 | GLU | A | 181 | -1.321 | -50.781 | 7.775 | 1.00 | 49.04 | O |
| ATOM | 2713 | OE2 | GLU | A | 181 | -0.518 | -50.574 | 5.732 | 1.00 | 48.35 | O |
| ATOM | 2714 | C | GLU | A | 181 | -2.811 | -47.632 | 10.027 | 1.00 | 39.89 | C |
| ATOM | 2715 | O | GLU | A | 181 | -3.125 | -48.577 | 10.754 | 1.00 | 39.81 | O |
| ATOM | 2717 | N | MET | A | 182 | -2.840 | -46.368 | 10.438 | 1.00 | 39.35 | N |
| ATOM | 2718 | CA | MET | A | 182 | -3.399 | -46.011 | 11.722 | 1.00 | 38.92 | C |
| ATOM | 2720 | CB | MET | A | 182 | -2.992 | -44.589 | 12.136 | 1.00 | 38.53 | C |
| ATOM | 2723 | CG | MET | A | 182 | -1.592 | -44.498 | 12.787 | 1.00 | 37.73 | C |
| ATOM | 2726 | SD | MET | A | 182 | -1.129 | -42.822 | 13.310 | 1.00 | 34.01 | S |
| ATOM | 2727 | CE | MET | A | 182 | 0.574 | -43.048 | 13.786 | 1.00 | 34.19 | C |
| ATOM | 2731 | C | MET | A | 182 | -4.917 | -46.148 | 11.615 | 1.00 | 39.25 | C |
| ATOM | 2732 | O | MET | A | 182 | -5.519 | -47.010 | 12.272 | 1.00 | 39.36 | O |
| ATOM | 2734 | N | ALA | A | 183 | -5.519 | -45.320 | 10.761 | 1.00 | 39.15 | N |
| ATOM | 2735 | CA | ALA | A | 183 | -6.974 | -45.289 | 10.569 | 1.00 | 39.02 | C |
| ATOM | 2737 | CB | ALA | A | 183 | -7.326 | -44.548 | 9.275 | 1.00 | 38.79 | C |
| ATOM | 2741 | C | ALA | A | 183 | -7.627 | -46.683 | 10.596 | 1.00 | 38.82 | C |
| ATOM | 2742 | O | ALA | A | 183 | -8.561 | -46.902 | 11.368 | 1.00 | 38.96 | O |
| ATOM | 2744 | N | SER | A | 184 | -7.116 | -47.617 | 9.792 | 1.00 | 38.77 | N |
| ATOM | 2745 | CA | SER | A | 184 | -7.605 | -49.014 | 9.749 | 1.00 | 38.98 | C |
| ATOM | 2747 | CB | SER | A | 184 | -6.678 | -49.877 | 8.890 | 1.00 | 38.86 | C |
| ATOM | 2750 | OG | SER | A | 184 | -6.559 | -49.351 | 7.586 | 1.00 | 39.28 | O |
| ATOM | 2752 | C | SER | A | 184 | -7.730 | -49.708 | 11.108 | 1.00 | 39.27 | C |
| ATOM | 2753 | O | SER | A | 184 | -8.301 | -50.781 | 11.200 | 1.00 | 39.52 | O |
| ATOM | 2755 | N | ARG | A | 185 | -7.152 | -49.118 | 12.145 | 1.00 | 39.75 | N |
| ATOM | 2756 | CA | ARG | A | 185 | -7.150 | -49.696 | 13.480 | 1.00 | 39.90 | C |
| ATOM | 2758 | CB | ARG | A | 185 | -5.725 | -50.107 | 13.827 | 1.00 | 40.06 | C |
| ATOM | 2761 | CG | ARG | A | 185 | -5.047 | -50.681 | 12.615 | 1.00 | 41.02 | C |
| ATOM | 2764 | CD | ARG | A | 185 | -3.666 | -51.231 | 12.835 | 1.00 | 42.83 | C |
| ATOM | 2767 | NE | ARG | A | 185 | -3.146 | -51.627 | 11.526 | 1.00 | 45.27 | N |
| ATOM | 2769 | CZ | ARG | A | 185 | -2.028 | -52.312 | 11.316 | 1.00 | 46.99 | C |
| ATOM | 2770 | NH1 | ARG | A | 185 | -1.255 | -52.695 | 12.334 | 1.00 | 47.24 | N |
| ATOM | 2773 | NH2 | ARG | A | 185 | -1.683 | -52.612 | 10.069 | 1.00 | 47.68 | N |
| ATOM | 2776 | C | ARG | A | 185 | -7.696 | -48.682 | 14.465 | 1.00 | 39.80 | C |
| ATOM | 2777 | O | ARG | A | 185 | -7.506 | -48.802 | 15.670 | 1.00 | 39.41 | O |
| ATOM | 2779 | N | SER | A | 186 | -8.389 | -47.681 | 13.932 | 1.00 | 40.05 | N |
| ATOM | 2780 | CA | SER | A | 186 | -9.030 | -46.664 | 14.741 | 1.00 | 40.57 | C |
| ATOM | 2782 | CB | SER | A | 186 | -10.206 | -47.281 | 15.541 | 1.00 | 40.69 | C |
| ATOM | 2785 | OG | SER | A | 186 | -11.017 | -48.135 | 14.736 | 1.00 | 40.64 | O |
| ATOM | 2787 | C | SER | A | 186 | -8.050 | -45.948 | 15.689 | 1.00 | 40.70 | C |
| ATOM | 2788 | O | SER | A | 186 | -8.476 | -45.360 | 16.679 | 1.00 | 41.28 | O |
| ATOM | 2790 | N | LEU | A | 187 | -6.751 | -45.986 | 15.384 | 1.00 | 40.68 | N |
| ATOM | 2791 | CA | LEU | A | 187 | -5.736 | -45.307 | 16.194 | 1.00 | 40.33 | C |
| ATOM | 2793 | CB | LEU | A | 187 | -4.403 | -46.057 | 16.133 | 1.00 | 40.08 | C |
| ATOM | 2796 | CG | LEU | A | 187 | -4.357 | -47.541 | 16.534 | 1.00 | 39.09 | C |
| ATOM | 2798 | CD1 | LEU | A | 187 | -3.067 | -48.181 | 16.053 | 1.00 | 38.05 | C |
| ATOM | 2802 | CD2 | LEU | A | 187 | -4.505 | -47.732 | 18.021 | 1.00 | 37.25 | C |

FIG.16-25

| | | | | | | | | | | | |
|---|---|---|---|---|---|---|---|---|---|---|---|
| ATOM | 2806 | C | LEU | A | 187 | -5.532 | -43.881 | 15.688 | 1.00 | 40.83 | C |
| ATOM | 2807 | O | LEU | A | 187 | -5.029 | -43.024 | 16.414 | 1.00 | 41.20 | O |
| ATOM | 2809 | N | TRP | A | 188 | -5.920 | -43.630 | 14.441 | 1.00 | 41.26 | N |
| ATOM | 2810 | CA | TRP | A | 188 | -5.656 | -42.345 | 13.795 | 1.00 | 41.52 | C |
| ATOM | 2812 | CB | TRP | A | 188 | -6.150 | -42.339 | 12.343 | 1.00 | 41.50 | C |
| ATOM | 2815 | CG | TRP | A | 188 | -6.158 | -40.966 | 11.809 | 1.00 | 41.20 | C |
| ATOM | 2816 | CD1 | TRP | A | 188 | -7.246 | -40.187 | 11.564 | 1.00 | 41.75 | C |
| ATOM | 2818 | NE1 | TRP | A | 188 | -6.854 | -38.950 | 11.114 | 1.00 | 42.16 | N |
| ATOM | 2820 | CE2 | TRP | A | 188 | -5.483 | -38.908 | 11.087 | 1.00 | 42.58 | C |
| ATOM | 2821 | CD2 | TRP | A | 188 | -5.014 | -40.163 | 11.532 | 1.00 | 41.22 | C |
| ATOM | 2822 | CE3 | TRP | A | 188 | -3.637 | -40.383 | 11.606 | 1.00 | 41.13 | C |
| ATOM | 2824 | CZ3 | TRP | A | 188 | -2.777 | -39.363 | 11.228 | 1.00 | 41.93 | C |
| ATOM | 2826 | CH2 | TRP | A | 188 | -3.271 | -38.117 | 10.792 | 1.00 | 42.24 | C |
| ATOM | 2828 | CZ2 | TRP | A | 188 | -4.615 | -37.871 | 10.713 | 1.00 | 42.53 | C |
| ATOM | 2830 | C | TRP | A | 188 | -6.292 | -41.168 | 14.514 | 1.00 | 41.88 | C |
| ATOM | 2831 | O | TRP | A | 188 | -5.659 | -40.115 | 14.695 | 1.00 | 41.56 | O |
| ATOM | 2833 | N | ASP | A | 189 | -7.552 | -41.342 | 14.894 | 1.00 | 42.52 | N |
| ATOM | 2834 | CA | ASP | A | 189 | -8.345 | -40.228 | 15.412 | 1.00 | 43.24 | C |
| ATOM | 2836 | CB | ASP | A | 189 | -9.828 | -40.605 | 15.492 | 1.00 | 43.54 | C |
| ATOM | 2839 | CG | ASP | A | 189 | -10.722 | -39.489 | 15.019 | 1.00 | 45.48 | C |
| ATOM | 2840 | OD1 | ASP | A | 189 | -11.025 | -39.463 | 13.797 | 1.00 | 47.35 | O |
| ATOM | 2841 | OD2 | ASP | A | 189 | -11.083 | -38.618 | 15.854 | 1.00 | 47.65 | O |
| ATOM | 2842 | C | ASP | A | 189 | -7.820 | -39.746 | 16.764 | 1.00 | 43.04 | C |
| ATOM | 2843 | O | ASP | A | 189 | -7.793 | -38.551 | 17.034 | 1.00 | 42.91 | O |
| ATOM | 2845 | N | SER | A | 190 | -7.384 | -40.684 | 17.596 | 1.00 | 43.12 | N |
| ATOM | 2846 | CA | SER | A | 190 | -6.683 | -40.353 | 18.825 | 1.00 | 43.43 | C |
| ATOM | 2848 | CB | SER | A | 190 | -6.379 | -41.629 | 19.605 | 1.00 | 43.34 | C |
| ATOM | 2851 | OG | SER | A | 190 | -5.852 | -41.319 | 20.879 | 1.00 | 44.13 | O |
| ATOM | 2853 | C | SER | A | 190 | -5.380 | -39.593 | 18.517 | 1.00 | 43.77 | C |
| ATOM | 2854 | O | SER | A | 190 | -5.183 | -38.458 | 18.961 | 1.00 | 43.68 | O |
| ATOM | 2856 | N | PHE | A | 191 | -4.513 | -40.227 | 17.733 | 1.00 | 44.05 | N |
| ATOM | 2857 | CA | PHE | A | 191 | -3.239 | -39.649 | 17.347 | 1.00 | 44.52 | C |
| ATOM | 2859 | CB | PHE | A | 191 | -2.602 | -40.522 | 16.265 | 1.00 | 44.54 | C |
| ATOM | 2862 | CG | PHE | A | 191 | -1.213 | -40.111 | 15.864 | 1.00 | 43.80 | C |
| ATOM | 2863 | CD1 | PHE | A | 191 | -0.143 | -40.272 | 16.740 | 1.00 | 44.21 | C |
| ATOM | 2865 | CE1 | PHE | A | 191 | 1.145 | -39.922 | 16.358 | 1.00 | 43.71 | C |
| ATOM | 2867 | CZ | PHE | A | 191 | 1.379 | -39.413 | 15.079 | 1.00 | 42.78 | C |
| ATOM | 2869 | CE2 | PHE | A | 191 | 0.330 | -39.261 | 14.199 | 1.00 | 42.36 | C |
| ATOM | 2871 | CD2 | PHE | A | 191 | -0.961 | -39.616 | 14.589 | 1.00 | 42.74 | C |
| ATOM | 2873 | C | PHE | A | 191 | -3.418 | -38.219 | 16.860 | 1.00 | 45.33 | C |
| ATOM | 2874 | O | PHE | A | 191 | -2.665 | -37.342 | 17.254 | 1.00 | 45.14 | O |
| ATOM | 2876 | N | ARG | A | 192 | -4.426 | -37.972 | 16.026 | 1.00 | 46.63 | N |
| ATOM | 2877 | CA | ARG | A | 192 | -4.671 | -36.612 | 15.538 | 1.00 | 47.77 | C |
| ATOM | 2879 | CB | ARG | A | 192 | -5.832 | -36.549 | 14.539 | 1.00 | 48.21 | C |
| ATOM | 2882 | CG | ARG | A | 192 | -5.687 | -35.388 | 13.549 | 1.00 | 49.97 | C |
| ATOM | 2885 | CD | ARG | A | 192 | -7.011 | -34.760 | 13.077 | 1.00 | 52.52 | C |
| ATOM | 2888 | NE | ARG | A | 192 | -6.735 | -33.566 | 12.262 | 1.00 | 54.29 | N |
| ATOM | 2890 | CZ | ARG | A | 192 | -7.644 | -32.844 | 11.606 | 1.00 | 54.80 | C |
| ATOM | 2891 | NH1 | ARG | A | 192 | -8.935 | -33.168 | 11.646 | 1.00 | 55.57 | N |
| ATOM | 2894 | NH2 | ARG | A | 192 | -7.251 | -31.785 | 10.903 | 1.00 | 54.56 | N |
| ATOM | 2897 | C | ARG | A | 192 | -4.955 | -35.644 | 16.683 | 1.00 | 48.26 | C |
| ATOM | 2898 | O | ARG | A | 192 | -4.364 | -34.566 | 16.741 | 1.00 | 48.45 | O |
| ATOM | 2900 | N | GLN | A | 193 | -5.842 | -36.035 | 17.598 | 1.00 | 48.69 | N |
| ATOM | 2901 | CA | GLN | A | 193 | -6.274 | -35.139 | 18.681 | 1.00 | 49.13 | C |
| ATOM | 2903 | CB | GLN | A | 193 | -7.613 | -35.613 | 19.253 | 1.00 | 49.42 | C |
| ATOM | 2906 | CG | GLN | A | 193 | -8.767 | -35.559 | 18.245 | 1.00 | 50.46 | C |
| ATOM | 2909 | CD | GLN | A | 193 | -10.039 | -36.207 | 18.776 | 1.00 | 51.87 | C |
| ATOM | 2910 | OE1 | GLN | A | 193 | -10.338 | -36.119 | 19.972 | 1.00 | 52.98 | O |
| ATOM | 2911 | NE2 | GLN | A | 193 | -10.796 | -36.860 | 17.888 | 1.00 | 51.85 | N |
| ATOM | 2914 | C | GLN | A | 193 | -5.256 | -34.950 | 19.822 | 1.00 | 49.03 | C |
| ATOM | 2915 | O | GLN | A | 193 | -5.313 | -33.953 | 20.546 | 1.00 | 49.13 | O |
| ATOM | 2917 | N | SER | A | 194 | -4.325 | -35.883 | 19.977 | 1.00 | 48.96 | N |
| ATOM | 2918 | CA | SER | A | 194 | -3.383 | -35.835 | 21.102 | 1.00 | 49.13 | C |

FIG.16-26

| | | | | | | | | | | | |
|---|---|---|---|---|---|---|---|---|---|---|---|
| ATOM | 2920 | CB | SER | A | 194 | -2.706 | -37.200 | 21.295 | 1.00 | 49.05 | C |
| ATOM | 2923 | OG | SER | A | 194 | -1.924 | -37.556 | 20.168 | 1.00 | 48.43 | O |
| ATOM | 2925 | C | SER | A | 194 | -2.318 | -34.719 | 21.008 | 1.00 | 49.40 | C |
| ATOM | 2926 | O | SER | A | 194 | -1.701 | -34.367 | 22.015 | 1.00 | 49.53 | O |
| ATOM | 2928 | N | GLU | A | 195 | -2.107 | -34.160 | 19.820 | 1.00 | 49.59 | N |
| ATOM | 2929 | CA | GLU | A | 195 | -1.167 | -33.060 | 19.656 | 1.00 | 49.84 | C |
| ATOM | 2931 | CB | GLU | A | 195 | -0.885 | -32.832 | 18.168 | 1.00 | 49.58 | C |
| ATOM | 2934 | CG | GLU | A | 195 | 0.398 | -32.064 | 17.912 | 1.00 | 49.65 | C |
| ATOM | 2937 | CD | GLU | A | 195 | 0.694 | -31.811 | 16.441 | 1.00 | 48.50 | C |
| ATOM | 2938 | OE1 | GLU | A | 195 | 0.088 | -32.456 | 15.572 | 1.00 | 47.38 | O |
| ATOM | 2939 | OE2 | GLU | A | 195 | 1.553 | -30.956 | 16.152 | 1.00 | 48.72 | O |
| ATOM | 2940 | C | GLU | A | 195 | -1.711 | -31.784 | 20.312 | 1.00 | 50.65 | C |
| ATOM | 2941 | O | GLU | A | 195 | -2.155 | -30.867 | 19.625 | 1.00 | 50.92 | O |
| ATOM | 2943 | N | ARG | A | 196 | -1.684 | -31.732 | 21.645 | 1.00 | 51.54 | N |
| ATOM | 2944 | CA | ARG | A | 196 | -2.200 | -30.571 | 22.402 | 1.00 | 52.12 | C |
| ATOM | 2946 | CB | ARG | A | 196 | -3.042 | -31.017 | 23.606 | 1.00 | 52.42 | C |
| ATOM | 2949 | CG | ARG | A | 196 | -4.243 | -31.923 | 23.284 | 1.00 | 53.48 | C |
| ATOM | 2952 | CD | ARG | A | 196 | -4.777 | -32.581 | 24.568 | 1.00 | 54.83 | C |
| ATOM | 2955 | NE | ARG | A | 196 | -5.630 | -33.736 | 24.296 | 1.00 | 55.74 | N |
| ATOM | 2957 | CZ | ARG | A | 196 | -5.990 | -34.655 | 25.195 | 1.00 | 57.08 | C |
| ATOM | 2958 | NH1 | ARG | A | 196 | -5.583 | -34.586 | 26.464 | 1.00 | 57.73 | N |
| ATOM | 2961 | NH2 | ARG | A | 196 | -6.769 | -35.664 | 24.819 | 1.00 | 57.50 | N |
| ATOM | 2964 | C | ARG | A | 196 | -1.047 | -29.719 | 22.913 | 1.00 | 52.08 | C |
| ATOM | 2965 | O | ARG | A | 196 | -0.327 | -30.128 | 23.829 | 1.00 | 52.03 | O |
| ATOM | 2967 | O11 | tte | B | 801 | 10.835 | -36.373 | 17.796 | 1.00 | 42.05 | O |
| ATOM | 2968 | C10 | tte | B | 801 | 10.316 | -35.557 | 18.550 | 1.00 | 40.00 | C |
| ATOM | 2969 | C5 | tte | B | 801 | 8.873 | -35.153 | 18.337 | 1.00 | 39.47 | C |
| ATOM | 2970 | C6 | tte | B | 801 | 7.809 | -35.410 | 19.226 | 1.00 | 39.38 | C |
| ATOM | 2972 | C1 | tte | B | 801 | 6.496 | -35.030 | 18.895 | 1.00 | 39.35 | C |
| ATOM | 2973 | O7 | tte | B | 801 | 5.447 | -35.260 | 19.747 | 1.00 | 38.95 | O |
| ATOM | 2975 | C2 | tte | B | 801 | 6.242 | -34.403 | 17.681 | 1.00 | 38.89 | C |
| ATOM | 2976 | O8 | tte | B | 801 | 4.967 | -34.019 | 17.368 | 1.00 | 38.97 | O |
| ATOM | 2978 | C3 | tte | B | 801 | 7.291 | -34.164 | 16.799 | 1.00 | 38.72 | C |
| ATOM | 2979 | O9 | tte | B | 801 | 7.090 | -33.549 | 15.599 | 1.00 | 38.53 | O |
| ATOM | 2981 | C4 | tte | B | 801 | 8.587 | -34.545 | 17.128 | 1.00 | 38.93 | C |
| ATOM | 2983 | O12 | tte | B | 801 | 11.220 | -35.067 | 19.560 | 1.00 | 40.90 | O |
| ATOM | 2984 | C13 | tte | B | 801 | 10.646 | -34.543 | 20.741 | 1.00 | 41.82 | C |
| ATOM | 2986 | C14 | tte | B | 801 | 10.591 | -32.999 | 20.659 | 1.00 | 42.19 | C |
| ATOM | 2988 | C19 | tte | B | 801 | 11.286 | -32.627 | 19.406 | 1.00 | 41.36 | C |
| ATOM | 2989 | C20 | tte | B | 801 | 12.663 | -32.838 | 19.328 | 1.00 | 41.52 | C |
| ATOM | 2991 | C21 | tte | B | 801 | 13.349 | -32.548 | 18.152 | 1.00 | 41.30 | C |
| ATOM | 2992 | O25 | tte | B | 801 | 14.596 | -32.713 | 18.106 | 1.00 | 40.42 | O |
| ATOM | 2993 | C22 | tte | B | 801 | 12.637 | -32.067 | 17.056 | 1.00 | 40.80 | C |
| ATOM | 2994 | O26 | tte | B | 801 | 13.259 | -31.813 | 16.006 | 1.00 | 39.62 | O |
| ATOM | 2995 | C24 | tte | B | 801 | 10.560 | -32.161 | 18.303 | 1.00 | 40.37 | C |
| ATOM | 2997 | C23 | tte | B | 801 | 11.245 | -31.870 | 17.117 | 1.00 | 41.43 | C |
| ATOM | 2998 | O32 | tte | B | 801 | 10.614 | -31.426 | 16.117 | 1.00 | 39.59 | O |
| ATOM | 2999 | C18 | tte | B | 801 | 11.449 | -35.083 | 21.917 | 1.00 | 40.77 | C |
| ATOM | 3002 | C17 | tte | B | 801 | 10.752 | -34.444 | 23.085 | 1.00 | 41.20 | C |
| ATOM | 3003 | C16 | tte | B | 801 | 10.617 | -33.070 | 22.993 | 1.00 | 41.65 | C |
| ATOM | 3004 | O15 | tte | B | 801 | 11.135 | -32.467 | 21.865 | 1.00 | 41.79 | O |
| ATOM | 3005 | C27 | tte | B | 801 | 10.240 | -35.151 | 24.162 | 1.00 | 40.94 | C |
| ATOM | 3006 | O33 | tte | B | 801 | 10.387 | -36.498 | 24.231 | 1.00 | 39.60 | O |
| ATOM | 3008 | C28 | tte | B | 801 | 9.590 | -34.451 | 25.183 | 1.00 | 42.18 | C |
| ATOM | 3010 | C29 | tte | B | 801 | 9.456 | -33.054 | 25.106 | 1.00 | 42.77 | C |
| ATOM | 3011 | O31 | tte | B | 801 | 8.828 | -32.352 | 26.102 | 1.00 | 42.73 | O |
| ATOM | 3013 | C30 | tte | B | 801 | 9.964 | -32.366 | 24.001 | 1.00 | 41.87 | C |
| ATOM | 3015 | MN | MN | D | 901 | 12.532 | -31.587 | 14.372 | 1.00 | 25.44 | MN |
| ATOM | 3016 | MN | MN | D | 902 | 15.458 | -32.653 | 16.373 | 1.00 | 30.83 | MN |
| ATOM | 3017 | OH2 | HOH | Z | 2 | 13.415 | -51.245 | 18.884 | 1.00 | 26.91 | O |
| ATOM | 3020 | OH2 | HOH | Z | 3 | 16.730 | -33.917 | -3.716 | 1.00 | 25.18 | O |
| ATOM | 3023 | OH2 | HOH | Z | 4 | 2.436 | -30.369 | -0.702 | 1.00 | 39.86 | O |
| ATOM | 3026 | OH2 | HOH | Z | 5 | 36.083 | -30.269 | 12.439 | 1.00 | 58.91 | O |

FIG.16-27

| | | | | | | | | | | | |
|---|---|---|---|---|---|---|---|---|---|---|---|
| ATOM | 3029 | OH2 | HOH | Z | 6 | -5.686 | -30.717 | 12.774 | 1.00 | 40.87 | O |
| ATOM | 3032 | OH2 | HOH | Z | 7 | 9.268 | -52.765 | 11.043 | 1.00 | 29.78 | O |
| ATOM | 3035 | OH2 | HOH | Z | 8 | 16.565 | -46.983 | 10.118 | 1.00 | 43.71 | O |
| ATOM | 3038 | OH2 | HOH | Z | 10 | 13.737 | -26.906 | 3.048 | 1.00 | 36.56 | O |
| ATOM | 3041 | OH2 | HOH | Z | 11 | 13.318 | -28.904 | 17.467 | 1.00 | 38.71 | O |
| ATOM | 3044 | OH2 | HOH | Z | 12 | -2.332 | -42.550 | 24.481 | 1.00 | 35.70 | O |
| ATOM | 3047 | OH2 | HOH | Z | 13 | 20.526 | -35.810 | 18.407 | 1.00 | 23.17 | O |
| ATOM | 3050 | OH2 | HOH | Z | 14 | 2.036 | -35.807 | 20.623 | 1.00 | 27.82 | O |
| ATOM | 3053 | OH2 | HOH | Z | 15 | 17.502 | -51.219 | 12.607 | 1.00 | 31.36 | O |
| ATOM | 3056 | OH2 | HOH | Z | 17 | 10.285 | -17.576 | 5.959 | 1.00 | 34.10 | O |
| ATOM | 3059 | OH2 | HOH | Z | 18 | 19.185 | -28.489 | 22.437 | 1.00 | 31.79 | O |
| ATOM | 3062 | OH2 | HOH | Z | 19 | -8.668 | -42.953 | 17.301 | 1.00 | 33.17 | O |
| ATOM | 3065 | OH2 | HOH | Z | 20 | 1.902 | -50.725 | 10.398 | 1.00 | 48.28 | O |
| ATOM | 3068 | OH2 | HOH | Z | 21 | 4.812 | -40.883 | 30.946 | 1.00 | 36.95 | O |
| ATOM | 3071 | OH2 | HOH | Z | 23 | 0.803 | -39.798 | 24.130 | 1.00 | 22.17 | O |
| ATOM | 3074 | OH2 | HOH | Z | 24 | 29.680 | -32.800 | 22.760 | 1.00 | 24.02 | O |
| ATOM | 3077 | OH2 | HOH | Z | 26 | 10.321 | -47.201 | 9.731 | 1.00 | 31.65 | O |
| ATOM | 3080 | OH2 | HOH | Z | 27 | 33.994 | -31.256 | 17.131 | 1.00 | 26.61 | O |
| ATOM | 3083 | OH2 | HOH | Z | 28 | 9.636 | -48.440 | 32.425 | 1.00 | 44.68 | O |
| ATOM | 3086 | OH2 | HOH | Z | 29 | 17.662 | -32.975 | 16.700 | 1.00 | 25.53 | O |
| ATOM | 3089 | OH2 | HOH | Z | 30 | 11.999 | -33.828 | -8.615 | 1.00 | 33.84 | O |
| ATOM | 3092 | OH2 | HOH | Z | 31 | 15.640 | -30.617 | 16.684 | 1.00 | 25.52 | O |
| ATOM | 3095 | OH2 | HOH | Z | 32 | 1.758 | -19.230 | 9.258 | 1.00 | 52.92 | O |
| ATOM | 3098 | OH2 | HOH | Z | 33 | -0.001 | -23.575 | 5.431 | 1.00 | 46.79 | O |
| ATOM | 3101 | OH2 | HOH | Z | 34 | 12.384 | -30.143 | 25.192 | 1.00 | 54.67 | O |
| ATOM | 3104 | OH2 | HOH | Z | 36 | 25.120 | -37.878 | 8.328 | 1.00 | 36.86 | O |
| ATOM | 3107 | OH2 | HOH | Z | 37 | 13.744 | -27.369 | -4.131 | 1.00 | 46.71 | O |
| ATOM | 3110 | OH2 | HOH | Z | 38 | 18.892 | -27.020 | 3.282 | 1.00 | 29.31 | O |
| ATOM | 3113 | OH2 | HOH | Z | 40 | 4.643 | -45.577 | 1.211 | 1.00 | 43.16 | O |

Figure 17: H1N1 PA structure with EMBL-R05-1 bound structure
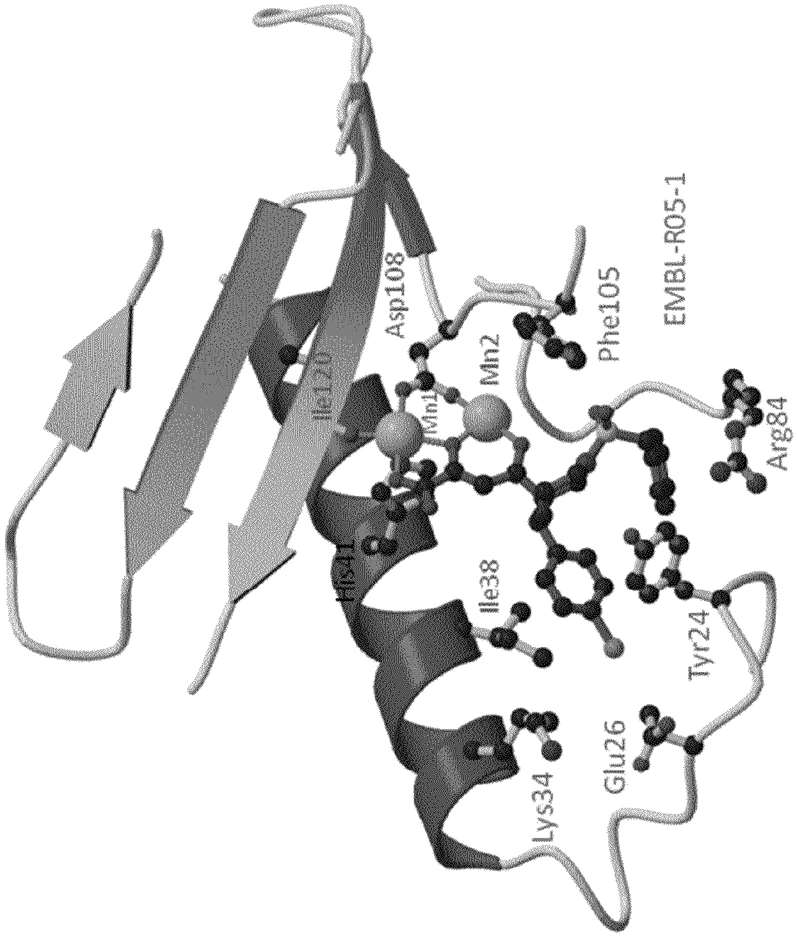

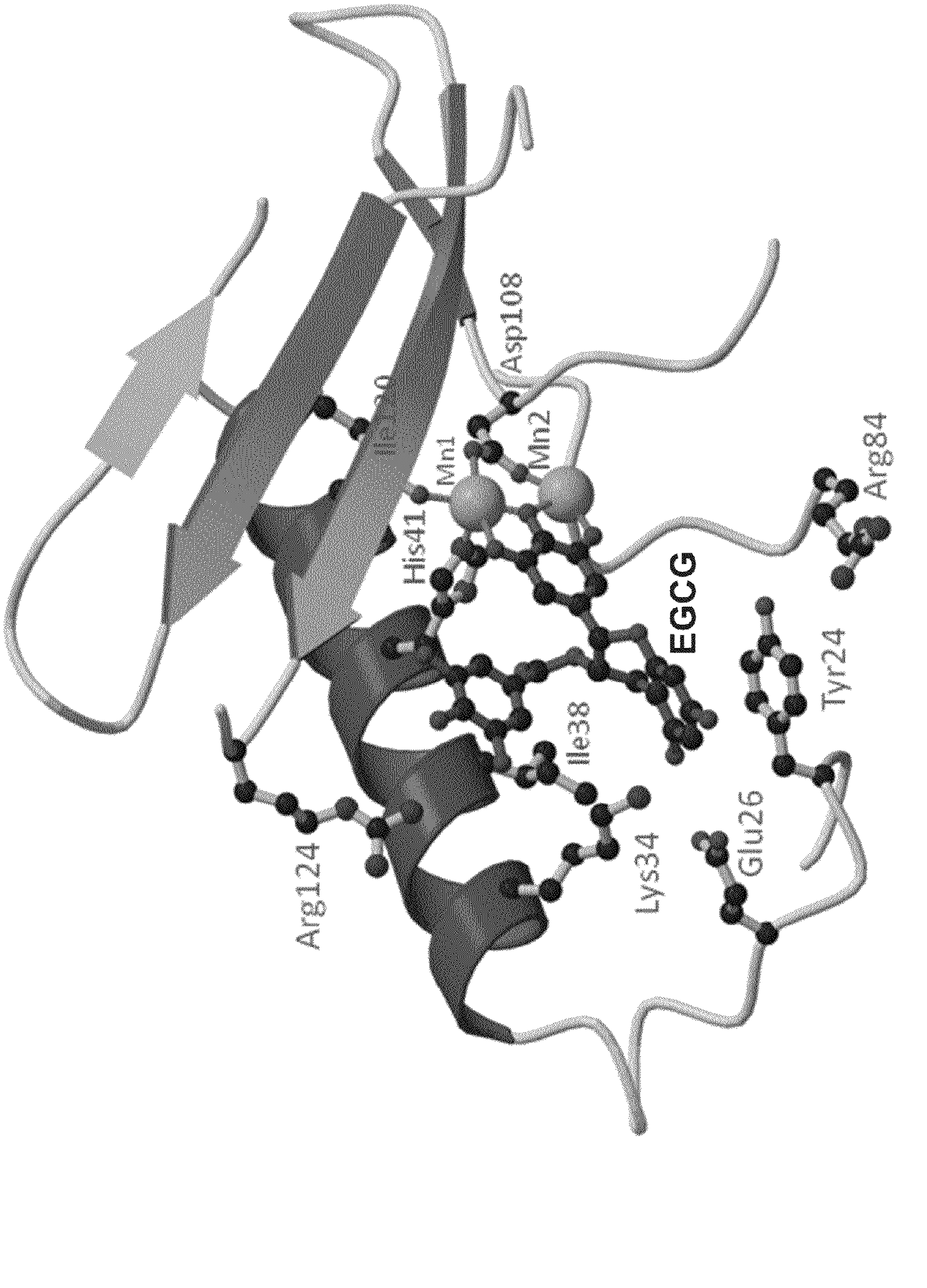
Figure 18A: H1N1 PA structure with EGCG bound structure

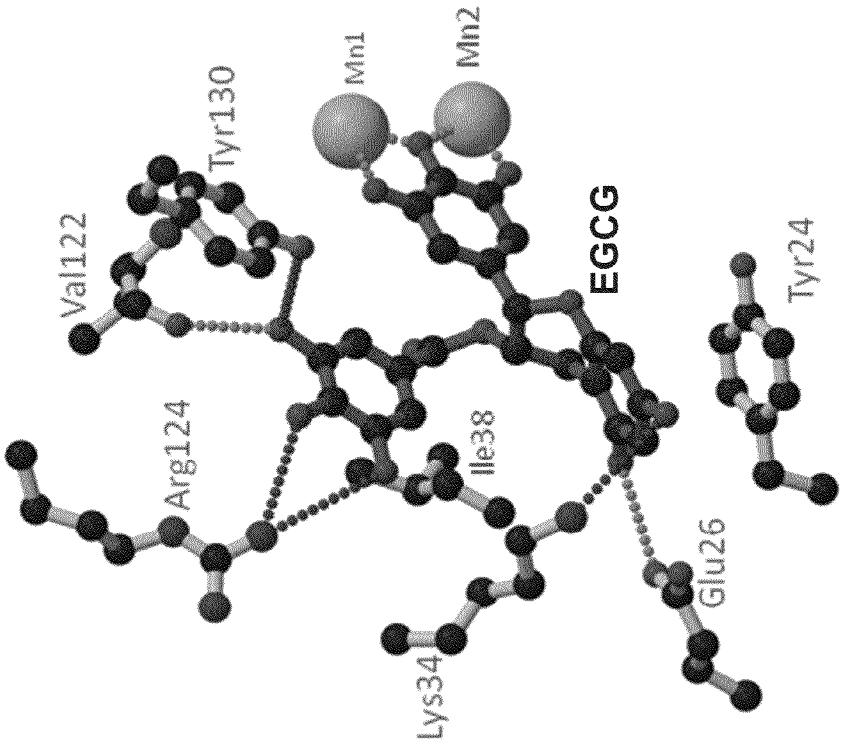
Figure 18B: H1N1 PA structure with EGCG bound structure

SEQUENCE LISTING

```
<160> NUMBER OF SEQ ID NOS: 16

<210> SEQ ID NO 1
<211> LENGTH: 2151
<212> TYPE: DNA
<213> ORGANISM: Influenza A pandemic H1N1 virus (A/California/04/2009)
<220> FEATURE:
<221> NAME/KEY: CDS
<222> LOCATION: (1)..(2151)
<223> OTHER INFORMATION: PA-subunit of the Influenza A pandemic H1N1
      virus (A/California/04/2009) RNA-dependent RNA polymerase

<400> SEQUENCE: 1

atg gaa gac ttt gtg cga caa tgc ttc aat cca atg atc gtc gag ctt       48
Met Glu Asp Phe Val Arg Gln Cys Phe Asn Pro Met Ile Val Glu Leu
1               5                   10                  15

gcg gaa aag gca atg aaa gaa tat ggg gaa gat ccg aaa atc gaa act       96
Ala Glu Lys Ala Met Lys Glu Tyr Gly Glu Asp Pro Lys Ile Glu Thr
            20                  25                  30

aac aag ttt gct gca ata tgc aca cat ttg gaa gtt tgt ttc atg tat      144
Asn Lys Phe Ala Ala Ile Cys Thr His Leu Glu Val Cys Phe Met Tyr
        35                  40                  45

tcg gat ttc cat ttc atc gac gaa cgg ggt gaa tca ata att gta gaa      192
Ser Asp Phe His Phe Ile Asp Glu Arg Gly Glu Ser Ile Ile Val Glu
    50                  55                  60

tct ggt gac ccg aat gca cta ttg aag cac cga ttt gag ata att gaa      240
Ser Gly Asp Pro Asn Ala Leu Leu Lys His Arg Phe Glu Ile Ile Glu
65                  70                  75                  80

gga aga gac cga atc atg gcc tgg aca gtg gtg aac agt ata tgt aac      288
Gly Arg Asp Arg Ile Met Ala Trp Thr Val Val Asn Ser Ile Cys Asn
                85                  90                  95

aca aca ggg gta gag aag cct aaa ttt ctt cct gat ttg tat gat tac      336
Thr Thr Gly Val Glu Lys Pro Lys Phe Leu Pro Asp Leu Tyr Asp Tyr
            100                 105                 110

aaa gag aac cgg ttc att gaa att gga gta aca cgg agg gaa gtc cac      384
Lys Glu Asn Arg Phe Ile Glu Ile Gly Val Thr Arg Arg Glu Val His
        115                 120                 125

ata tat tac cta gag aaa gcc aac aaa ata aaa tct gag aag aca cac      432
Ile Tyr Tyr Leu Glu Lys Ala Asn Lys Ile Lys Ser Glu Lys Thr His
    130                 135                 140

att cac atc ttt tca ttc act gga gag gag atg gcc acc aaa gcg gac      480
Ile His Ile Phe Ser Phe Thr Gly Glu Glu Met Ala Thr Lys Ala Asp
145                 150                 155                 160
```

-continued

```
tac acc ctt gac gaa gag agc agg gca aga atc aaa act agg ctt ttc      528
Tyr Thr Leu Asp Glu Glu Ser Arg Ala Arg Ile Lys Thr Arg Leu Phe
                165                 170                 175

act ata aga caa gaa atg gcc agt agg agt cta tgg gat tcc ttt cgt      576
Thr Ile Arg Gln Glu Met Ala Ser Arg Ser Leu Trp Asp Ser Phe Arg
            180                 185                 190

cag tcc gaa aga ggc gaa gag aca att gaa gaa aaa ttt gag att aca      624
Gln Ser Glu Arg Gly Glu Glu Thr Ile Glu Glu Lys Phe Glu Ile Thr
        195                 200                 205

gga act atg cgc aag ctt gcc gac caa agt ctc cca ccg aac ttc ccc      672
Gly Thr Met Arg Lys Leu Ala Asp Gln Ser Leu Pro Pro Asn Phe Pro
    210                 215                 220

agc ctt gaa aac ttt aga gcc tat gta gat gga ttc gag ccg aac ggc      720
Ser Leu Glu Asn Phe Arg Ala Tyr Val Asp Gly Phe Glu Pro Asn Gly
225                 230                 235                 240

tgc att gag ggc aag ctt tcc caa atg tca aaa gaa gtg aac gcc aaa      768
Cys Ile Glu Gly Lys Leu Ser Gln Met Ser Lys Glu Val Asn Ala Lys
                245                 250                 255

att gaa cca ttc ttg agg acg aca cca cgc ccc ctc aga ttg cct gat      816
Ile Glu Pro Phe Leu Arg Thr Thr Pro Arg Pro Leu Arg Leu Pro Asp
            260                 265                 270

ggg cct ctt tgc cat cag cgg tca aag ttc ctg ctg atg gat gct ctg      864
Gly Pro Leu Cys His Gln Arg Ser Lys Phe Leu Leu Met Asp Ala Leu
        275                 280                 285

aaa tta agt att gaa gac ccg agt cac gag ggg gag gga ata cca cta      912
Lys Leu Ser Ile Glu Asp Pro Ser His Glu Gly Glu Gly Ile Pro Leu
    290                 295                 300

tat gat gca atc aaa tgc atg aag aca ttc ttt ggc tgg aaa gag cct      960
Tyr Asp Ala Ile Lys Cys Met Lys Thr Phe Phe Gly Trp Lys Glu Pro
305                 310                 315                 320

aac ata gtc aaa cca cat gag aaa ggc ata aat ccc aat tac ctc atg     1008
Asn Ile Val Lys Pro His Glu Lys Gly Ile Asn Pro Asn Tyr Leu Met
                325                 330                 335

gct tgg aag cag gtg cta gca gag cta cag gac att gaa aat gaa gag     1056
Ala Trp Lys Gln Val Leu Ala Glu Leu Gln Asp Ile Glu Asn Glu Glu
            340                 345                 350

aag atc cca agg aca aag aac atg aag aga aca agc caa ttg aag tgg     1104
Lys Ile Pro Arg Thr Lys Asn Met Lys Arg Thr Ser Gln Leu Lys Trp
        355                 360                 365

gca ctc ggt gaa aat atg gca cca gaa aaa gta gac ttt gat gac tgc     1152
Ala Leu Gly Glu Asn Met Ala Pro Glu Lys Val Asp Phe Asp Asp Cys
    370                 375                 380

aaa gat gtt gga gac ctt aaa cag tat gac agt gat gag cca gag ccc     1200
Lys Asp Val Gly Asp Leu Lys Gln Tyr Asp Ser Asp Glu Pro Glu Pro
385                 390                 395                 400

aga tct cta gca agc tgg gtc caa aat gaa ttc aat aag gca tgt gaa     1248
Arg Ser Leu Ala Ser Trp Val Gln Asn Glu Phe Asn Lys Ala Cys Glu
                405                 410                 415

ttg act gat tca agc tgg ata gaa ctt gat gaa ata gga gaa gat gtt     1296
Leu Thr Asp Ser Ser Trp Ile Glu Leu Asp Glu Ile Gly Glu Asp Val
            420                 425                 430

gcc ccg att gaa cat atc gca agc atg agg agg aac tat ttt aca gca     1344
Ala Pro Ile Glu His Ile Ala Ser Met Arg Arg Asn Tyr Phe Thr Ala
        435                 440                 445

gaa gtg tcc cac tgc agg gct act gaa tac ata atg aag gga gtg tac     1392
Glu Val Ser His Cys Arg Ala Thr Glu Tyr Ile Met Lys Gly Val Tyr
    450                 455                 460

ata aat acg gcc ttg ctc aat gca tcc tgt gca gcc atg gat gac ttt     1440
Ile Asn Thr Ala Leu Leu Asn Ala Ser Cys Ala Ala Met Asp Asp Phe
465                 470                 475                 480
```

-continued

```
cag ctg atc cca atg ata agc aaa tgt agg acc aaa gaa gga aga cgg      1488
Gln Leu Ile Pro Met Ile Ser Lys Cys Arg Thr Lys Glu Gly Arg Arg
                485                 490                 495

aaa aca aac ctg tat ggg ttc att ata aaa gga agg tct cat ttg aga      1536
Lys Thr Asn Leu Tyr Gly Phe Ile Ile Lys Gly Arg Ser His Leu Arg
            500                 505                 510

aat gat act gat gtg gtg aac ttt gta agt atg gag ttc tca ctc act      1584
Asn Asp Thr Asp Val Val Asn Phe Val Ser Met Glu Phe Ser Leu Thr
        515                 520                 525

gac ccg aga ctg gag cca cac aaa tgg gaa aaa tac tgt gtt ctt gaa      1632
Asp Pro Arg Leu Glu Pro His Lys Trp Glu Lys Tyr Cys Val Leu Glu
    530                 535                 540

ata gga gac atg ctc ttg agg act gcg ata ggc caa gtg tcg agg ccc      1680
Ile Gly Asp Met Leu Leu Arg Thr Ala Ile Gly Gln Val Ser Arg Pro
545                 550                 555                 560

atg ttc cta tat gtg aga acc aat gga acc tcc aag atc aag atg aaa      1728
Met Phe Leu Tyr Val Arg Thr Asn Gly Thr Ser Lys Ile Lys Met Lys
                565                 570                 575

tgg ggc atg gaa atg agg cgc tgc ctt ctt cag tct ctt cag cag att      1776
Trp Gly Met Glu Met Arg Arg Cys Leu Leu Gln Ser Leu Gln Gln Ile
            580                 585                 590

gag agc atg att gag gcc gag tct tct gtc aaa gag aaa gac atg acc      1824
Glu Ser Met Ile Glu Ala Glu Ser Ser Val Lys Glu Lys Asp Met Thr
        595                 600                 605

aag gaa ttc ttt gaa aac aaa tcg gaa aca tgg cca atc gga gag tca      1872
Lys Glu Phe Phe Glu Asn Lys Ser Glu Thr Trp Pro Ile Gly Glu Ser
    610                 615                 620

ccc agg gga gtg gag gaa ggc tct att ggg aaa gtg tgc agg acc tta      1920
Pro Arg Gly Val Glu Glu Gly Ser Ile Gly Lys Val Cys Arg Thr Leu
625                 630                 635                 640

ctg gca aaa tct gta ttc aac agt cta tat gcg tct cca caa ctt gag      1968
Leu Ala Lys Ser Val Phe Asn Ser Leu Tyr Ala Ser Pro Gln Leu Glu
                645                 650                 655

ggg ttt tcg gct gaa tct aga aaa ttg ctt ctc att gtt cag gca ctt      2016
Gly Phe Ser Ala Glu Ser Arg Lys Leu Leu Leu Ile Val Gln Ala Leu
            660                 665                 670

agg gac aac ctg gaa cct gga acc ttc gat ctt ggg ggg cta tat gaa      2064
Arg Asp Asn Leu Glu Pro Gly Thr Phe Asp Leu Gly Gly Leu Tyr Glu
        675                 680                 685

gca atc gag gag tgc ctg att aat gat ccc tgg gtt ttg ctt aat gca      2112
Ala Ile Glu Glu Cys Leu Ile Asn Asp Pro Trp Val Leu Leu Asn Ala
    690                 695                 700

tct tgg ttc aac tcc ttc ctc aca cat gca ctg aag tag                  2151
Ser Trp Phe Asn Ser Phe Leu Thr His Ala Leu Lys
705                 710                 715


<210> SEQ ID NO 2
<211> LENGTH: 716
<212> TYPE: PRT
<213> ORGANISM: Influenza A pandemic H1N1 virus (A/California/04/2009)

<400> SEQUENCE: 2

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asp Glu Arg Gly Glu Ser Ile Ile Val Glu
    50                  55                  60
```

-continued

```
Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu Glu Thr Ile Glu Glu Lys Phe Glu Ile Thr
        195                 200                 205

Gly Thr Met Arg Lys Leu Ala Asp Gln Ser Leu Pro Pro Asn Phe Pro
    210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
            260                 265                 270

Gly Pro Leu Cys His Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
            340                 345                 350

Lys Ile Pro Arg Thr Lys Asn Met Lys Arg Thr Ser Gln Leu Lys Trp
        355                 360                 365

Ala Leu Gly Glu Asn Met Ala Pro Glu Lys Val Asp Phe Asp Asp Cys
    370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480
```

-continued

Gln Leu Ile Pro Met Ile Ser Lys Cys Arg Thr Lys Glu Gly Arg Arg
485 490 495

Lys Thr Asn Leu Tyr Gly Phe Ile Ile Lys Gly Arg Ser His Leu Arg
500 505 510

Asn Asp Thr Asp Val Val Asn Phe Val Ser Met Glu Phe Ser Leu Thr
515 520 525

Asp Pro Arg Leu Glu Pro His Lys Trp Glu Lys Tyr Cys Val Leu Glu
530 535 540

Ile Gly Asp Met Leu Leu Arg Thr Ala Ile Gly Gln Val Ser Arg Pro
545 550 555 560

Met Phe Leu Tyr Val Arg Thr Asn Gly Thr Ser Lys Ile Lys Met Lys
565 570 575

Trp Gly Met Glu Met Arg Arg Cys Leu Leu Gln Ser Leu Gln Gln Ile
580 585 590

Glu Ser Met Ile Glu Ala Glu Ser Ser Val Lys Glu Lys Asp Met Thr
595 600 605

Lys Glu Phe Phe Glu Asn Lys Ser Glu Thr Trp Pro Ile Gly Glu Ser
610 615 620

Pro Arg Gly Val Glu Glu Gly Ser Ile Gly Lys Val Cys Arg Thr Leu
625 630 635 640

Leu Ala Lys Ser Val Phe Asn Ser Leu Tyr Ala Ser Pro Gln Leu Glu
645 650 655

Gly Phe Ser Ala Glu Ser Arg Lys Leu Leu Leu Ile Val Gln Ala Leu
660 665 670

Arg Asp Asn Leu Glu Pro Gly Thr Phe Asp Leu Gly Gly Leu Tyr Glu
675 680 685

Ala Ile Glu Glu Cys Leu Ile Asn Asp Pro Trp Val Leu Leu Asn Ala
690 695 700

Ser Trp Phe Asn Ser Phe Leu Thr His Ala Leu Lys
705 710 715

<210> SEQ ID NO 3
<211> LENGTH: 6
<212> TYPE: PRT
<213> ORGANISM: artificial
<220> FEATURE:
<223> OTHER INFORMATION: synthetic sequence
<220> FEATURE:
<221> NAME/KEY: CHAIN
<222> LOCATION: (1)..(6)
<223> OTHER INFORMATION: amino-terminal linker

<400> SEQUENCE: 3

Met Gly Ser Gly Met Ala
1 5

<210> SEQ ID NO 4
<211> LENGTH: 11
<212> TYPE: PRT
<213> ORGANISM: Influenza A pandemic H1N1 virus (A/California/04/2009)
<220> FEATURE:
<221> NAME/KEY: peptide
<222> LOCATION: (1)..(11)
<223> OTHER INFORMATION: residues 20 to 30 of the PA-subunit of the Influenza A pandemic H1N1 virus (A/California/04/2009) RNA-dependent RNA polymerase

<400> SEQUENCE: 4

Ala Met Lys Glu Tyr Gly Glu Asp Pro Lys Ile
1 5 10

<210> SEQ ID NO 5
<211> LENGTH: 9
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(9)
<223> OTHER INFORMATION: residues 32 to 40 of the PA-subunit of the Influenza A pandemic H1N1 virus (A/California/04/2009) RNA-dependent RNA polymerase

<400> SEQUENCE: 5

Thr Asn Lys Phe Ala Ala Ile Cys Thr
1               5

<210> SEQ ID NO 6
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 41 to 51 of the PA-subunit of the Influenza A pandemic H1N1 virus (A/California/04/2009) RNA-dependent RNA polymerase

<400> SEQUENCE: 6

His Leu Glu Val Cys Phe Met Tyr Ser Asp Phe
1               5                   10

<210> SEQ ID NO 7
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 80 to 90 of the PA-subunit of the Influenza A pandemic H1N1 virus (A/California/04/2009) RNA-dependent RNA polymerase

<400> SEQUENCE: 7

Glu Gly Arg Asp Arg Ile Met Ala Trp Thr Val
1               5                   10

<210> SEQ ID NO 8
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 100 to 110 of the PA-subunit of the Influenza A pandemic H1N1 virus (A/California/04/2009) RNA-dependent RNA polymerase

<400> SEQUENCE: 8

Val Glu Lys Pro Lys Phe Leu Pro Asp Leu Tyr
1               5                   10

<210> SEQ ID NO 9
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 115 to 125 of the PA-subunit of the Influenza A pandemic H1N1 virus (A/California/04/2009) RNA-dependent RNA polymerase -continued

<400> SEQUENCE: 9

Asn Arg Phe Ile Glu Ile Gly Val Thr Arg Arg
1 5 10

<210> SEQ ID NO 10
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(1)
<223> OTHER INFORMATION: residues 130 to 140 of the PA-subunit of the Influenza A pandemic H1N1 virus (A/California/04/2009) RNA-dependent RNA polymerase

<400> SEQUENCE: 10

Tyr Tyr Leu Glu Lys Ala Asn Lys Ile Lys Ser
1 5 10

<210> SEQ ID NO 11
<211> LENGTH: 11
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(11)
<223> OTHER INFORMATION: residues 176 to 186 of the PA-subunit of the Influenza A pandemic H1N1 virus (A/California/04/2009) RNA-dependent RNA polymerase

<400> SEQUENCE: 11

Phe Thr Ile Arg Gln Glu Met Ala Ser Arg Ser
1 5 10

<210> SEQ ID NO 12
<211> LENGTH: 7
<212> TYPE: PRT
<213> ORGANISM: artificial
<220> FEATURE:
<223> OTHER INFORMATION: synthetic
<220> FEATURE:
<221> NAME/KEY: PEPTIDE
<222> LOCATION: (1)..(7)
<223> OTHER INFORMATION: TEV protease recognition site

<400> SEQUENCE: 12

Glu Asn Leu Tyr Phe Gln Gly
1 5

<210> SEQ ID NO 13
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: residues 1 to 198 of the PA-subunit of the Influenza A pandemic H1N1 virus (A/California/04/2009) RNA-dependent RNA polymerase

<400> SEQUENCE: 13

Met Glu Asp Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe His Phe Ile Asp Glu Arg Gly Glu Ser Ile Ile Val Glu
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu
        195

<210> SEQ ID NO 14
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: residues 1-198 of the PA-subunit of the Influenza A pandemic H1N1 virus (A/California/04/2009) RNA-dependent RNA polymerase with residues 52-64 replaced with glycine

<400> SEQUENCE: 14

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe Gly Gly Gly Gly Gly Gly Gly Gly Gly Gly Gly Gly Gly
    50                  55                  60

Ser Gly Asp Pro Asn Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
180 185 190

Gln Ser Glu Arg Gly Glu
195

<210> SEQ ID NO 15
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: amino acid residues 1-198 of PA-subunit of the Influenza A pandemic H1N1 virus (A/California/04/2009) RNA-dependent RNA polymerase with residues 52-72 replaced with Glycine

<400> SEQUENCE: 15

Met Glu Asp Phe Val Arg Gln Cys Phe Asn Pro Met Ile Val Glu Leu
1 5 10 15

Ala Glu Lys Ala Met Lys Glu Tyr Gly Glu Asp Pro Lys Ile Glu Thr
20 25 30

Asn Lys Phe Ala Ala Ile Cys Thr His Leu Glu Val Cys Phe Met Tyr
35 40 45

Ser Asp Phe Gly Gly Gly Gly Gly Gly Gly Gly Gly Gly Gly Gly Gly
50 55 60

Gly Gly Gly Gly Gly Gly Gly Gly Lys His Arg Phe Glu Ile Ile Glu
65 70 75 80

Gly Arg Asp Arg Ile Met Ala Trp Thr Val Val Asn Ser Ile Cys Asn
85 90 95

Thr Thr Gly Val Glu Lys Pro Lys Phe Leu Pro Asp Leu Tyr Asp Tyr
100 105 110

Lys Glu Asn Arg Phe Ile Glu Ile Gly Val Thr Arg Arg Glu Val His
115 120 125

Ile Tyr Tyr Leu Glu Lys Ala Asn Lys Ile Lys Ser Glu Lys Thr His
130 135 140

Ile His Ile Phe Ser Phe Thr Gly Glu Glu Met Ala Thr Lys Ala Asp
145 150 155 160

Tyr Thr Leu Asp Glu Glu Ser Arg Ala Arg Ile Lys Thr Arg Leu Phe
165 170 175

Thr Ile Arg Gln Glu Met Ala Ser Arg Ser Leu Trp Asp Ser Phe Arg
180 185 190

Gln Ser Glu Arg Gly Glu
195

<210> SEQ ID NO 16
<211> LENGTH: 198
<212> TYPE: PRT
<213> ORGANISM: Influenza A pandemic H1N1 virus (A/California/04/2009)
<220> FEATURE:
<221> NAME/KEY: PEPTIDE
<222> LOCATION: (1)..(198)
<223> OTHER INFORMATION: amino acid residues 1-198 of PA-subunit of the Influenza A pandemic H1N1 virus (A/California/04/2009) RNA-dependent RNA polymerase with residues 52-69 replaced with Glycine -continued

```
<400> SEQUENCE: 16

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

Asn Lys Phe Ala Ala Ile Cys Thr His Leu Glu Val Cys Phe Met Tyr
        35                  40                  45

Ser Asp Phe Gly Gly Gly Gly Gly Gly Gly Gly Gly Gly Gly Gly Gly
    50                  55                  60

Gly Gly Gly Gly Gly Ala Leu Leu Lys His Arg Phe Glu Ile Ile Glu
65                  70                  75                  80

Gly Arg Asp Arg Ile Met Ala Trp Thr Val Val Asn Ser Ile Cys Asn
                85                  90                  95

Thr Thr Gly Val Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
            180                 185                 190

Gln Ser Glu Arg Gly Glu
        195
```

INFLUENZA A 2009 PANDEMIC H1N1 POLYPEPTIDE FRAGMENTS COMPRISING ENDONUCLEASE ACTIVITY AND THEIR USE

CROSS-REFERENCE TO RELATED APPLICATION

This application is a National Stage filing of International Application Serial No. PCT/EP2011/001274, filed Mar. 15, 2011, which claims the benefit of U.S. Provisional No. 61/340,335 filed Mar. 16, 2010, the disclosures of which are expressly incorporated herein by reference.

TECHNICAL FIELD OF INVENTION

The present invention relates to polypeptide fragments comprising an amino-terminal fragment of the PA subunit of a viral RNA-dependent RNA polymerase possessing endonuclease activity, wherein said PA subunit is from Influenza A 2009 pandemic H1N1 virus or is a variant thereof. This invention also relates to (i) crystals of the polypeptide fragments which are suitable for structure determination of said polypeptide fragments using X-ray crystallography and (ii) computational methods using the structural coordinates of said polypeptide to screen for and design compounds that modulate, preferably inhibit the endonucleolytically active site within the polypeptide fragment. In addition, this invention relates to methods identifying compounds that bind to the PA polypeptide fragments possessing endonuclease activity and preferably inhibit said endonucleolytic activity, preferably in a high throughput setting. This invention also relates to compounds which are able to modulate, preferably to inhibit, the endonuclease activity of the PA subunit polypeptide fragment or variant thereof of the present invention and pharmaceutical compositions comprising said compounds for the treatment of disease conditions caused by viral infections with viruses of the Orthomyxoviridae family, Bunyaviridae family and/or Arenviridae family, preferably caused by viral infections with Influenza A 2009 pandemic H1N1 virus. Preferably, said compounds are identifiable by the methods disclosed herein or said pharmaceutical compositions are producible by the methods disclosed herein.

BACKGROUND OF THE INVENTION

Influenza is responsible for much morbidity and mortality in the world and is considered by many as belonging to the most significant viral threats to humans. Annual Influenza epidemics swipe the globe and occasional new virulent strains cause pandemics of great destructive power. At present the primary means of controlling Influenza virus epidemics is vaccination. However, mutant Influenza viruses are rapidly generated which escape the effects of vaccination. In the light of the fact that it takes approximately 6 months to generate a new Influenza vaccine, alternative therapeutic means, i.e., antiviral medication, are required especially as the first line of defense against a rapidly spreading pandemic.

An excellent starting point for the development of antiviral medication is structural data of essential viral proteins. Thus, the crystal structure determination of the Influenza virus surface antigen neuraminidase (von Itzstein et al., 1993, Nature 363:418-423) led directly to the development of neuraminidase inhibitors with anti-viral activity preventing the release of virus from the cells, however, not the virus production. These and their derivatives have subsequently developed into the anti-Influenza drugs, zanamivir (Glaxo) and oseltamivir (Roche), which are currently being stockpiled by many countries as a first line of defense against an eventual pandemic. However, these medicaments provide only a reduction in the duration of the clinical disease. Alternatively, other anti-Influenza compounds such as amantadine and rimantadine target an ion channel protein, i.e., the M2 protein, in the viral membrane interfering with the uncoating of the virus inside the cell. However, they have not been extensively used due to their side effects and the rapid development of resistant virus mutants (Magden et al., 2005, Appl. Microbiol. Biotechnol. 66:612-621). In addition, more unspecific viral drugs, such as ribavirin, have been shown to work for treatment of Influenza infections (Eriksson et al., 1977, Antimicrob. Agents Chemother. 11:946-951). However, ribavirin is only approved in a few countries, probably due to severe side effects (Furuta et al., 2005, Antimicrob. Agents Chemother. 49:981-986). Clearly, new antiviral compounds are needed, preferably directed against different targets.

Influenza virus A, B, C and Isavirus as well as Thogotovirus belong to the family of Orthomyxoviridae which, as well as the family of the Bunyaviridae, including the Hantavirus, Nairovirus, Orthobunyavirus, Phlebovirus, and Tospovirus, are negative stranded RNA viruses. Their genome is segmented and comes in ribonucleoprotein particles that include the RNA dependent RNA polymerase which carries out (i) the initial copying of the single-stranded virion RNA (vRNA) into viral mRNAs and (ii) the vRNA replication. For the generation of viral mRNA the polymerase makes use of the so called "cap-snatching" mechanism (Plotch et al., 1981, Cell 23:847-858; Kukkonen et al., 2005, Arch. Virol. 150:533-556; Leahy et al., 1997, J. Virol. 71:8347-8351; Noah and Krug, 2005, Adv. Virus Res. 65:121-145). The polymerase is composed of three subunits: PB1 (polymerase basic protein), PB2, and PA. For the cap-snatching mechanism, the viral polymerase binds via its PB2 subunit to the 5' RNA cap of cellular mRNA molecules which are cleaved at nucleotide 10 to 13 by the endonucleolytic activity of the polymerase. The capped RNA fragments serve as primers for the synthesis of viral mRNAs by the nucleotidyl-transferase center in the PB 1 subunit (Li et al., 2001, EMBO J. 20:2078-2086). Finally, the viral mRNAs are 3'-end poly-adenylated by stuttering of the polymerase at an oligo-U motif at the 5'-end of the template. Recent studies have precisely defined the structural domain of PB2 responsible for cap-binding (Fechter et al., 2003, J. Biol. Chem. 278:20381-20388; Guilligay et al., 2008 Nat. Struct. Mol. Biol. 15:500-506). The endonucleolytic activity of the polymerase has hitherto been thought to reside in the PB 1 subunit (Li et al, supra).

The polymerase complex seems to be an appropriate antiviral drug target since it is essential for synthesis of viral mRNA and viral replication and contains several functional active sites likely to be significantly different from those found in host cell proteins (Magden et al., supra). Thus, for example, there have been attempts to interfere with the assembly of polymerase subunits by a 25-amino-acid peptide resembling the PA-binding domain within PB1 (Ghanem et al., 2007, J. Virol. 81:7801-7804). Moreover, there have been attempts to interfere with viral transcription by nucleoside analogs, such as 2'-deoxy-2'-fluoroguanosine (Tisdale et al., 1995, Antimicrob. Agents Chemother. 39:2454-2458) and it has been shown that T-705, a substituted pyrazine compound may function as a specific inhibitor of Influenza virus RNA polymerase (Furuta et al., supra). Furthermore, the endonuclease activity of the polymerase has been targeted and a series of 4-substituted 2,4-dioxobutanoic acid compounds has been identified as selective inhibitors of this activity in Influenza viruses (Tomassini et al., 1994, Antimicrob. Agents Chemother. 38:2827-2837). In addition, flutimide, a substituted 2,6-diketopiperazine, identified in extracts of *Delitschia confertaspora*, a fungal species, has been shown to inhibit the endonuclease of Influenza virus (Tomassini et al., 1996, Antimicrob. Agents Chemother. 40:1189-1193). However, the inhibitory action of compounds on the endonucleolytic activity of the viral polymerase was hitherto only studied in the context of the entire trimeric complex of the polymerase.

The PA subunit of the polymerase is functionally the least well-characterised, although it has been implicated in both cap-binding and endonuclease activity, vRNA replication, and a controversial protease activity. PA (716 residues in influenza A) is separable by trypsination at residue 213. The recently determined crystal structure of the C-terminal two-thirds of PA bound to a PB 1 N-terminal peptide provided the first structural insight into both a large part of the PA subunit, whose function, however, still remains unclear, and the exact nature of one of the critical inter-subunit interactions (He et al., 2008, Nature 454:1123-1126; Obayashi et al., 2008, Nature 454:1127-1131). Systematic mutation of conserved residues in the PA amino-terminal domain have identified residues important for protein stability, promoter binding, cap-binding and endonuclease activity of the polymerase complex (Hara et al., 2006, J. Virol. 80:7789-7798). The enzymology of the endonuclease within the context of intact viral ribonucleoprotein particles (RNPs) has been extensively studied.

It has been found recently that, contrary to the general opinion in the field, the endonucleolytic activity resides exclusively within the PA subunit of the RNA-dependent RNA polymerase of the Influenza A H3N2 virus (Dias et al., 2009).

The present inventors have now achieved to structurally characterize the PA domain of the Influenza A 2009 pandemic H1N1 virus by X-ray crystallography and identified the endonucleolytic active center within said domain. The present inventors surprisingly found that polypeptide fragments of the PA subunit of said virus readily crystallized and that, thus, said polypeptide fragments are very suitable to study the endonucleolytic activity of the RNA-dependent RNA polymerase of the Influenza A 2009 pandemic H1N1 virus in the context of said polypeptide fragments in order to simplify the development of new anti-viral compounds targeting the endonuclease activity of said viral polymerase as well as to optimize previously identified compounds.

The achievement of the present inventors to recombinantly produce PA polypeptide fragments possessing the endonucleolytic activity of the RNA-dependent RNA polymerase of the Influenza A 2009 pandemic H1N1 virus allows for performing in vitro high-throughput screening for inhibitors of a functional site on said viral polymerase using easily obtainable material from a straightforward expression system. Furthermore, the structural data of the endonucleolytic PA H1N1 polypeptide fragment as well as of the enzymatically active center therein allows for directed design of inhibitors and in silico screening for potentially therapeutic compounds.

The present inventors further managed, for the first time, the co-crystallization of a PA polypeptide fragment and of a variant thereof of the PA subunit of Influenza A 2009 pandemic H1N1 virus with a bound inhibitor and found that, thus, the development of new anti-viral compounds targeting the endonuclease activity of the RNA-dependent RNA polymerase of the Influenza A 2009 pandemic H1N1 virus can be improved. Particularly, the co-crystallization data show, for the first time, in detail which amino acids comprised in the active site of a PA polypeptide fragment of the PA subunit of Influenza A 2009 pandemic H1N1 virus are especially involved in compound binding. This new knowledge allows the optimized design of modifications to existing inhibitors in order to improve their potency or the design and optimization of novel inhibitors that effectively block endonuclease activity.

It is an object of the present invention to provide (i) high resolution structural data of the endonucleolytic amino-terminal domain of the viral polymerase H1N1 PA subunit by X-ray crystallography, (ii) high resolution structural data of the endonucleolytic amino-terminal domain of the viral polymerase H1N1 PA subunit co-crystallized with a known inhibitor by X-ray crystallography, (iii) computational as well as in vitro methods, preferably in a high-throughput setting, for identifying compounds that can modulate, preferably inhibit, the endonuclease activity of the viral polymerase of the Influenza A 2009 pandemic H1N1 virus, preferably by blocking the endonucleolytic active site within the H1N1 PA subunit, and (iv) pharmacological compositions comprising such compounds for the treatment of infectious diseases caused by viruses using the cap snatching mechanism for synthesis of viral mRNA.

SUMMARY OF THE INVENTION

In a first aspect, the present invention relates to a polypeptide fragment comprising an amino-terminal fragment of the PA subunit of a viral RNA-dependent RNA polymerase possessing endonuclease activity, wherein said PA subunit is from Influenza A pandemic 2009 H1N1 virus according to SEQ ID NO: 2 or is a variant thereof, wherein said variant comprises the amino acid serine at an amino acid position 186 according to SEQ ID NO: 2 or at an amino acid position corresponding thereto.

In a further aspect, the present invention relates to an isolated polynucleotide coding for an isolated polypeptide fragment according to the present invention.

In a further aspect, the present invention relates to a recombinant vector comprising the isolated polynucleotide according to the present invention.

In a further aspect, the present invention relates to a recombinant host cell comprising the isolated polynucleotide according to the present invention or the recombinant vector according to the present invention.

In a further aspect, the present invention relates to a method for identifying compounds, which modulate the endonuclease activity of the PA subunit of a RNA-dependent RNA polymerase from Influenza A 2009 pandemic H1N1 virus or a variant thereof comprising the steps of:

(a) constructing a computer model of the active site defined by (i) the structure coordinates of the polypeptide fragment according to the present invention as shown in FIG. 1, (ii) the structure coordinates of the polypeptide fragment according to the present invention as shown in FIG. 2, (iii) the structure coordinates of the polypeptide fragment according to the present invention as shown in FIG. 3, (iv) the structure coordinates of the polypeptide fragment according to the present invention as shown in FIG. 4, (v) the structure coordinates of the polypeptide fragment according to the present invention as shown in FIG. 5, (vi) the structure coordinates of the polypeptide fragment according to the present invention as shown in FIG. 15, or (vii) the structure coordinates of the polypeptide fragment according to the present invention as shown in FIG. 16, (b) selecting a potential modulating compound by a method selected from the group consisting of:

(i) assembling molecular fragments into said compound, (ii) selecting a compound from a small molecule database, and (iii) de novo ligand design of said compound;

(c) employing computational means to perform a fitting program operation between computer models of the said compound and the said active site in order to provide an energy-minimized configuration of the said compound in the active site; and (d) evaluating the results of said fitting operation to quantify the association between the said compound and the active site model, whereby evaluating the ability of said compound to associate with the said active site.

In a further aspect, the present invention relates to a method for identifying compounds, which modulate the endonuclease activity of the PA subunit of a RNA-dependent RNA polymerase from Influenza A 2009 pandemic H1N1 virus or a variant thereof comprising the steps of:

(i) contacting the polypeptide fragment or variant thereof according to the present invention or the recombinant host cell according to the present invention with a test compound, and (ii) analyzing the ability of said test compound to modulate the endonuclease activity of said PA subunit polypeptide fragment or variant thereof.

In a further aspect, the present invention relates to a compound which is able to modulate, preferably to inhibit, the endonuclease activity of the PA subunit polypeptide fragment or variant thereof according to the present invention. Preferably, said compound is identifiable by the (in vitro) methods according to the present inventions.

In a further aspect, the present invention relates to a pharmaceutical composition comprising the compound of the present invention or a pharmaceutically acceptable salt thereof and one or more pharmaceutically acceptable excipient(s) and/or carrier(s). Preferably, said pharmaceutical composition is producible according to the (in vitro) methods of the present invention.

In a further aspect, the present invention relates to an antibody directed against the active site of the PA subunit of the Influenza A 2009 pandemic H1N1 virus according to SEQ ID NO: 2 or a variant thereof, wherein said variant comprises the amino acid serine at an amino acid position 186 according to SEQ ID NO: 2 or at an amino acid position corresponding thereto.

In a further aspect, the present invention relates to the use of a compound according to the present invention, a pharmaceutical composition according to the present invention, or an antibody according to the present invention for the manufacture of a medicament for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

In a further aspect, the present invention relates to the use of 4-[3-[(4-chlorophenyl)methyl]-1-(phenylm ethyl)-3-piperidinyl]-2-hydroxy-4-oxo-2-butenoic acid (EMBL-R05-3), 4-[4-[(4-chlorophenyl)methyl]-1-(cyclohexylmethyl)-4-piperidinyl]-2-hydroxy-4-oxo-2-butenoic acid (EMBL-R05-2), 4-[3-[(4-chlorophenyl)methyl]-1-(phenylmethylsulpho)-3-piperidinyl]-2-hydroxy-4-oxo-2-butenoic acid (EMBL-R05-1), or [(2R,3R)-5,7-dihydroxy-2-(3,4,5-trihydroxyphenyl) chroman-3-yl]3,4,5-trihydroxybenzoate (EGCG) for the manufacture of a medicament for treating, ameliorating, or preventing disease conditions caused by viral infections with Influenza A 2009 pandemic H1N1 virus.

In a further aspect, the present invention relates to a compound according to the present invention, a pharmaceutical composition according to the present invention, or an antibody according to the present invention for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

In a further aspect, the present invention relates to 4-[3-[(4-chlorophenyl)methyl]-1-(phenylmethyl)-3-piperidinyl]-2-hydroxy-4-oxo-2-butenoic acid (EMBL-R05-3), 4-[4-[(4-chlorophenyl)methyl]-1-(cyclohexylmethyl)-4-piperidinyl]-2-hydroxy-4-oxo-2-butenoic acid (EMBL-R05-2), 4-[3-[(4-chlorophenyl)methyl]-1-(phenylmethylsulpho)-3-piperidinyl]-2-hydroxy-4-oxo-2-butenoic acid (EMBL-R05-1), or [(2R,3R)-5,7-dihydroxy-2-(3,4,5-trihydroxyphenyl) chroman-3-yl]3,4,5-trihydroxybenzoate (EGCG) for treating, ameliorating, or preventing disease conditions caused by viral infections with Influenza A 2009 pandemic H1N1 virus.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the polypeptide fragment of the present invention corresponds to amino acids 1 to 198 of the amino acid sequence set forth in SEQ ID NO: 2 and in another preferred embodiment the PA polypeptide fragment according to the present invention may be tagged with a peptide-tag that is preferably cleavable from the PA polypeptide fragment, preferably using a TEV protease, it is a preferred embodiment of the invention that the polypeptide fragment corresponding to amino acids 1 to 198 of the amino acid sequence set forth in SEQ ID NO: 2 is tagged with a peptide-tag that is cleavable from the PA polypeptide using a TEV protease.

Preferably, the terms used herein are defined as described in "A multilingual glossary of biotechnological terms: (IUPAC Recommendations)", H. G. W. Leuenberger, B. Nagel, and H. Kolbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular*

*Cloning: A Laboratory Manual,* $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. As used in this specification and the appended claims, the singular forms "a", "an", and "the" include plural referents, unless the content clearly dictates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

The term "polypeptide fragment" refers to a part of a protein which is composed of a single amino acid chain. The term "protein" comprises polypeptide fragments that resume a secondary and tertiary structure and additionally refers to proteins that are made up of several amino acid chains, i.e., several subunits, forming quaternary structures. The term "peptide" refers to short amino acid chains of up to 50 amino acids that do not necessarily assume secondary or tertiary structures. A "peptoid" is a peptidomimetic that results from the oligomeric assembly of N-substituted glycines.

Residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, e.g., (see website at ebi.ac.uk/clustalw) or Align (see website at ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Residues in two or more PA subunits are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20 or 30 amino acids.

The present invention relates to Influenza A 2009 pandemic H1N1 virus RNA-dependent RNA polymerase PA subunit fragments possessing endonuclease activity. The term "RNA-dependent RNA polymerase PA subunit" refers to the PA subunit of Influenza A 2009 pandemic H1N1 virus having an amino acid sequence as set forth in SEQ ID NO: 2. The term "RNA-dependent RNA polymerase PA subunit variant" refers to a PA subunit variant of Influenza A 2009 pandemic H1N1 virus which comprises the amino acid serine at an amino acid position 186 according to SEQ ID NO: 2 or at an amino acid position corresponding thereto and preferably has at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid sequence set forth in SEQ ID NO: 2. It is preferred that when a PA subunit variant is aligned with a PA subunit according to SEQ ID NO: 2 that the alignment will be over the entire length of the two polypeptides and, thus, that the alignment score will be determined on this basis. It is, however, possible that the PA subunit variant may comprise C-terminal/N-terminal or internal deletions or additions, e.g., through N- or C-terminal fusions. In this case, only the best aligned region is used for the assessment of similarity and identity, respectively. Preferably, fragments derived from these variants show the indicated similarity and identity, respectively, preferably within the region required for endonuclease activity. Accordingly, any alignment between SEQ ID NO: 2 and a PA subunit variant should preferably comprise the endonuclease active site. Thus, the above sequence similarity and identity to SEQ ID NO: 2 occurs at least over a length of 80, 90, 100, 110, 120, 130, 140, 150, 160, 165, 170, 180, 190, 200, 210, 220, 230, 240, 250, 300 or more amino acids, preferably comprising the endonuclease active site.

The polypeptide fragments of the present invention are, thus, based on Influenza A 2009 pandemic H1N1 virus RNA-dependent RNA polymerase PA subunit or variants thereof as defined above. Accordingly, in the following specification, the terms "polypeptide fragment(s)" and "PA polypeptide fragment(s)" always comprise fragments derived both from the PA protein as set out in SEQ ID NO: 2 and from PA protein variants thereof, as set out above, possessing endonuclease activity.

However, the specification also uses the terms "PA polypeptide fragment variants" or "PA fragment variants" to specifically refer to PA polypeptide fragments or PA fragments possessing endonuclease activity that are derived from Influenza A 2009 pandemic H1N1 virus RNA-dependent RNA polymerase PA subunit variants. The PA polypeptide fragments of the present invention, thus, preferably comprise, essentially consist or consist of sequences of the naturally occurring Influenza A 2009 pandemic H1N1 virus PA subunit. It is, however, also envisioned that the PA polypeptide fragment variants comprise the amino acid serine at an amino acid position 186 according to SEQ ID NO: 2 or at an amino acid position corresponding thereto and preferably further contain amino acid substitutions at 1, 2, 3, 4, 5, 6, 7, 8, 9, 10, 11, 12, 13, 14, 15 or more amino acid positions, and/or have at least 60%, 65%, 70%, 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid sequence set forth in SEQ ID NO: 2. It is understood that PA fragments of the present invention may comprise additional amino acids not derived from PA, like, e.g., tags, enzymes etc., such additional amino acids will not be considered in such an alignment, i.e., are excluded from the calculation of the alignment score. In a preferred embodiment, the above indicated alignment score is obtained when aligning the sequence of the fragment with SEQ ID NO: 2 at least over a length of 70, 80, 90, 100, 110, 120, 130, 140, 150, 160, 165, 170, 180, or 190 amino acids, wherein the sequence of SEQ ID NO: 2 preferably comprises the endonuclease active site.

In a preferred embodiment, the PA polypeptide fragment variants comprise at least the amino acid residues corresponding to amino acid residues 1 to 190 of Influenza A 2009 pandemic H1N1 virus PA subunit according to SEQ ID NO: 2 or consist of amino acid residues 1 to 190 of Influenza A 2009 pandemic H1N1 virus PA subunit according to SEQ ID NO: 2 and have at least 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 190 of the amino acid sequence set forth in SEQ ID NO: 2. More preferably, the PA polypeptide fragment variants comprise at least the amino acid residues corresponding to amino acid residues 1 to 198 of Influenza A 2009 pandemic H1N1 virus PA subunit according to SEQ ID NO: 2 or consist of amino acid residues 1 to 198 of Influenza A 2009 pandemic H1N1 virus PA subunit according to SEQ ID NO: 2 and have at least 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with the amino acid residues 1 to 198 of the amino acid sequence set forth in SEQ ID NO: 2. It is also preferred that the PA polypeptide fragment variants comprise at least the amino acid residues corresponding to amino acid residues 1 to 200 of Influenza A 2009 pandemic H1N1 virus PA subunit according to SEQ ID NO: 2 or consist of amino acid residues 1 to 200 of Influenza A 2009 pandemic H1N1 virus PA subunit according to SEQ ID NO: 2 and have at least 60%, more preferably 65%, more preferably 70%, more preferably 75%, more preferably 80%, 81%, 82%, 83%, 84%, 85%, 86%, 87%, 88%, 89%, 90%, 91%, 92%, 93%, 94%, 95%, 96%, 97%, 98%, 99% sequence similarity, preferably sequence identity over the entire length of the fragment using the best sequence alignment and/or over the region of the best sequence alignment, wherein the best sequence alignment is obtainable with art known tools, e.g., Align, using standard settings, preferably EMBOSS::needle, Matrix: Blosum62, Gap Open 10.0, Gap Extend 0.5, with amino acid residues 1 to 200 of the amino acid sequence set forth in SEQ ID NO: 2. It should be noted that all of the above mentioned preferred PA polypeptide fragment variants comprise the amino acid serine at an amino acid position 186 according to SEQ ID NO: 2 or at an amino acid position corresponding thereto.

In the context of the present invention, the term "PA-Nter" refers to a polypeptide fragment which consists of amino acid residues 1 to 198 of the amino acid sequence as set forth in SEQ ID NO: 2 (PA H1N1 1 to 198) and optionally of an additional amino-terminal linker, i.e. MGSGMA (SEQ ID NO: 3). In the context of the present invention, the term "PA-Nter mutant" refers to a polypeptide fragment (variant) which consists of amino acid residues 1 to 198 of the amino acid sequence as set forth in SEQ ID NO: 2 with amino acids 52 to 64 replaced by the amino acid glycine (PA H1N1 1 to 198 Δ52-64: Gly) and optionally of an additional amino-terminal linker, i.e. MGSGMA (SEQ ID NO: 3).

The term "sequence similarity" means that amino acids at the same position of the best sequence alignment are identical or similar, preferably identical. "Similar amino acids" possess similar characteristics, such as polarity, solubility, hydrophilicity, hydrophobicity, charge, or size. Similar amino acids are preferably leucine, isoleucine, and valine; phenylalanine, tryptophan, and tyrosine; lysine, arginine, and histidine; glutamic acid and aspartic acid; glycine, alanine, and serine; threonine, asparagine, glutamine, and methionine. The skilled person is well aware of sequence similarity searching tools, e.g., available on the World Wide Web (see website at ebi.ac.uk/Tools.similarity.html).

The term "soluble", as used herein, refers to a polypeptide fragment which remains in the supernatant after centrifugation for 30 min at 100,000×g in an aqueous buffer under physiologically isotonic conditions, for example, 0.14 M sodium chloride or sucrose, at a protein concentration of at least 200 μg/ml, preferably of at least 500 μg/ml, preferably of at least 1 mg/ml, more preferably of at least 2 mg/ml, even more preferably of at least 3 mg/ml, even more preferably of at least 4 mg/ml, most preferably of at least 5 mg/ml in the absence of denaturants such as guanidine or urea in effective concentrations. A protein fragment that is tested for its solubility is preferably expressed in one of the cellular expression systems indicated below.

The term "purified" in reference to a polypeptide, does not require absolute purity such as a homogenous preparation, rather it represents an indication that the polypeptide is relatively purer than in the natural environment. Generally, a purified polypeptide is substantially free of other proteins, lipids, carbohydrates, or other materials with which it is naturally associated, preferably at a functionally significant level, for example, at least 85% pure, more preferably at least 90% or 95% pure, most preferably at least 99% pure. The expression "purified to an extent to be suitable for crystallization" refers to a polypeptide that is 85% to 100%, preferably 90% to 100%, more preferably 95% to 100% or 98% to 100% pure and can be concentrated to higher than 3 mg/ml, preferably higher than 10 mg/ml, more preferably higher than 18 mg/ml without precipitation. A skilled artisan can purify a polypeptide using standard techniques for protein purification. A substantially pure polypeptide will yield a single major band on a non-reducing polyacrylamide gel.

The term "associate" as used in the context of identifying compounds with the methods of the present invention refers to a condition of proximity between a moiety (i.e., chemical entity or compound or portions or fragments thereof), and an endonuclease active site of the PA subunit. The association may be non-covalent, i.e., where the juxtaposition is energetically favored by, for example, hydrogen-bonding, van der Waals, electrostatic, or hydrophobic interactions, or it may be covalent.

The term "endonuclease activity" or "endonucleolytic activity" refers to an enzymatic activity which results in the cleavage of the phosphodiester bond within a polynucleotide chain. In the context of the present invention, the polypeptide fragments possess an endonucleolytic activity, which is preferably not selective for the polynucleotide type, i.e., the polypeptide fragments according to the present invention preferably exhibit endonucleolytic activity for DNA and RNA, preferably for single stranded DNA (ssDNA) or single stranded RNA (ssRNA). In this context, "Single stranded" means that a stretch of preferably at least 3 nucleotides, preferably at least 5 nucleotides, more preferably at least 10 nucleotides within the polynucleotide chain are single stranded, i.e., not base paired to another nucleotide. Preferably, the endonucleolytic activity of the polypeptide fragments according to the present invention is not dependent on recognition sites, i.e., specific nucleotide sequences, but results in unspecific cleavage of polynucleotide chains. For example, the skilled person may test for endonucleolytic activity of polypeptide fragments according to the present invention by incubating RNA or DNA substrates such as panhandle RNA or a linear or circular single stranded DNA, with or without the respective polypeptide fragment, for example, at 37° C. for a certain period of time such as for 5, 10, 20, 40, 60, or 80 minutes, and test for the integrity of the polynucleotides, for example, by gel electrophoresis.

The term "nucleotide" as used herein refers to a compound consisting of a purine, deazapurine, or pyrimidine nucleoside base, e.g., adenine, guanine, cytosine, uracil, thymine, deazaadenine, deazaguanosine, and the like, linked to a pentose at the position, including 2'-deoxy and 2'-hydroxyl forms, e.g., as described in Kornberg and Baker, DNA Replication, 2nd Ed. (Freeman, San Francisco, 1992) and further include, but are not limited to, synthetic nucleosides having modified base moieties and/or modified sugar moieties, e.g., described generally by Scheit, Nucleotide Analogs (John Wiley, N.Y., 1980).

The term "isolated polynucleotide" refers to polynucleotides that were (i) isolated from their natural environment, (ii) amplified by polymerase chain reaction, or (iii) wholly or partially synthesized, and means a single or double-stranded polymer of deoxyribonucleotide or ribonucleotide bases and includes DNA and RNA molecules, both sense and anti-sense strands. The term comprises cDNA, cRNA, genomic DNA, and recombinant DNA. A polynucleotide may consist of an entire gene, or a portion thereof.

The term "recombinant vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

"Recombinant host cell", as used herein, refers to a host cell that comprises a polynucleotide that codes for a polypeptide fragment of interest, i.e., the Influenza A pandemic H1N1 PA polypeptide fragment or variants thereof according to the invention. This polynucleotide may be found inside the host cell (i) freely dispersed as such, (ii) incorporated in a recombinant vector, or (iii) integrated into the host cell genome or mitochondrial DNA. The recombinant cell can be used for expression of a polynucleotide of interest or for amplification of the polynucleotide or the recombinant vector of the invention. The term "recombinant host cell" includes the progeny of the original cell which has been transformed, transfected, or infected with the polynucleotide or the recombinant vector of the invention. A recombinant host cell may be a bacterial cell such as an *E. coli* cell, a yeast cell such as *Saccharomyces cerevisiae* or *Pichia pastoris*, a plant cell, an insect cell such as SF9 or High Five cells, or a mammalian cell. Preferred examples of mammalian cells are Chinese hamster ovary (CHO) cells, green African monkey kidney (COS) cells, human embryonic kidney (HEK293) cells, HELA cells, and the like.

As used herein, the term "crystal" or "crystalline" means a structure (such as a three-dimensional solid aggregate) in which the plane faces intersect at definite angles and in which there is a regular structure (such as internal structure) of the constituent chemical species. The term "crystal" can include any one of: a solid physical crystal form such as an experimentally prepared crystal, a crystal structure derivable from the crystal (including secondary and/or tertiary and/or quaternary structural elements), a 2D and/or 3D model based on the crystal structure, a representation thereof such as a schematic representation thereof or a diagrammatic representation thereof, or a data set thereof for a computer. In one aspect, the crystal is usable in X-ray crystallography techniques. Here, the crystals used can withstand exposure to X-ray beams and are used to produce diffraction pattern data necessary to solve the X-ray crystallographic structure. A crystal may be characterized as being capable of diffracting X-rays in a pattern defined by one of the crystal forms depicted in T. L. Blundell and L. N. Johnson, "Protein Crystallography", Academic Press, New York (1976).

The term "unit cell" refers to a basic cubic or parallelepiped shaped block. The entire volume of a crystal may be constructed by regular assembly of such blocks. Each unit cell comprises a complete representation of the unit of pattern, the repetition of which builds up the crystal.

The term "space group" refers to the arrangement of symmetry elements of a crystal. In a space group designation the capital letter indicates the lattice type and the other symbols represent symmetry operations that can be carried out on the contents of the asymmetric unit without changing its appearance.

The term "structure coordinates" refers to a set of values that define the position of one or more amino acid residues with reference to a system of axes. The term refers to a data set that defines the three-dimensional structure of a molecule or molecules (e.g., Cartesian coordinates, temperature factors, and occupancies). Structural coordinates can be slightly modified and still render nearly identical three-dimensional structures. A measure of a unique set of structural coordinates is the root mean square deviation of the resulting structure. Structural coordinates that render three-dimensional structures (in particular, a three-dimensional structure of an enzymatically active center) that deviate from one another by a root mean square deviation of less than 3 Å, 2 Å, 1.5 Å, 1.0 Å, or 0.5 Å may be viewed by a person of ordinary skill in the art as very similar.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a variant of the PA polypeptide fragment or the enzymatically active center therein from the backbone of the PA polypeptide fragment or the enzymatically active center therein as defined by the structure coordinates of the PA polypeptide fragment PA-Nter according to FIG. 1.

As used herein, the term "constructing a computer model" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry, and other structure-based constraint models.

The term "fitting program operation" refers to an operation that utilizes the structure coordinates of a chemical entity, an enzymatically active center, a binding pocket, molecule or molecular complex, or portion thereof, to associate the chemical entity with the enzymatically active center, the binding pocket, molecule or molecular complex, or portion thereof. This may be achieved by positioning, rotating or translating the chemical entity in the enzymatically active center to match the shape and electrostatic complementarity of the enzymatically active center. Covalent interactions, non-covalent interactions such as hydrogen bond, electrostatic, hydrophobic, van der Waals interactions, and non-complementary electrostatic interactions such as repulsive charge-charge, dipole-dipole and charge-dipole interactions may be optimized. Alternatively, one may minimize the deformation energy of binding of the chemical entity to the enzymatically active center.

As used herein, the term "test compound" refers to an agent comprising a compound, molecule, or complex that is being tested for its ability to inhibit the endonucleolytic activity of the polypeptide fragment of interest, i.e., the PA polypeptide fragment of the invention or variants thereof possessing endonucleolytic acitvity. Test compounds can be any agents including, but not restricted to, peptides, peptoids, polypeptides, proteins (including antibodies), lipids, metals, nucleotides, nucleotide analogs, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term "small molecules" refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds. Well known methods may be used for attaching such a detectable label to a test compound. The test compound of the invention may also comprise complex mixtures of substances, such as extracts containing natural products, or the products of mixed combinatorial syntheses. These can also be tested and the component that inhibits the endonucleolytic activity of the target polypeptide fragment can be purified from the mixture in a subsequent step. Test compounds can be derived or selected from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant and animal cell and tissue extracts can be used. Additionally, test compounds can be synthetically produced using combinatorial chemistry either as individual compounds or as mixtures. A collection of compounds made using combinatorial chemistry is referred to herein as a combinatorial library.

In the context of the present invention, "a compound which modulates the endonucleolytic activity" may increase or decrease, preferably inhibit the endonucleolytic activity of the PA subunit of the Influenza A 2009 pandemic H1N1 virus or the Influenza A 2009 pandemic H1N1 virus RNA-dependent RNA polymerase or a variant thereof. Preferably, such a compound is specific for the endonucleolytic activity of the Influenza A 2009 pandemic H1N1 PA subunit or variant thereof and does not modulate, preferably decrease the endonucleolytic activity of other endonucleases, in particular mammalian endonucleases.

The term "a compound which decreases the endonucleolytic activity" means a compound which decreases the endonucleolytic activity of the PA subunit of the Influenza A 2009 pandemic H1N1 virus or the Influenza A 2009 pandemic H1N1 virus RNA-dependent RNA polymerase or a variant thereof by 50%, more preferably by 60%, even more preferably by 70%, even more preferably by 80%, even more preferably by 90%, and most preferably by 100% compared to the endonucleolytic activity of said PA subunit or a variant thereof without said compound but with otherwise the same reaction conditions, i.e., buffer conditions, reaction time and temperature.

It is most preferred that the compound which decreases the endonucleolytic activity of the PA subunit of the Influenza A 2009 pandemic H1N1 virus or a variant thereof inhibits said activity, i.e., decreases said activity by at least 95%, preferably by 100% compared to the activity without the compound. It is particularly preferred that the compound that decreases or inhibits the endonucleolytic activity of the PA subunit of the Influenza A 2009 pandemic H1N1 virus or a variant thereof specifically decreases or inhibits the endonucleolytic activity of said PA subunit or a variant thereof but does not inhibit the endonucleolytic activity of other endonucleases such as RNase H or restriction endonucleases to the same extent, preferably not at all. For example, the skilled person may set up the following samples with the same buffer and reaction conditions as well as substrate and endonuclease concentrations: (1) substrate such as panhandle RNA, endonucleolytically active PA H1N1 polypeptide fragment or variant thereof, (2) substrate such as panhandle RNA, endonucleolytically active PA H1N1 polypeptide fragment or variant thereof, test compound, (3) substrate such as panhandle RNA, reference endonuclease such as RNAse H, (4) substrate such as panhandle RNA, reference nucleotide such as RNAse H, test compound. After incubation of the samples, the skilled person may analyze the substrate, for example, by gel electrophoresis. Test compounds which result in cleaved substrate in sample (4) and intact substrate in sample (2) are preferred.

The term "in a high-throughput setting" refers to high-throughput screening assays and techniques of various types which are used to screen libraries of test compounds for their ability to inhibit the endonuclease activity of the polypeptide fragment of interest. Typically, the high-throughput assays are performed in a multi-well format and include cell-free as well as cell-based assays.

The term "antibody" refers to both monoclonal and polyclonal antibodies, i.e., any immunoglobulin protein or portion thereof which is capable of recognizing an antigen or hapten, i.e., the Influenza A 2009 pandemic H1N1 PA polypeptide fragment possessing endonucleolytic activity or a peptide thereof. In a preferred embodiment, the antibody is capable of binding to the enzymatically (endonucleolytically) active center within the Influenza A 2009 pandemic H1N1 PA polypeptide fragment or variant thereof Antigen-binding portions of the antibody may be produced by recombinant DNA techniques or by enzymatic or chemical cleavage of intact antibodies. In some embodiments, antigen-binding portions include Fab, Fab', F(ab')2, Fd, Fv, dAb, and complementarity determining region (CDR) fragments, single-chain antibodies (scFv), chimeric antibodies such as humanized antibodies, diabodies; and polypeptides that contain at least a portion of an antibody that is sufficient to confer specific antigen binding to the polypeptide.

The term "pharmaceutically acceptable salt" refers to a salt of a compound identifiable by the methods of the present invention or a compound of the present invention. Suitable pharmaceutically acceptable salts include acid addition salts which may, for example, be formed by mixing a solution of compounds of the present invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci. 66:1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The term "pharmaceutically acceptable carrier" includes, for example, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

DETAILED DESCRIPTION

The present inventors surprisingly found that a small independently folded domain derived from the N-terminus of the PA subunit of Influenza A 2009 pandemic H1N1 virus RNA-dependent RNA polymerase exhibits the functional properties of the endonuclease reported for the trimeric complex, although this activity was thought to be detectable only in the trimeric complex. Moreover, the inventors found that this PA polypeptide fragment can easily be produced by recombinant means and, thus, is suitable for in vitro studies on the endonucleolytic activity and its modulation. The present inventors surprisingly found that the domain derived from the N-terminus of the PA subunit of Influenza A 2009 pandemic H1N1 virus RNA-dependent RNA polymerase readily crystallized and that, thus, said domain is very dedicated for the identification, selection and design of new anti-viral compounds targeting the endonuclease activity of the Influenza A 2009 pandemic H1N1 polymerase as well as for the optimization of previously identified compounds by computer methods.

It is one aspect of the present invention to provide a polypeptide fragment comprising an amino-terminal fragment of the PA subunit of a viral RNA-dependent RNA polymerase possessing endonuclease activity, wherein said PA subunit is from Influenza A 2009 pandemic H1N1 virus according to SEQ ID NO: 2 or is a variant thereof, wherein said variant comprises the amino acid serine at an amino acid position 186 according to SEQ ID NO: 2 or at an amino acid position corresponding thereto.

In a preferred embodiment of the present invention, said variant comprises the amino acids 1 to 198 of the amino acid sequence set forth in SEQ ID NO: 2 with amino acids 52 to 64 replaced by the amino acid glycine (SEQ ID NO: 14). In a further preferred embodiment of the present invention, said variant comprises the amino acids 1 to 198 of the amino acid sequence set forth in SEQ ID NO: 2 with amino acids 52 to 72 replaced by the amino acid glycine SEQ ID NO:15). In another further preferred embodiment of the present invention, said variant comprises the amino acids 1 to 198 of the amino acid sequence set forth in SEQ ID NO: 2 with amino acids 52 to 69 replaced by the amino acid glycine (SEQ ID NO: 6).

It is preferred that the polypeptide fragment according to the present invention is soluble, preferably in an aqueous solution. The minimal length of the polypeptide fragment of the present invention is determined by its ability to cleave polynucleotide chains such as panhandle RNA or single stranded DNA, i.e., the minimal length of the polypeptide is determined by its endonucleolytic activity. Preferably, the endonuclease activity is not dependent on the polynucleotide type, and thus, may be exerted on DNA and RNA, preferably on single stranded DNA and RNA. Preferably, the endonuclease activity is not dependent on specific recognition sites within the substrate polynucleotide.

In a preferred embodiment, the polypeptide fragment according to the present invention is suitable for crystallization, i.e., preferably the polypeptide fragment is crystallizable. Preferably, the crystals obtainable from the polypeptide fragment according to the invention are suitable for structure determination of the polypeptide fragment using X-ray crystallography. Preferably, said crystals are greater than 25 micron cubes and preferably are radiation stable enough to permit more than 85% diffraction data completeness at resolution of preferably 3.5 Å or better to be collected upon exposure to monochromatic X-rays.

In one embodiment, the polypeptide fragment is crystallizable using (i) an aqueous protein solution, i.e. the crystallization solution, with a protein concentration of 5 to 20 mg/ml, e.g. of 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mg/ml, preferably of 8 to 15 mg/ml, most preferably of 10 to 15 mg/ml in a buffer system such as HEPES or Tris-HCl at concentrations ranging from 10 mM to 3 M, preferably 10 mM to 2 M, more preferably 20 mM to 1 M, at pH 3 to pH 9, preferably pH 4 to pH 9, more preferably pH 7 to pH 9, and (ii) a precipitant/reservoir solution comprising one or more substances such as sodium formate, ammonium sulphate, lithium sulphate, magnesium acetate, manganese acetate, sodium chloride, glycerol or ethylene glycol.

Optionally, the protein solution may contain one or more salts such as monovalent salts, e.g., NaCl, KCl, or LiCl, preferably NaCl, at concentrations ranging from 10 mM to 1 M, preferably 20 mM to 500 mM, more preferably 50 mM to 200 mM, and/or divalent salts, e.g., $MnCl_2$, $CaCl_2$, $MgCl_2$, $ZnCl_2$, or $CoCl_2$, preferably $MgCl_2$ and $MnCl_2$, at concentrations ranging from 0.1 to 50 mM, preferably 0.5 to 25 mM, more preferably 1 to 10 mM or 1 to 5 mM.

Preferably, the precipitant/reservoir solution comprises sodium formate at concentrations ranging from 0.5 to 2 M, preferably 1 to 1.8 M, a buffer system such as HEPES at concentrations ranging from 10 mM to 1 M, preferably 50 mM to 500 mM, more preferably 75 to 150 mM, at preferably pH 4 to 8, more preferably pH 5 to 7, and/or ethylene glycol at concentrations ranging from 1% to 20%, preferably 2% to 8%, more preferably 2 to 5%.

The PA polypeptide fragment or variant thereof is preferably 85% to 100% pure, more preferably 90% to 100% pure, even more preferably 95% to 100% pure in the crystallization solution. To produce crystals, the protein solution suitable for crystallization may be mixed with an equal volume of the precipitant solution.

In a preferred embodiment, the crystallization medium comprises 0.05 to 2 μl, preferably 0.8 to 1.2 μl, of protein solution suitable for crystallization mixed with a similar, preferably equal volume of precipitant solution comprising 1.0 to 2.0 M sodium formate, 80 to 120 mM HEPES pH 6.5 to pH 7.5, and 2 to 5% glycol or glycerol.

In another embodiment, the precipitant solution comprises, preferably essentially consists of or consists of 1.6 M sodium formate, 0.1 M HEPES pH 7.0, and 5% glycol or glycerol, and the crystallization/protein solution comprises, preferably essentially consists or consists of 10 to 15 mg/ml in 20 mM HEPES pH 7.5, 150 mM NaCl, 2.0 mM $MnCl_2$, and 2.0 mM $MgCl_2$.

In another embodiment, the PA polypeptide fragment is co-crystallizable with a compound, preferably with a compound that modulates, preferably inhibits, the endonuclease activity of the PA polypeptide fragment, preferably with a compound according to Tables 1 or 2, using (i) an aqueous protein solution with a concentration of the PA polypeptide fragment of 5 to 20 mg/ml, e.g., 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 mg/ml, preferably of 8 to 15 mg/ml, most preferably of 10 to 15 mg/ml in a buffer system such as HEPES or Tris-HCl at concentrations ranging from 10 mM to 3 M, preferably 10 mM to 2 M, more preferably 20 mM to 1 M, at pH 3 to pH 9, preferably pH 4 to pH 9, more preferably pH 7 to pH 9, and (ii) a precipitant/reservoir solution comprising one or more substances such as sodium formate, ammonium sulphate, lithium sulphate, magnesium acetate, manganese acetate, sodium chloride, ethylene glycol, glycerol, or PEG. For co-crystallization, a compound, preferably a compound that modulates, e.g. inhibits, the endonuclease activity of the PA polypeptide fragment, preferably a compound according to Tables 1 or 2, is added to the aqueous protein solution to a final concentration of between 0.5 and 5 mM, preferably of between 1.5 and 5 mM, i.e. 0.5, 1, 1.5, 2, 2.5, 3, 4.5 or 5 mM.

Optionally, the protein solution may contain one or more salts such as monovalent salts, e.g., NaCl, KCl, or LiCl, preferably NaCl, at concentrations ranging from 10 mM to 1 M, preferably 20 mM to 500 mM, more preferably 50 mM to 200 mM, and/or divalent salts, e.g., $MnCl_2$, $CaCl_2$, $MgCl_2$, $ZnCl_2$, or $CoCl_2$, preferably $MgCl_2$ and $MnCl_2$, at concentrations ranging from 0.1 to 50 mM, preferably 0.5 to 25 mM, more preferably 1 to 10 mM or 1 to 5 mM.

Preferably, the precipitant/reservoir solution comprises ammonium sulphate at concentrations ranging from 0.1 to 2.5 M, preferably 0.1 to 2.0 M, a buffer system such as Bis-Tris at concentrations ranging from 10 mM to 1 M, preferably 50 mM to 500 mM, more preferably 75 to 150 mM, at preferably pH 4 to 7, more preferably pH 5 to 6, and/or PEG such as PEG 3350 at concentrations ranging from 1% to 30%, preferably 15% to 30%, more preferably 20 to 25%.

The PA polypeptide fragment or variant thereof is preferably 85% to 100% pure, more preferably 90% to 100% pure, even more preferably 95% to 100% pure in the protein solution. For co-crystallization, the aqueous protein solution comprising the PA polypeptide fragment or variant thereof and the compound may be mixed with an equal volume of the precipitant solution.

In a preferred embodiment, the protein solution comprises, preferably essentially consists or consists of 10 to 15 mg/ml PA polypeptide fragment in 20 mM HEPES pH 7.5, 150 mM NaCl, 2.0 mM $MnCl_2$, and 2.0 mM $MgCl_2$ and 4-[3-[(4-chlorophenyl)methyl]-1-(phenylmethyl)-3-piperidinyl]-2-hydroxy-4-oxo-2-butenoic acid (EMBL-R05-3) in a final concentration of 1.5 mM, and the reservoir solution/precipitant solution comprises, preferably essentially consists of or consists of 2.0 M ammonium sulphate and 0.1M Bis-Tris pH5.5 (see also Table 1).

In another preferred embodiment, the protein solution comprises, preferably essentially consists or consists of 10 to 15 mg/ml PA polypeptide fragment in 20 mM HEPES pH 7.5, 150 mM NaCl, 2.0 mM $MnCl_2$, and 2.0 mM $MgCl_2$ and 4-[4-[(4-chlorophenyl)methyl]-1-(cyclohexylmethyl)-4-piperidinyl]-2-hydroxy-4-oxo-2-butenoic acid (EMBL-R05-2) in a final concentration of 1.5 mM, preferably soaked into crystals initially grown with ribo-Uridine Monophosphate (rUMP), and the reservoir solution/precipitant solution comprises, preferably essentially consists of or consists of 0.1 M ammonium sulphate, 0.1 M Bis-Tris pH5.5 and 25% (w/v) PEG 3350 (see also Table 1).

In a further preferred embodiment, the protein solution comprises, preferably essentially consists or consists of 10 to 15 mg/ml PA polypeptide fragment in 20 mM HEPES pH 7.5, 150 mM NaCl, 2.0 mM $MnCl_2$, and 2.0 mM $MgCl_2$ and ribo-Uridine Monophosphate (rUMP) in a final concentration of 5 mM, and the reservoir solution/precipitant solution comprises, preferably essentially consists of or consists of 0.1 M ammonium sulphate, 0.1 M Bis-Tris pH5.5 and 25% (w/v) PEG 3350 (see also Table 1).

Other preferred reservoir solutions/precipitant solutions for the co-crystallization of the PA polypeptide fragment or variant thereof, e.g. with 4-[3-[(4-chlorophenyl)methyl]-1-(phenylmethylsulpho)-3-piperidinyl]-2-hydroxy-4-oxo-2-butenoic acid (EMBL-R05-1) or with [(2R,3R)-5,7-dihydroxy-2-(3,4,5-trihydroxyphenyl)chroman-3-yl]3,4,5-trihydroxybenzoate (EGCG), can further be taken from Table 1.

Crystals can be grown by any method known to the person skilled in the art including, but not limited to, hanging and sitting drop techniques, sandwich-drop, dialysis, and microbatch or microtube batch devices. It would be readily apparent to one of skill in the art to vary the crystallization conditions disclosed above to identify other crystallization conditions that would produce crystals of PA polypeptide fragments of the inventions or variants thereof alone or in complex with a compound. Such variations include, but are not limited to, adjusting pH, protein concentration and/or crystallization temperature, changing the identity or concentration of salt and/or precipitant used, using a different method for crystallization, or introducing additives such as detergents (e.g., TWEEN 20 (monolaurate), LDOA, Brij 30 (4 lauryl ether)), sugars (e.g., glucose, maltose), organic compounds (e.g., dioxane, dimethylformamide), lanthanide ions, or poly-ionic compounds that aid in crystallizations. High throughput crystallization assays may also be used to assist in finding or optimizing the crystallization condition.

Microseeding may be used to increase the size and quality of crystals. In brief, micro-crystals are crushed to yield a stock seed solution. The stock seed solution is diluted in series. Using a needle, glass rod or strand of hair, a small sample from each diluted solution is added to a set of equilibrated drops containing a protein concentration equal to or less than a concentration needed to create crystals without the presence of seeds. The aim is to end up with a single seed crystal that will act to nucleate crystal growth in the drop.

The manner of obtaining the structure coordinates as shown in FIGS. 1 to 5, interpretation of the coordinates and their utility in understanding the protein structure, as described herein, are commonly understood by the skilled person and by reference to standard texts such as J. Drenth, "Principles of protein X-ray crystallography", $2^{nd}$ Ed., Springer Advanced Texts in Chemistry, New York (1999); and G. E. Schulz and R. H. Schirmer, "Principles of Protein Structure", Springer Verlag, N.Y. (1985). For example, X-ray diffraction data is first acquired, often using cryoprotected (e.g., with 20% to 30% glycerol) crystals frozen to 100 K, e.g., using a beamline at a synchrotron facility or a rotating anode as an X-ray source. Then, the phase problem is solved by a generally known method, e.g., multiwavelength anomalous diffraction (MAD), multiple isomorphous replacement (MIR), single wavelength anomalous diffraction (SAD), or molecular replacement (MR). The sub-structure may be solved using SHELXD (Schneider and Sheldrick, 2002, Acta Crystallogr. D. Biol. Crystallogr. (Pt 10 Pt 2), 1772-1779), phases calculated with SHARP (Vonrhein et al., 2006, Methods Mol. Biol. 364:215-30), and improved with solvent flattening and non-crystallographic symmetry averaging, e.g., with RESOLVE (Terwilliger, 2000, Acta Cryst. D. Biol. Crystallogr. 56:965-972). Model autobuilding can be done, e.g., with ARP/wARP (Perrakis et al., 1999, Nat. Struct. Biol. 6:458-63) and refinement with, e.g. REFMAC (Murshudov, 1997, Acta Crystallogr. D. Biol. Crystallogr. 53: 240-255).

Preferably, the amino terminal PA fragment comprised within the polypeptide fragment according to the present invention corresponds to, preferably essentially consists or consists of, at least amino acids 1 to 190, preferably amino acids 1 to 198, preferably amino acids 1 to 200, of the PA subunit of the RNA-dependent RNA polymerase of Influenza A 2009 pandemic H1N1 virus according to SEQ ID NO: 2 or variants thereof.

In a preferred embodiment, the polypeptide fragment according to the present invention is purified to an extent to be suitable for crystallization, preferably it is 85% to 100%, more preferably 90% to 100%, most preferably 95% to 100% pure. In another preferred embodiment, the polypeptide fragment according to the present invention is purified to an extent to be suitable for co-crystallization, preferably it is 85% to 100%, more preferably 90% to 100%, most preferably 95% to 100% pure.

In another embodiment, the polypeptide fragment according to the present invention is capable of binding to divalent cations. Preferably, the polypeptide fragment according to the present invention is bound to one or more divalent cation(s), preferably it is bound to two divalent cations. In this context, the divalent cation is preferably selected form the group consisting of manganese, cobalt, calcium, magnesium, and zinc, and is more preferably manganese or cobalt, most preferably manganese and/or magnesium. Thus, in a preferred embodiment, the polypeptide fragment of the present invention is present in complex with (i) two manganese cations, (ii) two magnesium cations, or (iii) one manganese and one magnesium cation. In a preferred embodiment, the divalent cations are coordinated by amino acids corresponding to amino acids Glu80 and Asp108 (second cation) and amino acids corresponding to amino acids His41, Asp108, Ile120 and Glu119 (first cation) as set forth in SEQ ID NO: 2. In preferred embodiment, the divalent cation is manganese for site 1 and manganese or magnesium for site 2, i.e. manganese for site 1 and magnesium for site 2 (see FIG. 6) or manganese for site 1 and manganese for site 2 (see FIGS. 7 to 10, 17 and 18)

In a further embodiment, the polypeptide fragment according to the present invention is a polypeptide fragment, wherein the N-terminus is identical to or corresponds to amino acid position 15 or lower, e.g., at position 15, 14, 13, 12, 11, 10, 9, 8, 7, 6, 5, 4, 3, 2, or 1, and the C-terminus is identical to or corresponds to an amino acid at a position selected from positions 186 to 200, e.g., 186, 187, 188, 189, 190, 191, 192, 193, 194, 195, 196, 197, 198, 199, or 200 of the amino acid sequence of the PA subunit according to SEQ ID NO: 2, preferably the C-terminus is identical to or corresponds to an amino acid at a position selected from 190 to 200, more preferably 190 to 198 of the amino acid sequence of the PA subunit according to SEQ ID NO: 2, or is a variant thereof, wherein said variant comprises the amino acid serine at an amino acid position 186 according to SEQ ID NO: 2 or at an amino acid position corresponding thereto and retains the endonuclease activity.

In a preferred embodiment of the present invention, said variant comprises SEQ ID NO: 14 (the amino acids 1 to 198 of the amino acid sequence set forth in SEQ ID NO: 2 with amino acids 52 to 64 replaced by the amino acid glycine). In a more preferred embodiment of the present invention, said variant consists of SEQ ID NO: 14 (the amino acids 1 to 198 of the amino acid sequence set forth in SEQ ID NO: 2 with amino acids 52 to 64 replaced by the amino acid glycine) and optionally of an amino-terminal linker having the amino acid sequence MGSGMA (SEQ ID NO: 3).

In a further preferred embodiment of the present invention, said variant comprises SEQ ID NO: 15 (the amino acids 1 to 198 of the amino acid sequence set forth in SEQ ID NO: 2 with amino acids 52 to 72 replaced by the amino acid glycine). In a more preferred embodiment of the present invention, said variant consists of SEQ ID NO: 15 (the amino acids 1 to 198 of the amino acid sequence set forth in SEQ ID NO: 2 with amino acids 52 to 72 replaced by the amino acid glycine) and optionally of an amino-terminal linker having the amino acid sequence MGSGMA (SEQ ID NO: 3).

In another further preferred embodiment of the present invention, said variant comprises SEQ ID NO: 16 (the amino acids 1 to 198 of the amino acid sequence set forth in SEQ ID NO: 2 with amino acids 52 to 69 replaced by the amino acid glycine). In a more preferred embodiment of the present invention, said variant consists of SEQ ID NO: 16 (the amino acids 1 to 198 of the amino acid sequence set forth in SEQ ID NO: 2 with amino acids 52 to 69 replaced by the amino acid glycine) and optionally of an amino-terminal linker having the amino acid sequence MGSGMA (SEQ ID NO: 3).

Preferably, said polypeptide fragment has or corresponds to an amino acid sequence selected from the group of amino acid sequences consisting of amino acids 5 to 190, 10 to 190, 15 to 190, 20 to 190, 5 to 198, 10 to 198, 15 to 198, 20 to 198 of the amino acid sequence set forth in SEQ ID NO: 2 and variants thereof, wherein said variants comprises the amino acid serine at an amino acid position 186 according to SEQ ID NO: 2 or at an amino acid position corresponding thereto and retain the endonuclease activity.

In a further embodiment, the polypeptide fragment (variant) according to the present invention (a) consists of SEQ ID NO: 13 (amino acids 1 to 198 of the amino acid sequence set forth in SEQ ID NO: 2) and optionally of an amino-terminal linker having the amino acid sequence MGSGMA (SEQ ID NO: 3) and has the structure defined by (i) the structure coordinates as shown in FIG. 1, (ii) the structure coordinates as shown in FIG. 2, (iii) the structure coordinates as shown in FIG. 3, (iv) the structure coordinates as shown in FIG. 4, or (v) the structure coordinates as shown in FIG. 5, or (b) consists of SEQ ID NO: 14 (amino acids 1 to 198 of the amino acid sequence set forth in SEQ ID NO: 2 with amino acids 52 to 64 replaced by the amino acid glycine) and optionally of an amino-terminal linker having the amino acid sequence MGSGMA (SEQ ID NO: 3) and has the structure defined by (vi) the structure coordinates as shown in FIG. 15, or (vii) the structure coordinates as shown in FIG. 16.

It is preferred that said polypeptide fragment according to the present invention has the crystal structure defined by the structure coordinates as shown in FIG. 1 without co-crystallization with a compound (native structure).

It is further preferred that said polypeptide fragment (variant) according to the present invention has the crystal structure defined by the structure coordinates as shown in FIG. 2 to 5, 15 or 16 after co-crystallization with a compound, preferably with a compound that modulates, preferably inhibits, the endonuclease activity of said polypeptide fragment.

It is particularly preferred that said polypeptide fragment (variant) has the structure defined by the structure coordinates as shown in FIG. 2 to 5, 15 or 16 after co-crystallization with a compound according to Tables 1 or 2, i.e. the structure defined by the structure coordinates as shown in FIGS. 2 and 3 after co-crystallization with 4-[3-[(4-chlorophenypmethyl]-1-(phenylmethyl)-3-piperidinyl]-2-hydroxy-4-oxo-2-butenoic acid (EMBL-R05-3), the structure defined by the structure coordinates as shown in FIG. 4 after co-crystallization with 4-[4-[(4-chlorophenyl)methyl]-1-(cyclohexylmethyl)-4-piperidinyl]-2-hydroxy-4-oxo-2-butenoic acid, (EMBL-R05-2), the structure defined by the structure coordinates as shown in FIG. 5 after co-crystallization with ribouridine monophosphate (rUMP), the structure defined by the structure coordinates as shown in FIG. 15 after co-crystallization with 4-[3-[(4-chlorophenyl)methyl]-1-(phenylmethylsulpho)-3-piperidinyl]-2-hydroxy-4-oxo-2-butenoic acid (EMBL-R05-1), or the structure defined by the structure coordinates as shown in FIG. 16 after co-crystallization with [(2R,3R)-5,7-dihydroxy-2-(3,4,5-trihydroxyphenyl)chroman-3-yl]3,4,5-trihydroxybenzoate (EGCG).

Considering the above, the skilled person will readily understand that said polypeptide fragment (variant) has a crystal structure which is only defined by the structure coordinates of its amino acids and optionally of its bound divalent cations comprised in FIG. 1, 2 to 5, 15 or 16 and that it is not defined by the structure coordinates of the respective compound used for co-crystallization which are also comprised in FIG. 2 to 5, 15 or 16, i.e. the compound EMBL-R05-3 has the residue descriptor ci3 in FIGS. 2 and 3, the compound EMBL-R05-2 has the residue descriptor cit in FIG. 4, the compound rUMP has the residue descriptor U in FIG. 5, the compound EMBL-R05-1 has the residue descriptor ci1 in FIG. 15 and the compound EGCG has the residue descriptor tte in FIG. 16.

It is also preferred that said polypeptide fragment (variant) having the structure defined by the structure coordinates as shown in FIG. 1 has a crystalline form with space group C2 and unit cell dimensions of a=26.36 nm±0.5 nm, b=6.62 nm±0.3 nm, c=6.63 nm±0.3 nm, α=90 deg, β=96±2 deg, γ=90 deg, having the structure defined by the structure coordinates as shown in FIGS. 2 to 5 has a crystalline form with space group $P2_12_12_1$ and unit cell dimensions of a=5.46±0.3 nm, b=12.25±0.4 nm, c=13.0±0.3 nm, α=90 deg, β=90 deg, γ=90 deg, having the structure defined by the structure coordinates as shown in FIG. 15 has a crystalline form with space group P $6_222$ and unit cell dimensions of a=7.50 nm±0.3 nm, b=7.50 nm±0.3 nm, c=12.00 nm±0.5 nm, α=90 deg, β=90 deg, γ=120 deg, or having the structure defined by the structure coordinates as shown in FIG. 16 has a crystalline form with space group $P6_422$ and unit cell dimensions of a=9.99 nm±0.5 nm, b=9.99 nm±0.5 nm, c=8.27 nm±0.3 nm, α=90 deg, β=90 deg, γ=120 deg.

Preferably, the crystal of the polypeptide fragment (variant) diffracts X-rays to a resolution of 2.8 Å or higher, preferably 2.6 Å or higher, more preferably 2.5 Å or higher, even more preferably 2.4 Å or higher, most preferably 2.1 Å or higher or 1.9 Å or higher. For example, the crystal of the polypeptide fragment (variant) diffracts X-rays to a resolution of 1.9, 2.0, 2.1, 2.2, 2.3, 2.4, 2.5, 2.6, 2.7, 2.8 Å or higher.

It is another aspect of the present invention to provide an isolated polynucleotide coding for the above-mentioned (isolated) PA polypeptide fragments and variants thereof according to the present invention.

In a preferred embodiment of the present invention, the isolated polynucleotide codes for the PA polypeptide fragment which comprises SEQ ID NO: 13 (the amino acids 1 to 198 of the amino acid sequence set forth in SEQ ID NO: 2).

In another preferred embodiment of the present invention, the isolated polynucleotide codes for the PA polypeptide fragment variant which comprises SEQ ID NO: 14 the amino acids 1 to 198 of the amino acid sequence set forth in SEQ ID NO: 2 with amino acids 52 to 64 replaced by the amino acid glycine).

In a further preferred embodiment of the present invention, the isolated polynucleotide codes for the PA polypeptide fragment variant which comprises SEQ ID NO: 15 (the amino acids 1 to 198 of the amino acid sequence set forth in SEQ ID NO: 2 with amino acids 52 to 72 replaced by the amino acid glycine).

In another further preferred embodiment of the present invention, the isolated polynucleotide codes for the PA polypeptide fragment variant which comprises SEQ ID NO: 16 (the amino acids 1 to 198 of the amino acid sequence set forth in SEQ ID NO: 2 with amino acids 52 to 69 replaced by the amino acid glycine).

The molecular biology methods applied for obtaining such isolated nucleotide fragments are generally known to the person skilled in the art (for standard molecular biology methods see Sambrook et al., Eds., "Molecular Cloning: A Laboratory Manual", Cold Spring Harbor Laboratory Press, Cold Spring Harbor, N.Y. (1989), which is incorporated herein by reference). For example, RNA can be isolated from Influenza A 2009 pandemic H1N1 virus infected cells and cDNA generated applying reverse transcription polymerase chain reaction (RT-PCR) using either random primers (e.g., random hexamers of decamers) or primers specific for the generation of the fragments of interest. The fragments of interest can then be amplified by standard PCR using fragment specific primers.

The isolated polynucleotides coding for the Influenza A 2009 pandemic H1N1 virus RNA-dependent RNA polymerase PA subunit fragments are derived from SEQ ID NO: 1. In this context, "derived" refers to the fact that SEQ ID NO: 1 encodes the full-length PA polypeptide and, thus, polynucleotides coding for preferred PA polypeptide fragments may comprise deletions at the 3'- and/or 5'-ends of the polynucleotides as required by the respectively encoded PA polypeptide fragments.

In another aspect, the present invention relates to a recombinant vector comprising the isolated polynucleotide according to the present invention. The person skilled in the art is well aware of techniques used for the incorporation of polynucleotide sequences of interest into vectors (also see Sambrook et al., 1989, supra). Such vectors include any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors may be expression vectors suitable for prokaryotic or eukaryotic expression. Said plasmids may include an origin of replication (ori), a multiple cloning site, and regulatory sequences such as promoter (constitutive or inducible), transcription initiation site, ribosomal binding site, transcription termination site, polyadenylation signal, and selection marker such as antibiotic resistance or auxotrophic marker based on complementation of a mutation or deletion. In one embodiment the polynucleotide sequence of interest is operably linked to the regulatory sequences.

In another embodiment, said vector includes nucleotide sequences coding for epitope-, peptide-, or protein-tags that facilitate purification of polypeptide fragments of interest. Such epitope-, peptide-, or protein-tags include, but are not limited to, hemagglutinin- (HA-), FLAG-, myc-tag, poly-His-tag, glutathione-S-transferase- (GST-), maltose-binding-protein-(MBP-), NusA-, and thioredoxin-tag, or fluorescent protein-tags such as (enhanced) green fluorescent protein ((E)GFP), (enhanced) yellow fluorescent protein ((E)YFP), red fluorescent protein (RFP) derived from Discosoma species (DsRed) or monomeric (mRFP), cyan fluorescence protein (CFP), and the like. In a preferred embodiment, the epitope-, peptide-, or protein-tags can be cleaved off the polypeptide fragment of interest, for example, using a protease such as thrombin, Factor Xa, PreScission, TEV protease, and the like. Preferably, the tag can be cleaved of with a TEV protease. The recognition sites for such proteases are well known to the person skilled in the art. For example, the seven amino acid consensus sequence of the TEV protease recognition site is Glu-X-X-Tyr-X-Gln-Gly/Ser, wherein X may be any amino acid and is in the context of the present invention preferably Glu-Asn-Leu-Tyr-Phe-Gln-Gly (SEQ ID NO: 12). In another embodiment, the vector includes functional sequences that lead to secretion of the polypeptide fragment of interest into the culture medium of the recombinant host cells or into the periplasmic space of bacteria. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

In another aspect, the present invention provides a recombinant host cell comprising the isolated polynucleotide according to the present invention or the recombinant vector according to the present invention. The recombinant host cells may be prokaryotic cells such as archea and bacterial cells or eukaryotic cells such as yeast, plant, insect, or mammalian cells. In a preferred embodiment the host cell is a bacterial cell such as an *E. coli* cell. The person skilled in the art is well aware of methods for introducing said isolated polynucleotide or said recombinant vector into said host cell. For example, bacterial cells can be readily transformed using, for example, chemical transformation, e.g., the calcium chloride method, or electroporation. Yeast cells may be transformed, for example, using the lithium acetate transformation method or electroporation. Other eukaryotic cells can be transfected, for example, using commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), electroporation, or viral infection. In a preferred embodiment of the invention, the recombinant host cell expresses the polynucleotide fragment of interest. In an even more preferred embodiment, said expression leads to soluble polypeptide fragments of the invention. These polypeptide fragments may be purified using protein purification methods well known to the person skilled in the art, optionally taking advantage of the above-mentioned epitope-, peptide-, or protein-tags.

In another aspect, the present invention relates to a method for identifying compounds, which modulate the endonuclease activity of the PA subunit of a RNA-dependent RNA polymerase from Influenza A 2009 pandemic H1N1 virus or a variant thereof comprising the steps of:

(a) constructing a computer model of the active site defined by (i) the structure coordinates of the polypeptide fragment according to the present invention as shown in FIG. 1, (ii) the structure coordinates of the polypeptide fragment according to the present invention as shown in FIG. 2, (iii) the structure coordinates of the polypeptide fragment according to the present invention as shown in FIG. 3, (iv) the structure coordinates of the polypeptide fragment according to the present invention as shown in FIG. 4, (v) the structure coordinates of the polypeptide fragment according to the present invention as shown in FIG. 5, (vi) the structure coordinates of the polypeptide fragment (variant) according to the present invention as shown in FIG. 15, and/or (vii) the structure coordinates of the polypeptide fragment (variant) according to the present invention as shown in FIG. 16, (b) selecting a potential modulating compound by a method selected from the group consisting of:

(i) assembling molecular fragments into said compound, (ii) selecting a compound from a small molecule database, and (iii) de novo ligand design of said compound;

(c) employing computational means to perform a fitting program operation between computer models of the said compound and the said active site in order to provide an energy-minimized configuration of the said compound in the active site; and (d) evaluating the results of said fitting operation to quantify the association between the said compound and the active site model, whereby evaluating the ability of said compound to associate with the said active site.

In a preferred embodiment, a computer model of the active site defined by (i) the structure coordinates of the polypeptide fragment according to the present invention (i.e. amino acid structure coordinates) as shown in FIG. 1 and the structure coordinates of the divalent cations as shown in FIG. 1, (ii) the structure coordinates of the polypeptide fragment according to the present invention (i.e. amino acid structure coordinates) as shown in FIG. 2 and the structure coordinates of the divalent cations as shown in FIG. 2, (iii) the structure coordinates of the polypeptide fragment according to the present invention as shown in FIG. 3 and the structure coordinates of the divalent cations as shown in FIG. 3, (iv) the structure coordinates of the polypeptide fragment according to the present invention as shown in FIG. 4 and the structure coordinates of the divalent cations as shown in FIG. 4, (v) the structure coordinates of the polypeptide fragment according to the present invention as shown in FIG. 5 and the structure coordinates of the divalent cations as shown in FIG. 5, (vi) the structure coordinates of the polypeptide fragment (variant) according to the present invention (i.e. amino acid structure coordinates) as shown in FIG. 15 and the structure coordinates of the divalent cations as shown in FIG. 15, and/or (vii) the structure coordinates of the polypeptide fragment (variant) according to the present invention (i.e. amino acid structure coordinates) as shown in FIG. 16 and the structure coordinates of the divalent cations as shown in FIG. 16 is constructed in step a) of the method of the present invention.

Preferably, the modulating compound associates with, preferably binds to, the endonucleolytically active site within the PA subunit of a RNA-dependent RNA polymerase from Influenza A 2009 pandemic H1N1 virus or variant thereof. The modulating compound may increase or decrease, preferably decrease said endonucleolytic activity.

In a preferred embodiment of this aspect of the present invention, the compound that modulates the endonuclease activity of the PA subunit of a RNA-dependent RNA polymerase from Influenza A 2009 pandemic H1N1 virus or variant thereof decreases said activity, more preferably said compound inhibits said activity. Preferably, the compound decreases the endonucleolytic activity of the PA subunit of a RNA-dependent RNA polymerase from Influenza A 2009 pandemic H1N1 virus or variant thereof by 50%, more preferably by 60%, even more preferably by 70%, even more preferably by 80%, even more preferably by 90%, and most preferably by 100% compared to the endonucleolytic activity of said PA subunit or a variant thereof without said compound but with otherwise the same reaction conditions, i.e., buffer conditions, reaction time and temperature. It is particularly preferred that the compound specifically decreases or inhibits the endonucleolytic activity of the PA subunit of a RNA-dependent RNA polymerase from Influenza A 2009 pandemic H1N1 virus or variant thereof but does not decrease or inhibit the endonucleolytic activity of other endonucleases, in particular of mammalian endonucleases, to the same extent, preferably not at all.

The present invention permits the use of molecular design techniques to identify, select, or design compounds that potentially modulate the endonucleolytic activity of the PA subunit of a RNA-dependent RNA polymerase from Influenza A 2009 pandemic H1N1 virus or variant thereof; based on the structure coordinates of the (native) endonucleolytically active site according to FIG. 1. For the first time, the present invention further permits the optimized identification, selection and design of compounds that potentially modulate the endonucleolytic activity of the PA subunit of a RNA-dependent RNA polymerase from Influenza A 2009 pandemic H1N1 virus or variant thereof, based on the structure coordinates of the endonucleolytically active site according to FIG. 2 to 5, 15 or 16. Said structure coordinates have been achieved from polypeptide fragments (polypeptide fragment variants) according to the present invention which have been co-crystallized with a modulating compound, preferably with 4-[3-[(4-chlorophenyl)methyl]-1-(phenylmethyl)-3-piperidinyl]-2-hydroxy-4-oxo-2-butenoic acid (EMBL-R05-3) (see FIGS. 2 and 3), with 4-[4-[(4-chlorophenyl)methyl]-1-(cyclohexylmethyl)-4-piperidinyl]-2-hydroxy-4-oxo-2-butenoic acid (EMBL-R05-2) (see FIG. 4), with ribo-Uridine monophosphate (rUMP) (see FIG. 5), with 4-[3-[(4-chlorophenyl)methyl]-1-(phenylmethylsulpho)-3-piperidinyl]-2-hydroxy-4-oxo-2-butenoic acid (EMBL-R05-1) (see FIG. 15), or with [(2R,3R)-5,7-dihydroxy-2-(3,4,5-trihydroxyphenyl)chroman-3-yl]3,4,5-trihydroxybenzoate (EGCG) (see FIG. 16) (see also Tables 1 or 2). The present inventors have namely surprisingly found that the structure coordinates of the polypeptide fragment (variant) of the present invention without bound compound (i.e. native polypeptide fragment (variant)) (see, for example, FIG. 1) differ from the structure coordinates of the polypeptide fragment (variant) of the present invention with bound compound (see, for example, FIG. 2 to 5, 15 or 16) as said polypeptide fragment (variant) changes its conformation after compound binding. Thus, this new three-dimensional knowledge allows the optimized design of modifications to existing inhibitors in order to improve their potency or the design and optimization of novel inhibitors that effectively block endonuclease activity.

Such predictive models are valuable in light of the higher costs associated with the preparation and testing of the many diverse compounds that may possibly modulate the endonucleolytic activity. In order to use the structure coordinates generated for the Influenza A 2009 pandemic H1N1 PA polypeptide fragment (variant) it is necessary to convert the structure coordinates into a three-dimensional shape. This is achieved through the use of commercially available software that is capable of generating three-dimensional graphical representations of molecules or portions thereof from a set of structure coordinates. An example for such a computer program is MODELER (Sali and Blundell, 1993, J. Mol. Biol. 234:779-815 as implemented in the Insight II Homology software package (Insight II (97.0), Molecular Simulations Incorporated, San Diego, Calif.)).

One skilled in the art may use several methods to screen chemical entities or fragments for their ability to modulate the endonucleolytic activity of the Influenza A 2009 pandemic H1N1 PA subunit or Influenza A 2009 pandemic H1N1 PA subunit PA polypeptide variants. This process may begin by a visual inspection of, for example, a three-dimensional computer model of the endonucleolytically active site of PA based on the structural coordinates according to FIG. 1 to 5, 15 or 16. Selected fragments or chemical compounds may then be positioned in a variety of orientations or docked within the active site. Docking may be accomplished using software such as Cerius, Quanta, and Sybyl (Tripos Associates, St. Louis, Mo.), followed by energy minimization and molecular dynamics with standard molecular dynamics force fields such as OPLS-AA, CHARMM, and AMBER. Additional specialized computer programs that may assist the person skilled in the art in the process of selecting suitable compounds or fragments include, for example, (i) AUTODOCK (Goodsell et al., 1990, Proteins: Struct., Funct., Genet. 8: 195-202; AUTODOCK is available from The Scripps Research Institute, La Jolla, Calif.) and (ii) DOCK (Kuntz et al., 1982, J. Mol. Biol. 161:269-288; DOCK is available from the University of California, San Francisco, Calif.).

Once suitable compounds or fragments have been selected, they can be designed or assembled into a single compound or complex. This manual model building is performed using software such as Quanta or Sybyl. Useful programs aiding the skilled person in connecting individual compounds or fragments include, for example, (i) CAVEAT (Bartlett et al., 1989, in Molecular Recognition in Chemical and Biological Problems, Special Publication, Royal Chem. Soc. 78:182-196; Lauri and Bartlett, 1994, J. Comp. Aid. Mol. Des. 8:51-66; CAVEAT is available from the University of California, Berkley, Calif.), (ii) 3D Database systems such as ISIS (MDL Information Systems, San Leandro, Calif.; reviewed in Martin, 1992, J. Med. Chem. 35:2145-2154), and (iii) HOOK (Eisen et al., 1994, Proteins: Struct., Funct., Genet. 19:199-221; HOOK is available from Molecular Simulations Incorporated, San Diego, Calif.).

Another approach enabled by this invention, is the computational screening of small molecule databases for compounds that can bind in whole or part to the endonucleolytically active site of the Influenza A 2009 pandemic H1N1 PA subunit or active sites of Influenza A 2009 pandemic H1N1 PA polypeptide variants. In this screening, the quality of fit of such compounds to the active site may be judged either by shape complementarity or by estimated interaction energy (Meng et al., 1992, J. Comp. Chem. 13:505-524).

Alternatively, a potential modulator for the endonucleolytic activity of the Influenza A 2009 pandemic H1N1 PA subunit or Influenza A 2009 pandemic H1N1 polypeptide variant thereof, preferably an inhibitor of the endonucleolytic activity, may be designed de novo on the basis of the 3D structure of the PA polypeptide fragment according to FIGS. 1 to 5. There are various de novo ligand design methods available to the person skilled in the art. Such methods include (i) LUDI (Bohm, 1992, J. Comp. Aid. Mol. Des. 6:61-78; LUDI is available from Molecular Simulations Incorporated, San Diego, Calif.), (ii) LEGEND (Nishibata and Itai, Tetrahedron 47:8985-8990; LEGEND is available from Molecular Simulations Incorporated, San Diego, Calif.), (iii) LeapFrog (available from Tripos Associates, St. Louis, Mo.), (iv) SPROUT (Gillet et al., 1993, J. Comp. Aid. Mol. Des. 7:127-153; SPROUT is available from the University of Leeds, UK), (v) GROUPBUILD (Rotstein and Murcko, 1993, J. Med. Chem. 36:1700-1710), and (vi) GROW (Moon and Howe, 1991, Proteins 11:314-328).

In addition, several molecular modeling techniques (hereby incorporated by reference) that may support the person skilled in the art in de novo design and modeling of potential modulators and/or inhibitors of the endonucleolytically active site, preferably binding partners of the endonucleolytically active site, have been described and include, for example, Cohen et al., 1990, J. Med. Chem. 33:883-894; Navia and Murcko, 1992, Curr. Opin. Struct. Biol. 2:202-210; Balbes et al., 1994, Reviews in Computational Chemistry, Vol. 5, Lipkowitz and Boyd, Eds., VCH, New York, pp. 37-380; Guida, 1994, Curr. Opin. Struct. Biol. 4:777-781.

A molecule designed or selected as binding to the endonucleolytically active site of the Influenza A 2009 pandemic H1N1 PA subunit or variants thereof may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the binding compound and the binding pocket in a bound state, preferably make a neutral or favorable contribution to the enthalpy of binding. Specific computer programs that can evaluate a compound deformation energy and electrostatic interaction are available in the art. Examples of suitable programs include (i) Gaussian 92, revision C (Frisch, Gaussian, Incorporated, Pittsburgh, Pa.), (ii) AMBER, version 4.0 (Kollman, University of California, San Francisco, Calif.), (iii) QUANTA/CHARMM (Molecular Simulations Incorporated, San Diego, Calif.), (iv) OPLS-AA (Jorgensen, 1998, Encyclopedia of Computational Chemistry, Schleyer, Ed., Wiley, New York, Vol. 3, pp. 1986-1989), and (v) Insight IUDiscover (Biosysm Technologies Incorporated, San Diego, Calif.). These programs may be implemented, for instance, using a Silicon Graphics workstation, IRIS 4D/35 or IBM RISC/6000 workstation model 550. Other hardware systems and software packages are known to those skilled in the art.

Once a molecule of interest has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It should, of course, be understood that components known in the art to alter conformation should be avoided. Such substituted chemical compounds may then be analyzed for efficiency of fit to the endonucleolytically active site of the Influenza A 2009 pandemic H1N1 PA subunit or variant thereof by the same computer methods described in detail above.

In one embodiment of the above-described method of the present invention, the endonucleolytically active site of the Influenza A 2009 pandemic H1N1 PA subunit or variant thereof comprises amino acids Glu80, Glu119, Asp108, Ile120, and His41 of the PA subunit according to SEQ ID NO: 2 or amino acids corresponding thereto. In another embodiment, said active site comprises amino acids Glu80, Glu119, Asp108, Ile120, His41 and Lys34 of the PA subunit according to SEQ ID NO: 2 or amino acids corresponding thereto. In another embodiment, said active site comprises amino acids Glu80, Glu119, Asp108, Ile120, His41 and Tyr24 of the PA subunit according to SEQ ID NO: 2 or amino acids corresponding thereto. In another embodiment, said active site comprises amino acids Glu80, Glu119, Asp108, Ile120, His41 and Arg84 of the PA subunit according to SEQ ID NO: 2 or amino acids corresponding thereto. In another embodiment, said active site comprises amino acids Glu80, Glu119, Asp108, Ile120, His41 and Phe105 of the PA subunit according to SEQ ID NO: 2 or amino acids corresponding thereto. In another embodiment, said active site comprises amino acids Glu80, Glu119, Asp108, Ile120, His41, and Tyr130 of the PA subunit according to SEQ ID NO: 2 or amino acids corresponding thereto. In another embodiment, said active site comprises amino acids Glu80, Glu119, Asp108, Ile120, His41, and Ile38 of the PA subunit according to SEQ ID NO: 2 or amino acids corresponding thereto. In another embodiment, said active site comprises amino acids Glu80, Glu119, Asp108, Ile120, His41, and Arg124 of the PA subunit according to SEQ ID NO: 2 or amino acids corresponding thereto. In another embodiment, said active site comprises amino acids Glu80, Glu119, Asp108, Ile120, His41, Lys34, and Tyr24 of the PA subunit according to SEQ ID NO: 2 or amino acids corresponding thereto. In another embodiment, said active site comprises amino acids Glu80, Glu119, Asp108, Ile120, His41, Lys34, Tyr24, and Arg84 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, and Phe105 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, Phe105, and Tyr130 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, Phe105, Tyr130, and Ile38 of the PA subunit according to SEQ ID NO: 2 or amino acids corresponding thereto. In another embodiment, said active site comprises amino acids Glu80, Glu119, Asp108, Ile120, His41, Lys34, Tyr24, Arg84, Phe105, Tyr130, Ie38 and Arg124 of the PA subunit according to SEQ ID NO: 2 or amino acids corresponding thereto.

In yet another embodiment, said active site comprises amino acids Glu80, Glu119, Asp108, Ile120, His41, Lys34, Tyr24, Arg84, Phe105, Tyr130, Ile38, and Glu26 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124 and Glu26 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, and Lys134 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, and Lys134 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Gly26 and Lys134 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Gly26 and Lys134 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Leu106, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Leu106, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Lys134, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Lys134, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Lys134, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Lys134, and Lys137 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, Lys134, and Leu106 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, Lys134, and Leu106 of the PA subunit according to SEQ ID NO: 2 or amino acids corresponding thereto. In yet another embodiment, said active site comprises amino acids Glu80, Glu119, Asp108, Ile120, His41, Lys34, Tyr24, Arg84, Phe105, Tyr130, Ile38, Glu26, Lys134, Leu106, and Lys137 of the PA subunit according to SEQ ID NO: 2 or amino acids corresponding thereto, or amino acids Glu80, Glu119, Asp108, Ile120, His41, Lys34, Tyr24, Arg84, Phe105, Tyr130, Ile38, Arg124, Glu26, Lys134, Leu106, and Lys137 of the PA subunit according to SEQ ID NO: 2 or amino acids corresponding thereto.

In a further embodiment, said active site comprises amino acids Glu80, Glu119, Asp108, Ile120, His41, and Glu26 of the PA subunit according to SEQ ID NO: 2 or amino acids corresponding thereto. In a further embodiment, said active site comprises amino acids Glu80, Glu119, Asp108, Ile120, His41, and Lys134 of the PA subunit according to SEQ ID NO: 2 or amino acids corresponding thereto. In a further embodiment, said active site comprises amino acids Glu80, Glu119, Asp108, Ile120, His41, and Leu106 of the PA subunit according to SEQ ID NO: 2 or amino acids corresponding thereto. In a further embodiment, said active site comprises amino acids Glu80, Glu119, Asp108, Ile120, His41, and Lys137 of the PA subunit according to SEQ ID NO: 2 or amino acids corresponding thereto. In a further embodiment, said active site comprises amino acids Glu80, Glu119, Asp108, Ile120, His41, Glu26, and Lys134 of the PA subunit according to SEQ ID NO: 2 or amino acids corresponding thereto. In a further embodiment, said active site comprises amino acids Glu80, Glu119, Asp108, Ile120, His41, Glu26, Lys134, and Leu106 of the PA subunit according to SEQ ID NO: 2 or amino acids corresponding thereto. In a further embodiment, said active site comprises amino acids Glu80, Glu119, Asp108, Ile120, His41, Glu26, Lys134, Leu106, and Lys137 of the PA subunit according to SEQ ID NO: 2 or amino acids corresponding thereto.

In one embodiment of the above-described method of the invention, the endonucleolytically active site of the Influenza A 2009 pandemic H1N1 PA subunit or variant thereof is defined by the structure coordinates of the PA subunit SEQ ID NO: 2 amino acids Glu80, Glu119, Asp108, Ile120, and His41 according to FIGS. 1 to 5 or by the structure coordinates of the PA subunit amino acids Glu, Glu, Asp, Ile, and His corresponding to amino acids Glu80, Glu119, Asp108, Ile120, and His41 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Lys34 according to FIGS. 1 to 5 or by the structure coordinates of the PA subunit amino acids Glu, Glu, Asp, Ile, His and Lys corresponding to amino acids Glu80, Glu119, Asp108, Ile120, and His41 and Lys34 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Tyr24 according to FIGS. 1 to 5 or by the structure coordinates of the PA subunit amino acids Glu, Glu, Asp, Ile, His, and Tyr corresponding to amino acids Glu80, Glu119, Asp108, Ile120, His41 and Tyr24 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Arg84 according to FIGS. 1 to 5 or by the structure coordinates of the PA subunit amino acids Glu, Glu, Asp, Ile, His and Arg corresponding to amino acids Glu80, Glu119, Asp108, Ile120, His41 and Arg84 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Phe105 according to FIGS. 1 to 5 or by the structure coordinates of the PA subunit amino acids Glu, Glu, Asp, Ile, His and Phe corresponding to amino acids Glu80, Glu119, Asp108, Ile120, His41 and Phe105 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41 and Tyr130 according to FIGS. 1 to 5 or by the structure coordinates of the PA subunit amino acids Glu, Glu, Asp, Ile, His and Tyr corresponding to amino acids Glu80, Glu119, Asp108, Ile120, His41 and Tyr130 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, and Ile38 according to FIGS. 1 to 5 or by the structure coordinates of the PA subunit amino acids Glu, Glu, Asp, Ile, His and Ile corresponding to amino acids Glu80, Glu119, Asp108, Ile120, His41 and Ile38 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, and Arg124 according to FIGS. 1 to 5 or by the structure coordinates of the PA subunit amino acids Glu, Glu, Asp, Ile, His, and Arg corresponding to amino acids Glu80, Glu119, Asp108, Ile120, His41, and Arg124 of SEQ ID NO: 2, respectively, according to FIG. 15 or 16.

In another embodiment, said active site is defined by the structure coordinates of the PA subunit SEQ ID NO: 2 amino acids Glu80, Glu119, Asp108, Ile120, His41, Lys34, and Tyr24 according to FIGS. 1 to 5 or by the structure coordinates of the PA subunit amino acids Glu, Glu, Asp, Ile, His, Lys, and Tyr corresponding to amino acids Glu80, Glu119, Asp108, Ile120, His41, Lys34, and Tyr24 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, and Arg84 according to FIGS. 1 to 5 or by the structure coordinates of the PA subunit amino acids Glu, Glu, Asp, Ile, His, Lys, Tyr, and Arg corresponding to amino acids Glu80, Glu119, Asp108, Ile120, His41, Lys34, Tyr24, and Arg84 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, and Phe105 according to FIGS. 1 to 5 or by the structure coordinates of the PA subunit amino acids Glu, Glu, Asp, Ile, His, Lys, Tyr, Arg, and Phe corresponding to amino acids Glu80, Glu119, Asp108, Ile120, His41, Lys34, Tyr24, Arg84, and Phel 05 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, Phe105, and Tyr130 according to FIGS. 1 to 5 or by the structure coordinates of the PA subunit amino acids Glu, Glu, Asp, Ile, His, Lys, Tyr, Arg, Phe, and Tyr corresponding to amino acids Glu80, Glu119, Asp108, Ile120, His41, Lys34, Tyr24, Arg84, Phe105, and Tyr130 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, and Ile38 according to FIGS. 1 to 5 or by the structure coordinates of the PA subunit amino acids Glu, Glu, Asp, Ile, His, Lys, Tyr, Arg, Phe, Tyr, and Ile corresponding to amino acids Glu80, Glu119, Asp108, Ile120, His41, Lys34, Tyr24, Arg84, Phe105, Tyr130, and Ile38 of SEQ ID NO: 2, respectively, according to FIG. 15 or 16. In another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Arg124 according to FIGS. 1 to 5 or by the structure coordinates of the PA subunit amino acids Glu, Glu, Asp, Ile, His, Lys, Tyr, Arg, Phe, Tyr, Ile, and Arg corresponding to amino acids Glu80, Glu119, Asp108, Ile120, His41, Lys34, Tyr24, Arg84, Phe105, Tyr130, Ile38, and Arg124 of SEQ ID NO: 2, respectively, according to FIG. 15 or 16.

In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Glu26 according to FIGS. 1 to 5 or by the structure coordinates of the PA subunit amino acids Glu, Glu, Asp, Ile, His, Lys, Tyr, Arg, Phe, Tyr, Ile, and Glu corresponding to amino acids Glu80, Glu119, Asp108, Ile120, His41, Lys34, Tyr24, Arg84, Phe105, Tyr130, Ile38, and Glu26 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Lys134 according to FIGS. 1 to 5 or by the structure coordinates of the PA subunit amino acids Glu, Glu, Asp, Ile, His, Lys, Tyr, Arg, Phe, Tyr, Ile, and Lys corresponding to amino acids Glu80, Glu119, Asp108, Ile120, His41, Lys34, Tyr24, Arg84, Phe105, Tyr130, Ile38, and Lys134 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Leu106 according to FIGS. 1 to 5 or by the structure coordinates of the PA subunit amino acids Glu, Glu, Asp, Ile, His, Lys, Tyr, Arg, Phe, Tyr, Ile, and Leu corresponding to amino acids Glu80, Glu119, Asp108, Ile120, His41, Lys34, Tyr24, Arg84, Phe105, Tyr130, Ile38, and Leu106, of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, and Lys137 according to FIGS. 1 to 5 or by the structure coordinates of the PA subunit amino acids Glu, Glu, Asp, Ile, His, Lys, Tyr, Arg, Phe, Tyr, Ile, and Lys corresponding to amino acids Glu80, Glu119, Asp108, Ile120, His41, Lys34, Tyr24, Arg84, Phe105, Tyr130, Ile38, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Gly26 and Lys134 according to FIGS. 1 to 5 or by the structure coordinates of the PA subunit amino acids Glu, Glu, Asp, Ile, His, Lys, Tyr, Arg, Phe, Tyr, Ile, Glu, and Lys corresponding to amino acids Glu80, Glu119, Asp108, Ile120, His41, Lys34, Tyr24, Arg84, Phe105, Tyr130, Ile38, Glu26, and Lys134 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Leu106, and Lys137 according to FIGS. 1 to 5 or by the structure coordinates of the PA subunit amino acids Glu, Glu, Asp, Ile, His, Lys, Tyr, Arg, Phe, Tyr, Ile, Leu, and Lys corresponding to amino acids Glu80, Glu119, Asp108, Ile120, His41, Lys34, Tyr24, Arg84, Phe105, Tyr130, Ile38, Leu106, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, and Lys137 according to FIGS. 1 to 5 or by the structure coordinates of the PA subunit amino acids Glu, Glu, Asp, Ile, His, Lys, Tyr, Arg, Phe, Tyr, Ile, Glu, and Lys corresponding to amino acids Glu80, Glu119, Asp108, Ile120, His41, Lys34, Tyr24, Arg84, Phe105, Tyr130, Ile38, Glu26, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, and Leu106 according to FIGS. 1 to 5 or by the structure coordinates of the PA subunit amino acids Glu, Glu, Asp, Ile, His, Lys, Tyr, Arg, Phe, Tyr, Ile, Glu, and Leu, corresponding to amino acids Glu80, Glu119, Asp108, Ile120, His41, Lys34, Tyr24, Arg84, Phe105, Tyr130, Ile38, Glu26, and Leu106 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Lys134, and Leu106 according to FIGS. 1 to 5 or by the structure coordinates of the PA subunit amino acids Glu, Glu, Asp, Ile, His, Lys, Tyr, Arg, Phe, Tyr, Ile, Lys, and Leu corresponding to amino acids Glu80, Glu119, Asp108, Ile120, His41, Lys34, Tyr24, Arg84, Phe105, Tyr130, Ile38, Lys134, and Leu106 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Lys134, and Lys137 according to FIGS. 1 to 5 or by the structure coordinates of the PA subunit amino acids Glu, Glu, Asp, Ile, His, Lys, Tyr, Arg, Phe, Tyr, Ile, Lys, and Lys corresponding to amino acids Glu80, Glu119, Asp108, Ile120, His41, Lys34, Tyr24, Arg84, Phe105, Tyr130, Ile38, Lys134, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, Lys134, and Leu106 according to FIGS. 1 to 5 or by the structure coordinates of the PA subunit amino acids Glu, Glu, Asp, Ile, His, Lys, Tyr, Arg, Phe, Tyr, Ile, Glu, Lys, and Leu corresponding to amino acids Glu80, Glu119, Asp108, Ile120, His41, Lys34, Tyr24, Arg84, Phe105, Tyr130, Ile38, Glu26, Lys134, and Leu106 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Glu26, Lys134, Leu106, and Lys137 according to FIGS. 1 to 5 or by the structure coordinates of the PA subunit amino acids Glu, Glu, Asp, Ile, His, Lys, Tyr, Arg, Phe, Tyr, Ile, Glu, Lys, Leu, and Lys corresponding to amino acids Glu80, Glu119, Asp108, Ile120, His41, Lys34, Tyr24, Arg84, Phe105, Tyr130, Ile38, Glu26, Lys134, Leu106, and Lys137 of SEQ ID NO: 2, respectively, according to FIG. 15 or 16. In yet another embodiment, said active site is defined by the structure coordinates of the PA subunit SEQ ID NO: 2 amino acids Glu80, Glu119, Asp108, Ile120, His41, Lys34, Tyr24, Arg84, Phe105, Tyr130, Ile38, Arg124, Glu26, Lys134, Leu106, and Lys137 according to FIGS. 1 to 5 or by the structure coordinates of the PA subunit amino acids Glu, Glu, Asp, Ile, His, Lys, Tyr, Arg, Phe, Tyr, Ile, Arg, Glu, Lys, Leu, and Lys corresponding to amino acids Glu80, Glu119, Asp108, Ile120, His41, Lys34, Tyr24, Arg84, Phe105, Tyr130, Ile38, Arg124, Glu26, Lys134, Leu106, and Lys137 of SEQ ID NO: 2, respectively, according to FIG. 15 or 16.

In a further embodiment, said active site is defined by the structure coordinates of the PA subunit SEQ ID NO: 2 amino acids Glu80, Glu119, Asp108, Ile120, His41, and Glu26 according to FIGS. 1 to 5 or by the structure coordinates of the PA subunit amino acids Glu, Glu, Asp, Ile, His, and Glu corresponding to amino acids Glu80, Glu119, Asp108, Ile120, His41, and Glu26 of SEQ ID NO: 2, respectively, according to FIG. 15 or 16. In a further embodiment, said active site is defined by the structure coordinates of the PA subunit SEQ ID NO: 2 amino acids. Glu80, Glu119, Asp108, Ile120, His41, and Lys134 according to FIGS. 1 to 5 or by the structure coordinates of the PA subunit amino acids Glu, Glu, Asp, Ile, His, and Lys corresponding to amino acids Glu80, Glu119, Asp108, Ile120, His41, and Lys134 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, and Leu106 according to FIGS. 1 to 5 or by the structure coordinates of the PA subunit amino acids Glu, Glu, Asp, Ile, His, and Leu corresponding to amino acids Glu80, Glu119, Asp108, Ile120, His41, and Leu106 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, and Lys137 according to FIGS. 1 to 5 or by the structure coordinates of the PA subunit amino acids Glu, Glu, Asp, Ile, His, and Lys corresponding to amino acids Glu80, Glu119, Asp108, Ile120, His41, and Lys137 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, Glu26, and Lys134 according to FIGS. 1 to 5 or by the structure coordinates of the PA subunit amino acids Glu, Glu, Asp, Ile, His, Glu, and Lys corresponding to amino acids Glu80, Glu119, Asp108, Ile120, His41, Glu26, and Lys134 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, Glu26, Lys134, and Leu106 according to FIGS. 1 to 5 or by the structure coordinates of the PA subunit amino acids Glu, Glu, Asp, Ile, His, Glu, Lys, and Leu corresponding to amino acids Glu80, Glu119, Asp108, Ile120, His41, Glu26, Lys134, and Leu106 of SEQ ID NO: 2, respectively, according to FIG. 15 or 16. In a further embodiment, said active site is defined by the structure coordinates of the PA subunit SEQ ID NO: 2 amino acids Glu80, Glu119, Asp108, Ile120, His41, Glu26, Lys134, Leu106, and Lys137 according to FIGS. 1 to 5 or by the structure coordinates of the PA subunit amino acids Glu, Glu, Asp, Ile, His, Glu, Lys, Leu, and Lys corresponding to amino acids Glu80, Glu119, Asp108, Ile120, His41, Glu26, Lys134, Leu106, and Lys137 of SEQ ID NO: 2, respectively, according to FIG. 15 or 16.

The inventors of the present invention have surprisingly found that the amino acids His 41, Glu80, Asp108, Glu119, and Ile120 according to SEQ ID NO: 2 within the active site of Influenza A 2009 pandemic H1N1 PA subunit are required for divalent cation binding (see for example FIGS. 1 and 6), while the amino acids Tyr24, Lys34, Ile38, Arg84, Phe105, and Tyr130 according to SEQ ID NO: 2 within the active site of Influenza A 2009 pandemic H1N1 PA subunit are required for compound (i.e. inhibitor) binding in the structures shown in FIGS. 2 to 5 (see also FIGS. 7 to 10 and Tables 1 and 2) and are those amino acids which conformation changes from the unligated structure (see FIGS. 1 and 6). In addition, the inventors of the present invention determined that the amino acid residues Leu106, Lys134, Lys137 and Glue26 according to SEQ ID NO: 2 within the active site of Influenza A 2009 pandemic H1N1 PA subunit are also required to make contacts with the tested compounds (see Tables 1 and 2, FIGS. 2 to 5 and FIGS. 7 to 10). See also FIGS. 15 to 19. In addition, the inventors of the present invention have found that the amino acid Arg124 within the active site of Influenza A 2009 pandemic H1N1 PA subunit is required for compound (i.e. inhibitor) interaction in the structures shown in FIGS. 16 and 18. This three-dimensional knowledge of the compound/ligand interacting residues and the plasticity of the active site is important for the optimised design of modifications to existing inhibitors in order to improve their potency. In addition, the design, identification and selection of new anti viral compounds that interact with these amino acids is, thus, highly preferable.

If computer modeling according to the methods described hereinabove indicates binding of a compound to the active site of the Influenza A 2009 pandemic H1N1 PA subunit or a variant thereof, said compound may be synthesized and optionally said compound or a pharmaceutically acceptable salt thereof may be formulated with one or more pharmaceutically acceptable excipient(s) and/or carrier(s). Thus, the above-described method may comprise the further step of (e) synthesizing said compound and optionally formulating said compound or a, pharmaceutically acceptable salt thereof with one or more pharmaceutically acceptable excipient(s) and/or carrier(s).

Optionally, the ability of said compound or of a pharmaceutically acceptable salt thereof or of a formulation thereof to modulate, preferably decrease, more preferably inhibit, the endonucleolytic activity of the Influenza A 2009 pandemic H1N1 PA subunit or variant thereof may be tested in vitro or in vivo comprising the further step of (f) contacting said compound with the PA polypeptide fragment or variant thereof according to the present invention or the recombinant host cell according to the present invention and determine the ability of said compound to (i) bind to the active site and/or (ii) modulate, preferably decrease, more preferably inhibit, the endonucleolytic activity of the Influenza A 2009 pandemic H1N1 PA subunit polypeptide fragment or variant thereof. The quality of fit of such compounds to the active site may be judged either by shape complementarity or by estimated interaction energy (Meng et al., 1992, J. Comp. Chem. 13:505-524). Methods for synthesizing said compounds are well known to the person skilled in the art or such compounds may be commercially available.

It is another aspect of the present invention to provide a compound which is able to modulate, preferably to decrease, more preferably to inhibit, the endonuclease activity of the Influenza A 2009 pandemic H1N1 PA subunit or variant thereof according to the present invention. It is preferred that the compound is able to modulate, preferably to decrease, more preferably to inhibit, the endonuclease activity of the PA subunit or variant thereof according to the present invention by associating with, preferably by binding to, the endonucleolytically active site of said PA subunit or variant thereof.

It is also an aspect of the present invention to provide a compound which is able to modulate, preferably to decrease, more preferably to inhibit, the endonuclease activity of the Influenza A 2009 pandemic H1N1 PA subunit polypeptide fragment or variant thereof according to the present invention. It is preferred that the compound is able to modulate, preferably to decrease, more preferably to inhibit, the endonuclease activity of the PA subunit polypeptide fragment or variant thereof according to the present invention by associating with, preferably by binding to, the endonucleolytically active site of said PA subunit polypeptide fragment or variant thereof.

It is further an aspect of the present invention to provide a compound which is able to modulate, preferably to decrease, more preferably to inhibit, the endonuclease activity of the PA subunit of other viruses, preferably of viruses of the Orthomyxoviridae family, Bunyaviridae family and/or Arenviridae family. It is preferred that the compound is able to modulate, preferably to decrease, more preferably to inhibit, the endonuclease activity of the PA subunit of other viruses, preferably of viruses of the Orthomyxoviridae family, Bunyaviridae family and/or Arenviridae family, by associating with, preferably by binding to, the endonucleolytically active site of said PA subunit.

Preferably, the endonucleolytically active site of the above-mentioned PA subunits or variants thereof, or PA subunit polypeptide fragments or variants thereof has the structure as defined above.

Thus, it is preferred that said active site comprises amino acids Glu80, Glu119, Asp108, Ile120, and His41 of the PA subunit according to SEQ ID NO: 2 or amino acids corresponding thereto.

It is more preferred that said active site comprises amino acids Glu80, Glu119, Asp108, Ile120, His41, Lys34, Tyr24, Arg84, Phe105, Tyr130, and Ile38 of the PA subunit according to SEQ ID NO: 2 or amino acids corresponding thereto, or comprises amino acids Glu80, Glu119, Asp108, Ile120, His41 Lys34, Tyr24, Arg84, Phe105, Tyr130, Ile38, and Arg124 of the PA subunit according to SEQ ID NO: 2 or amino acids corresponding thereto.

It is also more preferred that said active site comprises amino acids Glu80, Glu119, Asp108, Ile120, His41, Glu26, Lys134, Leu106, and Lys137 of the PA subunit according to SEQ ID NO: 2 or amino acids corresponding thereto.

It is most preferred that said active side comprises amino acids Glu80, Glu119, Asp108, Ile120, His41 Lys34, Tyr24, Arg84, Phe105, Tyr130, Ile38, Glu26, Lys134, Leu106, and Lys137 of the PA subunit according to SEQ ID NO: 2 or amino acids corresponding thereto, or comprises amino acids Glu80, Glu119, Asp108, Ile120, His41 Lys34, Tyr24, Arg84, Phe105, Tyr130, Ile38, Arg124, Glu26, Lys134, Leu106, and Lys137 of the PA subunit according to SEQ ID NO: 2 or amino acids corresponding thereto.

Preferably, the endonucleolytically active site of the above-mentioned PA subunits or variants thereof, or PA subunit polypeptide fragments or variants thereof is defined by the structure coordinates of the PA subunit as mentioned above.

The ability of a compound to associate with, preferably to bind to, the endonucleolytically active site of the afore-mentioned PA subunit or variant thereof, or PA subunit polypeptide fragment or variant thereof, and/or to modulate, preferably to decrease, more preferably to inhibit the endonucleolytic activity of the PA subunit or variant thereof, or PA subunit polypeptide fragment or variant thereof can easily be assessed. For example, the purified PA subunit or PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit or PA subunit polypeptide fragment is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. Further suitable methods are described below.

Preferably, said compound is identifiable by the above-described method. More preferably, said compound is identified by the above-described method.

The compound identifiable by the above-described method may be able to modulate the endonuclease activity of the Influenza A 2009 pandemic H1N1 PA subunit or variant thereof. The compound identifiable by the above-described method may be able to modulate, preferably to decrease, more preferably to inhibit, the endonuclease activity of the Influenza A 2009 pandemic H1N1 PA subunit polypeptide fragment or variant thereof according to the present invention. It is also possible that the compound identifiable by the above-mentioned method may be able to modulate, preferably to decrease, most preferably to inhibit, the endonuclease activity of the PA subunit of other viruses, preferably of viruses of the Orthomyxoviridae family, Bunyaviridae family and/or Arenviridae family.

Compounds of the present invention can be any agents including, but not restricted to, peptides, peptoids, polypeptides, proteins (including antibodies), lipids, metals, nucleotides, nucleosides, nucleic acids, small organic or inorganic molecules, chemical compounds, elements, saccharides, isotopes, carbohydrates, imaging agents, lipoproteins, glycoproteins, enzymes, analytical probes, polyamines, and combinations and derivatives thereof. The term “small molecules” refers to molecules that have a molecular weight between 50 and about 2,500 Daltons, preferably in the range of 200-800 Daltons. In addition, a test compound according to the present invention may optionally comprise a detectable label. Such labels include, but are not limited to, enzymatic labels, radioisotope or radioactive compounds or elements, fluorescent compounds or metals, chemiluminescent compounds and bioluminescent compounds.

In a preferred embodiment of the compound according to the present invention, the compound is not a 4-substituted 2-dioxobutanoic acid, a 4-substituted 4-dioxobutanoic acid, a 4-substituted 2,4-dioxobutanoic acid, a 2,6-diketopiperazine or a derivative thereof, a substituted 2,6-diketopiperazine or a derivative thereof, pyrazine-2,6-dione or a substituted pyrazine-2,6-dione such as flutimide, an N-hydroxamic acid, or an N-hydroxymide.

In particular, the compound according to the present invention is not a compound according to Formula I:

Formula I

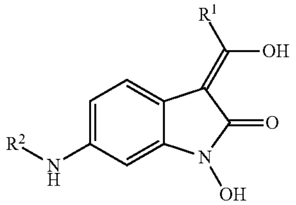

$R^1$ = Me, Et, Ph
$R^2$ = acyl, carbamoyl, sulfonyl.

In another preferred embodiment of the compound according to the present invention, the compound is not 4-[3-[(4-chlorophenyl)methyl]-1-(phenylmethyl)-3-piperidinyl]-2-hydroxy-4-oxo-2-butenoic acid, 4-[4-[(4-chlorophenypmethyl]-1-(cyclohexylmethyl)-4-piperidinyl]-2-hydroxy-4-oxo-2-butenoic acid, 4-[3-[(4-chlorophenyl)methyl]-1-(phenylmethylsulpho)-3-piperidinyl]-2-hydroxy-4-oxo-2-butenoic acid, ribo-Uridine Monophosphate (rUMP), desoxy-thymidinmonophosphat (dTMP), or 2.4-dioxo-4-phenylbutanoic acid (DPBA).

In a further preferred embodiment of the compound according to the present invention, the compound is not a catechin, preferably not a (−)-epigallocatechin gallate (EGCG), such as [(2R,3R)-5,7-dihydroxy-2-(3,4,5-trihydroxyphenyl)chroman-3-yl]3,4,5-trihydroxybenzoate, a (−)-epicatechin gallate (ECG), (−)-epigallocatechin (EGC), (−)-epicatechin (EC), or gallic acid (GA). In another preferred embodiment of the compound of the present invention, the compound is not a phenethylphenylphthalimide, a phenethylphenylphthalimide analog derived from thalidomide or raltegravir (also a diketobutanoic acid derivative).

In a further aspect, the present invention provides a (an in vitro) method for identifying compounds, which modulate, preferably decrease, more preferably inhibit, the endonuclease activity of the PA subunit of a RNA-dependent RNA polymerase from Influenza A 2009 pandemic H1N1 virus or a variant thereof comprising the steps of:

(i) contacting said polypeptide fragment or variant thereof according to the present invention or said recombinant host cell according to the present invention with a test compound, and (ii) analyzing the ability of said test compound to modulate, preferably to decrease, more preferably to inhibit, the endonuclease activity of said PA subunit polypeptide fragment or variant thereof.

It is preferred that said compounds modulate, preferably decrease, more preferably inhibit, the endonuclease activity of the PA subunit of a RNA-dependent RNA polymerase from Influenza A 2009 pandemic H1N1 virus or a variant thereof by associating with, preferably by binding to, the endonucleolytically active site of said PA subunit.

In another further aspect, the present invention provides a (an in vitro) method for identifying compounds, which bind to the endonucleolytically active site, (and) preferably modulate, more preferably decrease, most preferably inhibit, the endonuclease activity of the PA subunit of a RNA-dependent RNA polymerase from Influenza A 2009 pandemic H1N1 virus or a variant thereof comprising the steps of:

(i) contacting said polypeptide fragment or variant thereof according to the present invention or said recombinant host cell according to the present invention with a test compound, and (ii) analyzing the ability of said test compound to bind to the endonucleolytically site, (and) preferably to modulate, more preferably to decrease, most preferably to inhibit, the endonuclease activity of said PA subunit polypeptide fragment or variant thereof.

In one embodiment, the interaction between the Influenza A 2009 pandemic H1N1 PA polypeptide fragment or variant thereof and a test compound may be analyzed in form of a pull down assay. For example, the PA polypeptide fragment or variant thereof according to the invention may be purified and may be immobilized on beads. In one embodiment, the PA polypeptide fragment immobilized on beads may be contacted, for example, with (i) another purified protein, polypeptide fragment, or peptide, (ii) a mixture of proteins, polypeptide fragments, or peptides, or (iii) a cell or tissue extract, and binding of proteins, polypeptide fragments, or peptides may be verified by polyacrylamide gel electrophoresis in combination with coomassie staining or Western blotting. Unknown binding partners may be identified by mass spectrometric analysis.

In another embodiment, the interaction between the Influenza A 2009 pandemic H1N1 PA polypeptide fragment or variant thereof and a test compound may be analyzed in form of an enzyme-linked immunosorbent assay (ELISA)-based experiment. In one embodiment, the PA polypeptide fragment or variant thereof according to the invention may be immobilized on the surface of an ELISA plate and contacted with the test compound. Binding of the test compound may be verified, for example, for proteins, polypeptides, peptides, and epitope-tagged compounds by antibodies specific for the test compound or the epitope-tag. These antibodies might be directly coupled to an enzyme or detected with a secondary antibody coupled to said enzyme that—in combination with the appropriate substrates—carries out chemiluminescent reactions (e.g., horseradish peroxidase) or colorimetric reactions (e.g., alkaline phosphatase). In another embodiment, binding of compounds that cannot be detected by antibodies might be verified by labels directly coupled to the test compounds. Such labels may include enzymatic labels, radioisotope or radioactive compounds or elements, fluorescent compounds or metals, chemiluminescent compounds and bioluminescent compounds. In another embodiment, the test compounds might be immobilized on the ELISA plate and contacted with the PA polypeptide fragment or variants thereof according to the invention. Binding of said polypeptide may be verified by a PA polypeptide fragment specific antibody and chemiluminescence or colorimetric reactions as described above.

In a further embodiment, purified Influenza A 2009 pandemic H1N1 PA polypeptide fragments or variants may be incubated with a peptide array and binding of the PA polypeptide fragments to specific peptide spots corresponding to a specific peptide sequence may be analyzed, for example, by PA polypeptide specific antibodies, antibodies that are directed against an epitope-tag fused to the PA polypeptide fragment, or by a fluorescence signal emitted by a fluorescent tag coupled to the PA polypeptide fragment.

In another embodiment, the recombinant host cell according to the present invention is contacted with a test compound. This may be achieved by co-expression of test proteins or polypeptides and verification of interaction, for example, by fluorescence resonance energy transfer (FRET) or co-immunoprecipitation. In another embodiment, directly labeled test compounds may be added to the medium of the recombinant host cells. The potential of the test compound to penetrate membranes and bind to the PA polypeptide fragment may be, for example, verified by immunoprecipitation of said polypeptide and verification of the presence of the label.

In another embodiment, the ability of the test compound to modulate, preferably decrease, more preferably inhibit the endonucleolytic activity of the Influenza A 2009 pandemic H1N1 PA subunit polypeptide fragment or variant thereof is assessed. For example, the purified PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit polypeptide is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. This experimental setting may be applied in a multi-well plate format and is suitable for high throughput screening of compounds regarding their ability to modulate, decrease, or inhibit the endonuclease activity of the Influenza A 2009 pandemic H1N1 PA subunit polypeptide fragment or variants thereof.

Preferably, the ability of the test compound to inhibit the endonuclease activity of the Influenza A 2009 pandemic H1N1 PA subunit polypeptide fragment or variant thereof is analyzed in the above-described methods.

In a preferred embodiment, the above-described methods for identifying compounds which associate with, preferably bind to, the endonucleolytically active site, modulate, decrease, and/or inhibit the endonucleolytic activity of the Influenza A 2009 pandemic H1N1 PA subunit polypeptide fragment or variant thereof are performed in a high-throughput setting. In a preferred embodiment, said methods are carried out in a multi-well microtiter plate as described above using PA polypeptide fragments or variants thereof according to the present invention and labeled test compounds.

In a preferred embodiment, the test compounds are derived from libraries of synthetic or natural compounds. For instance, synthetic compound libraries are commercially available from Maybridge Chemical Co. (Trevillet, Cornwall, UK), ChemBridge Corporation (San Diego, Calif.), or Aldrich (Milwaukee, Wis.). A natural compound library is, for example, available from TimTec LLC (Newark, Del.). Alternatively, libraries of natural compounds in the form of bacterial, fungal, plant, and animal extracts can be used. Additionally, test compounds can be synthetically produced using combinatorial chemistry either as individual compounds or as mixtures.

In another embodiment, the inhibitory effect of the identified compound on the Influenza A 2009 pandemic H1N1 virus life cycle may be tested in an in vivo setting. A cell line that is susceptible for Influenza virus infection such as 293T human embryonic kidney cells, Madin-Darby canine kidney cells, or chicken embryo fibroblasts may be infected with Influenza A 2009 pandemic H1N1 virus in presence or absence of the identified compound. In a preferred embodiment, the identified compound may be added to the culture medium of the cells in various concentrations. Viral plaque formation may be used as read out for the infectious capacity of the Influenza A 2009 pandemic H1N1 virus and may be compared between cells that have been treated with the identified compound and cells that have not been treated.

In a further embodiment of the invention, the test compound applied in any of the above described methods is a small molecule. In a preferred embodiment, said small molecule is derived from a library, e.g., a small molecule inhibitor library. In another embodiment, said test compound is a peptide or protein. In a preferred embodiment, said peptide or protein is derived from a peptide or protein library.

In another embodiment of the above-described methods for computational as well as in vitro identification of compounds that associate with, preferably bind to, the endonucleolytically active site, modulate, decrease, and/or inhibit the endonucleolytic activity of the Influenza A 2009 pandemic H1N1 PA subunit polypeptide fragment or variant thereof according to the present invention, said methods further comprise the step of formulating said compound or a pharmaceutically acceptable salt thereof with one or more pharmaceutically acceptable excipient(s) and/or carrier(s).

As already mentioned above, it is an aspect of the present invention to provide a compound which is able to modulate, preferably to decrease, more preferably to inhibit, the endonuclease activity of the Influenza A 2009 pandemic H1N1 PA subunit or variant thereof according to the present invention. It is preferred that the compound is able to modulate, preferably to decrease, more preferably to inhibit, the endonuclease activity of the PA subunit or variant thereof according to the present invention by associating with, preferably by binding to, the endonucleolytically active site of said PA subunit or variant thereof.

It is also an aspect of the present invention to provide a compound which is able to modulate, preferably to decrease, more preferably to inhibit, the endonuclease activity of the Influenza A 2009 pandemic H1N1 PA subunit polypeptide fragment or variant thereof according to the present invention. It is preferred that the compound is able to modulate, preferably to decrease, more preferably to inhibit, the endonuclease activity of the PA subunit polypeptide fragment or variant thereof according to the present invention by associating with, preferably by binding to, the endonucleolytically active site of said PA subunit polypeptide fragment or variant thereof.

It is further an aspect of the present invention to provide a compound which is able to modulate, preferably to decrease, more preferably to inhibit, the endonuclease activity of the PA subunit of other viruses, preferably of viruses of the Orthomyxoviridae family, Bunyaviridae family and/or Arenviridae family. It is preferred that the compound is able to modulate, preferably to decrease, more preferably to inhibit, the endonuclease activity of the PA subunit of other viruses, preferably of viruses of the Orthomyxoviridae family, Bunyaviridae family and/or Arenviridae family, by associating with, preferably by binding to, the endonucleolytically active site of said PA subunit.

The ability of a compound to associate with, preferably to bind to, the endonucleolytically active site of the afore-mentioned PA subunit or variant thereof, or PA subunit polypeptide fragment or variant thereof, and/or to modulate, preferably to decrease, more preferably to inhibit the endonucleolytic activity of the PA subunit or variant thereof, or PA subunit polypeptide fragment or variant thereof can easily be assessed. For example, the purified PA subunit or PA subunit polypeptide fragment and a substrate thereof such as panhandle RNA or single stranded DNA are contacted in presence or absence of varying amounts of the test compound and incubated for a certain period of time, for example, for 5, 10, 15, 20, 30, 40, 60, or 90 minutes. The reaction conditions are chosen such that the PA subunit or PA subunit polypeptide fragment is endonucleolytically active without the test compound. The substrate is then analyzed for degradation/endonucleolytic cleavage, for example, by gel electrophoresis. Alternatively, such a test may comprise a labeled substrate molecule which provides a signal when the substrate molecule is endonucleolytically cleaved but does not provide a signal if it is intact. For example, the substrate polynucleotide chain may be labeled with fluorescent reporter molecule and a fluorescence quencher such that the fluorescent reporter is quenched as long as the substrate polynucleotide chain is intact. In case the substrate polynucleotide chain is cleaved, the fluorescent reporter and the quencher are separated, thus, the fluorescent reporter emits a signal which may be detected, for example, by an ELISA reader. Further suitable methods are described below.

Preferably, said compound is identifiable by the above-described (in vitro) methods. More preferably, said compound is identified by the above-described (in vitro) methods.

The compound identifiable by the above described (in vitro) methods may be able to modulate the endonuclease activity of the Influenza A 2009 pandemic H1N1 PA subunit or variant thereof. The compound identifiable by the above-described (in vitro) methods may be able to modulate, preferably to decrease, more preferably to inhibit, the endonuclease activity of the Influenza A 2009 pandemic H1N1 PA subunit polypeptide fragment or variant thereof according to the present invention.

It is also possible that the compound identifiable by the above-described (in vitro) methods may be able to modulate, preferably to decrease, most preferably to inhibit, the endonuclease activity of the PA subunit of other viruses, preferably of viruses of the Orthomyxoviridae family, Bunyaviridae family and/or Arenviridae family.

Compounds of the present invention can be any agents as described above for the in silico screening methods. In a preferred embodiment of the compound according to the present invention, the compound is not a 4-substituted 2-dioxobutanoic acid, a 4-substituted 4-dioxobutanoic acid, a 4-substituted 2,4-dioxobutanoic acid, 2,6-diketopiperazine or a derivative thereof, a substituted 2,6-diketopiperazine or a derivative thereof, a pyrazine-2,6-dione or a substituted pyrazine-2,6-dione such as flutimide, an N-hydroxamic acid, or an N-hydroxymide.

In particular, the compound according to the present invention is not a compound according to Formula I:

Formula I

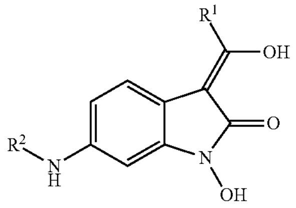

$R^1$ = Me, Et, Ph
$R^2$ = acyl, carbamoyl, sulfonyl.

In another preferred embodiment of the compound according to the present invention, the compound is not 4-[3-[(4-chlorophenyl)methyl]-1-(phenylmethyl)-3-piperidinyl]-2-hydroxy-4-oxo-2-butenoic acid, 4-[4-[(4-chlorophenyl) methyl]-1-(cyclohexylmethyl)-4-piperidinyl]-2-hydroxy-4-oxo-2-butenoic acid, 4-[3-[(4-chlorophenyl)methyl]-1-(phenylmethylsulpho)-3-piperidinyl]-2-hydroxy-4-oxo-2-butenoic acid, ribo-Uridine Monophosphate (rUMP), desoxy-thymidinmonophosphat (dTMP), or 2.4-dioxo-4-phenylbutanoic acid (DPBA).

In a further preferred embodiment of the compound according to the present invention, the compound is not a catechin, preferably not a (−)-epigallocatechin gallate (EGCG), such as [(2R,3R)-5,7-dihydroxy-2-(3,4,5-trihydroxyph enyl)chroman-3-yl]3,4,5-trihydroxybenzoate, a (−)-epicatechin gallate (ECG), (−)-epigallocatechin (EGC), (−)-epicatechin (EC), or gallic acid (GA). In another preferred embodiment of the compound of the present invention, the compound is not a phenethylphenylphthalimide, a phenethylphenylphthalimide analog derived from thalidomide or raltegravir (also a diketobutanoic acid derivative).

It is an aspect of the present invention to provide a pharmaceutical composition comprising the afore-mentioned compound of the present invention or a pharmaceutically acceptable salt thereof. It is also an aspect of the present invention to provide a pharmaceutical composition comprising the afore-mentioned compound of the present invention or a pharmaceutically acceptable salt thereof and one or more pharmaceutically acceptable excipient(s) and/or carrier(s).

As already mentioned above, the compound comprised in the pharmaceutical compositions of the present invention (i) is able to modulate, preferably to decrease, more preferably to inhibit, the endonuclease activity of the Influenza A 2009 pandemic H1N1 PA subunit or variant thereof according to the present invention, e.g. by binding to the endonucleolytically active site of said subunit or variant thereof, (ii) is able to modulate, preferably to decrease, more preferably to inhibit, the endonuclease activity of the Influenza A 2009 pandemic H1N1 PA subunit polypeptide fragment or variant thereof according to the present invention, e.g. by binding to the endonucleolytically active site of said polypeptide fragment or variant thereof, or (iii) is able to modulate, preferably to decrease, more preferably to inhibit, the endonuclease activity of the PA subunit of other viruses, preferably of viruses of the Orthomyxoviridae family, Bunyaviridae family and/or Arenviridae family, e.g. by binding to the endonucleolytically active site of said PA subunit. Preferably, the compound comprised in the pharmaceutical compositions of the present invention is identifiable by the above-described methods. More preferably, the compound comprised in the pharmaceutical compositions of the present invention is identified by the above-described methods.

Preferably, said pharmaceutical composition(s) is (are) producible according to the afore-mentioned methods.

A compound according to the present invention can be administered alone but, in human therapy, will generally be administered in admixture with a suitable pharmaceutical excipient, diluent, or carrier selected with regard to the intended route of administration and standard pharmaceutical practice (see hereinafter).

In the aspect of computational modeling or screening of a binding partner for the endonucleolytically active site, a modulator, and/or inhibitor of the endonucleolytic activity of the Influenza A 2009 pandemic H1N1 PA subunit polypeptide fragment or variant thereof according to the present invention, it may be possible to introduce into the molecule of interest, chemical moieties that may be beneficial for a molecule that is to be administered as a pharmaceutical. For example, it may be possible to introduce into or omit from the molecule of interest, chemical moieties that may not directly affect binding of the molecule to the target area but which contribute, for example, to the overall solubility of the molecule in a pharmaceutically acceptable carrier, the bioavailability of the molecule and/or the toxicity of the molecule. Considerations and methods for optimizing the pharmacology of the molecules of interest can be found, for example, in "Goodman and Gilman's The Pharmacological Basis of Therapeutics", 8$^{th}$ Edition, Goodman, Gilman, Rall, Nies, & Taylor, Eds., Pergamon Press (1985); Jorgensen & Duffy, 2000, Bioorg. Med. Chem. Lett. 10:1155-1158. Furthermore, the computer program "Qik Prop" can be used to provide rapid predictions for physically significant descriptions and pharmaceutically-relevant properties of an organic molecule of interest. A 'Rule of Five' probability scheme can be used to estimate oral absorption of the newly synthesized compounds (Lipinski et al., 1997, Adv. Drug Deliv. Rev. 23:3-25). Programs suitable for pharmacophore selection and design include (i) DISCO (Abbot Laboratories, Abbot Park, Ill.), (ii) Catalyst (Bio-CAD Corp., Mountain View, Calif.), and (iii) Chem DBS-3D (Chemical Design Ltd., Oxford, UK).

The pharmaceutical composition contemplated by the present invention may be formulated in various ways well known to one of skill in the art. For example, the pharmaceutical composition of the present invention may be in solid form such as in the form of tablets, pills, capsules (including soft gel capsules), cachets, lozenges, ovules, powder, granules, or suppositories, or in liquid form such as in the form of elixirs, solutions, emulsions, or suspensions.

Solid administration forms may contain excipients such as microcrystalline cellulose, lactose, sodium citrate, calcium carbonate, dibasic calcium phosphate, glycine, and starch (preferably corn, potato, or tapioca starch), disintegrants such as sodium starch glycolate, croscarmellose sodium, and certain complex silicates, and granulation binders such as polyvinylpyrrolidone, hydroxypropylmethyl cellulose (HPMC), hydroxypropylcellulose (HPC), sucrose, gelatin, and acacia. Additionally, lubricating agents such as magnesium stearate, stearic acid, glyceryl behenate, and talc may be included. Solid compositions of a similar type may also be employed as fillers in gelatin capsules. Preferred excipients in this regard include lactose, starch, a cellulose, milk sugar, or high molecular weight polyethylene glycols.

For aqueous suspensions, solutions, elixirs, and emulsions suitable for oral administration the compound may be combined with various sweetening or flavoring agents, coloring matter or dyes, with emulsifying and/or suspending agents and with diluents such as water, ethanol, propylene glycol, and glycerin, and combinations thereof.

The pharmaceutical composition of the present invention may contain release rate modifiers including, for example, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer, and mixtures thereof.

The pharmaceutical composition of the present invention may be in the form of fast dispersing or dissolving dosage formulations (FDDFs) and may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavoring, polyethylene glycol, fumed silica, silicon dioxide, sodium starch glycolate, sodium stearyl fumarate, sorbitol, xylitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

The pharmaceutical composition of the present invention suitable for parenteral administration is best used in the form of a sterile aqueous solution which may contain other substances, for example, enough salts or glucose to make the solution isotonic with blood. The aqueous solutions should be suitably buffered (preferably to a pH of from 3 to 9), if necessary.

The pharmaceutical composition suitable for intranasal administration and administration by inhalation is best delivered in the form of a dry powder inhaler or an aerosol spray from a pressurized container, pump, spray or nebulizer with the use of a suitable propellant, e.g., dichlorodifluoromethane, trichlorofluoromethane, dichlorotetrafluoroethane, a hydrofluoroalkane such as 1,1,1,2-tetrafluoroethane (HFA 134A.TM.) or 1,1,1,2,3,3,3-heptafluoropropane (HFA 227EA.TM.), carbon dioxide, or another suitable gas. The pressurized container, pump, spray or nebulizer may contain a solution or suspension of the active compound, e.g., using a mixture of ethanol and the propellant as the solvent, which may additionally contain a lubricant, e.g., sorbitan trioleate.

In another aspect, the present invention provides an antibody directed against the active site of the PA subunit of the Influenza A 2009 pandemic H1N1 virus according to SEQ ID NO: 2 or a variant thereof, wherein said variant comprises the amino acid serine at an amino acid position 186 according to SEQ ID NO: 2 or at an amino acid position corresponding thereto.

In a preferred embodiment, said antibody recognizes the endonuclease domain by recognition of a polypeptide fragment selected from the group of polypeptides defined by SEQ ID NO: 4 to 11, i.e., amino acids 20 to 30 (SEQ ID NO: 4), 32 to 40 (SEQ ID NO: 5), 41 to 51 (SEQ ID NO: 6), 80 to 90 (SEQ ID NO: 7), 100 to 110 (SEQ ID NO: 8), 115 to 125 (SEQ ID NO: 9), 130 to 140 (SEQ ID NO: 10), and 176 to 186 (SEQ ID NO: 11) of the amino acid sequence as set forth in SEQ ID NO: 2.

In particular, said antibody specifically binds to an epitope comprising one or more of above indicated amino acids, which define the active site. In this context, the term epitope has its art recognized meaning and preferably refers to stretches of 4 to 20 amino acids, preferably 5 to 18, 5 to 15, or 7 to 14 amino acids, e.g. stretches of 4, 5, 6, 7, 8, 9, 10, 11, 12, 13, 14, 15, 16, 17, 18, 19, or 20 amino acids. Accordingly, preferred epitopes have a length of 4 to 20, 5 to 18, preferably 5 to 15, or 7 to 14 amino acids, e.g. have a length of 4, 5, 6, 7, 8, 9, 10, 11, 12, 13, 14, 15, 16, 17, 18, 19, or 20 amino acids, and/or comprise one or more of Lys34, Glu26, Ile38, Tyr24, His41, Glu80, Arg84, Leu106, Asp108, Glu119, Ile120, Arg124, Tyr130, Lys134, Phe105, and Lys137 of SEQ ID NO: 2 or one or more corresponding amino acid(s). Thus, in a preferred embodiment, said antibody recognizes a polypeptide fragment of a length between 5 and 15 amino acids of the amino acid sequence as set forth in SEQ ID NO: 2, wherein the polypeptide fragment comprises one or more amino acid residues selected from the group consisting of Lys34, Glu26, Ile38, Tyr24, His41, Glu80, Arg84, Leu106, Asp108, Glu119, Ile120, Tyr130, Lys134, Phe105, Lys137, and Arg124.

The antibody of the present invention may be a monoclonal or polyclonal antibody or portions thereof. Antigen-binding portions may be produced by recombinant DNA techniques or by enzymatic or chemical cleavage of intact antibodies. In some embodiments, antigen-binding portions include Fab, Fab', $F(ab')_2$, Fd, Fv, dAb, and complementarity determining region (CDR) fragments, single-chain antibodies (scFv), chimeric antibodies such as humanized antibodies, diabodies, and polypeptides that contain at least a portion of an antibody that is sufficient to confer specific antigen binding to the polypeptide. The antibody of the present invention is generated according to standard protocols. For example, a polyclonal antibody may be generated by immunizing an animal such as mouse, rat, rabbit, goat, sheep, pig, cattle, or horse with the antigen of interest optionally in combination with an adjuvant such as Freund's complete or incomplete adjuvant, RIBI (muramyl dipeptides), or ISCOM (immunostimulating complexes) according to standard methods well known to the person skilled in the art. The polyclonal antiserum directed against the endonuclease domain of Influenza A 2009 pandemic H1N1 PA or fragments thereof is obtained from the animal by bleeding or sacrificing the immunized animal. The serum (i) may be used as it is obtained from the animal, (ii) an immunoglobulin fraction may be obtained from the serum, or (iii) the antibodies specific for the endonuclease domain of Influenza A 2009 pandemic H1N1 PA or fragments thereof may be purified from the serum. Monoclonal antibodies may be generated by methods well known to the person skilled in the art. In brief, the animal is sacrificed after immunization and lymph node and/or splenic B cells are immortalized by any means known in the art. Methods of immortalizing cells include, but are not limited to, transfecting them with oncogenes, infecting them with an oncogenic virus and cultivating them under conditions that select for immortalized cells, subjecting them to carcinogenic or mutating compounds, fusing them with an immortalized cell, e.g., a myeloma cell, and inactivating a tumor suppressor gene. Immortalized cells are screened using the H1N1 PA endonuclease domain or a fragment thereof. Cells that produce antibodies directed against the H1N1 PA endonuclease domain or a fragment thereof, e.g., hybridomas, are selected, cloned, and further screened for desirable characteristics including robust growth, high antibody production, and desirable antibody characteristics. Hybridomas can be expanded (i) in vivo in syngeneic animals, (ii) in animals that lack an immune system, e.g., nude mice, or (iii) in cell culture in vitro. Methods of selecting, cloning, and expanding hybridomas are well known to those of ordinary skill in the art. The skilled person may refer to standard texts such as "Antibodies: A Laboratory Manual", Harlow and Lane, Eds., Cold Spring Harbor Laboratory Press, Cold Spring Harbor, N.Y. (1990), which is incorporated herein by reference, for support regarding generation of antibodies.

In another aspect, the present invention relates to the use of the compound(s) according the present invention, the pharmaceutical composition(s) according to the present invention, or the antibody according to the present invention for the manufacture of a medicament for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

Said compound (i) is able to modulate, preferably to decrease, more preferably to inhibit, the endonuclease activity of the Influenza A 2009 pandemic H1N1 PA subunit or variant thereof according to the present invention, e.g. by binding to the endonucleolytically active site of said PA subunit or variant thereof, (ii) is able to modulate, preferably to decrease, more preferably to inhibit, the endonuclease activity of the Influenza A 2009 pandemic H1N1 PA subunit polypeptide fragment or variant thereof according to the present invention, e.g. by binding to the endonucleolytically active site of said PA subunit polypeptide fragment or variant thereof, or (iii) is able to modulate, preferably to decrease, more preferably to inhibit, the endonuclease activity of the PA subunit of other viruses, preferably of viruses of the Orthomyxoviridae family, Bunyaviridae family and/or Arenviridae family, e.g. by binding to the endonucleolytically active site of said PA subunit.

It is preferred that said compound(s) is (are) identifiable by the above-described methods. It is further preferred that said pharmaceutical composition(s) is (are) producible according to the afore-mentioned methods. Thus, preferably, the present invention relates to the use of a compound identifiable by the above-described methods that is able to bind to the endonucleolytically active site of the Influenza A 2009 pandemic H1N1 PA subunit polypeptide fragment or variant thereof, and/or is able to modulate, preferably to decrease, more preferably to inhibit the endonucleolytic activity of the Influenza A 2009 pandemic H1N1 PA subunit polypeptide fragment or variant thereof, or the pharmaceutical composition producible according to the afore-mentioned methods for the manufacture of a medicament for treating, ameliorating, or preventing disease conditions caused by viral infections with viruses of the Orthomyxoviridae family Bunyaviridae family and/or Arenviridae family, preferably caused by viral infections with Influenza A 2009 pandemic H1N1 virus.

In a further aspect, the present invention relates to the compound(s) according the present invention, the pharmaceutical composition(s) according to the present invention, or the antibody according to the present invention for treating, ameliorating, or preventing disease conditions caused by viral infections with viruses of the Orthomyxoviridae family, Bunyaviridae family and/or Arenviridae family, preferably caused by viral infections with Influenza A 2009 pandemic H1N1 virus.

Said compound (i) is able to modulate, preferably to decrease, more preferably to inhibit, the endonuclease activity of the Influenza A 2009 pandemic H1N1 PA subunit or variant thereof according to the present invention, e.g. by binding to the endonucleolytically active site of said PA subunit or variant thereof, (ii) is able to modulate, preferably to decrease, more preferably to inhibit, the endonuclease activity of the Influenza A 2009 pandemic H1N1 PA subunit polypeptide fragment or variant thereof according to the present invention, e.g. by binding to the endonucleolytically active site of said PA subunit polypeptide fragment or variant thereof, or (iii) is able to modulate, preferably to decrease, more preferably to inhibit, the endonuclease activity of the PA subunit of other viruses, preferably of viruses of the Orthomyxoviridae family, Bunyaviridae family and/or Arenviridae family, e.g. by binding to the endonucleolytically active site of said PA subunit.

It is preferred that said compound(s) is (are) identifiable by the above-described methods. It is further preferred that said pharmaceutical composition(s) is (are) producible according to the afore-mentioned methods. Thus, preferably, the present invention relates to a compound identifiable by the above-described methods that is able to bind to the endonucleolytically active site of the Influenza A 2009 pandemic H1N1 PA subunit polypeptide fragment or variant thereof, and/or is able to modulate, preferably to decrease, more preferably to inhibit the endonucleolytic activity of the Influenza A 2009 pandemic H1N1 PA subunit polypeptide fragment or variant thereof, or the pharmaceutical composition producible according to the afore-mentioned methods for treating, ameliorating, or preventing disease conditions caused by viral infections with viruses of the Orthomyxoviridae family Bunyaviridae family and/or Arenviridae family, preferably caused by viral infections with Influenza A 2009 pandemic H1N1 virus.

In another aspect, the present invention relates to the use of the compound 4-[3-[(4-chlorophenyl)methyl]-1-(phenylmethyl)-3-piperidinyl]-2-hydroxy-4-oxo-2-butenoic acid (EMBL-R05-3), of the compound 4-[4-[(4-chlorophenyl) methyl]-1-(cyclohexylmethyl)-4-piperidinyl]-2-hydroxy-4-oxo-2-butenoic acid (EMBL-R05-2), of the compound 4-[3-[(4-chlorophenyl)methyl]-1-(phenylmethylsulpho)-3-piperidinyl]-2-hydroxy-4-oxo-2-butenoic acid (EMBL-R05-1), or of the compound [(2R,3R)-5,7-dihydroxy-2-(3,4,5-trihydroxyphenyl)chroman-3-yl]3,4,5-trihydroxybenzoate (EGCG) for the manufacture of a medicament for treating, ameliorating, or preventing disease conditions caused by viral infections with Influenza A 2009 pandemic H1N1 virus, as the inventors of the present invention have determined that said compounds are able to bind to the endonucleolytically active site of the Influenza A 2009 pandemic H1N1 PA subunit polypeptide fragment or variant thereof, and are able to modulate, i.e. to inhibit, the endonucleolytic activity of the Influenza A 2009 pandemic H1N1 PA subunit polypeptide fragment or variant thereof.

In an further aspect, the present invention relates to 4-[3-[(4-chlorophenyl)methyl]-1-(phenylmethyl)-3-piperidinyl]-2-hydroxy-4-oxo-2-butenoic acid (EMBL-R05-3), 4-[4-[(4-chlorophenyl)methyl]-1-(cyclohexylmethyl)-4-piperidinyl]-2-hydroxy-4-oxo-2-butenoic acid (EMBL-R05-2), 4-[3-[(4-chlorophenyl)methyl]-1-(phenylmethylsulpho)-3-piperidinyl]-2-hydroxy-4-oxo-2-butenoic acid (EMBL-R05-1), or [(2R,3R)-5,7-dihydroxy-2-(3,4,5-trihydroxyphenyl) chroman-3-yl]3,4,5-trihydroxybenzoate (EGCG) for treating, ameliorating, or preventing disease conditions caused by viral infections with Influenza A 2009 pandemic H1N1 virus.

In another aspect, the present invention relates to the use of a 4-substituted 2,4-dioxobutanoic acid compound or a green tea catechin for treating, ameliorating, or preventing disease conditions caused by viral infections with Influenza A 2009 pandemic H1N1 virus.

For treating, ameliorating, or preventing said disease conditions the medicament of the present invention can be administered to an animal patient, preferably a mammalian patient, preferably a human patient, orally, buccally, sublingually, intranasally, via pulmonary routes such as by inhalation, via rectal routes, or parenterally, for example, intracavernosally, intravenously, intra-arterially, intraperitoneally, intrathecally, intraventricularly, intra-urethrally intrasternally, intracranially, intramuscularly, or subcutaneously, they may be administered by infusion or needleless injection techniques.

The pharmaceutical compositions of the present invention may be formulated in various ways well known to one of skill in the art and as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation administered in the use of the present invention may be varied or adjusted from about 1 mg to about 1000 mg per $m^2$, preferably about 5 mg to about 150 mg/$m^2$ according to the particular application and the potency of the active component.

The compounds employed in the medical use of the invention are administered at an initial dosage of about 0.05 mg/kg to about 20 mg/kg daily. A daily dose range of about 0.05 mg/kg to about 2 mg/kg is preferred, with a daily dose range of about 0.05 mg/kg to about 1 mg/kg being most preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Various modifications and variations of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The following figures and examples are merely illustrative of the present invention and should not be construed to limit the scope of the invention as indicated by the appended claims in any way.

BRIEF DESCRIPTION OF THE DRAWINGS

FIGS. 1-5 (common annotation): Refined atomic structure coordinates for PA polypeptide fragment amino acids 1 to 198 according to amino acids 1 to 198 of the amino acid sequence set forth in SEQ ID NO: 2 (PA H1N1 1 to 198), with or without bound compounds. For each structure there are generally four molecules in the crystallographic asymmetric unit (ASU) denoted A, B, C and D. In FIGS. 1 to 5, however, only one selected molecule is shown (see below). The file header gives information about the structure refinement. "Atom" refers to the element whose coordinates are measured. The first letter in the column defines the element. The 3-letter code of the respective amino acid is given and the amino acid sequence position. The first 3 values in the line "Atom" define the atomic position of the element as measured. The fourth value corresponds to the occupancy and the fifth (last) value is the temperature factor (B factor). The occupancy factor refers to the fraction of the molecules in which each atom occupies the position specified by the coordinates. A value of "1" indicates that each atom has the same conformation, i.e., the same position, in all equivalent molecules of the crystal. B is a thermal factor that measures movement of the atom around its atomic center. This nomenclature corresponds to the Protein Data Bank (PDB) format.

FIG. 1: (Sheets labelled FIG. 1-1 to FIG. 1-28) Structural co-ordinates of the native (i.e. without compound/ligand) H1N1 PA endonuclease domain in standard Protein Data Bank (PDB) format. Only the chain A (with associated divalent cations, i.e. one magnesium and one manganese ion, and water molecules) from the asymmetric unit is included. Chains B, C and D are very similar.

FIG. 2: (Sheets labelled FIG. 2-1 to FIG. 2-29) Structural co-ordinates of the H1N1 PA endonuclease domain with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format. Only the chain A (with associated divalent cations, i.e. two manganese ions, and water molecules) from the asymmetric unit is included. The compound EMBL-R05-3 has residue descriptor ci3.

FIG. 3: (Sheets labelled FIG. 3-1 to FIG. 3-28) Structural co-ordinates of the H1N1 PA endonuclease domain with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format. Only the chain D (with associated divalent cations, i.e. two manganese ions, and water molecules) from the asymmetric unit is included. The compound EMBL-05-03 has a different configuration than in chain A (FIG. 2). Said compound has residue descriptor ci3.

FIG. 4: (Sheets labelled FIG. 4-1 to FIG. 4-29) Structural co-ordinates of the H1N1 PA endonuclease domain with bound [4-[(4-chlorophenyl)methyl]-1-(cyclohexylmethyl)-4-piperidinyl]-2-hydroxy-4-oxo-2-butenoic acid (EMBL-R05-2) in standard Protein Data Bank (PDB) format. Only the chain A (with associated divalent cations, i.e. two manganese ions, and water molecules) from the asymmetric unit is included. Chains B, C and D are very similar. The compound EMBL-R05-2 has residue descriptor ci2.

FIG. 5: (Sheets labelled FIG. 5-1 to FIG. 5-27) Structural co-ordinates of the H1N1 PA endonuclease domain with bound ribo-Uridine Monophosphate (rUMP) in standard Protein Data Bank (PDB) format. Only the chain A (with associated divalent cations, i.e. two manganese ions, and water molecules) from the asymmetric unit is included. Chains B, C and D are very similar. The compound rUMP has residue descriptor U.

FIG. 6: Diagram using the structural co-ordinates of FIG. 1 illustrating the endonuclease active site (PA polypeptide fragment (chain A)), showing the divalent cations (one manganese and one magnesium) and key active site residues.

FIG. 7: (A) Diagram using the structural co-ordinates of FIG. 2 illustrating the endonuclease active site (PA polypeptide fragment (chain A)), showing the bound compound EMBL-R05-3, the divalent cations (two manganese) and key active site residues that interact with the compound (notably Arg84) or are close to it and (B) Diagram comparing the co-ordinates of FIG. 1 (chain subjacent on left hand side) and FIG. 2 showing change in conformation of the loop in the vicinity of Tyr24 upon binding of EMBL-R05-3 (chain A). Tyr24 side-chain moves to partially stack with the chlorobenzene of EMBL-R05-3.

FIG. 8: Diagram using the structural co-ordinates of FIG. 3 illustrating the endonuclease active site (PA polypeptide fragment (chain D)), showing the bound compound EMBL-R05-3, the divalent cations (two manganese) and key active site residues that interact with the compound (notably Tyr24 and Arg84) or are close to it.

FIG. 9: Diagram using the structural co-ordinates of FIG. 4 illustrating the endonuclease active site (PA polypeptide fragment (chain A)), showing the bound compound EMBL-R05-2, the divalent cations (two manganese) and key active site residues that interact with the compound (notably Tyr24 and Phel 05) or are close to it.

FIG. 10: Diagram using the structural co-ordinates of FIG. 5 illustrating the endonuclease active site (PA polypeptide fragment (chain A)), showing the bound compound rUMP, the divalent cations (two manganese) and key active site residues that interact with the compound (notably Tyr24 and Lys34) or are close to it.

FIG. 11: 15% PAGE gels and gel filtration profile from a typical purification of H1N1 PA1-198 (SEQ ID NO: 13). The arrow indicates faint traces of residual MBP.

FIGS. 15-16 (common annotation): Refined atomic structure coordinates for PA polypeptide fragment amino acids 1 to 198 of the amino acid sequence set forth in SEQ ID NO: 2 with amino acids 52 to 64 replaced by the amino acid glycine (PA H1N1 1 to 198 Δ52-64: Gly (SEQ ID NO:14)) with bound compounds. For each structure there is one molecule in the crystallographic asymmetric unit (ASU). The file header gives information about the structure refinement. "Atom" refers to the element whose coordinates are measured. The first letter in the column defines the element. The 3-letter code of the respective amino acid is given and the amino acid sequence position. The first 3 values in the line "Atom" define the atomic position of the element as measured. The fourth value corresponds to the occupancy and the fifth (last) value is the temperature factor (B factor). The occupancy factor refers to the fraction of the molecules in which each atom occupies the position specified by the coordinates. A value of "1" indicates that each atom has the same conformation, i.e., the same position, in all equivalent molecules of the crystal. B is a thermal factor that measures movement of the atom around its atomic center. This nomenclature corresponds to the Protein Data Bank (PDB) format.

FIG. 15: (Sheets labelled FIG. 15-1 to FIG. 15-28) Structural co-ordinates of the H1N1 PA endonuclease domain with bound 4-[3-[(4-chlorophenyl)methyl]-1-(phenylmethylsulpho)-3-piperidinyl]-2-hydroxy-4-oxo-2-butenoic acid (EMBL-R05-1) in standard Protein Data Bank (PDB) format. The chain A (with associated divalent cations, i.e. two manganese ions, and water molecules) from the asymmetric unit is included. The compound EMBL-R05-1 has residue descriptor ci1.

FIG. 16: (Sheets labelled FIG. 16-1 to FIG. 16-27) Structural co-ordinates of the H1N1 PA endonuclease domain with bound epigallocatechin 3-gallate (EGCG) in standard Protein Data Bank (PDB) format. The chain A (with associated divalent cations, i.e. two manganese ions, and water molecules) from the asymmetric unit is included. The compound EGCG has residue descriptor tte.

FIG. 17: Diagram using the structural co-ordinates of FIG. 15 illustrating the endonuclease active site (PA polypeptide fragment), showing the bound compound EMBL-R05-1, the divalent cations (two manganese) and key active site residues that interact with the compound (notably Tyr24 and Arg84) or are close to it.

FIG. 18: (A) Diagram using the structural co-ordinates of FIG. 16 illustrating the endonuclease active site (PA polypeptide fragment), showing the bound compound EGCG, the divalent cations (two manganese ions) and key active site residues that interact with the compound or are close to it. (B) Bound EGCG, the divalent cations (two manganese ions) and key active site residues that interact with the compound or are close to it. Interactions less than 3.3 Å (grey dotted lines), additional possible interactions less than 4 Å (dark grey dotted lines).

As shown in FIG. 19, the mode of binding of the three diketo inhibitors to the metals is conserved (although there is some variability in exact position) but the two 'arms' of each compound are inserted into different combinations of the pockets 1 to 4. EMBL-R05-1 has a similar configuration to EMBL-R05-3D, with the two arms occupying pockets 2 and 3. EMBL-R05-3A occupies pockets 2 and 4. EMBL-R05-2, which differs notably from R05-1 and R05-3 in the point of substitution on the piperidinyl ring (Table 2) occupies pocket 3 and uniquely pocket 1 (FIG. 7B). The green tea compound EGCG occupies pockets 3 and 4. More potent and specific compounds could be perhaps designed that occupy more than two of the pockets.

EXAMPLES

The Examples are designed in order to further illustrate the present invention and serve a better understanding. They are not to be construed as limiting the scope of the invention in any way.

1. Methods 1.1 Cloning, Expression and Purification of PA-Nter (PA H1N1 1 to 198 (SEQ ID NO:13)) and PA-Nter Mutant (PA H1N1 1 to 198 Δ52-64: Gly (SEQ ID NO:14)) from Influenza Strain A/California/04/2009-H1N1

The DNA coding for PA-Nter (residues 1-198 (SEQ ID NO:13)) (see SEQ ID NO: 1 and 2) from influenza strain A/California/04/2009-H1N1 was synthesized (PA H1N1 1 to 198 (SEQ ID NO:13)) and sub-cloned in the expression vector pESPRIT002 (EMBL) by GeneArt, Regensburg, Germany. The sequence was designed to contain a MGSGMA (SEQ ID NO: 3) polypeptide linker between the tobacco etch virus (TEV) cleavage site at the N-terminus to obtain 100% cleavage by TEV protease.

To further improve crystallisation properties, a deletion of part of the flexible loop (52-73) was engineered by site directed mutagenesis. To this end, a PCR amplification of the whole vector containing the wild-type gene was performed using two primers flanking the mutation site, one of them phosphorylated, and TurboPfu polymerase (Stratagene). Subsequently template vector was digested with DpnI (New England Biolabs) and the mutated vector was re-ligated. In the PA-Nter mutant, the amino acid sequence encompassing amino acids 52-64 was replaced by a single glycine (PA H1N1 1 to 198 Δ52-64: Gly (SEQ ID NO:14).

The wild-type and mutant plasmids were transformed to *E. coli* BL21(DE3) (Stratagene) and the protein was expressed in LB medium overnight at 20° C. after induction at an OD 0.8-1.0 with 0.2 mM isopropyl-β-thiogalactopyranoside (IPTG). The protein was purified by an immobilized metal affinity column (IMAC). A second IMAC step was performed after cleavage by the His-tagged TEV protease, followed by gel filtration on a Superdex 75 column (GE Healthcare). Finally, the protein was concentrated to 10-15 mg/ml. See FIG. 11.

1.2 Compounds

Compounds used for co-crystallisation are given in Table 2. Compound rUMP was purchased from Sigma. Compounds EMBL-R05-1, EMBL-R05-2, and EMBL-R05-3 (first described in {Tomassini, 1994 #397}) were custom synthesised by Shanghai ChemPartner. EGCG was purchased from Sigma (E4143).

1.3 Crystallization

Figure 12:
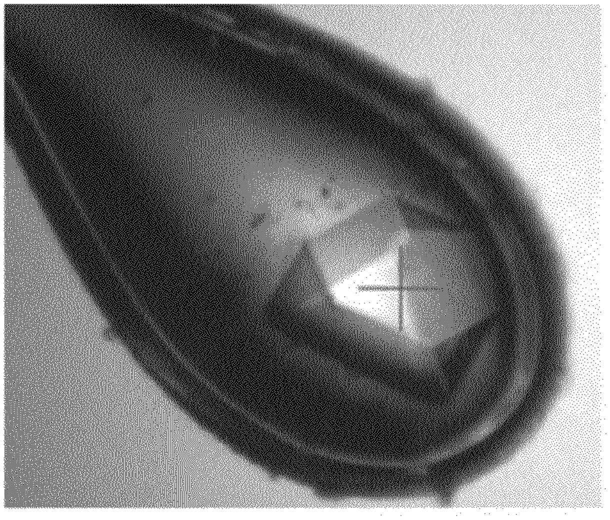
FIG. 12: Frozen crystal of H1N1 PA-Nter co-crystallised with rUMP in the P212121 space-group.

Initial sitting drop screening was carried out at 20° C. mixing 100 nL of protein solution (15 mg/mL) with 100 nL of reservoir solution using a Cartesian robot at the EMBL Grenoble crystallization platform. Around 600 conditions were screened. Subsequently, larger crystals were obtained at 20° C. by the hanging drop method mixing protein and reservoir solutions in a ratio of 1:1. The protein solution contained 10-15 mg/mL of PA-N-ter in 20 mM HEPES pH 7.5, 150 mM NaCl, 2 mM $MnCl_2$, 2 mM $MgCl_2$. The refined reservoir compositions for native crystals and co-crystallization with different compounds/ligands are listed in Table 1. For co-crystallisations, compounds/ligands rUMP, EMBL-R05-3 and EGCG were added to the protein solution to final concentrations of 5 mM, 1.5 mM and 5 mM, respectively. Native crystals and those co-crystallized with EMBL-R05-3 and EGCG were flash frozen in liquid nitrogen in their reservoir solution with additional 25% glycerol as cryo-protectant. Co-crystals with rUMP were frozen in their reservoir solution with additonal rUMP at 10 mM concentration and additional 20% glycerol as cryoprotectant. The structure with EMBL-R05-2 was obtained by soaking co-crystals of PA-N-ter and rUMP for 2 h with reservoir solution containing 1.5 mM EMBL-R05-2 and no rUMP (the inhibitor displaces the rUMP) followed by cryo protection in reservoir solution containing 20% glycerol and 1.5 mM EMBL-R05-2. FIG. 12 shows a typical co-crystal with rUMP. The structure with EMBL-R05-1 was obtained by soaking co-crystals of PA-N-ter mutant and dTMP for 2 h with reservoir solution containing the inhibitor followed by cryo protection in reservoir solution containing 20% glycerol and the inhibitor. See also Table 2 for the compounds/ligands.

TABLE 1

Summary of crystallisation conditions and crystallographic parameters for various compounds

| Fragment/ Figure(s) | Compound/ Ligand (final concentration) | Crystallisation reservoir condition | Space group and unit cell parameters | Resolution Refinement R-factor/R-free |
|---|---|---|---|---|
| PA H1N1 1 to 198 fragment (SEQ ID NO: 13) (chain A), see FIGS. 1 and 6 | No compound (native) | 1.6M sodium formate 0.1M HEPES pH7 5% Glycerol | C2 4 Molecules/ASU 263.630 66.240 66.32 90.00 95.98 90.00 | 2.1 Å 0.222/0.268 |
| PA H1N1 1 to 198 fragment (SEQ ID NO: 13) (chain A), see FIGS. 2 and 7 PA H1N1 fragment (chain D), see FIGS. 3 and 8 | EMBL-R05-3 (1.5 mM) | 2.0M ammonium sulphate 0.1M BisTris pH5.5 | P $2_12_12_1$ 4 Molecules/ASU 54.57 122.54 129.78 90.00 90.00 90.00 | 2.5 Å 0.205/0.276 |
| PA H1N1 1 to 198 Fragment (SEQ ID NO: 13) (chain A), see FIGS. 4 and 9 | EMBL-R05-2 (1.5 mM, soaked into crystals initially grown with rUMP) | 0.1M ammonium sulphate 0.1M Bis-Tris pH5.5 25% (w/v) PEG 3350 | P $2_12_12_1$ 4 Molecules/ASU 56.59 120.81 128.20 90.00 90.00 90.00 | 2.07 Å 0.205/0.259 |
| PA H1N1 1 to 198 Fragment (SEQ ID NO: 13) (chain A), see FIGS. 5 and 10 | rUMP (5.0 mM) | 0.1M ammonium sulphate 0.1M Bis-Tris pH5.5 25% (w/v) PEG 3350 | P $2_12_12_1$ 4 Molecules/ASU 54.94 120.11 128.05 90.00 90.00 90.00 | 2.05 Å 0.206/0.246 |

TABLE 1-continued

Summary of crystallisation conditions and crystallographic parameters for various compounds

| Fragment/ Figure(s) | Compound/ Ligand (final concentration) | Crystallisation reservoir condition | Space group and unit cell parameters | Resolution Refinement R-factor/R-free |
|---|---|---|---|---|
| PA H1N1 1-198 Δ52-64: Gly Fragment (SEQ ID NO: 14) (chain A) see FIGS. 15 and 17 | EMBL-R05-1 (1.5 mM, soaked into crystals initially grown with dTMP) | 25-30% PEG4K 0.1M Tris pH8.5 0.2M NaCl | P $6_222$ (180) 1 molecule/ASU a = b = 75.06 c = 120.05 Å | 1.9 Å 0.201/0.251 |
| PA H1N1 1-198 Δ52-64: Gly Fragment (SEQ ID NO: 14) (chain A) see FIGS. 16 and 18 | EGCG (5 mM) | 10% peg 3350, 0.1M NaCl, 0.1M Hepes, pH 7.0 | $P6_422$ (181) 1 molecule/ASU a = b = 99.9 c = 82.7 Å | 2.65 Å 0.250/0.304 |

TABLE 2

Compounds used

| Compound | CA Index Name | Formula | Chemical structure |
|---|---|---|---|
| EMBL-R05-3 (Tomassini et al. Antimicrob Agents Chemother 1994, 38:2827-2837) | 4-[3-[(4-chlorophenyl)methyl]-1-(phenylmethyl)-3-piperidinyl]-2-hydroxy-4-oxo-2-butenoic acid | C23 H24 Cl N O4 | 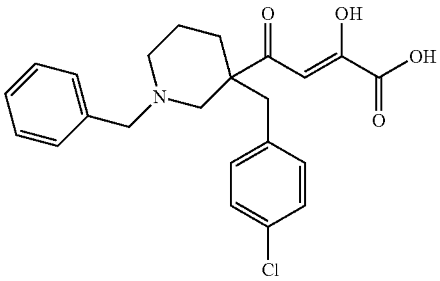 [SMILES: O=C(O)/C(O)=C/C(=O)C1(Cc2ccc(Cl)cc2)CCCN(Cc2ccccc2)C1] |
| EMBL-R05-2 (Tomassini et al. Antimicrob Agents Chemother 1994, 38:2827-2837) | 4-[4-[(4-chlorophenyl)methyl]-1-(cyclohexylmethyl)-4-piperidinyl]-2-hydroxy-4-oxo-2-butenoic acid | C23 H30 Cl N O4 | 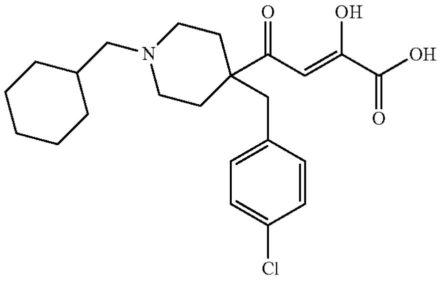 [SMILES: O=C(O)/C(O)=C/C(=O)C1(Cc2ccc(Cl)cc2)CCN(CC2CCCCC2)CC1] |
| rUMP (ribo-uridine monophosphate) | 5'-Uridylic acid | C9 H13 N2 O9 P | 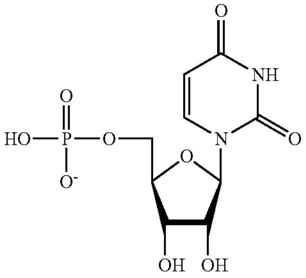 |

TABLE 2-continued

| Compounds used | | | |
|---|---|---|---|
| Compound | CA Index Name | Formula | Chemical structure |
| EMBL-R05-1 (Tomassini et al. Antimicrob Agents Chemother 1994, 38:2827-2837) | 4-[3-[(4-chlorophenyl)methyl]-1-(phenylmethylsulpho)-3-piperidinyl]-2-hydroxy-4-oxo-2-butenoic acid | C23 H24 Cl N S O6 | 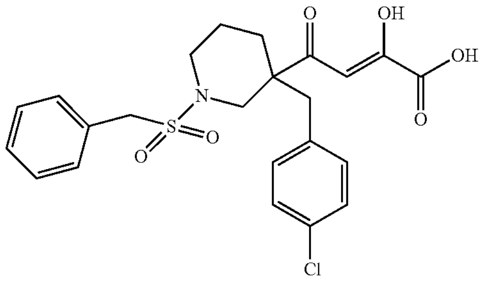 [SMILES: O=C(O)/C(O)=C/C(=O)C1(Cc2ccc(Cl)cc2)CCCN(S(=O)(=O)Cc2ccccc2)C1] |
| (−)-Epigallocatechin gallate (EGCG) | [(2R,3R)-5,7-dihydroxy-2-(3,4,5-trihydroxyphenyl)chroman-3-yl]3,4,5-trihydroxybenzoate | C22 H18 O11 | 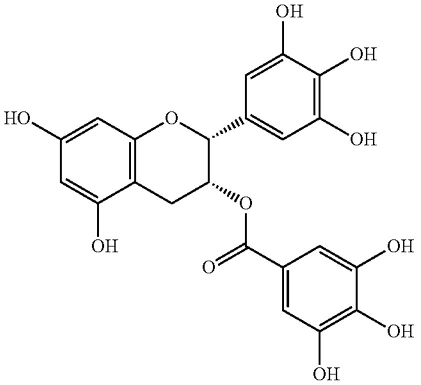 [SMILES: O=C(O[C@@H]1Cc2c(O)cc(O)cc2O[C@@H]1c1cc(O)c(O)c(O)c1)c1cc(O)c(O)c(O)c1] |

1.4 Crystal Structure Determination

Diffraction data were collected on various beamlines at the European Synchrotron Radiation Facility. Data sets were integrated with XDS and scaled with XSCALE. Subsequent data analysis was performed with the CCP4i programme suite. The initial H1N1 structure was solved with molecular replacement with PHASER using the previously determined H3N2 PA N-ter structure (Dias et al., Nature 2009). Subsequent co-crystal structures were determined with PHASER using the H1N1 structure. Refinement was carried out with REFMAC and/or model building with COOT or O. In the C2 and $P2_12_12_1$ crystal forms there are four molecules per asymmetric unit. However due to structural variations between the molecules due to plasticity (in particular the 53-73 region) and the generally good resolution, NCS restraints were not applied.

2. Results 2.1 PA H1N1 Polypeptide Fragment or PA H1N1 Polypeptide Fragment Variant Generation and Crystallisation The inventors of the present invention found that a polypeptide fragment comprising amino acids 1 to 198 of SEQ ID NO: 2 of influenza strain A/California/04/2009-H1N1 (2009 pandemic strain) (PA H1N1 1 to 198) readily crystallised with and without relevant compounds/ligands (see FIGS. 1 to 10). Crystallisation properties could further be improved with a polypeptide fragment variant comprising amino acids 1 to 198 of SEQ ID NO: 2 of influenza strain A/California/04/2009-H1N1 (2009 pandemic strain) with amino acids 52 to 64 replaced by the amino acid glycine (PA H1N1 1 to 198 Δ52-64: Gly) (see FIGS. 15 to 18).

Thus, in contrast to the numerous unsuccessful attempts undertaken in the prior art, the inventors of the present invention were able to obtain structures of PA H1N1 polypeptide fragments or PA H1N1 polypeptide fragment variants with and without compounds/ligands.

The structures of PA H1N1 polypeptide fragments or PA H1N1 polypeptide fragment variants with and without compounds/ligands are described below. All these structures show in detail how these compounds/ligands bind directly to the metal ions as well as interacting with a number of residues in the active site. Furthermore several of the interacting residues change conformation upon ligand binding, information which was unavailable before. This three-dimensional knowledge of the ligand interacting residues and the regions of plasticity of the active site is critical for the optimised design of modifications to existing inhibitors to improve their potency or for structure based design and optimisation of novel inhibitors that effectively block endonuclease activity.

2.2 H1N1 PA Native Structure

Structural co-ordinates of the native (i.e. without compound/ligand) H1N1 PA endonuclease domain (PA H1N1 1 to 198 (SEQ ID NO:13)) (chain A) in standard Protein Data Bank (PDB) format are shown in FIG. 1. Only the chain A (with associated divalent cations, i.e. one magnesium and one manganese ion, and water molecules) from the asymmetric unit is included. Chains B, C and D are very similar. A diagram using the structural co-ordinates of FIG. 1 illustrating the endonuclease active site (PA polypeptide fragment (chain A)) is shown in FIG. 6. It shows the divalent cations (one manganese and one magnesium) and key active site residues.

2.3 EMBL-R05-3-Bound Structure

Structural co-ordinates of the H1N1 PA endonuclease domain (PA H1N1 1 to 198 (SEQ ID NO:13)) (chain A) with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format are shown in FIG. 2. Only the chain A (with associated divalent cations, i.e. two manganese ions, and water molecules) from the asymmetric unit is included. The compound EMBL-R05-3 has residue descriptor ci3. A diagram using the structural co-ordinates of FIG. 2 illustrating the endonuclease active site (PA polypeptide fragment (chain A)) is shown in FIG. 7A. It shows the bound compound EMBL-R05-3, the divalent cations (two manganese) and key active site residues that interact with the compound (notably Arg84) or are close to it.

A diagram comparing the co-ordinates of FIG. 1 (chain subjacent on left hand side) and FIG. 2 showing change in conformation of the loop in the vicinity of Tyr24 upon binding of EMBL-R05-3 (chain A) is shown in FIG. 7B. The loop around Tyr24 is poorly ordered in the native structure. Tyr24 side-chain moves to partially stack with the chlorobenzene of EMBL-R05-3. This indicates a plasticity of the active site and an induced fit mode of ligand binding. An important conclusion for designing more potent inhibitors is to ensure that the extensions ('arms') to any ion-binding scaffold optimise interactions in one or more pocket(s). Imperfect matching will lead to residual flexibility and sub-optimal potency, as seems to be the case for the current compounds, none of which exhibit very well defined, full occupancy binding modes.

Further, structural co-ordinates of the H1N1 PA endonuclease domain (PA H1N1 1 to 198 (SEQ ID NO:13)) (chain D) with bound 4-[3-[(4-chlorophenyl)methyl]-1-(phenylmethyl)-3-piperidinyl]-2-hydroxy-4-oxo-2-butenoic acid (EMBL-R05-3) in standard Protein Data Bank (PDB) format are shown in FIG. 3. Only the chain D (with associated divalent cations, i.e. two manganese ions, and water molecules) from the asymmetric unit is included. The compound EMBL-05-3 has a different configuration than in chain A (FIG. 2). Said compound has residue descriptor ci3. A diagram using the structural co-ordinates of FIG. 3 illustrating the endonuclease active site (PA polypeptide fragment (chain D)) is shown in FIG. 8. It shows the bound compound EMBL-R05-3, the divalent cations (two manganese) and key active site residues that interact with the compound (notably Tyr24 and Arg84) or are close to it.

2.4 EMBL-R05-2-Bound Structure

Structural co-ordinates of the H1N1 PA endonuclease domain (PA H1N1 1 to 198 (SEQ ID NO:13)) (chain A) with bound 4-[4-[(4-chlorophenyl)methyl]-1-(cyclohexylmethyl)-4-piperidinyl]-2-hydroxy-4-oxo-2-butenoic acid (EMBL-R05-2) in standard Protein Data Bank (PDB) format are shown in FIG. 4. Only the chain A (with associated divalent cations, i.e. two manganese ions, and water molecules) from the asymmetric unit is included. Chains B, C and D are very similar. The compound EMBL-R05-2 has residue descriptor cit. A diagram using the structural co-ordinates of FIG. 4 illustrating the endonuclease active site (PA polypeptide fragment (chain A)) is shown in FIG. 9. It shows the bound compound EMBL-R05-2, the divalent cations (two manganese) and key active site residues that interact with the compound (notably Tyr24 and Phe105) or are close to it.

2.5 Ribo-Uridine Monosphosphate (rUMP)-Bound Structure

Structural co-ordinates of the H1N1 PA endonuclease domain (PA H1N1 1 to 198 (SEQ ID NO:13)) (chain A) with bound ribo-Uridine Monophosphate (rUMP) in standard Protein Data Bank (PDB) format are shown in FIG. 5. Only the chain A (with associated divalent cations, i.e. two manganese ions, and water molecules) from the asymmetric unit is included. Chains B, C and D are very similar. The compound rUMP has residue descriptor U.

Figure 14:
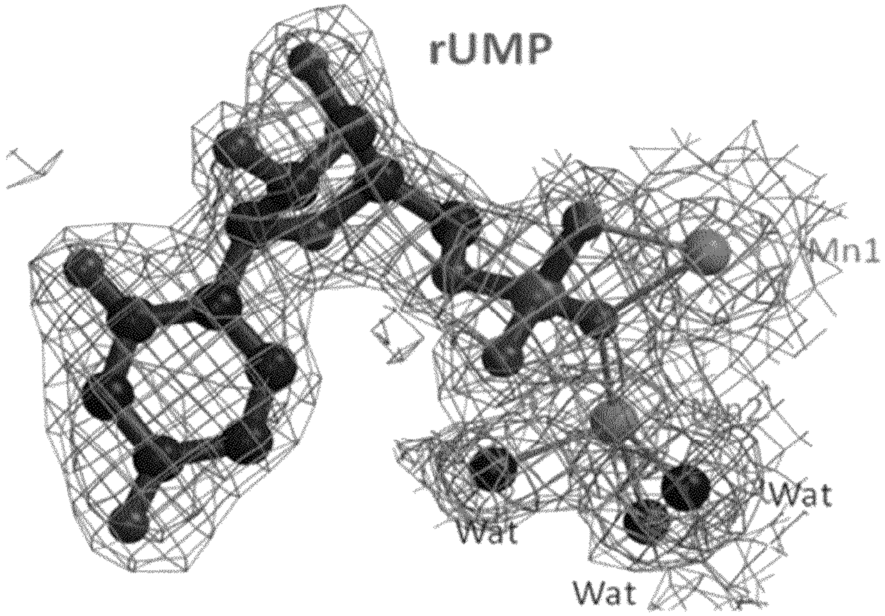
FIG. 14: Electron density for rUMP and divalent cations (manganese, Mn1 and Mn2) in co-crystals with H1N1 PA-Nter. Refined 2Fo-Fc electron density contoured at 1.1 σ. Unbiased Fo-Fc electron density contoured at 2.8 σ. Anomalous difference map contoured at 4σ.

Co-crystallisation trials with rUMP gave large, well-ordered crystals in a new orthorhombic space-group (FIGS. 12 and 14).

A diagram using the structural co-ordinates of FIG. 5 illustrating the endonuclease active site (PA polypeptide fragment (chain A)) is shown in FIG. 10. It shows the bound compound rUMP, the divalent cations (two manganese) and key active site residues that interact with the compound (notably Tyr24 and Lys34) or are close to it. The rUMP binds with two oxygens of the phosphate completing the co-ordination sphere of Mn1, one of them also co-ordinating Mn2. The base is well stacked on Tyr24 and Lys34 makes a hydrogen bond to the O2 position. The ribose hydroxyl groups do not make hydrogen bonds to the protein, consistent with the fact that deoxy ribose binds equally well and the protein is a DNAase as much as an RNAase {Dias, 2009 #448}.

The conformation observed for rUMP is quite different from that previously published (PDB entry 3hw3 {Zhao, 2009 #444}). The latter structure was obtained by soaking nucleotides into existing crystals of the endonuclease in the absence of manganese and the electron density is very poor. In this structure, a water molecule replaces Mn1 and a magnesium ion replaces Mn2. This difference in metal ligation is reflected in the altered conformation of Glu119. The ribose and base positions are quite different from the positions in the structure provided herein and unable to interact with Lys34 or Tyr24. The differences between the two structures may reflect firstly the lack of manganese and secondly the fact that soaking pre-grown crystals does not allow the active site to adapt to the ligand as is more likely the case for co-crystallisation.

2.6 EMBL-R05-1-Bound Structure

Structural co-ordinates of the H1N1 PA endonuclease domain (PA H1N1 1 to 198 Δ52-64: Gly (SEQ ID NO: 14)) with bound 4-[3-[(4-chlorophenyl)methyl]-1-(phenylmethylsulpho)-3-piperidinyl]-2-hydroxy-4-oxo-2-butenoic acid (EMBL-R05-1) in standard Protein Data Bank (PDB) format are shown in FIG. 15. The chain (with associated divalent cations, i.e. two manganese ions, and water molecules) from the asymmetric unit is included. The compound EMBL-R05-1 has residue descriptor ci1. A diagram using the structural co-ordinates of FIG. 15 illustrating the endonuclease active site (PA polypeptide fragment) is shown in FIG. 17. It shows the bound compound EMBL-R05-1, the divalent cations (two manganese) and key active site residues that interact with the compound (notably Tyr24 and Arg84) or are close to it.

2.7 EGCG-Bound Structure

Epigallocatechin 3-gallate (EGCG), is the ester of epigallocatechin and gallic acid and is the most abundant catechin in green tea. It has recently been reported that EGCG inhibits the influenza endonuclease {Kuzuhara, 2009 #629}. Co-crystallisation of PA H1N1 1 to 198 Δ52-64: Gly (SEQ ID NO: 14) with (−)-Epigallocatechin gallate gave a new crystal form (Table 1) diffracting to 2.65 Å resolution. The compound was clearly observed in the active site. Strong extra density also exists around a 2-fold crystallographic axis and most likely represents other EGCG molecules trapped by crystal packing Structural co-ordinates of the H1N1 PA endonuclease domain (PA H1N1 1 to 198 Δ52-64: Gly (SEQ ID NO: 14)) with bound epigallocatechin 3-gallate (EGCG) in standard Protein Data Bank (PDB) format is shown in FIG. 16. The chain (with associated divalent cations, i.e. two manganese ions, and water molecules) from the asymmetric unit is included. The compound EGCG has residue descriptor tte. A diagram using the structural co-ordinates of FIG. 16 illustrating the endonuclease active site (PA polypeptide fragment) is shown in FIG. 18A. It shows the bound compound EGCG, the divalent cations (two manganese ions) and key active site residues that interact with the compound or are close to it. FIG. 18B shows the bound EGCG, the divalent cations (two manganese ions) and key active site residues that interact with the compound or are close to it. Interactions less than 3.3 Å (grew dotted lines), additional possible interactions less than 4 Å (dark grey dotted lines) are shown.

2.8 Superposition of all Diketo Inhibitor Compounds

Figure 19:
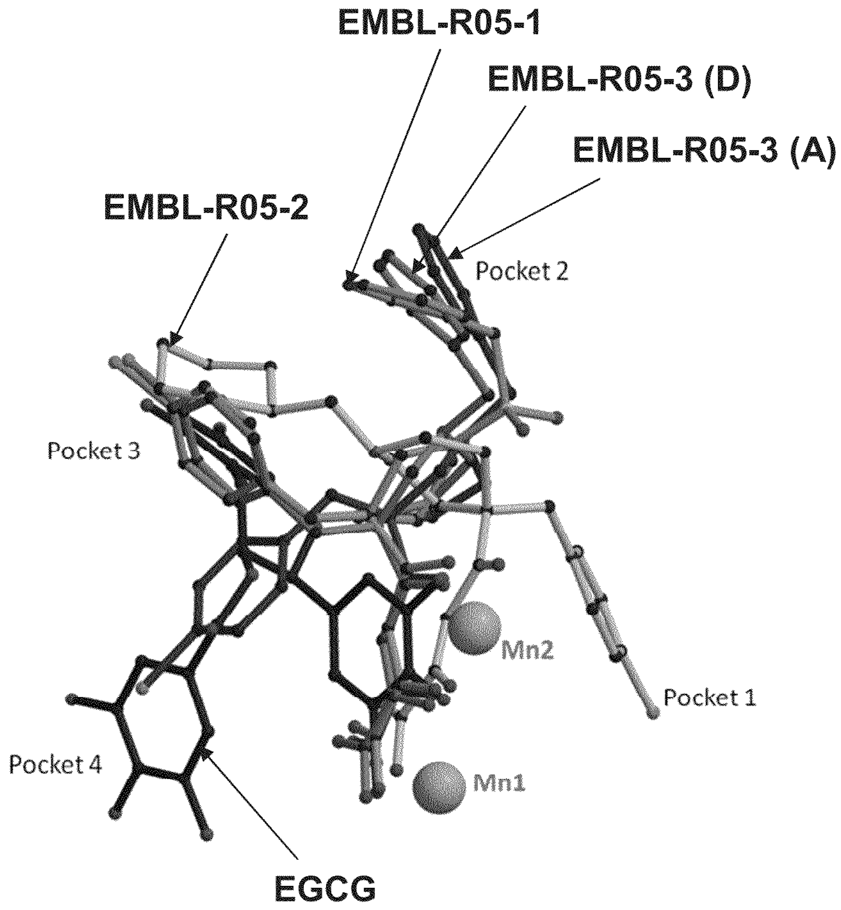
FIG. 19: Superposition of all diketo inhibitor compounds (EMBL-R05-1, EMBL-R05-2, and EMBL-R05-3A and D) and EGCG bound in PA active site.

A superposition of all diketo inhibitor compounds (EMBL-R05-1, EMBL-R05-2, and EMBL-R05-3A and D) and EGCG bound in PA active site is shown in FIG. 19. As shown in FIG. 19, the mode of binding of the three diketo inhibitors to the metals is conserved (although there is some variability in exact position) but the two 'arms' of each compound are inserted into different combinations of the pockets 1 to 4. EMBL-R05-1 has a similar configuration to EMBL-R05-3D, with the two arms occupying pockets 2 and 3. EMBL-R05-3A occupies pockets 2 and 4. EMBL-R05-2, which differs notably from R05-1 and R05-3 in the point of substitution on the piperidinyl ring (Table 2) occupies pocket 3 and uniquely pocket 1 (FIG. 7B). The green tea compound EGCG occupies pockets 3 and 4. More potent and specific compounds could be perhaps designed that occupy more than two of the pockets.

2.9 Divalent Cation Binding

Figure 13:
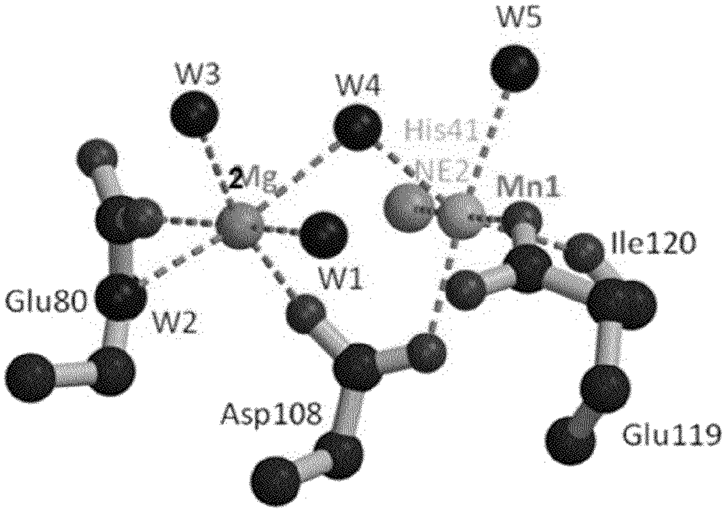
FIG. 13: Divalent ion co-ordination in the native endonuclease structure.

In the native structure (FIG. 1 and FIG. 6), two divalent cations are observed in the active site. These are identified (using magnitude of electron density and anomalous scattering, data not shown) to be a manganese atom in site 1 (Mn1 in FIG. 13), ligated by His41, Asp108, Glu119, Ile120 and two water molecules (W4 and W5) and a magnesium ion in site 2 (Mg2 in FIG. 13), ligated by Glu80 and Asp108 and four water molecules (W1, W2, W3 and W4). In the other structures (FIGS. 2-5 and FIGS. 7-10 as well as FIGS. 15-18) the ions in both site 1 and site 2 are manganese ions (Mn1 and Mn2), as identified by magnitude of electron density and anomalous scattering (e.g. for rUMP, see FIG. 14).

The invention claimed is:

1. A polypeptide consisting of an amino-terminal linker of SEQ ID NO:3 and an amino acid sequence having at least 95% sequence identity to residues 1-190 of SEQ ID NO:2 comprising a serine residue at a position corresponding to serine 186.

2. The polypeptide of claim 1, which is soluble and remains in the supernatant after centrifugation for 30 min at 100,000×g in an aqueous buffer under physiologically isotonic conditions.

3. The polypeptide of claim 1, wherein the amino acid sequence corresponds to amino acids 198 of SEQ ID NO: 2.

4. The polypeptide of claim 1 to which two divalent cations are bound.

5. The polypeptide of claim 4, wherein the divalent cation is manganese and/or magnesium.

6. The polypeptide of claim 1, wherein the polypeptide consists of SEQ ID NO: 3 and SEQ ID NO: 13.

7. The polypeptide fragment of claim 6, wherein the polypeptide is in a crystal form selected from the group consisting of a crystal in space group C2 with unit cell dimensions of a=263.6 Å±5 Å, b=66.2 Å±3 Å, c=66.3 Å±3 Å, α=90 deg, β=96±2 deg, γ=90 deg, and a crystal in space group $P2_12_12_1$ with unit cell dimensions of a=54.6 Å±3 Å, b=122.5 Å±4 Å, c=130.0 Å±3 Å, α=90 deg, β=90 deg, γ=90 deg.

8. The crystal of claim 7, wherein the crystal diffracts X-rays to a resolution of 2.6 Å or higher.

9. The crystal of claim 7, wherein the crystal diffracts X-rays to a resolution of 2.1 Å or higher.

10. The crystal of claim 7, wherein crystal diffracts X-rays to a resolution of 1.9 Å or higher.

11. A polypeptide comprising the amino acid sequence according to SEQ ID NO: 14.

12. The polypeptide of claim 11, further comprising an amino-terminal linker consisting of SEQ ID NO: 3.

13. A polypeptide consisting of the N-terminal linker of SEQ ID NO:3 and the amino acid sequence according to of SEQ ID NO:14.

14. The polypeptide of claim 13, wherein the polypeptide is in a crystal form selected from the group consisting of a crystal in space group P $6_222$ with unit cell dimensions of a=75.0 Å±3 Å, b=75.0 Å±3 Å, c=120.0 Å±5 Å, α=90 deg, β=90 deg, γ=120 deg, and a crystal in space group $P6_422$ with unit cell dimensions of a=99.9 Å±5 Å, b=99.9 Å±5, c=82.7 Å±3 Å, α=90 deg, β=90 deg, γ=120 deg.

* * * * *

UNITED STATES PATENT AND TRADEMARK OFFICE

CERTIFICATE OF CORRECTION

PATENT NO. : 9,181,307 B2
APPLICATION NO. : 13/635064
DATED : November 10, 2015
INVENTOR(S) : Stephen Cusack et al.

It is certified that error appears in the above-identified patent and that said Letters Patent is hereby corrected as shown below:

In the claims,

Claim 3, Column 79, Line 48

Insert --1 to-- before 198

Signed and Sealed this
Fifth Day of April, 2016

Michelle K. Lee
*Director of the United States Patent and Trademark Office*